(12) United States Patent
Boloor

(10) Patent No.: US 10,023,592 B2
(45) Date of Patent: Jul. 17, 2018

(54) BROMODOMAIN INHIBITORS

(71) Applicant: Celgene Quanticel Research, Inc., San Diego, CA (US)

(72) Inventor: Amogh Boloor, San Diego, CA (US)

(73) Assignee: Celgene Quanticel Research, Inc., San Diego, CA (US)

( * ) Notice: Subject to any disclaimer, the term of this patent is extended or adjusted under 35 U.S.C. 154(b) by 0 days.

(21) Appl. No.: 15/436,340

(22) Filed: Feb. 17, 2017

(65) Prior Publication Data

US 2017/0158709 A1    Jun. 8, 2017

Related U.S. Application Data

(60) Division of application No. 14/789,881, filed on Jul. 1, 2015, now Pat. No. 9,598,372, which is a continuation of application No. 14/658,048, filed on Mar. 13, 2015, now Pat. No. 9,115,114, which is a continuation of application No. 14/517,705, filed on Oct. 17, 2014, now Pat. No. 9,034,900.

(60) Provisional application No. 61/931,467, filed on Jan. 24, 2014, provisional application No. 61/893,133, filed on Oct. 18, 2013.

(51) Int. Cl.

| | | |
|---|---|---|
| *C07D 401/04* | (2006.01) |
| *A61K 31/44* | (2006.01) |
| *A61K 31/47* | (2006.01) |
| *A61K 31/505* | (2006.01) |
| *C07D 498/04* | (2006.01) |
| *C07D 217/24* | (2006.01) |
| *C07D 413/04* | (2006.01) |
| *C07D 471/04* | (2006.01) |
| *C07D 405/04* | (2006.01) |
| *C07D 213/64* | (2006.01) |
| *C07D 241/20* | (2006.01) |
| *C07D 213/73* | (2006.01) |
| *C07D 213/74* | (2006.01) |
| *C07D 487/04* | (2006.01) |
| *C07D 237/14* | (2006.01) |
| *C07D 401/14* | (2006.01) |
| *C07D 417/14* | (2006.01) |
| *C07D 405/12* | (2006.01) |
| *C07D 409/04* | (2006.01) |
| *C07D 405/06* | (2006.01) |
| *C07D 413/06* | (2006.01) |
| *C07D 491/048* | (2006.01) |
| *C07D 495/04* | (2006.01) |
| *C07D 401/12* | (2006.01) |
| *C07D 213/69* | (2006.01) |
| *C07D 213/70* | (2006.01) |

(52) U.S. Cl.
CPC ......... *C07D 498/04* (2013.01); *C07D 213/64* (2013.01); *C07D 213/69* (2013.01); *C07D 213/70* (2013.01); *C07D 213/73* (2013.01); *C07D 213/74* (2013.01); *C07D 217/24* (2013.01); *C07D 237/14* (2013.01); *C07D 241/20* (2013.01); *C07D 401/04* (2013.01); *C07D 401/12* (2013.01); *C07D 401/14* (2013.01); *C07D 405/04* (2013.01); *C07D 405/06* (2013.01); *C07D 405/12* (2013.01); *C07D 409/04* (2013.01); *C07D 413/04* (2013.01); *C07D 413/06* (2013.01); *C07D 417/14* (2013.01); *C07D 471/04* (2013.01); *C07D 487/04* (2013.01); *C07D 491/048* (2013.01); *C07D 495/04* (2013.01)

(58) Field of Classification Search
None
See application file for complete search history.

(56) References Cited

U.S. PATENT DOCUMENTS

| | | |
|---|---|---|
| 3,816,422 A | 6/1974 | Stahle et al. |
| 4,711,956 A | 12/1987 | Atanassova et al. |
| 6,486,155 B1 | 11/2002 | Pamukcu et al. |
| 7,265,120 B2 | 9/2007 | Tsutsumi et al. |
| 8,513,232 B2 | 8/2013 | Bacon et al. |
| 8,969,341 B2 | 3/2015 | Furet et al. |
| 8,975,417 B2 | 3/2015 | Blank et al. |
| 9,034,900 B2 | 5/2015 | Michael et al. |
| 2006/0287341 A1 | 12/2006 | Wu et al. |
| 2007/0099911 A1 | 5/2007 | Kelly et al. |
| 2007/0213323 A1 | 9/2007 | Imogai et al. |
| 2009/0054434 A1 | 2/2009 | Hu et al. |
| 2010/0256698 A1 | 10/2010 | Trotter et al. |
| 2012/0208814 A1 | 8/2012 | Demont et al. |
| 2013/0331382 A1 | 12/2013 | Hubbard et al. |
| 2014/0349990 A1 | 11/2014 | Blank et al. |

(Continued)

FOREIGN PATENT DOCUMENTS

| | | |
|---|---|---|
| CN | 103183675 A | 7/2013 |
| DE | 2011970 A1 | 11/1971 |

(Continued)

OTHER PUBLICATIONS

Search Report dated Apr. 11, 2017, in related Singapore Application No. 11201602996R, filed Oct. 17, 2014.

(Continued)

*Primary Examiner* — Zinna Northington Davis
(74) *Attorney, Agent, or Firm* — Wiley & Rein LLP

(57) ABSTRACT

The present invention relates to substituted heterocyclic derivative compounds, compositions comprising said compounds, and the use of said compounds and compositions for epigenetic regulation by inhibition of bromodomain-mediated recognition of acetyl lysine regions of proteins, such as histones. Said compositions and methods are useful for the treatment of cancer and neoplastic disease.

27 Claims, No Drawings

(56) References Cited

U.S. PATENT DOCUMENTS

| | | |
|---|---|---|
| 2015/0005340 A1 | 1/2015 | Gong |
| 2015/0051208 A1 | 2/2015 | Engelhardt et al. |
| 2015/0183784 A1 | 7/2015 | Bennett et al. |

FOREIGN PATENT DOCUMENTS

| | | |
|---|---|---|
| DE | 2356005 A1 | 5/1975 |
| JP | 2005089352 A | 4/2005 |
| WO | 0023487 A1 | 4/2000 |
| WO | 03/097613 A1 | 11/2003 |
| WO | 2004029051 A1 | 4/2004 |
| WO | 2004/058729 A1 | 7/2004 |
| WO | 2005030791 A2 | 4/2005 |
| WO | 2005063768 A1 | 7/2005 |
| WO | 2005095384 A1 | 10/2005 |
| WO | 2006030032 A1 | 3/2006 |
| WO | 2006112666 A1 | 10/2006 |
| WO | 2007012421 A1 | 2/2007 |
| WO | 2007012422 A1 | 2/2007 |
| WO | 2008077550 A1 | 7/2008 |
| WO | 2008077551 A1 | 7/2008 |
| WO | 2008077556 A1 | 7/2008 |
| WO | 2009097567 A1 | 8/2009 |
| WO | 2009158396 A1 | 12/2009 |
| WO | 2010069504 A1 | 6/2010 |
| WO | 2011044157 A1 | 4/2011 |
| WO | 2011/054848 A1 | 5/2011 |
| WO | 2011112766 A2 | 9/2011 |
| WO | 2012000595 A1 | 1/2012 |
| WO | 2012/150234 A1 | 11/2012 |
| WO | 2012171337 A1 | 12/2012 |
| WO | 2013/027168 A1 | 2/2013 |
| WO | 2013064984 A1 | 5/2013 |
| WO | 2013142390 A1 | 9/2013 |
| WO | 2014191894 A1 | 12/2014 |
| WO | 2014191896 A1 | 12/2014 |
| WO | 2014191911 A1 | 12/2014 |
| WO | 2014206150 A1 | 12/2014 |
| WO | 2014206345 A1 | 12/2014 |
| WO | 2014210425 A1 | 12/2014 |
| WO | 2015022332 A1 | 2/2015 |

OTHER PUBLICATIONS

Written Opinion dated Apr. 26, 2017, in related Singapore Application No. 11201602996R, filed Oct. 17, 2014.
Alvarez et al, Product class 6: isoquinolinones. Science of Synthesis 15:839-906 (2005).
Becknell et al., Synthesis and evaluation of pyridone-phenoxypropyl-R-2-methylpyrrolidine analogues as histamine H3 receptor antagonists. Bioorganic & Medicinal Chemistry Letters 21(23):7076-7080 (2011).
Berti., A new type of electrophilic transposition: Passage of a phthalimidine derivative to an isocarbostyril. Gazzetta Chimica Italiana 90:559-72 (1960).
Berti et al., Mechanism of the cyclization of the amides of o-(2-chlorovinyl)benzoic acids. Annali di Chimica 49:1253-68 (1959).
Briet et al., Synthesis of novel substituted isoquinolones. Tetrahedron 58(29):5761-5766 (2002).
CAS Structure Search dated Jun. 25, 2013.
CAS Structure Search dated May 30, 2014.
Chao et al., Substituted isoquinolines and quinazolines as potential antiinflammatory agents. Synthesis and biological evaluation of inhibitors of tumor necrosis factor alpha. J. Met Chem. 42:3860-3873 (1999).
Coskun et al., Novel Methods for the Synthesis of 4-Arylisoquinolinium Perchlorates and 4-Arylisoquinolin-1-ones. Synthetic Communications 35(18):2435-2443 (2005).
Couture et al., A new synthetic route to 2-alkyl-4-aryl-1(2H)-isoquinolones and 2-alkyl-4-aryl-1,2,3,4,-tetrahydroisoquinolines. Tetrahedron 52(12):4433-48 (1996).

Couture et al., Base-induced cyclization of trimethoxy-o-aroyldiphenylphosphoryl methylbenzamide: a formal synthesis of (±) cherylline and (±) cherylline dimethylether. Tetrahedron Letters 37(21):3697-3700 (1999).
Couture et al., Total syntheses of (±) -cherylline and (±) -latifine. J. Chem. Soc., Perkin Trans. 1:789-794 (1999).
Dey et al., Brd4 marks select genes on mitotic chromatin and directs postmitotic transcription. Mol. Biol. Cell 20:4899-4909 (2009).
Filippakopoulos et al., Selective Inhibition of BET Bromodomains. Nature 468(7327):1067-73 (2010).
French et al., BRD4 bromodomain gene rearrangement in aggressive carcinoma with translocation t(15;19). Am J. Pathol. 159:1987-1992 (2001).
French et al., BRD4-NUT fusion oncogene: a novel mechanism in aggressive carcinoma. Cancer Res. 63:304-307 (2003).
Gore et al., Efficient synthesis of (±) latifine dimethyl ether. Journal of the Chemical Society, Perkin Transactions 1: Organic and Bio-Organic Chemistry (3):481-3 (1972-1999) (1988).
Hares et al., Synthesis and Antibacterial Activity of Some 4-Oxopyrrolo [1,2-a] pyrimidine 3-Carboxylic Acid Derivatives. Egyptian Journal of Pharmaceutical Sciences 32(1-2) 303-14 (1991).
Hargreaves et al., Control of inducible gene expression by signal-dependent transcriptional elongation. Cell 138:129-145 (2009).
Henry et al., Preparation and fluorescence of substituted 2-methyl-isoquinolones, Journal of Organic Chemistry 40 (12):1760-6 (1975).
International Search Report and Written Opinion dated Jan. 21, 2015 issued in International Application No. PCT/US2014/61261, filed Oct. 17, 2014.
Jang et al., The bromodomain protein Brd4 is a positive regulatory component of P-TEFb and stimulates RNA polymerase II-dependent transcription. Mol. Cell 19:523-534 (2005).
Kihara et al., New reduction reaction of benzylic alcohols with acid and proof of the intermolecular hydride shift mechanism. Heterocycles 53(2):359-372 (2000).
Kihara et al., Stereoselective intermolecular hydride shift mechanism of the new reduction of benzylic alcohols with acid. Heterocycles 48(12):2473-2476 (1998).
Leroy et al., The double bromodomain proteins Brd2 and Brd3 couple histone acetylation to transcription. Mol Cell 30:51-60 (2008).
Mishra et al., Diversely Substituted Imidazo[1,2-α]pyrazine-8-oxo-3carbaldehydes: An Iodine-Mediated Cyclization/Oxidation Approach. European Journal of Organic Chemistry 2013(4):693-700 (2013).
Moehrle et al., Carbinolamines from substituted tetrahydroisoquinolines, Archiv der Pharmazie (Weinhelm, Germany) 321(10):759-64 (CAPLUS Accession No. 1989:23703) (1988).
Mukaiyama et al., Synthesis and c-Src inhibitory activity of imidazo[1,5-a]pyrazine derivatives as an agent for treatment of acute ischemic stroke. Bioorganic & Medicinal Chemistry 15(2):868-885 (2007).
Narasimhan et al., An Efficient Sythesis of 4Aryl-1,2,3,4-tetrahydrosisoquinolines. Journal of the Chemical Society, Chemical Communications (3):191-2 (1987).
Natsugari et al., Novel, Potent, and Orally Active Substance P Antagonists: Synthesis and Antagonist Activity of N-Benzylcarboxamide Derivatives of Pyrido[3,4-b]pyridine. Journal of Medicinal Chemistry 38(16):3106-20 (1995).
Nicodeme et al., Suppression of inflammation by a Synthetic Histone Mimic. Nature 468(7327):1119-23 (2010).
Phelps et al., Clinical response and pharmacokinetics from a phase 1 study of an active dosing schedule of flavopiridol in relapsed chronic lymphocytic leukemia. Blood 113:2637-2645 (2009).
Rahl et al., c-Myc regulates transcriptional pause release, Cell 141:432-445 (2010).
Staehle et al., RingschluBreaktionen mit 2-Aminoimidazolinen. Liebigs Annalen Chemie, pp. 1275-1281 (1973) (English Abstract).
Svechkarev et al., Synthesis and spectral properties of new luminescent compounds with intramolecular proton phototransfer reaction which are derivatives of 2-(N-methylisoquinolon-1(2H)-4-yl)-

(56) References Cited

OTHER PUBLICATIONS hydroxychromone, Visnik Kharkivs'nogo Universitetu im. V. N. Karazina 770:201-207 (CAPLUS Accession No. 2008:1015841) (2007) (English Abstract).

Vachhani et al., A facile diversity-oriented synthesis of imidazo[1,2-a]pyrazinones via gold-catalyszed regioselective heteroannulation of propnylaminopyrazinones. Tetrahedron 69(1):359-365 (2013).

Wang et al., A novel synthesis of arylpyrrolo[1,2-a]pyrazinone derivatives. Molecules 9(7):574-582 (2004).

Xie et al., Synthesis, single-crystal characterization and preliminary biological evaluation of novel ferrocenyl pyrazolo [1,5-a]pyrazin-4(5H)-one derivatives. European Journal of Medicinal Chemistry 45(1):210-218 (2010).

Yang et al., Multisite protein modification and intramolecular signaling. Oncogene 24:1653-1662 (2005).

Yang et al., Recruitment of P-TEFb for stimulation of transcriptional elongation by the bromodomain protein Brd4, Mol. Cell 19:535-545 (2005).

Gentile et al., Bioorganic & Medicinal Chemistry Letters 21(16):4823-4827 (2011).

Extended European Search Report dated Feb. 1, 2018, in related European Patent Application No. 17175464.1 (which is based on EP Pat. Appln. No. 14854531.2), filed Jun. 12, 2017.

BROMODOMAIN INHIBITORS

CROSS REFERENCE

This Application is a division of U.S. application Ser. No. 14/789,881, filed Jul. 1, 2015 (now U.S. Pat. No. 9,598,372), which is a continuation of U.S. patent application Ser. No. 14/658,048, filed Mar. 13, 2015 (now U.S. Pat. No. 9,115,114), which is a continuation of U.S. patent application Ser. No. 14/517,705, filed Oct. 17, 2014 (now U.S. Pat. No. 9,034,900), which claims the priority benefit of U.S. Provisional Applications No. 61/893,133, filed Oct. 18, 2013, and No. 61/931,467, filed Jan. 24, 2014, the contents of which are hereby incorporated by reference in their entireties for all purposes.

BACKGROUND

A need exists in the art for an effective treatment of cancer and neoplastic disease.

BRIEF SUMMARY OF THE INVENTION

Provided herein are substituted heterocyclic derivative compounds and pharmaceutical compositions comprising said compounds. The subject compounds and compositions are useful for epigenetic regulation by inhibition of bromodomain-mediated recognition of acetyl lysine regions of proteins, such as histones. Furthermore, the subject compounds and compositions are useful for the treatment of cancer, such as NUT midline carcinoma, Burkitts lymphoma, prostate cancer, breast cancer, bladder cancer, lung cancer and/or melanoma and the like. The substituted heterocyclic derivative compounds described herein are based upon isoquinolinones and related heterocyclic structures. Said isoquinolinones and related heterocyclic structures are substituted at the 4-position with a group such as an aryl, a heteroaryl and the like, and on the nitrogen atom of the isoquinolinone or related heterocyclic structure with a small alkyl group, such as a methyl group.

One embodiment provides a compound of Formula (I), or a pharmaceutically acceptable salt thereof,

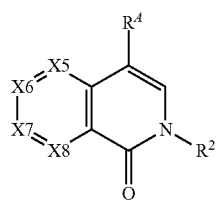

Formula (I)

wherein, $R^2$ is selected from $CH_3$, $CH_2CH_3$, $CH_2CF_3$, $CH_2F$, $CHF_2$, $CF_3$, $CH_2D$, $CHD_2$, or $CD_3$;

X5 is C—$R^5$ or N;
X6 is C—$R^6$ or N;
X7 is C—$R^7$ or N;
X8 is C—$R^8$ or N; wherein no more than two of X5, X6, X7, or X8 may be N;

$R^5$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^6$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^7$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^8$ is hydrogen, halogen, or alkyl;

$R^A$ is

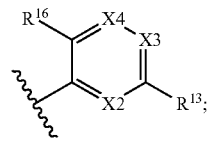

X2 is N or C—$R^{12}$, wherein $R^{12}$ is hydrogen, halogen, alkyl, or alkoxy;

$R^{13}$ is —Y—Z;

Y is selected from a bond, —$CH_2$—, —$CH(C_1$-$C_4$ alkyl)-;

Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$COR^{21}$, —$OC(O)N(R^{22})_2$, —$OSO_2N(R^{22})_2$, or —$N(R^{22})SO_3R^{21}$;

X3 is N or C—$R^{14}$, wherein $R^{14}$ is hydrogen, halogen, —CN, alkyl, cycloalkyl, or alkoxy;

X4 is N or C—$R^{15}$, wherein $R^{15}$ is hydrogen, halogen, alkyl, —CN, or alkoxy;

$R^{16}$ is hydrogen, halogen, or —W—X, wherein W is a bond, —O—, —S—, or —NH—, and X is selected from alkyl, aryl, aralkyl, cycloalkyl, cycloalkylalkyl, alkynyl, cycloalkylalkynyl, heterocyclyl, heterocyclylalkyl, heteroaryl, or heteroarylalkyl;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

One embodiment provides a compound of Formula (II), or a pharmaceutically acceptable salt thereof,

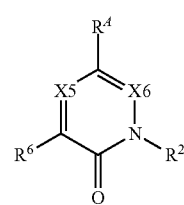

Formula (II)

wherein, $R^2$ is alkyl, cycloalkyl, cycloalkylalkyl, heterocyclylalkyl, aralkyl, or heteroarylalkyl;

X6 is C—H or N;

X5 is C—$R^5$ or N; provided that if X6 is N, then X5 is C—$R^5$, and if X5 is N, then X6 is CH;

$R^5$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^6$ is hydrogen, halogen, —OH, —CN, alkyl, cycloalkyl, cycloalkylalkyl, amino, alkylamino, dialkylamino, cycloalkylalkylamino, alkoxy, —S-alkyl, cycloalkylalkoxy, heterocyclyl, aralkoxy, heteroaryloxy, aryloxy, alkynyloxy, or —N(H)COalkyl;

$R^4$ is

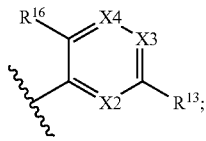

X2 is N or C—$R^{12}$, wherein $R^{12}$ is hydrogen, halogen, alkyl, or alkoxy;

$R^{13}$ is —Y—Z;

Y is selected from a bond, —$CH_2$—, or —CH($C_1$-$C_4$alkyl)-;

Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$COR^{21}$, —$OC(O)N(R^{22})_2$, —$OSO_2N(R^{22})_2$, or —$N(R^{22})SO_3R^{21}$;

X3 is N or C—$R^{14}$, wherein $R^{14}$ is hydrogen, halogen, —CN, alkyl, cycloalkyl, or alkoxy;

X4 is N or C—$R^{15}$, wherein $R^{15}$ is hydrogen, halogen, —CN, alkyl, alkoxy, aryloxy, aralkyloxy, cycloalkylalkyloxy, heterocyclyloxy, heteroarylalkyloxy, or alkynyloxy;

$R^{16}$ is hydrogen, halogen, —N(H)COX, or —W—X, wherein W is a bond, —O—, —S—, or —NH—, and X is selected from alkyl, aryl, aralkyl, cycloalkyl, cycloalkylalkyl, alkynyl, cycloalkylalkynyl, heterocyclyl, heterocyclylalkyl, heteroaryl, or heteroarylalkyl;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl; and provided that when X6 is N, then $R^5$ and $R^6$ are not hydrogen.

One embodiment provides a pharmaceutical composition comprising a compound of Formula (I), or a pharmaceutically acceptable salt thereof, and a pharmaceutically acceptable excipient. One embodiment provides a pharmaceutical composition comprising a compound of Formula (II), or a pharmaceutically acceptable salt thereof, and a pharmaceutically acceptable excipient.

One embodiment provides a method of treating cancer in a patient in need thereof, comprising administering to the patient a compound of Formula (I), or a pharmaceutically acceptable salt thereof. One embodiment provides a method of treating cancer in a patient in need thereof, comprising administering to the patient a compound of Formula (II), or a pharmaceutically acceptable salt thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

"Amino" refers to the —NH2 radical.
"Cyano" refers to the —CN radical.
"Nitro" refers to the —NO2 radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—NH2 radical.
"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_1$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)2, —C(O)R$^a$, —C(O)OR$^a$, —C(O)N(R$^a$)$_2$, —N(R$^a$)C(O)OR$^a$, —OC(O)—N(R$^a$)2, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoro-methyl), heterocyclylalkyl (optionally substituted with halogen, hydroxy, methoxy, or trifluoro-methyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoro-methyl), carbocyclylalkyl (optionally substituted with halogen, hydroxy, methoxy, or trifluoro-methyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)2, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoro-methyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)2, —N(R$^a$)C(O)

$R^a$, —N($R^a$)S(O)$_t R^a$ (where t is 1 or 2), —S(O)$_t$O$R^a$ (where t is 1 or 2), —S(O)$_t R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atoms (e.g., $C_2$ alkynylene). In other embodiments, an alkynylene comprises five to eight carbon atoms (e.g., $C_5$-$C_8$ alkynylene). In other embodiments, an alkynylene comprises two to five carbon atoms (e.g., $C_2$-$C_5$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, cyano, trimethylsilanyl, —O$R^a$, —S$R^a$, —OC(O)—$R^a$, —N($R^a$)$_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t R^a$ (where t is 1 or 2), —S(O)$_t$O$R^a$ (where t is 1 or 2), —S(O)$_t R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—O$R^a$, —$R^b$—OC(O)—$R^a$, —$R^b$—OC(O)—O$R^a$, —$R^b$—OC(O)—N($R^a$)$_2$, —$R^b$—N(Ra)$_2$, —$R^b$—C(O)$R^a$, —$R^b$—C(O)O$R^a$, —$R^b$C(O)N($R^a$)$_2$, —$R^b$—O—$R^e$—C(O)N(Ra)$_2$, —$R^b$—N($R^a$)C(O)O$R^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t$O$R^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula —$R^c$-aryl where $R^c$ is an alkylene chain as defined above, for example, methylene, ethylene, and the like. The alkylene chain part of the aralkyl radical is optionally substtuted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl may be saturated, (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(Ra)_2$, —$R^b$—$C(O)R^a$, —$R^b$—$C(O)OR^a$, —$R^b C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkoxy" refers to a radical bonded through an oxygen atom of the formula —O—$R^c$-carbocyclyl where $R^c$ is an alkylene chain as defined above. The alkylene chain and the carbocyclyl radical is optionally substituted as defined above.

"Carbocyclylalkynyl" refers to a radical of the formula —$R^c$-carbocyclyl, where $R^c$ is an alkynylene chain as defined above. The carbocyclyl part of the carbocyclylalkynyl radical is optionally substituted as described above for an carbocyclyl group. In some embodiments the carbocyclyl group is a cycloalkyl group. The alkynylene chain part of the carbocyclylalkynyl radical is optionally substituted as defined above for an alkynylene chain.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

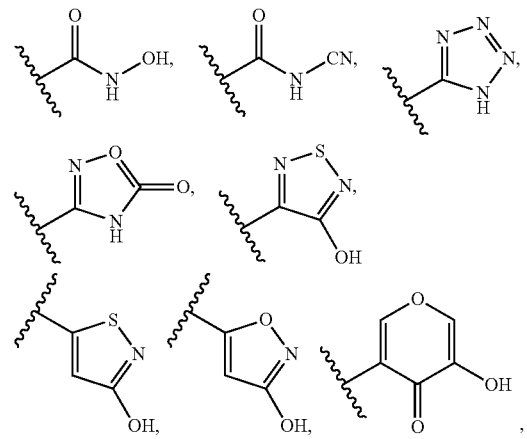

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical may be optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, iso-xazolidinyl, morpholinyl, octahydroindolyl, octahydroisoindolyl, 2-oxopiperazinyl, 2-oxo-piperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(Ra)_2$, —$R^b$—$C(O)R^a$, —$R^b$—$C(O)OR^a$, —$R^bC(O)N(R^a)_2$, —$R^b$—O—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O-Rc-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benz-oxazolyl, benzodioxolyl, benzodioxinyl, benzopyranyl, benzopyranonyl, benzofuranyl, benzo-furanonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]-pyrimidinyl, 5,6,7,8,9,10-hexahydrocycloocta[d]pyridazinyl, 5,6,7,8,9,10-hexahydrocycloocta[d]-pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octa-hydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thia-diazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—OC (O)—OR$^a$, —R$^b$—OC(O)—N(R$^a$)$_2$, —R$^b$—N(Ra)$_2$, —R$^b$—C(O)Ra, —R$^b$—C(O)OR$^a$, —R$^b$C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —R$^c$-heteroaryl, where R$^c$ is an alkylene chain as defined above.

alkylene chain. The heteroaryl part of the heteroarylalkyl radical is optionally substituted as defined above for a heteroaryl group.

"Heteroarylalkoxy" refers to a radical bonded through an oxygen atom of the formula —O—R$^c$-heteroaryl, where R$^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein may contain one or more asymmetric centers and may thus give rise to enantiomers, diastereomers, and other stereoisomeric forms that may be defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans). Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

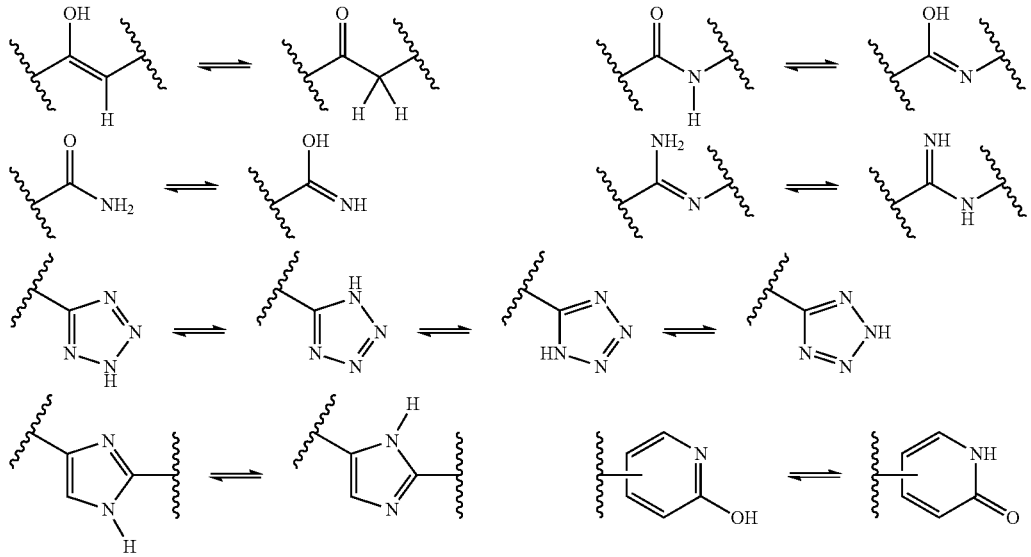

If the heteroaryl is a nitrogen-containing heteroaryl, the heteroaryl is optionally attached to the alkyl radical at the nitrogen atom. The alkylene chain of the heteroarylalkyl radical is optionally substituted as defined above for an "Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the substituted heterocyclic derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc., and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluene-sulfonates, phenylacetates, citrates, lactates, malates, tartrates, methanesulfonates, and the like. Also contemplated are salts of amino acids, such as arginates, gluconates, and galacturonates (see, e.g., Berge S M et al., *Pharmaceutical Salts*, J. Pharm. Sci. 66:1-19 (1997)). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H, DESIGN OF PRODRUGS (1985) pp. 7-9, 21-24 (Elsevier, Amsterdam).

A discussion of prodrugs is provided in Higuchi, T, et al., "Pro-drugs as Novel Delivery Systems," A.C.S. Symposium Series, Vol. 14, and in BIOREVERSIBLE CARRIERS IN DRUG DESIGN, ed. Edward B. Roche, American Pharmaceutical Association and Pergamon Press, 1987. The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2$H), tritium ($^3$H), iodine-125 ($^{125}$I) or carbon-14 ($^{14}$C). Isotopic substitution with $^2$H, $^{11}$C, $^{13}$C, $^{14}$C, $^{15}$C, $^{12}$N, $^{13}$N, $^{15}$N, $^{16}$N, $^{16}$O, $^{17}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$Cl, $^{79}$Br, $^{81}$Br, $^{125}$I are all contemplated. All isotopic variations of the compounds of the present invention, whether radioactive or not, are encompassed within the scope of the present invention.

In certain embodiments, the compounds disclosed herein have some or all of the $^1$H atoms replaced with $^2$H atoms. The methods of synthesis for deuterium-containing substituted heterocyclic derivative compounds are known in the art and include, by way of non-limiting example only, the following synthetic methods.

Deuterated starting materials are readily available and are subjected to the synthetic methods described herein to provide for the synthesis of deuterium-containing substituted heterocyclic derivative compounds. Large numbers of deuterium-containing reagents and building blocks are available commerically from chemical vendors, such as Aldrich Chemical Co.

Deuterium-transfer reagents suitable for use in nucleophilic substitution reactions, such as iodomethane-d$_3$ (CD$_3$I), are readily available and may be employed to transfer a deuterium-substituted carbon atom under nucleophilic substitution reaction conditions to the reaction substrate. The use of CD$_3$I is illustrated, by way of example only, in the reaction schemes below.

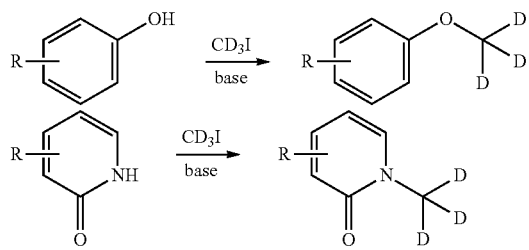

Deuterium-transfer reagents, such as lithium aluminum deuteride (LiAlD$_4$), are employed to transfer deuterium under reducing conditions to the reaction substrate. The use of LiAlD$_4$ is illustrated, by way of example only, in the reaction schemes below.

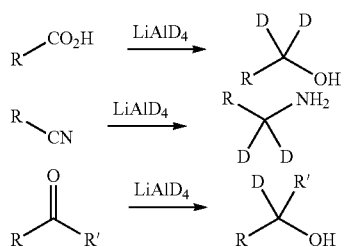

Deuterium gas and palladium catalyst are employed to reduce unsaturated carbon-carbon linkages and to perform a reductive substitution of aryl carbon-halogen bonds as illustrated, by way of example only, in the reaction schemes below.

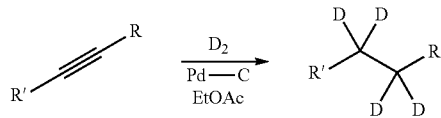

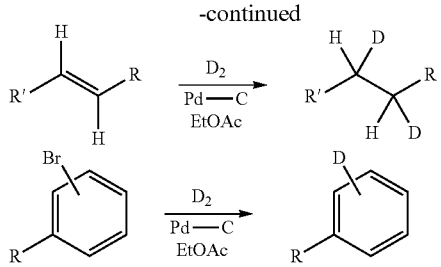

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^1$H hydrogen atoms. In one embodiment, the level of deuterium incorporation is determined by synthetic methods in which a deuterated synthetic building block is used as a starting material.

Substituted Heterocyclic Derivative Compounds

Substituted heterocyclic derivative compounds are described herein that are bromodomain inhibitors. These compounds, and compositions comprising these compounds, are useful for the treatment of cancer and neoplastic disease. The compounds described herein may, therefore, be useful for treating NUT midline carcinoma, Burkitts lymphoma, prostate cancer, breast cancer, bladder cancer, lung cancer and/or melanoma and the like.

One embodiment provides a compound of Formula (I), or a pharmaceutically acceptable salt thereof, Formula (I)

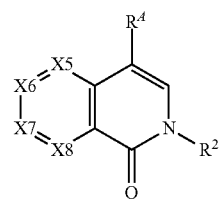

wherein,
R$^2$ is selected from CH$_3$, CH$_2$CH$_3$, CH$_2$CF$_3$, CH$_2$F, CHF$_2$, CF$_3$, CH$_2$D, CHD$_2$, or CD$_3$;
X5 is C—R$^5$ or N;
X6 is C—R$^6$ or N;
X7 is C—R$^7$ or N;
X8 is C—R$^8$ or N; wherein no more than two of X5, X6, X7, or X8 may be N;
R$^5$ is hydrogen, halogen, —OH, —CN, —OR$^{61}$, —NHR$^{61}$, —N(R$^{61}$)$_2$, alkyl, cycloalkyl, cycloalkylalkyl, aryl, aralkyl, heterocyclyl, heterocyclylalkyl, heteroaryl, or heteroarylalkyl, wherein each R$^{61}$ is independently selected from alkyl, cycloalkyl, cycloalkylalkyl, aryl, aralkyl, heterocyclyl, heterocyclylalkyl, heteroaryl, or heteroarylalkyl;

$R^6$ is hydrogen, halogen, —OH, —CN, —OR$^{61}$, —NHR$^{61}$, —N(R$^{61}$)$_2$, alkyl, cycloalkyl, cycloalkylalkyl, aryl, aralkyl, heterocyclyl, heterocyclylalkyl, heteroaryl, or heteroarylalkyl, wherein each R$^{61}$ is independently selected from alkyl, cycloalkyl, cycloalkylalkyl, aryl, aralkyl, heterocyclyl, heterocyclylalkyl, heteroaryl, or heteroarylalkyl;

$R^7$ is hydrogen, halogen, —OH, —CN, —OR$^{61}$, —NHR$^{61}$, —N(R$^{61}$)$_2$, alkyl, cycloalkyl, cycloalkylalkyl, aryl, aralkyl, heterocyclyl, heterocyclylalkyl, heteroaryl, or heteroarylalkyl, wherein each R$^{61}$ is independently selected from alkyl, cycloalkyl, cycloalkylalkyl, aryl, aralkyl, heterocyclyl, heterocyclylalkyl, heteroaryl, or heteroarylalkyl;

$R^8$ is hydrogen, halogen, or alkyl;

$R^A$ is

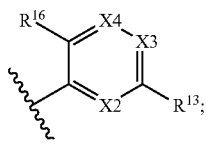

X2 is N or C—R$^{12}$, wherein R$^{12}$ is hydrogen, halogen, alkyl, or alkoxy;

$R^{13}$ is —Y—Z;

Y is selected from a bond, —CH$_2$—, —CH(C$_1$-C$_4$ alkyl)-;

Z is selected from —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —COR$^{21}$, —OC(O)N(R$^{22}$)$_2$, —OSO$_2$N(R$^{22}$)$_2$, or —N(R$^{22}$)SO$_3$R$^{21}$;

X3 is N or C—R$^{14}$, wherein R$^{14}$ is hydrogen, halogen, —CN, alkyl, cycloalkyl, or alkoxy;

X4 is N or C—R$^{15}$, wherein R$^{15}$ is hydrogen, halogen, alkyl, —CN, or alkoxy;

$R^{16}$ is hydrogen, halogen, or —W—X, wherein W is a bond, —O—, —S—, or —NH—, and X is selected from alkyl, aryl, aralkyl, cycloalkyl, cycloalkylalkyl, alkynyl, cycloalkylalkynyl, heterocyclyl, heterocyclylalkyl, heteroaryl, or heteroarylalkyl; each R$^{21}$ is independently selected from alkyl, cycloalkyl, cycloalkylalkyl, aryl, aralkyl, heterocyclyl, heterocyclylalkyl, heteroaryl, or heteroarylalkyl; and each R$^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (I), wherein R$^2$ is CH$_3$. Another embodiment provides a compound of Formula (I), wherein R$^2$ is CD$_3$. Another embodiment provides a compound of Formula (I), wherein X5 is N. Another embodiment provides a compound of Formula (I), wherein X6 is N. Another embodiment provides a compound of Formula (I), wherein X7 is N. Another embodiment provides a compound of Formula (I), wherein X8 is N. Another embodiment provides a compound of Formula (I), wherein none of X5, X6, X7, or X8 is N. Another embodiment provides a compound of Formula (I), wherein R$^5$ and R$^8$ are hydrogen. Another embodiment provides a compound of Formula (I), wherein R$^5$, R$^6$, R$^7$ and R$^8$ are hydrogen. Another embodiment provides a compound of Formula (I), wherein R$^7$ is a halogen. Another embodiment provides a compound of Formula (I), wherein R$^6$ is a halogen. Another embodiment provides a compound of Formula (I), wherein R$^6$ is a heteroaryl. Another embodiment provides a compound of Formula (I), wherein R$^6$ is an aryl. Another embodiment provides a compound of Formula (I), wherein R$^6$ is an alkyl. Another embodiment provides a compound of Formula (I), wherein R$^6$ is an aryl.

Another embodiment provides a compound of Formula (I), wherein Y is a bond. Another embodiment provides a compound of Formula (I), wherein Y is a —CH$_2$—. Another embodiment provides a compound of Formula (I), wherein Z is —SO$_2$R$^{21}$. Another embodiment provides a compound of Formula (I), wherein Z is —N(R$^{22}$)SO$_2$R$^{21}$. Another embodiment provides a compound of Formula (I), wherein Z is —SO$_2$N(R$^{22}$)$_2$. Another embodiment provides a compound of Formula (I), wherein Z is —N(R$^{22}$)SO$_2$N(R$^{22}$)$_2$. Another embodiment provides a compound of Formula (I), wherein Z is —CON(R$^{22}$)$_2$. Another embodiment provides a compound of Formula (I), wherein Z is —N(R$^{22}$)CO$_2$R$^{21}$. Another embodiment provides a compound of Formula (I), wherein Z is —N(R$^{22}$)CON(R$^{22}$)$_2$. Another embodiment provides a compound of Formula (I), wherein R21 is alkyl, cycloalkyl, or cycloalkylalkyl. Another embodiment provides a compound of Formula (I), wherein R$^{21}$ is alkyl. Another embodiment provides a compound of Formula (I), wherein R$^{14}$ is hydrogen, halogen, or alkyl. Another embodiment provides a compound of Formula (I), wherein X4 is C—R$^{15}$. Another embodiment provides a compound of Formula (I), wherein W is —O—. Another embodiment provides a compound of Formula (I), wherein W is —NH—. Another embodiment provides a compound of Formula (I), wherein X is alkyl. Another embodiment provides a compound of Formula (I), wherein X is aryl. Another embodiment provides a compound of Formula (I), wherein X is cycloalkylalkyl. Another embodiment provides a compound of Formula (I), wherein W is —O— and X is alkyl. Another embodiment provides a compound of Formula (I), wherein W is —O— and X is aryl. Another embodiment provides a compound of Formula (I), wherein W is —O— and X is cycloalkylalkyl. Another embodiment provides a compound of Formula (I), wherein R$^5$ and R$^8$ are hydrogen. Another embodiment provides a compound of Formula (I), wherein R$^5$ and R$^8$ are hydrogen, and R$^6$ is heteroaryl.

One embodiment provides a compound of Formula (Ia), or a pharmaceutically acceptable salt thereof,

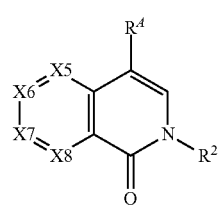

Formula (Ia)

wherein,

R$^2$ is selected from CH$_3$, CH$_2$CH$_3$, CH$_2$CF$_3$, CH$_2$F, CHF$_2$, CF$_3$, CH$_2$D, CHD$_2$, or CD$_3$;

X5 is C—R$^5$ or N;

X6 is C—R$^6$ or N;

X7 is C—R$^7$ or N;

X8 is C—R$^8$ or N; wherein no more than two of X5, X6, X7, or X8 may be N;

R$^5$ is hydrogen, halogen, —OH, —CN, —OR$^{61}$, —NHR$^{61}$, —N(R$^{61}$)$_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^6$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^7$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^8$ is hydrogen, halogen, or alkyl;

$R^4$ is

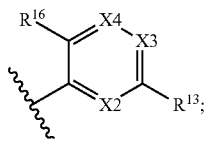

X2 is N or C—$R^{12}$, wherein $R^{12}$ is hydrogen, halogen, alkyl, or alkoxy;

$R^{13}$ is —Y—Z;

Y is selected from a bond, or —$CH_2$—;

Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$;

X3 is N or C—$R^{14}$, wherein $R^{14}$ is hydrogen, halogen, —CN, alkyl, cycloalkyl, or alkoxy;

X4 is N or C—$R^{15}$, wherein $R^{15}$ is hydrogen, halogen, alkyl, —CN, or alkoxy;

$R^{16}$ is hydrogen, halogen, or —W—X, wherein W is a bond, —O—, —S—, or —NH—, and X is selected from alkyl, aryl, aralkyl, cycloalkyl, cycloalkylalkyl, heterocyclyl, heterocyclylalkyl, heteroaryl, or heteroarylalkyl;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (Ia), wherein $R^2$ is $CH_3$. Another embodiment provides a compound of Formula (Ia), wherein $R^2$ is $CD_3$. Another embodiment provides a compound of Formula (Ia), wherein X5 is N. Another embodiment provides a compound of Formula (Ia), wherein X6 is N. Another embodiment provides a compound of Formula (Ia), wherein X7 is N. Another embodiment provides a compound of Formula (Ia), wherein X8 is N. Another embodiment provides a compound of Formula (Ia), wherein none of X5, X6, X7, or X8 is N. Another embodiment provides a compound of Formula (Ia), wherein $R^5$ and $R^8$ are hydrogen. Another embodiment provides a compound of Formula (Ia), wherein $R^5$, $R^6$, $R^7$ and $R^8$ are hydrogen. Another embodiment provides a compound of Formula (Ia), wherein $R^7$ is a halogen. Another embodiment provides a compound of Formula (Ia), wherein $R^6$ is a halogen. Another embodiment provides a compound of Formula (Ia), wherein $R^6$ is a heteroaryl. Another embodiment provides a compound of Formula (Ia), wherein $R^6$ is an aryl. Another embodiment provides a compound of Formula (Ia), wherein $R^6$ is an alkyl. Another embodiment provides a compound of Formula (Ia), wherein $R^6$ is an aryl.

Another embodiment provides a compound of Formula (Ia), wherein Y is a bond. Another embodiment provides a compound of Formula (Ia), wherein Y is a —$CH_2$—. Another embodiment provides a compound of Formula (Ia), wherein Z is —$SO2R^{21}$. Another embodiment provides a compound of Formula (Ia), wherein Z is —$N(R^{22})SO_2R^{21}$. Another embodiment provides a compound of Formula (Ia), wherein Z is —$SO_2N(R^{22})_2$. Another embodiment provides a compound of Formula (Ia), wherein Z is —$N(R^{22})SO_2N(R^{22})_2$. Another embodiment provides a compound of Formula (Ia), wherein Z is —$CON(R^{22})_2$. Another embodiment provides a compound of Formula (Ia), wherein Z is —$N(R^{22})CO_2R^{21}$. Another embodiment provides a compound of Formula (Ia), wherein Z is —$N(R^{22})CON(R^{22})_2$. Another embodiment provides a compound of Formula (Ia), wherein $R^{21}$ is alkyl, cycloalkyl, or cycloalkylalkyl. Another embodiment provides a compound of Formula (Ia), wherein $R^{21}$ is alkyl. Another embodiment provides a compound of Formula (Ia), wherein $R^{14}$ is hydrogen, halogen, or alkyl. Another embodiment provides a compound of Formula (Ia), wherein X4 is C—$R^{15}$. Another embodiment provides a compound of Formula (Ia), wherein W is —O—. Another embodiment provides a compound of Formula (Ia), wherein W is —NH—. Another embodiment provides a compound of Formula (Ia), wherein X is alkyl. Another embodiment provides a compound of Formula (Ia), wherein X is aryl. Another embodiment provides a compound of Formula (Ia), wherein X is cycloalkylalkyl. Another embodiment provides a compound of Formula (Ia), wherein W is —O— and X is alkyl. Another embodiment provides a compound of Formula (Ia), wherein W is —O— and X is aryl. Another embodiment provides a compound of Formula (Ia), wherein W is —O— and X is cycloalkylalkyl. Another embodiment provides a compound of Formula (Ia), wherein $R^5$ and $R^8$ are hydrogen. Another embodiment provides a compound of Formula (Ia), wherein $R^5$ and $R^8$ are hydrogen, and $R^6$ is heteroaryl.

One embodiment provides a compound, or a pharmaceutically acceptable salt thereof, having the structure of Formula (Ib),

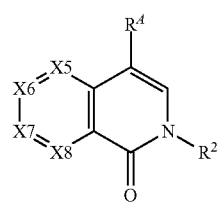

Formula (Ib)

wherein, $R^2$ is selected from $CH_3$;

X5 is C—H;

X6 is C—$R^6$;

X7 is C—$R^7$;

X8 is C—H;

$R^6$ is hydrogen, or halogen;
$R^7$ is hydrogen, or halogen;
$R^4$ is

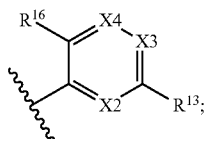

X2 is C—H;
$R^{13}$ is —Y—Z;
Y is selected from a bond, or —CH$_2$—;
Z is selected from —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;
X3 is C—R$^{14}$, wherein R$^{14}$ is hydrogen, halogen, C$_1$-C$_3$ alkyl, or C$_1$-C$_3$ alkoxy;
X4 is C—R$^{15}$, wherein R$^{15}$ is hydrogen, or halogen;
R$^{16}$ is —W—X, wherein W is a bond, —O—, —S—, or —NH—, and X is selected from alkyl, aryl, aralkyl, cycloalkyl, cycloalkylalkyl, heterocyclyl, heterocyclylalkyl, heteroaryl, or heteroarylalkyl;
each R$^{21}$ is independently selected from alkyl, cycloalkyl, cycloalkylalkyl, aryl, aralkyl, heterocyclyl, heterocyclylalkyl, heteroaryl, or heteroarylalkyl; and
each R$^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound, or a pharmaceutically acceptable salt thereof, having the structure of Formula (Ib), wherein R$^6$ is halogen, and R$^7$ is hydrogen.

Another embodiment provides a compound, or a pharmaceutically acceptable salt thereof, having the structure of Formula (Ib), wherein R$^6$ is hydrogen, and R$^7$ is halogen.

Another embodiment provides a compound, or a pharmaceutically acceptable salt thereof, having the structure of Formula (Ib), wherein R$^6$ is hydrogen, and R$^7$ is hydrogen.

Another embodiment provides a compound, or a pharmaceutically acceptable salt thereof, having the structure of Formula (Ib), wherein Y is —CH2-. Another embodiment provides a compound, or a pharmaceutically acceptable salt thereof, having the structure of Formula (Ib), wherein Y is —CH$_2$—, and Z is —SO$_2$R$^{21}$, or —N(R$^{22}$)SO$_2$R$^{21}$. Another embodiment provides a compound, or a pharmaceutically acceptable salt thereof, having the structure of Formula (Ib), wherein R$^{22}$ is hydrogen or methyl.

Another embodiment provides a compound, or a pharmaceutically acceptable salt thereof, having the structure of Formula (Ib), wherein Y is a bond. Another embodiment provides a compound, or a pharmaceutically acceptable salt thereof, having the structure of Formula (Ib), wherein Y is a bond, and Z is —N(R$^{22}$)SO$_2$R$^{21}$, or —N(R$^{22}$)SO$_2$N(R$^{22}$)$_2$. Another embodiment provides a compound, or a pharmaceutically acceptable salt thereof, having the structure of Formula (Ib), wherein Y is a bond, and Z is —SO$_2$R$^{21}$. Another embodiment provides a compound, or a pharmaceutically acceptable salt thereof, having the structure of Formula (Ib), wherein Y is a bond, Z is —SO$_2$R$^{21}$, and R$^{21}$ is heterocyclyl, or heterocyclylalkyl. Another embodiment provides a compound, or a pharmaceutically acceptable salt thereof, having the structure of Formula (Ib), wherein Y is a bond, Z is —SO$_2$R$^{21}$, and R$^{21}$ is alkyl, cycloalkyl, or cycloalkylalkyl. Another embodiment provides a compound, or a pharmaceutically acceptable salt thereof, having the structure of Formula (Ib), wherein Y is a bond, Z is —SO$_2$R$^{21}$, R$^{21}$ is alkyl, and the alkyl is a C$_1$-C$_4$ alkyl.

Another embodiment provides a compound, or a pharmaceutically acceptable salt thereof, having the structure of Formula (Ib), wherein Y is a bond, and Z is —SO$_2$N(R$^{22}$)$_2$. Another embodiment provides a compound, or a pharmaceutically acceptable salt thereof, having the structure of Formula (Ib), wherein R$^{22}$ is hydrogen or methyl. Another embodiment provides a compound, or a pharmaceutically acceptable salt thereof, having the structure of Formula (Ib), wherein Y is a bond, Z is —SO$_2$N(R$^{22}$)$_2$, and at least one R$^{22}$ is alkyl, cycloalkyl, or aralkyl.

Another embodiment provides a compound, or a pharmaceutically acceptable salt thereof, having the structure of Formula (Ib), wherein R$^{21}$ is heterocyclyl, or heterocyclylalkyl. Another embodiment provides a compound, or a pharmaceutically acceptable salt thereof, having the structure of Formula (Ib), wherein R$^{22}$ is hydrogen or methyl. Another embodiment provides a compound, or a pharmaceutically acceptable salt thereof, having the structure of Formula (Ib), wherein at least one R$^{22}$ is alkyl, cycloalkyl, or aralkyl.

Another embodiment provides a compound, or a pharmaceutically acceptable salt thereof, having the structure of Formula (Ib), wherein R$^{21}$ is alkyl, cycloalkyl, or cycloalkylalkyl.

Another embodiment provides a compound, or a pharmaceutically acceptable salt thereof, having the structure of Formula (Ib), wherein the alkyl is a C$_1$-C$_4$ alkyl. Another embodiment provides a compound, or a pharmaceutically acceptable salt thereof, having the structure of Formula (Ib), wherein the C$_1$-C$_4$ alkyl is a C$_1$ alkyl.

Another embodiment provides a compound, or a pharmaceutically acceptable salt thereof, having the structure of Formula (Ib), wherein R$^{14}$ is hydrogen, and R$^{15}$ is hydrogen.

Another embodiment provides a compound, or a pharmaceutically acceptable salt thereof, having the structure of Formula (Ib), wherein W is —NH—. Another embodiment provides a compound, or a pharmaceutically acceptable salt thereof, having the structure of Formula (Ib), wherein W is —S—. Another embodiment provides a compound, or a pharmaceutically acceptable salt thereof, having the structure of Formula (Ib), wherein W is a bond. Another embodiment provides a compound, or a pharmaceutically acceptable salt thereof, having the structure of Formula (Ib), wherein W is —O—.

Another embodiment provides a compound, or a pharmaceutically acceptable salt thereof, having the structure of Formula (Ib), wherein X is alkyl. Another embodiment provides a compound, or a pharmaceutically acceptable salt thereof, having the structure of Formula (Ib), wherein W is —NH—, and X is alkyl. Another embodiment provides a compound, or a pharmaceutically acceptable salt thereof, having the structure of Formula (Ib), wherein W is —O— and X is alkyl. Another embodiment provides a compound, or a pharmaceutically acceptable salt thereof, having the structure of Formula (Ib), wherein W is a bond, and X is alkyl.

Another embodiment provides a compound, or a pharmaceutically acceptable salt thereof, having the structure of Formula (Ib), wherein X is cycloalkylalkyl. Another embodiment provides a compound, or a pharmaceutically acceptable salt thereof, having the structure of Formula (Ib), wherein W is —NH—, and X is cycloalkylalkyl. Another embodiment provides a compound, or a pharmaceutically acceptable salt thereof, having the structure of Formula (Ib), wherein W is —O— and X is cycloalkylalkyl. Another embodiment provides a compound, or a pharmaceutically acceptable salt thereof, having the structure of Formula (Ib), wherein W is a bond, and X is cycloalkylalkyl.

Another embodiment provides a compound, or a pharmaceutically acceptable salt thereof, having the structure of Formula (Ib), wherein X is aryl. Another embodiment provides a compound, or a pharmaceutically acceptable salt thereof, having the structure of Formula (Ib), wherein W is —NH—, and X is aryl. Another embodiment provides a compound, or a pharmaceutically acceptable salt thereof, having the structure of Formula (Ib), wherein W is —O—, and X is aryl. Another embodiment provides a compound, or a pharmaceutically acceptable salt thereof, having the structure of Formula (Ib), wherein W is a bond, and X is aryl.

Another embodiment provides a compound, or a pharmaceutically acceptable salt thereof, having the structure of Formula (Ib), wherein Y is a bond, Z is —SO$_2$R$^{21}$, W is —O—, and X is aryl or cycloalkylalkyl. Another embodiment provides a compound, or a pharmaceutically acceptable salt thereof, having the structure of Formula (Ib), wherein Y is a bond, Z is —SO$_2$R$^{21}$, W is —O—, and X is cycloalkylalkyl.

One embodiment provides a compound of Formula (II), or a pharmaceutically acceptable salt thereof,

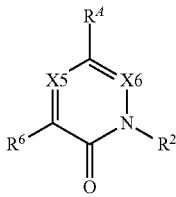

Formula (II)

wherein,
R$^2$ is alkyl, cycloalkyl, cycloalkylalkyl, heterocyclylalkyl, aralkyl, or heteroarylalkyl;
X6 is C—H or N;
X5 is C—R$^5$ or N; provided that if X6 is N, then X5 is C—R$^5$, and if X5 is N, then X6 is CH;
R$^5$ is hydrogen, halogen, —OH, —CN, —OR$^{61}$, —NHR$^{61}$, —N(R$^{61}$)$_2$, alkyl, cycloalkyl, cycloalkylalkyl, aryl, aralkyl, heterocyclyl, heterocyclylalkyl, heteroaryl, or heteroarylalkyl, wherein each R$^{61}$ is independently selected from alkyl, cycloalkyl, cycloalkylalkyl, aryl, aralkyl, heterocyclyl, heterocyclylalkyl, heteroaryl, or heteroarylalkyl;
R$^6$ is hydrogen, halogen, —OH, —CN, alkyl, cycloalkyl, cycloalkylalkyl, amino, alkylamino, dialkylamino, cycloalkylalkylamino, alkoxy, —S— alkyl, cycloalkylalkoxy, heterocyclyl, aralkoxy, heteroaryloxy, aryloxy, alkynyloxy, or —N(H)CO alkyl;
R$^A$ is

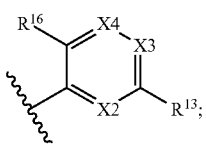

X2 is N or C—R$^{12}$, wherein R$^{12}$ is hydrogen, halogen, alkyl, or alkoxy;
R$^{13}$ is —Y—Z;
Y is selected from a bond, —CH$_2$—, or —CH(C$_1$-C$_4$alkyl)-;
Z is selected from —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —COR$^{21}$, —OC(O)N(R$^{22}$)$_2$, —OSO$_2$N(R$^{22}$)$_2$, or —N(R$^{22}$)SO$_3$R$^{21}$;
X3 is N or C—R$^{14}$, wherein R$^{14}$ is hydrogen, halogen, —CN, alkyl, cycloalkyl, or alkoxy;
X4 is N or C—R$^{15}$, wherein R$^{15}$ is hydrogen, halogen, —CN, alkyl, alkoxy, aryloxy, aralkyloxy, cycloalkylalkyloxy, heterocyclyloxy, heteroarylalkyloxy, or alkynyloxy;
R$^{16}$ is hydrogen, halogen, —N(H)COX, or —W—X, wherein W is a bond, —O—, —S—, or —NH—, and X is selected from alkyl, aryl, aralkyl, cycloalkyl, cycloalkylalkyl, alkynyl, cycloalkylalkynyl, heterocyclyl, heterocyclylalkyl, heteroaryl, or heteroarylalkyl;
each R$^{21}$ is independently selected from alkyl, cycloalkyl, cycloalkylalkyl, aryl, aralkyl, heterocyclyl, heterocyclylalkyl, heteroaryl, or heteroarylalkyl; and
each R$^{22}$ is independently selected from hydrogen, alkyl, cycloalkyl, cycloalkylalkyl, aryl, aralkyl, heterocyclyl, heterocyclylalkyl, heteroaryl, or heteroarylalkyl; and
provided that when X6 is N, then R$^5$ and R$^6$ are not hydrogen.

One embodiment provides a compound of Formula (IIa), or a pharmaceutically acceptable salt thereof,

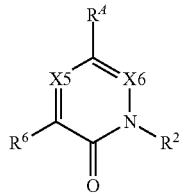

Formula (IIa)

wherein,
R$^2$ is CH$_3$, CH$_2$CH$_3$, CH$_2$CF$_3$, CH$_2$F, CHF$_2$, CF$_3$, CH$_2$D, CHD$_2$, or CD$_3$;
X6 is C—H or N;
X5 is C—R$^5$ or N; provided that if X6 is N, then X5 is C—R$^5$, and if X5 is N, then X6 is CH;
R$^5$ is hydrogen, halogen, —OH, —CN, —OR$^{61}$, —NHR$^{61}$, —N(R$^{61}$)$_2$, alkyl, cycloalkyl, cycloalkylalkyl, aryl, aralkyl, heterocyclyl, heterocyclylalkyl, heteroaryl, or heteroarylalkyl, wherein each R$^{61}$ is independently selected from alkyl, cycloalkyl, cycloalkylalkyl, aryl, aralkyl, heterocyclyl, heterocyclylalkyl, heteroaryl, or heteroarylalkyl;
R$^6$ is hydrogen, halogen, —OH, —CN, alkyl, cycloalkyl, cycloalkylalkyl, amino, alkylamino, dialkylamino, cycloalkylalkylamino, alkoxy, or cycloalkylalkoxy;
R$^A$ is

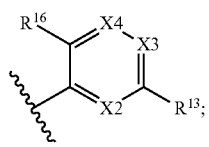

X2 is N or C—$R^{12}$, wherein $R^{12}$ is hydrogen, halogen, alkyl, or alkoxy;

$R^{13}$ is —Y—Z;

Y is selected from a bond, or —$CH_2$—;

Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$;

X3 is N or C—$R^{14}$, wherein $R^{14}$ is hydrogen, halogen, —CN, alkyl, cycloalkyl, or alkoxy;

X4 is N or C—$R^{15}$, wherein $R^{15}$ is hydrogen, halogen, —CN, alkyl, or alkoxy;

$R^{16}$ is hydrogen, halogen, or —W—X, wherein W is a bond, —O—, —S—, or —NH—, and X is selected from alkyl, aryl, aralkyl, cycloalkyl, cycloalkylalkyl, heterocyclyl, heterocyclylalkyl, heteroaryl, or heteroarylalkyl;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl; and provided that when X6 is N, then $R^5$ and $R^6$ are not hydrogen.

Another embodiment provides a compound of Formula (IIa), wherein X2 is N. Another embodiment provides a compound of Formula (IIa), wherein X3 is N. Another embodiment provides a compound of Formula (IIa), wherein X4 is N. Another embodiment provides a compound of Formula (IIa), wherein X2 and X3 are N. Another embodiment provides a compound of Formula (IIa), wherein X2 is C—$R^{12}$, X3 is C—$R^{14}$, and X4 is C—$R^{15}$.

Another embodiment provides a compound of Formula (IIa), wherein $R^2$ is $CH_3$. Another embodiment provides a compound of Formula (IIa), wherein X6 is C—H. Another embodiment provides a compound of Formula (IIa), wherein X6 is N. Another embodiment provides a compound of Formula (IIa), wherein X5 is C—$R^5$. Another embodiment provides a compound of Formula (IIa), wherein X5 is N. Another embodiment provides a compound of Formula (IIa), wherein $R^5$ is hydrogen, halogen, or alkyl. Another embodiment provides a compound of Formula (IIa), wherein $R^6$ is hydrogen, halogen, or alkyl.

Another embodiment provides a compound of Formula (IIa), wherein Y is a bond. Another embodiment provides a compound of Formula (IIa), wherein Y is a —$CH_2$—. Another embodiment provides a compound of Formula (IIa), wherein Z is —$SO_2R^{21}$. Another embodiment provides a compound of Formula (IIa), wherein Z is —$N(R^{22})SO_2R^{21}$. Another embodiment provides a compound of Formula (IIa), wherein Z is —$SO_2N(R^{22})_2$. Another embodiment provides a compound of Formula (IIa), wherein Z is —$N(R^{22})SO_2N(R^{22})_2$. Another embodiment provides a compound of Formula (IIa), wherein Z is —$CON(R^{22})_2$. Another embodiment provides a compound of Formula (IIa), wherein Z is —$N(R^{22})CO_2R^{21}$. Another embodiment provides a compound of Formula (IIa), wherein Z is —$N(R^{22})CON(R^{22})_2$. Another embodiment provides a compound of Formula (IIa), wherein $R^{21}$ is alkyl, cycloalkyl, or cycloalkylalkyl. Another embodiment provides a compound of Formula (IIa), wherein $R^{21}$ is alkyl. Another embodiment provides a compound of Formula (IIa), wherein $R^{14}$ is hydrogen, halogen, or alkyl. Another embodiment provides a compound of Formula (IIa), wherein X4 is C—$R^{15}$. Another embodiment provides a compound of Formula (IIa), wherein W is —O—. Another embodiment provides a compound of Formula (IIa), wherein W is —NH—. Another embodiment provides a compound of Formula (IIa), wherein X is alkyl. Another embodiment provides a compound of Formula (IIa), wherein X is aryl. Another embodiment provides a compound of Formula (IIa), wherein X is cycloalkylalkyl. Another embodiment provides a compound of Formula (IIa), wherein W is —O— and X is alkyl. Another embodiment provides a compound of Formula (IIa), wherein W is —O— and X is aryl. Another embodiment provides a compound of Formula (IIa), wherein W is —O— and X is cycloalkylalkyl. Another embodiment provides a compound of Formula (IIa), wherein the $R^6$ is CD3.

One embodiment provides a compound of Formula (IIb), or a pharmaceutically acceptable salt thereof,

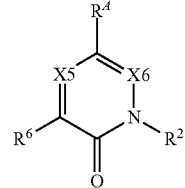

Formula (IIb)

wherein, $R^2$ is $CH_3$;

X6 is C—H;

X5 is C—$R^5$;

$R^5$ is hydrogen;

$R^6$ is halogen or alkyl;

$R^4$ is

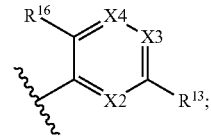

X2 is N;

$R^{13}$ is —Y—Z;

Y is selected from a bond, or —$CH_2$—;

Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$;

X3 is N;

X4 is C—$R^{15}$, wherein $R^{15}$ is hydrogen, halogen, —CN, alkyl, or alkoxy;

$R^{16}$ is —W—X, wherein W is a bond, —O—, —S—, or —NH—, and X is selected from alkyl, aryl, aralkyl, cycloalkyl, cycloalkylalkyl, heterocyclyl, heterocyclylalkyl, heteroaryl, or heteroarylalkyl;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (IIb), wherein $R^6$ is halogen. Another embodiment provides a compound of Formula (IIb), wherein $R^6$ is alkyl. Another embodiment provides a compound of Formula (IIb), wherein R⁶ is $C_1$-$C_3$ alkyl. Another embodiment provides a compound of Formula (IIb), wherein R⁶ is $C_1$ alkyl.

Another embodiment provides a compound of Formula (IIb), wherein Y is a bond. Another embodiment provides a compound of Formula (IIb), wherein Y is a —$CH_2$—. Another embodiment provides a compound of Formula (IIb), wherein Z is —$SO_2R^{21}$. Another embodiment provides a compound of Formula (IIb), wherein Z is —$N(R^{22})SO_2R^{21}$. Another embodiment provides a compound of Formula (IIb), wherein Z is —$SO_2N(R^{22})_2$. Another embodiment provides a compound of Formula (IIb), wherein Z is —$N(R^{22})SO_2N(R^{22})_2$. Another embodiment provides a compound of Formula (IIb), wherein Z is —$CON(R^{22})_2$. Another embodiment provides a compound of Formula (IIb), wherein Z is —$N(R^{22})CO_2R^{21}$. Another embodiment provides a compound of Formula (IIb), wherein Z is —$N(R^{22})CON(R^{22})_2$. Another embodiment provides a compound of Formula (IIb), wherein $R^{21}$ is alkyl, cycloalkyl, or cycloalkylalkyl. Another embodiment provides a compound of Formula (IIb), wherein $R^{21}$ is alkyl. Another embodiment provides a compound of Formula (IIb), wherein $R^{21}$ is $C_1$-$C_2$ alkyl.

Another embodiment provides a compound of Formula (IIb), wherein W is —O—. Another embodiment provides a compound of Formula (IIb), wherein W is —NH—. Another embodiment provides a compound of Formula (IIb), wherein W is a bond. Another embodiment provides a compound of Formula (IIb), wherein X is alkyl. Another embodiment provides a compound of Formula (IIb), wherein X is aryl. Another embodiment provides a compound of Formula (IIb), wherein X is cycloalkylalkyl. Another embodiment provides a compound of Formula (IIb), wherein W is —O— and X is alkyl. Another embodiment provides a compound of Formula (IIb), wherein W is —O— and X is aryl. Another embodiment provides a compound of Formula (IIb), wherein W is —O— and X is cycloalkylalkyl. Another embodiment provides a compound of Formula (IIb), wherein W is a bond and X is alkyl. Another embodiment provides a compound of Formula (IIb), wherein W is a bond and X is aryl. Another embodiment provides a compound of Formula (IIb), wherein W is a bond and X is cycloalkylalkyl. Another embodiment provides a compound of Formula (IIb), wherein the R⁶ is $CD_3$.

One embodiment provides a compound of Formula (III), or a pharmaceutically acceptable salt thereof,

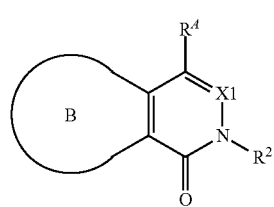

Formula (III)

wherein,
R² is $CH_3$, $CH_2CH_3$, $CH_2CF_3$, $CH_2F$, $CHF_2$, $CF_3$, $CH_2D$, $CHD_2$, or $CD_3$;
X1 is C—H or N;
ring B is an optionally substituted 5- or 6-membered heterocyclic ring containing at least one oxygen or nitrogen atom;
$R^A$ is

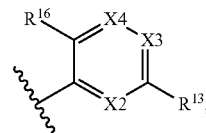

X2 is N or C—$R^{12}$, wherein $R^{12}$ is hydrogen, halogen, alkyl, or alkoxy;
$R^{13}$ is —Y—Z;
Y is selected from a bond, —$CH_2$—, or —$CH(C_1$-$C_4$ alkyl)-;
Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$;
X3 is N or C—$R^{14}$, wherein $R^{14}$ is hydrogen, halogen, —CN, alkyl, cycloalkyl, or alkoxy; or optionally when X4 is C—$R^{15}$, $R^{14}$ and $R^{15}$ connect to form a ring;
X4 is N or C—$R^{15}$, wherein $R^{15}$ is hydrogen, halogen, —CN, alkyl, or alkoxy;
$R^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl; or optionally when X4 is C—$R^{15}$, $R^{16}$ and $R^{15}$ connect to form a ring;
each $R^{21}$ is independently selected from alkyl, cycloalkyl, cycloalkylalkyl, aryl, aralkyl, heterocyclyl, heterocyclylalkyl, heteroaryl, or heteroarylalkyl; and
each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (III), wherein X2 is N. Another embodiment provides a compound of Formula (III), wherein X3 is N. Another embodiment provides a compound of Formula (III), wherein X4 is N. Another embodiment provides a compound of Formula (III), wherein X2 and X3 are N. Another embodiment provides a compound of Formula (III), wherein X2 is C—$R^{12}$, X3 is C—$R^{14}$, and X4 is C—$R^{15}$.

Another embodiment provides a compound of Formula (III), having the structure of Formula (IIIa):

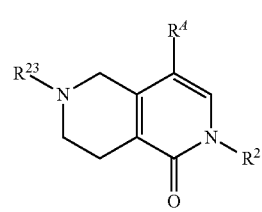

Formula (IIIa)

wherein,
ring B is a 6-membered ring having one nitrogen atom;
$R^{23}$ is selected from alkyl, aryl, aralkyl, cycloalkyl, cycloalkylalkyl, —$COR^{24}$, —$CO_2R^{24}$, —$CONH(R^{24})$, $CON(R^{24})_2$, or —$SO_2R^{24}$; and
each $R^{24}$ is independently selected from alkyl, aryl, aralkyl, cycloalkyl, cycloalkylalkyl, heterocyclyl, heterocyclylalkyl, heteroaryl, or heteroarylalkyl.

Another embodiment provides a compound of Formula (III), wherein $R^2$ is $CH_3$. Another embodiment provides a compound of Formula (III), wherein X1 is C—H. Another embodiment provides a compound of Formula (III), wherein X1 is N.

Another embodiment provides a compound of Formula (III), wherein Y is a bond. Another embodiment provides a compound of Formula (III), wherein Y is a —$CH_2$—. Another embodiment provides a compound of Formula (III), wherein Z is —$SO_2R^{21}$. Another embodiment provides a compound of Formula (III), wherein Z is —$N(R^{22})SO_2R^{21}$. Another embodiment provides a compound of Formula (III), wherein Z is —$SO_2N(R^{22})_2$. Another embodiment provides a compound of Formula (III), wherein Z is —$N(R^{22})SO_2N(R^{22})_2$. Another embodiment provides a compound of Formula (III), wherein Z is —$CON(R^{22})_2$. Another embodiment provides a compound of Formula (III), wherein Z is —$N(R^{22})CO2R^{21}$. Another embodiment provides a compound of Formula (III), wherein Z is —$N(R^{22})CON(R^{22})_2$. Another embodiment provides a compound of Formula (III), wherein $R^{21}$ is alkyl, cycloalkyl, or cycloalkylalkyl. Another embodiment provides a compound of Formula (III), wherein $R^{21}$ is alkyl. Another embodiment provides a compound of Formula (III), wherein $R^{14}$ is hydrogen, halogen, or alkyl. Another embodiment provides a compound of Formula (III), wherein X4 is C—$R^{15}$. Another embodiment provides a compound of Formula (III), wherein W is —O—. Another embodiment provides a compound of Formula (III), wherein W is —NH—. Another embodiment provides a compound of Formula (III), wherein X is alkyl. Another embodiment provides a compound of Formula (III), wherein X is alkynyl. Another embodiment provides a compound of Formula (III), wherein X is aryl. Another embodiment provides a compound of Formula (III), wherein X is cycloalkylalkyl. Another embodiment provides a compound of Formula (III), wherein X is cycloalkylalkynyl. Another embodiment provides a compound of Formula (III), wherein W is —O— and X is alkyl. Another embodiment provides a compound of Formula (III), wherein W is —O— and X is alkynyl. Another embodiment provides a compound of Formula (III), wherein W is —O— and X is aryl. Another embodiment provides a compound of Formula (III), wherein W is —O— and X is cycloalkylalkyl. Another embodiment provides a compound of Formula (III), wherein W is —O— and X is cycloalkylalkynyl.

One embodiment provides a compound of Formula (IV), or a pharmaceutically acceptable salt thereof,

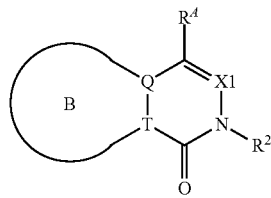

Formula (IV)

wherein,
Q is N and T is C, or Q is C and T is N;
Ring B is an optionally substituted 5-membered aromatic nitrogen-containing heteroaryl ring containing one or more nitrogen atoms;
$R^2$ is selected from $CH_3$, $CH_2CH_3$, $CH_2CF_3$, $CH_2F$, $CHF_2$, $CF_3$, $CH_2D$, $CHD_2$, or $CD_3$;
X1 is C—H or N;
$R^A$ is

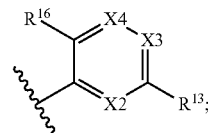

X2 is N or C—$R^{12}$, wherein $R^{12}$ is hydrogen, halogen, alkyl, or alkoxy;
$R^{13}$ is —Y—Z;
Y is selected from a bond, or —$CH_2$—;
Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$;
X3 is N or C—$R^{14}$, wherein $R^{14}$ is hydrogen, halogen, —CN, alkyl, cycloalkyl, or alkoxy;
X4 is N or C—$R^{15}$, wherein $R^{15}$ is hydrogen, halogen, —CN, alkyl, or alkoxy;
$R^{16}$ is hydrogen, halogen, or —W—X, wherein W is a bond, —O—, —S—, or —NH—, and X is selected from alkyl, aryl, aralkyl, cycloalkyl, cycloalkylalkyl, heterocyclyl, heterocyclylalkyl, heteroaryl, or heteroarylalkyl;
each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (IV), wherein X2 is N. Another embodiment provides a compound of Formula (IV), wherein X3 is N. Another embodiment provides a compound of Formula (IV), wherein X4 is N. Another embodiment provides a compound of Formula (IV), wherein X2 and X3 are N. Another embodiment provides a compound of Formula (IV), wherein X2 is C—$R^{12}$, X3 is C—$R^{14}$, and X4 is C—$R^{15}$.

Another embodiment provides a compound of Formula (IV), wherein the compound of Formula (IV) is selected from the group:

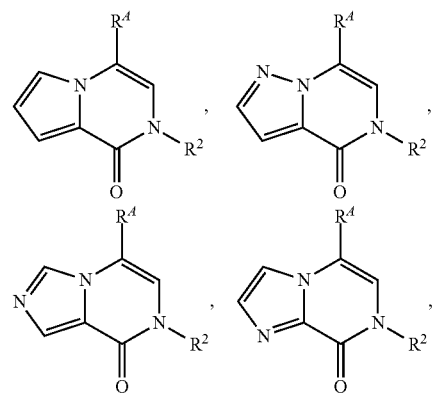

-continued

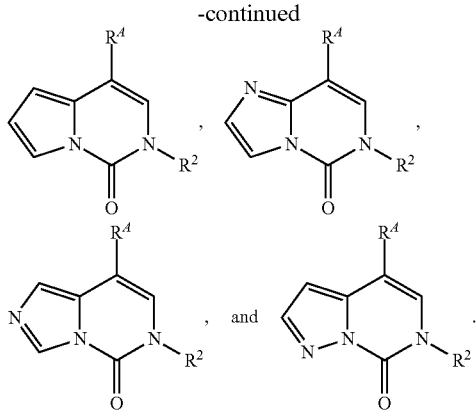

Another embodiment provides a compound of Formula (IV), wherein the compound of Formula (IV) has the structure:

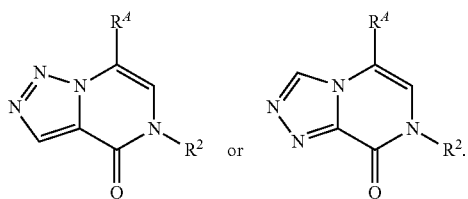

Another embodiment provides a compound of Formula (IV), wherein Q is N and T is C. Another embodiment provides a compound of Formula (IV), wherein Q is C and T is N. Another embodiment provides a compound of Formula (IV), wherein $R^2$ is $CH_3$. Another embodiment provides a compound of Formula (IV), wherein X1 is C—H. Another embodiment provides a compound of Formula (IV), wherein X1 is N.

Another embodiment provides a compound of Formula (IV), wherein Y is a bond. Another embodiment provides a compound of Formula (IV), wherein Y is a —$CH_2$—. Another embodiment provides a compound of Formula (IV), wherein Z is —$SO_2R^{21}$. Another embodiment provides a compound of Formula (IV), wherein Z is —$N(R^{22})SO_2R^{21}$. Another embodiment provides a compound of Formula (IV), wherein Z is —$SO_2N(R^{22})_2$. Another embodiment provides a compound of Formula (IV), wherein Z is —$N(R^{22})SO_2N(R^{22})_2$. Another embodiment provides a compound of Formula (IV), wherein Z is —$CON(R^{22})_2$. Another embodiment provides a compound of Formula (IV), wherein Z is —$N(R^{22})CO2R^{21}$. Another embodiment provides a compound of Formula (IV), wherein Z is —$N(R^{22})CON(R^{22})_2$. Another embodiment provides a compound of Formula (IV), wherein $R^{21}$ is alkyl, cycloalkyl, or cycloalkylalkyl. Another embodiment provides a compound of Formula (IV), wherein $R^{21}$ is alkyl. Another embodiment provides a compound of Formula (IV), wherein $R^{14}$ is hydrogen, halogen, or alkyl. Another embodiment provides a compound of Formula (IV), wherein X4 is C—$R^{15}$. Another embodiment provides a compound of Formula (IV), wherein W is —O—. Another embodiment provides a compound of Formula (IV), wherein W is —NH—. Another embodiment provides a compound of Formula (IV), wherein X is alkyl. Another embodiment provides a compound of Formula (IV), wherein X is aryl. Another embodiment provides a compound of Formula (IV), wherein X is cycloalkylalkyl. Another embodiment provides a compound of Formula (IV), wherein W is —O— and X is alkyl. Another embodiment provides a compound of Formula (IV), wherein W is —O— and X is aryl. Another embodiment provides a compound of Formula (IV), wherein W is —O— and X is cycloalkylalkyl.

Another embodiment provides a compound of Formula (V), or a pharmaceutically acceptable salt thereof,

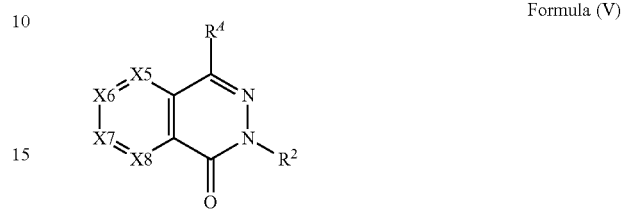

Formula (V)

wherein,
$R^2$ is selected from $CH_3$, $CH_2CH_3$, $CH_2CF_3$, $CH_2F$, $CHF_2$, $CF_3$, $CH_2D$, $CHD_2$, or $CD_3$;
X5 is C—$R^5$ or N;
X6 is C—$R^6$ or N;
X7 is C—$R^7$ or N;
X8 is C—$R^8$ or N; wherein no more than two of X5, X6, X7, or X8 may be N;
$R^5$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;
$R^6$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;
$R^7$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;
$R^8$ is hydrogen, halogen, or alkyl;
$R^A$ is

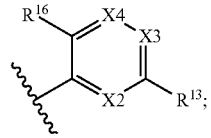

X2 is N or C—$R^{12}$, wherein $R^{12}$ is hydrogen, halogen, alkyl, or alkoxy;
$R^{13}$ is —Y—Z;
Y is selected from a bond, or —$CH_2$—;
Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$;

X3 is N or C—R$^{14}$, wherein R$^{14}$ is hydrogen, halogen, alkyl, cycloalkyl, or alkoxy;

X4 is N or C—R$^{15}$, wherein R$^{15}$ is hydrogen, halogen, alkyl, or alkoxy;

R$^{16}$ is hydrogen, halogen, or —W—X, wherein W is a bond, —O—, —S—, or —NH—, and X is selected from alkyl, aryl, aralkyl, cycloalkyl, cycloalkylalkyl, heterocyclyl, heterocyclylalkyl, heteroaryl, or heteroarylalkyl;

each R$^{21}$ is independently selected from alkyl, cycloalkyl, cycloalkylalkyl, aryl, aralkyl, heterocyclyl, heterocyclylalkyl, heteroaryl, or heteroarylalkyl; and each R$^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (V), wherein X2 is N. Another embodiment provides a compound of Formula (V), wherein X3 is N. Another embodiment provides a compound of Formula (V), wherein X4 is N. Another embodiment provides a compound of Formula (V), wherein X2 and X3 are N. Another embodiment provides a compound of Formula (V), wherein X2 is C—R$^{12}$, X3 is C—R$^{14}$, and X4 is C—R$^{15}$.

Another embodiment provides a compound of Formula (V), wherein R$^2$ is CH$_3$. Another embodiment provides a compound of Formula (V), wherein R$^2$ is CD$_3$. Another embodiment provides a compound of Formula (V), wherein X5 is N. Another embodiment provides a compound of Formula (V), wherein X6 is N. Another embodiment provides a compound of Formula (V), wherein X7 is N. Another embodiment provides a compound of Formula (V), wherein X8 is N. Another embodiment provides a compound of Formula (V), wherein none of X5, X6, X7, or X8 is N. Another embodiment provides a compound of Formula (V), wherein R$^5$ and R$^8$ are hydrogen. Another embodiment provides a compound of Formula (V), wherein R$^5$, R$^6$, R$^7$ and R$^8$ are hydrogen. Another embodiment provides a compound of Formula (V), wherein R$^7$ is a halogen. Another embodiment provides a compound of Formula (V), wherein R$^6$ is a halogen. Another embodiment provides a compound of Formula (V), wherein R$^6$ is a heteroaryl. Another embodiment provides a compound of Formula (V), wherein R$^6$ is an aryl. Another embodiment provides a compound of Formula (V), wherein R$^6$ is an alkyl. Another embodiment provides a compound of Formula (V), wherein R6 is an aryl.

Another embodiment provides a compound of Formula (V), wherein Y is a bond. Another embodiment provides a compound of Formula (V), wherein Y is a —CH$_2$—. Another embodiment provides a compound of Formula (V), wherein Z is —SO$_2$R$^{21}$. Another embodiment provides a compound of Formula (V), wherein Z is —N(R$^{22}$)SO$_2$R$^{21}$. Another embodiment provides a compound of Formula (V), wherein Z is —SO$_2$N(R$^{22}$)$_2$. Another embodiment provides a compound of Formula (V), wherein Z is —N(R$^{22}$)SO$_2$N(R$^{22}$)$_2$. Another embodiment provides a compound of Formula (V), wherein Z is —CON(R$^{22}$)$_2$. Another embodiment provides a compound of Formula (V), wherein Z is —N(R$^{22}$)CO$_2$R21. Another embodiment provides a compound of Formula (V), wherein Z is —N(R$^{22}$)CON(R$^{22}$)$_2$. Another embodiment provides a compound of Formula (V), wherein R$^{21}$ is alkyl, cycloalkyl, or cycloalkylalkyl. Another embodiment provides a compound of Formula (V), wherein R$^{21}$ is alkyl. Another embodiment provides a compound of Formula (V), wherein R$^{14}$ is hydrogen, halogen, or alkyl. Another embodiment provides a compound of Formula (V), wherein X4 is C—R$^{15}$. Another embodiment provides a compound of Formula (V), wherein W is —O—. Another embodiment provides a compound of Formula (V), wherein W is —NH—. Another embodiment provides a compound of Formula (V), wherein X is alkyl. Another embodiment provides a compound of Formula (V), wherein X is aryl. Another embodiment provides a compound of Formula (V), wherein X is cycloalkylalkyl. Another embodiment provides a compound of Formula (V), wherein W is —O— and X is alkyl. Another embodiment provides a compound of Formula (V), wherein W is —O— and X is aryl. Another embodiment provides a compound of Formula (V), wherein W is —O— and X is cycloalkylalkyl. Another embodiment provides a compound of Formula (V), wherein R$^5$ and R$^8$ are hydrogen. Another embodiment provides a compound of Formula (V), wherein R$^5$ and R$^8$ are hydrogen, and R$^6$ is heteroaryl.

One embodiment provides a compound of Formula (VIa), or a pharmaceutically acceptable salt thereof,

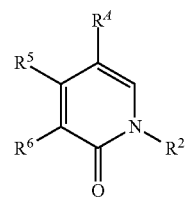

Formula (VIa)

wherein,
R$^2$ is CH$_3$ or CD$_3$;
R$^5$ is hydrogen or CH$_3$;
R$^6$ is hydrogen, CH$_3$, Cl, F, Br, NH$_2$, N(CH$_3$)$_2$, NH(alkyl), or CD$_3$;
R$^4$ is

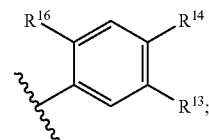

R$^{13}$ is —Y—Z;
Y is selected from a bond or —CH$_2$—;
Z is —SO$_2$R$^{21}$;
R$^{14}$ is hydrogen, F, or Cl;
R$^{16}$ is —W—X, wherein W is —O— or —NH—, and X is selected from CH$_3$, CH$_2$CH$_3$, CH$_2$CH$_2$CH$_3$, CH(CH$_3$)$_2$, cyclopropyl, cyclobutyl, cyclopentyl, cyclohexyl, CH$_2$-(cyclopropyl), C$_6$H$_5$, 4-fluoro(C$_6$H$_4$), 2,4-difluoro(C$_6$H$_3$), 2-fluoro(C$_6$H$_4$), 4-tetrahydropyranyl, 3-tetrahydropyranyl, oxolan-3-yl, 4,4-difluorocyclohexyl, and 4-hydroxycyclohexyl; and each R$^{21}$ is CH$_3$ or CH$_2$CH$_3$.

Another embodiment provides a compound of Formula (VIa), wherein Y is a bond. Another embodiment provides a compound of Formula (VIa), wherein Y is —CH$_2$—. Another embodiment provides a compound of Formula (VIa), wherein W is —O—. Another embodiment provides a compound of Formula (VIa), wherein W is —NH—. Another embodiment provides a compound of Formula (VIa), wherein R$^2$ is CH$_3$. Another embodiment provides a compound of Formula (VIa), wherein R$^2$ is CD$_3$.

One embodiment provides a compound of Formula (VIb), or a pharmaceutically acceptable salt thereof,

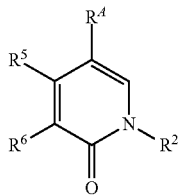

wherein, $R^2$ is $CH_3$ or $CD_3$;

$R^5$ is hydrogen or $CH_3$;

$R^6$ is hydrogen, $CH_3$, Cl, F, Br, $NH_2$, $N(CH_3)_2$, NH(alkyl), or $CD_3$;

$R^A$ is

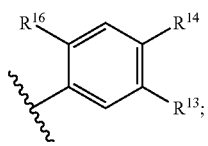

$R^{13}$ is —$NHSO_2R^{21}$;

$R^{14}$ is hydrogen, F, or Cl;

$R^{16}$ is —W—X, wherein W is —O— or —NH—, and X is selected from $CH_3$, $CH_2CH_3$, $CH_2CH_2CH_3$, $CH(CH_3)_2$, cyclopropyl, cyclobutyl, cyclopentyl, cyclohexyl, $CH_2$-(cyclopropyl), $C_6H_5$, 4-fluoro($C_6H_4$), 2,4-difluoro($C_6H_3$), 2-fluoro($C_6H_4$), 4-tetrahydropyranyl, 3-tetrahydropyranyl, oxolan-3-yl, 4,4-difluorocyclohexyl, and 4-hydroxycyclohexyl; and each $R^{21}$ is $CH_3$ or $CH_2CH_3$.

Another embodiment provides a compound of Formula (VIb), wherein W is —O—. Another embodiment provides a compound of Formula (VIb), wherein W is —NH—. Another embodiment provides a compound of Formula (VIb), wherein $R^2$ is $CH_3$. Another embodiment provides a compound of Formula (VIb), wherein $R^2$ is $CD_3$.

One embodiment provides a compound of Formula (VIc), or a pharmaceutically acceptable salt thereof, Formula (VIc)

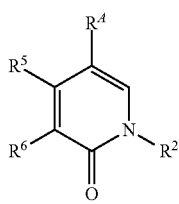

wherein, $R^2$ is $CH_3$ or $CD_3$;

$R^5$ is hydrogen or $CH_3$;

$R^6$ is hydrogen, $CH_3$, Cl, F, Br, $NH_2$, $N(CH_3)_2$, NH(alkyl), or $CD_3$;

$R^A$ is

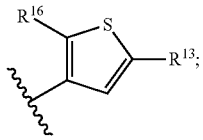

$R^{13}$ is —Y—Z;

Y is selected from a bond or —$CH_2$—;

Z is —$SO_2R^{21}$;

$R^{16}$ is —W—X, wherein W is —O— or —NH—, and X is selected from $CH_3$, $CH_2CH_3$, $CH_2CH_2CH_3$, $CH(CH_3)_2$, cyclopropyl, cyclobutyl, cyclopentyl, cyclohexyl, $CH_2$-(cyclopropyl), $C_6H_5$, 4-fluoro($C_6H_4$), 2,4-difluoro($C_6H_3$), 2-fluoro($C_6H_4$), 4-tetrahydropyranyl, 3-tetrahydropyranyl, oxolan-3-yl, 4,4-difluorocyclohexyl, and 4-hydroxycyclohexyl; and each $R^{21}$ is $CH_3$ or $CH_2CH_3$.

Another embodiment provides a compound of Formula (VIc), wherein Y is a bond. Another embodiment provides a compound of Formula (VIc), wherein Y is —CH2-. Another embodiment provides a compound of Formula (VIc), wherein W is —O—. Another embodiment provides a compound of Formula (VIc), wherein W is —NH—. Another embodiment provides a compound of Formula (VIc), wherein $R^2$ is $CH_3$. Another embodiment provides a compound of Formula (VIc), wherein $R^2$ is $CD_3$.

One embodiment provides a compound of Formula (VId), or a pharmaceutically acceptable salt thereof, Formula (VId)

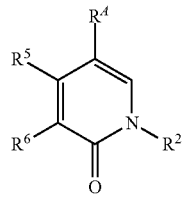

wherein, $R^2$ is $CH_3$ or $CD_3$;

$R^5$ is hydrogen or $CH_3$;

$R^6$ is hydrogen, $CH_3$, Cl, F, Br, $NH_2$, $N(CH_3)_2$, NH(alkyl), or $CD_3$;

$R^A$ is

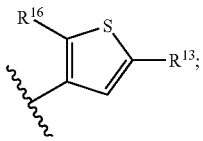

$R^{13}$ is —$NHSO_2R^{21}$;

$R^{16}$ is —W—X, wherein W is —O— or —NH—, and X is selected from $CH_3$, $CH_2CH_3$, $CH_2CH_2CH_3$, $CH(CH_3)_2$, cyclopropyl, cyclobutyl, cyclopentyl, cyclohexyl, $CH_2$-(cyclopropyl), $C_6H_5$, 4-fluoro($C_6H_4$), 2,4-difluoro($C_6H_3$), 2-fluoro($C_6H_4$), 4-tetrahydropyranyl, 3-tetrahydropyranyl, oxolan-3-yl, 4,4-difluorocyclohexyl, and 4-hydroxycyclohexyl; and each $R^{21}$ is $CH_3$ or $CH_2CH_3$.

Another embodiment provides a compound of Formula (VId), wherein W is —O—. Another embodiment provides a compound of Formula (VId), wherein W is —NH—. Another embodiment provides a compound of Formula (VId), wherein R2 is CH3. Another embodiment provides a compound of Formula (VId), wherein R2 is CD$_3$.

One embodiment provides a compound of Formula (VIe), or a pharmaceutically acceptable salt thereof,

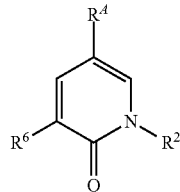

Formula (VIe)

wherein, $R^2$ is hydrogen, CH$_3$, or CHF$_2$;

$R^6$ is CH$_3$, CD$_3$, cyclopropyl, NH(CH$_3$), NH(CH$_2$CH$_3$), F, or Cl;

$R^A$ is

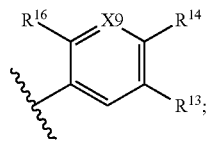

$R^{13}$ is —Y—Z;

Y is selected from —NH— or —CH$_2$—;

Z is selected from —SO$_2$R$^{21}$;

$R^{14}$ is hydrogen, CH$_3$, or F;

X9 is N or CH;

$R^{16}$ is —W—X, wherein W is —O— or —NH—, and X is selected from CH$_3$, CH$_2$CH$_3$, CH$_2$CH$_2$CH$_3$, CH$_2$-(cyclopropyl), CH$_2$CH$_2$CFH$_2$, 2,4-difluoro(C$_6$H$_3$), 2,3-difluoro(C$_6$H$_3$), 2-chloro-4-fluoro(C$_6$H$_3$), 2-fluoro (C$_6$H$_4$), and 2-chloro(C$_6$H$_4$); and each $R^{21}$ is independently selected from CH$_3$, CH$_2$CH$_3$, CH$_2$CH$_2$CH$_3$, CH$_2$CH$_2$CHF$_2$, CH$_2$-(cyclopropyl), and cyclopropyl.

Another embodiment provides a compound of Formula (VIe), wherein Y is —NH—. Another embodiment provides a compound of Formula (VIe), wherein Y is —CH$_2$—. Another embodiment provides a compound of Formula (VIe), wherein W is —O—. Another embodiment provides a compound of Formula (VIe), wherein W is —NH—. Another embodiment provides a compound of Formula (VIe), wherein X9 is N. Another embodiment provides a compound of Formula (VIe), wherein X9 is CH. Another embodiment provides a compound of Formula (VIe), wherein R$^2$ is hydrogen. Another embodiment provides a compound of Formula (VIe), wherein R$^2$ is CH$_3$. Another embodiment provides a compound of Formula (VIe), wherein R$^2$ is CHF$_2$.

One embodiment provides a compound of Formula (VII), or a pharmaceutically acceptable salt thereof,

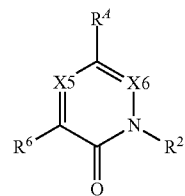

Formula (VII)

wherein, $R^2$ is CH$_3$, CH$_2$CH$_3$, CH$_2$CF$_3$, CH$_2$F, CHF$_2$, CF$_3$, CH$_2$D, CHD$_2$, or CD$_3$;

X6 is C—H or N;

X5 is C—R$^5$ or N; provided that if X6 is N, then X5 is C—R$^5$, and if X5 is N, then X6 is CH;

$R^5$ is hydrogen, halogen, —OH, —CN, —OR$^{61}$, —NHR$^{61}$, —N(R$^{61}$)$_2$, alkyl, cycloalkyl, cycloalkylalkyl, aryl, aralkyl, heterocyclyl, heterocyclylalkyl, heteroaryl, or heteroarylalkyl, wherein each R$^{61}$ is independently selected from alkyl, cycloalkyl, cycloalkylalkyl, aryl, aralkyl, heterocyclyl, heterocyclylalkyl, heteroaryl, or heteroarylalkyl;

$R^6$ is hydrogen, halogen, —OH, —CN, alkyl, alkynyl, cycloalkyl, cycloalkylalkyl, cycloalkylalkynyl, amino, alkylamino, dialkylamino, heterocyclyl, cycloalkylalkylamino, alkoxy, cycloalkyloxy, cycloalkylalkoxy, alkyl-S—, cycloalkyl-S—, and cycloalkylalkyl-S—;

$R^A$ is

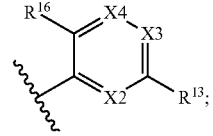

X2 is N or C—R$^{12}$, wherein R$^{12}$ is hydrogen, halogen, alkyl, or alkoxy;

$R^{13}$ is —Y—Z;

Y is selected from a bond, —CH$_2$—, or —CH(C$_1$-C$_4$ alkyl)-;

Z is selected from —SO$_2$R$^{21}$, —N(R$^{22}$)SO$_2$R$^{21}$, —SO$_2$N (R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, vN(R$^{22}$) COR$^{21}$, —OC(O)N(R$^{22}$)$_2$, —OSO$_2$N(R$^{22}$)$_2$, or —N(R$^{22}$)SO$_3$R$^{21}$;

X3 is N or C—R$^{14}$, wherein R$^{14}$ is hydrogen, halogen, —CN, alkyl, cycloalkyl, or alkoxy; or optionally when X4 is C—R$^{15}$, R$^{14}$ and R$^{15}$ connect to form a ring;

X4 is N or C—R$^{15}$, wherein R$^{15}$ is hydrogen, halogen, —CN, alkyl, or alkoxy;

$R^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl; or optionally when X4 is C—R$^{15}$, R$^{16}$ and R$^{15}$ connect to form a ring;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (VII), wherein X2 is N. Another embodiment provides a compound of Formula (VII), wherein X3 is N. Another embodiment provides a compound of Formula (VII), wherein X4 is N. Another embodiment provides a compound of Formula (VII), wherein X2 and X3 are N. Another embodiment provides a compound of Formula (VII), wherein X2 is C—$R^{12}$, X3 is C—$R^{14}$, and X4 is C—$R^{15}$.

Another embodiment provides a compound of Formula (VII), wherein $R^2$ is $CH_3$. Another embodiment provides a compound of Formula (VII), wherein X6 is C—H. Another embodiment provides a compound of Formula (VII), wherein X6 is N. Another embodiment provides a compound of Formula (VII), wherein X5 is C—$R^5$. Another embodiment provides a compound of Formula (VII), wherein X5 is N. Another embodiment provides a compound of Formula (VII), wherein $R^5$ is hydrogen, halogen, or alkyl. Another embodiment provides a compound of Formula (VII), wherein $R^6$ is hydrogen, halogen, or alkyl. Another embodiment provides a compound of Formula (VII), wherein $R^6$ is heterocyclyl. Another embodiment provides a compound of Formula (VII), wherein $R^6$ is cycloalkylalkynyl. Another embodiment provides a compound of Formula (VII), wherein $R^6$ is alkoxy, cycloalkyloxy, or cycloalkylalkoxy.

Another embodiment provides a compound of Formula (VII), wherein Y is a bond. Another embodiment provides a compound of Formula (VII), wherein Y is a —$CH_2$—. Another embodiment provides a compound of Formula (VII), wherein Z is —$SO_2R^{21}$. Another embodiment provides a compound of Formula (VII), wherein Z is —$N(R^{22})SO_2R^{21}$. Another embodiment provides a compound of Formula (VII), wherein Z is —$SO_2N(R^{22})_2$. Another embodiment provides a compound of Formula (VII), wherein Z is —$N(R^{22})SO_2N(R^{22})_2$. Another embodiment provides a compound of Formula (VII), wherein Z is —$CON(R^{22})_2$. Another embodiment provides a compound of Formula (VII), wherein Z is —$N(R^{22})CO_2R^{21}$. Another embodiment provides a compound of Formula (VII), wherein Z is —$N(R^{22})CON(R^{22})_2$. Another embodiment provides a compound of Formula (VII), wherein $R^{21}$ is alkyl, cycloalkyl, or cycloalkylalkyl. Another embodiment provides a compound of Formula (VII), wherein $R^{21}$ is alkyl. Another embodiment provides a compound of Formula (VII), wherein $R^{14}$ is hydrogen, halogen, or alkyl. Another embodiment provides a compound of Formula (VII), wherein X4 is C—$R^{15}$. Another embodiment provides a compound of Formula (VII), wherein W is —O—. Another embodiment provides a compound of Formula (VII), wherein W is —NH—. Another embodiment provides a compound of Formula (VII), wherein X is alkyl. Another embodiment provides a compound of Formula (VII), wherein X is alkynyl. Another embodiment provides a compound of Formula (VII), wherein X is aryl. Another embodiment provides a compound of Formula (VII), wherein X is cycloalkylalkyl. Another embodiment provides a compound of Formula (VII), wherein X is cycloalkylalkynyl. Another embodiment provides a compound of Formula (VII), wherein W is —O— and X is alkyl. Another embodiment provides a compound of Formula (VII), wherein W is —O— and X is alkynyl. Another embodiment provides a compound of Formula (VII), wherein W is —O— and X is aryl. Another embodiment provides a compound of Formula (VII), wherein W is —O— and X is cycloalkylalkyl. Another embodiment provides a compound of Formula (VII), wherein W is —O— and X is cycloalkylalkynyl.

Another embodiment provides a compound of Formula (VII), wherein the $R^6$ is $CD_3$.

One embodiment provides a compound of Formula (VIIa), or a pharmaceutically acceptable salt thereof,

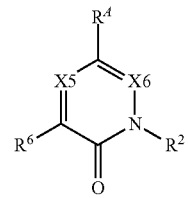

Formula (VIIa)

wherein, $R^2$ is $CH_3$, $CH_2CH_3$, $CH_2CF_3$, $CH_2F$, $CHF_2$, $CF_3$, $CH_2D$, $CHD_2$, or $CD_3$;

X6 is C—H or N;

X5 is C—$R^5$ or N; provided that if X6 is N, then X5 is C—$R^5$, and if X5 is N, then X6 is CH;

$R^5$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^6$ is hydrogen, halogen, —OH, —CN, alkyl, alkynyl, cycloalkyl, cycloalkylalkyl, cycloalkylalkynyl, amino, alkylamino, dialkylamino, heterocyclyl, cycloalkylalkylamino, alkoxy, cycloalkyloxy, cycloalkylalkoxy, alkyl-S—, cycloalkyl-S—, and cycloalkylalkyl-S—;

$R^A$ is

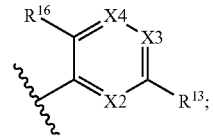

X2 is N or C—$R^{12}$, wherein $R^{12}$ is hydrogen, halogen, alkyl, or alkoxy;

$R^{13}$ is —Y—Z;

Y is selected from a bond, —$CH_2$—, or —$CH(C_1$-$C_4$ alkyl)-;

Z is selected from —$N(R^{22})SO_2R^{21}$, —$N(R^{22})CO_2R^{21}$, —$N(R^{22})COR^{21}$, or —$N(R^{22})SO_3R^{21}$;

X3 is N or C—$R^{14}$, wherein $R^{14}$ is hydrogen, halogen, —CN, alkyl, cycloalkyl, or alkoxy; or optionally when X4 is C—$R^{15}$, $R^{14}$ and $R^{15}$ connect to form a ring;

X4 is N or C—$R^{15}$, wherein $R^{15}$ is hydrogen, halogen, —CN, alkyl, or alkoxy;

$R^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl; or optionally when X4 is C—$R^{15}$, $R^{16}$ and $R^{15}$ connect to form a ring;

each $R^{21}$ is independently selected from alkyl, cycloalkyl, cycloalkylalkyl, aryl, aralkyl, heterocyclyl, heterocyclylalkyl, heteroaryl, or heteroarylalkyl; or optionally when $R^{21}$ and $R^{22}$ are alkyl, $R^{21}$ and $R^{22}$ connect to form a ring; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (VIIa), wherein X2 is N. Another embodiment provides a compound of Formula (VIIa), wherein X3 is N. Another embodiment provides a compound of Formula (VIIa), wherein X4 is N. Another embodiment provides a compound of Formula (VIIa), wherein X2 and X3 are N. Another embodiment provides a compound of Formula (VIIa), wherein X2 is C—$R^{12}$, X3 is C—$R^{14}$, and X4 is C—$R^{15}$.

Another embodiment provides a compound of Formula (VIIa), wherein $R^2$ is $CH_3$. Another embodiment provides a compound of Formula (VIIa), wherein X6 is C—H. Another embodiment provides a compound of Formula (VIIa), wherein X6 is N. Another embodiment provides a compound of Formula (VIIa), wherein X5 is C—$R^5$. Another embodiment provides a compound of Formula (VIIa), wherein X5 is N. Another embodiment provides a compound of Formula (VIIa), wherein $R^5$ is hydrogen, halogen, or alkyl. Another embodiment provides a compound of Formula (VIIa, wherein $R^6$ is hydrogen, halogen, or alkyl. Another embodiment provides a compound of Formula (VIIa), wherein $R^6$ is heterocyclyl. Another embodiment provides a compound of Formula (VIIa), wherein $R^6$ is cycloalkylalkynyl. Another embodiment provides a compound of Formula (VIIa), wherein $R^6$ is alkoxy, cycloalkyloxy, or cycloalkylalkoxy.

Another embodiment provides a compound of Formula (VIIa), wherein Y is a bond. Another embodiment provides a compound of Formula (VIIa), wherein Y is a —$CH_2$—. Another embodiment provides a compound of Formula (VIIa), wherein Z is —$N(R^{22})SO_2R^{21}$. Another embodiment provides a compound of Formula (VIIa), wherein Z is —$N(R^{22})CO_2R^{21}$. Another embodiment provides a compound of Formula (VIIa), wherein R21 is alkyl, cycloalkyl, or cycloalkylalkyl. Another embodiment provides a compound of Formula (VIIa), wherein $R^{21}$ is alkyl. Another embodiment provides a compound of Formula (VIIa), wherein $R^{22}$ is alkyl. Another embodiment provides a compound of Formula (VIIa), wherein both $R^{21}$ and $R^{22}$ are alkyl and connect to form a ring. Another embodiment provides a compound of Formula (VIIa), wherein $R^{14}$ is hydrogen, halogen, or alkyl. Another embodiment provides a compound of Formula (VIIa), wherein X4 is C—$R^{15}$. Another embodiment provides a compound of Formula (VIIa), wherein W is —O—. Another embodiment provides a compound of Formula (VIIa), wherein W is —NH—. Another embodiment provides a compound of Formula (VIIa), wherein X is alkyl. Another embodiment provides a compound of Formula (VIIa), wherein X is alkynyl. Another embodiment provides a compound of Formula (VIIa), wherein X is aryl. Another embodiment provides a compound of Formula (VIIa), wherein X is cycloalkylalkyl. Another embodiment provides a compound of Formula (VIIa), wherein X is cycloalkylalkynyl. Another embodiment provides a compound of Formula (VIIa), wherein W is —O— and X is alkyl. Another embodiment provides a compound of Formula (VIIa), wherein W is —O— and X is alkynyl. Another embodiment provides a compound of Formula (VIIa), wherein W is —O— and X is aryl. Another embodiment provides a compound of Formula (VIIa), wherein W is —O— and X is cycloalkylalkyl. Another embodiment provides a compound of Formula (VIIa), wherein W is —O— and X is cycloalkylalkynyl. Another embodiment provides a compound of Formula (VIIa), wherein the $R^6$ is $CD_3$.

One embodiment provides a compound of Formula (VIII), or a pharmaceutically acceptable salt thereof,

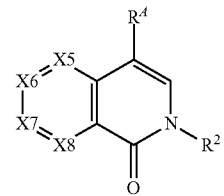

Formula (VIII)

wherein, $R^2$ is selected from $CH_3$, $CH_2CH_3$, $CH_2CF_3$, $CH_2F$, $CHF_2$, $CF_3$, $CH_2D$, $CHD_2$, or $CD_3$;

X5 is C—$R^5$ or N;

X6 is C—$R^6$ or N;

X7 is C—$R^7$ or N;

X8 is C—$R^8$ or N; wherein no more than two of X5, X6, X7, or X8 may be N;

$R^5$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^6$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^7$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^8$ is hydrogen, halogen, or alkyl;

$R^A$ is

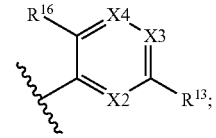

X2 is N or C—$R^{12}$, wherein $R^{12}$ is hydrogen, halogen, alkyl, or alkoxy;

$R^{13}$ is —Y—Z;

Y is selected from a bond, —$CH_2$—, or —$CH(C_1$-$C_4$ alkyl)-;

Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$;

X3 is N or C—$R^{14}$, wherein $R^{14}$ is hydrogen, halogen, —CN, alkyl, cycloalkyl, or alkoxy; or optionally when X4 is C—$R^{15}$, $R^{14}$ and $R^{15}$ connect to form a ring;

X4 is N or C—$R^{15}$, wherein $R^{15}$ is hydrogen, halogen, —CN, alkyl, or alkoxy;

$R^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl; or optionally when X4 is C—$R^{15}$, $R^{16}$ and $R^{15}$ connect to form a ring;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (VIII), wherein $R^2$ is $CH_3$. Another embodiment provides a compound of Formula (VIII), wherein $R^2$ is $CD_3$. Another embodiment provides a compound of Formula (VIII), wherein X5 is N. Another embodiment provides a compound of Formula (VIII), wherein X6 is N. Another embodiment provides a compound of Formula (VIII), wherein X7 is N. Another embodiment provides a compound of Formula (VIII), wherein X8 is N. Another embodiment provides a compound of Formula (VIII), wherein none of X5, X6, X7, or X8 is N. Another embodiment provides a compound of Formula (VIII), wherein $R^5$ and $R^8$ are hydrogen. Another embodiment provides a compound of Formula (VIII), wherein $R^5$, $R^6$, $R^7$ and $R^8$ are hydrogen. Another embodiment provides a compound of Formula (VIII), wherein $R^7$ is a halogen. Another embodiment provides a compound of Formula (VIII), wherein $R^6$ is a halogen. Another embodiment provides a compound of Formula (VIII), wherein $R^6$ is a heteroaryl. Another embodiment provides a compound of Formula (VIII), wherein $R^6$ is an aryl. Another embodiment provides a compound of Formula (VIII), wherein $R^6$ is an alkyl. Another embodiment provides a compound of Formula (VIII), wherein $R^6$ is an aryl.

Another embodiment provides a compound of Formula (VIII), wherein Y is a bond. Another embodiment provides a compound of Formula (VIII), wherein Y is a —$CH_2$—. Another embodiment provides a compound of Formula (VIII), wherein Z is —$SO_2R^{21}$. Another embodiment provides a compound of Formula (VIII), wherein Z is —$N(R^{22})SO_2R^{21}$. Another embodiment provides a compound of Formula (VIII), wherein Z is —$SO_2N(R^{22})_2$. Another embodiment provides a compound of Formula (VIII), wherein Z is —$N(R^{22})SO_2N(R^{22})_2$. Another embodiment provides a compound of Formula (VIII), wherein Z is —$CON(R^{22})2$. Another embodiment provides a compound of Formula (VIII), wherein Z is —$N(R^{22})CO_2R^{21}$. Another embodiment provides a compound of Formula (VIII), wherein Z is —$N(R^{22})CON(R^{22})_2$. Another embodiment provides a compound of Formula (VIII), wherein $R^{21}$ is alkyl, cycloalkyl, or cycloalkylalkyl. Another embodiment provides a compound of Formula (VIII), wherein R21 is alkyl. Another embodiment provides a compound of Formula (VIII), wherein $R^{14}$ is hydrogen, halogen, or alkyl. Another embodiment provides a compound of Formula (VIII), wherein X4 is C—$R^{15}$. Another embodiment provides a compound of Formula (VIII), wherein W is —O—. Another embodiment provides a compound of Formula (VIII), wherein W is —NH—. Another embodiment provides a compound of Formula (VIII), wherein X is alkyl. Another embodiment provides a compound of Formula (VIII), wherein X is aryl. Another embodiment provides a compound of Formula (VIII), wherein X is cycloalkylalkyl.

Another embodiment provides a compound of Formula (VIII), wherein W is —O— and X is alkyl. Another embodiment provides a compound of Formula (VIII), wherein W is —O— and X is aryl. Another embodiment provides a compound of Formula (VIII), wherein W is —O— and X is cycloalkylalkyl. Another embodiment provides a compound of Formula (VIII), wherein $R^5$ and $R^8$ are hydrogen. Another embodiment provides a compound of Formula (VIII), wherein $R^5$ and $R^8$ are hydrogen, and $R^6$ is heteroaryl.

One embodiment provides a compound of Formula (VIIIa), or a pharmaceutically acceptable salt thereof, Formula (VIIIa)

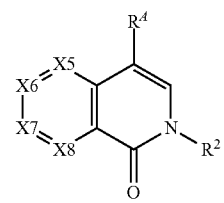

wherein, $R^2$ is selected from $CH_3$, $CH_2CH_3$, $CH_2CF_3$, $CH_2F$, $CHF_2$, $CF_3$, $CH_2D$, $CHD_2$, or $CD_3$;

X5 is C—$R^5$ or N;

X6 is C—$R^6$ or N;

X7 is C—$R^7$ or N;

X8 is C—$R^8$ or N; wherein no more than two of X5, X6, X7, or X8 may be N;

$R^5$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^6$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^7$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^8$ is hydrogen, halogen, or alkyl;

$R^A$ is

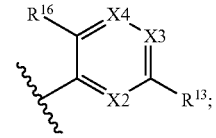

X2 is N or C—$R^{12}$, wherein $R^{12}$ is hydrogen, halogen, alkyl, or alkoxy;

$R^{13}$ is —Y—Z;

Y is selected from a bond, —CH$_2$—, or —CH(C$_1$-C$_4$ alkyl)-;

Z is selected from —N(R$^{22}$)SO$_2$R$^{21}$, —N(R$^{22}$)CO$_2$R$^{21}$, —N(R$^{22}$)COR$^{21}$, or —N(R$^{22}$)SO$_3$R$^{21}$; X3 is N or C—R$^{14}$, wherein R$^{14}$ is hydrogen, halogen, —CN, alkyl, cycloalkyl, or alkoxy; or optionally when X4 is C—R$^{15}$, R$^{14}$ and R$^{15}$ connect to form a ring;

X4 is N or C—R$^{15}$, wherein R$^{15}$ is hydrogen, halogen, —CN, alkyl, or alkoxy;

R$^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl; or optionally when X4 is C—R$^{15}$, R$^{16}$ and R$^{15}$ connect to form a ring;

each R$^{21}$ is independently selected from alkyl, cycloalkyl, cycloalkylalkyl, aryl, aralkyl, heterocyclyl, heterocyclylalkyl, heteroaryl, or heteroarylalkyl; or optionally when R$^{21}$ and R$^{22}$ are alkyl, R$^{21}$ and R$^{22}$ connect to form a ring; and each R$^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (VIIIa), wherein R$^2$ is CH$_3$. Another embodiment provides a compound of Formula (VIIIa), wherein R$^2$ is CD$_3$. Another embodiment provides a compound of Formula (VIIIa), wherein X5 is N. Another embodiment provides a compound of Formula (VIIIa), wherein X6 is N. Another embodiment provides a compound of Formula (VIIIa), wherein X7 is N. Another embodiment provides a compound of Formula (VIIIa), wherein X8 is N. Another embodiment provides a compound of Formula (VIIIa), wherein none of X5, X6, X7, or X8 is N. Another embodiment provides a compound of Formula (VIIIa), wherein R$^5$ and R$^8$ are hydrogen. Another embodiment provides a compound of Formula (VIIIa), wherein R$^5$, R$^6$, R$^7$ and R$^8$ are hydrogen. Another embodiment provides a compound of Formula (VIIIa), wherein R$^7$ is a halogen. Another embodiment provides a compound of Formula (VIIIa), wherein R$^6$ is a halogen. Another embodiment provides a compound of Formula (VIIIa), wherein R$^6$ is a heteroaryl. Another embodiment provides a compound of Formula (VIIIa), wherein R$^6$ is an aryl. Another embodiment provides a compound of Formula (VIIIa), wherein R$^6$ is an alkyl. Another embodiment provides a compound of Formula (VIIIa), wherein R$^6$ is an aryl.

Another embodiment provides a compound of Formula (VIIIa), wherein Y is a bond. Another embodiment provides a compound of Formula (VIIIa), wherein Y is a —CH$_2$—. Another embodiment provides a compound of Formula (VIIIa), wherein Z is —N(R$^{22}$)SO$_2$R$^{21}$. Another embodiment provides a compound of Formula (VIIIa), wherein Z is —N(R$^{22}$)CO$_2$R$^{21}$. Another embodiment provides a compound of Formula (VIIIa), wherein R$^{21}$ is alkyl, cycloalkyl, or cycloalkylalkyl. Another embodiment provides a compound of Formula (VIIIa), wherein R$^{21}$ is alkyl. Another embodiment provides a compound of Formula (VIIIa), wherein R$^{22}$ is alkyl. Another embodiment provides a compound of Formula (VIIIa), wherein both R$^{21}$ and R$^{22}$ are alkyl and connect to form a ring. Another embodiment provides a compound of Formula (VIIIa), wherein R$^{14}$ is hydrogen, halogen, or alkyl. Another embodiment provides a compound of Formula (VIIIa), wherein X4 is C—R$^{15}$. Another embodiment provides a compound of Formula (VIIIa), wherein W is —O—. Another embodiment provides a compound of Formula (VIIIa), wherein W is —NH—. Another embodiment provides a compound of Formula (VIIIa), wherein X is alkyl. Another embodiment provides a compound of Formula (VIIIa), wherein X is aryl. Another embodiment provides a compound of Formula (VIIIa), wherein X is cycloalkylalkyl. Another embodiment provides a compound of Formula (VIIIa), wherein W is —O— and X is alkyl. Another embodiment provides a compound of Formula (VIIIa), wherein W is —O— and X is aryl. Another embodiment provides a compound of Formula (VIIIa), wherein W is —O— and X is cycloalkylalkyl. Another embodiment provides a compound of Formula (VIIIa), wherein R$^5$ and R$^8$ are hydrogen. Another embodiment provides a compound of Formula (VIIIa), wherein R$^5$ and R$^8$ are hydrogen, and R$^6$ is heteroaryl.

One embodiment provides a compound of Formula (IX), or a pharmaceutically acceptable salt thereof,

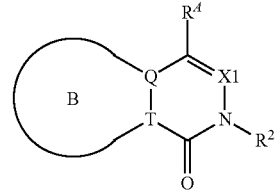

Formula (IX)

wherein,

Q is N and T is C, or Q is C and T is N;

Ring B is an optionally substituted 5-membered aromatic nitrogen-containing heteroaryl ring containing one or more nitrogen atoms;

R$^2$ is selected from CH$_3$, CH$_2$CH$_3$, CH$_2$CF$_3$, CH$_2$F, CHF$_2$, CF$_3$, CH$_2$D, CHD$_2$, or CD$_3$;

X1 is C—H or N;

R$^4$ is

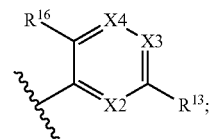

X2 is N or C—R$^{12}$, wherein R$^{12}$ is hydrogen, halogen, alkyl, or alkoxy;

R$^{13}$ is —Y—Z;

Y is selected from a bond, —CH$_2$—, or —CH(C$_1$-C$_4$ alkyl)-;

Z is selected from —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;

X3 is N or C—R$^{14}$, wherein R$^{14}$ is hydrogen, halogen, —CN, alkyl, cycloalkyl, or alkoxy; or optionally when X4 is C—R$^{15}$, R$^{14}$ and R$^{15}$ connect to form a ring;

X4 is N or C—R$^{15}$, wherein R$^{15}$ is hydrogen, halogen, —CN, alkyl, or alkoxy;

R$^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl; or optionally when X4 is C—R$^{15}$, R$^{16}$ and R$^{15}$ connect to form a ring;

each R$^{21}$ is independently selected from alkyl, cycloalkyl, cycloalkylalkyl, aryl, aralkyl, heterocyclyl, heterocyclylalkyl, heteroaryl, or heteroarylalkyl; and each R$^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (IX), wherein X2 is N. Another embodiment provides a compound of Formula (IX), wherein X3 is N. Another embodiment provides a compound of Formula (IX), wherein X4 is N. Another embodiment provides a compound of Formula (IX), wherein X2 and X3 are N. Another embodiment provides a compound of Formula (IX), wherein X2 is C—R$^{12}$, X3 is C—R$^{14}$, and X4 is C—R$^{15}$.

Another embodiment provides a compound of Formula (IX), wherein the compound of Formula (IX) is selected from the group:

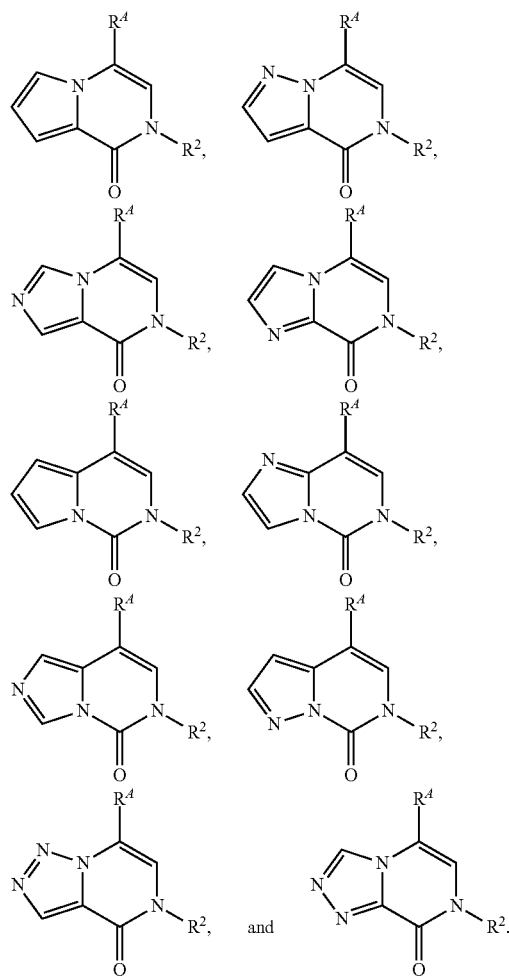

Another embodiment provides a compound of Formula (IX), wherein Q is N and T is C. Another embodiment provides a compound of Formula (IX), wherein Q is C and T is N. Another embodiment provides a compound of Formula (IX), wherein R$^2$ is CH$_3$. Another embodiment provides a compound of Formula (IX), wherein X1 is C—H. Another embodiment provides a compound of Formula (IX), wherein X1 is N.

Another embodiment provides a compound of Formula (IX), wherein Y is a bond. Another embodiment provides a compound of Formula (IX), wherein Y is a —CH$_2$—. Another embodiment provides a compound of Formula (IX), wherein Z is —SO$_2$R$^{21}$. Another embodiment provides a compound of Formula (IX), wherein Z is —N(R$^{22}$)SO$_2$R$^{21}$. Another embodiment provides a compound of Formula (IX), wherein Z is —SO$_2$N(R$^{22}$)$_2$. Another embodiment provides a compound of Formula (IX), wherein Z is —N(R$^{22}$)SO$_2$N(R$^{22}$)$_2$. Another embodiment provides a compound of Formula (IX), wherein Z is —CON(R$^{22}$)$_2$. Another embodiment provides a compound of Formula (IX), wherein Z is —N(R$^{22}$)CO$_2$R$^{21}$. Another embodiment provides a compound of Formula (IX), wherein Z is —N(R$^{22}$)CON(R$^{22}$)$_2$. Another embodiment provides a compound of Formula (IX), wherein R$^{21}$ is alkyl, cycloalkyl, or cycloalkylalkyl. Another embodiment provides a compound of Formula (IX), wherein R$^{21}$ is alkyl.

Another embodiment provides a compound of Formula (IX), wherein R14 is hydrogen, halogen, or alkyl. Another embodiment provides a compound of Formula (IX), wherein X4 is C—R$^{15}$. Another embodiment provides a compound of Formula (IX), wherein W is —O—. Another embodiment provides a compound of Formula (IX), wherein W is —NH—. Another embodiment provides a compound of Formula (IX), wherein X is alkyl. Another embodiment provides a compound of Formula (IX), wherein X is aryl. Another embodiment provides a compound of Formula (IX), wherein X is cycloalkylalkyl. Another embodiment provides a compound of Formula (IX), wherein W is —O— and X is alkyl. Another embodiment provides a compound of Formula (IX), wherein W is —O— and X is aryl. Another embodiment provides a compound of Formula (IX), wherein W is —O— and X is cycloalkylalkyl.

One embodiment provides a compound of Formula (XII), or a pharmaceutically acceptable salt thereof,

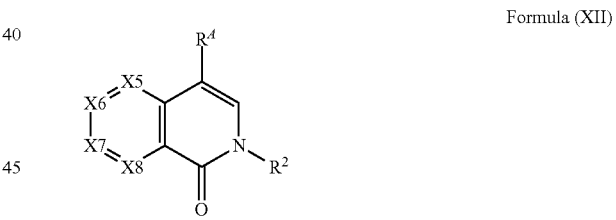

Formula (XII)

wherein,

R$^2$ is selected from CH$_3$, CH$_2$CH$_3$, CH$_2$CF$_3$, CH$_2$F, CHF$_2$, CF$_3$, CH$_2$D, CHD$_2$, or CD$_3$;

X5 is C—R$^5$ or N;

X6 is C—R$^6$ or N;

X7 is C—R$^7$ or N;

X8 is C—R$^8$ or N; wherein no more than two of X5, X6, X7, or X8 may be N;

R$^5$ is hydrogen, halogen, —OH, —CN, —OR$^{61}$, —NHR$^{61}$, —N(R$^{61}$)$_2$, alkyl, cycloalkyl, cycloalkylalkyl, aryl, aralkyl, heterocyclyl, heterocyclylalkyl, heteroaryl, or heteroarylalkyl, wherein each R$^{61}$ is independently selected from alkyl, cycloalkyl, cycloalkylalkyl, aryl, aralkyl, heterocyclyl, heterocyclylalkyl, heteroaryl, or heteroarylalkyl;

R$^6$ is hydrogen, halogen, —OH, —CN, —OR$^{61}$, —NHR$^{61}$, —N(R$^{61}$)$_2$, alkyl, cycloalkyl, cycloalkylalkyl, aryl, aralkyl, heterocyclyl, heterocyclylalkyl, heteroaryl, or heteroarylalkyl, wherein each R$^{61}$ is independently selected from alkyl, cycloalkyl, cycloalkylalkyl, aryl, aralkyl, heterocyclyl, heterocyclylalkyl, heteroaryl, or heteroarylalkyl;

$R^7$ is hydrogen, halogen, —OH, —CN, —OR$^{61}$, —NHR$^{61}$, —N(R$^{61}$)$_2$, alkyl, cycloalkyl, cycloalkylalkyl, aryl, aralkyl, heterocyclyl, heterocyclylalkyl, heteroaryl, or heteroarylalkyl, wherein each R$^{61}$ is independently selected from alkyl, cycloalkyl, cycloalkylalkyl, aryl, aralkyl, heterocyclyl, heterocyclylalkyl, heteroaryl, or heteroarylalkyl;

$R^8$ is hydrogen, halogen, or alkyl;

$R^A$ is

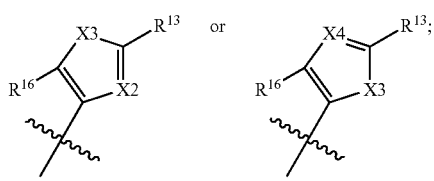

X2 is N or C—R$^{12}$, wherein R$^{12}$ is hydrogen, halogen, alkyl, or alkoxy;

$R^{13}$ is —Y—Z;

Y is selected from a bond, —CH$_2$—, or —CH(C$_1$-C$_4$ alkyl)-;

Z is selected from —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;

X3 is S;

X4 is N or C—R$^{14}$, wherein R$^{14}$ is hydrogen, halogen, alkyl, or alkoxy;

$R^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (XII), wherein R$^2$ is CH$_3$. Another embodiment provides a compound of Formula (XII), wherein R$^2$ is CD$_3$. Another embodiment provides a compound of Formula (XII), wherein X5 is N. Another embodiment provides a compound of Formula (XII), wherein X6 is N. Another embodiment provides a compound of Formula (XII), wherein X7 is N. Another embodiment provides a compound of Formula (XII), wherein X8 is N. Another embodiment provides a compound of Formula (XII), wherein none of X5, X6, X7, or X8 is N. Another embodiment provides a compound of Formula (XII), wherein R$^5$ and R$^8$ are hydrogen. Another embodiment provides a compound of Formula (XII), wherein R$^5$, R$^6$, R$^7$, and R$^8$ are hydrogen. Another embodiment provides a compound of Formula (XII), wherein R$^7$ is a halogen. Another embodiment provides a compound of Formula (XII), wherein R$^6$ is a halogen. Another embodiment provides a compound of Formula (XII), wherein R$^6$ is a heteroaryl. Another embodiment provides a compound of Formula (XII), wherein R$^6$ is an aryl. Another embodiment provides a compound of Formula (XII), wherein R$^6$ is an alkyl. Another embodiment provides a compound of Formula (XII), wherein R$^6$ is an aryl.

Another embodiment provides a compound of Formula (XII), wherein Y is a bond. Another embodiment provides a compound of Formula (XII), wherein Y is a —CH$_2$—. Another embodiment provides a compound of Formula (XII), wherein Z is —SO$_2$R$^{21}$. Another embodiment provides a compound of Formula (XII), wherein Z is —N(R$^{22}$)SO$_2$R$^{21}$. Another embodiment provides a compound of Formula (XII), wherein Z is —SO$_2$N(R$^{22}$)$_2$. Another embodiment provides a compound of Formula (XII), wherein Z is —N(R$^{22}$)SO$_2$N(R$^{22}$)$_2$. Another embodiment provides a compound of Formula (XII), wherein Z is —CON(R$^{22}$)$_2$. Another embodiment provides a compound of Formula (XII), wherein Z is —N(R$^{22}$)CO$_2$R$^{21}$. Another embodiment provides a compound of Formula (XII), wherein Z is —N(R$^{22}$)CON(R$^{22}$)$_2$. Another embodiment provides a compound of Formula (XII), wherein R$^{21}$ is alkyl, cycloalkyl, or cycloalkylalkyl. Another embodiment provides a compound of Formula (XII), wherein R$^{21}$ is alkyl. Another embodiment provides a compound of Formula (XII), wherein W is —O—. Another embodiment provides a compound of Formula (XII), wherein W is —NH—. Another embodiment provides a compound of Formula (XII), wherein X is alkyl. Another embodiment provides a compound of Formula (XII), wherein X is aryl. Another embodiment provides a compound of Formula (XII), wherein X is cycloalkylalkyl. Another embodiment provides a compound of Formula (XII), wherein W is —O— and X is alkyl. Another embodiment provides a compound of Formula (XII), wherein W is —O— and X is aryl. Another embodiment provides a compound of Formula (XII), wherein W is —O— and X is cycloalkylalkyl. Another embodiment provides a compound of Formula (XII), wherein R$^5$ and R$^8$ are hydrogen. Another embodiment provides a compound of Formula (XII), wherein R$^5$ and R$^8$ are hydrogen, and R$^6$ is heteroaryl.

Another embodiment provides a compound of Formula (XII), wherein $R^A$ is

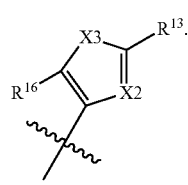

Another embodiment provides a compound of Formula (XII), wherein R$^A$ is

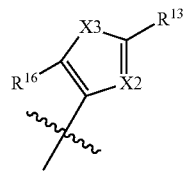

and X2 is N.

Another embodiment provides a compound of Formula (XII), wherein R$^A$ is

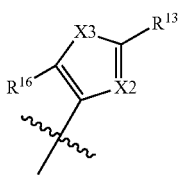

and X2 is C—R$^{12}$.

Another embodiment provides a compound of Formula (XII), wherein R$^4$ is

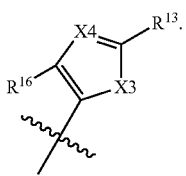

Another embodiment provides a compound of Formula (XII), wherein R$^4$ is

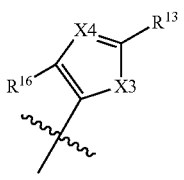

and X4 is N.

Another embodiment provides a compound of Formula (XII), wherein R$^4$ is

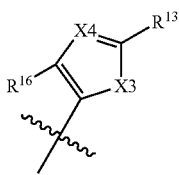

and X4 is C—R$^{14}$.

One embodiment provides a compound of Formula (XIII), or a pharmaceutically acceptable salt thereof, Formula (XIII)

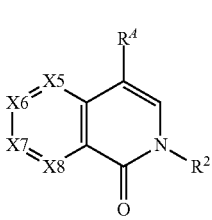

wherein,
R$^2$ is selected from CH$_3$, CH$_2$CH$_3$, CH$_2$CF$_3$, CH$_2$F, CHF$_2$, CF$_3$, CH$_2$D, CHD$_2$, or CD$_3$;
X5 is C—R$^5$ or N;
X6 is C—R$^6$ or N;
X7 is C—R$^7$ or N;
X8 is C—R$^8$ or N; wherein no more than two of X5, X6, X7, or X8 may be N;
R$^5$ is hydrogen, halogen, —OH, —CN, —OR$^{61}$, —NHR$^{61}$, —N(R$^{61}$)$_2$, alkyl, cycloalkyl, cycloalkylalkyl, aryl, aralkyl, heterocyclyl, heterocyclylalkyl, heteroaryl, or heteroarylalkyl, wherein each R$^{61}$ is independently selected from alkyl, cycloalkyl, cycloalkylalkyl, aryl, aralkyl, heterocyclyl, heterocyclylalkyl, heteroaryl, or heteroarylalkyl;
R$^6$ is hydrogen, halogen, —OH, —CN, —OR$^{61}$, —NHR$^{61}$, —N(R$^{61}$)$_2$, alkyl, cycloalkyl, cycloalkylalkyl, aryl, aralkyl, heterocyclyl, heterocyclylalkyl, heteroaryl, or heteroarylalkyl, wherein each R$^{61}$ is independently selected from alkyl, cycloalkyl, cycloalkylalkyl, aryl, aralkyl, heterocyclyl, heterocyclylalkyl, heteroaryl, or heteroarylalkyl;
R$^7$ is hydrogen, halogen, —OH, —CN, —OR$^{61}$, —NHR$^{61}$, —N(R$^{61}$)$_2$, alkyl, cycloalkyl, cycloalkylalkyl, aryl, aralkyl, heterocyclyl, heterocyclylalkyl, heteroaryl, or heteroarylalkyl, wherein each R$^{61}$ is independently selected from alkyl, cycloalkyl, cycloalkylalkyl, aryl, aralkyl, heterocyclyl, heterocyclylalkyl, heteroaryl, or heteroarylalkyl;
R$^8$ is hydrogen, halogen, or alkyl;
R$^4$ is

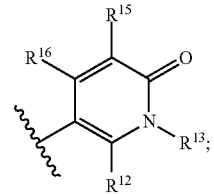

R$^{12}$ is hydrogen or C$_1$-C$_4$ alkyl;
R$^{13}$ is —Y—Z;
Y is selected from —CH$_2$—, or —CH(C$_1$-C$_4$ alkyl)-;
Z is selected from —SO$_2$R$^{21}$, —SO$_2$N(R$^{22}$)$_2$, or —CON(R$^{22}$)$_2$;
R$^{15}$ is hydrogen, halogen or C$_1$-C$_4$ alkyl;
R$^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl; or optionally, R$^{16}$ and R$^{15}$ connect to form a ring;
each R$^{21}$ is independently selected from alkyl, cycloalkyl, cycloalkylalkyl, aryl, aralkyl, heterocyclyl, heterocyclylalkyl, heteroaryl, or heteroarylalkyl; and
each R$^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (XIII), wherein R$^2$ is CH$_3$. Another embodiment provides a compound of Formula (XIII), wherein R$^2$ is CD$_3$. Another embodiment provides a compound of Formula (XIII), wherein X5 is N. Another embodiment provides a compound of Formula (XIII), wherein X6 is N. Another embodiment provides a compound of Formula (XIII), wherein X7 is N. Another embodiment provides a compound of Formula (XIII), wherein X8 is N. Another embodiment provides a compound of Formula (XIII), wherein none of X5, X6, X7, or X8 is N. Another embodiment provides a compound of Formula Formula (XIII), wherein $R^5$ and $R^8$ are hydrogen. Another embodiment provides a compound of Formula (XIII), wherein $R^5$, $R^6$, $R^7$, and $R^8$ are hydrogen. Another embodiment provides a compound of Formula (XIII), wherein $R^7$ is a halogen. Another embodiment provides a compound of Formula (XIII), wherein $R^6$ is a halogen. Another embodiment provides a compound of Formula (XIII), wherein $R^6$ is a heteroaryl. Another embodiment provides a compound of Formula (XIII), wherein $R^6$ is an aryl. Another embodiment provides a compound of Formula (XIII), wherein $R^6$ is an alkyl. Another embodiment provides a compound of Formula (XIII), wherein $R^6$ is an aryl.

Another embodiment provides a compound of Formula (XIII), wherein Y is a —$CH_2$—. Another embodiment provides a compound of Formula (XIII), wherein Z is —$SO_2R^{21}$. Another embodiment provides a compound of Formula (XIII), wherein Z is —$SO_2N(R^{22})_2$. Another embodiment provides a compound of Formula (XIII), wherein Z is —$CON(R^{22})_2$. Another embodiment provides a compound of Formula (XIII), wherein $R^{21}$ is alkyl, cycloalkyl, or cycloalkylalkyl. Another embodiment provides a compound of Formula (XIII), wherein $R^{21}$ is alkyl. Another embodiment provides a compound of Formula (XIII), wherein W is —O—. Another embodiment provides a compound of Formula (XIII), wherein W is —NH—. Another embodiment provides a compound of Formula (XIII), wherein X is alkyl. Another embodiment provides a compound of Formula (XIII), wherein X is aryl. Another embodiment provides a compound of Formula (XIII), wherein X is cycloalkylalkyl. Another embodiment provides a compound of Formula (XIII), wherein W is —O— and X is alkyl. Another embodiment provides a compound of Formula (XIII), wherein W is —O— and X is aryl. Another embodiment provides a compound of Formula (XIII), wherein W is —O— and X is cycloalkylalkyl. Another embodiment provides a compound of Formula (XIII), wherein $R^5$ and $R^8$ are hydrogen. Another embodiment provides a compound of Formula (XIII), wherein $R^5$ and $R^8$ are hydrogen, and $R^6$ is heteroaryl.

One embodiment provides a compound of Formula (XIV), or a pharmaceutically acceptable salt thereof,

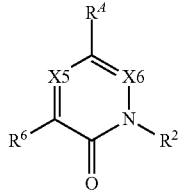

Formula (XIV)

wherein,
$R^2$ is $CH_3$, $CH_2CH_3$, $CH_2CF_3$, $CH_2F$, $CHF_2$, $CF_3$, $CH_2D$, $CHD_2$, or $CD_3$;
X6 is C—H or N;
X5 is C—$R^5$ or N; provided that if X6 is N, then X5 is C—$R^5$, and if X5 is N, then X6 is CH;
$R^5$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^6$ is hydrogen, halogen, —OH, —CN, alkyl, alkynyl, cycloalkyl, cycloalkylalkyl, cycloalkylalkynyl, amino, alkylamino, dialkylamino, heterocyclyl, cycloalkylalkylamino, alkoxy, cycloalkyloxy, cycloalkylalkoxy, alkyl-S—, cycloalkyl-S—, and cycloalkylalkyl-S—;
$R^4$ is

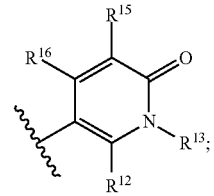

$R^{12}$ is hydrogen or $C_1$-$C_4$ alkyl;
$R^{13}$ is —Y—Z;
Y is selected from —$CH_2$—, or —$CH(C_1$-$C_4$ alkyl)-;
Z is selected from —$SO_2R^{21}$, —$SO_2N(R^{22})_2$, or —$CON(R^{22})_2$;
$R^{15}$ is hydrogen, halogen or $C_1$-$C_4$ alkyl;
$R^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl; or optionally, $R^{16}$ and $R^{15}$ connect to form a ring;
each $R^{21}$ is independently selected from alkyl, cycloalkyl, cycloalkylalkyl, aryl, aralkyl, heterocyclyl, heterocyclylalkyl, heteroaryl, or heteroarylalkyl; and
each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (XIV), wherein $R^2$ is $CH_3$. Another embodiment provides a compound of Formula (XIV), wherein X6 is C—H. Another embodiment provides a compound of Formula (XIV), wherein X6 is N. Another embodiment provides a compound of Formula (XIV), wherein X5 is C—$R^5$. Another embodiment provides a compound of Formula (XIV), wherein X5 is N. Another embodiment provides a compound of Formula (XIV), wherein $R^5$ is hydrogen, halogen, or alkyl. Another embodiment provides a compound of Formula (XIV), wherein $R^6$ is hydrogen, halogen, or alkyl. Another embodiment provides a compound of Formula (XIV), wherein $R^6$ is heterocyclyl. Another embodiment provides a compound of Formula (XIV), wherein $R^6$ is cycloalkylalkynyl. Another embodiment provides a compound of Formula (XIV), wherein $R^6$ is alkoxy, cycloalkyloxy, or cycloalkylalkoxy.

Another embodiment provides a compound of Formula (XIV), wherein Y is a —$CH_2$—. Another embodiment provides a compound of Formula (XIV), wherein Z is —$SO_2R^{21}$. Another embodiment provides a compound of Formula (XIV), wherein Z is —$SO_2N(R^{22})_2$. Another embodiment provides a compound of Formula (XIV), wherein Z is —$CON(R^{22})_2$. Another embodiment provides a compound of Formula (XIV), wherein $R^{21}$ is alkyl, cycloalkyl, or cycloalkylalkyl. Another embodiment provides a compound of Formula (XIV), wherein $R^{21}$ is alkyl. Another embodiment provides a compound of Formula (XIV), wherein W is —O—. Another embodiment provides a compound of Formula (XIV), wherein W is —NH—. Another embodiment provides a compound of Formula (XIV), wherein X is alkyl. Another embodiment provides a compound of Formula (XIV), wherein X is alkynyl. Another embodiment provides a compound of Formula (XIV), wherein X is aryl. Another embodiment provides a compound of Formula (XIV), wherein X is cycloalkylalkyl. Another embodiment provides a compound of Formula (XIV), wherein X is cycloalkylalkynyl. Another embodiment provides a compound of Formula (XIV), wherein W is —O— and X is alkyl. Another embodiment provides a compound of Formula (XIV), wherein W is —O— and X is alkynyl. Another embodiment provides a compound of Formula (XIV), wherein W is —O— and X is aryl. Another embodiment provides a compound of Formula (XIV), wherein W is —O— and X is cycloalkylalkyl. Another embodiment provides a compound of Formula (XIV), wherein W is —O— and X is cycloalkylalkynyl. Another embodiment provides a compound of Formula (XIV), wherein the $R^6$ is $CD_3$.

One embodiment provides a compound of Formula (XV), or a pharmaceutically acceptable salt thereof,

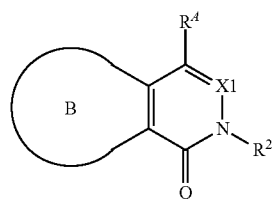

Formula (XV)

wherein,

Ring B is an optionally substituted 5-membered heteroaryl ring containing at least one oxygen or sulfur atom;

$R^2$ is selected from $CH_3$, $CH_2CH_3$, $CH_2CF_3$, $CH_2F$, $CHF_2$, $CF_3$, $CH_2D$, $CHD_2$, or $CD_3$;

X1 is C—H or N;

$R^4$ is

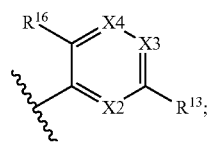

X2 is N or C—$R^{12}$, wherein $R^{12}$ is hydrogen, halogen, alkyl, or alkoxy;

$R^{13}$ is —Y—Z;

Y is selected from a bond, —$CH_2$—, or —CH($C_1$-$C_4$ alkyl)-;

Z is selected from v$SO_2R^{21}$, —N($R^{22}$)$SO_2R^{21}$, —$SO_2$N($R^{22}$)$_2$, —N($R^{22}$)$SO_2$N($R^{22}$)$_2$, —CON($R^{22}$)$_2$, —N($R^{22}$)$CO_2R^{21}$, —N($R^{22}$)CON($R^{22}$)$_2$, —N($R^{22}$)COR$^{21}$, —OC(O)N($R^{22}$)$_2$, —$OSO_2$N($R^{22}$)$_2$, or —N($R^{22}$)$SO_3R^{21}$;

X3 is N or C—$R^{14}$, wherein $R^{14}$ is hydrogen, halogen, —CN, alkyl, cycloalkyl, or alkoxy; or optionally when X4 is C—$R^{15}$, $R^{14}$ and $R^{15}$ connect to form a ring;

X4 is N or C—$R^{15}$, wherein $R^{15}$ is hydrogen, halogen, —CN, alkyl, or alkoxy;

$R^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl; or optionally when X4 is C—$R^{15}$, $R^{16}$ and $R^{15}$ connect to form a ring;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (XV), wherein X2 is N. Another embodiment provides a compound of Formula (XV), wherein X3 is N. Another embodiment provides a compound of Formula (XV), wherein X4 is N. Another embodiment provides a compound of Formula (XV), wherein X2 and X3 are N. Another embodiment provides a compound of Formula (XV), wherein X2 is C—$R^{12}$, X3 is C—$R^{14}$, and X4 is C—$R^{15}$.

Another embodiment provides a compound of Formula (XV), wherein the compound of Formula (XV) has a formula selected from:

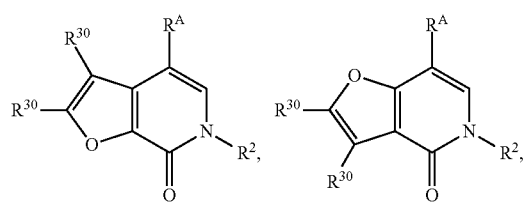

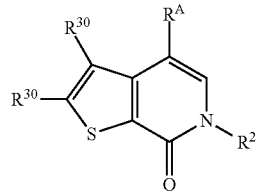

and

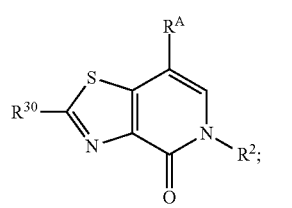

wherein each $R^{30}$ is independently selected from hydrogen, halogen, —CN, $C_1$-$C_4$ alkyl, —OH, —OR$^{31}$, —NHR$^{31}$, —N($R^{31}$)$_2$, —CONHR$^{31}$, or —CON($R^{31}$)$_2$; and $R^{31}$ is $C_1$-$C_4$ alkyl.

Another embodiment provides a compound of Formula (XV), wherein the compound of Formula (XV) has a formula selected from:

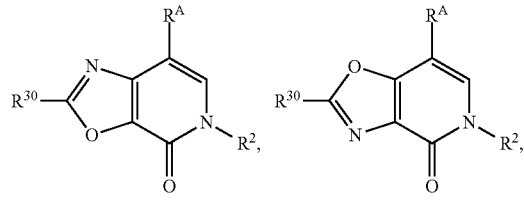

-continued

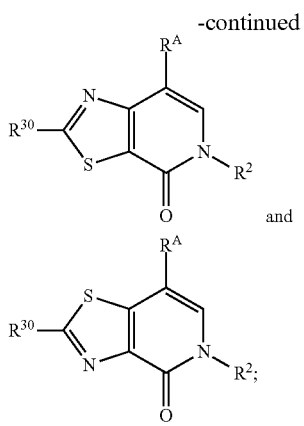

and wherein each R³⁰ is independently selected from hydrogen, halogen, —CN, $C_1$-$C_4$ alkyl, —OH, —OR³¹, —NHR³¹, —N(R³¹)$_2$, —CONHR³¹, or —CON(R³¹)$_2$; and R³¹ is $C_1$-$C_4$ alkyl.

Another embodiment provides a compound of Formula (XV), wherein the compound of Formula (XV) has a formula selected from:

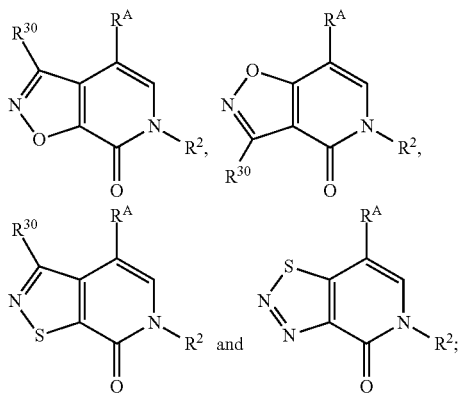

wherein each R³⁰ is independently selected from hydrogen, halogen, —CN, $C_1$-$C_4$ alkyl, —OH, —OR³¹, —NHR³¹, —N(R³¹)$_2$, —CONHR³¹, or —CON(R³¹)$_2$; and R³¹ is $C_1$-$C_4$ alkyl.

Another embodiment provides a compound of Formula (XV), wherein R² is CH₃. Another embodiment provides a compound of Formula (XV), wherein X1 is C—H. Another embodiment provides a compound of Formula (XV), wherein X1 is N.

Another embodiment provides a compound of Formula (XV), wherein Y is a bond. Another embodiment provides a compound of Formula (XV), wherein Y is a —CH₂—. Another embodiment provides a compound of Formula (XV), wherein Z is —SO₂R²¹. Another embodiment provides a compound of Formula (XV), wherein Z is —N(R²²)SO₂R²¹. Another embodiment provides a compound of Formula (XV), wherein Z is —SO₂N(R²²)₂. Another embodiment provides a compound of Formula (XV), wherein Z is —N(R²²)SO₂N(R²²)₂. Another embodiment provides a compound of Formula (XV), wherein Z is —CON(R²²)₂. Another embodiment provides a compound of Formula (XV), wherein Z is —N(R²²)CO₂R²¹. Another embodiment provides a compound of Formula (XV), wherein Z is —N(R²²)CON(R²²)₂. Another embodiment provides a compound of Formula (XV), wherein R²¹ is alkyl, cycloalkyl, or cycloalkylalkyl. Another embodiment provides a compound of Formula (XV), wherein R²¹ is alkyl.

Another embodiment provides a compound of Formula (XV), wherein X3 is C—R¹⁴. Another embodiment provides a compound of Formula (XV), wherein R¹⁴ is hydrogen, halogen, or alkyl. Another embodiment provides a compound of Formula (XV), wherein X4 is C—R¹⁵. Another embodiment provides a compound of Formula (XV), wherein W is —O—. Another embodiment provides a compound of Formula (XV), wherein W is —NH—. Another embodiment provides a compound of Formula (XV), wherein X is alkyl. Another embodiment provides a compound of Formula (XV), wherein X is alkynyl. Another embodiment provides a compound of Formula (XV), wherein X is aryl. Another embodiment provides a compound of Formula (XV), wherein X is cycloalkylalkyl. Another embodiment provides a compound of Formula (XV), wherein X is cycloalkylalkynyl. Another embodiment provides a compound of Formula (XV), wherein W is —O— and X is alkyl. Another embodiment provides a compound of Formula (XV), wherein W is —O— and X is aryl. Another embodiment provides a compound of Formula (XV), wherein W is —O— and X is alkynyl. Another embodiment provides a compound of Formula (XV), wherein W is —O— and X is cycloalkylalkyl. Another embodiment provides a compound of Formula (XV), wherein W is —O— and X is cycloalkylalkynyl.

Another embodiment provides a compound of Formula (XVI), or a pharmaceutically acceptable salt thereof, Formula (XVI)

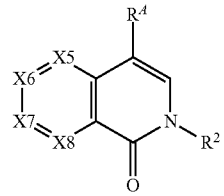

wherein,
R² is selected from CH₃, CH₂CH₃, CH₂CF₃, CH₂F, CHF₂, CF₃, CH₂D, CHD₂, or CD₃;
X5 is C—R⁵ or N;
X6 is C—R⁶ or N;
X7 is C—R⁷ or N;
X8 is C—R⁸ or N; wherein no more than two of X5, X6, X7, or X8 may be N;
R⁵ is hydrogen, halogen, —OH, —CN, —OR⁶¹, —NHR⁶¹, —N(R⁶¹)₂, alkyl, cycloalkyl, cycloalkylalkyl, aryl, aralkyl, heterocyclyl, heterocyclylalkyl, heteroaryl, or heteroarylalkyl, wherein each R⁶¹ is independently selected from alkyl, cycloalkyl, cycloalkylalkyl, aryl, aralkyl, heterocyclyl, heterocyclylalkyl, heteroaryl, or heteroarylalkyl;
R⁶ is hydrogen, halogen, —OH, —CN, —OR⁶¹, —NHR⁶¹, —N(R⁶¹)₂, alkyl, cycloalkyl, cycloalkylalkyl, aryl, aralkyl, heterocyclyl, heterocyclylalkyl, heteroaryl, or heteroarylalkyl, wherein each R⁶¹ is independently selected from alkyl, cycloalkyl, cycloalkylalkyl, aryl, aralkyl, heterocyclyl, heterocyclylalkyl, heteroaryl, or heteroarylalkyl;
R⁷ is hydrogen, halogen, —OH, —CN, —OR⁶¹, —NHR⁶¹, —N(R⁶¹)₂, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^8$ is hydrogen, halogen, or alkyl;

$R^4$ is

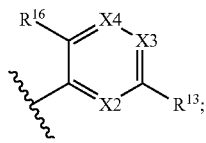

$X2$ is N or $C-R^{12}$, wherein $R^{12}$ is hydrogen, halogen, alkyl, or alkoxy;

$R^{13}$ is $-Y-Z$;

Y is selected from a bond, $-CH_2-$, or $-CH(C_1-C_4$ alkyl)-;

Z is selected from $-SO_2R^{21}$, $-N(R^{22})SO_2R^{21}$, $-SO_2N(R^{22})_2$, $-N(R^{22})SO_2N(R^{22})_2$, $-CON(R^{22})_2$, $-N(R^{22})CO_2R^{21}$, $-N(R^{22})CON(R^{22})_2$, $-N(R^{22})COR^{21}$, $-OC(O)N(R^{22})_2$, $-OSO_2N(R^{22})_2$, or $-N(R^{22})SO_3R^{21}$;

X3 is N or $C-R^{14}$, wherein $R^{14}$ is hydrogen, halogen, $-CN$, alkyl, cycloalkyl, or alkoxy; or optionally when X4 is $C-R^{15}$, $R^{14}$ and $R^{15}$ connect to form a ring;

X4 is N or $C-R^{15}$, wherein $R^{15}$ is hydrogen, halogen, $-CN$, alkyl, or alkoxy;

$R^{16}$ is hydrogen, halogen, or $-W-X$, wherein W is a bond, $-O-$, $-S-$, or $-NH-$, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl; or optionally when X4 is $C-R^{15}$, $R^{16}$ and $R^{15}$ connect to form a ring;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (XVI), wherein X2 is N. Another embodiment provides a compound of Formula (XVI), wherein X3 is N. Another embodiment provides a compound of Formula (XVI), wherein X4 is N. Another embodiment provides a compound of Formula (XVI), wherein X2 and X3 are N. Another embodiment provides a compound of Formula (XVI), wherein X2 is $C-R^{12}$, X3 is $C-R^{14}$, and X4 is $C-R^{15}$.

Another embodiment provides a compound of Formula (XVI), wherein $R^2$ is $CH_3$. Another embodiment provides a compound of Formula (XVI), wherein $R^2$ is $CD_3$. Another embodiment provides a compound of Formula (XVI), wherein X5 is N. Another embodiment provides a compound of Formula (XVI), wherein X6 is N. Another embodiment provides a compound of Formula (XVI), wherein X7 is N. Another embodiment provides a compound of Formula (XVI), wherein X8 is N. Another embodiment provides a compound of Formula (XVI), wherein none of X5, X6, X7, or X8 is N. Another embodiment provides a compound of Formula (XVI), wherein $R^5$ and $R^8$ are hydrogen. Another embodiment provides a compound of Formula (XVI), wherein $R^5$, $R^6$, $R^7$, and $R^8$ are hydrogen. Another embodiment provides a compound of Formula (XVI), wherein $R^7$ is a halogen. Another embodiment provides a compound of Formula (XVI), wherein $R^6$ is a halogen. Another embodiment provides a compound of Formula (XVI), wherein $R^6$ is a heteroaryl. Another embodiment provides a compound of Formula (XVI), wherein $R^6$ is an aryl. Another embodiment provides a compound of Formula (XVI), wherein $R^6$ is an alkyl. Another embodiment provides a compound of Formula (XVI), wherein $R^6$ is an aryl.

Another embodiment provides a compound of Formula (XVI), wherein Y is a bond. Another embodiment provides a compound of Formula (XVI), wherein Y is a $-CH_2-$. Another embodiment provides a compound of Formula (XVI), wherein Z is $-SO_2R^{21}$. Another embodiment provides a compound of Formula (XVI), wherein Z is $-N(R^{22})SO_2R^{21}$. Another embodiment provides a compound of Formula (XVI), wherein Z is $-SO_2N(R^{22})_2$. Another embodiment provides a compound of Formula (XVI), wherein Z is $-N(R^{22})SO_2N(R^{22})_2$. Another embodiment provides a compound of Formula (XVI), wherein Z is $-CON(R^{22})_2$. Another embodiment provides a compound of Formula (XVI), wherein Z is $-N(R^{22})CO_2R^{21}$. Another embodiment provides a compound of Formula (XVI), wherein Z is $-N(R^{22})CON(R^{22})_2$. Another embodiment provides a compound of Formula (XVI), wherein $R^{21}$ is alkyl, cycloalkyl, or cycloalkylalkyl. Another embodiment provides a compound of Formula (XVI), wherein $R^{21}$ is alkyl. Another embodiment provides a compound of Formula (XVI), wherein $R^{14}$ is hydrogen, halogen, or alkyl. Another embodiment provides a compound of Formula (XVI), wherein X4 is $C-R^{15}$. Another embodiment provides a compound of Formula (XVI), wherein W is $-O-$. Another embodiment provides a compound of Formula (XVI), wherein W is $-NH-$. Another embodiment provides a compound of Formula (XVI), wherein X is alkyl. Another embodiment provides a compound of Formula (XVI), wherein X is aryl. Another embodiment provides a compound of Formula (XVI), wherein X is cycloalkylalkyl. Another embodiment provides a compound of Formula (XVI), wherein W is $-O-$ and X is alkyl. Another embodiment provides a compound of Formula (XVI), wherein W is $-O-$ and X is aryl. Another embodiment provides a compound of Formula (XVI), wherein W is $-O-$ and X is cycloalkylalkyl. Another embodiment provides a compound of Formula (XVI), wherein $R^5$ and $R^8$ are hydrogen. Another embodiment provides a compound of Formula (XVI), wherein $R^5$ and $R^8$ are hydrogen, and $R^6$ is heteroaryl.

One embodiment provides a compound of Formula (XVII), or a pharmaceutically acceptable salt thereof,

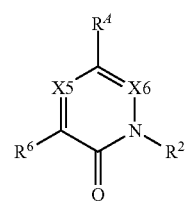

Formula (XVII)

wherein, $R^2$ is $CH_3$, $CH_2CH_3$, $CH_2CF_3$, $CH_2F$, $CHF_2$, $CF_3$, $CH_2D$, $CHD_2$, or $CD_3$;

X6 is $C-H$ or N;

X5 is $C-R^5$ or N; provided that if X6 is N, then X5 is $C-R^5$, and if X5 is N, then X6 is CH;

$R^5$ is hydrogen, halogen, —OH, —CN, —OR$^{61}$, —NHR$^{61}$, —N(R$^{61}$)$_2$, alkyl, cycloalkyl, cycloalkylalkyl, aryl, aralkyl, heterocyclyl, heterocyclylalkyl, heteroaryl, or heteroarylalkyl, wherein each R$^{61}$ is independently selected from alkyl, cycloalkyl, cycloalkylalkyl, aryl, aralkyl, heterocyclyl, heterocyclylalkyl, heteroaryl, or heteroarylalkyl;

$R^6$ is hydrogen, halogen, —OH, —CN, alkyl, alkynyl, cycloalkyl, cycloalkylalkyl, cycloalkylalkynyl, amino, alkylamino, dialkylamino, heterocyclyl, cycloalkylalkylamino, alkoxy, cycloalkyloxy, cycloalkylalkoxy, alkyl-S—, cycloalkyl-S—, and cycloalkylalkyl-S—;

$R^4$ is

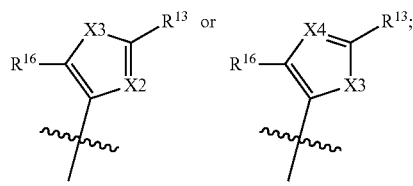

X2 is N or C—R$^{12}$, wherein R$^{12}$ is hydrogen, halogen, alkyl, or alkoxy;

R$^{13}$ is —Y—Z;

Y is selected from a bond, —CH$_2$—, or —CH(C$_1$-C$_4$ alkyl)-;

Z is selected from —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;

X3 is S;

X4 is N or C—R$^{14}$, wherein R$^{14}$ is hydrogen, halogen, alkyl, or alkoxy;

R$^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl;

each R$^{21}$ is independently selected from alkyl, cycloalkyl, cycloalkylalkyl, aryl, aralkyl, heterocyclyl, heterocyclylalkyl, heteroaryl, or heteroarylalkyl; and each R$^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (XVII), wherein RA is

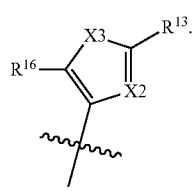

Another embodiment provides a compound of Formula (XVII), wherein RA is

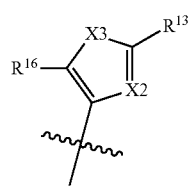

and X2 is N.

Another embodiment provides a compound of Formula (XVII), wherein RA is

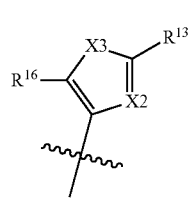

and X2 is C—R$^{12}$.

Another embodiment provides a compound of Formula (XVII), wherein RA is

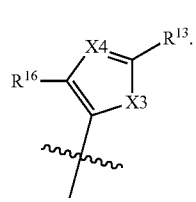

Another embodiment provides a compound of Formula (XVII), wherein RA is

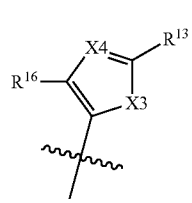

and X4 is N.

Another embodiment provides a compound of Formula (XVII), wherein RA is

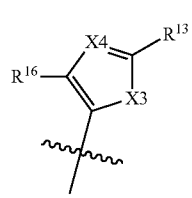

and X4 is C—R$^{14}$.

Another embodiment provides a compound of Formula (XVII), wherein R$^2$ is CH$_3$. Another embodiment provides a compound of Formula (XVII), wherein X6 is C—H. Another embodiment provides a compound of Formula (XVII), wherein X6 is N. Another embodiment provides a compound of Formula (XVII), wherein X5 is C—$R^5$. Another embodiment provides a compound of Formula (XVII), wherein X5 is N. Another embodiment provides a compound of Formula (XVII), wherein $R^5$ is hydrogen, halogen, or alkyl. Another embodiment provides a compound of Formula (XVII), wherein $R^6$ is hydrogen, halogen, or alkyl. Another embodiment provides a compound of Formula (XVII), wherein $R^6$ is heterocyclyl. Another embodiment provides a compound of Formula (XVII), wherein $R^6$ is cycloalkylalkynyl. Another embodiment provides a compound of Formula (XVII), wherein $R^6$ is alkoxy, cycloalkyloxy, or cycloalkylalkoxy.

Another embodiment provides a compound of Formula (XVII), wherein Y is a bond. Another embodiment provides a compound of Formula (XVII), wherein Y is a —$CH_2$—. Another embodiment provides a compound of Formula (XVII), wherein Z is —$SO_2R^{21}$. Another embodiment provides a compound of Formula (XVII), wherein Z is —$N(R^{22})SO_2R^{21}$. Another embodiment provides a compound of Formula (XVII), wherein Z is —$SO_2N(R^{22})_2$. Another embodiment provides a compound of Formula (XVII), wherein Z is —$N(R^{22})SO_2N(R^{22})_2$. Another embodiment provides a compound of Formula (XVII), wherein Z is —$CON(R^{22})_2$. Another embodiment provides a compound of Formula (XVII), wherein Z is —$N(R^{22})CO_2R^{21}$. Another embodiment provides a compound of Formula (XVII), wherein Z is —$N(R^{22})CON(R^{22})_2$. Another embodiment provides a compound of Formula (XVII), wherein $R^{21}$ is alkyl, cycloalkyl, or cycloalkylalkyl. Another embodiment provides a compound of Formula (XVII), wherein $R^{21}$ is alkyl. Another embodiment provides a compound of Formula (XVII), wherein W is —O—. Another embodiment provides a compound of Formula (XVII), wherein W is —NH—. Another embodiment provides a compound of Formula (XVII), wherein X is alkyl. Another embodiment provides a compound of Formula (XVII), wherein X is alkynyl. Another embodiment provides a compound of Formula (XVII), wherein X is aryl. Another embodiment provides a compound of Formula (XVII), wherein X is cycloalkylalkyl. Another embodiment provides a compound of Formula (XVII), wherein X is cycloalkylalkynyl. Another embodiment provides a compound of Formula (XVII), wherein W is —O— and X is alkyl. Another embodiment provides a compound of Formula (XVII), wherein W is —O— and X is alkynyl. Another embodiment provides a compound of Formula (XVII), wherein W is —O— and X is aryl. Another embodiment provides a compound of Formula (XVII), wherein W is —O— and X is cycloalkylalkyl. Another embodiment provides a compound of Formula (XVII), wherein W is —O— and X is cycloalkylalkynyl. Another embodiment provides a compound of Formula (XVII), wherein the $R^6$ is $CD_3$.

One embodiment provides a compound of Formula (XVIII), or a pharmaceutically acceptable salt thereof,

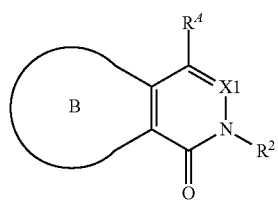

Formula (XVIII)

wherein, $R^2$ is $CH_3$, $CH_2CH_3$, $CH_2CF_3$, $CH_2F$, $CHF_2$, $CF_3$, $CH_2D$, $CHD_2$, or $CD_3$;

X1 is C—H or N;

ring B is an optionally substituted 5- or 6-membered heterocyclic ring containing at least one oxygen or nitrogen atom;

$R^A$ is

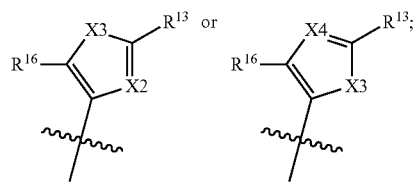

X2 is N or C—$R^{12}$, wherein $R^{12}$ is hydrogen, halogen, alkyl, or alkoxy;

$R^{13}$ is —Y—Z;

Y is selected from a bond, —$CH_2$—, or —$CH(C_1$-$C_4$ alkyl)-;

Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$;

X3 is S;

X4 is N or C—$R^{14}$, wherein $R^{14}$ is hydrogen, halogen, alkyl, or alkoxy;

$R^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

One embodiment provides a compound of Formula (XIX), or a pharmaceutically acceptable salt thereof,

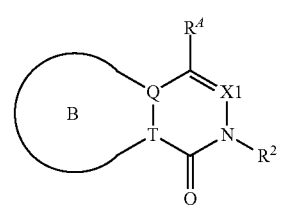

Formula (XIX)

wherein,

Q is N and T is C, or Q is C and T is N;

Ring B is an optionally substituted 5-membered aromatic nitrogen-containing heteroaryl ring containing one or more nitrogen atoms;

$R^2$ is selected from $CH_3$, $CH_2CH_3$, $CH_2CF_3$, $CH_2F$, $CHF_2$, $CF_3$, $CH_2D$, $CHD_2$, or $CD_3$;

X1 is C—H or N;

$R^A$ is

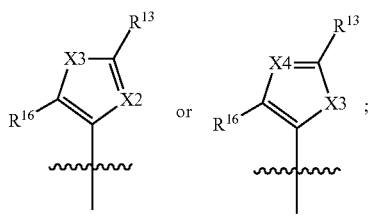

X2 is N or C—$R^{12}$, wherein $R^{12}$ is hydrogen, halogen, alkyl, or alkoxy;
$R^{13}$ is —Y—Z;
Y is selected from a bond, —$CH_2$—, or —$CH(C_1$-$C_4$ alkyl)-;
Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$;
X3 is S;
X4 is N or C—$R^{14}$, wherein $R^{14}$ is hydrogen, halogen, alkyl, or alkoxy;
$R^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl;
each $R^{21}$ is independently selected from alkyl, cycloalkyl, cycloalkylalkyl, aryl, aralkyl, heterocyclyl, heterocyclylalkyl, heteroaryl, or heteroarylalkyl; and
each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (XIX), wherein X2 is N. Another embodiment provides a compound of Formula (XIX), wherein X4 is N. Another embodiment provides a compound of Formula (XIX), wherein X2 is C—$R^{12}$. Another embodiment provides a compound of Formula (XIX), wherein X4 is C—$R^{14}$.

Another embodiment provides a compound of Formula (XIX), wherein the compound of Formula (XIX) is selected from the group:

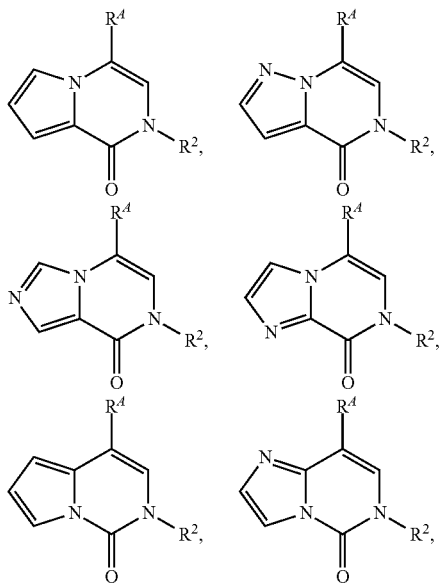

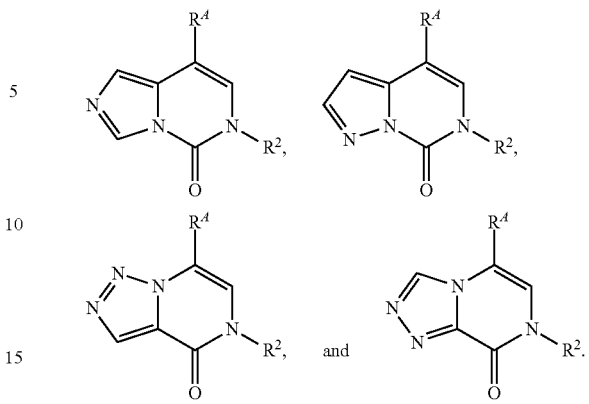

Another embodiment provides a compound of Formula (XIX), wherein Q is N and T is C. Another embodiment provides a compound of Formula (XIX), wherein Q is C and T is N. Another embodiment provides a compound of Formula (XIX), wherein $R^2$ is $CH_3$. Another embodiment provides a compound of Formula (XIX), wherein X1 is C—H. Another embodiment provides a compound of Formula (XIX), wherein X1 is N.

Another embodiment provides a compound of Formula (XIX), wherein Y is a bond. Another embodiment provides a compound of Formula (XIX), wherein Y is a —$CH_2$—. Another embodiment provides a compound of Formula (XIX), wherein Z is —$SO_2R^{21}$. Another embodiment provides a compound of Formula (XIX), wherein Z is —$N(R^{22})SO_2R^{21}$. Another embodiment provides a compound of Formula (XIX), wherein Z is —$SO_2N(R^{22})_2$. Another embodiment provides a compound of Formula (XIX), wherein Z is —$N(R^{22})SO_2N(R^{22})_2$. Another embodiment provides a compound of Formula (XIX), wherein Z is —$CON(R^{22})_2$. Another embodiment provides a compound of Formula (XIX), wherein Z is —$N(R^{22})CO_2R^{21}$. Another embodiment provides a compound of Formula (XIX), wherein Z is —$N(R^{22})CON(R^{22})_2$. Another embodiment provides a compound of Formula (XIX), wherein $R^{21}$ is alkyl, cycloalkyl, or cycloalkylalkyl. Another embodiment provides a compound of Formula (XIX), wherein $R^{21}$ is alkyl Another embodiment provides a compound of Formula (XIX), wherein W is —O—. Another embodiment provides a compound of Formula (XIX), wherein W is —NH—. Another embodiment provides a compound of Formula (XIX), wherein X is alkyl. Another embodiment provides a compound of Formula (XIX), wherein X is aryl. Another embodiment provides a compound of Formula (XIX), wherein X is cycloalkylalkyl. Another embodiment provides a compound of Formula (XIX), wherein W is —O— and X is alkyl. Another embodiment provides a compound of Formula (XIX), wherein W is —O— and X is aryl. Another embodiment provides a compound of Formula (XIX), wherein W is —O— and X is cycloalkylalkyl.

One embodiment provides a compound of Formula (XX), or a pharmaceutically acceptable salt thereof,

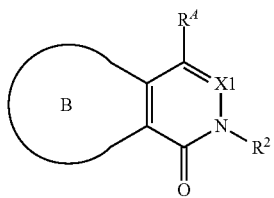

Formula (XX)

wherein,

Ring B is an optionally substituted 5-membered heteroaryl ring containing at least one oxygen or sulfur atom;

$R^2$ is selected from $CH_3$, $CH_2CH_3$, $CH_2CF_3$, $CH_2F$, $CHF_2$, $CF_3$, $CH_2D$, $CHD_2$, or $CD_3$;

X1 is C—H or N;

$R^A$ is

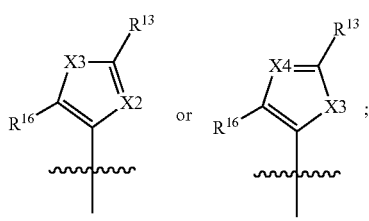

X2 is N or C—$R^{12}$, wherein $R^{12}$ is hydrogen, halogen, alkyl, or alkoxy;

$R^{13}$ is —Y—Z;

Y is selected from a bond, —$CH_2$—, or —$CH(C_1$-$C_4$ alkyl)-;

Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$OC(O)N(R^{22})_2$, —$OSO_2N(R^{22})_2$, or —$N(R^{22})SO_3R^{21}$;

X3 is S;

X4 is N or C—$R^{14}$, wherein $R^{14}$ is hydrogen, halogen, alkyl, or alkoxy;

$R^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (XX), wherein X2 is N. Another embodiment provides a compound of Formula (XX), wherein X4 is N. Another embodiment provides a compound of Formula (XX), wherein X2 is C—$R^{12}$. Another embodiment provides a compound of Formula (XX), wherein X4 is C—$R^{14}$.

Another embodiment provides a compound of Formula (XX), wherein the compound of Formula (XX) has a formula selected from:


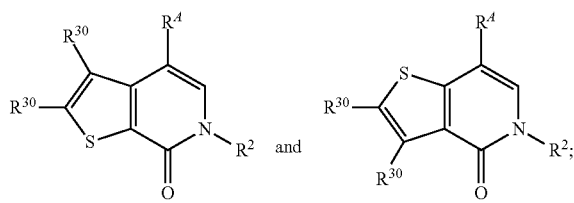

wherein each $R^{30}$ is independently selected from hydrogen, halogen, —CN, $C_1$-$C_4$ alkyl, —OH, —$OR^{31}$, —$NHR^{31}$, —$N(R^{31})_2$, —$CONHR^{31}$, —$CON(R^{31})_2$; and $R^{31}$ is $C_1$-$C_4$ alkyl.

Another embodiment provides a compound of Formula (XX), wherein the compound of Formula (XX) has a formula selected from:

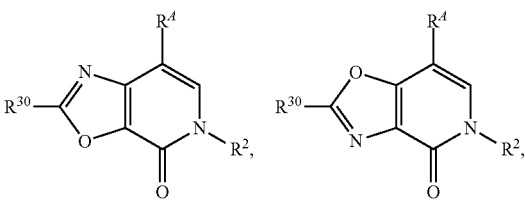

wherein each $R^{30}$ is independently selected from hydrogen, halogen, —CN, $C_1$-$C_4$ alkyl, —OH, —$OR^{31}$, —$NHR^{31}$, —$N(R^{31})_2$, —$CONHR^{31}$, —$CON(R^{31})_2$; and $R^{31}$ is $C_1$-$C_4$ alkyl.

Another embodiment provides a compound of Formula (XX), wherein the compound of Formula (XX) has a formula selected from:

-continued

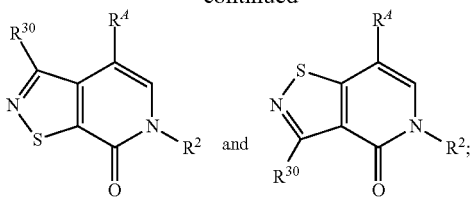 and 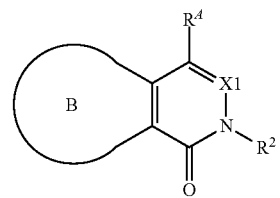

wherein each $R^{30}$ is independently selected from hydrogen, halogen, —CN, $C_1$-$C_4$ alkyl, —OH, —$OR^{31}$, —$NHR^{31}$, —$N(R^{31})_2$, —$CONHR^{31}$, —$CON(R^{31})_2$; and $R^{31}$ is $C_1$-$C_4$ alkyl.

Another embodiment provides a compound of Formula (XX), wherein R2 is CH3. Another embodiment provides a compound of Formula (XX), wherein X1 is C—H. Another embodiment provides a compound of Formula (XX), wherein X1 is N.

Another embodiment provides a compound of Formula (XX), wherein Y is a bond. Another embodiment provides a compound of Formula (XX), wherein Y is a —$CH_2$—. Another embodiment provides a compound of Formula (XX), wherein Z is —$SO_2R^{21}$. Another embodiment provides a compound of Formula (XX), wherein Z is —$N(R^{22})SO_2R^{21}$. Another embodiment provides a compound of Formula (XX), wherein Z is —$SO_2N(R^{22})_2$. Another embodiment provides a compound of Formula (XX), wherein Z is —$N(R^{22})SO_2N(R^{22})_2$. Another embodiment provides a compound of Formula (XX), wherein Z is —$CON(R^{22})_2$. Another embodiment provides a compound of Formula (XX), wherein Z is —$N(R^{22})CO_2R^{21}$. Another embodiment provides a compound of Formula (XX), wherein Z is —$N(R^{22})CON(R^{22})_2$. Another embodiment provides a compound of Formula (XX), wherein $R^{21}$ is alkyl, cycloalkyl, or cycloalkylalkyl. Another embodiment provides a compound of Formula (XV), wherein $R^{21}$ is alkyl.

Another embodiment provides a compound of Formula (XX), wherein W is —O—. Another embodiment provides a compound of Formula (XX), wherein W is —NH—. Another embodiment provides a compound of Formula (XX), wherein X is alkyl. Another embodiment provides a compound of Formula (XX), wherein X is alkynyl. Another embodiment provides a compound of Formula (XX), wherein X is aryl. Another embodiment provides a compound of Formula (XX), wherein X is cycloalkylalkyl. Another embodiment provides a compound of Formula (XX), wherein X is cycloalkylalkynyl. Another embodiment provides a compound of Formula (XX), wherein W is —O— and X is alkyl. Another embodiment provides a compound of Formula (XX), wherein W is —O— and X is aryl. Another embodiment provides a compound of Formula (XX), wherein W is —O— and X is alkynyl. Another embodiment provides a compound of Formula (XX), wherein W is —O— and X is cycloalkylalkyl. Another embodiment provides a compound of Formula (XX), wherein W is —O— and X is cycloalkylalkynyl.

One embodiment provides a compound of Formula (XXI), or a pharmaceutically acceptable salt thereof,

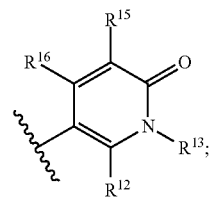

Formula (XXI)

wherein,
$R^2$ is $CH_3$, $CH_2CH_3$, $CH_2CF_3$, $CH_2F$, $CHF_2$, $CF_3$, $CH_2D$, $CHD_2$, or $CD_3$;
X1 is C—H or N;
ring B is an optionally substituted 5- or 6-membered heterocyclic ring containing at least one oxygen or nitrogen atom;
$R^A$ is $R^{12}$ is hydrogen or $C_1$-$C_4$ alkyl;
$R^{13}$ is —Y—Z;
Y is selected from —$CH_2$—, or —$CH(C_1$-$C_4$ alkyl)-;
Z is selected from —$SO_2R^{21}$, —$SO_2N(R^{22})_2$, or —$CON(R^{22})_2$;
$R^{15}$ is hydrogen, halogen or $C_1$-$C_4$ alkyl;
$R^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl; or optionally, $R^{16}$ and $R^{15}$ connect to form a ring;
each $R^{21}$ is independently selected from alkyl, cycloalkyl, cycloalkylalkyl, aryl, aralkyl, heterocyclyl, heterocyclylalkyl, heteroaryl, or heteroarylalkyl; and
each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

One embodiment provides a compound of Formula (XXII), or a pharmaceutically acceptable salt thereof,

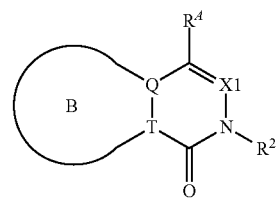

Formula (XXII)

wherein,
Q is N and T is C, or Q is C and T is N;
Ring B is an optionally substituted 5-membered aromatic nitrogen-containing heteroaryl ring containing one or more nitrogen atoms;

$R^2$ is selected from $CH_3$, $CH_2CH_3$, $CH_2CF_3$, $CH_2F$, $CHF_2$, $CF_3$, $CH_2D$, $CHD_2$, or $CD_3$;

X1 is C—H or N;

$R^A$ is

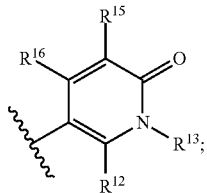

$R^{12}$ is hydrogen or $C_1$-$C_4$ alkyl;

$R^{13}$ is —Y—Z;

Y is selected from —$CH_2$—, or —CH($C_1$-$C_4$ alkyl)-;

Z is selected from —$SO_2R^{21}$, —$SO_2N(R^{22})_2$, or —CON$(R^{22})_2$;

$R^{15}$ is hydrogen, halogen or $C_1$-$C_4$ alkyl;

$R^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl; or optionally, $R^{16}$ and $R^{15}$ connect to form a ring;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (XXII), wherein the compound of Formula (XXII) is selected from the group:

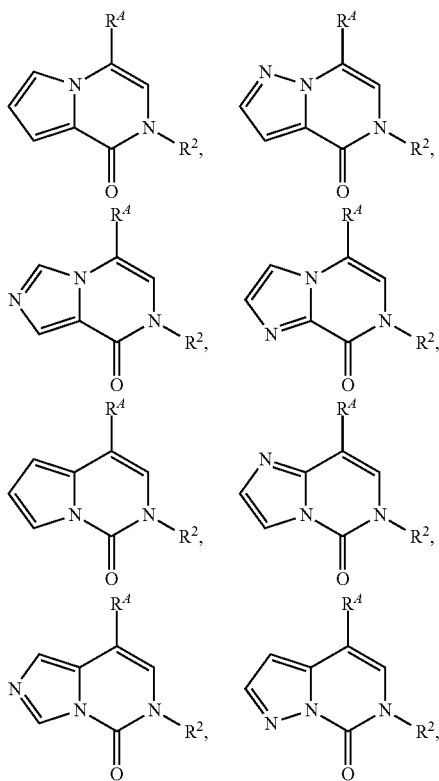

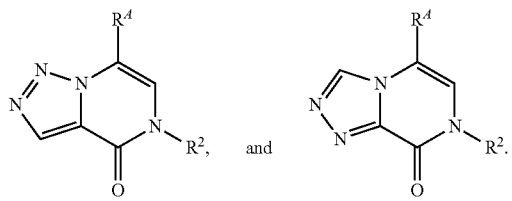

Another embodiment provides a compound of Formula (XXII), wherein Q is N and T is C. Another embodiment provides a compound of Formula (XXII), wherein Q is C and T is N. Another embodiment provides a compound of Formula (XXII), wherein $R^2$ is $CH_3$. Another embodiment provides a compound of Formula (XXII), wherein X1 is C—H. Another embodiment provides a compound of Formula (XXII), wherein X1 is N.

Another embodiment provides a compound of Formula (XXII), wherein Y is a —$CH_2$—. Another embodiment provides a compound of Formula (XXII), wherein Z is —$SO_2R^{21}$. Another embodiment provides a compound of Formula (XXII), wherein Z is —$SO_2N(R^{22})_2$. Another embodiment provides a compound of Formula (XXII), wherein Z is —CON$(R^{22})_2$. Another embodiment provides a compound of Formula (XXII), wherein $R^{21}$ is alkyl, cycloalkyl, or cycloalkylalkyl. Another embodiment provides a compound of Formula (XXII), wherein $R^{21}$ is alkyl.

Another embodiment provides a compound of Formula (XXII), wherein W is —O—. Another embodiment provides a compound of Formula (XXII), wherein W is —NH—. Another embodiment provides a compound of Formula (XXII), wherein X is alkyl. Another embodiment provides a compound of Formula (XXII), wherein X is aryl. Another embodiment provides a compound of Formula (XXII), wherein X is cycloalkylalkyl. Another embodiment provides a compound of Formula (XXII), wherein W is —O— and X is alkyl. Another embodiment provides a compound of Formula (XXII), wherein W is —O— and X is aryl. Another embodiment provides a compound of Formula (XXII), wherein W is —O— and X is cycloalkylalkyl.

One embodiment provides a compound of Formula (XXIII), or a pharmaceutically acceptable salt thereof, Formula (XXIII)

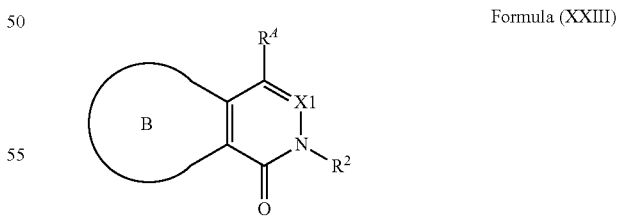

wherein,

Ring B is an optionally substituted 5-membered heteroaryl ring containing at least one oxygen or sulfur atom;

$R^2$ is selected from $CH_3$, $CH_2CH_3$, $CH_2CF_3$, $CH_2F$, $CHF_2$, $CF_3$, $CH_2D$, $CHD_2$, or $CD_3$;

X1 is C—H or N;

$R^A$ is

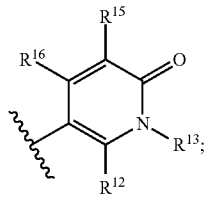

$R^{12}$ is hydrogen or $C_1$-$C_4$ alkyl;
$R^{13}$ is —Y—Z;
Y is selected from —$CH_2$—, or —CH($C_1$-$C_4$ alkyl)-;
Z is selected from —$SO_2R^{21}$, —$SO_2N(R^{22})_2$, or —CON($R^{22})_2$;
$R^{15}$ is hydrogen, halogen or $C_1$-$C_4$ alkyl;
$R^{16}$ is hydrogen, halogen, or —W—X, wherein W is a bond, —O—, —S—, or —NH—, and X is selected from alkyl, alkynyl, aryl, aralkyl, cycloalkyl, cycloalkylalkyl, cycloalkylalkynyl, heterocyclyl, heterocyclylalkyl, heteroaryl, or heteroarylalkyl; or optionally, $R^{16}$ and $R^{15}$ connect to form a ring;
each $R^{21}$ is independently selected from alkyl, cycloalkyl, cycloalkylalkyl, aryl, aralkyl, heterocyclyl, heterocyclylalkyl, heteroaryl, or heteroarylalkyl; and
each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (XXIII), wherein the compound of Formula (XXIII) has a formula selected from:

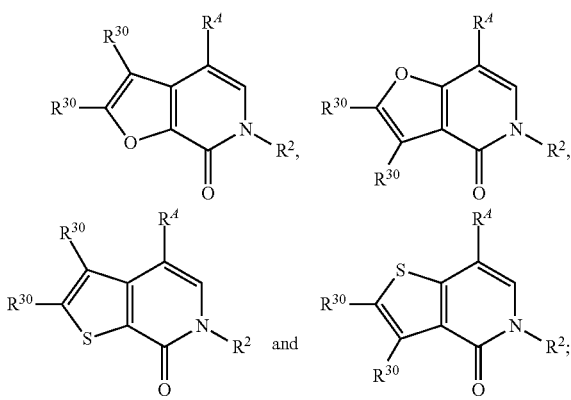

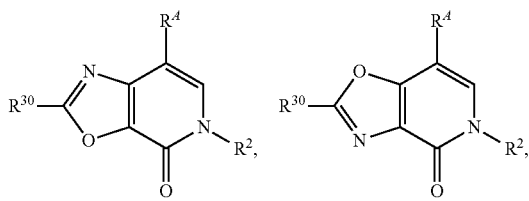

wherein each $R^{30}$ is independently selected from hydrogen, halogen, —CN, $C_1$-$C_4$ alkyl, —OH, —$OR^{31}$, —$NHR^{31}$, —$N(R^{31})_2$, —$CONHR^{31}$, —$CON(R^{31})_2$; and $R^{31}$ is $C_1$-$C_4$ alkyl.

Another embodiment provides a compound of Formula (XXIII), wherein the compound of Formula (XXIII) has a formula selected from:

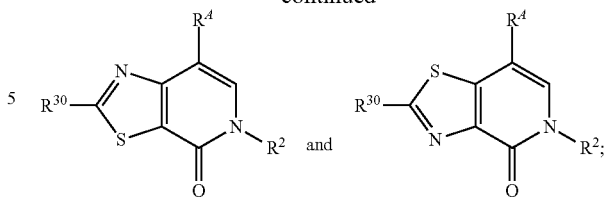

wherein each $R^{30}$ is independently selected from hydrogen, halogen, —CN, $C_1$-$C_4$ alkyl, —OH, —$OR^{31}$, —$NHR^{31}$, —$N(R^{31})_2$, —$CONHR^{31}$, —$CON(R^{31})_2$; and $R^{31}$ is $C_1$-$C_4$ alkyl.

Another embodiment provides a compound of Formula (XXIII), wherein the compound of Formula (XXIII) has a formula selected from:

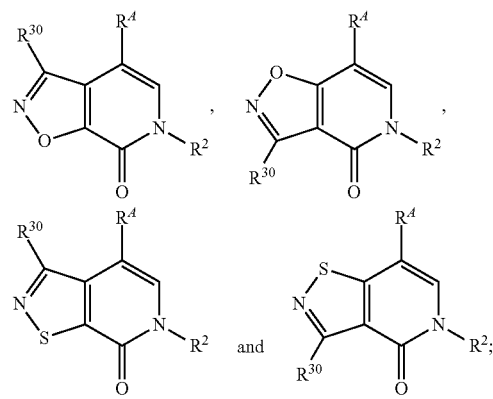

wherein each $R^{30}$ is independently selected from hydrogen, halogen, —CN, $C_1$-$C_4$ alkyl, —OH, —$OR^{31}$, —$NHR^{31}$, —$N(R^{31})_2$, —$CONHR^{31}$, —$CON(R^{31})_2$; and $R^{31}$ is $C_1$-$C_4$ alkyl.

Another embodiment provides a compound of Formula (XXIII), wherein $R^2$ is $CH_3$. Another embodiment provides a compound of Formula (XXIII), wherein X1 is C—H. Another embodiment provides a compound of Formula (XXIII), wherein X1 is N.

Another embodiment provides a compound of Formula (XXIII), wherein Y is a —$CH_2$—. Another embodiment provides a compound of Formula (XXIII), wherein Z is —$SO_2R^{21}$. Another embodiment provides a compound of Formula (XXIII), wherein Z is —$SO_2N(R^{22})_2$. Another embodiment provides a compound of Formula (XXIII), wherein Z is —$CON(R^{22})_2$. Another embodiment provides a compound of Formula (XXIII), wherein $R^{21}$ is alkyl, cycloalkyl, or cycloalkylalkyl. Another embodiment provides a compound of Formula (XXIII), wherein $R^{21}$ is alkyl.

Another embodiment provides a compound of Formula (XXIII), wherein W is —O—. Another embodiment provides a compound of Formula (XXIII), wherein W is —NH—. Another embodiment provides a compound of Formula (XXIII), wherein X is alkyl. Another embodiment provides a compound of Formula (XXIII), wherein X is alkynyl. Another embodiment provides a compound of Formula (XXIII), wherein X is aryl. Another embodiment provides a compound of Formula (XXIII), wherein X is cycloalkylalkyl. Another embodiment provides a compound of Formula (XXIII), wherein X is cycloalkylalkynyl. Another embodiment provides a compound of Formula (XXIII), wherein W is —O— and X is alkyl. Another embodiment provides a compound of Formula (XXIII), wherein W is —O— and X is aryl. Another embodiment provides a compound of Formula (XXIII), wherein W is —O— and X is alkynyl. Another embodiment provides a compound of Formula (XXIII), wherein W is —O— and X is cycloalkylalkyl. Another embodiment provides a compound of Formula (XXIII), wherein W is —O— and X is cycloalkylalkynyl.

One embodiment provides a compound of Formula (XXIV), or a pharmaceutically acceptable salt thereof,

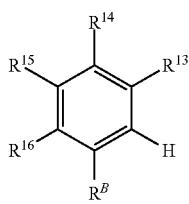

Formula (XXIV)

wherein,
R$^{13}$ is —Y—Z;
Y is selected from a bond, or —CH$_2$—;
Z is selected from —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —COR$^{21}$, —OC(O)N(R$^{22}$)$_2$, —OSO$_2$N(R$^{22}$)$_2$, —N(R$^{22}$)SO$_3$R$^{21}$, or —N(R$^{22}$)$_2$;
R$^{14}$ is hydrogen, halogen, C$_1$-C$_3$ alkyl, or C$_1$-C$_3$ alkoxy;
R$^{15}$ is halogen or U—V, wherein U is a bond, —O—, or —CH$_2$—; and V is —CN, alkyl, alkynyl, aryl, aralkyl, cycloalkyl, cycloalkylalkyl, heterocyclyl, heterocyclylalkyl, heteroaryl, or heteroarylalkyl;
R$^{16}$ is hydrogen;
each R$^{21}$ is independently selected from alkyl, cycloalkyl, cycloalkylalkyl, aryl, aralkyl, heterocyclyl, heterocyclylalkyl, heteroaryl, or heteroarylalkyl;
each R$^{22}$ is independently selected from hydrogen, alkyl, cycloalkyl, cycloalkylalkyl, aryl, aralkyl, heterocyclyl, heterocyclylalkyl, heteroaryl, or heteroarylalkyl;
R$^B$ is

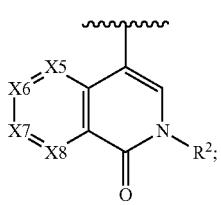

wherein
R$^2$ is CH$_3$;
X5 is C—H;
X6 is C—R$^6$;
X7 is C—R$^7$;
X8 is C—H;
R$^6$ is hydrogen, or halogen;
R$^7$ is hydrogen, or halogen; or
R$^B$ is

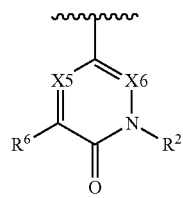

wherein
R$^2$ is CH$_3$;
X6 is C—H;
X5 is C—R$^5$;
R$^5$ is hydrogen, or halogen;
R$^6$ is hydrogen, alkyl, alkoxy, or halogen; or
R$^B$ is

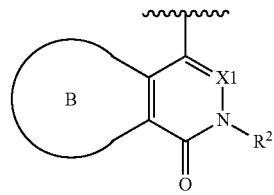

wherein
Ring B is an optionally substituted 5-membered heteroaryl ring containing at least one oxygen or sulfur atom;
R$^2$ is CH$_3$; and
X1 is C—H.

Another embodiment provides a compound of Formula (XXIV), or a pharmaceutically acceptable salt thereof, wherein Y is —CH$_2$—. Another embodiment provides a compound of Formula (XXIV), or a pharmaceutically acceptable salt thereof, wherein Y is a bond.

Another embodiment provides a compound of Formula (XXIV), or a pharmaceutically acceptable salt thereof, wherein Z is —SO$_2$R$^{21}$, —N(R$^{22}$)SO$_2$R$^{21}$, or —N(R$^{22}$)$_2$.

Another embodiment provides a compound of Formula (XXIV), or a pharmaceutically acceptable salt thereof, wherein Z is —SO$_2$R$^{21}$ or —N(R$^{22}$)SO$_2$R$^{21}$. Another embodiment provides a compound of Formula (XXIV), or a pharmaceutically acceptable salt thereof, wherein Z is —N(R$^{22}$)SO$_2$R$^{21}$. Another embodiment provides a compound of Formula (XXIV), or a pharmaceutically acceptable salt thereof, wherein Z is —SO$_2$R$^{21}$.

Another embodiment provides a compound of Formula (XXIV), or a pharmaceutically acceptable salt thereof, wherein R$^{21}$ is heterocyclyl or heterocyclylalkyl. Another embodiment provides a compound of Formula (XXIV), or a pharmaceutically acceptable salt thereof, wherein R$^{21}$ is alkyl, cycloalkyl, or cycloalkylalkyl. Another embodiment provides a compound of Formula (XXIV), or a pharmaceutically acceptable salt thereof, wherein R$^{21}$ is alkyl, and the alkyl is a C$_1$-C$_4$ alkyl.

Another embodiment provides a compound of Formula (XXIV), or a pharmaceutically acceptable salt thereof, wherein R$^{22}$ is alkyl, cycloalkyl, or aralkyl. Another embodiment provides a compound of Formula (XXIV), or a pharmaceutically acceptable salt thereof, wherein R$^{22}$ is hydrogen or methyl.

Another embodiment provides a compound of Formula (XXIV), or a pharmaceutically acceptable salt thereof, wherein R$^{14}$ is hydrogen.

Another embodiment provides a compound of Formula (XXIV), or a pharmaceutically acceptable salt thereof, wherein U is a bond. Another embodiment provides a compound of Formula (XXIV), or a pharmaceutically acceptable salt thereof, wherein U is —O—.

Another embodiment provides a compound of Formula (XXIV), or a pharmaceutically acceptable salt thereof, wherein U is —CH₂—.

Another embodiment provides a compound of Formula (XXIV), or a pharmaceutically acceptable salt thereof, wherein V is alkyl. Another embodiment provides a compound of Formula (XXIV), or a pharmaceutically acceptable salt thereof, wherein V is aryl. Another embodiment provides a compound of Formula (XXIV), or a pharmaceutically acceptable salt thereof, wherein V is aralkyl. Another embodiment provides a compound of Formula (XXIV), or a pharmaceutically acceptable salt thereof, wherein V is cycloalkylalkyl. Another embodiment provides a compound of Formula (XXIV), or a pharmaceutically acceptable salt thereof, wherein V is heterocyclylalkyl. Another embodiment provides a compound of Formula (XXIV), or a pharmaceutically acceptable salt thereof, wherein V is heteroaryl. Another embodiment provides a compound of Formula (XXIV), or a pharmaceutically acceptable salt thereof, wherein V is heteroarylalkyl. Another embodiment provides a compound of Formula (XXIV), or a pharmaceutically acceptable salt thereof, wherein V is alkynyl.

Another embodiment provides a compound of Formula (XXIV), or a pharmaceutically acceptable salt thereof, wherein Y is a bond, Z is —N(R²²)SO₂R²¹, U is —O—, and V is aryl, aralkyl or cycloalkylalkyl. Another embodiment provides a compound of Formula (XXIV), or a pharmaceutically acceptable salt thereof, wherein Y is a bond, Z is —SO₂R²¹, U is —O—, and V is aryl, aralkyl or cycloalkylalkyl.

Another embodiment provides a compound of Formula (XXIV), or a pharmaceutically acceptable salt thereof, wherein RB is

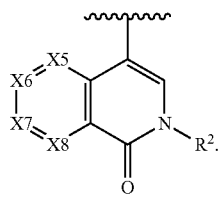

Another embodiment provides a compound of Formula (XXIV), or a pharmaceutically acceptable salt thereof, wherein R⁶ is halogen, and R⁷ is hydrogen. Another embodiment provides a compound of Formula (XXIV), or a pharmaceutically acceptable salt thereof, wherein R⁶ is hydrogen, and R⁷ is halogen. Another embodiment provides a compound of Formula (XXIV), or a pharmaceutically acceptable salt thereof, wherein R⁶ is hydrogen, and R⁷ is hydrogen.

Another embodiment provides a compound of Formula (XXIV), or a pharmaceutically acceptable salt thereof, wherein RB is

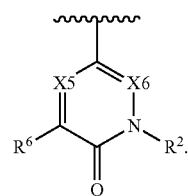

Another embodiment provides a compound of Formula (XXIV), or a pharmaceutically acceptable salt thereof, wherein R⁵ is hydrogen, and R⁶ is alkyl. Another embodiment provides a compound of Formula (XXIV), or a pharmaceutically acceptable salt thereof, wherein R⁶ is methyl.

Another embodiment provides a compound of Formula (XXIV), or a pharmaceutically acceptable salt thereof, wherein RB is

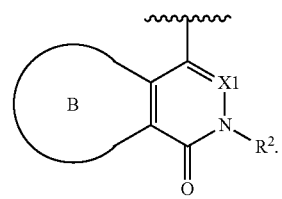

Another embodiment provides a compound of Formula (XXIV), or a pharmaceutically acceptable salt thereof, wherein Ring B is an optionally substituted 5-membered heteroaryl ring containing one oxygen.

One embodiment provides a compound of Formula (XXV), or a pharmaceutically acceptable salt thereof,

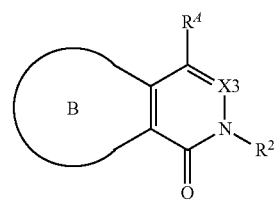

Formula (XXV)

wherein,
Ring B is an optionally substituted 5-, 6-, or 7-membered, non-aromatic carbocyclyl ring;
R² is selected from CH₃, CH₂CH₃, CH₂CF₃, CH₂F, CHF₂, CF₃, CH₂D, CHD₂, or CD₃;
X3 is C—H or N;
R⁴ is

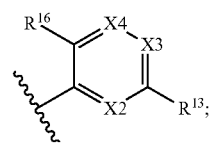

X2 is N or C—R¹², wherein R¹² is hydrogen, halogen, alkyl, or alkoxy;
R¹³ is —Y—Z;
Y is selected from a bond, or —CH₂—;
Z is selected from —SO₂R²¹, —N(R²²)SO₂R²¹, —SO₂N(R²²)₂, —N(R²²)SO₂N(R²²)₂, —CON(R²²)₂, —N(R$^{22}$)CO$_2$R$^{21}$, —N(R$^{22}$)CON(R$^{22}$)$_2$, —N(R$^{22}$)COR$^{21}$, —OC(O)N(R$^{22}$)$_2$, —OSO$_2$N(R$^{22}$)$_2$, or —N(R$^{22}$)SO$_3$R$^{21}$;

X3 is N or C—R$^{14}$, wherein R$^{14}$ is hydrogen, halogen, —CN, alkyl, cycloalkyl, or alkoxy;

X4 is N or C—R$^{15}$, wherein R$^{15}$ is hydrogen, halogen, —CN, alkyl, or alkoxy;

R$^{16}$ is hydrogen, halogen, or —W—X, wherein W is a bond, —O—, —S—, or —NH—, and X is selected from alkyl, aryl, aralkyl, cycloalkyl, cycloalkylalkyl, heterocyclyl, heterocyclylalkyl, heteroaryl, or heteroarylalkyl;

each R$^{21}$ is independently selected from alkyl, cycloalkyl, cycloalkylalkyl, aryl, aralkyl, heterocyclyl, heterocyclylalkyl, heteroaryl, or heteroarylalkyl; and each R$^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

Another embodiment provides a compound of Formula (XXV), or a pharmaceutically acceptable salt thereof, wherein Ring B is an optionally substituted 5-membered, non-aromatic carbocyclyl ring. Another embodiment provides a compound of Formula (XXV), or a pharmaceutically acceptable salt thereof, wherein Ring B is an optionally substituted 6-membered, non-aromatic carbocyclyl ring. Another embodiment provides a compound of Formula (XXV), or a pharmaceutically acceptable salt thereof, wherein Ring B is an optionally substituted 7-membered, non-aromatic carbocyclyl ring.

Another embodiment provides a compound of Formula (XXV), or a pharmaceutically acceptable salt thereof, wherein R$^2$ is CH$_3$.

Another embodiment provides a compound of Formula (XXV), or a pharmaceutically acceptable salt thereof, wherein X3 is C—H. Another embodiment provides a compound of Formula (XXV), or a pharmaceutically acceptable salt thereof, wherein X3 is N.

Another embodiment provides a compound of Formula (XXV), or a pharmaceutically acceptable salt thereof, wherein Y is a bond. Another embodiment provides a compound of Formula (XXV), or a pharmaceutically acceptable salt thereof, wherein Y is a —CH$_2$—.

Another embodiment provides a compound of Formula (XXV), or a pharmaceutically acceptable salt thereof, wherein Z is —SO$_2$R$^{21}$. Another embodiment provides a compound of Formula (XXV), or a pharmaceutically acceptable salt thereof, wherein Z is —N(R$^{22}$)SO$_2$R$^{21}$.

Another embodiment provides a compound of Formula (XXV), or a pharmaceutically acceptable salt thereof, wherein Z is —SO$_2$N(R$^{22}$)$_2$. Another embodiment provides a compound of Formula (XXV), or a pharmaceutically acceptable salt thereof, wherein Z is —N(R$^{22}$)SO$_2$N(R$^{22}$)$_2$. Another embodiment provides a compound of Formula (XXV), or a pharmaceutically acceptable salt thereof, wherein Z is —CON(R$^{22}$)$_2$. Another embodiment provides a compound of Formula (XXV), or a pharmaceutically acceptable salt thereof, wherein Z is —N(R$^{22}$)CO$_2$R$^{21}$. Another embodiment provides a compound of Formula (XXV), or a pharmaceutically acceptable salt thereof, wherein Z is —N(R$^{22}$)CON(R$^{22}$)$_2$.

Another embodiment provides a compound of Formula (XXV), or a pharmaceutically acceptable salt thereof, wherein R$^{21}$ is alkyl, cycloalkyl, or cycloalkylalkyl. Another embodiment provides a compound of Formula (XXV), or a pharmaceutically acceptable salt thereof, wherein R$^{21}$ is alkyl.

Another embodiment provides a compound of Formula (XXV), or a pharmaceutically acceptable salt thereof, wherein R$^{14}$ is hydrogen, halogen, or alkyl. Another embodiment provides a compound of Formula (XXV), or a pharmaceutically acceptable salt thereof, wherein X4 is C—R$^{15}$. Another embodiment provides a compound of Formula (XXV), or a pharmaceutically acceptable salt thereof, wherein W is —O—. Another embodiment provides a compound of Formula (XXV), or a pharmaceutically acceptable salt thereof, wherein W is —NH—.

Another embodiment provides a compound of Formula (XXV), or a pharmaceutically acceptable salt thereof, wherein X is alkyl. Another embodiment provides a compound of Formula (XXV), or a pharmaceutically acceptable salt thereof, wherein X is aryl. Another embodiment provides a compound of Formula (XXV), or a pharmaceutically acceptable salt thereof, wherein X is cycloalkylalkyl.

Another embodiment provides a compound of Formula (XXV), or a pharmaceutically acceptable salt thereof, wherein W is —O— and X is alkyl. Another embodiment provides a compound of Formula (XXV), or a pharmaceutically acceptable salt thereof, wherein W is —O— and X is aryl. Another embodiment provides a compound of Formula (XXV), or a pharmaceutically acceptable salt thereof, wherein W is —O— and X is cycloalkylalkyl.

In some embodiments, the substituted heterocyclic derivative compound disclosed herein has the structure provided in Table 1.

TABLE 1

| Chemical Synthesis Example | Structure | Name |
|---|---|---|
| 2 | 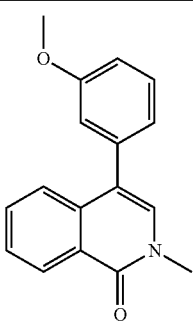 | 4-(3-methoxyphenyl)-2-methylisoquinolin-1-one |

TABLE 1-continued

| Chemical Synthesis Example | Structure | Name |
|---|---|---|
| 3 | 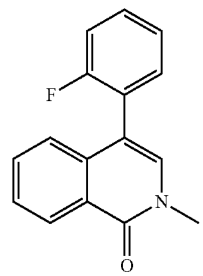 [SMILES: Cn1cc(-c2ccccc2F)c2ccccc2c1=O] | 4-(2-fluorophenyl)-2-methylisoquinolin-1-one |
| 4 | 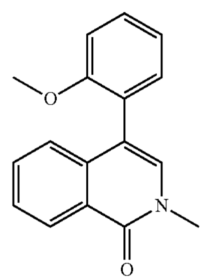 [SMILES: COc1ccccc1-c1cn(C)c(=O)c2ccccc12] | 4-(2-methoxyphenyl)-2-methylisoquinolin-1-one |
| 5 | 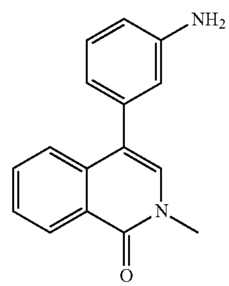 [SMILES: Cn1cc(-c2cccc(N)c2)c2ccccc2c1=O] | 4-(3-aminophenyl)-2-methylisoquinolin-1-one |
| 6 | 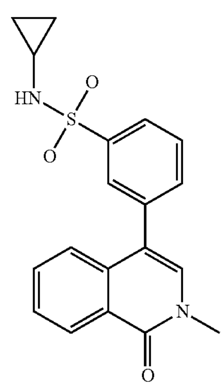 [SMILES: Cn1cc(-c2cccc(S(O)(O)NC3CC3)c2)c2ccccc2c1=O] | N-cyclopropyl-3-(2-methyl-1-oxoisoquinolin-4-yl)benzenesulfonamide |
| 7 | 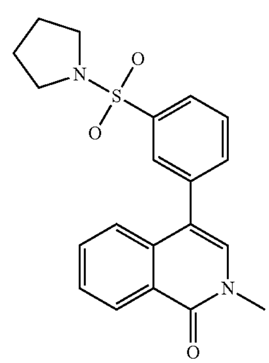 [SMILES: Cn1cc(-c2cccc(S(O)(O)N3CCCC3)c2)c2ccccc2c1=O] | 2-methyl-4-(3-pyrrolidin-1-ylsulfonylphenyl)isoquinolin-1-one |

TABLE 1-continued

| Chemical Synthesis Example | Structure | Name |
|---|---|---|
| 8 | 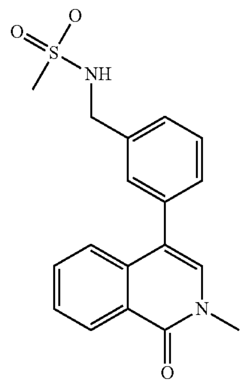 | N-[[3-(2-methyl-1-oxoisoquinolin-4-yl)phenyl]methyl]methanesulfonamide |
| 9 | 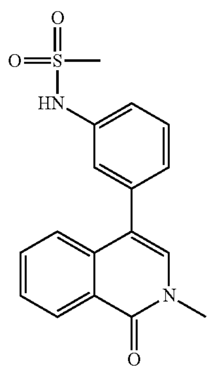 | N-[3-(2-methyl-1-oxoisoquinolin-4-yl)phenyl]methanesulfonamide |
| 10 | 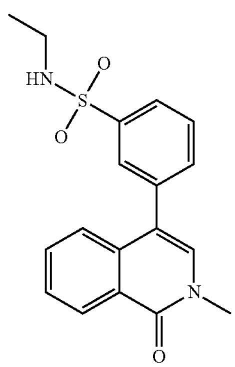 [SMILES: CCNS(O)(O)c1cccc(-c2cn(C)c(=O)c3ccccc23)c1] | N-ethyl-3-(2-methyl-1-oxo-isoquinolin-4-yl)benzenesulfonamide |
| 11 | 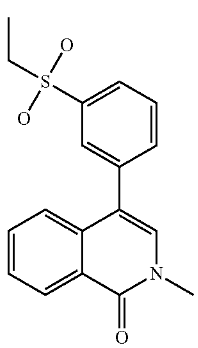 [SMILES: CCS(O)(O)c1cccc(-c2cn(C)c(=O)c3ccccc23)c1] | 4-(3-ethylsulfonylphenyl)-2-methylisoquinolin-1-one |

TABLE 1-continued

| Chemical Synthesis Example | Structure | Name |
|---|---|---|
| 12 | 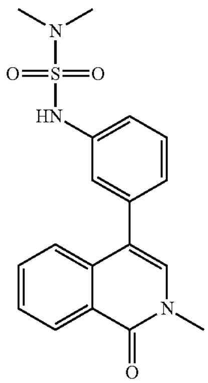 [SMILES: CN(C)S(=O)(=O)Nc1cccc(-c2cn(C)c(=O)c3ccccc23)c1] | 4-[3-(dimethylsulfamoylamino)phenyl]-2-methyl-1-oxoisoquinoline |
| 13 | 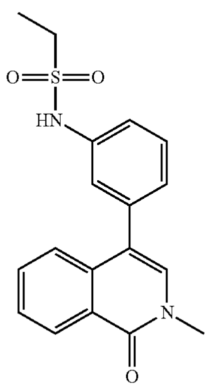 | N-[3-(2-methyl-1-oxoisoquinolin-4-yl)phenyl]ethanesulfonamide |
| 14 | 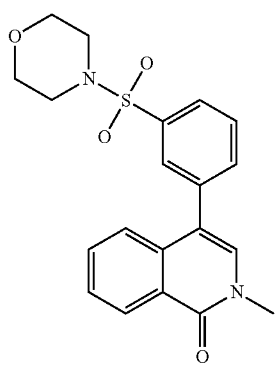 [SMILES: Cn1cc(-c2cccc(S(O)(O)N3CCOCC3)c2)c2ccccc2c1=O] | 2-methyl-4-(3-morpholin-4-yl-sulfonylphenyl)isoquinolin-1-one |
| 15 | 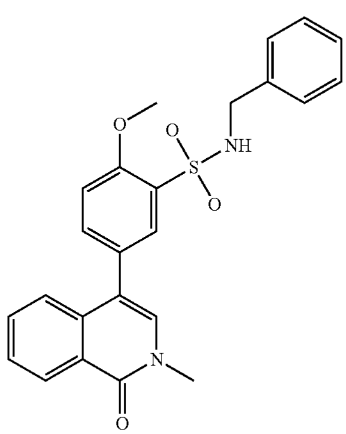 [SMILES: COc1ccc(-c2cn(C)c(=O)c3ccccc23)cc1S(O)(O)NCc1ccccc1] | N-benzyl-2-methoxy-5-(2-methyl-1-oxoisoquinolin-4-yl)benzenesulfonamide |

TABLE 1-continued

| Chemical Synthesis Example | Structure | Name |
|---|---|---|
| 16 | 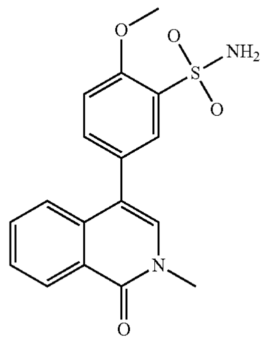 [SMILES: COc1ccc(-c2cn(C)c(=O)c3ccccc23)cc1S(N)(O)O] | 2-methoxy-5-(2-methyl-1-oxoisoquinolin-4-yl)benzenesulfonamide |
| 17 | 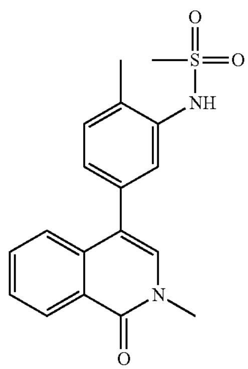 [SMILES: Cc1ccc(-c2cn(C)c(=O)c3ccccc23)cc1NS(C)(=O)=O] | N-[2-methyl-5-(2-methyl-1-oxoisoquinolin-4-yl)phenyl]methanesulfonamide |
| 18 | 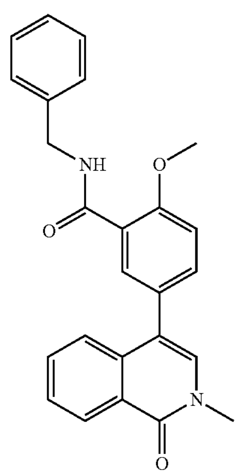 [SMILES: COc1ccc(-c2cn(C)c(=O)c3ccccc23)cc1C(=O)NCc1ccccc1] | N-benzyl-2-methoxy-5-(2-methyl-1-oxoisoquinolin-4-yl)benzamide |
| 19 | 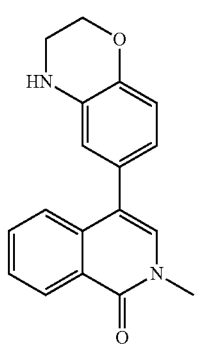 [SMILES: Cn1cc(-c2ccc3c(c2)NCCO3)c2ccccc2c1=O] | 4-(3,4-dihydro-2H-1,4-benzoxazin-6-yl)-2-methylisoquinolin-1-one |

TABLE 1-continued

| Chemical Synthesis Example | Structure | Name |
|---|---|---|
| 20 | 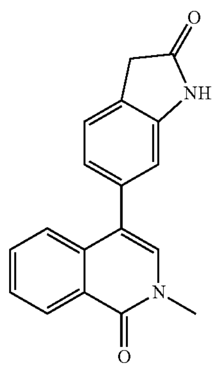 [SMILES: Cn1cc(-c2ccc3c(c2)NC(=O)C3)c2ccccc2c1=O] | 2-methyl-4-(2-oxo-1,3-dihydroindol-6-yl)isoquinolin-1-one |
| 21 | 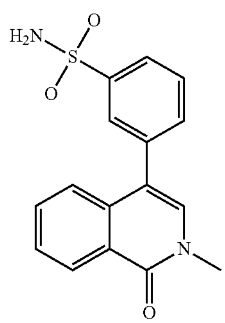 [SMILES: Cn1cc(-c2cccc(S(N)(O)O)c2)c2ccccc2c1=O] | 3-(2-methyl-1-oxoisoquinolin-4-yl)benzenesulfonamide |
| 22 | 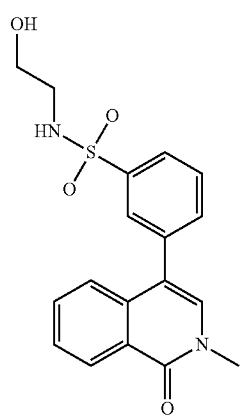 [SMILES: Cn1cc(-c2cccc(S(O)(O)NCCO)c2)c2ccccc2c1=O] | N-(2-hydroxyethyl)-3-(2-methyl-1-oxoisoquinolin-4-yl)benzenesulfonamide |
| 23 | 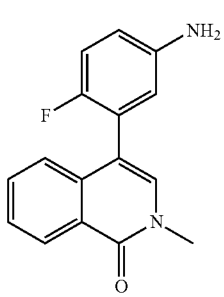 [SMILES: Cn1cc(-c2cc(N)ccc2F)c2ccccc2c1=O] | 4-(5-amino-2-fluorophenyl)-2-methylisoquinolin-1-one |

TABLE 1-continued

| Chemical Synthesis Example | Structure | Name |
|---|---|---|
| 24 | 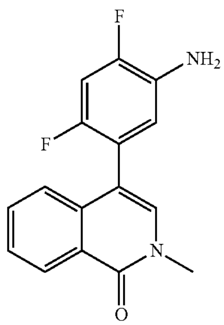 [SMILES: Cn1cc(-c2cc(N)c(F)cc2F)c2ccccc2c1=O] | 4-(5-amino-2,4-difluorophenyl)-2-methylisoquinolin-1-one |
| 25 | 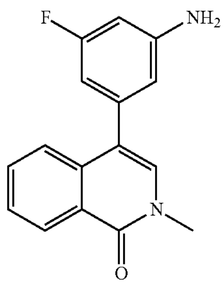 [SMILES: Cn1cc(-c2cc(N)cc(F)c2)c2ccccc2c1=O] | 4-(3-amino-5-fluorophenyl)-2-methylisoquinolin-1-one |
| 26 | 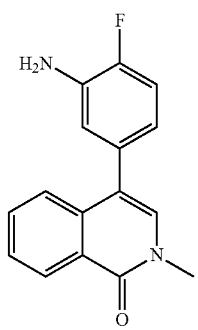 [SMILES: Cn1cc(-c2ccc(F)c(N)c2)c2ccccc2c1=O] | 4-(3-amino-4-fluorophenyl)-2-methylisoquinolin-1-one |
| 27 | 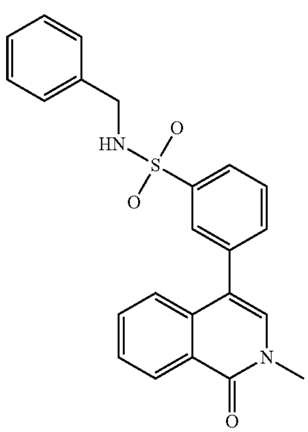 [SMILES: Cn1cc(-c2cccc(S(O)(O)NCc3ccccc3)c2)c2ccccc2c1=O] | N-benzyl-3-(2-methyl-1-oxoisoquinolin-4-yl)benzenesulfonamide |

TABLE 1-continued

| Chemical Synthesis Example | Structure | Name |
|---|---|---|
| 28 | 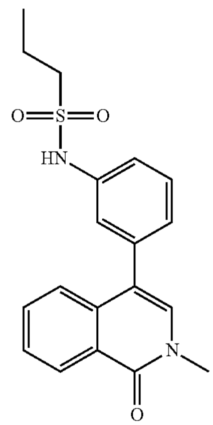 [SMILES: CCCS(=O)(=O)Nc1cccc(-c2cn(C)c(=O)c3ccccc23)c1] | N-[3-(2-methyl-1-oxoisoquinolin-4-yl)phenyl]propane-1-sulfonamide |
| 29 | 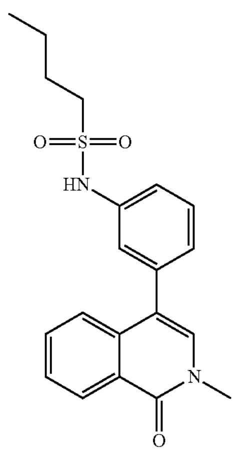 [SMILES: CCCCS(=O)(=O)Nc1cccc(-c2cn(C)c(=O)c3ccccc23)c1] | N-[3-(2-methyl-1-oxoisoquinolin-4-yl)phenyl]butane-1-sulfonamide |
| 30 | 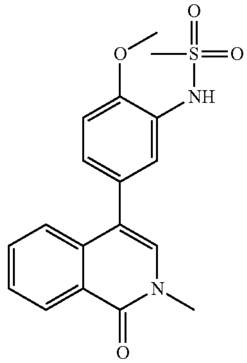 [SMILES: COc1ccc(-c2cn(C)c(=O)c3ccccc23)cc1NS(C)(=O)=O] | N-[2-methoxy-5-(2-methyl-1-oxoisoquinolin-4-yl)phenyl]methanesulfonamide |

TABLE 1-continued
| Chemical Synthesis Example | Structure | Name |
|---|---|---|
| 31 | 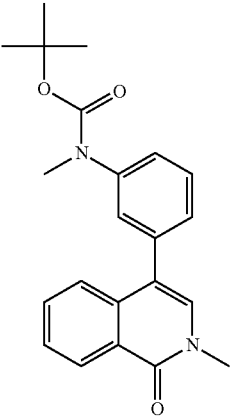 [SMILES: CN(C(=O)OC(C)(C)C)c1cccc(-c2cn(C)c(=O)c3ccccc23)c1] | tert-butyl N-methyl-N-[3-(2-methyl-1-oxoisoquinolin-4-yl)phenyl]carbamate |
| 32 | 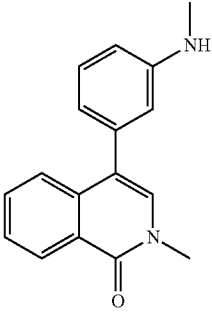 [SMILES: CNc1cccc(-c2cn(C)c(=O)c3ccccc23)c1] | 2-methyl-4-[3-(methylamino)phenyl]isoquinolin-1-one |
| 33 | 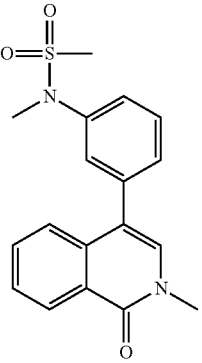 [SMILES: CN(c1cccc(-c2cn(C)c(=O)c3ccccc23)c1)S(C)(=O)=O] | N-methyl-N-[3-(2-methyl-1-oxoisoquinolin-4-yl)phenyl]methanesulfonamide |
| 34 | 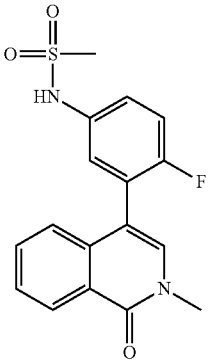 [SMILES: Cn1cc(-c2cc(NS(C)(=O)=O)ccc2F)c2ccccc2c1=O] | N-[4-fluoro-3-(2-methyl-1-oxoisoquinolin-4-yl)phenyl]methanesulfonamide |

TABLE 1-continued

| Chemical Synthesis Example | Structure | Name |
|---|---|---|
| 35 | 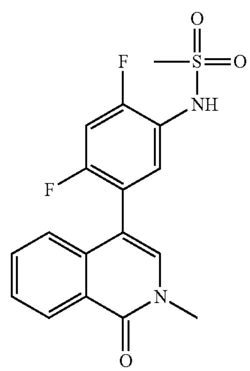 [SMILES: Cn1cc(-c2cc(NS(C)(=O)=O)c(F)cc2F)c2ccccc2c1=O] | N-[2,4-difluoro-5-(2-methyl-1-oxoisoquinolin-4-yl)phenyl]methanesulfonamide |
| 36 | 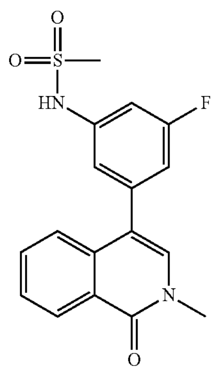 [SMILES: Cn1cc(-c2cc(F)cc(NS(C)(=O)=O)c2)c2ccccc2c1=O] | N-[3-fluoro-5-(2-methyl-1-oxoisoquinolin-4-yl)phenyl]methanesulfonamide |
| 37 | 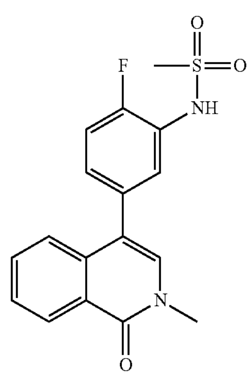 [SMILES: Cn1cc(-c2ccc(F)c(NS(C)(=O)=O)c2)c2ccccc2c1=O] | N-[2-fluoro-5-(2-methyl-1-oxoisoquinolin-4-yl)phenyl]methanesulfonamide |
| 38 | 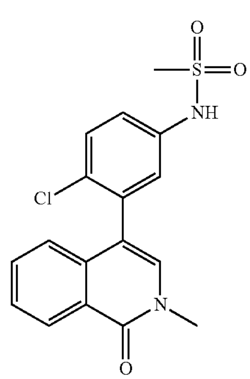 [SMILES: Cn1cc(-c2cc(NS(C)(=O)=O)ccc2Cl)c2ccccc2c1=O] | N-[4-chloro-3-(2-methyl-1-oxoisoquinolin-4-yl)phenyl]methanesulfonamide |

TABLE 1-continued

| Chemical Synthesis Example | Structure | Name |
|---|---|---|
| 39 | 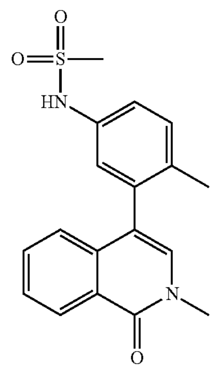 [SMILES: Cc1ccc(NS(C)(=O)=O)cc1-c1cn(C)c(=O)c2ccccc12] | N-[4-methyl-3-(2-methyl-1-oxoisoquinolin-4-yl)phenyl]methanesulfonamide |
| 40 | 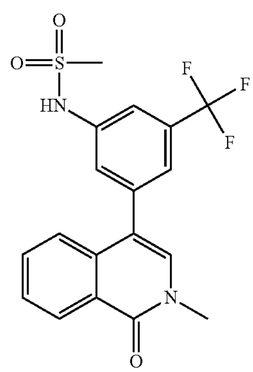 [SMILES: Cn1cc(-c2cc(NS(C)(=O)=O)cc(C(F)(F)F)c2)c2ccccc2c1=O] | N-[3-(2-methyl-1-oxoisoquinolin-4-yl)-5-(trifluoromethyl)phenyl]methanesulfonamide |
| 41 | 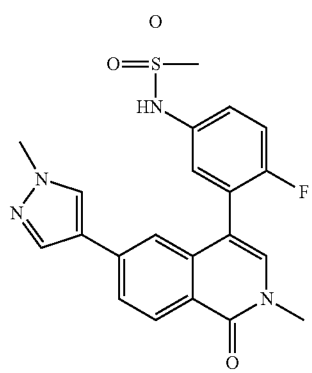 | N-[4-fluoro-3-[2-methyl-6-(1-methylpyrazol-4-yl)-1-oxoisoquinolin-4-yl]phenyl]methanesulfonamide |
| 42 | 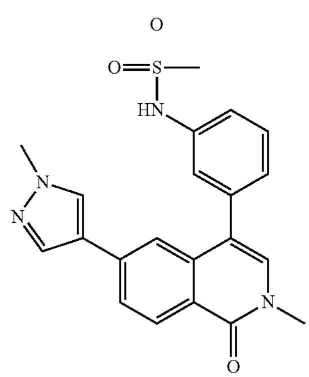 | N-[3-[2-methyl-6-(1-methylpyrazol-4-yl)-1-oxoisoquinolin-4-yl]phenyl]methanesulfonamide |

TABLE 1-continued

| Chemical Synthesis Example | Structure | Name |
|---|---|---|
| 43 | 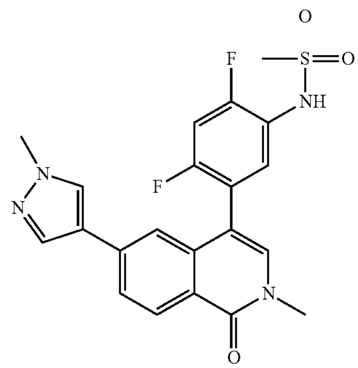 | N-[2,4-difluoro-5-[2-methyl-6-(1-methylpyrazol-4-yl)-1-oxoisoquinolin-4-yl]phenyl]methanesulfonamide |
| 44 | 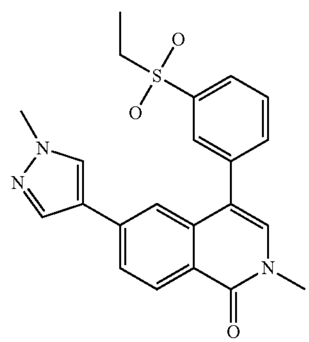 [SMILES: CCS(O)(O)c1cccc(-c2cn(C)c(=O)c3ccc(-c4cnn(C)c4)cc23)c1] | 4-(3-ethylsulfonylphenyl)-2-methyl-6-(1-methylpyrazol-4-yl)isoquinolin-1-one |
| 45 | 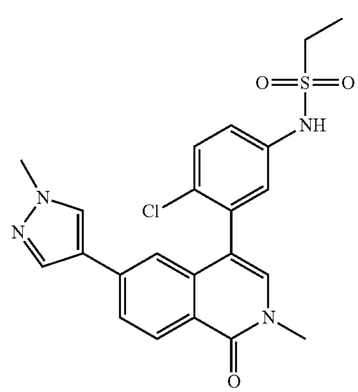 [SMILES: CCS(=O)(=O)Nc1ccc(Cl)c(-c2cn(C)c(=O)c3ccc(-c4cnn(C)c4)cc23)c1] | N-[4-chloro-3-[2-methyl-6-(1-methylpyrazol-4-yl)-1-oxoisoquinolin-4-yl]phenyl]ethanesulfonamide |
| 46 | 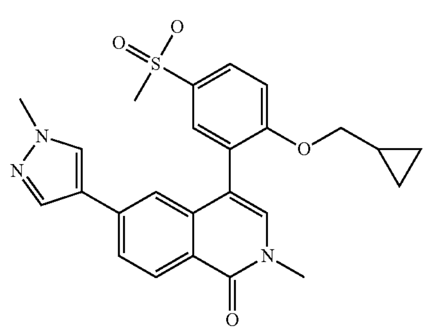 | 4-[2-(cyclopropylmethoxy)-5-methylsulfonylphenyl]-2-methyl-6-(1-methylpyrazol-4-yl)isoquinolin-1-one |

TABLE 1-continued
| Chemical Synthesis Example | Structure | Name |
|---|---|---|
| 47 | 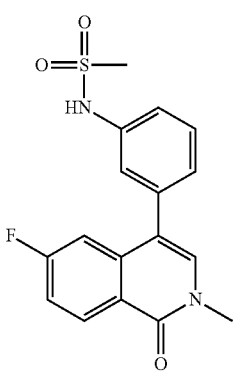 [SMILES: Cn1cc(-c2cccc(NS(C)(=O)=O)c2)c2cc(F)ccc2c1=O] | N-[3-(6-fluoro-2-methyl-1-oxoisoquinolin-4-yl)phenyl]methanesulfonamide |
| 48 | 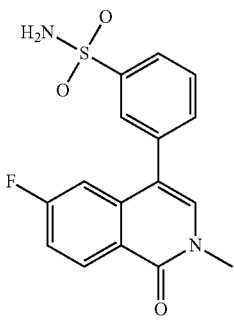 [SMILES: Cn1cc(-c2cccc(S(N)(O)O)c2)c2cc(F)ccc2c1=O] | 3-(6-fluoro-2-methyl-1-oxoisoquinolin-4-yl)benzenesulfonamide |
| 49 | 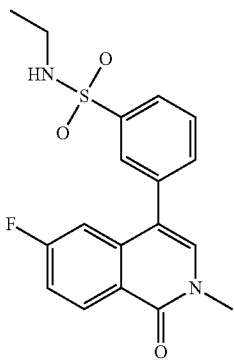 [SMILES: CCNS(O)(O)c1cccc(-c2cn(C)c(=O)c3ccc(F)cc23)c1] | N-ethyl-3-(6-fluoro-2-methyl-1-oxoisoquinolin-4-yl)benzenesulfonamide |
| 50 | 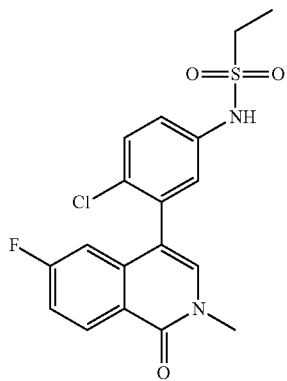 [SMILES: CCS(=O)(=O)Nc1ccc(Cl)c(-c2cn(C)c(=O)c3ccc(F)cc23)c1] | N-[4-chloro-3-(6-fluoro-2-methyl-1-oxoisoquinolin-4-yl)phenyl]ethanesulfonamide |

TABLE 1-continued

| Chemical Synthesis Example | Structure | Name |
|---|---|---|
| 51 | 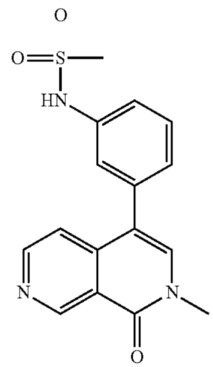 | N-[3-(2-methyl-1-oxo-2,7-naphthyridin-4-yl)phenyl]methanesulfonamide |
| 52 | 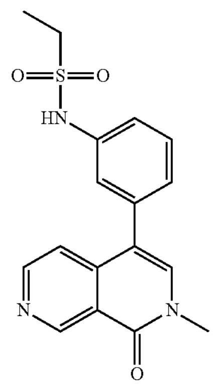 [SMILES: CCS(=O)(=O)Nc1cccc(-c2cn(C)c(=O)c3cnccc23)c1] | N-[3-(2-methyl-1-oxo-2,7-naphthyridin-4-yl)phenyl]ethanesulfonamide |
| 53 | 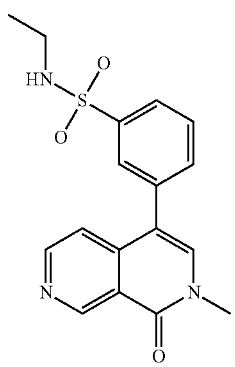 | N-ethyl-3-(2-methyl-1-oxo-2,7-naphthyridin-4-yl)benzenesulfonamide |
| 54 | 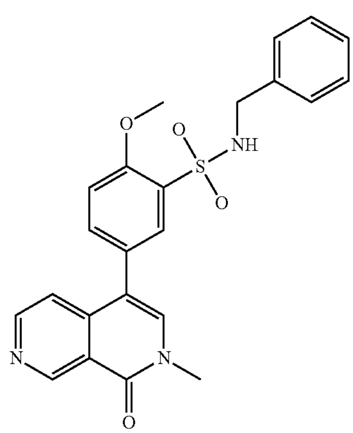 [SMILES: COc1ccc(-c2cn(C)c(=O)c3cnccc23)cc1S(O)(O)NCc1ccccc1] | N-benzyl-2-methoxy-5-(2-methyl-1-oxo-2,7-naphthyridin-4-yl)benzenesulfonamide |

TABLE 1-continued

| Chemical Synthesis Example | Structure | Name |
|---|---|---|
| 55 | 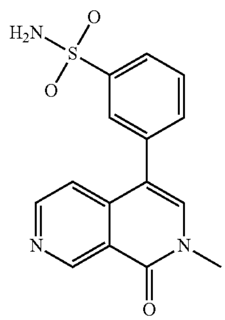 [SMILES: Cn1cc(-c2cccc(S(N)(O)O)c2)c2ccncc2c1=O] | 3-(2-methyl-1-oxo-2,7-naphthyridin-4-yl)benzenesulfonamide |
| 56 | 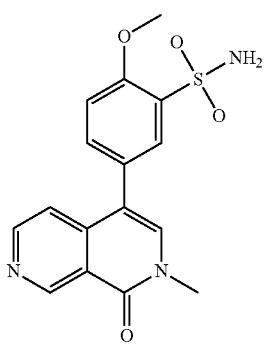 [SMILES: COc1ccc(-c2cn(C)c(=O)c3cnccc23)cc1S(N)(O)O] | 2-methoxy-5-(2-methyl-1-oxo-2,7-naphthyridin-4-yl)benzenesulfonamide |
| 57 | 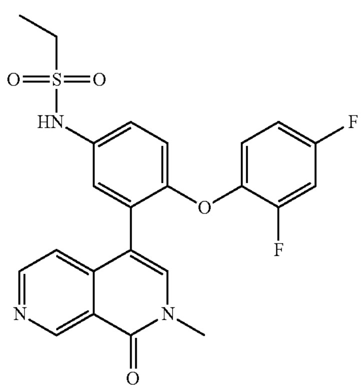 [SMILES: CCS(=O)(=O)Nc1ccc(Oc2ccc(F)cc2F)c(-c2cn(C)c(=O)c3cnccc23)c1] | N-[4-(2,4-difluorophenoxy)-3-(2-methyl-1-oxo-2,7-naphthyridin-4-yl)phenyl]ethanesulfonamide |
| 58 | 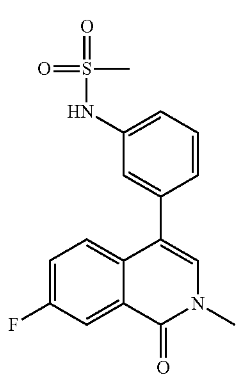 [SMILES: Cn1cc(-c2cccc(NS(C)(=O)=O)c2)c2ccc(F)cc2c1=O] | N-[3-(7-fluoro-2-methyl-1-oxoisoquinolin-4-yl)phenyl]methanesulfonamide |

TABLE 1-continued

| Chemical Synthesis Example | Structure | Name |
|---|---|---|
| 59 | 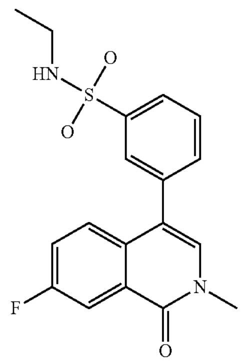 [SMILES: CCNS(O)(O)c1cccc(-c2cn(C)c(=O)c3cc(F)ccc23)c1] | N-ethyl-3-(7-fluoro-2-methyl-1-oxoisoquinolin-4-yl)benzenesulfonamide |
| 60 | 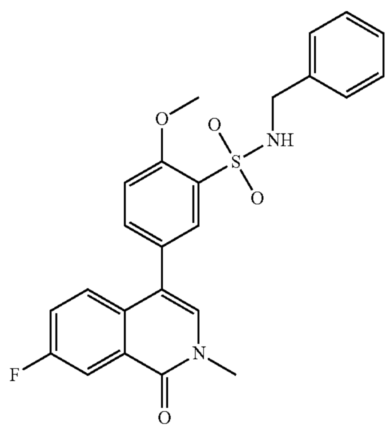 [SMILES: COc1ccc(-c2cn(C)c(=O)c3cc(F)ccc23)cc1S(O)(O)NCc1ccccc1] | N-benzyl-5-(7-fluoro-2-methyl-1-oxoisoquinolin-4-yl)-2-methoxybenzenesulfonamide |
| 61 | 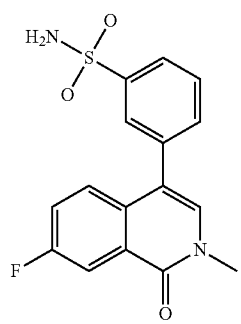 [SMILES: Cn1cc(-c2cccc(S(N)(O)O)c2)c2ccc(F)cc2c1=O] | 3-(7-fluoro-2-methyl-1-oxoisoquinolin-4-yl)benzenesulfonamide |
| 62 | 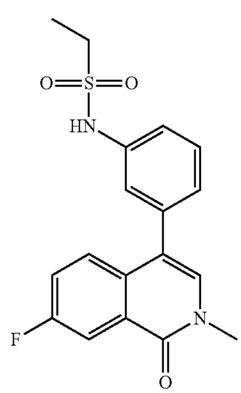 [SMILES: CCS(=O)(=O)Nc1cccc(-c2cn(C)c(=O)c3cc(F)ccc23)c1] | N-[3-(7-fluoro-2-methyl-1-oxoisoquinolin-4-yl)phenyl]ethanesulfonamide |

TABLE 1-continued

| Chemical Synthesis Example | Structure | Name |
|---|---|---|
| 63 | 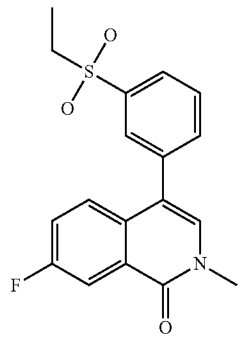 [SMILES: CCS(O)(O)c1cccc(-c2cn(C)c(=O)c3cc(F)ccc23)c1] | 4-(3-ethylsulfonylphenyl)-7-fluoro-2-methylisoquinolin-1-one |
| 64 | 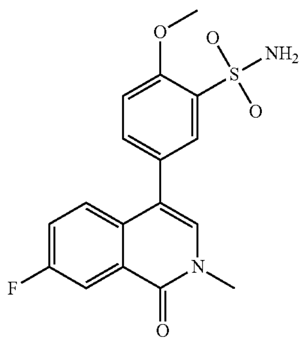 [SMILES: COc1ccc(-c2cn(C)c(=O)c3cc(F)ccc23)cc1S(N)(O)O] | 5-(7-fluoro-2-methyl-1-oxoisoquinolin-4-yl)-2-methoxybenzenesulfonamide |
| 65 | 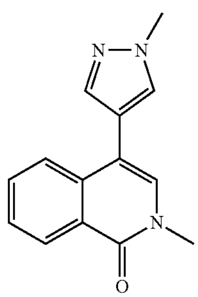 [SMILES: Cn1cc(-c2cn(C)c(=O)c3ccccc23)cn1] | 2-methyl-4-(1-methylpyrazol-4-yl)isoquinolin-1-one |
| 66 | 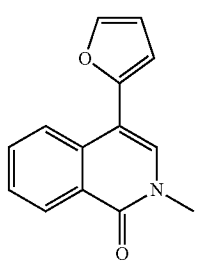 [SMILES: Cn1cc(-c2ccco2)c2ccccc2c1=O] | 4-(furan-2-yl)-2-methylisoquinolin-1-one |
| 67 | 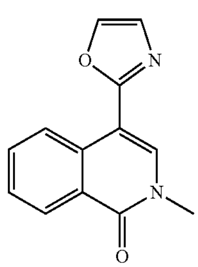 [SMILES: Cn1cc(-c2ncco2)c2ccccc2c1=O] | 2-methyl-4-(1,3-oxazol-2-yl)isoquinolin-1-one |

TABLE 1-continued

| Chemical Synthesis Example | Structure | Name |
|---|---|---|
| 68 | 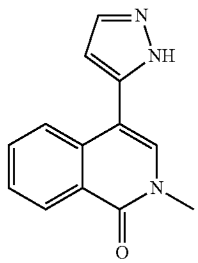 [SMILES: Cn1cc(-c2ccn[nH]2)c2ccccc2c1=O] | 2-methyl-4-(1H-pyrazol-5-yl)isoquinolin-1-one |
| 69 | 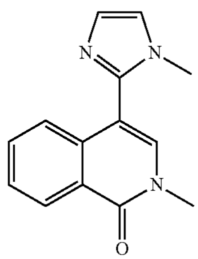 [SMILES: Cn1ccnc1-c1cn(C)c(=O)c2ccccc12] | 2-methyl-4-(1-methylimidazol-2-yl)isoquinolin-1-one |
| 70 | 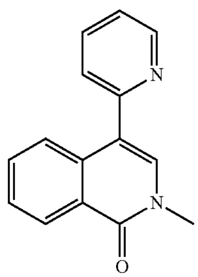 [SMILES: Cn1cc(-c2ccccn2)c2ccccc2c1=O] | 2-methyl-4-pyridin-2-ylisoquinolin-1-one |
| 71 | 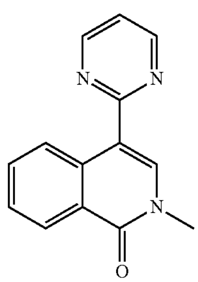 [SMILES: Cn1cc(-c2ncccn2)c2ccccc2c1=O] | 2-methyl-4-pyrimidin-2-ylisoquinolin-1-one |
| 72 | 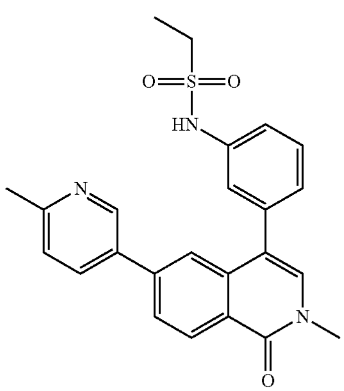 | N-[3-[2-methyl-6-(6-methylpyridin-3-yl)-1-oxoisoquinolin-4-yl]phenyl]ethanesulfonamide |

TABLE 1-continued

| Chemical Synthesis Example | Structure | Name |
|---|---|---|
| 73 | 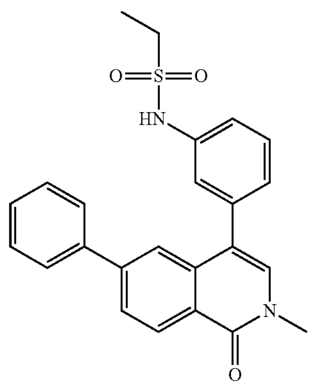 [SMILES: CCS(=O)(=O)Nc1cccc(-c2cn(C)c(=O)c3ccc(-c4ccccc4)cc23)c1] | N-[3-(2-methyl-1-oxo-6-phenylisoquinolin-4-yl)phenyl]ethanesulfonamide |
| 74 | 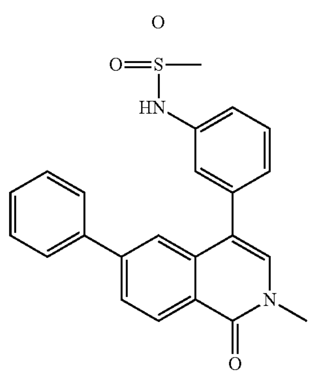 | N-[3-(2-methyl-1-oxo-6-phenylisoquinolin-4-yl)phenyl]methanesulfonamide |
| 75 | 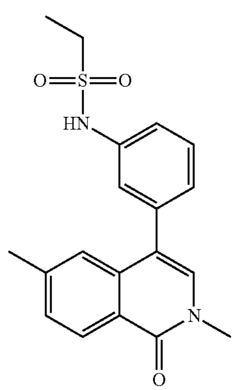 | N-[3-(2,6-dimethyl-1-oxoisoquinolin-4-yl)phenyl]ethanesulfonamide |
| 76 | 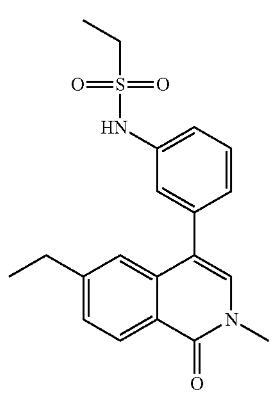 [SMILES: CCc1ccc2c(=O)n(C)cc(-c3cccc(NS(=O)(=O)CC)c3)c2c1] | N-[3-(6-ethyl-2-methyl-1-oxoisoquinolin-4-yl)phenyl]ethanesulfonamide |

TABLE 1-continued

| Chemical Synthesis Example | Structure | Name |
|---|---|---|
| 77 | 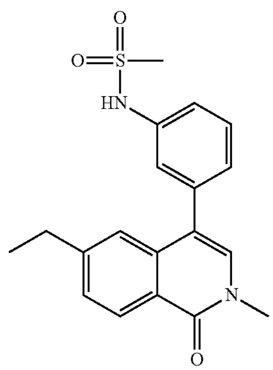 [SMILES: CCc1ccc2c(=O)n(C)cc(-c3cccc(NS(C)(=O)=O)c3)c2c1] | N-[3-(6-ethyl-2-methyl-1-oxoisoquinolin-4-yl)phenyl]methanesulfonamide |
| 78 | 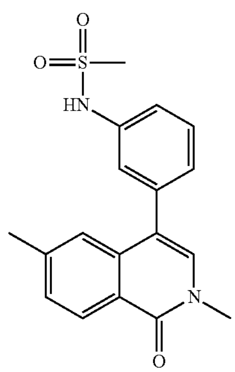 | N-[3-(2,6-dimethyl-1-oxoisoquinolin-4-yl)phenyl]methanesulfonamide |
| 79 | 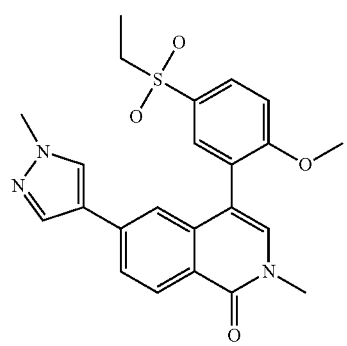 [SMILES: CCS(O)(O)c1ccc(OC)c(-c2cn(C)c(=O)c3ccc(-c4cnn(C)c4)cc23)c1] | 4-(5-ethylsulfonyl-2-methoxyphenyl)-2-methyl-6-(1-methylpyrazol-4-yl)isoquinolin-1-one |
| 80 | 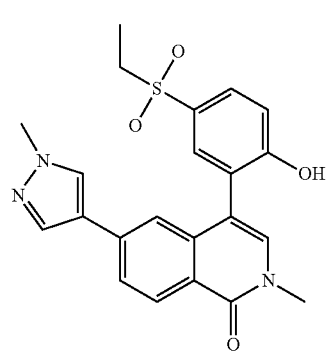 [SMILES: CCS(O)(O)c1ccc(O)c(-c2cn(C)c(=O)c3ccc(-c4cnn(C)c4)cc23)c1] | 4-(5-ethylsulfonyl-2-hydroxyphenyl)-2-methyl-6-(1-methylpyrazol-4-yl)isoquinolin-1-one |

TABLE 1-continued

| Chemical Synthesis Example | Structure | Name |
|---|---|---|
| 81 | 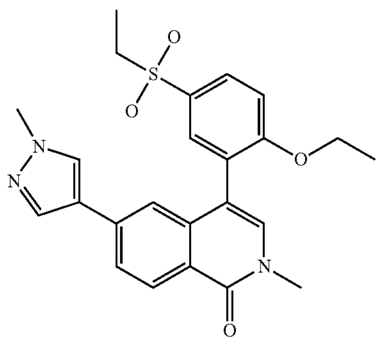 [SMILES: CCOc1ccc(S(O)(O)CC)cc1-c1cn(C)c(=O)c2ccc(-c3cnn(C)c3)cc12] | 4-(2-ethoxy-5-ethylsulfonylphenyl)-2-methyl-6-(1-methylpyrazol-4-yl)isoquinolin-1-one |
| 82 | 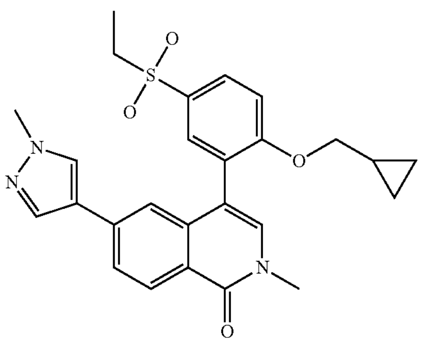 [SMILES: CCS(O)(O)c1ccc(OCC2CC2)c(-c2cn(C)c(=O)c3ccc(-c4cnn(C)c4)cc23)c1] | 4-[2-(cyclopropylmethoxy)-5-ethylsulfonylphenyl]-2-methyl-6-(1-methylpyrazol-4-yl)isoquinolin-1-one |
| 83 | 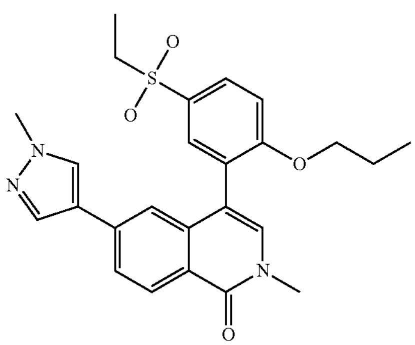 [SMILES: CCCOc1ccc(S(O)(O)CC)cc1-c1cn(C)c(=O)c2ccc(-c3cnn(C)c3)cc12] | 4-(5-ethylsulfonyl-2-propoxyphenyl)-2-methyl-6-(1-methylpyrazol-4-yl)isoquinolin-1-one |
| 84 | 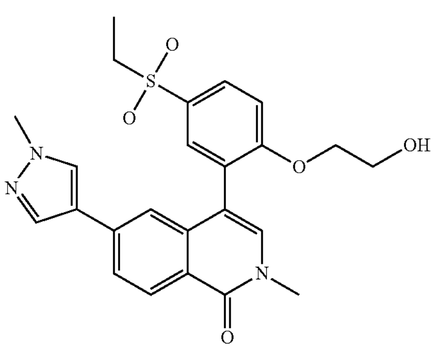 [SMILES: CCS(O)(O)c1ccc(OCCO)c(-c2cn(C)c(=O)c3ccc(-c4cnn(C)c4)cc23)c1] | 4-[5-ethylsulfonyl-2-(2-hydroxyethoxy)phenyl]-2-methyl-6-(1-methylpyrazol-4-yl)isoquinolin-1-one |

TABLE 1-continued

| Chemical Synthesis Example | Structure | Name |
|---|---|---|
| 85 | 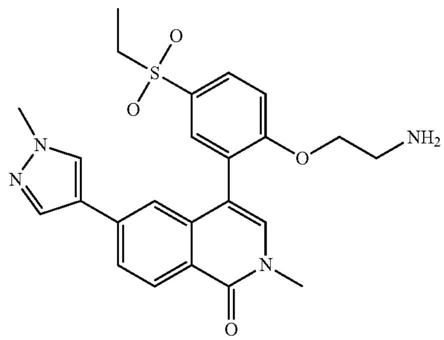 [SMILES: CCS(O)(O)c1ccc(OCCN)c(-c2cn(C)c(=O)c3ccc(-c4cnn(C)c4)cc23)c1] | 4-[2-(2-aminoethoxy)-5-ethylsulfonylphenyl]-2-methyl-6-(1-methylpyrazol-4-yl)isoquinolin-1-one |
| 86 | 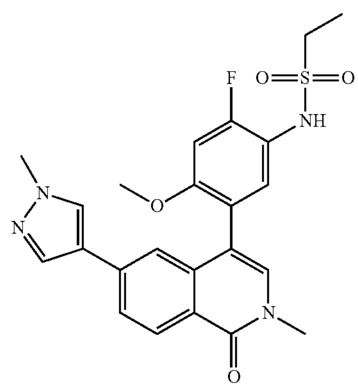 [SMILES: CCS(=O)(=O)Nc1cc(-c2cn(C)c(=O)c3ccc(-c4cnn(C)c4)cc23)c(OC)cc1F] | N-[2-fluoro-4-methoxy-5-[2-methyl-6-(1-methylpyrazol-4-yl)-1-oxoisoquinolin-4-yl]phenyl]ethanesulfonamide |
| 87 | 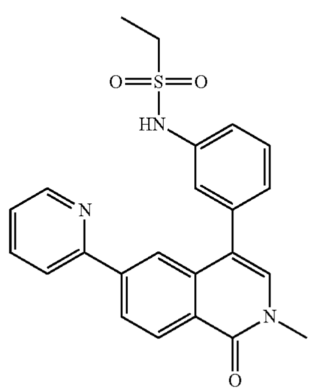 [SMILES: CCS(=O)(=O)Nc1cccc(-c2cn(C)c(=O)c3ccc(-c4ccccn4)cc23)c1] | N-[3-(2-methyl-1-oxo-6-pyridin-2-ylisoquinolin-4-yl)phenyl]ethanesulfonamide |
| 88 | 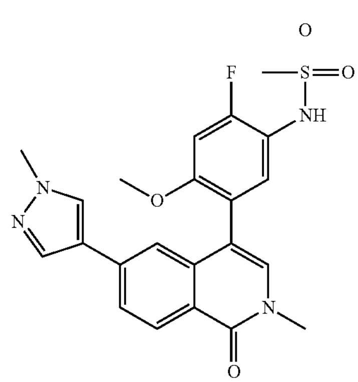 | 4-[4-fluoro-2-methoxy-5-(methylsulfonylmethyl)phenyl]-2-methyl-6-(1-methylpyrazol-4-yl)isoquinolin-1-one |

TABLE 1-continued
| Chemical Synthesis Example | Structure | Name |
|---|---|---|
| 89 | 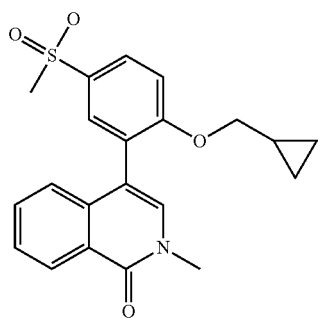 | 4-[2-(cyclopropylmethoxy)-5-methylsulfonylphenyl]-2-methylisoquinolin-1-one |
| 90 | 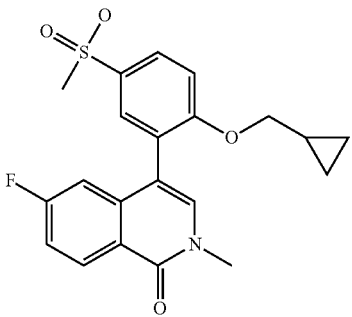 | 4-[2-(cyclopropylmethoxy)-5-methylsulfonylphenyl]-6-fluoro-2-methylisoquinolin-1-one |
| 91 | 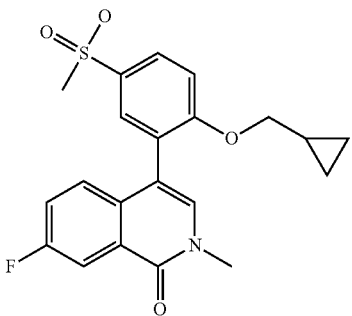 | 4-[2-(cyclopropylmethoxy)-5-methylsulfonylphenyl]-7-fluoro-2-methylisoquinolin-1-one |
| 92 | 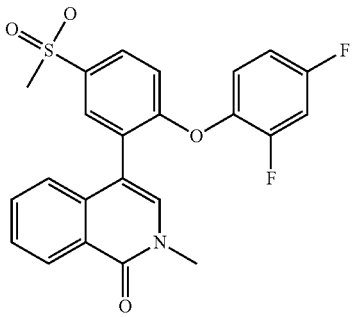 | 4-[2-(2,4-difluorophenoxy)-5-methylsulfonylphenyl]-2-methylisoquinolin-1-one |

TABLE 1-continued

| Chemical Synthesis Example | Structure | Name |
|---|---|---|
| 93 | 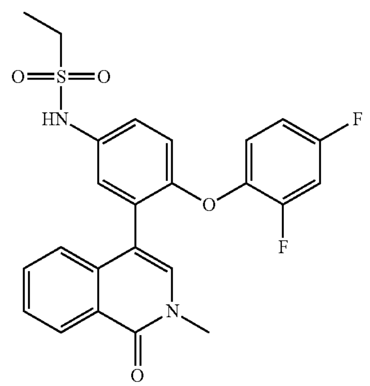 [SMILES: CCS(=O)(=O)Nc1ccc(Oc2ccc(F)cc2F)c(-c2cn(C)c(=O)c3ccccc23)c1] | N-[4-(2,4-difluorophenoxy)-3-(2-methyl-1-oxoisoquinolin-4-yl)phenyl]ethanesulfonamide |
| 94 | 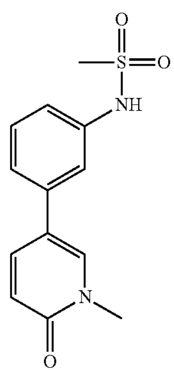 [SMILES: Cn1cc(-c2cccc(NS(C)(=O)=O)c2)ccc1=O] | N-[3-(1-methyl-6-oxopyridin-3-yl)phenyl]methanesulfonamide |
| 95 | 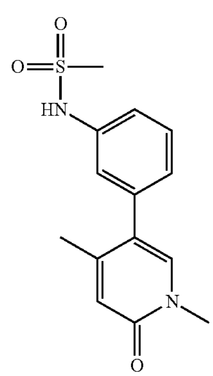 [SMILES: Cc1cc(=O)n(C)cc1-c1cccc(NS(C)(=O)=O)c1] | N-[3-(1,4-dimethyl-6-oxopyridin-3-yl)phenyl]methanesulfonamide |
| 96 | 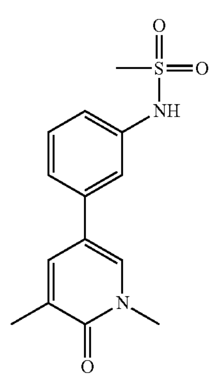 [SMILES: Cc1cc(-c2cccc(NS(C)(=O)=O)c2)cn(C)c1=O] | N-[3-(1,5-dimethyl-6-oxopyridin-3-yl)phenyl]methanesulfonamide |

TABLE 1-continued

| Chemical Synthesis Example | Structure | Name |
| --- | --- | --- |
| 97 | 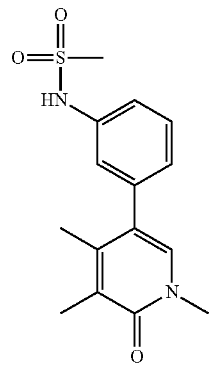 [SMILES: Cc1c(-c2cccc(NS(C)(=O)=O)c2)cn(C)c(=O)c1C] | N-[3-(1,4,5-trimethyl-6-oxopyridin-3-yl)phenyl]methanesulfonamide |
| 98 | 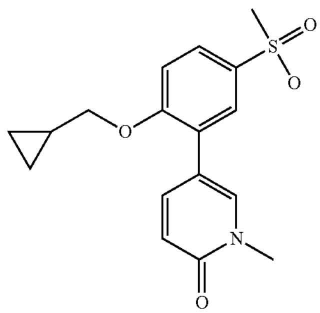 | 5-[2-(cyclopropylmethoxy)-5-methylsulfonylphenyl]-1-methylpyridin-2-one |
| 99 | 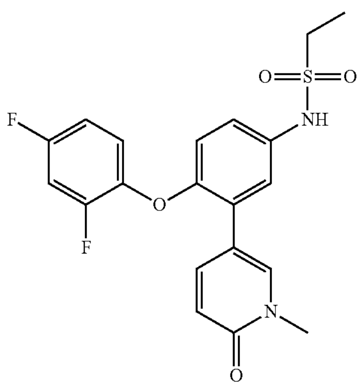 [SMILES: CCS(=O)(=O)Nc1ccc(Oc2ccc(F)cc2F)c(-c2ccc(=O)n(C)c2)c1] | N-[4-(2,4-difluorophenoxy)-3-(1-methyl-6-oxopyridin-3-yl)phenyl]ethanesulfonamide |
| 100 | 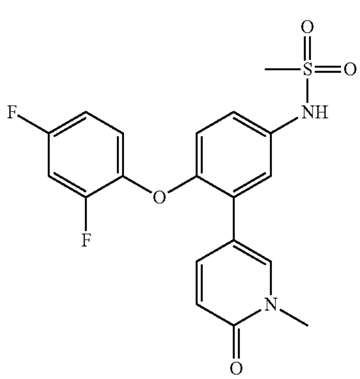 [SMILES: Cn1cc(-c2cc(NS(C)(=O)=O)ccc2Oc2ccc(F)cc2F)ccc1=O] | N-[4-(2,4-difluorophenoxy)-3-(1-methyl-6-oxopyridin-3-yl)phenyl]methanesulfonamide |

TABLE 1-continued

| Chemical Synthesis Example | Structure | Name |
|---|---|---|
| 101 | 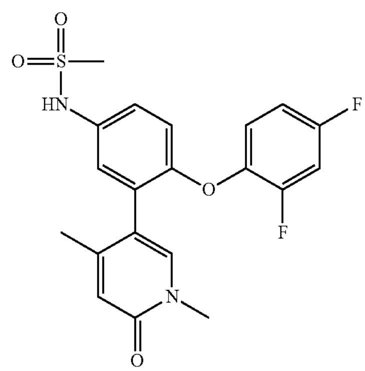 [SMILES: Cc1cc(=O)n(C)cc1-c1cc(NS(C)(=O)=O)ccc1Oc1ccc(F)cc1F] | N-[4-(2,4-difluorophenoxy)-3-(1,4-dimethyl-6-oxopyridin-3-yl)phenyl]methanesulfonamide |
| 102 | 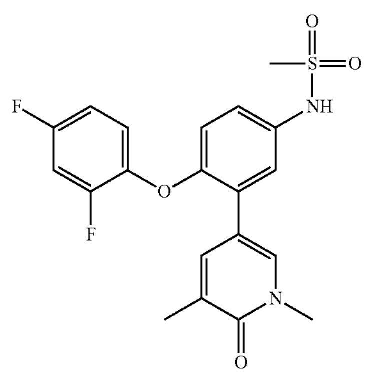 [SMILES: Cc1cc(-c2cc(NS(C)(=O)=O)ccc2Oc2ccc(F)cc2F)cn(C)c1=O] | N-[4-(2,4-difluorophenoxy)-3-(1,5-dimethyl-6-oxopyridin-3-yl)phenyl]methanesulfonamide |
| 103 | 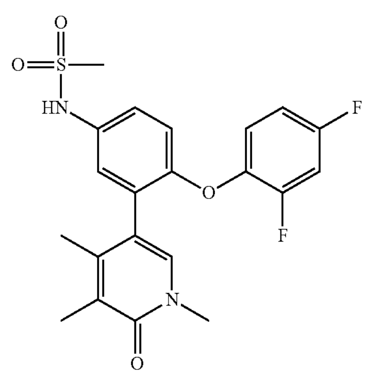 [SMILES: Cc1c(-c2cc(NS(C)(=O)=O)ccc2Oc2ccc(F)cc2F)cn(C)c(=O)c1C] | N-[4-(2,4-difluorophenoxy)-3-(1,4,5-trimethyl-6-oxopyridin-3-yl)phenyl]methanesulfonamide |
| 104 | 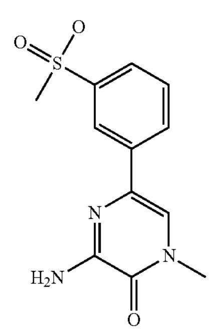 | 3-amino-1-methyl-5-(3-methylsulfonylphenyl)pyrazin-2-one |

TABLE 1-continued

| Chemical Synthesis Example | Structure | Name |
|---|---|---|
| 105 | 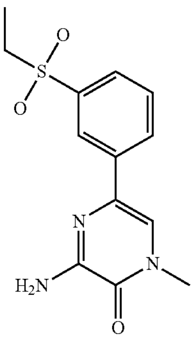 [SMILES: CCS(O)(O)c1cccc(-c2cn(C)c(=O)c(N)n2)c1] | 3-amino-5-(3-ethylsulfonylphenyl)-1-methylpyrazin-2-one |
| 106 | 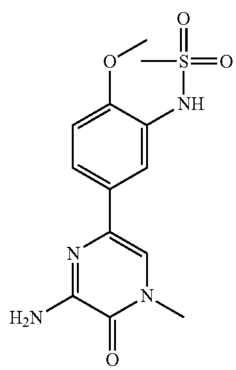 [SMILES: COc1ccc(-c2cn(C)c(=O)c(N)n2)cc1NS(C)(=O)=O] | N-[5-(6-amino-4-methyl-5-oxopyrazin-2-yl)-2-methoxyphenyl]methanesulfonamide |
| 107 | 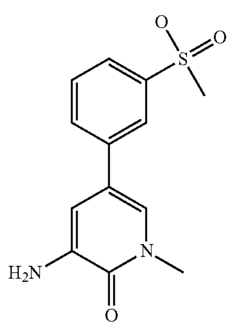 | 3-amino-1-methyl-5-(3-methylsulfonylphenyl)pyridin-2-one |
| 108 | 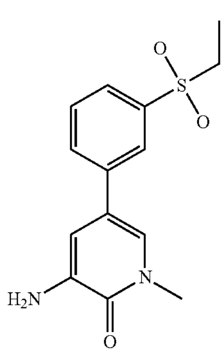 [SMILES: CCS(O)(O)c1cccc(-c2cc(N)c(=O)n(C)c2)c1] | 3-amino-5-(3-ethylsulfonylphenyl)-1-methylpyridin-2-one |

TABLE 1-continued

| Chemical Synthesis Example | Structure | Name |
|---|---|---|
| 109 | 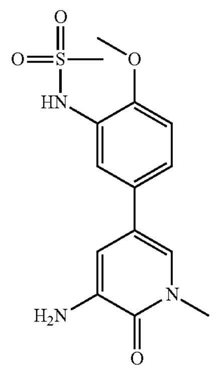 [SMILES: COc1ccc(-c2cc(N)c(=O)n(C)c2)cc1NS(C)(=O)=O] | N-[5-(5-amino-1-methyl-6-oxopyridin-3-yl)-2-methoxyphenyl]methanesulfonamide |
| 110 | 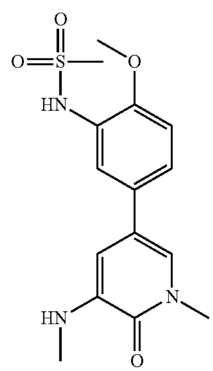 [SMILES: CNc1cc(-c2ccc(OC)c(NS(C)(=O)=O)c2)cn(C)c1=O] | N-[2-methoxy-5-[1-methyl-5-(methylamino)-6-oxopyridin-3-yl]phenyl]methanesulfonamide |
| 111 | 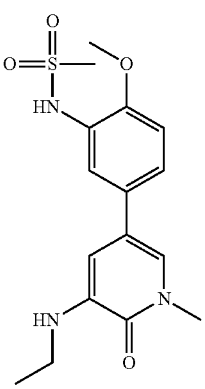 [SMILES: CCNc1cc(-c2ccc(OC)c(NS(C)(=O)=O)c2)cn(C)c1=O] | N-[5-[5-(ethylamino)-1-methyl-6-oxopyridin-3-yl]-2-methoxyphenyl]methanesulfonamide |
| 112 | 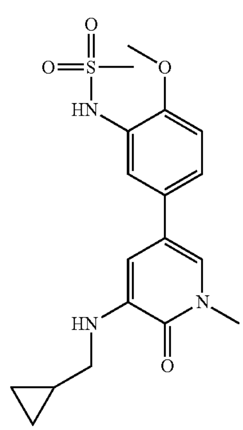 [SMILES: COc1ccc(-c2cc(NCC3CC3)c(=O)n(C)c2)cc1NS(C)(=O)=O] | N-[5-[5-(cyclopropylmethylamino)-1-methyl-6-oxopyridin-3-yl]-2-methoxyphenyl]methanesulfonamide |

TABLE 1-continued
| Chemical Synthesis Example | Structure | Name |
|---|---|---|
| 113 | 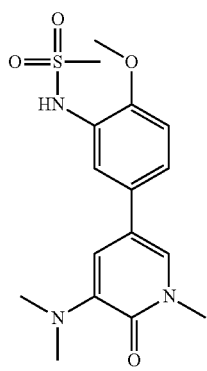 [SMILES: COc1ccc(-c2cc(N(C)C)c(=O)n(C)c2)cc1NS(C)(=O)=O] | N-[5-[5-(dimethylamino)-1-methyl-6-oxopyridin-3-yl]-2-methoxyphenyl] methanesulfonamide |
| 114 | 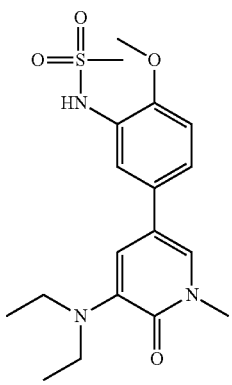 [SMILES: CCN(CC)c1cc(-c2ccc(OC)c(NS(C)(=O)=O)c2)cn(C)c1=O] | N-[5-[5-(diethylamino)-1-methyl-6-oxopyridin-3-yl]-2-methoxyphenyl]methanesulfonamide |
| 115 | 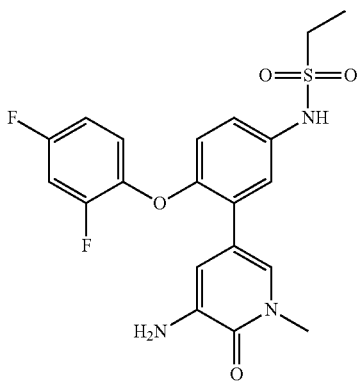 | N-[3-(5-amino-1-methyl-6-oxopyridin-3-yl)-4-(2,4-difluorophenoxy)phenyl]ethanesulfonamide |
| 116 | 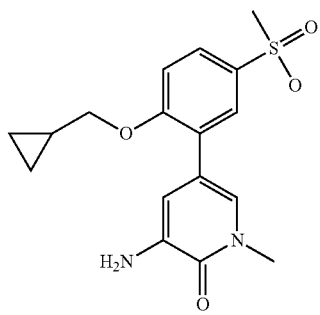 | 3-amino-5-[2-(cyclopropylmethoxy)-5-methylsulfonylphenyl]-1-methylpyridin-2-one |

TABLE 1-continued

| Chemical Synthesis Example | Structure | Name |
|---|---|---|
| 117 | 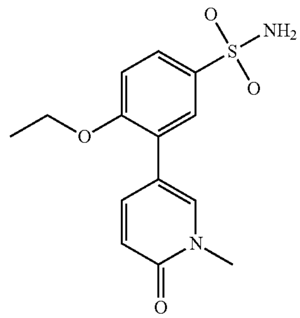 [SMILES: CCOc1ccc(S(N)(O)O)cc1-c1ccc(=O)n(C)c1] | 4-ethoxy-3-(1-methyl-6-oxopyridin-3-yl)benzenesulfonamide |
| 118 | 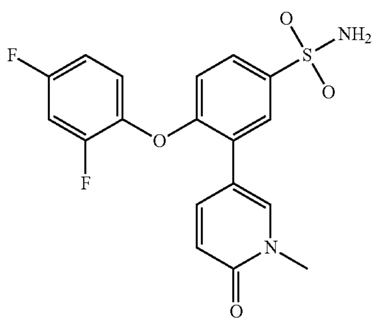 [SMILES: Cn1cc(-c2cc(S(N)(O)O)ccc2Oc2ccc(F)cc2F)ccc1=O] | 4-(2,4-difluorophenoxy)-3-(1-methyl-6-oxopyridin-3-yl)benzenesulfonamide |
| 119 | 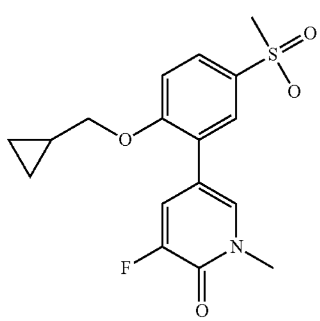 | 5-[2-(cyclopropylmethoxy)-5-methylsulfonylphenyl]-3-fluoro-1-methylpyridin-2-one |
| 120 | 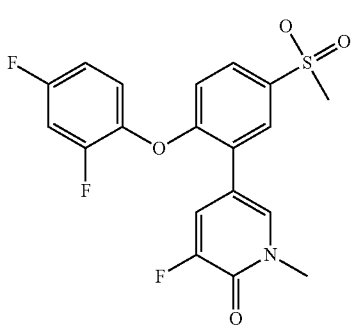 | 5-[2-(2,4-difluorophenoxy)-5-methylsulfonylphenyl]-3-fluoro-1-methylpyridin-2-one |

TABLE 1-continued

| Chemical Synthesis Example | Structure | Name |
|---|---|---|
| 121 | 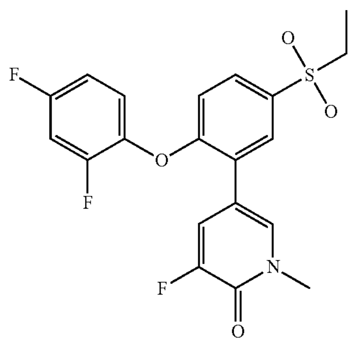 [SMILES: CCS(O)(O)c1ccc(Oc2ccc(F)cc2F)c(-c2cc(F)c(=O)n(C)c2)c1] | 5-[2-(2,4-difluorophenoxy)-5-ethylsulfonylphenyl]-3-fluoro-1-methylpyridin-2-one |
| 122 | 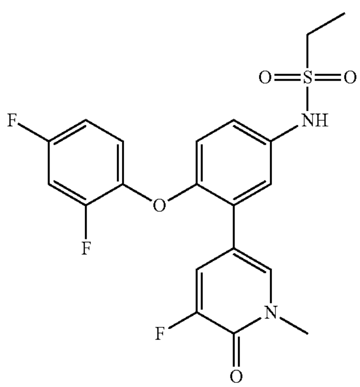 [SMILES: CCS(=O)(=O)Nc1ccc(Oc2ccc(F)cc2F)c(-c2cc(F)c(=O)n(C)c2)c1] | N-[4-(2,4-difluorophenoxy)-3-(5-fluoro-1-methyl-6-oxopyridin-3-yl)phenyl]ethanesulfonamide |
| 123 | 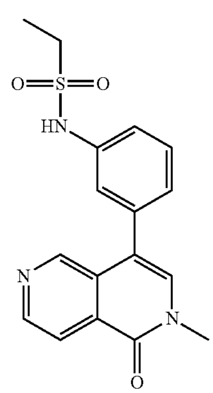 [SMILES: CCS(=O)(=O)Nc1cccc(-c2cn(C)c(=O)c3ccncc23)c1] | N-[3-(2-methyl-1-oxo-2,6-naphthyridin-4-yl)phenyl]ethanesulfonamide |
| 124 | 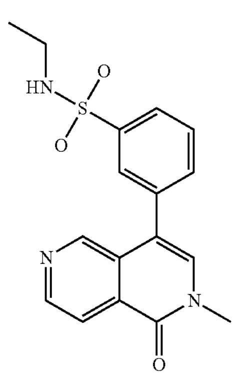 [SMILES: CCNS(O)(O)c1cccc(-c2cn(C)c(=O)c3ccncc23)c1] | N-ethyl-3-(2-methyl-1-oxo-2,6-naphthyridin-4-yl)benzenesulfonamide |

TABLE 1-continued

| Chemical Synthesis Example | Structure | Name |
| --- | --- | --- |
| 125 | 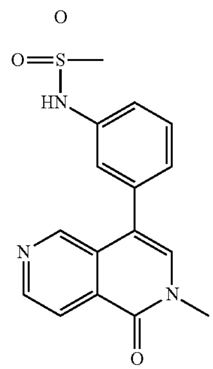 | N-[3-(2-methyl-1-oxo-2,6-naphthyridin-4-yl)phenyl]methanesulfonamide |
| 126 | 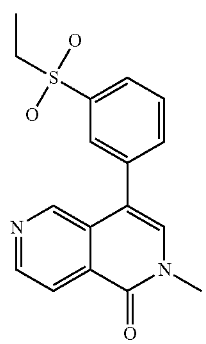 [SMILES: CCS(O)(O)c1cccc(-c2cn(C)c(=O)c3ccncc23)c1] | 4-(3-ethylsulfonylphenyl)-2-methyl-2,6-naphthyridin-1-one |
| 127 | 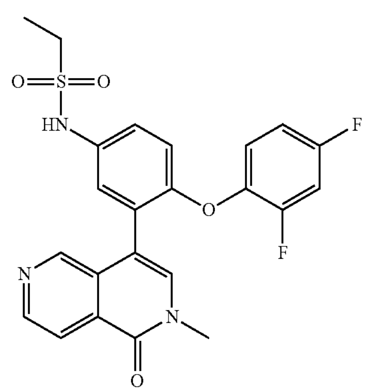 [SMILES: CCS(=O)(=O)Nc1ccc(Oc2ccc(F)cc2F)c(-c2cn(C)c(=O)c3ccncc23)c1] | N-[4-(2,4-difluorophenoxy)-3-(2-methyl-1-oxo-2,6-naphthyridin-4-yl)phenyl]ethanesulfonamide |
| 128 | 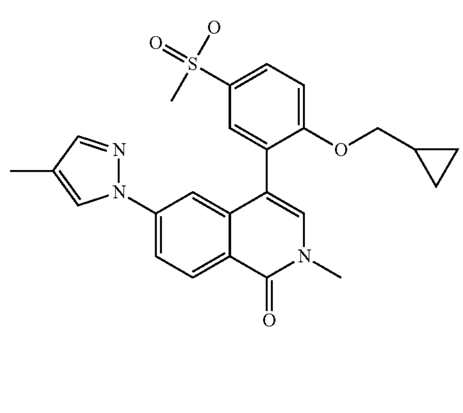 | 4-[2-(cyclopropylmethoxy)-5-methylsulfonylphenyl]-2-methyl-6-(4-methylpyrazol-1-yl)isoquinolin-1-one |

TABLE 1-continued

| Chemical Synthesis Example | Structure | Name |
|---|---|---|
| 129 | 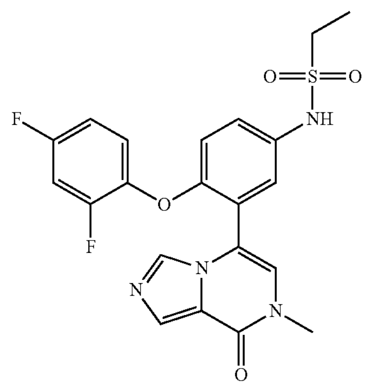 [SMILES: CCS(=O)(=O)Nc1ccc(Oc2ccc(F)cc2F)c(-c2cn(C)c(=O)c3cncn23)c1] | N-[4-(2,4-difluorophenoxy)-3-(7-methyl-8-oxoimidazo[1,5-a]pyrazin-5-yl)phenyl]ethanesulfonamide |
| 130 | 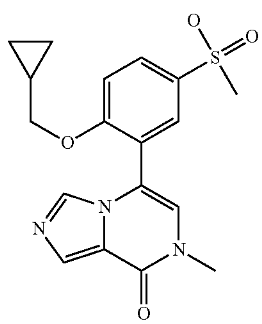 | 5-[2-(cyclopropylmethoxy)-5-methylsulfonylphenyl]-7-methylimidazo[1,5-a]pyrazin-8-one |
| 131 | 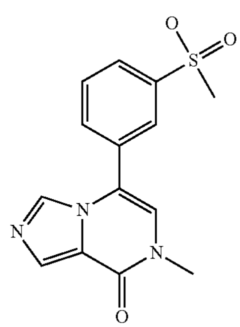 | 7-methyl-5-(3-methylsulfonylphenyl)imidazo[1,5-a]pyrazin-8-one |
| 132 | 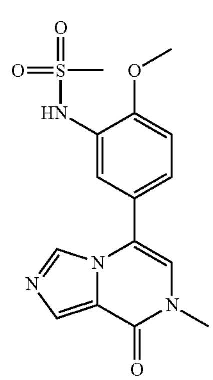 [SMILES: COc1ccc(-c2cn(C)c(=O)c3cncn23)cc1NS(C)(=O)=O] | N-[2-methoxy-5-(7-methyl-8-oxoimidazo[1,5-a]pyrazin-5-yl)phenyl]methanesulfonamide |

TABLE 1-continued

| Chemical Synthesis Example | Structure | Name |
|---|---|---|
| 133 | 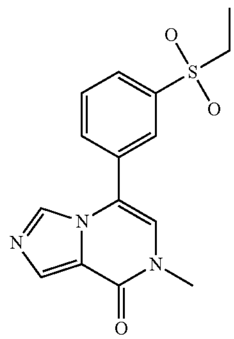 [SMILES: CCS(O)(O)c1cccc(-c2cn(C)c(=O)c3cncn23)c1] | 5-(3-ethylsulfonylphenyl)-7-methylimidazo[1,5-a]pyrazin-8-one |
| 134 | 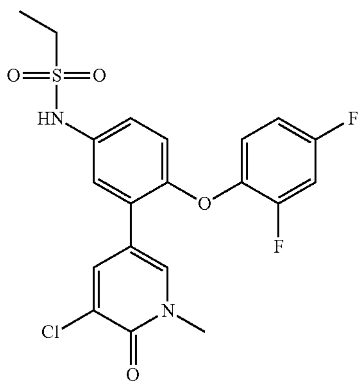 [SMILES: CCS(=O)(=O)Nc1ccc(Oc2ccc(F)cc2F)c(-c2cc(Cl)c(=O)n(C)c2)c1] | N-[3-(5-chloro-1-methyl-6-oxopyridin-3-yl)-4-(2,4-difluorophenoxy)phenyl]ethanesulfonamide |
| 135 | 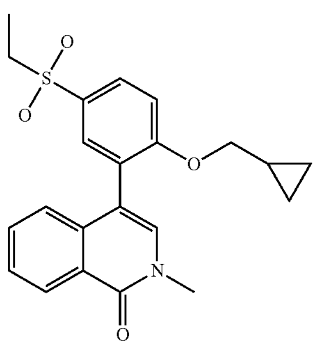 [SMILES: CCS(O)(O)c1ccc(OCC2CC2)c(-c2cn(C)c(=O)c3ccccc23)c1] | 4-[2-(cyclopropylmethoxy)-5-ethylsulfonylphenyl]-2-methylisoquinolin-1-one |
| 136 | 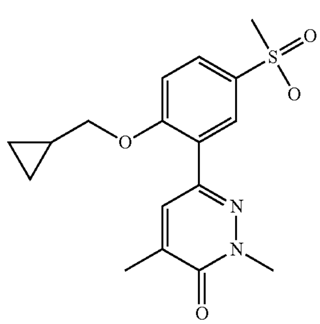 | 6-[2-(cyclopropylmethoxy)-5-methylsulfonylphenyl]-2,4-dimethylpyridazin-3-one |

TABLE 1-continued

| Chemical Synthesis Example | Structure | Name |
|---|---|---|
| 137 | 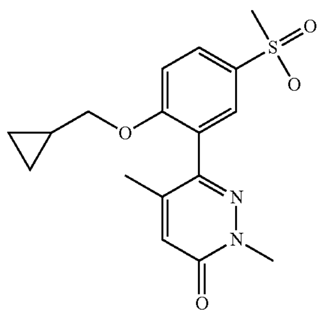 | 6-[2-(cyclopropylmethoxy)-5-methylsulfonylphenyl]-2,5-dimethylpyridazin-3-one |
| 138 | 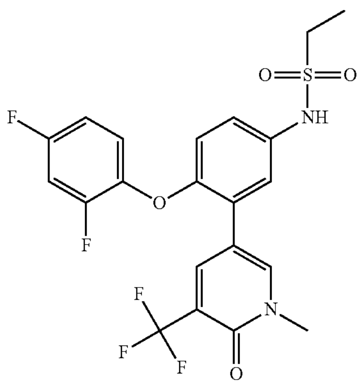 [SMILES: CCS(=O)(=O)Nc1ccc(Oc2ccc(F)cc2F)c(-c2cc(C(F)(F)F)c(=O)n(C)c2)c1] | N-[4-(2,4-difluorophenoxy)-3-[1-methyl-6-oxo-5-(trifluoromethyl)pyridin-3-yl]phenyl]ethanesulfonamide |
| 139 | 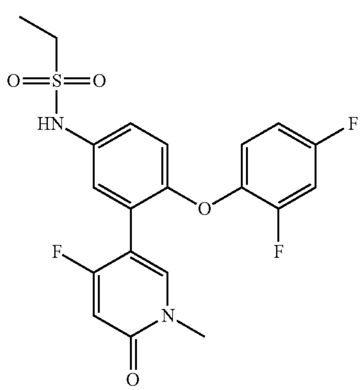 [SMILES: CCS(=O)(=O)Nc1ccc(Oc2ccc(F)cc2F)c(-c2cn(C)c(=O)cc2F)c1] | N-[4-(2,4-difluorophenoxy)-3-(4-fluoro-1-methyl-6-oxopyridin-3-yl)phenyl]ethanesulfonamide |
| 140 | 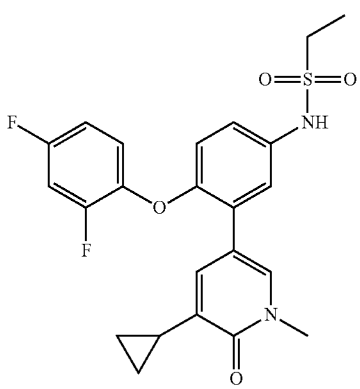 [SMILES: CCS(=O)(=O)Nc1ccc(Oc2ccc(F)cc2F)c(-c2cc(C3CC3)c(=O)n(C)c2)c1] | N-[3-(5-cyclopropyl-1-methyl-6-oxopyridin-3-yl)-4-(2,4-difluorophenoxy)phenyl]ethanesulfonamide |

TABLE 1-continued

| Chemical Synthesis Example | Structure | Name |
|---|---|---|
| 141 | 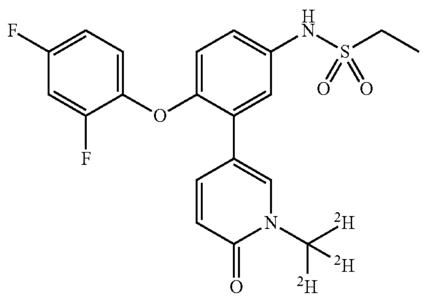 [SMILES: [2H]C([2H])([2H])n1cc(-c2cc(NS(=O)(=O)CC)ccc2Oc2ccc(F)cc2F)ccc1=O] | N-{4-(2,4-difluorophenoxy)-3-[1-($^2$H$_3$)methyl-6-oxopyridin-3-yl]phenyl}ethanesulfonamide |
| 142 | 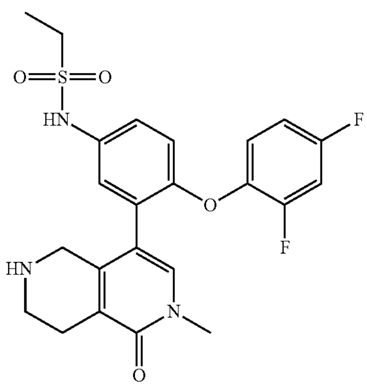 [SMILES: CCS(=O)(=O)Nc1ccc(Oc2ccc(F)cc2F)c(-c2cn(C)c(=O)c3c2CNCC3)c1] | N-[4-(2,4-difluorophenoxy)-3-(2-methyl-1-oxo-5,6,7,8-tetrahydro-2,6-naphthyridin-4-yl)phenyl]ethanesulfonamide |
| 143 | 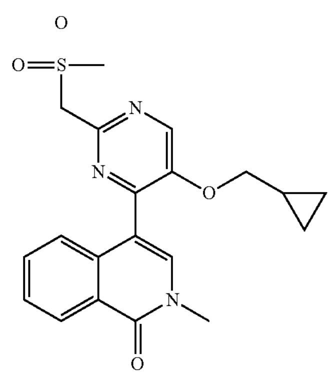 | 4-[5-(cyclopropylmethoxy)-2-(methylsulfonylmethyl)pyrimidin-4-yl]-2-methylisoquinolin-1-one |
| 144 | 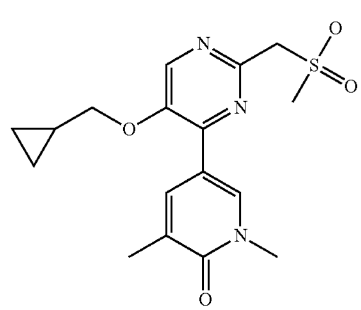 | 5-[5-(cyclopropylmethoxy)-2-(methylsulfonylmethyl)pyrimidin-4-yl]-1,3-dimethylpyridin-2-one |

TABLE 1-continued

| Chemical Synthesis Example | Structure | Name |
|---|---|---|
| 145 | 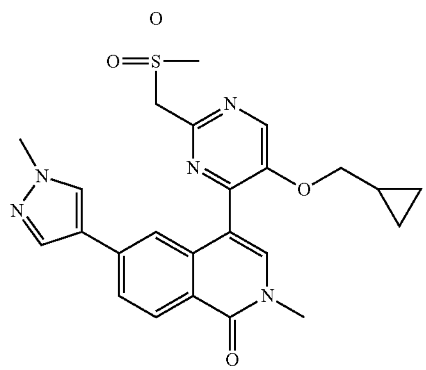 | 4-[5-(cyclopropylmethoxy)-2-(methylsulfonylmethyl)pyrimidin-4-yl]-2-methyl-6-(1-methylpyrazol-4-yl)isoquinolin-1-one |
| 146 | 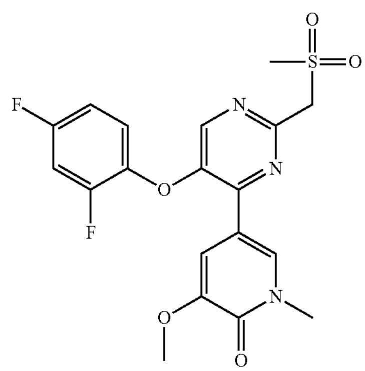 [SMILES: COc1cc(-c2nc(CS(C)(=O)=O)ncc2Oc2ccc(F)cc2F)cn(C)c1=O] | 5-[5-(2,4-difluorophenoxy)-2-(methylsulfonylmethyl)pyrimidin-4-yl]-3-methoxy-1-methylpyridin-2-one |
| 147 | 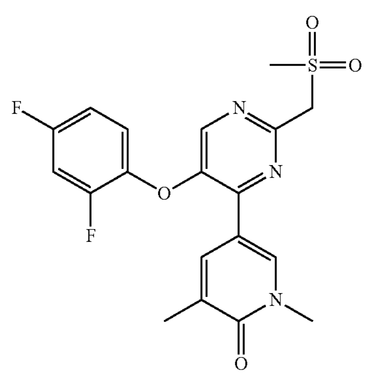 [SMILES: Cc1cc(-c2nc(CS(C)(=O)=O)ncc2Oc2ccc(F)cc2F)cn(C)c1=O] | 5-[5-(2,4-difluorophenoxy)-2-(methylsulfonylmethyl)pyrimidin-4-yl]-1,3-dimethylpyridin-2-one |
| 148 | 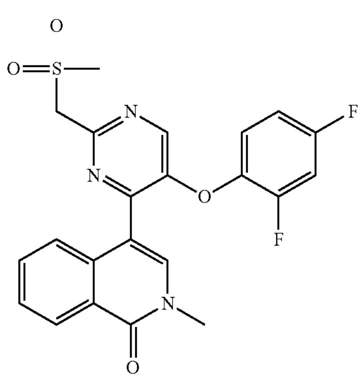 | 4-[5-(2,4-difluorophenoxy)-2-(methylsulfonylmethyl)pyrimidin-4-yl]-2-methylisoquinolin-1-one |

TABLE 1-continued

| Chemical Synthesis Example | Structure | Name |
|---|---|---|
| 149 | 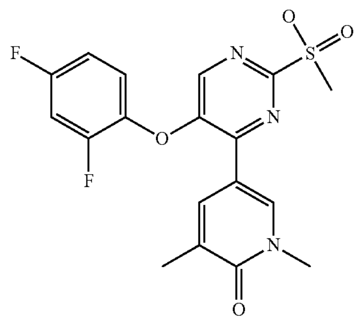 | 5-[5-(2,4-difluorophenoxy)-2-methylsulfonylpyrimidin-4-yl]-1,3-dimethylpyridin-2-one |
| 150 | 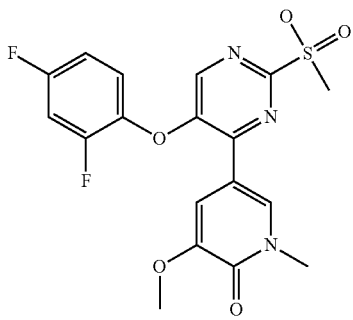 | 5-[5-(2,4-difluorophenoxy)-2-methylsulfonylpyrimidin-4-yl]-3-methoxy-1-methylpyridin-2-one |
| 151 | 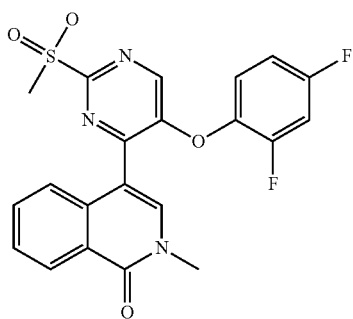 | 4-[5-(2,4-difluorophenoxy)-2-methylsulfonylpyrimidin-4-yl]-2-methylisoquinolin-1-one |
| 152 | 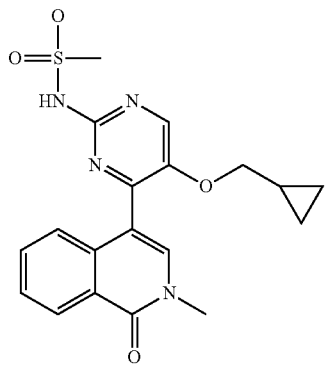 | N-[5-(cyclopropylmethoxy)-4-(2-methyl-1-oxoisoquinolin-4-yl)pyrimidin-2-yl]methanesulfonamide |

TABLE 1-continued

| Chemical Synthesis Example | Structure | Name |
|---|---|---|
| 153 | 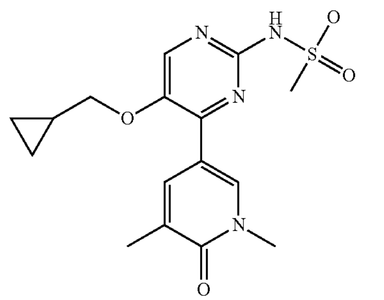 | N-[5-(cyclopropylmethoxy)-4-(1,5-dimethyl-6-oxopyridin-3-yl)pyrimidin-2-yl]methanesulfonamide |
| 154 | 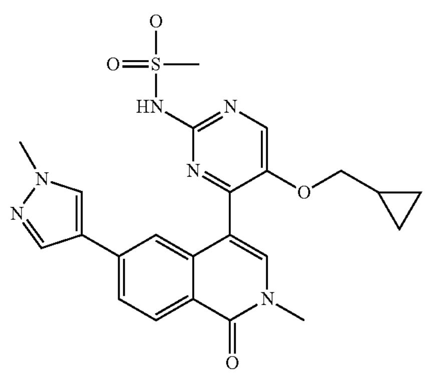 | N-[5-(cyclopropylmethoxy)-4-[2-methyl-6-(1-methylpyrazol-4-yl)-1-oxoisoquinolin-4-yl]pyrimidin-2-yl]methanesulfonamide |
| 155 | 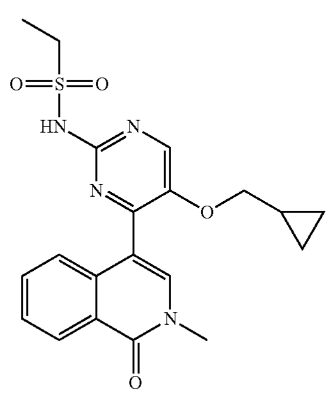 [SMILES: CCS(=O)(=O)Nc1ncc(OCC2CC2)c(-c2cn(C)c(=O)c3ccccc23)n1] | N-[5-(cyclopropylmethoxy)-4-(2-methyl-1-oxoisoquinolin-4-yl)pyrimidin-2-yl]ethanesulfonamide |
| 156 | 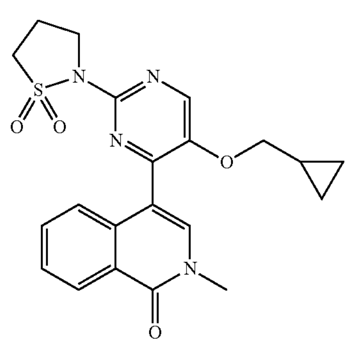 [SMILES: Cn1cc(-c2nc(N3CCCS3(=O)=O)ncc2OCC2CC2)c2ccccc2c1=O] | 4-[5-(cyclopropylmethoxy)-2-(1,1-dioxo-1,2-thiazolidin-2-yl)pyrimidin-4-yl]-2-methylisoquinolin-1-one |

TABLE 1-continued

| Chemical Synthesis Example | Structure | Name |
|---|---|---|
| 157 | 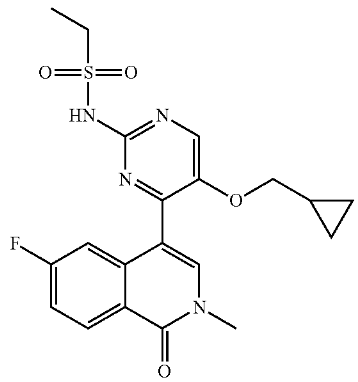 [SMILES: CCS(=O)(=O)Nc1ncc(OCC2CC2)c(-c2cn(C)c(=O)c3ccc(F)cc23)n1] | N-[5-(cyclopropylmethoxy)-4-(6-fluoro-2-methyl-1-oxoisoquinolin-4-yl)pyrimidin-2-yl] ethanesulfonamide |
| 158 | 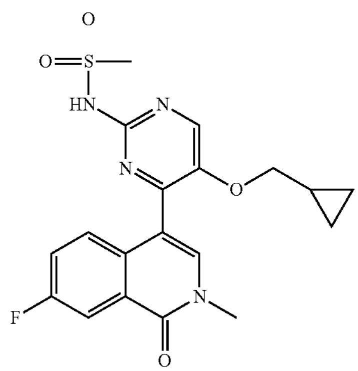 | N-[5-(cyclopropylmethoxy)-4-(7-fluoro-2-methyl-1-oxoisoquinolin-4-yl)pyrimidin-2-yl] methanesulfonamide |
| 159 | 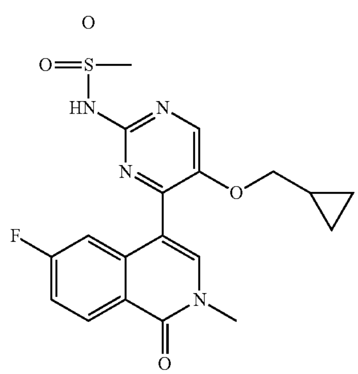 | N-[5-(cyclopropylmethoxy)-4-(6-fluoro-2-methyl-1-oxoisoquinolin-4-yl)pyrimidin-2-yl] methanesulfonamide |
| 160 | 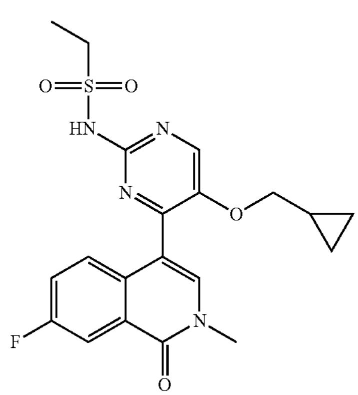 [SMILES: CCS(=O)(=O)Nc1ncc(OCC2CC2)c(-c2cn(C)c(=O)c3cc(F)ccc23)n1] | N-[5-(cyclopropylmethoxy)-4-(7-fluoro-2-methyl-1-oxoisoquinolin-4-yl)pyrimidin-2-yl] ethanesulfonamide |

TABLE 1-continued

| Chemical Synthesis Example | Structure | Name |
|---|---|---|
| 161 | 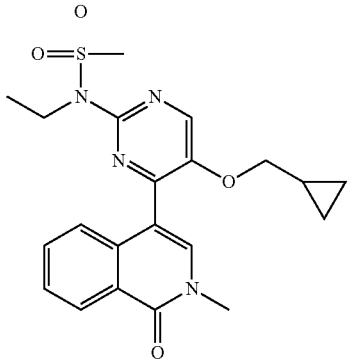 | N-[5-(cyclopropylmethoxy)-4-(2-methyl-1-oxoisoquinolin-4-yl)pyrimidin-2-yl]-N-ethylmethanesulfonamide |
| 162 | 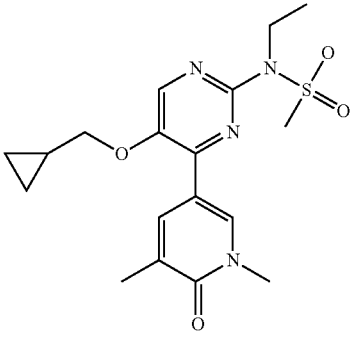 | N-[5-(cyclopropylmethoxy)-4-(1,5-dimethyl-6-oxopyridin-3-yl)pyrimidin-2-yl]-N-ethylmethanesulfonamide |
| 163 | 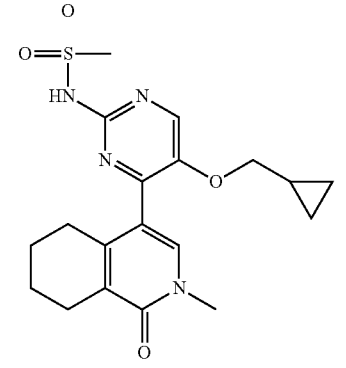 | N-[5-(cyclopropylmethoxy)-4-(2-methyl-1-oxo-5,6,7,8-tetrahydroisoquinolin-4-yl)pyrimidin-2-yl]methanesulfonamide |
| 164 | 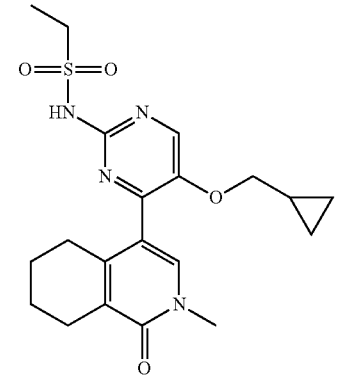 [SMILES: CCS(=O)(=O)Nc1ncc(OCC2CC2)c(-c2cn(C)c(=O)c3c2CCCC3)n1] | N-[5-(cyclopropylmethoxy)-4-(2-methyl-1-oxo-5,6,7,8-tetrahydroisoquinolin-4-yl)pyrimidin-2-yl]ethanesulfonamide |

TABLE 1-continued

| Chemical Synthesis Example | Structure | Name |
|---|---|---|
| 165 | 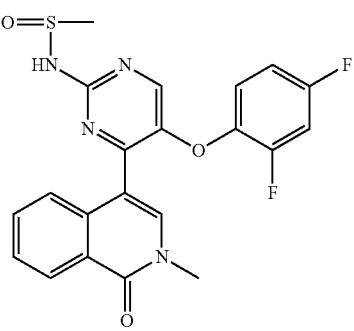 | N-[5-(2,4-difluorophenoxy)-4-(2-methyl-1-oxoisoquinolin-4-yl)pyrimidin-2-yl]methanesulfonamide |
| 166 | 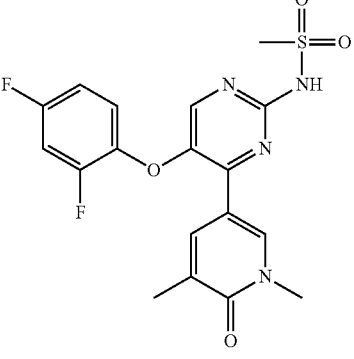 | N-[5-(2,4-difluorophenoxy)-4-(1,5-dimethyl-6-oxopyridin-3-yl)pyrimidin-2-yl]methanesulfonamide |
| 167 | 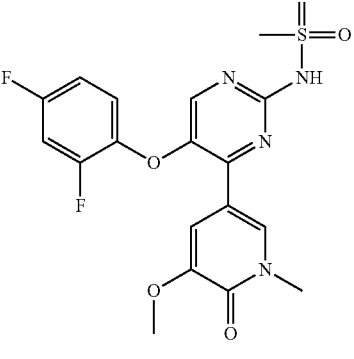 | N-[5-(2,4-difluorophenoxy)-4-(5-methoxy-1-methyl-6-oxopyridin-3-yl)pyrimidin-2-yl]methanesulfonamide |
| 168 | 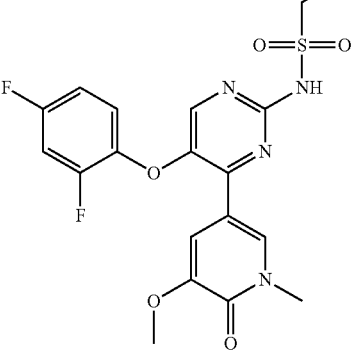 | N-[5-(2,4-difluorophenoxy)-4-(5-methoxy-1-methyl-6-oxopyridin-3-yl)pyrimidin-2-yl]ethanesulfonamide |

TABLE 1-continued

| Chemical Synthesis Example | Structure | Name |
|---|---|---|
| 169 | 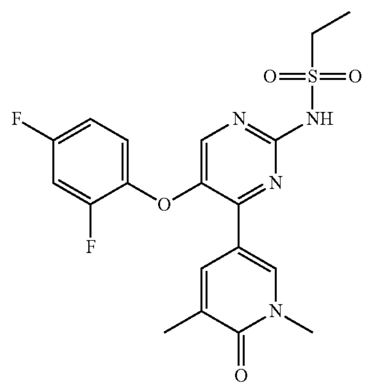 [SMILES: CCS(=O)(=O)Nc1ncc(Oc2ccc(F)cc2F)c(-c2cc(C)c(=O)n(C)c2)n1] | N-[5-(2,4-difluorophenoxy)-4-(1,5-dimethyl-6-oxopyridin-3-yl)pyrimidin-2-yl]ethanesulfonamide |
| 170 | 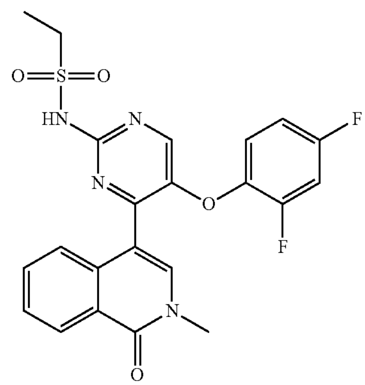 | N-[5-(2,4-difluorophenoxy)-4-(2-methyl-1-oxoisoquinolin-4-yl)pyrimidin-2-yl]ethanesulfonamide |
| 171 | 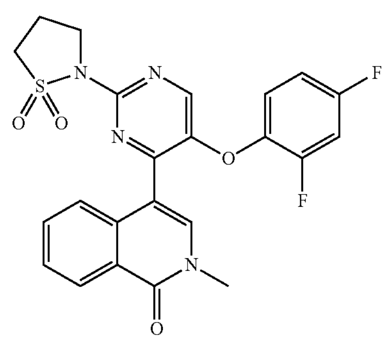 [SMILES: Cn1cc(-c2nc(N3CCCS3(=O)=O)ncc2Oc2ccc(F)cc2F)c2ccccc2c1=O] | 4-[5-(2,4-difluorophenoxy)-2-(1,1-dioxo-1,2-thiazolidin-2-yl)pyrimidin-4-yl]-2-methylisoquinolin-1-one |
| 172 | 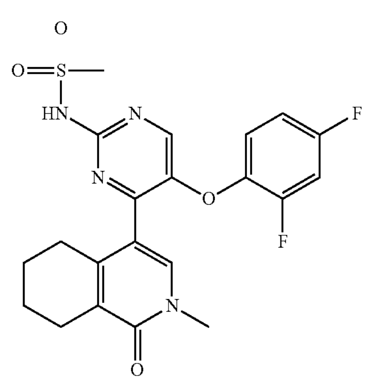 | N-[5-(2,4-difluorophenoxy)-4-(2-methyl-1-oxo-5,6,7,8-tetrahydroisoquinolin-4-yl)pyrimidin-2-yl]methanesulfonamide |

TABLE 1-continued
| Chemical Synthesis Example | Structure | Name |
|---|---|---|
| 173 | 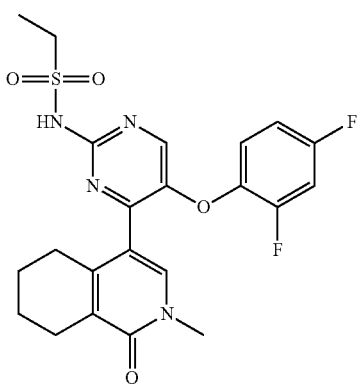 [SMILES: CCS(=O)(=O)Nc1ncc(Oc2ccc(F)cc2F)c(-c2cn(C)c(=O)c3c2CCCC3)n1] | N-[5-(2,4-difluorophenoxy)-4-(2-methyl-1-oxo-5,6,7,8-tetrahydroisoquinolin-4-yl)pyrimidin-2-yl]ethanesulfonamide |
| 174 | 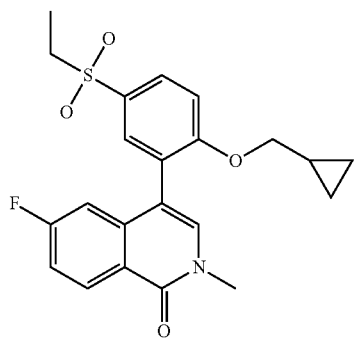 [SMILES: CCS(O)(O)c1ccc(OCC2CC2)c(-c2cn(C)c(=O)c3ccc(F)cc23)c1] | 4-[2-(cyclopropylmethoxy)-5-ethylsulfonylphenyl]-6-fluoro-2-methylisoquinolin-1-one |
| 175 | 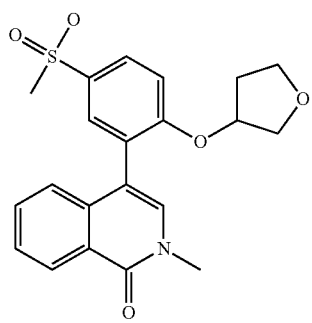 | 2-methyl-4-[5-methylsulfonyl-2-(oxolan-3-yloxy)phenyl]isoquinolin-1-one |
| 176 | 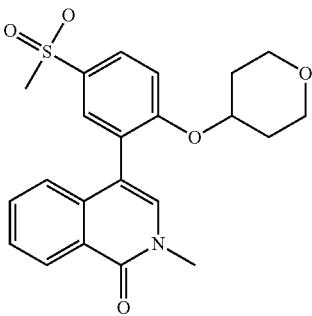 | 2-methyl-4-[5-methylsulfonyl-2-(oxan-4-yloxy)phenyl]isoquinolin-1-one |

TABLE 1-continued
| Chemical Synthesis Example | Structure | Name |
|---|---|---|
| 177 | 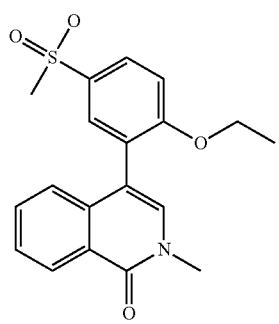 | 4-(2-ethoxy-5-methylsulfonylphenyl)-2-methylisoquinolin-1-one |
| 178 | 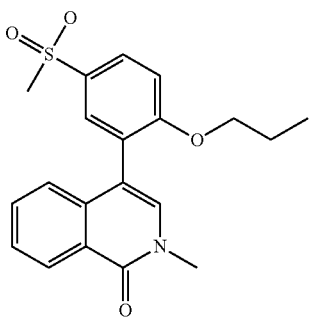 | 2-methyl-4-(5-methylsulfonyl-2-propoxyphenyl)isoquinolin-1-one |
| 179 | 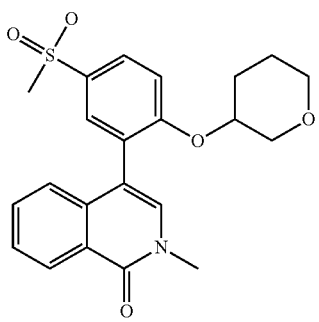 | 2-methyl-4-[5-methylsulfonyl-2-(oxan-3-yloxy)phenyl]isoquinolin-1-one |
| 180 | 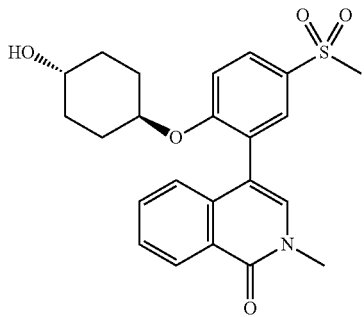 [SMILES: Cn1cc(-c2cc(S(C)(=O)=O)ccc2O[C@H]2CC[C@H](O)CC2)c2ccccc2c1=O] | 4-[2-(trans-4-hydroxycyclohexyl)oxy-5-methylsulfonylphenyl]-2-methylisoquinolin-1-one |

TABLE 1-continued
| Chemical Synthesis Example | Structure | Name |
|---|---|---|
| 181 | 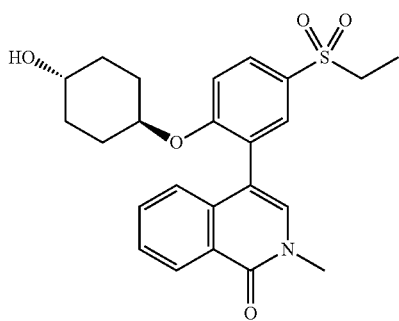 [SMILES: CCS(=O)(=O)c1ccc(O[C@H]2CC[C@H](O)CC2)c(-c2cn(C)c(=O)c3ccccc23)c1] | 4-[5-ethylsulfonyl-2-(trans-4-hydroxycyclohexyl)oxyphenyl]-2-methylisoquinolin-1-one |
| 182 | 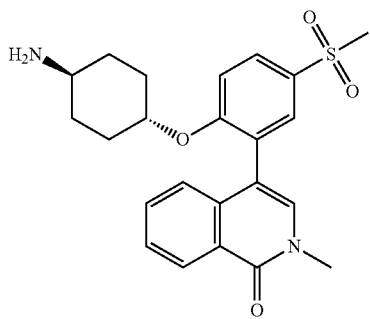 [SMILES: Cn1cc(-c2cc(S(C)(=O)=O)ccc2O[C@H]2CC[C@H](N)CC2)c2ccccc2c1=O] | 4-[2-(trans-4-aminocyclohexyl)oxy-5-methylsulfonylphenyl]-2-methylisoquinolin-1-one |
| 183 | 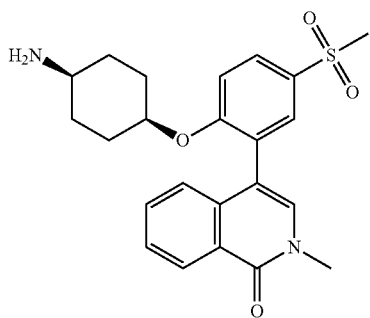 [SMILES: Cn1cc(-c2cc(S(C)(=O)=O)ccc2O[C@H]2CC[C@@H](N)CC2)c2ccccc2c1=O] | 4-[2-(cis-4-aminocyclohexyl)oxy-5-methylsulfonylphenyl]-2-methylisoquinolin-1-one |
| 184 | 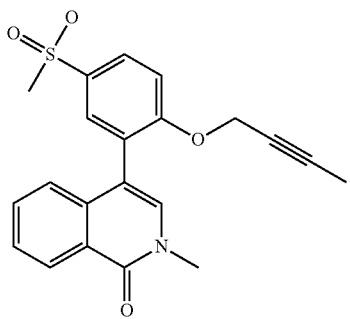 | 4-(2-but-2-ynoxy-5-methylsulfonylphenyl)-2-methylisoquinolin-1-one |

TABLE 1-continued

| Chemical Synthesis Example | Structure | Name |
|---|---|---|
| 185 | 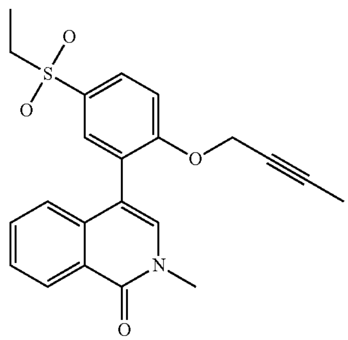 [SMILES: CC#CCOc1ccc(S(O)(O)CC)cc1-c1cn(C)c(=O)c2ccccc12] | 4-(2-but-2-ynoxy-5-ethylsulfonylphenyl)-2-methylisoquinolin-1-one |
| 186 | 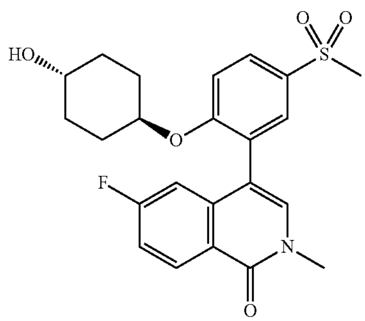 [SMILES: Cn1cc(-c2cc(S(C)(=O)=O)ccc2O[C@H]2CC[C@H](O)CC2)c2cc(F)ccc2c1=O] | 6-fluoro-4-[2-(trans-4-hydroxycyclohexyl)oxy-5-methylsulfonylphenyl]-2-methylisoquinolin-1-one |
| 187 | 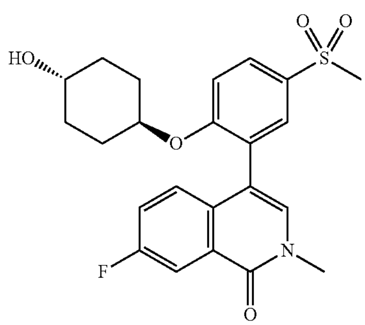 [SMILES: Cn1cc(-c2cc(S(C)(=O)=O)ccc2O[C@H]2CC[C@H](O)CC2)c2ccc(F)cc2c1=O] | 7-fluoro-4-[2-(trans-4-hydroxycyclohexyl)oxy-5-methylsulfonylphenyl]-2-methylisoquinolin-1-one |
| 188 | 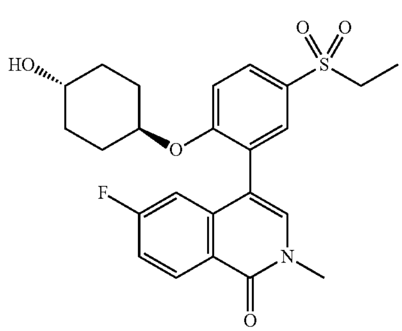 [SMILES: CCS(=O)(=O)c1ccc(O[C@H]2CC[C@H](O)CC2)c(-c2cn(C)c(=O)c3ccc(F)cc23)c1] | 4-[5-ethylsulfonyl-2-(trans-4-hydroxycyclohexyl)oxyphenyl]-6-fluoro-2-methylisoquinolin-1-one |

TABLE 1-continued
| Chemical Synthesis Example | Structure | Name |
|---|---|---|
| 189 | 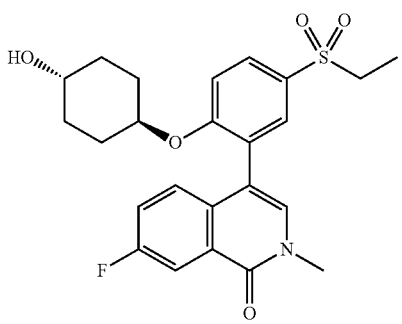 [SMILES: CCS(=O)(=O)c1ccc(O[C@H]2CC[C@H](O)CC2)c(-c2cn(C)c(=O)c3cc(F)ccc23)c1] | 4-[5-ethylsulfonyl-2-(trans-4-hydroxycyclohexyl)oxyphenyl]-7-fluoro-2-methylisoquinolin-1-one |
| 190 | 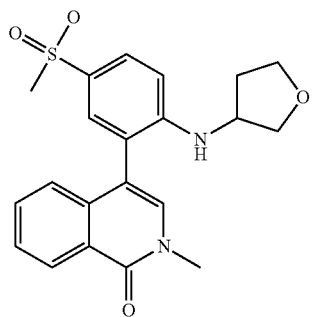 | 2-methyl-4-[5-methylsulfonyl-2-(oxolan-3-ylamino)phenyl]isoquinolin-1-one |
| 191 | 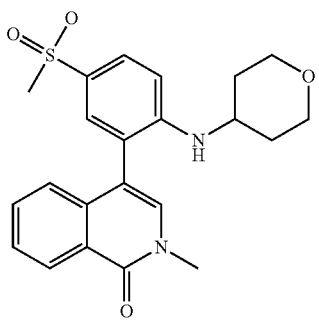 | 2-methyl-4-[5-methylsulfonyl-2-(oxan-4-ylamino)phenyl]isoquinolin-1-one |
| 192 | 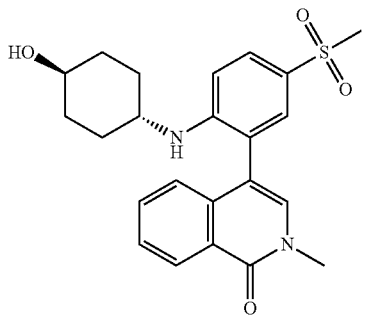 [SMILES: Cn1cc(-c2cc(S(C)(=O)=O)ccc2N[C@H]2CC[C@H](O)CC2)c2ccccc2c1=O] | 4-[2-[(trans-4-hydroxycyclohexyl)amino]-5-methylsulfonylphenyl]-2-methylisoquinolin-1-one |

TABLE 1-continued

| Chemical Synthesis Example | Structure | Name |
|---|---|---|
| 193 | 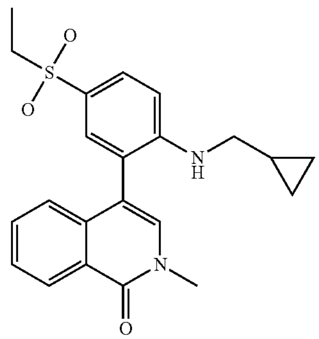 [SMILES: CCS(O)(O)c1ccc(NCC2CC2)c(-c2cn(C)c(=O)c3ccccc23)c1] | 4-[2-(cyclopropylmethylamino)-5-ethylsulfonylphenyl]-2-methylisoquinolin-1-one |
| 194 | 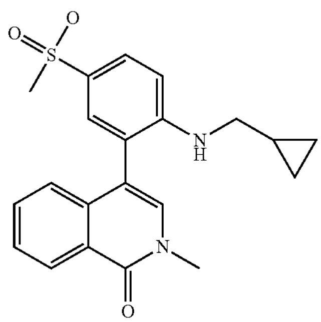 | 4-[2-(cyclopropylmethylamino)-5-methylsulfonylphenyl]-2-methylisoquinolin-1-one |
| 195 | 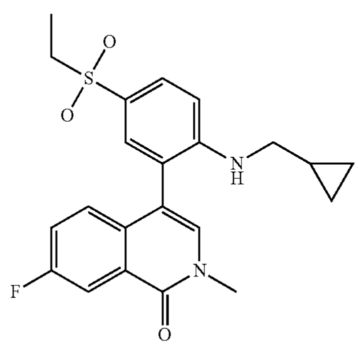 [SMILES: CCS(O)(O)c1ccc(NCC2CC2)c(-c2cn(C)c(=O)c3cc(F)ccc23)c1] | 4-[2-(cyclopropylmethylamino)-5-ethylsulfonylphenyl]-7-fluoro-2-methylisoquinolin-1-one |
| 196 | 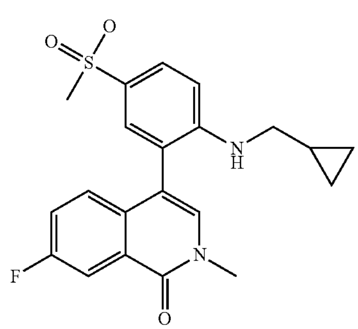 | 4-[2-(cyclopropylmethylamino)-5-methylsulfonylphenyl]-7-fluoro-2-methylisoquinolin-1-one |

TABLE 1-continued

| Chemical Synthesis Example | Structure | Name |
|---|---|---|
| 197 | 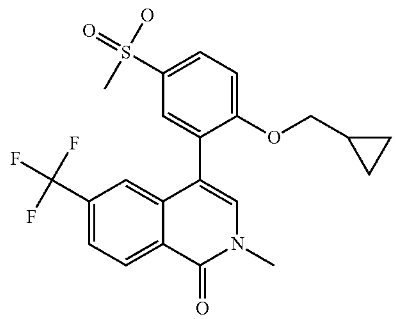 | 4-[2-(cyclopropylmethoxy)-5-methylsulfonylphenyl]-2-methyl-6-(trifluoromethyl)isoquinolin-1-one |
| 198 | 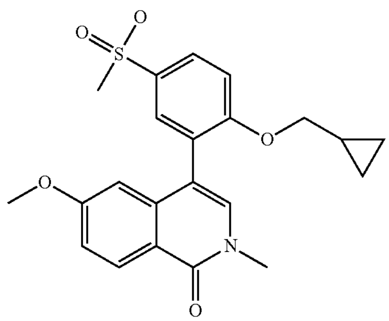 | 4-[2-(cyclopropylmethoxy)-5-methylsulfonylphenyl]-6-methoxy-2-methylisoquinolin-1-one |
| 199 | 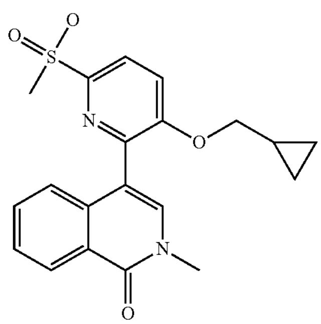 | 4-[3-(cyclopropylmethoxy)-6-methylsulfonylpyridin-2-yl]-2-methylisoquinolin-1-one |
| 200 | 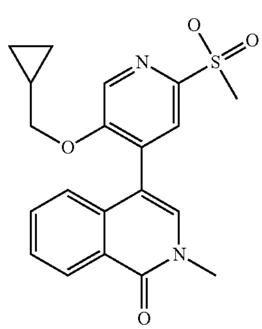 | 4-[5-(cyclopropylmethoxy)-2-methylsulfonylpyridin-4-yl]-2-methylisoquinolin-1-one |

TABLE 1-continued

| Chemical Synthesis Example | Structure | Name |
|---|---|---|
| 201 | 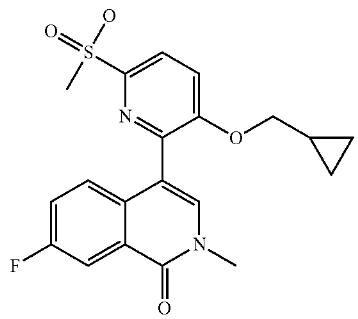 | 4-[3-(cyclopropylmethoxy)-6-methylsulfonylpyridin-2-yl]-7-fluoro-2-methylisoquinolin-1-one |
| 202 | 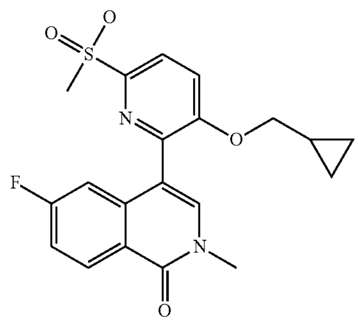 | 4-[3-(cyclopropylmethoxy)-6-methylsulfonylpyridin-2-yl]-6-fluoro-2-methylisoquinolin-1-one |
| 203 | 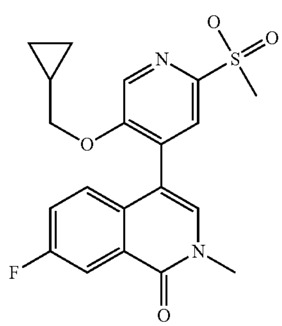 | 4-[5-(cyclopropylmethoxy)-2-methylsulfonylpyridin-4-yl]-7-fluoro-2-methylisoquinolin-1-one |
| 204 | 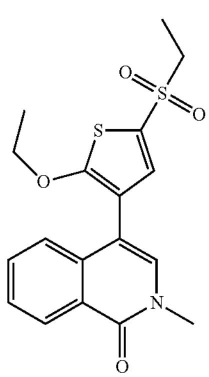 [SMILES: CCOc1sc(S(=O)(=O)CC)cc1-c1cn(C)c(=O)c2ccccc12] | 4-(2-ethoxy-5-ethylsulfonylthiophen-3-yl)-2-methylisoquinolin-1-one |

TABLE 1-continued

| Chemical Synthesis Example | Structure | Name |
|---|---|---|
| 205 | 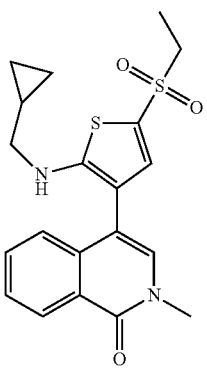 [SMILES: CCS(=O)(=O)c1cc(-c2cn(C)c(=O)c3ccccc23)c(NCC2CC2)s1] | 4-[2-(cyclopropylmethylamino)-5-ethylsulfonylthiophen-3-yl]-2-methylisoquinolin-1-one |
| 206 | 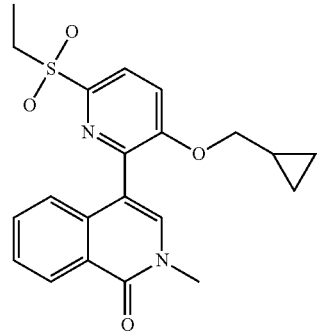 [SMILES: CCS(O)(O)c1ccc(OCC2CC2)c(-c2cn(C)c(=O)c3ccccc23)n1] | 4-[3-(cyclopropylmethoxy)-6-ethylsulfonylpyridin-2-yl]-2-methylisoquinolin-1-one |
| 207 | 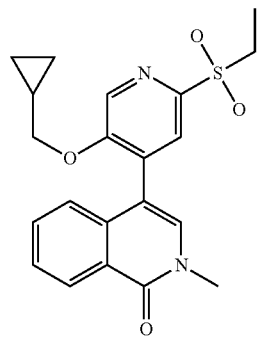 [SMILES: CCS(O)(O)c1cc(-c2cn(C)c(=O)c3ccccc23)c(OCC2CC2)cn1] | 4-[5-(cyclopropylmethoxy)-2-ethylsulfonylpyridin-4-yl]-2-methylisoquinolin-1-one |
| 208 | 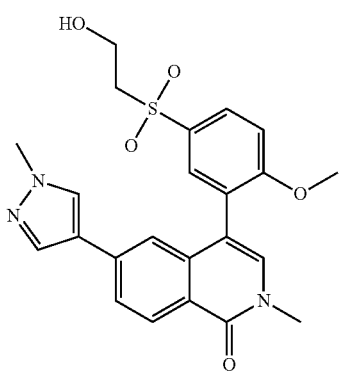 [SMILES: COc1ccc(S(O)(O)CCO)cc1-c1cn(C)c(=O)c2ccc(-c3cnn(C)c3)cc12] | 4-[5-(2-hydroxyethylsulfonyl)-2-methoxyphenyl]-2-methyl-6-(1-methylpyrazol-4-yl)isoquinolin-1-one |

TABLE 1-continued

| Chemical Synthesis Example | Structure | Name |
|---|---|---|
| 209 | 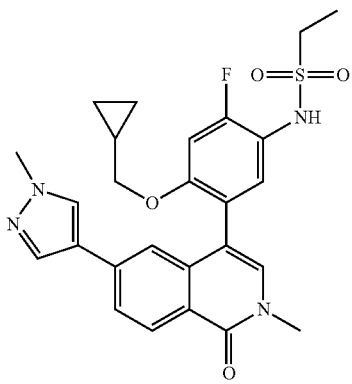 [SMILES: CCS(=O)(=O)Nc1cc(-c2cn(C)c(=O)c3ccc(-c4cnn(C)c4)cc23)c(OCC2CC2)cc1F] | N-[4-(cyclopropylmethoxy)-2-fluoro-5-[2-methyl-6-(1-methylpyrazol-4-yl)-1-oxoisoquinolin-4-yl]phenyl]ethanesulfonamide |
| 210 | 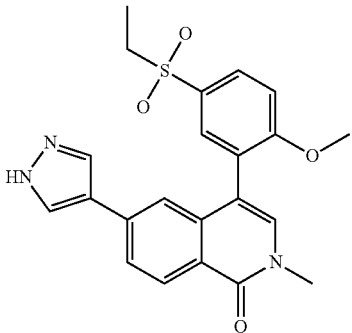 [SMILES: CCS(O)(O)c1ccc(OC)c(-c2cn(C)c(=O)c3ccc(-c4cn[nH]c4)cc23)c1] | 4-(5-ethylsulfonyl-2-methoxyphenyl)-2-methyl-6-(1H-pyrazol-4-yl)isoquinolin-1-one |
| 211 | 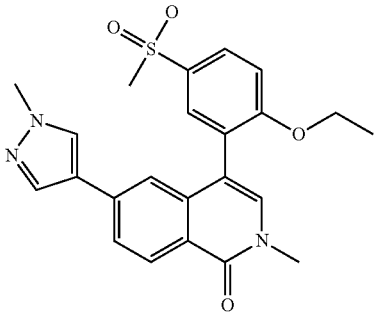 | 4-(2-ethoxy-5-methylsulfonylphenyl)-2-methyl-6-(1-methylpyrazol-4-yl)isoquinolin-1-one |
| 212 | 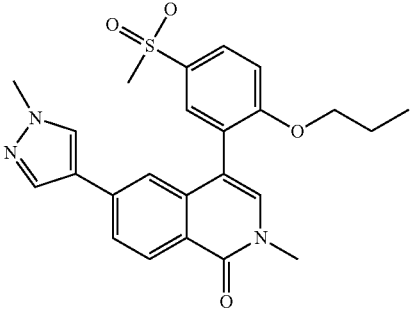 | 2-methyl-6-(1-methylpyrazol-4-yl)-4-(5-methylsulfonyl-2-propoxyphenyl)isoquinolin-1-one |

TABLE 1-continued

| Chemical Synthesis Example | Structure | Name |
|---|---|---|
| 213 | 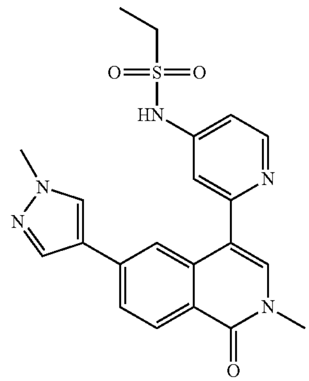 [SMILES: CCS(=O)(=O)Nc1ccnc(-c2cn(C)c(=O)c3ccc(-c4cnn(C)c4)cc23)c1] | N-[2-[2-methyl-6-(1-methylpyrazol-4-yl)-1-oxoisoquinolin-4-yl]pyridin-4-yl]ethanesulfonamide |
| 214 | 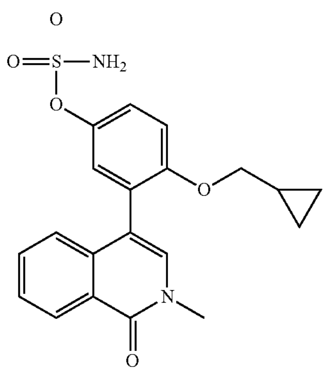 | [4-(cyclopropylmethoxy)-3-(2-methyl-1-oxoisoquinolin-4-yl)phenyl]sulfamate |
| 215 | 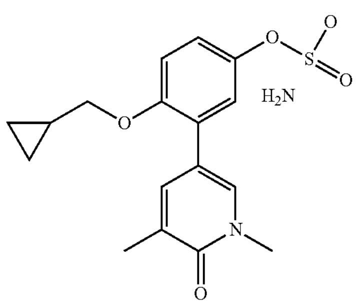 | [4-(cyclopropylmethoxy)-3-(1,5-dimethyl-6-oxopyridin-3-yl)phenyl]sulfamate |
| 216 | 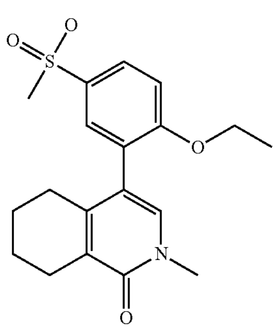 | 4-(2-ethoxy-5-methylsulfonylphenyl)-2-methyl-5,6,7,8-tetrahydro-isoquinolin-1-one |

TABLE 1-continued

| Chemical Synthesis Example | Structure | Name |
|---|---|---|
| 217 | 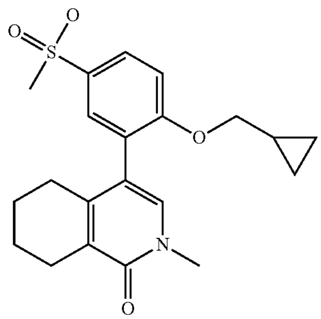 | 4-[2-(cyclopropylmethoxy)-5-methylsulfonylphenyl]-2-methyl-5,6,7,8-tetrahydroisoquinolin-1-one |
| 218 | 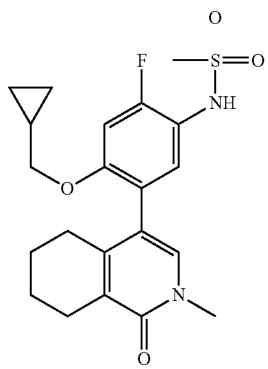 | N-[4-(cyclopropylmethoxy)-2-fluoro-5-(2-methyl-1-oxo-5,6,7,8-tetrahydroisoquinolin-4-yl)phenyl]methanesulfonamide |
| 219 | 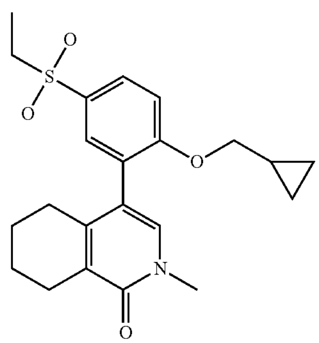 [SMILES: CCS(O)(O)c1ccc(OCC2CC2)c(-c2cn(C)c(=O)c3c2CCCC3)c1] | 4-[2-(cyclopropylmethoxy)-5-ethylsulfonylphenyl]-2-methyl-5,6,7,8-tetrahydroisoquinolin-1-one |
| 220 | 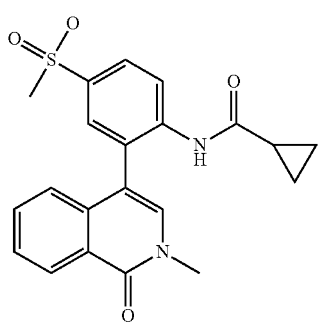 | N-[2-(2-methyl-1-oxoisoquinolin-4-yl)-4-methylsulfonylphenyl]-cyclopropanecarboxamide |

TABLE 1-continued

| Chemical Synthesis Example | Structure | Name |
|---|---|---|
| 221 | 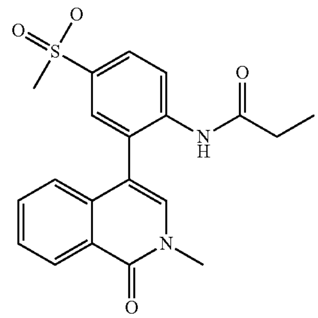 | N-[2-(2-methyl-1-oxoisoquinolin-4-yl)-4-methylsulfonylphenyl]propanamide |
| 222 | 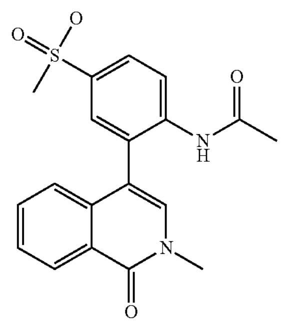 | N-[2-(2-methyl-1-oxoisoquinolin-4-yl)-4-methylsulfonylphenyl]acetamide |
| 223 | 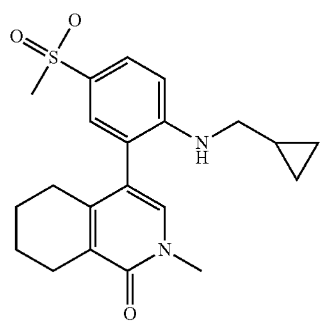 | 4-[2-(cyclopropylmethylamino)-5-methylsulfonylphenyl]-2-methyl-5,6,7,8-tetrahydroisoquinolin-1-one |
| 224 | 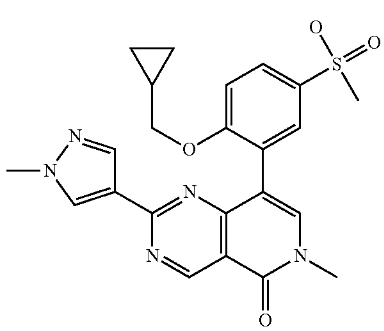 | 8-[2-(cyclopropylmethoxy)-5-methylsulfonylphenyl]-6-methyl-2-(1-methylpyrazol-4-yl)pyrido[4,3-d]pyrimidin-5-one |

TABLE 1-continued

| Chemical Synthesis Example | Structure | Name |
|---|---|---|
| 225 | 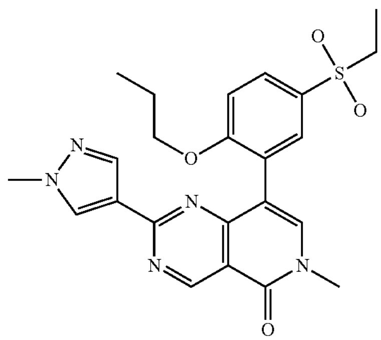 [SMILES: CCCOc1ccc(S(O)(O)CC)cc1-c1cn(C)c(=O)c2cnc(-c3cnn(C)c3)nc12] | 8-(5-ethylsulfonyl-2-propoxyphenyl)-6-methyl-2-(1-methylpyrazol-4-yl)pyrido[4,3-d]pyrimidin-5-one |
| 226 | 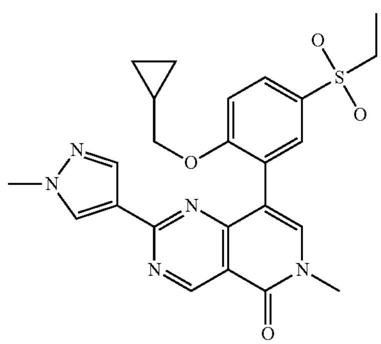 [SMILES: CCS(O)(O)c1ccc(OCC2CC2)c(-c2cn(C)c(=O)c3cnc(-c4cnn(C)c4)nc23)c1] | 8-[2-(cyclopropylmethoxy)-5-ethylsulfonylphenyl]-6-methyl-2-(1-methylpyrazol-4-yl)pyrido[4,3-d]pyrimidin-5-one |
| 227 | 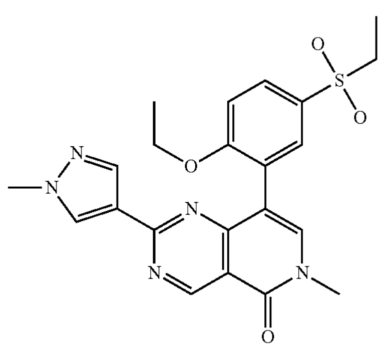 [SMILES: CCOc1ccc(S(O)(O)CC)cc1-c1cn(C)c(=O)c2cnc(-c3cnn(C)c3)nc12] | 8-(2-ethoxy-5-ethylsulfonylphenyl)-6-methyl-2-(1-methylpyrazol-4-yl)pyrido[4,3-d]pyrimidin-5-one |
| 228 | 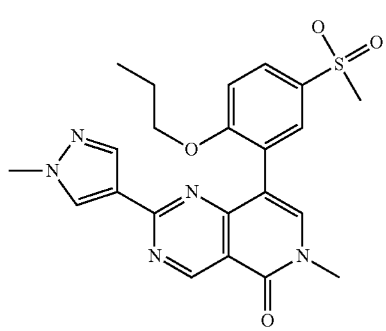 | 6-methyl-2-(1-methylpyrazol-4-yl)-8-(5-methylsulfonyl-2-propoxyphenyl)pyrido[4,3-d]pyrimidin-5-one |

TABLE 1-continued

| Chemical Synthesis Example | Structure | Name |
|---|---|---|
| 229 | 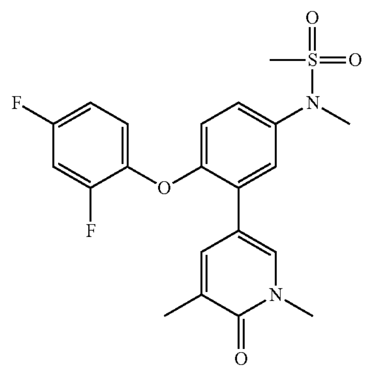 [SMILES: Cc1cc(-c2cc(N(C)S(C)(=O)=O)ccc2Oc2ccc(F)cc2F)cn(C)c1=O] | N-[4-(2,4-difluorophenoxy)-3-(1,5-dimethyl-6-oxopyridin-3-yl)phenyl]-N-methylmethanesulfonamide |
| 230 | 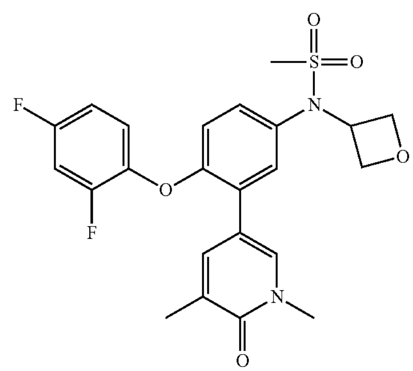 [SMILES: Cc1cc(-c2cc(N(C3COC3)S(C)(=O)=O)ccc2Oc2ccc(F)cc2F)cn(C)c1=O] | N-[4-(2,4-difluorophenoxy)-3-(1,5-dimethyl-6-oxopyridin-3-yl)phenyl]-N-(oxetan-3-yl)methanesulfonamide |
| 231 | 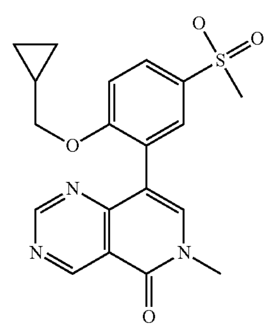 | 8-[2-(cyclopropylmethoxy)-5-methylsulfonylphenyl]-6-methylpyrido[4,3-d]pyrimidin-5-one |
| 232 | 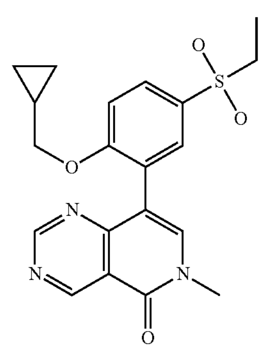 [SMILES: CCS(O)(O)c1ccc(OCC2CC2)c(-c2cn(C)c(=O)c3cncnc23)c1] | 8-[2-(cyclopropylmethoxy)-5-ethylsulfonylphenyl]-6-methylpyrido[4,3-d]pyrimidin-5-one |

TABLE 1-continued
| Chemical Synthesis Example | Structure | Name |
|---|---|---|
| 233 | 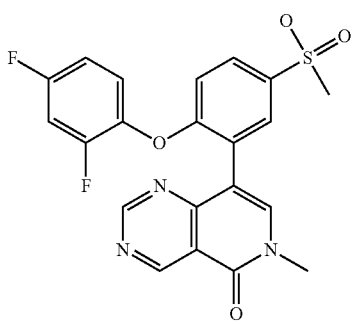 | 8-[2-(2,4-difluorophenoxy)-5-methylsulfonylphenyl]-6-methylpyrido[4,3-d]pyrimidin-5-one |
| 234 | 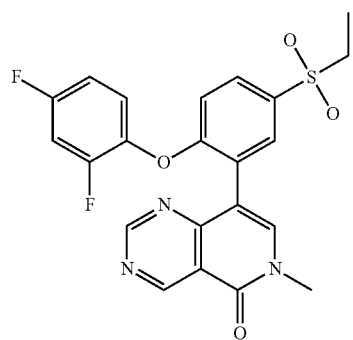 [SMILES: CCS(O)(O)c1ccc(Oc2ccc(F)cc2F)c(-c2cn(C)c(=O)c3cncnc23)c1] | 8-[2-(2,4-difluorophenoxy)-5-ethylsulfonylphenyl]-6-methylpyrido[4,3-d]pyrimidin-5-one |
| 235 | 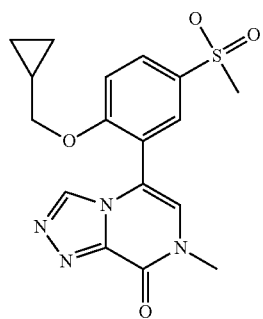 | 5-[2-(cyclopropylmethoxy)-5-methylsulfonylphenyl]-7-methyl-[1,2,4]triazolo[4,3-a]pyrazin-8-one |
| 236 | 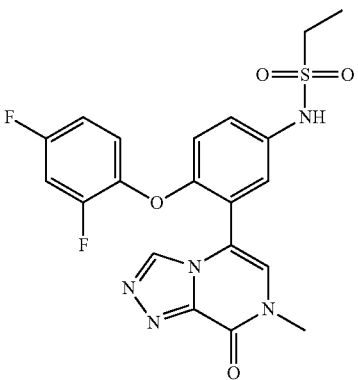 | N-[4-(2,4-difluorophenoxy)-3-(7-methyl-8-oxo-[1,2,4]triazolo[4,3-a]pyrazin-5-yl)phenyl]ethanesulfonamide |

TABLE 1-continued

| Chemical Synthesis Example | Structure | Name |
|---|---|---|
| 237 | 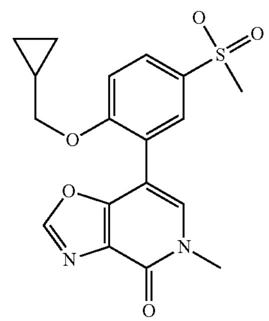 | 7-[2-(cyclopropylmethoxy)-5-methylsulfonylphenyl]-5-methyl-[1,3]oxazolo[4,5-c]pyridin-4-one |
| 238 | 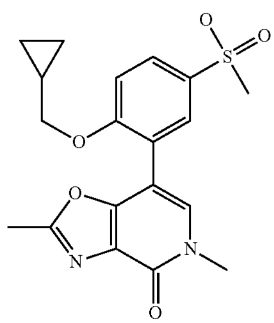 | 7-[2-(cyclopropylmethoxy)-5-methylsulfonylphenyl]-2,5-dimethyl-[1,3]oxazolo[4,5-c]pyridin-4-one |
| 239 | 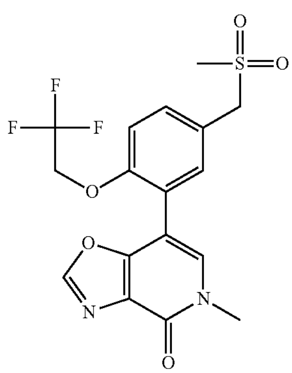 [SMILES: Cn1cc(-c2cc(CS(C)(=O)=O)ccc2OCC(F)(F)F)c2ocnc2c1=O] | 5-methyl-7-[5-(methylsulfonylmethyl)-2-(2,2,2-trifluoroethoxy)phenyl]-[1,3]oxazolo[4,5-c]pyridin-4-one |
| 240 | 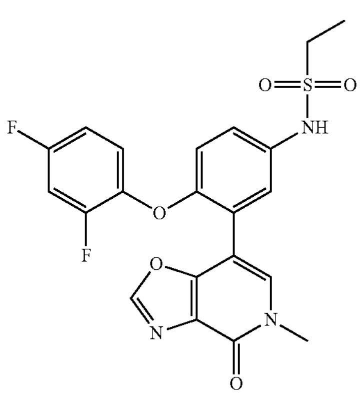 | N-[4-(2,4-difluorophenoxy)-3-(5-methyl-4-oxo-[1,3]oxazolo[4,5-c]pyridin-7-yl)phenyl]ethanesulfonamide |

TABLE 1-continued

| Chemical Synthesis Example | Structure | Name |
|---|---|---|
| 241 | 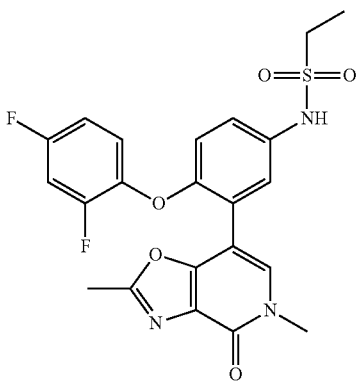 [SMILES: CCS(=O)(=O)Nc1ccc(Oc2ccc(F)cc2F)c(-c2cn(C)c(=O)c3nc(C)oc23)c1] | N-[4-(2,4-difluorophenoxy)-3-(2,5-dimethyl-4-oxo-[1,3]oxazolo-[4,5-c]pyridin-7-yl)phenyl]ethanesulfonamide |
| 242 | 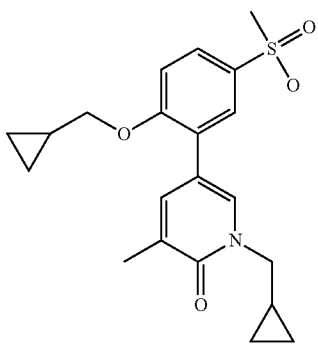 | 5-[2-(cyclopropylmethoxy)-5-methylsulfonylphenyl]-1-(cyclopropyl-methyl)-3-methylpyridin-2-one |
| 243 | 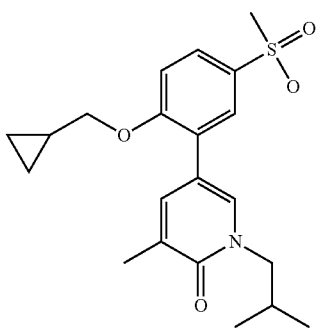 | 5-[2-(cyclopropylmethoxy)-5-methylsulfonylphenyl]-3-methyl-1-(2-methylpropyl)pyridin-2-one |
| 244 | 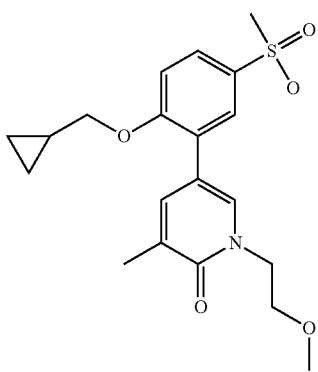 | 5-[2-(cyclopropylmethoxy)-5-methylsulfonylphenyl]-1-(2-methoxyethyl)-3-methylpyridin-2-one |

TABLE 1-continued

| Chemical Synthesis Example | Structure | Name |
|---|---|---|
| 245 | 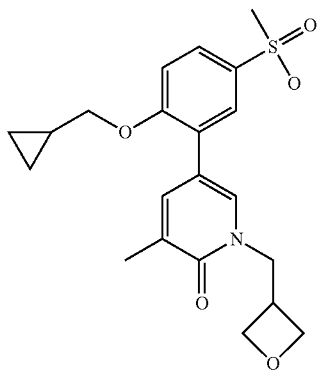 | 5-[2-(cyclopropylmethoxy)-5-methylsulfonylphenyl]-3-methyl-1-(oxetan-3-ylmethyl)pyridin-2-one |
| 246 | 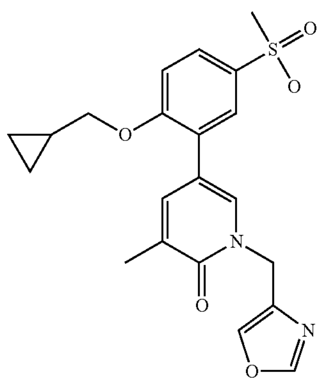 | 5-[2-(cyclopropylmethoxy)-5-methylsulfonylphenyl]-3-methyl-1-(1,3-oxazol-4-ylmethyl)pyridin-2-one |
| 247 | 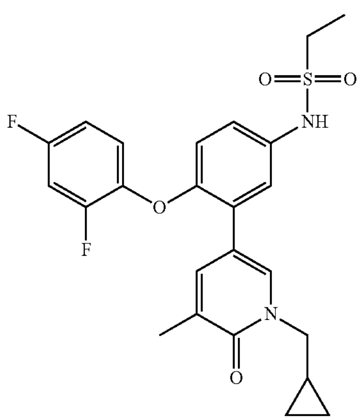 [SMILES: CCS(=O)(=O)Nc1ccc(Oc2ccc(F)cc2F)c(-c2cc(C)c(=O)n(CC3CC3)c2)c1] | N-[3-[1-(cyclopropylmethyl)-5-methyl-6-oxopyridin-3-yl]-4-(2,4-difluorophenoxy)phenyl]ethanesulfonamide |
| 248 | 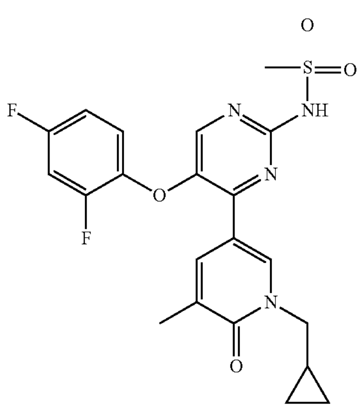 | N-[4-[1-(cyclopropylmethyl)-5-methyl-6-oxopyridin-3-yl]-5-(2,4-difluorophenoxy)pyrimidin-2-yl]methanesulfonamide |

TABLE 1-continued

| Chemical Synthesis Example | Structure | Name |
|---|---|---|
| 249 | 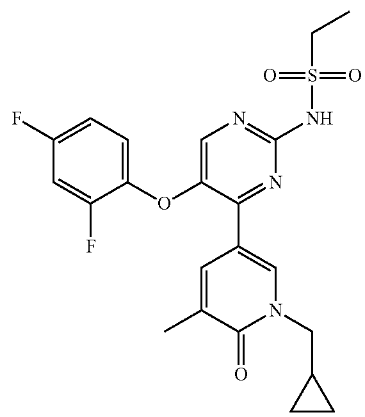 [SMILES: CCS(=O)(=O)Nc1ncc(Oc2ccc(F)cc2F)c(-c2cc(C)c(=O)n(CC3CC3)c2)n1] | N-[4-[1-(cyclopropylmethyl)-5-methyl-6-oxopyridin-3-yl]-5-(2,4-difluorophenoxy)pyrimidin-2-yl]ethanesulfonamide |
| 250 | 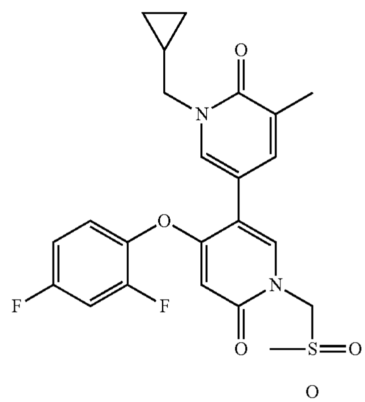 | 1-(cyclopropylmethyl)-5-[4-(2,4-difluorophenoxy)-1-(methylsulfonyl-methyl)-6-oxopyridin-3-yl]-3-methylpyridin-2-one |
| 251 | 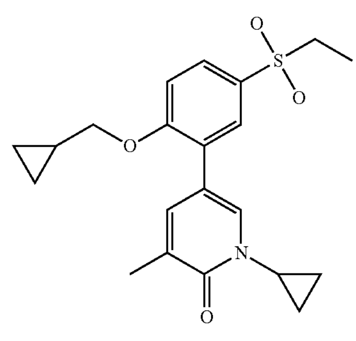 [SMILES: CCS(O)(O)c1ccc(OCC2CC2)c(-c2cc(C)c(=O)n(C3CC3)c2)c1] | 1-cyclopropyl-5-[2-(cyclopropylmethoxy)-5-ethylsulfonylphenyl]-3-methyl-pyridin-2-one |
| 252 | 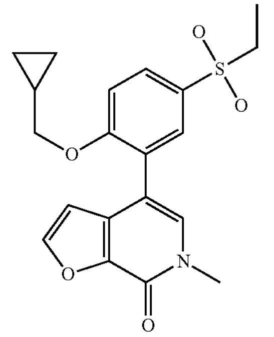 [SMILES: CCS(O)(O)c1ccc(OCC2CC2)c(-c2cn(C)c(=O)c3occc23)c1] | 4-[2-(cyclopropylmethoxy)-5-ethyl-sulfonylphenyl]-6-methylfuro[2,3-c]pyridin-7-one |

TABLE 1-continued

| Chemical Synthesis Example | Structure | Name |
|---|---|---|
| 253 | 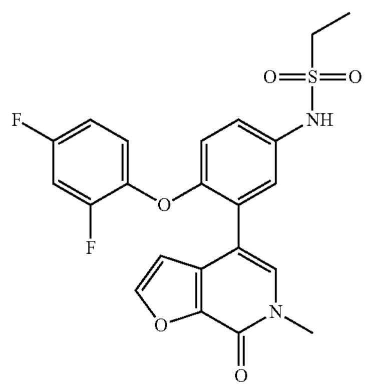 [SMILES: CCS(=O)(=O)Nc1ccc(Oc2ccc(F)cc2F)c(-c2cn(C)c(=O)c3occc23)c1] | N-[4-(2,4-difluorophenoxy)-3-(6-methyl-7-oxofuro[2,3-c]pyridin-4-yl)phenyl]ethanesulfonamide |
| 254 | 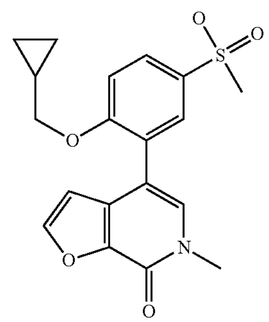 | 4-[2-(cyclopropylmethoxy)-5-methylsulfonylphenyl]-6-methylfuro[2,3-c]pyridin-7-one |
| 255 | 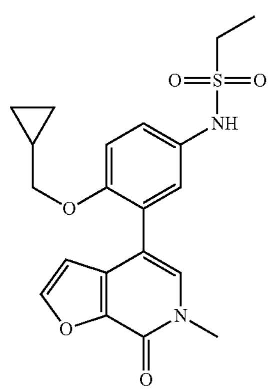 [SMILES: CCS(=O)(=O)Nc1ccc(OCC2CC2)c(-c2cn(C)c(=O)c3occc23)c1] | N-[4-(cyclopropylmethoxy)-3-(6-methyl-7-oxofuro[2,3-c]pyridin-4-yl)phenyl]ethanesulfonamide |
| 256 | 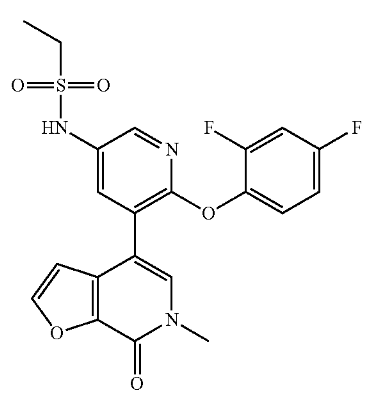 [SMILES: CCS(=O)(=O)Nc1cnc(Oc2ccc(F)cc2F)c(-c2cn(C)c(=O)c3occc23)c1] | N-[6-(2,4-difluorophenoxy)-5-(6-methyl-7-oxofuro[2,3-c]pyridin-4-yl)pyridin-3-yl]ethanesulfonamide |

TABLE 1-continued

| Chemical Synthesis Example | Structure | Name |
|---|---|---|
| 257 | 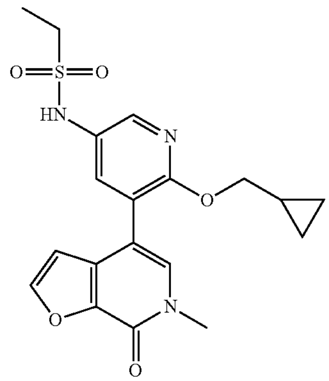 [SMILES: CCS(=O)(=O)Nc1cnc(OCC2CC2)c(-c2cn(C)c(=O)c3occc23)c1] | N-[6-(cyclopropylmethoxy)-5-(6-methyl-7-oxofuro[2,3-c]pyridin-4-yl)pyridin-3-yl]ethanesulfonamide |
| 258 | 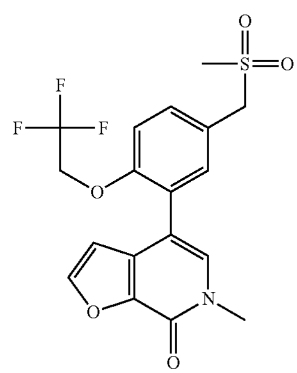 [SMILES: Cn1cc(-c2cc(CS(C)(=O)=O)ccc2OCC(F)(F)F)c2ccoc2c1=O] | 6-methyl-4-[5-(methylsulfonylmethyl)-2-(2,2,2-trifluoroethoxy)phenyl]furo[2,3-c]pyridin-7-one |
| 259 | 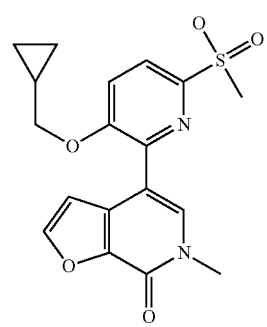 | 4-[3-(cyclopropylmethoxy)-6-methylsulfonylpyridin-2-yl]-6-methylfuro[2,3-c]pyridin-7-one |
| 260 | 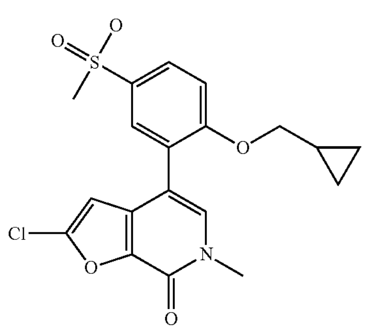 | 2-chloro-4-[2-(cyclopropylmethoxy)-5-methylsulfonylphenyl]-6-methylfuro[2,3-c]pyridin-7-one |

TABLE 1-continued

| Chemical Synthesis Example | Structure | Name |
|---|---|---|
| 261 | 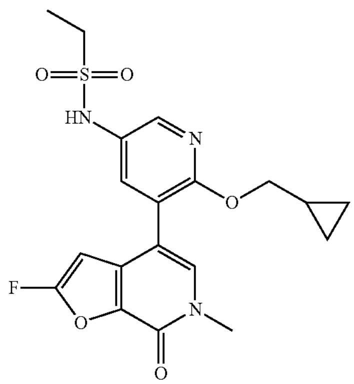 [SMILES: CCS(=O)(=O)Nc1cnc(OCC2CC2)c(-c2cn(C)c(=O)c3oc(F)cc23)c1] | N-[6-(cyclopropylmethoxy)-5-(2-fluoro-6-methyl-7-oxofuro[2,3-c]pyridin-4-yl)pyridin-3-yl]ethanesulfonamide |
| 262 | 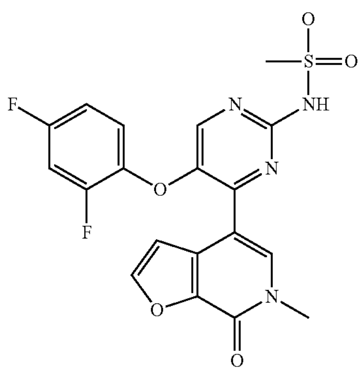 | N-[5-(2,4-difluorophenoxy)-4-(6-methyl-7-oxofuro[2,3-c]pyridin-4-yl)pyrimidin-2-yl]methanesulfonamide |
| 263 | 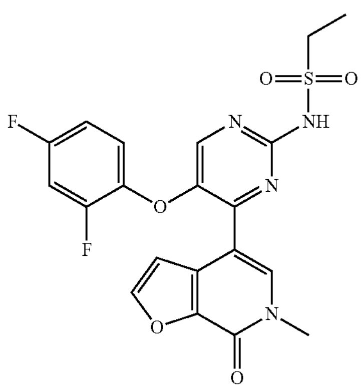 [SMILES: CCS(=O)(=O)Nc1ncc(Oc2ccc(F)cc2F)c(-c2cn(C)c(=O)c3occc23)n1] | N-[5-(2,4-difluorophenoxy)-4-(6-methyl-7-oxofuro[2,3-c]pyridin-4-yl)pyrimidin-2-yl]ethanesulfonamide |
| 264 | 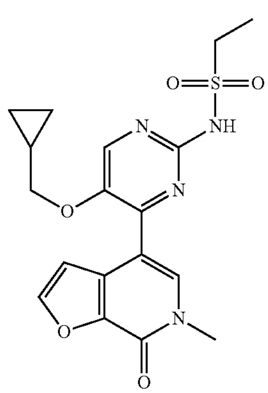 [SMILES: CCS(=O)(=O)Nc1ncc(OCC2CC2)c(-c2cn(C)c(=O)c3occc23)n1] | N-[5-(cyclopropylmethoxy)-4-(6-methyl-7-oxofuro[2,3-c]pyridin-4-yl)pyrimidin-2-yl]ethanesulfonamide |

TABLE 1-continued

| Chemical Synthesis Example | Structure | Name |
| --- | --- | --- |
| 265 | 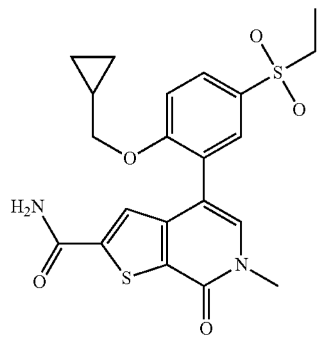 [SMILES: CCS(O)(O)c1ccc(OCC2CC2)c(-c2cn(C)c(=O)c3sc(C(N)=O)cc23)c1] | 4-[2-(cyclopropylmethoxy)-5-ethylsulfonylphenyl]-6-methyl-7-oxothieno[2,3-c]pyridine-2-carboxamide |
| 266 | 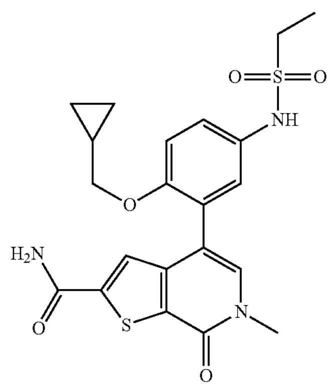 [SMILES: CCS(=O)(=O)Nc1ccc(OCC2CC2)c(-c2cn(C)c(=O)c3sc(C(N)=O)cc23)c1] | 4-[2-(cyclopropylmethoxy)-5-(ethylsulfonylamino)phenyl]-6-methyl-7-oxothieno[2,3-c]pyridine-2-carboxamide |
| 267 | 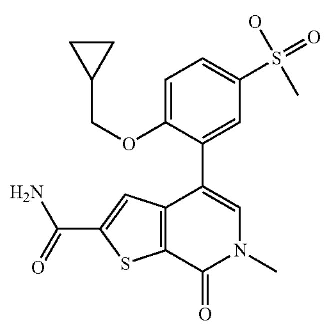 | 4-[2-(cyclopropylmethoxy)-5-methylsulfonylphenyl]-6-methyl-7-oxothieno[2,3-c]pyridine-2-carboxamide |
| 268 | 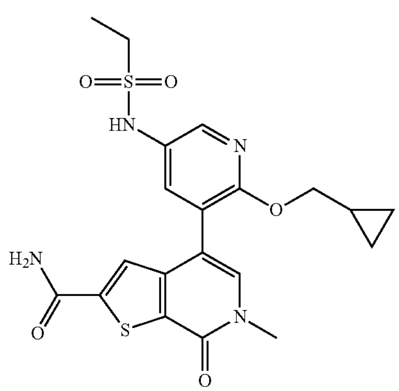 [SMILES: CCS(=O)(=O)Nc1cnc(OCC2CC2)c(-c2cn(C)c(=O)c3sc(C(N)=O)cc23)c1] | 4-[2-(cyclopropylmethoxy)-5-(ethylsulfonylamino)pyridin-3-yl]-6-methyl-7-oxothieno[2,3-c]pyridine-2-carboxamide |

TABLE 1-continued
| Chemical Synthesis Example | Structure | Name |
|---|---|---|
| 269 | 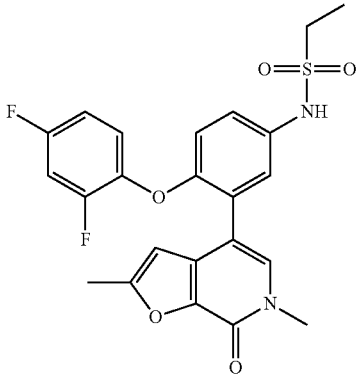 [SMILES: CCS(=O)(=O)Nc1ccc(Oc2ccc(F)cc2F)c(-c2cn(C)c(=O)c3oc(C)cc23)c1] | N-[4-(2,4-difluorophenoxy)-3-(2,6-dimethyl-7-oxofuro[2,3-c]pyridin-4-yl)phenyl]ethanesulfonamide |
| 270 | 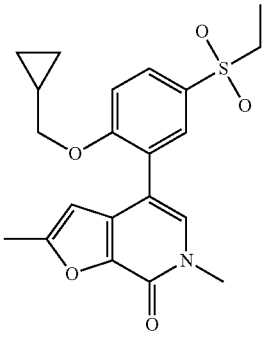 [SMILES: CCS(O)(O)c1ccc(OCC2CC2)c(-c2cn(C)c(=O)c3oc(C)cc23)c1] | 4-[2-(cyclopropylmethoxy)-5-ethylsulfonylphenyl]-2,6-dimethylfuro[2,3-c]pyridin-7-one |
| 271 | 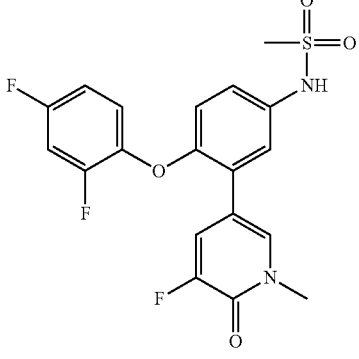 | N-[4-(2,4-difluorophenoxy)-3-(5-fluoro-1-methyl-6-oxopyridin-3-yl)phenyl]methanesulfonamide |
| 272 | 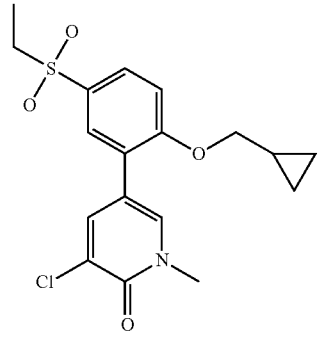 [SMILES: CCS(O)(O)c1ccc(OCC2CC2)c(-c2cc(Cl)c(=O)n(C)c2)c1] | 3-chloro-5-[2-(cyclopropylmethoxy)-5-ethylsulfonylphenyl]-1-methyl-pyridin-2-one |

TABLE 1-continued

| Chemical Synthesis Example | Structure | Name |
|---|---|---|
| 273 | 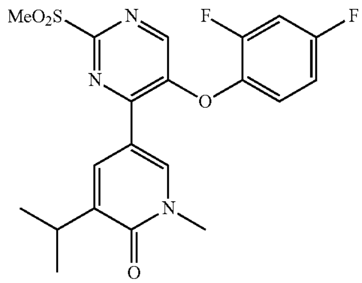 [SMILES: CC(C)c1cc(-c2nc(S(C)(=O)=O)ncc2Oc2ccc(F)cc2F)cn(C)c1=O] | 5-[5-(2,4-difluorophenoxy)-2-methylsulfonylpyrimidin-4-yl]-1-methyl-3-propan-2-ylpyridin-2-one |
| 274 | 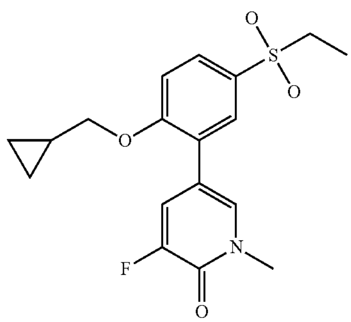 [SMILES: CCS(O)(O)c1ccc(OCC2CC2)c(-c2cc(F)c(=O)n(C)c2)c1] | 5-[2-(cyclopropylmethoxy)-5-ethylsulfonylphenyl]-3-fluoro-1-methylpyridin-2-one |
| 275 | 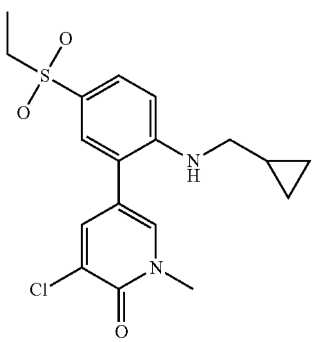 [SMILES: CCS(O)(O)c1ccc(NCC2CC2)c(-c2cc(Cl)c(=O)n(C)c2)c1] | 3-chloro-5-[2-(cyclopropylmethylamino)-5-ethylsulfonylphenyl]-1-methyl-pyridine-2-one |
| 276 | 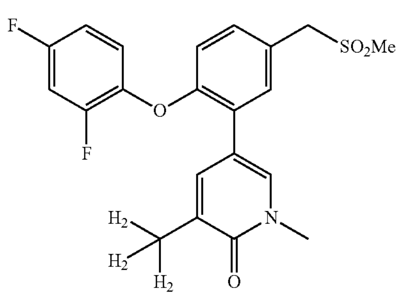 | 5-[2-(2,4-difluorophenoxy)-5-(methanesulfonylmethyl)phenyl]-3-($^{2}H_{3}$)methyl-1-methyl-1,2-dihydro-pyridin-2-one |
| 277 | 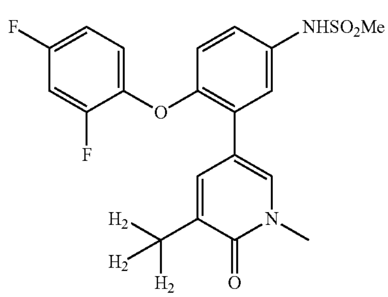 | N-[4-(2,4-difluorophenoxy)-3-[5-($^{2}H_{3}$)methyl-1-methyl-6-oxo-1,6-dihydropyridin-3-yl]phenyl]methanesulfonamide |

TABLE 1-continued

| Chemical Synthesis Example | Structure | Name |
|---|---|---|
| 278 | 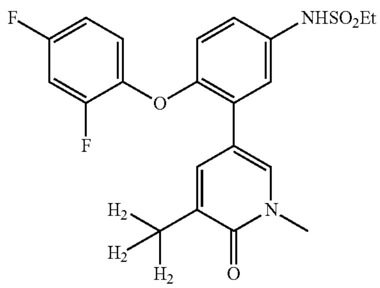 | N-[4-(2,4-difluorophenoxy)-3-[5-($^{2}$H$_{3}$)methyl-1-methyl-6-oxo-1,6-dihydropyridin-3-yl]phenyl]ethane-1-sulfonamide |
| 279 | 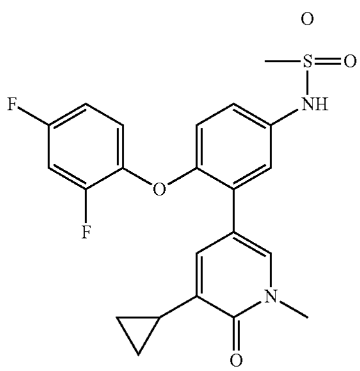 | N-[3-(5-cyclopropyl-1-methyl-6-oxopyridin-3-yl)-4-(2,4-difluoro-phenoxy)phenyl]methanesulfonamide |
| 280 | 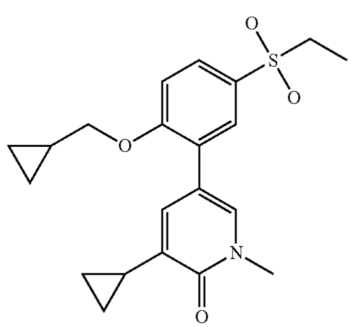 [SMILES: CCS(O)(O)c1ccc(OCC2CC2)c(-c2cc(C3CC3)c(=O)n(C)c2)c1] | 3-cyclopropyl-5-[2-(cyclopropylmethoxy)-5-ethylsulfonylphenyl]-1-methylpyridin-2-one |
| 281 | 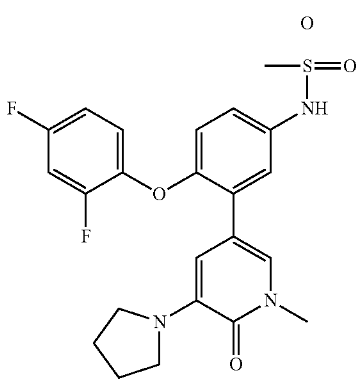 | N-[4-(2,4-difluorophenoxy)-3-(1-methyl-6-oxo-5-pyrrolidin-1-ylpyridin-3-yl)phenyl]methanesulfonamide |

TABLE 1-continued

| Chemical Synthesis Example | Structure | Name |
|---|---|---|
| 282 | 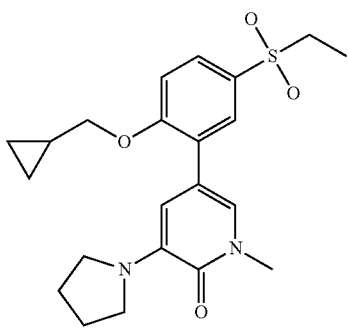 [SMILES: CCS(O)(O)c1ccc(OCC2CC2)c(-c2cc(N3CCCC3)c(=O)n(C)c2)c1] | 5-[2-(cyclopropylmethoxy)-5-ethylsulfonylphenyl]-1-methyl-3-pyrrolidin-1-ylpyridin-2-one |
| 283 | 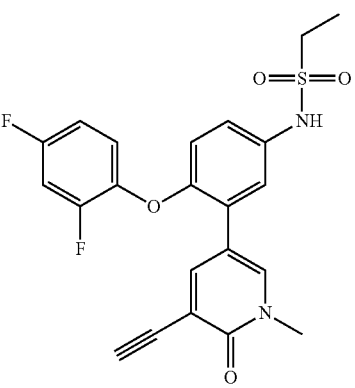 [SMILES: C#Cc1cc(-c2cc(NS(=O)(=O)CC)ccc2Oc2ccc(F)cc2F)cn(C)c1=O] | N-[4-(2,4-difluorophenoxy)-3-(5-ethynyl-1-methyl-6-oxopyridin-3-yl)phenyl]ethanesulfonamide |
| 284 | 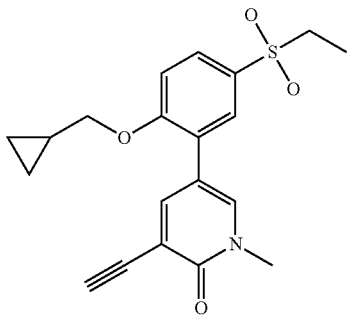 [SMILES: C#Cc1cc(-c2cc(S(O)(O)CC)ccc2OCC2CC2)cn(C)c1=O] | 5-[2-(cyclopropylmethoxy)-5-ethylsulfonylphenyl]-3-ethynyl-1-methylpyridin-2-one |
| 285 | 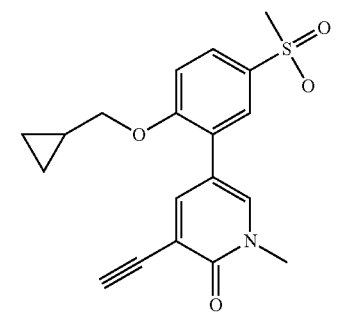 | 5-[2-(cyclopropylmethoxy)-5-methylsulfonylphenyl]-3-ethynyl-1-methylpyridin-2-one |

TABLE 1-continued

| Chemical Synthesis Example | Structure | Name |
|---|---|---|
| 286 | 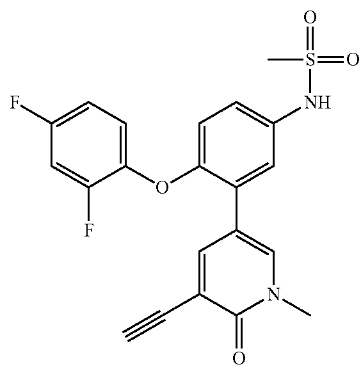 [SMILES: C#Cc1cc(-c2cc(NS(C)(=O)=O)ccc2Oc2ccc(F)cc2F)cn(C)c1=O] | N-[4-(2,4-difluorophenoxy)-3-(5-ethynyl-1-methyl-6-oxopyridin-3-yl)phenyl]methanesulfonamide |
| 287 | 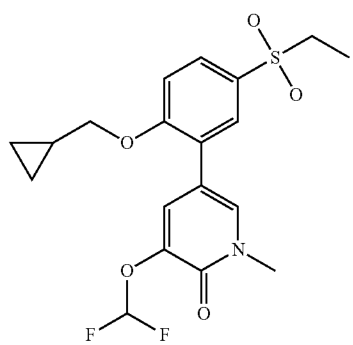 [SMILES: CCS(O)(O)c1ccc(OCC2CC2)c(-c2cc(OC(F)F)c(=O)n(C)c2)c1] | 5-[2-(cyclopropylmethoxy)-5-ethylsulfonylphenyl]-3-(difluoromethoxy)-1-methylpyridin-2-one |
| 288 | 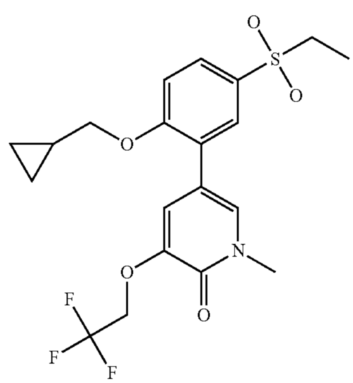 [SMILES: CCS(O)(O)c1ccc(OCC2CC2)c(-c2cc(OCC(F)(F)F)c(=O)n(C)c2)c1] | 5-[2-(cyclopropylmethoxy)-5-ethylsulfonylphenyl]-1-methyl-3-(2,2,2-trifluoroethoxy)pyridin-2-one |
| 289 | 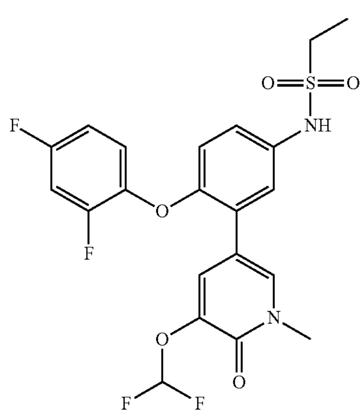 [SMILES: CCS(=O)(=O)Nc1ccc(Oc2ccc(F)cc2F)c(-c2cc(OC(F)F)c(=O)n(C)c2)c1] | N-[3-[5-(difluoromethoxy)-1-methyl-6-oxopyridin-3-yl]-4-(2,4-difluorophenoxy)phenyl]ethanesulfonamide |

TABLE 1-continued

| Chemical Synthesis Example | Structure | Name |
|---|---|---|
| 290 | 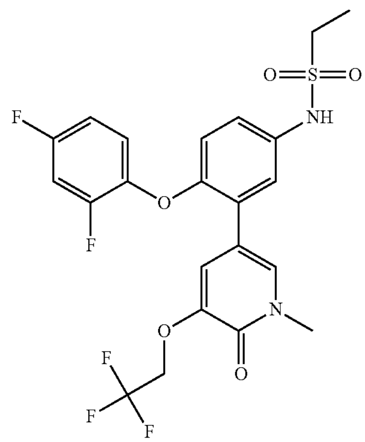 [SMILES: CCS(=O)(=O)Nc1ccc(Oc2ccc(F)cc2F)c(-c2cc(OCC(F)(F)F)c(=O)n(C)c2)c1] | N-[4-(2,4-difluorophenoxy)-3-[1-methyl-6-oxo-5-(2,2,2-trifluoroethoxy)pyridin-3-yl]phenyl]ethanesulfonamide |
| 291 | 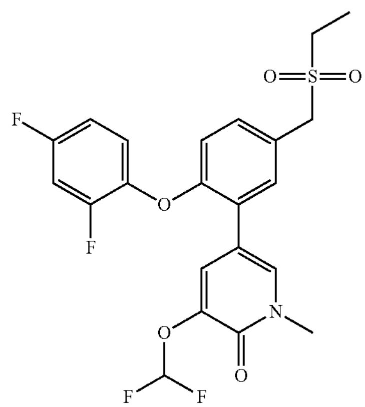 [SMILES: CCS(=O)(=O)Cc1ccc(Oc2ccc(F)cc2F)c(-c2cc(OC(F)F)c(=O)n(C)c2)c1] | 3-(difluoromethoxy)-5-[2-(2,4-difluorophenoxy)-5-(ethylsulfonylmethyl)phenyl]-1-methylpyridin-2-one |
| 292 | 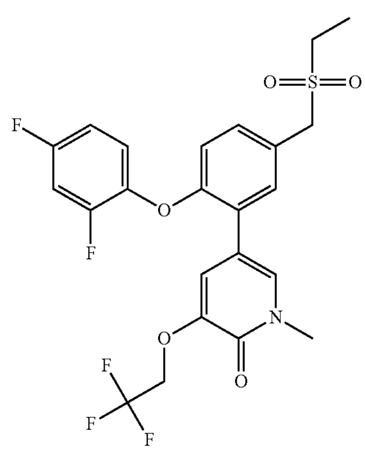 [SMILES: CCS(=O)(=O)Cc1ccc(Oc2ccc(F)cc2F)c(-c2cc(OCC(F)(F)F)c(=O)n(C)c2)c1] | 5-[2-(2,4-difluorophenoxy)-5-(ethylsulfonylmethyl)phenyl]-1-methyl-3-(2,2,2-trifluoroethoxy)pyridin-2-one |

TABLE 1-continued

| Chemical Synthesis Example | Structure | Name |
|---|---|---|
| 293 | 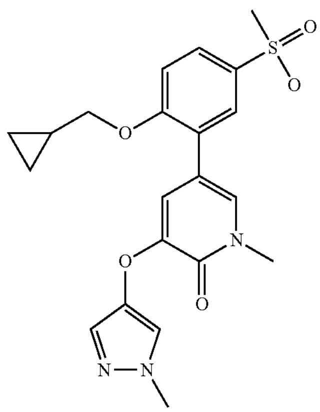 | 5-[2-(cyclopropylmethoxy)-5-methylsulfonylphenyl]-1-methyl-3-(1-methylpyrazol-4-yl)oxypyridin-2-one |
| 294 | 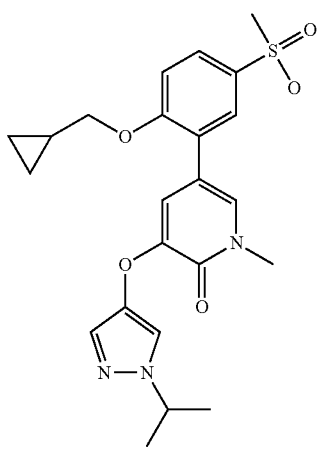 | 5-[2-(cyclopropylmethoxy)-5-methylsulfonylphenyl]-1-methyl-3-(1-propan-2-ylpyrazol-4-yl)oxypyridin-2-one |
| 295 | 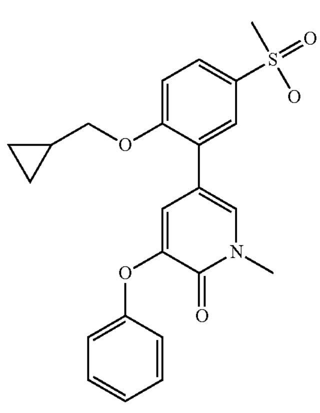 | 5-[2-(cyclopropylmethoxy)-5-methylsulfonylphenyl]-1-methyl-3-phenoxypyridin-2-one |

TABLE 1-continued
| Chemical Synthesis Example | Structure | Name |
|---|---|---|
| 296 | 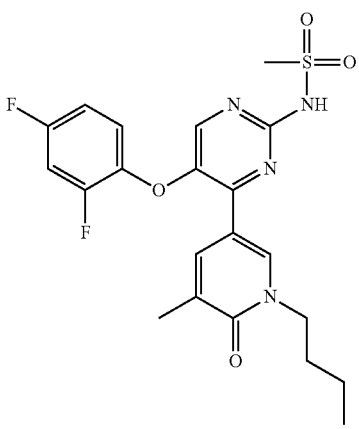 [SMILES: CCCCn1cc(-c2nc(NS(C)(=O)=O)ncc2Oc2ccc(F)cc2F)cc(C)c1=O] | N-[4-(1-butyl-5-methyl-6-oxopyridin-3-yl)-5-(2,4-difluorophenoxy)pyrimidin-2-yl]methanesulfonamide |
| 297 | 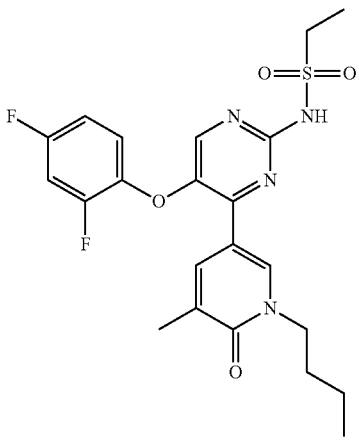 [SMILES: CCCCn1cc(-c2nc(NS(=O)(=O)CC)ncc2Oc2ccc(F)cc2F)cc(C)c1=O] | N-[4-(1-butyl-5-methyl-6-oxopyridin-3-yl)-5-(2,4-difluorophenoxy)pyrimidin-2-yl]ethanesulfonamide |
| 298 | 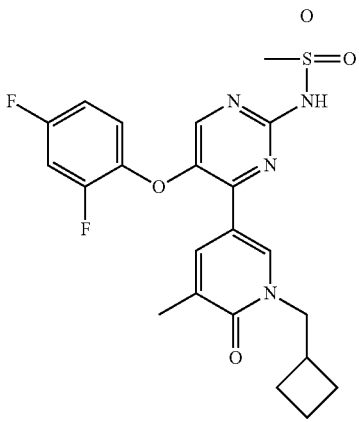 | N-[4-[1-(cyclobutylmethyl)-5-methyl-6-oxopyridin-3-yl]-5-(2,4-difluorophenoxy)pyrimidin-2-yl]methanesulfonamide |

TABLE 1-continued

| Chemical Synthesis Example | Structure | Name |
|---|---|---|
| 299 | 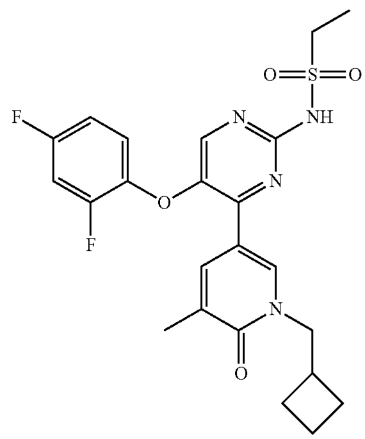 [SMILES: CCS(=O)(=O)Nc1ncc(Oc2ccc(F)cc2F)c(-c2cc(C)c(=O)n(CC3CCC3)c2)n1] | N-[4-[1-(cyclobutylmethyl)-5-methyl-6-oxopyridin-3-yl]-5-(2,4-difluorophenoxy)pyrimidin-2-yl]ethanesulfonamide |
| 300 | 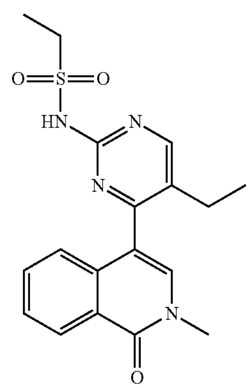 [SMILES: CCc1cnc(NS(=O)(=O)CC)nc1-c1cn(C)c(=O)c2ccccc12] | N-[5-ethyl-4-(2-methyl-1-oxoisoquinolin-4-yl)pyrimidin-2-yl]ethanesulfonamide |
| 301 | 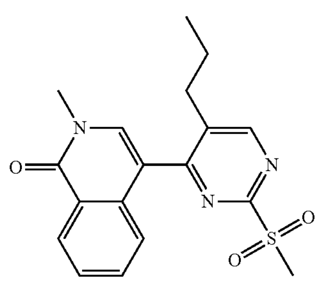 [SMILES: CCCc1cnc(S(C)(=O)=O)nc1-c1cn(C)c(=O)c2ccccc12] | 2-methyl-4-(2-methylsulfonyl-5-propylpyrimidin-4-yl)isoquinolin-1-one |
| 302 | 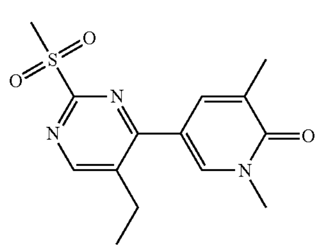 [SMILES: CCc1cnc(S(C)(=O)=O)nc1-c1cc(C)c(=O)n(C)c1] | 5-(5-ethyl-2-methylsulfonylpyrimidin-4-yl)-1,3-dimethylpyridin-2-one |

TABLE 1-continued

| Chemical Synthesis Example | Structure | Name |
|---|---|---|
| 303 | 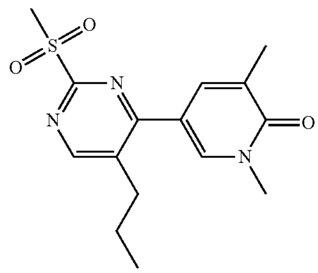 [SMILES: CCCc1cnc(S(C)(=O)=O)nc1-c1cc(C)c(=O)n(C)c1] | 1,3-dimethyl-5-(2-methylsulfonyl-5-propylpyrimidin-4-yl)pyridin-2-one |
| 304 | 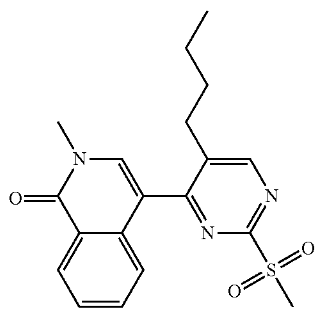 [SMILES: CCCCc1cnc(S(C)(=O)=O)nc1-c1cn(C)c(=O)c2ccccc12] | 4-(5-butyl-2-methylsulfonylpyrimidin-4-yl)-2-methylisoquinolin-1-one |
| 305 | 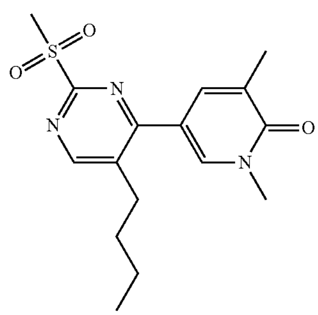 [SMILES: CCCCc1cnc(S(C)(=O)=O)nc1-c1cc(C)c(=O)n(C)c1] | 5-(5-butyl-2-methylsulfonylpyrimidin-4-yl)-1,3-dimethylpyridin-2-one |
| 306 | 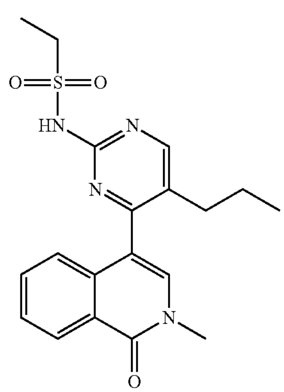 [SMILES: CCCc1cnc(NS(=O)(=O)CC)nc1-c1cn(C)c(=O)c2ccccc12] | N-[4-(2-methyl-1-oxoisoquinolin-4-yl)-5-propylpyrimidin-2-yl]ethanesulfonamide |

TABLE 1-continued
| Chemical Synthesis Example | Structure | Name |
|---|---|---|
| 307 | 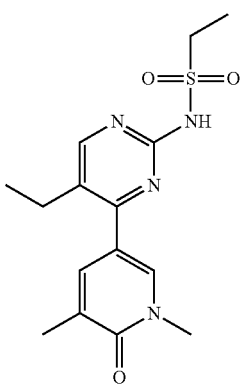 [SMILES: CCc1cnc(NS(=O)(=O)CC)nc1-c1cc(C)c(=O)n(C)c1] | N-[4-(1,5-dimethyl-6-oxopyridin-3-yl)-5-ethylpyrimidin-2-yl]ethanesulfonamide |
| 308 | 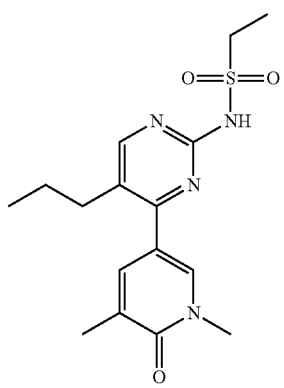 [SMILES: CCCc1cnc(NS(=O)(=O)CC)nc1-c1cc(C)c(=O)n(C)c1] | N-[4-(1,5-dimethyl-6-oxopyridin-3-yl)-5-propylpyrimidin-2-yl]ethanesulfonamide |
| 309 | 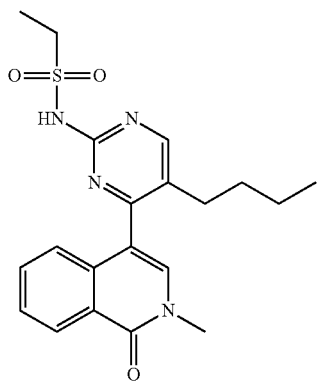 [SMILES: CCCCc1cnc(NS(=O)(=O)CC)nc1-c1cn(C)c(=O)c2ccccc12] | N-[5-butyl-4-(2-methyl-1-oxoisoquinolin-4-yl)pyrimidin-2-yl]ethanesulfonamide |
| 310 | 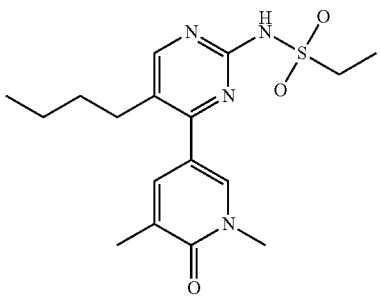 [SMILES: CCCCc1cnc(NS(O)(O)CC)nc1-c1cc(C)c(=O)n(C)c1] | N-[5-butyl-4-(1,5-dimethyl-6-oxopyridin-3-yl)pyrimidin-2-yl]ethanesulfonamide |

TABLE 1-continued

| Chemical Synthesis Example | Structure | Name |
| --- | --- | --- |
| 311 | 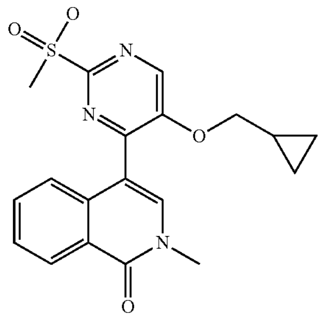 | 4-[5-(cyclopropylmethoxy)-2-methylsulfonylpyrimidin-4-yl]-2-methylisoquinolin-1-one |
| 312 | 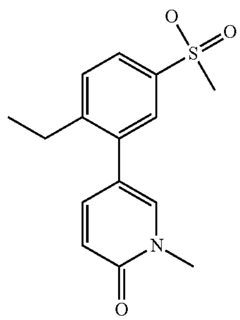 | 5-(2-ethyl-5-methylsulfonylphenyl)-1-methylpyridin-2-one |
| 313 | 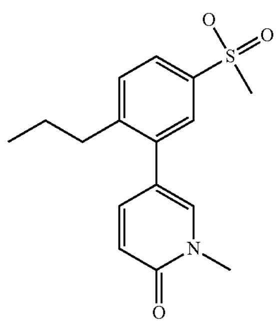 | 1-methyl-5-(5-methylsulfonyl-2-propylphenyl)pyridin-2-one |
| 314 | 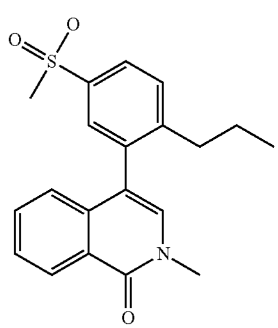 | 2-methyl-4-(5-methylsulfonyl-2-propylphenyl)isoquinolin-1-one |

TABLE 1-continued

| Chemical Synthesis Example | Structure | Name |
|---|---|---|
| 315 | 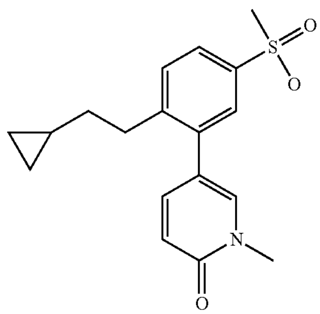 | 5-[2-(2-cyclopropylethyl)-5-methylsulfonylphenyl]-1-methylpyridin-2-one |
| 316 | 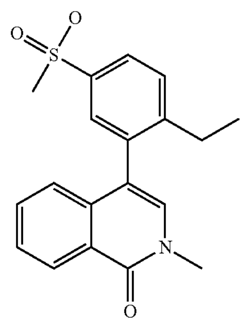 | 4-(2-ethyl-5-methylsulfonylphenyl)-2-methylisoquinolin-1-one |
| 317 | 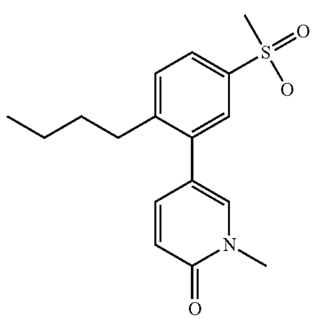 | 5-(2-butyl-5-methylsulfonylphenyl)-1-methylpyridin-2-one |
| 318 | 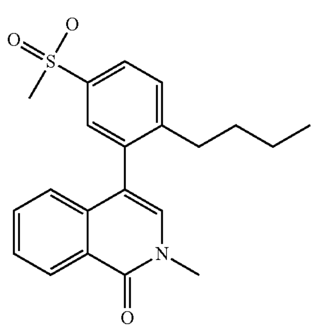 | 4-(2-butyl-5-methylsulfonylphenyl)-2-methylisoquinolin-1-one |

TABLE 1-continued

| Chemical Synthesis Example | Structure | Name |
|---|---|---|
| 319 | 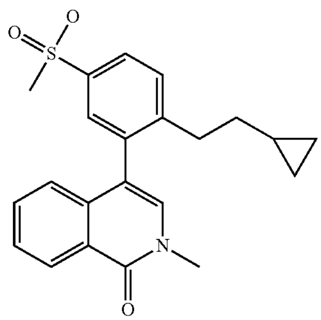 | 4-[2-(2-cyclopropylethyl)-5-methylsulfonylphenyl]-2-methylisoquinolin-1-one |
| 320 | 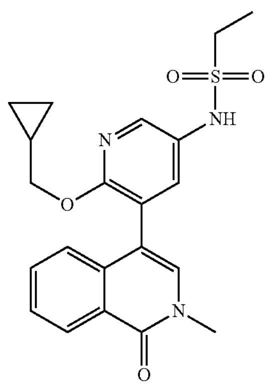 [SMILES: CCS(=O)(=O)Nc1cnc(OCC2CC2)c(-c2cn(C)c(=O)c3ccccc23)c1] | N-[6-(cyclopropylmethoxy)-5-(2-methyl-1-oxoisoquinolin-4-yl)pyridin-3-yl]ethanesulfonamide |
| 321 | 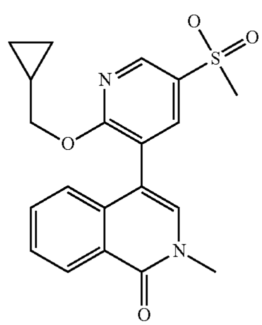 | 4-[2-(cyclopropylmethoxy)-5-methylsulfonylpyridin-3-yl]-2-methylisoquinolin-1-one |
| 322 | 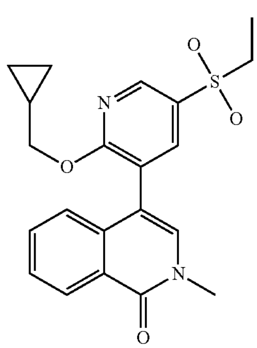 [SMILES: CCS(O)(O)c1cnc(OCC2CC2)c(-c2cn(C)c(=O)c3ccccc23)c1] | 4-[2-(cyclopropylmethoxy)-5-ethylsulfonylpyridin-3-yl]-2-methylisoquinolin-1-one |

TABLE 1-continued

| Chemical Synthesis Example | Structure | Name |
|---|---|---|
| 323 | 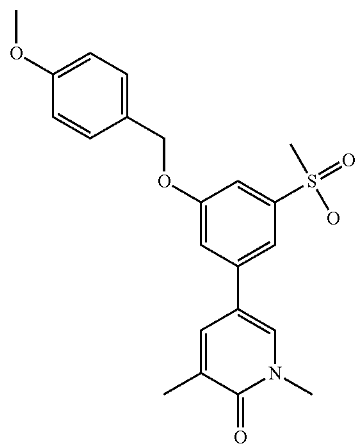 | 5-[3-[(4-methoxyphenyl)methoxy]-5-methylsulfonylphenyl]-1,3-dimethylpyridin-2-one |
| 324 | 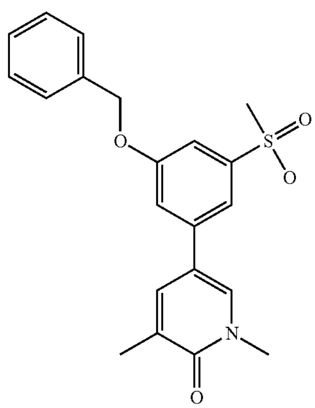 | 1,3-dimethyl-5-(3-methylsulfonyl-5-phenylmethoxyphenyl)pyridin-2-one |
| 325 | 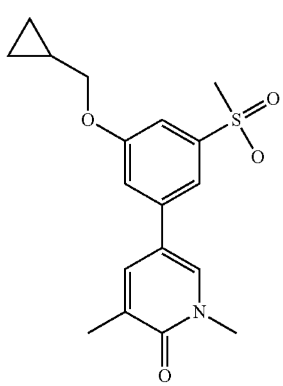 | 5-[3-(cyclopropylmethoxy)-5-methylsulfonylphenyl]-1,3-dimethylpyridin-2-one |

TABLE 1-continued
| Chemical Synthesis Example | Structure | Name |
|---|---|---|
| 326 | 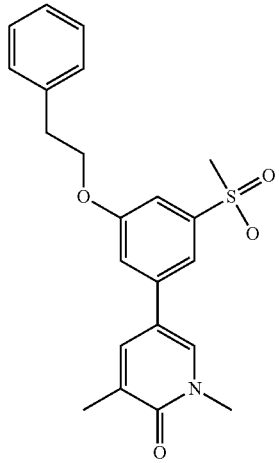 | 1,3-dimethyl-5-[3-methylsulfonyl-5-(2-phenylethoxy)phenyl]pyridin-2-one |
| 327 | 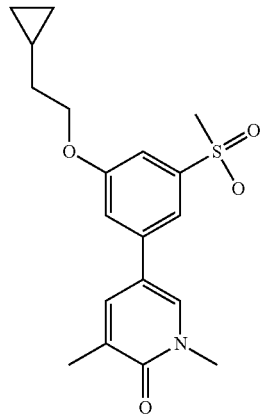 | 5-[3-(2-cyclopropylethoxy)-5-methylsulfonylphenyl]-1,3-dimethylpyridin-2-one |
| 328 | 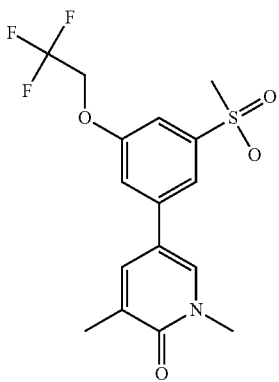 | 1,3-dimethyl-5-[3-methylsulfonyl-5-(2,2,2-trifluoroethoxy)phenyl]pyridin-2-one |

TABLE 1-continued

| Chemical Synthesis Example | Structure | Name |
|---|---|---|
| 329 | 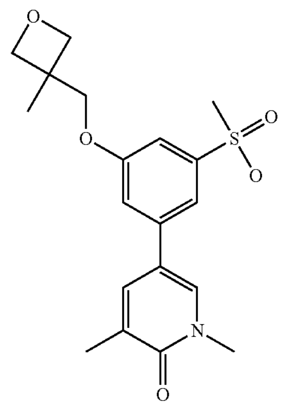 | 1,3-dimethyl-5-[3-[(3-methyloxetan-3-yl)methoxy]-5-methylsulfonylphenyl]pyridine-2-one |
| 330 | 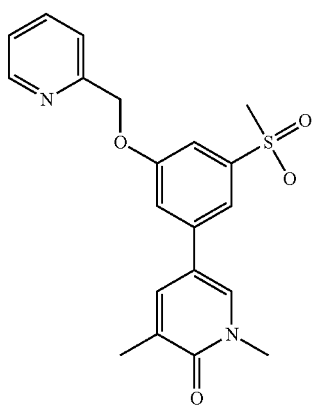 | 1,3-dimethyl-5-[3-methylsulfonyl-5-(pyridin-2-ylmethoxy)phenyl]pyridin-2-one |
| 331 | 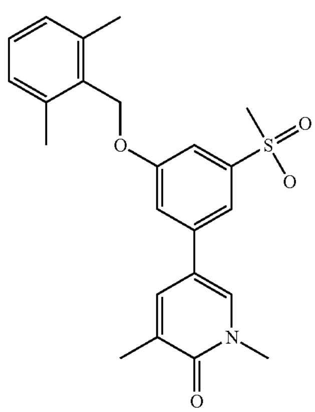 | 5-[3-[(2,6-dimethylphenyl)methoxy]-5-methylsulfonylphenyl]-1,3-dimethylpyridin-2-one |

TABLE 1-continued

| Chemical Synthesis Example | Structure | Name |
|---|---|---|
| 332 | 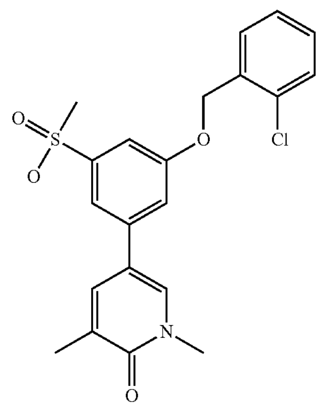 | 5-[3-[(2-chlorophenyl)methoxy]-5-methylsulfonylphenyl]-1,3-dimethylpyridin-2-one |
| 333 | 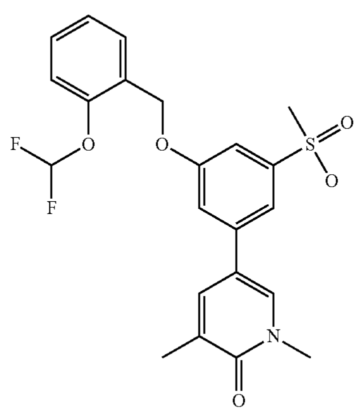 | 5-[3-[[2-(difluoromethoxy)phenyl]methoxy]-5-methylsulfonylphenyl]-1,3-dimethylpyridin-2-one |
| 334 | 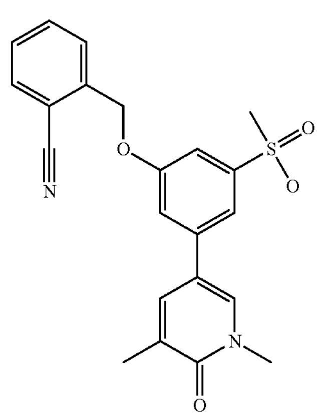 | 2-[[3-(1,5-dimethyl-6-oxopyridin-3-yl)-5-methylsulfonylphenoxy]methyl]benzonitrile |

TABLE 1-continued
| Chemical Synthesis Example | Structure | Name |
|---|---|---|
| 335 | 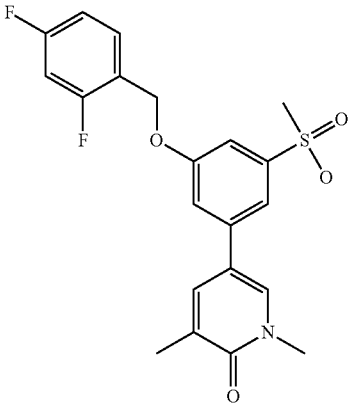 | 5-[3-[(2,4-difluorophenyl)methoxy]-5-methylsulfonylphenyl]-1,3-dimethylpyridin-2-one |
| 336 | 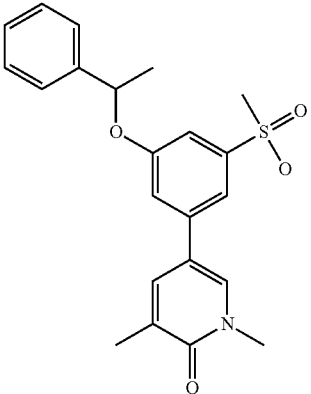 | 1,3-dimethyl-5-[3-methylsulfonyl-5-(1-phenylethoxy)phenyl]pyridin-2-one |
| 337 | 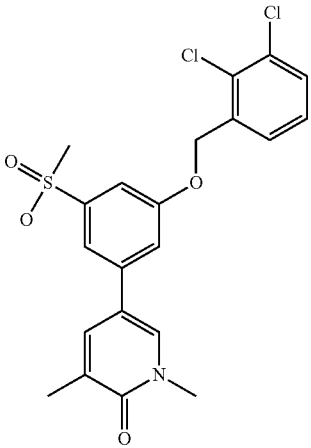 | 5-[3-[(2,3-dichlorophenyl)methoxy]-5-methylsulfonylphenyl]-1,3-dimethylpyridin-2-one |

TABLE 1-continued

| Chemical Synthesis Example | Structure | Name |
|---|---|---|
| 338 | 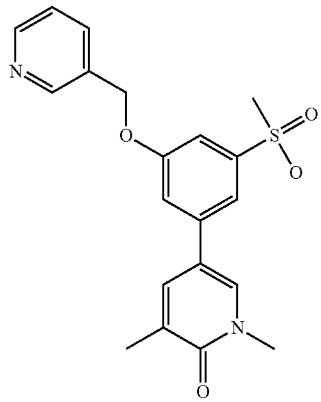 | 1,3-dimethyl-5-[3-methylsulfonyl-5-(pyridin-3-ylmethoxy)phenyl]pyridin-2-one |
| 339 | 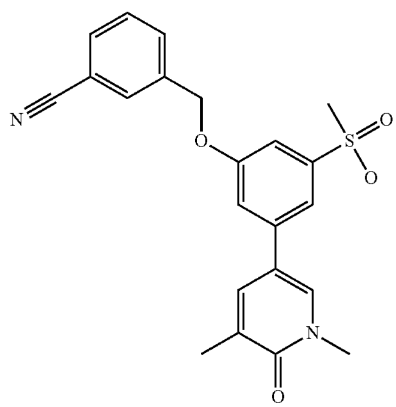 | 3-[[3-(1,5-dimethyl-6-oxopyridin-3-yl)-5-methylsulfonylphenoxy]methyl]benzonitrile |
| 340 | 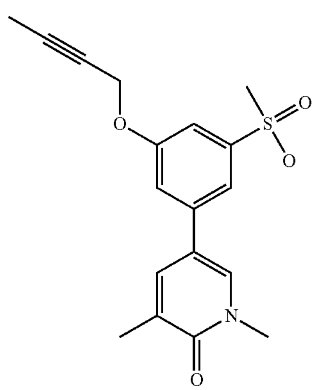 | 5-(3-but-2-ynoxy-5-methylsulfonylphenyl)-1,3-dimethylpyridin-2-one |

TABLE 1-continued
| Chemical Synthesis Example | Structure | Name |
|---|---|---|
| 341 | 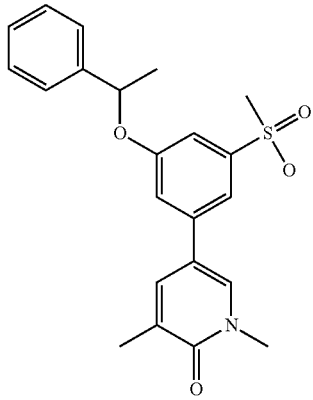 | 1,3-dimethyl-5-[3-methylsulfonyl-5-(1-phenylethoxy)phenyl]pyridin-2-one |
| 342 | 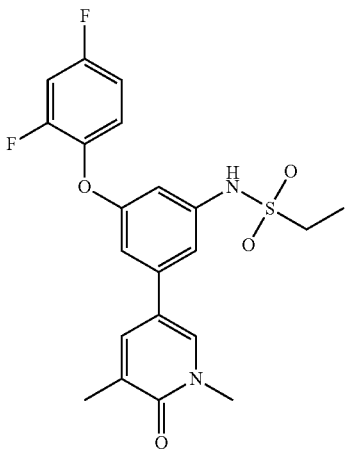 [SMILES: CCS(O)(O)Nc1cc(Oc2ccc(F)cc2F)cc(-c2cc(C)c(=O)n(C)c2)c1] | N-[3-(2,4-difluorophenoxy)-5-(1,5-dimethyl-6-oxopyridin-3-yl)phenyl]ethanesulfonamide |
| 343 | 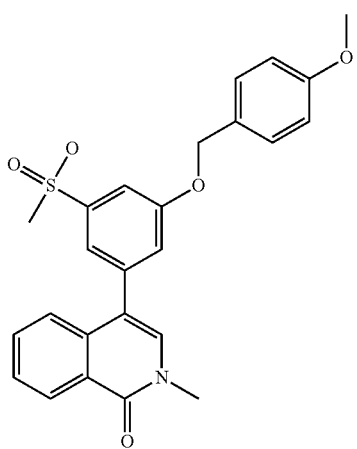 | 4-[3-[(4-methoxyphenyl)methoxy]-5-methylsulfonylphenyl]-2-methylisoquinolin-1-one |

TABLE 1-continued

| Chemical Synthesis Example | Structure | Name |
|---|---|---|
| 344 | 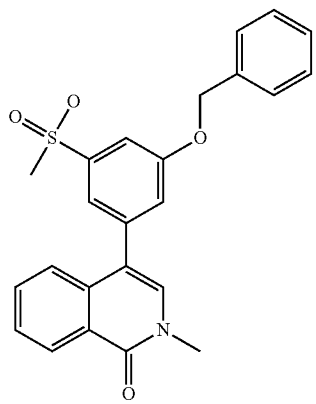 | 2-methyl-4-(3-methylsulfonyl-5-phenylmethoxyphenyl)isoquinolin-1-one |
| 345 | 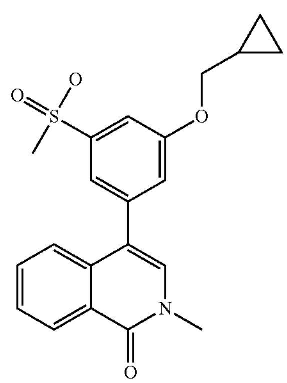 | 4-[3-(cyclopropylmethoxy)-5-methylsulfonylphenyl]-2-methylisoquinolin-1-one |
| 346 | 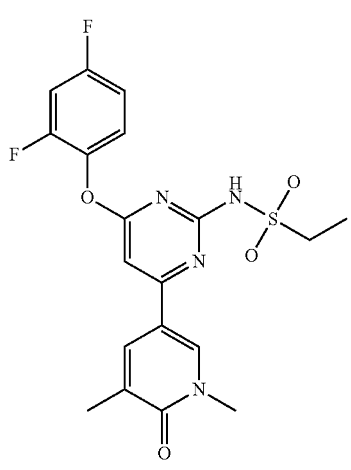 [SMILES: CCS(O)(O)Nc1nc(Oc2ccc(F)cc2F)cc(-c2cc(C)c(=O)n(C)c2)n1] | N-[4-(2,4-difluorophenoxy)-6-(1,5-dimethyl-6-oxopyridin-3-yl)pyrimidin-2-yl]ethanesulfonamide |

TABLE 1-continued

| Chemical Synthesis Example | Structure | Name |
|---|---|---|
| 347 | 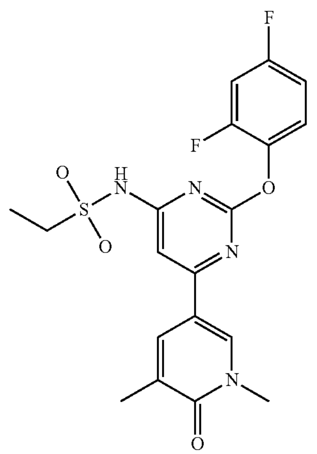 [SMILES: CCS(O)(O)Nc1cc(-c2cc(C)c(=O)n(C)c2)nc(Oc2ccc(F)cc2F)n1] | N-[2-(2,4-difluorophenoxy)-6-(1,5-dimethyl-6-oxopyridin-3-yl)pyrimidin-4-yl]ethanesulfonamide |
| 348 | 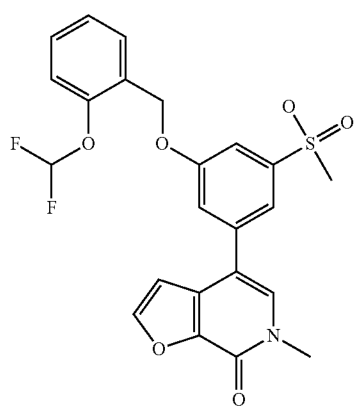 | 4-[3-[[2-(difluoromethoxy)phenyl]methoxy]-5-methylsulfonylphenyl]-6-methylfuro[2,3-c]pyridin-7-one |
| 349 | 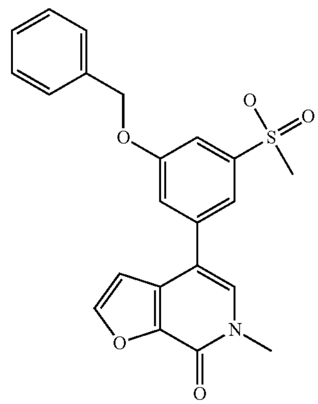 | 6-methyl-4-(3-methylsulfonyl-5-phenylmethoxyphenyl)furo[2,3-c]pyridin-7-one |

TABLE 1-continued

| Chemical Synthesis Example | Structure | Name |
|---|---|---|
| 350 | 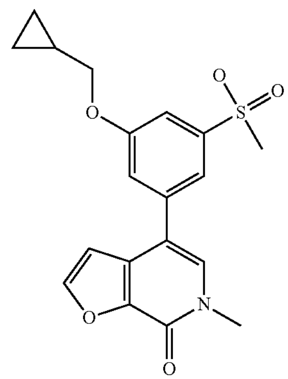 | 4-[3-(cyclopropylmethoxy)-5-methylsulfonylphenyl]-6-methylfuro[2,3-c]pyridin-7-one |
| 351 | 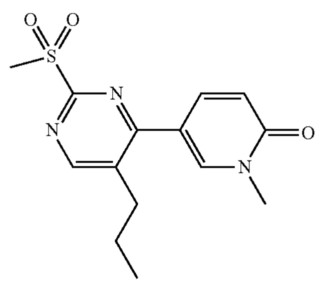 [SMILES: CCCc1cnc(S(C)(=O)=O)nc1-c1ccc(=O)n(C)c1] | 1-methyl-5-(2-methylsulfonyl-5-propylpyrimidin-4-yl)pyridin-2-one |
| 352 | 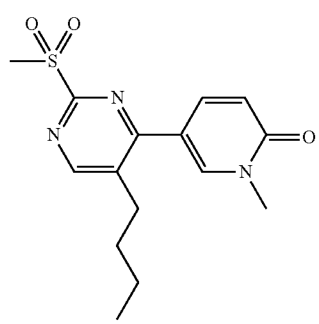 [SMILES: CCCCc1cnc(S(C)(=O)=O)nc1-c1ccc(=O)n(C)c1] | 5-(5-butyl-2-methylsulfonylpyrimidin-4-yl)-1-methylpyridin-2-one |
| 353 | 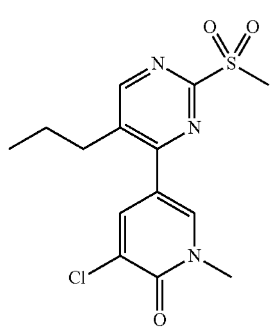 [SMILES: CCCc1cnc(S(C)(=O)=O)nc1-c1cc(Cl)c(=O)n(C)c1] | 3-chloro-1-methyl-5-(2-methylsulfonyl-5-propylpyrimidin-4-yl)pyridin-2-one |

TABLE 1-continued
| Chemical Synthesis Example | Structure | Name |
|---|---|---|
| 354 | 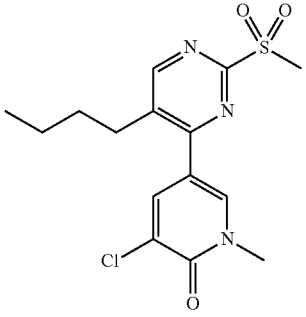 [SMILES: CCCCc1cnc(S(C)(=O)=O)nc1-c1cc(Cl)c(=O)n(C)c1] | 5-(5-butyl-2-methylsulfonylpyrimidin-4-yl)-3-chloro-1-methylpyridin-2-one |
| 355 | 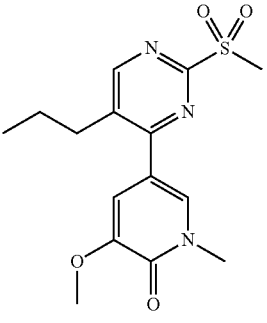 [SMILES: CCCc1cnc(S(C)(=O)=O)nc1-c1cc(OC)c(=O)n(C)c1] | 3-methoxy-1-methyl-5-(2-methylsulfonyl-5-propylpyrimidin-4-yl)pyridin-2-one |
| 356 | 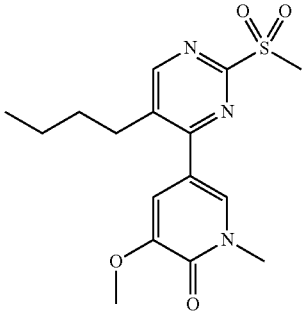 [SMILES: CCCCc1cnc(S(C)(=O)=O)nc1-c1cc(OC)c(=O)n(C)c1] | 5-(5-butyl-2-methylsulfonylpyrimidin-4-yl)-3-methoxy-1-methylpyridin-2-one |
| 357 | 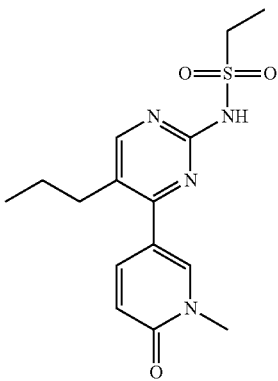 [SMILES: CCCc1cnc(NS(=O)(=O)CC)nc1-c1ccc(=O)n(C)c1] | N-[4-(1-methyl-6-oxopyridin-3-yl)-5-propylpyrimidin-2-yl]ethanesulfonamide |

TABLE 1-continued
| Chemical Synthesis Example | Structure | Name |
|---|---|---|
| 358 | 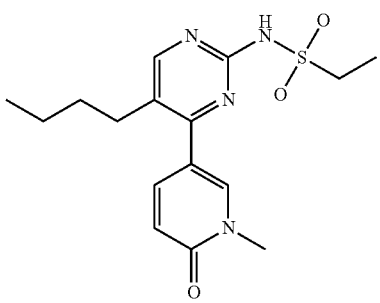 [SMILES: CCCCc1cnc(NS(O)(O)CC)nc1-c1ccc(=O)n(C)c1] | N-[5-butyl-4-(1-methyl-6-oxopyridin-3-yl)pyrimidin-2-yl]ethanesulfonamide |
| 359 | 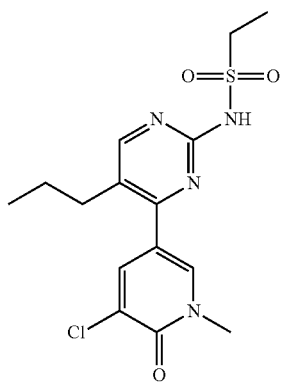 [SMILES: CCCc1cnc(NS(=O)(=O)CC)nc1-c1cc(Cl)c(=O)n(C)c1] | N-[4-(5-chloro-1-methyl-6-oxopyridin-3-yl)-5-propylpyrimidin-2-yl]ethanesulfonamide |
| 360 | 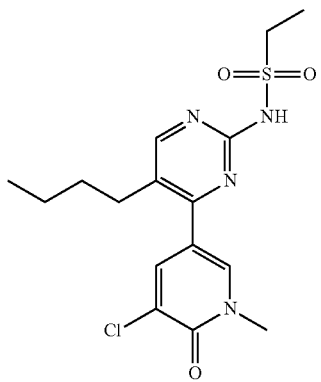 [SMILES: CCCCc1cnc(NS(=O)(=O)CC)nc1-c1cc(Cl)c(=O)n(C)c1] | N-[5-butyl-4-(5-chloro-1-methyl-6-oxopyridin-3-yl)pyrimidin-2-yl]ethanesulfonamide |
| 361 | 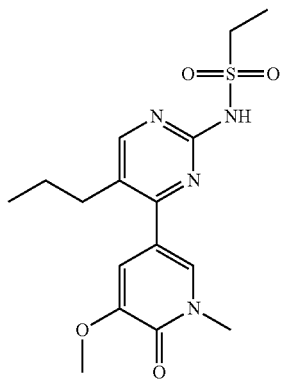 [SMILES: CCCc1cnc(NS(=O)(=O)CC)nc1-c1cc(OC)c(=O)n(C)c1] | N-[4-(5-methoxy-1-methyl-6-oxopyridin-3-yl)-5-propylpyrimidin-2-yl]ethanesulfonamide |

TABLE 1-continued

| Chemical Synthesis Example | Structure | Name |
|---|---|---|
| 362 | 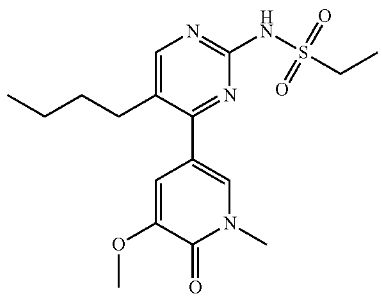 [SMILES: CCCCc1cnc(NS(=O)(=O)CC)nc1-c1cc(OC)c(=O)n(C)c1] | N-[5-butyl-4-(5-methoxy-1-methyl-6-oxopyridin-3-yl)pyrimidin-2-yl]ethanesulfonamide |
| 363 | 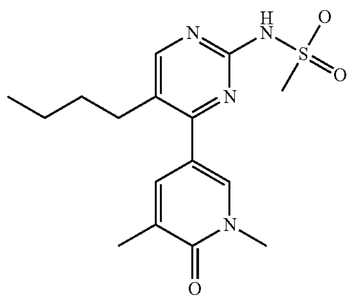 | N-[5-butyl-4-(1,5-dimethyl-6-oxopyridin-3-yl)pyrimidin-2-yl]methanesulfonamide |
| 364 | 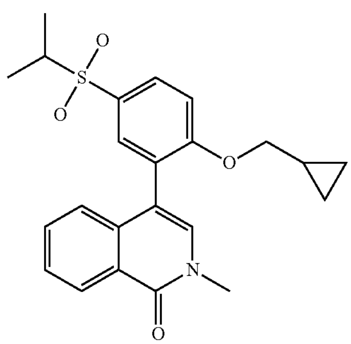 [SMILES: CC(C)S(O)(O)c1ccc(OCC2CC2)c(-c2cn(C)c(=O)c3ccccc23)c1] | 4-[2-(cyclopropylmethoxy)-5-propan-2-ylsulfonylphenyl]-2-methylisoquinolin-1-one |
| 365 | 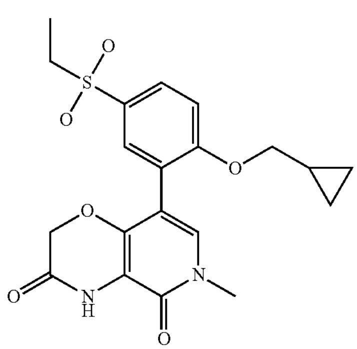 [SMILES: CCS(O)(O)c1ccc(OCC2CC2)c(-c2cn(C)c(=O)c3c2OCC(=O)N3)c1] | 8-[2-(cyclopropylmethoxy)-5-ethylsulfonylphenyl]-6-methyl-4H-pyrido[4,3-b][1,4]oxazine-3,5-dione |

TABLE 1-continued

| Chemical Synthesis Example | Structure | Name |
|---|---|---|
| 366 | 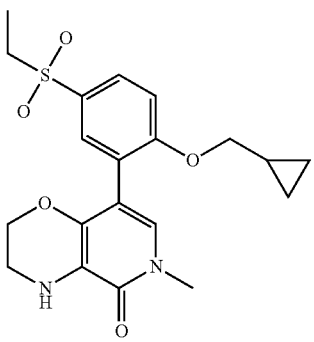 [SMILES: CCS(O)(O)c1ccc(OCC2CC2)c(-c2cn(C)c(=O)c3c2OCCN3)c1] | 8-[2-(cyclopropylmethoxy)-5-ethylsulfonylphenyl]-6-methyl-3,4-dihydro-2H-pyrido[4,3-b][1,4]oxazin-5-one |
| 367 | 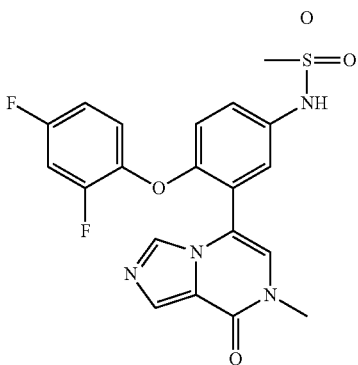 | N-[4-(2,4-difluorophenoxy)-3-(7-methyl-8-oxoimidazo[1,5-a]pyrazin-5-yl)phenyl]methanesulfonamide |
| 368 | 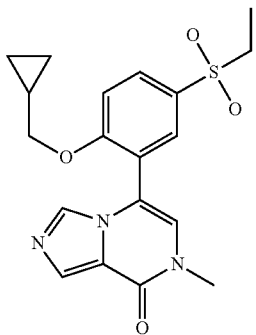 [SMILES: CCS(O)(O)c1ccc(OCC2CC2)c(-c2cn(C)c(=O)c3cncn23)c1] | 5-[2-(cyclopropylmethoxy)-5-ethylsulfonylphenyl]-7-methylimidazo[1,5-a]pyrazin-8-one |
| 369 | 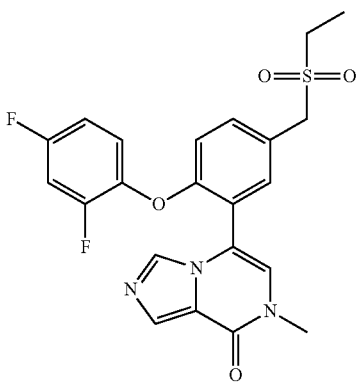 [SMILES: CCS(=O)(=O)Cc1ccc(Oc2ccc(F)cc2F)c(-c2cn(C)c(=O)c3cncn23)c1] | 5-[2-(2,4-difluorophenoxy)-5-(ethylsulfonylmethyl)phenyl]-7-methylimidazo[1,5-a]pyrazin-8-one |

TABLE 1-continued

| Chemical Synthesis Example | Structure | Name |
|---|---|---|
| 370 | 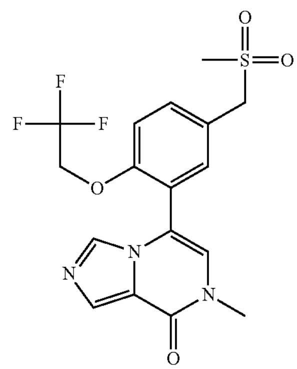 [SMILES: Cn1cc(-c2cc(CS(C)(=O)=O)ccc2OCC(F)(F)F)n2cncc2c1=O] | 7-methyl-5-[5-(methylsulfonylmethyl)-2-(2,2,2-trifluoroethoxy)phenyl]imidazo[1,5-a]pyrazin-8-one |
| 371 | 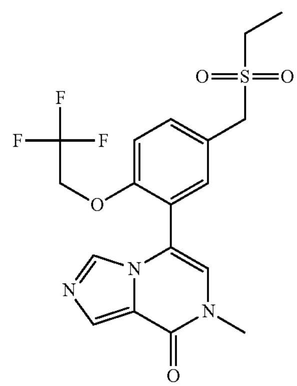 [SMILES: CCS(=O)(=O)Cc1ccc(OCC(F)(F)F)c(-c2cn(C)c(=O)c3cncn23)c1] | 5-[5-(ethylsulfonylmethyl)-2-(2,2,2-trifluoroethoxy)phenyl]-7-methylimidazo[1,5-a]pyrazin-8-one |
| 372 | 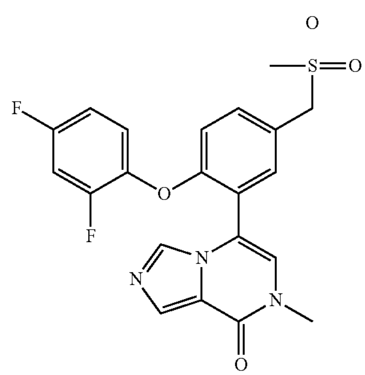 | 5-[2-(2,4-difluorophenoxy)-5-(methylsulfonylmethyl)phenyl]-7-methylimidazo[1,5-a]pyrazin-8-one |
| 373 | 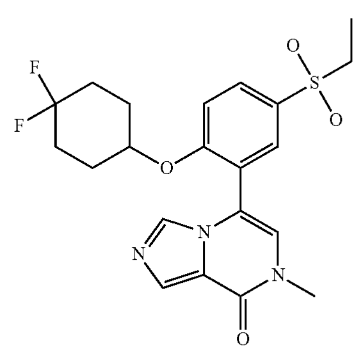 [SMILES: CCS(O)(O)c1ccc(OC2CCC(F)(F)CC2)c(-c2cn(C)c(=O)c3cncn23)c1] | 5-[2-(4,4-difluorocyclohexyl)oxy-5-ethylsulfonylphenyl]-7-methylimidazo[1,5-a]pyrazin-8-one |

TABLE 1-continued

| Chemical Synthesis Example | Structure | Name |
|---|---|---|
| 374 | 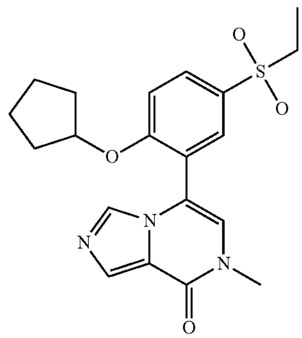 [SMILES: CCS(O)(O)c1ccc(OC2CCCC2)c(-c2cn(C)c(=O)c3cncn23)c1] | 5-(2-cyclopentyloxy-5-ethylsulfonylphenyl)-7-methylimidazo[1,5-a]pyrazin-8-one |
| 375 | 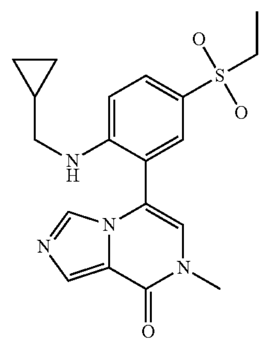 [SMILES: CCS(O)(O)c1ccc(NCC2CC2)c(-c2cn(C)c(=O)c3cncn23)c1] | 5-[2-(cyclopropylmethylamino)-5-ethylsulfonylphenyl]-7-methylimidazo[1,5-a]pyrazin-8-one |
| 376 | 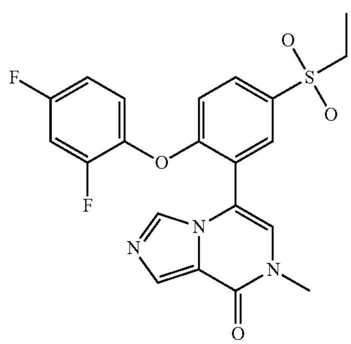 [SMILES: CCS(O)(O)c1ccc(Oc2ccc(F)cc2F)c(-c2cn(C)c(=O)c3cncn23)c1] | 5-[2-(2,4-difluorophenoxy)-5-ethylsulfonylphenyl]-7-methylimidazo[1,5-a]pyrazin-8-one |
| 377 | 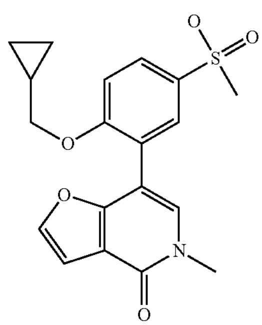 | 7-[2-(cyclopropylmethoxy)-5-methylsulfonylphenyl]-5-methylfuro[3,2-c]pyridin-4-one |

TABLE 1-continued

| Chemical Synthesis Example | Structure | Name |
|---|---|---|
| 378 | 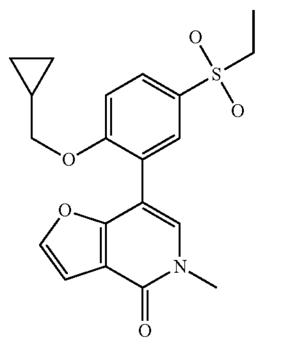 [SMILES: CCS(O)(O)c1ccc(OCC2CC2)c(-c2cn(C)c(=O)c3ccoc23)c1] | 7-[2-(cyclopropylmethoxy)-5-ethylsulfonylphenyl]-5-methylfuro[3,2-c]pyridin-4-one |
| 379 | 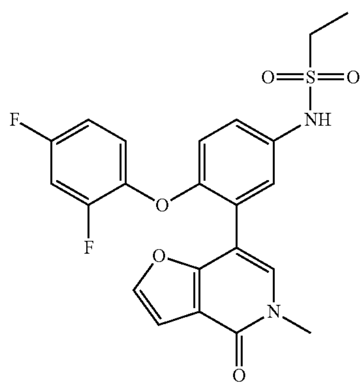 [SMILES: CCS(=O)(=O)Nc1ccc(Oc2ccc(F)cc2F)c(-c2cn(C)c(=O)c3ccoc23)c1] | N-[4-(2,4-difluorophenoxy)-3-(5-methyl-4-oxofuro[3,2-c]pyridin-7-yl)phenyl]ethanesulfonamide |
| 380 | 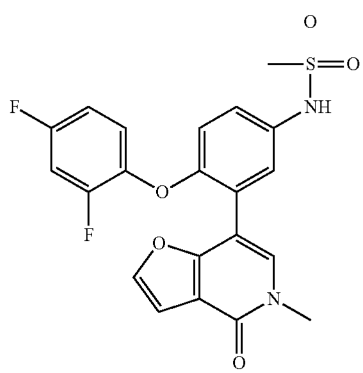 | N-[4-(2,4-difluorophenoxy)-3-(5-methyl-4-oxofuro[3,2-c]pyridin-7-yl)phenyl]methanesulfonamide |
| 381 | 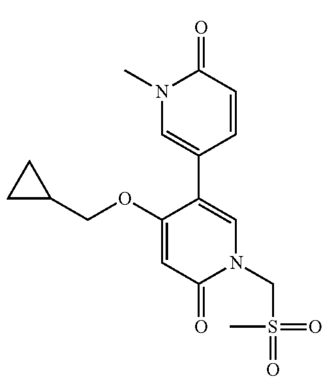 [SMILES: Cn1cc(-c2cn(CS(C)(=O)=O)c(=O)cc2OCC2CC2)ccc1=O] | 4-(cyclopropylmethoxy)-5-(1-methyl-6-oxopyridin-3-yl)-1-(methylsulfonylmethyl)pyridin-2-one |

TABLE 1-continued

| Chemical Synthesis Example | Structure | Name |
| --- | --- | --- |
| 382 | 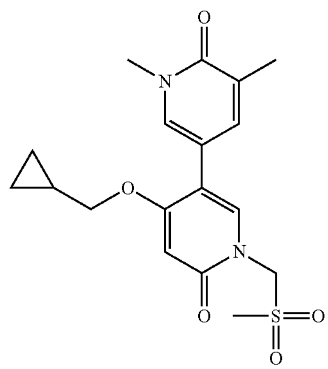 [SMILES: Cc1cc(-c2cn(CS(C)(=O)=O)c(=O)cc2OCC2CC2)cn(C)c1=O] | 5-[4-(cyclopropylmethoxy)-1-(methylsulfonylmethyl)-6-oxopyridin-3-yl]-1,3-dimethylpyridin-2-one |
| 383 | 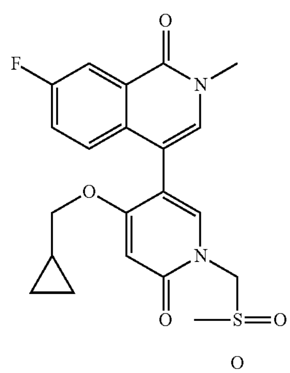 | 4-[4-(cyclopropylmethoxy)-1-(methylsulfonylmethyl)-6-oxopyridin-3-yl]-7-fluoro-2-methylisoquinolin-1-one |
| 384 | 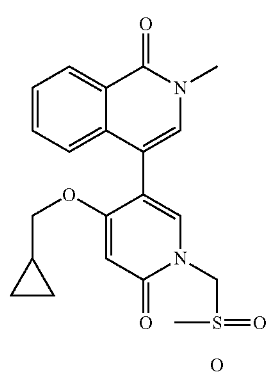 | 4-[4-(cyclopropylmethoxy)-1-(methylsulfonylmethyl)-6-oxopyridin-3-yl]-2-methylisoquinolin-1-one |
| 385 | 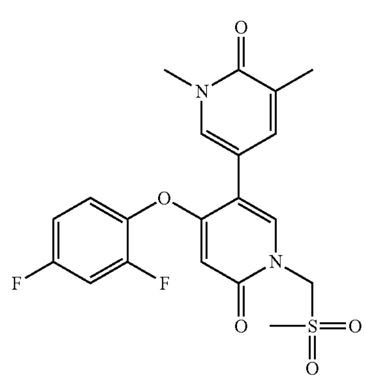 [SMILES: Cc1cc(-c2cn(CS(C)(=O)=O)c(=O)cc2Oc2ccc(F)cc2F)cn(C)c1=O] | 5-[4-(2,4-difluorophenoxy)-1-(methylsulfonylmethyl)-6-oxopyridin-3-yl]-1,3-dimethylpyridin-2-one |

TABLE 1-continued

| Chemical Synthesis Example | Structure | Name |
|---|---|---|
| 386 | 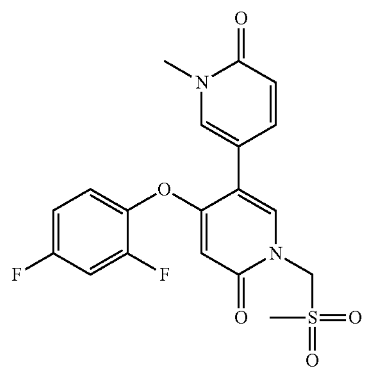 [SMILES: Cn1cc(-c2cn(CS(C)(=O)=O)c(=O)cc2Oc2ccc(F)cc2F)ccc1=O] | 4-(2,4-difluorophenoxy)-5-(1-methyl-6-oxopyridin-3-yl)-1-(methylsulfonylmethyl)pyridin-2-one |
| 387 | 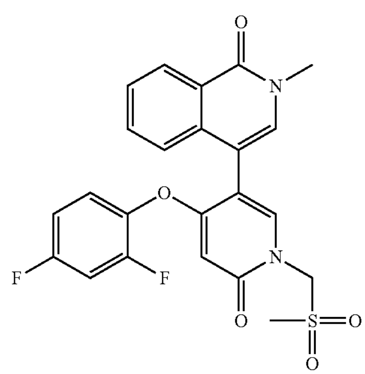 [SMILES: Cn1cc(-c2cn(CS(C)(=O)=O)c(=O)cc2Oc2ccc(F)cc2F)c2ccccc2c1=O] | 4-[4-(2,4-difluorophenoxy)-1-(methylsulfonylmethyl)-6-oxopyridin-3-yl]-2-methylisoquinolin-1-one |
| 388 | 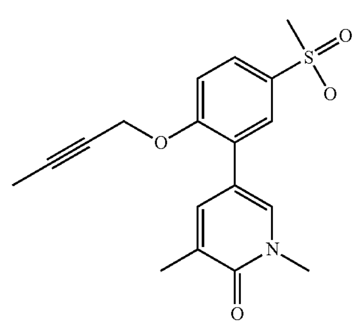 | 5-(2-but-2-ynoxy-5-methylsulfonylphenyl)-1,3-dimethylpyridin-2-one |
| 389 | 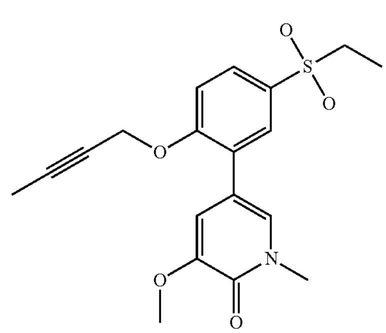 [SMILES: CC#CCOc1ccc(S(O)(O)CC)cc1-c1cc(OC)c(=O)n(C)c1] | 5-(2-but-2-ynoxy-5-ethylsulfonylphenyl)-3-methoxy-1-methylpyridin-2-one |

TABLE 1-continued

| Chemical Synthesis Example | Structure | Name |
|---|---|---|
| 390 | 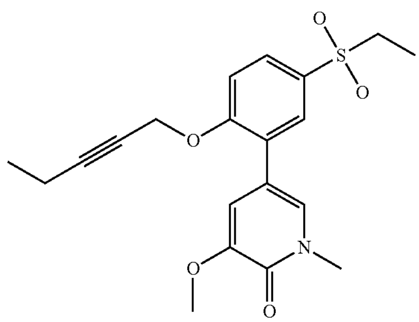 [SMILES: CCC#CCOc1ccc(S(O)(O)CC)cc1-c1cc(OC)c(=O)n(C)c1] | 5-(5-ethylsulfonyl-2-pent-2-ynoxyphenyl)-3-methoxy-1-methylpyridin-2-one |
| 391 | 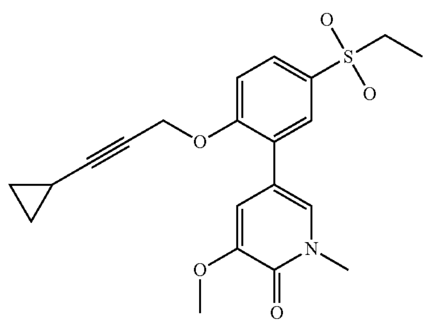 [SMILES: CCS(O)(O)c1ccc(OCC#CC2CC2)c(-c2cc(OC)c(=O)n(C)c2)c1] | 5-[2-(3-cyclopropylprop-2-ynoxy)-5-ethylsulfonylphenyl]-3-methoxy-1-methylpyridin-2-one |
| 392 | 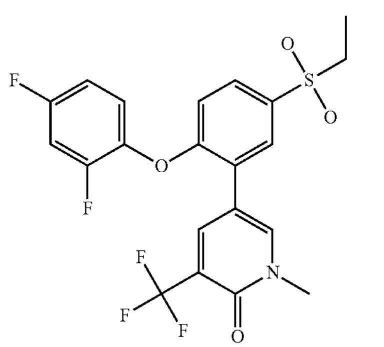 [SMILES: CCS(O)(O)c1ccc(Oc2ccc(F)cc2F)c(-c2cc(C(F)(F)F)c(=O)n(C)c2)c1] | 5-[2-(2,4-difluorophenoxy)-5-ethylsulfonylphenyl]-1-methyl-3-(trifluoromethyl)pyridin-2-one |
| 393 | 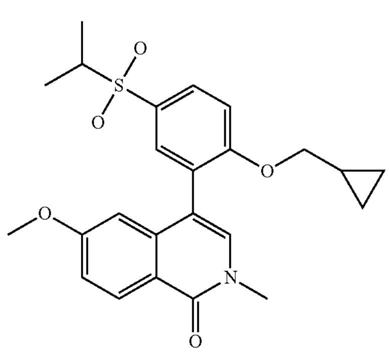 [SMILES: COc1ccc2c(=O)n(C)cc(-c3cc(S(O)(O)C(C)C)ccc3OCC3CC3)c2c1] | 4-[2-(cyclopropylmethoxy)-5-propan-2-ylsulfonylphenyl]-6-methoxy-2-methylisoquinolin-1-one |

TABLE 1-continued

| Chemical Synthesis Example | Structure | Name |
|---|---|---|
| 394 | 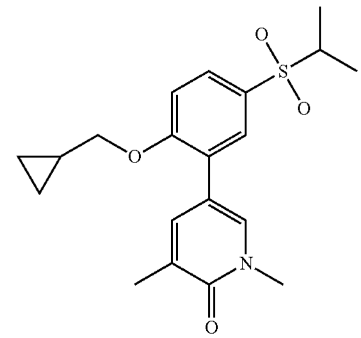 [SMILES: Cc1cc(-c2cc(S(O)(O)C(C)C)ccc2OCC2CC2)cn(C)c1=O] | 5-[2-(cyclopropylmethoxy)-5-propan-2-ylsulfonylphenyl]-1,3-dimethylpyridin-2-one |
| 395 | 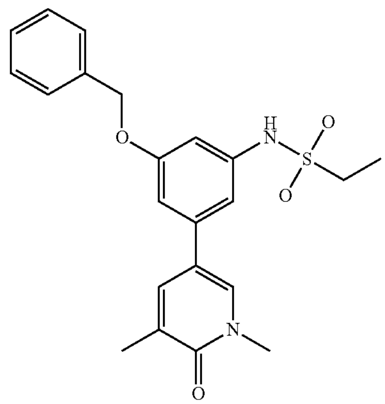 [SMILES: CCS(O)(O)Nc1cc(OCc2ccccc2)cc(-c2cc(C)c(=O)n(C)c2)c1] | N-[3-(1,5-dimethyl-6-oxopyridin-3-yl)-5-phenylmethoxyphenyl]ethanesulfonamide |
| 396 | 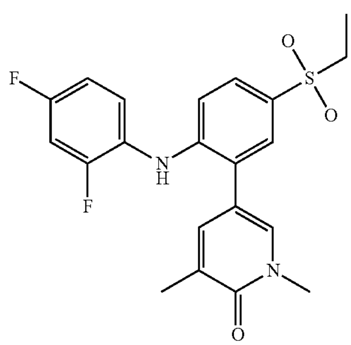 [SMILES: CCS(O)(O)c1ccc(Nc2ccc(F)cc2F)c(-c2cc(C)c(=O)n(C)c2)c1] | 5-[2-(2,4-difluoroanilino)-5-ethylsulfonylphenyl]-1,3-dimethylpyridin-2-one |
| 397 | 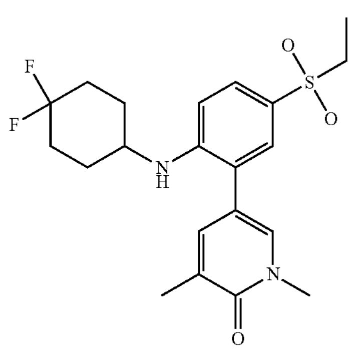 [SMILES: CCS(O)(O)c1ccc(NC2CCC(F)(F)CC2)c(-c2cc(C)c(=O)n(C)c2)c1] | 5-[2-[(4,4-difluorocyclohexyl)amino]-5-ethylsulfonylphenyl]-1,3-dimethylpyridin-2-one |

TABLE 1-continued

| Chemical Synthesis Example | Structure | Name |
|---|---|---|
| 398 | 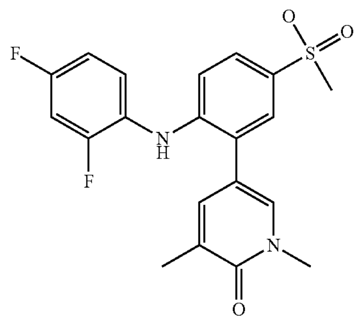 | 5-[2-(2,4-difluoroanilino)-5-methylsulfonylphenyl]-1,3-dimethylpyridin-2-one |
| 399 | 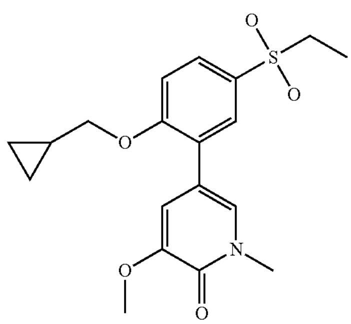 [SMILES: CCS(O)(O)c1ccc(OCC2CC2)c(-c2cc(OC)c(=O)n(C)c2)c1] | 5-[2-(cyclopropylmethoxy)-5-ethylsulfonylphenyl]-3-methoxy-1-methylpyridin-2-one |
| 400 | 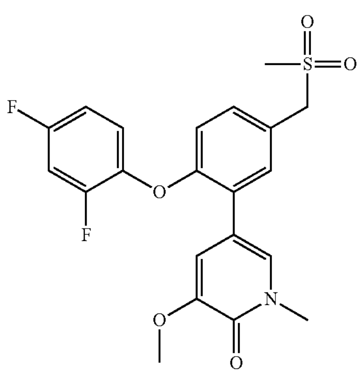 [SMILES: COc1cc(-c2cc(CS(C)(=O)=O)ccc2Oc2ccc(F)cc2F)cn(C)c1=O] | 5-[2-(2,4-difluorophenoxy)-5-(methylsulfonylmethyl)phenyl]-3-methoxy-1-methylpyridin-2-one |
| 401 | 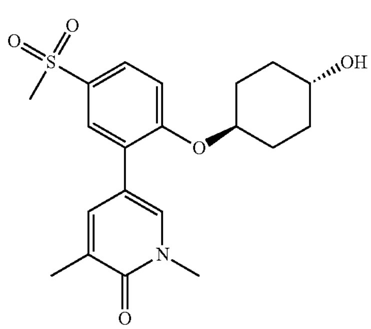 [SMILES: Cc1cc(-c2cc(S(C)(=O)=O)ccc2O[C@H]2CC[C@H](O)CC2)cn(C)c1=O] | 5-[2-(trans-4-hydroxycyclohexyl)oxy-5-methylsulfonylphenyl]-1,3-dimethylpyridin-2-one |

TABLE 1-continued
| Chemical Synthesis Example | Structure | Name |
|---|---|---|
| 402 | 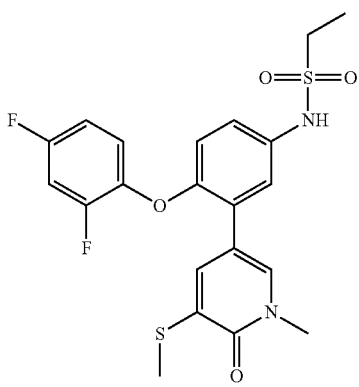 | N-[4-(2,4-difluorophenoxy)-3-(1-methyl-5-methylsulfanyl-6-oxopyridin-3-yl)phenyl]ethanesulfonamide |
| 403 | 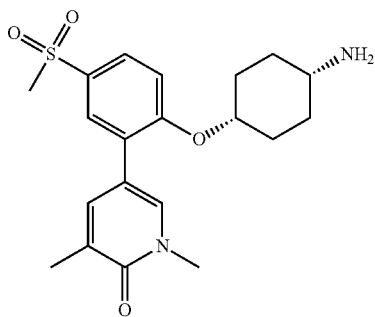 [SMILES: Cc1cc(-c2cc(S(C)(=O)=O)ccc2O[C@H]2CC[C@@H](N)CC2)cn(C)c1=O] | 5-[2-(cis-4-aminocyclohexyl)oxy-5-methylsulfonylphenyl]-1,3-dimethylpyridin-2-one |
| 404 | 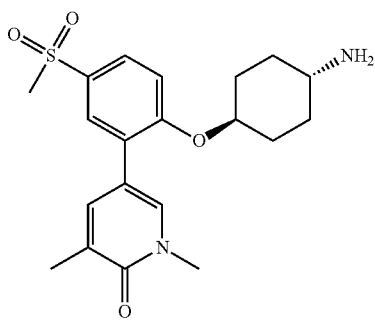 [SMILES: Cc1cc(-c2cc(S(C)(=O)=O)ccc2O[C@H]2CC[C@H](N)CC2)cn(C)c1=O] | 5-[2-(trans-4-aminocyclohexyl)oxy-5-methylsulfonylphenyl]-1,3-dimethylpyridin-2-one |
| 405 | 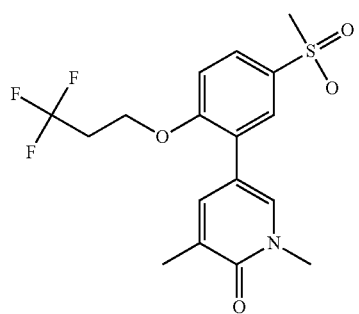 | 1,3-dimethyl-5-[5-methylsulfonyl-2-(3,3,3-trifluoropropoxy)phenyl]pyridin-2-one |

TABLE 1-continued

| Chemical Synthesis Example | Structure | Name |
|---|---|---|
| 406 | 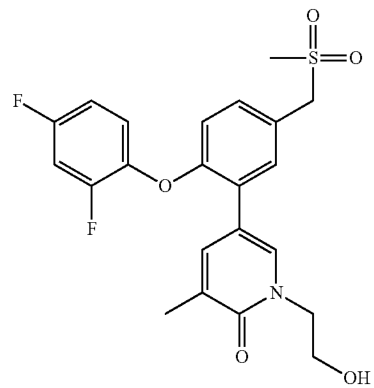 [SMILES: Cc1cc(-c2cc(CS(C)(=O)=O)ccc2Oc2ccc(F)cc2F)cn(CCO)c1=O] | 5-[2-(2,4-difluorophenoxy)-5-(methylsulfonylmethyl)phenyl]-1-(2-hydroxyethyl)-3-methylpyridin-2-one |
| 407 | 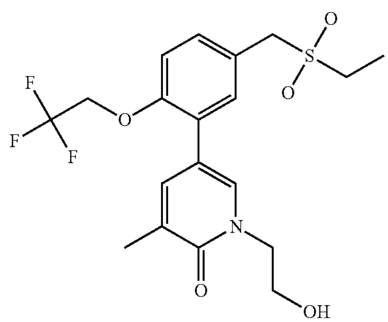 [SMILES: CCS(O)(O)Cc1ccc(OCC(F)(F)F)c(-c2cc(C)c(=O)n(CCO)c2)c1] | 5-[5-(ethylsulfonylmethyl)-2-(2,2,2-trifluoroethoxy)phenyl]-1-(2-hydroxyethyl)-3-methylpyridin-2-one |
| 408 | 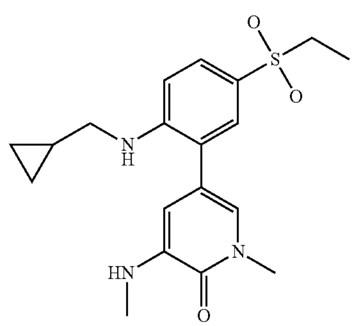 [SMILES: CCS(O)(O)c1ccc(NCC2CC2)c(-c2cc(NC)c(=O)n(C)c2)c1] | 5-[2-(cyclopropylmethylamino)-5-ethylsulfonylphenyl]-1-methyl-3-(methylamino)pyridin-2-one |
| 409 | 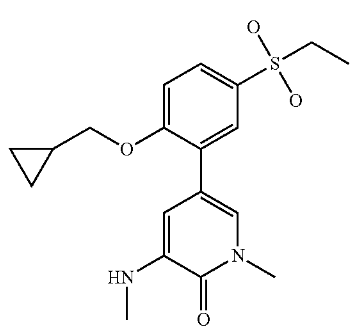 [SMILES: CCS(O)(O)c1ccc(OCC2CC2)c(-c2cc(NC)c(=O)n(C)c2)c1] | 5-[2-(cyclopropylmethoxy)-5-ethylsulfonylphenyl]-1-methyl-3-(methylamino)pyridin-2-one |

TABLE 1-continued

| Chemical Synthesis Example | Structure | Name |
|---|---|---|
| 410 | 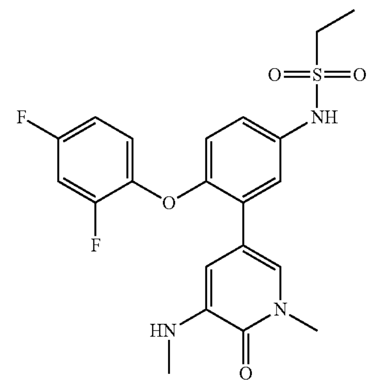 [SMILES: CCS(=O)(=O)Nc1ccc(Oc2ccc(F)cc2F)c(-c2cc(NC)c(=O)n(C)c2)c1] | N-[4-(2,4-difluorophenoxy)-3-[1-methyl-5-(methylamino)-6-oxopyridin-3-yl]phenyl]ethanesulfonamide |
| 411 | 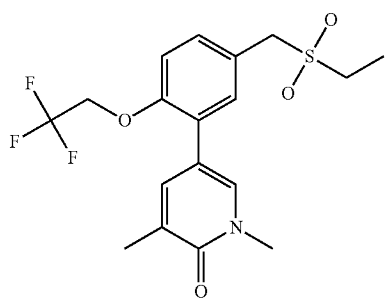 [SMILES: CCS(O)(O)Cc1ccc(OCC(F)(F)F)c(-c2cc(C)c(=O)n(C)c2)c1] | 5-[5-(ethylsulfonylmethyl)-2-(2,2,2-trifluoroethoxy)phenyl]-1,3-dimethylpyridin-2-one |
| 412 | 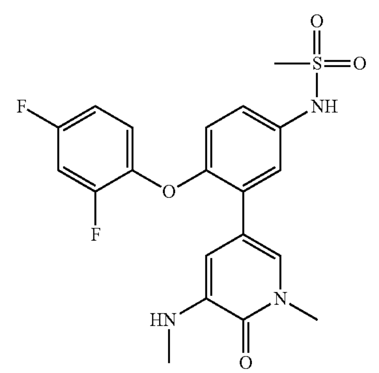 [SMILES: CNc1cc(-c2cc(NS(C)(=O)=O)ccc2Oc2ccc(F)cc2F)cn(C)c1=O] | N-[4-(2,4-difluorophenoxy)-3-[1-methyl-5-(methylamino)-6-oxopyridin-3-yl]phenyl]methanesulfonamide |
| 413 | 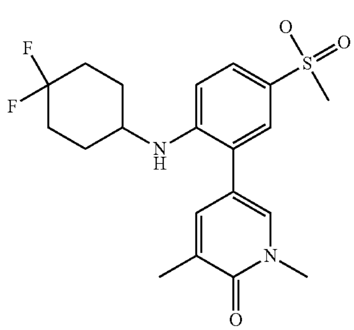 | 5-[2-[(4,4-difluorocyclohexyl)amino]-5-methylsulfonylphenyl]-1,3-dimethylpyridin-2-one |

TABLE 1-continued

| Chemical Synthesis Example | Structure | Name |
|---|---|---|
| 414 | 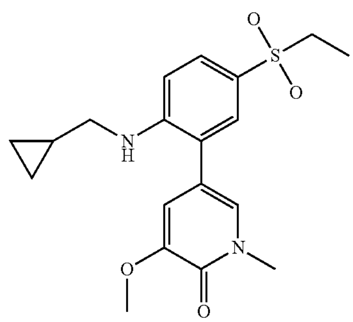 [SMILES: CCS(O)(O)c1ccc(NCC2CC2)c(-c2cc(OC)c(=O)n(C)c2)c1] | 5-[2-(cyclopropylmethylamino)-5-ethylsulfonylphenyl]-3-methoxy-1-methylpyridin-2-one |
| 415 | 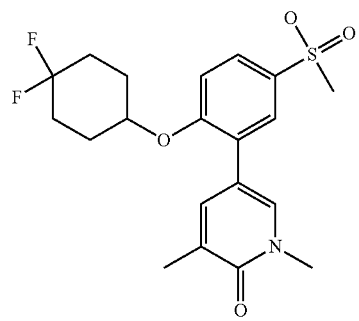 | 5-[2-(4,4-difluorocyclohexyl)oxy-5-methylsulfonylphenyl]-1,3-dimethylpyridin-2-one |
| 416 | 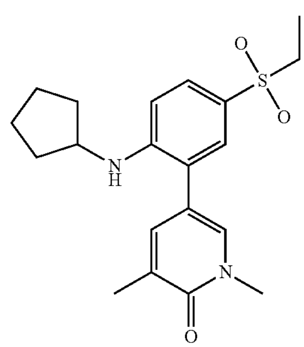 [SMILES: CCS(O)(O)c1ccc(NC2CCCC2)c(-c2cc(C)c(=O)n(C)c2)c1] | 5-[2-(cyclopentylamino)-5-ethylsulfonylphenyl]-1,3-dimethylpyridin-2-one |
| 417 | 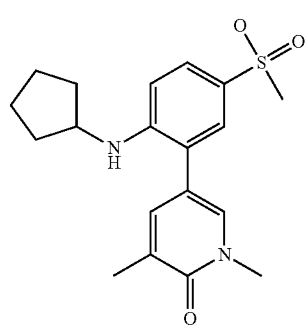 | 5-[2-(cyclopentylamino)-5-methylsulfonylphenyl]-1,3-dimethylpyridin-2-one |

TABLE 1-continued

| Chemical Synthesis Example | Structure | Name |
|---|---|---|
| 418 | 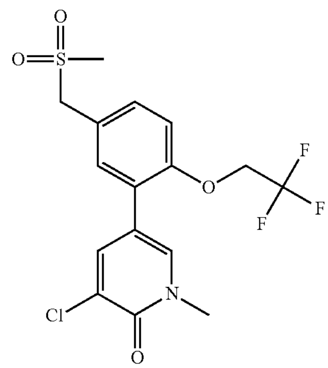 [SMILES: Cn1cc(-c2cc(CS(C)(=O)=O)ccc2OCC(F)(F)F)cc(Cl)c1=O] | 3-chloro-1-methyl-5-[5-(methylsulfonylmethyl)-2-(2,2,2-trifluoroethoxy)phenyl]pyridin-2-one |
| 419 | 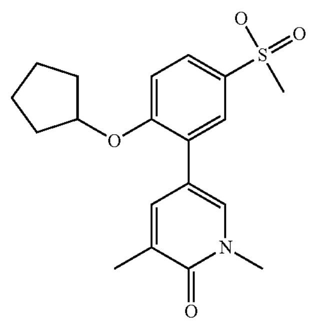 | 5-(2-cyclopentyloxy-5-methylsulfonylphenyl)-1,3-dimethylpyridin-2-one |
| 420 | 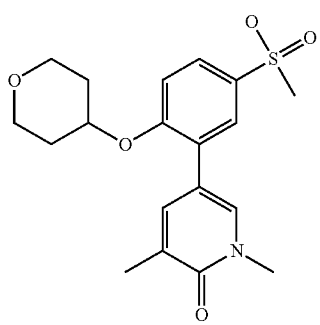 | 1,3-dimethyl-5-[5-methylsulfonyl-2-(oxan-4-yloxy)phenyl]pyridin-2-one |
| 421 | 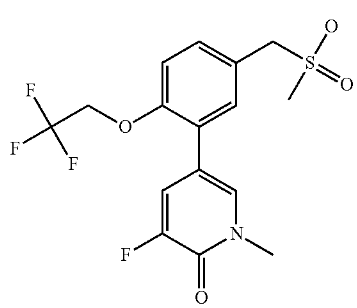 | 3-fluoro-1-methyl-5-[5-(methylsulfonylmethyl)-2-(2,2,2-trifluoroethoxy)phenyl]pyridin-2-one |

TABLE 1-continued

| Chemical Synthesis Example | Structure | Name |
|---|---|---|
| 422 | 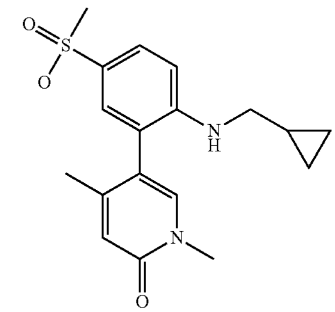 | 5-[2-(cyclopropylmethylamino)-5-methylsulfonylphenyl]-1,4-dimethylpyridin-2-one |
| 423 | 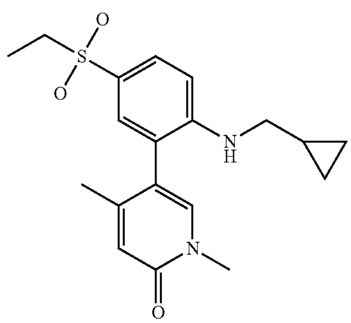 [SMILES: CCS(O)(O)c1ccc(NCC2CC2)c(-c2cn(C)c(=O)cc2C)c1] | 5-[2-(cyclopropylmethylamino)-5-ethylsulfonylphenyl]-1,4-dimethylpyridin-2-one |
| 424 | 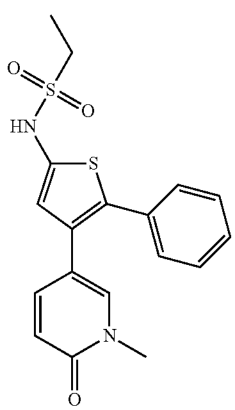 [SMILES: CCS(=O)(=O)Nc1cc(-c2ccc(=O)n(C)c2)c(-c2ccccc2)s1] | N-[4-(1-methyl-6-oxopyridin-3-yl)-5-phenylthiophen-2-yl]ethanesulfonamide |
| 425 | 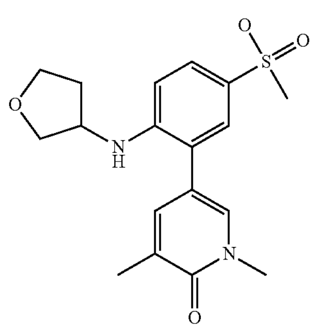 | 1,3-dimethyl-5-[5-methylsulfonyl-2-(oxolan-3-ylamino)phenyl]pyridin-2-one |

TABLE 1-continued

| Chemical Synthesis Example | Structure | Name |
|---|---|---|
| 426 | 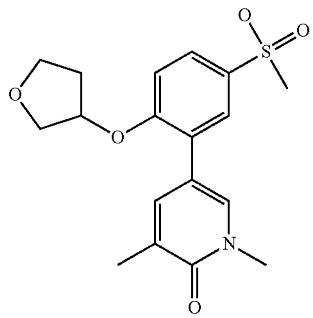 | 1,3-dimethyl-5-[5-methylsulfonyl-2-(oxolan-3-yloxy)phenyl]pyridin-2-one |
| 427 | 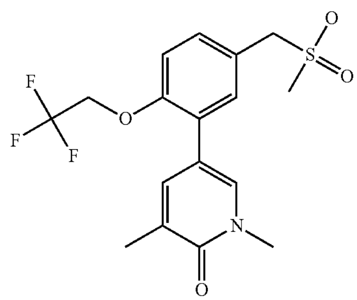 | 1,3-dimethyl-5-[5-(methylsulfonylmethyl)-2-(2,2,2-trifluoroethoxy)phenyl]pyridin-2-one |
| 428 | 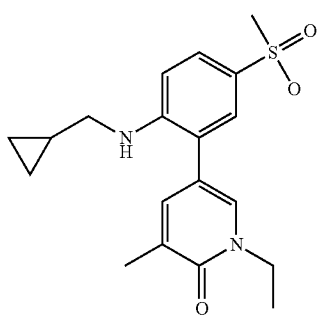 | 5-[2-(cyclopropylmethylamino)-5-methylsulfonylphenyl]-1-ethyl-3-methylpyridin-2-one |
| 429 | 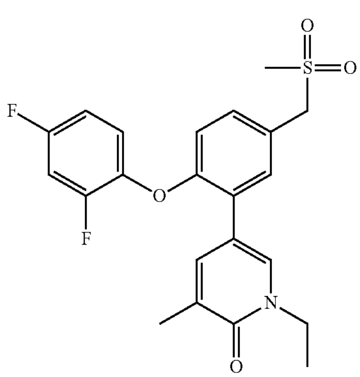 [SMILES: CCn1cc(-c2cc(CS(C)(=O)=O)ccc2Oc2ccc(F)cc2F)cc(C)c1=O] | 5-[2-(2,4-difluorophenoxy)-5-(methylsulfonylmethyl)phenyl]-1-ethyl-3-methylpyridin-2-one |

TABLE 1-continued

| Chemical Synthesis Example | Structure | Name |
|---|---|---|
| 430 | 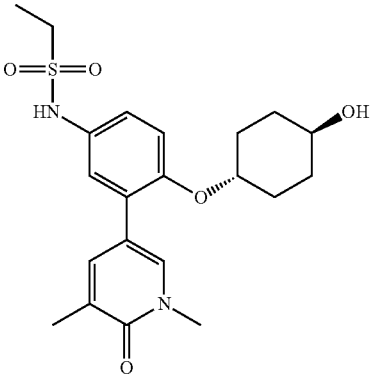 [SMILES: CCS(=O)(=O)Nc1ccc(O[C@H]2CC[C@H](O)CC2)c(-c2cc(C)c(=O)n(C)c2)c1] | N-[3-(1,5-dimethyl-6-oxopyridin-3-yl)-4-(trans-4-hydroxycyclohexyl)oxyphenyl]ethanesulfonamide |
| 431 | 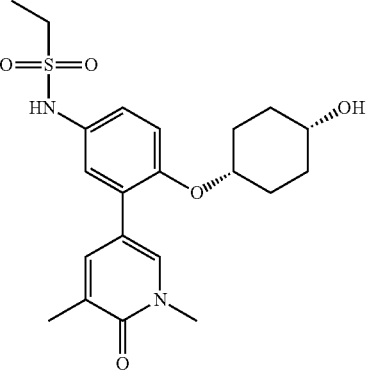 [SMILES: CCS(=O)(=O)Nc1ccc(O[C@H]2CC[C@@H](O)CC2)c(-c2cc(C)c(=O)n(C)c2)c1] | N-[3-(1,5-dimethyl-6-oxopyridin-3-yl)-4-(cis-4-hydroxycyclohexyl)oxyphenyl]ethanesulfonamide |
| 432 | 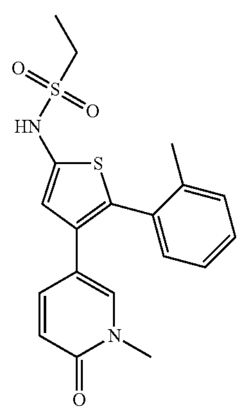 [SMILES: CCS(=O)(=O)Nc1cc(-c2ccc(=O)n(C)c2)c(-c2ccccc2C)s1] | N-[4-(1-methyl-6-oxopyridin-3-yl)-5-(2-methylphenyl)thiophen-2-yl]ethanesulfonamide |
| 433 | 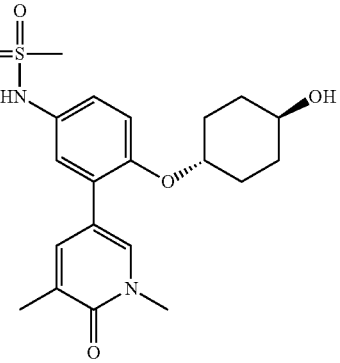 | N-[3-(1,5-dimethyl-6-oxopyridin-3-yl)-4-(trans-4-hydroxycyclohexyl)oxyphenyl]methanesulfonamide |

TABLE 1-continued

| Chemical Synthesis Example | Structure | Name |
|---|---|---|
| 434 | 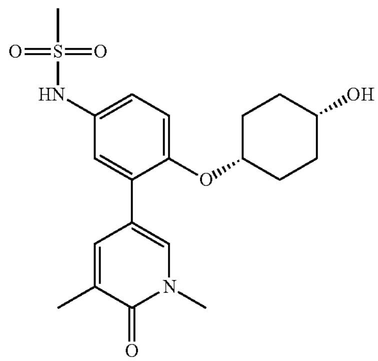 [SMILES: Cc1cc(-c2cc(NS(C)(=O)=O)ccc2O[C@H]2CC[C@@H](O)CC2)cn(C)c1=O] | N-[3-(1,5-dimethyl-6-oxopyridin-3-yl)-4-(cis-4-hydroxycyclohexyl)oxyphenyl]methanesulfonamide |
| 435 | 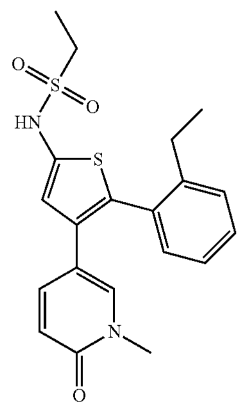 [SMILES: CCc1ccccc1-c1sc(NS(=O)(=O)CC)cc1-c1ccc(=O)n(C)c1] | N-[5-(2-ethylphenyl)-4-(1-methyl-6-oxopyridin-3-yl)thiophen-2-yl]ethanesulfonamide |
| 436 | 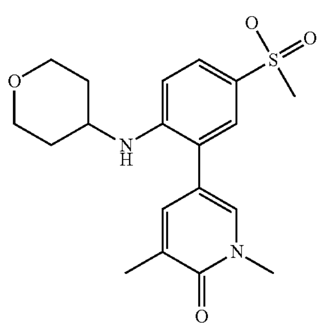 | 1,3-dimethyl-5-[5-methylsulfonyl-2-(oxan-4-ylamino)phenyl]pyridin-2-one |
| 437 | 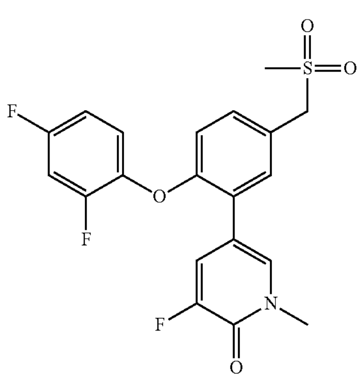 | 5-[2-(2,4-difluorophenoxy)-5-(methylsulfonylmethyl)phenyl]-3-fluoro-1-methylpyridin-2-one |

TABLE 1-continued

| Chemical Synthesis Example | Structure | Name |
|---|---|---|
| 438 | 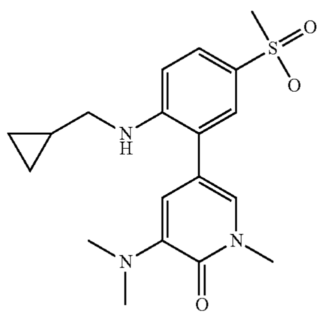 | 5-[2-(cyclopropylmethylamino)-5-methylsulfonylphenyl]-3-(dimethylamino)-1-methylpyridin-2-one |
| 439 | 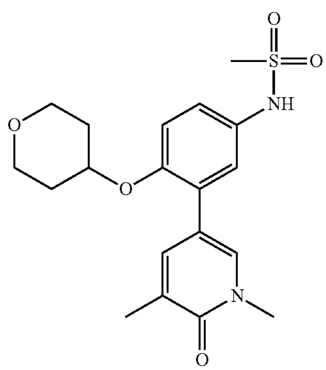 [SMILES: Cc1cc(-c2cc(NS(C)(=O)=O)ccc2OC2CCOCC2)cn(C)c1=O] | N-[3-(1,5-dimethyl-6-oxopyridin-3-yl)-4-(oxan-4-yloxy)phenyl]methanesulfonamide |
| 440 | 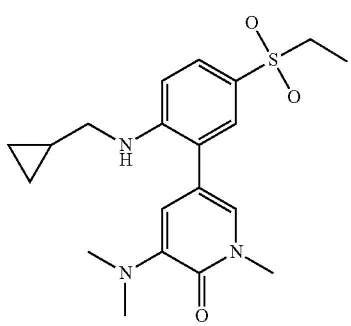 [SMILES: CCS(O)(O)c1ccc(NCC2CC2)c(-c2cc(N(C)C)c(=O)n(C)c2)c1] | 5-[2-(cyclopropylmethylamino)-5-ethylsulfonylphenyl]-3-(dimethylamino)-1-methylpyridin-2-one |
| 441 | 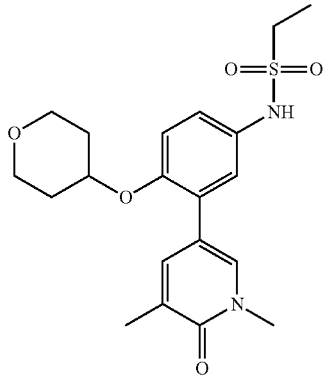 [SMILES: CCS(=O)(=O)Nc1ccc(OC2CCOCC2)c(-c2cc(C)c(=O)n(C)c2)c1] | N-[3-(1,5-dimethyl-6-oxopyridin-3-yl)-4-(oxan-4-yloxy)phenyl]ethanesulfonamide |

TABLE 1-continued

| Chemical Synthesis Example | Structure | Name |
|---|---|---|
| 442 | 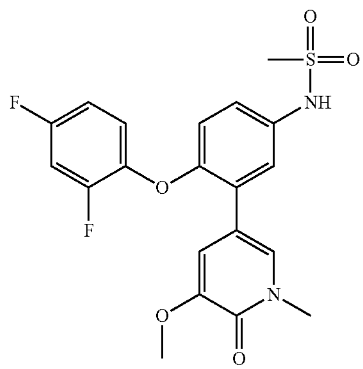 [SMILES: COc1cc(-c2cc(NS(C)(=O)=O)ccc2Oc2ccc(F)cc2F)cn(C)c1=O] | N-[4-(2,4-difluorophenoxy)-3-(5-methoxy-1-methyl-6-oxopyridin-3-yl)phenyl]methanesulfonamide |
| 443 | 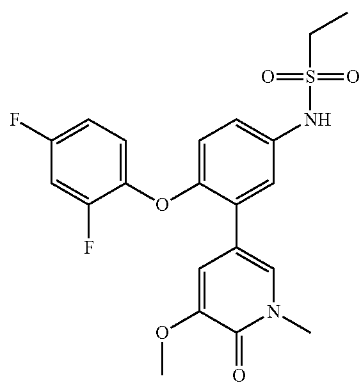 [SMILES: CCS(=O)(=O)Nc1ccc(Oc2ccc(F)cc2F)c(-c2cc(OC)c(=O)n(C)c2)c1] | N-[4-(2,4-difluorophenoxy)-3-(5-methoxy-1-methyl-6-oxopyridin-3-yl)phenyl]ethanesulfonamide |
| 444 | 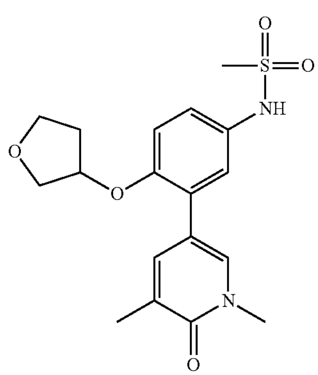 [SMILES: Cc1cc(-c2cc(NS(C)(=O)=O)ccc2OC2CCOC2)cn(C)c1=O] | N-[3-(1,5-dimethyl-6-oxopyridin-3-yl)-4-(oxolan-3-yloxy)phenyl]methanesulfonamide |
| 445 | 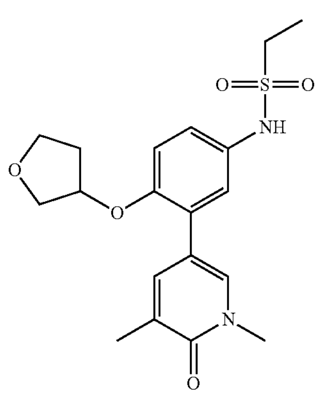 [SMILES: CCS(=O)(=O)Nc1ccc(OC2CCOC2)c(-c2cc(C)c(=O)n(C)c2)c1] | N-[3-(1,5-dimethyl-6-oxopyridin-3-yl)-4-(oxolan-3-yloxy)phenyl]ethanesulfonamide |

TABLE 1-continued

| Chemical Synthesis Example | Structure | Name |
|---|---|---|
| 446 | 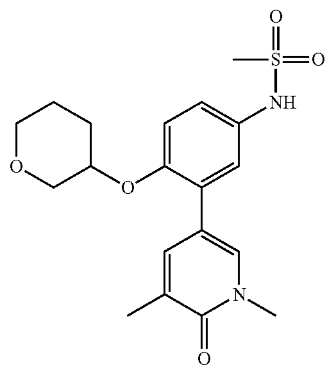 [SMILES: Cc1cc(-c2cc(NS(C)(=O)=O)ccc2OC2CCCOC2)cn(C)c1=O] | N-[3-(1,5-dimethyl-6-oxopyridin-3-yl)-4-(oxan-3-yloxy)phenyl]methanesulfonamide |
| 447 | 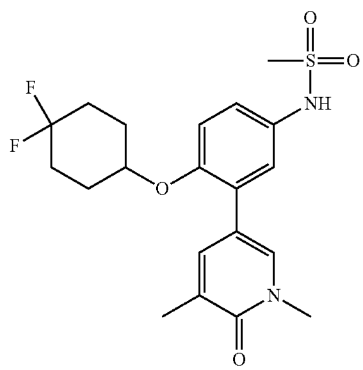 [SMILES: Cc1cc(-c2cc(NS(C)(=O)=O)ccc2OC2CCC(F)(F)CC2)cn(C)c1=O] | N-[4-(4,4-difluorocyclohexyl)oxy-3-(1,5-dimethyl-6-oxopyridin-3-yl)phenyl]methanesulfonamide |
| 448 | 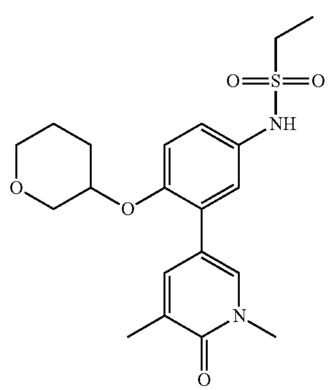 [SMILES: CCS(=O)(=O)Nc1ccc(OC2CCCOC2)c(-c2cc(C)c(=O)n(C)c2)c1] | N-[3-(1,5-dimethyl-6-oxopyridin-3-yl)-4-(oxan-3-yloxy)phenyl]ethanesulfonamide |
| 449 | 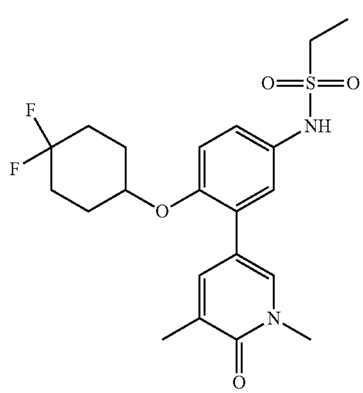 [SMILES: CCS(=O)(=O)Nc1ccc(OC2CCC(F)(F)CC2)c(-c2cc(C)c(=O)n(C)c2)c1] | N-[4-(4,4-difluorocyclohexyl)oxy-3-(1,5-dimethyl-6-oxopyridin-3-yl)phenyl]ethanesulfonamide |

TABLE 1-continued

| Chemical Synthesis Example | Structure | Name |
|---|---|---|
| 450 | 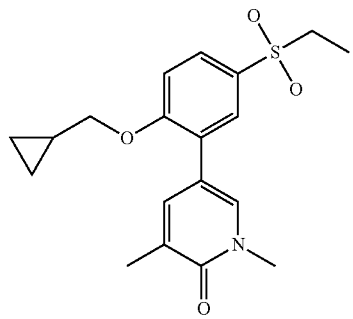 [SMILES: CCS(O)(O)c1ccc(OCC2CC2)c(-c2cc(C)c(=O)n(C)c2)c1] | 5-[2-(cyclopropylmethoxy)-5-ethylsulfonylphenyl]-1,3-dimethylpyridin-2-one |
| 451 | 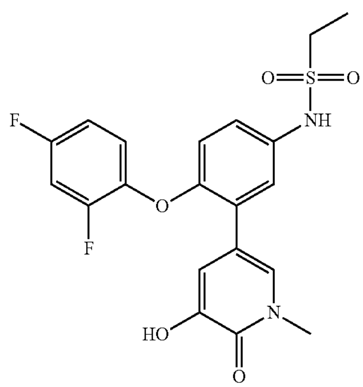 [SMILES: CCS(=O)(=O)Nc1ccc(Oc2ccc(F)cc2F)c(-c2cc(O)c(=O)n(C)c2)c1] | N-[4-(2,4-difluorophenoxy)-3-(5-hydroxy-1-methyl-6-oxopyridin-3-yl)phenyl]ethanesulfonamide |
| 452 | 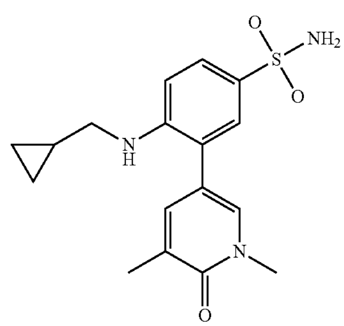 [SMILES: Cc1cc(-c2cc(S(N)(O)O)ccc2NCC2CC2)cn(C)c1=O] | 4-(cyclopropylmethylamino)-3-(1,5-dimethyl-6-oxopyridin-3-yl)benzenesulfonamide |
| 453 | 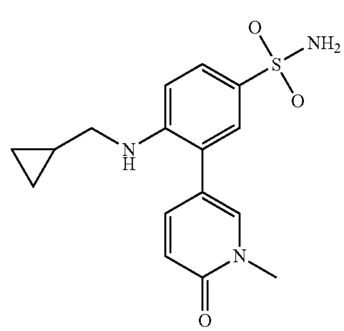 [SMILES: Cn1cc(-c2cc(S(N)(O)O)ccc2NCC2CC2)ccc1=O] | 4-(cyclopropylmethylamino)-3-(1-methyl-6-oxopyridin-3-yl)benzenesulfonamide |

TABLE 1-continued

| Chemical Synthesis Example | Structure | Name |
|---|---|---|
| 454 | 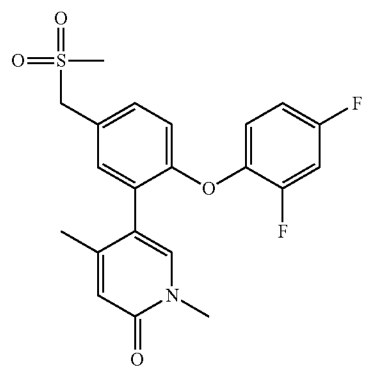 [SMILES: Cc1cc(=O)n(C)cc1-c1cc(CS(C)(=O)=O)ccc1Oc1ccc(F)cc1F] | 5-[2-(2,4-difluorophenoxy)-5-(methylsulfonylmethyl)phenyl]-1,4-dimethylpyridin-2-one |
| 455 | 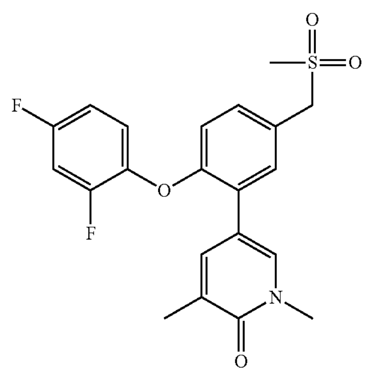 [SMILES: Cc1cc(-c2cc(CS(C)(=O)=O)ccc2Oc2ccc(F)cc2F)cn(C)c1=O] | 5-[2-(2,4-difluorophenoxy)-5-(methylsulfonylmethyl)phenyl]-1,3-dimethylpyridin-2-one |
| 456 | 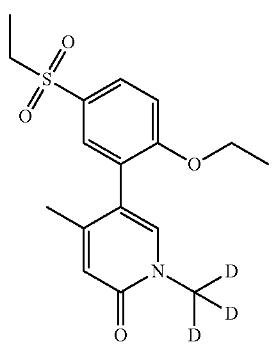 [SMILES: [2H]C([2H])([2H])n1cc(-c2cc(S(=O)(=O)CC)ccc2OCC)c(C)cc1=O] | 5-(2-ethoxy-5-ethylsulfonylphenyl)-1-($^2H_3$)methyl-4-methylpyridin-2-one |
| 457 | 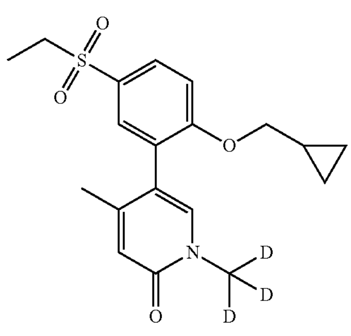 [SMILES: [2H]C([2H])([2H])n1cc(-c2cc(S(=O)(=O)CC)ccc2OCC2CC2)c(C)cc1=O] | 5-[2-(cyclopropylmethoxy)-5-ethylsulfonylphenyl]-1-($^2H_3$)methyl-4-methylpyridin-2-one |

TABLE 1-continued
| Chemical Synthesis Example | Structure | Name |
|---|---|---|
| 458 | 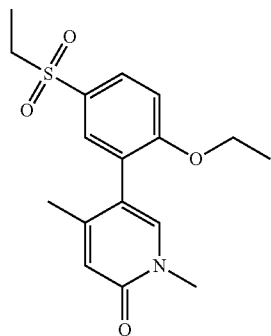 [SMILES: CCOc1ccc(S(=O)(=O)CC)cc1-c1cn(C)c(=O)cc1C] | 5-(2-ethoxy-5-ethylsulfonylphenyl)-1,4-dimethylpyridin-2-one |
| 459 | 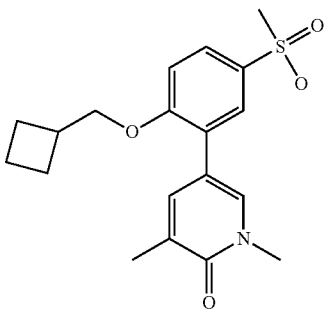 | 5-[2-(cyclobutylmethoxy)-5-methylsulfonylphenyl]-1,3-dimethylpyridin-2-one |
| 460 | 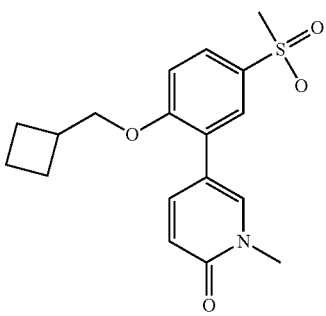 | 5-[2-(cyclobutylmethoxy)-5-methylsulfonylphenyl]-1-methylpyridin-2-one |
| 461 | 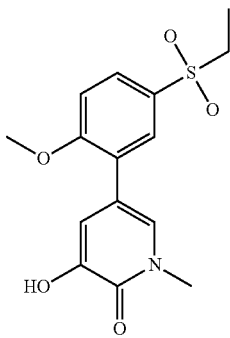 [SMILES: CCS(O)(O)c1ccc(OC)c(-c2cc(O)c(=O)n(C)c2)c1] | 5-(5-ethylsulfonyl-2-methoxyphenyl)-3-hydroxy-1-methylpyridin-2-one |

TABLE 1-continued

| Chemical Synthesis Example | Structure | Name |
|---|---|---|
| 462 | 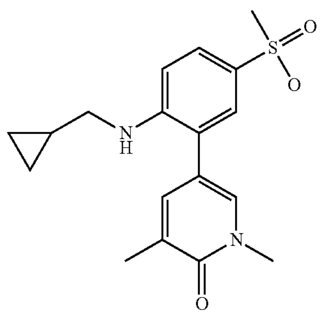 | 5-[2-(cyclopropylmethylamino)-5-methylsulfonylphenyl]-1,3-dimethylpyridin-2-one |
| 463 | 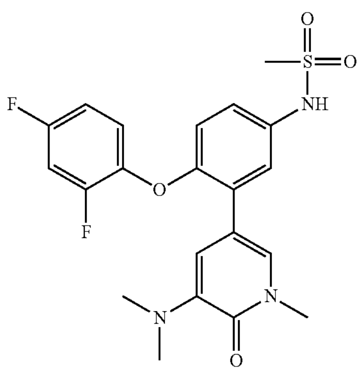 [SMILES: CN(C)c1cc(-c2cc(NS(C)(=O)=O)ccc2Oc2ccc(F)cc2F)cn(C)c1=O] | N-[4-(2,4-difluorophenoxy)-3-[5-(dimethylamino)-1-methyl-6-oxopyridin-3-yl]phenyl]methanesulfonamide |
| 464 | 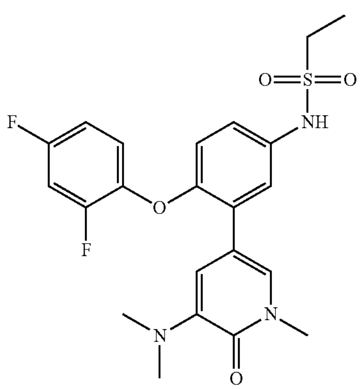 [SMILES: CCS(=O)(=O)Nc1ccc(Oc2ccc(F)cc2F)c(-c2cc(N(C)C)c(=O)n(C)c2)c1] | N-[4-(2,4-difluorophenoxy)-3-[5-(dimethylamino)-1-methyl-6-oxopyridin-3-yl]phenyl]ethanesulfonamide |
| 465 | 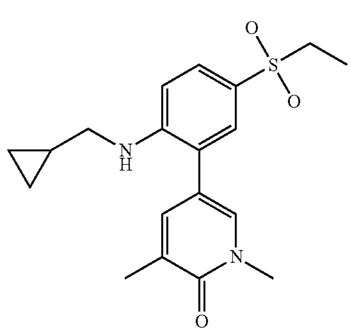 [SMILES: CCS(O)(O)c1ccc(NCC2CC2)c(-c2cc(C)c(=O)n(C)c2)c1] | 5-[2-(cyclopropylmethylamino)-5-ethylsulfonylphenyl]-1,3-dimethylpyridin-2-one |

TABLE 1-continued

| Chemical Synthesis Example | Structure | Name |
|---|---|---|
| 466 | 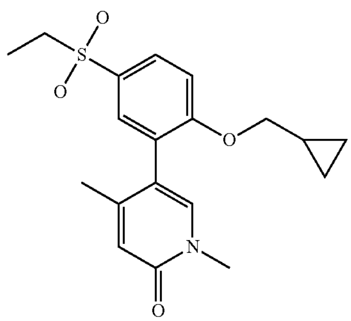 [SMILES: CCS(O)(O)c1ccc(OCC2CC2)c(-c2cn(C)c(=O)cc2C)c1] | 5-[2-(cyclopropylmethoxy)-5-ethylsulfonylphenyl]-1,4-dimethylpyridin-2-one |
| 467 | 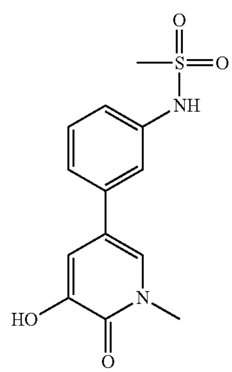 [SMILES: Cn1cc(-c2cccc(NS(C)(=O)=O)c2)cc(O)c1=O] | N-[3-(5-hydroxy-1-methyl-6-oxopyridin-3-yl)phenyl]methanesulfonamide |
| 468 | 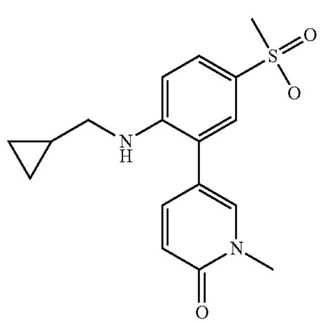 | 5-[2-(cyclopropylmethylamino)-5-methylsulfonylphenyl]-1-methylpyridin-2-one |
| 469 | 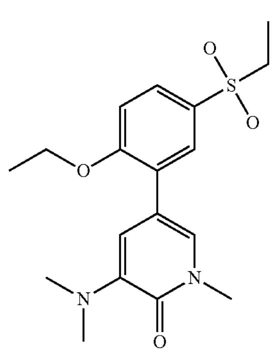 [SMILES: CCOc1ccc(S(O)(O)CC)cc1-c1cc(N(C)C)c(=O)n(C)c1] | 3-(dimethylamino)-5-(2-ethoxy-5-ethylsulfonylphenyl)-1-methylpyridin-2-one |

TABLE 1-continued
| Chemical Synthesis Example | Structure | Name |
|---|---|---|
| 470 | 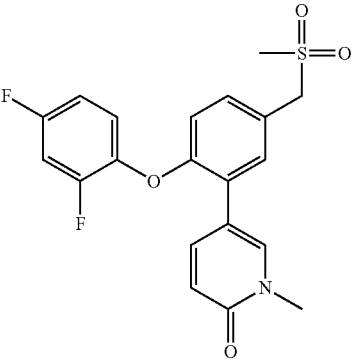 [SMILES: Cn1cc(-c2cc(CS(C)(=O)=O)ccc2Oc2ccc(F)cc2F)ccc1=O] | 5-[2-(2,4-difluorophenoxy)-5-(methylsulfonylmethyl)phenyl]-1-methylpyridin-2-one |
| 471 | 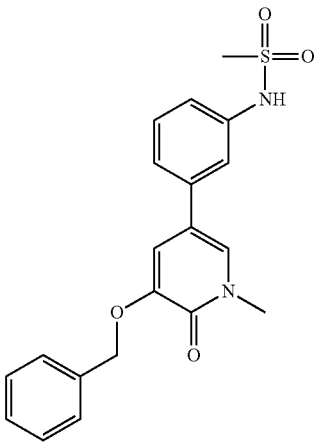 [SMILES: Cn1cc(-c2cccc(NS(C)(=O)=O)c2)cc(OCc2ccccc2)c1=O] | N-[3-(1-methyl-6-oxo-5-phenylmethoxypyridin-3-yl)phenyl]methanesulfonamide |
| 472 | 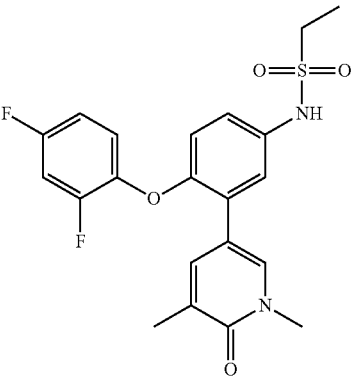 [SMILES: CCS(=O)(=O)Nc1ccc(Oc2ccc(F)cc2F)c(-c2cc(C)c(=O)n(C)c2)c1] | N-[4-(2,4-difluorophenoxy)-3-(1,5-dimethyl-6-oxopyridin-3-yl)phenyl]ethanesulfonamide |
| 473 | 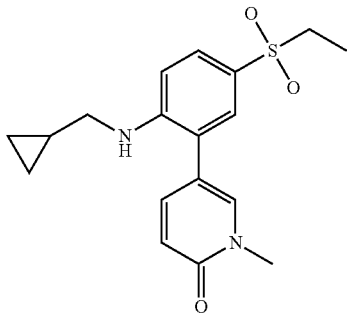 [SMILES: CCS(O)(O)c1ccc(NCC2CC2)c(-c2ccc(=O)n(C)c2)c1] | 5-[2-(cyclopropylmethylamino)-5-ethylsulfonylphenyl]-1-methylpyridin-2-one |

TABLE 1-continued

| Chemical Synthesis Example | Structure | Name |
|---|---|---|
| 474 | 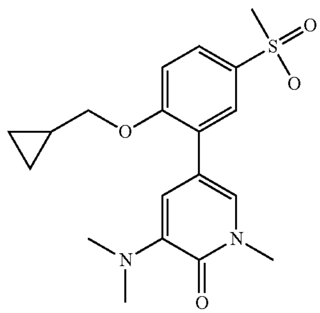 | 5-[2-(cyclopropylmethoxy)-5-methylsulfonylphenyl]-3-(dimethylamino)-1-methylpyridin-2-one |
| 475 | 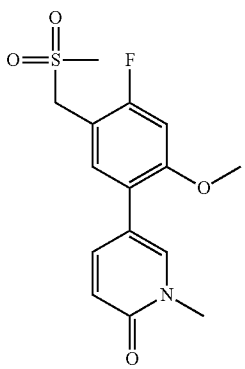 [SMILES: COc1cc(F)c(CS(C)(=O)=O)cc1-c1ccc(=O)n(C)c1] | 5-[4-fluoro-2-methoxy-5-(methylsulfonylmethyl)phenyl]-1-methylpyridin-2-one |
| 476 | 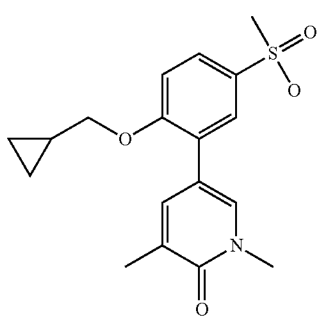 | 5-[2-(cyclopropylmethoxy)-5-methylsulfonylphenyl]-1,3-dimethylpyridin-2-one |
| 477 | 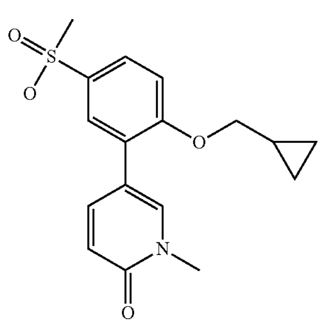 | 5-[2-(cyclopropylmethoxy)-5-methylsulfonylphenyl]-1,4-dimethylpyridin-2-one |

TABLE 1-continued

| Chemical Synthesis Example | Structure | Name |
|---|---|---|
| 478 | 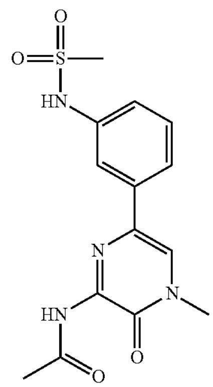 [SMILES: CC(=O)Nc1nc(-c2cccc(NS(C)(=O)=O)c2)cn(C)c1=O] | N-[6-[3-(methanesulfonamido)phenyl]-4-methyl-3-oxopyrazin-2-yl]acetamide |
| 479 | 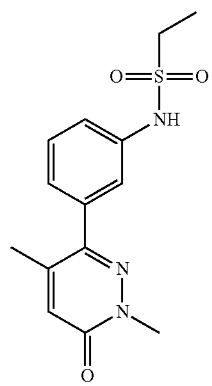 [SMILES: CCS(=O)(=O)Nc1cccc(-c2nn(C)c(=O)cc2C)c1] | N-[3-(1,4-dimethyl-6-oxopyridazin-3-yl)phenyl]ethanesulfonamide |
| 480 | 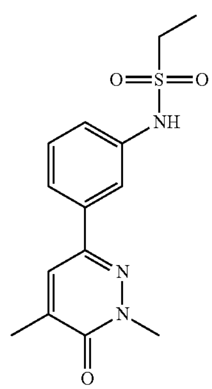 [SMILES: CCS(=O)(=O)Nc1cccc(-c2cc(C)c(=O)n(C)n2)c1] | N-[3-(1,5-dimethyl-6-oxopyridazin-3-yl)phenyl]ethanesulfonamide |
| 481 | 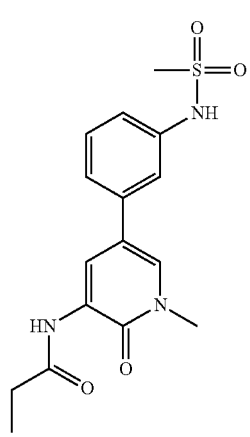 [SMILES: CCC(=O)Nc1cc(-c2cccc(NS(C)(=O)=O)c2)cn(C)c1=O] | N-[5-[3-(methanesulfonamido)phenyl]-1-methyl-2-oxopyridin-3-yl]propanamide |

TABLE 1-continued

| Chemical Synthesis Example | Structure | Name |
|---|---|---|
| 482 | 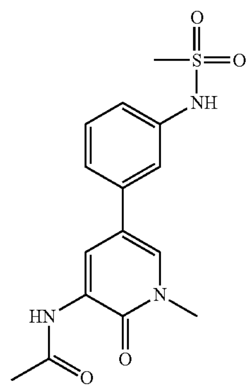 [SMILES: CC(=O)Nc1cc(-c2cccc(NS(C)(=O)=O)c2)cn(C)c1=O] | N-[5-[3-(methanesulfonamido)phenyl]-1-methyl-2-oxopyridin-3-yl]acetamide |
| 483 | 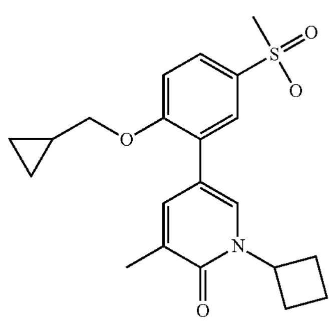 | 1-cyclobutyl-5-[2-(cyclopropylmethoxy)-5-methylsulfonylphenyl]-3-methylpyridin-2-one |
| 484 | 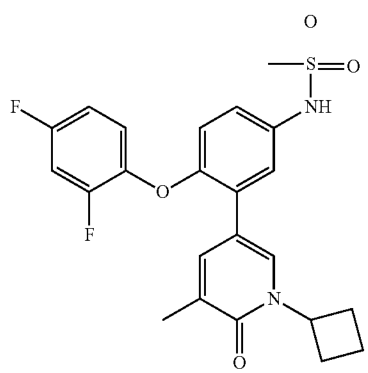 | N-[3-(1-cyclobutyl-5-methyl-6-oxopyridin-3-yl)-4-(2,4-difluorophenoxy)phenyl]methanesulfonamide |
| 485 | 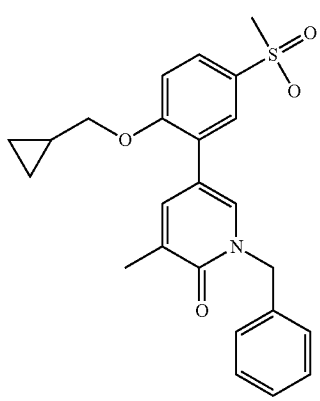 | 1-benzyl-5-[2-(cyclopropylmethoxy)-5-methylsulfonylphenyl]-3-methylpyridin-2-one |

TABLE 1-continued

| Chemical Synthesis Example | Structure | Name |
|---|---|---|
| 486 | 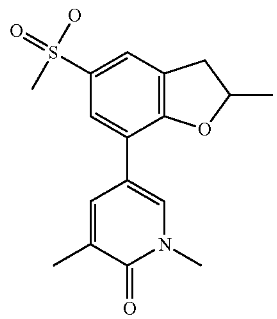 | 1,3-dimethyl-5-(2-methyl-5-methyl-sulfonyl-2,3-dihydro-1-benzofuran-7-yl)pyridin-2-one |
| 487 | 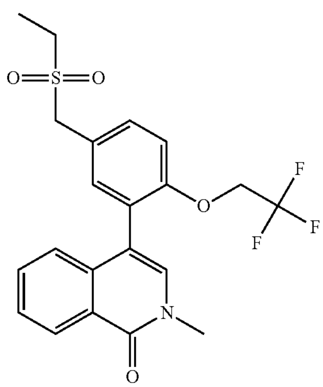 [SMILES: CCS(=O)(=O)Cc1ccc(OCC(F)(F)F)c(-c2cn(C)c(=O)c3ccccc23)c1] | 4-[5-(ethylsulfonylmethyl)-2-(2,2,2-trifluoroethoxy)phenyl]-2-methylisoquinolin-1-one |
| 488 | 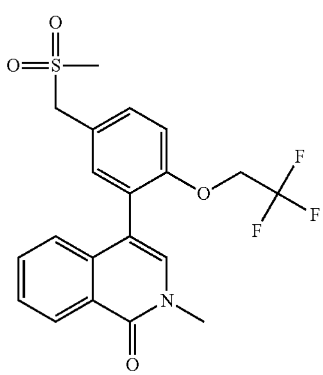 [SMILES: Cn1cc(-c2cc(CS(C)(=O)=O)ccc2OCC(F)(F)F)c2ccccc2c1=O] | 2-methyl-4-[5-(methylsulfonylmethyl)-2-(2,2,2-trifluoroethoxy)phenyl]isoquinolin-1-one |
| 489 | 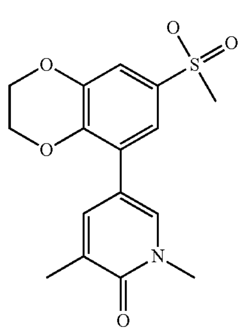 | 1,3-dimethyl-5-(7-methylsulfonyl-2,3-dihydro-1,4-benzodioxin-5-yl)pyridine-2-one |

TABLE 1-continued

| Chemical Synthesis Example | Structure | Name |
|---|---|---|
| 490 | 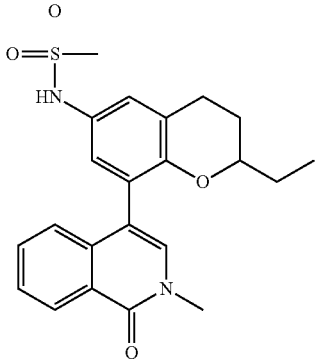 | N-[2-ethyl-8-(2-methyl-1-oxoisoquinolin-4-yl)-3,4-dihydro-2H-chromen-6-yl]methanesulfonamide |
| 491 | 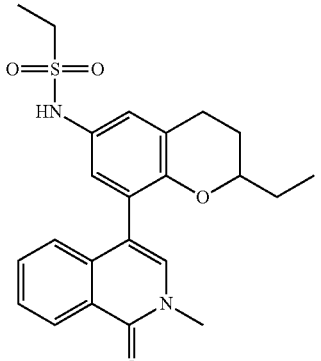 | N-[2-ethyl-8-(2-methyl-1-oxoisoquinolin-4-yl)-3,4-dihydro-2H-chromen-6-yl]ethanesulfonamide |
| 492 | 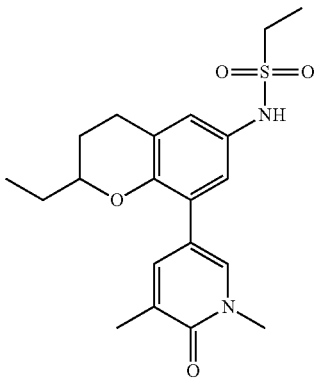 [SMILES: CCC1CCc2cc(NS(=O)(=O)CC)cc(-c3cc(C)c(=O)n(C)c3)c2O1] | N-[8-(1,5-dimethyl-6-oxopyridin-3-yl)-2-ethyl-3,4-dihydro-2H-chromen-6-yl]ethanesulfonamide |
| 493 | 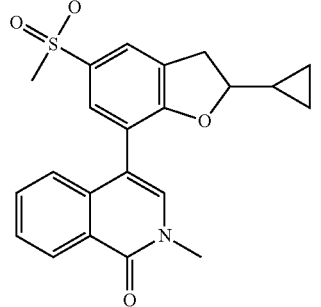 | 4-(2-cyclopropyl-5-methylsulfonyl-2,3-dihydro-1-benzofuran-7-yl)-2-methylisoquinolin-1-one |

TABLE 1-continued

| Chemical Synthesis Example | Structure | Name |
|---|---|---|
| 494 | 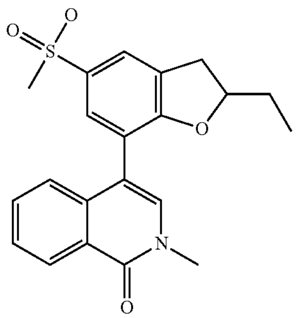 | 4-(2-ethyl-5-methylsulfonyl-2,3-dihydro-1-benzofuran-7-yl)-2-methylisoquinolin-1-one |
| 495 | 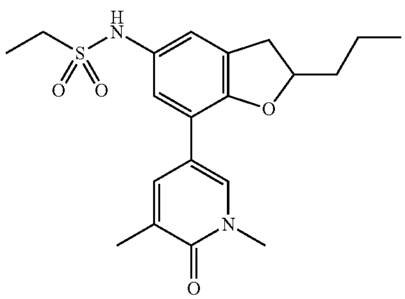 [SMILES: CCCC1Cc2cc(NS(=O)(=O)CC)cc(-c3cc(C)c(=O)n(C)c3)c2O1] | N-[7-(1,5-dimethyl-6-oxopyridin-3-yl)-2-propyl-2,3-dihydro-1-benzofuran-5-yl]ethanesulfonamide |
| 496 | 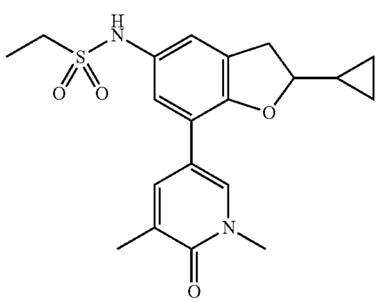 [SMILES: CCS(=O)(=O)Nc1cc2c(c(-c3cc(C)c(=O)n(C)c3)c1)OC(C1CC1)C2] | N-[2-cyclopropyl-7-(1,5-dimethyl-6-oxopyridin-3-yl)-2,3-dihydro-1-benzofuran-5-yl]ethanesulfonamide |
| 497 | 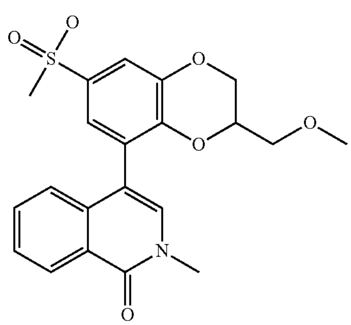 | 4-[3-(methoxymethyl)-7-methylsulfonyl-2,3-dihydro-1,4-benzodioxin-5-yl]-2-methylisoquinolin-1-one |
| 498 | 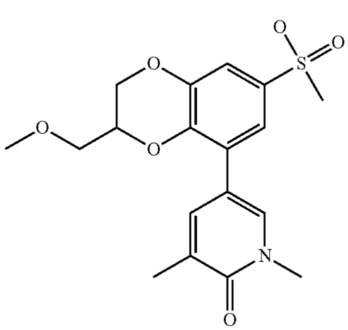 | 5-[3-(methoxymethyl)-7-methylsulfonyl-2,3-dihydro-1,4-benzodioxin-5-yl]-1,3-dimethylpyridin-2-one |

TABLE 1-continued

| Chemical Synthesis Example | Structure | Name |
| --- | --- | --- |
| 499 | 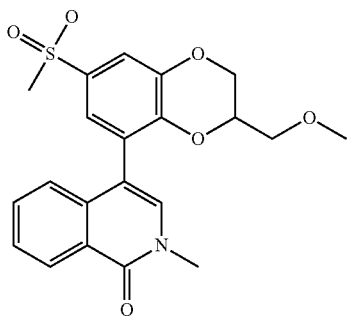 | 4-[3-(methoxymethyl)-7-methylsulfonyl-2,3-dihydro-1,4-benzodioxin-5-yl]-2-methylisoquinolin-1-one |
| 500 | 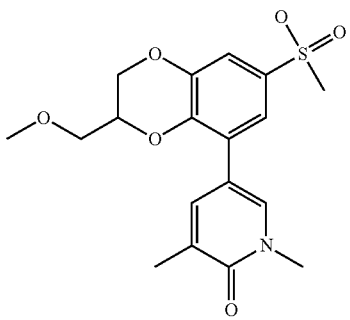 | 5-[3-(methoxymethyl)-7-methylsulfonyl-2,3-dihydro-1,4-benzodioxin-5-yl]-1,3-dimethylpyridin-2-one |
| 501 | 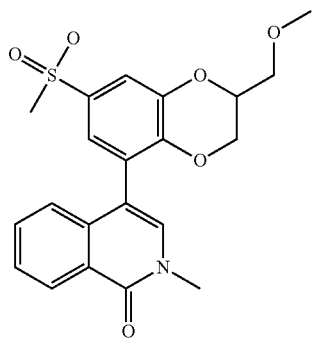 | 4-[2-(methoxymethyl)-7-methylsulfonyl-2,3-dihydro-1,4-benzodioxin-5-yl]-2-methylisoquinolin-1-one |
| 502 | 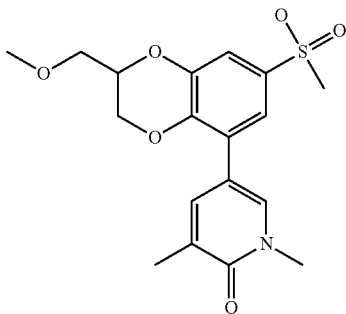 | 5-[2-(methoxymethyl)-7-methylsulfonyl-2,3-dihydro-1,4-benzodioxin-5-yl]-1,3-dimethylpyridin-2-one |

TABLE 1-continued

| Chemical Synthesis Example | Structure | Name |
|---|---|---|
| 503 | 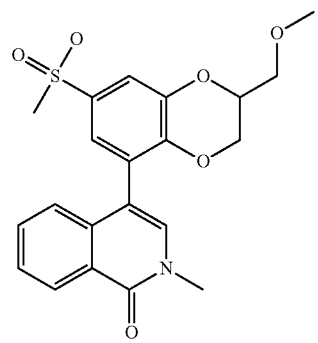 | 4-[2-(methoxymethyl)-7-methylsulfonyl-2,3-dihydro-1,4-benzodioxin-5-yl]-2-methylisoquinolin-1-one |
| 504 | 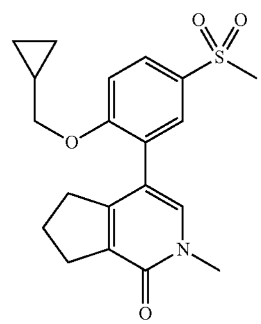 [SMILES: Cn1cc(-c2cc(S(C)(=O)=O)ccc2OCC2CC2)c2c(c1=O)CCC2] | 4-[2-(cyclopropylmethoxy)-5-methylsulfonylphenyl]-2-methyl-6,7-dihydro-5H-cyclopenta[c]pyridin-1-one |
| 505 | 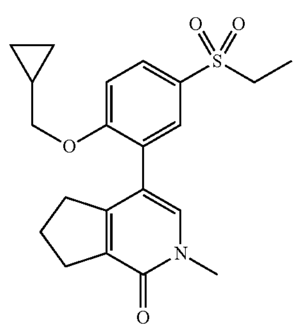 [SMILES: CCS(=O)(=O)c1ccc(OCC2CC2)c(-c2cn(C)c(=O)c3c2CCC3)c1] | 4-[2-(cyclopropylmethoxy)-5-ethylsulfonylphenyl]-2-methyl-6,7-dihydro-5H-cyclopenta[c]pyridin-1-one |
| 506 | 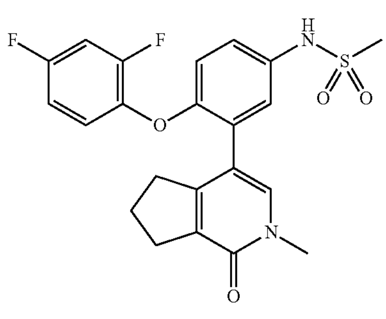 [SMILES: Cn1cc(-c2cc(NS(C)(=O)=O)ccc2Oc2ccc(F)cc2F)c2c(c1=O)CCC2] | N-[4-(2,4-difluorophenoxy)-3-(2-methyl-1-oxo-6,7-dihydro-5H-cyclopenta[c]pyridin-4-yl)phenyl]methanesulfonamide |

TABLE 1-continued

| Chemical Synthesis Example | Structure | Name |
|---|---|---|
| 507 | 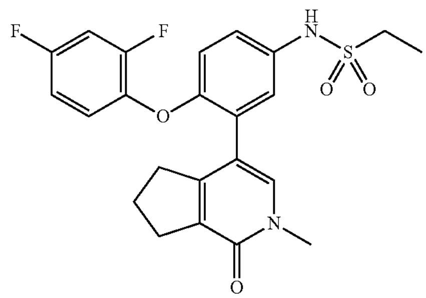 [SMILES: CCS(=O)(=O)Nc1ccc(Oc2ccc(F)cc2F)c(-c2cn(C)c(=O)c3c2CCC3)c1] | N-[4-(2,4-difluorophenoxy)-3-(2-methyl-1-oxo-6,7-dihydro-5H-cyclopenta[c]pyridin-4-yl)phenyl]ethanesulfonamide |
| 508 | 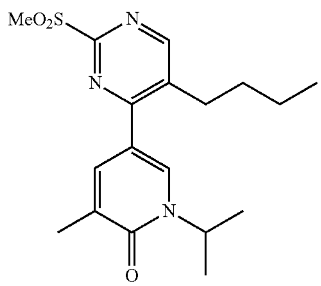 [SMILES: CCCCc1cnc(S(C)(=O)=O)nc1-c1cc(C)c(=O)n(C(C)C)c1] | 5-(5-butyl-2-methylsulfonylpyrimidin-4-yl)-3-methyl-1-propan-2-ylpyridin-2-one |
| 509 | 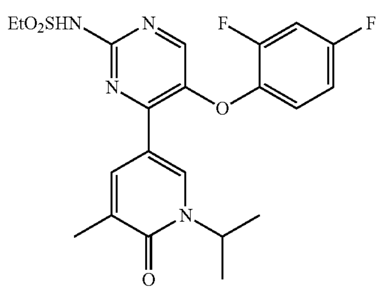 | N-[5-(2,4-difluorophenoxy)-4-(5-methyl-6-oxo-1-propan-2-ylpyridin-3-yl)pyrimidin-2-yl]ethanesulfonamide |
| 510 | 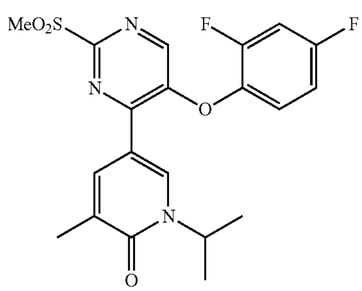 [SMILES: Cc1cc(-c2nc(S(C)(=O)=O)ncc2Oc2ccc(F)cc2F)cn(C(C)C)c1=O] | 5-[5-(2,4-difluorophenoxy)-2-methylsulfonylpyrimidin-4-yl]-3-methyl-1-propan-2-ylpyridin-2-one |
| 511 | 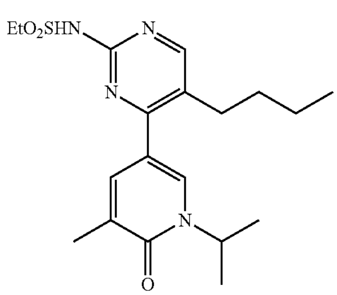 | N-[5-butyl-4-(5-methyl-6-oxo-1-propan-2-ylpyridin-3-yl)pyrimidin-2-yl]ethanesulfonamide |

TABLE 1-continued

| Chemical Synthesis Example | Structure | Name |
|---|---|---|
| 512 | 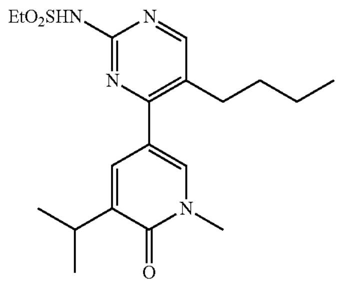 | N-[5-butyl-4-(1-methyl-6-oxo-5-propan-2-ylpyridin-3-yl)pyrimidin-2-yl]ethanesulfonamide |
| 513 | 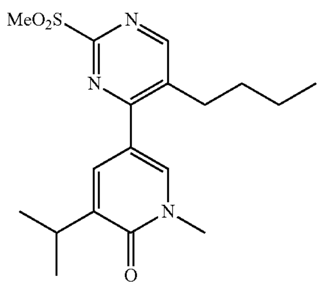 [SMILES: CCCCc1cnc(S(C)(=O)=O)nc1-c1cc(C(C)C)c(=O)n(C)c1] | 5-(5-butyl-2-methylsulfonylpyrimidin-4-yl)-1-methyl-3-propan-2-ylpyridin-2-one |
| 514 | 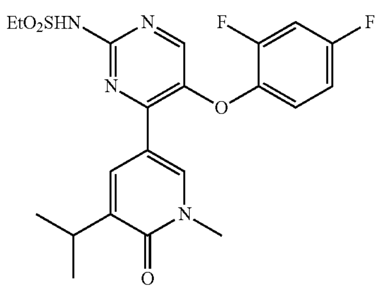 | N-[5-(2,4-difluorophenoxy)-4-(1-methyl-6-oxo-5-propan-2-ylpyridin-3-yl)pyrimidin-2-yl]ethanesulfonamide |

In some embodiments, the substituted heterocyclic derivative compound disclosed herein has the structure provided in Table 2.

TABLE 2

343
TABLE 2-continued
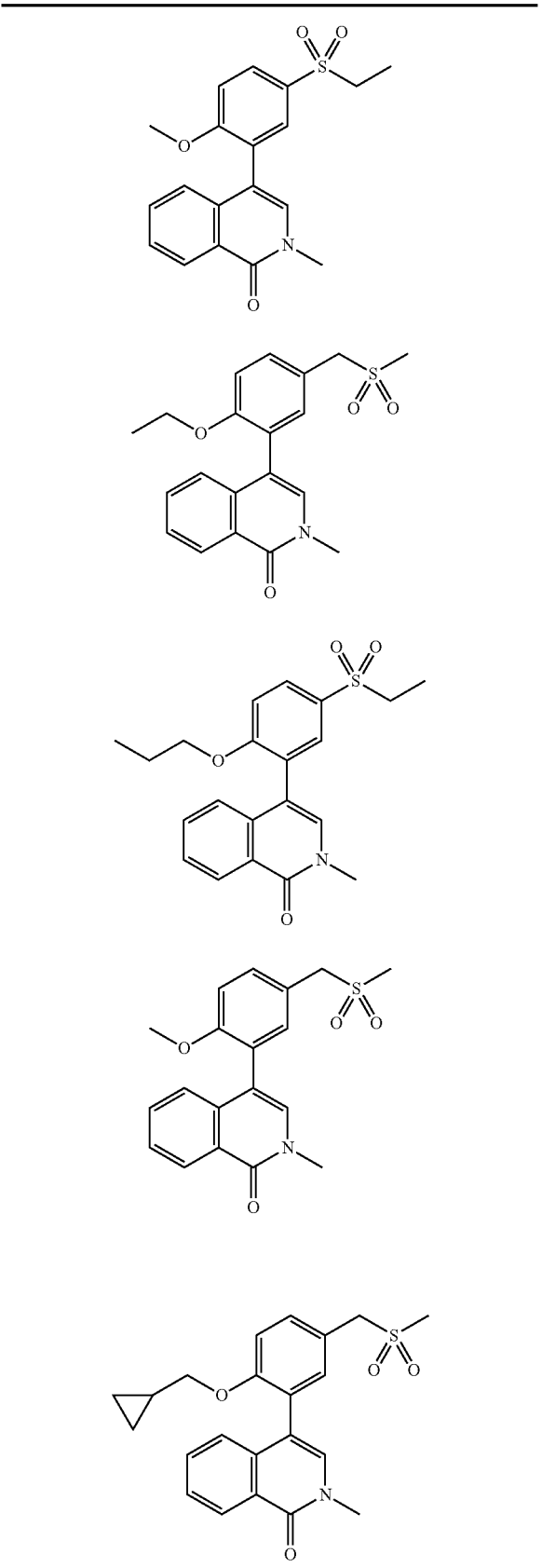
344
TABLE 2-continued
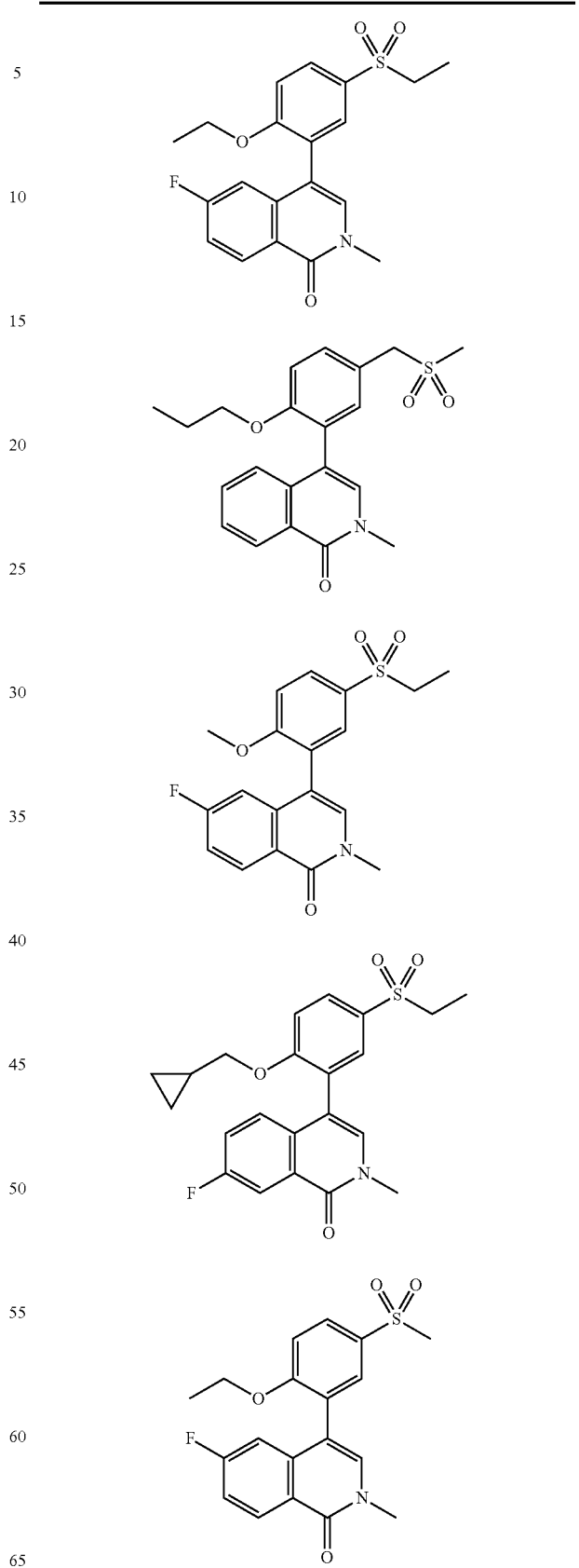

TABLE 2-continued
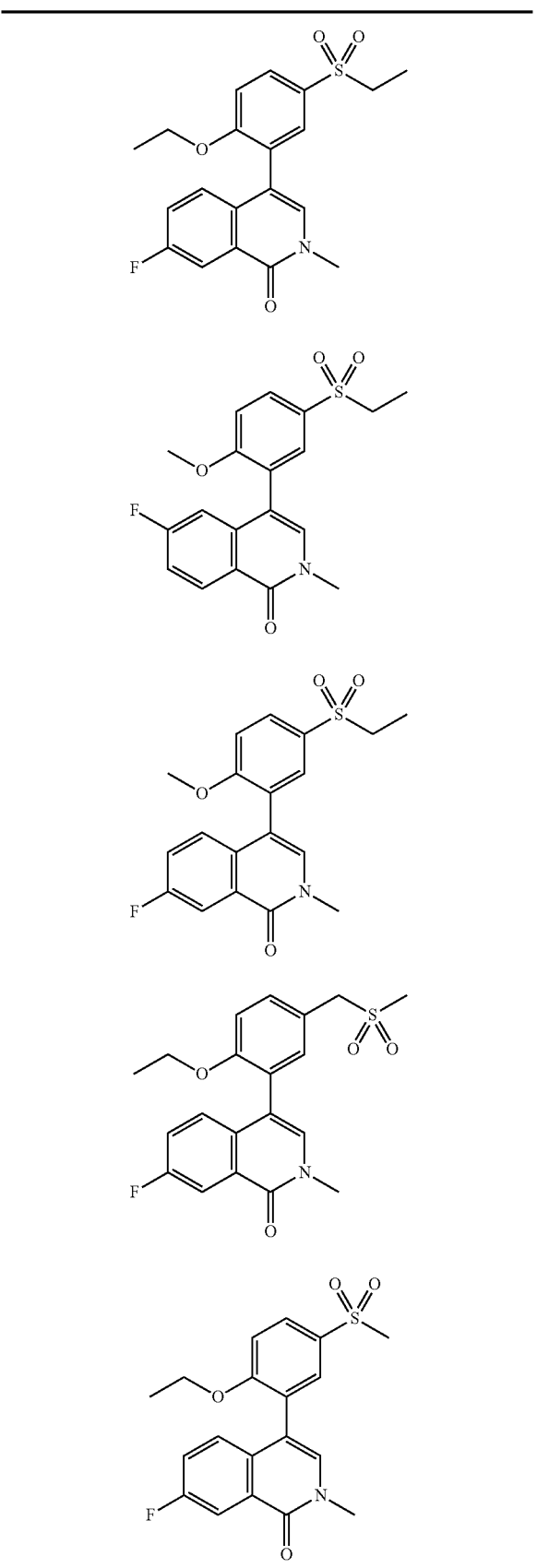
TABLE 2-continued
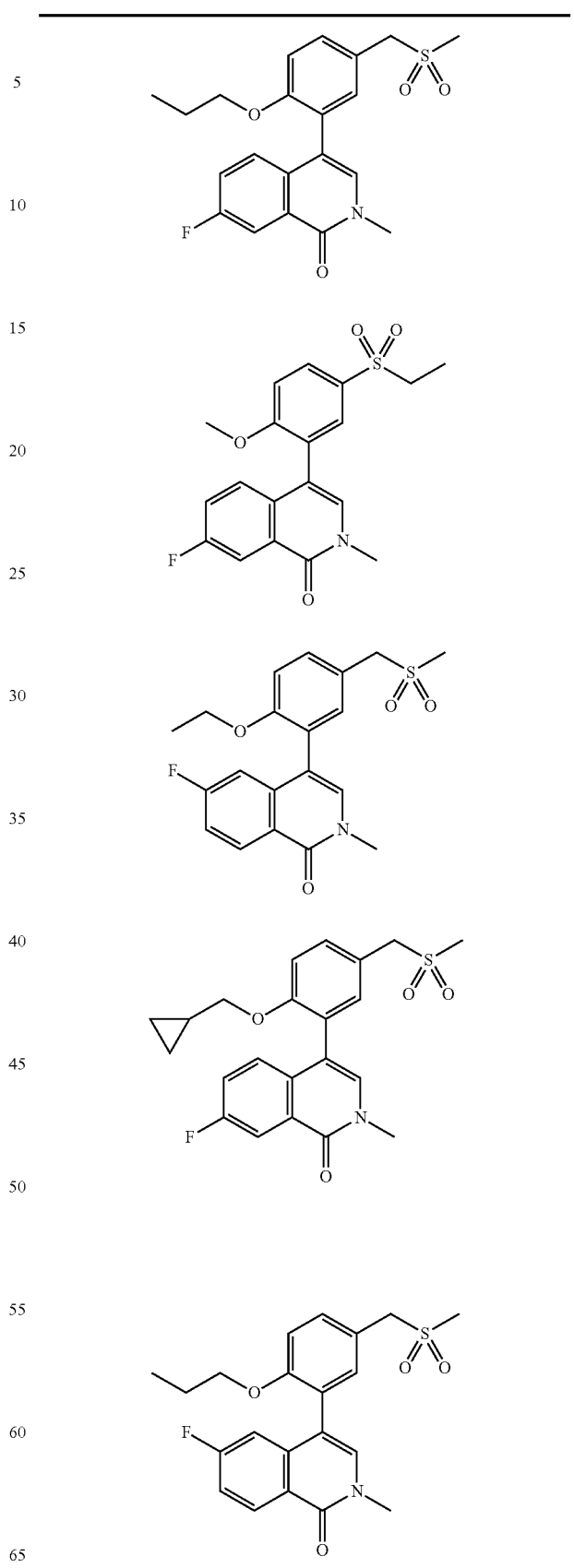

TABLE 2-continued
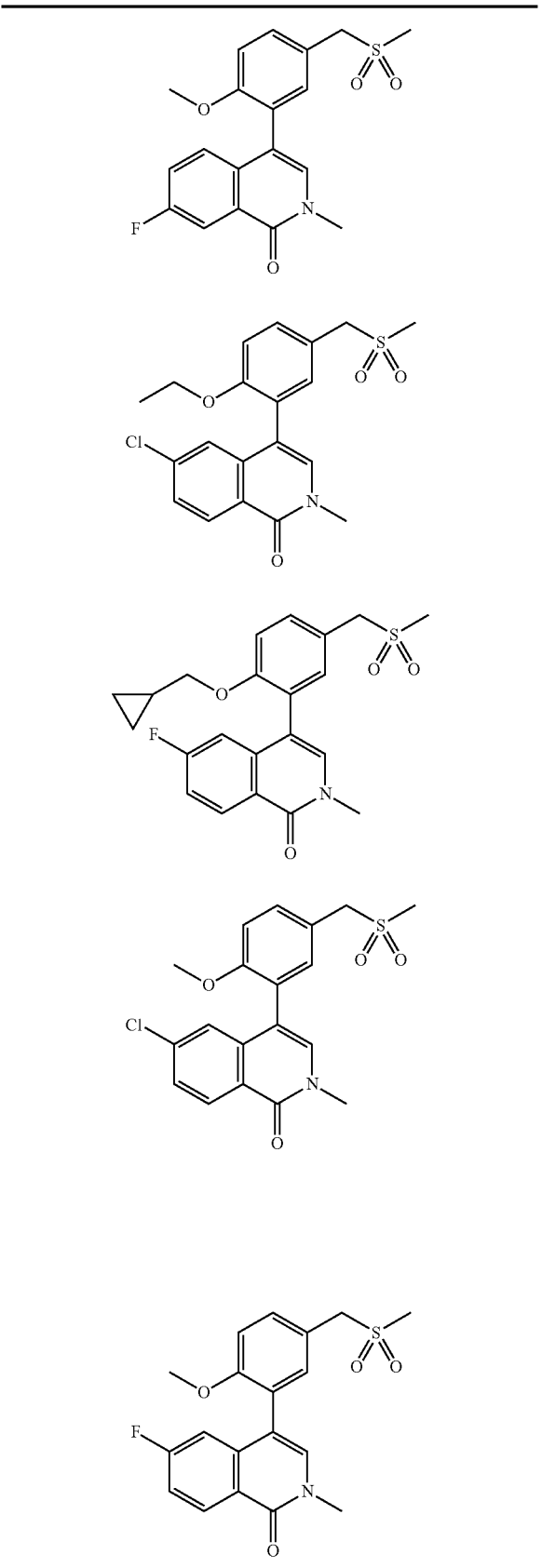
TABLE 2-continued
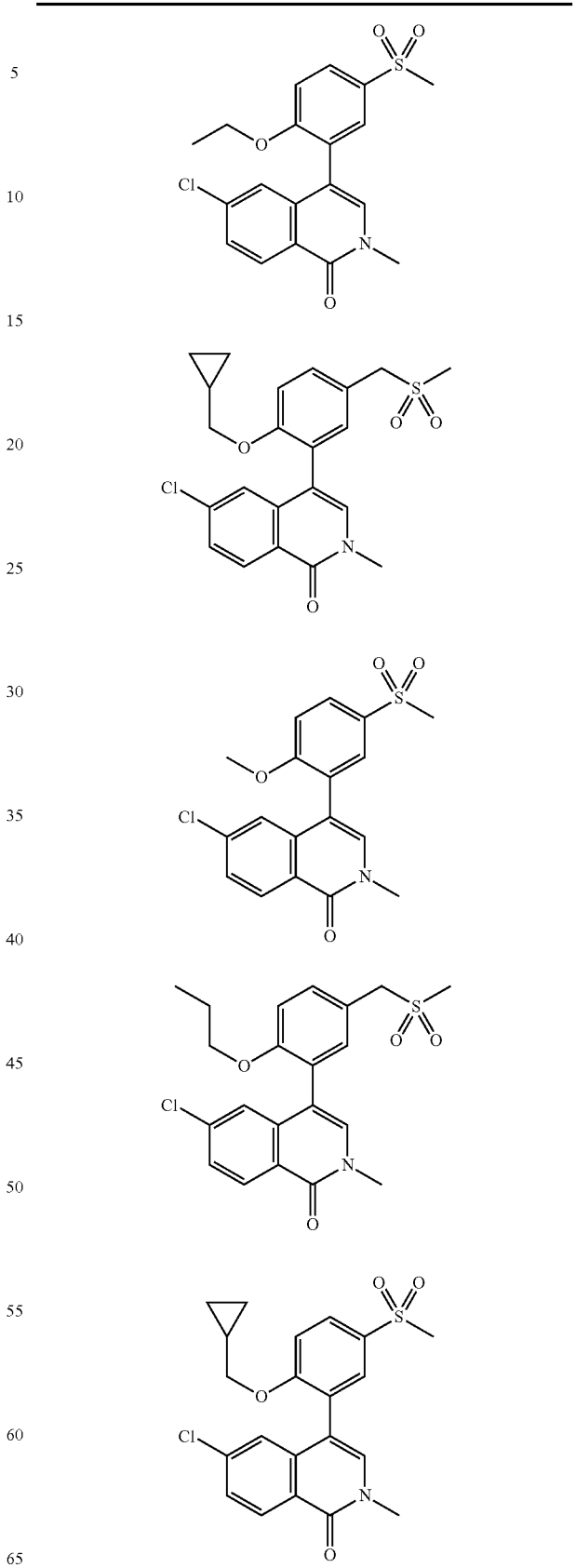

TABLE 2-continued
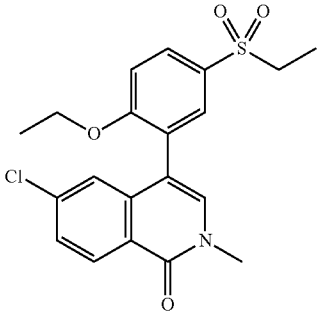 [SMILES: CCOc1ccc(S(=O)(=O)CC)cc1-c1cn(C)c(=O)c2ccc(Cl)cc12]
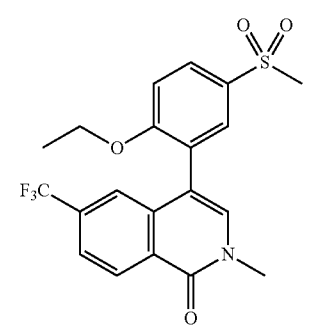 [SMILES: CCOc1ccc(S(C)(=O)=O)cc1-c1cn(C)c(=O)c2ccc(C(F)(F)F)cc12]
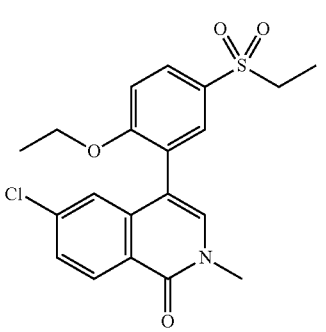 [SMILES: CCOc1ccc(S(=O)(=O)CC)cc1-c1cn(C)c(=O)c2ccc(Cl)cc12]
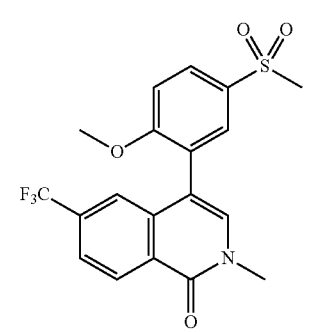 [SMILES: COc1ccc(S(C)(=O)=O)cc1-c1cn(C)c(=O)c2ccc(C(F)(F)F)cc12]
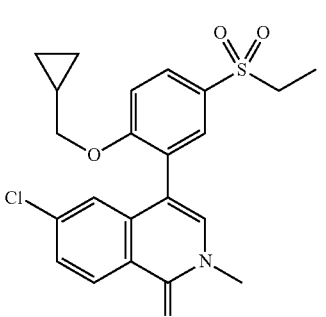
TABLE 2-continued
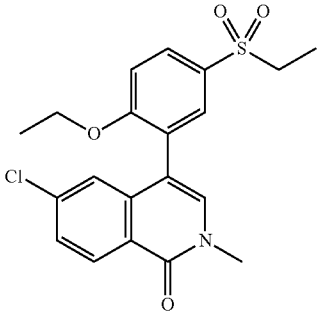 [SMILES: CCOc1ccc(S(=O)(=O)CC)cc1-c1cn(C)c(=O)c2ccc(Cl)cc12]
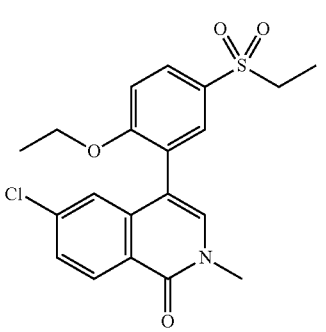 [SMILES: CCOc1ccc(S(=O)(=O)CC)cc1-c1cn(C)c(=O)c2ccc(Cl)cc12]
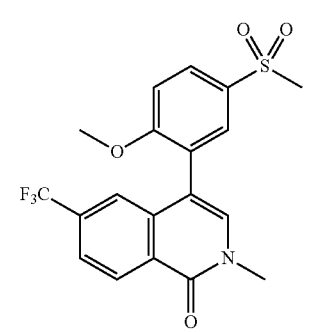 [SMILES: COc1ccc(S(C)(=O)=O)cc1-c1cn(C)c(=O)c2ccc(C(F)(F)F)cc12]
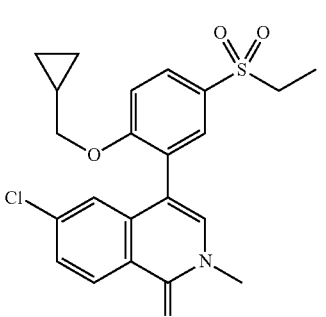
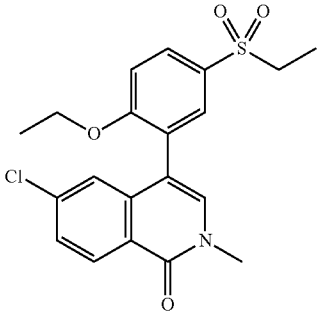 [SMILES: CCOc1ccc(S(=O)(=O)CC)cc1-c1cn(C)c(=O)c2ccc(Cl)cc12]

TABLE 2-continued
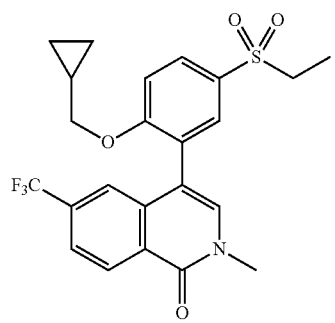 [SMILES: CCS(=O)(=O)c1ccc(OCC2CC2)c(-c2cn(C)c(=O)c3ccc(C(F)(F)F)cc23)c1]
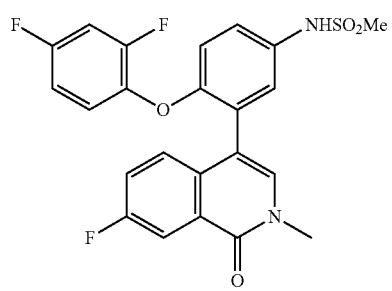
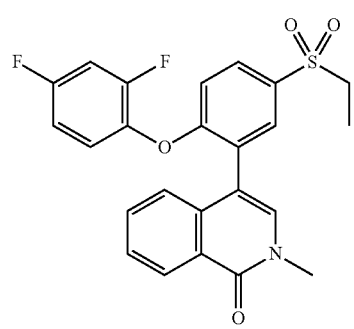 [SMILES: CCS(=O)(=O)c1ccc(Oc2ccc(F)cc2F)c(-c2cn(C)c(=O)c3ccccc23)c1]
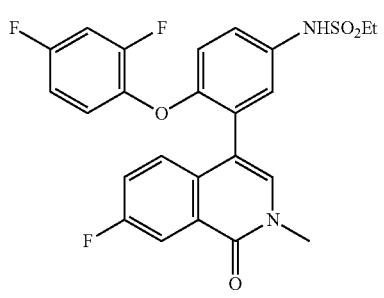
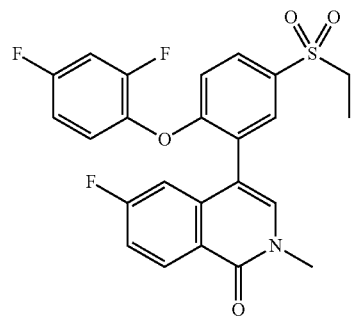 [SMILES: CCS(=O)(=O)c1ccc(Oc2ccc(F)cc2F)c(-c2cn(C)c(=O)c3ccc(F)cc23)c1]
TABLE 2-continued
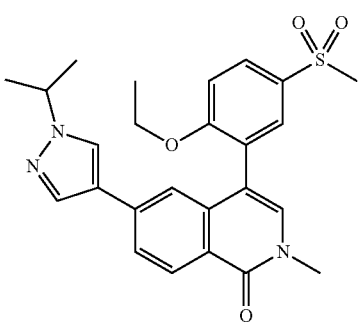 [SMILES: CCOc1ccc(S(C)(=O)=O)cc1-c1cn(C)c(=O)c2ccc(-c3cnn(C(C)C)c3)cc12]
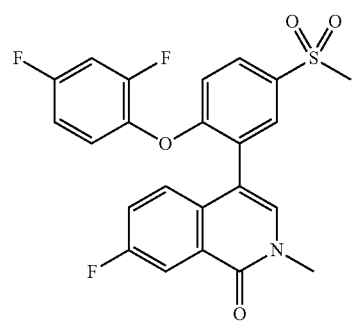 [SMILES: Cn1cc(-c2cc(S(C)(=O)=O)ccc2Oc2ccc(F)cc2F)c2ccc(F)cc2c1=O]
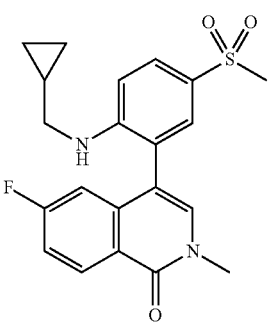
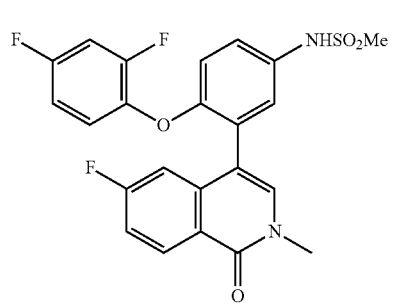
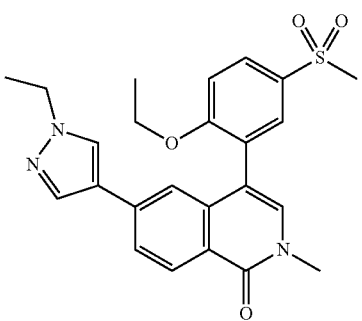 [SMILES: CCOc1ccc(S(C)(=O)=O)cc1-c1cn(C)c(=O)c2ccc(-c3cnn(CC)c3)cc12]

TABLE 2-continued
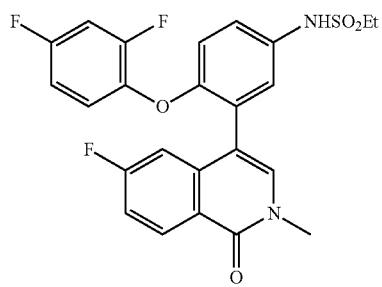
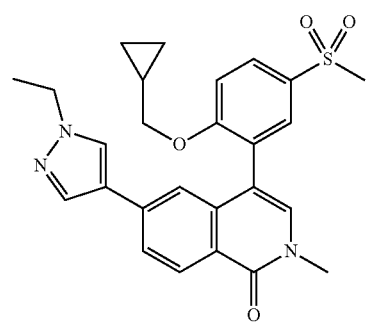 [SMILES: CCn1cc(-c2ccc3c(=O)n(C)cc(-c4cc(S(C)(=O)=O)ccc4OCC4CC4)c3c2)cn1]
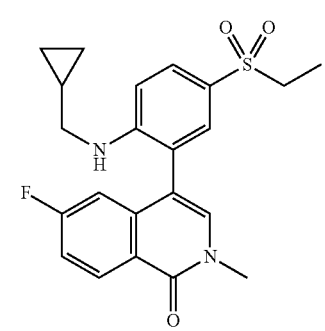 [SMILES: CCS(=O)(=O)c1ccc(NCC2CC2)c(-c2cn(C)c(=O)c3ccc(F)cc23)c1]
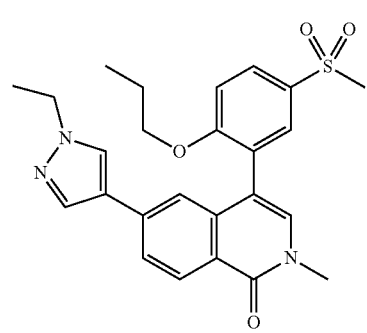 [SMILES: CCCOc1ccc(S(C)(=O)=O)cc1-c1cn(C)c(=O)c2ccc(-c3cnn(CC)c3)cc12]
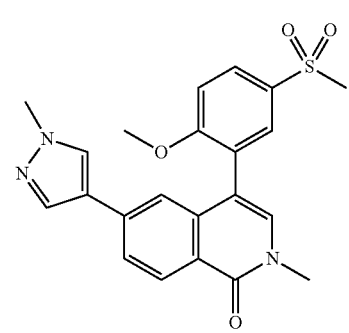 [SMILES: COc1ccc(S(C)(=O)=O)cc1-c1cn(C)c(=O)c2ccc(-c3cnn(C)c3)cc12]
TABLE 2-continued
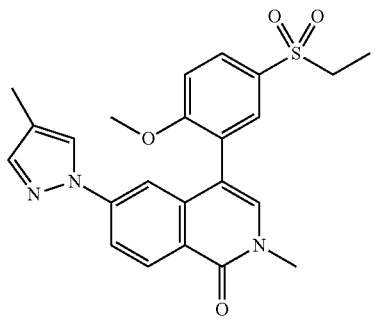 [SMILES: CCS(=O)(=O)c1ccc(OC)c(-c2cn(C)c(=O)c3ccc(-n4cc(C)cn4)cc23)c1]
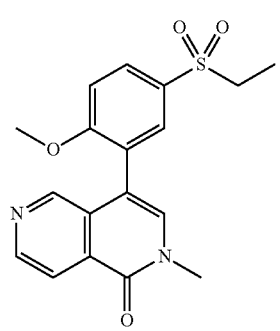 [SMILES: CCS(=O)(=O)c1ccc(OC)c(-c2cn(C)c(=O)c3ccncc23)c1]
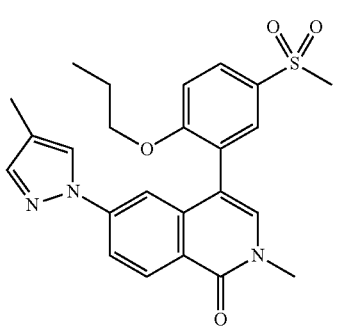 [SMILES: CCCOc1ccc(S(C)(=O)=O)cc1-c1cn(C)c(=O)c2ccc(-n3cc(C)cn3)cc12]
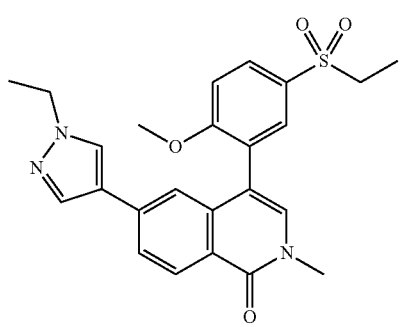 [SMILES: CCn1cc(-c2ccc3c(=O)n(C)cc(-c4cc(S(=O)(=O)CC)ccc4OC)c3c2)cn1]
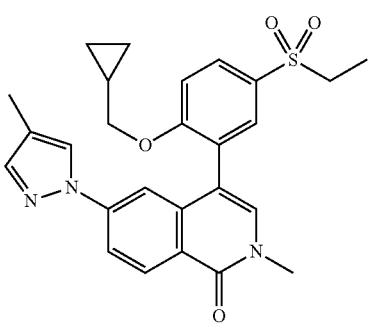 [SMILES: CCS(=O)(=O)c1ccc(OCC2CC2)c(-c2cn(C)c(=O)c3ccc(-n4cc(C)cn4)cc23)c1]

355
TABLE 2-continued
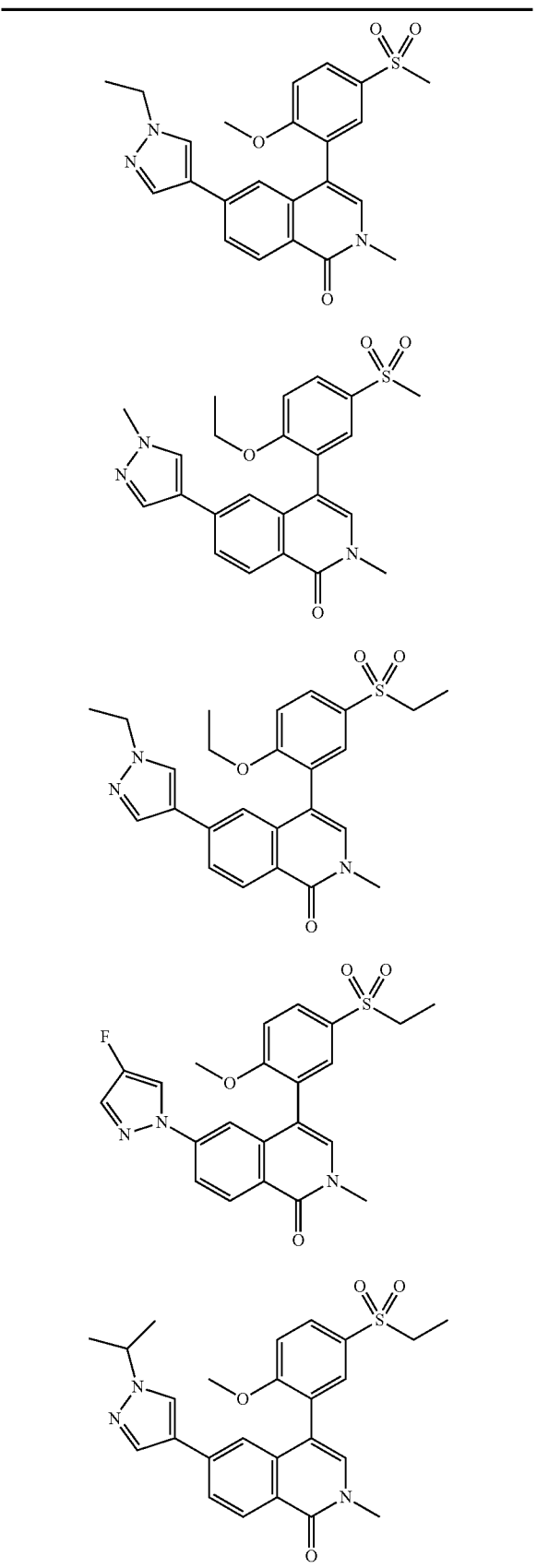
356
TABLE 2-continued
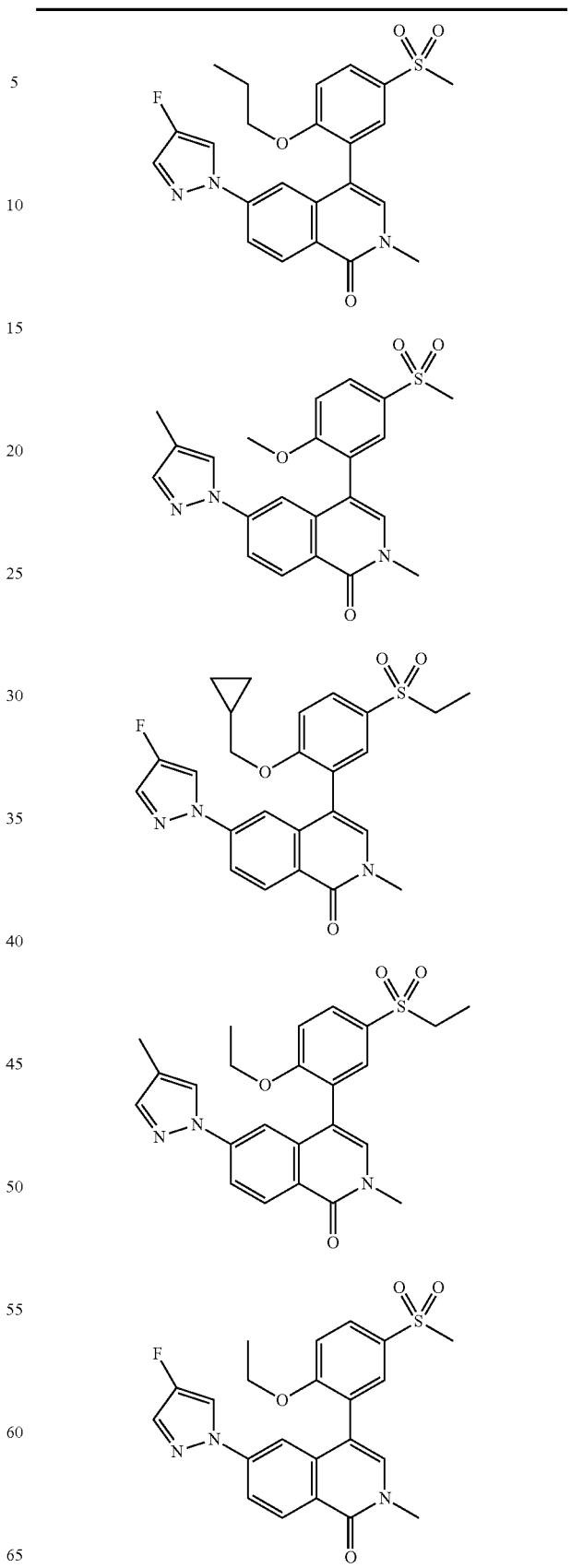

TABLE 2-continued
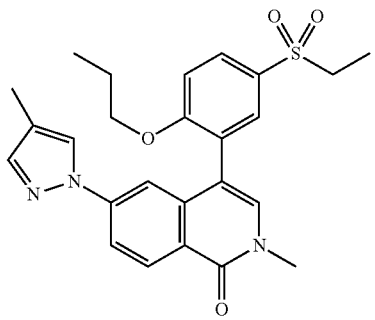 [SMILES: CCCOc1ccc(S(=O)(=O)CC)cc1-c1cn(C)c(=O)c2ccc(-n3cc(C)cn3)cc12]
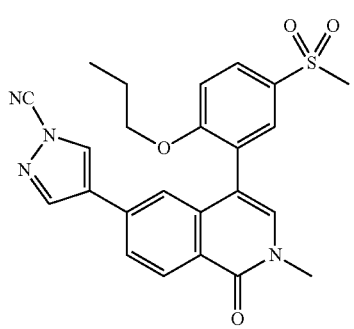 [SMILES: CCCOc1ccc(S(C)(=O)=O)cc1-c1cn(C)c(=O)c2ccc(-c3cnn(C#N)c3)cc12]
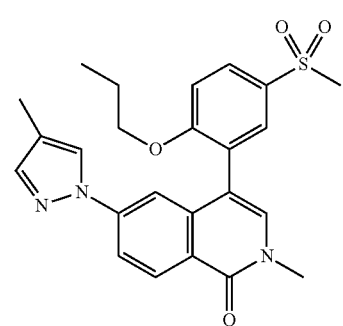 [SMILES: CCCOc1ccc(S(C)(=O)=O)cc1-c1cn(C)c(=O)c2ccc(-n3cc(C)cn3)cc12]
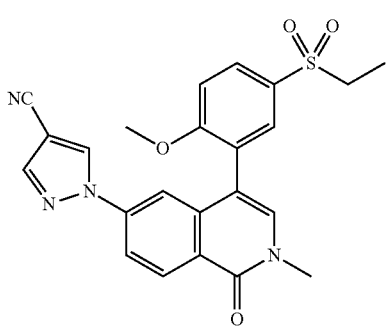 [SMILES: CCS(=O)(=O)c1ccc(OC)c(-c2cn(C)c(=O)c3ccc(-n4cc(C#N)cn4)cc23)c1]
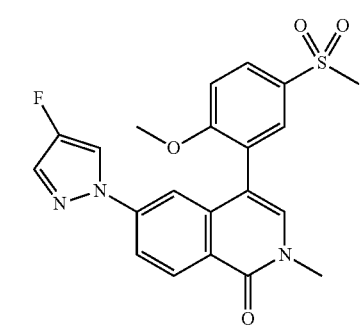 [SMILES: COc1ccc(S(C)(=O)=O)cc1-c1cn(C)c(=O)c2ccc(-n3cc(F)cn3)cc12]
TABLE 2-continued
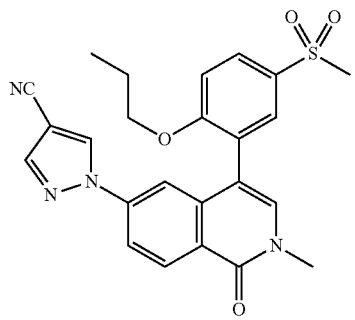 [SMILES: CCCOc1ccc(S(C)(=O)=O)cc1-c1cn(C)c(=O)c2ccc(-n3cc(C#N)cn3)cc12]
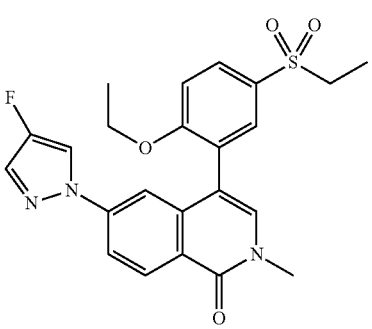 [SMILES: CCOc1ccc(S(=O)(=O)CC)cc1-c1cn(C)c(=O)c2ccc(-n3cc(F)cn3)cc12]
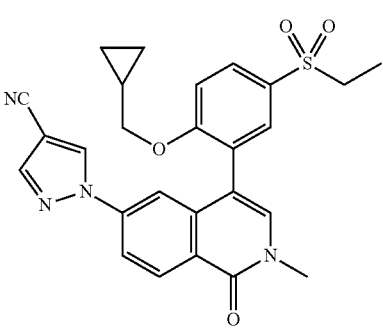 [SMILES: CCS(=O)(=O)c1ccc(OCC2CC2)c(-c2cn(C)c(=O)c3ccc(-n4cc(C#N)cn4)cc23)c1]
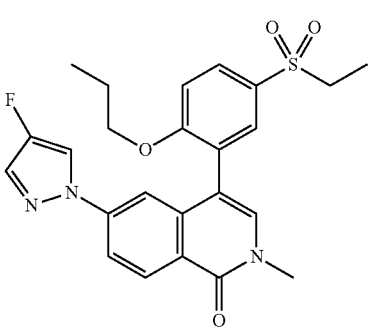 [SMILES: CCCOc1ccc(S(=O)(=O)CC)cc1-c1cn(C)c(=O)c2ccc(-n3cc(F)cn3)cc12]
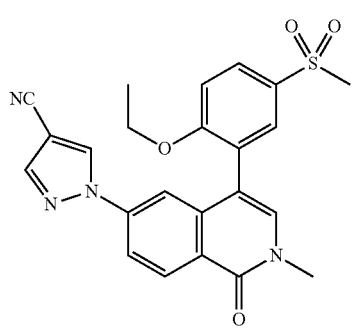 [SMILES: CCOc1ccc(S(C)(=O)=O)cc1-c1cn(C)c(=O)c2ccc(-n3cc(C#N)cn3)cc12]

TABLE 2-continued
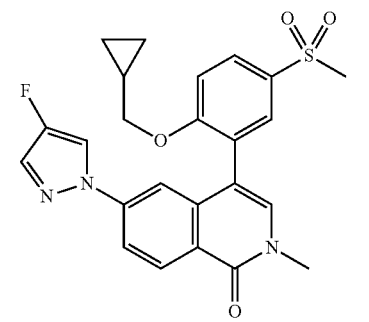 [SMILES: Cn1cc(-c2cc(S(C)(=O)=O)ccc2OCC2CC2)c2cc(-n3cc(F)cn3)ccc2c1=O]
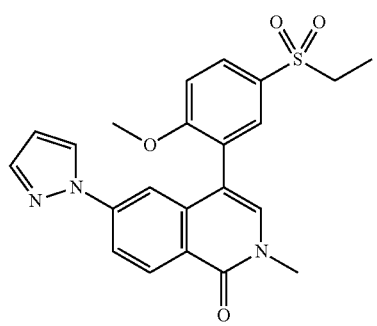 [SMILES: CCS(=O)(=O)c1ccc(OC)c(-c2cn(C)c(=O)c3ccc(-n4cccn4)cc23)c1]
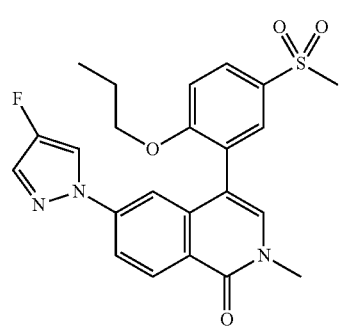 [SMILES: CCCOc1ccc(S(C)(=O)=O)cc1-c1cn(C)c(=O)c2ccc(-n3cc(F)cn3)cc12]
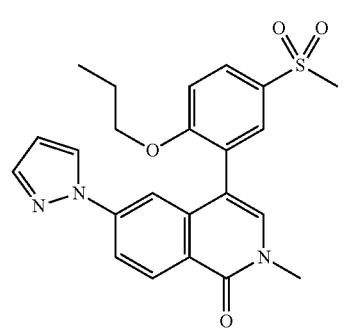 [SMILES: CCCOc1ccc(S(C)(=O)=O)cc1-c1cn(C)c(=O)c2ccc(-n3cccn3)cc12]
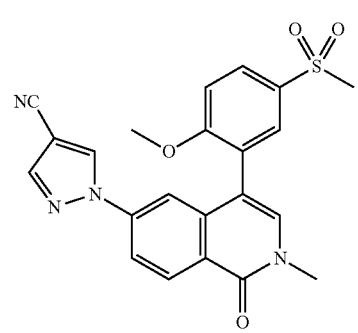 [SMILES: COc1ccc(S(C)(=O)=O)cc1-c1cn(C)c(=O)c2ccc(-n3cc(C#N)cn3)cc12]
TABLE 2-continued
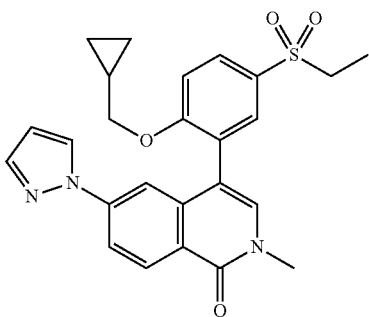 [SMILES: CCS(=O)(=O)c1ccc(OCC2CC2)c(-c2cn(C)c(=O)c3ccc(-n4cccn4)cc23)c1]
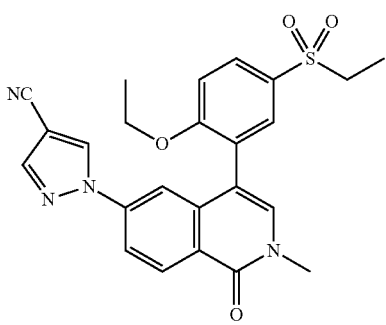 [SMILES: CCOc1ccc(S(=O)(=O)CC)cc1-c1cn(C)c(=O)c2ccc(-n3cc(C#N)cn3)cc12]
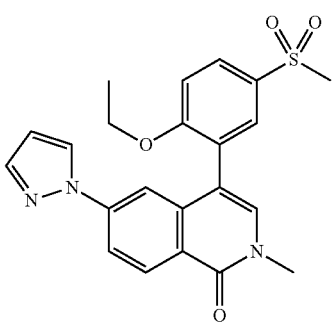 [SMILES: CCOc1ccc(S(C)(=O)=O)cc1-c1cn(C)c(=O)c2ccc(-n3cccn3)cc12]
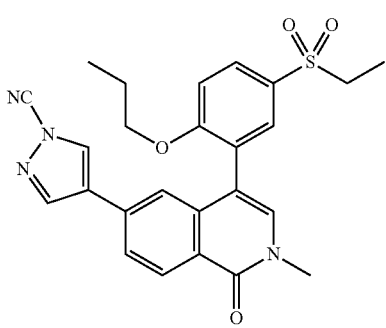 [SMILES: CCCOc1ccc(S(=O)(=O)CC)cc1-c1cn(C)c(=O)c2ccc(-c3cnn(C#N)c3)cc12]
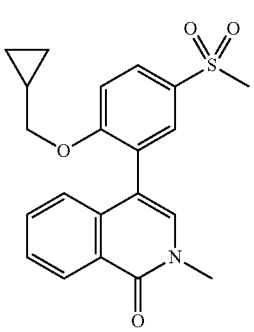 [SMILES: Cn1cc(-c2cc(S(C)(=O)=O)ccc2OCC2CC2)c2ccccc2c1=O]

361
TABLE 2-continued
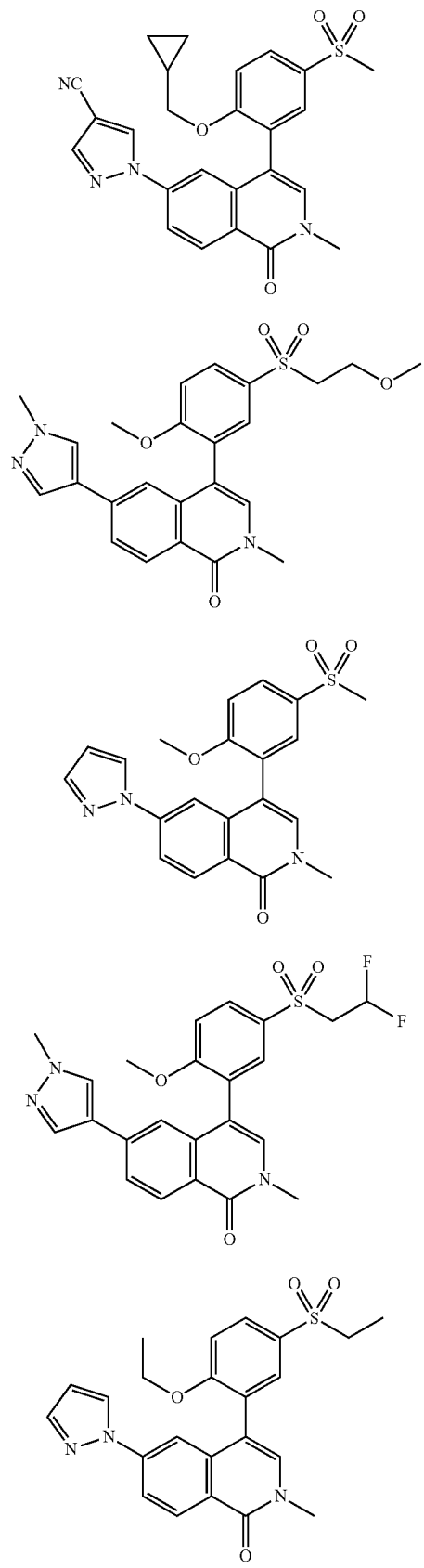
362
TABLE 2-continued
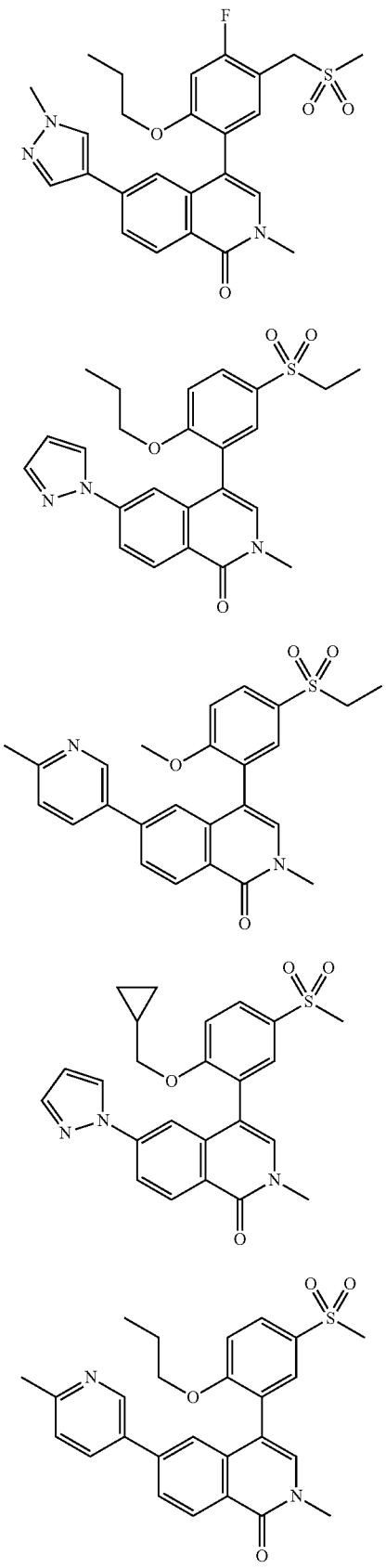

TABLE 2-continued
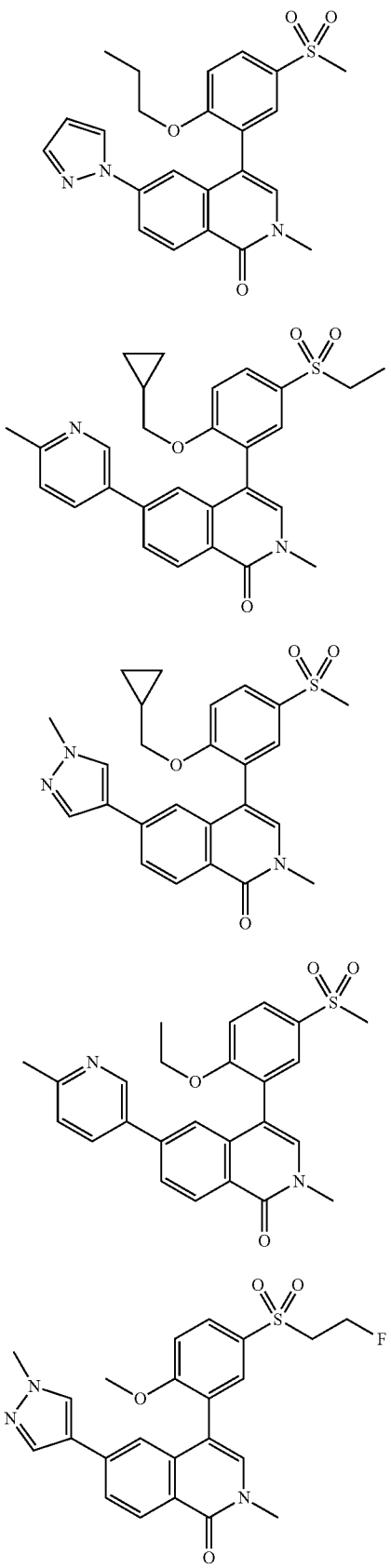
TABLE 2-continued
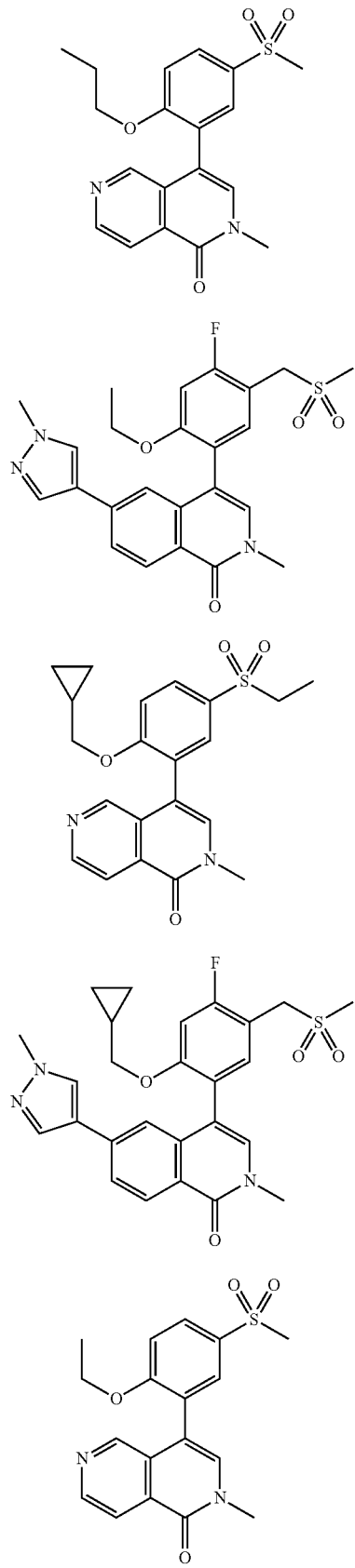

TABLE 2-continued
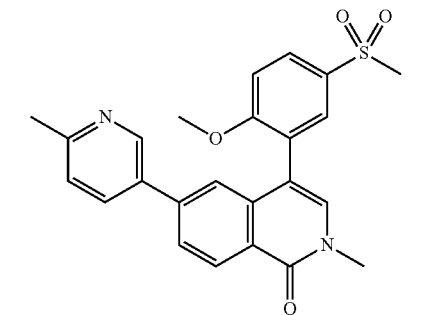
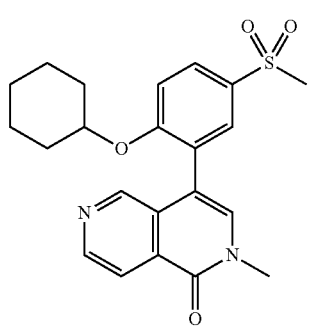 [SMILES: Cn1cc(-c2cc(S(C)(=O)=O)ccc2OC2CCCCC2)c2cnccc2c1=O]
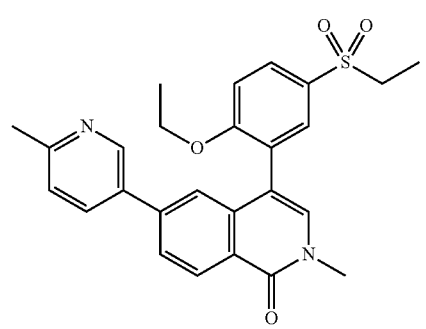 [SMILES: CCOc1ccc(S(=O)(=O)CC)cc1-c1cn(C)c(=O)c2ccc(-c3ccc(C)nc3)cc12]
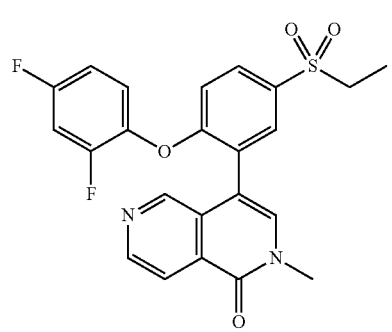 [SMILES: CCS(=O)(=O)c1ccc(Oc2ccc(F)cc2F)c(-c2cn(C)c(=O)c3ccncc23)c1]
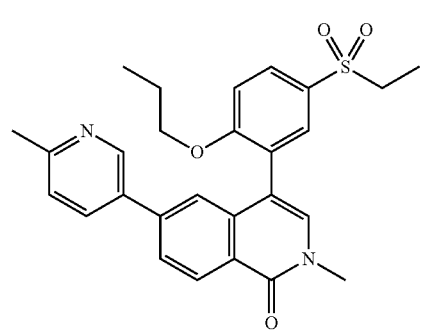 [SMILES: CCCOc1ccc(S(=O)(=O)CC)cc1-c1cn(C)c(=O)c2ccc(-c3ccc(C)nc3)cc12]
TABLE 2-continued
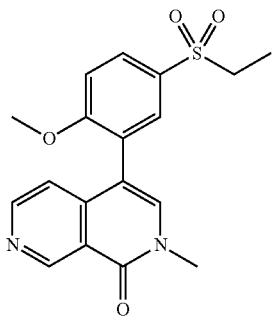 [SMILES: CCS(=O)(=O)c1ccc(OC)c(-c2cn(C)c(=O)c3cnccc23)c1]
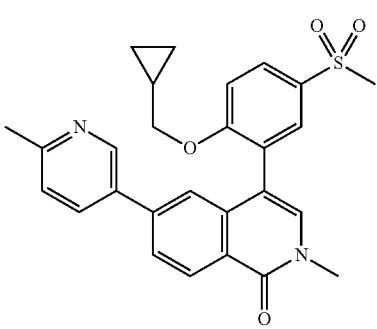
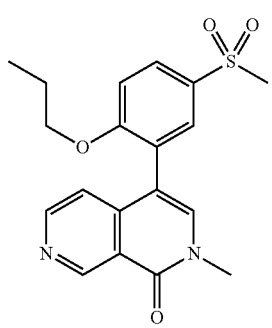 [SMILES: CCCOc1ccc(S(C)(=O)=O)cc1-c1cn(C)c(=O)c2cnccc12]
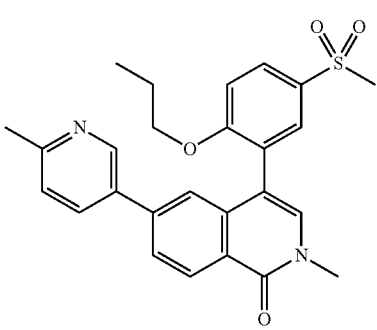
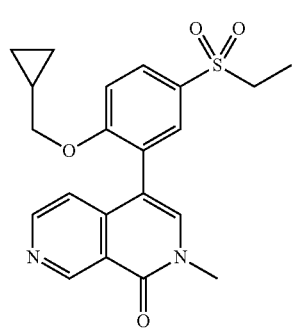 [SMILES: CCS(=O)(=O)c1ccc(OCC2CC2)c(-c2cn(C)c(=O)c3cnccc23)c1]

TABLE 2-continued
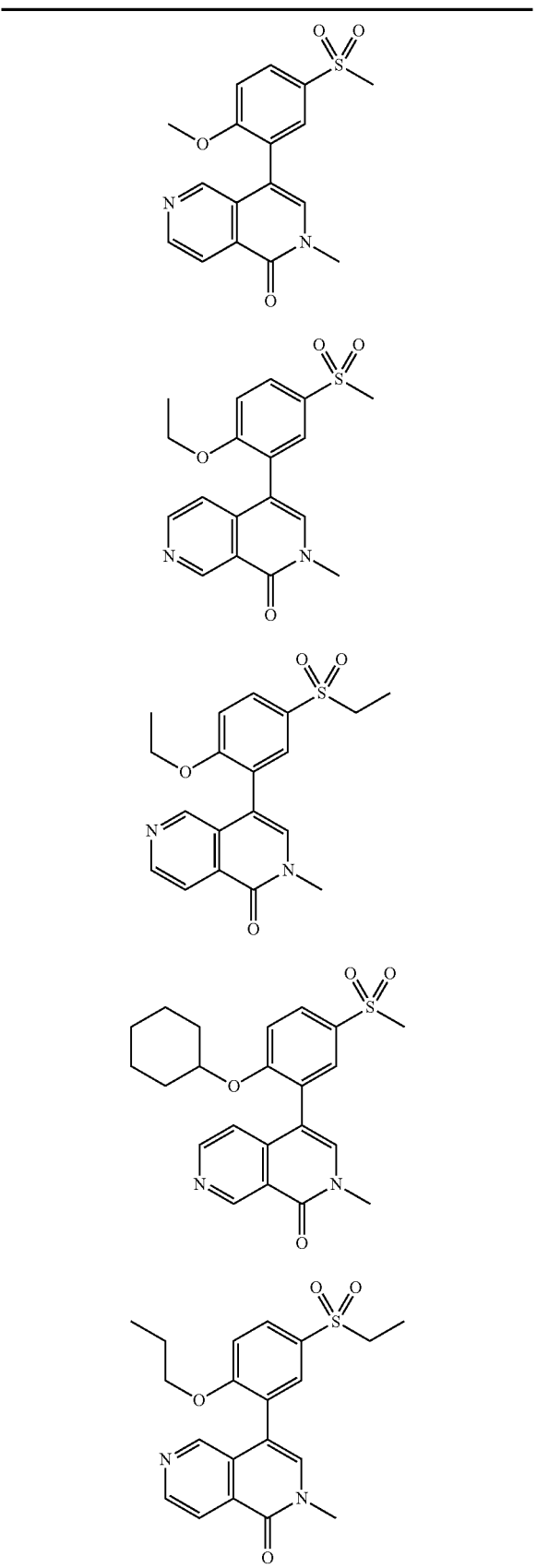
TABLE 2-continued
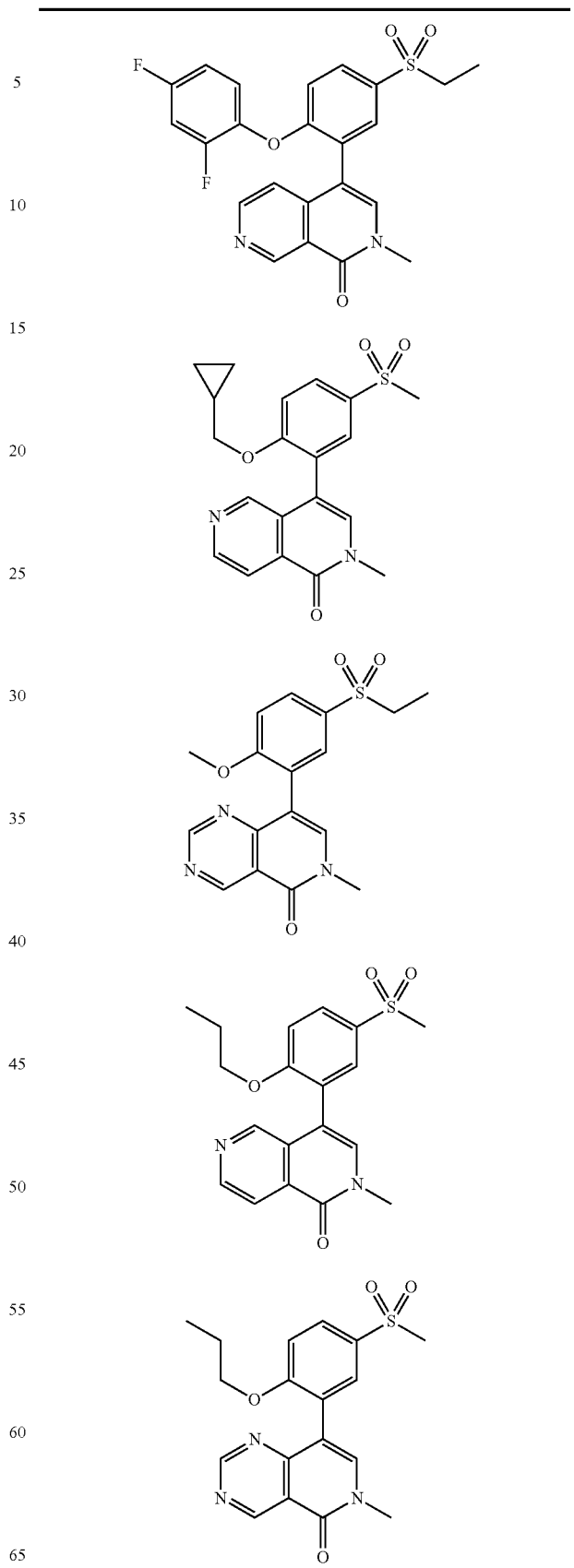

TABLE 2-continued
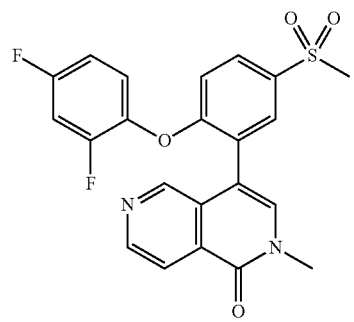 [SMILES: Cn1cc(-c2cc(S(C)(=O)=O)ccc2Oc2ccc(F)cc2F)c2cnccc2c1=O]
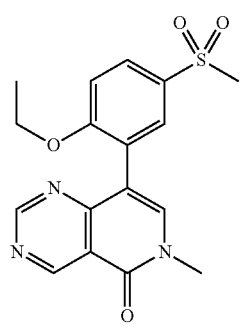 [SMILES: CCOc1ccc(S(C)(=O)=O)cc1-c1cn(C)c(=O)c2cncnc12]
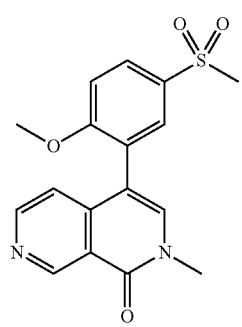
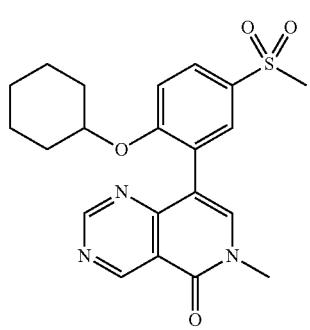 [SMILES: Cn1cc(-c2cc(S(C)(=O)=O)ccc2OC2CCCCC2)c2ncncc2c1=O]
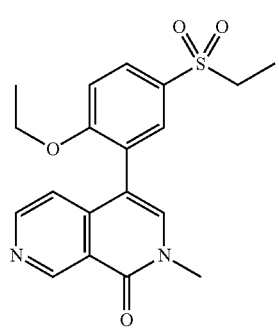
TABLE 2-continued
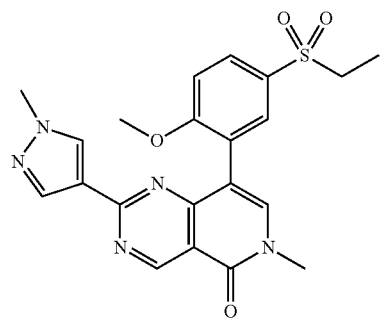 [SMILES: CCS(=O)(=O)c1ccc(OC)c(-c2cn(C)c(=O)c3cnc(-c4cnn(C)c4)nc23)c1]
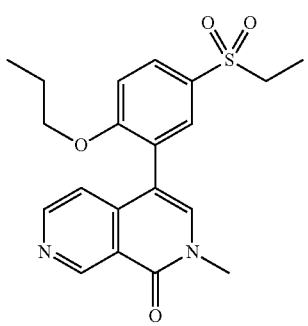
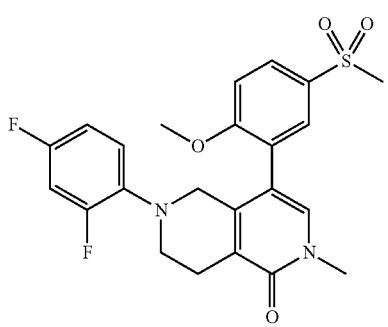
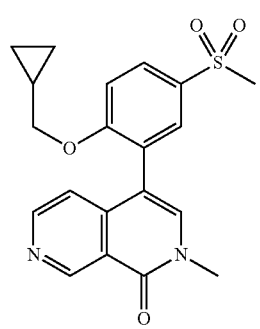 [SMILES: Cn1cc(-c2cc(S(C)(=O)=O)ccc2OCC2CC2)c2ccncc2c1=O]
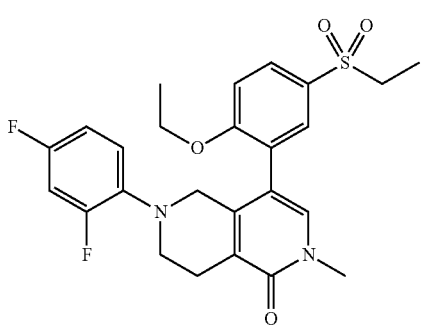 [SMILES: CCOc1ccc(S(=O)(=O)CC)cc1-c1cn(C)c(=O)c2c1CN(c1ccc(F)cc1F)CC2]

TABLE 2-continued
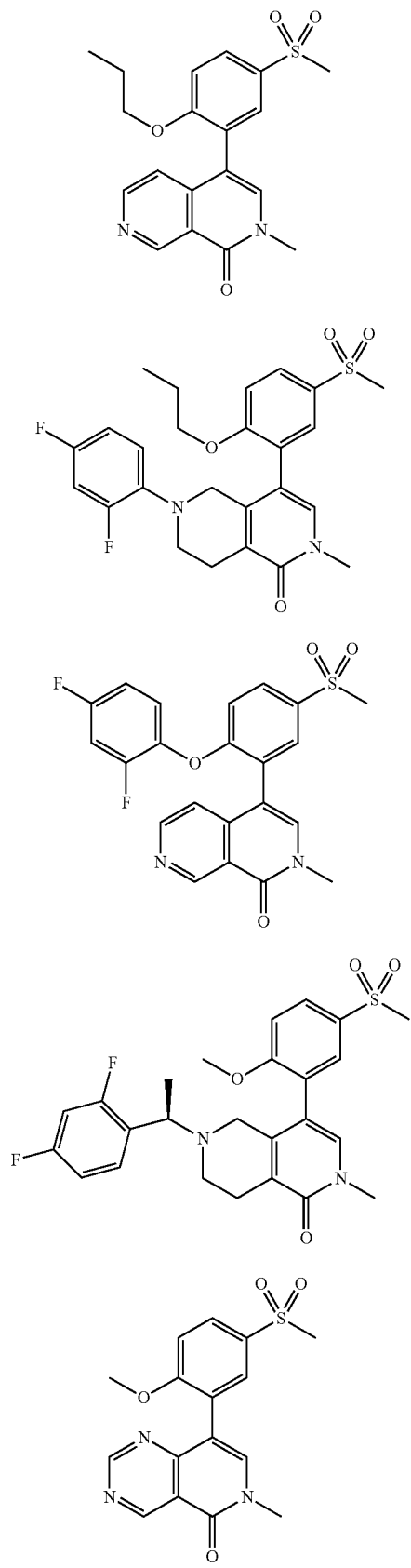
TABLE 2-continued
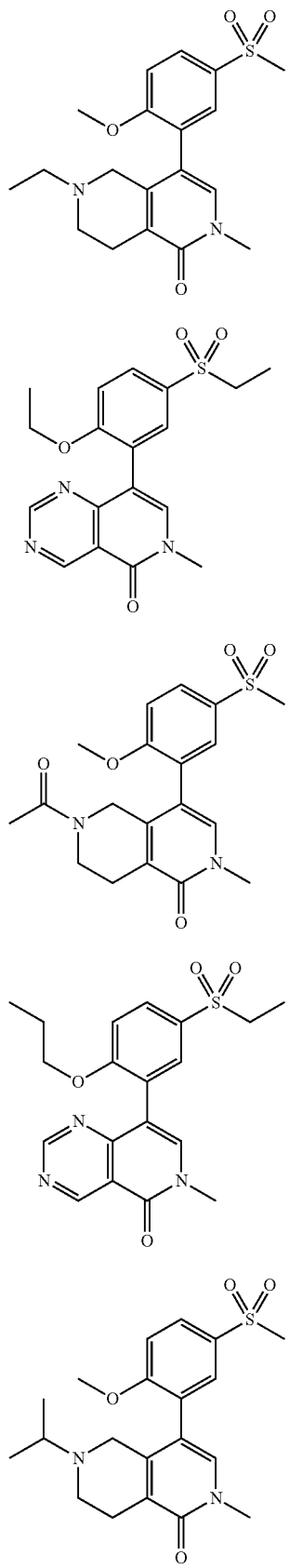

TABLE 2-continued
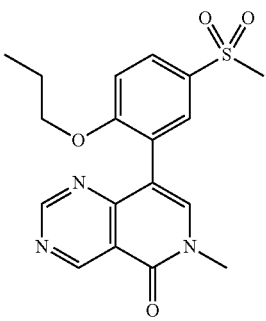
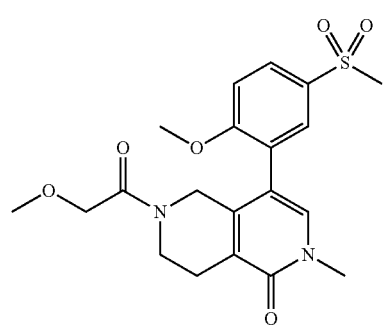
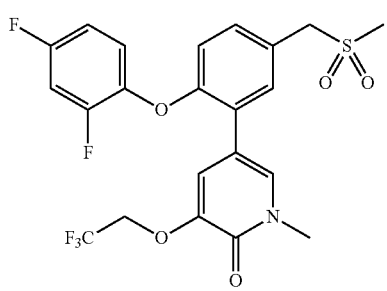 [SMILES: Cn1cc(-c2cc(CS(C)(=O)=O)ccc2Oc2ccc(F)cc2F)cc(OCC(F)(F)F)c1=O]
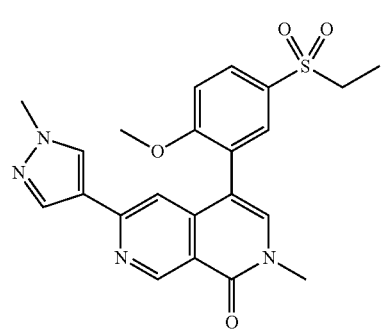 [SMILES: CCS(=O)(=O)c1ccc(OC)c(-c2cn(C)c(=O)c3cnc(-c4cnn(C)c4)cc23)c1]
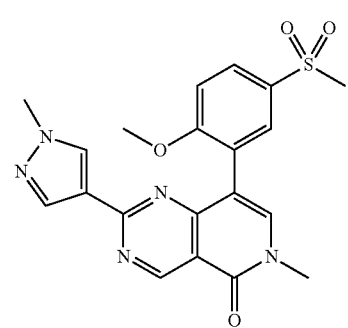 [SMILES: COc1ccc(S(C)(=O)=O)cc1-c1cn(C)c(=O)c2cnc(-c3cnn(C)c3)nc12]
TABLE 2-continued
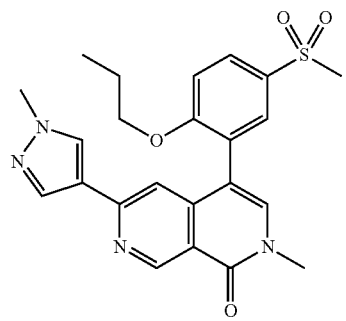 [SMILES: CCCOc1ccc(S(C)(=O)=O)cc1-c1cn(C)c(=O)c2cnc(-c3cnn(C)c3)cc12]
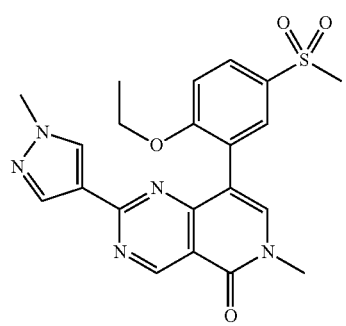 [SMILES: CCOc1ccc(S(C)(=O)=O)cc1-c1cn(C)c(=O)c2cnc(-c3cnn(C)c3)nc12]
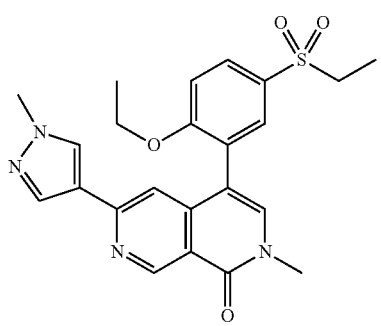 [SMILES: CCOc1ccc(S(=O)(=O)CC)cc1-c1cn(C)c(=O)c2cnc(-c3cnn(C)c3)cc12]
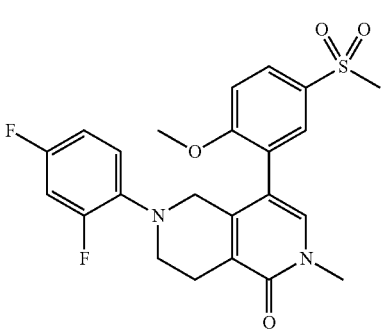
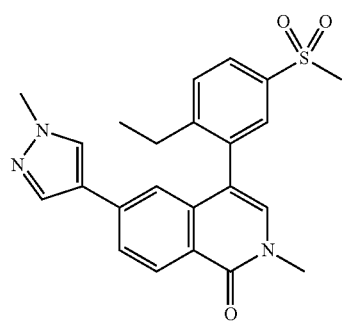 [SMILES: CCc1ccc(S(C)(=O)=O)cc1-c1cn(C)c(=O)c2ccc(-c3cnn(C)c3)cc12]

TABLE 2-continued
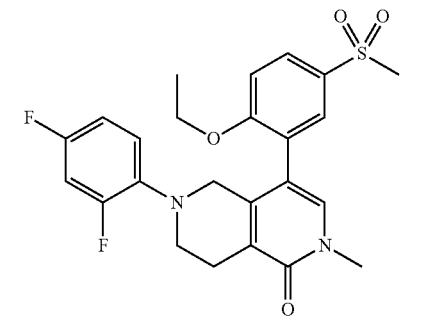 [SMILES: CCOc1ccc(S(C)(=O)=O)cc1-c1cn(C)c(=O)c2c1CN(c1ccc(F)cc1F)CC2]
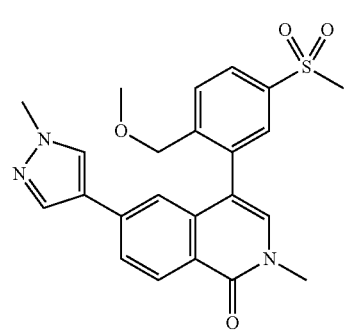 [SMILES: COCc1ccc(S(C)(=O)=O)cc1-c1cn(C)c(=O)c2ccc(-c3cnn(C)c3)cc12]
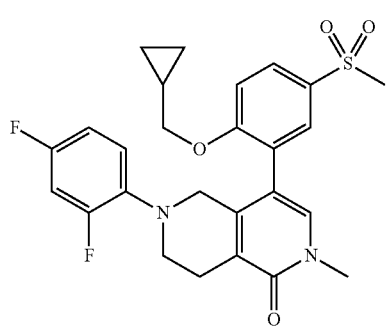 [SMILES: Cn1cc(-c2cc(S(C)(=O)=O)ccc2OCC2CC2)c2c(c1=O)CCN(c1ccc(F)cc1F)C2]
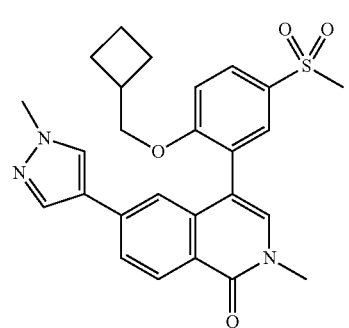 [SMILES: Cn1cc(-c2ccc3c(=O)n(C)cc(-c4cc(S(C)(=O)=O)ccc4OCC4CCC4)c3c2)cn1]
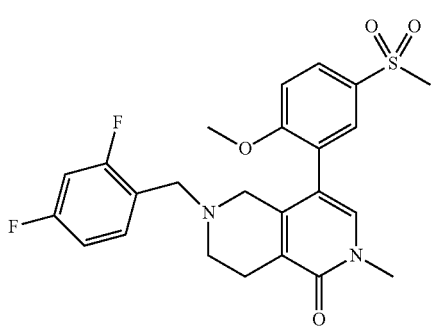 [SMILES: COc1ccc(S(C)(=O)=O)cc1-c1cn(C)c(=O)c2c1CN(Cc1ccc(F)cc1F)CC2]
TABLE 2-continued
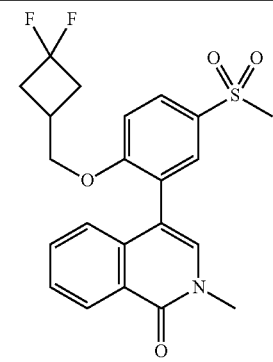
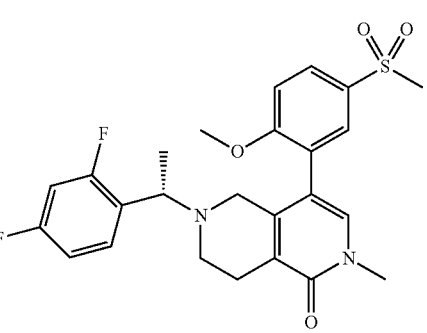
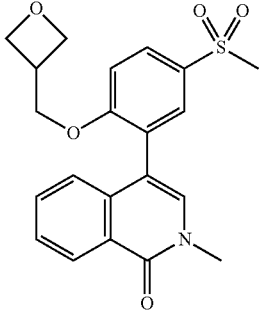 [SMILES: Cn1cc(-c2cc(S(C)(=O)=O)ccc2OCC2COC2)c2ccccc2c1=O]
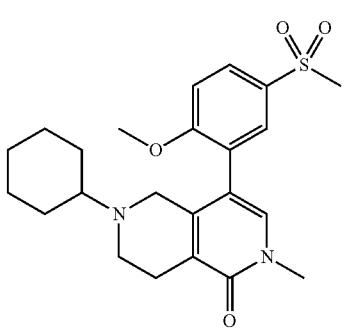 [SMILES: COc1ccc(S(C)(=O)=O)cc1-c1cn(C)c(=O)c2c1CN(C1CCCCC1)CC2]
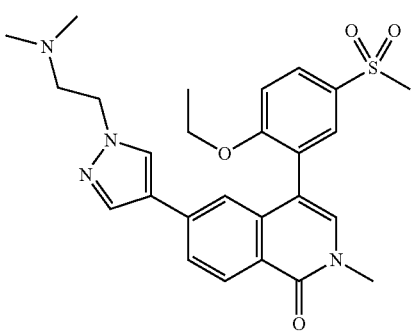

TABLE 2-continued
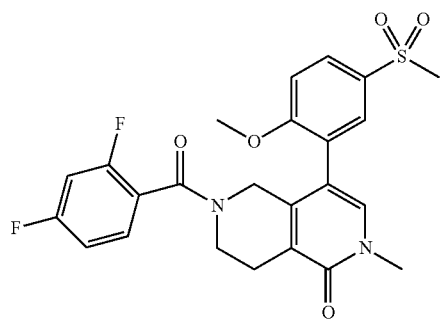 [SMILES: COc1ccc(S(C)(=O)=O)cc1-c1cn(C)c(=O)c2c1CN(C(=O)c1ccc(F)cc1F)CC2]
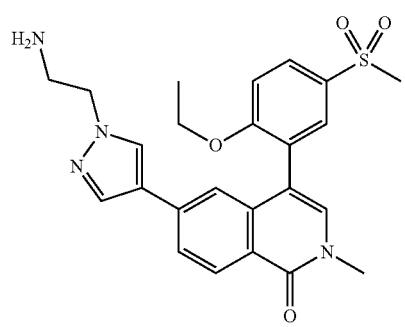 [SMILES: CCOc1ccc(S(C)(=O)=O)cc1-c1cn(C)c(=O)c2ccc(-c3cnn(CCN)c3)cc12]
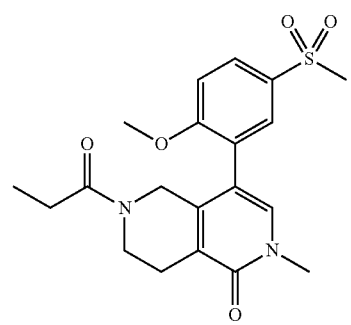 [SMILES: CCC(=O)N1CCc2c(c(-c3cc(S(C)(=O)=O)ccc3OC)cn(C)c2=O)C1]
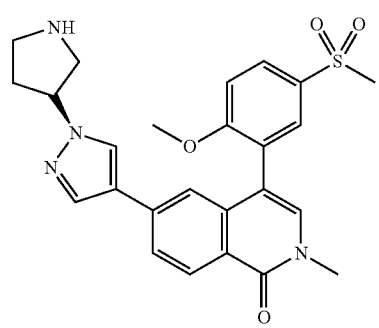
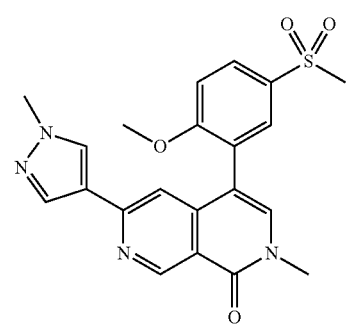 [SMILES: COc1ccc(S(C)(=O)=O)cc1-c1cn(C)c(=O)c2cnc(-c3cnn(C)c3)cc12]
TABLE 2-continued
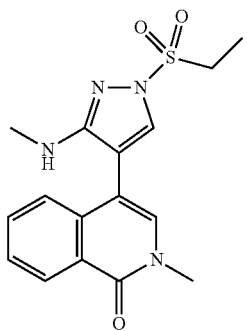 [SMILES: CCS(=O)(=O)n1cc(-c2cn(C)c(=O)c3ccccc23)c(NC)n1]
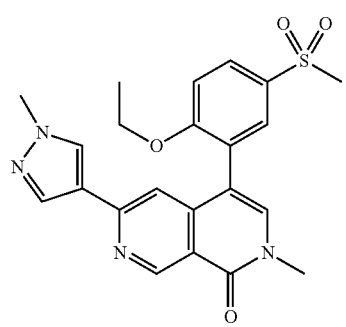 [SMILES: CCOc1ccc(S(C)(=O)=O)cc1-c1cn(C)c(=O)c2cnc(-c3cnn(C)c3)cc12]
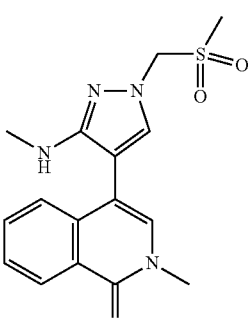
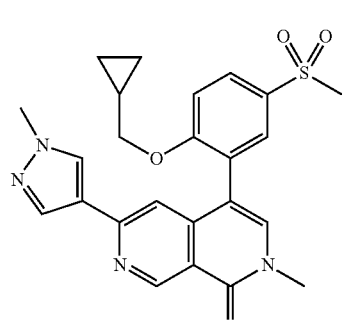
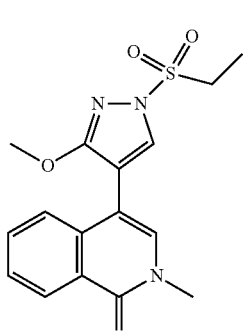

TABLE 2-continued
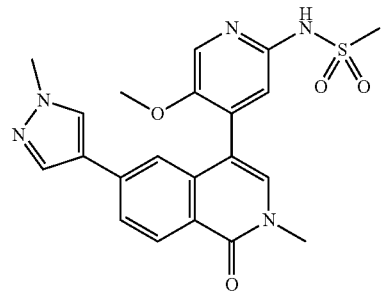 [SMILES: COc1cnc(NS(C)(=O)=O)cc1-c1cn(C)c(=O)c2ccc(-c3cnn(C)c3)cc12]
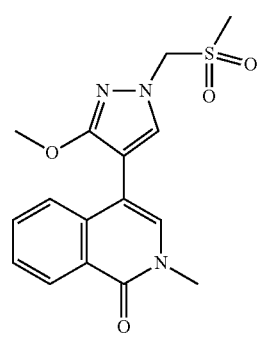 [SMILES: COc1nn(CS(C)(=O)=O)cc1-c1cn(C)c(=O)c2ccccc12]
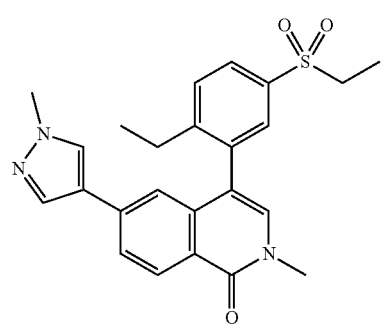 [SMILES: CCc1ccc(S(=O)(=O)CC)cc1-c1cn(C)c(=O)c2ccc(-c3cnn(C)c3)cc12]
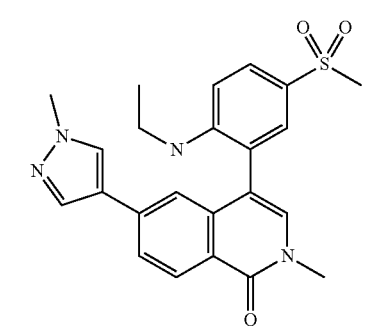 [SMILES: CCNc1ccc(S(C)(=O)=O)cc1-c1cn(C)c(=O)c2ccc(-c3cnn(C)c3)cc12]
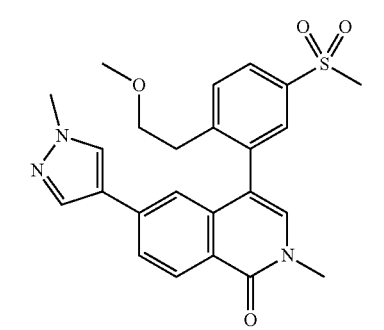
TABLE 2-continued
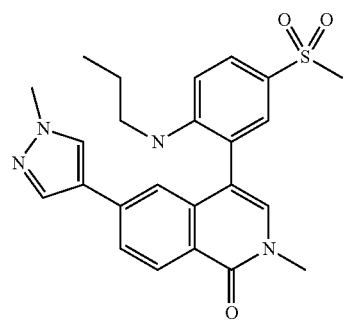 [SMILES: CCCNc1ccc(S(C)(=O)=O)cc1-c1cn(C)c(=O)c2ccc(-c3cnn(C)c3)cc12]
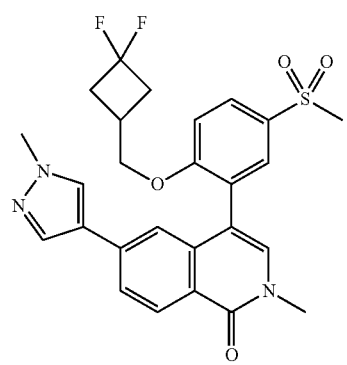 [SMILES: Cn1cc(-c2ccc3c(=O)n(C)cc(-c4cc(S(C)(=O)=O)ccc4OCC4CC(F)(F)C4)c3c2)cn1]
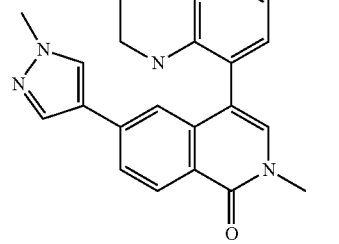
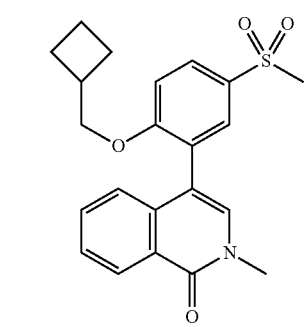 [SMILES: Cn1cc(-c2cc(S(C)(=O)=O)ccc2OCC2CCC2)c2ccccc2c1=O]
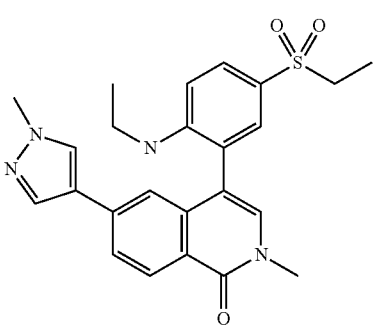 [SMILES: CCNc1ccc(S(=O)(=O)CC)cc1-c1cn(C)c(=O)c2ccc(-c3cnn(C)c3)cc12]

TABLE 2-continued
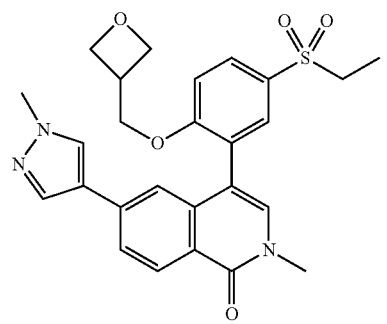 [SMILES: CCS(=O)(=O)c1ccc(OCC2COC2)c(-c2cn(C)c(=O)c3ccc(-c4cnn(C)c4)cc23)c1]
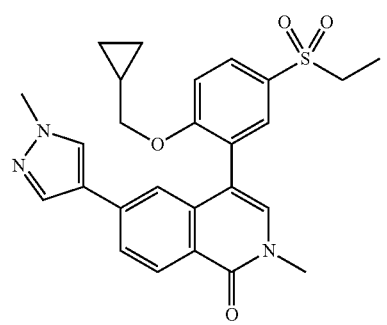 [SMILES: CCS(=O)(=O)c1ccc(OCC2CC2)c(-c2cn(C)c(=O)c3ccc(-c4cnn(C)c4)cc23)c1]
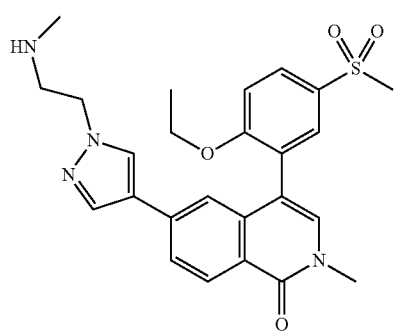 [SMILES: CCOc1ccc(S(C)(=O)=O)cc1-c1cn(C)c(=O)c2ccc(-c3cnn(CCNC)c3)cc12]
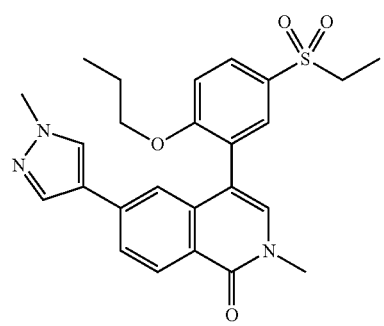 [SMILES: CCCOc1ccc(S(=O)(=O)CC)cc1-c1cn(C)c(=O)c2ccc(-c3cnn(C)c3)cc12]
TABLE 2-continued
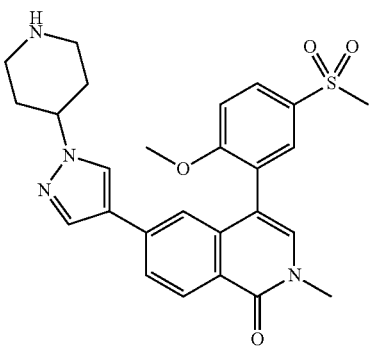 [SMILES: COc1ccc(S(C)(=O)=O)cc1-c1cn(C)c(=O)c2ccc(-c3cnn(C4CCNCC4)c3)cc12]
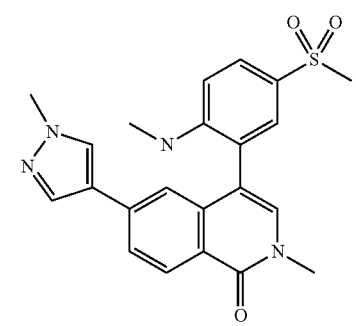 [SMILES: CNc1ccc(S(C)(=O)=O)cc1-c1cn(C)c(=O)c2ccc(-c3cnn(C)c3)cc12]
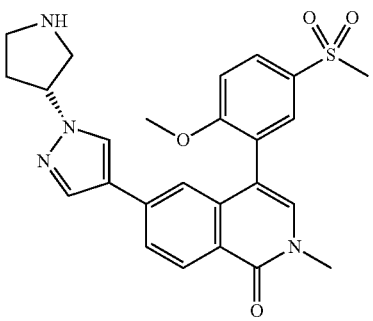
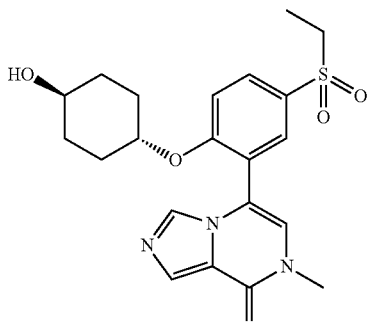
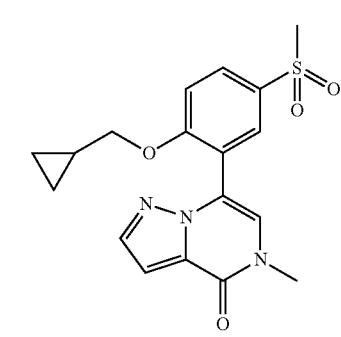 [SMILES: Cn1cc(-c2cc(S(C)(=O)=O)ccc2OCC2CC2)n2nccc2c1=O]

TABLE 2-continued
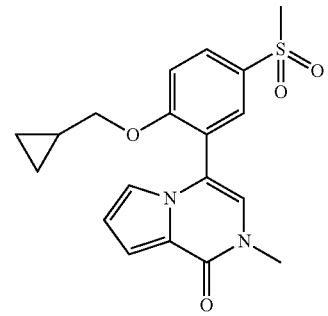 [SMILES: Cn1cc(-c2cc(S(C)(=O)=O)ccc2OCC2CC2)n2cccc2c1=O]
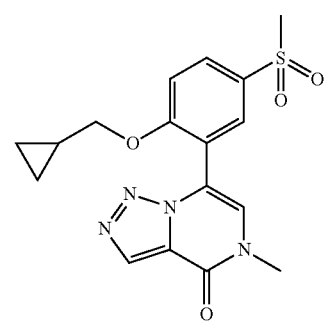 [SMILES: Cn1cc(-c2cc(S(C)(=O)=O)ccc2OCC2CC2)n2nncc2c1=O]
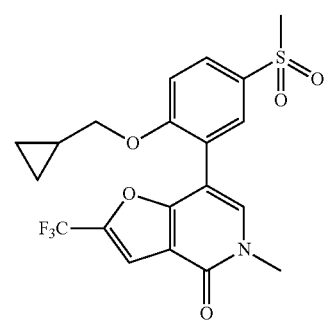 [SMILES: Cn1cc(-c2cc(S(C)(=O)=O)ccc2OCC2CC2)c2oc(C(F)(F)F)cc2c1=O]
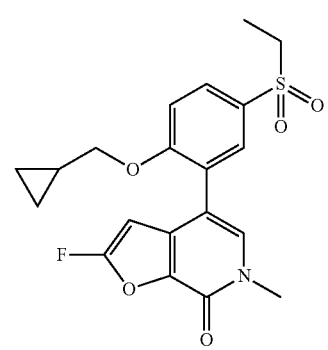 [SMILES: CCS(=O)(=O)c1ccc(OCC2CC2)c(-c2cn(C)c(=O)c3oc(F)cc23)c1]
TABLE 2-continued
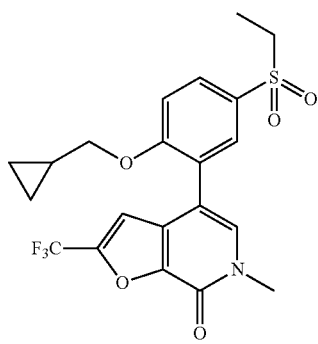 [SMILES: CCS(=O)(=O)c1ccc(OCC2CC2)c(-c2cn(C)c(=O)c3oc(C(F)(F)F)cc23)c1]
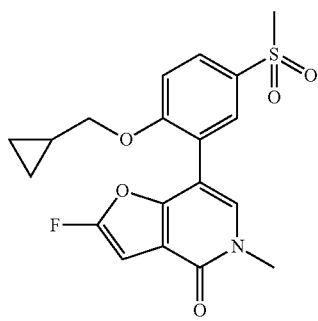 [SMILES: Cn1cc(-c2cc(S(C)(=O)=O)ccc2OCC2CC2)c2oc(F)cc2c1=O]
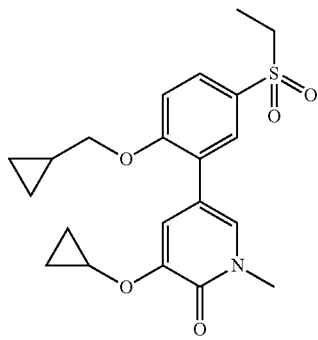 [SMILES: CCS(=O)(=O)c1ccc(OCC2CC2)c(-c2cc(OC3CC3)c(=O)n(C)c2)c1]
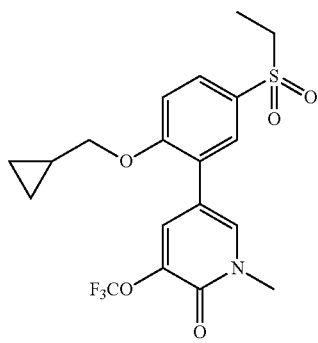 [SMILES: CCS(=O)(=O)c1ccc(OCC2CC2)c(-c2cc(OC(F)(F)F)c(=O)n(C)c2)c1]
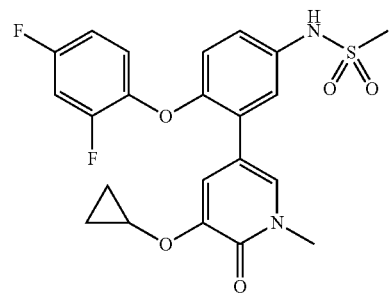 [SMILES: Cn1cc(-c2cc(NS(C)(=O)=O)ccc2Oc2ccc(F)cc2F)cc(OC2CC2)c1=O]

TABLE 2-continued
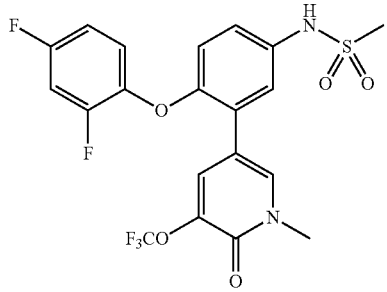 [SMILES: Cn1cc(-c2cc(NS(C)(=O)=O)ccc2Oc2ccc(F)cc2F)cc(OC(F)(F)F)c1=O]
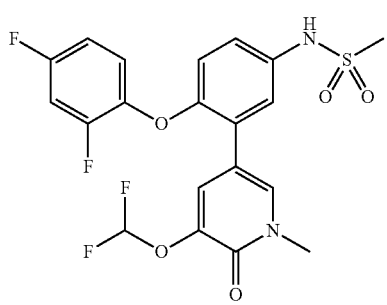 [SMILES: Cn1cc(-c2cc(NS(C)(=O)=O)ccc2Oc2ccc(F)cc2F)cc(OC(F)F)c1=O]
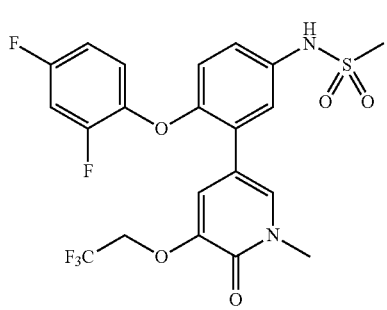 [SMILES: Cn1cc(-c2cc(NS(C)(=O)=O)ccc2Oc2ccc(F)cc2F)cc(OCC(F)(F)F)c1=O]
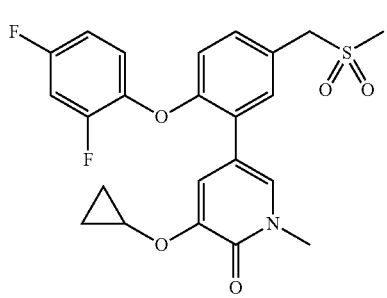 [SMILES: Cn1cc(-c2cc(CS(C)(=O)=O)ccc2Oc2ccc(F)cc2F)cc(OC2CC2)c1=O]
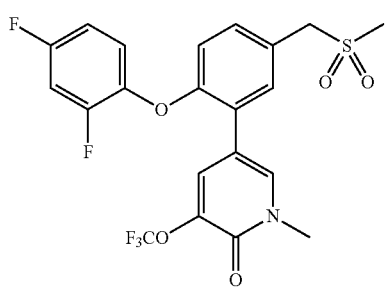 [SMILES: Cn1cc(-c2cc(CS(C)(=O)=O)ccc2Oc2ccc(F)cc2F)cc(OC(F)(F)F)c1=O]
TABLE 2-continued
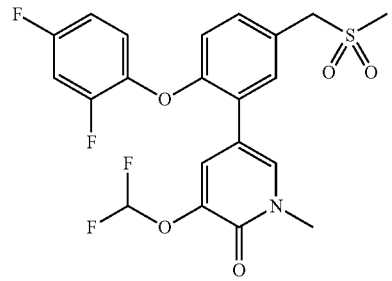 [SMILES: Cn1cc(-c2cc(CS(C)(=O)=O)ccc2Oc2ccc(F)cc2F)cc(OC(F)F)c1=O]
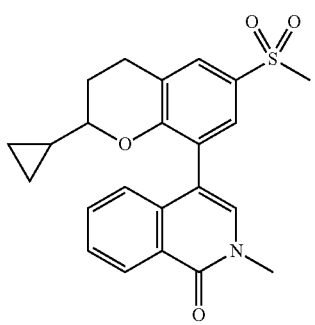 [SMILES: Cn1cc(-c2cc(S(C)(=O)=O)cc3c2OC(C2CC2)CC3)c2ccccc2c1=O]
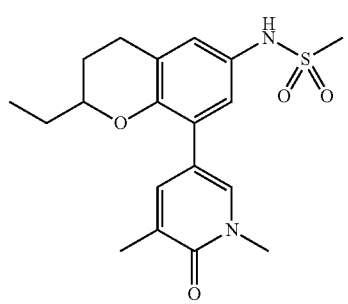 [SMILES: CCC1CCc2cc(NS(C)(=O)=O)cc(-c3cc(C)c(=O)n(C)c3)c2O1]
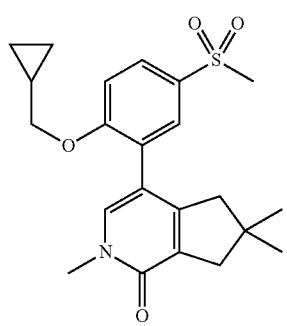 [SMILES: Cn1cc(-c2cc(S(C)(=O)=O)ccc2OCC2CC2)c2c(c1=O)CC(C)(C)C2]
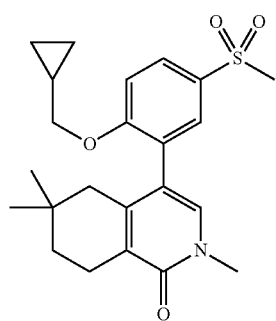

TABLE 2-continued
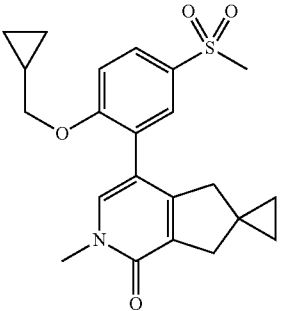 [SMILES: Cn1cc(-c2cc(S(C)(=O)=O)ccc2OCC2CC2)c2c(c1=O)CC1(CC1)C2]
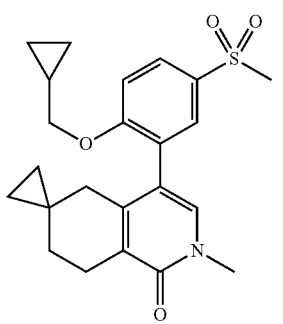 [SMILES: Cn1cc(-c2cc(S(C)(=O)=O)ccc2OCC2CC2)c2c(c1=O)CCC1(CC1)C2]
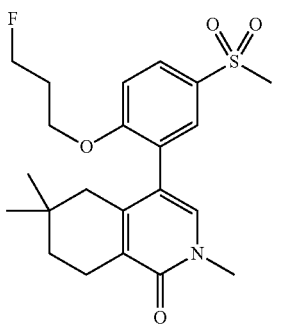
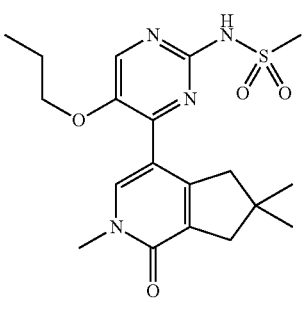 [SMILES: CCCOc1cnc(NS(C)(=O)=O)nc1-c1cn(C)c(=O)c2c1CC(C)(C)C2]
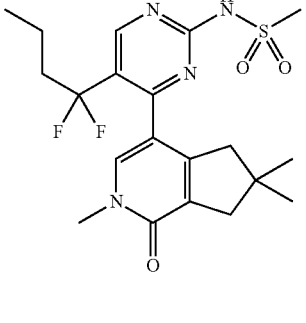
TABLE 2-continued
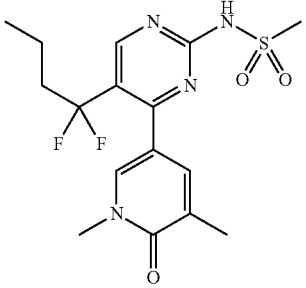 [SMILES: CCCC(F)(F)c1cnc(NS(C)(=O)=O)nc1-c1cc(C)c(=O)n(C)c1]
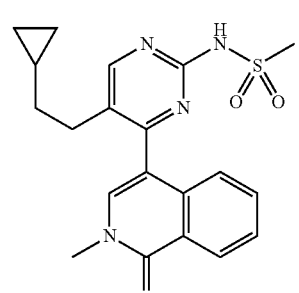
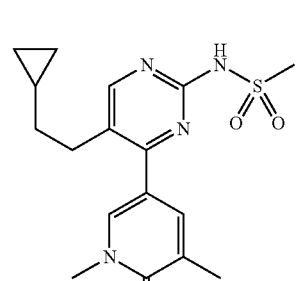
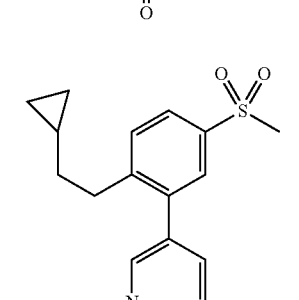

389
TABLE 2-continued
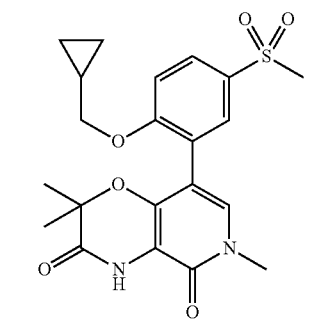
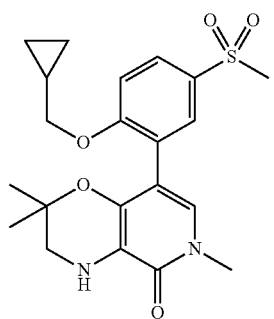
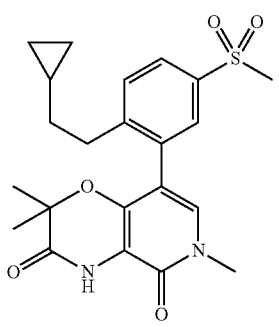
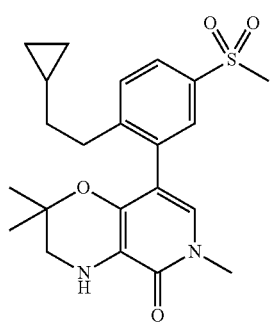
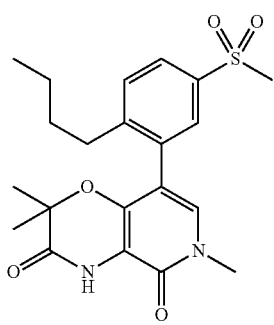 [SMILES: CCCCc1ccc(S(C)(=O)=O)cc1-c1cn(C)c(=O)c2c1OC(C)(C)C(=O)N2]
390
TABLE 2-continued
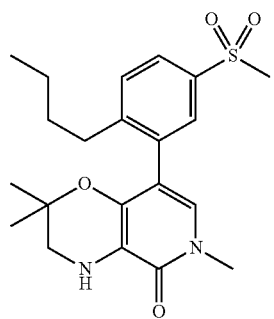
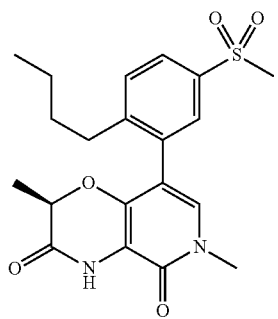 [SMILES: CCCCc1ccc(S(C)(=O)=O)cc1-c1cn(C)c(=O)c2c1O[C@H](C)C(=O)N2]
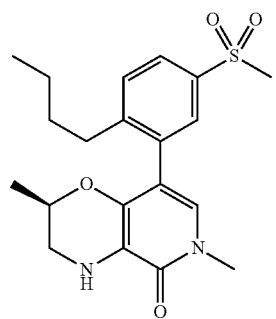 [SMILES: CCCCc1ccc(S(C)(=O)=O)cc1-c1cn(C)c(=O)c2c1O[C@H](C)CN2]
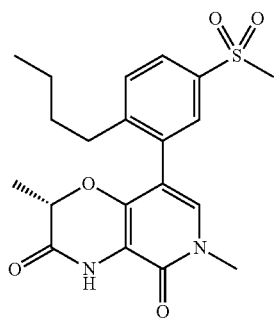 [SMILES: CCCCc1ccc(S(C)(=O)=O)cc1-c1cn(C)c(=O)c2c1O[C@@H](C)C(=O)N2]
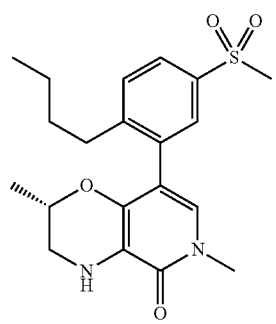 [SMILES: CCCCc1ccc(S(C)(=O)=O)cc1-c1cn(C)c(=O)c2c1O[C@@H](C)CN2]

TABLE 2-continued
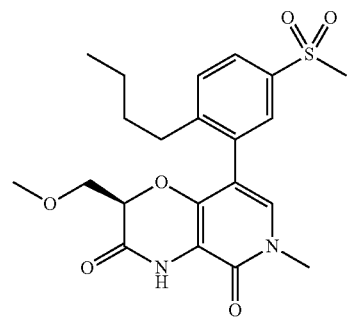
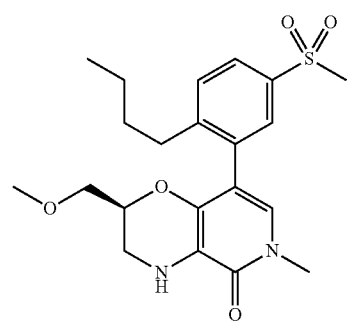
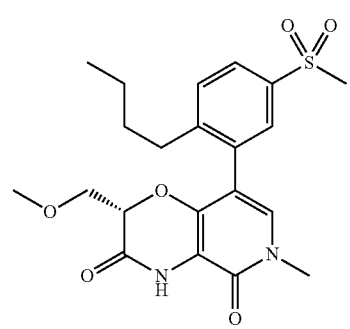
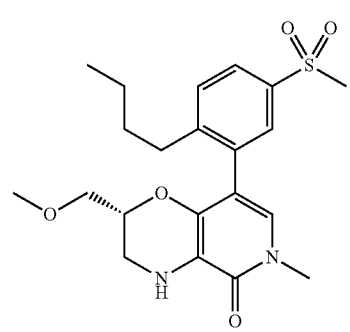
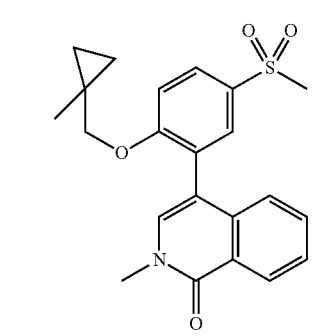 [SMILES: Cn1cc(-c2cc(S(C)(=O)=O)ccc2OCC2(C)CC2)c2ccccc2c1=O]
TABLE 2-continued
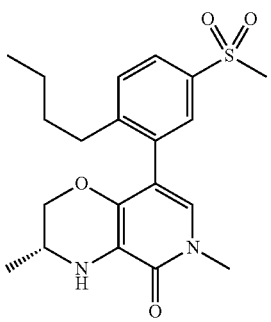 [SMILES: CCCCc1ccc(S(C)(=O)=O)cc1-c1cn(C)c(=O)c2c1OC[C@@H](C)N2]
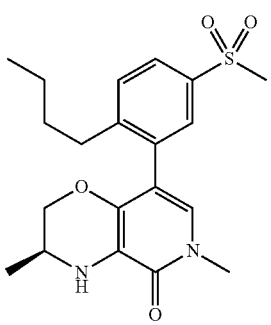 [SMILES: CCCCc1ccc(S(C)(=O)=O)cc1-c1cn(C)c(=O)c2c1OC[C@H](C)N2]
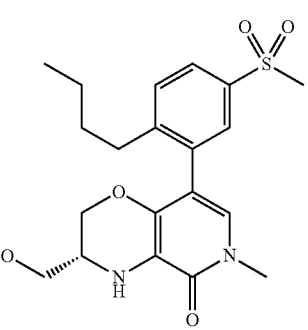
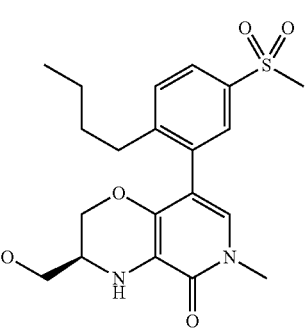
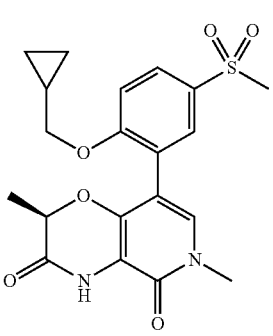

TABLE 2-continued
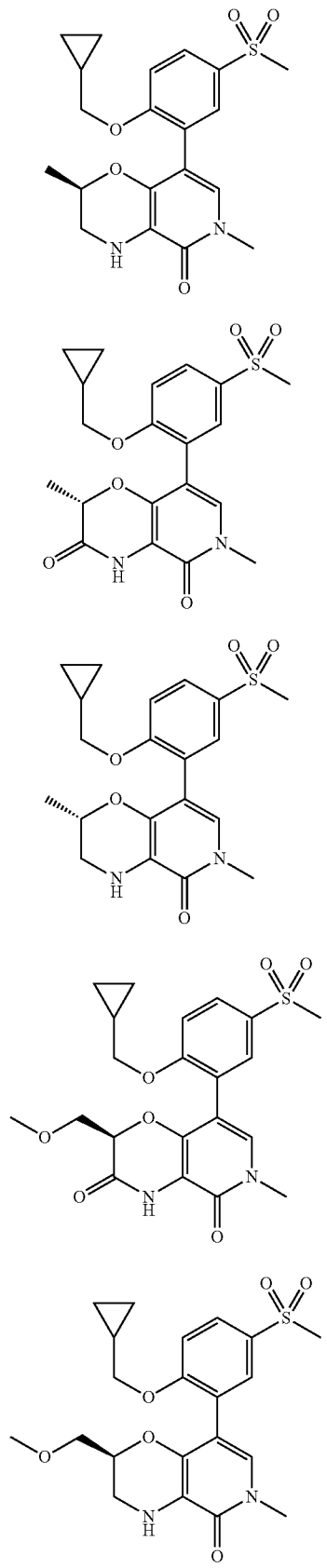
TABLE 2-continued
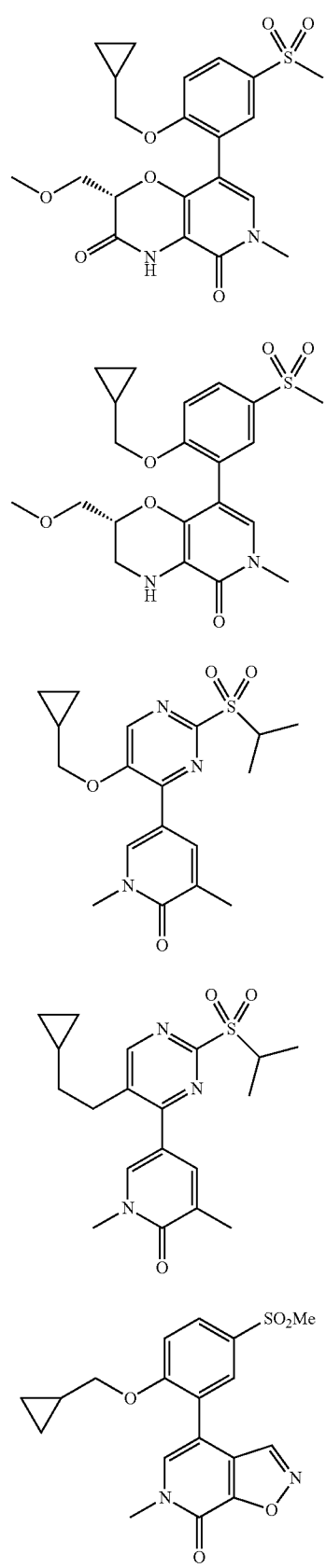

TABLE 2-continued
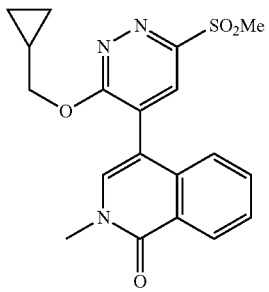 [SMILES: Cn1cc(-c2cc(S(C)(=O)=O)nnc2OCC2CC2)c2ccccc2c1=O]
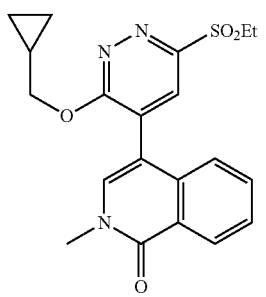
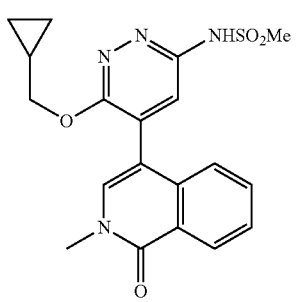
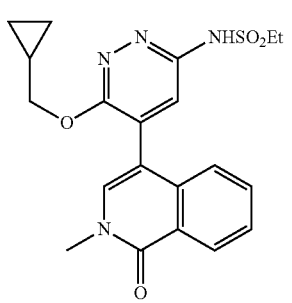
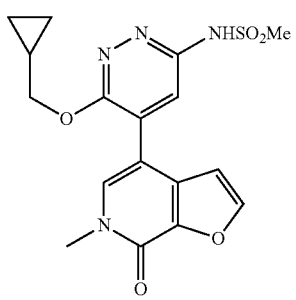
TABLE 2-continued
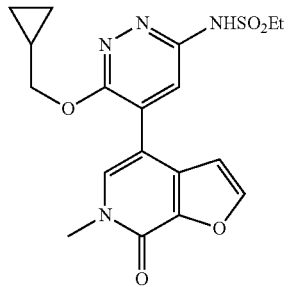
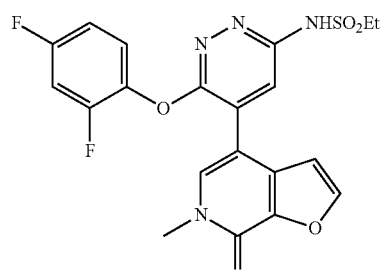
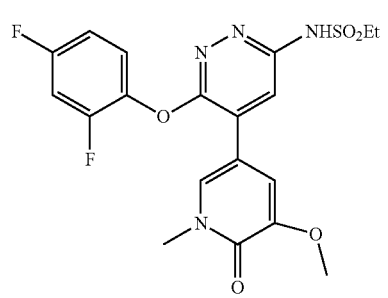
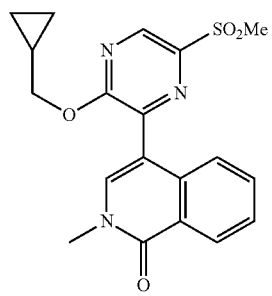 [SMILES: Cn1cc(-c2nc(S(C)(=O)=O)cnc2OCC2CC2)c2ccccc2c1=O]
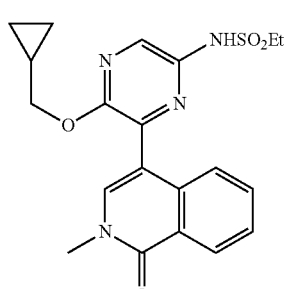

TABLE 2-continued

TABLE 2-continued
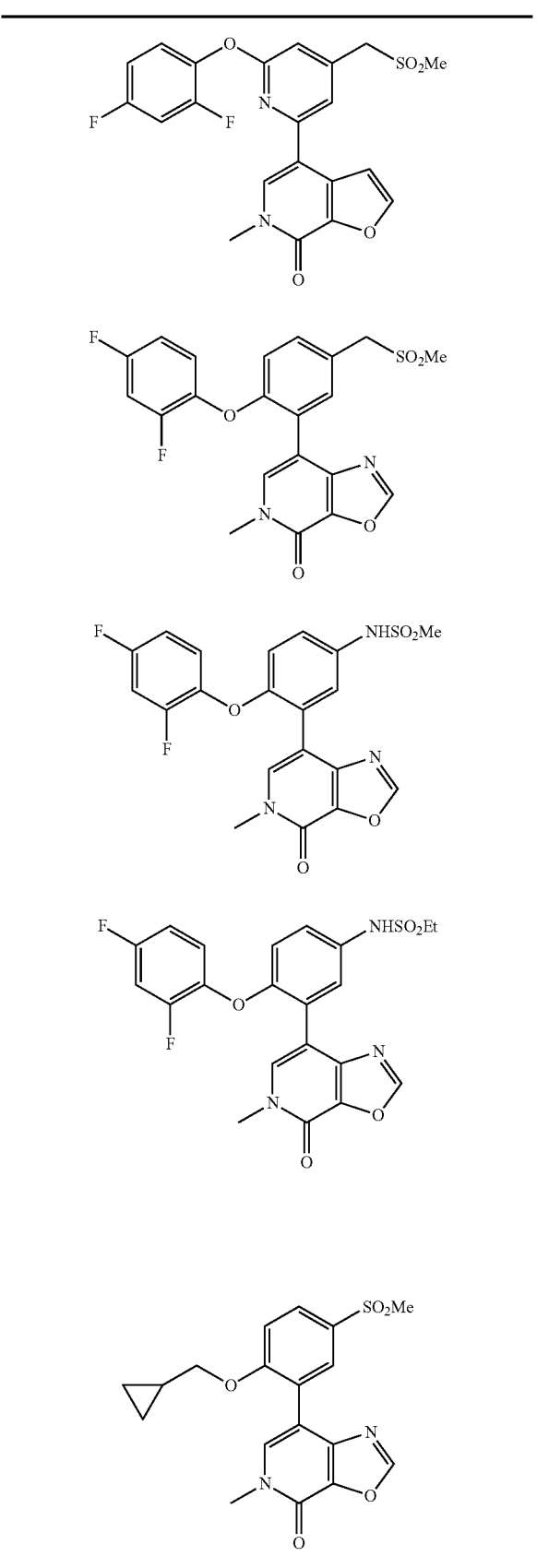
TABLE 2-continued
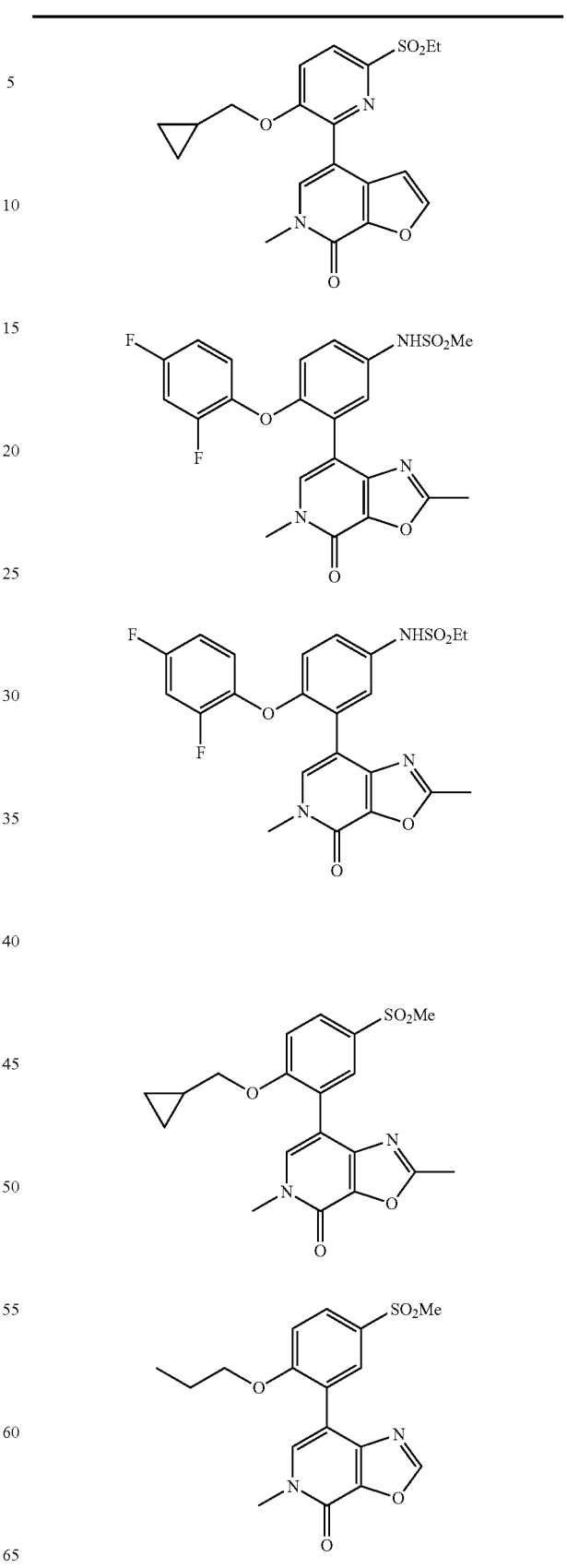

TABLE 2-continued
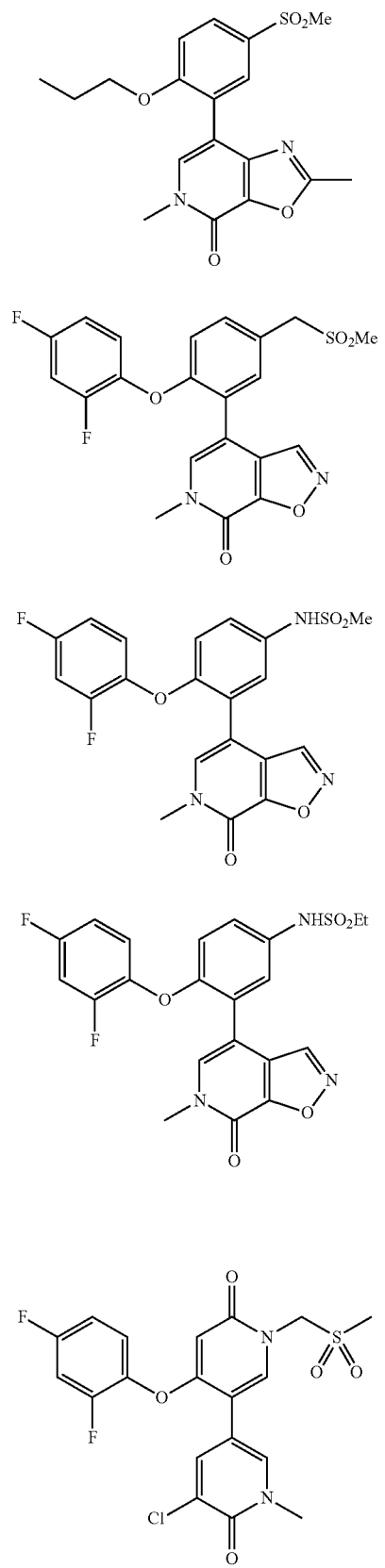
TABLE 2-continued
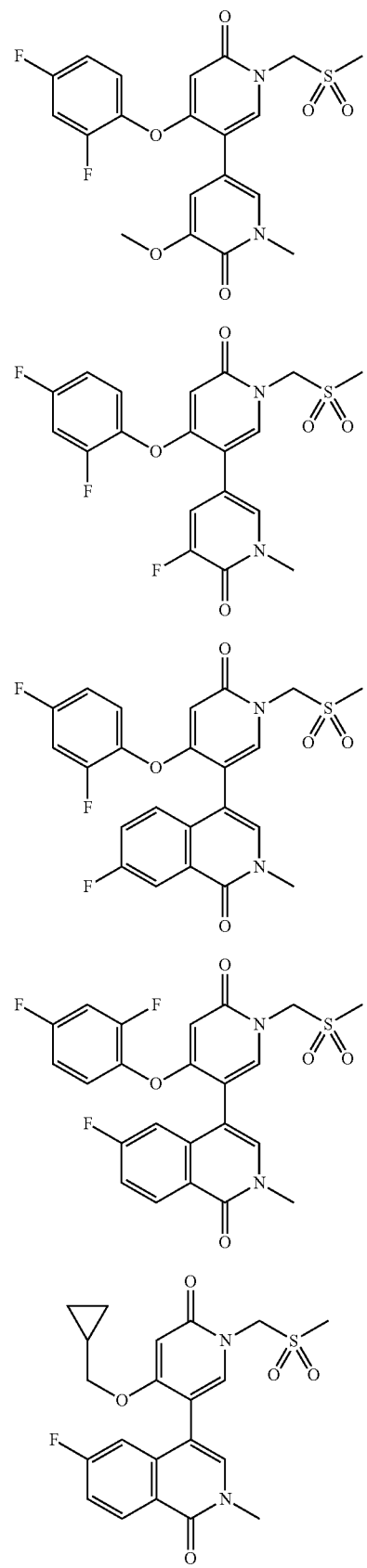

TABLE 2-continued
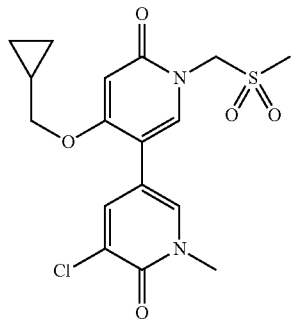 [SMILES: Cn1cc(-c2cn(CS(C)(=O)=O)c(=O)cc2OCC2CC2)cc(Cl)c1=O]
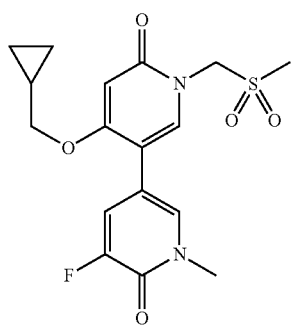 [SMILES: Cn1cc(-c2cn(CS(C)(=O)=O)c(=O)cc2OCC2CC2)cc(F)c1=O]
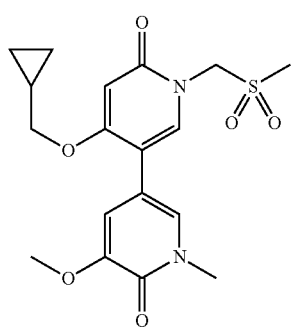 [SMILES: COc1cc(-c2cn(CS(C)(=O)=O)c(=O)cc2OCC2CC2)cn(C)c1=O]
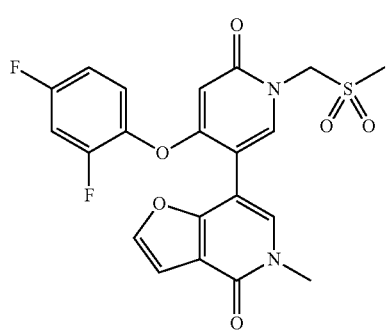 [SMILES: Cn1cc(-c2cn(CS(C)(=O)=O)c(=O)cc2Oc2ccc(F)cc2F)c2occc2c1=O]
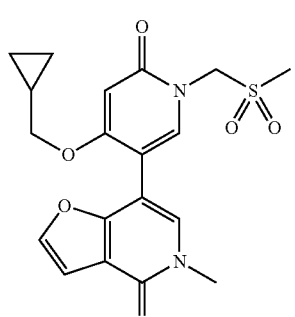
TABLE 2-continued
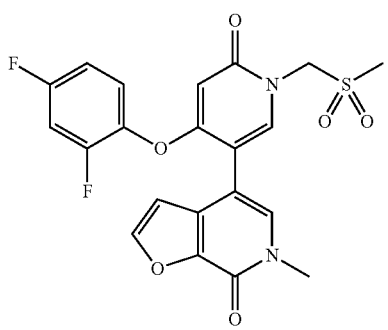 [SMILES: Cn1cc(-c2cn(CS(C)(=O)=O)c(=O)cc2Oc2ccc(F)cc2F)c2ccoc2c1=O]
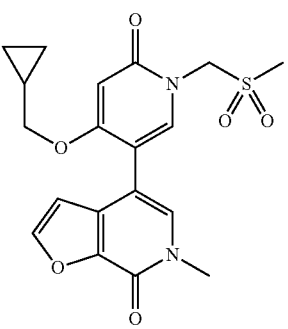 [SMILES: Cn1cc(-c2cn(CS(C)(=O)=O)c(=O)cc2OCC2CC2)c2ccoc2c1=O]
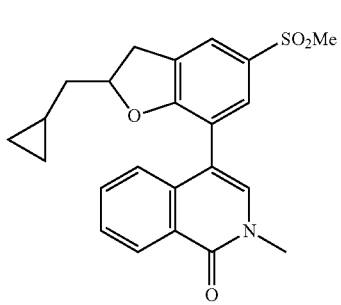 [SMILES: Cn1cc(-c2cc(S(C)(=O)=O)cc3c2OC(CC2CC2)C3)c2ccccc2c1=O]
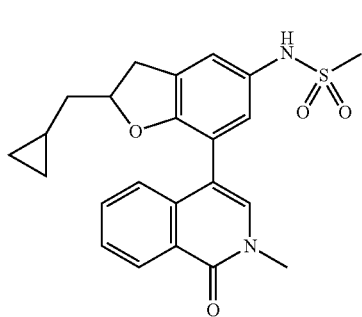 [SMILES: Cn1cc(-c2cc(NS(C)(=O)=O)cc3c2OC(CC2CC2)C3)c2ccccc2c1=O]
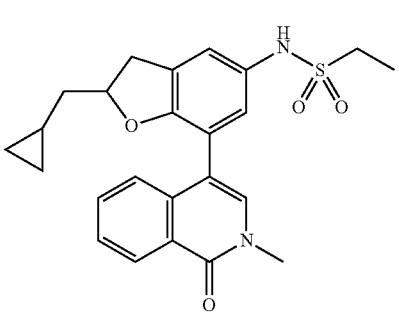 [SMILES: CCS(=O)(=O)Nc1cc2c(c(-c3cn(C)c(=O)c4ccccc34)c1)OC(CC1CC1)C2]

TABLE 2-continued
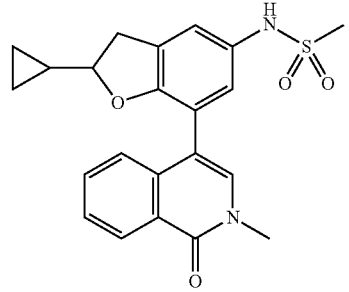 [SMILES: Cn1cc(-c2cc(NS(C)(=O)=O)cc3c2OC(C2CC2)C3)c2ccccc2c1=O]
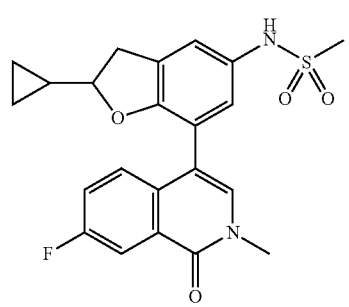 [SMILES: Cn1cc(-c2cc(NS(C)(=O)=O)cc3c2OC(C2CC2)C3)c2ccc(F)cc2c1=O]
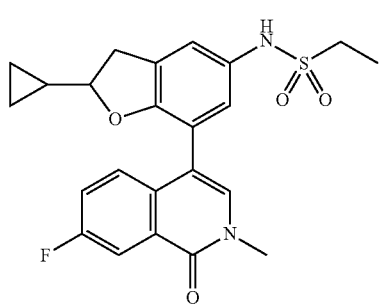 [SMILES: CCS(=O)(=O)Nc1cc2c(c(-c3cn(C)c(=O)c4cc(F)ccc34)c1)OC(C1CC1)C2]
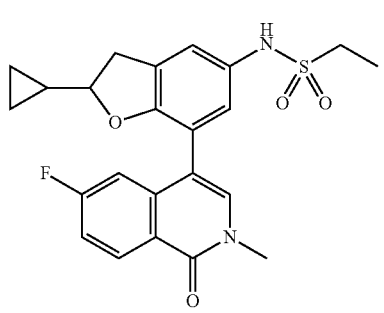 [SMILES: CCS(=O)(=O)Nc1cc2c(c(-c3cn(C)c(=O)c4ccc(F)cc34)c1)OC(C1CC1)C2]
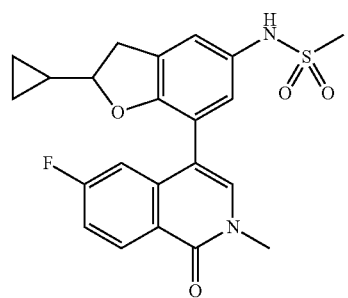 [SMILES: Cn1cc(-c2cc(NS(C)(=O)=O)cc3c2OC(C2CC2)C3)c2cc(F)ccc2c1=O]
TABLE 2-continued
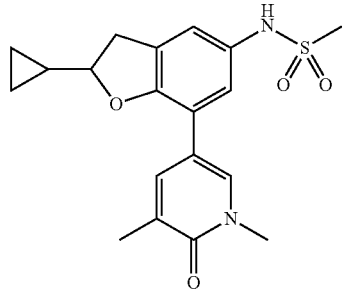 [SMILES: Cc1cc(-c2cc(NS(C)(=O)=O)cc3c2OC(C2CC2)C3)cn(C)c1=O]
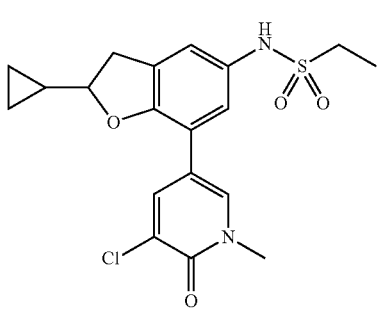 [SMILES: CCS(=O)(=O)Nc1cc2c(c(-c3cc(Cl)c(=O)n(C)c3)c1)OC(C1CC1)C2]
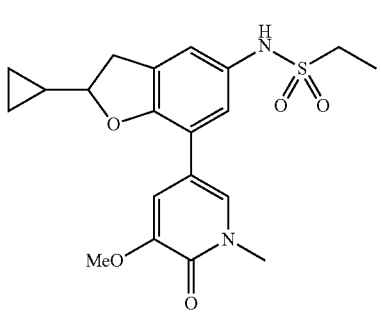 [SMILES: CCS(=O)(=O)Nc1cc2c(c(-c3cc(OC)c(=O)n(C)c3)c1)OC(C1CC1)C2]
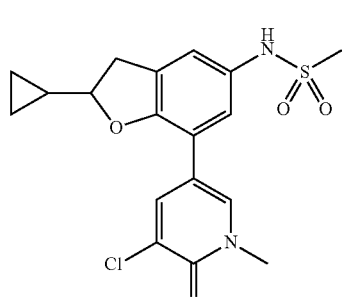
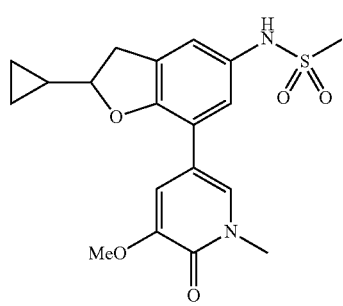 [SMILES: COc1cc(-c2cc(NS(C)(=O)=O)cc3c2OC(C2CC2)C3)cn(C)c1=O]

TABLE 2-continued

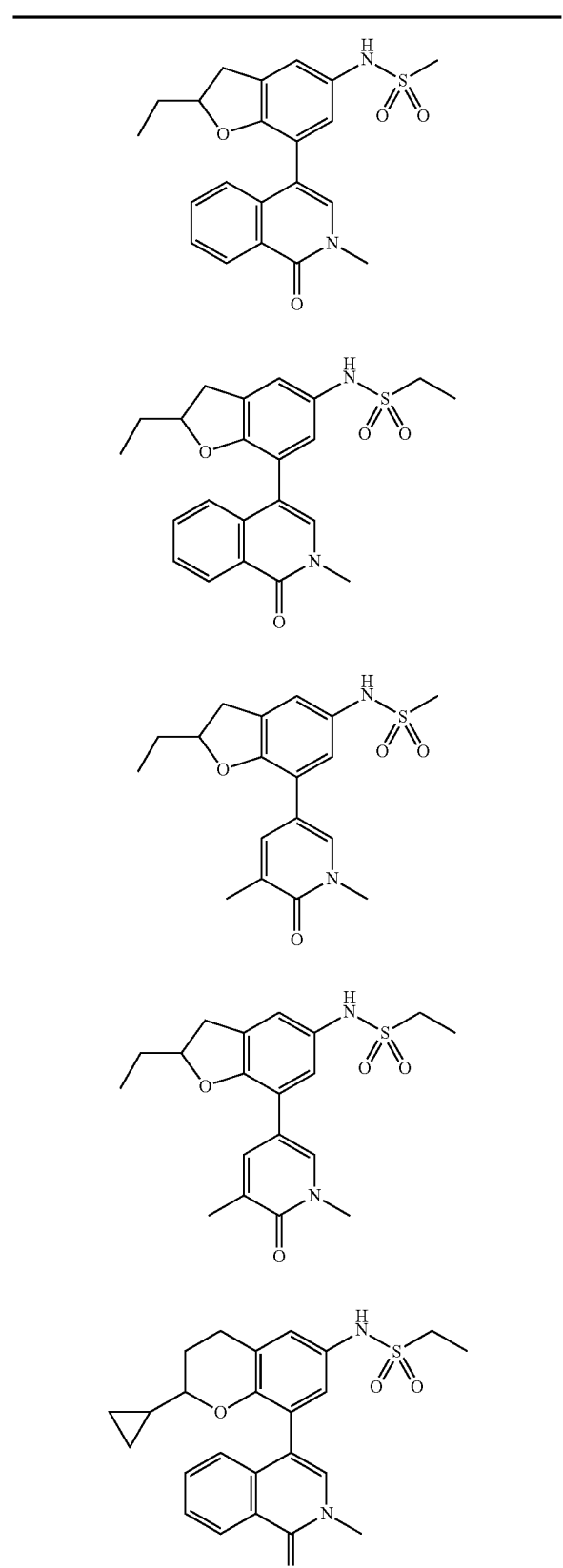

TABLE 2-continued

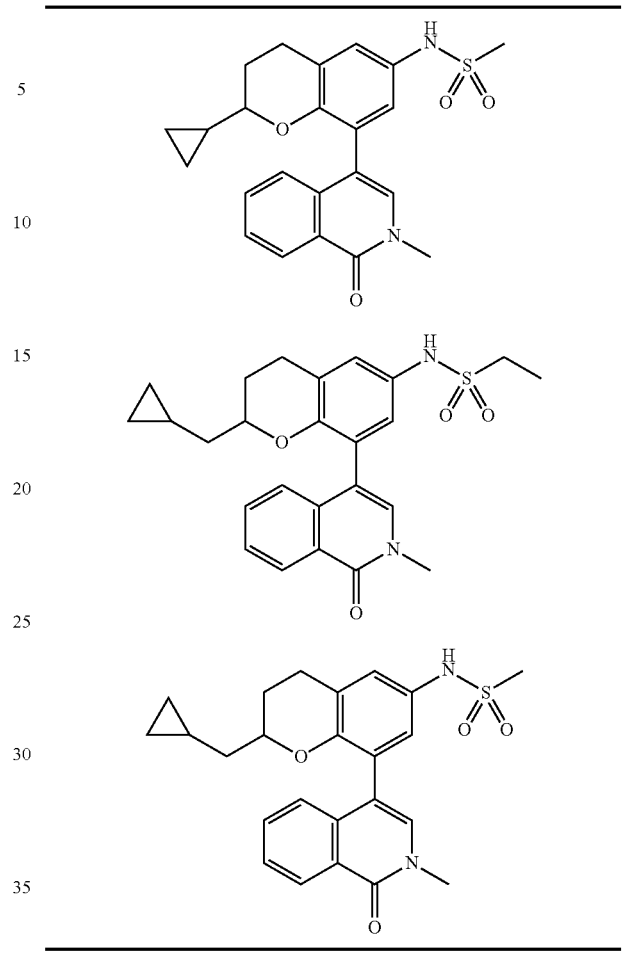

Preparation of the Substituted Heterocyclic Derivative Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen A G (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Methods known to one of ordinary skill in the art are identified through various reference books and databases. Suitable reference books and treatise that detail the synthesis of reactants useful in the preparation of compounds described herein, or provide references to articles that describe the preparation include, for example, SYNTHETIC ORGANIC CHEMISTRY, John Wiley & Sons, Inc., New York; Sandler et al., ORGANIC FUNCTIONAL GROUP PREPARATIONS, 2nd Ed., Academic Press, New York, 1983; House, MODERN SYNTHETIC REACTIONS, 2nd Ed., Benjamin, Inc. Menlo Park, Calif. 1972; Gilchrist, HETEROCYCLIC CHEMISTRY, 2nd Ed., John Wiley & Sons, New York, 1992; March, ADVANCED ORGANIC CHEMISTRY: REACTIONS, MECHANISMS & STRUCTURE, 4th Ed., Wiley-Interscience, New York, 1992. Additional suitable reference books and treatise that detail the synthesis of reactants useful in the preparation of compounds described herein, or provide references to articles that describe the preparation, include, for example, Fuhrhop and Penzlin, ORGANIC SYNTHESIS: CONCEPTS, METHODS, STARTING MATERIALS, SECOND, REVISED & ENLARGED EDITION (1994) John Wiley & Sons ISBN: 3-527-29074-5; Hoffman, ORGANIC CHEMISTRY, AN INTERMEDIATE TEXT (1996) Oxford University Press, ISBN 0-19-509618-5; Larock, COMPREHENSIVE ORGANIC TRANSFORMATIONS: A GUIDE TO FUNCTIONAL GROUP PREPARATIONS, 2nd Edition (1999) Wiley-VCH, ISBN: 0-471-19031-4; Otera (editor) MODERN CARBONYL CHEMISTRY (2000) Wiley-VCH, ISBN: 3-527-29871-1; Patai, PATAI'S 1992 GUIDE TO THE CHEMISTRY OF FUNCTIONAL GROUPS (1992) Interscience ISBN: 0-471-93022-9; Solomons, ORGANIC CHEMISTRY, 7TH EDITION (2000) John Wiley & Sons, ISBN: 0-471-19095-0; Stowell, INTERMEDIATE ORGANIC CHEMISTRY, 2nd Edition (1993) Wiley-Interscience, ISBN: 0-471-57456-2; INDUSTRIAL ORGANIC CHEMICALS: STARTING MATERIALS & INTERMEDIATES: AN ULLMANN'S ENCYCLOPEDIA (1999) John Wiley & Sons, ISBN: 3-527-29645-X, in 8 volumes; ORGANIC REACTIONS (1942-2000) John Wiley & Sons, in over 55 volumes; and CHEMISTRY OF FUNCTIONAL GROUPS, John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the substituted heterocyclic derivative compounds described herein is Stahl & Wermuth, HANDBOOK OF PHARMACEUTICAL SALTS, Verlag Helvetica Chimica Acta, Zurich, 2002.

General methods for the synthesis of substituted heterocyclic derivatives are provided in, but not limited to, the following references: WO 2009/158396; WO 2005/63768; WO 2006/112666; Briet et. al., Tetrahedron (2002), 58(29): 5761; WO 2008/77550; WO 2008/77551; WO 2008/77556; WO 2007/12421; WO 2007/12422; US 200799911; WO 2008/77550; Havera et al., J. Med. Chem. (1999), 42:3860; WO 2004/29051; and US 20090054434. Additional examples of the synthesis of substituted heterocyclic derivatives are found in the following references: WO 2012/171337; WO 2011/044157; WO 2009/097567; WO 2005/030791; EP 203216; Becknell et al., Bioorganic & Medicinal Chem. Letters (2011), 21(23):7076; Svechkarev et al., Visnik Kharkivs'kogo Natsional'nogo Universitetu im. V. N. Karazina (2007), 770:201; Coskun et al., Synthetic Communications (2005), 35(18):2435; Alvarez et al., Sci. Synth. (2005), 15, 839; Kihara et al., Heterocycles (2000), 53(2):359; Couture et al., J. Chem. Society, Perkin Transactions 1: Org. & Bio-Org. Chem. (1999), (7):789; Kihara et al., Heterocycles (1998), 48(12):2473; Couture et al., Tetrahedron (1996), 52(12), 4433; Couturre et al., Tetrahedron Letters (1996), 37(21):3697; Natsugari et al., J. Med. Chem. (1995), 38(16):3106; Moehrle et al., Archiv der Pharmazie (Weinheim, Germany) (1988), 321(10):759; Gore et al., J. Chem. Society, Perkin Transactions 1: Org. & Bio-Org. Chem. (1972-1999) (1988), (3):481; Narasimhan et al., J. Chem. Society, Chem. Communc'n (1987), (3):191; Henry et al., J. Org. Chem. (1975), 40(12):1760; Berti, Gazzetta Chimica Italiana (1960), 90:559; Berti et al., Annali di Chimica (Rome, Italy) (1959), 49:2110; Berti et al., Annali di Chimica (Rome, Italy) (1959), 49:1253; WO 2012/000595; Couture et al., Tetrahedron (1996), 52(12):4433; WO 2010/069504; WO 2010/069504; WO 2006/030032; WO 2005/095384; US20050222159; WO 2013/064984; Mishra et al., Eur. J. Org. Chem. (2013), 2013(4):693; Vachhani et al., Tetrahedron (2013), 69(1):359; Xie et al., European J. Med. Chem. (2010), 45(1):210; Mukaiyama et al., Bioorganic & Med. Chem. (2007), 15(2):868; JP2005/089352; Wang et al., Molecules (2004), 9(7):574; WO 2000/023487; US2006/0287341; CN103183675; Hares et al., Egyptian J. Pharm. Sci. (1991), 32(1-2): 303; DE2356005; DE2133898; DE2133998; U.S. Pat. No. 3,816, 422; DE2011970; and Staehle et al., Justus Liebigs Annalen der Chemie (1973), (8):1275.

In some embodiments, the substituted heterocyclic derivative compounds disclosed herein are prepared by the general synthetic routes described below in Schemes 1-6. These schemes are intended to exemplary to one of skill in the art and are not limiting. Additional methods for the synthesis of the substituted heterocyclic derivative compounds disclosed herein are readily available to one of skill in the art.

Scheme 1

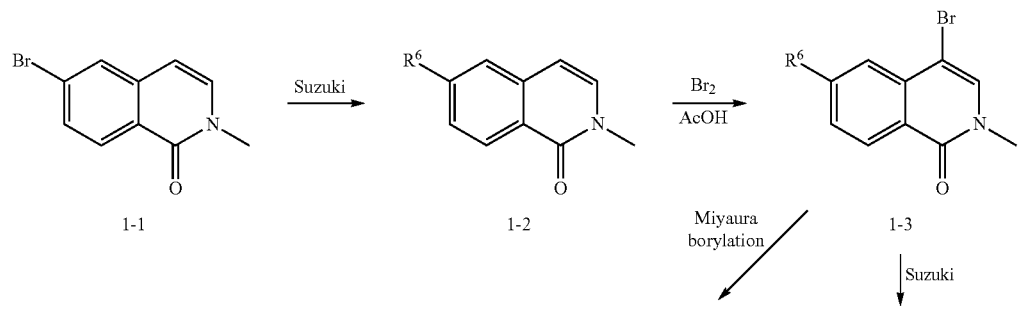

-continued

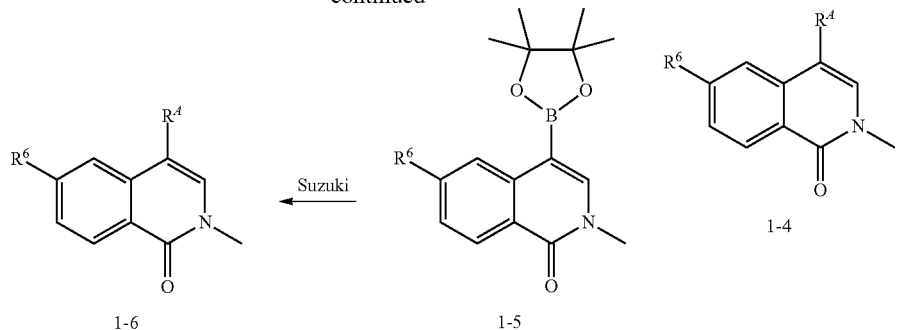

A method for preparing compounds of Formula (I) is provided in Scheme 1, above. 6-Bromo-2-methylisoquinolin-1(2H)-one (1-1) is subjected to a palladium-catalyzed cross coupling reaction to provide isoquinolinone 1-2. Bromination under acidic conditions provides compound 1-3. Further palladium-catalyzed cross coupling reaction with a boronic acid, or ester, provides the isoquinolinone 1-4. Alternatively, palladium-catalyzed cross coupling of compound 1-3 with 4,4,5,5-tetramethyl-2-(tetramethyl-1,3,2-dioxaborolan-2-yl)-1,3,2-dioxaborolane under the conditions described by Miyaura (Ishiyama et al., J. Org. Chem. 1995, 60, 7508-7510) provides the boron ester 1-5. Further palladium-catalyzed cross coupling reaction of compound 1-5 with a suitable halide provides the isoquinolinone 1-6.

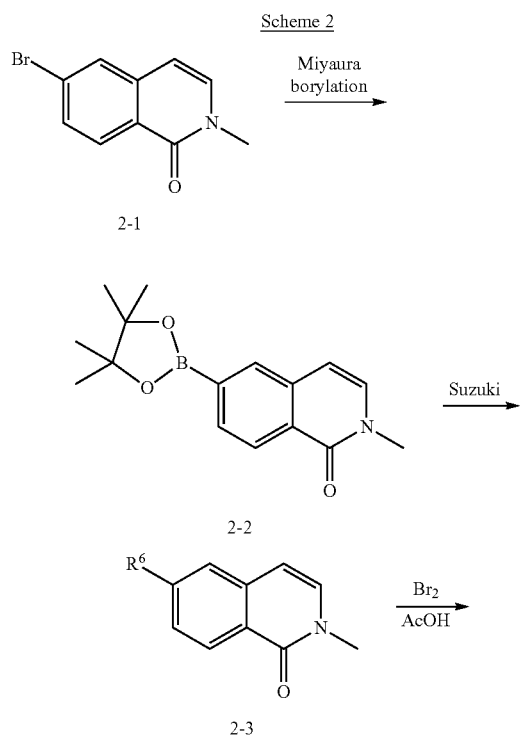

-continued

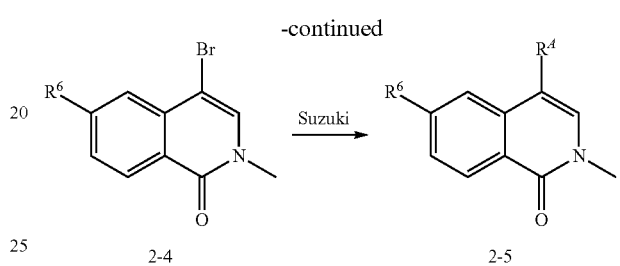

A method for preparing compounds of Formula (I) is provided in Scheme 2, above. 6-Bromo-2-methylisoquinolin-1(2H)-one (2-1) is subjected to a palladium-catalyzed cross coupling reaction with 4,4,5,5-tetramethyl-2-(tetramethyl-1,3,2-dioxaborolan-2-yl)-1,3,2-dioxaborolane to provide boron ester 2-2. Further palladium-catalyzed cross coupling reaction of compound 2-2 with a suitable halide provides compound 2-3. Bromination under acidic conditions provides compound 2-4. Further palladium-catalyzed cross coupling reaction with a boronic acid, or ester, provides the isoquinolinone 2-5.

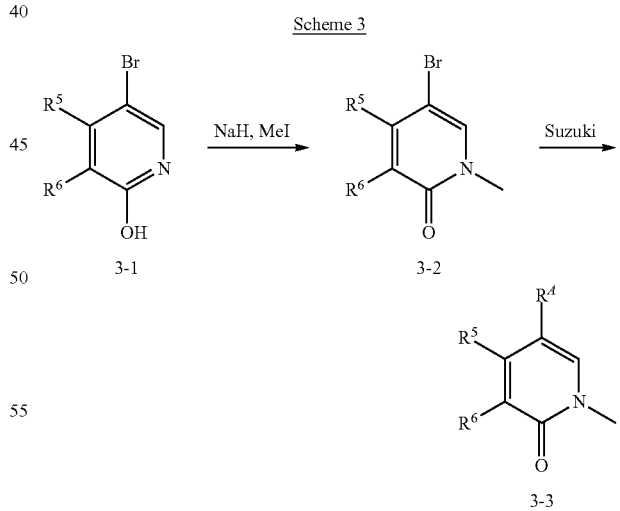

A method for preparing compounds of Formula (II) is provided in Scheme 3, above. 5-Bromopyridin-2-ol derivative (3-1) is subjected to alkylation with methyl iodide under basic conditions to provide the related 5-bromo-1-methylpyridin-2(1H)-one derivative (3-2). Further palladium-catalyzed cross coupling reaction of compound 3-2 with a suitable halide provides compound 3-3.

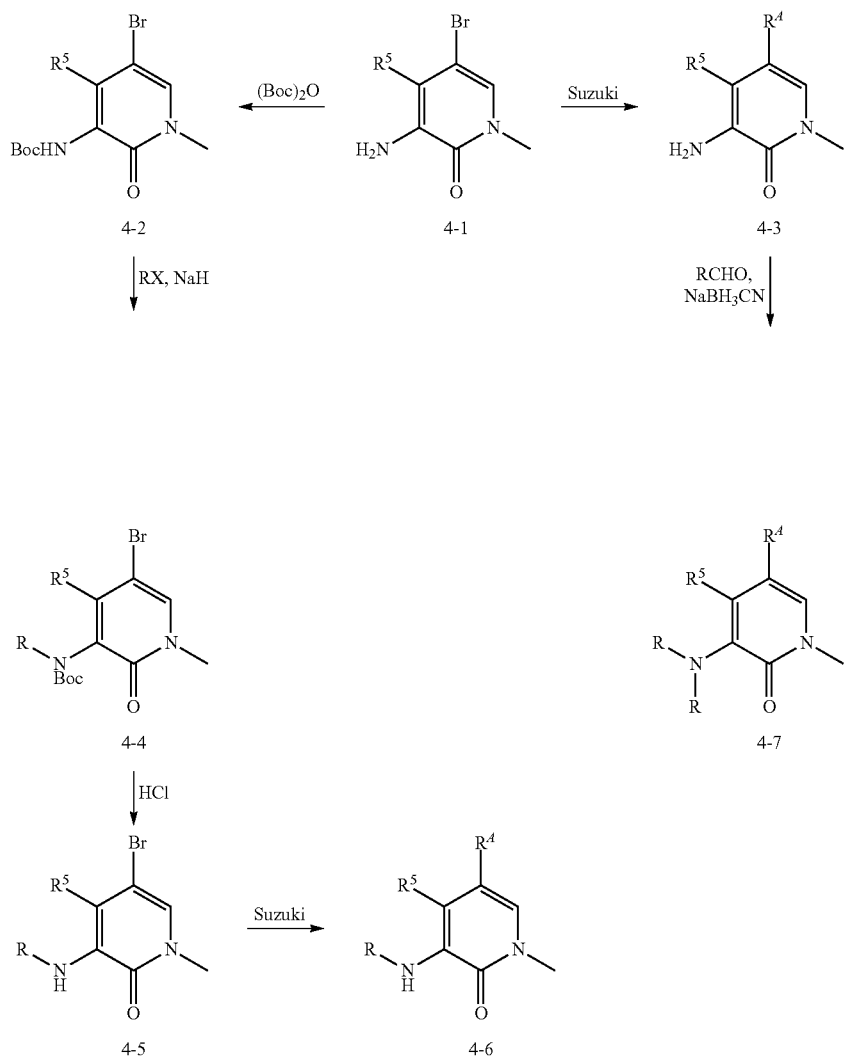

Scheme 4

A method for preparing compounds of Formula (II) is provided in Scheme 4, above. 3-Amino-5-bromo-1-methyl-pyridin-2(1H)-one derivative 4-1 is used as a starting material for several routes. In one route, compound 4-1 is directly subjected to a palladium-catalyzed cross coupling reaction to provide pyridone 4-3. The amino group of compound 4-3 is subjected to a reductive amination with an aldehyde and a reducing agent, such as sodium cyanoborohydride, to provide the substituted amino derivative compound 4-7. A second route involving selective alkylation of the amino group of compound 4-1 begins with protection of the amino group as the BOC carbamate. Alkylation of the carbamate under basic conditions followed by removal of the BOC carbamate under acidic conditions provides the secondary amine compound 4-5. Treatment of 4-5 with a suitable halide under palladium-catalyzed cross coupling conditions affords compound 4-6.

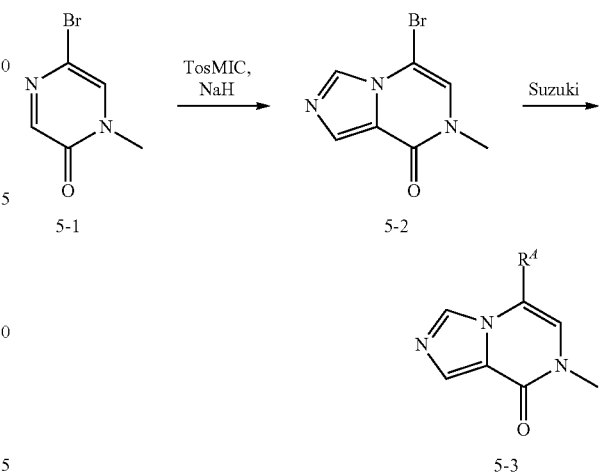

Scheme 5

A method for preparing compounds of Formula (IV) is provided in Scheme 5, above. 5-Bromo-1-methylpyrazin-2 (1H)-one (5-1) is subjected to an imidazole annulation reaction by treatment with tosylmethisocyanide (TosMIC) under basic conditions (Hoogenboom et al., Org. Syntheses, Coll. 6:987 (1988)) to provide 5-bromo-7-methylimidazo[1, 5-a]pyrazin-8(7H)-one (5-2). Palladium-catalyzed cross coupling reaction of compound 5-2 with a suitable halide provides the compound 5-3.

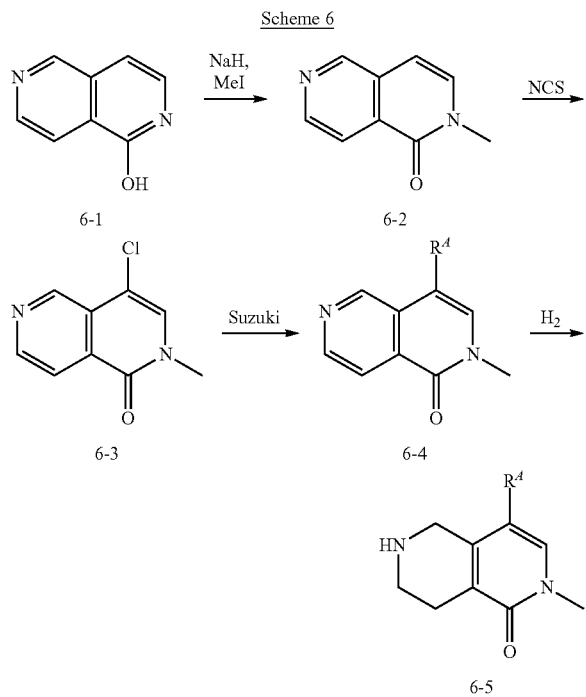

A method for preparing compounds of Formula (III) is provided in Scheme 6, above. 2,6-Naphthyridin-1-ol (6-1) is subjected to alkylation with methyl iodide under basic conditions to provide 2-methyl-2,6-naphthyridin-1(2H)-one (6-2). Chlorination of 6-2 with N-chlorosuccinimide provides chloro compound 6-3. Treatment of 6-3 under palladium-catalyzed cross coupling conditions with a suitable halide provides compound 6-4. Selective reduction of the 2,6-naphthyridinone derivative provides the 5,6,7,8-tetrahydro-2,6-naphthyridin-1(2H)-one derivative 6-5.

In each of the above reaction procedures or schemes, the various substituents may be selected from among the various substituents otherwise taught herein.

Pharmaceutical Compositions

In certain embodiments, the substituted heterocyclic derivative compound as described herein is administered as a pure chemical. In other embodiments, the substituted heterocyclic derivative compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in REMINGTON: SCIENCE & PRACTICE OF PHARMACY (Gennaro, 21st Ed. Mack Pub. Co., Easton, Pa. (2005)).

Accordingly, provided herein is a pharmaceutical composition comprising at least one substituted heterocyclic derivative compound, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a compound of Formula (I), (Ia), or (Ib), or a pharmaceutically acceptable salt thereof, and a pharmaceutically acceptable excipient. One embodiment provides a pharmaceutical composition comprising a compound of Formula (II), (IIa), or (IIb), or a pharmaceutically acceptable salt thereof, and a pharmaceutically acceptable excipient. One embodiment provides a pharmaceutical composition comprising a compound of Formula (III), or (IIIa), or a pharmaceutically acceptable salt thereof, and a pharmaceutically acceptable excipient. One embodiment provides a pharmaceutical composition comprising a compound of Formula (IV), or a pharmaceutically acceptable salt thereof, and a pharmaceutically acceptable excipient. One embodiment provides a pharmaceutical composition comprising a compound of Formula (V), or a pharmaceutically acceptable salt thereof, and a pharmaceutically acceptable excipient. One embodiment provides a pharmaceutical composition comprising a compound of Formula (VIa), (VIb), (VIc), (VId), or (VIe), or a pharmaceutically acceptable salt thereof, and a pharmaceutically acceptable excipient. One embodiment provides a pharmaceutical composition comprising a compound of Formula (VII) or (VIIa), or a pharmaceutically acceptable salt thereof, and a pharmaceutically acceptable excipient. One embodiment provides a pharmaceutical composition comprising a compound of Formula (VIII) or (VIIIa), or a pharmaceutically acceptable salt thereof, and a pharmaceutically acceptable excipient. One embodiment provides a pharmaceutical composition comprising a compound of Formula (IX), or a pharmaceutically acceptable salt thereof, and a pharmaceutically acceptable excipient. One embodiment provides a pharmaceutical composition comprising a compound of Formula (XII), or a pharmaceutically acceptable salt thereof, and a pharmaceutically acceptable excipient. One embodiment provides a pharmaceutical composition comprising a compound of Formula (XIII), or a pharmaceutically acceptable salt thereof, and a pharmaceutically acceptable excipient. One embodiment provides a pharmaceutical composition comprising a compound of Formula (XIV), or a pharmaceutically acceptable salt thereof, and a pharmaceutically acceptable excipient. One embodiment provides a pharmaceutical composition comprising a compound of Formula (XV), or a pharmaceutically acceptable salt thereof, and a pharmaceutically acceptable excipient. One embodiment provides a pharmaceutical composition comprising a compound of Formula (XVI), or a pharmaceutically acceptable salt thereof, and a pharmaceutically acceptable excipient. One embodiment provides a pharmaceutical composition comprising a compound of Formula (XVII), or a pharmaceutically acceptable salt thereof, and a pharmaceutically acceptable excipient. One embodiment provides a pharmaceutical composition comprising a compound of Formula (XVIII), or a pharmaceutically acceptable salt thereof, and a pharmaceutically acceptable excipient. One embodiment provides a pharmaceutical composition comprising a compound of Formula (XIX), or a pharmaceutically acceptable salt thereof, and a pharmaceutically acceptable excipient. One embodiment provides a pharmaceutical composition comprising a compound of Formula (XX), or a pharmaceutically acceptable salt thereof, and a pharmaceutically acceptable excipient. One embodiment provides a pharmaceutical composition comprising a compound of Formula (XXI), or a pharmaceutically acceptable salt thereof, and a pharmaceutically acceptable excipient. One embodiment provides a pharmaceutical composition comprising a compound of Formula (XXII), or a pharmaceutically acceptable salt thereof, and a pharmaceutically acceptable excipient. One embodiment provides a pharmaceutical composition comprising a compound of Formula (XXIII), or a pharmaceutically acceptable salt thereof, and a pharmaceutically acceptable excipient. One embodiment provides a pharmaceutical composition comprising a compound of Formula (XXIV), or a pharmaceutically acceptable salt thereof, and a pharmaceutically acceptable excipient. One embodiment provides a pharmaceutical composition comprising a compound of Formula (XXV), or a pharmaceutically acceptable salt thereof, and a pharmaceutically acceptable excipient.

In certain embodiments, the substituted heterocyclic derivative compound as described herein is substantially pure, in that it contains less than about 5%, or less than about 1%, or less than about 0.1%, of other organic small molecules, such as contaminating intermediates or by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. Suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. See, e.g., REMINGTON: SCIENCE & PRACTICE OF PHARMACY (21st Ed., Gennaro, ed., Mack Pub. Co., Easton, Pa. (2005).

The dose of the composition comprising at least one substituted heterocyclic derivative compound as described herein may differ, depending upon the patient's (e.g., human) condition, that is, stage of the disease, general health status, age, and other factors that a person skilled in the medical art will use to determine dose.

Pharmaceutical compositions may be administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses may generally be determined using experimental models and/or clinical trials. The optimal dose may depend upon the body mass, weight, or blood volume of the patient.

Oral doses typically range from about 1.0 mg to about 1000 mg, one to four times, or more, per day.

Bromodomain Inhibition

Chromatin is the complex of DNA and protein that makes up chromosomes. Histones are the major protein component of chromatin, acting as spools around which DNA winds. Changes in chromatin structure are affected by covalent modifications of histone proteins and by non-histone binding proteins. Several classes of enzymes are known which modify histones at various sites. Epigenetics is the study of heritable changes in gene expression caused by mechanisms other than the underlying DNA sequence. Molecular mechanisms that play a role in epigenetic regulation include DNA methylation and chromatin/histone modifications.

The genomes of eukaryotic organisms are highly organized within the nucleus of the cell. Tremendous compaction is required to package the 3 billion nucleotides of the human genome into the nucleus of a cell.

Histones are the chief protein components of chromatin. There are a total of six classes of histones (H1, H2A, H2B, H3, H4, and H5) organized into two classes: core histones (H2A, H2B, H3, and H4) and linker histones (H1 and H5). The basic unit of chromatin is the nucleosome, which consists of about 147 base pairs of DNA wrapped around the core histone octamer, consisting of two copies each of the core histones H2A, H2B, H3, and H4.

Basic nucleosome units are then further organized and condensed by the aggregation and folding of nucleosomes to form a highly condensed chromatin structure. A range of different states of condensation are possible, and the tightness of chromatin structure varies during the cell cycle, being most compact during the process of cell division.

Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications include acetylation, methylation, phosphorylation, ribosylation sumoylation, ubiquitination, citrullination, deimination, and biotinylation. The core of histones H2A and H3 can also be modified. Histone modifications are integral to diverse biological processes such as gene regulation, DNA repair, and chromosome condensation.

Histone Acetylation and Bromodomains

Histone acetylation is generally associated with the activation of gene transcription, as the modification is known to loosen the interaction of the DNA and the histone octamer by changing the electrostatics. In addition to this physical change, specific proteins are known to bind to acetylated lysine residues within histones in order to read the epigenetic code. Bromodomains are small (~110 amino acid) distinct domains within proteins that are known to bind to acetylated lysine residues commonly, but not exclusively, in the context of histones. Around 50 proteins are known to contain bromodomains, and they have a range of functions within the cell.

The BET family of bromodomain containing proteins comprises 4 proteins (BRD2, BRD3, BRD4 and BRD-t) which contain tandem bromodomains capable of binding to two acetylated lysine resides in close proximity, increasing the specificity of the interaction.

Bromodomain-containing proteins that recognize acetylated lysines on histones (such as BET proteins and non-BET proteins) have been implicated in proliferative disease. BRD4 knockout mice die shortly after implantation and are compromised in their ability to maintain an inner cell mass, and heterozygotes display pre- and postnatal growth defects associated with reduced proliferation rates. BRD4 regulates genes expressed during M/G1, including growth-associated genes, and remains bound to chromatin throughout the cell cycle (Dey et al. (2009) Mol. Biol. Cell 20:4899). BRD4 also physically associates with Mediator and P-TEFb (CDK9/cyclin T1) to facilitate transcriptional elongation (Yang et al. (2005) Oncogene 24:1653; Yang, et al. (2005)

Mol. Cell 19:535). CDK9 is a validated target in chronic lymphocytic leukemia (CLL), and is linked to c-Myc-dependent transcription (Phelps et al. Blood 113:2637; Rahl et al. (2010) Cell 141:432).

BRD4 is translocated to the NUT protein in patients with lethal midline carcinoma, an aggressive form of human squamous carcinoma. French, et al. (2001) Am. J. Pathol. 159:1987; French et al. (2003) Cancer Res. 63:304. In vitro analysis with RNAi supports a causal role for BRD4 in this recurrent t(15; 19) chromosomal translocation. Also, inhibition of the BRD4 bromodomains has been found to result in growth arrest/differentiation of BRD4-NUT cell lines in vitro and in vivo (Filippakopoulos et al., *Selective Inhibition of BET Bromodomains*, Nature (published online Sep. 24, 2010)).

Bromodomain-containing proteins (such as BET proteins) have also been implicated in inflammatory diseases. BET proteins (e.g., BRD2, BRD3, BRD4, and BRDT) regulate assembly of histone acetylation-dependent chromatin complexes that control inflammatory gene expression. Hargreaves et al. (2009) Cell 138:129; LeRoy et al. (2008) Mol. Cell 30:51; Jang, et al. (2005) Mol. Cell 19:523; Yang, et al. (2005) Mol. Cell 19:535. Key inflammatory genes (secondary response genes) are down-regulated upon bromodomain inhibition of the BET subfamily, and non-responsive genes (primary response genes) are poised for transcription. BET bromodomain inhibition protects against LPS-induced endotoxic shock and bacteria-induced sepsis in vivo (Nicodeme et al., *Suppression of Inflammation by a Synthetic Histone Mimic*, Nature (published online Nov. 10, 2010)).

Bromodomain-containing proteins (such as BET proteins) have also been found to play a role in viral infection. For example, BRD4 is implicated in the primary phase of human papilloma virus (HPV) infection, in which the viral genome is maintained in an extra-chromosomal episome in basal epithelia. In some strains of HPV, BRD4 binding to the HPV E2 protein functions to tether the viral genome to chromosomes. E2 is critical for both the repression of E6/E7 and the activation of HPV viral genes. Disruption of BRD4 or the BRD4-E2 interaction blocks E2-dependent gene activation. BRD4 also functions to tether other classes of viral genomes to host chromatin (e.g., Herpes virus, Epstein-Barr virus).

Bromodomain-containing proteins has also been found to bind to acetylated lysine residues on proteins other than histones. For example, the bromodomain of CREB binding protein transcriptional coactivator (CBP) allows for recognition of p53 with acetylated Lys382. The interaction between the bromodomain and acetyl-p53 follows DNA damage and promotes p53-induced transcriptional activation of the CDK inhibitor p21 and cell cycle arrest. Another novel bromodomain-containing protein is BAZ2B, whose biological function, is believed to function similarly to ACF1, the *Drosophila* BAZ2B ortholog. ACF complexes play roles in establishing regular nucleosome spacing during chromatin assembly and influencing different remodeling outcomes at target loci.

One embodiment provides a method of regulating gene transcription in a cell comprising exposing a bromodomain containing protein to a compound of Formula (I), (Ia), or (Ib). One embodiment provides a method of regulating gene transcription in a cell comprising exposing a bromodomain containing protein to a compound of Formula (II), (IIa), or (IIb). One embodiment provides a method of regulating gene transcription in a cell comprising exposing a bromodomain containing protein to a compound of Formula (III), or (IIIa). One embodiment provides a method of regulating gene transcription in a cell comprising exposing a bromodomain containing protein to a compound of Formula (IV). One embodiment provides a method of regulating gene transcription in a cell comprising exposing a bromodomain containing protein to a compound of Formula (V). One embodiment provides a method of regulating gene transcription in a cell comprising exposing a bromodomain containing protein to a compound of Formula (VIa), (VIb), (VIc), (VId), or (VIe). One embodiment provides a method of regulating gene transcription in a cell comprising exposing a bromodomain containing protein to a compound of Formula (VII) or (VIIa). One embodiment provides a method of regulating gene transcription in a cell comprising exposing a bromodomain containing protein to a compound of Formula (VIII), or (VIIIa). One embodiment provides a method of regulating gene transcription in a cell comprising exposing a bromodomain containing protein to a compound of Formula (IX). One embodiment provides a method of regulating gene transcription in a cell comprising exposing a bromodomain containing protein to a compound of Formula (XII). One embodiment provides a method of regulating gene transcription in a cell comprising exposing a bromodomain containing protein to a compound of Formula (XIII). One embodiment provides a method of regulating gene transcription in a cell comprising exposing a bromodomain containing protein to a compound of Formula (XIV). One embodiment provides a method of regulating gene transcription in a cell comprising exposing a bromodomain containing protein to a compound of Formula (XV). One embodiment provides a method of regulating gene transcription in a cell comprising exposing a bromodomain containing protein to a compound of Formula (XVI). One embodiment provides a method of regulating gene transcription in a cell comprising exposing a bromodomain containing protein to a compound of Formula (XVII). One embodiment provides a method of regulating gene transcription in a cell comprising exposing a bromodomain containing protein to a compound of Formula (XVIII). One embodiment provides a method of regulating gene transcription in a cell comprising exposing a bromodomain containing protein to a compound of Formula (XIX). One embodiment provides a method of regulating gene transcription in a cell comprising exposing a bromodomain containing protein to a compound of Formula (XX). One embodiment provides a method of regulating gene transcription in a cell comprising exposing a bromodomain containing protein to a compound of Formula (XXI). One embodiment provides a method of regulating gene transcription in a cell comprising exposing a bromodomain containing protein to a compound of Formula (XXII). One embodiment provides a method of regulating gene transcription in a cell comprising exposing a bromodomain containing protein to a compound of Formula (XXIII). One embodiment provides a method of regulating gene transcription in a cell comprising exposing a bromodomain containing protein to a compound of Formula (XXIV). One embodiment provides a method of regulating gene transcription in a cell comprising exposing a bromodomain containing protein to a compound of Formula (XXV).

One embodiment provides a method of inhibiting bromodomain-mediated recognition of an acetyl lysine region of a protein comprising exposing the bromodomain to a compound of Formula (I), (Ia), or (Ib). One embodiment provides a method of inhibiting bromodomain-mediated recognition of an acetyl lysine region of a protein comprising exposing the bromodomain to a compound of Formula (II), (IIa), or (IIb). One embodiment provides a method of inhibiting bromodomain-mediated recognition of an acetyl lysine region of a protein comprising exposing the bromodomain to a compound of Formula (III) or (IIIa). One embodiment provides a method of inhibiting bromodomain-mediated recognition of an acetyl lysine region of a protein comprising exposing the bromodomain to a compound of Formula (IV). One embodiment provides a method of inhibiting bromodomain-mediated recognition of an acetyl lysine region of a protein comprising exposing the bromodomain to a compound of Formula (V). One embodiment provides a method of inhibiting bromodomain-mediated recognition of an acetyl lysine region of a protein comprising exposing the bromodomain to a compound of Formula (VIa), (VIb), (VIc), (VId), or (VIe). One embodiment provides a method of inhibiting bromodomain-mediated recognition of an acetyl lysine region of a protein comprising exposing the bromodomain to a compound of Formula (VII) or (VIIa). One embodiment provides a method of inhibiting bromodomain-mediated recognition of an acetyl lysine region of a protein comprising exposing the bromodomain to a compound of Formula (VIII), or (VIIIa). One embodiment provides a method of inhibiting bromodomain-mediated recognition of an acetyl lysine region of a protein comprising exposing the bromodomain to a compound of Formula (IX). One embodiment provides a method of inhibiting bromodomain-mediated recognition of an acetyl lysine region of a protein comprising exposing the bromodomain to a compound of Formula (XII). One embodiment provides a method of inhibiting bromodomain-mediated recognition of an acetyl lysine region of a protein comprising exposing the bromodomain to a compound of Formula (XIII) One embodiment provides a method of inhibiting bromodomain-mediated recognition of an acetyl lysine region of a protein comprising exposing the bromodomain to a compound of Formula (XIV). One embodiment provides a method of inhibiting bromodomain-mediated recognition of an acetyl lysine region of a protein comprising exposing the bromodomain to a compound of Formula (XV). One embodiment provides a method of inhibiting bromodomain-mediated recognition of an acetyl lysine region of a protein comprising exposing the bromodomain to a compound of Formula (XVI). One embodiment provides a method of inhibiting bromodomain-mediated recognition of an acetyl lysine region of a protein comprising exposing the bromodomain to a compound of Formula (XVII). One embodiment provides a method of inhibiting bromodomain-mediated recognition of an acetyl lysine region of a protein comprising exposing the bromodomain to a compound of Formula (XVIII). One embodiment provides a method of inhibiting bromo-domain-mediated recognition of an acetyl lysine region of a protein comprising exposing the bromodomain to a compound of Formula (XIX). One embodiment provides a method of inhibiting bromodomain-mediated recognition of an acetyl lysine region of a protein comprising exposing the bromodomain to a compound of Formula (XX). One embodiment provides a method of inhibiting bromodomain-mediated recognition of an acetyl lysine region of a protein comprising exposing the bromodomain to a compound of Formula (XXI). One embodiment provides a method of inhibiting bromodomain-mediated recognition of an acetyl lysine region of a protein comprising exposing the bromodomain to a compound of Formula (XXII). One embodiment provides a method of inhibiting bromodomain-mediated recognition of an acetyl lysine region of a protein comprising exposing the bromodomain to a compound of Formula (XXIII) One embodiment provides a method of inhibiting bromodomain-mediated recognition of an acetyl lysine region of a protein comprising exposing the bromodomain to a compound of Formula (XXIV). One embodiment provides a method of inhibiting bromodomain-mediated recognition of an acetyl lysine region of a protein comprising exposing the bromodomain to a compound of Formula (XXV).

One embodiment provides a method of regulating gene transcription in a cell comprising exposing a bromodomain-containing protein to a compound of Formula (X), or a pharmaceutically acceptable salt thereof,

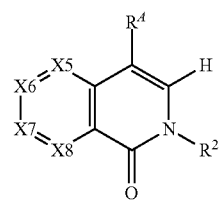

Formula (X)

wherein, $R^2$ is selected from $CH_3$, $CH_2CH_3$, $CH_2CF_3$, $CH_2F$, $CHF_2$, $CF_3$, $CH_2D$, $CHD_2$, or $CD_3$;

X5 is C—$R^5$ or N;

X6 is C—$R^6$ or N;

X7 is C—$R^7$ or N;

X8 is C—$R^8$ or N; wherein no more than two of X5, X6, X7, or X8 may be N;

$R^5$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^6$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^7$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^8$ is hydrogen, halogen, or alkyl; and $R^4$ is an aryl group or a heteroaryl group.

Another embodiment provides the method of regulating gene transcription in a cell, wherein the compound of Formula (X) has the structure wherein $R^4$ is a substituted phenyl group.

Another embodiment provides a method of inhibiting of bromodomain-mediated recognition of an acetyl lysine region of a protein comprising exposing the bromodomain to a compound of Formula (X). Another embodiment provides the method of inhibiting of bromodomain-mediated recognition of an acetyl lysine region of a protein, wherein the compound of Formula (X) has the structure wherein $R^4$ is a substituted phenyl group.

One embodiment provides a method of regulating gene transcription in a cell comprising exposing a bromodomain-containing protein to a compound of Formula (XI), or a pharmaceutically acceptable salt thereof, Formula (XI)

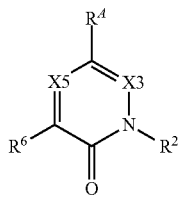

wherein,
R² is CH₃, CH₂CH₃, CH₂CF₃, CH₂F, CHF₂, CF₃, CH₂D, CHD₂, or CD₃;
X3 is C—H or N;
X5 is C—R⁵ or N; provided that if X3 is N, then X5 is C—R⁵, and if X5 is N, then X3 is CH;
R⁵ is hydrogen, halogen, —OH, —CN, —OR⁶¹, —NHR⁶¹, —N(R⁶¹)₂, alkyl, cycloalkyl, cycloalkylalkyl, aryl, aralkyl, heterocyclyl, heterocyclylalkyl, heteroaryl, or heteroarylalkyl, wherein each R⁶¹ is independently selected from alkyl, cycloalkyl, cycloalkylalkyl, aryl, aralkyl, heterocyclyl, heterocyclylalkyl, heteroaryl, or heteroarylalkyl;
R⁶ is hydrogen, halogen, —OH, —CN, alkyl, cycloalkyl, cycloalkylalkyl, amino, alkylamino, dialkylamino, cycloalkylalkylamino, alkoxy, or cycloalkylalkoxy; and R⁴ is an aryl group or a heteroaryl group.

Another embodiment provides the method of regulating gene transcription in a cell, wherein the compound of Formula (XI) has the structure wherein RA is a substituted phenyl group.

Another embodiment provides a method of inhibiting of bromodomain-mediated recognition of an acetyl lysine region of a protein comprising exposing the bromodomain to a compound of Formula (XI). Another embodiment provides the method of inhibiting of bromodomain-mediated recognition of an acetyl lysine region of a protein, wherein the compound of Formula (XI) has the structure wherein RA is a substituted phenyl group.

Methods of Treatment

Compounds and compositions described herein are generally useful for the inhibition of activity of one or more proteins involved in epigenetic regulation. Thus, one embodiment provides a method of modulating epigenetic regulation mediated by one or more proteins containing acetyl-lysine recognition motifs, also known as bromodomains (e.g., BET proteins, such as BRD2, BRD3, BRD4, and/or BRDT, and non-BET proteins, such as CBP, ATAD2A, GCN5L, BAZ2B, FALZ, TAF1, and/or BRPF1), by administering a substituted heterocyclic derivative compound as described herein.

In some embodiments, the substituted heterocyclic derivative compounds as described herein are capable of inhibiting the activity of a bromodomain-containing protein, such as a BET protein (BRD2, BRD3, BRD4 and/or BRDT), non-BET proteins (such as CBP, ATAD2A, GCN5L, BAZ2B, FALZ, TAF1, and/or BRPF1) or a mutant thereof, in a biological sample in manner useful for a variety of purposes that are known to one of skill in the art. Examples of such purposes include, but are not limited to, blood transfusion, organ-transplantation, biological specimen storage, and biological assays.

In some embodiments is provided a method of inhibiting the activity of a bromodomain-containing protein, such as a BET protein (BRD2, BRD3, BRD4 and/or BRDT), non-BET proteins (such as CBP, ATAD2A, GCN5L, BAZ2B, FALZ, TAF1, and/or BRPF1) or a mutant thereof, in a patient comprising the step of administering to said patient a substituted heterocyclic derivative compound as described herein, or a composition comprising said compound.

In some embodiments is provided a method of inhibiting the activity of a bromodomain-containing protein, such as a BET protein (BRD2, BRD3, BRD4 and/or BRDT), non-BET proteins (such as CBP, ATAD2A, GCN5L, BAZ2B, FALZ, TAF1, and/or BRPF1) or a mutant thereof, in a biological sample comprising the step of contacting said biological sample with a substituted heterocyclic derivative compound as described herein. In some embodiments, the bromodomain-containing protein is a BET protein. In some embodiments, the BET protein is BRD4.

In some embodiments is provided a method of inhibiting the activity of a bromodomain-containing protein, such as a BET protein (BRD2, BRD3, BRD4 and/or BRDT), non-BET proteins (such as CBP, ATAD2A, GCN5L, BAZ2B, FALZ, TAF1, and/or BRPF1) or a mutant thereof, in a patient in need thereof, comprising the step of administering to said patient a substituted heterocyclic derivative compound as described herein. In some embodiments, the bromodomain-containing protein is a BET protein. In some embodiments, the BET protein is BRD4.

Diseases and conditions treatable according to the methods of this invention include cancer, neoplastic disease and other proliferative disorders. Thus, one aspect is a method of treating a subject having cancer, a neoplastic disease and other proliferative disorder, the method comprising administration of a substituted heterocyclic derivative compound as described herein to the subject. In one embodiment, a human patient is treated with a substituted heterocyclic derivative compound as described herein and a pharmaceutically acceptable excipient, wherein said compound is present in an amount to measurably inhibit bromodomain-containing protein activity (such as BRD2, BRD3, BRD4, and/or BRDT) in the patient.

The invention further provides a method of treating a subject, such as a human, suffering from cancer, a neoplastic disease and other proliferative disorder. The method comprises administering to a subject in need of such treatment a therapeutically effective amount of one or more substituted heterocyclic derivative compound as described herein, which function by inhibiting a bromodomain and, in general, by modulating gene expression, to induce various cellular effects, in particular induction or repression of gene expression, arresting cell proliferation, inducing cell differentiation and/or inducing apoptosis.

The invention further provides a therapeutic method of modulating protein methylation, gene expression, cell proliferation, cell differentiation and/or apoptosis in vivo in conditions, illnesses, disorders or diseases disclosed herein, in particular cancer, inflammatory disease, and/or viral disease comprising administering to a subject in need of such therapy a pharmacologically active and therapeutically effective amount of one or more substituted heterocyclic derivative compound as described herein.

The invention further provides a method of regulating endogenous or heterologous promoter activity by contacting a cell with a substituted heterocyclic derivative compound as described herein.

The invention further relates to a method for treating or ameliorating cancer, neoplastic disease, or another proliferative disorder by administration of an effective amount of a substituted heterocyclic derivative compound as described herein, to a mammal, in particular a human, in need of such treatment. In some aspects of the invention, the disease to be treated by the methods of the present invention is cancer.

In certain embodiments, the cancer is NUT midline carcinoma, prostate cancer, breast cancer, bladder cancer, lung cancer, or melanoma. In another embodiment the cancer is Burkitts lymphoma.

One embodiment provides a method of treating cancer in a patient in need thereof, comprising administering to the patient a compound of Formula (I), (Ia), or (Ib), or a pharmaceutically acceptable salt thereof. One embodiment provides a method of treating cancer in a patient in need thereof, comprising administering to the patient a compound of Formula (II), (IIa), or (IIb), or a pharmaceutically acceptable salt thereof. One embodiment provides a method of treating cancer in a patient in need thereof, comprising administering to the patient a compound of Formula (III), or (IIIa), or a pharmaceutically acceptable salt thereof. One embodiment provides a method of treating cancer in a patient in need thereof, comprising administering to the patient a compound of Formula (IV), or a pharmaceutically acceptable salt thereof. One embodiment provides a method of treating cancer in a patient in need thereof, comprising administering to the patient a compound of Formula (V), or a pharmaceutically acceptable salt thereof. One embodiment provides a method of treating cancer in a patient in need thereof, comprising administering to the patient a compound of Formula (VIa), (VIb), (VIc), (VId), or (VIe), or a pharmaceutically acceptable salt thereof. One embodiment provides a method of treating cancer in a patient in need thereof, comprising administering to the patient a compound of Formula (VII) or (VIIa), or a pharmaceutically acceptable salt thereof. One embodiment provides a method of treating cancer in a patient in need thereof, comprising administering to the patient a compound of Formula (VIII) or (VIIIa), or a pharmaceutically acceptable salt thereof. One embodiment provides a method of treating cancer in a patient in need thereof, comprising administering to the patient a compound of Formula (IX), or a pharmaceutically acceptable salt thereof. One embodiment provides a method of treating cancer in a patient in need thereof, comprising administering to the patient a compound of Formula (XII), or a pharmaceutically acceptable salt thereof. One embodiment provides a method of treating cancer in a patient in need thereof, comprising administering to the patient a compound of Formula (XIII), or a pharmaceutically acceptable salt thereof. One embodiment provides a method of treating cancer in a patient in need thereof, comprising administering to the patient a compound of Formula (XIV), or a pharmaceutically acceptable salt thereof. One embodiment provides a method of treating cancer in a patient in need thereof, comprising administering to the patient a compound of Formula (XV), or a pharmaceutically acceptable salt thereof. One embodiment provides a method of treating cancer in a patient in need thereof, comprising administering to the patient a compound of Formula (XVI), or a pharmaceutically acceptable salt thereof. One embodiment provides a method of treating cancer in a patient in need thereof, comprising administering to the patient a compound of Formula (XVII), or a pharmaceutically acceptable salt thereof. One embodiment provides a method of treating cancer in a patient in need thereof, comprising administering to the patient a compound of Formula (XVIII), or a pharmaceutically acceptable salt thereof. One embodiment provides a method of treating cancer in a patient in need thereof, comprising administering to the patient a compound of Formula (XIX), or a pharmaceutically acceptable salt thereof. One embodiment provides a method of treating cancer in a patient in need thereof, comprising administering to the patient a compound of Formula (XX), or a pharmaceutically acceptable salt thereof. One embodiment provides a method of treating cancer in a patient in need thereof, comprising administering to the patient a compound of Formula (XXI), or a pharmaceutically acceptable salt thereof. One embodiment provides a method of treating cancer in a patient in need thereof, comprising administering to the patient a compound of Formula (XXII), or a pharmaceutically acceptable salt thereof. One embodiment provides a method of treating cancer in a patient in need thereof, comprising administering to the patient a compound of Formula (XXIII), or a pharmaceutically acceptable salt thereof. One embodiment provides a method of treating cancer in a patient in need thereof, comprising administering to the patient a compound of Formula (XXIV), or a pharmaceutically acceptable salt thereof. One embodiment provides a method of treating cancer in a patient in need thereof, comprising administering to the patient a compound of Formula (XXV), or a pharmaceutically acceptable salt thereof.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography (CC) and thin layer chromatography (TLC) were performed on silica gel unless otherwise noted. Spectra are given in ppm (δ) and coupling constants (J) are reported in Hertz. For $^1$H NMR spectra, the solvent peak was used as the reference peak.

Chemistry Example 1 is 2-methyl-4-phenylisoquinolin-1-one which was purchased from a commercial vendor.

Example 2:
4-(3-methoxyphenyl)-2-methylisoquinolin-1-one

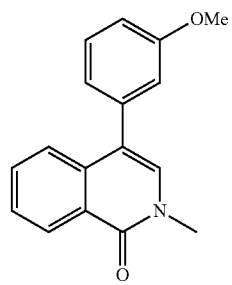 [SMILES: COc1cccc(-c2cn(C)c(=O)c3ccccc23)c1]

A mixture of 4-bromo-2-methylisoquinolin-1(2H)-one (100 mg, 0.42 mmol), and (3-methoxyphenyl)boronic acid (70 mg, 0.46 mmol), PPh$_3$ (66 mg, 0.25 mmol), Na$_2$CO$_3$ (133 mg, 1.26 mmol), and Pd(dppf)Cl$_2$ (62 mg, 0.084 mmol) in dioxane (2.5 mL) and H$_2$O (0.5 mL) was heated overnight at 90° C. Extractive work-up with EtOAc followed by preparative TLC (PE:EA=1:1) gave the title compound (18 mg, 0.07 mmol) as a white solid in 17% yield. $^1$H NMR (DMSO, 400 MHz): δ 8.30 (d, 1H, J=7.68), 7.68 (t, 1H, J=7.56), 7.50-7.55 (m, 3H), 7.40 (t, 1H, J=7.44), 6.97-7.00 (m, 3H), 3.78 (s, 3H), 3.54 (s, 3H). MS (m/z, relative intensity): 266 (Mt 1).

Examples 3-14: in Table 3 were prepared from 4-bromo-2-methylisoquinolin-1(2H)-one and the appropriate boronic acid/ester in a manner similar to Example 2.

TABLE 3

| Ex. No. | R$^1$ | Name | $^1$H NMR (ppm (d), 400 MHz) | MS (M + H) |
|---|---|---|---|---|
| 3 | 2-fluorophenyl | 4-(2-fluorophenyl)-2-methylisoquinolin-1-one | (DMSO-d$_6$) 3.57 (s, 3 H) 7.20 (d, J = 7.42 Hz, 1H) 7.31-7.41 (m, 2H) 7.42-7.61 (m, 4H) 7.64-7.73 (m, 1H) 8.32 (d, J = 7.81 Hz, 1H) | 254 |
| 4 | 2-methoxyphenyl | 4-(2-methoxyphenyl)-2-methylisoquinolin-1-one | (DMSO-d$_6$) 3.54 (s, 3 H) 3.67 (s, 3 H) 7.00-7.11 (m, 2H) 7.15 (d, J = 8.20 Hz, 1H) 7.25 (d, J = 6.83 Hz, 1H) 7.40 (s, 1H) 7.48 (dt, J = 15.91, 7.86 Hz, 2H) 7.61 (d, J = 7.42 Hz, 1H) 8.28 (d, J = 8.20 Hz, 1H) | 266 |
| 5 | 3-aminophenyl | 4-(3-aminophenyl)-2-methylisoquinolin-1-one | (DMSO-d$_6$) 3.55 (s, 3 H) 5.19 (br. s., 2H) 6.55 (d, J = 7.33 Hz, 1H) 6.60-6.64 (m, 2 H) 7.12 (t, J = 7.83 Hz, 1H) 7.43 (s, 1H) 7.51-7.62 (m, 2 H) 7.66-7.72 (m, 1H) 8.31 (d, J = 7.83 Hz, 1H) | 251 |
| 6 | 3-(N-cyclopropylsulfamoyl)phenyl | N-cyclopropyl-3-(2-methyl-1-oxoisoquinolin-4-yl)benzenesulfonamide | (DMSO-d$_6$) 0.36-0.41 (m, 2H) 0.47-0.52 (m, 2 H) 2.16 (br. s., 1H) 3.57 (s, 3 H) 7.44 (d, J = 8.20 Hz, 1 H) 7.54-7.61 (m, 2 H) 7.68-7.77 (m, 3H) 7.83-7.88 (m, 2H) 7.96 (br. s., 1H) 8.34 (d, J = 7.81 Hz, 1H) | 355 |
| 7 | 3-(pyrrolidin-1-ylsulfonyl)phenyl | 2-methyl-4-(3-pyrrolidin-1-ylsulfonylphenyl)isoquinolin-1-one | (DMSO-d$_6$) 1.67 (t, J = 6.64 Hz, 4H) 3.18 (t, J = 6.44 Hz, 4H) 3.57 (s, 3H) 7.42 (d, J = 8.20 Hz, 1H) 7.56 (t, J = 7.61 Hz, 1H) 7.61 (s, 1H) 7.68-7.80 (m, 4H) 7.85 (d, J = 6.83 Hz, 1H) 8.33 (d, J = 8.20 Hz, 1H) | 369 |
| 8 | 3-((methylsulfonamido)methyl)phenyl | N-[[3-(2-methyl-1-oxoisoquinolin-4-yl)phenyl]methyl]methanesulfonamide | (DMSO-d$_6$) 2.87 (s, 3H) 3.56 (s, 3H) 4.22 (d, J = 6.05 Hz, 2H) 7.31-7.44 (m, 3H) 7.45-7.62 (m, 5H) 7.64-7.72 (m, 1H) 8.32 (d, J = 7.61 Hz, 1H) | 343 |
| 9 | 3-(methylsulfonamido)phenyl | N-[3-(2-methyl-1-oxoisoquinolin-4-yl)phenyl]methanesulfonamide | (DMSO-d$_6$) 3.03 (s, 3 H) 3.55 (s, 3H) 7.16 (d, J = 7.61 Hz, 1 H) 7.23-7.28 (m, 2H) 7.45 (t, J = 8.30 Hz, 1H) 7.48-7.57 (m, 3 H) 7.67-7.72 (m, 1H) 8.31 (d, J = 7.03 Hz, 1H) 9.88 (br. s., 1 H) | 329 |
| 10 | 3-(N-ethylsulfamoyl)phenyl | N-ethyl-3-(2-methyl-1-oxoisoquinolin-4-yl)benzenesulfonamide | (DMSO-d$_6$) 0.92-1.02 (m, 3H) 2.76-2.86 (m, 2 H) 3.56 (s, 3H) 7.43 (d, J = 8.20 Hz, 1H) 7.53-7.60 (m, 2H) 7.64 (t, J = 5.66 Hz, 1H) 7.68-7.75 (m, 3 H) 7.80-7.88 (m, 2H) 8.29-8.36 (m, 1H) | 343 |

TABLE 3-continued

[Structure: 4-R¹-2-methylisoquinolin-1(2H)-one core]

| Ex. No. | R¹ | Name | ¹H NMR (ppm (d), 400 MHz) | MS (M + H) |
|---|---|---|---|---|
| 11 | [3-(ethylsulfonyl)phenyl] | 4-(3-ethylsulfonylphenyl)-2-methylisoquinolin-1-one | (CHLOROFORM-d) 1.33 (t, J = 7.42 Hz, 3H) 3.18 (q, J = 7.42 Hz, 2H) 3.65-3.69 (m, 3H) 7.10 (s, 1 H) 7.43 (d, J = 8.01 Hz, 1H) 7.51-7.57 (m, 1 H) 7.60-7.76 (m, 3H) 7.93-7.98 (m, 2 H) 8.53 (dd, J = 8.01, 0.98 Hz, 1H) | 328 |
| 12 | [3-(dimethylsulfamoylamino)phenyl] | 4-[3-(dimethylsulfamoylamino)phenyl]-2-methyl-1-oxoisoquinoline | (DMSO-d₆) 2.71 (s, 6 H) 3.55 (s, 3H) 7.10 (d, J = 7.03 Hz, 1H) 7.22-7.25 (m, 2H) 7.41 (t, J = 7.71 Hz, 1H) 7.48 (s, 1H) 7.50-7.56 (m, 2H) 7.67-7.72 (m, 1H) 8.31 (d, J = 7.81 Hz, 1H) 10.02 (br. s., 1H) | 358 |
| 13 | [3-(ethanesulfonamido)phenyl] | N-[3-(2-methyl-1-oxoisoquinolin-4-yl)phenyl]ethanesulfonamide | (DMSO-d₆) 1.20 (t, J = 7.13 Hz, 3H) 3.13 (q, J = 7.29 Hz, 2H) 3.55 (s, 3H) 7.14 (d, J = 7.03 Hz, 1H) 7.25 (br. s., 2 H) 7.38-7.59 (m, 4H) 7.69 (t, J = 7.61 Hz, 1H) 8.31 (d, J = 8.01 Hz, 1H) 9.92 (s, 1H) | 343 |
| 14 | [3-(morpholin-4-ylsulfonyl)phenyl] | 2-methyl-4-(3-morpholin-4-yl-sulfonylphenyl)isoquinolin-1-one | (DMSO-d₆) 3.02-3.09 (m, 4H) 3.68 (s, 3 H) 3.73-3.80 (m, 4H) 7.09 (s, 1 H) 7.43 (d, J = 7.81 Hz, 1H) 7.53-7.58 (m, 1H) 7.61-7.73 (m, 3H) 7.78-7.84 (m, 2H) 8.55 (d, J = 7.03 Hz, 1H) | 385 |

Example 15: N-benzyl-2-methoxy-5-(2-methyl-1-oxoisoquinolin-4-yl)benzenesulfonamide For about 3 min, N₂ was bubbled through the mixture of 4-bromo-2-methylisoquinolin-1(2H)-one (56 mg, 0.24 mmol), [3-(benzylsulfamoyl)-4-methoxyphenyl]boronic acid (83 mg, 0.26 mmol), aq 2M Na₂CO₃ (0.375 mL) and Pd(dppf)Cl₂ (9 mg, 0.001 mmol) in dioxane (1.5 mL) which was then microwaved at 120° C. for 1 hr and then filtered through a plug of anhydrous Na₂SO₄ using EtOAc to transfer and rinse. Silica gel chromatography, eluting with 0-60% EA in hexane over 6 min and continuing 60% isocratic EA gave the title compound (60 mg, 0.14 mmol) as a white solid in 58% yield. ¹H NMR (400 MHz, DMSO-d₆): δ 3.57 (s, 3H), 3.89 (s, 3H), 4.11 (d, J=6.32 Hz, 2H), 7.16-7.23 (m, 6H), 7.34 (d, J=8.08 Hz, 1H), 7.47 (s, 1H), 7.53-7.59 (m, 2H), 7.65 (d, J=2.27 Hz, 1H), 7.72-7.77 (m, 1H), 7.94 (t, J=6.32 Hz, 1H), 8.34 (d, J=7.33 Hz, 1H). LCMS (M+H)⁺: 435.

Examples 16-17 in Table 4 were prepared from 4-bromo-2-methylisoquinolin-1(2H)-one and the appropriate boronic acid/ester in a manner similar to Example 15.

TABLE 4

[Structure: 4-R₁-2-methyl-isoquinolin-1(2H)-one]

| Ex. No. | R¹ | Name | ¹H NMR (ppm (d), 400 MHz) | MS (M + H) |
|---|---|---|---|---|
| 16 | [4-OMe, 3-SO₂NH₂ phenyl] | 2-methoxy-5-(2-methyl-1-oxoisoquinolin-4-yl)benzenesulfonamide | (DMSO-d₆) 3.57 (s, 3 H) 3.97 (s, 3H) 7.18 (s, 2H) 7.35 (d, J = 8.59 Hz, 1H) 7.44 (d, J = 8.08 Hz, 1H) 7.50 (s, 1H) 7.57 (t, J = 7.45 Hz, 1H) 7.65 (dd, J = 8.46, 2.15 Hz, 1H) 7.71 (t, J = 7.58 Hz, 1 H) 7.76 (d, J = 2.27 Hz, 1H) 8.34 (d, J = 8.34 Hz, 1H) | 345 |
| 17 | [4-Me, 3-NHSO₂Me phenyl] | N-[2-methyl-5-(2-methyl-1-oxoisoquinolin-4-yl)phenyl]methanesulfonamide | (DMSO-d₆) 2.38 (s, 3H) 3.02 (s, 3H) 3.57 (s, 3 H) 7.24 (dd, J = 7.83, 1.77 Hz, 1H) 7.34 (d, J = 1.52 Hz, 1H) 7.38 (d, J = 7.83 Hz, 1H) 7.50 (s, 1H) 7.53-7.58 (m, 2H) 7.67-7.72 (m, 1H) 8.30-8.36 (m, 1H) 9.18 (s, 1H) | 343 |

Example 18: N-benzyl-2-methoxy-5-(2-methyl-1-oxoisoquinolin-4-yl)benzamide

Step 1: N-benzyl-5-bromo-2-methoxybenzamide

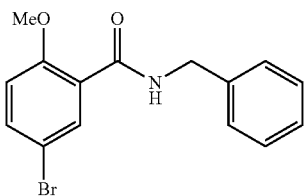 [SMILES: COc1ccc(Br)cc1C(=O)NCc1ccccc1]

To an icebath cooled mixture of 5-bromo-2-methoxybenzoic acid (439 mg, 1.9 mmol) in 1:1 CH₂Cl₂:DMF (4 mL) was added benzylamine (0.228 mL, 2.1 mmol), EDCI (438 mg, 2.3 mmol), HOBt (311 mg, 2.3 mmol) and NEtiPr₂ (0.496 mL, 2.85 mmol). The mixture was then stirred at room temp until the rxn was complete. Extractive work-up with EtOAc, washing with satd aq NaHCO₃, H₂O, satd aq KHSO₄, and brine gave the title compound (550 mg) after isolation which was carried forward without purification. LCMS (M+H)⁺: 320, 322.

Step 2: N-benzyl-2-methoxy-5-(tetramethyl-1,3,2-dioxaborolan-2-yl)benzamide

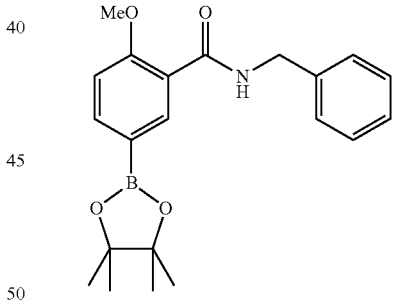

For about 3 min, N₂ was bubbled through a mixture of the title compound of N-benzyl-5-bromo-2-methoxybenzamide (174 mg, 0.54 mmol), 4,4,5,5-tetramethyl-2-(tetramethyl-1,3,2-dioxaborolan-2-yl)-1,3,2-dioxaborolane (166 mg, 0.65 mmol), potassium acetate (159 mg, 1.62 mmol) and Pd(dppf)Cl₂ (20 mg, 0.03 mmol) in anhydrous DMF (4.2 mL). After heating at 90° C. for about 2 hr under N₂, silica gel chromatography, eluting with 0-40% EA in hexane over 7 min and continuing 40% isocratic EA gave the title compound (138 mg, 0.38 mmol) as a white solid in 70% yield. LCMS (M+H)⁺: 368.

Step 3: N-benzyl-2-methoxy-5-(2-methyl-1-oxoisoquinolin-4-yl)benzamide

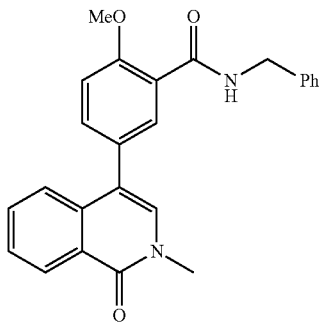 [SMILES: COc1ccc(-c2cn(C)c(=O)c3ccccc23)cc1C(=O)NCc1ccccc1]

For about 3 min, N₂ was bubbled through a mixture of N-benzyl-2-methoxy-5-(tetramethyl-1,3,2-dioxaborolan-2-yl)benzamide (51 mg, 0.14 mmol), 4-bromo-2-methylisoquinolin-1 (2H)-one (30 mg, 0.13 mmol), aq 1M K₃PO₄ (0.3 mL) and Pd(dppf)Cl₂ (10 mg, 0.013 mmol) in dioxane (1.15 mL) which was then microwaved at 100° C. for 1 hr. Work-up similar to Example 15 and purification by silica gel chromatography, eluting with 5-50% EA in hexane over 4 min and continuing 50% isocratic EA gave the title compound (37 mg, 0.14 mmol) as a tan solid in 71% yield. $^1$H NMR (400 MHz, DMSO-$d_6$) δ 3.57 (s, 3H), 3.97 (s, 3H), 4.52 (d, J=6.06 Hz, 2H), 7.21-7.37 (m, 6H), 7.47-7.51 (m, 2H), 7.56 (td, J=5.37, 2.15 Hz, 2H), 7.68-7.73 (m, 1H), 7.79 (d, J=2.27 Hz, 1H), 8.33 (d, J=7.83 Hz, 1H), 8.79 (t, J=6.06 Hz, 1H). LCMS (M+H)$^+$: 399.

Examples 19-31 in Table 5 were prepared from 4-bromo-2-methylisoquinolin-1(2H)-one and the appropriate boronic acid/ester in a manner similar to Example 18, step 3. For Examples 20-26 the microwave temp was increased to 120° C. Aniline hydrochlorides were prepared by treating the aniline with anhydrous HCl in methanol as the final step.

TABLE 5

| Ex. No. | R¹ | Name | $^1$H NMR (ppm (d), 400 MHz) | MS (M + H) |
|---|---|---|---|---|
| 19 | (3,4-dihydro-2H-1,4-benzoxazin-6-yl) | 4-(3,4-dihydro-2H-1,4-benzoxazin-6-yl)-2-methylisoquinolin-1-one | (DMSO-$d_6$) 3.50-3.59 (m, 3H) 4.14-4.19 (m, 2 H) 5.87 (br. s., 1H) 6.51 (dd, J = 8.08, 2.02 Hz, 1H) 6.61 (d, J = 2.02 Hz, 1 H) 6.74 (d, J = 8.08 Hz, 1H) 7.38 (s, 1H) 7.50-7.55 (m, 1H) 7.58 (d, J = 7.83 Hz, 1H) 7.66-7.72 (m, 1H) 8.30 (d, J = 8.08 Hz, 1H) | 293 |
| 20 | (2-oxo-1,3-dihydroindol-6-yl) | 2-methyl-4-(2-oxo-1,3-dihydroindol-6-yl)isoquinolin-1-one | (DMSO-$d_6$) 3.55 (s, 2H) 3.56 (s, 3 H) 6.85 (s, 1H) 7.00 (dd, J = 7.58, 1.52 Hz, 1H) 7.32 (d, J = 7.58 Hz, 1H) 7.49 (s, 1H) 7.53-7.58 (m, 2H) 7.67-7.72 (m, 1H) 8.31-8.35 (m, 1H) 10.47 (s, 1H) | 291 |
| 21 | (3-SO₂NH₂-phenyl) | 3-(2-methyl-1-oxoisoquinolin-4-yl)benzenesulfonamide | (DMSO-$d_6$) 3.59 (s, 3H) 7.43 (s, 2H) 7.48 (d, J = 8.08 Hz, 1H) 7.56-7.61 (m, 2H) 7.67-7.75 (m, 3H) 7.87-7.92 (m, 2H) 8.36 (d, J = 8.08 Hz, 1H) | 315 |
| 22 | (3-SO₂NHCH₂CH₂OH-phenyl) | N-(2-hydroxyethyl)-3-(2-methyl-1-oxoisoquinolin-4-yl)benzenesulfonamide | (DMSO-$d_6$) 2.85 (q, J = 6.06 Hz, 2H) 3.39 (q, J = 6.06 Hz, 2H) 3.59 (s, 3H) 4.70 (t, J = 5.56 Hz, 1H) 7.47 (d, J = 8.08 Hz, 1H) 7.56-7.59 (m, 1H) 7.61 (s, 1H) 7.66-7.77 (m, 4H) 7.83-7.88 (m, 2H) 8.36 (d, J = 8.08 Hz, 1H) | 359 |
| 23 | (4-F, 3-NH₂·HCl-phenyl) | 4-(5-amino-2-fluorophenyl)-2-methylisoquinolin-1-one hydrochloride | (DMSO-$d_6$) 3.57 (s, 3H partially obscured) 7.08-7.22 (m, 2H) 7.24 (d, J = 9.60 Hz, 1H) 7.32 (t, J = 9.09 Hz, 1H) 7.54-7.60 (m, 2H) 7.67-7.73 (m, 1H) 8.32 (d, J = 7.83 Hz, 1H) | 269 |

TABLE 5-continued

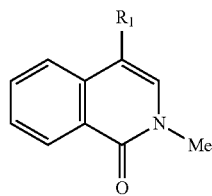

| Ex. No. | R¹ | Name | ¹H NMR (ppm (d), 400 MHz) | MS (M + H) |
|---|---|---|---|---|
| 24 | 2,4-difluoro-5-amino-phenyl (F, F, NH₂·HCl) | 4-(5-amino-2,4-difluorophenyl)-2-methylisoquinolin-1-one hydrochloride | (DMSO-d₆) 3.55 (s, 3H) 6.83 (dd, J = 9.73, 7.96 Hz, 1H) 7.19–7.28 (m, 2H) 7.51–7.58 (m, 2H) 7.67–7.72 (m, 1H) 8.30 (d, J = 8.08 Hz, 1H) | 287 |
| 25 | 3-amino-5-fluorophenyl (F, NH₂·HCl) | 4-(3-amino-5-fluorophenyl)-2-methylisoquinolin-1-one hydrochloride | (DMSO-d₆) 3.55 (s, 3 H) 6.47–6.56 (m, 2H) 6.59 (s, 1 H) 7.51 (s, 1H) 7.52–7.62 (m, 2H) 7.69–7.75 (m, 1H) 8.32 (d, J = 8.08 Hz, 1H) | 269 |
| 26 | 3-amino-4-fluorophenyl (F, NH₂) | 4-(3-amino-4-fluorophenyl)-2-methylisoquinolin-1-one hydrochloride | (DMSO-d₆) 3.55 (s, 3H) 6.64 (d, J = 2.53 Hz, 1H) 6.89 (dd, J = 8.59, 2.02 Hz, 1H) 7.13 (dd, J = 11.49, 8.21 Hz, 1H) 7.45 (s, 1 H) 7.52–7.58 (m, 2H) 7.67–7.74 (m, 1H) 8.32 (d, J = 7.07 Hz, 1H) | 269 |
| 27 | 3-(N-benzylsulfamoyl)phenyl | N-benzyl-3-(2-methyl-1-oxoisoquinolin-4-yl)benzenesulfonamide | (DMSO-d₆) 3.59 (s, 3H) 4.08 (d, J = 6.06 Hz, 2H) 7.17–7.29 (m, 5H) 7.40 (d, J = 7.83 Hz, 1H) 7.54 (s, 1H) 7.58 (t, J = 7.58 Hz, 1H) 7.68–7.76 (m, 3H) 7.80 (s, 1H) 7.85 (td, J = 4.48, 1.89 Hz, 1H) 8.26 (t, J = 6.32 Hz, 1H) 8.35 (d, J = 8.08 Hz, 1H) | 405 |
| 28 | 3-(propylsulfonylamino)phenyl | N-[3-(2-methyl-1-oxoisoquinolin-4-yl)phenyl]propane-1-sulfonamide | (DMSO-d₆) 0.96 (t, J = 7.45 Hz, 3H) 1.72 (sxt, J = 7.48 Hz, 2H) 3.10–3.15 (m, 2 H) 3.57 (s, 3H) 7.16 (d, J = 7.58 Hz, 1H) 7.26–7.30 (m, 2H) 7.43–7.59 (m, 4 H) 7.68–7.73 (m, 1H) 8.34 (d, J = 7.83 Hz, 1H) 9.91 (s, 1H) | 357 |
| 29 | 3-(butylsulfonylamino)phenyl | N-[3-(2-methyl-1-oxoisoquinolin-4-yl)phenyl]butane-1-sulfonamide | (DMSO-d₆) 0.84 (t, J = 7.33 Hz, 3H) 1.37 (sxt, J = 7.38 Hz, 2H) 1.67 (dt, J = 15.35, 7.61 Hz, 2H) 3.10–3.18 (m, 2H) 3.57 (s, 3H) 7.16 (d, J = 7.58 Hz, 1H) 7.24–7.33 (m, 2H) 7.41–7.60 (m, 4H) 7.64–7.74 (m, 1H) 8.34 (d, J = 8.08 Hz, 1H) 9.91 (s, 1H) | 371 |
| 30 | 4-methoxy-3-(methylsulfonylamino)phenyl (OMe, NHSO₂Me) | N-[2-methoxy-5-(2-methyl-1-oxoisoquinolin-4-yl)phenyl]methanesulfonamide | (DMSO-d₆) 3.00 (s, 3H) 3.57 (s, 3 H) 3.90 (s, 3H) 7.18–7.23 (m, 1H) 7.24–7.30 (m, 1H) 7.33 (d, J = 2.27 Hz, 1H) 7.47 (s, 1H) 7.55 (dd, J = 7.58, 5.05 Hz, 2 H) 7.65–7.73 (m, 1H) 8.31–8.37 (m, 1H) 9.04 (s, 1H) | 359 |
| 31 | 3-(N-methyl-N-tert-butoxycarbonyl-amino)phenyl (N(Me)CO₂tBu) | tert-butyl N-methyl-N-[3-(2-methyl-1-oxoisoquinolin-4-yl)phenyl]carbamate | (DMSO-d₆) 1.41 (s, 9H) 3.24 (s, 3H) 3.57 (s, 3H) 7.25 (d, J = 7.33 Hz, 1H) 7.32–7.38 (m, 2H) 7.44–7.60 (m, 4H) 7.67–7.73 (m, 1H) 8.34 (d, J = 7.83 Hz, 1H) | 365 |

Example 32: 2-methyl-4-[3-(methylamino)phenyl]isoquinolin-1-one Hydrochloride

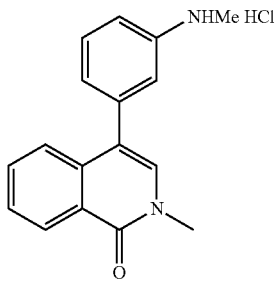

To the title compound of Example 31 (48 mg, 0.13 mmol) was added 4 M HCl in dioxane (3 mL). After stirring about 1 hr, the volatile components were removed under vacuum. Hexane was added and evaporated (×2). The resulting white solid was dried under vacuum to give the title compound (39 mg, 0.13 mmol) in quantitative yield. $^1$H NMR (400 MHz, DMSO-$d_6$): δ ppm 2.85 (s, 3H), 3.57 (s, 3H), 7.10 (br. s., 3H), 7.44 (br. s., 1H), 7.51-7.60 (m, 3H), 7.68-7.74 (m, 1H), 8.34 (d, J=7.58 Hz, 1H). LCMS (M+H)$^+$: 265.

Example 33: N-methyl-N-[3-(2-methyl-1-oxoisoquinolin-4-yl)phenyl]methanesulfonamide

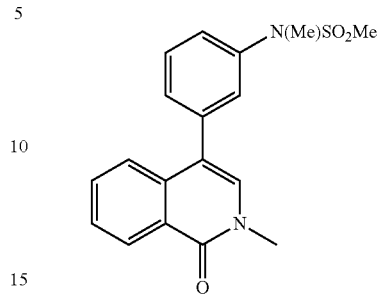

To the title compound of Example 32 (35 mg, 0.12 mmol) in anhydrous CH$_2$Cl$_2$ (0.3 mL), pyridine (0.1 mL) and NEtiPr$_2$ (0.021 mL, 0.12 mmol) was added methanesulfonyl chloride (0.011 mL, 0.14 mmol). After 0.5-1 hr, ice was added to the mixture followed by H$_2$O and EtOAc. Extractive work-up, washing with H$_2$O, a 1:1 aq satd KHSO$_4$:H$_2$O, and brine, and purification on silica gel eluting with 35-80% EA in hexane over 6 min and continuing 80% isocratic EA gave the title compound (22 mg, 0.06 mmol) as a cream solid in 54% yield. $^1$H NMR (400 MHz, DMSO-$d_6$): δ ppm 3.00 (s, 3H), 3.30 (s, 3H), 3.58 (s, 3H), 7.40 (d, J=7.58 Hz, 1H), 7.45-7.61 (m, 6H), 7.71 (td, J=7.58, 1.26 Hz, 1H), 8.34 (dd, J=8.21, 1.14 Hz, 1H). LCMS (M+H)$^+$: 343.

Examples 34-40 in Table 6 were prepared in one step by sulfonylation of the aniline Examples 23-26 from Table 5 using methanesulfonyl chloride in a manner similar to Example 33 (one step from the indicated Example No.) or in two steps from 4-bromo-2-methylisoquinolin-1(2H)-one and the appropriate aniline boronic acid/ester in a manner similar to Example 23 followed by sulfonylation of the aniline with methanesulfonyl chloride in a manner similar to Example 33 (two steps).

TABLE 6

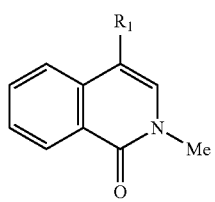

| Ex. No. | R$^1$ | Name | No. of steps (from Ex. No.) | $^1$H NMR (ppm (d), 400 MHz) | MS (M + H) |
|---|---|---|---|---|---|
| 34 | ![F-phenyl-NHSO2Me] | N-[4-fluoro-3-(2-methyl-1-oxoisoquinolin-4-yl)phenyl] methanesulfonamide | 1 step (from Ex. 23) | $^1$H NMR (400 MHz, DMSO-$d_6$) d ppm 3.04 (s, 3 H) 3.57 (s, 3H) 7.22-7.27 (m, 2H) 7.30-7.40 (m, 2H) 7.53-7.59 (m, 1H) 7.61 (s, 1H) 7.66-7.74 (m, 1H) 8.32 (d, J = 8.08 Hz, 1H) 9.83 (s, 1H) | 347 |

TABLE 6-continued

| Ex. No. | R¹ | Name | No. of steps (from Ex. No.) | ¹H NMR (ppm (d), 400 MHz) | MS (M + H) |
|---|---|---|---|---|---|
| 35 | (2,4-difluoro-5-NHSO₂Me-phenyl) | N-[2,4-difluoro-5-(2-methyl-1-oxoisoquinolin-4-yl)phenyl]methanesulfonamide | 1 step (from Ex. 24) | ¹H NMR (400 MHz, DMSO-d₆) d ppm 3.08 (s, 3H) 3.57 (s, 3H) 7.24 (d, J = 8.08 Hz, 1H) 7.45 (t, J = 8.21 Hz, 1H) 7.53-7.60 (m, 2H) 7.62 (s, 1H) 7.70 (t, J = 7.58 Hz, 1H) 8.32 (d, J = 7.83 Hz, 1H) 9.70 (s, 1H) | 365 |
| 36 | (3-fluoro-5-NHSO₂Me-phenyl) | N-[3-fluoro-5-(2-methyl-1-oxoisoquinolin-4-yl)phenyl]methanesulfonamide | 1 step (from Ex. 25) | ¹H NMR (400 MHz, DMSO-d₆) d ppm 3.12 (s, 3H) 3.57 (s, 3H) 7.01-7.13 (m, 3H) 7.54-7.63 (m, 3H) 7.70-7.77 (m, 1H) 8.33 (d, J = 8.08 Hz, 1H) 10.16 (s, 1H) | 347 |
| 37 | (2-fluoro-5-NHSO₂Me-phenyl) | N-[2-fluoro-5-(2-methyl-1-oxoisoquinolin-4-yl)phenyl]methanesulfonamide | 1 step (from Ex. 26) | ¹H NMR (400 MHz, DMSO-d₆) d ppm 3.09 (s, 3H) 3.57 (s, 3H) 7.28-7.36 (m, 1H) 7.39-7.48 (m, 2H) 7.49-7.60 (m, 3H) 7.67-7.74 (m, 1H) 8.34 (d, J = 8.08 Hz, 1H) 9.75 (s, 1H) | 347 |
| 38 | (4-chloro-3-NHSO₂Me-phenyl) | N-[4-chloro-3-(2-methyl-1-oxoisoquinolin-4-yl)phenyl]methanesulfonamide | 2 steps | ¹H NMR (400 MHz, DMSO-d₆) d ppm 3.08 (s, 3H) 3.56 (s, 3H) 7.07 (d, J = 7.83 Hz, 1H) 7.23 (d, J = 2.78 Hz, 1H) 7.33 (dd, J = 8.72, 2.65 Hz, 1H) 7.51-7.62 (m, 3H) 7.64-7.70 (m, 1H) 8.28-8.36 (m, 1H) 10.04 (s, 1H) | 363, 365 |
| 39 | (4-methyl-3-NHSO₂Me-phenyl) | N-[4-methyl-3-(2-methyl-1-oxoisoquinolin-4-yl)phenyl]methanesulfonamide | 2 steps | ¹H NMR (400 MHz, DMSO-d₆) d ppm 2.01 (s, 3H) 3.00 (s, 3H) 3.56 (s, 3H) 7.02 (d, J = 8.08 Hz, 1H) 7.06 (d, J = 2.53 Hz, 1H) 7.22 (dd, J = 8.21, 2.40 Hz, 1H) 7.33 (d, J = 8.34 Hz, 1H) 7.45 (s, 1H) 7.51-7.56 (m, 1H) 7.63-7.68 (m, 1H) 8.32 (d, J = 8.08 Hz, 1H) 9.71 (s, 1H) | 343 |
| 40 | (3-CF₃-5-NHSO₂Me-phenyl) | N-[3-(2-methyl-1-oxoisoquinolin-4-yl)-5-(trifluoromethyl)phenyl]methanesulfonamide | 2 steps | ¹H NMR (400 MHz, DMSO-d₆) d ppm 3.14 (s, 3H) 3.58 (s, 3H) 7.49-7.52 (m, 2H) 7.54-7.61 (m, 3H) 7.64 (s, 1H) 7.70-7.76 (m, 1H) 8.35 (d, J = 8.08 Hz, 1H) 10.29 (s, 1H) | 397 |

Example 41: N-[4-fluoro-3-[2-methyl-6-(1-methyl-pyrazol-4-yl)-1-oxoisoquinolin-4-yl]phenyl]methanesulfonamide

Step 1: 2-methyl-6-(1-methylpyrazol-4-yl)isoquinolin-1-one

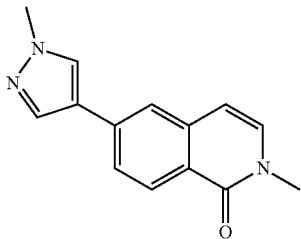 [SMILES: Cn1cc(-c2ccc3c(=O)n(C)ccc3c2)cn1]

A mixture of 6-bromo-2-methylisoquinolin-1-one (3.8 g, 16 mmol), 1-methyl-4-(tetramethyl-1,3,2-dioxaborolan-2-yl)-1H-pyrazole (6.69 g, 32 mmol), CsF (7.29 g, 48 mmol), Pd(PPh$_3$)$_2$Cl$_2$ (0.4 g, 1 mmol) in dioxane/H$_2$O (60/10 mL) was stirred at 90° C. for 12 hr under N$_2$. The mixture was concentrated and the residue was purified by silica gel chromatography (PE:EA=2:1) to give the title compound (3.1 g, 81%) as a yellow solid. $^1$H NMR (CDCl$_3$, 400 MHz): δ 8.40 (d, J=12 Hz, 1H), 7.87 (s, 1H), 7.74 (s, 1H), 7.59-7.56 (dt, J$_1$=4 Hz, J$_2$=8 Hz, 2H), 7.07 (d, J=4 Hz, 1H), 6.48 (d, J=8 Hz, 1H) 3.98 (s, 3H), 3.61 (s, 3H). LCMS: 240.0 (M+H)$^+$.

Step 2: 4-bromo-2-methyl-6-(1-methylpyrazol-4-yl)isoquinolin-1-one

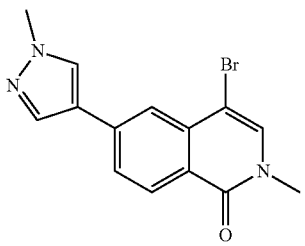 [SMILES: Cn1cc(-c2ccc3c(=O)n(C)cc(Br)c3c2)cn1]

Bromine (1.8 g, 11.25 mmol) in HOAc (6 mL) was added to the title compound of 2-methyl-6-(1-methylpyrazol-4-yl)isoquinolin-1-one (3 g, 12.5 mmol) in HOAc (24 mL) at 0° C. The mixture was stirred at 30° C. for 15 min, quenched with H$_2$O (100 mL), and the resulting yellow solid was collected by filtration to give the title compound (2.04 g, 56%). $^1$H NMR (CDCl$_3$, 400 MHz): δ 8.42 (d, J=8.4 Hz, 1H), 7.87 (d, J=28.8 Hz, 2H), 7.82 (d, J=15.6 Hz, 2H), 7.65 (d, J=8 Hz, 2H), 7.38 (s, 1H), 4.00 (s, 3H), 3.61 (s, 3H). LCMS: 318.0 (M+H)$^+$.

Step 3: 4-(5-amino-2-fluorophenyl)-2-methyl-6-(1-methylpyrazol-4-yl)isoquinolin-1-one

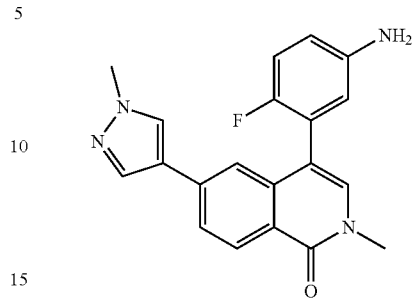

4-Bromo-2-methyl-6-(1-methylpyrazol-4-yl)isoquinolin-1-one (35 mg, 0.11 mmol), 4-fluoro-3-(4,4,5,5-tetramethyl-1,3,2-dioxaborolan-2-yl)aniline (29 mg, 0.12 mmol), Pd(dppf)Cl$_2$ (8 mg, 0.01 mmol) and aq 1 M K$_3$PO$_4$ (0.3 mL) in dioxane (1.2 mL) were microwaved at 120° C. for 1.25 hr. Work-up was similar to that described for Example 18, step 3. Silica gel chromatography, eluting with 100% EA followed by 10% methanol in EA, gave the title compound (25 mg, 0.07 mmol) as a cream solid in 64% yield. LCMS (M+H)$^+$: 349.

Step 4: N-[4-fluoro-3-[2-methyl-6-(1-methylpyrazol-4-yl)-1-oxoisoquinolin-4-yl]phenyl]methanesulfonamide

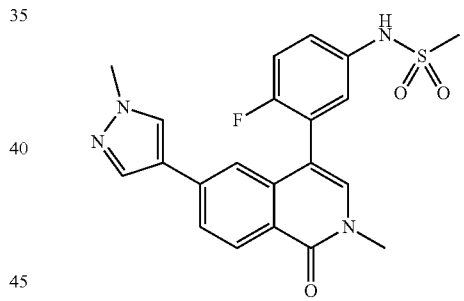

4-(5-Amino-2-fluorophenyl)-2-methyl-6-(1-methylpyrazol-4-yl)isoquinolin-1-one (25 mg, 0.07 mmol) in pyridine (0.1 mL) and anhydrous CH$_2$Cl$_2$ (0.3 mL) was treated with methanesulfonyl chloride (0.007 mL, 0.09 mmol) in a manner similar to Example 33. After a similar work-up, silica gel chromatography, eluting with 50-100% EA in hexane over 4 min and continuing isocratic 100% EA, gave the title compound (24 mg, 0.06 mmol) as a white solid in 78% yield. $^1$H NMR (400 MHz, DMSO-d$_6$) δ 3.06 (s, 3H), 3.56 (s, 3H), 3.85 (s, 3H), 7.22-7.45 (m, 4H), 7.59 (s, 1H), 7.76 (dd, J=8.34, 1.52 Hz, 1H), 7.85 (s, 1H), 8.16 (s, 1H), 8.29 (d, J=8.34 Hz, 1H), 9.82 (s, 1H). LCMS (M+H)$^+$: 427.

Examples 42-45 in Table 7 were prepared from title compound of Example 41, step 2, in one step using the appropriate phenyl boronic acid/ester in a manner similar to Example 18, step 3, (1 step) or in two steps from the aniline boronic acid/ester followed sulfonylation of the aniline with the either methanesulfonyl chloride or ethanesulfonyl chloride in a manner similar to Example 41, steps 3 and 4, (2 steps).

TABLE 7

| Ex. No. | R¹ | Name | No. of steps (from Ex. No.) | ¹H NMR (ppm (d), 400 MHz) | MS (M + H) |
|---|---|---|---|---|---|
| 42 | 3-(NHSO₂Me)phenyl | N-[3-[2-methyl-6-(1-methylpyrazol-4-yl)-1-oxoisoquinolin-4-yl]phenyl]methanesulfonamide | 1 step | (DMSO-d₆) 3.07 (s, 3H) 3.56 (s, 3H) 3.85 (s, 3H) 7.23 (d, J = 7.83 Hz, 1H) 7.28 (d, J = 8.08 Hz, 1H) 7.34 (s, 1H) 7.41-7.54 (m, 2H) 7.66 (s, 1H) 7.72-7.80 (m, 1H) 7.86 (s, 1H) 8.16 (s, 1H) 8.30 (d, J = 8.34 Hz, 1H) 9.87 (s, 1H) | 409 |
| 43 | 2,4-difluoro-5-(NHSO₂Me)phenyl | N-[2,4-difluoro-5-[2-methyl-6-(1-methylpyrazol-4-yl)-1-oxoisoquinolin-4-yl]phenyl]methanesulfonamide | 2 steps | (DMSO-d₆) 3.10 (s, 3H) 3.55 (s, 3H) 3.85 (s, 3H) 7.33 (s, 1H) 7.44-7.63 (m, 3H) 7.77 (dd, J = 8.59, 1.52 Hz, 1H) 7.89 (s, 1H) 8.19 (s, 1H) 8.28 (d, J = 8.34 Hz, 1H) 9.71 (s, 1H) | 445 |
| 44 | 3-(SO₂Et)phenyl | 4-(3-ethylsulfonylphenyl)-2-methyl-6-(1-methylpyrazol-4-yl)isoquinolin-1-one | 1 step | (DMSO-d₆) 1.17 (t, J = 7.33 Hz, 3H) 3.40 (q, J = 7.41 Hz, 2H) 3.58 (s, 3H) 3.85 (s, 3H) 7.56 (s, 1H) 7.63 (s, 1H) 7.75-8.00 (m, 6H) 8.16 (s, 1H) 8.32 (d, J = 8.34 Hz, 1H) | 409 |
| 45 | 4-chloro-3-(NHSO₂Et)phenyl | N-[4-chloro-3-[2-methyl-6-(1-methylpyrazol-4-yl)-1-oxoisoquinolin-4-yl]phenyl]ethanesulfonamide | 2 steps | (DMSO-d₆) 1.14-1.28 (m, 3H) 3.11-3.28 (m, 2H) 3.55 (s, 3H) 3.84 (s, 3H) 7.13 (s, 1H) 7.26 (d, J = 2.53 Hz, 1H) 7.36 (dd, J = 8.72, 2.65 Hz, 1H) 7.54 (s, 1H) 7.61 (d, J = 8.84 Hz, 1H) 7.72-7.77 (m, 1H) 7.81 (s, 1H) 8.12 (s, 1H) 8.28 (d, J = 8.34 Hz, 1H) 10.08 (s, 1H) | 457, 459 |

Example 46: 4-[2-(cyclopropylmethoxy)-5-methylsulfonylphenyl]-2-methyl-6-(1-methylpyrazol-4-yl)isoquinolin-1-one

Step 1: 2-bromo-1-(cyclopropylmethoxy)-4-methanesulfonylbenzene

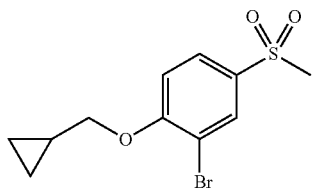 [SMILES: CS(=O)(=O)c1ccc(OCC2CC2)c(Br)c1]

A mixture of 2-bromo-4-methanesulfonylphenol (7.2 g, 29 mmol), (chloromethyl) cyclopropane (4.3 g, 32 mmol) and K$_2$CO$_3$ (8 g, 58 mmol) in acetone (80 mL) was stirred at 80° C. for 5 hr. The mixture was quenched with H$_2$O (40 mL). Extractive work-up with EtOAc and purification by preparative HPLC gave the title compound (2.5 g, 28.6%). $^1$H NMR (CDCl$_3$, 400 MHz): δ 8.12 (d, J=2.3 Hz, 1H), 7.84 (dd, J$_1$=2.3 Hz, J$_2$=8.7 Hz, 1H), 6.97 (d, J=8.8 Hz, 1H), 3.99 (d, J=6.7 Hz, 2H), 3.05 (s, 3H), 1.23-1.43 (m, 1H), 0.70 (d, J=7.9 Hz, 2H), 0.44 (d, J=5.4 Hz, 2H).

Step 2: 2-methyl-6-(1-methylpyrazol-4-yl)-4-(4,4,5,5-tetramethyl-1,3,2-dioxaborolan-2-yl) isoquinolin-1-one

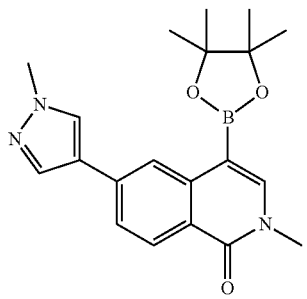 [SMILES: Cn1cc(-c2ccc3c(=O)n(C)cc(B4OC(C)(C)C(C)(C)O4)c3c2)cn1]

A mixture of the title compound of Example 41, step 2 (1.4 g, 4.41 mmol), 4,4,5,5-tetramethyl-2-(tetramethyl-1,3,2-dioxaborolan-2-yl)-1,3,2-dioxaborolane (2.24 g, 8.83 mmol), KOAc (1.08 g, 11.08 mmol), Pd(dppf)Cl$_2$ (100 mg, 0.137 mmol) in dioxane (50 mL) was stirred at 90° C. for 12 hr under N$_2$. Purification by CC on silica gel (PE:EA=3:1) gave the title compound (200 mg, 12%) as a yellow solid. $^1$H NMR (CDCl$_3$, 400 MHz): δ 8.55 (d, J=1.5 Hz, 1H), 8.40 (d, J=8.4 Hz, 1H), 7.90 (s, 1H), 7.71 (d, J=16.8 Hz, 2H), 4.00 (s, 3H), 3.63 (s, 3H), 1.40 (s, 12H).

Step 3: 4-[2-(cyclopropylmethoxy)-5-methylsulfonylphenyl]-2-methyl-6-(1-methylpyrazol-4-yl)isoquinolin-1-one

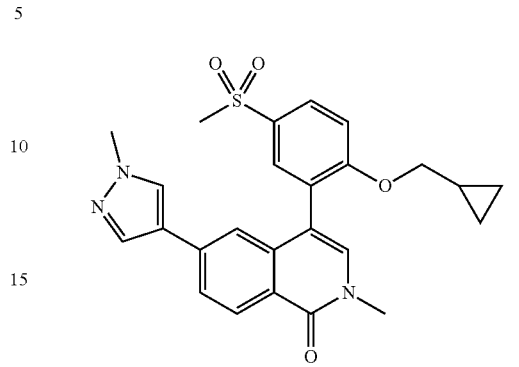

A mixture of 2-bromo-1-(cyclopropylmethoxy)-4-methanesulfonylbenzene (20.8 mg, 0.068 mmol), 2-methyl-6-(1-methylpyrazol-4-yl)-4-(4,4,5,5-tetramethyl-1,3,2-dioxaborolan-2-yl) isoquinolin-1-one (30 mg, 0.08 mmol), NaHCO$_3$ (14.28 mg, 0.17 mmol), and Pd(dppf)Cl$_2$ (10 mg, 0.014 mmol) in dioxane (2.0 mL) and H$_2$O (0.5 mL) was microwaved under N$_2$ at 100° C. for 30 min. Purification by preparative HPLC gave the title compound (11 mg, 28%) as a white solid. $^1$H NMR (CDCl$_3$, 400 MHz): δ 8.48 (d, J=8.4 Hz, 1H), 7.98-8.04 (m, 1H), 7.89 (d, J=2.4 Hz, 1H), 7.68 (s, 1H), 7.63 (s, 1H), 7.58-7.62 (m, 1H), 7.19-7.21 (m, 1H), 7.11-7.15 (m, 1H), 7.09 (s, 1H), 3.93 (s, 3H), 3.83-3.91 (m, 2H), 3.66 (s, 3H), 3.12 (s, 3H), 0.94-1.04 (m, 1H), 0.30-0.40 (m, 2H), 0.00-0.12 (m, 2H). LCMS: 464.1 (M+H)$^+$.

Example 47: N-[3-(6-fluoro-2-methyl-1-oxoisoquinolin-4-yl)phenyl]methanesulfonamide

Step 1: 6-fluoro-2-methylisoquinolin-1-one

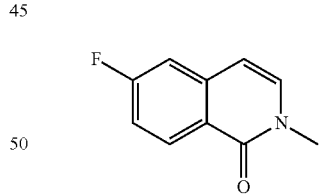

Sodium hydride (60% in mineral oil) (211 mg, 5.27 mmol) was added to 6-fluoro-1,2-dihydroisoquinolin-1-one (716 mg, 4.39 mmol) in anhydrous DMF (6 mL) cooled in an icebath. The mixture was stirred for about 30 min at room temp and methyl iodide (0.328 mL, 5.27 mmol) was added dropwise. After 1 hr, the rxn was judged to be about 60% complete and additional methyl iodide (0.2 mL, 3.2 mmol) was added. After about 1 hr, ice and H$_2$O and EtOAc were added to the mixture. After extractive work-up with EtOAc, the title compound (836 mg) was obtained as a cream solid and carried on without purification.

Step 2: 4-bromo-6-fluoro-2-methylisoquinolin-1-one

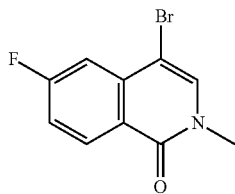

Bromine (232 mg, 1.45 mmol, 0.097 mL) in acetic acid (1.0 mL) was added dropwise, quickly to 6-fluoro-2-methylisoquinolin-1-one (283 mg, 1.61 mmol) in acetic acid (7.0 mL) under $N_2$ and cooled in an icebath. The icebath was removed and the thick suspension was stirred for 10 min at room temp. Ice and $H_2O$ and EtOAc were added. Extractive work-up with EtOAc, washing with aq 0.5N NaOH, $H_2O$, satd aq $KHSO_4$ and brine, gave the title compound as a cream solid (313 mg) which was carried on without purification.

Step 3: N-[3-(6-fluoro-2-methyl-1-oxoisoquinolin-4-yl)phenyl]methanesulfonamide

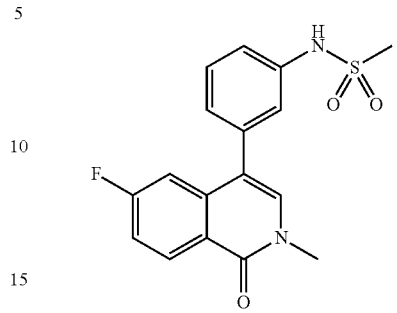

For about 3 min $N_2$ was bubbled through a mixture of 4-bromo-6-fluoro-2-methyl-isoquinolin-1-one (41 mg, 0.16 mmol), (3-methanesulfonamidophenyl)boronic acid (38 mg, 0.18 mmol), aq 1M $K_3PO_4$ (0.3 mL) and Pd(dppf)Cl$_2$ (12 mg, 0.016 mmol) in dioxane (1.2 mL) which was then microwaved for 1 hr at 120° C. Work-up was similar to that described for Example 18, step 3. Purification using silica gel chromatography, eluting with 40-80% EA in hexane over 5 min and continuing 80% isocratic EA gave the title compound (28 mg, 0.08 mmol) as a cream solid in a combined yield of 38% over steps 1-3. $^1$H NMR (400 MHz, DMSO-d$_6$): δ 3.06 (s, 3H), 3.56 (s, 3H), 7.15-7.22 (m, 2H), 7.25-7.31 (m, 2H), 7.41 (td, J=8.65, 2.65 Hz, 1H), 7.45-7.52 (m, 1H), 7.61 (s, 1H), 8.40 (dd, J=9.09, 6.06 Hz, 1H), 9.88 (s, 1H). LCMS (M+H)$^+$: 347.

Examples 48-50 in Table 8 were prepared from title compound of Example 47, step 2, in one step using the appropriate phenyl boronic acid/ester in a manner similar to Example 47, step 3 (one step) or in two steps from the appropriate aniline boronic acid/ester in a manner similar to Example 47, step 3 followed by sulfonylation of the aniline with either methanesulfonyl chloride or ethanesulfonyl chloride in a manner similar to Example 41, step 4 (two steps).

TABLE 8

| Ex. No. | R$^1$ | Name | No. of steps (from Ex. No.) | $^1$H NMR (ppm (d), 400 MHz) | MS (M + H) |
|---|---|---|---|---|---|
| 48 | ![structure with SO2NH2] | 3-(6-fluoro-2-methyl-1-oxoisoquinolin-4-yl)benzenesulfonamide | 1 | (DMSO-d$_6$) 3.58 (s, 3H) 7.11 (dd, J = 10.61, 2.53 Hz, 1H) 7.41-7.49 (m, 3H) 7.65-7.76 (m, 3H) 7.87-7.93 (m, 2H) 8.42 (dd, J = 8.84, 6.06 Hz, 1H) | 333 |

TABLE 8-continued

| Ex. No. | R[1] | Name | No. of steps (from Ex. No.) | $^1$H NMR (ppm (d), 400 MHz) | MS (M + H) |
|---|---|---|---|---|---|
| 49 | ![structure] | N-ethyl-3-(6-fluoro-2-methyl-1-oxoisoquinolin-4-yl)benzenesulfonamide | 1 | (DMSO-d6) 1.00 (t, J = 7.33 Hz, 3H) 2.81-2.89 (m, 2H) 3.58 (s, 3H) 7.09 (dd, J = 10.36, 2.53 Hz, 1H) 7.44 (td, J = 8.65, 2.40 Hz, 1H) 7.65 (t, J = 5.68 Hz, 1H) 7.69 (s, 1H) 7.72-7.79 (m, 2H) 7.82-7.90 (m, 2H) 8.42 (dd, J = 9.09, 6.06 Hz, 1H) | 361 |
| 50 | ![structure] | N-[4-chloro-3-(6-fluoro-2-methyl-1-oxoisoquinolin-4-yl)phenyl]ethanesulfonamide | 2 | (DMSO-d6) 1.22 (t, J = 7.33 Hz, 3H) 3.16-3.24 (m, 2H) 3.56 (s, 3H) 6.72 (dd, J = 10.23, 2.40 Hz, 1H) 7.24 (d, J = 2.53 Hz, 1H) 7.34 (dd, J = 8.59, 2.78 Hz, 1H) 7.40 (td, J = 8.72, 2.53 Hz, 1H) 7.60 (d, J = 8.84 Hz, 1H) 7.65 (s, 1H) 8.38 (dd, J = 8.84, 5.81 Hz, 1H) 9.86-10.28 (m, 1H) | 395, 397 |

Example 51: N-[3-(2-methyl-1-oxo-2,7-naphthyridin-4-yl)phenyl]methanesulfonamide Step 1: 2-methyl-2,7-naphthyridin-1-one

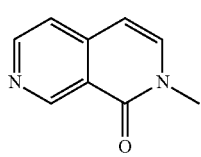

Sodium hydride (2.9 g, 72.5 mmol, 60% in oil) was added in portions to 2H-2,7-naphthyridin-1-one (3.5 g, 24.0 mmol) in dry DMF (50 mL) at 0° C. After stirring at 0° C. for 30 min, MeI (17.0 g, 118.7 mmol) was added and the mixture was stirred for an additional 30 min. Satd aq NH4Cl (250 mL) and EtOAc (100 mL) were added. Extractive work-up with EtOAc and purification by silica gel chromatography (DCM:MeOH=100:1 to 10:1) gave the title compound (0.5 g, 13.1%) as a yellow solid. $^1$H NMR (CDCl3, 400 MHz): δ 9.54 (1H, s), 8.64-8.62 (1H, d, J=5.6 Hz), 7.27-7.26 (1H, d, J=5.2 Hz), 7.22-7.20 (1H, d, J=5.6 Hz), 6.37-6.35 (1H, d, J=7.2 Hz), 3.54 (3H, s).

Step 2: 4-bromo-2-methyl-2,7-naphthyridin-1-one

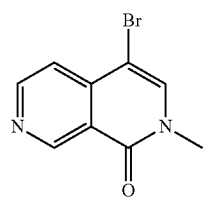

Bromine (1.1 g, 6.87 mmol) in acetic acid (10 mL) was added dropwise to 2-methyl-2,7-naphthyridin-1-one (1.1 g, 6.87 mmol) in acetic acid (60 mL) at 10-15° C. After stirring at 15° C. for 1 hr, the mixture was concentrated under vacuum. Purification by silica gel chromatography (DCM:MeOH=50:1 to 10:1) gave the title compound (0.45 g, 27.4%) as a yellow solid. $^1$H NMR (CDCl3, 400 MHz): δ 9.61 (1H, s), 8.86-8.85 (1H, d, J=5.6 Hz), 7.62-7.60 (1H, d, J=5.6 Hz), 7.56 (1H, s), 3.63 (3H, s).

Step 3: N-[3-(2-methyl-1-oxo-2,7-naphthyridin-4-yl)phenyl]methanesulfonamide

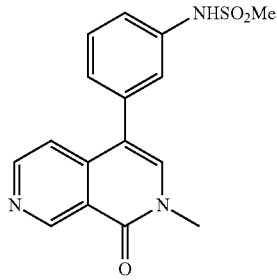

A mixture of 4-bromo-2-methyl-2,7-naphthyridin-1-one (50 mg, 0.21 mmol), [3-(methanesulfonamido)phenyl]boronic acid (68 mg, 0.31 mmol), Pd(dppf)Cl$_2$ (15.3 mg, 0.021 mmol) and aq K$_3$PO$_4$ (1 M, 0.3 mL, 0.3 mmol) in dioxane (3 mL) was microwaved at 90° C. for 40 min. Purification by silica gel chromatography (PE:EA=100:1 to 1:1) followed by preparative HPLC gave the title compound (48.1 mg, 69.8%) as a white solid. $^1$H NMR (400 MHz, Methanol-d$_4$): δ 9.56 (s, 1H), 8.68 (d, J=6.4 Hz, 1H), 7.96 (s, 1H), 7.81 (d, J=6.4 Hz, 1H), 7.51 (t, J=7.6 Hz, 1H), 7.37 (d, J=2.0 Hz, 1H), 7.34 (d, J=1.6 Hz, 1H), 7.26 (d, J=7.6 Hz, 1H), 3.71 (s, 3H), 3.03 (s, 3H). LCMS: 330.0 (M+H)$^+$.

Examples 52-56 in Table 9 were prepared from title compound of Example 51, step 2, in one step using the appropriate phenyl boronic acid/ester in a manner similar to Example 51, step 3.

TABLE 9

| Ex. No. | R$^1$ | Name | $^1$H NMR (ppm (d), 400 MHz) | MS (M + H) |
|---|---|---|---|---|
| 52 | 3-(ethylsulfonamido)phenyl | N-[3-(2-methyl-1-oxo-2,7-naphthyridin-4-yl)phenyl]ethanesulfonamide | 1H NMR (400 MHz, CDCl$_3$) d 9.71 (s, 1H), 8.72 (d, J = 6.0 Hz, 1 H), 7.48 (t, J = 7.6 Hz, 1H), 7.37 (d, J = 6.0 Hz, 1H), 7.29-7.26 (m, 3H), 7.20 (d, J = 7.6 Hz, 1H), 6.74 (s, 1H), 3.69 (s, 3H), 3.21 (q, J = 7.6 Hz, 2H), 1.43 (t, J = 7.6 Hz, 3H) | 344 |
| 53 | 3-(N-ethylsulfamoyl)phenyl | N-ethyl-3-(2-methyl-1-oxo-2,7-naphthyridin-4-yl)benzenesulfonamide | 1H NMR (400 MHz, CDCl$_3$) d 9.72 (s, 1H), 8.73 (d, J = 5.6 Hz, 1H), 7.95 (d, J = 7.2 Hz, 1H), 7.92 (s, 1H), 7.67-7.62 (m, 2H), 7.33 (s, 1H), 7.30 (d, J = 5.6 Hz, 1H), 4.48 (s, 1H), 3.70 (s, 3H), 3.13-3.12 (m, 2H), 1.18 (t, J = 7.2 Hz, 3H) | 344 |
| 54 | 3-(N-benzylsulfamoyl)-4-methoxyphenyl | N-benzyl-2-methoxy-5-(2-methyl-1-oxo-2,7-naphthyridin-4-yl)benzenesulfonamide | 1H NMR (400 MHz, CDCl$_3$) d 9.72 (s, 1H), 8.74 (d, J = 5.6 Hz, 1H), 7.93 (s, 1H), 7.54 (dd, J$_1$ = 8.4 Hz, J$_2$ = 2.4 Hz, 1H), 7.27-7.26 (s, 6H), 7.19 (d, J = 3.2 Hz, 1H) 7.06 (d, J = 8.4 Hz, 1H), 5.26 (s, 1H), 4.20 (d, J = 5.2 Hz, 2H), 3.96 (s, 3H), 3.70 (s, 3H) | 436 |
| 55 | 3-sulfamoylphenyl | 3-(2-methyl-1-oxo-2,7-naphthyridin-4-yl)benzenesulfonamide | 1H NMR (400 MHz, DMSO-d$_6$) d 9.46 (d, J = 9.2 Hz, 1H), 8.73 (d, J = 5.6 Hz, 1H), 7.89-7.88 (m, 3H), 7.73-7.69 (m, 2H), 7.39-7.38 (d, J = 5.2 Hz, 1H), 3.60 (s, 3H) | 316 |
| 56 | 4-methoxy-3-sulfamoylphenyl | 2-methoxy-5-(2-methyl-1-oxo-2,7-naphthyridin-4-yl)benzenesulfonamide | 1H NMR (400 MHz, DMSO-d$_6$) d 9.44 (s, 1H), 8.72 (d, J = 5.6 Hz, 1H), 7.80 (s, 1H), 7.77 (d, J = 2.4 Hz, 1H), 7.65-7.63 (dd, J$_1$ = 8.4 Hz, J$_2$ = 2.4 Hz, 1H), 7.34 (d, J = 8.4 Hz, 1H), 7.33 (d, J = 5.2 Hz, 1H), 3.97 (s, 3H), 3.59 (s, 3H) | 346 |

Example 57: N-[4-(2,4-difluorophenoxy)-3-(2-methyl-1-oxo-2,7-naphthyridin-4-yl)phenyl]ethanesulfonamide

Step 1: 4-(2,4-difluorophenoxy)-3-(4,4,5,5-tetramethyl-1,3,2-dioxaborolan-2-yl)aniline

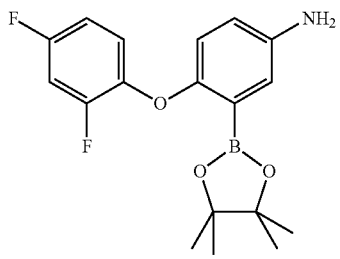 [SMILES: CC1(C)OB(c2cc(N)ccc2Oc2ccc(F)cc2F)OC1(C)C]

A mixture of 3-bromo-4-(2,4-difluorophenoxy)aniline (300 mg, 1 mmol), 4,4,5,5-tetramethyl-2-(4,4,5,5-tetramethyl-1,3,2-dioxaborolan-2-yl)-1,3,2-dioxaborolane (518 mg, 2 mmol), KOAc (300 mg, 3 mmol) and Pd(dppf)Cl$_2$ (73.2 mg, 0.1 mmol) in dioxane (6 mL) was microwaved at 100° C. for 2 hr. Purification by silica gel chromatography (PE:EA=10:1 to 5:1) gave the title compound (200 mg, 56%). LCMS: 348.0 (M+H)$^+$.

Step 2: 4-[5-amino-2-(2,4-difluorophenoxy)phenyl]-2-methyl-2,7-naphthyridin-1-one

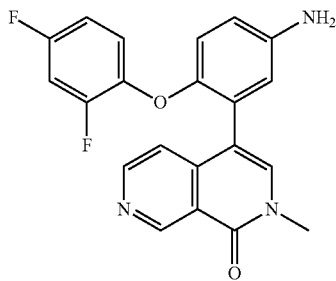 [SMILES: Cn1cc(-c2cc(N)ccc2Oc2ccc(F)cc2F)c2ccncc2c1=O]

For 5 min, N$_2$ was bubbled through a mixture of 4-(2,4-difluorophenoxy)-3-(4,4,5,5-tetramethyl-1,3,2-dioxaborolan-2-yl)aniline (64.8 mg, 0.187 mmol), the title compound of Example 51, step 2 (30.0 mg, 0.124 mmol), K$_2$CO$_3$ (51.6 mg, 0.374 mmol) and Pd(dppf)Cl$_2$ (18.3 mg, 0.025 mmol) in dioxane (2.0 mL) and H$_2$O (0.2 mL) which was then microwaved at 100° C. for 1 hr. Purification by preparative TLC (DCM:MeOH=20:1, Rf=0.5) gave the title compound (25.0 mg, 53%) as yellow gum. LCMS: 380.0 (M+H)$^+$.

Step 3: N-[4-(2,4-difluorophenoxy)-3-(2-methyl-1-oxo-2,7-naphthyridin-4-yl)phenyl]ethanesulfonamide

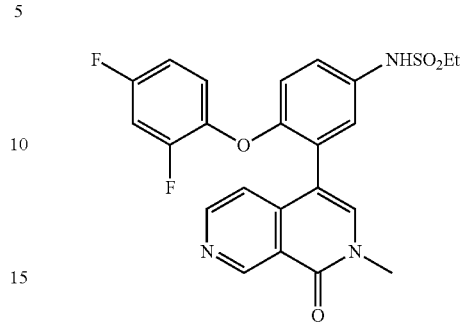

Ethanesulfonyl chloride (25.4 mg, 0.198 mmol) was added to 4-[5-amino-2-(2,4-difluorophenoxy)phenyl]-2-methyl-2,7-naphthyridin-1-one (25.0 mg, 0.066 mmol) and TEA (20.0 mg, 0.198 mmol) in DCM (5 mL) at 0° C. The mixture was stirred at room temp for 18 hr and then purified by preparative HPLC to give the title compound (8.5 mg, 27.4%) as yellow gum. $^1$H NMR (Methanol-d$_4$, 400 MHz): δ 9.54 (s, 1H), 8.68 (d, J=4.4 Hz, 1H), 8.00 (s, 1H), 7.66 (d, J=8.4 Hz, 1H), 7.38-7.33 (m, 2H), 7.09-6.99 (m, 2H), 6.96-6.94 (d, J=8.4 Hz, 1H), 6.91-6.85 (m, 1H), 3.70 (s, 3H), 3.15 (q, J=7.6 Hz, 2H), 1.35 (t, J=7.6 Hz, 3H). LCMS: 472.1 (M+H)$^+$.

Example 58: N-[3-(7-fluoro-2-methyl-1-oxoisoquinolin-4-yl)phenyl]methanesulfonamide

Step 1: 7-fluoro-2-methylisoquinolin-1-one

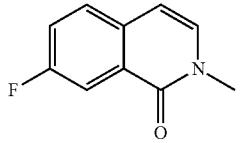

Under N$_2$, sodium hydride (710 mg, 29.4 mmol) was added to 7-fluoro-2H-isoquinolin-1-one (4 g, 24.55 mmol) in dry DMF (40 mL) at 0° C. After stirring at 0° C. for 20 min, CH$_3$I (5.2 g, 36.7 mmol) was added. The mixture was stirred at 26° C. for 2 hr. Satd aq NH$_4$Cl (20 mL) was added and after extractive work-up with EtOAc, purification by silica gel chromatography (PE:EA=10:1) gave the title compound (2.2 g, 50%) as an off-white solid. $^1$H NMR (CDCl$_3$, 400 MHz): δ 8.06 (dd, J$_1$=9.6 Hz, J$_2$=2.8 Hz, 1H), 7.50 (dd, J$_1$=8.8 Hz, J$_2$=5.2 Hz, 1H), 7.38-7.36 (m, 1H), 7.03 (d, J=7.6 Hz, 1H), 6.48 (d, J=7.2 Hz, 1H), 3.61 (s, 3H). LCMS: 178.1 [M+H]$^+$.

Step 2: 4-bromo-7-fluoro-2H-isoquinolin-1-one

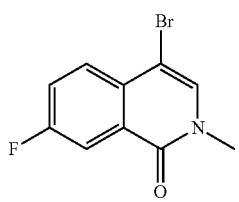

Bromine (3.8 g, 24 mmol) in acetic acid (6 mL) was added slowly to a mixture of 7-fluoro-2-methylisoquinolin-1-one (4 g, 22.4 mmol) in acetic acid (8 mL) at 0° C. After stirring at 26° C. for 2 hr, the mixture was poured into $H_2O$ (100 mL) and the solid was collected by filtration. Purification by silica gel chromatography (PE:EA=20:1) gave the title compound (1.4 g, 44%) as an off-white solid. $^1H$ NMR ($CDCl_3$, 400 MHz): δ 8.11 (d, J=9.2 Hz, 1H), 7.84 (dd, $J_1$=9.6 Hz, $J_2$=4.8 Hz, 1H), 7.49-7.45 (m, 1H), 7.34 (s, 1H), 3.62 (3H, s). LCMS: 255.9 [M+H]$^+$.

Step 3: N-[3-(7-fluoro-2-methyl-1-oxoisoquinolin-4-yl)phenyl]methanesulfonamide

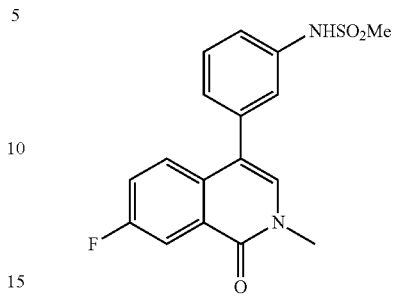

4-Bromo-7-fluoro-2H-isoquinolin-1-one was treated with [3-(methanesulfonamido)phenyl]boronic acid in a manner similar to Example 51, step 3. Isolation and purification also in a similar manner gave the title compound (18 mg, 26.5%) a white solid. $^1H$ NMR (400 MHz, $CDCl_3$): δ 8.17 (dd, $J_1$=9.2 Hz, $J_2$=2.8 Hz, 1H), 7.52 (dd, $J_1$=8.0 Hz, $J_2$=4.0 Hz 1H), 7.50-7.45 (m, 1H), 7.38-7.32 (m, 1H), 7.31-7.27 (m, 2H), 7.26-7.21 (m, 1H), 7.03 (s, 1H), 6.72 (brs, 1H), 3.67 (s, 3H), 3.09 (s, 3H). LCMS: 347.0 (M+H)$^+$.

Examples 59-64 in Table 10 were prepared from title compound of Example 58, step 2 using the appropriate phenyl boronic acid/ester in a manner similar to Example 18, step 3.

TABLE 10

| Ex. No. | $R^1$ | Name | $^1H$ NMR (ppm (δ), 400 MHz) | MS (M + H) |
|---|---|---|---|---|
| 59 | 3-substituted phenyl-SO$_2$NHEt | N-ethyl-3-(7-fluoro-2-methyl-1-oxoisoquinolin-4-yl)benzenesulfonamide | (CDCl$_3$) 8.17 (dd, $J_1$ = 9.6 Hz, $J_2$ = 2.4 Hz, 1H), 7.93-7.92 (m, 2H), 7.64-7.63 (s, 2H), 7.46-7.45 (m, 1H), 7.36-7.35 (m, 1H), 7.06 (s, 1H), 4.58 (brs, 1H), 3.14-3.07 (m, 2H), 1.16 (t, J = 7.2 Hz, 3H) | 361 |
| 60 | 4-methoxy-3-substituted phenyl-SO$_2$NHBn | N-benzyl-5-(7-fluoro-2-methyl-1-oxoisoquinolin-4-yl)-2-methoxybenzenesulfonamide | (CDCl$_3$) δ 8.20 (dd, $J_1$ = 9.3 Hz, $J_2$ = 2.8 Hz, 1H), 7.96 (d, J = 2.4 Hz, 1H), 7.54 (ddd, $J_1$ = 8.5 Hz, $J_2$ = 2.3 Hz, 1H), 7.47-7.44 (m, 1H), 7.41-7.36 (m, 1H), 7.30-7.25 (m, 3H), 7.22-7.20 (m, 2H), 7.06 (d, J = 8.5 Hz, 1H), 7.04 (s, 1H), 5.34 (t, J = 6.0 Hz, 1H), 4.21 (d, J = 6.3 Hz, 2H), 3.97 (s, 3H), 3.70 (s, 3H) | 453 |
| 61 | 3-substituted phenyl-SO$_2$NH$_2$ | 3-(7-fluoro-2-methhyl-1-oxoisoquinolin-4-yl)benzenesulfonamide | (CDCl$_3$) 7.13 (dd, $J_1$ = 9.6 Hz, $J_2$ = 2.8 Hz, 1H), 7.03-7.01 (m, 2H), 6.84-6.82 (m, 2H), 6.76-6.74 (m, 1H), 6.69 (s, 1H), 6.67-6.66 (m, 1H), 6.58-6.56 (m, 2H), 2.71 (s, 3H) | 333 |

TABLE 10-continued

[Structure: 7-fluoro-2-methyl-4-R₁-isoquinolin-1(2H)-one]

| Ex. No. | R¹ | Name | ¹H NMR (ppm (δ), 400 MHz) | MS (M + H) |
|---|---|---|---|---|
| 62 | [phenyl-NHSO₂Et] | N-[3-(7-fluoro-2-methyl-1-oxoisoquinolin-4-yl)phenyl]ethanesulfonamide | (CDCl₃) 8.17 (dd, J₁ = 9.2 Hz, J₂ = 2.8 Hz, 1H), 7.53 (dd, J₁ = 8.8 Hz, J₂ = 3.6 Hz, 1H), 7.44 (t, J = 8.4 Hz, 1H), 7.28-7.27 (m, 3H), 7.20 (d, J = 7.6 Hz, 1H), 7.03 (s, 1H), 6.79 (s, 1H), 3.67 (s, 3H), 3.20 (q, J = 7.2 Hz, 2H), 1.43 (t, J = 7.2 Hz, 3H) | 361 |
| 63 | [phenyl-SO₂Et] | 4-(3-ethylsulfonylphenyl)-7-fluoro-2-methylisoquinolin-1-one | (CDCl₃) 1.15 (t, J = 7.45 Hz, 3H) 3.38 (q, J = 7.41 Hz, 2H) 3.60 (s, 3H) 7.52-7.57 (m, 1H) 7.61-7.67 (m, 2H) 7.78-7.87 (m, 2H) 7.91-8.03 (m, 3H) | 346 |
| 64 | [methoxyphenyl-SO₂NH₂] | 5-(7-fluoro-2-methyl-1-oxoisoquinolin-4-yl)-2-methoxybenzenesulfonamide | (DMSO-d₆) δ 7.98 (d, J = 7.2 Hz, 1H), 7.74 (s, 1H), 7.65-7.61 (m, 2H), 7.51-7.48 (m, 2H), 7.35 (d, J = 8.4 Hz, 1H), 7.18 (s, 2H), 3.97 (s, 3H), 3.57 (s, 3H) | 363 |

Example 65:
2-methyl-4-(1-methylpyrazol-4-yl)isoquinolin-1-one

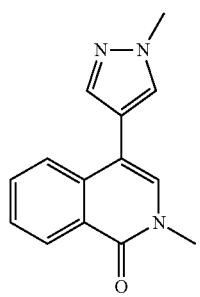 [SMILES: Cn1cc(-c2cn(C)c(=O)c3ccccc23)cn1]

For 3 min, N₂ was bubbled through a mixture of 4-bromo-2-methylisoquinolin-1(2H)-one (54 mg, 0.23 mmol), (1-methylpyrazol-4-yl)boronic acid (31 mg, 0.25 mmol), aq 2M Na₂CO₃ (0.375 mL) and Pd(dppf)Cl₂ (8 mg, 0.01 mmol) in 1,4-dioxane (1.5 mL) which was then microwaved at 120° C. for 1 hr. Work-up in a manner similar to Example 18, step 3, and two successive silica gel chromatographies, eluting with 15-80% EA in hexane over 6 min and continuing 80% isocratic EA followed by a second chromatography 15-100% EA in hexane over 6 min and continuing 100% isocratic EA gave the title compound (28 mg, 0.12 mmol) as a cream solid in 51% yield. ¹H NMR (400 MHz, DMSO-d₆): δ ppm 3.54 (s, 3H) 3.92 (s, 3H) 7.50 (s, 1H) 7.55 (ddd, J=8.02, 5.87, 2.27 Hz, 1H) 7.60-7.64 (m, 1H) 7.70-7.80 (m, 2H) 7.95 (s, 1H) 8.31 (d, J=7.83 Hz, 1H). LCMS (M+H)⁺: 240.

Examples 66-71 in Table 11 were prepared from 4-bromo-2-methylisoquinolin-1(2H)-one in a similar manner to Example 65 using commercially available boronic acids/esters or from commercially available tin compounds using standard Stille-type coupling conditions.

TABLE 11

| Ex. No. | R¹ | Name | ¹H NMR (ppm (δ), 400 MHz) | MS (M + H) |
|---|---|---|---|---|
| 66 | | 4-(furan-2-yl)-2-methylisoquinolin-1-one | (CHLOROFORM-d) 3.61-3.70 (m, 3H) 6.50-6.57 (m, 2H) 7.37 (s, 1H) 7.50-7.58 (m, 2 H) 7.69 (dd, J = 8.30, 7.03, 1.46 Hz, 1H) 7.93 (d, J = 8.20 Hz, 1H) 8.51 (dd, J = 8.01, 0.98 Hz, 1H) | 2.26 |
| 67 | | 2-methyl-4-(1,3-oxazol-2-yl)isoquinolin-1-one | (CHLOROFORM-d) 3.72 (s, 3H) 7.30 (s, 1H) 7.56-7.61 (m, 1H) 7.74 (s, 1H) 7.79 (ddd, J = 8.40, 7.03, 1.37 Hz, 1H) 7.99 (s, 1H) 8.52 (dd, J = 8.01, 0.98 Hz, 1H) 8.93 (d, J = 8.40 Hz, 1H) | 227 |
| 68 | | 2-methyl-4-(1H-pyrazol-5-yl)isoquinolin-1-one | (CHLOROFORM-d) 3.61-3.71 (m, 3H) 6.66 (br. s., 1H) 7.34 (s, 1H) 7.57 (t, J = 7.42 Hz, 1H) 7.68 (t, J = 7.52 Hz, 1H) 7.76 (d, J = 8.01 Hz, 1H) 7.83 (br. s., 1H) 8.52 (d, J = 7.81 Hz, 1H) | 226 |
| 69 | | 2-methyl-4-(1-methylimidazol-2-yl)isoquinolin-1-one | (METHANOL-d₄) 3.55 (s, 3 H) 3.65 (s, 3H) 7.10 (br. s., 1H) 7.17 (br. s., 1H) 7.28 (s, 1H) 7.54-7.62 (m, 2H) 7.71 (t, J = 7.61 Hz, 1H) 8.41 (d, J = 8.20 Hz, 1H) | 240 |
| 70 | | 2-methyl-4-pyridin-2-ylisoquinolin-1-one | (METHANOL-d₄) 3.69 (s, 3H) 7.48 (d, J = 5.86 Hz, 1H) 7.58 (br. s., 2H) 7.65 (d, J = 7.81 Hz, 1H) 7.71 (t, J = 7.22 Hz, 1H) 7.76-7.80 (m, 1H) 7.98 (t, J = 7.03 Hz, 1H) 8.42 (d, J = 7.81 Hz, 1H) 8.68 (d, J = 3.32 Hz, 1H) | 237 |
| 71 | | 2-methyl-4-pyrimidin-2-ylisoquinolin-1-one | (METHANOL-d₄) 3.73 (s, 3H) 7.41 (t, J = 4.88 Hz, 1H) 7.59 (t, J = 7.71 Hz, 1H) 7.76 (t, J = 7.71 Hz, 1H) 8.27 (s, 1H) 8.42 (d, J = 8.20 Hz, 1H) 8.82 (d, J = 8.40 Hz, 1H) 8.90 (d, J = 4.88 Hz, 2H) | 238 |

Example 72: N-[3-[2-methyl-6-(6-methylpyridin-3-yl)-1-oxoisoquinolin-4-yl]phenyl]ethanesulfonamide Step 1: 2-methyl-6-(6-methylpyridin-3-yl)isoquinolin-1-one

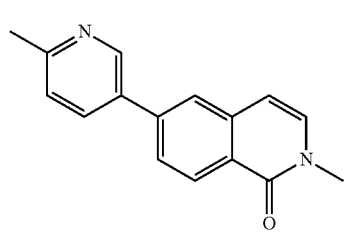

A mixture of 6-bromo-2-methylisoquinolin-1-one (160 mg, 0.67 mmol), (6-methylpyridin-3-yl)boronic acid (166 mg, 0.32 mmol), Pd(dppf)Cl₂ (60 mg, 0.08 mmol) and satd aq NaHCO₃ (0.6 mL) in dioxane (6.5 mL) was microwaved at 110° C. for 1.5 hr. Purification using silica gel chromatography (PE:EA=3:1 to 2:3) gave the title compound (160 mg, 95.2%) as a yellow solid. LCMS: 251.2 (M+H)⁺.

Step 2: 4-bromo-2-methyl-6-(6-methylpyridin-3-yl)isoquinolin-1-one

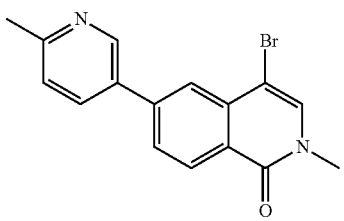

Bromine (97 mg, 0.61 mmol) in acetic acid (0.61 mL) was added dropwise to 2-methyl-6-(6-methylpyridin-3-yl)isoquinolin-1-one (160 mg, 0.64 mmol) in acetic acid (6 mL) at 0° C. After stirring at room temp for 17 min, H₂O (22 mL) was added and adjusted to pH 7-8 with 1M NaOH. Extractive work-up with EtOAc and purification by silica gel chromato-graphy (PE:EA=2:1-3:2) gave the title compound (135 mg, 64.3%) as a yellow solid. LCMS: 329.0 (M+H)+.

Step 3: N-[3-[2-methyl-6-(6-methylpyridin-3-yl)-1-oxoisoquinolin-4-yl]phenyl]ethanesulfonamide

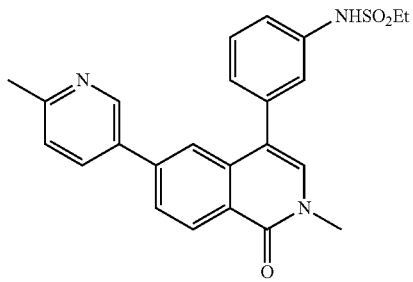

A mixture of 4-bromo-2-methyl-6-(6-methylpyridin-3-yl)isoquinolin-1-one (135 mg, 0.41 mmol), [3-(ethylsulfonylamino)phenyl]boronic acid (141 mg, 0.62 mmol), Pd(dppf)Cl$_2$ (35 mg, 0.05 mmol) and aq 1M K$_3$PO$_4$ (1.03 mL) in dioxane (6 mL) was microwaved at 100° C. for 1 hr. Purification by silica gel chromatography (PE:EA=3:1-1:2) followed by preparative HPLC gave the title compound (25 mg, 14.1%) as a white solid. $^1$H NMR (CDCl$_3$, 400 MHz): δ 8.74 (d, J=2.0 Hz, 1H), 8.41 (d, J=8.4 Hz, 1H), 7.96 (d, J=8.0 Hz, 1H), 7.86 (d, J=8.8 Hz, 1H), 7.75 (s, 1H), 7.58 (s, 1H), 7.47 (t, J=8.0 Hz, 1H), 7.39 (s, 1H), 7.35 (d, J=8.4 Hz, 1H), 7.30 (d, J=8.4 Hz, 1H), 7.24 (d, J=8.4 Hz, 1H), 3.59 (s, 3H), 3.59 (s, 3H), 3.15 (q, J=7.2 Hz, 2H), 1.19 (t, J=7.2 Hz, 3H). LCMS: 434.1 (M+H)+.

Examples 73-74 in Table 12 were prepared from 6-bromo-2-methylisoquinolin-1-one and phenylboronic acid in three steps in a manner similar to Example 72, steps 1-3. For Example 74, [3-(methanesulfonamido)phenyl]boronic acid was substituted for [3-(ethylsulfonyl-amino)phenyl]boronic acid in step 3.

TABLE 12

| Ex. No. | R$^1$ | Name | $^1$H NMR (ppm (δ), 400 MHz) | MS (M + H) |
|---|---|---|---|---|
| 73 | Ethyl | N-[3-(2-methyl-1-oxo-6-phenylisoquinolin-4-yl)phenyl]ethanesulfonamide | (DMSO-d$_6$) 9.94 (brs, 1H), 8.41 (d, J = 8.4 Hz, 1H), 7.85 (d, J = 8.4 Hz, 1H), 7.74 (s, 1H), 7.67 (d, J = 7.6 Hz, 2H), 7.57 (s, 1H), 7.50-7.45 (m, 3H), 7.42 (d, J = 7.6 Hz, 1 H), 7.38 (s, 1H), 7.30 (d, J = 8.0 Hz, 1 H), 7.23 (d, J = 7.6 Hz, 1H), 3.59 (s, 3H), 3.14 (q, J = 7.2 Hz, 2H), 1.19 (t, J = 7.2 Hz, 3H) | 419 |
| 74 | Methyl | N-[3-(2-methyl-1-oxo-6-phenylisoquinolin-4-yl)phenyl]methanesulfonamide | (CHLOROFORM-d) 8.60 (d, J = 8.4 Hz, 1H), 7.78 (dd, J$_1$ = 8.4 Hz, J$_2$ = 1.6 Hz, 1H), 7.72 (d, J = 1.2 Hz, 1H), 7.60-7.58 (m, 2H), 7.49-7.36 (m, 5H), 7.31 (d, J = 7.6 Hz, 1H), 7.26-7.23 (m, 1H), 7.10 (s, 1 H), 6.47 (s, 1H), 3.70 (s, 3H), 3.08 (s, 3H) | 405 |

Example 75: N-[3-(2,6-dimethyl-1-oxoisoquinolin-4-yl)phenyl]ethanesulfonamide

Step 1: 2,6-dimethylisoquinolin-1-one

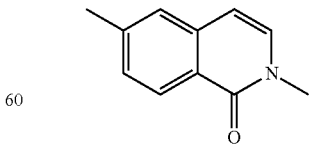

A mixture of 6-bromo-2-methylisoquinolin-1-one (200.0 mg, 0.84 mmol), methylboronic acid (251.0 mg, 4.2 mmol), Pd(PPh$_3$)$_4$ (93.0 mg, 0.08 mmol), K$_2$CO$_3$ (232.0 mg, 1.68 mmol) and H$_2$O (2 drops) in dioxane (10.0 mL) was microwaved at 120° C. for 1 hr. Purification by silica gel chromatography (PE:EA=5:1) gave the title compound (120.0 mg, 82.8%) as a light yellow solid. LCMS: 174.3 (M+H)+.

Step 2: 4-bromo-2,6-dimethylisoquinolin-1-one

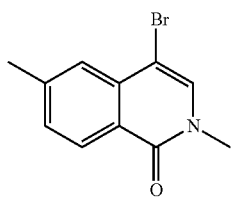

2,6-Dimethylisoquinolin-1-one (120.0 mg, 0.60 mmol) in acetic acid (4 mL) was treated with Br$_2$ (96 mg, 0.6 mmol) in acetic acid (0.6 mL) at 0° C. in a manner similar to Example 72, step 2. Isolation, also in a similar manner, gave the title compound (145.0 mg, 82.9%) as a white yellow solid. $^1$H NMR (CDCl$_3$, 400 MHz): δ 8.33 (d, J=8.0 Hz, 1H), 7.60 (s, 1H), 7.37 (d, J=8.0 Hz, 1H), 7.35 (s, 1H), 3.60 (s, 3H), 2.54 (s, 3H). LCMS: 252.1 (M+H)$^+$.

Step 3: N-[3-(2,6-dimethyl-1-oxoisoquinolin-4-yl)phenyl]ethanesulfonamide

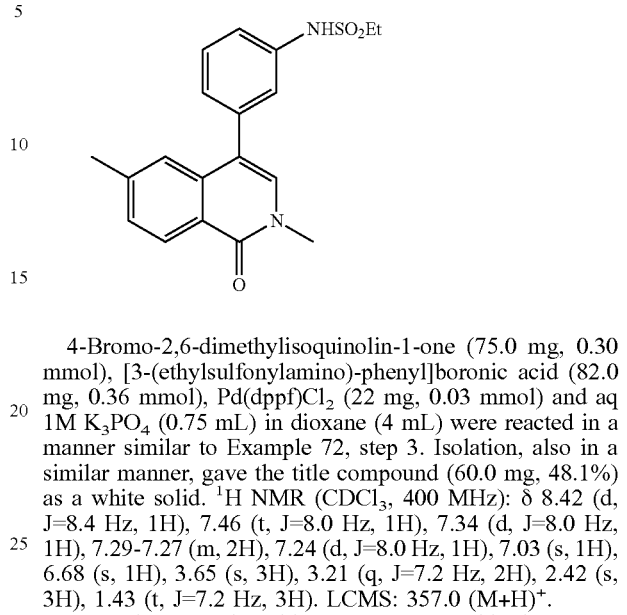

4-Bromo-2,6-dimethylisoquinolin-1-one (75.0 mg, 0.30 mmol), [3-(ethylsulfonylamino)-phenyl]boronic acid (82.0 mg, 0.36 mmol), Pd(dppf)Cl$_2$ (22 mg, 0.03 mmol) and aq 1M K$_3$PO$_4$ (0.75 mL) in dioxane (4 mL) were reacted in a manner similar to Example 72, step 3. Isolation, also in a similar manner, gave the title compound (60.0 mg, 48.1%) as a white solid. $^1$H NMR (CDCl$_3$, 400 MHz): δ 8.42 (d, J=8.4 Hz, 1H), 7.46 (t, J=8.0 Hz, 1H), 7.34 (d, J=8.0 Hz, 1H), 7.29-7.27 (m, 2H), 7.24 (d, J=8.0 Hz, 1H), 7.03 (s, 1H), 6.68 (s, 1H), 3.65 (s, 3H), 3.21 (q, J=7.2 Hz, 2H), 2.42 (s, 3H), 1.43 (t, J=7.2 Hz, 3H). LCMS: 357.0 (M+H)$^+$.

Examples 76-78 in Table 13 were prepared in three steps in a similar manner to Example 75 steps 1-3. For Examples 76 and 77, ethylboronic acid was substituted for methylboronic acid in step 1. For Examples 77 and 78, [3-(methanesulfonamido)phenyl]boronic acid was substituted for [3-(ethylsulfonylamino)phenyl]boronic acid in step 3.

TABLE 13

| Ex. No. | R$^1$ | R$^2$ | Name | 1H NMR (ppm (δ), 400 MHz) | MS (M + H) |
|---|---|---|---|---|---|
| 76 | Ethyl | Ethyl | N-[3-(6-ethyl-2-methyl-1-oxoisoquinolin-4-yl)phenyl]ethanesulfonamide | (CDCl$_3$) 8.41 (d, J = 8.4 Hz, 1H), 7.42 (t, J = 8.4 Hz, 1H), 7.38 (d, J = 8.4 Hz, 1H), 7.29-7.25 (m, 2H), 7.19 (d, J = 7.6 Hz, 1H), 7.00 (s, 1H), 6.90 (s, 1H), 3.61 (s, 3H), 3.17 (q, J = 7.6 Hz, 2H), 2.67 (q, J = 7.6 Hz, 2H), 1.39 (t, J = 7.6 Hz, 3H), 1.19 (t, J = 7.6 Hz, 3H) | 371 |
| 77 | Ethyl | Methyl | N-[3-(6-ethyl-2-methyl-1-oxoisoquinolin-4-yl)phenyl]methanesulfonamide | (CDC$_3$) 8.45 (d, J = 8.4 Hz, 1H), 7.48 (t, J = 8.0 Hz, 1H), 7.38 (d, J = 8.0 Hz, 1H), 7.32-7.26 (m, 5H), 7.04 (s, 1H), 6.66 (s, 1 H), 3.65 (s, 3 H), 3.10 (s, 3H), 2.70 (q, J = 7.6 Hz, 2H), 1.23 (t, J = 7.6 Hz, 3H) | 357 |
| 78 | Methyl | Methyl | N-[3-(2,6-dimethyl-1-oxoisoquinolin-4-yl)phenyl]methanesulfonamide | (DMSO-d$_6$) 9.88 (brs, 1H), 8.23 (d, J = 8.0 Hz, 1H), 7.49-7.45 (m, 2H), 7.39 (d, J = 8.4 Hz, 1H), 7.33 (s, 1H), 7.28-7.24 (m, 2H), 7.19 (d, J = 8.0 Hz, 1H), 3.55 (s, 3H), 3.06 (s, 3H), 2.39 (s, 3H) | 343 |

Example 79: 4-(5-ethylsulfonyl-2-methoxyphenyl)-2-methyl-6-(1-methylpyrazol-4-yl) isoquinolin-1-one Step 1: 2-bromo-4-ethylsulfanyl-1-fluorobenzene

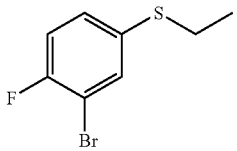

To a mixture of 3-bromo-4-fluorobenzenethiol (2.07 g, 10 mmol) and $K_2CO_3$ (4.14 g, 30 mmol) in acetone (20 mL) was added EtI (3.12 g, 20 mmol). The mixture was stirred at room temp for 12 hr, filtered, and the volatile components were removed under vacuum to give the title compound (2.34 g) as light yellow oil which was carried on without purification. $^1$H NMR (CDCl$_3$, 400 MHz): δ 7.54 (dd, $J_1$=6.4 Hz, $J_2$=2.4 Hz, 1H), 7.26-7.25 (m, 1H), 7.05 (t, J=8.4 Hz, 1H), 2.91 (q, J=7.6 Hz, 2H), 1.30 (t, J=7.6 Hz, 3H).

Step 2: 2-bromo-4-ethylsulfonyl-1-fluorobenzene

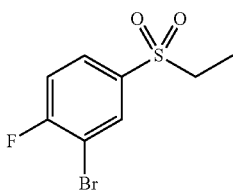

To 2-bromo-4-ethylsulfanyl-1-fluorobenzene (2.2 g, 9.36 mmol) in DCM (20 mL) was added m-CPBA (6.47 g, 37.4 mmol). The mixture was stirred at room temp for 12 hr. Aq satd $Na_2S_2O_3$ (100 mL) was added, and extractive work-up with $CH_2Cl_2$ gave the title compound (1.5 g, 50%) as a yellow solid which was carried on without purification. $^1$H NMR (CDCl$_3$, 400 MHz): δ 8.15 (dd, $J_1$=6.4 Hz, $J_2$=2.4 Hz, 1H), 7.88-7.85 (m, 1H), 7.32 (t, J=8.4 Hz, 1H), 3.14 (q, J=7.2 Hz, 2H), 1.31 (t, J=7.6 Hz, 3H).

Step 3: 2-bromo-4-ethylsulfonyl-1-methoxybenzene

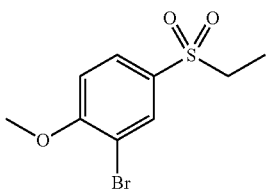

A mixture of 2-bromo-4-ethylsulfonyl-1-fluorobenzene (0.6 g, 2.25 mmol) and sodium methoxide (1.2 g, 22.2 mmol) in THF (20 mL) was stirred at room temp for 18 hr. Water (30 mL) was added and extractive work-up with EtOAc followed by silica gel chromatography (PE:EA=10:1-1:1) gave the title compound (0.5 g, 79.4%) as a yellow solid. $^1$H NMR (CDCl$_3$, 400 MHz): δ 8.08 (d, J=2.4 Hz, 1H), 7.87-7.84 (dd, $J_1$=8.6 Hz, $J_2$=2.4 Hz, 1H), 7.04 (d, J=8.8 Hz, 1H), 3.99 (s, 3H), 3.11 (q, J=7.4 Hz, 2H), 1.30 (t, J=7.4 Hz, 3H).

Step 4: 4-(5-ethylsulfonyl-2-methoxyphenyl)-2-methyl-6-(1-methylpyrazol-4-yl) isoquinolin-1-one

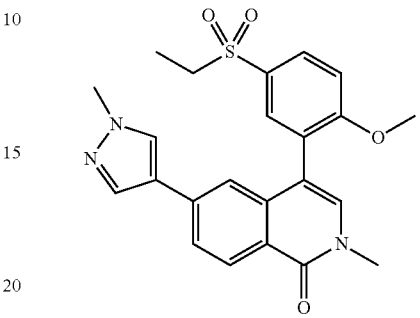

For 5 min $N_2$ was bubbled into a mixture of 2-bromo-4-ethylsulfonyl-1-methoxybenzene (300 mg, 1.07 mmol), the title compound of Example 46, step 2 (300 mg, 0.82 mmol), $K_3PO_4$ (435.6 mg, 2.05 mmol) and Pd(dppf)Cl$_2$ (120.2 mg, 0.16 mmol) in dioxane (8 mL) and $H_2O$ (0.8 mL) which was then microwaved at 110° C. for 30 min. Purification by silica gel chromatography (DCM:MeOH=100:0-20:1) gave the title compound (200 mg, 55.7%) as a yellow solid. $^1$H NMR (CDCl$_3$, 400 MHz): δ 8.51 (d, J=8.4 Hz, 1H), 8.03 (dd, $J_1$=8.8 Hz, $J_2$=2.8 Hz, 1H), 7.86 (d, J=2.4 Hz, 1H), 7.72 (s, 1H), 7.64 (s, 1H), 7.63-7.61 (m, 1H), 7.19 (d, J=8.8 Hz, 1H), 7.15 (d, J=1.2 Hz, 1H), 7.09 (s, 1H), 3.97 (s, 3H), 3.85 (s, 3H), 3.68 (s, 3H), 3.18 (q, J=7.6 Hz, 2H), 1.35 (t, J=7.6 Hz, 3H). LCMS: 438.1 (M+H)$^+$.

Example 80: 4-(5-ethylsulfonyl-2-hydroxyphenyl)-2-methyl-6-(1-methylpyrazol-4-yl) isoquinolin-1-one

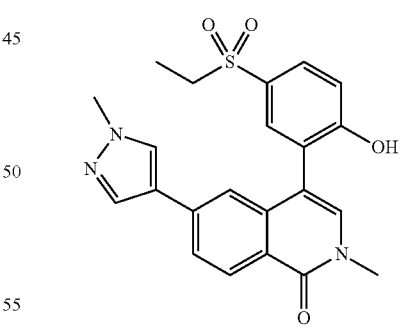

At −78° C., a 4 M soln of BBr$_3$ (2.3 mL, 9.2 mmol) in $CH_2Cl_2$ was added to the title compound of Example 79 (200.0 mg, 0.458 mmol) in dry $CH_2Cl_2$ (8 mL). The mixture was refluxed for 18 hr. Extractive work-up with $CH_2Cl_2$ and purification by silica gel chromatography (DCM:MeOH=100:1-20:1) gave the title compound (70 mg, 36.1%) as a brown solid. $^1$H NMR (CDCl$_3$, 400 MHz): δ 8.39 (d, J=8.4 Hz, 1H), 7.99 (s, 1H), 7.87 (dd, $J_1$=8.8 Hz, $J_2$=2.4 Hz, 1H), 7.80 (s, 1H), 7.79 (s, 1H), 7.76 (d, J=1.6 Hz, 1H), 7.39 (s, 1H), 7.35 (d, J=1.2 Hz, 1H), 7.18 (d, J=8.8 Hz, 1H), 3.91 (s, 3H), 3.67 (s, 3H), 3.25 (q, J=7.6 Hz, 2H), 1.27 (t, J=7.6 Hz, 3H). LCMS: 424.0 (M+H)+.

Example 81: 4-(2-ethoxy-5-ethylsulfonylphenyl)-2-methyl-6-(1-methylpyrazol-4-yl) isoquinolin-1-one

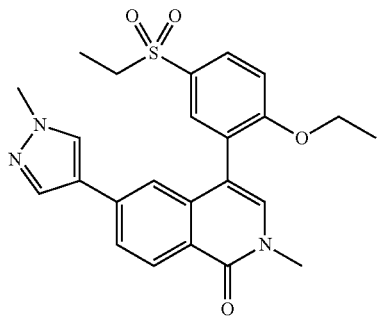 [SMILES: CCOc1ccc(S(=O)(=O)CC)cc1-c1cn(C)c(=O)c2ccc(-c3cnn(C)c3)cc12]

A mixture of the title compound of Example 80 (25.0 mg, 0.059 mmol), ethyl iodide (27.7 mg, 0.177 mmol), and K$_2$CO$_3$ (24.5 mg, 0.177 mmol) in acetone (2 mL) was stirred at room temp for 18 hr. After CH$_2$Cl$_2$ extractive work-up, purification by preparative TLC (PE:EA=2:1) gave the title compound (15.8 mg, 60%) as a white solid. $^1$H NMR (CDCl$_3$, 400 MHz): δ 8.48 (d, J=8.4 Hz, 1H), 7.97 (dd, J$_1$=8.4 Hz, J$_2$=2.4 Hz, 1H), 7.86 (d, J=2.4 Hz, 1H), 7.68 (s, 1H), 7.62 (s, 1H), 7.61 (dd, J$_1$=8.4 Hz, J$_2$=1.6 Hz, 1H), 7.17 (d, J=1.2 Hz, 1H), 7.15 (d, J=8.4 Hz, 1H), 7.08 (s, 1H), 4.3 (q, J=7.2 Hz, 2H), 3.94 (s, 3H), 3.66 (s, 3H), 3.17 (q, J=7.6 Hz, 2H), 1.35 (t, J=7.6 Hz, 3H), 1.18 (t, J=7.2 Hz, 3H). LCMS: 452.1 (M+H)+.

Examples 82-84 in Table 14, the title compound of Example 80 was O-alkylated with the appropriate alkyl halide in a similar manner to Example 81. Example 85 in Table 14 was prepared in two steps by O-alkylation with tert-butyl N-(2-bromoethyl)carbamate in a similar manner to Example 81 followed by deprotection of the the Boc group in a manner similar to Example 32.

TABLE 14

| Ex. No. | R$^1$ | Name | $^1$H NMR (ppm (δ), 400 MHz) | MS (M + H) |
|---|---|---|---|---|
| 82 | cyclopropylmethyl | 4-[2-(cyclopropylmethoxy)-5-ethylsulfonylphenyl]-2-methyl-6-(1-methylpyrazol-4-yl)isoquinolin-1-one | (CDCl$_3$) 8.51 (d, J = 8.4 Hz, 1 H), 7.97 (dd, J$_1$ = 8.4 Hz, J$_2$ = 2.4 Hz, 1 H), 7.88 (d, J = 2.8 Hz, 1 H), 7.70 (s, 1 H), 7.64 (s, 1 H), 7.62 (dd, J$_1$ = 8.4 Hz, J$_2$ = 1.6 Hz, 1 H), 7.21 (d, J = 1.6 Hz, 1 H), 7.13 (d, J = 8.8 Hz, 1 H), 7.11 (s, 1 H), 3.96 (s, 3 H), 3.91-3.86 (m, 2 H), 3.67 (s, 3 H), 3.17 (q, J = 7.6 Hz, 2 H), 1.34 (t, J = 7.6 Hz, 3 H), 0.99-0.96 (m, 1 H), 0.38-0.35 (m, 2 H), 0.10-0.02 (m, 2 H) | 478 |
| 83 | propyl | 4-(5-ethylsulfonyl-2-propoxyphenyl)-2-methyl-6-(1-methylpyrazol-4-yl) isoquinolin-1-one | (CDCl$_3$) 8.51 (d, J = 8.4 Hz, 1 H), 7.97 (dd, J$_1$ = 8.4 Hz, J$_2$ = 2.4 Hz, 1 H), 7.88 (d, J = 2.8 Hz, 1 H), 7.70 (s, 1 H), 7.64 (s, 1 H), 7.62 (dd, J$_1$ = 8.4 Hz, J$_2$ = 1.6 Hz, 1 H), 7.21 (d, J = 1.6 Hz, 1 H), 7.13 (d, J = 8.8 Hz, 1 H), 7.11 (s, 1 H), 3.96 (s, 3 H), 3.91-3.86 (m, 2 H), 3.67 (s, 3 H), 3.17 (q, J = 7.6 Hz, 2 H), 1.34 (t, J = 7.6 Hz, 3 H), 0.99-0.96 (m, 1 H), 0.38-0.35 (m, 2 H), 0.10-0.02 (m, 2 H) | 466 |
| 84 | 2-hydroxyethyl | 4-[5-ethylsulfonyl-2-(2-hydroxyethoxy)phenyl]-2-methyl-6-(1-methylpyrazol-4-yl)isoquinolin-1-one | (CDCl$_3$) 8.51 (d, J = 8.4 Hz, 1 H), 7.97 (dd, J$_1$ = 8.4 Hz, J$_2$ = 2.4 Hz, 1 H), 7.88 (d, J = 2.8 Hz, 1 H), 7.70 (s, 1 H), 7.64 (s, 1 H), 7.62 (dd, J$_1$ = 8.4 Hz, J$_2$ = 1.6 Hz, 1 H), 7.21 (d, J =1.6 Hz, 1 H), 7.13 (d, J = 8.8 Hz, 1 H), 7.11 (s, 1 H), 3.96 (s, 3 H), 3.91-3.86 (m, 2 H), 3.67 (s, 3 H), 3.17 (q, J = 7.6 Hz, 2 H), 1.34 (t, J = 7.6 Hz, 3 H), 0.99-0.96 (m, 1 H), 0.38-0.35 (m, 2 H), 0.10-0.02 (m, 2 H) | 468 |

TABLE 14-continued

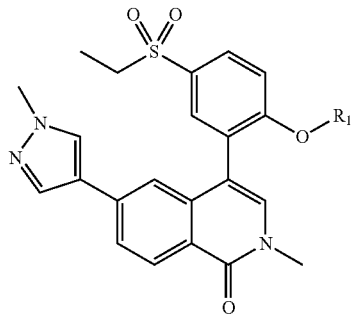

| Ex. No. | R¹ | Name | ¹H NMR (ppm (δ), 400 MHz) | MS (M + H) |
|---|---|---|---|---|
| 85 | 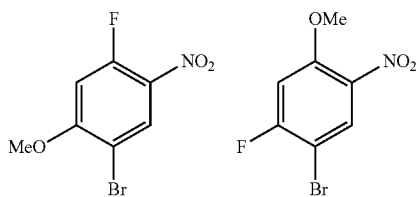 | 4-[2-(2-aminoethoxy)-5-ethylsulfonylphenyl]-2-methyl-6-(1-methylpyrazol-4-yl)isoquinolin-1-one | (Methanol-d₄) 8.38 (d, J= 8.4 Hz, 1 H), 8.06 (dd, J₁ = 8.4 Hz, J₂ = 2.4 Hz, 1 H), 8.05 (s, 1 H), 7.89 (d, J =2.4 Hz, 1 H), 7.83 (s, 1 H), 7.76 (dd, J₁ = 8.4 Hz, J₂ = 1.2 Hz, 1 H), 7.47 (d, J = 8.8 Hz, 1 H), 7.44 (s, 1 H), 7.27 (d, J = 1.2 Hz, 1 H), 4.46-4.32 (m, 2 H), 3.92 (s, 3 H), 3.67 (s, 3 H), 3.27 (q, J = 7.2 Hz, 2 H), 3.25-3.17 (m, 1 H), 3.04-2.96 (m, 1 H), 1.28 (t, J = 7.2 Hz, 3 H) | |

Example 86: N-[2-fluoro-4-methoxy-5-[2-methyl-6-(1-methylpyrazol-4-yl)-1-oxoisoquinolin-4-yl]phenyl]ethanesulfonamide Step 1: 1-bromo-4-fluoro-2-methoxy-5-nitrobenzene and 1-bromo-2-fluoro-4-methoxy-5-nitrobenzene

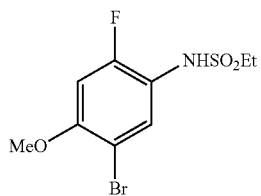

At 0° C., sodium methoxide (344 mg, 6.3 mmol) in dry MeOH (7 mL) was added dropwise to 1-bromo-2,4-difluoro-5-nitrobenzene (1 g, 4.2 mmol) in dry MeOH (18 mL). The mixture was stirred at room temp for 10 hr and then refluxed for 8 hr. After extractive work-up, purification by silica gel chromatography (PE:EA=1:0 to 10:1) gave a mixture of the two title compounds (765 mg, 72.9%) in about a 2:1 ratio as a yellow solid. LCMS: 249.9 (M+H)⁺.

Step 2: 5-bromo-2-fluoro-4-methoxyaniline

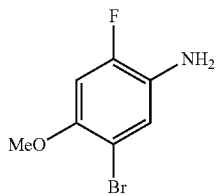 [SMILES: COc1cc(F)c(N)cc1Br]

Zinc dust (0.95 g, 14.5 mmol) was added to the mixture of two title compounds from step 1 (725 mg, 2.9 mmol) in 2:1 MeOH:satd aq NH₄Cl (10 mL) at 0° C. After stirring at room temp for 30 min, extractive work-upwith EtOAc and purification by silica gel chromatography (PE:EA=1:0 to 10:1) gave the title compound (260 mg, 41%) as a yellow solid free of the corresponding regioisomer. ¹H NMR (400 MHz, DMSO-d₆): δ 7.00 (d, J=9.6 Hz, 1H), 6.94 (d, J=13.2 Hz, 1H), 4.88 (s, 2H), 3.72 (s, 3H). LCMS: 219.9 (M+H)⁺.

Step 3: N-(5-bromo-2-fluoro-4-methoxyphenyl)ethanesulfonamide

At 0° C., ethansulfonylchloride (1.4 g, 10.9 mmol) was added dropwise to a soln of 5-bromo-2-fluoro-4-methoxyaniline (3.5 g, 24.0 mmol) in pyridine (1.3 g, 16.4 mmol) and dry CH₂Cl₂ (20 mL). After stirring at room temp for 10 hr, CH₂Cl₂ extractive work-up and purification by silica gel chromatography (PE:EA=10:0 to 3:1) gave the title compound (2.5 g, 73.5%) as a yellow solid. ¹H NMR (400 MHz, CDCl₃) δ 7.77 (d, J=8.4 Hz, 1H), 6.73 (d, J=11.6 Hz, 1H), 6.27 (s, 1H), 3.89 (s, 3H), 3.10 (q, J=7.6 Hz, 2H), 1.40 (t, J=7.6 Hz, 3H). LCMS: 334.0 (M+Na)⁺.

Step 4: N-[2-fluoro-4-methoxy-5-[2-methyl-6-(1-methylpyrazol-4-yl)-1-oxoisoquinolin-4-yl]phenyl]ethanesulfonamide

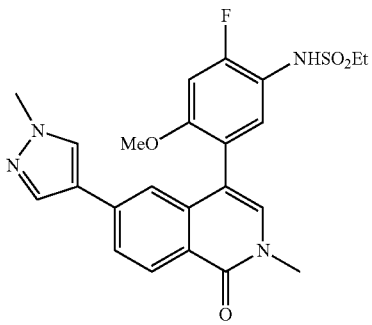

A mixture of N-(5-bromo-2-fluoro-4-methoxyphenyl)ethanesulfonamide (63 mg, 0.20 mmol), the title compound of Example 46, step 2 (75 mg, 0.21 mmol), Pd(dppf)Cl$_2$ (19 mg, 0.03 mmol) and aq K$_3$PO$_4$ (1 M, 0.5 mL, 0.5 mmol) in dioxane (3 mL) was microwaved at 100° C. for 1 hr. Purification by silica gel chromatography (PE:EA=1:1-1:4) followed by preparative HPLC gave the title compound (25 mg, 26.3%) as a white solid. $^1$H NMR (400 MHz, CDCl$_3$) δ 8.48 (d, J=8.4 Hz, 1H), 7.72 (s, 1H), 7.69 (s, 1H), 7.58 (d, J=7.2 Hz, 1H), 7.49 (d, J=9.2 Hz, 1H), 7.25 (s, 1H), 7.04 (s, 1H), 6.85 (d, J=12.0 Hz, 1H), 6.37 (s, 1H), 3.94 (s, 3H), 3.75 (s, 3H), 3.65 (s, 3H), 3.17 (q, J=7.2 Hz, 2H), 1.46 (t, J=7.2 Hz, 3H). LCMS: 471.1 (M+H)$^+$.

Example 87: N-[3-(2-methyl-1-oxo-6-pyridin-2-ylisoquinolin-4-yl)phenyl]ethanesulfonamide Step 1: 2-methyl-6-(4,4,5,5-tetramethyl-1,3,2-dioxaborolan-2-yl)isoquinolin-1-one

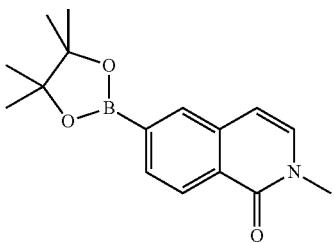

For 5 min N$_2$ was bubbled through a mixture of 6-bromo-2-methylisoquinolin-1-one (0.5 g, 2.1 mmol), 4,4,5,5-tetramethyl-2-(tetramethyl-1,3,2-dioxaborolan-2-yl)-1,3,2-dioxaborolane (0.8 g, 3.1 mmol), Pd(dppf)Cl$_2$ (153.6 mg, 0.21 mmol) and KOAc (0.51 g, 5.2 mmol) in dioxane (5 mL) which was then microwaved at 110° C. for 40 min. Purification by silica gel chromatography (PE:EA=20:1-5:1) gave the title compound (0.45 g, 75.0%) as yellow gum.

Step 2: 2-methyl-6-pyridin-2-ylisoquinolin-1-one

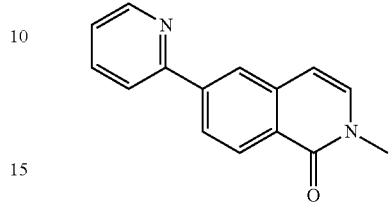

A mixture of 2-methyl-6-(4,4,5,5-tetramethyl-1,3,2-dioxaborolan-2-yl)isoquinolin-1-one (420 mg, 1.47 mmol), 2-bromopyridine (698 mg, 4.42 mmol), Pd(dppf)Cl$_2$ (107 mg, 0.15 mmol) and satd aq NaHCO$_3$ (3.5 mL) in DMSO (25 mL) was microwaved at 150° C. for 45 min. After extractive work-up with EtOAc, purification by silica gel chromatography (PE:EA=3:1-3:2) gave the title compound (160 mg, 46.0%) as a white solid. $^1$H NMR (CDCl$_3$, 400 MHz): δ 8.76 (d, J=4.8 Hz, 1H), 8.53 (d, J=8.0 Hz, 1H), 8.20 (d, J=1.2 Hz, 1H), 8.07 (dd, J$_1$=8.4 Hz, J$_2$=1.6 Hz, 1H), 7.85-7.82 (m, 2H), 7.34-7.30 (m, 1H), 7.11 (d, J=7.2 Hz, 1H), 6.6 (d, J=7.2 Hz, 1H), 3.64 (s, 3H). LCMS: 237.2 (M+H)$^+$.

Step 3: 4-bromo-2-methyl-6-pyridin-2-ylisoquinolin-1-one

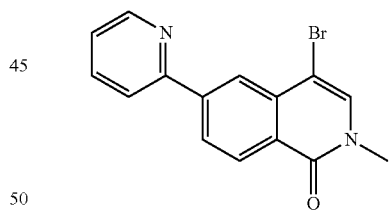

At 0° C., bromine (78 mg, 0.49 mmol) in acetic acid (0.3 mL) was added dropwise to 2-methyl-6-pyridin-2-ylisoquinolin-1-one (115 mg, 0.49 mmol) in acetic acid (20 mL). The mixture was stirred at room temp for 20 min. Extractive work-up with CH$_2$Cl$_2$ and purification by silica gel chromatography (PE:EA=5:1-1:1) gave the title compound (73.0 mg, 47.7%) as a yellow solid. $^1$H NMR (CDCl$_3$, 400 MHz): δ 8.79 (d, J=4.4 Hz, 1H), 8.55 (d, J=8.4 Hz, 1H), 8.44 (s, 1H), 8.19 (d, J=8.8 Hz, 1H), 7.90 (d, J=8.0 Hz, 1H), 7.85 (t, J=7.2 Hz, 1H), 7.42 (s, 1H), 7.36-7.34 (m, 1H), 3.64 (s, 3H). LCMS: 314.9 (M+H)$^+$.

Step 4: N-[3-(2-methyl-1-oxo-6-pyridin-2-ylisoquinolin-4-yl)phenyl]ethanesulfonamide

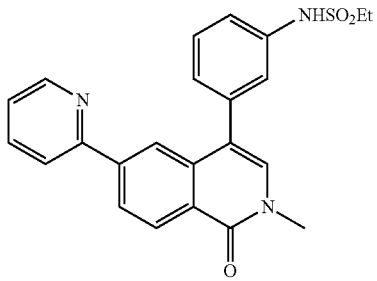

For 5 min, $N_2$ was bubbled through a mixture of 4-bromo-2-methyl-6-pyridin-2-yl-isoquinolin-1-one (48.1 mg, 0.153 mmol), [3-(ethylsulfonylamino)phenyl]boronic acid (35.0 mg, 0.153 mmol), Pd(dppf)Cl$_2$ (22.3 mg, 0.03 mmol) and aq 1M K$_3$PO$_4$ (0.38 mL, 0.38 mmol, 1M) in dioxane (5 mL) which was then microwaved at 80° C. for 20 min. Purification by silica gel chromatography (PE:EA=3:1 to 1:2) followed by preparative HPLC gave the title compound (2.5 mg, 3.9%) as a white solid. $^1$H NMR (Methanol-d4, 400 MHz): δ 8.69 (d, J=8.4 Hz, 1H), 8.59 (d, J=8.4 Hz, 1H), 8.23 (d, J=1.2 Hz, 1H), 8.15-8.22 (m, 1H), 8.10 (dd, J$_1$=8.4 Hz, J$_2$=1.6 Hz, 2H), 7.65-7.62 (m, 1H), 7.50-7.45 (m, 3H), 7.38-7.30 (m, 2H), 3.71 (s, 3H), 3.16 (q, J=7.2 Hz, 2H), 1.32 (t, J=7.2 Hz, 3H). LCMS: 420.1 (M+H)$^+$.

Example 88: 4-[4-fluoro-2-methoxy-5-(methylsulfonylmethyl)phenyl]-2-methyl-6-(1-methylpyrazol-4-yl)isoquinolin-1-one

Step 1: 4-[4-fluoro-2-methoxy-5-(methylsulfonylmethyl)phenyl]-2-methyl-6-(1-methylpyrazol-4-yl)isoquinolin-1-one

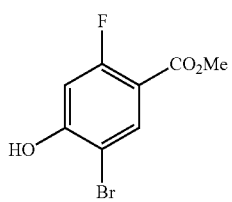 [SMILES: COC(=O)c1cc(Br)c(O)cc1F]

At 0-10° C., Br$_2$ (24 g, 150 mmol) in acetic acid (100 mL) was added drop-wise to a soln of methyl 2-fluoro-4-hydroxybenzoate (25.5 g, 150 mmol) in acetic acid (600 mL). The mixture was stirred at room temp overnight. Extractive work-up with EtOAc and purification by silica gel chromatography (100% DCM) gave the title compound (32.0 g, 86.5%) as a white solid. $^1$H NMR (Methanol-d$_4$, 400 MHz): δ 8.03 (d, J=7.2 Hz, 1H), 6.68 (d, J=12.0 Hz, 1H), 3.86 (s, 3H). LCMS: 249.1 (M+H)$^+$.

Step 2: 5-methyl 5-bromo-2-fluoro-4-methoxybenzoate

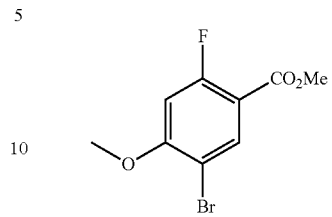

Methyl iodide (10.6 g, 74.9 mmol) was added drop-wise to 4-[4-fluoro-2-methoxy-5-(methylsulfonylmethyl)phenyl]-2-methyl-6-(1-methylpyrazol-4-yl)isoquinolin-1-one (6.0 g, 24.1 mmol) and K$_2$CO$_3$ (9.98 g, 72.3 mmol) in MeCN (120 mL). The mixture was heated at 80° C. overnight. Extractive work-up with EtOAc and purification by silica gel chromatography (PE:EA=60:1-40:1) gave the title compound (5.1 g, 80.4%) as a white solid which was carried on without purification. $^1$H NMR (CDCl$_3$, 400 MHz): δ 8.15 (d, J=7.6 Hz, 1H), 6.66 (d, J=12.0 Hz, 1H), 3.94 (s, 3H), 3.91 (s, 3H). LCMS: 263.0 (M+H)$^+$.

Step 3: (5-bromo-2-fluoro-4-methoxyphenyl)methanol

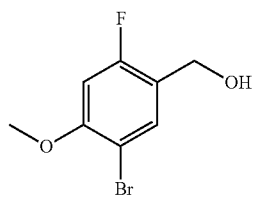

DIBAL-H (45.6 mL, 1M in toluene) was added drop-wise to a soln of 5-methyl 5-bromo-2-fluoro-4-methoxybenzoate (5.0 g, 19.0 mmol) in anhydrous CH$_2$Cl$_2$ (300 mL) at −78° C. The mixture was stirred at −78° C. for 3 hr and then quenched with MeOH and H$_2$O. The mixture was filtered and the filter cake rinsed with CH$_2$Cl$_2$. The filtrate was washed with brine, dried over Na$_2$SO$_4$, filtered, and concentrated to give the title compound (4.18 g, 94.4%) as a white solid which was carried on without purification. $^1$H NMR (DMSO-d$_6$, 400 MHz): δ 7.59 (d, J=7.6 Hz, 1H), 7.02 (d, J=12.4 Hz, 1H), 5.25 (t, J=5.6 Hz, 1H), 4.45 (d, J=5.6 Hz, 2H), 3.84 (s, 3H).

Step 4: 1-bromo-5-(bromomethyl)-4-fluoro-2-methoxybenzene

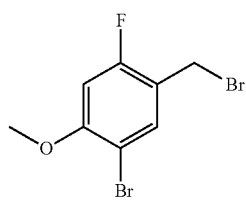

PBr₃ (4.7 g, 17.4 mmol) was added drop-wise to a soln of (5-bromo-2-fluoro-4-methoxyphenyl)methanol (4.1 g, 17.4 mmol) in anhydrous CH₂Cl₂ (40 mL) at 0° C. The mixture was stirred at room temp for 3 hr and poured into ice water. The pH was adjusted to pH 8 with satd aq NaHCO₃. Extractive work-up with CH₂Cl₂ gave the title compound (4.9 g, 94.8%) as a white solid which was carried on without purification. ¹H NMR (DMSO-d₆, 400 MHz): δ 7.56 (d, J=8.0 Hz, 1H), 6.65 (d, J=11.6 Hz, 1H), 4.46 (s, 2H), 3.89 (s, 3H).

Step 5: 1-bromo-4-fluoro-2-methoxy-5-(methylsulfanylmethyl)benzene

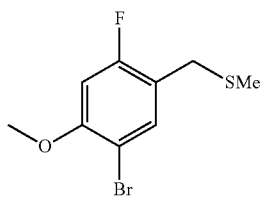

Thiomethoxide (1.19 g, 17.0 mmol) was added to a soln of 1-bromo-5-(bromo-methyl)-4-fluoro-2-methoxybenzene (4.9 g, 16.4 mmol) in anhydrous DMF (25 mL) at 0° C. The mixture was stirred at room temp for 5 hr, and then poured into H₂O (40 mL). Extractive work-up with EtOAc gave the title compound (4.3 g, 99.0%) as colorless oil which was carried on without purification. ¹H NMR (CDCl₃, 400 MHz): δ 7.50 (d, J=8.0 Hz, 1H), 6.64 (d, J=11.2 Hz, 1H), 3.88 (s, 3H), 3.63 (s, 2H), 2.04 (s, 3H).

Step 6: 1-bromo-4-fluoro-2-methoxy-5-(methylsulfonylmethyl)benzene

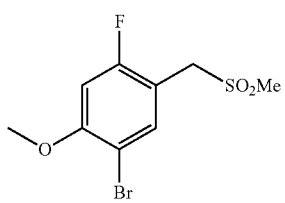

Oxone (20.9 g, 34.1 mmol) in H₂O (100 mL) was added drop-wise to a soln of 1-bromo-4-fluoro-2-methoxy-5-(methylsulfanylmethyl)benzene (4.3 g, 16.2 mmol) in MeOH (100 mL) at 0° C. The mixture was then stirred at room temp for 3 hr and then poured into H₂O. Extractive work-up with EtOAc, washing with satd aq Na₂SO₃ (40 mL) and brine, gave a solid that was triturated with 1:10 EA:MTBE to give the title compound (4.40 g, 93.0%) as a white solid. ¹H NMR (CDCl₃, 400 MHz): δ 7.66 (d, J=8.0 Hz, 1H), 6.72 (d, J=11.2 Hz, 1H), 4.22 (s, 2H), 3.92 (s, 3H), 2.83 (s, 3H). LCMS: 318.9 (M+Na)⁺.

Step 7: 4-[4-fluoro-2-methoxy-5-(methylsulfonylmethyl)phenyl]-2-methyl-6-(1-methylpyrazol-4-yl)isoquinolin-1-one

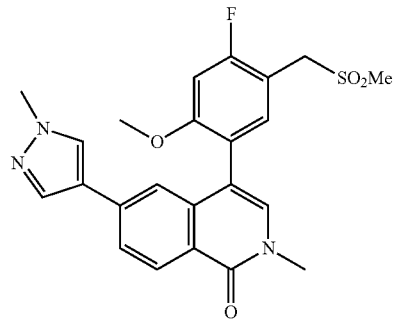 [SMILES: COc1cc(F)c(CS(C)(=O)=O)cc1-c1cn(C)c(=O)c2ccc(-c3cnn(C)c3)cc12]

1-Bromo-4-fluoro-2-methoxy-5-(methylsulfonylmethyl)benzene (34.0 mg, 0.114 mmol), the title compound of Example 46, step 2 (50.0 mg, 0.137 mmol), Pd(dppf)Cl₂ (20.0 mg, 0.027 mmol) and 1M aq K₃PO₄ (0.47 mL, 0.47 mmol) in dioxane (3.0 mL) were microwaved at 100° C. for 40 min. Preparative HPLC gave the title compound (10.0 mg, 18%) as a light yellow solid. ¹H NMR (CDCl₃, 400 MHz): δ 8.47 (d, J=8.0 Hz, 1H), 7.74 (s, 1H), 7.73 (s, 1H), 7.60 (d, J=8.4 Hz, 1H), 7.42 (d, J=8.4 Hz, 1H), 7.27 (s, 1H), 7.05 (s, 1H), 6.85 (d, J=12.0 Hz, 1H), 4.32 (d, J=6.4 Hz, 2H), 3.93 (s, 3H), 3.77 (s, 3H), 3.64 (s, 3H), 2.93 (s, 3H). LCMS: 456.1 (M+H)+.

Example 89: 4-[2-(cyclopropylmethoxy)-5-methylsulfonylphenyl]-2-methylisoquinolin-1-one Step 1: 2-methyl-4-(4,4,5,5-tetramethyl-1,3,2-dioxaborolan-2-yl)isoquinolin-1-one

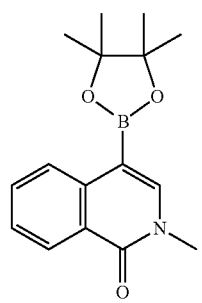 [SMILES: Cn1cc(B2OC(C)(C)C(C)(C)O2)c2ccccc2c1=O]

A suspension of 4-bromo-2-methylisoquinolin-1-one (100 mg, 0.42 mmol), bis(pinacolato)diboron (214 mg, 0.84 mmol), Pd(dppf)Cl₂ (31 mg, 0.04 mmol) and potassium acetate (104 mg, 1.05 mmol) in dioxane (2 mL) under N₂ was warmed to 90° C. for 135 min. It was then cooled to room temp and diluted with EtOAc (8 mL). The mixture was washed with aq satd soln of NaHCO₃ (8 mL) and brine (8 mL). The organic phase was separated, dried over Na₂SO₄, filtered and concentrated under reduced pressure. The residue was purified by normal phase CC (10%-90% EtOAc/Hexanes) to give the title compound (44 mg, 37%). ¹H NMR (CDCl₃, 400 MHz): δ 8.43 (d, J=7.9 Hz, 1H), 8.40 (dd, J=8.2

Hz, 0.9 Hz, 1H), 7.68 (s, 1H), 7.65 (ddd, J=8.2, 8.2, 1.1 Hz, 1H), 7.46 (t, J=7.5 Hz, 1H), 3.63 (s, 3H), 1.38 (s, 12H). LCMS (M+H)+: 286.

Step 2: 4-[2-(cyclopropylmethoxy)-5-methylsulfonylphenyl]-2-methylisoquinolin-1-one

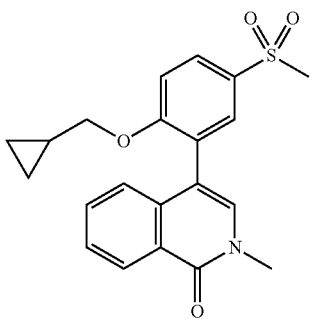 [SMILES: Cn1cc(-c2cc(S(C)(=O)=O)ccc2OCC2CC2)c2ccccc2c1=O]

The title compound was prepared in a manner similar to Example 18, step 3, substituting 2-bromo-1-(cyclopropylmethoxy)-4-methylsulfonylbenzene for 4-bromo-2-methylisoquinolin-1(2H)-one and 2-methyl-4-(4,4,5,5-tetramethyl-1,3,2-dioxaborolan-2-yl)isoquinolin-1-one for N-benzyl-2-methoxy-5-(tetramethyl-1,3,2-dioxaborolan-2-yl)benzamide. $^1$H NMR (DMSO-d6, 400 MHz): δ 0.09 (m, 2H), 0.29 (m, 1H), 0.35 (m, 1H), 0.94 (m, 1H), 3.22 (s, 3H), 3.57 (s, 3H), 3.95 (m, 2H), 7.16 (d, J=7.9 Hz, 1H), 7.37 (d, J=8.8 Hz, 1H), 7.53 (m, 2H), 7.65 (t, J=7.6 Hz, 1H), 7.81 (d, J=2.4 Hz, 1H), 7.97 (dd, J=8.8, 2.4 Hz, 1H), 8.30 (d, J=8.1 Hz, 1H). LCMS (M+H)+: 384.

Alternatively, 4-[2-(cyclopropylmethoxy)-5-methylsulfonylphenyl]-2-methyl-isoquinolin-1-one can be prepared as described below.

Step 1: 2-methyl-4-(4,4,5,5-tetramethyl-1,3,2-dioxaborolan-2-yl)isoquinolin-1-one

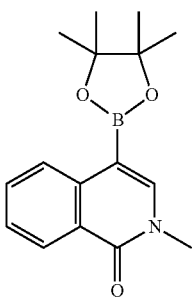 [SMILES: Cn1cc(B2OC(C)(C)C(C)(C)O2)c2ccccc2c1=O]

A mixture of 4-bromo-2-methylisoquinolin-1-one (8.0 g, 33.6 mmol), bis(pinacolato) diboron (17.1 g, 67.2 mmol), KOAc (6.6 g, 67.2 mmol), Pd$_2$(dba)$_3$ (3.1 g, 3.36 mmol) and X-Phos (1.6 g, 3.36 mmol) in anhydrous dioxane (200 mL) was stirred at 60° C. for 12 hr. The rxn mixture was concentrated and the residue was purified by CC on silica gel (PE:EA=15:1) to give the title compound (6.0 g, 62%) as a solid.

Step 2: 4-[2-(cyclopropylmethoxy)-5-methylsulfonylphenyl]-2-methylisoquinolin-1-one The title compound from Step 1 (5.0 g, 17.5 mmol), 2-bromo-1-(cyclopropylmethoxy)-4-methylsulfonylbenzene (6.4 g, 21 mmol), K$_3$PO$_4$ (9.3 g, 43.9 mmol) and Pd(dppf)Cl$_2$ (1.4 g, 1.75 mmol) in a dioxane/H$_2$O (100 mL/10 mL) mixture were stirred at 60° C. for 12 hr. The rxn mixture was concentrated under reduced pressure and the residue was purified by CC on silica gel (EA:DCM=1:4). Appropriate fractions were combined and concentrated under reduce pressure. The resultant solid was recrystallized from DCM:MTBE (1:1, 50 mL) to give the title compound (4.0 g, 60%) as a white solid. $^1$H NMR (CDCl$_3$, 400 MHz): δ 8.51 (dd, J$_1$=8.0 Hz, J$_2$=0.8 Hz, 1H), 7.98 (dd, J$_1$=8.4 Hz, J$_2$=2.4 Hz, 1H), 7.86 (d, J=2.4 Hz, 1H), 7.53 (m, 2H), 7.16 (d, J=7.6 Hz, 1H), 7.10 (m, 2H), 3.88 (m, 2H), 3.66 (s, 3H), 3.09 (s, 3H), 1.02-0.98 (m, 1H), 0.44-0.38 (m, 2H), 0.11-0.09 (m, 2H). LCMS: 384.1 (M+H)+.

Example 90: 4-[2-(cyclopropylmethoxy)-5-methylsulfonylphenyl]-6-fluoro-2-methylisoquinolin-1-one Step 1: 2-[2-(cyclopropylmethoxy)-5-methylsulfonylphenyl]-4,4,5,5-tetramethyl-1,3,2-dioxaborolane

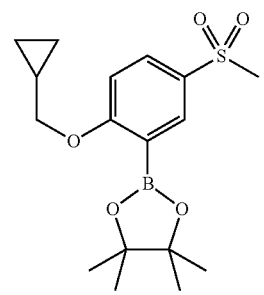 [SMILES: CC1(C)OB(c2cc(S(C)(=O)=O)ccc2OCC2CC2)OC1(C)C]

The title compound was prepared in a manner similar to Example 89, step 1, substituting 2-bromo-1-(cyclopropylmethoxy)-4-methylsulfonylbenzene for 4-bromo-2-methylisoquinolin-1-one. $^1$H NMR (CDCl$_3$, 400 MHz): δ 0.46 (m, 2H), 0.60 (m, 2H), 1.24 (m, 1H), 1.35 (s, 12H), 3.02 (s, 3H), 3.97 (d, J=6.0, 2H), 6.91 (d, J=8.7 Hz, 1H), 7.92 (dd, J=8.7, 2.5 Hz, 1H), 8.15 (d, J=2.4 Hz, 1H). LCMS (M+H)+: 353.

Step 2: 4-[2-(cyclopropylmethoxy)-5-methylsulfonylphenyl]-6-fluoro-2-methyl-isoquinolin-1-one

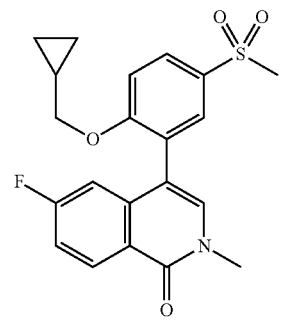 [SMILES: Cn1cc(-c2cc(S(C)(=O)=O)ccc2OCC2CC2)c2cc(F)ccc2c1=O]

The title compound was prepared in a manner similar to Example 18, step 3, substituting the title compound of Example 47, step 2 for 4-bromo-2-methylisoquinolin-1 (2H)-one and 2-[2-(cyclopropylmethoxy)-5-methylsulfonylphenyl]-4,4,5,5-tetramethyl-1,3,2-dioxaborolane for N-benzyl-2-methoxy-5-(tetramethyl-1,3,2-dioxaborolan-2-yl)

benz amide. ¹H NMR (DMSO-d₆, 400 MHz): δ 0.12 (m, 2H), 0.32 (m, 1H), 0.39 (m, 1H), 0.99 (m, 1H), 3.22 (s, 3H), 3.56 (s, 3H), 3.97 (m, 2H), 6.82 (dd, J=10.5, 2.4 Hz, 1H), 7.39 (m, 2H), 7.61 (s, 1H), 7.82 (d, J=2.3 Hz, 1H), 7.98 (dd, J=8.74, 2.4 Hz, 1H), 8.36 (dd, J=8.9, 6.1 Hz, 1H). LCMS (M+H)⁺: 402.

Example 91: 4-[2-(cyclopropylmethoxy)-5-methyl-sulfonylphenyl]-7-fluoro-2-methyl-isoquinolin-1-one

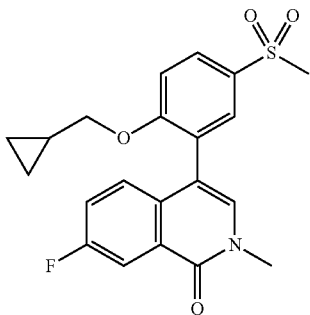 [SMILES: Cn1cc(-c2cc(S(C)(=O)=O)ccc2OCC2CC2)c2ccc(F)cc2c1=O]

The title compound was prepared in a manner similar to Example 18, step 3, substituting the title compound of Example 58, step 2 for 4-bromo-2-methylisoquinolin-1(2H)-one and 2-[2-(cyclopropylmethoxy)-5-methylsulfonyl-phenyl]-4,4,5,5-tetramethyl-1,3,2-dioxaborolane for N-benzyl-2-methoxy-5-(tetramethyl-1,3,2-dioxaborolan-2-yl)benzamide. ¹H NMR (DMSO-d₆, 400 MHz): δ 0.10 (m, 2H), 0.30 (m, 1H), 0.39 (m, 1H), 0.94 (m, 1H), 3.22 (s, 3H), 3.58 (s, 3H), 3.95 (m, 2H), 7.24 (dd, J=9, 5.3 Hz, 1H), 7.38 (d, J=8.8 Hz, 1H), 7.54 (s, 1H), 7.56 (m, 1H), 7.81 (d, J=2.4 Hz, 1H), 7.96 (m, 2H). LCMS (M+H)⁺: 402.

Example 92: 4-[2-(2,4-difluorophenoxy)-5-methyl-sulfonylphenyl]-2-methylisoquinolin-1-one

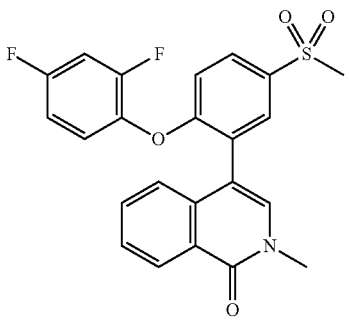

The title compound was prepared in a manner similar to Example 18, step 3, substituting 1-(2-bromo-4-methylsulfo-nylphenoxy)-2,4-difluorobenzene for 4-bromo-2-methyliso-quinolin-1(2H)-one, and 2-methyl-4-(4,4,5,5-tetramethyl-1,3,2-dioxaborolan-2-yl)isoquinolin-1-one for N-benzyl-2-methoxy-5-(tetramethyl-1,3,2-dioxaborolan-2-yl)benzamide. ¹H NMR (DMSO-d₆, 400 MHz): δ 3.27 (s, 3H), 3.58 (s, 3H), 7.03 (d, J=9.2 Hz, 1H), 7.13 (m, 1H), 7.35 (m, 2H), 7.48 (m, 1H), 7.54 (t, J=7.5, 1H), 7.67 (s, 1H), 7.69 (m, 1H), 7.97 (m, 1H), 7.98 (s, 1H), 8.30 (d, J=8.1, 1H). LCMS (M+H)⁺: 442.

Example 93: N-[4-(2,4-difluorophenoxy)-3-(2-methyl-1-oxoisoquinolin-4-yl)phenyl]ethanesulfona-mide

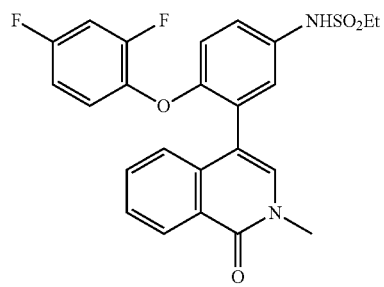

The title compound was prepared in a manner similar to Example 18, step 3, substituting N-[3-bromo-4-(2,4-difluo-rophenoxy)phenyl]ethanesulfonamide for 4-bromo-2-meth-ylisoquinolin-1(2H)-one and 2-methyl-4-(4,4,5,5-tetram-ethyl-1,3,2-dioxaborolan-2-yl)isoquinolin-1-one for N-benzyl-2-methoxy-5-(tetramethyl-1,3,2-dioxaborolan-2-yl)benzamide. ¹H NMR (DMSO-d₆, 400 MHz): δ 1.23 (t, J=7.3 Hz, 3H), 3.13 (q, J=7.8 Hz, 2H), 3.53 (s, 3H), 6.95 (m, 2H), 7.09 (m, 1H), 7.28 (m, 3H), 7.51 (m, 2H), 7.65 (t, J=6.9 Hz, 1H), 8.26 (d, J=0.8 Hz, 1H), 9.83 (s, 1H). LCMS (M+H)⁺: 471.

Example 94: N-[3-(1-methyl-6-oxopyridin-3-yl)phenyl]methanesulfonamide

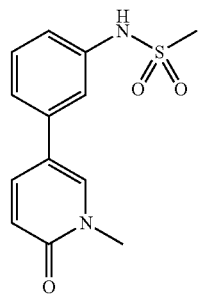 [SMILES: Cn1cc(-c2cccc(NS(C)(=O)=O)c2)ccc1=O]

A mixture of 5-bromo-1-methylpyridin-2-one (100 mg, 0.532 mmol), [3-(methane-sulfonamido)phenyl]boronic acid (171.1 mg, 0.798 mmol), KOAc (130.0 mg, 1.326 mmol) and Pd(dppf)Cl₂ (38.9 mg, 0.05 mmol) in dioxane/H₂O (2 mL/0.5 mL) was stirred at 90° C. for 20 min. The mixture was concentrated and the residue was purified by CC (PE:EA=1:1) to give the title compound (30.0 mg, 20%) as a brown solid. ¹H NMR (CDCl₃, 400 MHz): δ 7.65-7.60 (dd, J₁=7.6 Hz, J₂=2.4 Hz, 1H), 7.54 (d, J=2.4 Hz, 1H), 7.41 (t, J=8.0 Hz, 1H), 7.33 (s, 1H), 7.24 (d, J=7.6 Hz, 1H), 7.17 (d, J=7.6 Hz, 1H), 6.86 (brs, 1H), 6.67 (d, J=9.2 Hz, 1H), 3.65 (s, 3H), 3.05 (s, 3H). LCMS (M+H)⁺: 279.

Example 95: N-[3-(1,4-dimethyl-6-oxopyridin-3-yl)phenyl]methanesulfonamide

Step 1: 5-bromo-1,4-dimethylpyridin-2-one

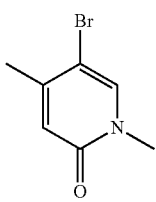

To a soln of 5-bromo-4-methylpyridin-2-ol (1.12 g, 6.0 mmol) in anhydrous THF (20 mL) was added NaH (288.0 mg, 12.0 mmol) and the rxn mixture was stirred at 0° C. for 30 min. Then, methyl iodide (1.7 g, 12.0 mmol) was added and stirred at room temp for 3 hr. Satd NH$_4$Cl (100 mL) was added and the resulting mixture was extracted with EtOAc (100 mL×3). The combined organic layers were washed with brine (100 mL), dried over anhydrous Na$_2$SO$_4$ and concentrated. The residue was purified by CC on silica gel (PE:EA=10:1-2:1) to give the title compound (1.0 g, 83.3%) as a yellow solid. $^1$H NMR (CDCl$_3$, 400 MHz): δ 7.44 (s, 1H), 6.94 (s, 1H), 3.51 (s, 3H), 2.24 (s, 3H). LCMS (M+H)$^+$: 202.

Step 2: N-[3-(1-methyl-6-oxopyridin-3-yl)phenyl]methanesulfonamide

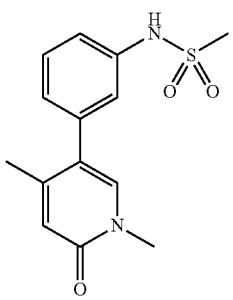

5-Bromo-1,4-dimethylpyridin-2-one was treated with [3-(methanesulfonamido)phenyl]boronic acid in a manner similar to Example 94 to give the title compound as a white solid. $^1$H NMR (CDCl$_3$, 400 MHz) δ 7.43 (t, J=8.0 Hz, 1H), 7.20 (d, J=8.0 Hz, 1H), 7.16 (s, 1H), 7.07 (d, J=7.6 Hz, 1H), 6.71 (s, 1H), 6.69 (s, 1H), 3.67 (s, 3H), 3.07 (s, 3H), 2.16 (s, 3H). LCMS (M+H)$^+$: 293.

Example 96: N-[3-(1,5-dimethyl-6-oxopyridin-3-yl)phenyl]methanesulfonamide

Step 1: 5-bromo-1,3-dimethylpyridin-2-one

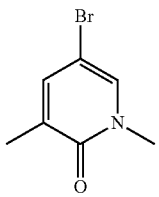

The title compound of step 1 was prepared in a manner similar to Example 95, step 1 using 5-bromo-3-methylpyridin-2-ol instead of 5-bromo-4-methylpyridin-2-ol to give 5-bromo-1,3-dimethylpyridin-2-one. $^1$H NMR (CDCl$_3$, 400 MHz): 7.30 (d, J=2.0 Hz, 1H), 7.26 (d, J=1.6 Hz, 1H), 3.53 (s, 3H), 2.16 (s, 3H). LCMS (M+H)$^+$: 202.

Step 2: N-[3-(1,5-dimethyl-6-oxopyridin-3-yl)phenyl]methanesulfonamide

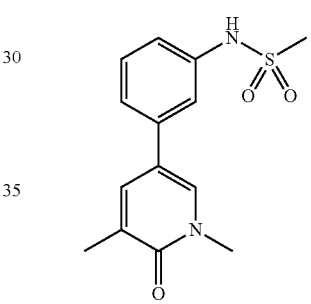

5-Bromo-1,3-dimethylpyridin-2-one was treated with [3-(methanesulfonamido)phenyl]boronic acid in a manner similar to Example 94 to give the title compound as a white solid. $^1$H NMR (DMSO-d6, 400 MHz): 9.74 (s, 1H), 7.91 (d, J=2.4 Hz, 1H), 7.62 (s, 1H), 7.37 (t, J=7.6 Hz, 1H), 7.32 (s, 1H), 7.29 (d, J=7.6 Hz, 1H), 7.13 (d, J=7.6 Hz, 1H), 3.52 (s, 3H), 3.02 (s, 3H), 2.08 (s, 3H). LCMS (M+H)$^+$: 293.

Example 97: N-[3-(1,4,5-trimethyl-6-oxopyridin-3-yl)phenyl]methanesulfonamide Step 1: 5-bromo-3,4-dimethyl-1H-pyridin-2-one

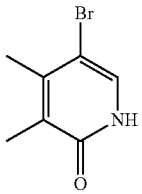

To a mixture of 5-bromo-3,4-dimethylpyridin-2-amine (0.6 g, 3.0 mmol) and H$_2$SO$_4$ (98%, 1.62 mL) and H$_2$O (18 mL) is added a soln of NaNO$_2$ (243.6 mg, 4.2 mmol) in H$_2$O (1.6 mL) drop-wise at 0° C. Then, it was stirred at 31° C. for 30 min and filtered. The resulting solid is washed with H$_2$O to provide the title compound (375.0 mg, 62%) as a white solid. $^1$H NMR (CDCl$_3$, 400 MHz): δ 7.48 (s, 1H), 2.32 (s, 3H), 2.19 (s, 3H). LCMS (M+H)$^+$: 202.

Step 2: 5-bromo-1,3,4-trimethylpyridin-2-one

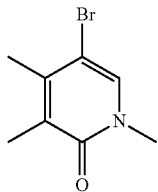

To a soln of 5-bromo-3,4-dimethyl-1H-pyridin-2-one (402.0 mg, 2.0 mmol) in anhydrous THF (20 mL) was added NaH (96.0 mg, 2.4 mmol). The resulting mixture was stirred at 0° C. for 30 min. Methyl iodide (568.0 mg, 4.0 mmol) was added and the rxn was stirred at 32° C. for 3 hr. Then, satd aq NH$_4$Cl (100 mL) was added and the mixture extracted with EtOAc (100 mL×3). The combined organic layers were washed with brine (100 mL), dried over Na$_2$SO$_4$, filtered and concentrated. The residue was purified by CC on silica gel (PE:EA=10:1-2:1) to give the title compound (350.0 mg, 80%) as a white solid. $^1$H NMR (CDCl$_3$, 400 MHz): δ 7.38 (s, 1H), 3.52 (s, 3H), 2.27 (s, 3H), 2.20 (s, 3H). LCMS (M+H)$^+$: 216.

Step 3: N-[3-(1,4,5-trimethyl-6-oxopyridin-3-yl)phenyl]methanesulfonamide

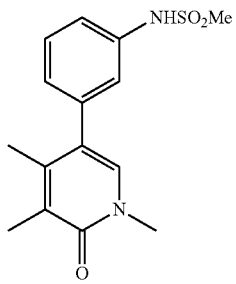

5-Bromo-1,3,4-trimethylpyridin-2-one was treated with [3-(methanesulfonamido)phenyl]boronic acid in a manner similar to Example 94 to give the title compound as a white solid. $^1$H NMR (CDCl$_3$, 400 MHz): δ 7.42 (s, 1H), 7.39 (t, J=7.6 Hz, 1H), 7.24 (s, 1H), 7.16 (s, 1H), 7.08 (s, 1H), 7.05 (d, J=7.6 Hz, 1H), 3.59 (s, 3H), 3.06 (s, 3H), 2.19 (s, 3H), 2.06 (s, 3H). LCMS (M+H)$^+$: 307.

Example 98: 5-[2-(cyclopropylmethoxy)-5-methylsulfonylphenyl]-1-methylpyridin-2-one Step 1: 1-methyl-5-(4,4,5,5-tetramethyl-1,3,2-dioxaborolan-2-yl)pyridin-2-one

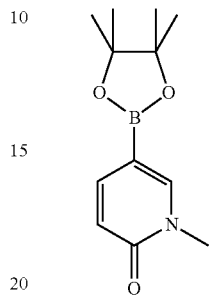

A soln of 5-bromo-1-methylpyridin-2-one (200.0 mg, 1.06 mmol), bis(pinacolato)-diboron (410.0 mg, 1.61 mmol), potassium acetate (270 mg, 2.67 mmol), Pd (dppf) Cl$_2$ (80 mg, 0.11 mmol) in dioxane (5 mL) was heated at 100° C. for 2 hr under microwave. The mixture was filtered, washed with H$_2$O and extracted with EtOAc (20 mL×3). The combined organics were dried over Na$_2$SO$_4$, filtered and concentrated to give the crude title compound (59.0 mg, 23.6%). LCMS (M+H)$^+$: 236.

Step 2: 5-[2-(cyclopropylmethoxy)-5-methylsulfonylphenyl]-1-methylpyridin-2-one

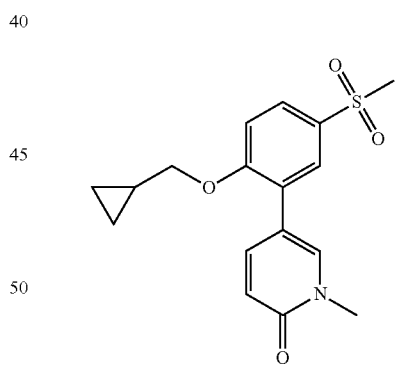

1-Methyl-5-(4,4,5,5-tetramethyl-1,3,2-dioxaborolan-2-yl)pyridin-2-one was treated with 2-bromo-1-(cyclopropylmethoxy)-4-methylsulfonylbenzene in a manner similar to Example 94 to give the title compound. $^1$H NMR (CDCl$_3$, 400 MHz): δ 7.86 (dd, J$_1$=8.8 Hz, J$_2$=2.4 Hz, 1H), 7.81 (d, J=2.0 Hz, 1H), 7.68-765 (m, 2H), 7.03 (d, J=8.4 Hz, 1H), 6.66 (d, J=8.8 Hz, 1H), 3.95 (d, J=6.8 Hz, 2H), 3.64 (s, 3H), 3.07 (s, 3H), 1.28-1.25 (m, 1H), 0.69-0.65 (m, 2H), 0.34-0.38 (m, 2H). LCMS (M+H)$^+$: 334.

Example 99: N-[4-(2,4-difluorophenoxy)-3-(1-methyl-6-oxopyridin-3-yl)phenyl]ethanesulfonamide Step 1: 5-[5-amino-2-(2,4-difluorophenoxy)phenyl]-1-methylpyridin-2-one

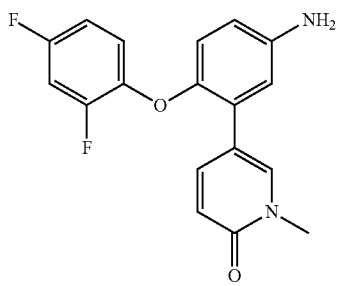 [SMILES: Cn1cc(-c2cc(N)ccc2Oc2ccc(F)cc2F)ccc1=O]

A mixture of the title compound of step 1 in Example 57 (100 mg, 0.289 mmol), 5-bromo-1-methylpyridin-2-one (45.27 mg, 0.240 mmol), $K_3PO_4$ (127.6 mg, 0.60 mmol) and Pd(dppf)Cl$_2$ (20 mg, 0.027 mmol) in dioxane/H$_2$O (4/0.5 mL) was stirred at 100° C. for 40 min under microwave. The mixture was concentrated and the residue was purified by CC on silica gel (PE:EA=1:2) to give the title compound (60 mg, 76%). LCMS (M+H)$^+$: 328.

Step 2: N-[4-(2,4-difluorophenoxy)-3-(1-methyl-6-oxopyridin-3-yl)phenyl]ethanesulfonamide

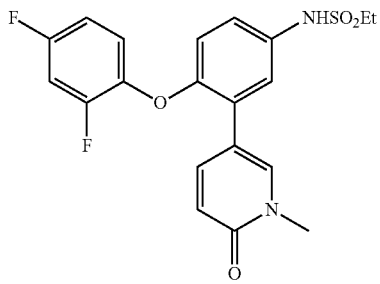

To a soln of 5-[5-amino-2-(2,4-difluorophenoxy)phenyl]-1-methylpyridin-2-one (30 mg, 0.09 mmol) in DCM (4 mL) was added TEA (27.3 mg, 0.27 mmol) and EtSO$_2$Cl (35.39 mg, 0.27 mmol). The mixture was stirred at 30° C. for 12 hR. H$_2$O (4 mL) was added and the mixture was extracted with DCM (4 mL×3). The organic layer was concentrated and the residue was purified by prep-HPLC to give the title compound (10 mg, 26%) as light yellow gum. $^1$H NMR (CDCl$_3$, 400 MHz): δ 7.68-7.66 (m, 2H), 7.28 (d, J=2.4 Hz, 1H), 7.13-7.10 (m, 1H), 7.09 (s, 1H), 7.00-6.92 (m, 2H), 6.84-6.86 (m, 1H), 6.78 (d, J=8.4 Hz, 1H), 6.73 (d, J=9.2 Hz, 1H), 3.65 (s, 3H), 3.14 (q, J=7.2 Hz, 2H), 1.41 (t, J=7.2 Hz, 3H). LCMS (M+H)$^+$: 421.

Example 100: N-[4-(2,4-difluorophenoxy)-3-(1-methyl-6-oxopyridin-3-yl)phenyl]methanesulfonamide Preparation was carried out in a manner similar to Example 99, substituting methane-sulfonyl chloride for ethanesulfonyl chloride in step 2 to give the title compound as a light yellow gum. $^1$H NMR (CDCl$_3$, 400 MHz): δ 7.64-7.62 (m, 2H), 7.29 (d, J=4.8 Hz, 1H), 7.13-7.12 (m, 1H), 6.69-6.95 (m, 2H), 6.79 (m, 1H), 6.79 (d, J=8.4 Hz, 1H), 6.62 (d, J=9.4 Hz, 1H), 3.61 (s, 3H), 3.04 (s, 3H). LCMS (M+H)$^+$: 407.

Example 101: N-[4-(2,4-difluorophenoxy)-3-(1,4-dimethyl-6-oxopyridin-3-yl)phenyl]methanesulfonamide Preparation was carried out in a manner similar to Example 100, substituting 5-bromo-1,4-dimethylpyridin-2-one for 5-bromo-1-methylpyridin-2-one in step 1 to give the title compound. $^1$H NMR (CDCl$_3$, 400 MHz) δ 7.21-7.16 (m, 4H), 6.95-6.93 (m, 2H), 6.86-6.80 (m, 1H), 6.77 (d, J=8.8 Hz, 1H), 6.53 (s, 1H), 3.57 (s, 3H), 3.04 (s, 3H), 2.10 (s, 3H). LCMS (M+H)$^+$: 421.

Example 102: N-[4-(2,4-difluorophenoxy)-3-(1,5-dimethyl-6-oxopyridin-3-yl)phenyl]methanesulfonamide

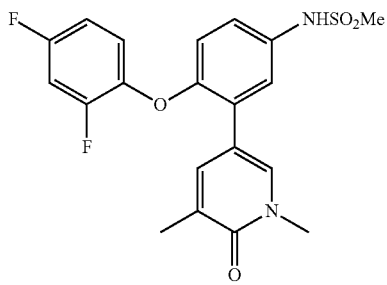

Preparation was carried out in a manner similar to Example 100, substituting 5-bromo-1,3-dimethylpyridin-2-one for 5-bromo-1-methylpyridin-2-one to give the title compound. $^1$H NMR (CDCl$_3$, 400 MHz): δ 7.53 (s, 2H), 7.40 (s, 1H), 7.31 (d, J=2.4 Hz, 1H), 7.17 (dd, J$_1$=8.8 Hz, J$_2$=2.4 Hz, 1H), 6.99-6.90 (m, 2H), 6.87-6.80 (m, 1H), 6.80 (d, J=8.8 Hz, 1H), 3.63 (s, 3H), 3.03 (s, 3H), 2.19 (s, 3H). LCMS (M+H)$^+$: 421.

Example 103: N-[4-(2,4-difluorophenoxy)-3-(1,4,5-trimethyl-6-oxopyridin-3-yl)phenyl]methanesulfonamide

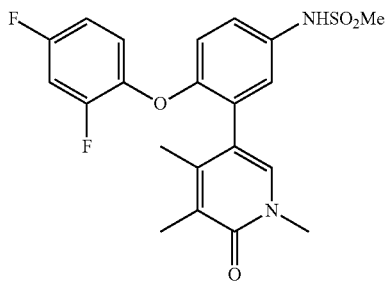

Preparation was carried out in a manner similar to Example 100, substituting 5-bromo-1,3,4-trimethylpyridin-2-one for 5-bromo-1-methylpyridin-2-one to give the title compound. $^1$H NMR (Methanol-d$_4$, 400 MHz): δ 7.65 (dd, J$_1$=8.8 Hz, J$_2$=2.4 Hz, 1H), 7.58 (d, J=2.8 Hz, 1H), 7.39 (s, 1H), 7.05-7.01 (m, 2H), 6.94-6.91 (m, 2H), 3.55 (s, 3H), 3.31 (s, 3H), 2.13 (s, 3H), 2.08 (s, 3H). LCMS (M+18+H)$^+$: 453.

Example 104: 3-amino-1-methyl-5-(3-methylsulfonylphenyl)pyrazin-2-one

Step 1: 3-amino-5-bromo-1-methylpyrazin-2-one

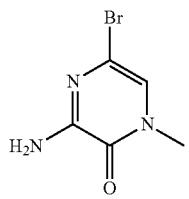

A soln of 3,5-dibromo-1-methylpyrazin-2-one (500.0 mg, 2.46 mmol), NH$_3$H$_2$O (5.0 mL) in dioxane (30.0 mL) was heated at 105° C. for 20 hr. The mixture was concentrated, diluted with EtOAc (50 mL) and filtrated to give the title compound (300.0 mg, 79.0%) which was carried on without purification. LCMS (M+H)$^+$: 204.

Step 2: 3-amino-1-methyl-5-(3-methylsulfonylphenyl)pyrazin-2-one

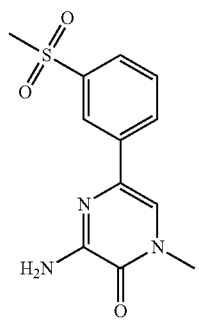

A soln of 3-amino-5-bromo-1-methylpyrazin-2-one (81.0 mg, 0.4 mmol), (3-methylsulfonylphenyl)boronic acid (120.0 mg, 0.6 mmol), Cs$_2$CO$_3$ (391.0 mg, 1.2 mmol), Pd(PPh$_3$)$_4$ (20.0 mg, 0.017 mmol) in dioxane (20.0 mL) and H$_2$O (2.0 mL) was stirred at 95° C. for 12 hr under N$_2$. The mixture was concentrated and purified by silica gel chromatography (PE:EA=3:2) to give the title compound (20.0 mg, 18%). $^1$H NMR (DMSO-d$_6$ 400 MHz): δ 8.35 (s, 1H), 8.11 (d, J=8.0 Hz, 1H), 7.80 (d, J=8.0 Hz, 1H), 7.73 (s, 1H), 7.66 (t, J=8.0 Hz, 1H), 6.93 (brs, 2H), 3.50 (s, 3H), 3.24 (s, 3H). LCMS (M+H)$^+$: 280.

Example 105: 3-amino-5-(3-ethylsulfonylphenyl)-1-methylpyrazin-2-one

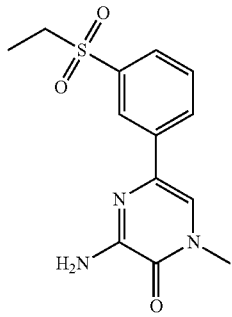 [SMILES: CCS(=O)(=O)c1cccc(-c2cn(C)c(=O)c(N)n2)c1]

Preparation was carried out in a manner similar to Example 104, step 2, substituting (3-ethylsulfonylphenyl)boronic acid for (3-methylsulfonylphenyl)boronic acid to give the title compound. $^1$H NMR (DMSO-$d_6$ 400 MHz): δ 8.30 (t, J=1.6 Hz, 1H), 8.11 (d, J=8.0 Hz, 1H), 7.74 (d, J=8.0 Hz, 1H), 7.71 (s, 1H), 7.65 (t, J=8.0 Hz, 1H), 6.90 (brs, 2H), 3.48 (s, 3H), 3.29 (q, J=7.2 Hz, 2H), 1.11 (t, J=7.2 Hz, 3H). LCMS (M+H)$^+$: 294.

Example 106: N-[5-(6-amino-4-methyl-5-oxopyrazin-2-yl)-2-methoxyphenyl]methanesulfonamide

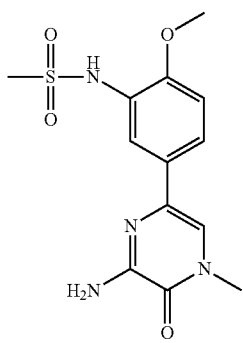

Preparation was carried out in a manner similar to Example 104, step 2, substituting [3-(methanesulfonamido)-4-methoxyphenyl]boronic acid for (3-methylsulfonylphenyl)boronic acid to give the title compound. $^1$H NMR (DMSO-$d_6$ 400 MHz): δ 8.91 (s, 1H), 7.68 (d, J=2.4 Hz, 1H), 7.61 (dd, $J_1$=8.8 Hz, $J_2$=2.4 Hz, 1H), 7.38 (s, 1H), 7.08 (d, J=8.8 Hz, 1H), 6.88-6.64 (m, 2H), 3.84 (s, 3H), 3.46 (s, 3H), 2.95 (s, 3H). LCMS (M+H)$^+$: 325.

Example 107: 3-amino-1-methyl-5-(3-methylsulfonylphenyl)pyridin-2-one

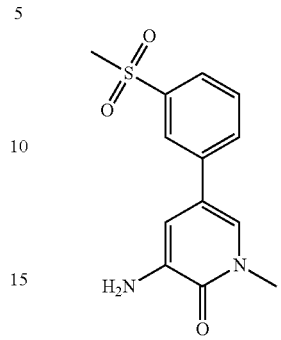

Preparation was carried out in a manner similar to Example 104, step 2, substituting 3-amino-5-bromo-1-methylpyridin-2-one for 3-amino-5-bromo-1-methylpyrazin-2-one to give the title compound. $^1$H NMR (Methanol-$d_4$, 400 MHz): δ 8.06 (t, J=2.0 Hz, 1H), 7.89-7.85 (m, 2H), 7.67 (t, J=8.0 Hz, 1H), 7.39 (d, J=2.0 Hz, 1H), 7.03 (d, J=2.4 Hz, 1H), 3.67 (s, 3H), 3.17 (s, 3H). LCMS (M+H)$^+$: 279.

Example 108: 3-amino-5-(3-ethylsulfonylphenyl)-1-methylpyridin-2-one

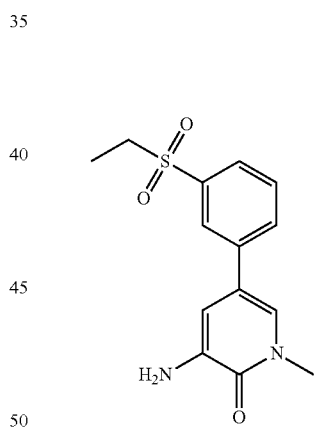

Preparation was carried out in a manner similar to Example 105, substituting 3-amino-5-bromo-1-methylpyridin-2-one for 3-amino-5-bromo-1-methylpyrazin-2-one to give the title compound. $^1$H NMR (Methanol-d4, 400 MHz) δ 8.01 (t, J=2.0 Hz, 1H), 7.88-7.83 (m, 2H), 7.68 (t, J=8.0 Hz, 1H), 7.39 (d, J=2.0 Hz, 1H), 7.03 (d, J=2.4 Hz, 1H), 3.67 (s, 3H), 3.26 (q, J=7.6 Hz, 2H), 1.25 (t, J=7.6 Hz, 3H). LCMS (M+H)$^+$: 293.

Example 109: N-[5-(5-amino-1-methyl-6-oxopyridin-3-yl)-2-methoxyphenyl]methanesulfonamide

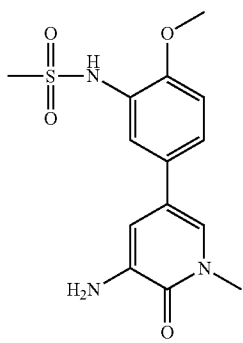

Preparation was carried out in a manner similar to Example 106, substituting 3-amino-5-bromo-1-methylpyridin-2-one for 3-amino-5-bromo-1-methylpyrazin-2-one to give the title compound. $^1$H NMR (Methanol-$d_4$, 400 MHz): δ 7.53 (d, J=2.4 Hz, 1H), 7.34 (dd, $J_1$=8.8 Hz, $J_2$=2.4 Hz, 1H), 7.18 (d, J=2.4 Hz, 1H), 7.09 (d, J=8.8 Hz, 1H), 6.96 (d, J=2.4 Hz, 1H), 3.92 (s, 3H), 3.64 (s, 3H), 2.94 (s, 3H). LCMS (M+H)$^+$: 324.

Example 110: N-[2-methoxy-5-[1-methyl-5-(methylamino)-6-oxopyridin-3-yl]phenyl]methanesulfonamide

Step 1: Tert-Butyl N-(5-bromo-1-methyl-2-oxopyridin-3-yl)carbamate

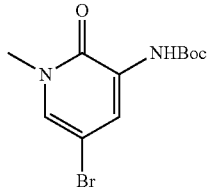 [SMILES: Cn1cc(Br)cc(NC(=O)OC(C)(C)C)c1=O]

To a soln of 3-amino-5-bromo-1-methylpyridin-2-one (404.0 mg, 2.0 mmol) in DCM (30 mL) was added (Boc)$_2$O (654.0 mg, 3.0 mmol), Et$_3$N (606.0 mg, 6.0 mmol) dropwise and DMAP (123.0 mg, 1.0 mmol). The rxn mixture was stirred for 12 hr at 30° C., quenched with satd aq NH$_4$Cl (50 mL), extracted with EA (50 mL), dried over Na$_2$SO$_4$, filtered and concentrated. Silica gel chromatography (PE:EA=2:1) gave the impure title compound (400.0 mg) as a green solid, which was carried on to the next step. LCMS (M-55)$^+$: 247.

Step 2: Tert-Butyl N-(5-bromo-1-methyl-2-oxopyridin-3-yl)-N-methylcarbamate

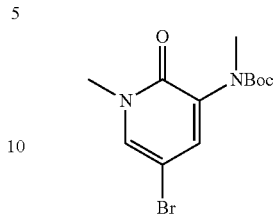

To a soln of tert-butyl N-(5-bromo-1-methyl-2-oxopyridin-3-yl)carbamate (150.0 mg, impure) in DMF (10 mL) was added NaH (60.0 mg, 1.5 mol, 60% in oil) in portions at 0° C. It was stirred for 30 min. Then CH$_3$I (231.0 mg, 1.5 mmol) was added dropwise at 0° C. The rxn mixture was stirred for 2 hr at 30° C. The rxn was quenched with satd aq NH$_4$Cl (15 mL), extracted with EA (20 mL), washed with brine (20 mL), dried over Na$_2$SO$_4$, filtered and concentrated to give the title compound (120.0 mg, crude) as a green solid, which was used directly in the next step without purification.

Step 3: 5-bromo-1-methyl-3-(methylamino)pyridin-2-one

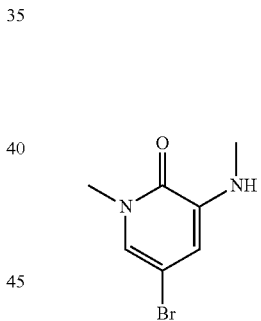

To a soln of tert-butyl N-(5-bromo-1-methyl-2-oxopyridin-3-yl)-N-methylcarbamate (94.8 mg, crude) in DCM (10 mL) was added HCl/dioxane (1 mL, 4 M) dropwise with stirring at 30° C. The rxn mixture was stirred at 30° C. for 30 min. The mixture was filtered and the filter cake collected. The filtrate was adjusted to pH 9 with satd aq NaHCO$_3$, extracted with EtOAc (20 mL), dried over Na$_2$SO$_4$, filtered and concentrated to give a green solid which was combined with the filter cake to give the title compound (43.2 mg). $^1$H NMR (CDCl$_3$ 400 MHz): δ 6.74 (d, J=2.4 Hz, 1H), 6.18 (d, J=2.4 Hz, 1H), 5.15 (s, 1H), 3.53 (s, 3H), 2.83 (s, 3H). LCMS (M+H)$^+$: 217.

Step 4: N-[2-methoxy-5-[1-methyl-5-(methyl-amino)-6-oxopyridin-3-yl]phenyl]methanesulfonamide

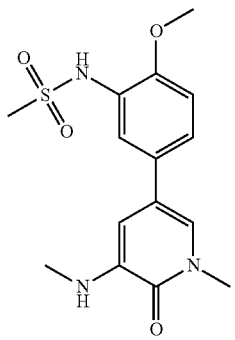

The title compound was prepared in a manner similar to Example 106, substituting the title compound of step 3 for 3-amino-5-bromo-1-methylpyrazin-2-one. ¹H NMR (Methanol-d₄, 400 MHz): δ 7.55 (d, J=2.0 Hz, 1H), 7.38 (dd, $J_1$=8.8, $J_2$=2.4 Hz, 1H), 7.13-7.08 (m, 2H), 6.52 (d, J=2.0 Hz, 1H), 3.93 (s, 3H), 3.63 (s, 3H), 2.94 (s, 3H), 2.88 (s, 3H). LCMS (M+H)⁺: 338.

Example 111: N-[5-[5-(ethylamino)-1-methyl-6-oxopyridin-3-yl]-2-methoxyphenyl]methanesulfonamide Step 1: Tert-Butyl N-(5-bromo-1-methyl-2-oxopyridin-3-yl)-N-ethylcarbamate

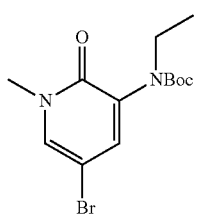 [SMILES: CCN(C(=O)OC(C)(C)C)c1cc(Br)cn(C)c1=O]

To a soln of the title compound from Example 110, step 1 (150.0 mg, crude) in DMF (10 mL) was added NaH (60.0 mg, 1.5 mmol, 60% in oil) in portions at 0° C. and stirred for 30 min. Then iodoethane (234.0 mg, 1.5 mmol) was added dropwise at 0° C. The rxn mixture was stirred for 2 hr at 30° C. It was then quenched with satd aq NH₄Cl (15 mL), extracted with EtOAc (20 mL), washed with brine (20 mL), dried over Na₂SO₄, filtered and concentrated to give the title compound (120.0 mg, crude) as a light green solid which was carried forward without purification.

Step 2: 5-bromo-3-(ethylamino)-1-methylpyridin-2-one

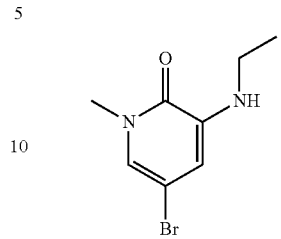

To a soln of tert-butyl N-(5-bromo-1-methyl-2-oxopyridin-3-yl)-N-ethylcarbamate (99.0 mg, crude) in DCM (10 mL) was added HCl/dioxane (1 mL, 4 M) dropwise with stirring at 30° C. The rxn mixture was stirred for 30 min at 30° C. Then the mixture was filtered and the filter cake collected. The filtrate was adjusted to pH 9 with satd aq NaHCO₃, extracted with EA (20 mL), dried over Na₂SO₄, filtered and concentrated to give a light green solid which is combined with the filter cake to give the title compound (46.0 mg) which was carried forward without purification. ¹H NMR (CDCl₃ 400 MHz): δ 6.72 (d, J=2.4 Hz, 1H), 6.20 (d, J=1.6 Hz, 1H), 3.51 (s, 3H), 3.09 (q, J=7.2 Hz, 2H), 1.27 (t, J=7.2 Hz, 3H). LCMS (M+H)⁺: 231.

Step 3: N-[5-[5-(ethylamino)-1-methyl-6-oxopyridin-3-yl]-2-methoxyphenyl]methanesulfonamide

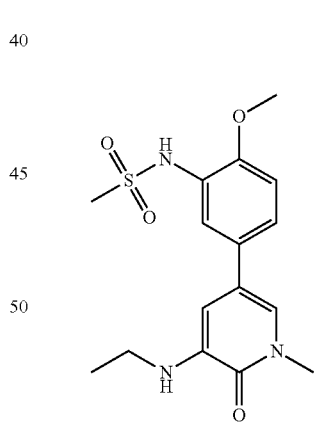

The title compound was prepared in a manner similar to Example 106, substituting the title compound of step 2 for 3-amino-5-bromo-1-methylpyrazin-2-one. ¹H NMR (CDCl₃ 400 MHz): δ 7.63 (d, J=2.0 Hz, 1H), 6.16 (dd, $J_1$=8.4 Hz, $J_1$=2.4 Hz, 1H), 6.95 (d, J=8.4 Hz, 1H), 6.82-6.80 (m, 1H), 6.39 (d, J=2.4 Hz, 1H), 3.93 (s, 3H), 3.64 (s, 3H), 3.19 (q, J=7.2 Hz, 2H), 2.98 (s, 3H), 1.32 (t, J=7.2 Hz, 3H). LCMS (M+H)⁺: 352.

Example 112: N-[5-[5-(cyclopropylmethylamino)-1-methyl-6-oxopyridin-3-yl]-2-methoxyphenyl]methanesulfonamide

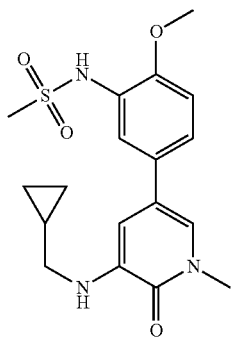

To a soln of compound from Example 109 (64.6 mg, 0.2 mmol) in MeOH (3 mL) and AcOH (0.3 mL) was added cyclopropanecarbaldehyde (14.0 mg, 0.2 mmol) dropwise with stirring at 30° C. NaBH$_3$CN (24.5 mg, 0.4 mol) was added in portions at 30° C. The rxn mixture was stirred for 2 hr at 30° C. It was then quenched with satd aq NH$_4$Cl (5 mL), extracted with EtOAc (20 mL), dried over Na$_2$SO$_4$, filtered and concentrated. The residue was purified by prep-HPLC to give the title compound (10.0 mg, 13.2%) as a light green solid. $^1$H NMR (Methanol-d$_4$ 400 MHz): δ 7.55 (d, J=2.4 Hz, 1H), 7.36 (dd, J=8.4, 2.4 Hz, 1H), 7.16-7.07 (m, 2H), 6.61 (d, J=2.4 Hz, 1H), 3.94 (s, 3H), 3.66 (s, 3H), 3.05 (s, 2H), 2.95 (s, 3H), 1.21-1.14 (m, 1H), 0.64-0.56 (m, 2H), 0.35-0.28 (m, 2H). LCMS (M+H)$^+$: 378.

Example 113: N-[5-[5-(dimethylamino)-1-methyl-6-oxopyridin-3-yl]-2-methoxyphenyl]methanesulfonamide

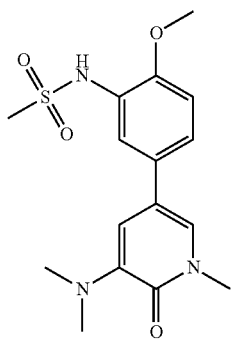

To a soln of compound from Example 109 (64.6 mg, 0.2 mmol) in MeOH (3 mL) and AcOH (0.3 mL) was added HCHO (30.0 mg, 1.0 mmol) dropwise with stirring at 30° C. NaBH$_3$CN (61 mg, 1.0 mol) was added in portions at 30° C. The rxn mixture was stirred for 2 hr at 30° C. It was then quenched with satd aq NH$_4$Cl (5 mL), extracted with EtOAc (20 mL), dried over Na$_2$SO$_4$, filtered and concentrated. The residue was purified by CC on silica gel (PE:EA=2:3) to give the title compound (30 mg, 43%) as a light green solid. $^1$H NMR (Methanol-d$_4$ 400 MHz): δ 7.54 (d, J=2.4 Hz, 1H), 7.47 (d, J=2.4 Hz, 1H), 7.37 (dd, J$_1$=2.4, J$_2$=8.4 Hz, 1H), 7.11 (d, J=8.4 Hz, 1H), 7.04 (d, J=2.4 Hz, 1H), 3.93 (s, 3H), 3.63 (s, 3H), 2.94 (s, 3H), 2.86 (s, 6H). LCMS (M+H)$^+$: 352.

Example 114: N-[5-[5-(diethylamino)-1-methyl-6-oxopyridin-3-yl]-2-methoxyphenyl]methanesulfonamide

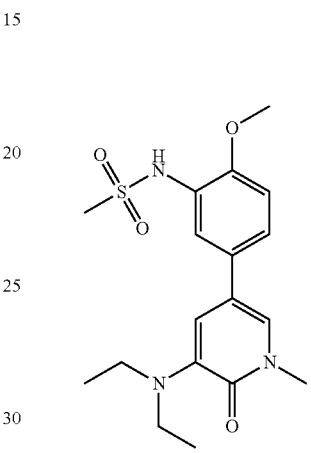

The title compound was prepared in a manner similar to Example 113, substituting acetaldehyde for formaldehyde. $^1$H NMR (Methanol-d$_4$ 400 MHz): δ 7.55 (d, J=2.4 Hz, 1H), 7.49 (d, J=2.4 Hz, 1H), 7.37 (dd, J$_1$=8.4 Hz, J$_2$=2.4 Hz, 1H), 7.17-7.11 (m, 1H), 7.06 (d, J=2.4 Hz, 1H), 3.95 (s, 3H), 3.65 (s, 3H), 3.34 (m, 4H), 2.97 (s, 3H), 1.11 (t, J=7.2 Hz, 6H). LCMS (M+H)$^+$: 380.

Example 115: N-[3-(5-amino-1-methyl-6-oxopyridin-3-yl)-4-(2,4-difluorophenoxy)phenyl]ethanesulfonamide Step 1: 3-amino-5-[5-amino-2-(2,4-difluorophenoxy)phenyl]-1-methylpyridin-2-one

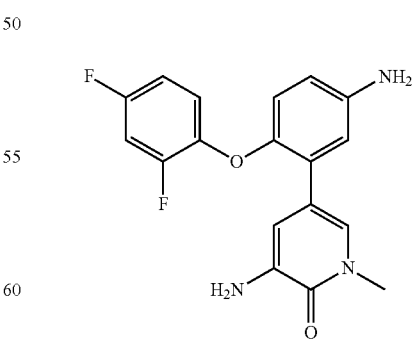

The title compound of step 1 was prepared in a manner similar to Example 107, substituting the title compound of Example 57, step 1 for (3-methylsulfonylphenyl)boronic acid. LCMS (M+H)$^+$: 344.

Step 2: N-[3-(5-amino-1-methyl-6-oxopyridin-3-yl)-4-(2,4-difluorophenoxy)phenyl]ethanesulfonamide

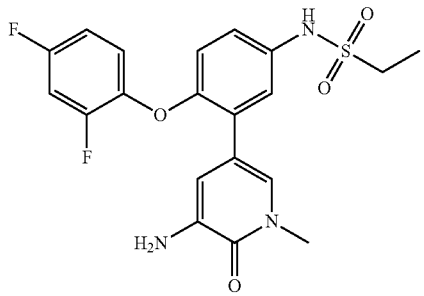 [SMILES: CCS(=O)(=O)Nc1ccc(Oc2ccc(F)cc2F)c(-c2cc(N)c(=O)n(C)c2)c1]

The title compound was prepared in a manner similar to Example 99, step 2. $^1$H NMR (DMSO-d6, 400 MHz): δ 9.78 (s, 1H), 7.45-7.39 (m, 1H), 7.23-7.22 (m, 2H), 7.14 (dd, J$_1$=7.2 Hz, J$_2$=1.6 Hz, 1H), 7.10-7.02 (m, 2H), 6.85 (d, J=8.8 Hz, 1H), 6.79 (d, J=2.0 Hz, 1H), 3.49 (s, 3H), 3.09 (q, J=7.2 Hz, 2H), 1.21 (t, J=7.6 Hz, 3H). LCMS (M+H)$^+$: 436.

Example 116: 3-amino-5-[2-(cyclopropylmethoxy)-5-methylsulfonylphenyl]-1-methylpyridin-2-one

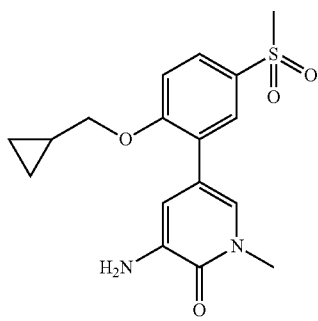 [SMILES: Cn1cc(-c2cc(S(C)(=O)=O)ccc2OCC2CC2)cc(N)c1=O]

The title compound was prepared in a manner similar to Example 107, substituting the title compound of Example 90, step 1 for (3-methylsulfonylphenyl)boronic acid. $^1$H NMR (CDCl$_3$, 400 MHz): δ 7.84-7.81 (m, 2H), 7.11 (d, J=2.0 Hz, 1H), 7.02 (d, J=2.4 Hz, 1H), 6.84 (d, J=2.4 Hz, 1H), 3.95 (d, J=6.8 Hz, 2H), 3.65 (s, 3H), 3.06 (s, 3H), 1.31-1.27 (m, 1H), 0.68 (q, J=5.6 Hz, 2H), 0.37 (q, J=5.2 Hz, 2H). LCMS (M+H)$^+$: 349.

Example 117: 4-ethoxy-3-(1-methyl-6-oxopyridin-3-yl)benzenesulfonamide

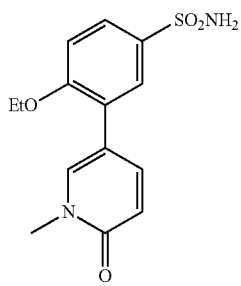 [SMILES: CCOc1ccc(S(N)(=O)=O)cc1-c1ccc(=O)n(C)c1]

A mixture of the title compound of Example 98, step 1 (40 mg, 0.17 mmol), Pd(dppf)Cl$_2$ (10 mg, 8%) and 3-bromo-4-ethoxybenzene-1-sulfonamide (48 mg, 0.17 mmol) was suspended in 1,4-dioxane (880 μL) and satd bicarbonate soln (aq) (220 μL). The mixture was heated to 95° C. using microwave irradiation (normal) for 60 min. The crude rxn mixture was filtered through a short plug of celite, the plug was washed with additional 1,4-dioxane (1 ml), and the combined filtrate was purified by prep-HPLC. The fractions were combined and lyophilized to give the title compound (14 mg, 27%) as a white solid. $^1$HNMR (DMSO, 400 MHz): δ 1.33 (t, J=6.9, 3H), 3.49 (s, 3H), 4.15 (q, J=6.9, 2H), 6.45 (d, J=9.4 Hz, 1H), 7.20-7.23 (m, 3H), 7.64 (dd, J=2.6, 9.4 Hz, 1H), 7.72-7.74 (m, 2H), 7.89 (d, J=2.6 Hz, 1H). LCMS (M+H)$^+$: 309.

Example 118: 4-(2,4-difluorophenoxy)-3-(1-methyl-6-oxopyridin-3-yl)benzenesulfonamide Step 1: 3-bromo-4-fluorobenzenesulfonamide

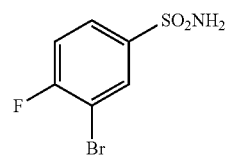 [SMILES: NS(=O)(=O)c1ccc(F)c(Br)c1]

A soln of 3-bromo-4-fluorobenzenesulfonyl chloride (1 g, 3.3 mmol, 90% pure) stirred at 0° C. in THF (15 ml) and DCM (5 ml) was treated with aq ammonium hydroxide (28%) by dropwise addition over 15 min. After stirring at 0° C. for 210 min, the mixture was acidified (pH 1) by addition of 1N HCl (aq). After the mixture was concentrated in vacuo to near dryness, it was treated with H$_2$O (50 ml), sonicated for 3 min and filtered. After the filter cake was washed sequentially with H$_2$O (50 ml) and hexanes (100 ml), it was dried in vacuo to afford the title compound (503 mg, 60%) as a white solid which was carried forward without purification. LCMS (M−H)$^−$: 253.

Step 2: 3-bromo-4-(2,4-difluorophenoxy)benzenesulfonamide

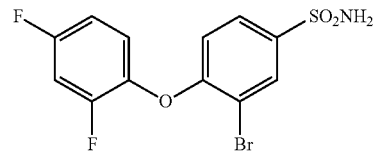 [SMILES: NS(=O)(=O)c1ccc(Oc2ccc(F)cc2F)c(Br)c1]

A soln of 3-bromo-4-fluorobenzenesulfonamide (400 mg, 1.6 mmol) and 2,4-difluorophenol (228 mg, 1.76 mmol) in DMSO (16 ml) was treated with cesium carbonate (1 g, 3.2 mmol). The resulting mixture was heated to 120° C. for 20 min by microwave irridation (normal). The mixture was treated with H$_2$O (100 ml) and extracted with EtOAc (3×50 ml). The combined organic extracts were washed with satd bicarbonate soln (aq), dried over Na$_2$SO$_4$, filtered and concentrated in vacuo to afford a tan solid. The solid was purified by silica gel chromatography (12 g ISCO, 30%

Step 3: 4-(2,4-difluorophenoxy)-3-(1-methyl-6-oxopyridin-3-yl)benzenesulfonamide

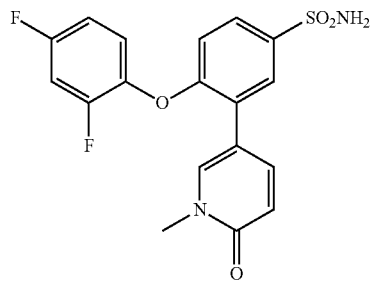 [SMILES: Cn1cc(-c2cc(S(N)(=O)=O)ccc2Oc2ccc(F)cc2F)ccc1=O]

3-Bromo-4-(2,4-difluorophenoxy)benzenesulfonamide (1 eq., 62 mg), the title compound of Example 98, step 1 (40 mg, 0.17 mmol), Pd(dppf)Cl$_2$ (10 mg, 8%) in 1,4-dioxane (880 µL) and satd bicarbonate soln (aq) (220 µL) were reacted at 105° C. for 30 min in a manner similar to Example 117. Work-up and preparative HPLC, also in a similar manner, gave the title compound (12 mg, 18%) as a white solid. $^1$H NMR (DMSO, 400 MHz): δ3.51 (s, 3H), 6.49 (d, J=9.4, 1H), 4.15 (q, J=6.9, 2H), 6.45 (d, J=9.4 Hz, 1H), 7.20-7.23 (m, 3H), 7.64 (dd, J=2.6, 9.4 Hz, 1H), 7.72-7.74 (m, 2H), 7.89 (d, J=2.6 Hz, 1H). LCMS (M+H)$^+$: 393.

Example 119: 5-[2-(cyclopropylmethoxy)-5-methylsulfonylphenyl]-3-fluoro-1-methylpyridin-2-one Step 1: 5-bromo-3-fluoro-1-methylpyridin-2-one

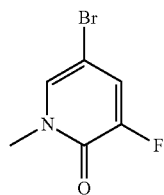

A mixture of 5-bromo-3-fluoropyridin-2-ol (1 g, 5.2 mmol), iodomethane (356 mg, 5.7 mmol) and K$_2$CO$_3$ (1.4 g, 10.4 mmol) in DMF (10 mL) was stirred at room temp for 12 hr. The mixture was treated with H$_2$O (70 ml) and extracted with EtOAc (3×50 ml). The combined organic extracts were washed with satd bicarbonate soln (aq), dried over Na$_2$SO$_4$, filtered and concentrated in vacuo to afford the title compound (1 g, 93%) as a white solid which was carried forward without purification. LCMS (M+H)$^+$: 207.

Step 2: 3-fluoro-1-methyl-5-(4,4,5,5-tetramethyl-1,3,2-dioxaborolan-2-yl)pyridin-2-one

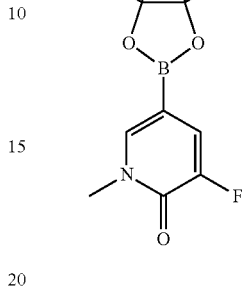

A mixture of 5-bromo-3-fluoro-1-methylpyridin-2-one (1 g, 4.9 mmol), 4,4,5,5-tetramethyl-2-(tetramethyl-1,3,2-dioxaborolan-2-yl)-1,3,2-dioxaborolane (2.5 g, 9.8 mmol), KOAc (1.2 g, 12.3 mmol), and Pd(dppf)Cl$_2$ (286 mg, 8%) was suspended in 1,4-dioxane (15 mL). After purging the rxn vial with N$_2$ for 5 min, the capped vial was stirred at 80° C. for 1 hr. The mixture was treated with H$_2$O (70 ml) and extracted with EtOAc (3×40 ml). The combined organic extracts were washed with brine, dried over Na$_2$SO$_4$, filtered and concentrated in vacuo to afford a dark residue. The residue was purified by silica gel chromatography (12 g ISCO, gradient 5% to 75% EtOAc in hexanes) to give the title compound (682 mg, 55%) as a reddish brown solid.

Step 3: 5-[2-(cyclopropylmethoxy)-5-methylsulfonylphenyl]-3-fluoro-1-methylpyridin-2-one

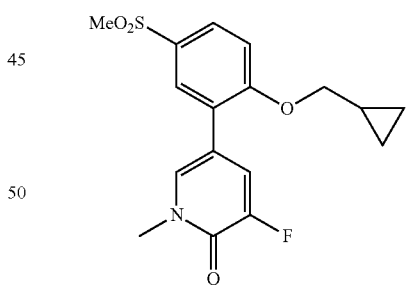

3-Fluoro-1-methyl-5-(4,4,5,5-tetramethyl-1,3,2-dioxaborolan-2-yl)pyridin-2-one (40 mg, 0.16 mmol), 2-bromo-1-(cyclopropylmethoxy)-4-methanesulfonylbenzene (49 mg, 0.16 mmol), and Pd(dppf)Cl$_2$ (12 mg, 10%) in 1,4-dioxane (880 µL) and satd bicarbonate soln (aq) (220 µL) were reacted, worked up, and purified in a manner similar to Example 117. The title compound (22 mg, 46%) was obtained as a tan solid. 1H NMR (400 MHz, DMSO-d6): δ 0.31-0.42 (m, 2H) 0.53-0.63 (m, 2H) 1.17-1.34 (m, 1H) 3.20 (s, 3H) 3.58 (s, 3H) 3.95-4.06 (m, 2H) 7.24-7.33 (m, 1H) 7.72-7.79 (m, 1H) 7.80-7.87 (m, 1H) 7.84 (s, 1H) 7.88-7.93 (m, 1H). LCMS (M+H)$^+$: 351.

Example 120: 5-[2-(2,4-difluorophenoxy)-5-methyl-sulfonylphenyl]-3-fluoro-1-methylpyridin-2-one

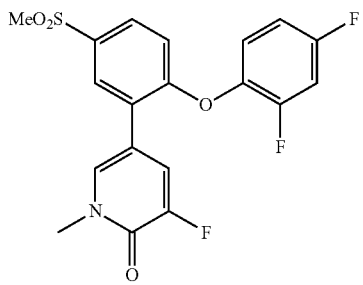 [SMILES: Cn1cc(-c2cc(S(C)(=O)=O)ccc2Oc2ccc(F)cc2F)cc(F)c1=O]

The title compound of Example 119, step 2 (40 mg, 0.16 mmol), 1-(2-bromo-4-methylsulfonylphenoxy)-2,4-difluorobenzene (58 mg, 0.16 mmol) and Pd(dppf)Cl$_2$ (12 mg, 10%) in 1,4-dioxane (880 μL) and satd bicarbonate soln (aq) (220 μL) were reacted, worked-up and purified in a manner similar to Example 117. The title compound (26 mg, 46%) was obtained as a tan solid. $^1$H NMR (400 MHz, DMSO-d6)L δ 3.25 (s, 3H) 3.60 (s, 3H) 6.91-6.99 (m, 1H) 7.16-7.30 (m, 1H) 7.49-7.62 (m, 2H) 7.76-7.86 (m, 2H) 8.00 (m, 2H). LCMS (M+H)$^+$: 410.

Example 121: 5-[2-(2,4-difluorophenoxy)-5-ethyl-sulfonylphenyl]-3-fluoro-1-methylpyridin-2-one

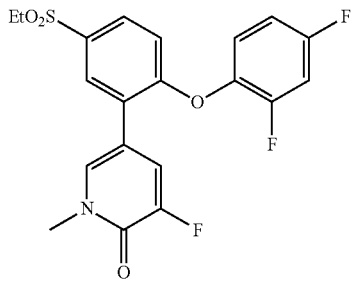

The title compound of Example 119, step 2 (40 mg, 0.16 mmol), 1-(2-bromo-4-ethylsulfonylphenoxy)-2,4-difluorobenzene (60 mg, 0.16 mmol), and Pd(dppf)Cl$_2$ (12 mg, 10%) in 1,4-dioxane (880 μL) and satd bicarbonate soln (aq) (220 μL) were reacted, worked up and purified in a manner similar to Example 117. The title compound (18 mg, 27%) was obtained as a tan solid. $^1$H NMR (400 MHz, DMSO-d$_6$): δ 1.13 (t, J=7.33 Hz, 3H) 3.34 (q, J=7.33 Hz, 2H) 3.59 (s, 3H) 6.92-6.98 (m, 1H) 7.19-7.27 (m, 1H) 7.50-7.61 (m, 2H) 7.76-7.84 (m, 2H) 7.92-7.96 (m, 1H) 7.97-8.01 (m, 1H). LCMS (M+H)$^+$: 424.

Example 122: N-[4-(2,4-difluorophenoxy)-3-(5-fluoro-1-methyl-6-oxopyridin-3-yl)phenyl]ethane-sulfonamide

Step 1: N-[3-bromo-4-(2,4-difluorophenoxy)phenyl]ethanesulfonamide

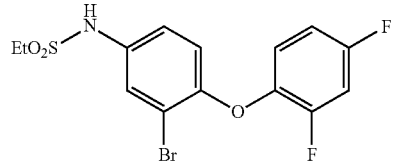

Ethylsulfonyl chloride (177 mg, 1.4 mmol) was added dropwise to a stirred soln of 3-bromo-4-(2,4-difluorophenoxy)aniline (328 mg, 1.1 mmol) and pyridine (178 μL, 2.2 mmol) in CH$_2$Cl$_2$ (2 ml) at 0° C. under N$_2$. After the mixture warmed to room temp and stirred overnight, it was treated with 1N HCl (10 ml) and extracted with CH$_2$Cl$_2$ (3×10 ml); the combined organic extracts were washed with satd bicarbonate soln (aq), dried over Na$_2$SO$_4$, filtered and concentrated in vacuo to give the title compound (430 mg, 99%) as a tan solid which was carried forward without purification. LCMS (M−H)$^−$: 391.

Step 2: N-[4-(2,4-difluorophenoxy)-3-(5-fluoro-1-methyl-6-oxopyridin-3-yl)phenyl]ethanesulfonamide

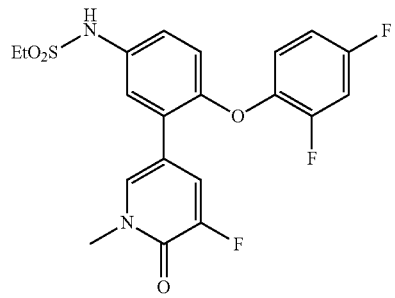

N-[3-Bromo-4-(2,4-difluorophenoxy)phenyl]ethanesulfonamide (77 mg, 0.2 mmol), the title compound of Example 119, step 2 (50 mg, 0.2 mmol), and Pd(dppf)Cl$_2$ (14 mg, 10%) in 1,4-dioxane (1 mL) and satd bicarbonate soln (aq) (333 μL) were reacted, worked up and purified in a manner similar to Example 117. The title compound (31 mg, 27%) was obtained as a tan solid. $^1$H NMR (400 MHz, DMSO-d$_6$): δ 1.22 (t, J=7.3, 3H) 3.11 (q, J=7.3 Hz, 2H) 3.55 (s, 3H) 6.86 (d, J=8.6 Hz, 1H) 7.02-7.12 (m, 1H) 7.13-7.23 (m, 2H) 7.26 (d, J=2.8 Hz, 1H) 7.35-7.52 (m, 1H) 7.60 (m, 1H) 7.79 (s, 1H) 9.48-9.96 (m, 1H). LCMS (M+H)$^+$: 439.

Example 123: N-[3-(2-methyl-1-oxo-2,6-naphthyridin-4-yl)phenyl]ethanesulfonamide

Step 1: 4-chloro-2-methyl-2,6-naphthyridin-1-one

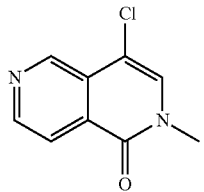

N-chlorosuccinimide (0.8 g, 6.2 mmol) was added in portions to a soln of 2-methyl-2,6-naphthyridin-1-one (1.0 g, 6.2 mmol) in acetonitrile (25 mL), and then heated at 65° C. for 18 hr. Extractive work-up with EtOAc and purification by silica gel chromatography (PE:EA=5:1~1:1) gave the title compound of step 1 (0.6 g, 56%) as a yellow solid. $^1$H NMR (CDCl$_3$, 400 MHz): δ 9.29 (s, 1H), 8.81 (d, J=3.6 Hz, 1H), 8.21 (d, J=5.2 Hz, 1H), 7.31 (s, 1H), 3.63 (s, 3H). LCMS: 195.0 (M+H)$^+$.

Step 2: N-[3-(2-methyl-1-oxo-2,6-naphthyridin-4-yl)phenyl]ethanesulfonamide

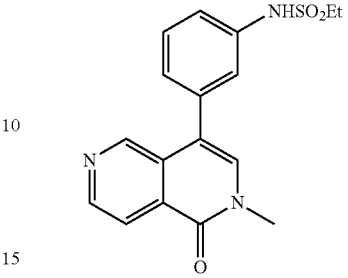

A mixture of 4-chloro-2-methyl-2,6-naphthyridin-1-one (50.0 mg, 0.26 mmol), [3-(ethylsulfonylamino)phenyl]boronic acid (88.0 mg, 0.38 mmol), Pd(dppf)Cl$_2$ (15.3 mg, 0.026 mmol) and K$_3$PO$_4$ (190 mg, 0.9 mmol) in dioxane (3 mL) and H$_2$O (0.5 mL) was microwaved at 120° C. under microwave for 2 hr. Purification by silica gel chromatography on (PE:EA=10:1 to 1:1) followed by preparative HPLC gave the title compound (5.9 mg, 6.8%) as a yellow solid. $^1$H NMR (Methanol-d4, 400 MHz): δ 8.99 (brs, 1H), 8.71 (d, J=6.0 Hz, 1H), 8.39 (d, J=5.6 Hz, 1H), 7.62 (s, 1H), 7.51 (t, J=8.0 Hz, 1H), 7.41-7.40 (m, 1H), 7.36 (dd, J$_1$=8.0 Hz, J$_2$=1.2 Hz, 1H), 7.29 (d, J=5.6 Hz, 1H), 3.72 (s, 3H), 3.17 (q, J=7.6 Hz, 2H), 1.35 (t, J=7.6 Hz, 3H). LCMS: 344.1 (M+H)$^+$.

Examples 124-126 in Table 15 were prepared from title compound of Example 123, step 1, using the appropriate phenyl boronic acid/ester in a manner similar to Example 123, step 2. Example 127 in Table 15 was prepared in two steps from the title compound of Example 123, step 1, and the title compound of Example 57, step 1, by coupling the aniline boronic ester in a manner similar to Example 123, step 1, except that the temp was raised from 120° C. to 150° C. and NMP was used instead of dioxane (step 1), followed by sulfonylation of the aniline in a manner similar to Example 57, step 3 (step 2).

TABLE 15

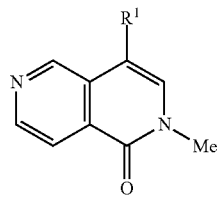

| Ex. No. | R$^1$ | Name | $^1$H NMR (ppm (δ, 400 MHz) | MS (M + H) |
|---|---|---|---|---|
| 124 | ![structure] | N-ethyl-3-(2-methyl-1-oxo-2,6-naphthyridin-4-yl)benzenesulfonamide | (Methanol-d$_4$) 8.86 (d, J = 0.8 Hz, 1H), 8.70 (d, J = 5.6 Hz, 1H), 8.28 (dd, J$_1$ = 5.6 Hz, J$_2$ = 0.8 Hz, 1H), 7.98-7.95 (m, 2H), 7.78-7.75 (m, 2 H), 7.60 (s, 1H), 3.71 (s, 3H), 2.98 (q, J = 7.2 Hz, 2H), 1.10 (t, J = 7.2 Hz, 3H) | 344 |
| 125 | ![structure] | N-[3-(2-methyl-1-oxo-2,6-naphthyridin-4-yl)phenyl]methanesulfonamide | (CD$_3$OD) 8.98 (s, 1H), 8.70 (d, J = 5.2 Hz, 1H), 8.34 (d, J = 5.2 Hz, 1H), 7.60 (s, 1H), 7.52 (t, J = 8.0 Hz, 1H), 7.40 (s, 1 H), 7.36 (d, J = 8.0 Hz, 1H), 7.31 (d, J = 8.0 Hz, 1H), 3.71 (s, 3H), 3.04 (s, 3H) | 330 |

TABLE 15-continued

| Ex. No. | R¹ | Name | ¹H NMR (ppm (δ, 400 MHz) | MS (M + H) |
|---|---|---|---|---|
| 126 | [3-ethylsulfonylphenyl group] | 4-(3-ethylsulfonylphenyl)-2-methyl-2,6-naphthyridin-1-one | (CD$_3$OD) 9.02 (s, 1H), 8.78 (d, J = 5.2 Hz, 1H), 8.57 (d, J = 5.2 Hz, 1H), 8.09 (s, 1H), 8.06 (d, J = 7.6 Hz, 1H), 7.93 (d, J = 7.6 Hz, 1H), 7.85 (t, J = 7.6 Hz, 1H), 7.80 (s, 1H), 3.74 (s, 3 H), 3.33 (q, J = 7.6 Hz, 2H), 1.29 (t, J = 7.6 Hz, 3H) | 329 |
| 127 | [2,4-difluorophenoxy-phenyl-ethanesulfonamide group] | N-[4-(2,4-difluorophenoxy)-3-(2-methyl-1-oxo-2,6-naphthyridin-4-yl) phenyl]ethanesulfonamide | (CD$_3$OD) 9.02 (s, 1H), 8.78 (d, J = 5.2 Hz, 1H), 8.57 (d, J = 5.2 Hz, 1H), 8.09 (s, 1H), 8.06 (d, J = 7.6 Hz, 1H), 7.93 (d, J = 7.6 Hz, 1H), 7.85 (t, J = 7.6 Hz, 1H), 7.80 (s, 1H), 3.74 (s, 3H), 3.33 (q, J = 7.6 Hz, 2H), 1.29 (t, J = 7.6 Hz, 3H) | 472 |

Example 128: 4-[2-(cyclopropylmethoxy)-5-methylsulfonylphenyl]-2-methyl-6-(4-methylpyrazol-1-yl)isoquinolin-1-one

Step 1: 2-methyl-6-(4-methylpyrazol-1-yl)isoquinolin-1-one

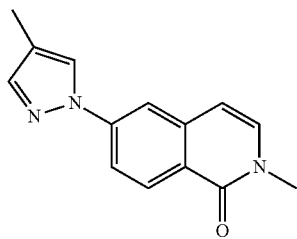 [SMILES: Cc1cnn(-c2ccc3c(=O)n(C)ccc3c2)c1]

6-Bromo-2-methylisoquinolin-1-one (300.0 mg, 1.27 mmol), 4-methyl-1H-pyrazole (210.0 mg, 2.54 mmol), CuI (30.0 mg, 0.127 mmol) and K$_2$CO$_3$ (360.0 mg, 2.54 mmol) in NMP (3.0 mL) were microwaved at 195° C. for 5 hr. Extractive work-up with EtOAc followed by silica gel chromatography (PE:EA=5:1) gave the title compound of step 1 (160.0 mg, 52%) as a light yellow solid. ¹H NMR (CDCl$_3$, 400 MHz): δ 8.49 (d, J=8.8 Hz, 1H), 7.84 (s, 1H), 7.83 (d, J=2.0 Hz, 1H), 7.74 (dd, J$_1$=8.8 Hz, J$_2$=2.0 Hz, 1H), 7.59 (s, 1H), 7.10 (d, J=7.6 Hz, 1H), 6.52 (d, J=7.6 Hz, 1H), 3.62 (s, 3H), 2.19 (s, 3H). LCMS: 240.0 (M+H)$^+$.

Step 2: 4-bromo-2-methyl-6-(4-methylpyrazol-1-yl)isoquinolin-1-one

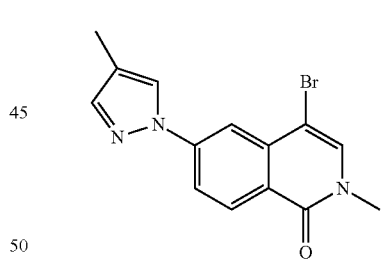

Bromine (94 mg, 0.59 mmol) in acetic acid (2 mL) was added drop-wise to a soln of 2-methyl-6-(4-methylpyrazol-1-yl)isoquinolin-1-one (140.0 mg, 0.583 mmol) in acetic acid (4 mL) at 0° C. The mixture was then stirred at room temp for 17 min and quenched with H$_2$O (10 mL). The pH was adjusted to about 7-8 with aq 1M NaOH. Extractive work-up with EtOAc followed by purification using silica gel chromatography (PE:EA=1:1) gave the title compound of step 2 (120.0 mg, 56%) as a light yellow solid. ¹H NMR (CDCl$_3$, 400 MHz): δ 8.51 (d, J=8.8 Hz, 1H), 8.06 (d, J=2.0 Hz, 1H), 7.89 (s, 1H), 7.87 (dd, J$_1$=8.8 Hz, J$_2$=2.0 Hz, 1H), 7.63 (s, 1H), 7.42 (s, 1H), 3.62 (s, 3H), 2.20 (s, 3H). LCMS: 319.8 (M+H)$^+$.

Step 3: 4-[2-(cyclopropylmethoxy)-5-methylsulfonylphenyl]-2-methyl-6-(4-methylpyrazol-1-yl)isoquinolin-1-one

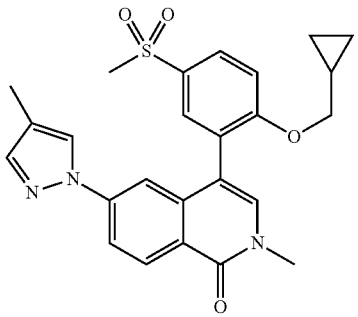 [SMILES: Cc1cnn(-c2ccc3c(=O)n(C)cc(-c4cc(S(C)(=O)=O)ccc4OCC4CC4)c3c2)c1]

4-Bromo-2-methyl-6-(4-methylpyrazol-1-yl)isoquinolin-1-one (40.0 mg, 0.126 mmol), the title compound of Example 90, step 1 (53.2 mg, 0.152 mmol), Pd(dppf)Cl$_2$ (200.0 mg, 0.05 mmol) and aq 1M K$_3$PO$_4$ (0.38 mL, 0.38 mmol) in dioxane (3 mL) were heat in a microwave at 100° C. for 1 hr. Purification by preparative HPLC gave the title compound (15.0 mg, 25%) as a white solid. $^1$H NMR (CDCl$_3$, 400 MHz): δ 8.57 (d, J=8.4 Hz, 1H), 8.00 (d, J=8.4 Hz, 1H), 7.90 (s, 1H), 7.75 (d, J=7.6 Hz, 1H), 7.73 (s, 1H), 7.54 (s, 1H), 7.50 (s, 1H), 7.14 (s, 1H), 7.12 (s, J=9.2 Hz, 1H), 3.96-3.83 (m, 2H), 3.68 (s, 3H), 3.13 (s, 3H), 2.15 (s, 3H), 1.01-0.94 (m, 1H), 0.38-0.28 (m, 2H), 0.08-0.02 (m, 2H). LCMS: 464.1 (M+H)$^+$.

Example 129: N-[4-(2,4-difluorophenoxy)-3-(7-methyl-8-oxoimidazo[1,5-a]pyrazin-5-yl)phenyl]ethanesulfonamide Step 1: 5-bromo-7-methylimidazo[1,5-a]pyrazin-8-one

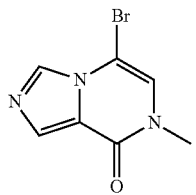

To a soln of 5-bromo-1-methylpyrazin-2-one (500.0 mg, 2.65 mmol) and (p-tolylsulfonyl)methyl isocyanide (573.0 mg, 2.94 mmol) in THF (4 mL) was added a suspension of NaH (235.0 mg, 5.9 mmol) in THF (2 mL) at 0° C. under N$_2$. After stirring at 0° C. for 30 min, the mixture was stirred at 30° C. for another 1.5 hr. The rxn mixture was quenched with H$_2$O (20 mL) at 0° C., and extracted with EtOAc (30 mL×2). The organic phases were combined, washed with brine (30 mL), dried over Na$_2$SO$_4$, filtered and evaporated.

The crude product was purified by CC (PE:EA=1/1) to give the title compound (300.0 mg, 50%) as a light yellow solid. $^1$H NMR (CDCl$_3$ 400 MHz): δ 8.06 (d, J=4.4 Hz, 1H), 6.61 (s, 1H), 3.48 (s, 3H). LCMS (M+H)$^+$: 228.

Step 2: 5-[5-amino-2-(2,4-difluorophenoxy)phenyl]-7-methylimidazo[1,5-a]pyrazin-8-one

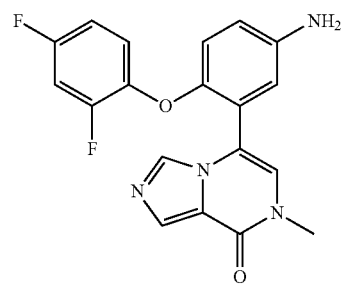 [SMILES: Cn1cc(-c2cc(N)ccc2Oc2ccc(F)cc2F)n2cncc2c1=O]

A soln of 5-bromo-7-methylimidazo[1,5-a]pyrazin-8-one (114.0 mg, 0.5 mmol), the title compound of Example 57, step 1 (208.0 mg, 0.6 mmol), Pd(dppf)$_2$Cl$_2$ (37.0 mg, 0.05 mmol), NaHCO$_3$ (126.0 mg, 1.5 mmol) in dioxane (10 mL) and H$_2$O (1 mL) was stirred in microwave at 110° C. under N$_2$ for 3 hr. The solvent was evaporated to give the crude product, which was purified by CC (PE:EA=3:1) to give the title compound (110 mg, 60%) as a yellow solid. $^1$H NMR (CDCl$_3$ 400 MHz): δ 7.94 (s, 1H), 7.82 (s, 1H), 6.93-6.82 (m, 2H), 6.79-6.74 (m, 4H), 6.41 (s, 1H), 3.50 (s, 3H). LCMS (M+H)$^+$: 369.

Step 3: N-[4-(2,4-difluorophenoxy)-3-(7-methyl-8-oxoimidazo[1,5-a]pyrazin-5-yl)phenyl]ethanesulfonamide

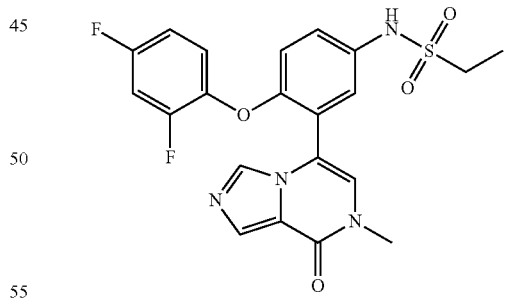

The title compound was prepared in a manner similar to Example 99, step 2, substituting the title compound of step 2 for the title compound of Example 99, step 1. $^1$H NMR (CDCl$_3$ 400 MHz): δ 8.57 (s, 1H), 8.14 (s, 1H), 7.50 (d, J=2.4 Hz, 1H), 7.30 (dd, J$_1$=8.8 Hz, J$_2$=2.4, 1H), 7.20-7.16 (m, 1H), 6.99-6.87 (m, 2H), 6.83 (s, 1H), 6.55 (d, J=8.8 Hz, 1H), 3.59 (s, 3H), 3.13 (q, J=7.2 Hz, 2H), 1.39 (t, J=7.2 Hz, 3H). LCMS (M+H)$^+$: 461.

Example 130: 5-[2-(cyclopropylmethoxy)-5-methyl-sulfonylphenyl]-7-methylimidazo[1,5-a]pyrazin-8-one

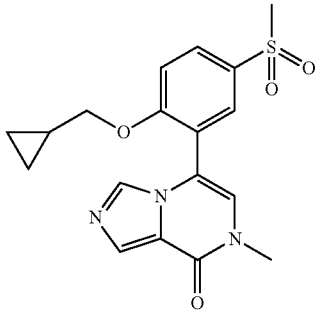 [SMILES: Cn1cc(-c2cc(S(C)(=O)=O)ccc2OCC2CC2)n2cncc2c1=O]

The title compound was prepared in a manner similar to Example 129, step 2, substituting 2-[2-(cyclopropyl-methoxy)-5-methylsulfonylphenyl]-4,4,5,5-tetramethyl-1,3,2-dioxaborolane for 4-(2,4-difluorophenoxy)-3-(4,4,5,5-tetramethyl-1,3,2-dioxaborolan-2-yl)aniline to give the title compound. $^1$H NMR (CDCl$_3$ 400 MHz): δ 8.08 (dd, J$_1$=8.8 Hz, J$_2$=2.4, 1H), 8.03 (s, 1H), 7.98 (d, J=2.4 Hz, 1H), 7.58 (s, 1H), 7.16 (d, J=8.8 Hz, 1H), 6.50 (s, 1H), 3.97 (d, J=7.2 Hz, 2H), 3.54 (s, 3H), 3.11 (s, 3H), 1.15-1.02 (m, 1H), 0.59-0.49 (m, 2H), 0.26-0.17 (m, 2H). LCMS (M+H)$^+$: 374.

Example 131: 7-methyl-5-(3-methylsulfonylphenyl)imidazo[1,5-a]pyrazin-8-one

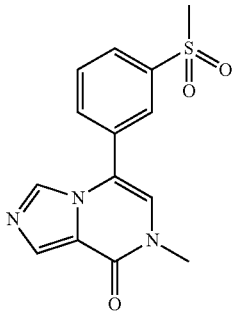 [SMILES: Cn1cc(-c2cccc(S(C)(=O)=O)c2)n2cncc2c1=O]

A soln of compound from Example 129, step 1 (80 mg, 0.35 mmol), (3-methyl-sulfonylphenyl)boronic acid (77 mg, 0.6 mmol), Na$_2$CO$_3$ (106 mg, 1 mmol), Pd(PPh$_3$)$_2$Cl$_2$ (30.0 mg) in dioxane (3 mL) and H$_2$O (0.5 mL) was stirred at 120° C. for 18 hr under N$_2$. After cooling to room temp, the mixture was filtered, concentrated and purified by prep-HPLC to give the title compound (20.0 mg, 20%). $^1$H NMR (Methanol-d4 400 MHz): δ 8.70-8.65 (m, 1H), 8.30-8.20 (m, 2H), 8.16 (d, J=8.0 Hz, 1H), 8.05 (d, J=8.0 Hz, 1H), 7.88 (t, J=8.0 Hz, 1H), 7.22 (s, 1H), 3.56 (s, 3H), 3.24 (s, 3H). LCMS (M+H)$^+$: 304.

Example 132: N-[2-methoxy-5-(7-methyl-8-oxoimidazo[1,5-a]pyrazin-5-yl)phenyl]methanesulfonamide

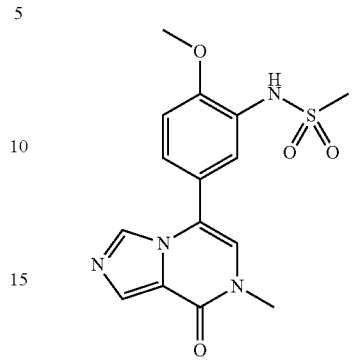

The title compound was prepared in a manner similar to Example 131, substituting [3-(methanesulfonamido)-4-methoxyphenyl]boronic acid for (3-methylsulfonylphenyl)boronic acid to give the title compound. $^1$H NMR (Methanol-d4 400 MHz): δ 8.81 (s, 1H), 8.29 (s, 1H), 7.70 (s, 1H), 7.50 (m, 2H), 7.28 (d, J=8.0 Hz, 1H), 7.12 (s, 1H), 4.01 (s, 3H), 3.56 (s, 3H), 3.08 (s, 3H). LCMS (M+H)$^+$: 349.

Example 133: 5-(3-ethylsulfonylphenyl)-7-methyl-imidazo[1,5-a]pyrazin-8-one

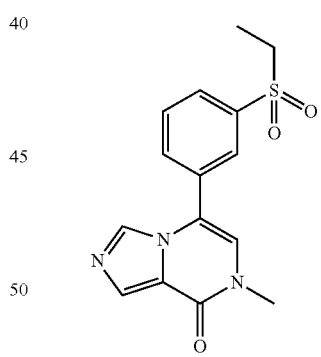

The title compound was prepared in a manner similar to Example 131, substituting (3-ethylsulfonylphenyl)boronic acid for (3-methylsulfonylphenyl)boronic acid to give the title compound. $^1$H NMR (Methanol-d4 400 MHz): δ 8.83 (s, 1H), 8.27 (s, 1H), 8.21 (s, 1H), 8.10 (d, J=7.6 Hz, 1H), 8.05 (d, J=8.0 Hz, 1H), 7.89 (t, J=8.0 Hz, 1H), 7.24 (s, 1H), 3.56 (s, 3H), 3.31 (q, J=7.6 Hz, 2H), 1.28 (t, J=7.6 Hz, 3H). LCMS (M+H)$^+$: 318.

511

Example 134: N-[3-(5-chloro-1-methyl-6-oxopyridin-3-yl)-4-(2,4-difluorophenoxy)phenyl]ethanesulfonamide

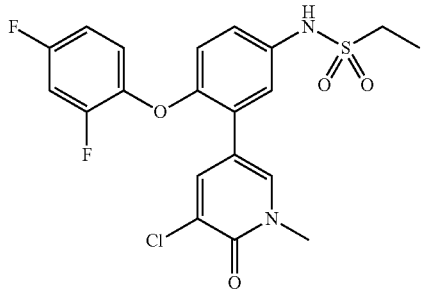 [SMILES: CCS(=O)(=O)Nc1ccc(Oc2ccc(F)cc2F)c(-c2cc(Cl)c(=O)n(C)c2)c1]

The title compound was prepared in a manner similar to Example 122, substituting 3-chloro-1-methyl-5-(4,4,5,5-tetramethyl-1,3,2-dioxaborolan-2-yl)pyridin-2-one for 3-fluoro-1-methyl-5-(4,4,5,5-tetramethyl-1,3,2-dioxaborolan-2-yl)pyridin-2-one. LCMS (M+H)⁺: 455.

Example 135: 4-[2-(cyclopropylmethoxy)-5-ethylsulfonylphenyl]-2-methylisoquinolin-1-one

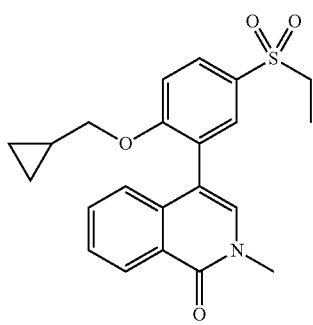 [SMILES: CCS(=O)(=O)c1ccc(OCC2CC2)c(-c2cn(C)c(=O)c3ccccc23)c1]

The title compound was prepared in a manner similar to Example 89, substituting 2-bromo-1-(cyclopropylmethoxy)-4-ethylsulfonylbenzene for 2-bromo-1-(cyclopropylmethoxy)-4-methylsulfonylbenzene. LCMS (M+H)⁺: 398.

Example 136: 6-[2-(cyclopropylmethoxy)-5-methylsulfonylphenyl]-2,4-dimethylpyridazin-3-one

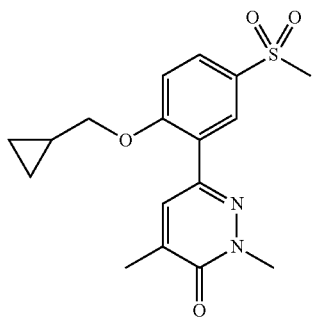 [SMILES: Cc1cc(-c2cc(S(C)(=O)=O)ccc2OCC2CC2)nn(C)c1=O]

512

The title compound was prepared in a manner similar to Example 90, substituting 6-chloro-2,4-dimethylpyridazin-3-one for 4-bromo-6-fluoro-2-methylisoquinolin-1-one. LCMS (M+H)⁺: 349.

Example 137: 6-[2-(cyclopropylmethoxy)-5-methylsulfonylphenyl]-2,5-dimethylpyridazin-3-one

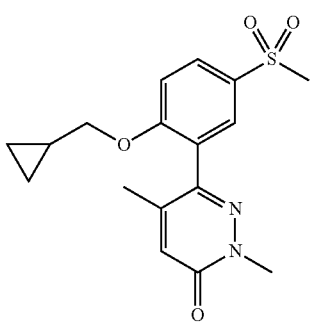 [SMILES: Cc1cc(=O)n(C)nc1-c1cc(S(C)(=O)=O)ccc1OCC1CC1]

The title compound was prepared in a manner similar to Example 90, substituting 6-chloro-2,5-dimethylpyridazin-3-one for 4-bromo-6-fluoro-2-methylisoquinolin-1-one. LCMS (M+H)⁺: 349.

Example 138: N-[4-(2,4-difluorophenoxy)-3-[1-methyl-6-oxo-5-(trifluoromethyl)pyridine-3-yl]phenyl]ethanesulfonamide

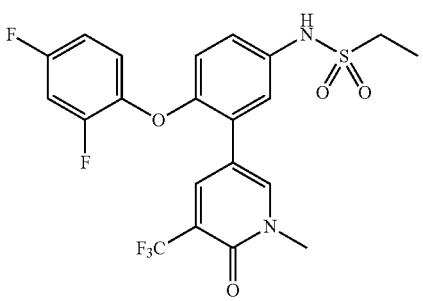

The title compound was prepared in a manner similar to Example 122, substituting 1-methyl-5-(4,4,5,5-tetramethyl-1,3,2-dioxaborolan-2-yl)-3-(trifluoromethyl)pyridin-2-one for 3-fluoro-1-methyl-5-(4,4,5,5-tetramethyl-1,3,2-dioxaborolan-2-yl)pyridin-2-one. LCMS (M+H)⁺ 489.

Example 139: N-[4-(2,4-difluorophenoxy)-3-(4-fluoro-1-methyl-6-oxopyridin-3-yl)phenyl]ethanesulfonamide

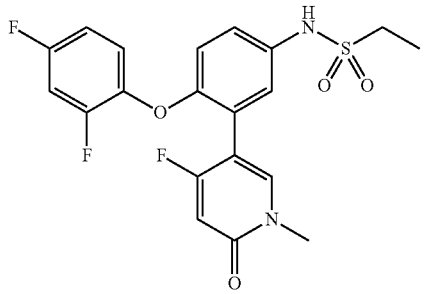 [SMILES: CCS(=O)(=O)Nc1ccc(Oc2ccc(F)cc2F)c(-c2cn(C)c(=O)cc2F)c1]

Step 1: 2-chloro-5-[2-(2,4-difluorophenoxy)-5-nitrophenyl]-4-fluoropyridine

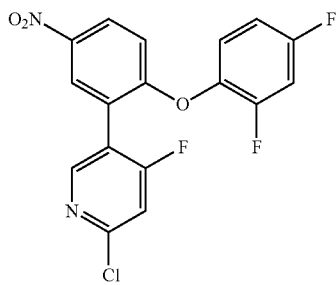 [SMILES: O=[N+]([O-])c1ccc(Oc2ccc(F)cc2F)c(-c2cnc(Cl)cc2F)c1]

A mixture of 2-chloro-4-fluoro-5-(4,4,5,5-tetramethyl-1,3,2-dioxaborolan-2-yl)pyridine (170 mg, 0.66 mmol), 2-bromo-1-(2,4-difluorophenoxy)-4-nitrobenzene (326 mg, 0.98 mmol), Pd$_2$(dba)$_3$ (30 mg, 5%), and tricyclohexylphosphine (280 mg, 10%) was suspended in 1,4-dioxane (4 mL) and aq 1M K$_3$PO$_4$ (2 mL). The mixture was heated to 70° C. using microwave irradiation (normal) for 45 min. The crude rxn mixture was filtered through a short plug of celite and the celite plug was washed with EtOAc (~50 mL). The filtrate was washed with H$_2$O (2×30 mL), brine, dried over Na$_2$SO$_4$, filtered and concentrated in vacuo. The resulting residue was purified by silica gel CC (12 g ISCO, gradient 5-75% EtOAc in hexanes) to afford the free base of the desired product, 2-chloro-5-[2-(2,4-difluorophenoxy)-5-nitrophenyl]-4-fluoropyridine as a yellow solid (144 mg, 57%). LCMS (M+H)$^+$: 381.

Step 2: 5-[2-(2,4-difluorophenoxy)-5-nitrophenyl]-4-fluoro-1-methylpyridin-2-one

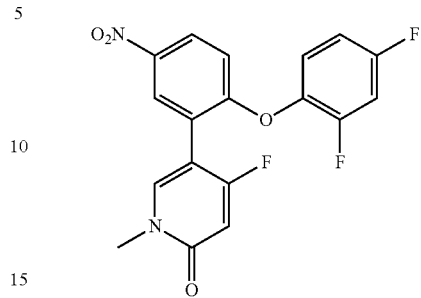

A mixture of 2-chloro-5-[2-(2,4-difluorophenoxy)-5-nitrophenyl]-4-fluoropyridine (140 mg, 0.37 mmol), KOH (62 mg, 1.11 mmol), Pd$_2$(dba)$_3$ (17 mg, 5%), and XPhos (18 mg, 10%) was suspended in 1,4-dioxane (1.9 mL) and H$_2$O (316 µL). After purging the rxn vial with N$_2$ for 5 min, the capped vial was stirred at 100° C. for 1 hr. After the mixture cooled to room temp, it was treated with 1N HCl (aq) (1 mL) and EtOAc (5 mL). The biphasic mixture was filtered through a short plug of celite and the celite plug was washed with EtOAc (~50 mL). The filtrate was washed with H$_2$O (2×30 mL), brine, dried over Na$_2$SO$_4$, filtered and concentrated in vacuo to afford a orange solid, 5-[2-(2,4-difluorophenoxy)-5-nitrophenyl]-4-fluoropyridin-2-ol (LCMS (M+H)$^+$363). After the solid was diluted with DMF (2.4 mL), it was treated with K$_2$CO$_3$ (112 mg) and MeI (23 µL). After stirring at room temp for 5 hr, the mixture was treated with H$_2$O (10 mL) and extracted with EtOAc (3×10 mL); the combined organic extracts were washed with satd bicarbonate soln (aq), dried over Na$_2$SO$_4$, filtered, concentrated in vacuo. The resulting residue was purified by silica gel CC (4 g ISCO, gradient 05-95% EtOAc in hexanes) to afford the desired product, 5-[2-(2,4-difluorophenoxy)-5-nitrophenyl]-4-fluoro-1-methylpyridin-2-one as a tan solid (95 mg). LCMS (M+H)$^+$: 377.

Step 3: 5-[5-amino-2-(2,4-difluorophenoxy)phenyl]-4-fluoro-1-methylpyridin-2-one

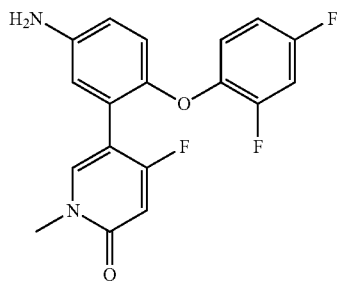 [SMILES: Cn1cc(-c2cc([N+](=O)[O-])ccc2Oc2ccc(F)cc2F)c(F)cc1=O]

A mixture of 5-[2-(2,4-difluorophenoxy)-5-nitrophenyl]-4-fluoro-1-methylpyridin-2-one (90 mg, 0.24 mmol), ammonium chloride (26 mg, 0.48 mmol), iron powder (67 mg, 1.2 mmol) suspended in THF (500 µL), H$_2$O (180 µL), and EtOH (500 µL) was heated to 100° C. using microwave irradiation (normal) for 3 hr. The crude rxn mixture was filtered through a short plug of celite and the celite plug was washed with heated (50° C.) MeOH (~10 mL). The resulting filtrate was concentrated in vacuo. The resulting residue was diluted with EtOAc (20 ml) and washed with satd bicarbonate soln (aq), dried over anhydrous magnesium sulfate, filtered, and concentrated in vacuo to afford the desired product, 5-[5-amino-2-(2,4-difluorophenoxy)-phenyl]-4-fluoro-1-methylpyridin-2-one (75 mg, 90%). LCMS (M+H)+: 347. The material was carried forward without any further purification.

Step 4: N-[4-(2,4-difluorophenoxy)-3-(4-fluoro-1-methyl-6-oxopyridin-3-yl)phenyl]ethanesulfonamide

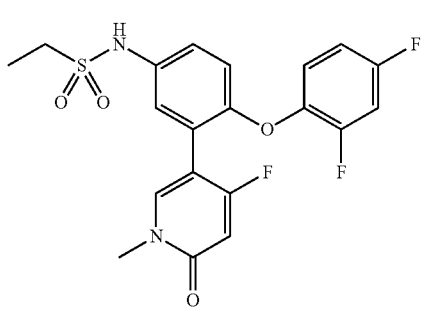 [SMILES: CCS(=O)(=O)Nc1ccc(Oc2ccc(F)cc2F)c(-c2cn(C)c(=O)cc2F)c1]

Ethylsulfonyl chloride (177 mg, 1.4 mmol) was added dropwise to a stirred soln of 5-[5-amino-2-(2,4-difluorophenoxy)phenyl]-4-fluoro-1-methylpyridin-2-one (72 mg, 0.21 mmol) and pyridine (50 pt, 0.63 mmol) in CH$_2$Cl$_2$ (500 μL) at 0° C. under N$_2$. After the mixture was allowed to warm to room temp and stir for 2 hr, it was treated with 1N HCl (3 mL) and extracted with CH$_2$Cl$_2$ (3×10 mL); the combined organic extracts were washed with satd bicarbonate soln (aq), dried over Na$_2$SO$_4$, filtered and concentrated in vacuo. The resulting residue was purified by silica gel CC (4 g ISCO, gradient 0-10% MeOH in CH$_2$Cl$_2$) to afford the desired product, N-[4-(2,4-difluorophenoxy)-3-(4-fluoro-1-methyl-6-oxopyridin-3-yl)phenyl]ethanesulfonamide (66 mg, 72%) as a white solid. $^1$H NMR (400 MHz, DMSO-d6): δ 1.18-1.26 (m, 3H), 3.07-3.16 (m, 2H), 3.45 (s, 3H), 6.22-6.33 (m, 1H), 6.82-6.93 (m, 1H), 7.01-7.16 (m, 2H), 7.18-7.28 (m, 2H), 7.38-7.49 (m, 1H), 7.95-8.05 (m, 1H), 9.77-9.87 (s, 1H). LCMS (M+H)+: 439.

Example 140: N-[3-(5-cyclopropyl-1-methyl-6-oxopyridin-3-yl)-4-(2,4-difluorophenoxy)phenyl]ethanesulfonamide

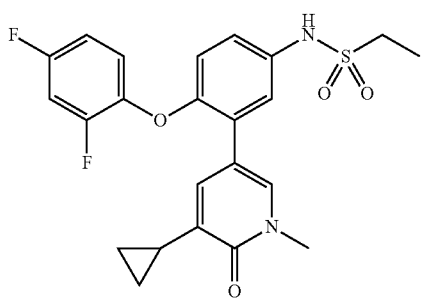 [SMILES: CCS(=O)(=O)Nc1ccc(Oc2ccc(F)cc2F)c(-c2cc(C3CC3)c(=O)n(C)c2)c1]

The title compound was prepared in a manner similar to Example 122, substituting 3-cyclopropyl-1-methyl-5-(4,4,5,5-tetramethyl-1,3,2-dioxaborolan-2-yl)pyridin-2-one for 3-fluoro-1-methyl-5-(4,4,5,5-tetramethyl-1,3,2-dioxaborolan-2-yl)pyridin-2-one. LCMS (M+H)+: 461.

Example 141: N-{4-(2,4-difluorophenoxy)-3-[1-($^2$H$_3$)methyl-6-oxopyridin-3-yl]phenyl}ethanesulfonamide

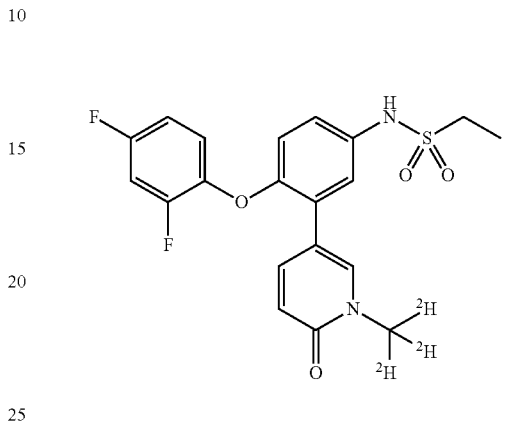

The title compound was prepared in a manner similar to Example 122, substituting 1-($^2$H$_3$)methyl-5-(4,4,5,5-tetramethyl-1,3,2-dioxaborolan-2-yl)pyridin-2-one for 3-fluoro-1-methyl-5-(4,4,5,5-tetramethyl-1,3,2-dioxaborolan-2-yl)pyridin-2-one. LCMS (M+H)+: 424.

Example 142: N-[4-(2,4-difluorophenoxy)-3-(2-methyl-1-oxo-5,6,7,8-tetrahydro-2,6-naphthyridin-4-yl)phenyl]ethanesulfonamide

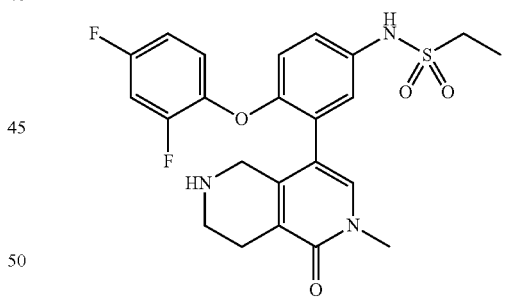

The title compound of Example 127 (240 mg, 0.5 mmol) was hydrogenated (50 psi) at room temp in anhydrous EtOH (30 mL) for 18 hr using PtO$_2$ (0.1 g). Purification by preparative HPLC gave the title compound (40 mg, 16.7%) as a white solid. $^1$H NMR (Methanol-d4, 400 MHz): δ 7.36 (s., 1H), 7.23 (dd, J$_1$=8.8 Hz, J$_2$=2.8 Hz 1H), 7.14 (d, J=2.8 Hz, 1H), 7.06-6.96 (m, 2H), 6.91-6.86 (m, 2H), 3.83-3.49 (m, 2H), 3.53 (s, 3H), 3.16-2.89 (m, 2H), 3.08 (q, J=7.2 Hz, 2H), 2.55 (t, J=6.0 Hz, 2H), 2.55 (t, J=7.2 Hz, 3H). LCMS (M+H)+: 476.

Example 143: 4-[5-(cyclopropylmethoxy)-2-(methylsulfonylmethyl)pyrimidin-4-yl]-2-methylisoquinolin-1-one

Step 1: 5-(cyclopropylmethoxy)-2-(methylsulfonylmethyl)pyrimidin-4-ol

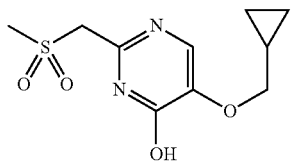 [SMILES: CS(=O)(=O)Cc1ncc(OCC2CC2)c(O)n1]

To the title compound of Example 152, step 1 (5.00 g, 31.6 mmol) in THF (50 mL) at 0° C. was added NaH (1.26 g, 31.6 mmol, 60% in mineral oil). Ethyl formate (2.57 g, 34.76 mmol) was added at 0° C. and the mixture was heated at 70° C. for 2 h. The mixture was then cooled to room temp and a pre-mixed soln of 2-(methylsulfonyl)-ethanimidamide (6.44 g 47.4 mmol) and EtONa (4.3 g, 63.2 mmol) in ethanol (50 mL) was added dropwise. The mixture was heated at 90° C. for 12 hr, cooled to room temp, and solvent was removed under vacuum. H$_2$O (50 mL) was added to the residue and the pH was adjusted to 5 with 1M HCl. The resulting precipitate was collected and washed with H$_2$O (100 ml), EtOH (50 ml) and MeOH (30 mL) to give the title compound (1.9 g, yield: 23.4%) as a white solid. $^1$H NMR (DMSO-d6, 400 MHz): δ 11.49 (s, 1H), 6.83 (s, 1H), 6.49 (s, 2H), 3.63 (d, J=6.8 Hz, 2H), 3.04 (s, 3H), 1.14-1.10 (m, 1H), 0.52-0.49 (m, 2H), 0.27-0.24 (m, 2H). LCMS: 259.0 (M+1)$^+$.

Step 2: 4-chloro-5-(cyclopropylmethoxy)-2-(methylsulfonylmethyl)pyrimidine

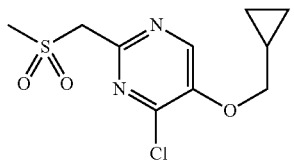 [SMILES: CS(=O)(=O)Cc1ncc(OCC2CC2)c(Cl)n1]

To the title compound of step 1 (1.9 g, 7.36 mmol) in MeCN (30 mL) was added Me$_4$NCl (1.6 g, 14.72 mmol) and POCl$_3$ (6.8 g, 44.16 mmol). The mixture was heated at 80° C. for 6 hr. After concentration under vacuum, the residue was subjected to EA extractive work-up. Trituration with MeOH (20 mL) gave the title compound (1 g, yield: 49.3%) as a white solid. $^1$H NMR (CDCl$_3$, 400 MHz): δ 7.60 (s, 1H), 5.50 (s, 2H), 3.85 (d, J=6.8 Hz, 2H), 3.09 (s, 3H), 1.31-1.28 (m, 1H), 0.70-0.65 (m, 2H), 0.39-0.36 (m, 2H). LCMS: 277.1 (M+1)$^+$.

Step 3: 4-[5-(cyclopropylmethoxy)-2-(methylsulfonylmethyl)pyrimidin-4-yl]-2-methylisoquinolin-1-one

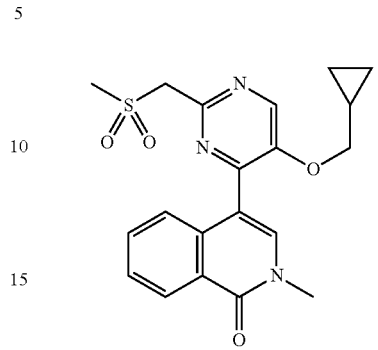

The title compound of step 2 (100 mg, 0.36 mmol), the title compound of Example 89, step 1 (124 mg, 0.43 mmol), Pd(dppf)Cl$_2$ (27 mg, 0.03 mmol) and K$_3$PO$_4$ (154 mg, 0.72 mmol) in dioxane (5 mL) and H$_2$O (5 drops) were N$_2$ purged and heated to 70° C. for 18 hr. After concentration under vacuum, the residue was purified using silica gel chromatography followed by prep-HPLC to give the title compound (61.7 mg, 42.7%) as a yellow solid. $^1$H NMR (DMSO-d6, 400 MHz) δ 8.29 (d, J=7.2 Hz, 1H), 7.69-7.65 (m, 3H), 7.53 (t, J=7.2 Hz, 1H), 7.44 (d, J=8.0 Hz, 1H), 3.76 (d, J=6.8 Hz, 2H), 3.58 (s, 3H), 3.26 (s, 3H), 0.94-0.88 (m, 1H), 0.35-0.31 (m, 2H), 0.10-0.08 (m, 2H). LCMS: 400.1 (M+1)$^+$.

Example 144: 5-[5-(cyclopropylmethoxy)-2-(methylsulfonylmethyl)pyrimidin-4-yl]-1,3-dimethylpyridin-2-one

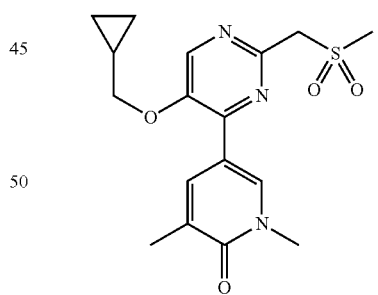

The title compound of Example 143, step 2 was reacted with 1,3-dimethyl-5-(4,4,5,5-tetramethyl-1,3,2-dioxaborolan-2-yl)pyridin-2-one in a manner similar to Example 143, step 3 to give the title compound. $^1$H NMR (CDCl$_3$, 400 MHz): δ 8.49 (d, J=2.0 Hz, 1H), 8.18 (s, 1H), 7.60 (s, 1H), 3.86 (d, J=6.8 Hz, 2H), 3.67 (s, 3H), 3.11 (s, 3H), 2.24 (s, 3H), 1.29-1.27 (m, 1H), 0.72-0.67 (m, 2H), 0.39-0.35 (m, 2H). LCMS: 364.1 (M+1)$^+$.

Example 145: 4-[5-(cyclopropylmethoxy)-2-(methylsulfonylmethyl)pyrimidin-4-yl]-2-methyl-6-(1-methylpyrazol-4-yl)isoquinolin-1-one

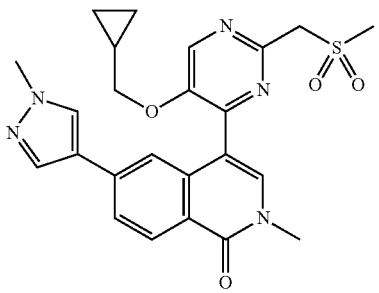 [SMILES: Cn1cc(-c2ccc3c(=O)n(C)cc(-c4nc(CS(C)(=O)=O)ncc4OCC4CC4)c3c2)cn1]

The title compound of Example 143, step 2 was reacted with the title compound of Example 46, step 2 in a manner similar to Example 143, step 3 to give the title compound. ¹H NMR (DMSO-d6, 400 MHz) δ 8.26 (d, J=8.4 Hz, 1H), 8.23 (s, 1H), 7.91 (s, 1H), 7.5 (d, J=8.4 Hz, 1H), 7.70 (s, 1H), 7.66 (s, 1H), 7.52 (s, 1H), 3.87 (s, 3H), 3.85-3.80 (m, 4H), 3.57 (s, 3H), 3.28 (s, 3H), 0.88-0.87 (m, 1H), 0.30-0.25 (m, 2H), 0.07-0.04 (m, 2H). LCMS: 480.2 (M+1)⁺.

Example 146: 5-[5-(2,4-difluorophenoxy)-2-(methylsulfonylmethyl)pyrimidin-4-yl]-3-methoxy-1-methylpyridin-2-one

Step 1: 5-(2,4-difluorophenoxy)-2-(methylsulfonylmethyl)pyrimidin-4-ol

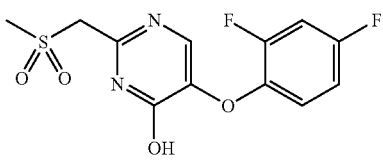 [SMILES: CS(=O)(=O)Cc1ncc(Oc2ccc(F)cc2F)c(O)n1]

To a stirred suspension of NaH (960 mg, 24 mmol, 60% in mineral oil) in anhydrous THF (33 mL) was added ethyl formate (1.8 g, 24.3 mmol) and 2-(2,4-difluorophenoxy) acetic acid ethyl ester (4.3 g, 19.9 mmol) in anhydrous THF (10 mL). The suspension was stirred at room temp for 0.5 hr and then refluxed for 3 hr, cooled, and concentrated under vacuum. The residue was dissolved in EtOH (50 mL) and 2-(methylsulfonyl)-ethanimidamide (3.0 g, 22.1 mmol) was added and the mixture was refluxed for 18 hr. After concentration under vacuum, H₂O (50 mL) was added and the pH was adjusted to pH 5 with acetic acid. After EA extractive work-up, the residue was dissolved in EA (20 mL) and PE (150 mL) was added. The resulting precipitate (3.0 g, crude) was collected as a grey solid to give the title compound. LCMS: 317.1 (M+1)⁺.

Step 2: 4-chloro-5-(2,4-difluorophenoxy)-2-(methylsulfonylmethyl)pyrimidine

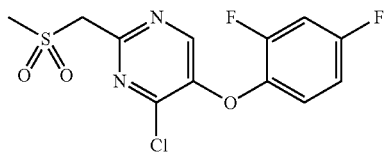 [SMILES: CS(=O)(=O)Cc1ncc(Oc2ccc(F)cc2F)c(Cl)n1]

To the title compound of step 1 (3.0 g) and N(CH₃)₄Cl (1.6 g, 14.2 mmol) in anhydrous MeCN (30 mL), POCl₃ (8.7 g, 56.9 mmol) was added dropwise. The mixture was stirred at room temp for 0.5 hr and then at 70° C. for 6 hr. After concentration under vacuum, H₂O was added and EA extractive work-up was carried out to give the title compound (3.0 g) as a light yellow solid. LCMS: 335.1 (M+1)⁺.

Step 3: 5-[5-(2,4-difluorophenoxy)-2-(methylsulfonylmethyl)pyrimidin-4-yl]-3-methoxy-1-methylpyridin-2-one

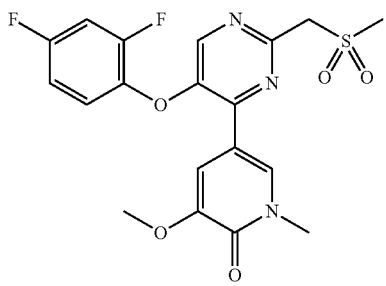 [SMILES: COc1cc(-c2nc(CS(C)(=O)=O)ncc2Oc2ccc(F)cc2F)cn(C)c1=O]

The title compound of Example 287, step 1 was treated with 4,4,5,5-tetramethyl-2-(tetramethyl-1,3,2-dioxaborolan-2-yl)-1,3,2-dioxaborolane in a manner similar to that outlined for Example 119, step 2 to give 3-methoxy-1-methyl-5-(4,4,5,5-tetramethyl-1,3,2-dioxaborolan-2-yl)pyridin-2-one which was then reacted with the title compound of step 2 in a manner similar to Example 143, step 3 to give the title compound. ¹H NMR (DMSO-d6, 400 MHz) δ 8.37 (s, 1H), 8.36 (d, J=2.0 Hz, 1H), 7.62 (d, J=2.0 Hz, 1H), 7.60-7.54 (m, 1H), 7.51-7.45 (m, 1H), 7.22-7.18 (m, 1H), 4.78 (s, 2H), 3.77 (s, 3H), 3.56 (s, 3H), 3.20 (s, 3H). LCMS: 438.1 (M+1)⁺.

Example 147: 5-[5-(2,4-difluorophenoxy)-2-(methylsulfonylmethyl)pyrimidin-4-yl]-1,3-dimethylpyridin-2-one

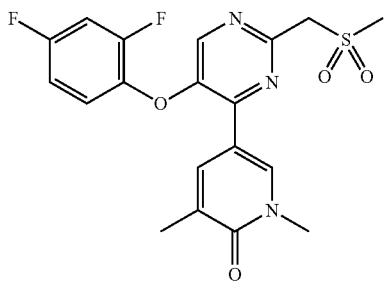 [SMILES: Cc1cc(-c2nc(CS(C)(=O)=O)ncc2Oc2ccc(F)cc2F)cn(C)c1=O]

The title compound of Example 146, step 2 was reacted with 1,3-dimethyl-5-(4,4,5,5-tetramethyl-1,3,2-dioxaborolan-2-yl)pyridin-2-one in a manner similar to Example 143, step 3 to give the title compound. ¹H NMR (DMSO-d6, 400 MHz): δ 8.58 (d, J=2.0 Hz, 1H), 8.35 (s, 1H), 8.13 (s, 1H), 7.60-7.54 (m, 1H), 7.52-7.46 (m, 1H), 7.22-7.17 (m, 1H), 4.76 (s, 2H), 3.56 (s, 3H), 3.18 (s, 3H), 2.08 (s, 3H). LCMS: 422.1 (M+1)⁺.

Example 148: 4-[5-(2,4-difluorophenoxy)-2-(methylsulfonylmethyl)pyrimidin-4-yl]-2-methylisoquinolin-1-one

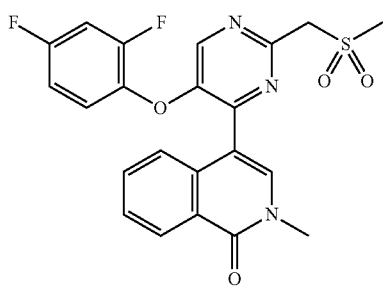 [SMILES: Cn1cc(-c2nc(CS(C)(=O)=O)ncc2Oc2ccc(F)cc2F)c2ccccc2c1=O]

The title compound of Example 146, step 2 was reacted with the title compound of Example 89, step 1 in a manner similar to Example 143, step 3 to give the title compound. ¹H NMR (DMSO-d6, 400 MHz): δ 8.62 (s, 1H), 8.28 (d, J=8.0 Hz, 1H), 7.91 (s, 1H), 7.69-7.68 (m, 2H), 7.58-7.54 (m, 1H), 7.45-7.34 (m, 2H), 7.07-7.03 (m, 1H), 4.83 (s, 2H), 3.58 (s, 3H), 3.17 (s, 3H). LCMS: 458.1 (M+1)⁺.

Example 149: 5-[5-(2,4-difluorophenoxy)-2-methylsulfonylpyrimidin-4-yl]-1,3-dimethylpyridin-2-one Step 1: 5-(2,4-difluorophenoxy)-2-methylsulfanylpyrimidin-4-ol

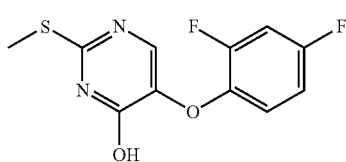 [SMILES: CSc1ncc(Oc2ccc(F)cc2F)c(O)n1]

To a soln of 2-(2,4-difluorophenoxy)acetic acid ethyl ester (8.0 g, 37.01 mmol) and ethyl formate (4.11 g, 55.51 mmol) in dry THF (200 mL) was added NaH (1.55 g, 38.75 mmol) slowly at 0° C. The mixture was then refluxed for 2 hr. In a separate flask, sodium ethoxide (3.02 g, 44.41 mmol) and S-methylthiopseudourea hemisulfate (6.17 g, 44.41 mmol) in EtOH (100 mL) were stirred at 20° C. for 2 hr and then the resulting mixture was added to the above THF soln. The combined mixture was refluxed for 12 hr. After concentration under vacuum, H₂O (20 mL) and HCl (10 mL, aq 1N) were added. The suspended solids were collected and washed with H₂O (50 mL×3) and EtOH (50 mL×3) and dried to give the title compound (6.0 g, 60.0% yield) as a light yellow solid. ¹H NMR (DMSO-d6, 400 MHz): δ 7.84 (s, 1H), 7.42-7.34 (m, 1H), 7.04-7.01 (m, 1H), 6.95 (t, J=9.6 Hz, 1H), 2.47 (s, 3H). LCMS: 271.1 (M+1)⁺.

Step 2: 4-chloro-5-(2,4-difluorophenoxy)-2-methylsulfanylpyrimidine

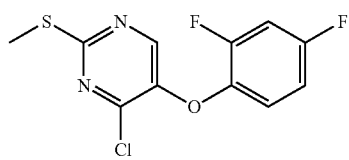 [SMILES: CSc1ncc(Oc2ccc(F)cc2F)c(Cl)n1]

The title compound of step 1 (5.30 g, 19.63 mmol), POCl₃ (18.06 g, 117.78 mmol), (Me)₄NCl (3.23 g, 29.47 mmol) in dry CH₃CN (60 mL) was refluxed for 12 hr. The mixture was poured into ice-water (50 mL) and subjected to EA extractive work-up. Concentration under vacuum gave impure title compound (4.0 g), which was carried on to the next step. LCMS: 288.99 (M+1)⁺.

Step 3: 4-chloro-5-(2,4-difluorophenoxy)-2-methylsulfonylpyrimidine

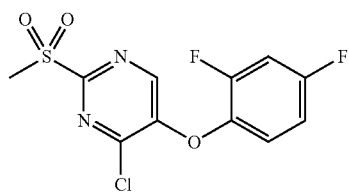 [SMILES: CS(=O)(=O)c1ncc(Oc2ccc(F)cc2F)c(Cl)n1]

To a soln of the title compound of step 2 (4.60 g, 15.93 mmol) in CH₂Cl₂ (200 mL) was added mCPBA (13.75 g, 79.68 mmol) slowly at 0° C. The mixture was stirred at 20° C. for 12 hr and then sat. aq Na₂SO₃ (200 mL) was added. EA extractive work-up and silica gel chromatography gave the title compound (2.0 g, 39.1% yield) as a yellow solid. ¹H NMR (CDCl₃, 400 MHz): δ 8.18 (s, 1H), 7.31-7.27 (m, 1H), 7.10-7.01 (m, 2H), 3.36 (s, 3H). LCMS: 320.8 (M+1)⁺.

Step 4: 5-[5-(2,4-difluorophenoxy)-2-methylsulfonylpyrimidin-4-yl]-1,3-dimethylpyridin-2-one

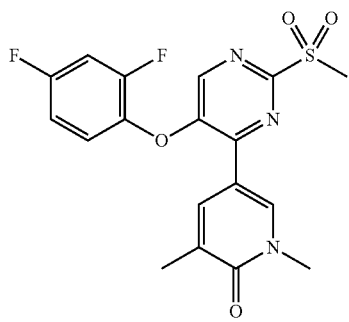 [SMILES: Cc1cc(-c2nc(S(C)(=O)=O)ncc2Oc2ccc(F)cc2F)cn(C)c1=O]

A mixture of the title compound from step 3 (100 mg, 0.31 mmol), 1,3-dimethyl-5-(4,4,5,5-tetramethyl-1,3,2-dioxaborolan-2-yl)pyridin-2-one (93 mg, 0.37 mmol), Pd(dppf)Cl₂ (23 mg, 0.31 mmol) and K₃PO₄ (199 mg, 0.94 mmol) in dioxane/H₂O (3 mL/0.5 mL) was N₂ purged and heated at 70° C. for 12 hr. Concentration under vacuum and silica gel chromatography (PE:EA=3:1~0:1) followed by prep-HPLC gave the title compound (45 mg, 35.4%). $^1$H NMR (CDCl$_3$, 400 MHz): δ 8.57 (s, 1H), 8.25 (s, 1H), 8.15 (s, 1H), 7.25-7.24 (m, 1H), 7.12-7.07 (m, 1H), 7.03 (t, J=8.0 Hz, 1H), 3.68 (s, 3H), 3.38 (s, 3H), 2.25 (s, H). LCMS: 407.9 (M+1)$^+$.

Example 150: 5-[5-(2,4-difluorophenoxy)-2-methyl-sulfonylpyrimidin-4-yl]-3-methoxy-1-methylpyridin-2-one

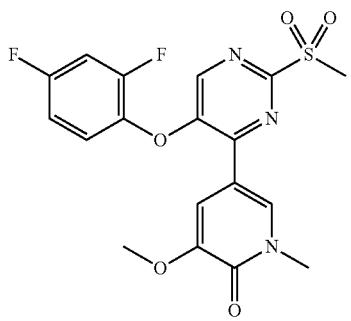 [SMILES: COc1cc(-c2nc(S(C)(=O)=O)ncc2Oc2ccc(F)cc2F)cn(C)c1=O]

The title compound of Example 149, step 3 was reacted with 3-methoxy-1-methyl-5-(4,4,5,5-tetramethyl-1,3,2-dioxaborolan-2-yl)pyridin-2-one (see Example 146, step 3) in a manner similar to Example 149, step 4 to give the title compound. $^1$H NMR (CDCl$_3$, 400 MHz): δ 8.35 (d, J=2.0 Hz, 1H), 8.18 (s, 1H), 7.70 (d, J=2.0 Hz, 1H), 7.25-7.22 (m, 1H), 7.12-7.08 (m, 1H), 7.08-7.04 (m, 1H), 3.93 (s, 3H), 3.70 (s, 3H), 3.38 (s, 3H). LCMS: 423.9 (M+1)$^+$.

Example 151: 4-[5-(2,4-difluorophenoxy)-2-methyl-sulfonylpyrimidin-4-yl]-2-methylisoquinolin-1-one

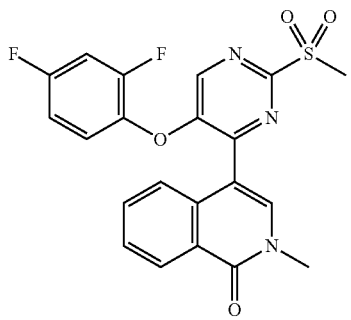

The title compound of Example 149, step 3 was reacted with the title compound of Example 89, step 1 in a manner similar to Example 149, step 4 to give the title compound. $^1$H NMR (CDCl$_3$, 400 MHz): δ 8.52 (d, J=8.0 Hz, 1H), 8.32 (s, 1H), 7.68 (s, 3H), 7.59-7.56 (m, 1H), 7.14-7.08 (m, 1H), 7.05-7.00 (m, 1H), 6.96-6.92 (m, 1H), 3.72 (s, 3H), 3.39 (s, 3H). LCMS: 443.9 (M+1)$^+$.

Example 152: N-[5-(cyclopropylmethoxy)-4-(2-methyl-1-oxoisoquinolin-4-yl)pyrimidin-2-yl]methanesulfonamide Step 1: Ethyl 2-(cyclopropylmethoxy)acetate

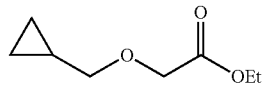 [SMILES: CCOC(=O)COCC1CC1]

Diazoacetic acid ethyl ester (80.00 g, 0.70 mol) was added dropwise to cyclopropanemethanol (60.66 g, 0.84 mol) and [Rh(Ac$_2$O)$_2$]$_2$ (3.1 g, 7.02 mmol) in anhydrous CH$_2$Cl$_2$ (800 mL) at 0° C. The mixture was stirred at 0° C. for 30 min and at room temp for 4 hr. CH$_2$Cl$_2$ extractive work-up and silica gel chromatography (PE:EA=100:1~50:1) gave the title compound (100 g, 90.4% yield) as a colorless oil. $^1$H NMR (CDCl$_3$, 400 MHz): δ 4.23-4.19 (m, 2H), 4.09 (s, 2H), 3.38-3.36 (m, 2H), 1.27 (t, J=7.2 Hz, 3H), 1.10-1.07 (m, 1H), 0.57-0.52 (m, 2H), 0.24-0.20 (m, 2H).

Step 2: 5-(cyclopropylmethoxy)-2-methylsulfanylpyrimidin-4-ol

To a stirred suspension of NaH (35.20 g, 0.88 mol, 60% in mineral oil) in anhydrous THF (1000 mL) was added ethyl formate (88.80 g, 0.90 mol) and the title compound of step 1 (126.0 g, 0.80 mol) in anhydrous THF (100 mL). The mixture was stirred at room temp for 0.5 hr and refluxed for 3 hr. In a separate flask, S-methylthiopseudourea hemisulfate (133.44 g, 0.96 mol) and sodium ethoxide (65.28 g, 0.96 mol) in EtOH (200 mL) were stirred at room temp for 1 hr, whereupon this mixture was added to the above mixture. There combined mixture was refluxed for 15 hr, cooled, and the pH was adjusted to 5 with acetic acid. After concentration under vacuum, silica gel chromatography (DCM:MeOH=50:1 to 10:1) gave the title compound (30.00 g, 17.7% yield) as a yellow solid. $^1$H NMR (CDCl$_3$, 400 MHz): δ 12.08 (s, 1H), 7.49 (s, 1H), 3.83-3.80 (m, 2H), 2.55 (s, 3H), 1.37-1.28 (m, 1H), 0.65-0.62 (m, 2H), 0.37-0.34 (m, 2H).

Step 3: 4-chloro-5-(cyclopropylmethoxy)-2-methyl-sulfanylpyrimidine

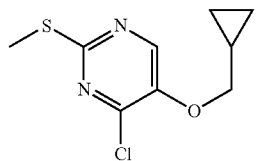

To the title compound of step 2 (29.00 g, 136.79 mmol) and N(CH₃)₄Cl (22.47 g, 205.19 mmol) in anhydrous MeCN (300 mL), was added POCl₃ (123.93 g, 820.74 mmol). The mixture was stirred at room temp for 30 min and at 70° C. for 1 hr. After concentration under vacuum, EA extractive work-up and silica gel chromatography (PE:EA=50:1~5:1) gave the title compound (20 g, 63.6% yield) as a white solid. ¹H NMR (CDCl₃, 400 MHz): δ 8.16 (s, 1H), 3.95 (d, J=6.8 Hz, 2H), 2.56 (s, 3H), 1.33-1.28 (m, 1H), 0.72-0.70 (m, 2H), 0.41-0.37 (m, 2H). LCMS: 230.9 (M+1)⁺.

Step 4: 4-chloro-5-(cyclopropylmethoxy)-2-methyl-sulfonylpyrimidine

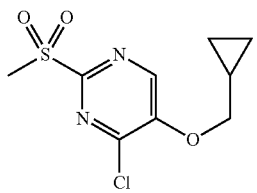 [SMILES: CS(=O)(=O)c1ncc(OCC2CC2)c(Cl)n1]

To the title compound of step 3 (19.0 g, 82.60 mmol) in dry CH₂Cl₂ (200 mL) at 0° C., m-CPBA (42.62 g, 247.80 mmol) was added over 15 min. The mixture was stirred at 0° C. for 30 min and at room temp overnight. Sat. aq Na₂SO₃ (100 mL) was added and CH₂Cl₂ extractive work-up was carried out. Trituration with MTBE (300 mL) gave the title compound (17 g, 78.3% yield) as a white solid. ¹H NMR (CDCl₃, 400 MHz): δ 8.37 (s, 1H), 4.13 (d, J=6.8 Hz, 2H), 3.33 (s, 3H), 1.39-1.35 (m, 1H), 0.79-0.74 (m, 2H), 0.49-0.45 (m, 2H). LCMS: 263.0 (M+1)⁺.

Step 5: 4-[5-(cyclopropylmethoxy)-2-methylsulfonylpyrimidin-4-yl]-2-methylisoquinolin-1-one

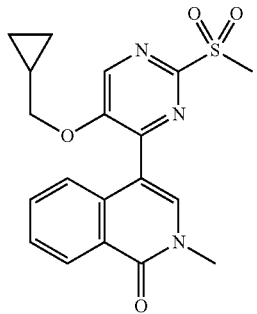 [SMILES: Cn1cc(-c2nc(S(C)(=O)=O)ncc2OCC2CC2)c2ccccc2c1=O]

The title compound of step 4 (5.00 g, 19.08 mmol), the title compound of Example 89, step 1 (5.98 g, 20.99 mmol), K₃PO₄ (12.13 g, 57.24 mmol), and Pd(dppf)Cl₂ (1.40 g, 1.91 mmol) in dioxane/H₂O (50 mL/5 mL) were N₂ purged and heated at 80° C. for 8 hr. Silica gel chromatography (PE:EA=10:1~1:1) to gave the title compound (5.01 g, yield: 68%) as a yellow solid. ¹H NMR (CDCl₃, 400 MHz): δ 8.53 (s, 2H), 7.67-7.63 (m, 2H), 7.57-7.52 (m, 2H), 4.06 (d, J=6.8 Hz, 2H), 3.71 (s, 3H), 3.37 (s, 3H), 1.17 (m, 1H), 0.61 (m, 2H), 0.30 (m, 2H). LCMS: 386.1 (M+1)⁺.

Step 6: N-[5-(cyclopropylmethoxy)-4-(2-methyl-1-oxoisoquinolin-4-yl)pyrimidin-2-yl]methanesulfonamide

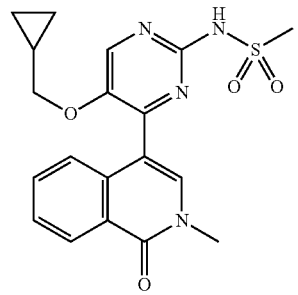 [SMILES: Cn1cc(-c2nc(NS(C)(=O)=O)ncc2OCC2CC2)c2ccccc2c1=O]

Sodium hydride (0.93 g, 23.37 mmol, 60% in mineral oil) was added to MeSO₂NH₂ (2.22 g, 23.37 mmol) in dry DMF (30 mL) at 0° C. over 15 min. The mixture was stirred at 0° C. for 1 hr and the title compound of step 5 (3.00 g, 7.79 mmol) was added. The mixture was heated at 60° C. for 6 hr. After cooling, ice water was added and the pH was adjusted to 5 with acetic acid. The suspended solids were collected and washed with MTBE (50 mL) to afford the title compound (3 g, yield: 96.7%) as an off-white solid. ¹H NMR (CDCl₃, 400 MHz): δ 9.80 (s, 1H), 8.53 (d, J=8.0 Hz, 1H), 8.42 (s, 1H), 7.97 (d, J=8.4 Hz, 1H), 7.70 (m, 2H), 7.56 (t, J=7.6 Hz, 1H), 3.87 (d, J=7.2 Hz, 2H), 3.70 (s, 3H), 3.39 (s, 3H), 1.12 (m, 1H), 0.58 (m, 2H), 0.24 (m, 2H). LCMS: 401.1 (M−1)⁺.

Example 153: N-[5-(cyclopropylmethoxy)-4-(1,5-dimethyl-6-oxopyridin-3-yl)pyrimidin-2-yl]methanesulfonamide

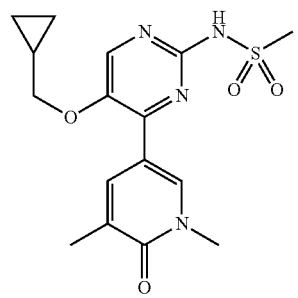 [SMILES: Cc1cc(-c2nc(NS(C)(=O)=O)ncc2OCC2CC2)cn(C)c1=O]

The title compound of Example 152, step 4 was reacted with 1,3-dimethyl-5-(4,4,5,5-tetramethyl-1,3,2-dioxaborolan-2-yl)pyridin-2-one in a manner similar to Example 152, step 5 and the resulting product was treated with MeSO₂NH₂ in a manner similar to Example 152, step 6 to give the title compound. ¹H NMR (DMSO-d6, 400 MHz): δ 10.97 (s, 1H), 8.67 (s, 1H), 8.42 (s, 1H), 8.14 (s, 1H), 4.03 (d, J=6.4 Hz, 2H), 3.54 (s, 3H), 3.35 (s, 3H), 2.08 (s, 3H), 1.33-1.31 (m, 1H), 0.63-0.61 (m, 2H), 0.38-0.37 (m, 2H). LCMS: 365.0 (M+1)⁺.

Example 154: N-[5-(cyclopropylmethoxy)-4-[2-methyl-6-(1-methylpyrazol-4-yl)-1-oxoisoquinolin-4-yl]pyrimidin-2-yl]methanesulfonamide

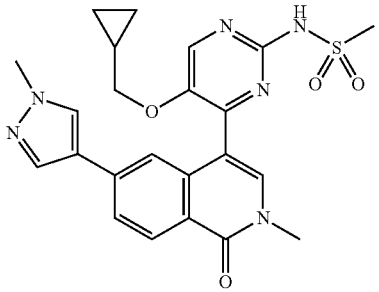 [SMILES: Cn1cc(-c2ccc3c(=O)n(C)cc(-c4nc(NS(C)(=O)=O)ncc4OCC4CC4)c3c2)cn1]

The title compound of Example 152, step 4 was reacted with the title compound of Example 46 step 2 in a manner similar to Example 152, step 5 and the resulting product was treated with MeSO$_2$NH$_2$ in a manner similar to Example 152, step 6 to give the title compound. $^1$H NMR (CDCl$_3$, 400 MHz): δ 11.15 (s, 1H), 8.56 (s, 1H), 8.27 (s, 1H), 8.25 (d, J=7.6 Hz, 1H), 7.98 (s, 1H), 7.79 (s, 1H), 7.77 (d, J=9.6 Hz, 1H), 7.70 (s, 1H), 3.95 (d, J=7.2 Hz, 2H), 3.85 (s, 3H), 3.57 (s, 3H), 3.32 (s, 3H), 1.00-0.99 (m, 1H), 0.37-0.32 (m, 2H), 0.14-0.12 (m, 2H). LCMS: 481.0 (M+1)$^+$.

Example 155: N-[5-(cyclopropylmethoxy)-4-(2-methyl-1-oxoisoquinolin-4-yl)pyrimidin-2-yl]ethanesulfonamide

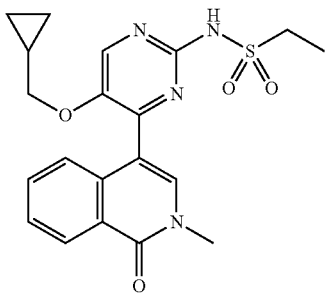 [SMILES: CCS(=O)(=O)Nc1ncc(OCC2CC2)c(-c2cn(C)c(=O)c3ccccc23)n1]

The title compound of Example 152, step 5 was treated with EtSO$_2$NH$_2$ instead of MeSO$_2$NH$_2$ in a manner similar to Example 152, step 6 to give the title compound. $^1$H NMR (CDCl$_3$, 400 MHz) δ 9.00 (s, 1H), 8.53 (d, J=8.0 Hz, 1H), 8.38 (s, 1H), 7.97 (d, J=8.0 Hz, 1H), 7.69 (m, 2H), 7.57 (t, J=7.6 Hz, 1H), 3.86 (d, J=6.8 Hz, 2H), 3.70 (s, 3H), 3.63 (q, J=7.2 Hz, 2H), 1.43 (t, J=7.2 Hz, 3H), 1.13 (m, 1H), 0.57 (m, 2H), 0.25 (m, 2H). LCMS: 415.0 (M+1)$^+$.

Example 156: 4-[5-(cyclopropylmethoxy)-2-(1,1-dioxo-1,2-thiazolidin-2-yl)pyrimidin-4-yl]-2-methyl-isoquinolin-1-one

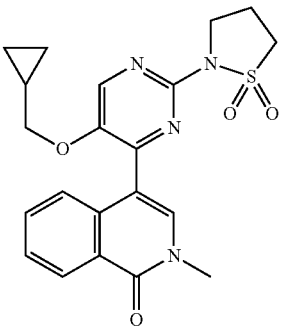 [SMILES: Cn1cc(-c2nc(N3CCCS3(=O)=O)ncc2OCC2CC2)c2ccccc2c1=O]

The title compound of Example 152, step 5 was treated with 1,1-dioxidoisothiazolidine instead of MeSO$_2$NH$_2$ in a manner similar to Example 152, step 6 to give the title compound. $^1$H NMR (DMSO-d6, 400 MHz): δ 8.56 (s, 1H), 8.30 (d, J=8.0 Hz, 1H), 7.86 (s, 1H), 7.77 (d, J=8.0 Hz, 1H), 7.67 (t, J=7.6 Hz, 1H), 7.55 (t, J=7.6 Hz, 1H), 3.93-3.91 (m, 4H), 3.59 (s, 3H), 2.38-2.31 (m, 2H), 1.06-1.01 (m, 1H), 0.44-0.39 (m, 2H), 0.20-0.16 (m, 2H). LCMS: 427.1 (M+H)$^+$.

Example 157: N-[5-(cyclopropylmethoxy)-4-(6-fluoro-2-methyl-1-oxoisoquinolin-4-yl)pyrimidin-2-yl]ethanesulfonamide

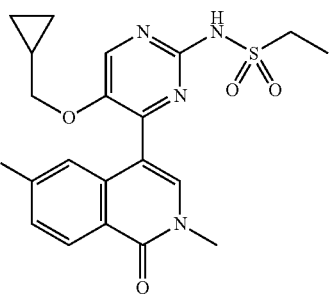

The title compound of Example 47, step 2 was treated with 4,4,5,5-tetramethyl-2-(tetramethyl-1,3,2-dioxaborolan-2-yl)-1,3,2-dioxaborolane in a manner similar to Example 89, step 1 and the resulting 6-fluoro-2-methyl-4-(4,4,5,5-tetramethyl-1,3,2-dioxaborolan-2-yl)isoquinolin-1-one was coupled to the title compound of Example 152, step 4 in a manner similar to Example 152, step 5 and the resulting 4-[5-(cyclopropylmethoxy)-2-methylsulfonylpyrimidin-4-yl]-6-fluoro-2-methyl-isoquinolin-1-one was treated with EtSO$_2$NH$_2$ instead of MeSO$_2$NH$_2$ in a manner similar to Example 152, step 6 to give the title compound. $^1$H NMR (DMSO-d6, 400 MHz): δ 11.04 (brs, 1H), 8.54 (s, 1H), 8.36 (dd, J$_1$=9.2 Hz, J$_2$=2.4 Hz, 1H), 8.01 (s, 1H), 7.65 (dd, J$_1$=11.2 Hz, J$_2$=2.4 Hz, 1H), 7.45-7.38 (m, 1H), 3.95 (d, J=6.8 Hz, 2H), 3.58 (s, 3H), 3.48 (q, J=7.2 Hz, 2H), 1.22 (t, J=7.2 Hz, 3H), 1.16-1.04 (m, 1H), 0.50-0.42 (m, 2H), 0.27-0.20 (m, 2H). LCMS: 433.0 (M+1)$^+$.

Example 158: N-[5-(cyclopropylmethoxy)-4-(7-fluoro-2-methyl-1-oxoisoquinolin-4-yl)pyrimidin-2-yl]methanesulfonamide

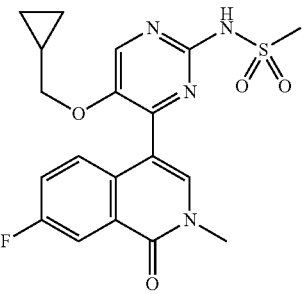 [SMILES: Cn1cc(-c2nc(NS(C)(=O)=O)ncc2OCC2CC2)c2ccc(F)cc2c1=O]

The title compound of Example 58, step 2 was treated with 4,4,5,5-tetramethyl-2-(tetramethyl-1,3,2-dioxaborolan-2-yl)-1,3,2-dioxaborolane in a manner similar to Example 89, step 1 and the resulting 7-fluoro-2-methyl-4-(4,4,5,5-tetramethyl-1,3,2-dioxaborolan-2-yl)-isoquinolin-1-one was coupled to the title compound of Example 152, step 4 in a manner similar to Example 152, step 5 and the resulting 4-[5-(cyclopropylmethoxy)-2-methylsulfonylpyrimidin-4-yl]-7-fluoro-2-methylisoquinolin-1-one was treated with MeSO$_2$NH$_2$ in a manner similar to Example 152, step 6 to give the title compound. $^1$H NMR (DMSO-d6, 400 MHz): δ 11.15 (s, 1H), 8.55 (s, 1H), 8.36 (dd, J$_1$=9.2 Hz, J$_2$=6.0 Hz, 1H), 8.00 (s, 1H), 7.60 (dd, J$_1$=11.2 Hz, J$_2$=2.4 Hz, 1H), 7.44-7.37 (m, 1H), 3.95 (d, J=7.2 Hz, 2H), 3.58 (s, 3H), 3.32 (s, 3H), 1.15-1.03 (m, 1H), 0.49-0.42 (m, 2H), 0.26-0.20 (m, 2H). LCMS: 419.0 (M+1)$^+$.

Example 159: N-[5-(cyclopropylmethoxy)-4-(6-fluoro-2-methyl-1-oxoisoquinolin-4-yl)pyrimidin-2-yl]methanesulfonamide

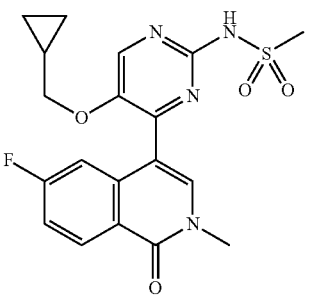 [SMILES: Cn1cc(-c2nc(NS(C)(=O)=O)ncc2OCC2CC2)c2cc(F)ccc2c1=O]

The title compound of Example 47, step 2 was treated with 4,4,5,5-tetramethyl-2-(tetramethyl-1,3,2-dioxaborolan-2-yl)-1,3,2-dioxaborolane in a manner similar to Example 89, step 1 and the resulting 6-fluoro-2-methyl-4-(4,4,5,5-tetramethyl-1,3,2-dioxaborolan-2-yl)isoquinolin-1-one was coupled to the title compound of Example 152, step 4 in a manner similar to Example 152, step 5 and the resulting 4-[5-(cyclopropylmethoxy)-2-methylsulfonylpyrimidin-4-yl]-6-fluoro-2-methylisoquinolin-1-one was treated with MeSO$_2$NH$_2$ in a manner similar to Example 152, step 6 to give the title compound. $^1$H NMR (DMSO-d6, 400 MHz): δ 11.14 (brs, 1H), 8.56 (s, 1H), 7.96 (dd, J$_1$=9.2 Hz, J$_2$=3.2 Hz, 1H), 7.88 (s, 1H), 7.85 (dd, J$_1$=9.2 Hz, J$_2$=3.6 Hz, 1H), 7.62-7.55 (m, 1H), 3.94 (d, J=6.8 Hz, 2H), 3.60 (s, 3H), 3.32 (s, 3H), 1.11-0.99 (m, 1H), 0.47-0.40 (m, 2H), 0.23-0.16 (m, 2H). LCMS: 419.0 (M+1)$^+$.

Example 160: N-[5-(cyclopropylmethoxy)-4-(7-fluoro-2-methyl-1-oxoisoquinolin-4-yl)pyrimidin-2-yl]ethanesulfonamide

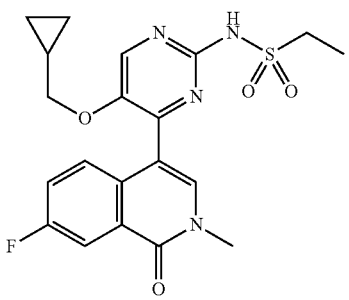 [SMILES: CCS(=O)(=O)Nc1ncc(OCC2CC2)c(-c2cn(C)c(=O)c3cc(F)ccc23)n1]

The title compound of Example 58, step 2 was treated with 4,4,5,5-tetramethyl-2-(tetramethyl-1,3,2-dioxaborolan-2-yl)-1,3,2-dioxaborolane in a manner similar to Example 89, step 1 and the resulting 7-fluoro-2-methyl-4-(4,4,5,5-tetramethyl-1,3,2-dioxaborolan-2-yl)isoquinolin-1-one was coupled to the title compound of Example 152, step 4 in a manner similar to Example 152, step 5 and the resulting 4-[5-(cyclopropylmethoxy)-2-methylsulfonylpyrimidin-4-yl]-7-fluoro-2-methylisoquinolin-1-one was treated with EtSO$_2$NH$_2$ instead of MeSO$_2$NH$_2$ in a manner similar to Example 152, step 6 to give the title compound. $^1$H NMR (CDCl3 400 MHz): δ 8.53 (dd, J$_1$=8.8 Hz, J$_2$=6.0 Hz, 1H), 8.40 (s, 1H), 7.77 (s, 1H), 7.69 (dd, J=8.8 Hz, 1H), 7.27-7.23 (m, 1H), 3.88 (d, J=6.8 Hz, 2H), 3.69 (s, 3H), 3.60 (q, J=7.2 Hz, 2H), 1.43 (t, J=7.2 Hz, 3H), 1.16-1.13 (m, 1H), 0.62-0.56 (m, 2H), 0.27-0.26 (m, 2H). LCMS: 433.2 (M+1)$^+$.

Example 161: N-[5-(cyclopropylmethoxy)-4-(2-methyl-1-oxoisoquinolin-4-yl)pyrimidin-2-yl]-N-ethylmethanesulfonamide

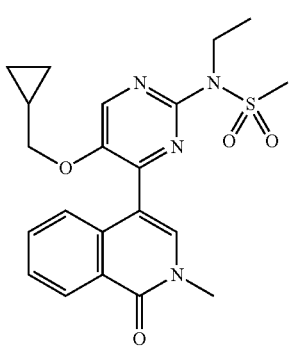 [SMILES: CCN(c1ncc(OCC2CC2)c(-c2cn(C)c(=O)c3ccccc23)n1)S(C)(=O)=O]

Ethyl iodide (95 mg, 0.6 mmol) and K$_2$CO$_3$ (55 mg, 0.4 mmol) were added to a soln of the title compound of Example 152 (80 mg, 0.2 mmol) in MeCN (5 mL). After refluxing 1 hr, the mixture was cooled, concentrated under vacuum and subjected to CH$_2$Cl$_2$ extractive work-up. HPLC purification gave the title compound (13.42 mg, yield: 15.2%) as a yellow solid. $^1$H NMR (DMSO-d6, 400 MHz)

δ 8.63 (s, 1H), 8.32 (d, J=8.0 Hz, 1H), 7.90 (s, 1H), 7.77 (d, J=8.0 Hz, 1H), 7.69 (t, J=7.6 Hz, 1H), 7.56 (t, J=7.6 Hz, 1H), 4.02 (q, J=6.8 Hz, 2H), 3.97 (d, J=7.2 Hz, 1H), 3.60 (s, 3H), 3.43 (s, 3H), 1.25 (t, J=6.8 Hz, 1H), 1.10-1.07 (m, 1H), 0.46-0.42 (m, 2H), 0.24-0.20 (m, 2H). LCMS: 429.1 (M+H)⁺.

Example 162: N-[5-(cyclopropylmethoxy)-4-(1,5-dimethyl-6-oxopyridin-3-yl)pyrimidin-2-yl]-N-ethyl-methanesulfonamide

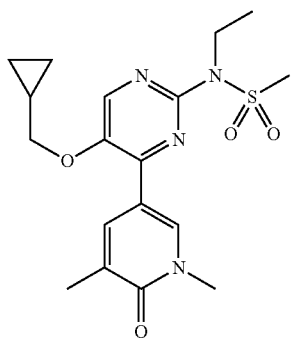 [SMILES: CCN(c1ncc(OCC2CC2)c(-c2cc(C)c(=O)n(C)c2)n1)S(C)(=O)=O]

The title compound of Example 153 was treated with ethyl iodide in a manner similar to Example 161 to give the title compound. ¹H NMR (400 MHz, DMSO-d₆): δ ppm 0.36-0.42 (m, 2H) 0.60-0.66 (m, 2H) 1.25 (t, J=6.82 Hz, 3H) 1.29-1.40 (m, 1H) 2.09 (s, 3H) 3.48 (s, 3H) 3.56 (s, 3H) 3.88-4.20 (m, 4H) 8.13 (s, 1H) 8.49 (s, 1H) 8.69 (s, 1H). LCMS: 393 (M+H)⁺.

Example 163: N-[5-(cyclopropylmethoxy)-4-(2-methyl-1-oxo-5,6,7,8-tetrahydroisoquinolin-4-yl)pyrimidin-2-yl]methanesulfonamide Step 1:
2-methyl-5,6,7,8-tetrahydroisoquinolin-1-one

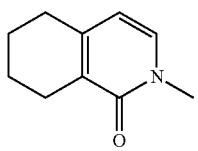

The title compound was prepared from the N-methylation of 5,6,7,8-tetrahydroisoquinolin-1(2H)-one in a manner similar to Example 47, step 1. ¹H NMR (CDCl₃, 400 MHz): δ 7.02 (d, J=7.2 Hz, 1H), 5.90 (d, J=7.2 Hz, 1H), 3.49 (s, 3H), 2.54-2.45 (m, 4H), 1.74-1.69 (m, 4H).

Step 2: 4-bromo-2-methyl-5,6,7,8-tetrahydroisoquinolin-1-one

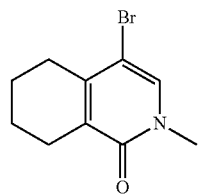

The title compound was prepared from the bromination of the title compound of step 1 in a manner similar to Example 47, step 2. LCMS: 241.9 (M+H)⁺.

Step 3: 2-methyl-4-(4,4,5,5-tetramethyl-1,3,2-dioxaborolan-2-yl)-5,6,7,8-tetrahydroisoquinolin-1-one

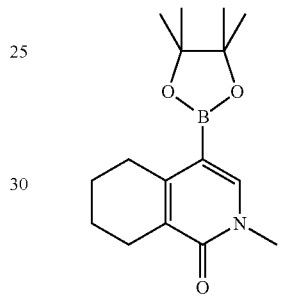

The title compound of step 2 (3.3 g, 13.7 mmol), 4,4,5,5-tetramethyl-2-(tetramethyl-1,3,2-dioxaborolan-2-yl)-1,3,2-dioxaborolane (6.96 g, 27.4 mmol), Pd₂(dba)₃ (400 mg, 0.43 mmol), X-phos (400 mg, 0.84 mmol) and anhydrous KOAc (1.02 g, 41.1 mmol) in anhydrous dioxane (50 mL) were heated at 50° C. under N₂ for 12 hr. Silica gel chromatography (PE:EA=5:1) gave the title compound (1.5 g, yield: 38%) as a yellow solid. ¹H NMR (CDCl₃, 400 MHz): δ 7.62 (s, 1H), 5.28 (s, 3H), 2.82-2.76 (m, 2H), 2.55-2.33 (m, 2H), 1.72-1.70 (m, 4H), 1.31 (s, 12H). LCMS: 290.0 (M+H)⁺.

Step 4: 4-[5-(cyclopropylmethoxy)-2-methylsulfonylpyrimidin-4-yl]-2-methyl-5,6,7,8-tetrahydroisoquinolin-1-one

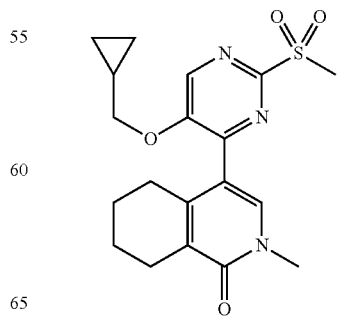

The title compound of step 3 (200 mg, 0.69 mmol), the title compound of Example 152, step 4 (218 mg, 0.83 mmol), K₃PO₄ (440 mg, 2.07 mmol) and Pd(dppf)Cl₂ (51 mg, 0.7 mmol) in 6:1 dioxane/H₂O (7 mL) were purged with N₂ and heated at 70° C. for 8 hr. After silica gel chromatography (PE:EA=1:1), the title compound (180 mg, yield: 67%) was obtained as a light yellow solid. ¹H NMR (CDCl₃, 400 MHz): δ 8.42 (s, 1H), 7.48 (s, 1H), 4.04 (d, J=7.2 Hz, 2H), 3.60 (s, 3H), 3.35 (s, 3H), 2.65-2.62 (m, 2H), 2.54-2.50 (m, 2H), 1.80-1.78 (m, 2H), 1.77-1.67 (m, 2H), 1.28-1.25 (m, 1H), 0.73-0.71 (m, 2H), 0.41-0.38 (m, 2H).

Step 5: N-[5-(cyclopropylmethoxy)-4-(2-methyl-1-oxo-5,6,7,8-tetrahydroisoquinolin-4-yl)pyrimidin-2-yl]methanesulfonamide

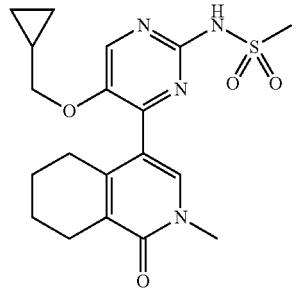 [SMILES: Cn1cc(-c2nc(NS(C)(=O)=O)ncc2OCC2CC2)c2c(c1=O)CCCC2]

The title compound of step 4 was treated with MeSO₂NH₂ in a manner similar to Example 152, step 6 to give the title compound. ¹H NMR (CDCl₃, 400 MHz): δ 8.18 (s, 1H), 7.38 (s, 1H), 3.74 (d, J=6.4 Hz, 2H), 3.51 (s, 3H), 3.28 (s, 3H), 2.60-2.53 (m, 2H), 2.50-2.46 (m, 2H), 1.74-1.71 (m, 2H), 1.64-1.59 (m, 2H), 1.13-1.10 (m, 1H), 0.60-0.58 (m, 2H), 0.25-0.24 (m, 2H). LCMS: 405.1 (M+H)⁺.

Example 164: N-[5-(cyclopropylmethoxy)-4-(2-methyl-1-oxo-5,6,7,8-tetrahydroisoquinolin-4-yl)pyrimidin-2-yl]ethanesulfonamide

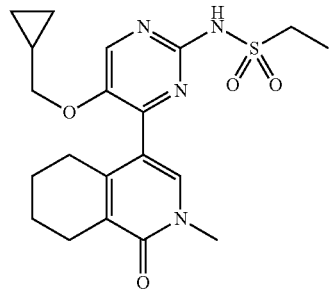 [SMILES: CCS(=O)(=O)Nc1ncc(OCC2CC2)c(-c2cn(C)c(=O)c3c2CCCC3)n1]

The title compound of Example 163, step 4 was treated with treated with EtSO₂NH₂ instead of MeSO₂NH₂ in a manner similar to Example 152, step 6 to give the title compound. ¹H NMR (DMSO-d6, 400 MHz): δ 8.32 (s, 1H), 7.64 (s, 1H), 3.83 (d, J=6.8 Hz, 2H), 3.44 (s, 3H), 3.30-3.20 (m, 2H), 2.47-2.41 (m, 4H), 1.67-1.57 (m, 4H), 1.19-1.13 (m, 4H), 0.51-0.49 (m, 2H), 0.24-0.22 (m, 2H). LCMS: 419.1 (M+H)⁺.

Example 165: N-[5-(2,4-difluorophenoxy)-4-(2-methyl-1-oxoisoquinolin-4-yl)pyrimidin-2-yl]methanesulfonamide

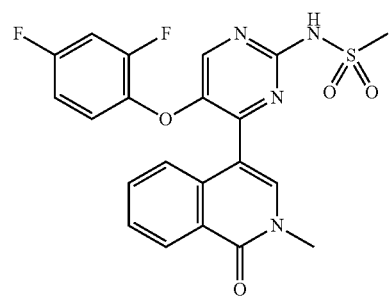 [SMILES: Cn1cc(-c2nc(NS(C)(=O)=O)ncc2Oc2ccc(F)cc2F)c2ccccc2c1=O]

The title compound of Example 151 was treated with MeSO₂NH₂ in a manner similar to Example 152, step 6 to give the title compound. ¹H NMR (DMSO-d6, 400 MHz) δ 11.50 (s, 1H), 8.59 (s, 1H), 8.25 (s, J=8.0 Hz, 1H), 7.87 (s, 1H), 7.77 (d, J=8.0 Hz, 1H), 7.67 (t, J=8.0 Hz, 1H), 7.54 (t, J=7.2 Hz, 1H), 7.34-7.28 (m, 1H), 7.20-7.13 (m, 1H), 6.90 (t, J=8.8 Hz, 1H), 3.54 (s, 3H), 3.35 (s, 3H). LCMS: 459.0 (M+1)⁺.

Example 166: N-[5-(2,4-difluorophenoxy)-4-(1,5-dimethyl-6-oxopyridin-3-yl)pyrimidin-2-yl]methanesulfonamide

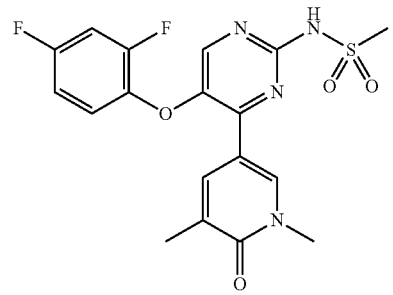 [SMILES: Cc1cc(-c2nc(NS(C)(=O)=O)ncc2Oc2ccc(F)cc2F)cn(C)c1=O]

The title compound of Example 149, step 4 was treated with MeSO₂NH₂ in a manner similar to Example 152, step 6 to give the title compound. ¹H NMR (CDCl₃, 400 MHz) δ 8.42 (s, 1H), 8.36 (s, 1H), 8.10-8.12 (m, 2H), 6.98-7.05 (m, 2H), 6.87-6.92 (m, 1H), 3.64 (s, 3H), 3.45 (s, 3H), 2.22 (s, 3H). LCMS: 423.0 (M+1)⁺.

Example 167: N-[5-(2,4-difluorophenoxy)-4-(5-methoxy-1-methyl-6-oxopyridin-3-yl)pyrimidin-2-yl]methanesulfonamide

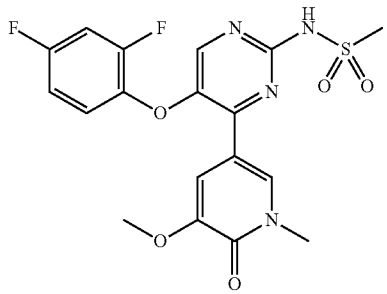 [SMILES: COc1cc(-c2nc(NS(C)(=O)=O)ncc2Oc2ccc(F)cc2F)cn(C)c1=O]

The title compound of Example 150 was treated with MeSO$_2$NH$_2$ in a manner similar to Example 152, step 6 to give the title compound. $^1$H NMR (DMSO-d6, 400 MHz): δ 11.37 (s, 1H), 8.34 (s, 1H), 8.26 (s, 1H), 7.58 (s, 1H), 7.54-7.50 (m, 1H), 7.28-7.23 (m, 1H), 7.10-7.06 (m, 1H), 3.74 (s, 3H), 3.52 (s, 3H), 3.39 (s, 3H). LCMS: 439.0 (M+1)$^+$.

Example 168: N-[5-(2,4-difluorophenoxy)-4-(5-methoxy-1-methyl-6-oxopyridin-3-yl)pyrimidin-2-yl]ethanesulfonamide

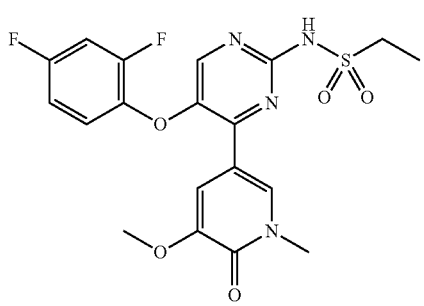 [SMILES: CCS(=O)(=O)Nc1ncc(Oc2ccc(F)cc2F)c(-c2cc(OC)c(=O)n(C)c2)n1]

The title compound of Example 150 was treated with EtSO$_2$NH$_2$ instead of MeSO$_2$NH$_2$ in a manner similar to Example 152, step 6 to give the title compound. $^1$H NMR (CDCl$_3$, 400 MHz): δ 8.35 (d, J=2.0 Hz, 1H), 8.18 (s, 1H), 7.70 (d, J=2.0 Hz, 1H), 7.25-7.22 (m, 1H), 7.12-7.07 (m, 1H), 7.04-7.01 (m, 1H), 3.93 (s, 3H), 3.70 (s, 3H), 3.38 (s, 3H). LCMS: 423.9 (M+1)$^+$.

Example 169: N-[5-(2,4-difluorophenoxy)-4-(1,5-dimethyl-6-oxopyridin-3-yl)pyrimidin-2-yl]ethanesulfonamide

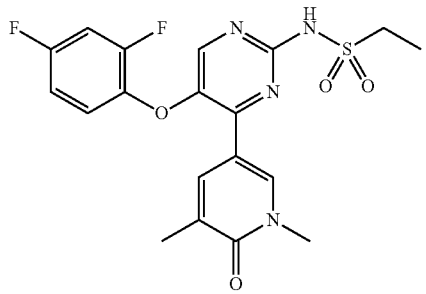 [SMILES: CCS(=O)(=O)Nc1ncc(Oc2ccc(F)cc2F)c(-c2cc(C)c(=O)n(C)c2)n1]

The title compound of Example 149, step 4 was treated with EtSO$_2$NH$_2$ instead of MeSO$_2$NH$_2$ in a manner similar to Example 152, step 6 to give the title compound. $^1$H NMR (DMSO-d6, 400 MHz): δ 9.07 (s, 1H), 8.42 (s, 1H), 8.15 (s, 1H), 8.11 (s, 1H), 7.03-6.97 (m, 1H), 6.91-6.87 (m, 1H), 3.66-3.61 (m, 5H), 2.22 (s, 3H), 1.44 (t, J=7.6 Hz, 3H). LCMS: 437.0 (M+1)$^+$.

Example 170: N-[5-(2,4-difluorophenoxy)-4-(2-methyl-1-oxoisoquinolin-4-yl)pyrimidin-2-yl]ethanesulfonamide

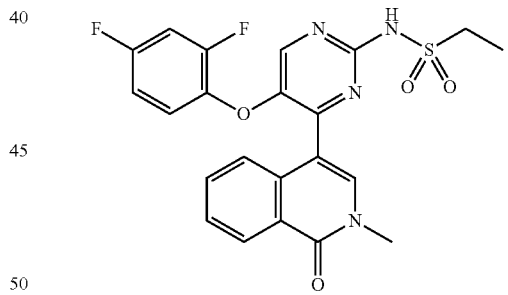

The title compound of Example 151 was treated with EtSO$_2$NH$_2$ instead of MeSO$_2$NH$_2$ in a manner similar to Example 152, step 6 to give the title compound. $^1$H NMR (CDCl$_3$, 400 MHz): δ 9.15 (s, 1H), 8.49 (d, J=7.6 Hz, 1H), 8.34 (s, 1H), 8.02 (d, J=8.0 Hz, 1H), 7.71-7.67 (m, 2H), 7.54 (t, J=7.6 Hz, 1H), 6.92-6.86 (m, 2H), 6.79-6.75 (m, 1H), 3.67 (s, 3H), 3.58 (q, J=7.6 Hz, 2H), 1.39 (t, J=7.6 Hz, 3H). LCMS: 473.0 (M+1)$^+$.

Example 171: 4-[5-(2,4-difluorophenoxy)-2-(1,1-dioxo-1,2-thiazolidin-2-yl)pyrimidin-4-yl]-2-methyl-isoquinolin-1-one

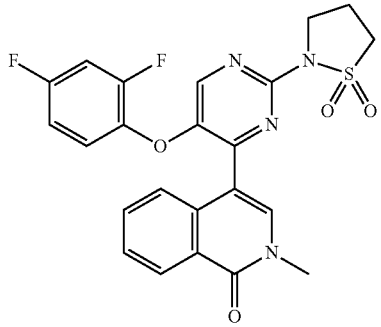 [SMILES: Cn1cc(-c2nc(N3CCCS3(=O)=O)ncc2Oc2ccc(F)cc2F)c2ccccc2c1=O]

The title compound of Example 151 was treated with 1,1-dioxidoisothiazolidine instead of MeSO$_2$NH$_2$ in a manner similar to Example 152, step 6 to give the title compound. $^1$H NMR (DMSO-d6, 400 MHz): δ 8.63 (s, 1H), 8.24 (d, J=8.0 Hz, 1H), 7.86 (s, 1H), 7.83 (d, J=8.0 Hz, 1H), 7.65 (t, J=7.2 Hz, 1H), 7.53 (t, J=7.2 Hz, 1H), 7.31-7.26 (m, 1H), 7.13-7.07 (m, 1H), 6.89-6.87 (m, 1H), 3.97 (t, J=6.4 Hz, 2H), 3.57 (t, J=7.2 Hz, 2H), 3.54 (s, 3H), 2.40-2.33 (m, 2H). LCMS: 485.2 (M+H)$^+$.

Example 172: N-[5-(2,4-difluorophenoxy)-4-(2-methyl-1-oxo-5,6,7,8-tetrahydroisoquinolin-4-yl)pyrimidin-2-yl]methanesulfonamide

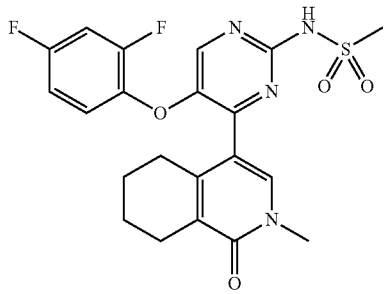 [SMILES: Cn1cc(-c2nc(NS(C)(=O)=O)ncc2Oc2ccc(F)cc2F)c2c(c1=O)CCCC2]

The title compound of Example 149, step 3 was reacted with the title compound of Example 163, step 3 in a manner similar to Example 163, step 4 and the resulting product was treated with MeSO$_2$NH$_2$ in a manner similar to Example 163, step 5 to give the title compound. $^1$H NMR (DMSO-d6, 400 MHz): δ 8.16 (s, 1H), 7.46 (s, 1H), 7.25-7.20 (m, 1H), 6.90-6.84 (m, 2H), 3.34 (s, 3H), 2.80 (s, 3H), 2.41-2.29 (m, 4H), 1.60-1.48 (m, 4H). LCMS: 463.1 (M+H)$^+$.

Example 173: N-[5-(2,4-difluorophenoxy)-4-(2-methyl-1-oxo-5,6,7,8-tetrahydroisoquinolin-4-yl)pyrimidin-2-yl]ethanesulfonamide

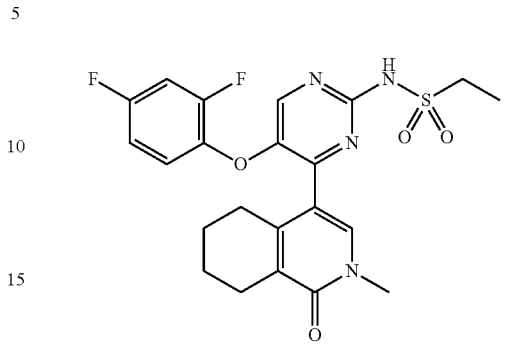

The title compound of Example 149, step 3 was reacted with the title compound of Example 163, step 3, in a manner similar to Example 163, step 4, and the resulting 4-[5-(2,4-difluorophenoxy)-2-methylsulfonylpyrimidin-4-yl]-2-methyl-5,6,7,8-tetrahydroisoquinolin-1-one was treated with EtSO$_2$NH$_2$ instead of MeSO$_2$NH$_2$ in a manner similar to Example 163, step 5, to give the title compound. $^1$H NMR (DMSO-d6, 400 MHz): δ 8.38 (s, 1H), 7.61 (s, 1H), 7.35-7.31 (m, 1H), 7.04-6.95 (m, 2H), 3.41 (s, 3H), 3.30-3.20 (m, 2H), 2.42-2.40 (m, 2H), 2.32-2.30 (m, 2H), 1.61-1.51 (m, 4H), 1.18 (t, J=7.2 Hz, 3H). LCMS: 477.1 (M+H)$^+$.

Example 174: 4-[2-(cyclopropylmethoxy)-5-ethylsulfonylphenyl]-6-fluoro-2-methylisoquinolin-1-one

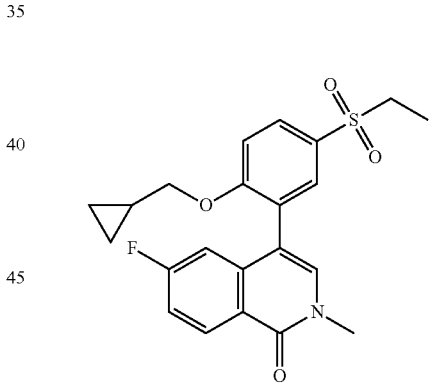

A mixture of 4-bromo-6-fluoro-2-methylisoquinolin-1-one (500.00 mg, 1.95 mmol), 2-[2-(cyclopropylmethoxy)-5-ethylsulfonylphenyl]-4,4,5,5-tetramethyl-1,3,2-dioxaborolane (1.07 g, 2.92 mmol), K$_3$PO$_4$ (1.24 g, 5.85 mmol) and Pd(dppf)Cl$_2$ (0.1 g, cat.) in dioxane/H$_2$O (30 mL/4 mL) was stirred at 70° C. for 12 hr under Ar. The mixture was concentrated and the residue purified by CC (PE:EA=1:1) to give a pink solid. The pink solid was further purified by CC (DCM:EA=4:1) to afford the title compound (0.13 g, 16%) as a light yellow solid. $^1$H NMR (CDCl$_3$, 400 MHz): δ 8.54 (brs, 1H), 7.96 (dd, J$_1$=8.8 Hz, J$_2$=2.4 Hz, 1H), 7.81 (d, J=2.0 Hz, 1H), 7.22-7.20 (m, 1H), 7.15-7.13 (m, 1H), 7.1 (d, J=8.8 Hz, 1H), 6.78 (dd, J$_1$=10.4 Hz, J$_2$=2.4 Hz, 1H), 3.90 (t, J=7.6 Hz, 2H), 3.68 (s, 3H), 3.15 (q, J=7.6 Hz, 2H), 1.33 (t, J=7.6 Hz, 3H), 1.06-1.02 (m, 1H), 0.50-0.43 (m, 2H), 0.15-0.14 (m, 2H). LCMS (M+H)$^+$: 416.0.

Example 175: 2-methyl-4-[5-methylsulfonyl-2-(oxolan-3-yloxy)phenyl]isoquinolin-1-one Step 1: 4-(2-fluoro-5-methylsulfonylphenyl)-2-methylisoquinolin-1-one

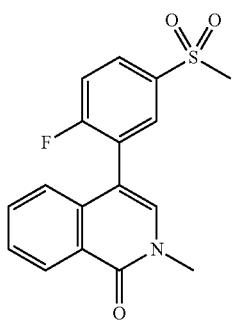

A mixture of compound 2-methyl-4-(4,4,5,5-tetramethyl-1,3,2-dioxaborolan-2-yl) isoquinolin-1-one (4.1 g, 14.5 mmol), 2-bromo-4-methylsulfonyl-1-fluorobenzene (3.5 g, 13.8 mmol) prepared in a similar manner to Example 79 steps 1-2, CsF (6.3 g, 41.3 mmol), and Pd(dppf)Cl$_2$ (1.0 g, 1.38 mmol) in DME (70 mL) and MeOH (35 ml) was stirred at 70° C. for 12 hr under N$_2$. The mixture was concentrated and the residue was purified by CC (PE:EA=2:1~0:1) to give the title compound (3.4 g, 74.4%) as a red solid. LCMS (M+H)$^+$: 331.9 (M+1)$^+$.

Step 2: 2-methyl-4-[5-methylsulfonyl-2-(oxolan-3-yloxy)phenyl]isoquinolin-1-one

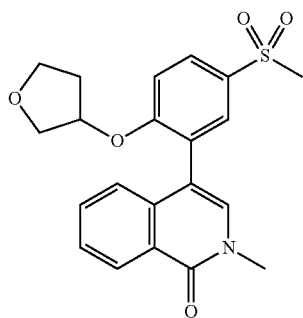 [SMILES: Cn1cc(-c2cc(S(C)(=O)=O)ccc2OC2CCOC2)c2ccccc2c1=O]

To a soln of oxolan-3-ol (175.0 mg, 1.99 mmol) in anhydrous DMF (3 mL) was added NaH (66.0 mg, 1.65 mmol, 60% in mineral oil) at 0° C. and then stirred at 0° C. for 0.5 hr. 4-(2-fluoro-5-methylsulfonylphenyl)-2-methyl-isoquinolin-1-one (110.0 mg, 0.33 mmol) was added. The mixture was stirred at 0° C. for 0.5 hr and then at room temp for 3 hr. It was then quenched with aq sat'd NH$_4$Cl (20 mL) and extracted with EA (20 mL×3). The combined organic layers were washed with brine (40 mL), dried over Na$_2$SO$_4$, and concentrated under reduced pressure to afford a crude product which was purified by prep-HPLC to give the title compound (62.0 mg, 39.7%) as a light yellow solid. $^1$H NMR (CDCl$_3$, 400 MHz): δ 8.51 (d, J=7.6 Hz, 1H), 8.00 (dd, J$_1$=8.8 Hz, J$_2$=2.4 Hz, 1H), 7.89 (d, J=2.4 Hz, 1H), 7.58-7.51 (m, 2H), 7.11-7.03 (m, 3H), 5.01-4.98 (m, 1H), 3.97 (dd, J$_1$=10.4 Hz, J$_2$=4.8 Hz, 1H), 3.76-3.70 (m, 2H), 3.67 (s, 3H), 3.61-3.42 (m, 1H), 3.11 (s, 3H), 2.18-1.88 (m, 2H). LCMS (M+H)$^+$: 400.0 (M+1)$^+$.

Example 176: 2-methyl-4-[5-methylsulfonyl-2-(oxan-4-yloxy)phenyl]isoquinolin-1-one

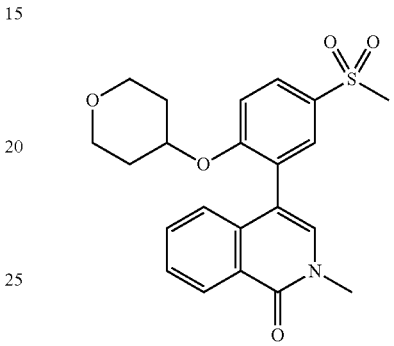

The title compound was prepared in a manner similar to Example 175, by substituting oxan-4-ol for oxolan-3-ol in step 2. $^1$H NMR (CDCl$_3$, 400 MHz): δ 8.52 (d, J=7.6 Hz, 1H), 8.00 (dd, J$_1$=8.8 Hz, J$_2$=2.4 Hz, 1H), 7.89 (d, J=2.4 Hz, 1H), 7.63-7.50 (m, 2H), 7.19 (d, J=7.6 Hz, 1H), 7.11 (d, J=8.8 Hz, 1H), 7.09 (s, 1H), 4.65-4.61 (m, 1H), 3.71 (s, 3H), 3.53-3.45 (m, 4H), 3.11 (s, 3H), 1.92-1.88 (m, 2H), 1.62-1.54 (m, 2H). LCMS (M+H)$^+$: 414.1 (M+1)$^+$.

Example 177: 4-(2-ethoxy-5-methylsulfonylphenyl)-2-methylisoquinolin-1-one

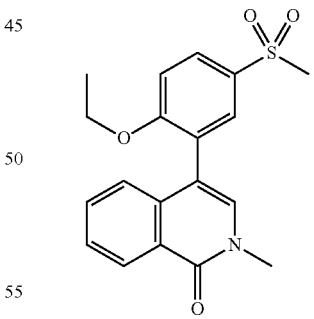

The title compound was prepared in a manner similar to Example 175, by substituting ethanol for oxolan-3-ol in step 2. $^1$H NMR (CDCl$_3$, 400 MHz): δ 8.52 (d, J=8.0 Hz, 1H), 8.01 (dd, J$_1$=8.8 Hz, J$_2$=2.4 Hz, 1H), 7.86 (d, J=2.4 Hz, 1H), 7.57 (t, J=7.2 Hz, 1H), 7.52 (t, J=7.2 Hz, 1H), 7.13 (t, J=7.2 Hz, 2H), 7.08 (s, 1H), 4.12-4.09 (m, 2H), 3.68 (s, 3H), 3.10 (s, 3H), 1.18 (t, J=7.2 Hz, 1H). LCMS (M+H)$^+$: 358.0 (M+1)$^+$.

Example 178: 2-methyl-4-(5-methylsulfonyl-2-propoxyphenyl)isoquinolin-1-one

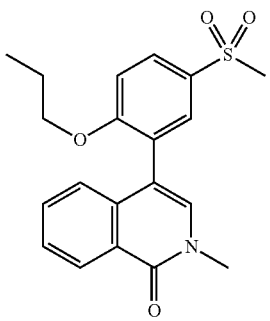 [SMILES: CCCOc1ccc(S(C)(=O)=O)cc1-c1cn(C)c(=O)c2ccccc12]

The title compound was prepared in a manner similar to Example 175, by substituting propan-1-ol for oxolan-3-ol in step 2. $^1$H NMR (CDCl$_3$, 400 MHz): δ 8.51 (d, J=8.0 Hz, 1H), 8.00 (dd, J$_1$=8.8 Hz, J$_2$=2.4 Hz, 1H), 7.86 (d, J=2.4 Hz, 1H), 7.56 (t, J=7.2 Hz, 1H), 7.50 (t, J=7.2 Hz, 1H), 7.14 (d, J=7.2 Hz, 1H), 7.12 (d, J=8.8 Hz, 1H), 7.07 (s, 1H), 4.00-3.94 (m, 2H), 3.67 (s, 3H), 3.10 (s, 3H), 1.60-1.52 (m, 2H), 0.68 (t, J=7.2 Hz, 1H). LCMS (M+H)$^+$: 372.0 (M+1)$^+$.

Example 179: 2-methyl-4-[5-methylsulfonyl-2-(oxan-3-yloxy)phenyl]isoquinolin-1-one

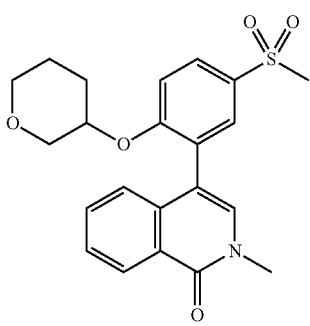 [SMILES: Cn1cc(-c2cc(S(C)(=O)=O)ccc2OC2CCCOC2)c2ccccc2c1=O]

The title compound was prepared in a manner similar to Example 175, by substituting oxan-3-ol for oxolan-3-ol in step 2. $^1$H NMR (CDCl$_3$, 400 MHz): δ 8.51 (d, J=8.0 Hz, 1H), 7.98 (dd, J$_1$=8.8 Hz, J$_2$=2.4 Hz, 1H), 7.88 (d, J=2.4 Hz, 1H), 7.56 (t, J=7.2 Hz, 1H), 7.52 (t, J=7.2 Hz, 1H), 7.18 (d, J=8.0 Hz, 1H), 7.12-7.06 (m, 2H), 4.43-4.41 (m, 1H), 3.79-3.78 (m, 1H), 3.67 (s, 3H), 3.66-3.63 (m, 1H), 3.39-3.34 (m, 2H), 3.10 (s, 3H), 2.02-1.93 (m, 2H), 1.59-1.48 (m, 2H). LCMS (M+H)$^+$: 414.1 (M+1)$^+$.

Example 180: 4-[2-(trans-4-hydroxycyclohexyl)oxy-5-methylsulfonylphenyl]-2-methylisoquinolin-1-one

Step 1: 4-[2-[4-[tert-butyl(dimethyl)silyl]oxycyclohexyl]oxy-5-methylsulfonylphenyl]-2-methylisoquinolin-1-one

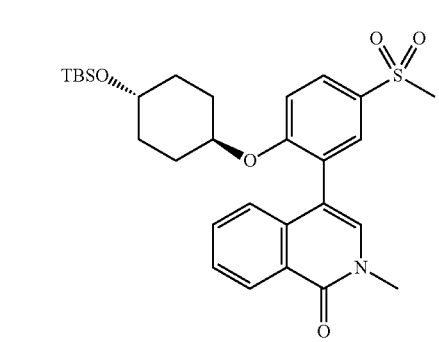 [SMILES: Cn1cc(-c2cc(S(C)(=O)=O)ccc2O[C@H]2CC[C@H](O[Si](C)(C)C(C)(C)C)CC2)c2ccccc2c1=O]

The title compound was prepared in a manner similar to Example 175, by substituting trans-4-[tert-butyl(dimethyl)silyl]oxycyclohexan-1-ol for oxolan-3-ol in step 2. LCMS (M+H)$^+$542.2 (M+1)$^+$.

Step 2: 4-[2-(trans-4-hydroxycyclohexyl)oxy-5-methylsulfonylphenyl]-2-methylisoquinolin-1-one

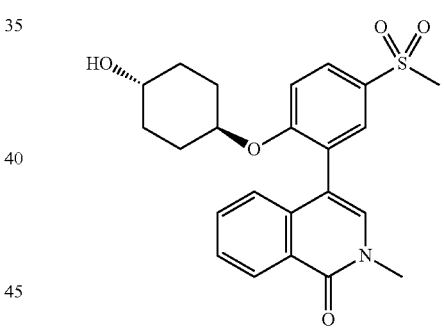

To a soln of the title compound from step 1 (180.0 mg, 0.33 mmol) in dry MeOH (5 mL) and DCM (3 mL) was added dropwise HCl/MeOH (0.3 mL, 1.2 mmol, 4M) at 0° C. and then stirred at room temp for 20 min. TLC showed the starting material was consumed completely. The mixture was concentrated and the residue was purified by prep-HPLC to afford the title compound (130.0 mg, 97.8%) as a white solid. $^1$H NMR (CDCl$_3$, 400 MHz): δ 8.50 (d, J=7.6 Hz, 1H), 7.98 (dd, J$_1$=8.8 Hz, J$_2$=2.8 Hz, 1H), 7.86 (d, J=2.4 Hz, 1H), 7.55 (t, J=6.8 Hz, 1H), 7.51 (t, J=6.8 Hz, 1H), 7.16 (d, J=7.6 Hz, 1H), 7.11 (d, J=8.8 Hz, 1H), 7.05 (s, 1H), 4.42-4.35 (m, 1H), 3.67 (s, 3H), 3.65-3.62 (m, 1H), 3.10 (s, 3H), 2.01-1.89 (m, 2H), 1.71-1.65 (m, 2H), 1.36-1.34 (m, 4H). LCMS (M+H)$^+$: 428.1 (M+1)$^+$.

Example 181: 4-[5-ethylsulfonyl-2-(trans-4-hydroxycyclohexyl)oxyphenyl]-2-methylisoquinolin-1-one Step 1: 4-[2-[4-[tert-butyl(dimethyl)silyl]oxycyclohexyl]oxy-5-ethylsulfonylphenyl]-2-methylisoquinolin-1-one

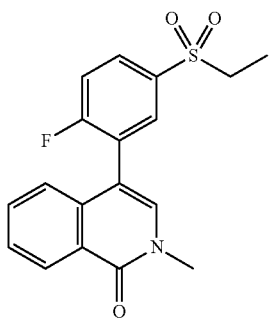 [SMILES: CCS(=O)(=O)c1ccc(F)c(-c2cn(C)c(=O)c3ccccc23)c1]

The title compound was prepared in a manner similar to Example 175 by substituting 2-bromo-4-ethylsulfonyl-1-fluorobenzene for 2-bromo-4-methylsulfonyl-1-fluorobenzene in step 1. LCMS (M+H)$^+$: 345.9 (M+1)$^+$.

Step 2: 4-[5-ethylsulfonyl-2-(trans-4-hydroxycyclohexyl)oxyphenyl]-2-methylisoquinolin-1-one

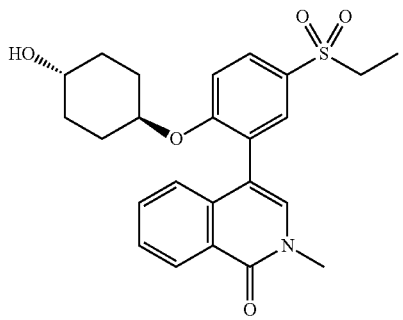 [SMILES: CCS(=O)(=O)c1ccc(O[C@H]2CC[C@H](O)CC2)c(-c2cn(C)c(=O)c3ccccc23)c1]

To a soln of trans-1,4-cyclohexanediol (504.0 mg, 4.34 mmol) in anhydrous DMF (4 mL) was added NaH (139.0 mg, 3.47 mmol, 60% in mineral oil) at 0° C. and then stirred at 0° C. for 1 hr. The compound from step 1 (100.0 mg, 0.29 mmol) was added. The mixture was stirred at 0° C. for 0.5 hr and then at room temp 18 hr. It was then quenched with MeOH (4 mL) and filtered. The filtrate was purified by prep-HPLC to give the title compound (37.0 mg, 30.0%) as an off-white solid. $^1$H NMR (CDCl$_3$, 40 MHz): δ 8.51 (d, J=7.6 Hz, 1H), 7.94 (dd, J$_1$=8.8 Hz, J$_2$=2.4 Hz, 1H), 7.83 (d, J=2.0 Hz, 1H), 7.56 (t, J=6.8 Hz, 1H), 7.51 (t, J=6.8 Hz, 1H), 7.16 (d, J=7.6 Hz, 1H), 7.11 (d, J=8.8 Hz, 1H), 7.05 (s, 1H), 4.43-4.18 (m, 1H), 3.67 (s, 3H), 3.65-3.62 (m, 1H), 3.16 (q, J=7.6 Hz, 2H), 2.00-1.90 (m, 2H), 1.71-1.65 (m, 2H), 1.42-1.30 (m, 7H). LCMS (M+H)$^+$: 442.0 (M+1)$^+$.

Example 182: 4-[2-(trans-4-aminocyclohexyl)oxy-5-methylsulfonylphenyl]-2-methylisoquinolin-1-one

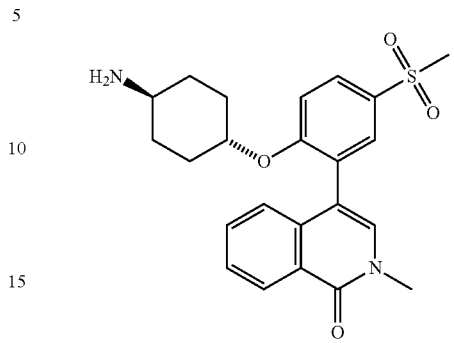

A mixture of 4-(2-fluoro-5-methylsulfonylphenyl)-2-methylisoquinolin-1-one (200 mg, 0.60 mmol), trans-4-aminocyclohexan-1-ol (278 mg, 2.42 mmol) and Cs$_2$CO$_3$ (591 mg, 1.81 mmol) in DMSO (4 mL) was stirred at 120° C. for 12 hr. H$_2$O (20 mL) was added and the mixture was extracted with EtOAc (3×20 mL). The combined organic layers were washed with brine (20 mL), dried over Na$_2$SO$_4$ and concentrated. The residue was purified by prep-HPLC to give the title compound (103.15 mg, 36.9%) as its hydrochloride salt. $^1$H NMR (DMSO-d6, 400 MHz): δ 8.28 (d, J=8.0 Hz, 1H), 8.10 (s, 3H), 7.95 (dd, J$_1$=8.8 Hz, J$_2$=2.4 Hz, 1H), 7.80 (d, J=2.4 Hz, 1H), 7.63 (t, J=7.2 Hz, 1H), 7.51-7.49 (m, 3H), 7.14 (d, J=8.0 Hz, 1H), 4.50-4.44 (m, 1H), 3.56 (s, 3H), 3.22 (s, 3H), 2.95-2.85 (m, 1H), 2.00-1.94 (m, 2H), 1.84 (d, J=11.2 Hz, 2H), 1.47-1.41 (m, 2H), 1.20-1.12 (m, 2H). LCMS (M+H)$^+$: 427.1 (M+H)$^+$.

Example 183: 4-[2-(cis-4-aminocyclohexyl)oxy-5-methylsulfonylphenyl]-2-methylisoquinolin-1-one

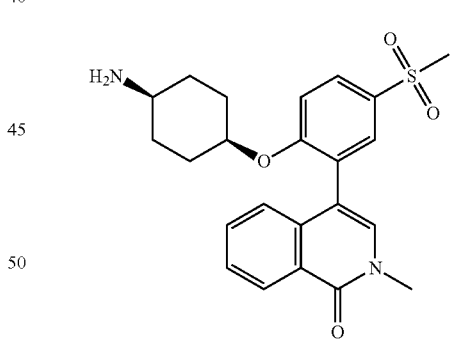

To compound cis-4-aminocyclohexan-1-ol (275 mg, 1.81 mmol) in DMF (3 mL), was added NaH (127 mg, 3.17 mmol, 60% in mineral oil) in one portion at 0° C. The mixture was stirred at 0° C. for 30 min, 4-(2-fluoro-5-methylsulfonylphenyl)-2-methylisoquinolin-1-one (150.00 mg, 0.45 mmol) was added in one portion and the mixture stirred at 0° C. for 2 hr. The rxn was diluted with H$_2$O (20 mL) and extracted with EA (3×20 mL). The combined organic layers were washed with satd brine (2×20 mL), dried with anhydrous Na$_2$SO$_4$, filtered and concentrated in vacuum. The residue was purified by prep-HPLC to give the title compound as its hydrochloride salt (91.01 mg, 47.1%). $^1$H NMR (DMSO-d6, 400 MHz): δ 8.29 (d, J=8.0 Hz, 1H), 8.00 (s, 3H), 7.95 (dd, J$_1$=8.8 Hz, J$_2$=2.0 Hz, 1H), 7.81 (d, J=2.0 Hz, 1H), 7.64 (t, J=7.2 Hz, 1H), 7.56 (s, 1H), 7.51 (t, J=7.2 Hz, 1H), 7.40 (d, J=8.8 Hz, 1H), 7.40 (d, J=8.0 Hz, 1H), 4.70 (s, 1H), 3.59 (s, 3H), 3.22 (s, 3H), 2.96-2.94 (m, 1H), 1.85-1.82 (m, 1H), 1.64-1.46 (m, 5H), 1.32-1.26 (m, 1H), 1.04-0.98 (m, 1H). LCMS (M+H)$^+$: 427.0 (M+H)$^+$.

Example 184: 4-(2-but-2-ynoxy-5-methylsulfonylphenyl)-2-methylisoquinolin-1-one

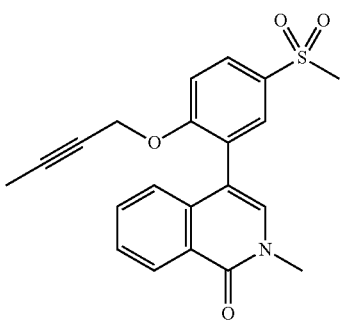 [SMILES: CC#CCOc1ccc(S(C)(=O)=O)cc1-c1cn(C)c(=O)c2ccccc12]

The title compound was prepared in a manner similar to Example 175, by substituting but-2-yn-1-ol for oxolan-3-ol in step 2. $^1$H NMR (CDCl$_3$, 400 MHz): δ 8.52 (d, J=7.6 Hz, 1H), 8.03 (d, J=8.8 Hz, 1H), 7.87 (s, 1H), 7.59-7.50 (m, 2H), 7.32 (d, J=8.8 Hz, 1H), 7.15 (d, J=8.4 Hz, 1H), 7.64 (t, J=8.0 Hz, 1H), 7.08 (s, 1H), 4.68 (s, 2H), 3.67 (s, H), 3.11 (s, 1H), 1.85 (s, 1H). LCMS (M+H)$^+$: 382.1 (M+H)$^+$.

Example 185: 4-(2-but-2-ynoxy-5-ethylsulfonylphenyl)-2-methylisoquinolin-1-one

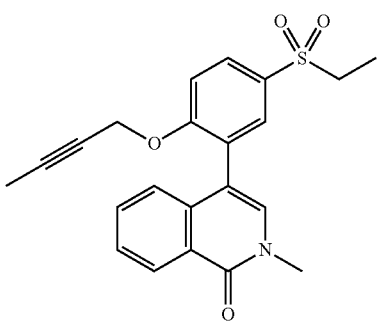 [SMILES: CC#CCOc1ccc(S(=O)(=O)CC)cc1-c1cn(C)c(=O)c2ccccc12]

The title compound was prepared in a manner similar to Example 181, by substituting but-2-yn-1-ol for trans-1,4-cyclohexanediol in step 2. $^1$H NMR (CDCl$_3$, 400 MHz) δ: 8.51 (d, J=7.6 Hz, 1H), 8.00 (dd, J$_1$=8.8 Hz, J$_2$=2.0 Hz, 1H), 7.83 (s, 1H), 7.61 (d, J=7.6 Hz, 1H), 7.55 (d, J=7.6 Hz, 1H), 7.33 (d, J=8.8 Hz, 1H), 7.18 (d, J=8.0 Hz, 1H), 7.12 (s, 1H), 4.68 (s, 2H), 3.72 (s, 3H), 3.17 (q, J=7.2 Hz, 2H), 1.85 (s, 3H), 1.34 (t, J=7.2 Hz, 3H). LCMS (M+H)$^+$: 396.0 (M+H)$^+$.

Example 186: 6-fluoro-4-[2-(trans-4-hydroxycyclohexyl)oxy-5-methylsulfonylphenyl]-2-methylisoquinolin-1-one Step 1: 6-fluoro-4-(2-fluoro-5-methylsulfonylphenyl)-2-methylisoquinolin-1-one

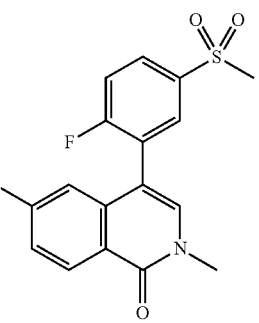

The title compound was prepared in a manner similar to Example 174, by substituting 2-(2-fluoro-5-methylsulfonylphenyl)-4,4,5,5-tetramethyl-1,3,2-dioxaborolane for 2-[2-(cyclopropylmethoxy)-5-ethylsulfonylphenyl]-4,4,5,5-tetramethyl-1,3,2-dioxaborolane. LCMS (M+H)$^+$: 349.9 (M+H)$^+$.

Step 2: 4-[2-[4-[tert-butyl(dimethyl)silyl]oxycyclohexyl]oxy-5-methylsulfonylphenyl]-6-fluoro-2-methylisoquinolin-1-one

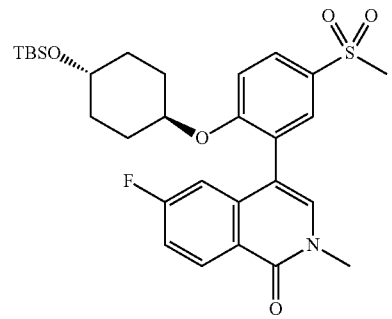 [SMILES: Cn1cc(-c2cc(S(C)(=O)=O)ccc2O[C@H]2CC[C@H](O[Si](C)(C)C(C)(C)C)CC2)c2cc(F)ccc2c1=O]

The title compound was prepared in a manner similar to Example 180 step 1, by substituting 6-fluoro-4-(2-fluoro-5-methylsulfonylphenyl)-2-methylisoquinolin-1-one for 4-(2-fluoro-5-methylsulfonylphenyl)-2-methylisoquinolin-1-one. The crude product was used directly in the next step without further purification. LCMS (M+H)$^+$: 560.3 (M+H)$^+$.

Step 3: 6-fluoro-4-[2-(trans-4-hydroxycyclohexyl)oxy-5-methylsulfonylphenyl]-2-methylisoquinolin-1-one

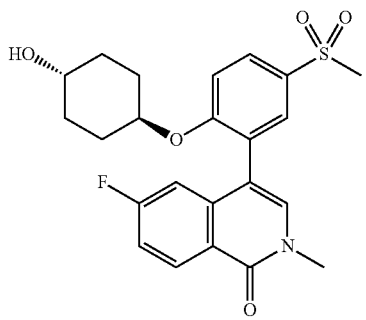

The tert-butyl(dimethyl)silyl ether was deprotected in a manner similar to Example 180 step 2. ¹H NMR (CDCl₃, 400 MHz): δ 8.53-8.49 (m, 1H), 7.99 (dd, $J_1$=8.8 Hz, $J_2$=2.4 Hz, 1H), 7.85 (d, J=2.0 Hz, 1H), 7.21-7.18 (m, 1H), 7.12 (d, J=8.8 Hz, 1H), 7.08 (s, 1H), 6.78 (dd, $J_1$=10.0 Hz, $J_2$=2.4 Hz, 1H), 4.46-4.44 (m, 1H), 3.66-3.65 (m, 4H), 3.10 (s, 3H), 2.02-1.99 (m, 2H), 1.73-1.71 (m, 2H), 1.43-1.37 (m, 4H). LCMS (M+H)⁺: 446.0 (M+H)⁺.

Example 187: 7-fluoro-4-[2-(trans-4-hydroxycyclohexyl)oxy-5-methylsulfonylphenyl]-2-methylisoquinolin-1-one

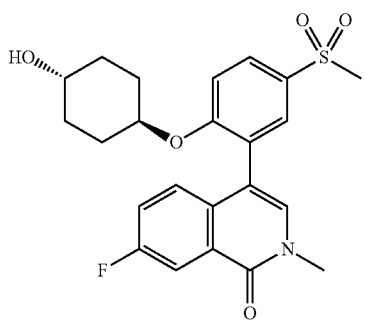

The title compound was prepared in a manner similar to Example 186, by substituting 4-bromo-7-fluoro-2-methylisoquinolin-1-one for 4-bromo-6-fluoro-2-methylisoquinolin-1-one in step 1. ¹H NMR (CDCl₃, 400 MHz): δ 8.16-8.14 (m, 1H), 7.99 (dd, $J_1$=8.8 Hz, $J_2$=2.4 Hz, 1H), 7.86 (d, J=2.4 Hz, 1H), 7.28-7.27 (m, 1H), 7.18-7.12 (m, 2H), 7.01 (s, 1H), 4.43-4.42 (m, 1H), 3.67-3.66 (m, 4H), 3.10 (s, 3H), 1.98-1.97 (m, 2H), 1.72-1.71 (m, 2H), 1.39-1.32 (m, 4H). LCMS (M+H)⁺: 446.0 (M+H)⁺.

Example 188: 4-[5-ethylsulfonyl-2-(trans-4-hydroxycyclohexyl)oxyphenyl]-6-fluoro-2-methylisoquinolin-1-one

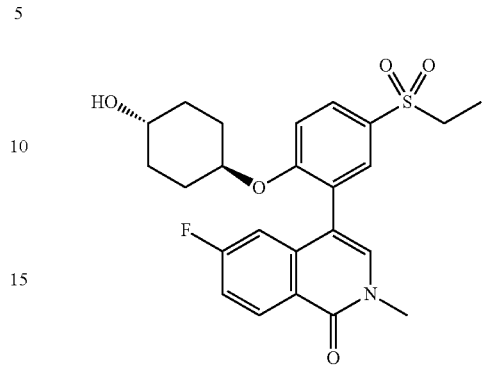

The title compound was prepared in a manner similar to Example 186, by substituting 2-(5-ethylsulfonyl-2-fluorophenyl)-4,4,5,5-tetramethyl-1,3,2-dioxaborolane for 2-(2-fluoro-5-methylsulfonylphenyl)-4,4,5,5-tetramethyl-1,3,2-dioxaborolane in step 1. ¹H NMR (CDCl₃, 400 MHz): δ 8.53-8.50 (m, 1H), 7.97-7.94 (m, 1H), 7.82 (d, J=2.4 Hz, 1H), 7.22-7.18 (m, 1H), 7.13 (d, J=8.8 Hz, 1H), 7.08 (s, 1H), 6.79-6.76 (m, 1H), 4.46-4.44 (m, 1H), 3.70-3.64 (m, 4H), 3.16 (q, J=7.6 Hz, 2H), 2.00-1.88 (m, 3H), 1.72-1.71 (m, 2H), 1.40-1.30 (m, 7H). LCMS (M+H)⁺: 460.1 (M+H)⁺.

Example 189: 4-[5-ethylsulfonyl-2-(trans-4-hydroxycyclohexyl)oxyphenyl]-7-fluoro-2-methylisoquinolin-1-one

Step 1: 4-(5-ethylsulfonyl-2-fluorophenyl)-7-fluoro-2-methylisoquinolin-1-one

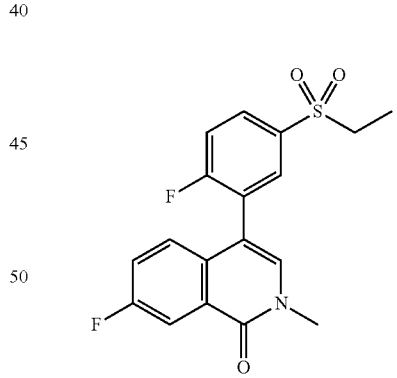

A mixture of 4-bromo-7-fluoro-2-methylisoquinolin-1-one (100 mg, 0.39 mmol), 2-(5-ethylsulfonyl-2-fluorophenyl)-4,4,5,5-tetramethyl-1,3,2-dioxaborolane (148 mg, 0.47 mmol), Pd(dppf)Cl₂ (29 mg, 0.04 mmol) and K₃PO₄ (207 mg, 0.98 mmol) in dioxane (6 mL) and H₂O (1 mL) was heated to 70° C. for 18 hr under N₂. The mixture was concentrated and the residue was purified by CC on silica gel (PE:EA=1:1) to give compound 12 (70 mg, yield: 49%) as a yellow solid. LCMS (M+H)⁺: 364.1 (M+H)⁺.

Step 2: 4-[2-[4-[tert-butyl(dimethyl)silyl]oxycyclohexyl]oxy-5-ethylsulfonylphenyl]-7-fluoro-2-methylisoquinolin-1-one

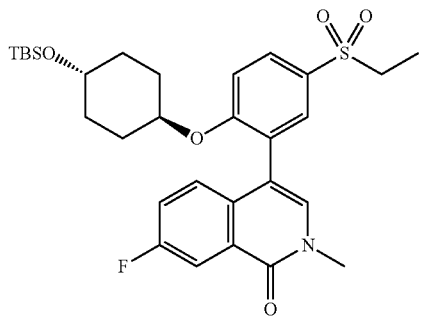 [SMILES: CCS(=O)(=O)c1ccc(O[C@H]2CC[C@H](O[Si](C)(C)C(C)(C)C)CC2)c(-c2cn(C)c(=O)c3cc(F)ccc23)c1]

To a soln of trans-4-[tert-butyl(dimethyl)silyl]oxycyclohexan-1-ol (87 mg, 0.38 mmol) in dry DMF (2 mL) was added NaH (15 mg, 0.38 mmol, 60% in mineral oil) in portions under $N_2$ at 0° C. and the mixture was stirred at 20° C. for 1 hr. Then the title compound from step 1 (70 mg, 0.19 mmol) was added and the mixture was stirred at 20° C. for 4 hr. The mixture was quenched with $H_2O$ (5 mL) and extracted with EtOAc (3×5 mL). The combined organic layers were dried over $Na_2SO_4$ and concentrated to give the title compound as a yellow gum (65 mg) which was used directly in the next step without further purification. LCMS $(M+H)^+$: 574.3 $(M+H)^+$.

Step 3: 4-[5-ethylsulfonyl-2-(trans-4-hydroxycyclohexyl)oxyphenyl]-7-fluoro-2-methylisoquinolin-1-one

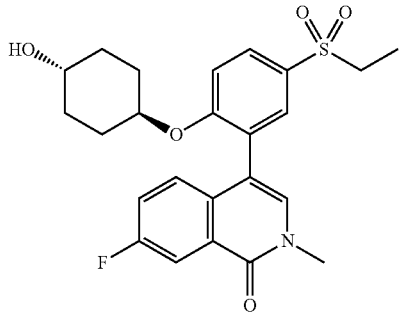 [SMILES: CCS(=O)(=O)c1ccc(O[C@H]2CC[C@H](O)CC2)c(-c2cn(C)c(=O)c3cc(F)ccc23)c1]

The tert-butyl(dimethyl)silyl ether was deprotected in a manner similar to Example 180 step 2. $^1$H NMR (CDCl$_3$, 400 MHz): δ 8.16 (dd, $J_1$=9.2 Hz, $J_2$=2.4 Hz, 1H), δ 7.96 (dd, $J_1$=8.4 Hz, $J_2$=2.4 Hz, 1H), 7.82 (d, J=2.4 Hz, 1H), 7.32-7.29 (m, 1H), 7.18-7.11 (m, 2H), 7.01 (s, 1H), 4.42-4.42 (m, 1H), 3.67 (s, 3H), 3.18 (q, J=7.6 Hz, 2H), 1.97-1.88 (m, 3H), 1.72-1.71 (m, 2H), 1.40-1.32 (m, 7H). LCMS $(M+H)^+$: 460.1 $(M+H)^+$.

Example 190: 2-methyl-4-[5-methylsulfonyl-2-(oxolan-3-ylamino)phenyl]isoquinolin-1-one

Step 1: N-(2-bromo-4-methylsulfonylphenyl)oxolan-3-amine

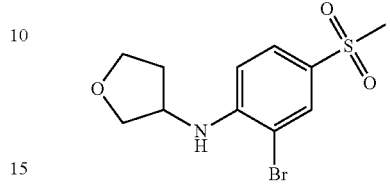

A mixture of 2-bromo-1-fluoro-4-methylsulfonylbenzene (0.8 g, 3.16 mmol), oxolan-3-amine (1.38 g, 15.8 mmol) and $K_2CO_3$ (0.87 g, 6.32 mmol) in DMSO (15 mL) was stirred at 100° C. for 5 hr. It was cooled to room temp and $H_2O$ (50 mL) was added. The mixture was extracted with EtOAc (50 mL×3) and the combined organic layers were washed with brine (50 mL), dried over $Na_2SO_4$, filtered and concentrated. The residue was purified by CC (PE:EA=50:1~3:1) to give the title compound (0.7 g, yield: 69.16%). $^1$H NMR (CDCl$_3$, 400 MHz): δ 8.00 (d, J=1.2 Hz, 1H), 7.74 (d, J=8.8 Hz, 1H), 6.67 (d, J=8.8 Hz, 1H), 5.03 (d, J=6.4 Hz, 1H), 4.23-4.13 (m, 1H), 4.07-3.98 (m, 2H), 3.96-3.87 (m, 1H), 3.83-3.76 (m, 1H), 3.03 (s, 3H), 2.43-2.32 (m, 1H), 1.98-1.88 (m, 1H). LCMS $(M+H)^+$: 320.0; $(M+H)^+$: 322.0.

Step 2: 2-methyl-4-[5-methylsulfonyl-2-(oxolan-3-ylamino)phenyl]isoquinolin-1-one

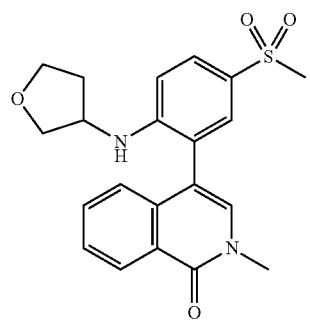 [SMILES: Cn1cc(-c2cc(S(C)(=O)=O)ccc2NC2CCOC2)c2ccccc2c1=O]

A mixture of 2-methyl-4-(4,4,5,5-tetramethyl-1,3,2-dioxaborolan-2-yl)isoquinolin-1-one (100 mg, 0.35 mmol), the compound from Step 1 (102 mg, 0.32 mmol), $K_3PO_4$ (186 mg, 0.88 mmol) and Pd(dppf)Cl$_2$ (29 mg, 0.04 mmol) in dioxane (5 mL) and $H_2O$ (1 mL) was purged three times with $N_2$ and then stirred at 70° C. for 18 hr under $N_2$. The mixture was filtered and concentrated. The residue was purified by prep-HPLC to give the title compound (56.02 mg, yield: 40.1%) as a light yellow solid. $^1$H NMR (CDCl$_3$, 400 MHz): δ 8.54 (d, J=8.0 Hz, 1H), 7.89 (dd, $J_1$=8.4 Hz, $J_2$=2.4 Hz, 1H), 7.69 (s, 1H), 7.64-7.52 (m, 2H), 7.13 (s, 1H), 7.13-7.08 (m, 1H), 6.78 (dd, $J_1$=8.8 Hz, $J_2$=5.6 Hz, 1H), 4.17 (s, 2H), 3.94-3.86 (m, 1H), 3.79-3.72 (m, 1H), 3.72-3.64 (m, 1H), 3.67 (s, 3H), 3.58-3.49 (m, 1H), 3.07 (s, 3H), 2.32-2.18 (m, 1H), 1.76-1.63 (m, 1H). LCMS $(M+H)^+$: 399.1 $(M+H)^+$.

Example 191: 2-methyl-4-[5-methylsulfonyl-2-(oxan-4-ylamino)phenyl]isoquinolin-1-one Step 1: N-(2-bromo-4-methylsulfonylphenyl)oxan-4-amine

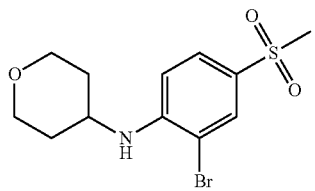 [SMILES: CS(=O)(=O)c1ccc(NC2CCOCC2)c(Br)c1]

The title compound was prepared in a manner similar to Example 190 step 1, by substituting oxan-3-amine for oxolan-3-amine. $^1$H NMR (CDCl$_3$, 400 MHz): δ 7.98 (d, J=1.8 Hz, 1H), 7.70 (dd, J$_1$=8.8 Hz, J$_2$=1.8 Hz, 1H), 6.70 (d, J=8.8 Hz, 1H), 4.85 (d, J=7.2 Hz, 1H), 4.08-3.99 (m, 2H), 3.69-3.60 (m, 1H), 3.60-3.52 (m, 2H), 3.03 (s, 3H), 2.10-2.02 (m, 2H), 1.68-1.55 (m, 2H). LCMS (M+H)$^+$: 334.0; (M+H)$^+$: 336.0.

Step 2: 2-methyl-4-[5-methylsulfonyl-2-(oxan-4-ylamino)phenyl]isoquinolin-1-one

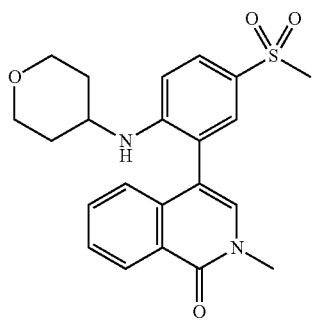 [SMILES: Cn1cc(-c2cc(S(C)(=O)=O)ccc2NC2CCOCC2)c2ccccc2c1=O]

The title compound was prepared in a manner similar to Example 190 step 2, by substituting N-(2-bromo-4-methylsulfonylphenyl)oxan-4-amine for N-(2-bromo-4-methylsulfonylphenyl)oxolan-3-amine. $^1$H NMR (CDCl$_3$, 400 MHz) δ 8.52 (d, J=7.6 Hz, 1H), 7.85 (dd, J$_1$=8.8 Hz, J$_2$=2.0 Hz, 1H), 7.67 (d, J=2.0 Hz, H), 7.63-7.52 (m, 2H), 7.16-7.11 (m, 2H), 6.81 (d, J=8.8 Hz, 1H), 4.00 (d, J=7.6 Hz, 1H), 3.93-3.82 (m, 2H), 3.64 (s, 3H), 3.63-3.54 (m, 1H), 3.51-3.42 (m, 2H), 3.06 (s, 3H), 1.95-1.87 (m, 2H), 1.37-1.24 (m, 1H). LCMS (M+H)$^+$: 413.0 (M+H)$^+$.

Example 192: 4-[2-[(trans-4-hydroxycyclohexyl)amino]-5-methylsulfonylphenyl]-2-methylisoquinolin-1-one

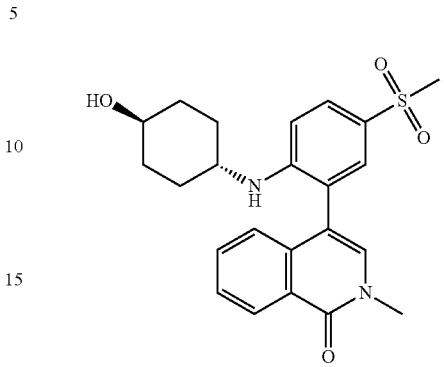

A mixture of 4-(2-fluoro-5-methylsulfonylphenyl)-2-methylisoquinolin-1-one (150 mg, 0.45 mmol) and trans-4-aminocyclohexan-1-ol (417 mg, 3.62 mmol) in NMP (0.2 mL) was heated for 20 min at 200-300° C. The cooled brownish residue was purified by prep-HPLC to give the title compound (55.64 mg, 28.8%) as a yellow solid. $^1$H NMR (CDCl$_3$, 400 MHz): δ 8.54 (d, J=8.0 Hz, 1H), 7.86 (dd, J$_1$=8.8 Hz, J$_2$=2.4 Hz, 1H), 7.66 (d, J=2.4 Hz, 1H), 7.60-7.55 (m, 2H), 7.15-7.13 (m, 2H), 6.79 (d, J=8.8 Hz, 1H), 3.91-3.85 (m, 1H), 3.67 (s, 3H), 3.63-3.55 (m, 1H), 3.37-3.34 (m, 1H), 3.06 (s, 3H), 2.04-1.92 (m, 5H), 1.44-1.35 (m, 2H), 1.11-1.02 (m, 2H). LCMS (M+H)$^+$: 427.1 (M+H)$^+$.

Example 193: 4-[2-(cyclopropylmethylamino)-5-ethylsulfonylphenyl]-2-methylisoquinolin-1-one

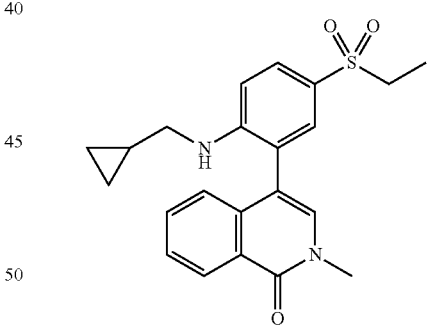

The title compound was prepared in a manner similar to Example 190 step 2, by substituting 2-bromo-N-(cyclopropylmethyl)-4-ethylsulfonylaniline for N-(2-bromo-4-methylsulfonylphenyl)oxolan-3-amine. $^1$H NMR (CDCl$_3$, 400 MHz): δ 8.51 (d, J=7.6 Hz, 1H), 7.80 (dd, J$_1$=8.8 Hz, J$_2$=2.0 Hz, 1H), 7.61-7.51 (m, 3H), 7.15 (d, J=8.0 Hz, 1H), 7.13 (s, 1H), 6.76 (d, J=8.8 Hz, 1H), 4.32 (t, J=4.8 Hz, 1H), 3.62 (s, 3H), 3.09 (q, J=7.2 Hz, 2H), 3.01 (m, 2H), 1.29 (t, J=7.2 Hz, 3H), 0.95-0.89 (m, 1H), 0.46-0.38 (m, 2H), 0.12-0.05 (m, 2H). LCMS (M+H)$^+$: 397.1 (M+H)$^+$.

Example 194: 4-[2-(cyclopropylmethylamino)-5-methylsulfonylphenyl]-2-methylisoquinolin-1-one

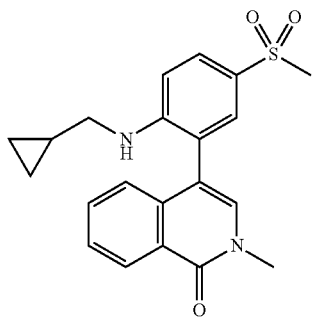 [SMILES: Cn1cc(-c2cc(S(C)(=O)=O)ccc2NCC2CC2)c2ccccc2c1=O]

The title compound was prepared in a manner similar to Example 190 step 2, by substituting 2-bromo-N-(cyclopropylmethyl)-4-methylsulfonylaniline for N-(2-bromo-4-methylsulfonylphenyl)oxolan-3-amine. $^1$H NMR (CDCl$_3$, 400 MHz) δ 8.54 (d, J=7.6 Hz, 1H), 7.80 (dd, J$_1$=8.8 Hz, J$_2$=2.4 Hz, 1H), 7.67 (d, J=2.4 Hz, 1H), 7.60-7.55 (m, 2H), 7.17 (d, J=8.0 Hz, 1H), 7.15 (s, 1H), 6.77 (d, J=8.8 Hz, 1H), 4.24-4.23 (m, 1H), 3.66 (s, 3H), 3.06 (s, 3H), 3.03-2.99 (m, 2H), 0.93-0.91 (m, 1H), 0.45-0.37 (m, 2H), 0.12-0.054 (m, 2H). LCMS (M+H)$^+$: 383.1 (M+H)$^+$.

Example 195: 4-[2-(cyclopropylmethylamino)-5-ethylsulfonylphenyl]-7-fluoro-2-methylisoquinolin-1-one

Step 1: 7-fluoro-2-methyl-4-(4,4,5,5-tetramethyl-1,3,2-dioxaborolan-2-yl)isoquinolin-1-one

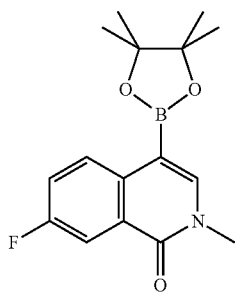 [SMILES: Cn1cc(B2OC(C)(C)C(C)(C)O2)c2ccc(F)cc2c1=O]

A mixture of compound 4-bromo-7-fluoro-2-methylisoquinolin-1-one (1.2 g, 4.69 mmol), bis(pinacolato)diboron (2.38 g, 9.37 mmol), AcOK (1.38 g, 14.07 mmol), Pd$_2$(dba)$_3$ (429 mg, 0.47 mmol) and X-phos (224 mg, 0.47 mmol) in dioxane (20 mL) was stirred at 70° C. for 18 hr under N$_2$. The mixture was concentrated and the residue was purified by CC to give the title compound (0.8 g, yield: 56.3%). $^1$H NMR (CDCl$_3$, 400 MHz) δ 8.42 (dd, J$_1$=9.2 Hz, J$_2$=4.2 Hz, 1H), 8.06 (dd, J$_1$=9.2 Hz, J$_2$=2.8 Hz, 1H), 7.65 (s, 1H), 7.42-7.35 (m, 1H), 3.64 (s, 3H), 1.38 (s, 12H). LCMS (M+H)$^+$: 304.1 (M+H)$^+$.

Step 2: 4-[2-(cyclopropylmethylamino)-5-ethylsulfonylphenyl]-7-fluoro-2-methylisoquinolin-1-one

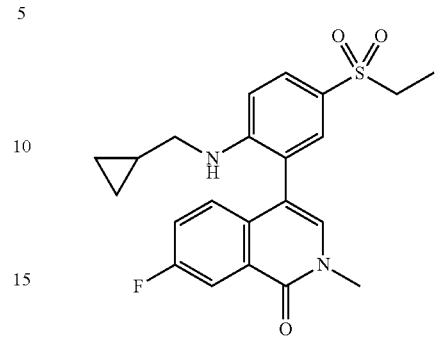

The title compound was prepared in a manner similar to Example 193, by substituting 7-fluoro-2-methyl-4-(4,4,5,5-tetramethyl-1,3,2-dioxaborolan-2-yl)isoquinolin-1-one for 2-methyl-4-(4,4,5,5-tetramethyl-1,3,2-dioxaborolan-2-yl)isoquinolin-1-one. $^1$H NMR (CDCl$_3$, 400 MHz): δ 8.17 (d, J=8.4 Hz, 1H), 7.82 (d, J=8.4 Hz, 1H), 7.61 (s, 1H), 7.38-7.29 (m, 1H), 7.21-7.13 (m, 1H), 7.11 (s, 1H), 6.77 (d, J=8.4 Hz, 1H), 3.67 (s, 3H), 3.11 (q, J=7.2 Hz, 2H), 3.01 (d, J=6.8 Hz, 2H), 1.31 (t, J=7.2 Hz, 3H), 0.99-0.85 (m, 1H), 0.51-0.36 (m, 2H), 0.17-0.02 (m, 2H). LCMS (M+H)$^+$: 415.1 (M+H)$^+$.

Example 196: 4-[2-(cyclopropylmethylamino)-5-methylsulfonylphenyl]-7-fluoro-2-methylisoquinolin-1-one

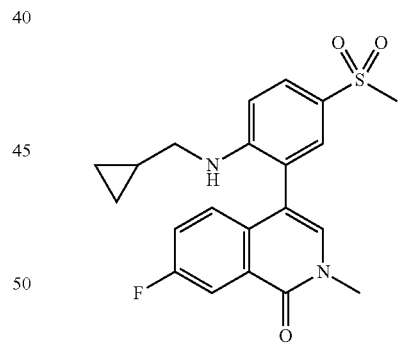

The title compound was prepared in a manner similar to Example 195, by substituting 2-bromo-N-(cyclopropylmethyl)-4-methylsulfonylaniline for 2-bromo-N-(cyclopropylmethyl)-4-ethylsulfonylaniline in step 2. $^1$H NMR (CDCl$_3$, 400 MHz): δ 8.19 (dd, J$_1$=9.2 Hz, J$_2$=2.8 Hz, 1H), 7.86 (dd, J$_1$=8.8 Hz, J$_2$=2.0 Hz, 1H), 7.66 (d, J=2.4 Hz, 1H), 7.37-7.30 (m, 1H), 7.18 (dd, J$_1$=8.8 Hz, J$_2$=4.8 Hz, 1H), 7.11 (s, 1H), 6.77 (d, J=8.8 Hz, 1H), 4.14 (s, 1H), 3.68 (s, 3H), 3.06 (s, 3H), 3.01 (d, J=6.8 Hz, 2H), 0.98-0.84 (m, 1H), 0.51-0.37 (m, 2H), 0.16-0.02 (m, 2H). LCMS (M+H)$^+$: 401.1 (M+H)$^+$.

Example 197: 4-[2-(cyclopropylmethoxy)-5-methylsulfonylphenyl]-2-methyl-6-(trifluoromethoxy)isoquinolin-1-one

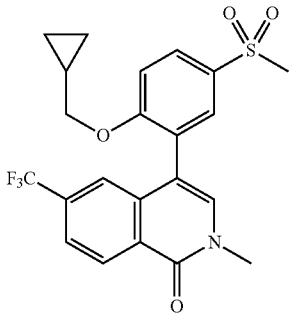 [SMILES: Cn1cc(-c2cc(S(C)(=O)=O)ccc2OCC2CC2)c2cc(C(F)(F)F)ccc2c1=O]

A mixture of 4-bromo-2-methyl-6-(trifluoromethyl)isoquinolin-1-one (40 mg, 0.13 mmol), 2-[2-(cyclopropylmethoxy)-5-methylsulfonylphenyl]-4,4,5,5-tetramethyl-1,3,2-dioxaborolane (46 mg, 0.13 mmol), $K_3PO_4$ (68 mg, 0.33 mmol) and Pd(dppf)$Cl_2$ (10 mg, 0.01 mmol) in dioxane (0.9 mL) and $H_2O$ (0.09 mL) was degassed with $N_2$ for 10 min and then stirred at 60° C. for 1.6 hr. The rxn mixture was diluted with EtOAc (5 mL), dried over $Na_2SO_4$, filtered and concentrated under reduced pressure. The residue was purified by normal phase silica gel CC to give the title compound (27 mg, 46%). $^1$H NMR (DMSO-d6, 400 MHz): δ 8.51 (d, $J_1$=8.4 Hz, 1H), 8.0 (dd, $J_1$=8.7 Hz, $J_2$=2.5 Hz, 1H), 7.87 (s, 1H), 7.85 (m, 1H), 7.72 (s, 1H), 7.39 (m, 2H), 4.02 (m, 1H), 3.86 (m, 1H), 3.61 (s, 3H), 3.23 (s, 3H), 0.90 (m, 1H), 0.31 (m, 2H), 0.09 (m, 2H). LCMS (M+H)$^+$: 452.2.

Example 198: 4-(2-(cyclopropylmethoxy)-5-(methylsulfonyl)phenyl)-6-methoxy-2-methylisoquinolin-1(2H)-one

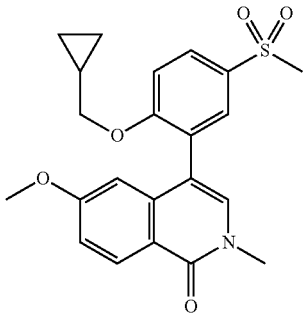

The title compound of Example 90, step 2 (30 mg, 0.075 mmol) in N,N-dimethyl-acetamide was treated with excess 25% sodium methoxide in methanol and heated at 85° C. until complete. Silica gel chromatography (40-80% EA in hexane over 8 min, then isocratic) gave the title compound 23 mg, 0.056 mmol, 74%) as a white solid. $^1$H NMR (400 MHz, DMSO-d$_6$): δ ppm 0.06-0.20 (m, 2H) 0.27-0.43 (m, 2H) 0.83-1.05 (m, 1H) 3.22 (s, 3H) 3.53 (s, 3H) 3.73 (s, 3H) 3.83-4.16 (m, 2H) 6.47 (s, 1H) 7.04-7.20 (m, 1H) 7.36 (d, J=8.59 Hz, 1H) 7.50 (s, 1H) 7.81 (s, 1H) 7.96 (d, J=6.82 Hz, 1H) 8.23 (d, J=8.59 Hz, 1H). LCMS: 414 (M+H)$^+$.

Example 199: 4-[3-(cyclopropylmethoxy)-6-methylsulfonylpyridin-2-yl]-2-methylisoquinolin-1-one Step 1: 6-methylsulfonylpyridin-3-ol

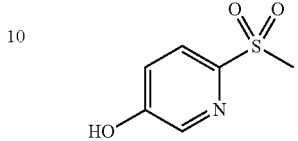

A mixture of 6-chloropyridin-3-ol (2.00 g, 15.44 mmol), MeSO$_2$Na (2.36 g, 23.16 mmol), CuI (882.16 mg, 4.63 mmol), L-proline (533.28 mg, 4.63 mmol), and $K_2CO_3$ (640.19 mg, 4.63 mmol) in DMSO (20 mL) were charged into a microwave tube. The sealed tube was heated at 140° C. for 3 hr under microwave. After cooling to room temp, $H_2O$ (100 mL) was added. The mixture was extracted with EtOAc (100 mL×3). The combined organic layers were washed with brine (100 mL), dried over $Na_2SO_4$, filtered and concentrated under reduced pressure. The residue was purified by CC to give the title compound (1.2 g, 44.8%) as a yellow solid. $^1$H NMR (Methanol-d$_4$, 400 MHz): δ 8.24 (d, J=2.4 Hz, 1H), 7.94 (d, J=8.4 Hz, 1H), 7.37 (dd, $J_1$=8.8 Hz, $J_2$=2.8 Hz, 1H), 3.15 (s, 3H).

Step 2: 2-iodo-6-methylsulfonylpyridin-3-ol and 4-iodo-6-methylsulfonylpyridin-3-ol

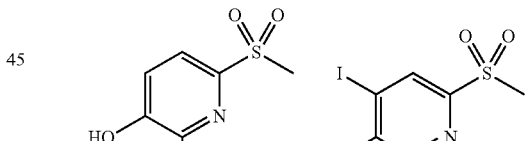

A mixture of the title compound from Step 1 (3.0 g, 17.34 mmol), $I_2$ (6.6 g, 26.01 mmol), NaHCO$_3$ (2.2 g, 26.20 mmol) and KI (0.72 g, 4.34 mmol) in THF (30 mL) and $H_2O$ (30 mL) was stirred at 60° C. for 18 hr. $H_2O$ (100 mL) was added and the mixture was extracted with EtOAc (100 mL×3). The combined organic layers were washed with brine (100 mL), dried over $Na_2SO_4$, filtered and concentrated under reduced pressure. The residue was purified by preparative HPLC to give 4-iodo-6-methylsulfonylpyridin-3-ol (700.0 mg) and 2-iodo-6-methylsulfonylpyridin-3-ol (700.0 mg). 2-iodo-6-methylsulfonylpyridin-3-ol: $^1$H NMR (CDCl$_3$, 400 MHz): δ 12.08 (brs, 1H), 7.86 (d, J=8.4 Hz, 1H), 7.31 (d, J=8.4 Hz, 1H), 3.19 (s, 3H). 4-iodo-6-methylsulfonylpyridin-3-ol: $^1$H NMR (CDCl$_3$, 400 MHz): δ 12.0 (brs, 1H), 8.24 (s, 1H), 8.17 (s, 1H), 3.20 (s, 3H).

Step 3: 3-(cyclopropylmethoxy)-2-iodo-6-methylsulfonylpyridine

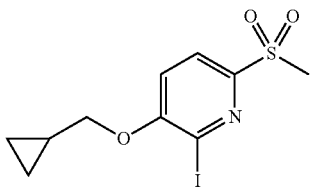 [SMILES: CS(=O)(=O)c1ccc(OCC2CC2)c(I)n1]

A mixture of 2-iodo-6-methylsulfonylpyridin-3-ol (500.0 mg, 1.67 mmol), bromomethylcyclopropane (248.4 mg, 1.84 mmol) and K$_2$CO$_3$ (461.3 mg, 33.4 mmol) in ACN (15 mL) was stirred at 80° C. for 4 hr. H$_2$O (30 mL) was added and the mixture was extracted with EtOAc (30 mL×3). The combined organic layers were washed with brine (30 mL), dried over Na$_2$SO$_4$, filtered and concentrated to give the title compound (500.0 mg, 84.8%). $^1$H NMR (CDCl$_3$, 400 MHz): δ 7.96 (d, J=8.8 Hz, 1H), 7.52 (d, J=8.4 Hz, 1H), 4.09 (d, J=6.8 Hz, 2H), 3.22 (s, 3H), 1.36-1.22 (m, 1H), 0.69-0.57 (m, 2H), 0.43-0.37 (m, 2H). LCMS: 354.0 (M+1)$^+$.

Step 4

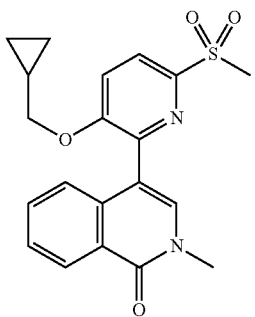 [SMILES: Cn1cc(-c2nc(S(C)(=O)=O)ccc2OCC2CC2)c2ccccc2c1=O]

A mixture of 3-(cyclopropylmethoxy)-2-iodo-6-methylsulfonylpyridine (140.0 mg, 0.40 mmol), 2-methyl-4-(4,4,5,5-tetramethyl-1,3,2-dioxaborolan-2-yl)isoquinolin-1-one (136.5 mg, 0.48 mmol), K$_3$PO$_4$ (252.7 mg, 1.19 mmol) and Pd(dppf)Cl$_2$ (29.2 mg, 0.04 mmol) in dioxane (5 mL) and H$_2$O (1 mL) was stirred at 70° C. for 18 hr under N$_2$. The mixture was filtered and concentrated. The residue was purified by prep-HPLC to give the title compound (81.0 mg, 53.1%). $^1$H NMR (CDCl$_3$, 400 MHz): δ 8.33 (dd, J$_1$=8.4 Hz, J$_2$=1.2 Hz, 1H), 8.07 (d, J=8.4 Hz, 1H), 7.83 (d, J=8.8 Hz, 1H), 7.74 (s, 1H), 7.67 (t, J=8.4 Hz, 1H), 7.55 (t, J=8.4 Hz, 1H), 7.39 (d, J=8.0 Hz, 1H), 4.01 (d, J=6.8 Hz, 2H), 3.60 (s, 3H), 3.25 (s, 3H), 1.10-0.98 (m, 1H), 0.45-0.37 (m, 2H), 0.23-0.17 (m, 2H). LCMS: 385.1 (M+1)$^+$.

Example 200: 4-[5-(cyclopropylmethoxy)-2-methylsulfonylpyridin-4-yl]-2-methylisoquinolin-1-one

Step 1: 5-(cyclopropylmethoxy)-4-iodo-2-methylsulfonylpyridine

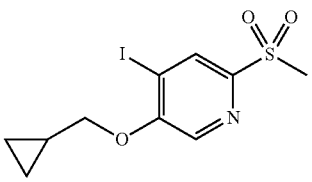 [SMILES: CS(=O)(=O)c1cc(I)c(OCC2CC2)cn1]

The title compound was prepared in a manner similar to Example 199 Step 3, by substituting 4-iodo-6-methylsulfonylpyridin-3-ol for 2-iodo-6-methylsulfonylpyridin-3-ol. $^1$H NMR (CDCl$_3$, 400 MHz): δ 8.35 (s, 1H), 8.32 (s, 1H), 4.20 (d, J=7.2 Hz, 2H), 3.23 (s, 3H), 1.36-1.25 (m, 1H), 0.67-0.58 (m, 2H), 0.44-0.37 (m, 2H). LCMS: 354.0 (M+1)$^+$.

Step 2: 4-[5-(cyclopropylmethoxy)-2-methylsulfonylpyridin-4-yl]-2-methylisoquinolin-1-one

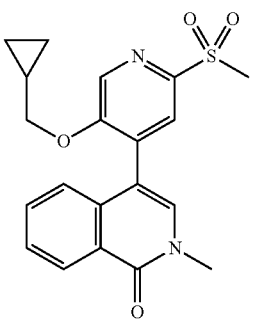 [SMILES: Cn1cc(-c2cc(S(C)(=O)=O)ncc2OCC2CC2)c2ccccc2c1=O]

The title compound was prepared in a manner similar to Example 199 Step 4, by substituting 5-(cyclopropylmethoxy)-4-iodo-2-methylsulfonylpyridine for 3-(cyclopropylmethoxy)-2-iodo-6-methylsulfonylpyridine. $^1$H NMR (CDCl$_3$, 400 MHz): δ 8.66 (s, 1H), 8.31 (d, J=8.0 Hz, 1H), 7.96 (s, 1H), 7.70-7.66 (m, 2H), 7.57-7.54 (t, J=7.2 Hz, 1H), 7.22 (d, J=8.0 Hz, 1H), 4.12 (d, J=6.8 Hz, 2H), 3.57 (s, 3H), 3.28 (s, 3H), 1.05-0.92 (m, 1H), 0.43-0.27 (m, 2H), 0.18-0.10 (m, 2H). LCMS: 385.1 (M−1)$^+$.

Example 201: 4-[3-(cyclopropylmethoxy)-6-methyl-sulfonylpyridin-2-yl]-7-fluoro-2-methylisoquinolin-1-one

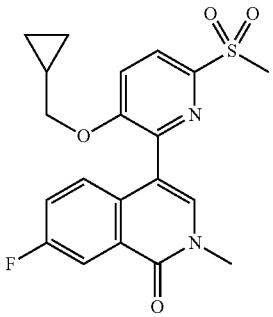 [SMILES: Cn1cc(-c2nc(S(C)(=O)=O)ccc2OCC2CC2)c2ccc(F)cc2c1=O]

The title compound was prepared in a manner similar to Example 199 Step 4, by substituting 7-fluoro-2-methyl-4-(4,4,5,5-tetramethyl-1,3,2-dioxaborolan-2-yl)isoquinolin-1-one for 2-methyl-4-(4,4,5,5-tetramethyl-1,3,2-dioxaborolan-2-yl)isoquinolin-1-one. $^1$H NMR (DMSO-d6, 400 MHz): δ 8.07 (d, J=8.4 Hz, 1H), 7.97 (d, J=7.6 Hz, 1H), 7.83 (d, J=8.4 Hz, 1H), 7.75 (s, 1H), 7.65-7.45 (m, 2H), 4.01 (d, J=6.4 Hz, 2H), 3.61 (s, 3H), 3.25 (s, 3H), 1.11-0.98 (m, 1H), 0.48-0.35 (m, 2H), 0.27-0.15 (m, 2H). LCMS: 403.1 (M+1)$^+$.

Example 202: 4-[3-(cyclopropylmethoxy)-6-methyl-sulfonylpyridin-2-yl]-6-fluoro-2-methylisoquinolin-1-one

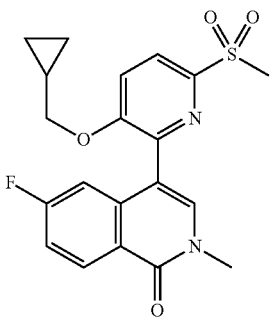

The title compound was prepared in a manner similar to Example 199 Step 4, by substituting 6-fluoro-2-methyl-4-(4,4,5,5-tetramethyl-1,3,2-dioxaborolan-2-yl)isoquinolin-1-one for 2-methyl-4-(4,4,5,5-tetramethyl-1,3,2-dioxaborolan-2-yl)isoquinolin-1-one. $^1$H NMR (DMSO-d$_6$, 400 MHz): δ 8.37 (dd, J$_1$=8.8 Hz, J$_2$=6.4 Hz, 1H), 8.07 (d, J=8.4 Hz, 1H), 7.84 (s, 1H), 7.82 (d, J=8.8 Hz, 1H), 7.45-7.36 (td, J$_1$=10.8 Hz, J$_2$=2.4 Hz, 1H), 7.18 (dd, J$_1$=10.8 Hz, J$_2$=2.4 Hz, 1H), 4.03 (d, J=7.2 Hz, 2H), 3.59 (s, 3H), 3.25 (s, 3H), 1.15-1.03 (m, 1H), 0.48-0.39 (m, 2H), 0.28-0.20 (m, 2H). LCMS: 403.1 (M+1)$^+$.

Example 203: 4-[5-(cyclopropylmethoxy)-2-methyl-sulfonylpyridin-4-yl]-7-fluoro-2-methylisoquinolin-1-one

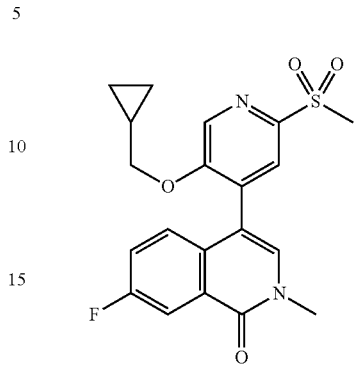

The title compound was prepared in a manner similar to Example 200 Step 2, by substituting 7-fluoro-2-methyl-4-(4,4,5,5-tetramethyl-1,3,2-dioxaborolan-2-yl)isoquinolin-1-one for 2-methyl-4-(4,4,5,5-tetramethyl-1,3,2-dioxaborolan-2-yl)isoquinolin-1-one. $^1$H NMR (DMSO-d6, 400 MHz): δ 8.08 (d, J=8.4 Hz, 1H), 7.97 (dd, J$_1$=9.2 Hz, J$_2$=2.8 Hz, 1H), 7.83 (d, J=8.4 Hz, 1H), 7.75 (s, 1H), 7.62-7.55 (td, J$_1$=9.2 Hz, J$_2$=2.4 Hz, 1H), 7.50 (dd, J$_1$=9.2 Hz, J$_2$=5.2 Hz, 1H), 4.01 (d, J=6.8 Hz, 2H), 3.61 (s, 3H), 3.25 (s, 3H), 1.11-0.99 (m, 1H), 0.46-0.39 (m, 2H), 0.24-0.18 (m, 2H). LCMS: 403.2 (M+1)$^+$.

Example 204: 4-(2-ethoxy-5-ethylsulfonylthiophen-3-yl)-2-methylisoquinolin-1-one

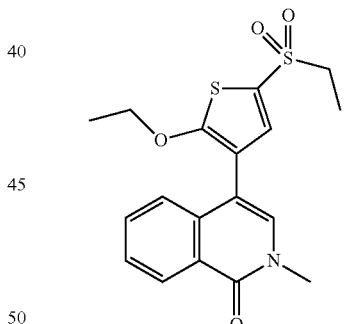

A mixture of 3-bromo-2-ethoxy-5-ethylsulfonylthiophene (18.0 mg, 0.06 mmol), 2-methyl-4-(4,4,5,5-tetramethyl-1,3,2-dioxaborolan-2-yl)isoquinolin-1-one (24 mg, 0.08 mmol), K$_3$PO$_4$ (42 mg, 0.20 mmol) and Pd(dppf)Cl$_2$ (6 mg, 0.008 mmol) in dioxane (0.5 mL) and H$_2$O (0.05 mL) was stirred at 60° C. for 1.5 hr. The rxn mixture was then poured over H$_2$O (6 mL) and extracted with EtOAc (2×5 mL). The combined organic layers were dried over Na$_2$SO$_4$, filtered and concentrated under reduced pressure. The residue was purified by normal phase silica gel CC to give the title compound (10.5 mg, 46%). $^1$H NMR (DMSO-d$_6$, 400 MHz): δ 8.29 (d, J=7.9 Hz, 1H), 7.71 (dd, J=7.6, 7.6 Hz, 1H), 7.57 (m, 3H), 7.35 (d, J=7.9 Hz, 1H), 4.25 (m, 2H), 3.54 (s, 3H), 3.38 (m, 2H), 1.24 (m, 6H). LCMS: 378.05 (M+1)$^+$.

Example 205: 4-[2-(cyclopropylmethylamino)-5-ethylsulfonylthiophen-3-yl]-2-methylisoquinolin-1-one

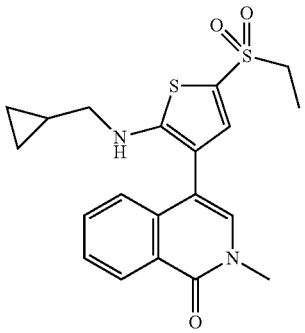 [SMILES: CCS(=O)(=O)c1cc(-c2cn(C)c(=O)c3ccccc23)c(NCC2CC2)s1]

The title compound was prepared in a manner similar to Example 204, by substituting 3-bromo-N-(cyclopropylmethyl)-5-ethylsulfonylthiophen-2-amine for 3-bromo-2-ethoxy-5-ethylsulfonylthiophene. $^1$H NMR (DMSO-d6, 400 MHz): δ 8.30 (d, J=8.0 Hz, 1H), 7.70 (m, 1H), 7.53 (dd, J=7.6, 7.6 Hz, 1H), 7.5 (s, 1H), 7.32 (s, 1H), 7.26 (d, J=8.0 Hz, 1H), 6.91 (m, 1H), 3.53 (s, 3H), 3.25 (m, 2H), 2.95 (m, 2H), 1.20 (dd, J=7.3, 7.3 Hz, 3H), 1.05 (m, 1H), 0.43 (m, 2H), 0.18 (m, 2H). LCMS: 403.1 (M+1)$^+$.

Example 206: 4-[3-(cyclopropylmethoxy)-6-ethylsulfonylpyridin-2-yl]-2-methylisoquinolin-1-one

Step 1: 5-bromo-2-ethylsulfanylpyridine

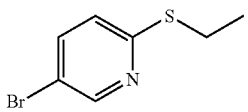

To a soln of 2,5-dibromopyridine (25 g, 105.5 mmol) in anhydrous DMSO (50 mL) at room temp was added NaSEt (13.3 g, 158.3 mmol) in one portion. The mixture was stirred for 18 hr. It was then diluted with H$_2$O (500 mL) and extracted with EtOAc (200 mL×3). The combined organic layers were washed by brine and dried over Na$_2$SO$_4$, filtered and concentrated under reduced pressure. The residue was purified by CC (PE:EA=20:1~10:1) to afford the title compound as light yellow oil (21 g yield: 91.3%). $^1$H NMR (CDCl$_3$, 400 MHz): δ 8.49 (dd, J$_1$=2.0 Hz, J$_2$=0.4 Hz, 1H), 7.59 (dd, J$_1$=8.8 Hz, J$_2$=2.4 Hz, 1H), 7.08 (dd, J$_1$=8.4 Hz, J$_2$=0.8 Hz, 1H), 3.16 (q, J=7.2 Hz, 2H), 1.38 (t, 3H). LCMS: 217.8 (M+1)$^+$; 219.8.

Step 2: 5-bromo-2-ethylsulfonylpyridine

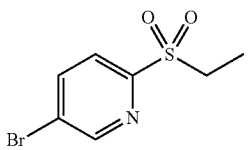

To a soln of the title compound form Step 1 (21 g, 96.3 mmol) in DCM (200 mL) was added m-CPBA (58.2 g, 289 mmol, 85% purity) slowly at 0° C. and then stirred at 20° C. for 3 hr. The rxn mixture was quenched with sat. aq Na$_2$SO$_3$ (200 mL) and then extracted with DCM (200 mL×2). The combined organic layers were washed with sat. aq NaHCO$_3$ (200 mL), H$_2$O (200 mL), and brine (200 mL), dried over Na$_2$SO$_4$, filtered and concentrated under reduced pressure to give 22 g of crude (~90% purity) title compound as a white solid that was used in the next step without further purification. $^1$H NMR (CDCl$_3$, 400 MHz): δ 8.82 (d, J=2.0 Hz, 1H), 8.13 (dd, J$_1$=8.4 Hz, J$_2$=2.0 Hz, 1H), 8.01 (d, J=8.0 Hz), 3.43 (q, J=7.2 Hz, 2H), 1.33 (t, J=7.2 Hz, 3H). LCMS: 249.8 (M+1)$^+$; 251.8.

Step 3: 2-ethylsulfonyl-5-methoxypyridine

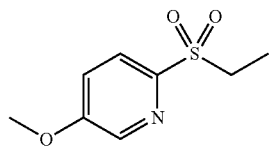

To a soln of the title compound form Step 2 (21 g, 84 mmol) in MeOH (150 mL) was added MeONa (11.3 g, 210 mmol). The mixture was refluxed for 5 hr, then cooled to room temp and concentrated under reduced pressure. The residue was triturated with isopropyl ether and filtered. The filtrate was concentrated under reduced pressure to give the title compound (4.5 g, yield, 23% two steps) as yellow oil. $^1$H NMR (CDCl$_3$, 400 MHz): δ 8.42 (d, J=2.8 Hz, 1H), 8.07 (d, J=8.4 Hz 1H), 7.37 (dd, J$_1$=8.8 Hz, J$_2$=2.8 Hz, 1H), 3.97 (s, 1H), 3.38 (q, J=7.2 Hz, 2H), 1.30 (t, J=7.2 Hz, 3H).

Step 4: 6-ethylsulfonylpyridin-3-ol

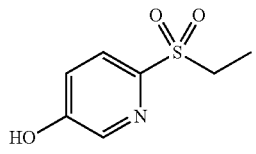

The title compound form Step 3 (4.5 g, 22.4 mmol) and pyridinium hydrochloride (26 g, 224 mmol) was heated to 160° C. for 4 hr. It was cooled to room temp, diluted with H$_2$O (100 mL) and extracted with EtOAc (100 mL×3). The combined organic layers were washed with brine (200 mL), dried over Na$_2$SO$_4$ and concentrated. The residue was purified by CC to afford the title compound (3 g, 72%) as a yellow solid. $^1$H NMR (DMSO-d6, 400 MHz): δ 8.87 (s, 1H), 8.86 (s, 1H), 8.45 (d, J=8.4 Hz, 1H), 7.93 (dd, J$_1$=8.8 Hz, J$_2$=2.4 Hz, 1H), 3.82 (q, J=7.2 Hz, 2H), 1.72 (t, J=7.2 Hz, 3H). LCMS: 187.9 (M+1)$^+$.

Step 5: 6-ethylsulfonyl-2-iodopyridin-3-ol and 6-ethylsulfonyl-4-iodopyridin-3-ol

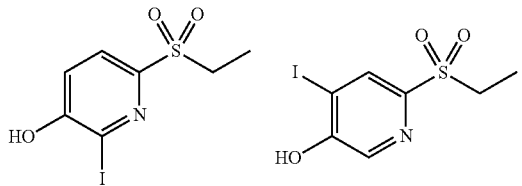

To a soln of the title compound from Step 4 (3 g, 16 mmol) in a mixture of THF (20 mL) and H$_2$O (20 mL) was added KI (662 mg, 4 mmol) and iodine (6.1 g, 24 mmol). The rxn was stirred at room temp for 1 hr and then heated to 60° C. for another 17 hr. The rxn mixture was then cooled to room temp and concentrated under reduced pressure to remove the THF. The mixture was diluted with H$_2$O (100 mL) and extracted with DCM (10 mL×3). The combined organic layers were washed with brine, dried over Na$_2$SO$_4$, filtered and concentrated. The residue was purified by prep-HPLC to afford 6-ethylsulfonyl-2-iodopyridin-3-ol and 6-ethyl-sulfonyl-4-iodopyridin-3-ol as white solids. 6-ethyl-sulfonyl-2-iodopyridin-3-ol: $^1$H NMR (DMSO-d$_6$, 400 MHz): δ 7.85 (d, J=8.4 Hz, 1H), 7.31 (d, J=8.4 Hz, 1H), 3.30 (q, J=7.2 Hz, 2H), 1.11 (t, J=7.2 Hz 3H). LCMS: 313.8 (M+1)$^+$; 6-ethylsulfonyl-4-iodopyridin-3-ol: $^1$H NMR (DMSO-d$_6$, 400 MHz) δ 8.23 (s, 1H), 8.18 (s, 1H), 3.31 (q, J=7.2 Hz, 2H, overlapped with solvent peak), 1.10 (t, J=7.2 Hz 3H). LCMS: 313.8 (M+1)$^+$.

Step 6: 3-(cyclopropylmethoxy)-6-ethylsulfonyl-2-iodopyridine

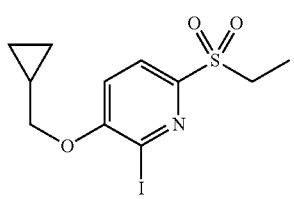 [SMILES: CCS(=O)(=O)c1ccc(OCC2CC2)c(I)n1]

The title compound was prepared in a manner similar to Example 199 Step 3, by substituting 6-ethylsulfonyl-2-iodopyridin-3-ol for 2-iodo-6-methylsulfonylpyridin-3-ol. $^1$H NMR (CDCl$_3$, 400 MHz): δ 7.98 (d, J=8.4 Hz, 1H), 7.06 (d, J=8.4 Hz 1H), 4.02 (d, J=6.8 Hz 2H), 3.40 (q, J=7.2 Hz, 2H), 1.38-1.26 (m, 4H), 0.77-0.73 (m, 2H), 0.49-0.46 (m, 2H). LCMS: 367.8 (M−1)$^+$.

Step 7: 4-[3-(cyclopropylmethoxy)-6-ethylsulfonylpyridin-2-yl]-2-methylisoquinolin-1-one

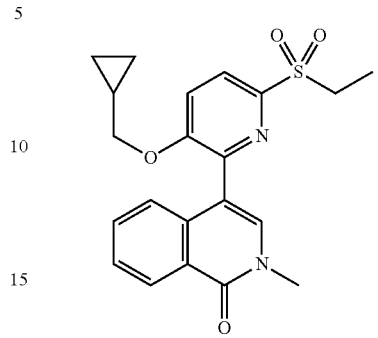

To a soln of the title compound from Step 6 (45 mg, 0.12 mmol) and 2-methyl-4-(4,4,5,5-tetramethyl-1,3,2-dioxaborolan-2-yl)isoquinolin-1-one (50 mg, 0.16 mmol) in dioxane (2.5 mL) and H$_2$O (0.5 mL) was added Pd(dppf)Cl$_2$ (9 mg, 0.013 mmol) and K$_3$PO$_4$ (86 mg, 0.4 mmol) in one portion at room temp under N$_2$. The mixture was stirred for 12 hr at 90° C. under N$_2$. H$_2$O (15 mL) was added and the mixture was extracted with DCM (30 mL×3). The combined organic phases were dried over Na$_2$SO$_4$, filtered, concentrated under reduced pressure. The residue was purified by prep-HPLC to give the title compound (16 mg, yield: 32%) as a white solid. $^1$H NMR (CDCl$_3$, 400 MHz) δ 8.52 (d, J=7.6 Hz, 1H), 8.11 (d, J=8.8 Hz 1H), 7.61-7.56 (m, 1H), 7.53-7.49 (m, 1H), 7.42 (d, J=8.8 Hz 1H), 7.38 (s, 1H), 7.34 (d, J=7.6 Hz 1H), 3.92 (d, J=7.2 Hz 2H), 3.68 (s, 3H), 3.41 (q, J=6.8 Hz, 2H), 1.33 (t, 3H), 1.08-1.02 (m, 1H), 0.54-0.48 (m, 2H), 0.22-0.21 (m, 2H). LCMS: 399.1 (M+1)$^+$.

Example 207: 4-[5-(cyclopropylmethoxy)-2-ethylsulfonylpyridin-4-yl]-2-methylisoquinolin-1-one

Step 1: 5-(cyclopropylmethoxy)-2-ethylsulfonyl-4-iodopyridine

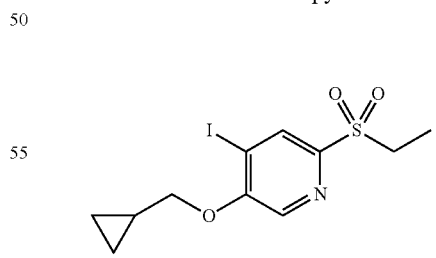

The title compound was prepared in a manner similar to Example 199 Step 3, by substituting 6-ethylsulfonyl-4-iodopyridin-3-ol for 2-iodo-6-methylsulfonylpyridin-3-ol. $^1$H NMR (CDCl$_3$, 400 MHz) δ 8.48 (s, 1H), 8.11 (s, 1H), 4.12 (d, J=6.8 Hz 2H), 3.37 (q, J=7.6 Hz, 2H), 1.39-1.27 (m, 4H), 0.76-0.73 (m, 2H), 0.48-0.46 (m, 2H). LCMS: 367.8 (M+1)$^+$.

Step 2: 4-[5-(cyclopropylmethoxy)-2-ethylsulfonylpyridin-4-yl]-2-methylisoquinolin-1-one

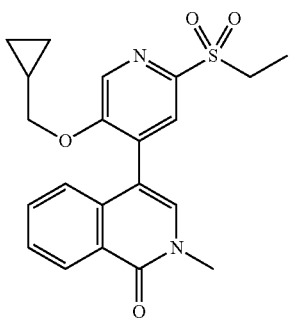 [SMILES: CCS(=O)(=O)c1cc(-c2cn(C)c(=O)c3ccccc23)c(OCC2CC2)cn1]

The title compound was prepared in a manner similar to Example 206 Step 7, by substituting 6-ethylsulfonyl-4-iodopyridin-3-ol for 3-(cyclopropylmethoxy)-6-ethylsulfonyl-2-iodopyridine. $^1$H NMR (CDCl$_3$, 400 MHz): δ 8.54-8.52 (m, 1H), 8.45 (s, 1H), 8.05 (s, 1H), 7.63-7.58 (m, 1H), 7.56-7.52 (m, 1H), 7.16 (d, J=8.8 Hz 1H), 4.01 (d, J=7.2 Hz 2H), 3.68 (s, 3H), 3.44 (q, J=7.2 Hz, 2H), 1.36 (t, 3H), 1.09-1.05 (m, 1H), 0.50-0.48 (m, 2H), 0.19-0.18 (m, 2H). LCMS: 399.1 (M+1)$^+$.

Example 208: 4-[5-(2-hydroxyethylsulfonyl)-2-methoxyphenyl]-2-methyl-6-(1-methylpyrazol-4-yl)isoquinolin-1-one

Step 1: 2-(4-methoxyphenyl)sulfanylethyl acetate

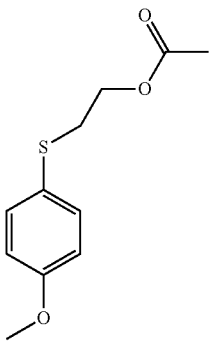

4-methoxybenzene-1-thiol (15.7 g, 0.11 mol), 2-bromoethyl acetate (18.8 g, 0.11 mol), and K$_2$CO$_3$ (46.6 g, 0.34 mol) in acetone (200 mL) were stirred at room temp for 12 hr. Then the mixture was filtered. After CH$_2$Cl$_2$ extractive work-up and silica gel chromatography (PE:EA=1:0~10:1) the title compound (21.1 g, 83.3%) was obtained as a colorless oil. $^1$H NMR (CDCl$_3$, 400 MHz): δ 7.40 (dd, J$_1$=6.8 Hz, J$_2$=2.0 Hz, 2H), 6.86 (dd, J$_1$=6.8 Hz, J$_2$=2.0 Hz, 2H), 4.18 (t, J=7.2 Hz, 2H), 3.80 (s, 3H), 3.02 (t, J=7.2 Hz, 2H), 2.03 (s, 3H). LCMS: 139.0 (M−87)$^+$.

Step 2: 2-(4-methoxyphenyl)sulfonylethyl acetate

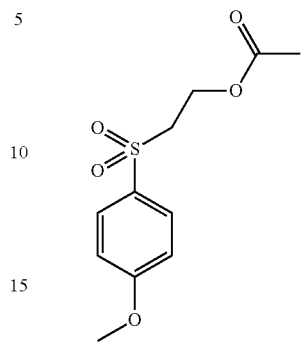

m-CPBA (80.3 g, 467 mmol) was added to the title compound of step 1 (21.1 g, 93.4 mmol) in CH$_2$Cl$_2$ (500 mL). After stirring at room temp for 12 hr, the mixture was subjected to CH$_2$Cl$_2$ extractive work-up and silica gel chromatography (PE:EA=1:0-1:1) to give the title compound (20.0 g, 83.3%) as a colorless oil. $^1$H NMR (CDCl$_3$, 400 MHz): δ 7.85 (dd, J$_1$=6.8 Hz, J$_2$=2.0 Hz, 2H), 7.04 (dd, J$_1$=6.8 Hz, J$_2$=2.0 Hz, 2H), 4.39 (t, J=6.0 Hz, 2H), 3.90 (s, 3H), 3.43 (t, J=6.0 Hz, 2H), 1.89 (s, 3H). LCMS: 280.9 (M+Na)$^+$.

Step 3: 2-(3-bromo-4-methoxyphenyl)sulfonylethanol

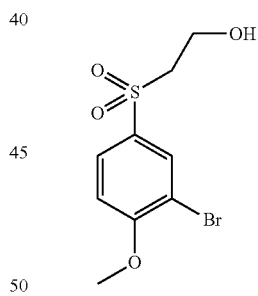

Br$_2$ (25 g, 155.0 mmol) was added dropwise over 30 min to the title compound of step 2 (8.0 g, 31.0 mmol) in acetic acid (100 mL) at 0° C. The mixture was heated at 50° C. for 12 hr. Aq Na$_2$SO$_3$ (200 mL) was added and the pH was adjusted to 8 with sat. aq NaHCO$_3$. The mixture was subjected to EA extractive work-up and silica gel chromatography (PE:EA=1:0-1:1) to give the title compound (2.7 g, 27.3%) as a white solid. $^1$H NMR (CDCl$_3$, 400 MHz): δ 8.11 (d, J=2.4 Hz, 1H), 7.87 (dd, J$_1$=8.8 Hz, J$_2$=2.4 Hz, 1H), 7.04 (d, J=2.4 Hz, 1H), 4.05-4.00 (m, 5H), 3.34-3.67 (m, 3H). LCMS: 316.9, 318.9 (M+Na)$^+$.

Step 4: 2-[2-(3-bromo-4-methoxyphenyl)sulfonylethoxy]oxane

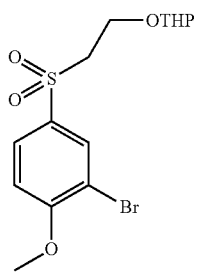

To the title compound of step 3 (1.0 g, 3.4 mmol) in CH$_2$Cl$_2$ (10 mL) was added 3,4-dihydro-2H-pyran (1.4 g, 17.0 mmol) followed by pyridinium p-toluensulfonate (64.6 mg, 0.34 mmol). After stirring at room temp for 12 hr, the mixture was subjected to CH$_2$Cl$_2$ extractive work-up and silica gel chromatography (PE:EA=1:0-5:1) to give the title compound (1.1 g, 85.6%) as a yellow oil. $^1$H NMR (CDCl$_3$, 400 MHz): δ 8.11 (d, J=2.4 Hz, 1H), 7.86 (dd, J$_1$=8.8 Hz, J$_2$=2.4 Hz, 1H), 7.00 (d, J=8.8 Hz, 1H), 4.51 (dd, J$_1$=4.0 Hz, J$_2$=2.4 Hz, 1H), 4.09-4.03 (m, 1H), 3.98 (s, 3H), 3.84-3.79 (m, 1H), 3.79-3.74 (m, 1H), 3.50-3.46 (m, 1H), 3.45-3.42 (m, 2H), 1.58-1.37 (m, 6H). LCMS: 401.0, 403.0 (M+Na)$^+$.

Step 5: 2-[2-methoxy-5-[2-(oxan-2-yloxy)ethylsulfonyl]phenyl]-4,4,5,5-tetramethyl-1,3,2-dioxaborolane

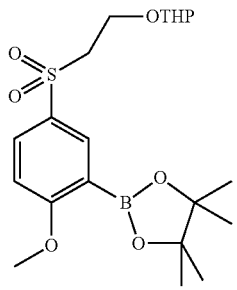

The title compound of step 4 (700 mg, 1.8 mmol), 4,4,5,5-tetramethyl-2-(tetramethyl-1,3,2-dioxaborolan-2-yl)-1,3,2-dioxaborolane (938 mg, 3.6 mmol) Pd(dppf)Cl$_2$ (263 mg, 0.36 mmol) and AcOK (1.05 g, 10.8 mmol) in 1,4-dioxane (7 mL) was stirred at 70° C. for 12 hr. After silica gel CC (PE:EA=1:0~1:1) the title compound (300 mg, 39.2%) was obtained as a yellow oil. $^1$H NMR (CDCl$_3$, 400 MHz): δ 8.20 (d, J=2.4 Hz, 1H), 7.94 (dd, J$_1$=8.8 Hz, J$_2$=2.8 Hz, 1H), 6.95 (d, J=8.8 Hz, 1H), 4.52 (t, J=4.0 Hz, 1H), 4.08-4.01 (m, 2H), 3.91 (s, 3H), 3.82-3.74 (m, 2H), 3.43 (t, J=2.4 Hz, 2H), 1.58-1.42 (m, 6H), 1.35 (s, 12H). LCMS: 343.0 (M+H-THP)$^+$.

Step 6: 4-[2-methoxy-5-[2-(oxan-2-yloxy)ethylsulfonyl]phenyl]-2-methyl-6-(1-methylpyrazol-4-yl)isoquinolin-1-one

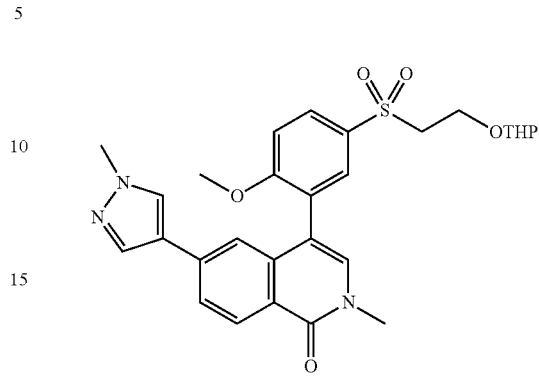

The title compound of step 5 (325 mg, 0.76 mmol), the title compound of Example 41, step 2 (201 mg, 0.64 mmol), Pd(dppf)Cl$_2$ (66 mg, 0.08 mmol) and AcOK (125 mg, 1.28 mmol) in 1,4-dioxane (6 mL) were heated at 70° C. for 12 hr. After silica gel CC (PE:EA=5:1~0:1) the title compound (80 mg, 23.6%) was obtained as a gray solid. $^1$H NMR (CDCl$_3$, 400 MHz): δ 8.48 (d, J=8.4 Hz, 1H), 8.03 (dd, J$_1$=8.8 Hz, J$_2$=2.4 Hz, 1H), 7.88 (d, J=2.4 Hz, 1H), 7.58-7.69 (m, 2H), 7.14-7.18 (m, 2H), 7.06 (s, 1H), 4.50 (t, J=4.4 Hz, 2H), 4.06-4.15 (m, 1H), 3.93 (s, 3H), 3.84-3.90 (m, 1H), 3.84 (s, 3H), 3.71-3.80 (m, 2H), 3.65 (s, 3H), 3.49 (t, J=5.6 Hz, 2H), 3.41-3.47 (m, 1H), 1.25-1.67 (m, 6H). LCMS: 538.2 (M+H)$^+$; 454.1 (M+H-THP)$^+$.

Step 7: 4-[5-(2-hydroxyethylsulfonyl)-2-methoxyphenyl]-2-methyl-6-(1-methylpyrazol-4-yl)isoquinolin-1-one

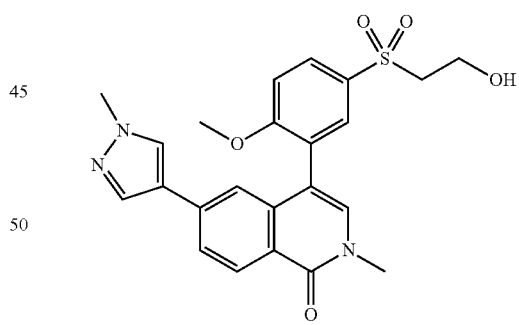

The title compound of step 6 (80 mg, 0.15 mmol) and pyridinium p-toluensulfonate (59 mg, 0.31 mmol) in DCM (2 mL) were stirred at room temp for 5 hr. After purification by prep-TLC (DCM:MeOH=10:1), the title compound (16.47 mg, 24.4%) was obtained as an off-white solid. $^1$H NMR (CDCl$_3$, 400 MHz): δ 8.49 (d, J=8.4 Hz, 1H), 8.05 (dd, J$_1$=8.8 Hz, J$_2$=2.4 Hz, 1H), 7.88 (d, J=2.4 Hz, 1H), 7.68 (s, 1H), 7.59-7.62 (m, 2H), 7.20 (d, J=8.8 Hz, 1H), 7.12 (d, J=1.2 Hz, 1H), 7.07 (s, 1H), 4.03-4.11 (m, 2H), 3.94 (s, 3H), 3.86 (s, 3H), 3.66 (s, 3H), 4.16 (t, J=5.2 Hz, 2H), 2.72 (t, J=6.4 Hz, 1H). LCMS: 454.1 (M+H)$^+$.

Example 209: N-[4-(cyclopropylmethoxy)-2-fluoro-5-[2-methyl-6-(1-methylpyrazol-4-yl)-1-oxoisoquinolin-4-yl]phenyl]ethanesulfonamide

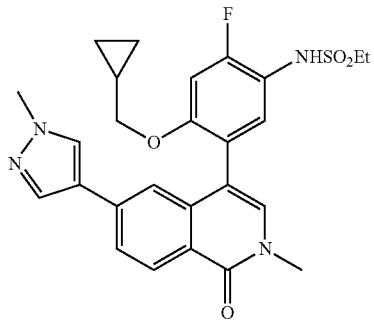

The title compound was prepared in 4 steps in a similar manner as Example 86 except that the alkoxide of cyclopropylmethanol was substituted for sodium methoxide in step 1. $^1$H NMR (DMSO-d$_6$, 400 MHz): δ 9.46 (s, 1H), 8.26 (d, J=8.4 Hz, 1H), 8.17 (s, 1H), 7.84 (s, 1H), 7.34 (d, J=8.0 Hz, 1H), 7.42 (s, 1H), 7.27-7.25 (m, 1H), 7.16 (d, J=12.4 Hz, 1H), 3.97-3.96 (m, 2H, overlapped with solvent peak), 3.85 (s, 3H), 3.54 (s, 3H), 3.13-3.07 (m, 2H), 1.30-1.26 (m, 2H), 0.91-0.90 (m, 1H), 0.27-0.22 (m, 2H), 0.04-0.09 (m, 2H). LCMS: 511.1 (M+1)$^+$.

Example 210: 4-(5-ethylsulfonyl-2-methoxyphenyl)-2-methyl-6-(1H-pyrazol-4-yl) isoquinolin-1-one

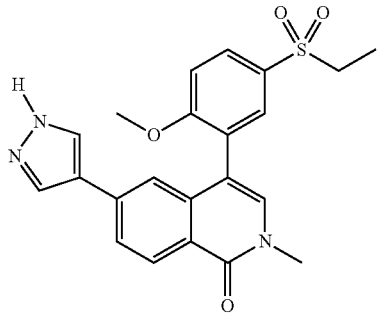 [SMILES: CCS(=O)(=O)c1ccc(OC)c(-c2cn(C)c(=O)c3ccc(-c4cn[nH]c4)cc23)c1]

The title compound was prepared in a similar manner to Example 79 using 4-(tetramethyl-1,3,2-dioxaborolan-2-yl)-1H-pyrazole instead of 1-methyl-4-(tetramethyl-1,3,2-dioxaborolan-2-yl)-1H-pyrazole. $^1$H NMR (DMSO-d6, 400 MHz) δ 8.26 (d, J=8.4 Hz, 1H), 8.02 (s, 2H), 7.97-8.00 (m, 1H), 7.75-7.79 (m, 2H), 7.50 (s, 1H), 7.42 (d, J=8.8 Hz, 1H), 7.16 (d, J=1.2 Hz, 1H), 3.82 (s, 3H), 3.54 (s, 3H), 3.31 (q, J=7.2 Hz, 2H), 1.13 (t, J=7.2 Hz, 3H). LCMS: 424.0 (M+1)$^+$.

Example 211: 4-(2-ethoxy-5-methylsulfonylphenyl)-2-methyl-6-(1-methylpyrazol-4-yl) isoquinolin-1-one

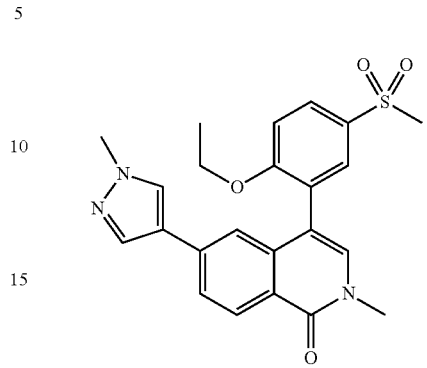

2-(2-ethoxy-5-methanesulfonylphenyl)-4,4,5,5-tetramethyl-1,3,2-dioxaborolane was prepared in a similar manner to Example 90, step 1 and coupled to the title compound of Example 41, step 2 in a manner similar to Example 90, step 2 to give the title compound. $^1$H NMR (CDCl$_3$, 400 MHz) δ 8.48 (d, J=8.4 Hz, 1H), 8.06-8.02 (m, 1H), 7.89 (d, J=2.8 Hz, 1H), 7.68 (s, 1H), 7.62 (s, 1H), 7.61 (d, J=1.6 Hz, 1H), 7.18 (d, J=1.2 Hz, 1H), 7.14 (d, J=8.8 Hz, 1H), 7.08 (s, 1H), 4.12 (q, J=7.2 Hz, 2H), 3.94 (s, 3H), 3.66 (s, 3H), 3.12 (s, 3H), 1.17 (t, J=7.2 Hz, 3H). LCMS: 438.1 (M+1)$^+$.

Example 212: 2-methyl-6-(1-methylpyrazol-4-yl)-4-(5-methylsulfonyl-2-propoxyphenyl)isoquinolin-1-one

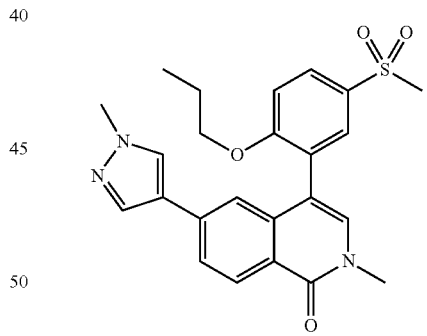

2-(5-methanesulfonyl-2-propoxyphenyl)-4,4,5,5-tetramethyl-1,3,2-dioxaborolane was prepared in a similar manner to Example 90, step 1 and coupled to the title compound of Example 41, step 2 in a manner similar to Example 90, step 2 to give the title compound. $^1$H NMR (CDCl$_3$, 400 MHz): δ 8.49 (d, J=8.4 Hz, 1H), 8.02 (s, J=6.8 Hz, 1H), 7.90 (d, J=2.4 Hz, 1H), 7.68 (s, 1H), 7.61 (s, 1H), 7.60 (d, J=6.8 Hz, 1H), 7.18 (s, 1H), 7.15 (d, J=8.8 Hz, 1H), 7.08 (s, 1H), 4.00 (m, 2H) 3.93 (s, 3H), 3.66 (s, 3H), 3.12 (s, 3H), 1.56 (m, 2H), 0.65 (t, J=7.2 Hz, 3H). LCMS: 452.0 (M+1)$^+$.

Example 213: N-[2-[2-methyl-6-(1-methylpyrazol-4-yl)-1-oxoisoquinolin-4-yl]pyridin-4-yl]ethanesulfonamide

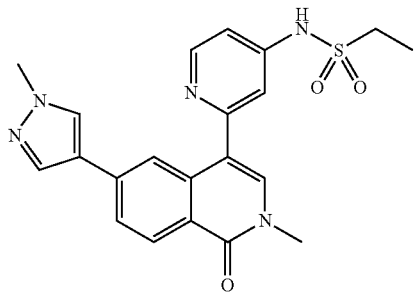 [SMILES: CCS(=O)(=O)Nc1ccnc(-c2cn(C)c(=O)c3ccc(-c4cnn(C)c4)cc23)c1]

The title compound was prepared after 2-chloropyridin-4-amine was sufonylated with ethanesulfonyl chloride and the resulting product was coupled to the title compound of Example 46, step 2. $^1$H NMR (CDCl$_3$, 400 MHz): δ 10.65 (brs, 1H), 8.56 (s, 1H), 8.29 (d, J=8.4 Hz, 1H), 8.22 (s, 1H), 8.01-7.73 (m, 4H), 7.37 (s, 1H), 7.18 (s, 1H), 3.87 (s, 3H), 3.59 (s, 3H), 1.25 (t, J=7.2 Hz, 3H). LCMS: 424.0 (M+1)$^+$.

Example 214: [4-(cyclopropylmethoxy)-3-(2-methyl-1-oxoisoquinolin-4-yl)phenyl]sulfamate Step 1: [3-bromo-4-(cyclopropylmethoxy)phenyl]sulfamate

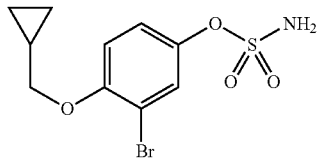 [SMILES: NS(=O)(=O)Oc1ccc(OCC2CC2)c(Br)c1]

3-bromo-4-(cyclopropylmethoxy)phenol (970 mg, 4.0 mmol) and sulfamoyl chloride (1.95 g, 16.0 mmol) in DMA (15 mL) were stirred at room temp for 5 hr. Extractive work-up from EA and H$_2$O gave the title compound (1.0 g, yield: 78.0%) which was carried on without purification. $^1$H NMR (CDCl$_3$, 400 MHz): δ 7.28 (d, J=2.8 Hz, 1H), 7.24 (dd, J$_1$=8.8 Hz, J$_2$=2.8 Hz, 1H), 6.88 (d, J=8.8 Hz, 1H), 5.07 (s, 2H), 3.89 (d, J=6.8 Hz, 2H), 1.35-1.25 (m, 1H), 0.70-0.63 (m, 2H), 0.43-0.36 (m, 2H). LCMS: 322.0 (M+1)$^+$.

Step 2: [4-(cyclopropylmethoxy)-3-(2-methyl-1-oxoisoquinolin-4-yl)phenyl]sulfamate

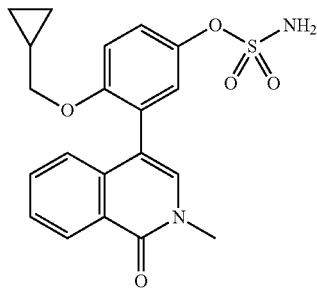 [SMILES: Cn1cc(-c2cc(OS(N)(=O)=O)ccc2OCC2CC2)c2ccccc2c1=O]

The title compound of step 1 (300 mg, 0.935 mmol), the title compound of Example 89, step 1 (293 mg, 1.028 mmol), K$_3$PO$_4$ (595 mg, 2.805 mmol) and Pd(dppf)Cl$_2$ (15 mg) in dioxane (5 mL) and H$_2$O (1 mL) were heated at 70° C. for 18 hr under N$_2$ whereupon it was discovered that the sulfamoyl group had been cleaved to the phenol. HPLC purification gave the phenol (59 mg, 0.184 mmol) which was again treated with sulfamoyl chloride (100 mg, 0.87 mmol) in DMA (3 mL) in a manner similar to step 1. Preparative HPLC gave the title compound (64.21 mg, yield: 87.02%) as grey solid. $^1$H NMR (CDCl$_3$, 400 MHz): δ 8.48 (d, J=8.0 Hz, 1H), 7.56 (t, J=7.6 Hz, 1H), 7.49 (d, J=7.6 Hz, 1H), 7.35 (dd, J$_1$=9.2 Hz, J$_2$=2.4 Hz, 1H), 7.30-7.27 (m, 1H), 7.26-7.22 (m, 1H), 7.04 (s, 1H), 6.98 (d, J=9.2 Hz, 1H), 5.14 (s, 2H), 3.82-3.73 (m, 2H), 3.62 (s, 3H), 1.03-1.90 (m, 1H), 0.45-0.32 (m, 2H), 0.13-0.03 (m, 2H). LCMS: 401.0 (M+1)$^+$.

Example 215: [4-(cyclopropylmethoxy)-3-(1,5-dimethyl-6-oxopyridin-3-yl)phenyl]sulfamate

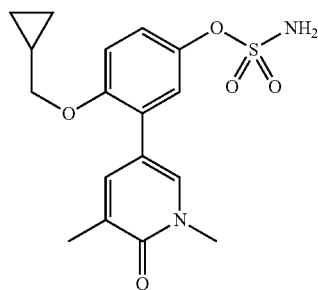 [SMILES: Cc1cc(-c2cc(OS(N)(=O)=O)ccc2OCC2CC2)cn(C)c1=O]

The title compound was prepared in a similar manner to Example 214, step 2 except that 1,3-dimethyl-5-(4,4,5,5-tetramethyl-1,3,2-dioxaborolan-2-yl)-2 (1H)-pyridinone was substituted for the title compound of Example 89, step 1. $^1$H NMR (CDCl$_3$, 400 MHz): δ 7.54 (d, J=2.0 Hz, 1H), 7.50 (s, 1H), 7.23-7.18 (m, 2H), 6.92-6.87 (m, 1H), 5.20 (s, 2H), 3.84 (d, J=6.8 Hz, 2H), 3.61 (s, 3H), 2.20 (s, 3H), 1.25-1.17 (m, 1H), 0.66-0.59 (m, 1H), 0.36-0.29 (m, 1H). LCMS: 365.1 (M+1)$^+$.

Example 216: 4-(2-ethoxy-5-methylsulfonylphenyl)-2-methyl-5,6,7,8-tetrahydroisoquinolin-1-one

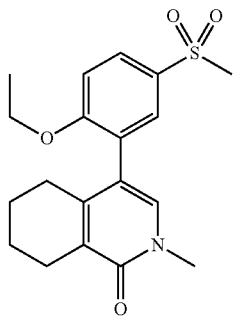 [SMILES: CCOc1ccc(S(C)(=O)=O)cc1-c1cn(C)c(=O)c2c1CCCC2]

2-bromo-1-ethoxy-4-methanesulfonylbenzene was prepared in a similar manner as Example 46, step 1 except that iodoethane was substituted for (chloromethyl)cyclopropane.

The title compound of Example 163, step 3 and 2-bromo-1-ethoxy-4-methanesulfonylbenzene were reacted in a similar manner as in Example 89, step 2 to give the title compound. ¹H NMR (CDCl₃, 400 MHz): δ 7.92 (dd, J₁=8.8 Hz, J₂=2.0 Hz, 1H), 7.68 (d, J=2.0 Hz, 1H), 7.03 (d, J=8.8 Hz, 1H), 6.69 (d, J=8.8 Hz, 1H), 4.20 (q, J=7.2 Hz, 2H), 3.59 (s, 3H), 3.08 (s, 3H), 2.70-2.60 (m, 2H), 2.33-2.18 (m, 2H), 1.65-1.61 (m, 4H), 1.45-1.02 (t, J=7.2 Hz, 3H). LCMS: 362.0 (M+H)⁺.

Example 217: 4-[2-(cyclopropylmethoxy)-5-methyl-sulfonylphenyl]-2-methyl-5,6,7,8-tetrahydroisoquinolin-1-one

The title compound of Example 163, step 3 and 2-bromo-1-(cyclopropylmethoxy)-4-methylsulfonylbenzene were reacted in a similar manner as in Example 89, step 2 to give the title compound. ¹H NMR (CDCl₃, 400 MHz): δ 7.92 (dd, J₁=8.4 Hz, J₂=2.0 Hz, 1H), 7.70 (d, J=2.0 Hz, 1H), 7.06 (s, 1H), 7.02 (d, J=8.4 Hz, 1H), 3.92-3.87 (m, 2H), 3.62 (s, 3H), 3.08 (s, 3H), 2.70-2.60 (m, 2H), 2.40-2.30 (m, 2H), 1.77-1.64 (m, 4H), 1.21-1.17 (m, 1H), 0.63-0.61 (m, 2H), 0.29-0.27 (m, 2H). LCMS: 388.1 (M+H)⁺.

Example 218: N-[4-(cyclopropylmethoxy)-2-fluoro-5-(2-methyl-1-oxo-5,6,7,8-tetrahydroisoquinolin-4-yl)phenyl]methanesulfonamide

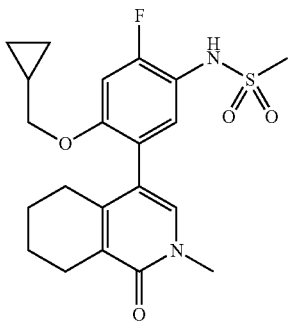 [SMILES: Cn1cc(-c2cc(NS(C)(=O)=O)c(F)cc2OCC2CC2)c2c(c1=O)CCCC2]

N-[5-bromo-4-(cyclopropylmethoxy)-2-fluorophenyl]methanesulfonamide was prepared in three steps in a similar manner as Example 86 except that the alkoxide of cyclopropylmethanol was substituted for sodium methoxide in step 1 and methanesulfonylchloride was substituted for ethansulfonylchloride in step 3. The title compound of Example 163, step 3 and N-[5-bromo-4-(cyclopropylmethoxy)-2-fluorophenyl]methanesulfonamide were reacted in a similar manner as in Example 89, step 2 to give the title compound. ¹H NMR (CDCl₃, 400 MHz): δ 7.29 (d, J=9.2 Hz, 1H), 6.96 (s, 1H), 6.70 (d, J=12.0 Hz, 1H), 6.21 (s, 1H), 3.76-3.75 (m, 2H), 3.56 (s, 3H), 3.02 (s, 3H), 2.70-2.60 (m, 2H), 2.36-2.17 (m, 2H), 1.80-1.70 (m, 2H), 1.69-1.64 (m, 2H), 1.20-1.10 (m, 1H), 0.60-0.50 (m, 2H), 0.27-0.25 (m, 2H). LCMS: 421.1 (M+H)⁺.

Example 219: 4-[2-(cyclopropylmethoxy)-5-ethyl-sulfonylphenyl]-2-methyl-5,6,7,8-tetrahydroisoquinolin-1-one

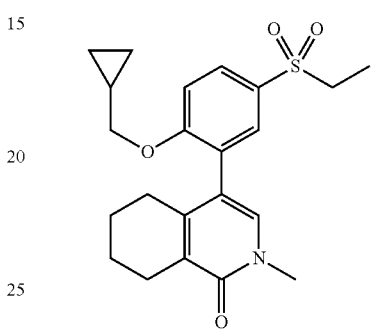

2-bromo-1-(cyclopropylmethoxy)-4-(ethanesulfonyl)benzene was prepared in a similar manner as Example 79, step 3 except that the alkoxide of cyclopropylmethanol was substituted for sodium methoxide. The title compound of Example 163, step 3 and 2-bromo-1-(cyclopropylmethoxy)-4-(ethanesulfonyl)benzene were reacted in a similar manner as in Example 89, step 2 to give the title compound. ¹H NMR (DMSO-d6, 400 MHz): δ 7.83 (dd, J₁=8.8 Hz, J₂=2.4 Hz, 1H), 7.56 (d, J=2.4 Hz, 1H), 7.43 (s, 1H), 7.65 (d, J=8.8 Hz, 1H), 4.02-3.90 (m, 2H), 3.43 (s, 3H), 3.29-3.23 (m, 2H), 2.49-2.44 (m, 4H), 1.61-1.50 (m, 4H), 1.15-1.08 (m, 5H), 0.53-0.51 (m, 2H), 0.29-0.27 (m, 2H). LCMS: 402.0 (M+H)⁺.

Example 220: N-[2-(2-methyl-1-oxoisoquinolin-4-yl)-4-methylsulfonylphenyl]cyclopropanecarboxamide

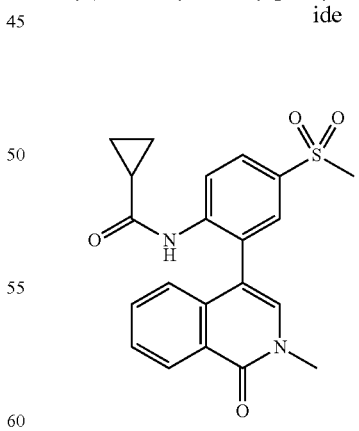

2-bromo-4-methanesulfonylaniline was coupled to the title compound of Example 89, step 1 in a manner similar to Example 89, step 2. The resulting product was reacted with cyclopropanecarbonyl chloride using diisopropylethylamine in THF to prepare the title compound. ¹H NMR (CDCl₃, 400 MHz): δ 9.38 (s, 1H), 8.34 (d, J=8.0 Hz, 1H), 8.23 (d, J=8.8

Hz, 1H), 7.96 (d, J=8.8 Hz, 1H), 7.83 (s, 1H), 7.53-7.64 (m, 3H), 6.94 (d, J=8.0 Hz, 1H), 3.59 (s, 3H), 3.25 (m, 3H), 1.64 (brs, 1H), 0.52-0.75 (m, 4H). LCMS: 397.0 (M+1)⁺.

Example 221: N-[2-(2-methyl-1-oxoisoquinolin-4-yl)-4-methylsulfonylphenyl]propanamide

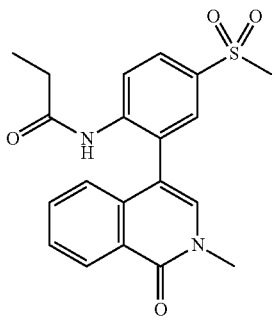 [SMILES: CCC(=O)Nc1ccc(S(C)(=O)=O)cc1-c1cn(C)c(=O)c2ccccc12]

The title compound was prepared in the same manner as Example 220 except that propanoyl chloride was substituted for cyclopropanecarbonyl chloride. ¹H NMR (CDCl₃, 400 MHz): δ 8.70 (d, J=8.8 Hz, 1H), 8.57 (d, J=6.4 Hz, 1H), 8.04 (dd, J=2.0, 8.8 Hz, 1H), 7.88 (d, J=2.0 Hz, 1H), 7.55-7.65 (m, 2H), 7.19 (s, 1H), 7.01-7.20 (m, 2H), 3.67 (s, 3H), 3.11 (s, 3H), 2.00-2.21 (m, 2H), 0.93 (t, J=7.2 Hz, 3H). LCMS: 385.0 (M+1)⁺.

Example 222: N-[2-(2-methyl-1-oxoisoquinolin-4-yl)-4-methylsulfonylphenyl]acetamide

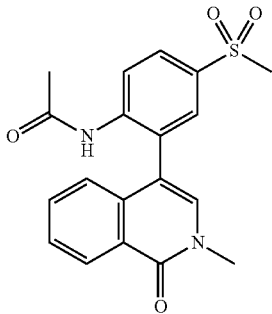 [SMILES: CC(=O)Nc1ccc(S(C)(=O)=O)cc1-c1cn(C)c(=O)c2ccccc12]

The title compound was prepared in the same manner as Example 220 except that acetyl chloride was substituted for cyclopropanecarbonyl chloride. ¹H NMR (CDCl₃, 400 MHz): δ 8.67 (d, J=8.8 Hz, 1H), 8.51 (d, J=7.6 Hz, 1H), 8.03 (dd, J=2.0, 6.8 Hz, 1H), 7.86 (d, J=2.0 Hz, 1H), 7.62-7.67 (m, 1H), 7.57-7.62 (m, 1H), 7.36 (s, 1H), 7.16 (s, 1H), 7.07-7.10 (m, 1H), 3.54 (s, 3H), 3.10 (s, 3H), 1.96 (s, 3H). LCMS: 371.0 (M+1)⁺.

Example 223: 4-[2-(cyclopropylmethylamino)-5-methylsulfonylphenyl]-2-methyl-5,6,7,8-tetrahydroisoquinolin-1-one

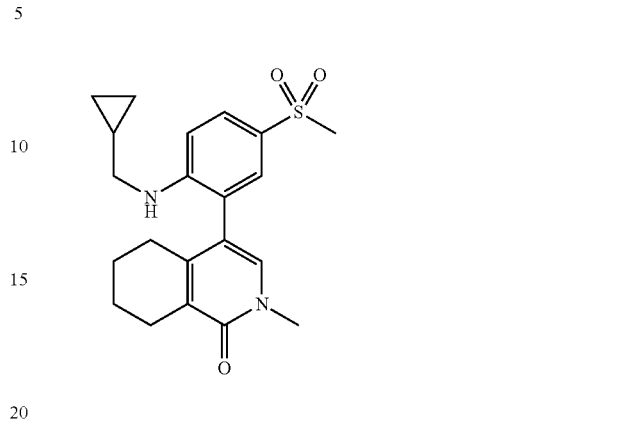

The sulfonyl compound of Example 194 was coupled as described in Example 163 to give the title compound. ¹H NMR (CDCl₃, 400 MHz): δ 7.89 (dd, J₁=8.8 Hz, J₂=2.4 Hz, 1H), 7.51 (d, J=2.4 Hz, 1H), 7.10 (s, 1H), 6.69 (d, J=8.8 Hz, 1H), 3.62 (s, 3H), 3.04-3.02 (m, 5H), 2.67-2.62 (m, 2H), 2.26-2.24 (m, 2H), 1.78-1.76 (m, 2H), 1.75-1.74 (m, 2H), 1.05-1.02 (m, 1H), 0.58-0.54 (m, 2H), 0.23-0.21 (m, 2H). LCMS: 387.0 (M+H)⁺.

Example 224: 8-[2-(cyclopropylmethoxy)-5-methylsulfonylphenyl]-6-methyl-2-(1-methylpyrazol-4-yl)pyrido[4,3-d]pyrimidin-5-one Step 1: Ethyl 4-methyl-2-(1-methylpyrazol-4-yl)pyrimidine-5-carboxylate

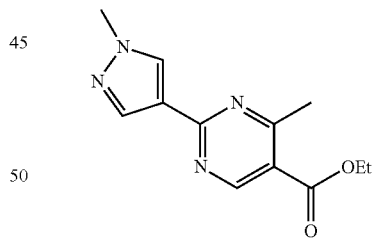

Ethyl 2-chloro-4-methylpyrimidine-5-carboxylate (1.0 g, 5.0 mmol), 1-methyl-4-(tetramethyl-1,3,2-dioxaborolan-2-yl)-1H-pyrazole (1.24 g, 6.0 mmol), K₃PO₄ (3.18 mg, 15.0 mmol) and Pd(dppf)Cl₂ (100 mg) in dioxane (15 mL) and H₂O (3 mL) were heated at 120° C. for 18 hr under N₂. Silica gel chromatography (PE:EA=3:1 to 1:1) gave the title compound (72 mg, yield: 32.0%). ¹H NMR (CDCl₃, 400 MHz): δ 9.08 (s, 1H), 8.22 (s, 1H), 8.15 (s, 1H), 4.40 (q, J=7.2 Hz, 2H), 3.98 (s, 3H), 2.82 (s, 3H), 1.42 (t, J=7.2 Hz, 3H). LCMS: 247.1 (M+1)⁺.

Step 2: Ethyl 4-[(E)-2-(dimethylamino)ethenyl]-2-(1-methylpyrazol-4-yl)pyrimidine-5-carboxylate and ethyl 2-(1-methylpyrazol-4-yl)-4-[(E)-2-pyrrolidin-1-ylethenyl]pyrimidine-5-carboxylate

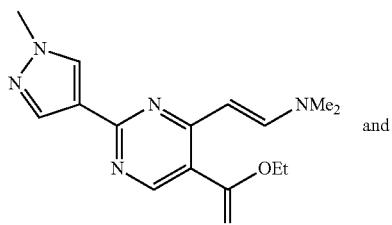

and

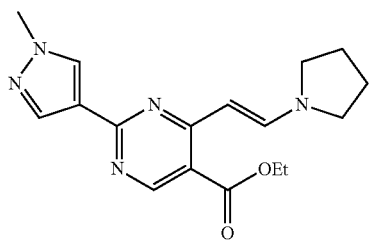

The title compound from step 1 (800 mg, 3.22 mmol), DMF-DMA (15.0 mL) and pyrrolidine (3.0 mL) were heated at 120° C. for 5 hr. Extractive work-up with EA gave a mixture of title compounds (500 mg, ~70:30 by LCMS) which were carried on without purification. LCMS: 328.1 (M+1)⁺.

Step 3: 6-methyl-2-(1-methylpyrazol-4-yl)pyrido[4,3-d]pyrimidin-5-one

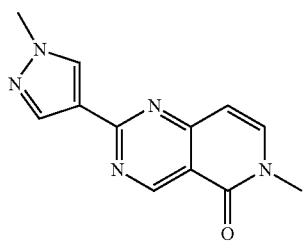 [SMILES: Cn1cc(-c2ncc3c(=O)n(C)ccc3n2)cn1]

The mixture of title compounds from step 2 (500 mg) was treated with ethanolic methylamine (15 mL, 30% $CH_3NH_2$ in EtOH) and heated at 80° C. for 5 hr. After concentration, the resulting solids were triturated with hexane (10 mL) and collected to give the title compound (220 mg, 55.0%). $^1$H NMR (CDCl₃, 400 MHz): δ 9.57 (s, 1H), 8.27 (s, 1H), 8.21 (s, 1H), 7.46 (d, J=7.6 Hz, 1H), 6.59 (d, J=7.6 Hz, 1H), 4.00 (s, 3H), 3.61 (s, 3H). LCMS: 242.0 (M+1)⁺.

Step 4: 8-bromo-6-methyl-2-(1-methylpyrazol-4-yl)pyrido[4,3-d]pyrimidin-5-one

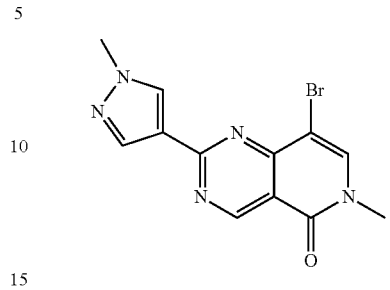

The title compound from step 3 (220 mg, 0.912 mmol) and Br₂ (146 mg, 0.912 mmol) in HOAc (15 mL) were stirred at room temp for 2 hr. H₂O (150 mL) was added, and the resulting solid was collected and triturated with DCM:PE=10:1 (10 mL) to give the title compound (200 mg, yield: 69.0%). $^1$H NMR (CDCl₃, 400 MHz): δ 9.54 (s, 1H), 8.33 (s, 1H), 8.27 (s, 1H), 7.77 (s, 1H), 4.01 (s, 3H), 3.62 (s, 3H).

Step 5: 8-[2-(cyclopropylmethoxy)-5-methylsulfonylphenyl]-6-methyl-2-(1-methylpyrazol-4-yl)pyrido[4,3-d]pyrimidin-5-one

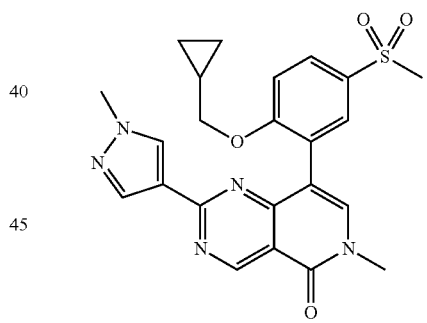

The title compound of step 4 (200 mg, 0.627 mmol), the title compound of Example 90, step 1 (266 mg, 0.752 mmol), K₃PO₄ (400 mg, 1.881 mmol) and Pd(dppf)Cl₂ (10 mg) in dioxane (4 mL) and H₂O (1 mL) were heated at 70° C. for 18 hr under N₂. After preparative HPLC, the title compound (104.5 mg, 35.8%) was obtained as an off white solid. $^1$H NMR (CDCl₃, 400 MHz): δ 9.64 (s, 1H), 8.24-8.18 (m, 2H), 8.07 (s, 1H), 7.96 (dd, $J_1$=8.8 Hz, $J_2$=2.4 Hz, 1H), 7.77 (s, 1H), 7.10 (d, J=8.8 Hz, 1H), 3.95 (s, 3H), 3.91 (d, J=7.2 Hz, 2H), 3.68 (s, 3H), 3.12 (s, 3H), 1.13-1.01 (m, 1H), 0.54-0.44 (m, 2H), 0.21-0.14 (m, 1H). LCMS: 466.1 (M+1)⁺.

Example 225: 8-(5-ethylsulfonyl-2-propoxyphenyl)-6-methyl-2-(1-methylpyrazol-4-yl)pyrido[4,3-d]pyrimidin-5-one

Step 1: 2-bromo-4-ethylsulfonyl-1-propoxybenzene

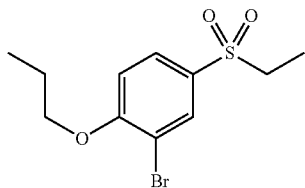 [SMILES: CCCOc1ccc(S(=O)(=O)CC)cc1Br]

To a soln of n-propanol (224 mg, 3.74 mmol) in THF (10 mL) was added NaH (112 mg, 2.80 mmol, 60% in mineral oil) at 0° C. After stirring at 0° C. for 30 min, 2-bromo-4-(ethanesulfonyl)-1-fluorobenzene (500 mg, 1.87 mmol) was added and the mixture was stirred at room temp for 4 hr. Addition of satd $NH_4Cl$ (10 mL) followed by EA extractive work-up gave the title compound (300 mg, yield: 52.3%) which was carried on directly.

Step 2: 2-(5-ethylsulfonyl-2-propoxyphenyl)-4,4,5,5-tetramethyl-1,3,2-dioxaborolane

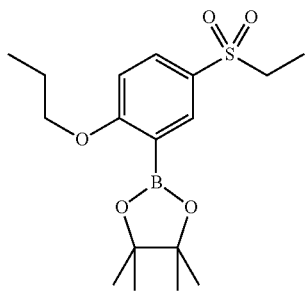 [SMILES: CCCOc1ccc(S(=O)(=O)CC)cc1B1OC(C)(C)C(C)(C)O1]

The title compound of step 1 (300 mg, 0.98 mmol), 4,4,5,5-tetramethyl-2-(tetramethyl-1,3,2-dioxaborolan-2-yl)-1,3,2-dioxaborolane (622 mg, 2.45 mmol), KOAc (288 mg, 2.94 mmol), $Pd_2(dba)_3$ (92 mg, 0.10 mmol), and X-Phos (62 mg, 0.13 mmol) in dioxane (5 mL) were purged with Ar and heated at 70° C. for 12 hr. $CH_2Cl_2$ extractive work-up and silica gel chromatography (PE:EA=20:1~5:1) gave the title compound (200 mg, yield: 57.7%) as a grey solid. $^1$H NMR ($CDCl_3$, 400 MHz): δ 8.13 (s, 1H), 7.91 (d, J=8.8 Hz, 1H), 6.95 (d, J=8.8 Hz, 1H), 4.02 (t, J=5.6 Hz, 2H), 3.13 (q, J=7.2 Hz, 2H), 1.89 (q, J=6.8 Hz, 2H), 1.36-1.25 (m, 15H), 1.12 (t, J=6.8 Hz, 3H). LCMS: 272.9 (M+1)$^+$.

Step 3: 8-(5-ethylsulfonyl-2-propoxyphenyl)-6-methyl-2-(1-methylpyrazol-4-yl)pyrido[4,3-d]pyrimidin-5-one

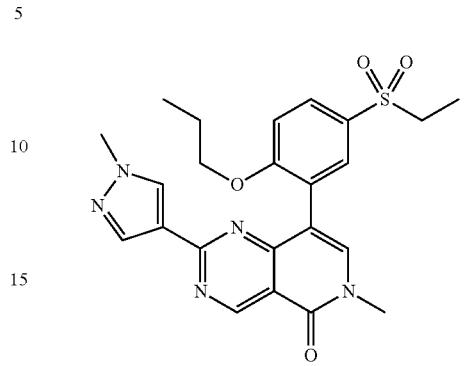

The title compound of step 2 (60 mg, 0.17 mmol), the title compound of Example 224, step 4 (64 mg, 0.20 mmol), $K_3PO_4$ (108 mg, 0.51 mmol), and $Pd(dppf)Cl_2$ (15 mg, 0.02 mmol) in dioxane (8 mL) were purged with $N_2$ and heated at 70° C. for 18 hr. $CH_2Cl_2$ extractive work-up and preparative HPLC gave the title compound (66.11 mg, yield: 83.3%) as a grey solid. $^1$H NMR ($CDCl_3$, 400 MHz): δ 9.64 (s, 1H), 8.19 (s, 1H), 8.12 (d, J=2.4 Hz, 1H), 8.06 (s, 1H), 7.96 (dd, $J_1$=8.8 Hz, $J_2$=2.4 Hz, 1H), 7.70 (s, 1H), 7.15 (d, J=8.4 Hz, 1H), 4.03-3.95 (m, 5H), 3.67 (s, 3H), 3.20 (q, J=7.2 Hz, 2H), 1.67-1.60 (m, 2H), 1.36 (t, J=7.2 Hz, 3H), 0.81 (t, J=7.2 Hz, 3H). LCMS: 468.2 (M+1)$^+$.

Example 226: 8-[2-(cyclopropylmethoxy)-5-ethylsulfonylphenyl]-6-methyl-2-(1-methylpyrazol-4-yl)pyrido[4,3-d]pyrimidin-5-one

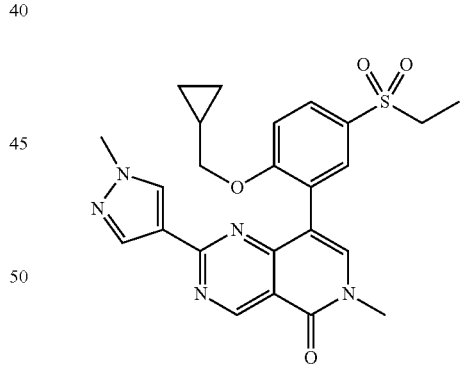

The title compound was prepared in three steps in a similar manner as Example 225 except that cyclopropylmethanol was substituted for n-propanol in step 1. $^1$H NMR ($CDCl_3$, 400 MHz): δ 9.64 (s, 1H), 8.22 (s, 1H), 8.17 (d, J=2.0 Hz, 1H), 8.07 (s, 1H), 7.92 (dd, $J_1$=8.4 Hz, $J_2$=2.0 Hz, 1H), 7.77 (s, 1H), 7.10 (d, J=8.4 Hz, 1H), 3.96 (s, 3H), 3.90 (d, J=6.8 Hz, 2H), 3.68 (s, 3H), 3.17 (q, J=7.2 Hz, 2H), 1.33 (t, J=7.2 Hz, 3H), 1.08-1.06 (m, 1H), 0.52-0.47 (m, 2H), 0.21-0.17 (m, 2H). LCMS: 480.2 (M+H)$^+$.

Example 227: 8-(2-ethoxy-5-ethylsulfonylphenyl)-6-methyl-2-(1-methylpyrazol-4-yl)pyrido[4,3-d]pyrimidin-5-one

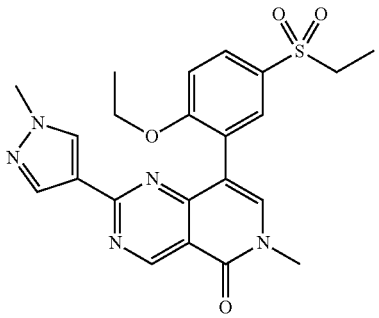 [SMILES: CCOc1ccc(S(=O)(=O)CC)cc1-c1cn(C)c(=O)c2cnc(-c3cnn(C)c3)nc12]

The title compound was prepared in three steps in a similar manner as Example 225 except that ethanol was substituted for n-propanol in step 1. $^1$H NMR (CDCl$_3$, 400 MHz): δ 9.64 (s, 1H), 8.19 (s, 1H), 8.10 (s, 1H), 8.06 (s, 1H), 7.94 (d, J=8.8 Hz, 1H), 7.69 (s, 1H), 7.13 (d, J=8.8 Hz, 1H), 4.13 (q, J=6.8 Hz, 2H), 3.95 (s, 3H), 3.67 (s, 3H), 3.17 (q, J=7.2 Hz, 2H), 1.34 (t, J=7.2 Hz, 3H), 0.81 (t, J=6.8 Hz, 3H). LCMS: 454.1 (M+H)$^+$.

Example 228: 8-(2-ethoxy-5-ethylsulfonylphenyl)-6-methyl-2-(1-methylpyrazol-4-yl)pyrido[4,3-d]pyrimidin-5-one

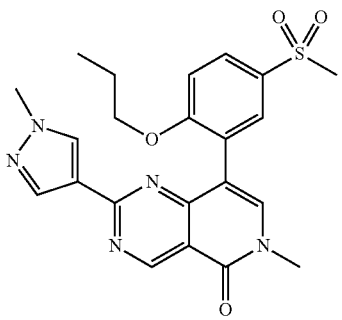 [SMILES: CCCOc1ccc(S(C)(=O)=O)cc1-c1cn(C)c(=O)c2cnc(-c3cnn(C)c3)nc12]

2-bromo-4-methylsulfonyl-1-propoxybenzene was prepared in a similar manner as Example 46, step 1 except that 1-chloropropane was substituted for (chloromethyl)cyclopropane and the resulting product was used to prepare 4,4,5,5-tetramethyl-2-(5-methylsulfonyl-2-propoxyphenyl)-1,3,2-dioxaborolane in a manner similar to Example 225, step 2 which was then used to prepare the title compound in a manner similar as Example 225, step 3. $^1$H NMR (CDCl$_3$, 400 MHz): δ 9.64 (s, 1H), 8.19 (s, 1H), 8.16 (d, J=2.4 Hz, 1H), 8.07 (s, 1H), 7.99 (dd, J$_1$=8.8 Hz, J$_2$=2.4 Hz, 1H), 7.70 (s, 1H), 7.14 (d, J=8.8 Hz, 1H), 4.01 (t, J=6.4 Hz, 2H), 3.96 (s, 3H), 3.68 (s, 3H), 3.12 (s, 3H), 1.67-1.61 (m, 2H), 0.78 (t, J=7.2 Hz, 3H). LCMS: 454.1 (M+H)$^+$.

Example 229: N-[4-(2,4-difluorophenoxy)-3-(1,5-dimethyl-6-oxopyridin-3-yl)phenyl]-N-methylmethanesulfonamide

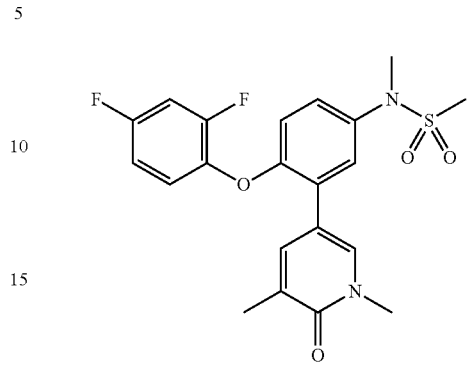

The title compound of Example 102 (56 mg, 0.13 mmol) in DMF (0.2 mL) was treated with NaH (60% dispersion in oil, 6 mg, 0.16 mmol). After about 15 min, methyl iodide (0.012 mL, 0.2 mmol) was added. After complete rxn, silica gel chromatography gave the title compound (55 mg, 0.13 mmol) as a cream colored solid. $^1$H NMR (400 MHz, DMSO-d$_6$): δ ppm 1.96-2.17 (s, 3H) 2.98 (s, 3H) 3.25 (s, 3H) 3.49 (s, 3H) 6.82 (d, J=8.84 Hz, 1H) 7.21-7.40 (m, 3H) 7.40-7.54 (m, 2H) 7.59 (s, 1H) 7.82 (d, J=2.53 Hz, 1H). LCMS (M+H)$^+$: 435.

Example 230: N-[4-(2,4-difluorophenoxy)-3-(1,5-dimethyl-6-oxopyridin-3-yl)phenyl]-N-(oxetan-3-yl)methanesulfonamide

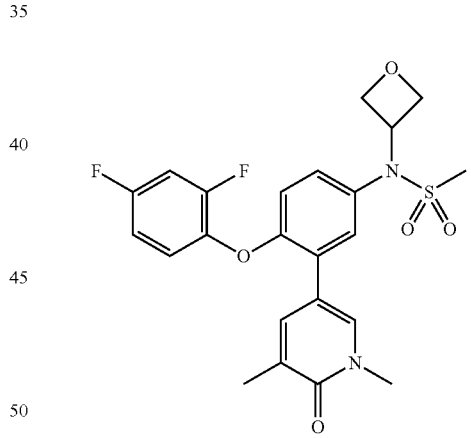

The title compound of Example 102 (46 mg, 0.11 mmol), Cs$_2$CO$_3$ (150 mg, 0.46 mmol), KI (10 mg, 0.06 mmol) and oxetan-3-yl 4-methylbenzenesulfonate (30 mg, 0.13 mmol) in DMF (0.9 mL) were microwaved at 130° C. for 2 hr. Additional oxetan-3-yl 4-methylbenzenesulfonate (65 mg, 0.29 mmol) and Cs2CO3 (126 mg, 0.39 mmol) were added and microwave resumed at 130° C. for 2 hr more. The mixture was purified by silica gel chromatography (EA) to give the title compound (20 mg, 0.04 mmol) as cream solids in 38% yield. $^1$H NMR (400 MHz, DMSO-d$_6$): δ ppm 2.03 (s, 3H) 2.98 (s, 3H) 3.50 (s, 3H) 4.41 (t, J=6.82 Hz, 2H) 4.58 (t, J=6.95 Hz, 2H) 5.30 (quin, J=7.01 Hz, 1H) 6.83 (d, J=8.84 Hz, 1H) 7.06-7.20 (m, 1H) 7.22-7.35 (m, 2H) 7.39 (d, J=2.53 Hz, 1H) 7.43-7.57 (m, 1H) 7.60 (s, 1H) 7.83 (d, J=2.27 Hz, 1H). LCMS (M+H)$^+$: 477.

Example 231: 8-[2-(cyclopropylmethoxy)-5-methyl-sulfonylphenyl]-6-methylpyrido[4,3-d]pyrimidin-5-one Step 1: 6H-pyrido[4,3-d]pyrimidin-5-one

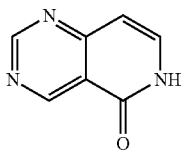 [SMILES: O=c1[nH]ccc2ncncc12]

Under N$_2$, ethyl 3-oxobutanoate (40.12 g, 0.31 mol) and 1,3,5-triazine (25.00 g, 0.31 mol) in dry EtOH (90 mL) were heated at 80° C. for 2 hr and EtONa (8.39 g, 0.12 mol) was added and heating continued at 80° C. for 18 hr. The mixture was concentrated and H$_2$O (300 mL) was added. Acidification with concentrated HCl (50 mL) resulted in a precipitate which was collected and washed with cold acetone (20 mL) and dried under vacuum to give the title compound (1.20 g, yield: 2.6%) as a brown solid. $^1$H NMR (DMSO-d$_6$, 400 MHz): δ 11.92 (brs, 1H), 9.41 (s, 1H), 9.32 (s, 1H), 7.72 (dd, J$_1$=7.6 Hz, J$_2$=6.4 Hz, 1H), 6.57 (d, J=7.6 Hz, 1H).

Step 2: 8-bromo-6H-pyrido[4,3-d]pyrimidin-5-one

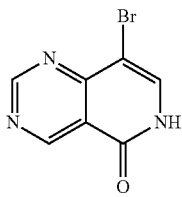

To the title compound of step 1 (200 mg, 1.36 mmol) in DMF (20 mL) was added NBS (242 mg, 1.36 mmol) at 0° C. The resulting mixture was stirred at 15° C. for 2 hr, and then concentrated and treated with acetone (20 mL). The resulting solid was collected to give the title compound (220 mg, yield: 71.6%) as a yellow solid. $^1$H NMR (DMSO-d$_6$, 400 MHz): δ 12.25 (brs, 1H), 9.46 (s, 1H), 9.42 (s, 1H), 8.12 (d, J=6.0 Hz, 1H).

Step 3: 8-bromo-6-methylpyrido[4,3-d]pyrimidin-5-one

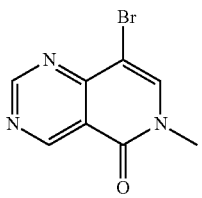

Sodium hydride (21 mg, 0.53 mmol, 60% in mineral oil) was added to the title compound of step 2 (100 mg, 0.44 mmol) in DMF (10 mL) at 0° C. After stirring 0.5 hr, MeI (126 mg, 0.88 mmol) was added and stirring continued at 0° C. for 2 hr. Following extractive work-up with EA, the title compound (80 mg, yield: 75.3%) was obtained as a yellow solid. $^1$H NMR (DMSO-d6, 400 MHz): δ 9.47 (s, 1H), 9.46 (s, 1H), 8.53 (s, 1H), 3.54 (s, 3H). LCMS: 240.0; 242.0 (M+H)$^+$.

Step 4: 8-[2-(cyclopropylmethoxy)-5-methylsulfonylphenyl]-6-methylpyrido[4,3-d]pyrimidin-5-one

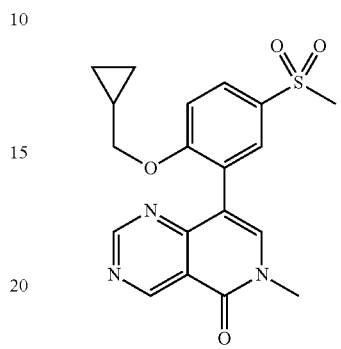

The title compound of step 3 (100 mg, 0.42 mmol), the title compound of Example 90, step 1 (147 mg, 0.42 mmol), Pd(dppf)Cl$_2$ (62 mg, 0.08 mmol), K$_3$PO$_4$ (221 mg, 1.04 mmol) in dioxane (4 mL) and H$_2$O (0.5 mL) was purged with N$_2$ and heated at 100° C. for 18 hr. Following CH$_2$Cl$_2$ extractive work-up, silica gel chromatography (PE:EA=2:1~0:1) and preparative HPLC, the title compound (54.57 mg, yield: 34.2%) was obtained as a yellow solid. $^1$H NMR (DMSO-d$_6$, 400 MHz): δ 9.54 (s, 1H), 9.30 (s, 1H), 8.18 (s, 1H), 7.93 (dd, J$_1$=8.8 Hz, J$_2$=2.4 Hz, 1H), 7.85 (d, J=2.4 Hz, 1H), 7.31 (d, J=8.8 Hz, 1H), 3.91 (d, J=6.8 Hz, 2H), 3.61 (s, 3H), 3.20 (s, 3H), 0.94-0.92 (m, 1H), 0.35-0.30 (m, 2H), 0.10-0.06 (m, 2H). LCMS: 386.0 (M+H)$^+$.

Example 232: 8-[2-(cyclopropylmethoxy)-5-ethylsulfonylphenyl]-6-methylpyrido[4,3-d]pyrimidin-5-one

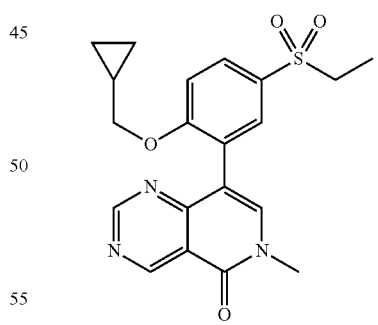

2-[2-(cyclopropylmethoxy)-5-ethylsulfonylphenyl]-4,4,5,5-tetramethyl-1,3,2-dioxaborolane as prepared in Example 226 was reacted with the title compound of 231, step 3 in a manner similar to 231, step 4 to give the title compound. $^1$H NMR (DMSO-d$_6$, 400 MHz): δ 9.54 (s, 1H), 9.30 (s, 1H), 8.17 (s, 1H), 7.88 (dd, J$_1$=8.8 Hz, J$_2$=2.4 Hz, 1H), 7.80 (d, J=2.4 Hz, 1H), 7.31 (d, J=8.8 Hz, 1H), 3.92 (d, J=6.8 Hz, 2H), 3.61 (s, 3H), 3.27 (q, J=7.2 Hz, 2H), 1.14 (t, J=7.2 Hz, 3H), 0.94-0.93 (m, 1H), 0.34-0.32 (m, 2H), 0.10-0.08 (m, 2H). LCMS: 400.0 (M+H)$^+$.

Example 233: 8-[2-(2,4-difluorophenoxy)-5-methylsulfonylphenyl]-6-methylpyrido[4,3-d]pyrimidin-5-one Step 1: 8-(2-fluoro-5-methylsulfonylphenyl)-6-methylpyrido[4,3-d]pyrimidin-5-one

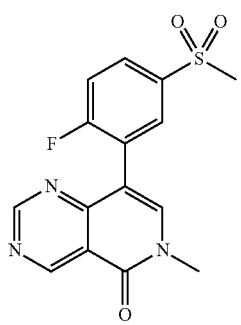 [SMILES: Cn1cc(-c2cc(S(C)(=O)=O)ccc2F)c2ncncc2c1=O]

2-bromo-1-fluoro-4-methylsulfonylbenzene was substituted for the title compound of Example 225, step 1 and was converted to 2-(2-fluoro-5-methylsulfonylphenyl)-4,4,5,5-tetramethyl-1,3,2-dioxaborolane in a manner similar to Example 225, step 2 and then reacted with the title compound of Example 231, step 3 in a manner similar to Example 231, step 4. LCMS: 333.9 (M+H)$^+$.

Step 2: 8-[2-(2,4-difluorophenoxy)-5-methylsulfonylphenyl]-6-methylpyrido[4,3-d]pyrimidin-5-one

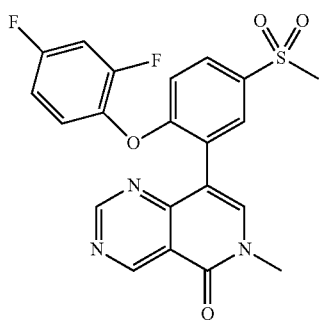 [SMILES: Cn1cc(-c2cc(S(C)(=O)=O)ccc2Oc2ccc(F)cc2F)c2ncncc2c1=O]

The title compound of step 2 (60 mg, crude), 2,4-difluorophenol (35 mg, 0.27 mmol) and Cs$_2$CO$_3$ (176 mg, 0.54 mmol) in DMSO (2 mL) was heated at 100° C. for 12 hr. EA extractive work-up and preparative HPLC gave the title compound (10.04 mg, yield: 13.6% for two steps) as a yellow solid. $^1$H NMR (CDCl$_3$, 400 MHz): δ 9.73 (s, 1H), 9.34 (s, 1H), 8.02 (d, J=2.4 Hz, 1H), 7.92 (dd, J$_1$=8.8 Hz, J$_2$=2.4 Hz, 1H), 7.72 (s, 1H), 7.19-7.17 (m, 1H), 6.97-6.89 (m, 3H), 3.72 (s, 3H), 3.12 (s, 3H). LCMS: 444.1 (M+H)$^+$.

Example 234: 8-[2-(2,4-difluorophenoxy)-5-ethylsulfonylphenyl]-6-methylpyrido[4,3-d]pyrimidin-5-one Step 1: 1-(2-bromo-4-ethylsulfonylphenoxy)-2,4-difluorobenzene

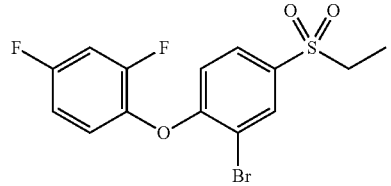 [SMILES: CCS(=O)(=O)c1ccc(Oc2ccc(F)cc2F)c(Br)c1]

2-bromo-1-fluoro-4-ethylsulfonylbenzene (130 mg, 0.49 mmol), 2,4-difluorophenol (78 mg, 0.60 mmol) and Cs$_2$CO$_3$ (478 mg, 1.47 mmol) in DMSO (5 mL) were heated at 100° C. for 12 hr. EA extractive work-up gave the title compound (150 mg, yield: 80.5%) as a grey solid. $^1$H NMR (CDCl$_3$, 400 MHz): δ 8.18 (d, J=2.0 Hz, 1H), δ 7.75 (dd, J$_1$=8.4 Hz, J$_2$=1.6 Hz, 1H), 7.22-7.16 (m, 1H), 7.06-6.95 (m, 2H), 6.80 (d, J=8.8 Hz, 1H), 3.16 (q, J=7.2 Hz, 2H), 1.33 (t, J=7.6 Hz, 3H). LCMS: 395.8 (M+NH$_4$)$^+$.

Step 2: 2-[2-(2,4-difluorophenoxy)-5-ethylsulfonylphenyl]-4,4,5,5-tetramethyl-1,3,2-dioxaborolane

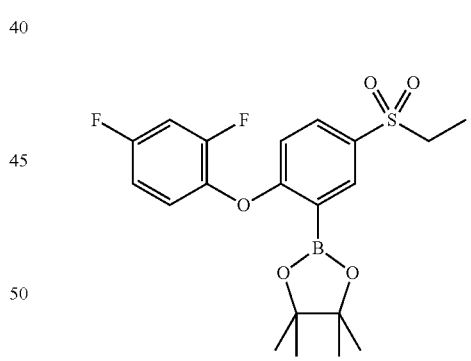

The title compound of step 1 was substituted for the title compound of Example 225, step 1 and reacted in a similar manner as Example 225, step 2. $^1$H NMR (CDCl$_3$, 400 MHz): δ 8.11 (d, J=2.8 Hz, 1H), δ 7.95 (dd, J$_1$=8.8 Hz, J$_2$=2.4 Hz, 1H), 7.55-7.50 (m, 1H), 7.29-7.23 (m, 1H), 7.16-7.12 (m, 1H), 6.99 (d, J=8.8 Hz, 1H), 3.32 (q, J=7.2 Hz, 2H), 1.26 (s, 12H), 1.12 (t, J=7.2 Hz, 3H). LCMS: 342.8 (M+H) (free boronic acid)$^+$.

Step 3: 8-[2-(2,4-difluorophenoxy)-5-ethylsulfonyl-phenyl]-6-methylpyrido[4,3-d]pyrimidin-5-one

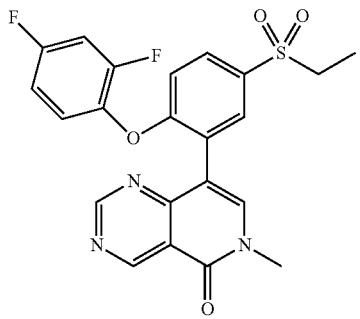 [SMILES: CCS(=O)(=O)c1ccc(Oc2ccc(F)cc2F)c(-c2cn(C)c(=O)c3cncnc23)c1]

The title compound of step 2 was substituted for the title compound of Example 225, step 2 and the title compound of Example 231, step 3 was substituted for the title compound of Example 224, step 4 and reacted in a similar manner as Example 225, step 3. $^1$H NMR (CDCl$_3$, 400 MHz): δ 9.60 (s, 1H), 9.27 (s, 1H), 8.12 (s, 1H), 8.02 (d, J=2.0 Hz, 1H), 7.94 (dd, J$_1$=8.8 Hz, J$_2$=2.0 Hz, 1H), 7.32-7.25 (m, 1H), 7.15-7.09 (m, 1H), 7.03-6.97 (m, 2H), 3.70 (s, 3H), 3.27 (q, J=7.6 Hz, 2H), 1.30 (t, J=7.2 Hz, 3H). LCMS: 458.0 (M+H)$^+$.

Example 235: 5-[2-(cyclopropylmethoxy)-5-methyl-sulfonylphenyl]-7-methyl-[1,2,4]triazolo[4,3-a]pyrazin-8-one Step 1: 5-bromo-7H-[1,2,4]triazolo[4,3-a]pyrazin-8-one

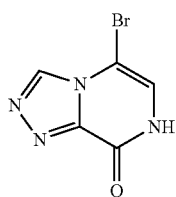

To a soln of 5-bromo-8-methoxy-[1,2,4]triazolo[4,3-a]pyrazine (Borchardt WO 2011/112766) (500 mg, 2.18 mmol) in HOAc (3 mL) was added HCl (1N, 5.00 mL). The mixture was heated at 110° C. for 4 hr and concentrated to give the title compound (400 mg, yield: 85%) as a yellow solid which was carried on without purification. $^1$H NMR (DMSO-d6, 400 MHz): δ 11.78 (s, 1H), 9.25 (s, 1H), 7.25 (d, J=6.0 Hz, 1H). LCMS: 214.9 (M+H)$^+$.

Step 2: 5-bromo-7-methyl-[1,2,4]triazolo[4,3-a]pyrazin-8-one

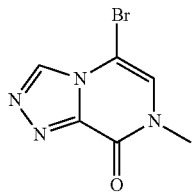

To a soln of the title compound of step 1 (400 mg, 1.86 mmol) in DMF (4 mL) was added NaH (149 mg, 3.72 mmol, 60% in mineral oil) in portions at 0° C. under N$_2$. The mixture was stirred at 20° C. for 1 hr, and methyl iodide (792 mg, 5.58 mmol) was added. After stirring at 20° C. for 5 hr, H$_2$O was added. Methylene chloride:2-propanol (10:1) extractive work-up gave the title compound (200 mg, yield: 47%) as a light yellow solid which was carried on without purification. $^1$H NMR (DMSO-d6, 400 MHz): δ 9.26 (s, 1H), 7.60 (s, 1H), 3.42 (s, 3H). LCMS: 228.9 (M+H)$^+$.

Step 3: 5-[2-(cyclopropylmethoxy)-5-methylsulfo-nylphenyl]-7-methyl-[1,2,4]triazolo[4,3-a]pyrazin-8-one

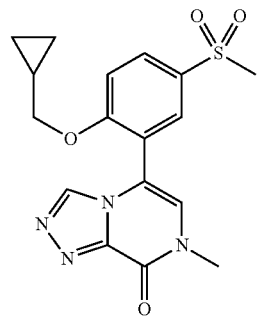 [SMILES: Cn1cc(-c2cc(S(C)(=O)=O)ccc2OCC2CC2)n2cnnc2c1=O]

The title compound of step 2 (40 mg, 0.175 mmol), the title compound of Example 90, step 1 (62 mg, 0.175 mmol), K$_3$PO$_4$ (93 mg, 0.438 mmol) and Pd(dppf)Cl$_2$ (13 mg, 0.018 mmol) in dioxane (2 mL) and H$_2$O (1 mL) was N$_2$ purged and microwaved at 70° C. for 2 hr. Silica gel chromatography (PE:EA=1:4) followed by preparative HPLC gave the title compound (31.89 mg, yield: 48.6%) as an off-white solid. $^1$H NMR (DMSO-d6, 400 MHz): δ 8.91 (s, 1H), 8.06 (dd, J$_1$=8.8 Hz, J$_2$=2.4 Hz, 1H), 7.96 (d, J=2.4 Hz, 1H), 7.43-7.04 (m, 2H), 4.04 (d, J=6.8 Hz, 2H), 3.52 (s, 3H), 3.23 (s, 3H), 0.99-0.96 (m, 1H), 0.41-0.36 (m, 2H), 0.23-0.20 (m, 2H). LCMS: 375.0 (M+H)$^+$.

Example 236: N-[4-(2,4-difluorophenoxy)-3-(7-methyl-8-oxo-[1,2,4]triazolo[4,3-a]pyrazin-5-yl)phenyl]ethanesulfonamide

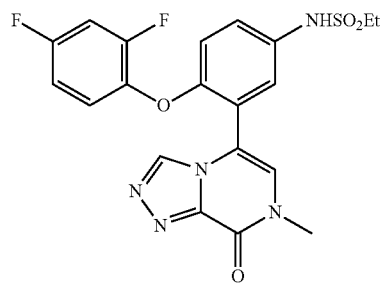

The title compound of Example 235, step 2 (40 mg, 0.175 mmol), N-[4-(2,4-difluoro-phenoxy)-3-(4,4,5,5-tetram-ethyl-1,3,2-dioxaborolan-2-yl)phenyl]ethanesulfonamide (77 mg, 0.175 mmol), K$_3$PO$_4$ (93 mg, 0.438 mmol) and Pd(dppf)Cl$_2$ (13 mg, 0.018 mmol) in dioxane (2 mL) and H$_2$O (1 mL) was N$_2$ purged and microwaved at 70° C. for 2 hr. Preparative HPLC gave the title compound (38.75 mg, yield: 49.3%) as an off-white solid. $^1$H NMR (CDCl$_3$, 400 MHz): δ 8.60 (s, 1H), 7.64 (d, J=2.8 Hz, 1H), 7.45 (dd, J$_1$=8.8 Hz, J$_2$=2.8 Hz, 1H), 7.10-7.05 (m, 1H), 6.99-6.88 (m, 3H), 6.74 (d, J=8.8 Hz, 1H), 3.67 (s, 3H), 3.18 (q, J=7.2 Hz, 2H), 1.40 (t, J=7.2 Hz, 3H). LCMS: 462.0 (M+H)$^+$.

Example 237: 7-[2-(cyclopropylmethoxy)-5-methyl-sulfonylphenyl]-5-methyl-[1,3]oxazolo[4,5-c]pyridin-4-one Step 1: 3-nitro-4-hydroxy-1-methylpyridin-2-one

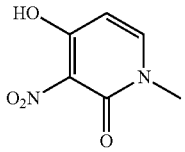

To 4-hydroxy-3-nitro-1H-pyridin-2-one (300 mg, 1.9 mmol) in DMF (5 mL) was added NaH (176 mg, 4.4 mmol, 60% in mineral oil) at 0° C. under N$_2$. After stirring at 0° C. for 30 min, CH$_3$I (272 mg, 1.9 mmol) in DMF (5 mL) was added dropwise, and the mixture was stirred for 2 hr at 25° C. Satd aq NH$_4$Cl was added, the pH was adjusted to ~3 with 1N HCl and EA extractive work-up gave a residue that was triturated with MeOH (0.5 ml):EA (10 mL):PE (5 mL). After filtration, the trituratate was evaporated to give the title compound (300 mg, 91%) as a yellow solid. $^1$H NMR (CDCl$_3$, 400 MHz): δ 7.75 (d, J=7.2 Hz, 1H), 6.17 (d, J=7.2 Hz, 1H) 3.54 (s, 3H). LCMS: 171.0 (M+1)$^+$.

Step 2: 1-methyl-3-nitro-4-phenylmethoxypyridin-2-one

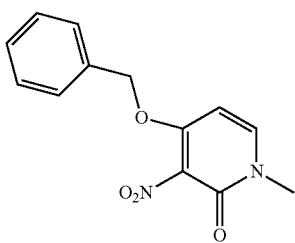 [SMILES: Cn1ccc(OCc2ccccc2)c([N+](=O)[O-])c1=O]

To the title compound of step 1 (300 mg, 1.7 mmol) in CH$_3$CN (15 mL) was added K$_2$CO$_3$ (726 mg, 5.2 mmol) at 25° C. under N$_2$. After stirring for 30 min, benzyl bromide (450 mg, 2.6 mmol) was added, and the mixture was heated at 50° C. for 20 hr. Following CH$_2$Cl$_2$ extractive work-up, the residue was triturated with PE:EA (3:1) to give the title compound (250 mg, 54%) as a yellow solid. $^1$H NMR (CDCl$_3$, 400 MHz): δ 7.43-7.29 (m, 6H), 6.12 (d, J=7.2 Hz, 1H), 5.27 (s, 2H), 3.57 (s, 3H). LCMS: 261.0 (M+1)$^+$.

Step 3: 3-amino-4-hydroxy-1-methylpyridin-2-one Hydrochloride

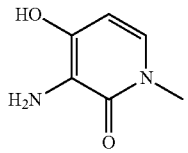

To the title compound of step 2 (2.00 g, 7.69 mmol, 1.00 Eq) in MeOH (50 mL)/EtOH (50 mL)/DMF (10 mL) was added Pd—C (10%, 0.2 g) under N$_2$. The suspension was purged with H$_2$ three times and hydrogenated under a balloon for 5 h. The catalyst was removed by filtration, and anhydrous HCl in methanol (10 mL, 1.25 M) was added. Concentration left a residue which was treated a second time with HCl in methanol. Evaporation of the volatile components and trituration with DCM (30 mL)/hexane (30 mL) gave the title compound (1.29 g, 7.30 mmol, yield: 95%) as a pink HCl salt after drying. $^1$H NMR (DMSO-d6, 400 MHz): δ 9.45-8.02 (br, 3H), 7.64 (d, J=7.6 Hz, 1H), 3.27 (d, J=7.6 Hz, 1H), 3.43 (s, 3H). LCMS: 163.0 (M+Na)$^+$.

Step 4: 5-methyl-[1,3]oxazolo[4,5-c]pyridin-4-one

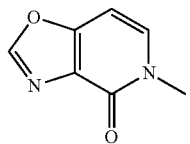

The title compound of step 3 (500 mg, 2.8 mmol) in triethyl orthoformate (10 mL) was refluxed for 5 hr. The mixture was concentrated in vacuo at 55° C. and purified by silica gel chromatography (PE:EA=1:1) to give the title compound (130 mg, yield: 30%) as a yellow solid. $^1$H NMR (CDCl$_3$, 400 MHz): δ 7.99 (s, 1H), 7.36 (d, J=8.0 Hz, 1H), 6.60 (d, J=8.0 Hz, 1H), 3.69 (s, 3H).

Step 5: 7-bromo-5-methyl-[1,3]oxazolo[4,5-c]pyridin-4-one

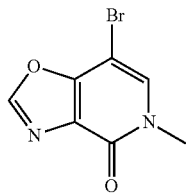

To the title compound of step 4 (100 mg, 0.7 mmol) in CH$_3$CN (5 mL) was added NBS (154 mg, 0.8 mmol) at 20° C. After 2 hr, the mixture was concentrated in vacuum at 45° C. Purification by silica gel chromatography (PE:EA=5:1~2:1) to gave the title compound (70 mg, yield: 45%) as a yellow solid. $^1$H NMR (CDCl$_3$, 400 MHz): δ 8.04 (s, 1H), 7.52 (s, 1H), 3.69 (s, 3H).

Step 6: 7-[2-(cyclopropylmethoxy)-5-methylsulfonylphenyl]-5-methyl-[1,3]oxazolo[4,5-c]pyridin-4-one

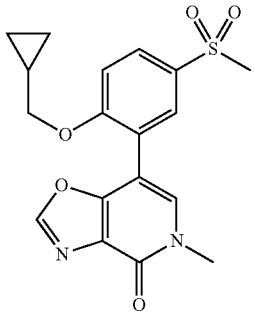 [SMILES: Cn1cc(-c2cc(S(C)(=O)=O)ccc2OCC2CC2)c2ocnc2c1=O]

The title compound of step 5 (60 mg, 0.3 mmol) in dioxane (2 mL) and H$_2$O (0.4 mL) was stirred at 15° C. under N$_2$ for 30 min. Pd(dppf)Cl$_2$ (19 mg, 0.026 mmol), the title compound of Example 90, step 1 (120 mg, 0.3 mmol) and K$_3$PO$_4$ (166 mg, 0.8 mmol,) were added at 15° C. under N$_2$. The rxn mixture was heated at 60° C. for 12 hr. Purification by silica gel chromatography (EA) and preparative HPLC gave the title compound (20.63 mg, 20%) as a yellow solid. $^1$H NMR (CDCl$_3$, 400 MHz): δ 8.03 (d, J=2.0 Hz, 1H), 8.02 (s, 1H), 7.96 (dd, J$_1$=8.4 Hz, J$_2$=2.0 Hz, 1H), 7.09 (d, J=8.4 Hz, 1H), 3.96 (d, J=6.8 Hz, 2H), 3.76 (s, 3H), 3.1 (s, 3H), 1.18 (m, 1H), 0.60 (m, 2H), 0.30 (m, 2H). LCMS: 375.1 (M+H)$^+$.

Example 238: 7-[2-(cyclopropylmethoxy)-5-methylsulfonylphenyl]-2,5-dimethyl-[1,3]oxazolo[4,5-c]pyridin-4-one

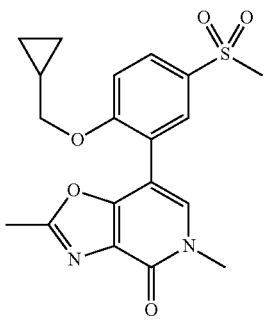

The title compound was prepared from the title compound of Example 237, step 3 in a similar manner as Example 237, steps 4-6 except that triethyl orthoacetate was substituted for triethyl orthoformate. $^1$H NMR (400 MHz, DMSO-d$_6$): δ ppm 0.25 (q, J=4.72 Hz, 2H) 0.48 (q, J=5.89 Hz, 2H) 1.11 (m, 1H) 2.54 (s, 3H) 3.21 (s, 3H) 3.60 (s, 3H) 4.00 (d, J=6.82 Hz, 2H) 7.34 (d, J=8.59 Hz, 1H) 7.88-7.98 (m, 3H). LCMS: 389 (M+H)$^+$.

Example 239: 5-methyl-7-[5-(methylsulfonylmethyl)-2-(2,2,2-trifluoroethoxy)phenyl]-[1,3]oxazolo[4,5-c]pyridin-4-one

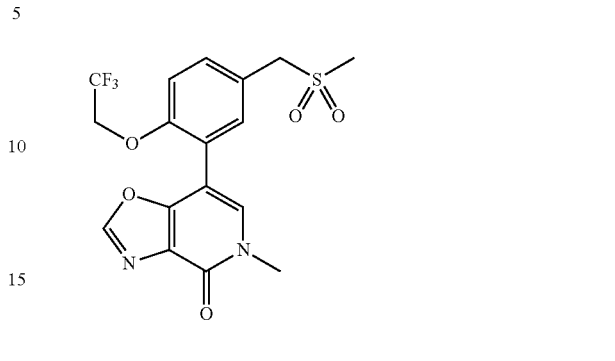

The title compound of Example 237, step 5 and the title compound of Example 370, step 1 were reacted in a manner similar to Example 237, step 6 to give the title compound. $^1$H NMR (CDCl$_3$, 400 MHz): δ 8.00 (s, 1H), 7.62 (s, 1H), 7.60 (s, 1H), 7.47 (d, J=8.4 Hz, 1H), 7.02 (d, J=8.4 Hz, 1H), 4.42 (q, J=8.0 Hz, 2H), 4.28 (s, 2H), 3.74 (s, 3H), 2.87 (s, 3H). LCMS: 417.0 (M+H)$^+$.

Example 240: N-[4-(2,4-difluorophenoxy)-3-(5-methyl-4-oxo-[1,3]oxazolo[4,5-c]pyridin-7-yl)phenyl]ethanesulfonamide

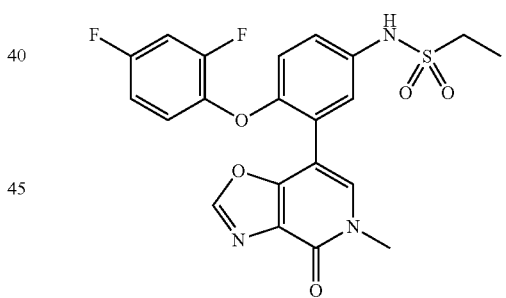

N-[4-(2,4-difluorophenoxy)-3-(4,4,5,5-tetramethyl-1,3,2-dioxaborolan-2-yl)phenyl]ethanesulfonamide was prepared from the title compound of Example 122, step 1 and 4,4,5,5-tetramethyl-2-(tetramethyl-1,3,2-dioxaborolan-2-yl)-1,3,2-dioxaborolane in a manner similar to Example 208, step 5 and reacted with the title compound of Example 237, step 5 in a manner similar to Example 237, step 6. $^1$H NMR (CDCl$_3$, 400 MHz): δ 8.01 (s, 1H), 7.31 (d, J=8.4 Hz, 1H), 7.67 (s, 1H), 7.48 (d, J=2.4 Hz, 1H), 7.22 (dd, J$_1$=8.8 Hz, J$_2$=2.4 Hz, 1H), 7.18 (m, 1H), 7.03 (m, 1H), 6.84 (m, 2H), 3.74 (s, 3H), 3.17 (q, J=7.2 Hz, 2H), 1.43 (t, J=7.2 Hz, 3H). LCMS: 462.1 (M+H)$^+$.

Example 241: N-[4-(2,4-difluorophenoxy)-3-(2,5-dimethyl-4-oxo-[1,3]oxazolo[4,5-c]pyridin-7-yl)phenyl]ethanesulfonamide

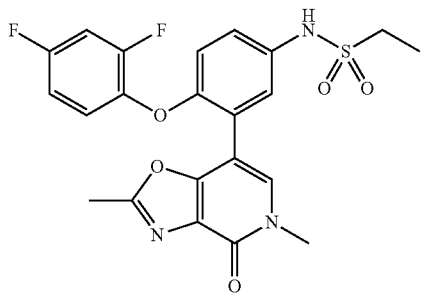

7-bromo-2,5-dimethyl-[1,3]oxazolo[4,5-c]pyridin-4-one prepared in Example 238 and N-[4-(2,4-difluorophenoxy)-3-(4,4,5,5-tetramethyl-1,3,2-dioxaborolan-2-yl)phenyl]ethanesulfonamide prepared in Example 240 were reacted in a manner similar to Example 237, step 6 to give the title compound. $^1$H NMR (400 MHz, DMSO-$d_6$): δ ppm 1.23 (t, J=6.95 Hz, 3H) 2.45 (s, 3H) 3.13 (d, J=7.83 Hz, 2H) 3.58 (s, 3H) 6.95 (d, J=8.59 Hz, 1H) 7.03-7.30 (m, 3H) 7.30-7.48 (m, 2H) 7.91 (s, 1H) 9.86 (s, 1H). LCMS: 476 (M+H)$^+$.

Example 242: 5-[2-(cyclopropylmethoxy)-5-methylsulfonylphenyl]-1-(cyclopropylmethyl)-3-methylpyridin-2-one

Step 1: 5-[2-(cyclopropylmethoxy)-5-methylsulfonylphenyl]-3-methyl-1H-pyridin-2-one

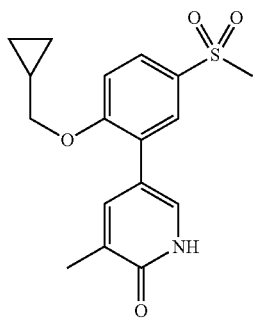 [SMILES: Cc1cc(-c2cc(S(C)(=O)=O)ccc2OCC2CC2)c[nH]c1=O]

5-bromo-3-methyl-1H-pyridin-2-one (950 mg, 5.05 mmol), the title compound of Example 90, step 1 (2.93 g, 5.95 mmol), Pd(dppf)Cl$_2$ (365 mg, 0.5 mmol) and K$_3$PO$_4$ (2.14 g, 10.1 mmol) in dioxane (30 mL) and H$_2$O (5 mL) was purged with N$_2$ and heated at 70° C. for 12 hr. Silica gel chromatography (PE:DCM:EA=3:0:1-0:1:3) gave impure title compound (990 mg) as a yellow solid which was used directly in the next step. $^1$H NMR (CDCl$_3$, 400 MHz): δ 12.57 (brs, 1H), 7.84 (d, J=8.8 Hz, 1H), 7.82 (s, 1H), 7.65 (s, 1H), 7.03 (d, J=8.8 Hz, 1H), 3.96 (d, J=7.2 Hz, 1H), 3.07 (s, 3H), 2.24 (s, 3H), 1.40-1.25 (m, 1H), 0.67-0.65 (m, 2H), 0.37-0.36 (m, 2H). LCMS: 334.1 (M+1)$^+$

Step 2: 5-[2-(cyclopropylmethoxy)-5-methylsulfonylphenyl]-1-(cyclopropylmethyl)-3-methylpyridin-2-one

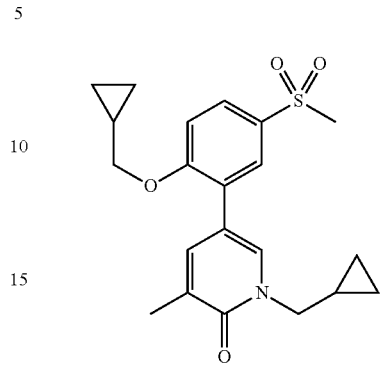

The title compound of step 1 (80 mg), K$_2$CO$_3$ (77 mg, 0.56 mmol) bromomethylcyclopropane (62 mg, 0.46 mmol) in DMF (2 mL) were heated at 70° C. for 4 hr. EA extractive work-up and preparative HPLC gave the title compound (17 mg) as a yellow solid. $^1$H NMR (CDCl$_3$, 400 MHz): δ 7.85-7.83 (m, 2H), 7.67 (d, J=2.0 Hz, 1H), 7.53 (s, 1H), 7.03 (d, J=9.2 Hz, 1H), 3.95 (d, J=6.8 Hz, 1H), 3.89 (d, J=7.2 Hz, 1H), 3.07 (s, 3H), 2.23 (s, 3H), 1.34-1.26 (m, 2H), 0.68-0.65 (m, 2H), 0.65-0.61 (m, 2H), 0.44-0.43 (m, 2H), 0.38-0.37 (m, 2H). LCMS: 388.2 (M+1)$^+$.

Example 243: 5-[2-(cyclopropylmethoxy)-5-methylsulfonylphenyl]-3-methyl-1-(2-methylpropyl)pyridin-2-one

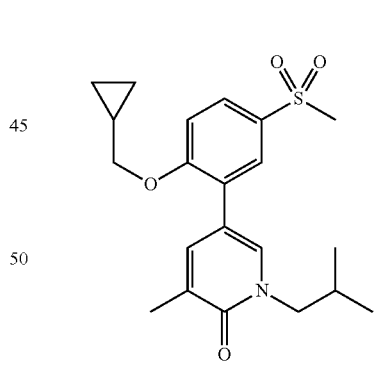

The title compound from Example 242, step 1 was reacted in a manner similar to Example 242, step 2 except that 1-bromo-2-methylpropane was substituted for bromomethylcyclopropane to give the title compound. $^1$H NMR (CDCl$_3$, 400 MHz); δ 7.85-7.82 (m, 2H), 7.56 (s, 1H), 7.53 (s, 1H), 7.03 (d, J=8.4 Hz, 1H), 3.94 (d, J=7.2 Hz, 1H), 3.83 (d, J=7.2 Hz, 1H), 3.07 (s, 3H), 2.30-2.26 (m, 1H), 2.23 (s, 3H), 1.28-1.27 (m, 1H), 1.00 (s, 3H), 0.98 (s, 3H), 0.69-0.65 (m, 2H), 0.38-0.35 (m, 2H). LCMS: 390.2 (M+1)$^+$.

Example 244: 5-[2-(cyclopropylmethoxy)-5-methyl-sulfonylphenyl]-1-(2-methoxyethyl)-3-methylpyridin-2-one

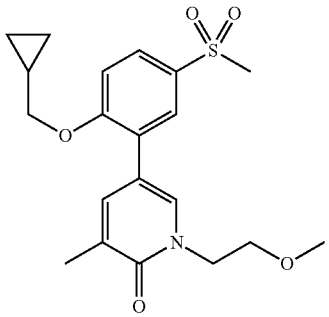 [SMILES: COCCn1cc(-c2cc(S(C)(=O)=O)ccc2OCC2CC2)cc(C)c1=O]

The title compound from Example 242, step 1 was reacted in a manner similar to Example 242, step 2 except that 1-bromo-2-methoxyethane was substituted for bromomethylcyclopropane to give the title compound. $^1$H NMR (CDCl$_3$, 400 MHz): δ 7.86-7.83 (m, 2H), 7.65 (d, J=1.6 Hz, 1H), 7.59 (s, 1H), 7.03 (d, J=8.4 Hz, 1H), 4.22 (t, J=4.8 Hz, 1H), 3.96 (d, J=6.8 Hz, 1H), 3.74 (t, J=4.8 Hz, 1H), 3.34 (s, 3H), 3.07 (s, 3H), 2.23 (s, 3H), 1.30-1.27 (m, 1H), 0.70-0.66 (m, 2H), 0.40-0.36 (m, 2H). LCMS: 392.2 (M+1)$^+$.

Example 245: 5-[2-(cyclopropylmethoxy)-5-methyl-sulfonylphenyl]-3-methyl-1-(oxetan-3-ylmethyl)pyridin-2-one

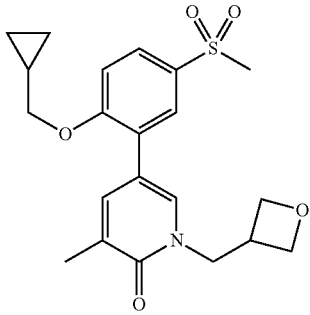 [SMILES: Cc1cc(-c2cc(S(C)(=O)=O)ccc2OCC2CC2)cn(CC2COC2)c1=O]

Sodium hydride (42 mg, 1.04 mmol, 60% in mineral oil) was added to the title compound from Example 242, step 1 (80 mg) in anhydrous DMF (4 mL) After stirring 1 hr, oxetan-3-ylmethyl methanesulfonate (173 mg, 1.04 mmol) was added and stirring continued for 18 hr. EA extractive work-up from 1 M HCl and preparative HPLC purification gave the title compound (24.0 mg) as an off-white solid. $^1$H NMR (CDCl$_3$, 400 MHz): δ 7.85 (d, J=8.8 Hz, 1H), 7.82 (s, 1H), 7.62 (s, 1H), 7.51 (s, 1H), 7.03 (d, J=8.8 Hz, 1H), 4.83 (t, J=7.2 Hz, 1H), 4.57 (t, J=6.4 Hz, 1H), 4.30 (d, J=7.2 Hz, 1H), 3.95 (d, J=6.8 Hz, 1H), 3.62-3.56 (m, 1H), 3.07 (s, 3H), 2.21 (s, 3H), 1.32-1.27 (m, 1H), 0.72-0.68 (m, 2H), 0.40-0.36 (m, 2H). LCMS: 404.1 (M+1)$^+$.

Example 246: 5-[2-(cyclopropylmethoxy)-5-methyl-sulfonylphenyl]-3-methyl-1-(1,3-oxazol-4-ylmethyl)pyridin-2-one

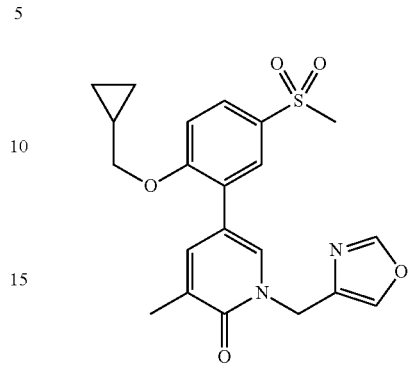

The title compound from Example 242, step 1 was reacted in a manner similar to Example 245 except that 1,3-oxazol-4-ylmethyl methanesulfonate was substituted for oxetan-3-ylmethyl methanesulfonate to give the title compound. $^1$H NMR (CDCl$_3$, 400 MHz): δ 7.82 (s, 5H), 7.52 (s, 1H), 7.01 (d, J=9.2 Hz, 1H), 5.11 (s, 2H), 3.94 (d, J=6.8 Hz, 1H), 3.06 (s, 3H), 2.21 (s, 3H), 1.27-1.24 (m, 1H), 0.68-0.65 (m, 2H), 0.37-0.36 (m, 2H). LCMS: 415.1 (M+1)$^+$.

Example 247: N-[3-[1-(cyclopropylmethyl)-5-methyl-6-oxopyridin-3-yl]-4-(2,4-difluoro-phenoxy)phenyl]ethanesulfonamide

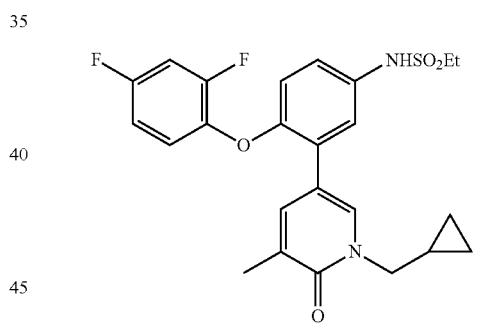

5-bromo-3-methyl-1H-pyridin-2-one was N-alkylated with bromomethylcyclopropane to give 5-bromo-1-(cyclopropylmethyl)-3-methylpyridin-2-one. 5-bromo-1-(cyclopropylmethyl)-3-methylpyridin-2-one (100 mg, 0.41 mmol), [2-(2,4-difluorophenoxy)-5-(ethylsulfonylamino)phenyl] boronic acid (217 mg, 0.5 mol), K$_3$PO$_4$ (263 mg, 1.24 mmol) and Pd(dppf)Cl$_2$ (30 mg, 41.3 μmol) in dioxane (8 mL)/H$_2$O (1 mL) were purged with N$_2$ and heated at 70-80° C. for 12 hr. Preparative HPLC gave the title compound (56.0 mg, 28.6% yield) as dull-red semisolid. $^1$H NMR (CDCl$_3$, 400 MHz): δ 7.74 (s, 1H), 7.61 (s, 1H), 7.28 (d, J=2.0 Hz, 1H), 7.10-7.15 (m, 1H), 6.92-7.00 (m, 2H), 6.82-6.89 (m, 1H), 6.80 (d, J=8.8 Hz, 1H), 6.71 (br. s., 1H), 3.93 (d, J=7.2 Hz, 3H), 3.12-3.21 (m, 2H), 2.24 (s, 3H), 1.42 (t, J=7.2 Hz, 3H), 1.22-1.33 (m, 1H), 0.57-0.67 (m, 2H), 0.36-0.43 (m, 2H). LCMS: 475.1 (M+1)$^+$.

Example 248: N-[4-[1-(cyclopropylmethyl)-5-methyl-6-oxopyridin-3-yl]-5-(2,4-difluorophenoxy)pyrimidin-2-yl]methanesulfonamide

Step 1: 5-bromo-1-(cyclopropylmethyl)-3-methyl-pyridin-2-one

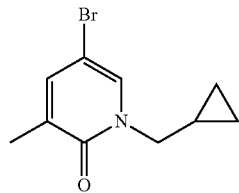

Potassium carbonate (1.32 g, 9.57 mmol) was added to 5-bromo-3-methyl-2-hydroxy-pyridine (600 mg, 3.19 mmol) and bromomethylcyclopropane (861 mg, 6.38 mmol) in DMF (6 mL). After heating at 70° C. for 3 hr, EA extractive work-up and silca gel chromatography (PE:EA=30:1~10:1), the title compound (510 mg, yield: 66.0%) was obtained as a white solid. $^1$H NMR (CDCl$_3$, 400 MHz): δ 7.39 (d, J=2.0 Hz, 1H), 7.26 (d, J=2.0 Hz, 1H), 3.77 (d, J=6.8 Hz, 2), 2.15 (s, 3H), 0.65-0.60 (m, 2H), 0.40-0.37 (m, 2H). LCMS: 242.1, 244.1 (M+H)$^+$.

Step 2: 1-(cyclopropylmethyl)-3-methyl-5-(4,4,5,5-tetramethyl-1,3,2-dioxaborolan-2-yl)pyridin-2-one

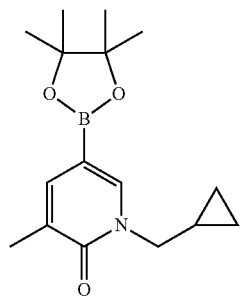 [SMILES: Cc1cc(B2OC(C)(C)C(C)(C)O2)cn(CC2CC2)c1=O]

The title compound of step 1 (480 mg, 1.98 mmol), 4,4,5,5-tetramethyl-2-(tetramethyl-1,3,2-dioxaborolan-2-yl)-1,3,2-dioxaborolane (1.01 g, 3.96 mmol), KOAc (582 mg, 5.94 mmol) and Pd(dppf)Cl$_2$ (146 mg, 0.20 mmol) in dioxane (9 mL) was purged with N$_2$ and heated to 70° C. for 8 hr. After silca gel chromatography (PE:EA=30:1~10:1) the title compound (415 mg, ~70% purity on $^1$H NMR, yield: 55.1%) was obtained as light yellow oil. $^1$H NMR (CDCl$_3$, 400 MHz): δ 7.69 (s, 1H), 7.49 (s, 1H), 3.82 (d, J=6.8 Hz, 2H), 2.14 (s, 3H), 1.32 (s, 12H), 1.27-1.1.16 (m, 1H), 0.61-0.56 (m, 2H), 0.42-0.39 (m, 2H). LCMS: 290.3 (M+H)$^+$.

Step 3: 1-(cyclopropylmethyl)-5-[5-(2,4-difluorophenoxy)-2-methylsulfonyl-pyrimidin-4-yl]-3-methylpyridin-2-one

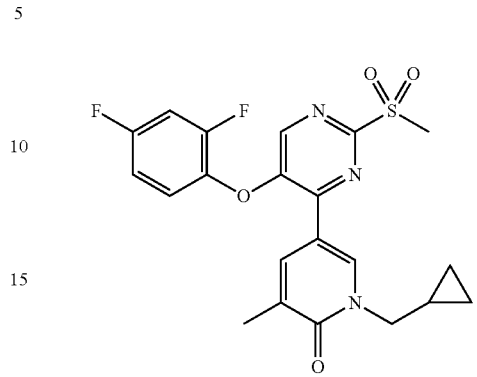

The title compound of Example 149, step 3 (200 mg, 0.62 mmol), the title compound of step 2 (250 mg, 0.69 mmol, 70% purity), Pd(dppf)Cl$_2$ (88 mg, 0.12 mmol) and K$_3$PO$_4$ (3M, 0.6 mL) in dioxane (6 mL) were purged with N$_2$ and heated to 70° C. for 4 hr. After silica gel chromatography (PE:EA=3:1~1:1) the title compound (220 mg, yield: 78.8%) was obtained as a yellow solid. $^1$H NMR (CDCl$_3$, 400 MHz): δ 7.45 (d, J=2.0 Hz, 1H), 8.25 (s, 1H), 8.16 (s, 1H), 7.24-7.22 (m, 1H), 7.12-7.10 (m, 1H), 7.10-7.03 (m, 1H), 3.92 (d, J=7.2 Hz, 2H), 3.38 (s, 3H), 2.26 (s, 3H), 1.27-1.21 (m, 1H), 0.65-0.60 (m, 2H), 0.42-0.38 (m, 2H). LCMS: 448.1 (M+H)$^+$.

Step 4: N-[4-[1-(cyclopropylmethyl)-5-methyl-6-oxopyridin-3-yl]-5-(2,4-difluorophenoxy)pyrimidin-2-yl]methanesulfonamide

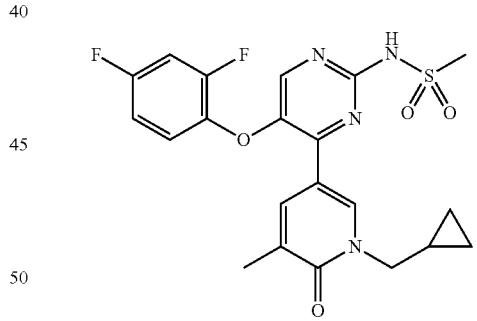

Methanesulfonamide (68 mg, 0.71 mmol), NaH (28 mg, 0.7 mmol, 60% in mineral oil) and the title compound from step 3 (80 mg, 0.18 mmol) in DMF (2 mL) were reacted in a similar manner as Example 152, step 6 to give the title compound (45.00 mg, yield: 54.4%) as an off-white solid. $^1$H NMR (CDCl$_3$, 400 MHz) δ 8.81 (s, 1H), 8.60 (d, J=2.0 Hz, 1H), 8.14 (s, 1H), 8.12 (s, 1H), 7.05-6.98 (m, 2H), 6.91-6.89 (m, 1H), 3.87 (d, J=7.2 Hz, 2H), 3.45 (s, 3H), 2.23 (s, 3H), 1.25-1.22 (m, 1H), 0.64-0.59 (m, 2H), 0.40-0.37 (m, 2H). LCMS: 463.1 (M+H)$^+$.

Example 249: N-[4-[1-(cyclopropylmethyl)-5-methyl-6-oxopyridin-3-yl]-5-(2,4-difluorophenoxy)pyrimidin-2-yl]ethanesulfonamide

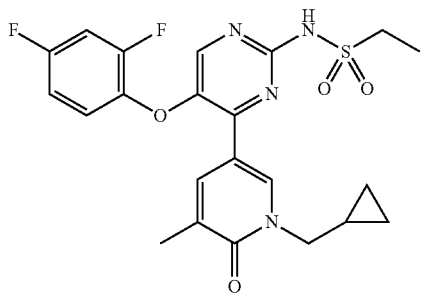 [SMILES: CCS(=O)(=O)Nc1ncc(Oc2ccc(F)cc2F)c(-c2cc(C)c(=O)n(CC3CC3)c2)n1]

The title compound of Example 248, step 3 was treated with EtSO$_2$NH$_2$ instead of MeSO$_2$NH$_2$ in a manner similar to Example 248, step 4 to give the title compound. $^1$H NMR (CDCl$_3$, 400 MHz): δ 9.09 (s, 1H), 8.60 (s, 1H), 8.16 (s, 1H), 8.11 (s, 1H), 7.04-6.96 (m, 2H), 6.91-6.89 (m, 1H), 3.87 (d, J=7.2 Hz, 2H), 3.64 (q, J=7.2 Hz, 2H), 2.22 (s, 3H), 1.44 (t, J=7.2 Hz, 3H), 1.25-1.23 (m, 1H), 0.62-0.60 (m, 2H), 0.38-0.37 (m, 2H). LCMS: 477.2 (M+H)$^+$.

Example 250: 1-(cyclopropylmethyl)-5-[6-(2,4-difluorophenoxy)-3-(methylsulfonylmethyl)-4-oxocyclohexa-1,5-dien-1-yl]-3-methylpyridin-2-one

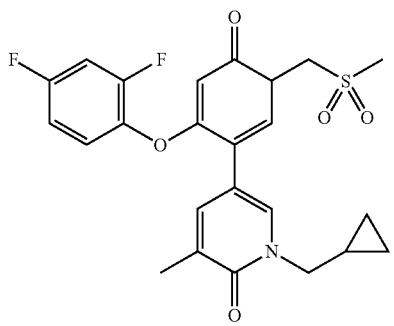 [SMILES: Cc1cc(C2=CC(CS(C)(=O)=O)C(=O)C=C2Oc2ccc(F)cc2F)cn(CC2CC2)c1=O]

The title compound from Example 248, step 2 was reacted with the title compound of Example 381, step 4 in a manner similar to Example 248, step 3 to give the title compound. $^1$H NMR (CDCl$_3$, 400 MHz): δ 7.47 (s, 1H), 7.41 (s, 1H), 7.37 (s, 1H), 7.18-7.16 (m, 1H), 7.04-7.02 (m, 1H), 7.01-6.98 (m, 1H), 5.69 (s, 1H), 5.17 (s, 2H), 3.86 (d, J=7.2 Hz, 2H), 2.99 (s, 3H), 2.20 (s, 3H), 1.28-1.27 (m, 1H), 0.65-0.60 (m, 2H), 0.42-0.39 (m, 2H). LCMS: 477.1 (M+H)$^+$.

Example 251: 1-cyclopropyl-5-[2-(cyclopropylmethoxy)-5-ethylsulfonylphenyl]-3-methylpyridin-2-one Step 1: 5-bromo-1-cyclopropyl-3-methylpyridin-2-one

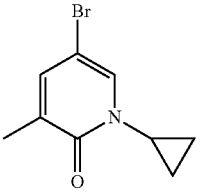

At room temp, NBS (63 mg, 0.35 mmol) was added to 1-cyclopropyl-3-methylpyridin-2-one (Racine et al., Chem. Communications 2013, 49(67) 7412-14) (53 mg, 0.36 mmol) in CH$_3$CN (0.7 mL). After 1 hr, EA extractive work-up from sat'd aq NaHCO$_3$ gave the title compound as yellow solids in quantitative yield.

Step 2: 1-cyclopropyl-5-[2-(cyclopropylmethoxy)-5-ethylsulfonylphenyl]-3-methylpyridin-2-one

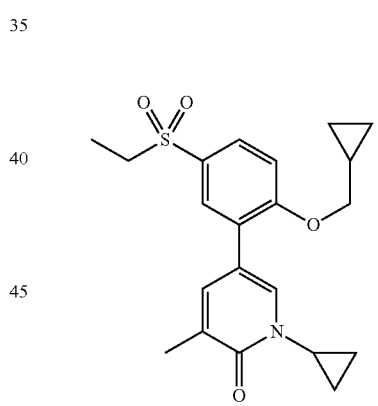

The title compound of step 1 was reacted with 2-[2-(cyclopropylmethoxy)-5-ethylsulfonylphenyl]-4,4,5,5-tetramethyl-1,3,2-dioxaborolane in a manner similar to Example 224, step 5. Silica gel chromatography (40-75% EA in hexane) gave the title compound (31 mg, 0.08 mmol, 42%) as a tan foam that turned to a glass upon standing. $^1$H NMR (400 MHz, CDCl$_3$): δ ppm 0.36-0.42 (m, 2H) 0.60-0.75 (m, 2H) 0.81-1.02 (m, 1H, partially obscured) 1.05-1.37 (m, 7H, partially obscured) 2.22 (s, 3H) 3.12 (q, J=7.41 Hz, 2H) 3.43 (br. s. 1H) 3.94 (d, J=6.82 Hz, 2H) 7.01 (d, J=9.35 Hz, 1H) 7.45-7.53 (m, 1H) 7.62 (br. s., 1H) 7.72-7.83 (m, 2H). LCMS: 388 (M+1)$^+$.

Example 252: 4-[2-(cyclopropylmethoxy)-5-ethyl-sulfonylphenyl]-6-methylfuro[2,3-c]pyridine-7-one

Step 1: 4-bromo-6H-furo[2,3-c]pyridin-7-one

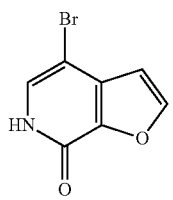

A mixture of 6H-furo[2,3-c]pyridin-7-one (1.0 g, 7.4 mmol) in DMF (30 mL) was treated with NBS (1.32 g, 7.4 mmol) in three equal portions at 0° C. After the resulting mixture was stirred at 15° C. for 2 hr, it was treated with H$_2$O (100 mL) and extracted with EtOAc (30 mL×3). The combined organic layers were washed with brine (30 mL), dried over Na$_2$SO$_4$, filtered, and concentrated in vacuo. The residue was purified by chromatography on silica gel (PE: EtOAc=3:1) to give the title compound (600 mg, 38%) as a yellow solid. $^1$H NMR (DMSO-d6, 400 MHz): δ 11.92 (s, 1H), 8.23 (s, J=2.0 Hz, 1H), 7.47 (s, 1H), 6.88 (m, 1H), 6.88 (s, 1H).

Step 2: 4-bromo-6-methylfuro[2,3-c]pyridin-7-one

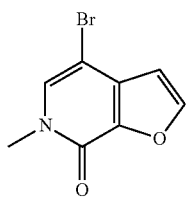

To a soln of the title compound of step 1 (500 mg, 2.3 mmol) stirred at 0° C. in DMF (5 mL) was added NaH (68 mg, 2.81 mmol, 60% in mineral oil). After stirring at 0° C. for 30 min, methyl iodide (400 mg, 2.8 mmol) was added dropwise. The icebath was removed, and mixture was stirred at room temp for 4 hr. The rxn mixture was treated with satd NH$_4$Cl (aq 30 mL) and extracted with EtOAc (30 mL×2). The combined organic layers were washed with brine (30 mL), dried over Na$_2$SO$_4$, filtered, and concentrated in vacuo. The residue was purified by chromatography on silica gel (PE:EtOAc=10:1) to give the title compound (500 mg, 94%). $^1$H NMR (CDCl$_3$, 400 MHz): δ 7.78 (d, J=2.0 Hz, 1H), 7.30 (s, 1H), 6.70 (d, J=2.0 Hz, 1H), 3.66 (s, 3H). LCMS: (M+H)$^+$229.

Step 3: 4-[2-(cyclopropylmethoxy)-5-ethylsulfonyl-phenyl]-6-methylfuro[2,3-c]pyridine-7-one

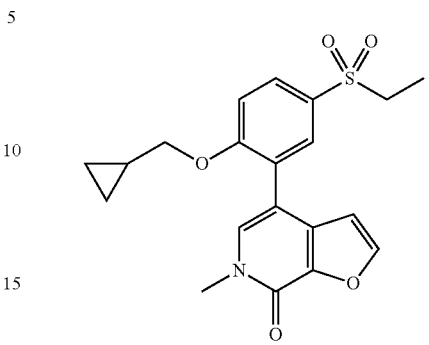

A mixture of the title compound of step 2 (150 mg, 0.66 mmol), 2-[2-(cyclopropylmethoxy)-5-ethylsulfonylphenyl]-4,4,5,5-tetramethyl-1,3,2-dioxaborolane (336 mg, 1.0 mmol), NaHCO$_3$ (167 mg, 1.99 mmol), Pd(dppf)Cl$_2$ (35 mg, 0.048 mmol) in dioxane/H$_2$O (10 mL/2.5 mL) was bubbled with Ar for 5 min. The sealed vial was stirred at 80° C. for 18 hr. The rxn mixture was concentrated, treated with DCM (30 mL), washed with H$_2$O (30 mL) and brine (30 mL), dried over Na$_2$SO$_4$, filtered and concentrated in vacuo. The resulting residue was purified by prep-HPLC to give the title compound (63 mg, 25%) as a yellow solid. $^1$H NMR (CDCl$_3$, 400 MHz): δ 7.90-7.86 (m, 2H), 7.75 (d, J=1.6 Hz, 1H), 7.31 (s, 1H), 7.09 (d, J=8.4 Hz, 1H), 6.57 (d, J=1.6 Hz, 1H), 3.95 (d, J=6.8 Hz, 2H), 3.74 (s, 3H), 3.18-3.12 (q, J=7.6 Hz, 2H), 1.34 (t, J=7.6 Hz, 3H), 1.16-1.15 (m, 1H), 0.61-0.55 (m, 2H), 0.31-0.27 (m, 2H). LCMS (M+H)$^+$: 388.

Example 253: N-[4-(2,4-difluorophenoxy)-3-(6-methyl-7-oxofuro[2,3-c]pyridin-4-yl)phenyl]ethanesulfonamide

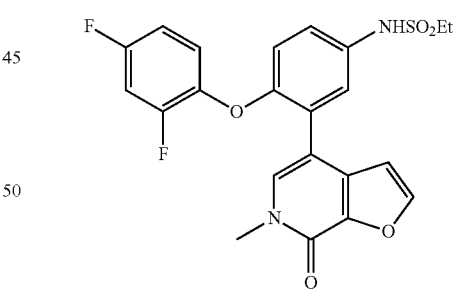

The title compound was prepared in a manner similar to step 3 of Example 252, by substituting N-[4-(2,4-difluorophenoxy)-3-(4,4,5,5-tetramethyl-1,3,2-dioxaborolan-2-yl)phenyl]ethanesulfonamide for 2-[2-(cyclopropylmethoxy)-5-ethylsulfonylphenyl]-4,4,5,5-tetramethyl-1,3,2-dioxaborolane. $^1$H NMR (CDCl$_3$, 400 MHz): δ 7.74 (s, 1H) 7.38 (m, 2H) 7.15 (m, 1H) 6.93-9.92 (m, 2H) 6.82-6.76 (m, 3H) 6.44 (s, 1H) 3.72 (s, 3H) 3.19-3.16 (q, J=7.2 Hz, 2H) 1.45 (t, J=7.2 Hz, 3H). LCMS (M+H)$^+$: 461.

Example 254: 4-[2-(cyclopropylmethoxy)-5-methyl-sulfonylphenyl]-6-methylfuro[2,3-c]pyridine-7-one

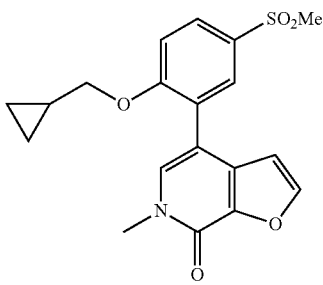 [SMILES: Cn1cc(-c2cc(S(C)(=O)=O)ccc2OCC2CC2)c2ccoc2c1=O]

A mixture of 2-[2-(cyclopropylmethoxy)-5-methylsulfonylphenyl]-4,4,5,5-tetramethyl-1,3,2-dioxaborolane (115 mg, 0.33 mmol), 4-bromo-6-methyl-6H,7H-furo[2,3-c]pyridin-7-one (75 mg, 0.33 mmol), K₃PO₄ (175 mg, 0.83 mmol), Pd(dppf)Cl₂ (24 mg, 10%) in dioxane/H₂O (2.2 mL/200 µL) was bubbled with N₂ for 5 min. The sealed vial was stirred at 70° C. for 90 min. The rxn mixture was filtered through a short plug of celite; the celite plug was washed with EtOAc (15 mL). The filtrate was washed with H₂O and brine. The organic layer was dried over Na₂SO₄, filtered and concentrated in vacuo to afford a brown residue. The resulting residue was purified by prep-HPLC to afford the title compound (60 mg, 49%) as a white solid. LCMS (M+H)⁺: 374.

Example 255: N-[4-(cyclopropylmethoxy)-3-(6-methyl-7-oxofuro[2,3-c]pyridine-4-yl)phenyl]ethanesulfonamide

Step 1: 2-bromo-1-(cyclopropylmethoxy)-4-nitrobenzene

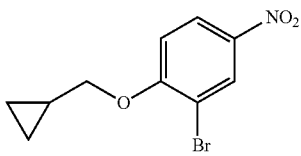

A 0.2 M soln of cyclopropyl methanol (441 µL, 5.5 mmol) in THF stirred at 0° C. under N₂ was treated with two equal portions of KOtBu (579 mg, 5.2 mmol). After 5 min the icebath was removed; the mixture was stirred for 30 min at room temp before resubmerging in the icebath and cooling to 0° C. A soln of 2-bromo-1-fluoro-4-nitro-benzene (1 g, 4.5 mmol) in THF (3 mL) was added dropwise. After 20 min, the icebath was removed and the mixture was stirred overnight. The rxn mixture was quenched with H₂O (50 mL) and extracted with EtOAc (3×50 ml). The combined organic layers were washed brine (30 mL), dried over Na₂SO₄, filtered and concentrated in vacuo. The resulting residue was purified by silica gel CC using a gradient of EtOAc (5 to 50%) in hexanes to afford the title compound (1.07 g, 88%) as a yellow solid.

Step 2: 3-bromo-4-(cyclopropylmethoxy)aniline

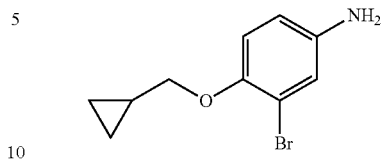

A mixture of 2-bromo-1-(cyclopropylmethoxy)-4-nitrobenzene (1.07 g, 3.9 mmol), ammonium chloride (421 mg, 7.8 mmol), and iron powder (1.1 g, 20 mmol) suspended in THF (6.5 mL), H₂O (2.5 mL) and EtOH (6.5 mL) was heated to 95° C. using microwave irradiation (normal) for 3 hr. The crude rxn mixture was filtered through a short plug of celite; the celite plug was washed with MeOH (~10 mL). The resulting filtrate was concentrated in vacuo. The resulting residue was diluted with EtOAc (50 ml) and washed with satd bicarbonate soln (aq), dried over anhydrous magnesium sulfate, filtered, and concentrated in vacuo to afford the title compound, (939 mg, 90%). The material was carried forward without any further purification. LCMS (M+H)⁺: 242.

Step 3: N-[3-bromo-4-(cyclopropylmethoxy)phenyl]ethane-1-sulfonamide

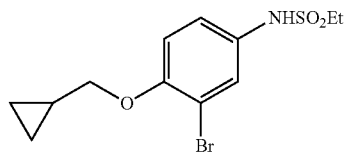

Ethylsulfonyl chloride (233 µL, 2.4 mmol) was added to a stirred soln of 3-bromo-4-(cyclopropylmethoxy)aniline (520 mg, 2.2 mmol) and pyridine (520 µL, 6.5 mmol) in DCM (4 mL) at 0° C. under N₂. After the mixture was allowed to warm to room temp and stirred for 12 hr, it was treated with 1N HCl (15 mL) and extracted with DCM (3×15 mL); the combined organic extracts were washed with satd bicarbonate soln (aq), dried over Na₂SO₄, filtered and concentrated in vacuo. The resulting residue was purified by silica gel CC using a gradient of EtOAc (10 to 100%) in hexanes to afford the title compound (711 mg, 98%) as a yellow solid. LCMS (M+H)⁺: 335.

Step 4: N-[4-(cyclopropylmethoxy)-3-(tetramethyl-1,3,2-dioxaborolan-2-yl)phenyl]ethane-1-sulfonamide

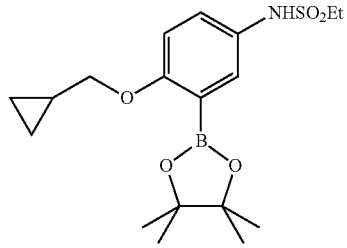

A mixture of N-[3-bromo-4-(cyclopropylmethoxy)phenyl]ethane-1-sulfonamide (711 mg, 2.1 mmol), 4,4,5,5-tetramethyl-2-(tetramethyl-1,3,2-dioxaborolan-2-yl)-1,3,2-dioxaborolane (1.1 g, 4.3 mmol), KOAc (470 mg, 4.8 mmol), Pd$_2$(dba)$_3$ (59 mg. 3%), and 1,3,5,7-Tetramethyl-6-phenyl-2,4,8-trioxa-6-phosphaadamantane (62 mg, 10%) was suspended in anhydrous dioxane (14 mL). The stirred mixture was capped and purged with N$_2$ for 6 min using an oil bubbler as an outlet. After the N$_2$ inlet and outlet were removed, the capped flask was stirred at 70° C. for 3 hr. After cooling to ~35° C., the rxn mixture was filtered through a short plug of celite; the celite plug was washed with EtOAc (75 mL). The filtrate was treated with H$_2$O and extracted with EtOAc; the combined organic layers were washed with brine, dried over Na$_2$SO$_4$, filtered and concentrated in vacuo to afford a tan residue. The residue was purified by silica gel CC using a gradient of EtOAc (5 to 100%) in hexanes to afford the title compound (527 mg, 65%). LCMS (M+H)$^+$: 382.

Step 5: N-[4-(cyclopropylmethoxy)-3-(6-methyl-7-oxofuro[2,3-c]pyridin-4-yl)phenyl]ethanesulfonamide

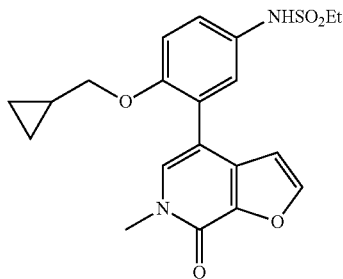

A mixture of N-[4-(cyclopropylmethoxy)-3-(tetramethyl-1,3,2-dioxaborolan-2-yl)phenyl]ethane-1-sulfonamide (138 mg, 0.38 mmol), 4-bromo-6-methyl-6H,7H-furo[2,3-c]pyridine-7-one (75 mg, 0.33 mmol), K$_3$PO$_4$ (175 mg, 0.83 mmol), Pd(dppf)Cl$_2$ (24 mg, 10%) in dioxane (2.2 mL) and H$_2$O (200 µL) was bubbled with N$_2$ for 5 min. The sealed vial was stirred at 70° C. for 4 hr. After the rxn mixture was filtered through a short plug of celite, the celite plug was washed with EtOAc (15 mL). The filtrate was washed with H$_2$O and brine; the organic layer was dried over Na$_2$SO$_4$, filtered and concentrated in vacuo to afford a tan residue. The resulting residue was purified by prep-HPLC to afford the title compound (21 mg, 16%) as a tan solid. $^1$H NMR (400 MHz, DMSO-d$_6$): δ ppm 0.15-0.28 (m, 2H) 0.35-0.52 (m, 2H) 0.95-1.13 (m, 1H) 1.14-1.26 (m, 3H) 2.98-3.09 (m, 2H) 3.57-3.65 (m, 3H) 3.77-3.87 (m, 2H) 7.04-7.22 (m, 3H) 7.55-7.64 (m, 1H) 8.05-8.17 (m, 1H) 9.49-9.57 (m, 1H). LCMS (M+H)$^+$: 403.

Example 256: N-[6-(2,4-difluorophenoxy)-5-(6-methyl-7-oxofuro[2,3-c]pyridin-4-yl)pyridine-3-yl]ethanesulfonamide Step 1:
3-bromo-2-(2,4-difluorophenoxy)-5-nitropyridine

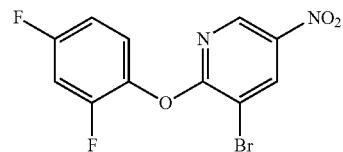

A soln of 3-bromo-2-chloro-5-nitropyridine (2.4 g, 10 mmol) and 2,4-difluorophenol (1 mL, 11 mmol) in NMP (20 ml) was treated with cesium carbonate (3.9 g, 12 mmol). The resulting mixture was heated to 60° C. for 12 hr. The mixture was treated with H$_2$O (100 ml) and extracted with EtOAc (3×50 ml); the combined organic extracts were washed with satd bicarbonate soln (aq), dried over Na$_2$SO$_4$, filtered and concentrated in vacuo to afford a yellow solid. The solid was purified by silica gel CC (gradient of 5 to 30% EtOAc in hexanes) to afford the free base of the title compound (2 g, 59%) as a yellow solid. LCMS (M+H)$^+$: 332.

Step 2:
5-bromo-6-(2,4-difluorophenoxy)pyridin-3-amine

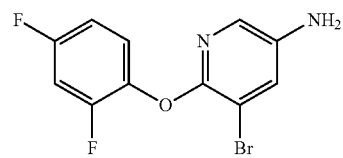 [SMILES: Nc1cnc(Oc2ccc(F)cc2F)c(Br)c1]

A mixture of 3-bromo-2-(2,4-difluorophenoxy)-5-nitropyridine (1.9 g, 5.9 mmol), ammonium chloride (637 mg, 11.8 mmol), and iron powder (1.65 g, 30 mmol) suspended in THF (10 mL), H$_2$O (3 mL), and EtOH (10 mL) was heated to 90° C. using microwave irradiation (normal) for 5 hr. The crude rxn mixture was filtered through a short plug of celite; the celite plug was washed with warm (50° C.) MeOH (~50 mL). The resulting filtrate was concentrated in vacuo. The resulting residue was diluted with EtOAc (100 ml) and washed with satd bicarbonate soln (aq), dried over anhydrous magnesium sulfate, filtered, and concentrated in vacuo to afford the title compound, (824 mg, 46%). LCMS (M+H)$^+$: 302.

Step 3: 6-(2,4-difluorophenoxy)-5-(4,4,5,5-tetramethyl-1,3,2-dioxaborolan-2-yl)pyridine-3-amine

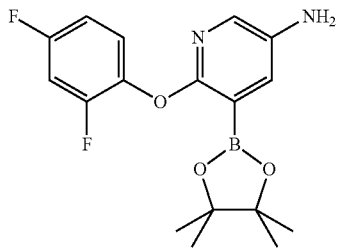 [SMILES: CC1(C)OB(c2cc(N)cnc2Oc2ccc(F)cc2F)OC1(C)C]

A mixture of 5-bromo-6-(2,4-difluorophenoxy)pyridin-3-amine (400 mg, 1.33 mmol), 4,4,5,5-tetramethyl-2-(tetramethyl-1,3,2-dioxaborolan-2-yl)-1,3,2-dioxaborolane (675 mg, 2.7 mmol), KOAc (325 mg, 3.3 mmol), Pd$_2$(dba)$_3$ (36 mg, 3%), and 1,3,5,7-tetramethyl-6-phenyl-2,4,8-trioxa-6-phosphaadamantane (38 mg, 10%) was suspended in dioxane (9 mL). The stirred rxn mixture was capped and purged with N$_2$ for 5 to 7 min using an oil bubbler as an outlet. After the N$_2$ inlet and outlet were removed, the capped vial was stirred at 80° C. for 3 hr. After cooling to room temp, the rxn mixture was filtered through a short plug of celite; the celite plug was washed with EtOAc (50 mL). The filtrate was treated with H$_2$O and extracted with EtOAc; the combined organic layers were washed with brine, dried over Na$_2$SO$_4$, filtered and concentrated in vacuo to afford a tan residue. The residue was purified by silica gel CC using a gradient (20-70%) of EtOAc in hexanes to afford the title compound (163 mg, 35%). LCMS (M+H)$^+$: 349.

Step 4: N-[6-(2,4-difluorophenoxy)-5-(4,4,5,5-tetramethyl-1,3,2-dioxaborolan-2-yl)pyridin-3-yl]ethanesulfonamide

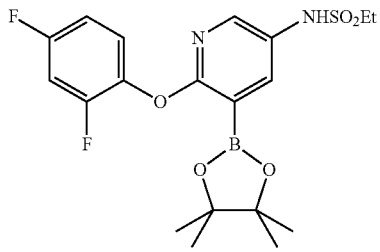

Ethylsulfonyl chloride (50 μL, 52 mmol) was added to a stirred soln of 6-(2,4-difluorophenoxy)-5-(4,4,5,5-tetramethyl-1,3,2-dioxaborolan-2-yl)pyridin-3-amine (163 mg, 0.5 mmol) and pyridine (113 μL) in DCM (2.4 mL) at 0° C. under N$_2$. After the mixture was allowed to warm to room temp and stir for 12 hr, it was treated with H$_2$O (15 mL) and extracted with DCM (3×15 mL); the combined organic extracts were washed with satd bicarbonate soln (aq), dried over Na$_2$SO$_4$, filtered and concentrated in vacuo. The resulting residue was purified by CC using a gradient of EtOAc (0 to 100%) in DCM to afford the title compound (181 mg, 88%) as a tan solid. LCMS (M+H)$^+$: 441.

Step 5: N-[6-(2,4-difluorophenoxy)-5-(6-methyl-7-oxofuro[2,3-c]pyridin-4-yl)pyridin-3-yl]ethanesulfonamide

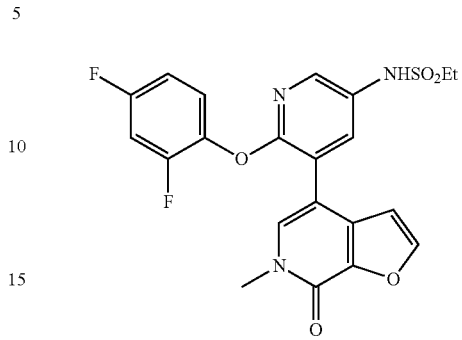

A mixture of N-[6-(2,4-difluorophenoxy)-5-(4,4,5,5-tetramethyl-1,3,2-dioxaborolan-2-yl)pyridin-3-yl]ethanesulfonamide (145 mg, 0.38 mmol), 4-bromo-6-methyl-6H,7H-furo[2,3-c]pyridin-7-one (75 mg, 0.33 mmol), K$_3$PO$_4$ (175 mg, 0.83 mmol), Pd(dppf)Cl$_2$ (24 mg, 10%) in dioxane/H$_2$O (2.2 mL/200 μL) was bubbled with N$_2$ for 5 min. The sealed vial was stirred at 70° C. for 4 hr. After the rxn mixture was filtered through a short plug of celite, the plug was washed with EtOAc (15 mL). The filtrate was washed with H$_2$O and brine, the organic layer was dried over Na$_2$SO$_4$, filtered and concentrated in vacuo to afford a tan residue. The resulting residue was purified by prep-HPLC to afford the title compound (50 mg, 33%) as a white solid. $^1$H NMR (400 MHz, DMSO-d$_6$): δ ppm 1.18-1.28 (m, 3H) 3.10-3.21 (m, 2H) 3.59-3.65 (m, 3H) 6.85-6.95 (m, 1H) 7.07-7.19 (m, 1H) 7.35-7.51 (m, 2H) 7.73-7.79 (m, 1H) 7.80-7.85 (m, 1H) 7.90-7.97 (m, 1H) 8.14-8.20 (m, 1H) 9.78-10.09 (m, 1H). LCMS (M+H)$^+$: 461.

Example 257: N-[6-(cyclopropylmethoxy)-5-(6-methyl-7-oxofuro[2,3-c]pyridin-4-yl)pyridine-3-yl]ethanesulfonamide

Step 1: 3-bromo-2-(cyclopropylmethoxy)-5-nitropyridine

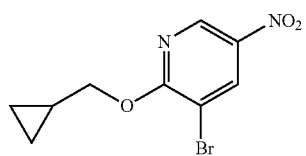 [SMILES: O=[N+]([O-])c1cnc(OCC2CC2)c(Br)c1]

A soln of 3-bromo-2-chloro-5-nitropyridine (2.4 g, 10 mmol) and cyclopropylmethanol (970 μL, 12 mmol) in THF (50 ml) was treated with KOtBu (3.3 g, 15 mmol). After stirring at room temp for 12 hr, the mixture was treated with H$_2$O (150 ml) and extracted with EtOAc (3×50 ml); the combined organic extracts were washed with brine, dried over Na$_2$SO$_4$, filtered and concentrated in vacuo to afford a yellow solid. The solid was purified by CC using EtOAc (5% to 30%) in hexanes to afford the title compound (1.3 g, 48%) as a yellow solid. LCMS (M+H)$^+$: 274.

Step 2:
5-bromo-6-(cyclopropylmethoxy)pyridin-3-amine

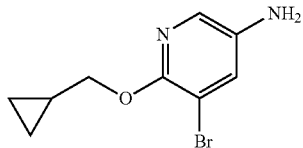

A mixture of 3-bromo-2-(cyclopropylmethoxy)-5-nitropyridine (1 g, 3.7 mmol), ammonium chloride (600 mg, 11.1 mmol), and iron powder (1.05 g, 19 mmol) suspended in THF (6.2 mL), H$_2$O (2.3 mL) and EtOH (6.2 mL) was heated to 100° C. using microwave irradiation (normal) for 5 hr. The crude rxn mixture was filtered through a short plug of celite; the celite plug was washed with warm (50° C.) MeOH (50 mL). The resulting filtrate was concentrated in vacuo. The resulting residue was diluted with EtOAc (100 ml) and washed with satd bicarbonate soln (aq), dried over anhydrous magnesium sulfate, filtered, and concentrated in vacuo to afford the title compound, (539 mg, 60%). LCMS (M+H)$^+$: 244.

Step 3: N-[5-bromo-6-(cyclopropylmethoxy)pyridin-3-yl]ethanesulfonamide

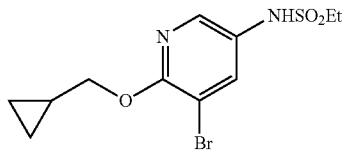

Ethylsulfonyl chloride (170 μL, 1.8 mmol) was added to a stirred soln of 5-bromo-6-(cyclopropylmethoxy)pyridin-3-amine (440 mg, 1.8 mmol) and pyridine (725 μL) in DCM (4.5 mL) at 0° C. under N$_2$. After the mixture was allowed to warm to room temp and stirred for 12 hr, it was treated with 1N HCl (15 mL) and extracted with DCM (3×15 mL); the combined organic extracts were washed with satd bicarbonate soln (aq), dried over Na$_2$SO$_4$, filtered and concentrated in vacuo. The resulting residue was purified by silica gel CC using a gradient of EtOAc (0 to 100%) in DCM to afford the title compound (181 mg, 88%) as a tan solid. LCMS (M+H)$^+$: 336.

Step 4: N-[6-(cyclopropylmethoxy)-5-(4,4,5,5-tetramethyl-1,3,2-dioxaborolan-2-yl)pyridin-3-yl]ethanesulfonamide

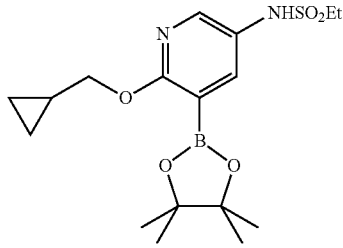

A mixture of N-[5-bromo-6-(cyclopropylmethoxy)pyridin-3-yl]ethanesulfonamide (150 mg, 0.45 mmol), 4,4,5,5-tetramethyl-2-(tetramethyl-1,3,2-dioxaborolan-2-yl)-1,3,2-dioxaborolane (285 mg, 1.13 mmol), KOAc (132 mg, 1.35 mmol), and Pd(dppf)$_2$(Cl)$_2$ (33 mg, 10%) was suspended in anhydrous dioxane (5 mL). The stirred rxn mixture was capped and purged with N$_2$ for 5 min using an oil bubbler as an outlet. After the N$_2$ inlet and outlet were removed, the capped vial was stirred at 70° C. for 3 hr. After cooling to room temp, the rxn mixture was filtered through a short plug of celite; the celite plug was washed with EtOAc. The filtrate was treated with H$_2$O and separated; after the aq layer was washed with EtOAC (3×25 mL), the combined organic layers were washed with brine, dried over Na$_2$SO$_4$, filtered and concentrated in vacuo to afford a dark tan residue. The residue was purified by silica gel CC using a gradient of 5 to 70% EtOAc in hexanes to afford the title compound (112 mg, 65%). LCMS (M+H)$^+$: 383.

Step 5: N-[6-(cyclopropylmethoxy)-5-(6-methyl-7-oxofuro[2,3-c]pyridin-4-yl)pyridin-3-yl]ethanesulfonamide

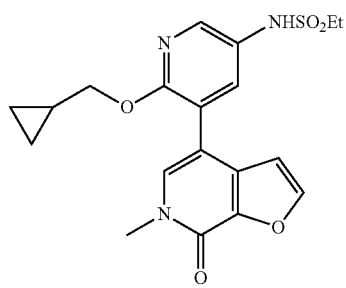

A mixture of N-[6-(cyclopropylmethoxy)-5-(4,4,5,5-tetramethyl-1,3,2-dioxaborolan-2-yl)pyridin-3-yl]ethanesulfonamide (145 mg, 0.38 mmol), 4-bromo-6-methyl-6H,7H-furo[2,3-c]pyridin-7-one (25 mg, 0.11 mmol), K$_3$PO$_4$ (58 mg, 0.28 mmol), Pd(dppf)Cl$_2$ (8 mg, 10%) in dioxane/H$_2$O (1 mL/100 μL) was bubbled with N$_2$ for 5 min. The sealed vial was stirred at 65° C. for 12 hr. The rxn mixture was filtered through a short plug of celite; the celite plug was washed with EtOAc (15 mL). The filtrate was washed with H$_2$O and brine; the organic layer was dried over Na$_2$SO$_4$, filtered and concentrated in vacuo to afford a tan residue. The resulting residue was purified by prep-HPLC to afford the title compound (21 mg, 48%) as a white solid. $^1$H NMR (400 MHz, DMSO-d$_6$): δ ppm 0.23-0.32 (m, 2H) 0.41-0.52 (m, 2H) 1.08-1.19 (m, 1H) 1.20-1.29 (m, 3H) 3.05-3.16 (m, 2H) 3.58-3.63 (m, 3H) 3.64-3.66 (m, 1H) 4.08-4.17 (m, 2H) 6.72-6.82 (m, 1H) 7.58-7.65 (m, 1H) 7.67-7.73 (m, 1H) 7.95-8.06 (m, 1H) 8.10-8.18 (m, 1H) 9.41-9.86 (m, 1H). LCMS (M+H)$^+$: 404.

Example 258: 6-methyl-4-[5-(methylsulfonylmethyl)-2-(2,2-trifluoroethoxy)phenyl]furo[2,3-c]pyridin-7-one

Step 1: 6-methyl-4-(4,4,5,5-tetramethyl-1,3,2-dioxaborolan-2-yl)furo[2,3-c]pyridin-7-one

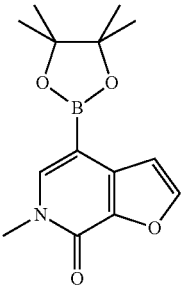 [SMILES: Cn1cc(B2OC(C)(C)C(C)(C)O2)c2ccoc2c1=O]

A soln of 4-bromo-6-methylfuro[2,3-c]pyridin-7-one (200 mg, 0.88 mmol), 4,4,5,5-tetramethyl-2-(tetramethyl-1,3,2-dioxaborolan-2-yl)-1,3,2-dioxaborolane (447 mg, 1.76 mmol), KOAc (259 mg, 2.64 mmol), $Pd_2(dba)_3$ (82 mg, 0.09 mmol), X-Phos (52 mg, 0.11 mmol) in dioxane (5 mL) was bubbled with $N_2$ for 5 min and then stirred at 70° C. for 12 hr. The rxn mixture was concentrated, treated with DCM (30 mL), washed with $H_2O$ (30 mL) and brine (30 mL), dried over $Na_2SO_4$, filtered and concentrated. The residue was purified by column chromatog (PE:EA=20:1~5:1) to give the title compound (130 mg, 54%) as a gray solid. $^1$H NMR (CDCl$_3$, 400 MHz): δ 7.73 (s, 1H) 7.62 (s, 1H) 7.01 (s, 1H) 3.68 (s, 3H) 1.35 (s, 12H). LCMS (M+H)$^+$: 276.

Step 2: 6-methyl-4-[5-(methylsulfonylmethyl)-2-(2,2,2-trifluoroethoxy)phenyl]furo[2,3-c]pyridin-7-one

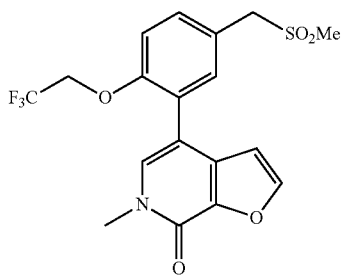 [SMILES: Cn1cc(-c2cc(CS(C)(=O)=O)ccc2OCC(F)(F)F)c2ccoc2c1=O]

A mixture of 2-bromo-4-(methylsulfonylmethyl)-1-(2,2,2-trifluoroethoxy)benzene (100 mg, 0.29 mmol), 6-methyl-4-(4,4,5,5-tetramethyl-1,3,2-dioxaborolan-2-yl)furo[2,3-c]pyridin-7-one (96 mg, 0.35 mmol), $K_3PO_4$ (184 mg, 0.87 mmol), Pd(dppf)Cl$_2$ (22 mg, 10%) in dioxane/H$_2$O (2 mL/1 mL) was bubbled with $N_2$ for 5 min. The sealed vial was heated at 70° C. for 2 hr. The rxn mixture was filtered through a short plug of celite; the celite plug was washed with EtOAc (15 mL). The filtrate was washed with H$_2$O and brine; the organic layer was dried over Na$_2$SO$_4$, filtered and concentrated in vacuo. The resulting residue was purified by prep-HPLC to afford the title compound (40 mg, 33%) as an off-white solid. $^1$H NMR (CDCl$_3$, 400 MHz): δ 7.76 (d, J=2.0 Hz, 1H) 7.53 (d, J=2.0 Hz, 1H) 7.41-7.38 (m, 1H) 7.37 (s, 1H) 7.02 (d, J=8.4, 1H) 6.72 (d, J=2.0 Hz, 2H) 4.37 (q, J=8.0 Hz, 2H) 4.27 (s, 2H) 3.73 (s, 3H) 2.89 (s, 3H). LCMS (M+H)$^+$: 416.

Example 259: 4-[3-(cyclopropylmethoxy)-6-methylsulfonylpyridin-2-yl]-6-methylfuro[2,3-c]pyridin-7-one

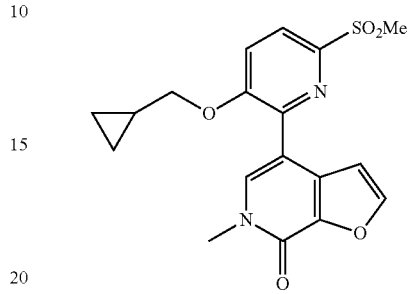

A mixture of 6-methyl-4-(4,4,5,5-tetramethyl-1,3,2-dioxaborolan-2-yl)furo[2,3-c]pyridin-7-one (50 mg, 0.18 mmol), 3-(cyclopropylmethoxy)-2-iodo-6-methylsulfonylpyridine (53 mg, 0.15 mmol), K$_3$PO$_4$ (114 mg, 0.54 mmol), Pd(dppf)Cl$_2$ (13 mg, 0.018 mmol) in dioxane (5 mL) was bubbled with N$_2$ for 5 min and then stirred at 70° C. for 12 hr. The rxn mixture was concentrated, treated with DCM (30 mL), washed with H$_2$O (30 mL) and brine (30 mL), dried over Na$_2$SO$_4$, filtered and concentrated. The residue was purified by prep-HPLC to give the title compound (35 mg, yield: 52%) as an off-white solid. $^1$H NMR (CDCl$_3$, 400 MHz): δ 8.42 (s, 1H) 8.10 (s, 1H) 7.81 (d, J=1.6 Hz, 1H) 7.51 (s, 1H) 6.66 (d, J=1.6 Hz, 1H) 4.08 (d, J=7.6 Hz, 2H) 3.77 (s, 3H) 3.26 (s, 3H) 1.26-1.19 (m, 1H) 0.68-0.63 (m, 2H) 0.37-0.33 (m, 2H). LCMS (M+H)$^+$: 375.

Example 260: 2-chloro-4-[2-(cyclopropylmethoxy)-5-methylsulfonylphenyl]-6-methylfuro[2,3-c]pyridin-7-one

Step 1: 2-chloro-7-methoxyfuro[2,3-c]pyridine

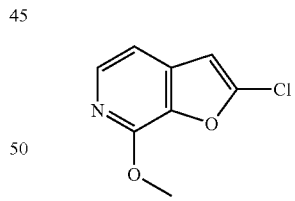

A 0.13 M soln of 7-methoxyfuro[2,3-c]pyridine (250 mg, 1.7 mmol) in THF stirred at −78° C. under an atmosphere of N$_2$ was treated with n-BuLi (1.6M in hexanes, 450 µL, 5.2 mmol) dropwise over 30 sec. The mixture was warmed gradually to −15° C. over a period of 7-10 min. After 1 hr at −15° C., the mixture was cooled to −65° C. and was treated with a 0.26 M soln of hexachloroethane (473 mg, 2 mmol) in THF by dropwise addition over 3 min. After stirring at −65° C. for 15 min, the mixture was gradually warmed to room temp. After the mixture was allowed to stir overnight, it was quenched with H$_2$O (5 mL) and extracted with EtOAc (3×15 ml). The combined organic layers were washed brine (10 mL), dried over Na$_2$SO$_4$, filtered and concentrated in vacuo. The resulting residue was purified by silica gel CC using a gradient of EtOAc (5 to 30%) in hexanes to afford the title compound (266 mg, 87%) as an amber oil. ¹H NMR (400 MHz, DMSO-d₆): δ ppm 3.99-4.08 (m, 3H) 7.13 (s, 1H) 7.25 (d, J=5.31 Hz, 1H) 7.95 (d, J=5.31 Hz, 1H). LCMS (M+H)⁺: 184.

Step 2: 2-chlorofuro[2,3-c]pyridin-7-ol

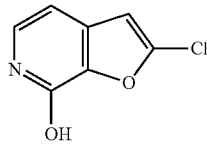 [SMILES: Oc1nccc2cc(Cl)oc12]

A 0.25M soln of 2-chloro-7-methoxyfuro[2,3-c]pyridine (263 mg, 1.4 mmol) in DCM stirred at −0° C. under an atmosphere of N₂ was treated with BBr₃ (1 M in DCM, 4.3 mL, 4.3 mmol) dropwise over 5 min. The mixture was allowed to warm gradually to room temp. After the mixture was allowed to stir overnight, it was poured into ice-water and extracted with DCM (3×15 mL). The combined organic layers were washed with H₂O and brine (10 mL), dried over Na₂SO₄, filtered and concentrated in vacuo. The resulting residue was purified by silica gel CC using a gradient of EtOAc (15 to 75%) in hexanes to afford the title compound (115 mg, 47%) as light yellow solid. LCMS (M+H)⁺: 170.

Step 3: 4-bromo-2-chlorofuro[2,3-c]pyridin-7-ol

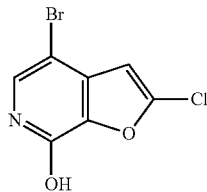 [SMILES: Oc1ncc(Br)c2cc(Cl)oc12]

A 0.15 M soln of 2-chlorofuro[2,3-c]pyridin-7-ol (113 mg, 0.7 mmol) in DMF stirred in the dark at 0° C. under an atmosphere of N₂ was treated with NBS (120 mg, 0.7 mmol) in three equal portions. The icebath was removed; the mixture was stirred at room temp for 3 hr. The rxn mixture was treated with a 10% aq soln of sodium thiosulfate (5 ml) and was extracted with EtOAc (3×30 mL). The combined organic layers were washed with H₂O (15 mL), brine (20 mL), dried over Na₂SO₄, filtered, and concentrated in vacuo. The residue was purified by chromatography on silica gel (hexanes:EtOAc=4:1) to afford the title compound (145 mg, 87%) as a white solid. LCMS (M+H)⁺: 249.

Step 4: 4-bromo-2-chloro-6-methylfuro[2,3-c]pyridin-7-one

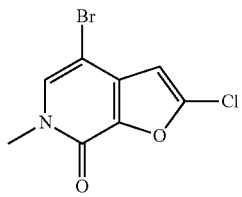

A 0.2 M soln of 4-bromo-2-chlorofuro[2,3-c]pyridin-7-ol (143 mg, 0.6 mmol) and K₂CO₃ (200 mg, 1.45 mmol) in DMF stirred at 0° C. under N₂ was treated with MeI (99 mg, 0.7 mmol). The icebath was removed and the mixture stirred at room temp overnight. The rxn mixture was treated H₂O (15 mL) and extracted with EtOAc (3×10 mL). The combined organic layers were washed with H₂O (15 mL), brine (20 mL), dried over Na₂SO₄, filtered, and concentrated in vacuo. The residue was purified by chromatography on silica gel using a gradient of EtOAc (10% to 100%) in hexanes to afford the title compound (113 mg, 85%) as a white solid. LCMS (M+H)⁺: 263.

Step 5: 2-chloro-4-[2-(cyclopropylmethoxy)-5-methylsulfonylphenyl]-6-methylfuro[2,3-c]pyridin-7-one

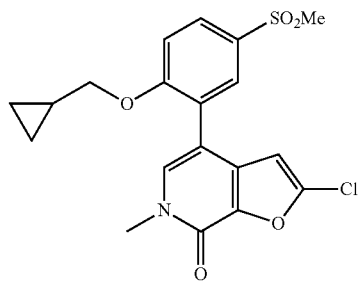 [SMILES: Cn1cc(-c2cc(S(C)(=O)=O)ccc2OCC2CC2)c2cc(Cl)oc2c1=O]

A mixture of 2-[2-(cyclopropylmethoxy)-5-methylsulfonylphenyl]-4,4,5,5-tetramethyl-1,3,2-dioxaborolane (33 mg, 0.09 mmol), 4-bromo-2-chloro-6-methylfuro[2,3-c]pyridin-7-one (25 mg, 0.09 mmol), K₃PO₄ (50 mg, 0.24 mmol), Pd(dppf)Cl₂ (7 mg, 10%) in dioxane/H₂O (700 μL/70 μL) was bubbled with N₂ for 5 min. The sealed vial was stirred at 70° C. for 90 min. The rxn mixture was filtered through a short plug of celite; the celite plug was washed with EtOAc (10 mL). The filtrate was washed with H₂O and brine; the organic layer was dried over Na₂SO₄, filtered and concentrated in vacuo to afford a tan residue. The resulting residue was purified by prep-HPLC to afford the title compound (27 mg, 69%) as an off-white solid. ¹H NMR (400 MHz, DMSO-d₆): δ ppm 0.23-0.34 (m, 2H) 0.44-0.55 (m, 2H) 1.00-1.13 (m, 1H) 3.19-3.24 (m, 3H) 3.61 (s, 3H) 3.94-4.05 (m, 2H) 6.82-6.89 (m, 1H) 7.10-7.16 (m, 1H) 7.26-7.35 (m, 1H) 7.70-7.78 (m, 1H) 7.87-7.94 (m, 1H). LCMS (M+H)⁺: 409.

Example 261: 2-fluoro-4-[2-(cyclopropylmethoxy)-5-methylsulfonylphenyl]-6-methylfuro[2,3-c]pyridin-7-one Step 1: 2-fluoro-7-methoxyfuro[2,3-c]pyridine

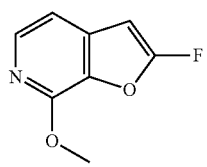

The title compound was prepared in a manner similar to step 1 of Example 260, by substituting N-Fluorobenzenesulfonamide for hexachloroethane. ¹H NMR (400 MHz, DMSO-d₆): δ ppm 4.01 (s, 3H) 6.46 (m, 1H) 7.25 (d, J=5.4 Hz, 1H) 7.96 (d, J=5.4 Hz, 1H). LCMS (M+H)⁺: 168.

Step 2: 2-fluorofuro[2,3-c]pyridin-7-ol

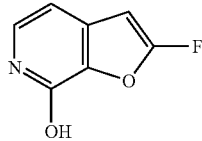 [SMILES: Oc1nccc2cc(F)oc12]

The title compound was prepared in a manner similar to step 2 of Example 260, by substituting 2-fluoro-7-methoxyfuro[2,3-c]pyridine for 2-chloro-7-methoxyfuro[2,3-c]pyridine. LCMS (M+H)⁺: 154.

Step 3: 4-bromo-2-fluorofuro[2,3-c]pyridin-7-ol

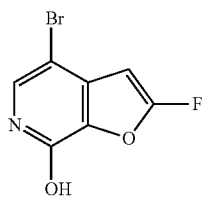 [SMILES: Oc1ncc(Br)c2cc(F)oc12]

The title compound was prepared in a manner similar to step 3 of Example 260, by substituting 2-fluorofuro[2,3-c]pyridin-7-ol for 2-chlorofuro[2,3-c]pyridin-7-ol. LCMS (M+H)⁺: 233.

Step 4: 4-bromo-2-fluoro-6-methylfuro[2,3-c]pyridin-7-one

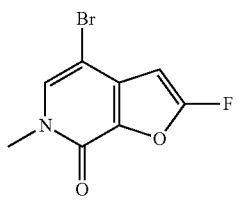

The title compound was prepared in a manner similar to step 4 of Example 260, by substituting 4-bromo-2-fluorofuro[2,3-c]pyridin-7-ol for 4-bromo-2-chlorofuro[2,3-c]pyridin-7-ol. LCMS: (M+H)⁺247.

Step 5: 2-fluoro-4-[2-(cyclopropylmethoxy)-5-methylsulfonylphenyl]-6-methylfuro[2,3-c]pyridin-7-one

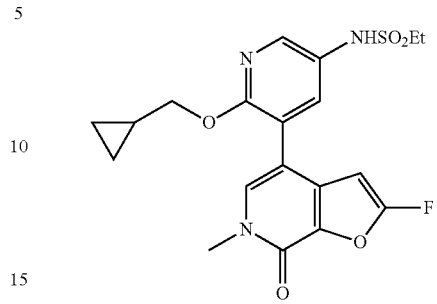

A mixture of N-[6-(cyclopropylmethoxy)-5-(4,4,5,5-tetramethyl-1,3,2-dioxaborolan-2-yl)pyridin-3-yl]ethanesulfonamide (31 mg, 0.08 mmol), 4-bromo-2-fluoro-6-methylfuro[2,3-c]pyridin-7-one (20 mg, 0.08 mmol), K₃PO₄ (36 mg, 0.17 mmol), Pd(dppf)Cl₂ (6 mg, 8%) in dioxane/H₂O (830 μL/100 μL) was bubbled with N₂ for 10 min. The sealed vial was stirred at 67° C. for 90 min. The rxn mixture was filtered through a short plug of celite; the celite plug was washed with EtOAc (15 mL). The filtrate was washed with H₂O and brine; the organic layer was dried over Na₂SO₄, filtered and concentrated in vacuo to afford a tan residue. The resulting residue was purified by CC using MeOH (0% to 2%) in DCM. The fractions were combined and concentrated in vacuo to afford a white solid (10 mg). The solid had a minor impurity (LCMS (M+H)⁺: 578); therefore, it was diluted in MeOH (1 mL) and 1N NaOH(aq) (500 μL) and purified by prep-HPLC to afford the title compound (6 mg, 17%) as a white solid. ¹H NMR (400 MHz, DMSO-d₆): δ ppm 0.28 (m, 2H) 0.43-0.58 (m, 2H) 0.56-0.58 (m, 1H) 1.24 (m, 3H) 3.09 (m, 2H) 3.60 (s, 3H) 4.12 (m, 2H) 6.16-6.34 (m, 1H) 7.52-7.72 (m, 1H) 7.77 (s, 1H) 7.90-8.14 (m, 1H) 9.37-10.62 (bs, 1H). LCMS (M+H)⁺: 422.

Example 262: N-[5-(2,4-difluorophenoxy)-4-(6-methyl-7-oxofuro[2,3-c]pyridin-4-yl)pyrimidin-2-yl]methanesulfonamide Step 1: 4-[5-(2,4-difluorophenoxy)-2-methylsulfonylpyrimidin-4-yl]-6-methylfuro[2,3-c]pyridin-7-one

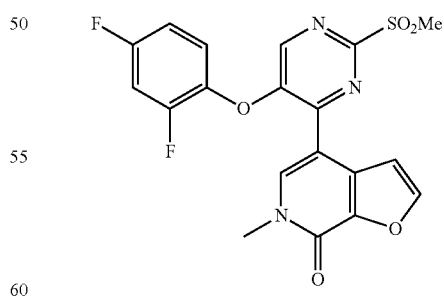

A mixture of 4-chloro-5-(2,4-difluorophenoxy)-2-methylsulfonylpyrimidine (155 mg, 0.48 mmol), 4-bromo-2-fluoro-6-methylfuro[2,3-c]pyridin-7-one (120 mg, 0.44 mmol), NaHCO₃ (92 mg, 1.1 mmol), Pd(dppf)Cl₂ (32 mg, 10%) in dioxane/H₂O (4 mL/200 μL) was bubbled with N₂ for 7 min. The sealed vial was stirred at 70° C. for 8 hr.

LCMS analysis showed complete consumption of the limiting reagent. The rxn mixture was filtered through a short plug of celite; the celite plug was washed with DCM. The filtrate was concentrated in vacuo. The resulting residue was purified by CC using EtOAc (10 to 100%) in DCM to afford the title compound (151 mg, 79%) as a yellow solid. LCMS (M+H)+: 434.

Step 2: N-[5-(2,4-difluorophenoxy)-4-(6-methyl-7-oxofuro[2,3-c]pyridin-4-yl)pyrimidin-2-yl]methanesulfonamide

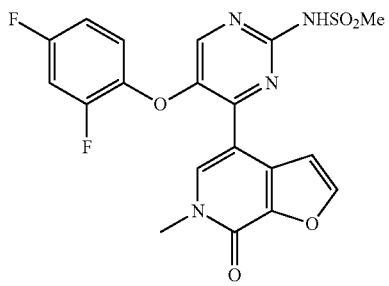

A soln of methanesulfonamide (61 mg, 0.65 mmol) in DMF (2 mL) stirred at 0° C. under $N_2$ was treated with NaH (99 mg, 0.7 mmol). After the icebath was removed, the mixture was stirred at room temp for 15 min. The resulting suspension was treated with a soln of 4-[5-(2,4-difluorophenoxy)-2-methylsulfonylpyrimidin-4-yl]-6-methylfuro[2,3-c]pyridin-7-one (70 mg, 0.16 mmol) in DMF (1 mL). After the $N_2$ inlet was removed, the capped mixture was heated to 70° C. for 3 hr. After cooling to 0° C., the rxn mixture was stirred vigorously and treated $H_2O$ (500 μL). After 5 min, the cooled mixture was treated with 1N $HCl_{(aq)}$ (1 mL). The resulting suspension was filtered; the filter cake was washed with additional 1N $HCl_{(aq)}$ (1 mL) and isopropyl ether (5 mL) to afford the title compound (50 mg, 70%) as an off-white solid. $^1$H NMR (400 MHz, DMSO-d6): δ ppm 3.34 (s, 3H) 3.60 (s, 3H) 7.06 (m, 1H) 7.28 (m, 1H) 7.49 (m, 1H) 7.80 (s, 1H) 8.23 (s, 1H) 8.43 (m, 2H) 11.50 (bs, 1H). LCMS (M+H)+: 449.

Example 263: N-[5-(2,4-difluorophenoxy)-4-(6-methyl-7-oxofuro[2,3-c]pyridin-4-yl)pyrimidin-2-yl]ethanesulfonamide

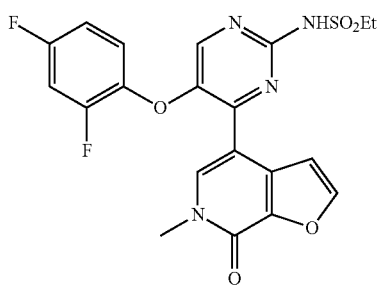

The title compound (46 mg, 62%) was prepared in a manner similar to step 2 of Example 262, by substituting ethanesulfonamide for methanesulfonamide. $^1$H NMR (400 MHz, DMSO-d6): δ ppm 1.20-1.27 (m, 3H) 3.43-3.57 (m, 2H) 3.57-3.67 (s, 3H) 7.00-7.13 (m, 1H) 7.20-7.37 (m, 1H) 7.41-7.54 (m, 1H) 7.72-7.87 (m, 1H) 8.15-8.28 (m, 1H) 8.30-8.49 (m, 2H) 11.25-11.48 (bs, 1H). LCMS: (M+H)+ 463.

Example 264: N-[5-(cyclopropylmethoxy)-4-(6-methyl-7-oxofuro[2,3-c]pyridin-4-yl)pyrimidin-2-yl]ethanesulfonamide Step 1: 4-[5-(cyclopropylmethoxy)-2-methylsulfonylpyrimidin-4-yl]-6-methylfuro[2,3-c]pyridin-7-one

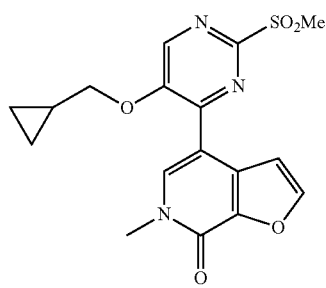 [SMILES: Cn1cc(-c2nc(S(C)(=O)=O)ncc2OCC2CC2)c2ccoc2c1=O]

The title compound was prepared in a manner similar to step 1 of Example 262, by substituting 4-chloro-5-(cyclopropylmethoxy)-2-methylsulfonylpyrimidine for 4-chloro-5-(2,4-difluorophenoxy)-2-methylsulfonylpyrimidine. LCMS (M+H)+: 376.

Step 2: N-[5-(cyclopropylmethoxy)-4-(6-methyl-7-oxofuro[2,3-c]pyridin-4-yl)pyrimidin-2-yl]ethanesulfonamide

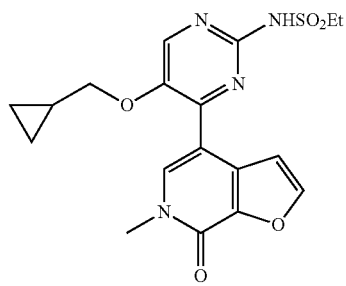

The title compound was prepared in a manner similar to step 2 of Example 262, by substituting ethanesulfonamide for methanesulfonamide and by substituting 4-[5-(cyclopropylmethoxy)-2-methylsulfonylpyrimidin-4-yl]-6-methylfuro[2,3-c]pyridin-7-one for 4-[5-(2,4-difluorophenoxy)-2-methylsulfonylpyrimidin-4-yl]-6-methylfuro[2,3-c]pyridin-7-one. LCMS (M+H)+: 405.

Example 265: 4-[2-(cyclopropylmethoxy)-5-ethylsulfonylphenyl]-6-methyl-7-oxothieno[2,3-c]pyridine-2-carboxamide

Step 1: Methyl 4-bromo-6-methyl-7-oxothieno[2,3-c]pyridine-2-carboxylate

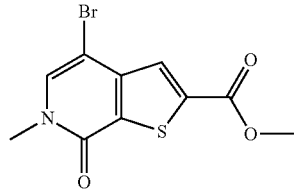

To a soln of methyl 4-bromo-7-hydroxythieno[2,3-c]pyridine-2-carboxylate (300 mg, 1.04 mmol) stirred at 0° C. in DMF (6.6 mL) under $N_2$ was added $K_2CO_3$ (358 mg, 2.6 mmol). After stirring at 0° C. for 15 min, methyl iodide (177 mg, 1.3 mmol) was added dropwise. The icebath was removed, and mixture was stirred at room temp for 20 min, 50° C. for 2 hr, and room temp for another 10 hr. The rxn mixture was treated with $H_2O$ (8 mL) and extracted with EtOAc (30 mL×3). The combined organic layers were washed with brine (30 mL), dried over $Na_2SO_4$, filtered, and concentrated in vacuo. The residue was purified by silica gel chromatography using a gradient of EtOAc (10 to 100%) in DCM to afford the title compound (284 mg, 90%) as a white solid. LCMS (M+H)$^+$: 303.

Step 2: 4-bromo-6-methyl-7-oxothieno[2,3-c]pyridine-2-carboxamide

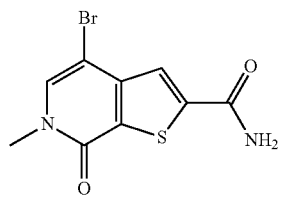

Using a sealed tube, a soln of methyl 4-bromo-6-methyl-7-oxothieno[2,3-c]pyridine-2-carboxylate (250 mg, 65 mmol) in MeOH (6 mL) stirred at room temp was treated with 2N $NH_3$ in MeOH (8 ml). The sealed tube was heated to 45° C. for 60 hr. After cooling to 0° C., the resulting suspension was filtered; the filter cake was washed with cooled (0° C.) MeOH (3 mL) and isopropyl ether (3 mL) to afford the title compound (215 mg, 95%) as a white solid. LCMS (M+H)$^+$: 288.

Step 3: 4-[2-(cyclopropylmethoxy)-5-ethylsulfonylphenyl]-6-methyl-7-oxothieno[2,3-c]pyridine-2-carboxamide

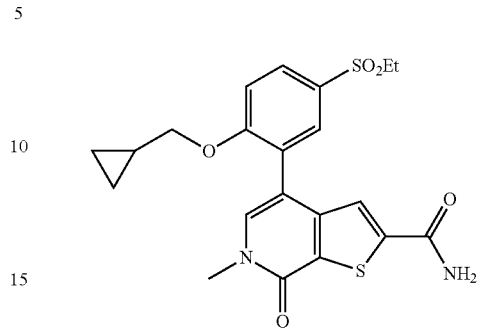

A mixture of 2-[2-(cyclopropylmethoxy)-5-ethylsulfonylphenyl]-4,4,5,5-tetramethyl-1,3,2-dioxaborolane (77 mg, 0.22 mmol), 4-bromo-6-methyl-7-oxothieno[2,3-c]pyridine-2-carboxamide (50 mg, 0.18 mmol), $K_3PO_4$ (93 mg, 0.44 mmol), Pd(dppf)Cl$_2$ (13 mg, 10%) in dioxane/$H_2O$ (1.6 mL/160 µL) was bubbled with $N_2$ for 5 min. The sealed vial was stirred at 65° C. for 3 hr. The rxn mixture was filtered through a short plug of celite; the celite plug was washed with EtOAc (15 mL). The filtrate was washed with $H_2O$ and brine; the organic layer was dried over $Na_2SO_4$, filtered and concentrated in vacuo to afford a tan residue. The resulting residue was purified by prep-HPLC to afford the title compound (20 mg, 26%) as a white solid. $^1$H NMR (400 MHz, DMSO-d$_6$): δ ppm 0.20 (m, 2H) 0.36 (m, 2H) 0.98 (m, 1H) 1.14 (m, 3H) 3.21-3.31 (m, 2H) 3.61 (s, 3H) 3.98 (m, 2H) 7.38 (d, J=8.6 Hz, 1H) 7.65-7.75 (m, 3H) 7.78 (d, J=2.0 Hz, 1H) 7.91 (dd, J=8.6, 2.0 Hz, 1H) 8.24 (s, 1H). LCMS (M+H)$^+$: 447.

Example 266: 4-[2-(cyclopropylmethoxy)-5-(ethylsulfonylamino)phenyl]-6-methyl-7-oxothieno[2,3-c]pyridine-2-carboxamide

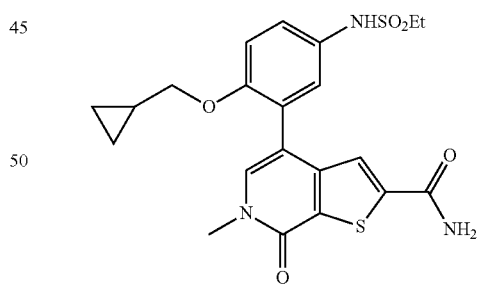

The title compound was prepared in a manner similar to step 3 of Example 265, by substituting N-[4-(cyclopropylmethoxy)-3-(tetramethyl-1,3,2-dioxaborolan-2-yl)phenyl]ethane-1-sulfonamide for 2-[2-(cyclopropylmethoxy)-5-ethylsulfonylphenyl]-4,4,5,5-tetramethyl-1,3,2-dioxaborolane. $^1$H NMR (400 MHz, DMSO-d$_6$): δ ppm 0.09-0.19 (m, 2H) 0.27-0.39 (m, 2H) 0.86-1.02 (m, 1H) 1.18-1.27 (m, 3H) 2.97-3.09 (m, 2H) 3.59 (s, 3H) 3.77-3.86 (m, 2H) 7.07-7.16 (m, 2H) 7.21-7.27 (m, 1H) 7.53-7.58 (m, 1H) 7.61-7.67 (m, 1H) 7.67-7.72 (m, 1H) 8.19-8.30 (m, 1H) 9.46-9.60 (m, 1H). LCMS (M+H)$^+$: 462.

621

Example 267: 4-[2-(cyclopropylmethoxy)-5-methyl-sulfonylphenyl]-6-methyl-7-oxothieno[2,3-c]pyridine-2-carboxamide

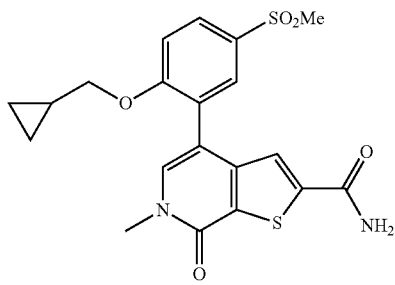 [SMILES: Cn1cc(-c2cc(S(C)(=O)=O)ccc2OCC2CC2)c2cc(C(N)=O)sc2c1=O]

The title compound was prepared in a manner similar to step 3 of Example 265, by substituting 2-[2-(cyclopropylmethoxy)-5-methylsulfonylphenyl]-4,4,5,5-tetramethyl-1,3,2-dioxaborolane for 2-[2-(cyclopropylmethoxy)-5-ethylsulfonylphenyl]-4,4,5,5-tetramethyl-1,3,2-dioxaborolane. $^1$H NMR (400 MHz, DMSO-$d_6$): δ ppm 0.11-0.26 (m, 2H) 0.27-0.41 (m, 2H) 0.89-1.05 (m, 1H) 3.21 (s, 3H) 3.61 (s, 3H) 3.91-4.04 (m, 2H) 7.34-7.41 (m, 1H) 7.63-7.76 (m, 3H) 7.81-7.88 (m, 1H) 7.92-7.99 (m, 1H) 8.21-8.29 (m, 1H). LCMS (M+H)$^+$: 433.

Example 268: 4-[2-(cyclopropylmethoxy)-5-(ethyl-sulfonylamino)pyridin-3-yl]-6-methyl-7-oxothieno[2,3-c]pyridine-2-carboxamide

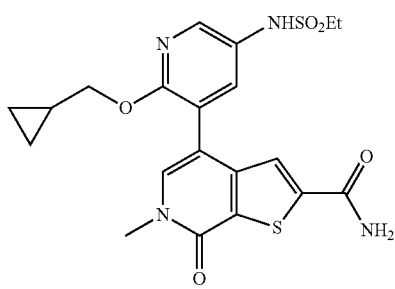

The title compound was prepared in a manner similar to step 3 of Example 265, by substituting N-[6-(cyclopropyl-methoxy)-5-(4,4,5,5-tetramethyl-1,3,2-dioxaborolan-2-yl)pyridin-3-yl]ethane-sulfonamide for 2-[2-(cyclopropyl-methoxy)-5-ethylsulfonylphenyl]-4,4,5,5-tetramethyl-1,3,2-di-oxaborolane. $^1$H NMR (400 MHz, DMSO-$d_6$): δ ppm 0.17-0.35 (m, 2H) 0.39-0.57 (m, 2H) 1.23 (m, 4H) 3.00-3.17 (m, 2H) 3.60 (s, 3H) 4.01-4.26 (m, 2H) 6.11-6.40 (m, 1H) 7.52-7.69 (m, 1H) 7.74-7.84 (m, 1H) 7.94-8.09 (m, 1H) 9.14-10.31 (m, 1H). LCMS: (M+H)$^+$463.

622

Example 269: N-[4-(2,4-difluorophenoxy)-3-(2,6-dimethyl-7-oxofuro[2,3-c]pyridin-4-yl)phenyl]ethanesulfonamide Step 1: 7-methoxy-2-methylfuro[2,3-c]pyridine

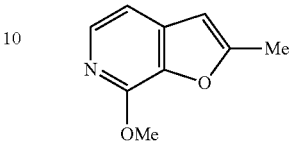

To a soln of 7-methoxyfuro[2,3-c]pyridine (2.9 g, 19.6 mmol) in THF (20 mL) stirred under Ar was added n-BuLi (7.8 mL, 19.6 mmol) at −78° C.; the mixture was transferred to a −30° C. icebath and was stirred for 2 hr. The mixture was cooled to −78° C. and MeI (4.2 g, 29.4 mmol) was added. After the mixture was stirred at room temp for 18 hr, the rxn mixture was quenched with H$_2$O (30 mL) and extracted with DCM (50 mL×3). The combined organic layers were washed with brine (30 mL×3), dried over Na$_2$SO$_4$ and concentrated in vacuo to afford the title compound (3.2 g, 100%) as a yellow solid. The material was carried forward without any further purification. LCMS (M+H)$^+$: 164.

Step 2: 4-bromo-7-methoxy-2-methylfuro[2,3-c]pyridine

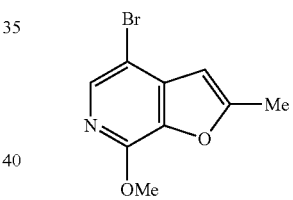

A soln of 7-methoxy-2-methylfuro[2,3-c]pyridine (3.2 g, 19.6 mmol) in ACN (30 mL) was treated with NBS (3.5 g, 19.7 mmol). After the mixture was stirred at room temp for 18 hr, it was concentrated in vacuo and purified by silica gel chromatography (PE:EA=30:1~5:1) to afford the title compound (3.0 g, 64%) as a yellow solid. LCMS (M+H)$^+$: 243.

Step 3: 4-bromo-2-methyl-6H-furo[2,3-c]pyridin-7-one

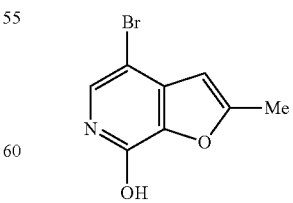

To a mixture of 4-bromo-7-methoxy-2-methylfuro[2,3-c]pyridine (3.0 g, 12.4 mmol) in DCM (30 mL) was stirred at 0° C. under N$_2$ was added BBr$_3$ (15.5 g, 62.0 mmol) dropwise. The mixture was stirred at 0° C. for 3 hr. The mixture was concentrated in vacuo to afford the title compound (2.50 g, 88%). The material was immediately used in the next step without any further purification. LCMS (M+H)⁺: 229.

Step 4: 4-bromo-2,6-dimethylfuro[2,3-c]pyridin-7-one

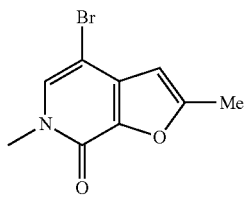

The title compound was prepared in a manner similar to step 2 of Example 252, by substituting 4-bromo-2-methyl-6H-furo[2,3-c]pyridin-7-one for 4-bromo-6H,7H-furo[2,3-c]-pyridin-7-one. ¹H NMR (CDCl₃, 400 MHz): δ 7.26 (s, 1H), 6.32 (s, 1H), 3.64 (s, 3H), 2.49 (s, 3H). LCMS (M+H)⁺: 243.

Step 5: N-[4-(2,4-difluorophenoxy)-3-(2,6-dimethyl-7-oxofuro[2,3-c]pyridin-4-yl)phenyl]ethanesulfonamide

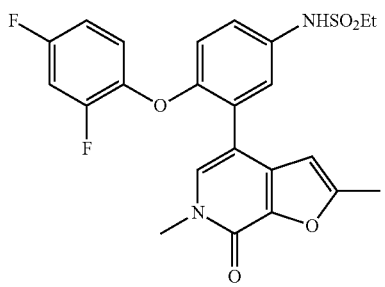

A mixture of 4-bromo-2,6-dimethylfuro[2,3-c]pyridin-7-one (200 mg, 0.83 mol), N-[4-(2,4-difluorophenoxy)-3-(4,4,5,5-tetramethyl-1,3,2-dioxaborolan-2-yl)phenyl]ethanesulfonamide (364 mg, 0.99 mmol), Pd(dppf)Cl₂ (66 mg, 0.09 mmol), K₃PO₄ (527 mg, 2.49 mmol) in dioxane/H₂O (4 mL/1 mL) was bubbled with Ar for 5 min. The mixture was heated at 70° C. for 18 hr. After cooling to room temp, the rxn mixture was poured into H₂O (10 mL) and extracted with EtOAc (40 mL×3). The combined organic layers were washed with brine (20 mL×2), dried over Na₂SO₄, filtered, and concentrated in vacuo. The residue was purified by prep-HPLC to afford the title compound (49 mg, 12%) as a yellow solid. ¹H NMR (CDCl₃, 400 MHz): δ 7.35-7.33 (m, 2H) 7.12 (m, 1H) 6.95-6.89 (m, 2H) 6.81 (m, 2H) 6.43 (s, 1H) 6.38 (s, 1H) 3.71 (s, 3H) 3.16 (q, J=7.2 Hz, 2H) 2.47 (s, 3H) 1.43 (t, J=7.2 Hz, 3H). LCMS (M+H)⁺: 475.

Example 270: 4-[2-(cyclopropylmethoxy)-5-ethylsulfonylphenyl]-2,6-dimethylfuro[2,3-c]pyridine-7-one

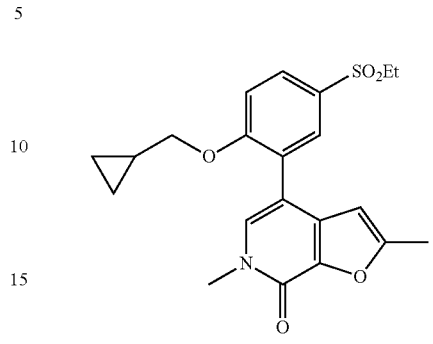

The title compound was prepared in a manner similar to step 5 of Example 269, by substituting 2-[2-(cyclopropylmethoxy)-5-ethylsulfonylphenyl]-4,4,5,5-tetramethyl-1,3,2-dioxaborolane for N-[4-(2,4-difluorophenoxy)-3-(4,4,5,5-tetramethyl-1,3,2-dioxaborolan-2-yl)phenyl]ethanesulfonamide. ¹H NMR (CDCl₃, 400 MHz): δ 7.89 (dd, J₁=8.8 Hz, J₂=2.4 Hz, 1H) 7.85 (d, J=2.4 Hz, 1H) 7.34 (s, 1H) 7.09 (d, J=8.8 Hz, 1H) 6.24 (s, 1H) 3.94 (m, 2H) 3.78 (s, 3H) 3.14 (q, J=7.2 Hz, 2H) 2.48 (s, 3H) 1.32 (t, J=7.2 Hz, 3H) 1.18-1.16 (m, 1H) 0.64-0.59 (m, 2H) 0.32-0.28 (m, 2H). LCMS (M+H)⁺: 402.

Example 271: N-[4-(2,4-difluorophenoxy)-3-(5-fluoro-1-methyl-6-oxopyridin-3-yl)phenyl]methanesulfonamide

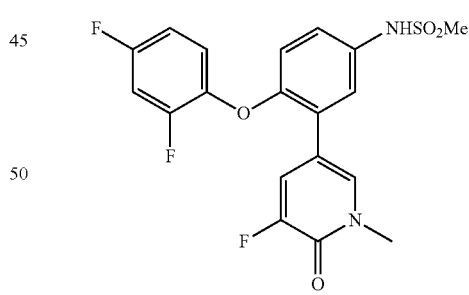

The title compound was prepared in a manner similar to Example 122, substituting N-[3-bromo-4-(2,4-difluorophenoxy)phenyl]methanesulfonamide for N-[3-Bromo-4-(2,4-difluoro-phenoxy)phenyl]ethanesulfonamide. ¹H NMR (400 MHz, DMSO-d₆): δ ppm 2.98-3.07 (m, 3H) 3.52-3.60 (m, 3H) 6.80-6.94 (m, 1H) 7.10 (s, 1H) 7.14-7.24 (m, 1H) 7.24-7.28 (m, 1H) 7.38-7.51 (m, 1H) 7.57-7.66 (m, 1H) 7.76-7.86 (m, 1H) 9.67-9.76 (m, 1H). LCMS (M+H)⁺: 425.

Example 272: 3-chloro-5-[2-(cyclopropylmethoxy)-5-ethylsulfonylphenyl]-1-methylpyridin-2-one

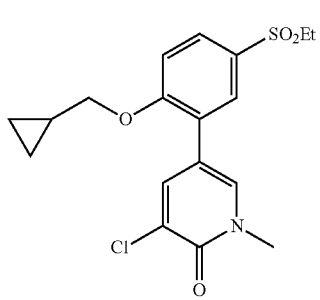

The title compound was prepared in a manner similar to Example 119, substituting 3-chloro-1-methyl-5-(4,4,5,5-tetramethyl-1,3,2-dioxaborolan-2-yl)pyridin-2-one for 3-fluoro-1-methyl-5-(4,4,5,5-tetramethyl-1,3,2-dioxaborolan-2-yl)pyridin-2-one, and 2-bromo-1-(cyclopropylmethoxy)-4-ethylsulfonylbenzene for 2-bromo-1-(cyclopropylmethoxy)-4-methanesulfonylbenzene. LCMS (M+H)$^+$: 382.

Example 273: 5-[5-(2,4-difluorophenoxy)-2-methylsulfonylpyrimidin-4-yl]-1-methyl-3-propan-2-ylpyridin-2-one

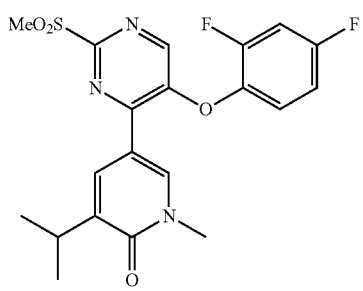

The title compound was prepared in three steps. Using conditions similar to those described by Malhotra et al., in Organic Letters 2013, 15(14): 3698-3701 (supporting information, compounds 4c and 3a), 3,5-dibromo-1-methylpyridin-2-one was alkylated at the 3-position using isopropylmagnesium bromide to give 5-bromo-1-methyl-3-propan-2-ylpyridin-2-one which was then reacted with 4,4,5,5-tetramethyl-2-(tetramethyl-1,3,2-dioxaborolan-2-yl)-1,3,2-dioxaborolane using conditions similar to those described in Example 248, step 2 to give the pinacol ester, 1-methyl-3-propan-2-yl-5-(4,4,5,5-tetramethyl-1,3,2-dioxaborolan-2-yl)pyridin-2-one. This pinacol ester was then substituted for the pinacol ester of Example 149, step 4 and reacted in the same manner to obtain the title compound. LCMS (M+H)$^+$: 436.

Example 274: 5-[2-(cyclopropylmethoxy)-5-ethylsulfonylphenyl]-3-fluoro-1-methylpyridin-2-one

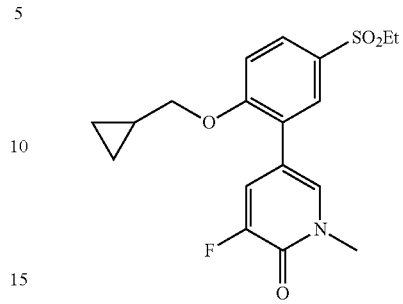

The title compound was prepared in a manner similar to Example 119, substituting 2-bromo-1-(cyclopropylmethoxy)-4-ethylsulfonylbenzene for 2-bromo-1-(cyclopropylmethoxy)-4-methanesulfonylbenzene. LCMS (M+H)$^+$: 366.

Example 275: 3-chloro-5-[2-(cyclopropylmethoxy)-5-ethylsulfonylphenyl]-1-methylpyridin-2-one

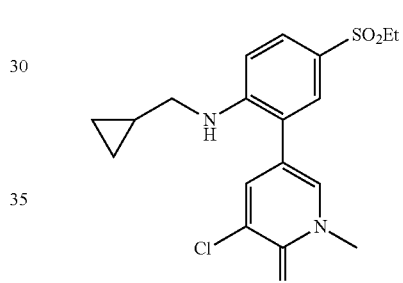

The title compound was prepared in a manner similar to Example 119, substituting 3-chloro-1-methyl-5-(4,4,5,5-tetramethyl-1,3,2-dioxaborolan-2-yl)pyridin-2-one for 3-fluoro-1-methyl-5-(4,4,5,5-tetramethyl-1,3,2-dioxaborolan-2-yl)pyridin-2-one, and N-(cyclopropylmethyl)-4-ethylsulfonyl-2-(4,4,5,5-tetramethyl-1,3,2-dioxaborolan-2-yl)aniline for 2-bromo-1-(cyclopropylmethoxy)-4-methanesulfonylbenzene. LCMS (M+H)$^+$: 381.

Example 276: 5-[2-(2,4-difluorophenoxy)-5-(methanesulfonylmethyl)phenyl]-3-($^2$H$_3$)methyl-1-methyl-1,2-dihydropyridin-2-one

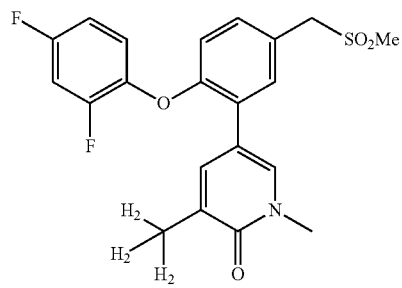

The title compound was prepared in a manner similar to Example 119, substituting 3-($^2$H$_3$)methyl-1-methyl-5-(tetramethyl-1,3,2-dioxaborolan-2-yl)-1,2-dihydropyridin-2-one for 3-fluoro-1-methyl-5-(4,4,5,5-tetramethyl-1,3,2-dioxaborolan-2-yl)pyridin-2-one, and 2-bromo-1-(2,4-difluorophen-oxy)-4-(methylsulfonylmethyl)benzene for 2-bromo-1-(cyclopropylmethoxy)-4-methanesulfonyl-benzene. $^1$H NMR (400 MHz, DMSO-d$_6$): δ ppm 2.93 (s, 3H) 3.49 (s, 3H) 4.42-4.52 (m, 2H) 6.81-6.89 (m, 1H) 7.04-7.16 (m, 1H) 7.20-7.29 (m, 1H) 7.30-7.35 (m, 1H) 7.43-7.51 (m, 2H) 7.53-7.57 (m, 1H) 7.75-7.82 (m, 1H). LCMS (M+H)$^+$: 423.

Example 277: N-[4-(2,4-difluorophenoxy)-3-[5-($^2$H$_3$)methyl-1-methyl-6-oxo-1,6-dihydropyridin-3-yl]phenyl]methanesulfonamide

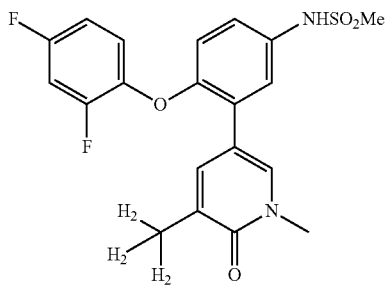

The title compound was prepared in a manner similar to Example 122, substituting N-[3-bromo-4-(2,4-difluorophenoxy)phenyl]methanesulfonamide for N-[3-Bromo-4-(2,4-difluoro-phen-oxy)phenyl]ethanesulfonamide, and 3-($^2$H$_3$)methyl-1-methyl-5-(tetramethyl-1,3,2-dioxaborolan-2-yl)-1,2-dihydropyridin-2-one for 3-fluoro-1-methyl-5-(4,4,5,5-tetramethyl-1,3,2-dioxaborolan-2-yl)pyridin-2-one. $^1$H NMR (400 MHz, DMSO-d$_6$): δ ppm 2.98-3.05 (m, 3H) 3.44-3.50 (m, 3H) 6.84-6.92 (m, 1H) 7.01-7.18 (m, 3H) 7.21-7.26 (m, 1H) 7.38-7.47 (m, 1H) 7.47-7.51 (m, 1H) 7.73-7.79 (m, 1H) 9.61-9.78 (bs, 1H). LCMS (M+H)$^+$: 424.

Example 278: N-[4-(2,4-difluorophenoxy)-3-[5-($^2$H$_3$)methyl-1-methyl-6-oxo-1,6-dihydropyridin-3-yl]phenyl]ethane-1-sulfonamide

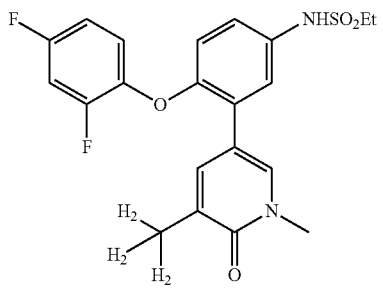

The title compound was prepared in a manner similar to Example 122, substituting 3-($^2$H$_3$)methyl-1-methyl-5-(tetramethyl-1,3,2-dioxaborolan-2-yl)-1,2-dihydropyridin-2-one for 3-fluoro-1-methyl-5-(4,4,5,5-tetramethyl-1,3,2-dioxaborolan-2-yl)pyridin-2-one. $^1$H NMR (400 MHz, DMSO-d$_6$): δ ppm 1.19-1.25 (m, 3H) 3.05-3.16 (m, 2H) 3.45-3.49 (m, 3H) 6.85-6.92 (m, 1H) 6.99-7.20 (m, 4H) 7.23 (m, 1H) 7.38-7.46 (m, 1H) 7.46-7.50 (m, 1H) 7.71-7.79 (m, 1H) 9.60-9.85 (m, 1H). LCMS (M+H)$^+$: 438.

Example 279: N-[3-(5-cyclopropyl-1-methyl-6-oxopyridin-3-yl)-4-(2,4-difluorophenoxy)phenyl]methanesulfonamide

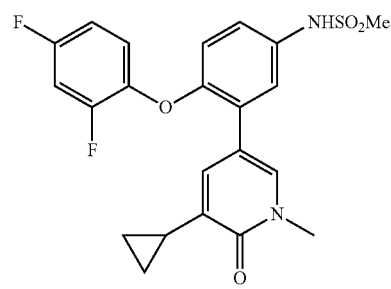

The title compound was prepared in a manner similar to Example 122, substituting 3-cyclopropyl-1-methyl-5-(4,4,5,5-tetramethyl-1,3,2-dioxaborolan-2-yl)pyridin-2-one for 3-fluoro-1-methyl-5-(4,4,5,5-tetramethyl-1,3,2-dioxaborolan-2-yl)pyridin-2-one, and N-[3-bromo-4-(2,4-difluorophenoxy)phenyl]methanesulfonamide for N-[3-bromo-4-(2,4-difluorophenoxy)phenyl]ethanesulfonamide. $^1$H NMR (400 MHz, DMSO-d$_6$): δ ppm 0.46-0.54 (m, 2H) 0.77-0.88 (m, 2H) 1.93-2.07 (m, 1H) 2.98-3.05 (m, 3H) 3.44-3.51 (m, 3H) 6.89-6.95 (m, 1H) 7.00-7.12 (m, 3H) 7.13-7.19 (m, 1H) 7.21-7.25 (m, 1H) 7.39-7.48 (m, 1H) 7.71 (s, 1H) 9.56-9.82 (bs, 1H). LCMS (M+H)$^+$: 447.

Example 280: 3-cyclopropyl-5-[2-(cyclopropylmethoxy)-5-ethylsulfonylphenyl]-1-methylpyridin-2-one

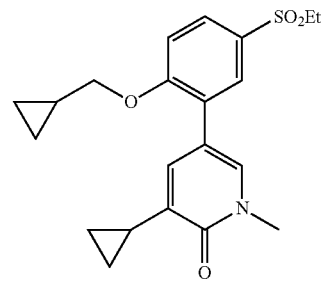

The title compound was prepared in a manner similar to Example 119, substituting 3-cyclopropyl-1-methyl-5-(4,4,5,5-tetramethyl-1,3,2-dioxaborolan-2-yl)pyridin-2-one for 3-fluoro-1-methyl-5-(4,4,5,5-tetramethyl-1,3,2-dioxaborolan-2-yl)pyridin-2-one and 2-bromo-1-(cyclo-propylmethoxy)-4-ethylsulfonylbenzene for 2-bromo-1-(cyclopropylmethoxy)-4-methanesulfonyl-benzene. $^1$H NMR (400 MHz, DMSO-d$_6$): δ ppm 0.33-0.41 (m, 2H) 0.55-0.61 (m, 2H) 0.63-0.69 (m, 2H) 0.83-0.91 (m, 2H) 1.07-1.14 (m, 3H) 1.19-1.25 (m, 2H) 2.01-2.12 (m, 1H) 3.23-3.30 (m, 2H) 3.52 (s, 3H) 3.92-4.00 (m, 2H) 7.22-7.29 (m, 2H) 7.70-7.80 (m, 3H). LCMS (M+H)$^+$: 388.

Example 281: N-[4-(2,4-difluorophenoxy)-3-(1-methyl-6-oxo-5-pyrrolidin-1-ylpyridin-3-yl)phenyl]methanesulfonamide

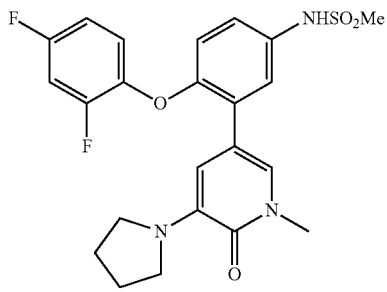

The title compound was prepared in a manner similar to Example 122, substituting 1-methyl-3-pyrrolidin-1-yl-5-(4,4,5,5-tetramethyl-1,3,2-dioxaborolan-2-yl)pyridin-2-one for 3-fluoro-1-methyl-5-(4,4,5,5-tetramethyl-1,3,2-dioxaborolan-2-yl)pyridin-2-one and N-[3-bromo-4-(2,4-difluorophenoxy)phenyl]methanesulfonamide for N-[3-bromo-4-(2,4-difluorophenoxy)phenyl]ethanesulfonamide. LCMS (M+H)+: 476.

Example 282: 5-[2-(cyclopropylmethoxy)-5-ethylsulfonylphenyl]-1-methyl-3-pyrrolidin-1-ylpyridin-2-one

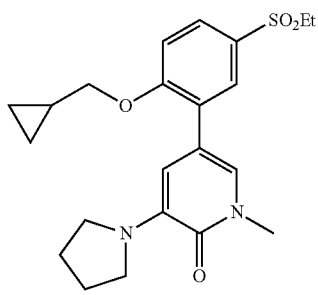

The title compound was prepared in a manner similar to Example 119, substituting 1-methyl-3-pyrrolidin-1-yl-5-(4,4,5,5-tetramethyl-1,3,2-dioxaborolan-2-yl)pyridin-2-one for 3-fluoro-1-methyl-5-(4,4,5,5-tetramethyl-1,3,2-dioxaborolan-2-yl)pyridin-2-one, and 2-bromo-1-(cyclo-propylmethoxy)-4-ethylsulfonylbenzene for 2-bromo-1-(cyclopropylmethoxy)-4-methane-sulfonyl-benzene. $^1$H NMR (400 MHz, DMSO-d$_6$): δ ppm 0.33-0.40 (m, 2H) 0.53-0.61 (m, 2H) 1.08-1.14 (m, 3H) 1.20-1.29 (m, 1H) 1.81-1.90 (m, 4H) 3.23-3.30 (m, 2H) 3.35-3.35 (m, 1H) 3.35-3.40 (m, 3H) 3.48 (s, 3H) 3.94-4.03 (m, 2H) 6.60-6.66 (m, 1H) 7.21-7.28 (m, 1H) 7.31-7.38 (m, 1H) 7.68-7.79 (m, 2H). LCMS (M+H)+: 417.

Example 283: N-[4-(2,4-difluorophenoxy)-3-(5-ethynyl-1-methyl-6-oxopyridin-3-yl)phenyl]ethanesulfonamide Step 1: 5-bromo-3-iodo-1-methylpyridin-2-one

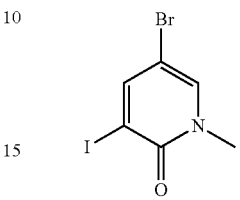

To a soln of 5-bromo-3-iodo-1H-pyridin-2-one (12.0 g, 40.01 mmol) stirred in dry DMF (120 mL) at 0° C. under N$_2$ was added NaH (2.4 g, 60.02 mmol, 60% in mineral oil). After the mixture was stirred at 0° C. for 1 hr, iodomethane (11.4 g, 80.03 mmol) was added dropwise. The icebath was removed, and the rxn was stirred at room temp for 1 hr. The mixture was poured into ice water (200 mL); the resulting precipitate was filtered, collected and dried to give the title compound (12 g, 95%) as a light yellow solid. The material was used without any further purification. $^1$H NMR (CDCl$_3$, 400 MHz): δ 8.01 (d, J=3.2 Hz, 1H), 7.46 (d, J=3.2 Hz, 1H), 3.60 (s, 3H). LCMS (M+H)+: 315.

Step 2: 5-bromo-1-methyl-3-(2-trimethylsilylethynyl)pyridin-2-one

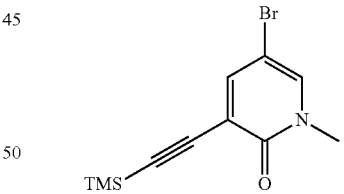

A mixture of 5-bromo-3-iodo-1-methylpyridin-2-one (8.0 g, 25.48 mmol), ethynyltri-methylsilane (2.7 g, 27.52 mmol), CuI (485 mg, 2.55 mmol), Pd(PPh$_3$)$_2$Cl$_2$ (1.79 g, 2.55 mmol) and triethylamine (12.9 g, 127.4 mmol) in dry THF (100 mL) was heated to 60° C. under N$_2$ for 2 hr. The mixture was concentrated and the residue was purified by CC on silica gel (PE:EA=5:1) to give the title compound (6 g, 82%) as a yellow solid. $^1$H NMR (CDCl$_3$, 400 MHz): δ 7.61 (d, J=2.4 Hz, H), 7.42 (d, J=2.4 Hz, 1H), 3.54 (s, 3H), 0.25 (s, 9H). LCMS (M+H)+: 285.

Step 3: 1-methyl-5-(4,4,5,5-tetramethyl-1,3,2-dioxaborolan-2-yl)-3-(2-trimethylsilylethynyl)pyridin-2-one

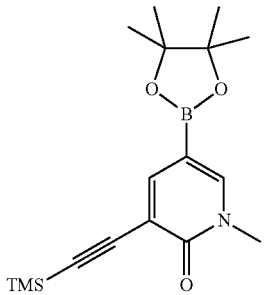 [SMILES: Cn1cc(B2OC(C)(C)C(C)(C)O2)cc(C#C[Si](C)(C)C)c1=O]

A mixture of 5-bromo-1-methyl-3-(2-trimethylsilylethynyl)pyridin-2-one (9.0 g, 31.67 mmol), 4,4,5,5-tetramethyl-2-(tetramethyl-1,3,2-dioxaborolan-2-yl)-1,3,2-dioxaborolane (20.1 g, 79.16 mmol), Pd$_2$(dba)$_3$ (1.8 g, 3.17 mmol), X-Phos (1.5 g, 3.17 mmol) and KOAc (18.65 g, 189.99 mmol) in anhydrous dioxane (200 mL) was stirred at 70° C. under Ar for 12 hr. After the mixture was concentrated in vacuo, the residue was purified by CC (PE:EA=4:1) to give the title compound (3.5 g, 33%) as an off-white solid. $^1$H NMR (CDCl$_3$, 400 MHz): δ 7.88 (d, J=2.0 Hz, 1H), 7.75 (d, J=2.0 Hz, 1H), 3.56 (s, 3H), 1.31 (s, 12H), 0.25 (s, 9H). LCMS (M+H)$^+$: 332 and 250.

Step 4: N-[4-(2,4-difluorophenoxy)-3-[1-methyl-6-oxo-5-(2-trimethylsilylethynyl)pyridine-3-yl]phenyl]ethanesulfonamide

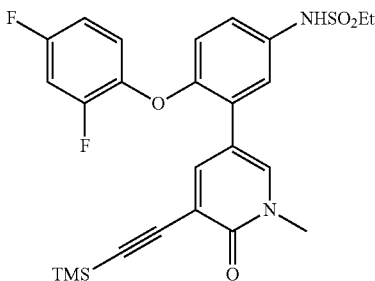

A mixture of 1-methyl-5-(4,4,5,5-tetramethyl-1,3,2-dioxaborolan-2-yl)-3-(2-trimethyl-silylethynyl)pyridin-2-one (200 mg, 0.6 mmol), N-[3-Bromo-4-(2,4-difluorophenoxy)phenyl]-ethanesulfonamide (197 mg, 0.5 mmol), Pd(dppf)Cl$_2$ (37 mg, 0.05 mmol), and K$_3$PO$_4$ (267 mg, 1.26 mmol) in dioxane (6 mL) and H$_2$O (0.6 mL) was stirred at 70° C. under Ar for 12 hr. After the mixture was concentrated, the residue was purified by CC (PE:EA=2:1) to give the title compound (100 mg, 38%) as a yellow solid. $^1$H NMR (CDCl$_3$, 400 MHz): δ 7.82 (d, J=2.4 Hz, 1H), 7.67 (d, J=2.4 Hz, 1H), 7.23 (d, J=2.4 Hz, 1H), 7.16-7.12 (m, 1H), 6.99-6.91 (m, 2H), 6.87-6.83 (m, 1H), 6.78 (m, 1H), 6.65 (s, 1H), 3.61 (s, 3H), 3.14 (q, J=7.2 Hz, 2H), 1.42 (t, J=7.2 Hz, 3H), 0.24 (s, 9H). LCMS (M+H)$^+$: 517.

Step 5: N-[4-(2,4-difluorophenoxy)-3-(5-ethynyl-1-methyl-6-oxopyridin-3-yl)phenyl]ethanesulfonamide

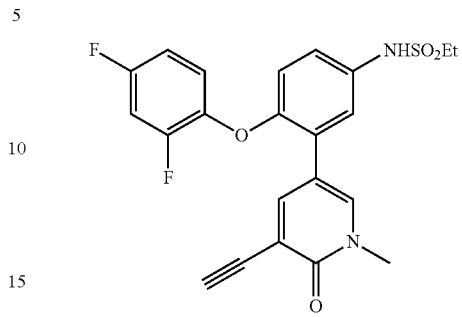

To a mixture of N-[4-(2,4-difluorophenoxy)-3-[1-methyl-6-oxo-5-(2-trimethylsilyl-ethynyl)pyridin-3-yl]phenyl]ethanesulfonamide (100 mg, 0.19 mmol) in EtOH (10 mL) was added K$_2$CO$_3$ (157 mg, 1.14 mmol). The rxn was stirred at 20° C. for 12 hr and poured into H$_2$O (30 mL) and extracted with DCM (20 mL×3). The organic phase was washed with brine (20 mL), dried over anhydrous MgSO$_4$ and concentrated in vacuo. The residue was purified by prep-HPLC to afford the title compound (48 mg, 56%) as an off-white solid. $^1$H NMR (CDCl$_3$, 400 MHz): δ 7.90 (d, J=2.4 Hz, 1H), 7.69 (d, J=2.4 Hz, 1H), 7.26 (d, J=2.8 Hz, 1H), 7.14-7.11 (m, 1H), 7.01-6.94 (m, 2H), 6.89-6.86 (m, 1H), 6.77 (d, J=8.8 Hz, 1H), 6.55 (s, 1H), 3.67 (s, 3H), 3.34 (s, 1H), 3.14 (q, J=7.2 Hz, 2H), 1.42 (t, J=7.2 Hz, 3H). LCMS (M+H)$^+$: 445.

Example 284: 5-[2-(cyclopropylmethoxy)-5-ethylsulfonylphenyl]-3-ethynyl-1-methylpyridin-2-one

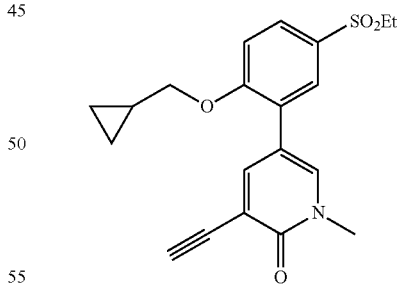

The title compound was prepared in a manner similar to Example 283, substituting 2-bromo-1-(cyclopropylmethoxy)-4-ethylsulfonylbenzene for N-[3-Bromo-4-(2,4-difluorophenoxy)phenyl]ethanesulfonamide in Step 4. $^1$H NMR (CDCl$_3$, 400 MHz): δ 7.93 (d, J=2.4 Hz, 1H), 7.84-7.81 (m, 1H), 7.76 (d, J=2.4 Hz, 1H), 7.68 (d, J=2.8 Hz, 1H), 7.03 (d, J=8.4 Hz, 1H), 3.96 (d, J=7.2 Hz, 2H), 3.66 (s, 3H), 3.35 (s, 1H), 3.13 (q, J=7.2 Hz, 2H), 1.32-1.27 (m, 4H), 0.71-0.67 (m, 2H), 0.40-0.37 (m, 2H). LCMS (M+H)$^+$: 372.

Example 285: 5-[2-(cyclopropylmethoxy)-5-methyl-sulfonylphenyl]-3-ethynyl-1-methylpyridin-2-one

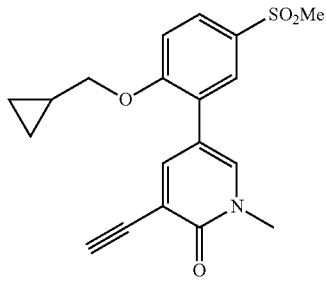 [SMILES: C#Cc1cc(-c2cc(S(C)(=O)=O)ccc2OCC2CC2)cn(C)c1=O]

The title compound was prepared in a manner similar to Example 283, substituting 2-bromo-1-(cyclopropyl-methoxy)-4-methylsulfonylbenzene for N-[3-Bromo-4-(2,4-difluorophenoxy)phenyl]ethanesulfonamide in Step 4. $^1$H NMR: (CDCl$_3$, 400 MHz): δ 7.92 (d, J=2.0 Hz, 1H), 7.86 (d, J=8.8 Hz, 1H), 7.81 (s, 1H), 7.69 (d, J=1.6 Hz, 1H), 7.04 (d, J=8.4 Hz, 1H), 3.96 (d, J=6.8 Hz, 3H), 3.65 (s, 3H), 3.34 (s, 1H), 3.07 (s, 3H), 1.28-1.27 (m, 1H), 0.70-0.68 (m, 2H), 0.38-0.37 (m, 2H). LCMS (M+H)$^+$: 358.

Example 286: N-[4-(2,4-difluorophenoxy)-3-(5-ethynyl-1-methyl-6-oxopyridin-3-yl)phenyl]methanesulfonamide

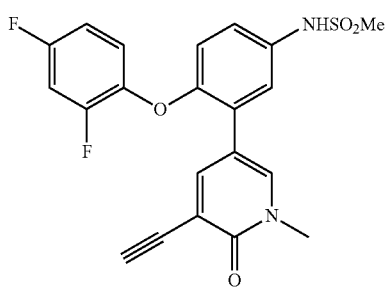

The title compound was prepared in a manner similar to Example 283, substituting N-[3-bromo-4-(2,4-difluorophenoxy)phenyl]methanesulfonamide for N-[3-Bromo-4-(2,4-difluorophenoxy)phenyl]ethanesulfonamide in Step 4. $^1$H NMR (CDCl$_3$, 400 MHz): δ 7.89 (d, J=3.2 Hz, 1H), 7.69 (d, J=3.2 Hz, 1H), 7.26-7.25 (m, 1H), 7.15-7.10 (m, 1H), 7.03-6.94 (m, 2H), 6.91-6.84 (m, 1H), 6.78 (d, J=11.6 Hz, 1H), 6.45 (s, 1H), 3.66 (s, 3H), 3.35 (s, 1H), 3.04 (s, 3H). LCMS (M+H)$^+$: 431.

Example 287: 5-[2-(cyclopropylmethoxy)-5-ethyl-sulfonylphenyl]-3-(difluoromethoxy)-1-methylpyridin-2-one

Step 1: 5-bromo-3-methoxy-1-methylpyridin-2-one

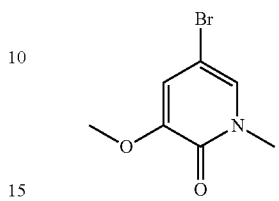

To a soln of 5-bromo-3-hydroxy-1H-pyridin-2-one (5.00 g, 26.31 mmol) in DMF (100 mL) stirred at 0° C. was added NaH (2.16 g, 53.95 mmol, 60% in mineral oil). After 30 min, iodomethane (9.33 g, 65.78 mmol) was added over a period of 5 min. After the mixture was stirred at room temp for 12 hr, it was quenched with H$_2$O (20 mL) and extracted with EtOAc (100 mL×3). The combined organic layers were washed with brine (100 mL×3), dried over Na$_2$SO$_4$, and concentrated in vacuo to give the title compound (5.5 g, 96%). The material was carried forward without further purification. LCMS (M+H)$^+$: 219.

Step 2: 5-bromo-3-hydroxy-1-methylpyridin-2-one

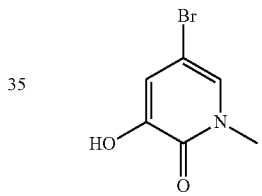

To a soln of 5-bromo-3-methoxy-1-methylpyridin-2-one (5.60 g, 25.7 mmol) stirred at 0° C. in DCM (100 mL) was added BBr$_3$ (12.87 g, 51.4 mmol). The icebath was removed and the mixture was stirred at room temp for 5 hr. After the mixture was cooled to 0° C., it was quenched with MeOH (5 mL), concentrated to near dryness and purified by CC on silica gel to give title compound (3 g, 57%) as a white solid. $^1$H NMR (CDCl3, 400 MHz): δ 7.49 (s, 1H), 6.80 (s, 1H), 3.44 (s, 3H). LCMS (M+H)$^+$: 205.

Step 3: 5-[2-(cyclopropylmethoxy)-5-ethylsulfonyl-phenyl]-3-hydroxy-1-methylpyridin-2-one

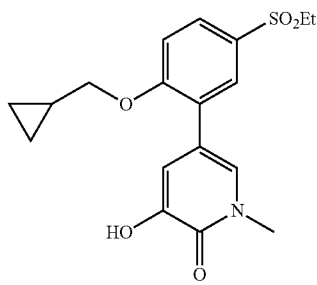

To a mixture of 5-bromo-3-hydroxy-1-methylpyridin-2-one (1.00 g, 4.9 mmol), 2-[2-(cyclopropylmethoxy)-5-ethylsulfonylphenyl]-4,4,5,5-tetramethyl-1,3,2-dioxaborolane (1.80 g, 4.9 mmol) in dioxane (30 mL) and H$_2$O (5 mL) was added K$_3$PO$_4$ (3.12 g, 14.7 mmol), Pd(dppf)Cl$_2$ (358 mg, 0.49 mmol). After purging the mixture with N$_2$, the mixture was stirred at 90° C. under microwave irradiation for 1 hr. After the mixture was filtered, the filtrate was concentrated to dryness. The resulting residue was purified by prep-HPLC to give the title compound (0.9 g, 51%) as a purple solid. $^1$H NMR (CDCl$_3$, 400 MHz): δ 7.81 (dd, J$_1$=8.8 Hz, J$_2$=2.4 Hz, 1H), 7.77 (d, J=2.4 Hz, 1H), 7.16-7.15 (m, 2H), 3.95 (d, J=6.8 Hz, 2H), 3.70 (s, 3H), 3.12 (q, J=7.6 Hz, 2H), 1.32-1.27 (m, 4H), 0.70-0.67 (m, 2H), 0.39-0.36 (m, 2H). LCMS (M+H)$^+$: 364.

Step 4: 5-[2-(cyclopropylmethoxy)-5-ethylsulfonylphenyl]-3-(difluoromethoxy)-1-methylpyridin-2-one

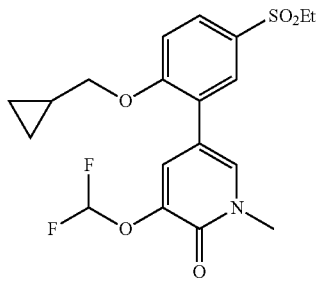

A mixture of 5-[2-(cyclopropylmethoxy)-5-ethylsulfonylphenyl]-3-hydroxy-1-methylpyridin-2-one (50 mg, 0.14 mmol), sodium chlorodifluoroacetate (252 mg, 1.65 mmol), K$_2$CO$_3$ (70 mg, 0.51 mmol) in dioxane (4 mL) was stirred at 100° C. for 18 hr. After the mixture was filtered, the filtrate was concentrated in vacuo. The residue was purified by prep-HPLC to give the title compound (16 mg, 28%) as a light pink solid. $^1$H NMR (CDCl$_3$, 400 MHz): δ 7.84 (m, 1H) 7.77 (d, J=2.4 Hz, 1H) 7.63 (d, J=2.4 Hz, 1H) 7.49 (d, J=2.4 Hz, 1H) 7.04 (m, 1H) 3.95 (m, 2H) 3.69 (s, 3H) 3.13 (m, 3H) 1.33-1.26 (m, 4H) 0.72-0.67 (m, 2H) 0.39-0.36 (m, 2H). LCMS (M+H)$^+$: 414.

Example 288: 5-[2-(cyclopropylmethoxy)-5-ethylsulfonylphenyl]-1-methyl-3-(2,2,2-trifluoroethoxy)pyridin-2-one

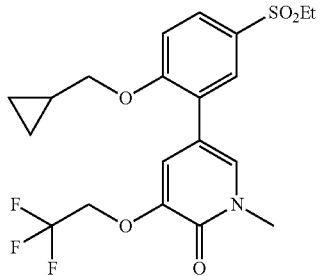

A mixture of 5-[2-(cyclopropylmethoxy)-5-ethylsulfonylphenyl]-3-hydroxy-1-methylpyridin-2-one (50 mg, 0.14 mmol), 2,2,2-trifluoroethyl trifluoromethanesulfonate (33 mg, 0.14 mmol), Cs$_2$CO$_3$ (134.48 mg, 0.42 mmol) in DMF (2 mL) was stirred at 20° C. for 2 hr. After the mixture was filtered, the filtrate was concentrated in vacuo. The residue was purified by prep-HPLC to give the title compound (29 mg, 47%) as an off-white solid. $^1$H NMR (CDCl$_3$, 400 MHz): δ 7.84 (m, 1H), 7.77 (m, 1H), 7.41 (m, 2H), 7.04 (m, 1H), 4.58 (m, 2H), 3.95 (m, 2H), 3.70 (s, 3H), 3.14 (m, 2H), 1.33-1.27 (m, 4H), 0.72-0.69 (m, 2H), 0.39-0.35 (m, 2H). LCMS (M+H)$^+$: 446.

Example 289: N-[3-[5-(difluoromethoxy)-1-methyl-6-oxopyridin-3-yl]-4-(2,4-difluorophenoxy)phenyl]ethanesulfonamide Step 1: 5-bromo-3-(difluoromethoxy)-1-methylpyridin-2-one

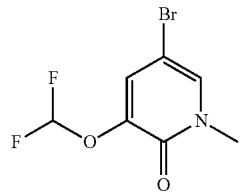

The title compound was prepared in a manner similar to step 4 in Example 287, substituting 5-bromo-3-hydroxy-1-methylpyridin-2-one for 5-[2-(cyclopropylmethoxy)-5-ethylsulfonylphenyl]-3-hydroxy-1-methylpyridin-2-one. LCMS (M+H)$^+$: 255.

Step 2: N-[3-[5-(difluoromethoxy)-1-methyl-6-oxopyridin-3-yl]-4-(2,4-difluorophenoxy)phenyl]ethanesulfonamide

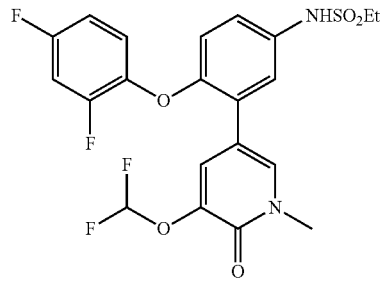

A mixture of 5-bromo-3-(difluoromethoxy)-1-methylpyridin-2-one (50 mg, 0.20 mmol), N-[4-(2,4-difluorophenoxy)-3-(4,4,5,5-tetramethyl-1,3,2-dioxaborolan-2-yl)phenyl]ethanesulfonamide (88 mg, 0.18 mmol), Pd(dppf)Cl$_2$ (11 mg) and K$_3$PO$_4$ (85 mg, 0.40 mmol) in dioxane (5 mL) and H$_2$O (5 drops) was purged with N$_2$, capped, and heated to 70° C. for 8 hr. After the mixture was filtered, the filtrate was concentrated in vacuo and purified by prep-HPLC to afford the title compound (13 mg, 13%) as a white solid. $^1$H NMR (CDCl$_3$, 400 MHz): δ 7.53 (m, 2H) 7.25 (m, 1H) 7.05 (m, 1H) 7.12 (m, 1H) 7.02-6.97 (m, 2H) 6.97-6.95 (m, 1H) 6.77 (m, 1H) 6.48 (bs, 1H) 3.67 (s, 3H) 3.15 (q, J=7.4 Hz, 2H) 1.42 (t, J=7.4 Hz, 3H). LCMS: (M+H)$^+$487.

Example 290: N-[4-(2,4-difluorophenoxy)-3-[1-methyl-6-oxo-5-(2,2,2-trifluoroethoxy)pyridin-3-yl]phenyl]ethanesulfonamide Step 1: 5-bromo-1-methyl-3-(2,2,2-trifluoroethoxy)pyridin-2-one

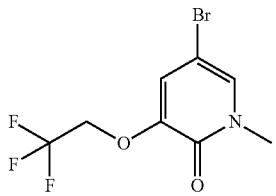

The title compound was prepared in a manner similar to Example 288, substituting 5-bromo-3-hydroxy-1-methylpyridin-2-one for 5-[2-(cyclopropylmethoxy)-5-ethylsulfonylphenyl]-3-hydroxy-1-methylpyridin-2-one. LCMS (M+H)+: 287.

Step 2: N-[4-(2,4-difluorophenoxy)-3-[1-methyl-6-oxo-5-(2,2,2-trifluoroethoxy)pyridine-3-yl]phenyl]ethanesulfonamide

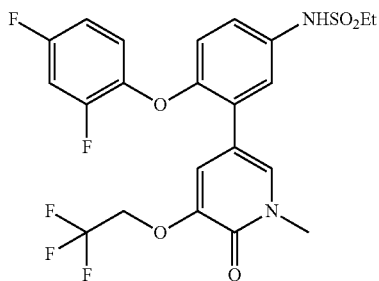

A mixture of 5-bromo-1-methyl-3-(2,2,2-trifluoroethoxy)pyridin-2-one (50 mg, 0.18 mmol), N-[4-(2,4-difluorophenoxy)-3-(4,4,5,5-tetramethyl-1,3,2-dioxaborolan-2-yl)phenyl]ethanesulfonamide (79 mg, 0.18 mmol), Pd(dppf)Cl$_2$ (11 mg) and K$_3$PO$_4$ (76 mg, 0.36 mmol) in dioxane (5 mL) and H$_2$O (5 drops) was purged with N$_2$, capped, and heated to 70° C. for 8 hr. After the mixture was filtered, the filtrate was concentrated in vacuo and purified by prep-HPLC to afford the title compound (11 mg, 11%) as a white solid. $^1$H NMR (CDCl$_3$, 400 MHz): δ 7.39 (m, 1H) 7.32 (m, 1H) 7.25 (d, J=2.8 Hz, 1H) 7.12 (dd, J$_1$=2.8 Hz, J$_2$=8.8 Hz, 1H) 6.99-6.93 (m, 2H) 6.88-6.83 (m, 1H) 6.79 (d, J=8.8 Hz, 1H) 6.47 (b.s., 1H) 4.56 (m, 2H) 3.65 (s, 3H) 3.15 (q, J=7.2 Hz, 2H) 1.42 (t, J=7.2 Hz, 3H). LCMS (M+H)+: 519.

Example 291: 3-(difluoromethoxy)-5-[2-(2,4-difluorophenoxy)-5-(ethylsulfonylmethyl)phenyl]-1-methylpyridin-2-one

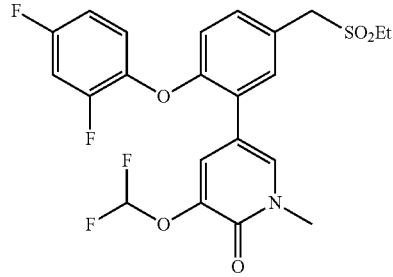

A mixture of 5-bromo-3-(difluoromethoxy)-1-methylpyridin-2-one (50 mg, 0.20 mmol), 2-[2-(2,4-difluorophenoxy)-5-(ethylsulfonylmethyl)phenyl]-4,4,5,5-tetramethyl-1,3,2-dioxaborolane (79 mg, 0.18 mmol), Pd(dppf)Cl$_2$ (11 mg) and K$_3$PO$_4$ (76 mg, 0.36 mmol) in dioxane (5 mL) and H$_2$O (5 drops) was purged with N$_2$, capped, and heated to 70° C. for 8 hr. After the mixture was filtered, the filtrate was concentrated in vacuo and purified by prep-HPLC to afford the title compound (21 mg, 22%) as a white solid. $^1$H NMR (CDCl$_3$, 400 MHz): δ 7.62 (d, J=2.0 Hz, 1H) 7.54 (d, J=2.0 Hz, 1H) 7.40 (d, J=2.0 Hz, 1H) 7.29 (d, J=2.0 Hz, 1H) 7.09-6.96 (m, 3H) 6.93-6.88 (m, 1H) 6.78 (m, 1H) 4.21 (s, 2H) 3.70 (s, 3H) 2.97 (q, J=7.6 Hz, 2H) 1.43 (t, J=7.6 Hz, 3H). LCMS (M+H)+: 486.

Example 292: 5-[2-(2,4-difluorophenoxy)-5-(ethylsulfonylmethyl)phenyl]-1-methyl-3-(2,2,2-trifluoroethoxy)pyridin-2-one

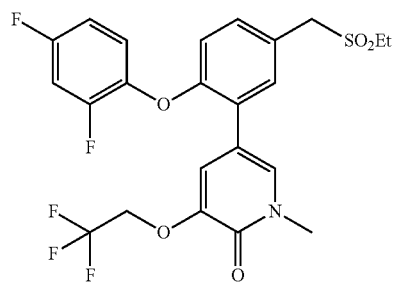

A mixture of 5-bromo-1-methyl-3-(2,2,2-trifluoroethoxy)pyridin-2-one (50 mg, 0.18 mmol), 2-[2-(2,4-difluorophenoxy)-5-(ethylsulfonylmethyl)phenyl]-4,4,5,5-tetramethyl-1,3,2-dioxaborolane (88 mg, 0.20 mmol), Pd(dppf)Cl$_2$ (11 mg) and K$_3$PO$_4$ (85 mg, 0.40 mmol) in dioxane (5 mL) and H$_2$O (5 drops) was purged with N$_2$, capped, and heated to 70° C. for 8 hr. After the mixture was filtered, the filtrate was concentrated in vacuo and purified by prep-HPLC to afford the title compound (21 mg, 22%) as a white solid. $^1$H NMR (CDCl$_3$, 400 MHz): δ 7.41 (m, 2H) 7.35 (m, 1H) 7.30 (m, 1H) 7.07-6.96 (m, 2H) 6.92-6.87 (m, 1H) 6.80 (m, 1H), 4.51 (m, 2H) 4.21 (s, 2H) 3.69 (s, 3H) 2.97 (m, 2H) 1.44 (m, 3H). LCMS (M+H)+: 518.

Example 293: 5-[2-(cyclopropylmethoxy)-5-methylsulfonylphenyl]-1-methyl-3-(1-methylpyrazol-4-yl)oxypyridin-2-one

Step 1: 5-bromo-1-methyl-3-(1-methylpyrazol-4-yl)oxypyridin-2-one

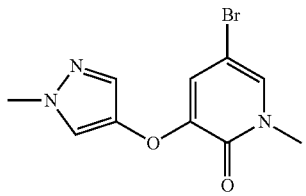

A 0.3M soln of 5-bromo-3-chloro-1-methylpyridin-2-one (124 mg, 0.56 mmol) in DMF was treated with $Cs_2CO_3$ (546 mg, 1.7 mmol). The mixture was sonicated for 30 sec before heating to 140° C. by microwave irradiation (normal) for 150 min. The resulting suspension was diluted with $H_2O$ and extracted with EtOAc (15 mL×3). The combined organic layers were washed with brine, dried over $Na_2SO_4$, and concentrated in vacuo. The resulting solid was purified by silica gel CC using a gradient of EtOAc (5 to 60%) in hexanes to afford the title compound (33 mg, 19%) as a tan solid. LCMS: $(M+H)^+$ 285.

Step 2: 5-[2-(cyclopropylmethoxy)-5-methylsulfonylphenyl]-1-methyl-3-(1-methylpyrazol-4-yl)oxypyridin-2-one

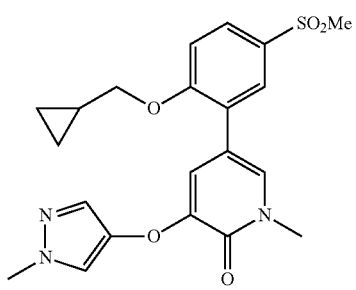 [SMILES: Cn1cc(Oc2cc(-c3cc(S(C)(=O)=O)ccc3OCC3CC3)cn(C)c2=O)cn1]

A mixture of 5-bromo-1-methyl-3-(1-methylpyrazol-4-yl)oxypyridin-2-one (30 mg, 0.11 mmol), 2-[2-(cyclopropylmethoxy)-5-methylsulfonylphenyl]-4,4,5,5-tetramethyl-1,3,2-dioxaborolane (44 mg, 0.16 mmol), $Pd(dppf)Cl_2$ (8 mg) and $K_3PO_4$ (57 mg, 0.26 mmol) in dioxane (1.5 mL) and $H_2O$ (200 μL) was purged with $N_2$, capped, and heated to 75° C. for 12 hr. After the mixture was filtered through a short bed of celite, the filtrate was concentrated in vacuo and purified by prep-HPLC to afford the title compound (35 mg, 78%) as an off-white solid. $^1H$ NMR (400 MHz, DMSO-$d_6$): δ ppm 0.12-0.36 (m, 2H) 0.46-0.61 (m, 2H) 0.99-1.17 (m, 1H) 3.14-3.23 (m, 3H) 3.55-3.60 (m, 3H) 3.75-3.83 (m, 3H) 3.88-3.96 (m, 2H) 7.18-7.32 (m, 2H) 7.32-7.40 (m, 1H) 7.68-7.91 (m, 4H). LCMS $(M+H)^+$: 430.

Example 294: 5-[2-(cyclopropylmethoxy)-5-methylsulfonylphenyl]-1-methyl-3-(1-propan-2-ylpyrazol-4-yl)oxypyridin-2-one

Step 1: 1-propan-2-ylpyrazol-4-ol

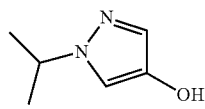

A 0.4 M soln of 1-propan-2-yl-4-(4,4,5,5-tetramethyl-1,3,2-dioxaborolan-2-yl) pyrazole (472 mg, 2 mmol) in THF stirred at 0° C. was treated with a 2.5 M aq soln of NaOH (1.6 mL, 4 mmol) and 30% $H_2O_{2(aq)}$ (453 μl, 4 mmol). The icebath was removed and the mixture was allowed to stir at room temp for 1 hr. After adjustment to pH 3 by the addition of aq 2N $H_2SO_4$, the mixture was extracted with DCM. The combined organic layers were washed with brine, dried over $MgSO_4$, filtered, and concentrated in vacuo. The resulting solid was purified by silica gel CC using EtOAc (5 to 90%) in hexanes to afford the title compound (240 mg, 95%) as a white solid. LCMS $(M+H)^+$: 127.

Step 2: 5-[2-(cyclopropylmethoxy)-5-methylsulfonylphenyl]-3-iodo-1-methylpyridin-2-one

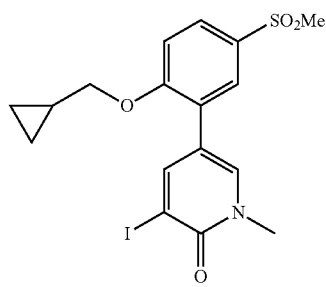 [SMILES: Cn1cc(-c2cc(S(C)(=O)=O)ccc2OCC2CC2)cc(I)c1=O]

A 0.2 M soln of the title compound (264 mg, 0.8 mmol) from Example 98 in DMF stirred at 0° C. was treated with three equal portions of N-iodosuccinimide (187 mg, 84 mmol). After 15 min, the icebath was removed and the mixture was stirred at room temp for 2 hr. The rxn mixture was treated with 10% sodium thiosulfate (aq) (5 mL) and extracted with EtOAc (20 mL×3). The combined organic layers were washed with $H_2O$ and brine, dried over $MgSO_4$, filtered, and concentrated in vacuo to afford a crude solid. The resulting solid was purified by silica gel CC using a gradient of EtOAc (0 to 100%) in DCM to afford the title compound (333 mg, 91%) as a white solid. LCMS $(M+H)^+$: 460.

Step 3: 5-[2-(cyclopropylmethoxy)-5-methylsulfonylphenyl]-1-methyl-3-(1-propan-2-yl-pyrazol-4-yl)oxypyridin-2-one

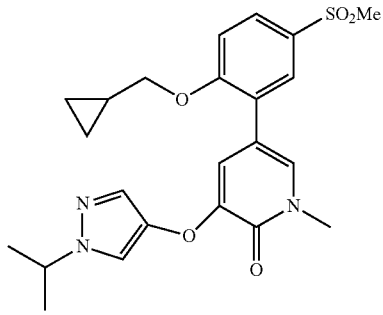 [SMILES: CC(C)n1cc(Oc2cc(-c3cc(S(C)(=O)=O)ccc3OCC3CC3)cn(C)c2=O)cn1]

A mixture of 5-[2-(cyclopropylmethoxy)-5-methylsulfonylphenyl]-3-iodo-1-methylpyridin-2-one (91 mg, 0.2 mmol), 1-propan-2-ylpyrazol-4-ol (45 mg, 0.36 mmol), CuI (4 mg, 10%), 2,2,6,6-tetramethyl-3,5-heptanedione (8 µL, 0.04 mmol) and $K_3PO_4$ (85 mg, 0.4 mmol) in DMSO (1 mL) was purged with $N_2$ for 10 min, capped, and heated to 110° C. for 13 hr. After the mixture was filtered through a short bed of celite, the filtrate was concentrated in vacuo and purified by prep-HPLC to afford the title compound (36 mg, 40%) as a white solid. $^1$H NMR (400 MHz, DMSO-$d_6$): δ ppm 0.18-0.26 (m, 2H) 0.44-0.53 (m, 2H) 1.03-1.10 (m, 1H) 1.37-1.43 (m, 6H) 3.17-3.21 (m, 3H) 3.54-3.61 (m, 3H) 3.87-3.93 (m, 2H) 4.33-4.46 (m, 1H) 7.20-7.25 (m, 1H) 7.25-7.28 (m, 1H) 7.33-7.36 (m, 1H) 7.70-7.74 (m, 1H) 7.76-7.85 (m, 4H). LCMS (M+H)$^+$: 458.

Example 295: 5-[2-(cyclopropylmethoxy)-5-methylsulfonylphenyl]-1-methyl-3-phenoxypyridin-2-one

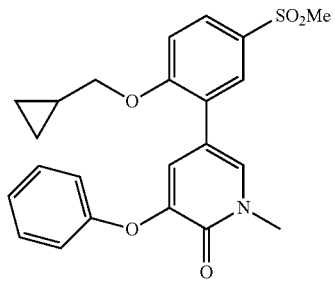 [SMILES: Cn1cc(-c2cc(S(C)(=O)=O)ccc2OCC2CC2)cc(Oc2ccccc2)c1=O]

The title compound was prepared in a manner similar to Step 3 of Example 294, substituting phenol for 1-propan-2-ylpyrazol-4-ol. $^1$H NMR (400 MHz, DMSO-$d_6$): δ ppm 0.23-0.30 (m, 2H) 0.41-0.50 (m, 2H) 1.05-1.16 (m, 1H) 3.17-3.22 (m, 3H) 3.54-3.61 (m, 3H) 3.88-3.97 (m, 2H) 6.95-7.01 (m, 2H) 7.04-7.11 (m, 1H) 7.21-7.27 (m, 1H) 7.30-7.37 (m, 2H) 7.49-7.54 (m, 1H) 7.77-7.83 (m, 1H) 7.83-7.92 (m, 2H). LCMS (M+H)$^+$: 426.

Example 296: N-[4-(1-butyl-5-methyl-6-oxopyridin-3-yl)-5-(2,4-difluorophenoxy)pyrimidin-2-yl]methanesulfonamide

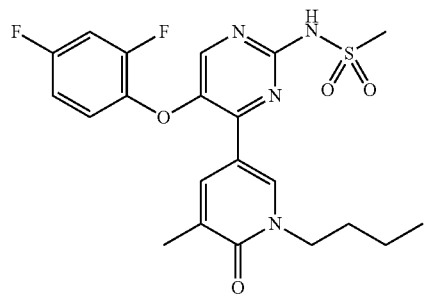 [SMILES: CCCCn1cc(-c2nc(NS(C)(=O)=O)ncc2Oc2ccc(F)cc2F)cc(C)c1=O]

The title compound was prepared in four steps in a similar manner to Example 248 except that 1-iodobutane was substituted for bromomethylcyclopropane in step 1. $^1$H NMR (CDCl$_3$, 400 MHz): δ 8.95 (s, 1H), 8.40 (s, 1H), 8.17 (s, 1H), 8.09 (s, 1H), 7.04-6.95 (m, 2H), 6.90-6.88 (m, 1H), 4.01 (t, J=6.8 Hz, 2H), 3.45 (s, 3H), 2.22 (s, 3H), 1.75-1.72 (m, 2H), 1.39-1.33 (m, 2H), 0.93 (t, J=7.2 Hz, 3H). LCMS: 465.1 (M+H)$^+$.

Example 297: N-[4-(1-butyl-5-methyl-6-oxopyridin-3-yl)-5-(2,4-difluorophenoxy)pyrimidin-2-yl]ethanesulfonamide

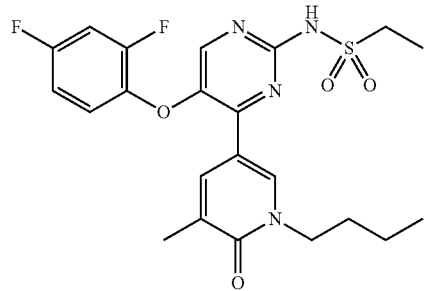 [SMILES: CCCCn1cc(-c2nc(NS(=O)(=O)CC)ncc2Oc2ccc(F)cc2F)cc(C)c1=O]

The title compound was prepared in four steps in a similar manner to Example 248 except that 1-iodobutane was substituted for bromomethylcyclopropane in step 1 and EtSO$_2$NH$_2$ was substituted for MeSO$_2$NH$_2$ in step 4. $^1$H NMR (CDCl$_3$, 400 MHz): δ 8.83 (s, 1H), 8.38 (s, 1H), 8.16 (s, 1H), 8.08 (s, 1H), 7.04-6.95 (m, 2H), 6.94-6.88 (m, 1H), 4.00 (t, J=7.2 Hz, 2H), 3.64 (q, J=7.2 Hz, 2H), 2.21 (s, 3H), 1.75-1.72 (m, 2H), 1.45 (t, J=7.2 Hz, 3H), 1.37-1.33 (m, 2H), 0.93 (t, J=7.2 Hz, 3H). LCMS: 479.1 (M+H)$^+$.

Example 298: N-[4-[1-(cyclobutylmethyl)-5-methyl-6-oxopyridin-3-yl]-5-(2,4-difluorophenoxy)pyrimidin-2-yl]methanesulfonamide

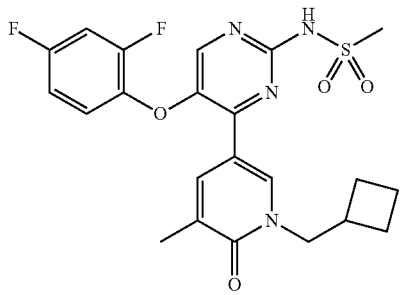 [SMILES: Cc1cc(-c2nc(NS(C)(=O)=O)ncc2Oc2ccc(F)cc2F)cn(CC2CCC2)c1=O]

The title compound was prepared in four steps in a similar manner to Example 248 except that 1-(bromomethyl)cyclobutane was substituted for bromomethylcyclopropane in step 1. $^1$H NMR (CDCl$_3$, 400 MHz): δ 8.96 (s, 1H), 8.39 (s, 1H), 8.14 (s, 1H), 8.09 (s, 1H), 7.02-6.96 (m, 2H), 6.91-6.89 (m, 1H), 4.03 (d, J=7.2 Hz, 2H), 3.44 (s, 3H), 2.82-2.74 (m, 1H), 2.21 (s, 3H), 2.04-2.03 (m, 2H), 1.89-1.85 (m, 2H), 1.79-1.74 (m, 2H). LCMS: 477.1 (M+H)$^+$.

Example 299: N-[4-[1-(cyclobutylmethyl)-5-methyl-6-oxopyridin-3-yl]-5-(2,4-difluorophenoxy)pyrimidin-2-yl]ethanesulfonamide

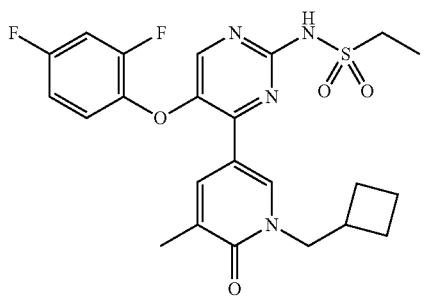 [SMILES: CCS(=O)(=O)Nc1ncc(Oc2ccc(F)cc2F)c(-c2cc(C)c(=O)n(CC3CCC3)c2)n1]

The title compound was prepared in four steps in a similar manner to Example 248 except that 1-(bromomethyl)cyclobutane was substituted for bromomethylcyclopropane in step 1 and EtSO$_2$NH$_2$ was substituted for MeSO$_2$NH$_2$ in step 4. $^1$H NMR (CDCl$_3$, 400 MHz): δ 8.38 (d, J=2.4 Hz, 1H), 8.13 (s, 1H), 8.08 (s, 1H), 7.04-6.98 (m, 2H), 6.97-6.88 (m, 1H), 4.02 (d, J=7.2 Hz, 2H), 3.63 (q, J=7.2 Hz, 2H), 2.80-2.76 (m, 1H), 2.20 (s, 3H), 2.04-2.03 (m, 2H), 1.89-1.76 (m, 4H), 1.44 (t, J=7.2 Hz, 3H). LCMS: 491.1 (M+H)$^+$.

Example 300: N-[5-ethyl-4-(2-methyl-1-oxoisoquinolin-4-yl)pyrimidin-2-yl]ethanesulfonamide Step 1

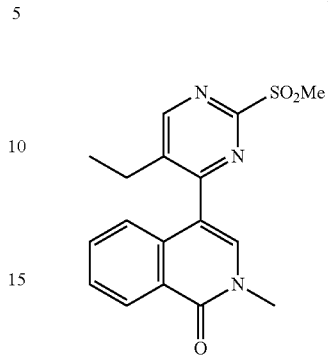

4-chloro-5-ethyl-2-methylsulfonylpyrimidine was prepared in a manner similar to Example 152, steps 2-4 except that ethyl butanoate was substituted for ethyl 2-(cyclopropylmeth-oxy)acetate in step 2. Thus prepared, 4-chloro-5-ethyl-2-methylsulfonylpyrimidine and the title compound of Example 89, step 1 were reacted in a similar manner as Example 152, step 5. Silica gel chromatography (PE:EA=1:1~0:1) gave the title compound (120 mg, yield: 77%) as a yellow solid. $^1$H NMR (CDCl$_3$, 400 MHz): δ 8.90 (s, 1H), 8.55 (d, J=8 Hz, 1H), 7.64-7.55 (m, 2H), 7.28 (s, 1H), 7.07 (d, J=8 Hz, 1H), 3.69 (s, 3H), 3.39 (s, 3H), 2.67 (q, J=8 Hz, 2H), 1.17 (t, J=8 Hz, 3H). LCMS: 344.0 (M+1)$^+$.

Step 2: N-[5-ethyl-4-(2-methyl-1-oxoisoquinolin-4-yl)pyrimidin-2-yl]ethanesulfonamide

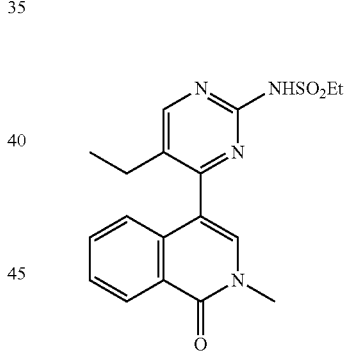

The title compound of step 1 was treated with EtSO$_2$NH$_2$ in a manner similar to Example 155 to give the title compound. $^1$H NMR (CDCl$_3$, 400 MHz): δ 8.59 (s, 1H), 8.53 (d, J=8 Hz, 1H), 7.63 (t, J=8 Hz, 1H), 7.55 (t, J=8 Hz, 1H), 7.23 (d, J=12 Hz, 1H), 7.17 (s, 1H), 3.68 (s, 3H), 3.64 (t, J=8 Hz, 2H), 2.52 (q, J=8 Hz, 2H), 1.44 (t, J=8 Hz, 3H), 1.09 (t, J=8 Hz, 3H). LCMS: 373.0 (M+1)$^+$.

Examples 301, 303-305 in Table 16 were prepared in a similar multi-step manner as Example 300, step 1 wherein ethyl pentanoate was converted to 4-chloro-2-methylsulfonyl-5-propylpyrimidine and ethyl hexanoate was converted to 5-butyl-4-chloro-2-methylsulfonylpyrimidine. Thus prepared, both the 4-chloro-2-methylsulfonyl-5-propylpyrimidine and the 5-butyl-4-chloro-2-methylsulfonylpyrimidine were each coupled to the title compound of Example 89, step 1 or 1,3-dimethyl-5-(4,4,5,5-tetramethyl-1,3,2-dioxaborolan-2-yl)-2(1H)-pyridinone in a manner similar to Example 152, step 5 to give the title compounds. Example 302 was prepared from 4-chloro-5-ethyl-2-methylsulfonylpyrimidine (described in Example 300, step 1) and 1,3-dimethyl-5-(4,4,5,5-tetramethyl-1,3,2-dioxaborolan-2-yl)-2(1H)-pyridinone which were also reacted in a manner similar to Example 152, step 5.

Example 302 in Table 16 was prepared from 4-chloro-5-ethyl-2-methylsulfonylpyrimidine (described in Example 300, step 1) and 1,3-dimethyl-5-(4,4,5,5-tetramethyl-1,3,2-dioxaborolan-2-yl)-2(1H)-pyridinone which were also reacted in a manner similar to Example 152, step 5.

TABLE 16

| Ex. No. | Structure | Name | 1H NMR (ppm (δ), 400 MHz) | MS (M + H) |
|---|---|---|---|---|
| 301 | 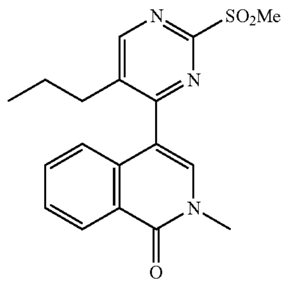 [SMILES: CCCc1cnc(S(C)(=O)=O)nc1-c1cn(C)c(=O)c2ccccc12] | 2-methyl-4-(2-methylsulfonyl-5-propylpyrimidin-4-yl)isoquinolin-1-one | (CDCl$_3$, 400 MHz) δ 8.88 (s, 1H), 8.54 (d, J = 8 Hz, 1H), 7.65-7.55 (m, 2H), 7.06 (d, J = 8 Hz, 1H), 3.69 (s, 3H), 3.39 (s, 3H), 2.61 (t, J = 8 Hz, 2H), 1.56-1.50 (m, 2H), 0.83 (t, J = 7.6 Hz, 3H). | 358 |
| 302 | 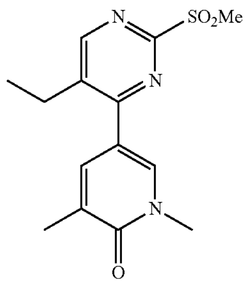 [SMILES: CCc1cnc(S(C)(=O)=O)nc1-c1cc(C)c(=O)n(C)c1] | 5-(5-ethyl-2-methylsulfonylpyrimidin-4-yl)-1,3-dimethylpyridin-2-one | (CDCl$_3$, 400 MHz) δ 8.73 (s, 1 H), 7.84 (s, 1 H), 7.55 (s, 1 H), 3.67 (s, 3 H), 3.37 (s, 3 H), 2.90 (q, J = 7.6 Hz, 2 H), 2.23 (s, 3 H), 1.33 (t, J = 7.6 Hz, 3 H) | 308 |
| 303 | 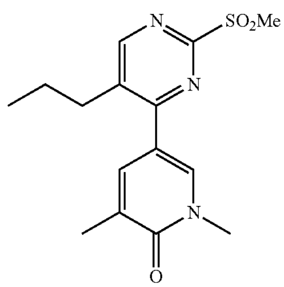 [SMILES: CCCc1cnc(S(C)(=O)=O)nc1-c1cc(C)c(=O)n(C)c1] | 1,3-dimethyl-5-(2-methylsulfonyl-5-propylpyrimidin-4-yl)pyridine-2-one | | 322 |
| 304 | 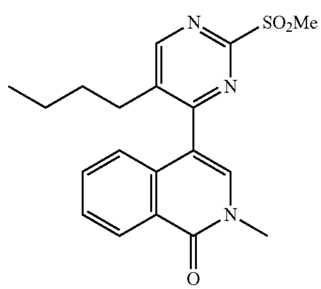 [SMILES: CCCCc1cnc(S(C)(=O)=O)nc1-c1cn(C)c(=O)c2ccccc12] | 4-(5-butyl-2-methylsulfonylpyrimidin-4-yl)-2-methylisoquinolin-1-one | | 372 |
| 305 | 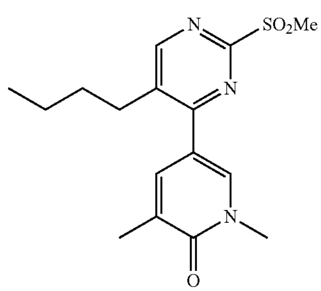 [SMILES: CCCCc1cnc(S(C)(=O)=O)nc1-c1cc(C)c(=O)n(C)c1] | 5-(5-butyl-2-methylsulfonylpyrimidin-4-yl)-1,3-dimethylpyridin-2-one | (CDCl3, 400 MHz) δ 8.70 (s, 1H), 7.84 (s, 1H), 7.55 (s, 1H), 3.67 (s, 3H), 3.37 (s, 3H), 2.84 (t, J = 8.0 Hz, 2H), 2.24 (s, 3H), 1.68 (m, 2H, overlapped with H$_2$O peak), 1.41 (m, 2H), 0.96 (t, J = 7.2 Hz, 3H). | 336 |

Examples 306-310 in Table 17 were prepared in a similar manner as Example 300, step 2 wherein Examples 301-305 were each treated with EtSO₂NH₂ to give the title compound.

TABLE 17

| Ex. No. | Structure | Name | ¹H NMR (ppm (δ), 400 MHz) | MS (M + H) | Prepared from Ex. No. |
|---|---|---|---|---|---|
| 306 | 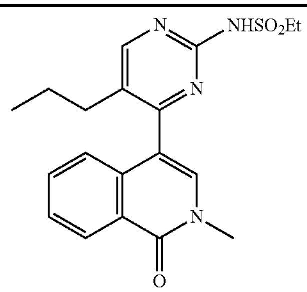 | N-[4-(2-methyl-1-oxoisoquinolin-4-yl)-5-propylpyrimidin-2-yl]ethanesulfonamide | (CDCl₃, 400 MHz) δ 8.58 (s, 1H), 8.54 (d, J = 8 Hz, 1H), 7.64 (t, J = 8 Hz, 1H), 7.56 (t, J = 8 Hz, 1H), 7.24 (s, 1H), 7.18 (s, 1H), 3.69 (s, 3H), 3.67-3.61 (m, 2H), 2.47 (t, J = 8 Hz, 2H), 1.51-1.47 (t, J = 8 Hz, 2H), 1.45-1.41 (t, J = 8 Hz, 3H), 0.81 (t, J = 8 Hz, 3H). | 387 | 301 |
| 307 | 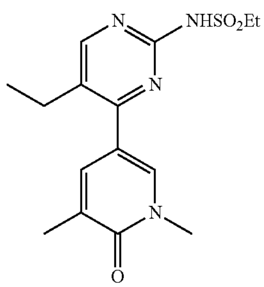 | N-[4-(1,5-dimethyl-6-oxopyridin-3-yl)-5-ethylpyrimidin-2-yl]ethanesulfonamide | (CDCl3, 400 MHz) δ 8.47 (s, 1H), 7.69 (s, 1H), 7.55 (s, 1H), 3.67 (m, 5H), 2.75 (q, J = 8 Hz, 2H), 2.24 (s, 3H), 1.45 (t, J = 8 Hz, 3H), 1.26 (t, J = 8 Hz, 3H) | 337 | 302 |
| 308 | 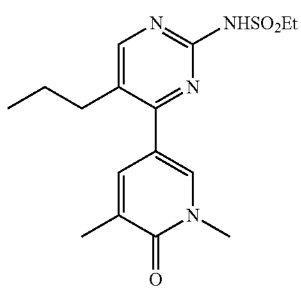 | N-[4-(1,5-dimethyl-6-oxopyridin-3-yl)-5-propylpyrimidin-2-yl]ethanesulfonamide | (CDCl3, 400 MHz) δ 8.42 (s, 1H), 7.67 (d, J = 2 Hz, 1H), 7.53 (s, 1H), 3.69 (t, J = 8 Hz, 2H), 3.65 (d, J = 8 Hz, 3H), 2.66 (q, J = 8 Hz, 2H), 2.23 (s, 3H), 1.62-1.60 (m, 2H), 1.45 (t, J = 8 Hz, 3H), 0.98 (t, J = 8 Hz, 3H) | 351 | 303 |
| 309 | 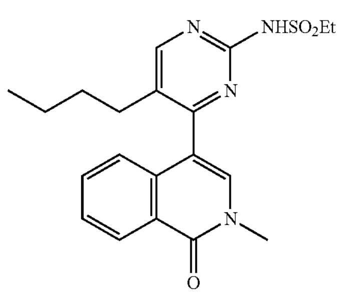 | N-[5-butyl-4-(2-methyl-1-oxoisoquinolin-4-yl)pyrimidin-2-yl]ethanesulfonamide | (CDC13, 400 MHz) δ 8.57 (s, 1H), 8.53 (d, J = 8 Hz, 1H), 7.65-7.61 (m, 1H), 7.58-7.53 (m, 1H), 7.24 (d, J = 8 Hz, 1H), 7.17 (s, 1H), 3.68 (s, 3H), 3.67-3.61 (m, 2H), 2.48 (t, J = 8 Hz, 2H), 1.46-1.39 (m, 5H), 1.23-1.16 (m, 2H), 0.76 (t, J = 7.2 Hz, 3H) | 401 | 304 |
| 310 | 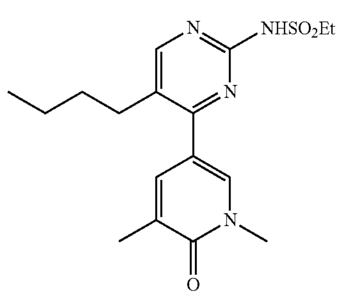 | N-[5-butyl-4-(1,5-dimethyl-6-oxopyridin-3-yl)pyrimidin-2-yl]ethanesulfonamide | (CDCl3, 400 MHz) δ 8.47 (s, 1H), 7.71 (s, 1H), 7.55 (s, 1H), 3.68-3.62 (m, 5H), 2.69 (t, J = 8 Hz, 2H), 2.23 (s, 3H), 1.55-1.46 (m, 2H), 1.40-1.37 (m, 5H), 0.94 (t, J = 7.2 Hz, 3H) | 365 | 305 |

Example 311: 4-[5-(cyclopropylmethoxy)-2-methyl-sulfonylpyrimidin-4-yl]-2-methylisoquinolin-1-one

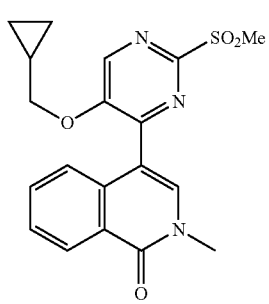 [SMILES: Cn1cc(-c2nc(S(C)(=O)=O)ncc2OCC2CC2)c2ccccc2c1=O]

The title compound of Example 152, step 5 was purified by preparative HPLC to give a cream colored powder. $^1$H NMR (CDCl$_3$, 400 MHz): δ 8.53 (s, 2H), 7.67-7.63 (m, 2H), 7.57-7.52 (m, 2H), 4.06 (d, J=6.8 Hz, 1H), 3.71 (s, 3H), 3.37 (s, 3H), 1.17 (m, 1H), 0.61 (m, 2H), 0.30 (m, 2H). LCMS: 386.1 (M+1)$^+$.

Example 312: 5-(2-ethyl-5-methylsulfonylphenyl)-1-methylpyridin-2-one

Step 1: 1-ethyl-4-methylsulfonyl-2-nitrobenzene

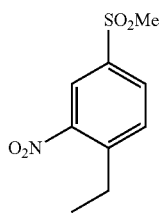

Bromo-4-methylsulfonyl-2-nitrobenzene (2 g, 7.0 mmol), ethylboronic acid (0.57 g, 7.7 mmol), K$_2$CO$_3$ (3.0 g, 21 mmol), Pd(dppf)Cl$_2$ (0.29 g, 0.35 mmol) in 1,4-dioxane/H$_2$O (4:1) (24 mL) were heated at 85° C. under N$_2$ overnight. Silica gel chromatography (PE:EA=6:1) gave the title compound (0.66 g, 40%) as a brown solid.

Step 2: 2-ethyl-5-methylsulfonylaniline

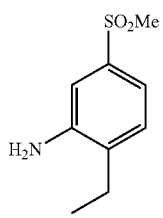

The title compound of step 1 (0.6 g, 2.6 mmol) and palladium on carbon (0.18 g) in CH$_3$OH (20 mL) was hydrogenated at 1 atm. for 6 hr. Silica gel chromatography (PE:EA=6:1) gave the title compound (0.49 g, 94%) as a brown liquid.

Step 3: 1-ethyl-2-iodo-4-methylsulfonylbenzene

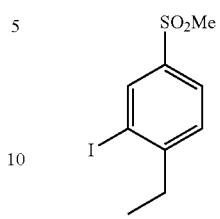

To the title compound of step 2 (155 mg, 0.8 mmol) in 5M HCl (3 mL) and H$_2$O (4 mL), cooled to 0° C., was added NaNO$_2$ (66 mg, 0.96 mmol). After stirring 0° C. for 30 min, KI (1.33 g, 8 mmol) in H$_2$O (2 mL) was added and the mixture was warmed to room temp and stirred 1 hr. Silica gel chromatography (PE:EA=3:1) gave the title compound (213 mg, 86%) as a brown solid.

Step 4: 5-(2-ethyl-5-methylsulfonylphenyl)-1-methylpyridin-2-one

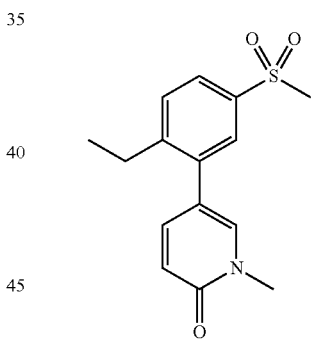

The title compound of step 3 (62 mg, 0.2 mmol), 1-methyl-5-(4,4,5,5-tetramethyl-1,3,2-dioxaborolan-2-yl)pyridin-2-one (57 mg, 0.24 mmol), K$_2$CO$_3$ (82 mg, 0.6 mmol), Pd(dppf)Cl$_2$ (6.2 mg) in 1,4-dioxane/H$_2$O (4:1) (5 mL) were heated at 85° C. under N$_2$ overnight. Silica gel chromatography (PE:EA=1:1) gave the title compound (56.6 mg, 97%) as a brown oil. $^1$H NMR (300 MHz, CDCl$_3$): δ 1.66 (3H, t, J=6.0 Hz), 2.63-2.71 (2H, m), 3.05 (3H, s), 3.60 (3H, s), 6.64 (1H, d, J=9.0 Hz), 7.28-7.33 (2H, m), 7.48 (1H, d, J=9.0 Hz), 7.70 (1H, s), 7.82-7.85 (1H, m). LCMS: 292 (M+1)$^+$.

Example 313: 1-methyl-5-(5-methylsulfonyl-2-propylphenyl)pyridin-2-one

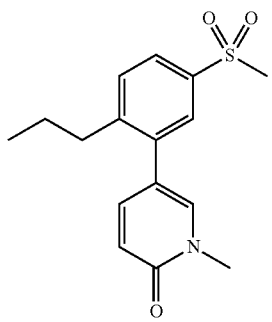 [SMILES: CCCc1ccc(S(C)(=O)=O)cc1-c1ccc(=O)n(C)c1]

The title compound was prepared in four steps in a similar manner to Example 312, steps 1-4 except that propylboronic acid was substituted for ethylboronic acid in step 1. $^1$H NMR (CDCl$_3$, 400 MHz): δ 7.91 (d, J=6.8 Hz, 1H), 7.77 (d, J=15.2 Hz, 2H), 7.62-7.58 (m, 2H), 6.66 (d, J=8.4 Hz, 1H), 3.67 (s, 3H), 3.16 (s, 3H), 2.74-2.78 (m, 2H), 1.63-1.58 (m, 2H), 0.93-0.90 (m, 3H). LCMS: 306 (M+1)$^+$.

Example 314: 2-methyl-4-(5-methylsulfonyl-2-propylphenyl)isoquinolin-1-one

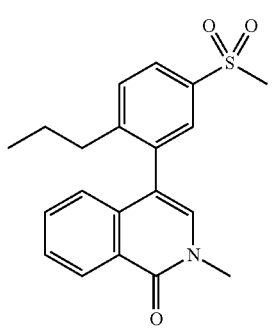 [SMILES: CCCc1ccc(S(C)(=O)=O)cc1-c1cn(C)c(=O)c2ccccc12]

The title compound was prepared in four steps in a similar manner to Example 312, steps 1-4, except that propylboronic acid was substituted for ethylboronic acid in step 1 and the title compound of Example 89, step 1 was substituted for 1-methyl-5-(4,4,5,5-tetramethyl-1,3,2-dioxaborolan-2-yl)pyridin-2-one in step 4. $^1$H NMR (CD$_3$OD, 400 MHz): δ 8.67 (d, J=8.0 Hz, 1H), 8.20 (dd, J$_1$=1.6 Hz, J$_2$=2.4 Hz, 1H), 7.84 (s, 1H), 7.71-7.67 (m, 2H), 7.63-7.59 (m, 1H), 7.42 (s, 1H), 7.08 (d, J=8.8 Hz, 1H), 3.71 (s, 3H), 3.18 (m, 3H), 2.64-2.57 (m, 1H), 2.51-2.44 (m, 1H), 1.59-1.50 (m, 2H), 0.82-0.78 (m, 3H).). LCMS: 356 (M+1)$^+$.

Example 315: 5-[2-(2-cyclopropylethyl)-5-methylsulfonylphenyl]-1-methylpyridin-2-one

Step 1: 2-(2-cyclopropylethynyl)-5-methylsulfonylaniline

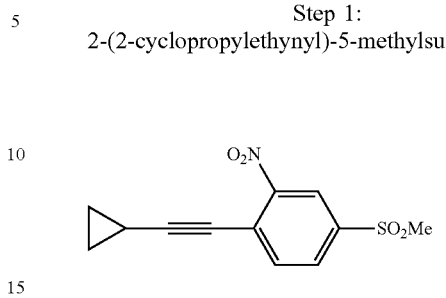

Bromo-4-methylsulfonyl-2-nitrobenzene (1.5 g, 5.36 mmol), ethynylcyclopropane (0.7 g, 10.72 mmol), K$_2$CO$_3$ (1.5 g, 10.72 mmol) in CH$_3$CN (30 ml), Pd(ACN)$_2$Cl$_2$ (55.5 mg, 0.21 mmol) and X-phos (128 mg, 0.27 mmol) under N$_2$ were heated at 45° C. for 3 hr. EA extractive work-up and preparative TLC (PE:EtOAc=5:1) gave the title compound (1.2 g).

Step 2: 2-(2-cyclopropylethyl)-5-methylsulfonylaniline

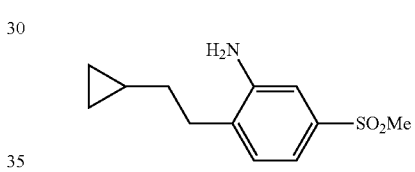

The title compound of step 1 (1.2 g) was hydrogenated in MeOH (45 mL) in a manner similar to Example 312, step 2. Preparative HPLC gave the title compound (422 mg, 41%). $^1$H NMR (CDCl$_3$, 400 MHz): δ 7.19-7.13 (m, 3H), 2.95 (s, 3H), 2.60-2.56 (m, 2H), 1.50-1.44 (m, 2H) 0.68-0.65 (m, 1H), 0.43-0.38 (m, 2H), 0.03-0.01 (m, 2H).

Step 3: 1-(2-cyclopropylethyl)-2-iodo-4-methylsulfonylbenzene

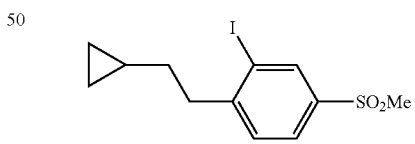

The title compound of step 2 (442 mg, 1.85 mmol) in 5M HCl (10 mL) was treated with NaNO$_2$ (167 mg, 2.41 mmol) followed by KI (3.07 g, 18.50 mmol) in H$_2$O (8 ml) in a manner similar to Example 312, step 3. EA extractive work-up and silica gel chromatography (PE:EA=10:1) gave the title compound (600 mg, 93%). $^1$H NMR (CDCl$_3$, 400 MHz): δ 8.27 (d, J=1.6 Hz, 1H), 7.74 (dd, J$_1$=1.6 Hz, J$_2$=6.4 Hz, 1H), 7.32 (d, J=7.6 Hz, 1H), 2.98 (s, 3H), 2.86-2.82 (m, 2H), 1.47-1.41 (m, 2H), 0.69-0.64 (m, 1H), 1.42-0.37 (m, 2H), 0.04-0.01 (m, 2H).

Step 4: 5-[2-(2-cyclopropylethyl)-5-methylsulfonyl-phenyl]-1-methylpyridin-2-one

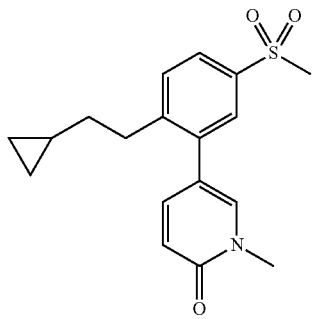 [SMILES: Cn1cc(-c2cc(S(C)(=O)=O)ccc2CCC2CC2)ccc1=O]

The title compound of step 3 (120 mg, 0.34 mmol), 1-methyl-5-(4,4,5,5-tetramethyl-1,3,2-dioxaborolan-2-yl)pyridin-2-one (89 mg, 0.37 mmol), Na2CO3 (72 mg, 0.68 mmol) and Pd(dppf)Cl$_2$ (15 mg) in DMF/H$_2$O (6 ml/1.5 ml) under N$_2$ were heated at 100° C. for 1 hr. EA extractive work-up and preparative TLC (PE:EtOAc=0:1) gave the title compound (62 mg, 55%). $^1$H NMR (CD$_3$OD, 400 MHz): δ 7.92 (dd, J$_1$=2.4 Hz, J$_2$=5.6 Hz, 1H), 7.81 (d, J=2 Hz, 1H), 7.78 (d, J=2.4 Hz, 1H), 7.65-7.61 (m, 2H), 6.69 (m, J=9.2 Hz, 1H), 3.69 (s, 3H), 3.17 (s, 3H), 2.89-2.86 (m, 2H), 1.51-1.45 (m, 2H), 0.68-0.65 (m, 1H), 0.45-0.40 (m, 2H), 0.04-0.00 (m, 2H). LCMS: 332 (M+1)$^+$.

Example 316: 4-(2-ethyl-5-methylsulfonylphenyl)-2-methylisoquinolin-1-one

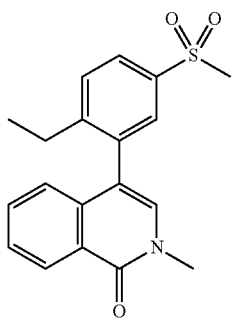 [SMILES: CCc1ccc(S(C)(=O)=O)cc1-c1cn(C)c(=O)c2ccccc12]

The title compound of Example 312, step 3 was reacted with the title compound of Example 89, step 1 in a manner similar to Example 312, step 4 to give the title compound. $^1$H NMR (400 MHz, CDCl$_3$): δ 1.10 (3H, t, J=8.0 Hz), 2.51-2.56 (2H, m), 3.10 (3H, s), 3.67 (3H, s), 6.97-7.02 (2H, m), 7.52-7.59 (3H, m), 7.80 (1H, s), 7.97 (1H, d, J=8.0 Hz), 8.54 (1H, d, J=8.0 Hz). LCMS: 342 (M+1)$^+$.

Example 317: 5-(2-butyl-5-methylsulfonylphenyl)-1-methylpyridin-2-one

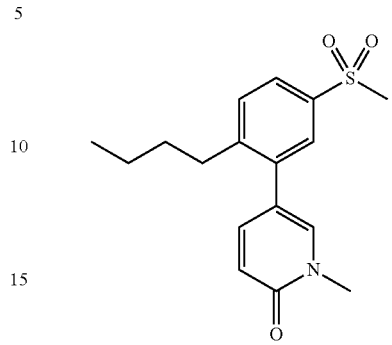

The title compound was prepared in four steps in a similar manner to Example 312, steps 1-4, except that butylboronic acid was substituted for ethylboronic acid in step 1. $^1$H NMR (400 MHz, MeOH-d$_4$): δ 0.89 (3H, t, J=8.0 Hz), 1.28-1.35 (2H, m), 1.54-1.58 (2H, m), 2.73-2.77 (2H, m), 3.16 (3H, s), 3.67 (3H, s), 6.67 (1H, d, J=4.0 Hz), 7.58-7.62 (2H, m), 7.78 (2H, d, J=12.0 Hz), 7.89-7.92 (1H, m). LCMS: 320 (M+1)$^+$.

Example 318: 4-(2-butyl-5-methylsulfonylphenyl)-2-methylisoquinolin-1-one

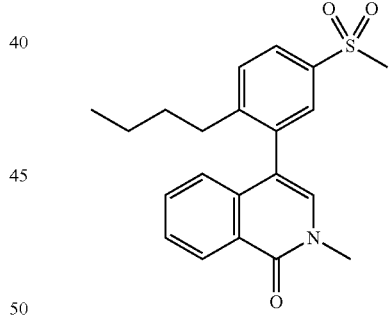

The title compound was prepared in four steps in a similar manner to Example 312, steps 1-4, except that butylboronic acid was substituted for ethylboronic acid in step 1 and the title compound of Example 89, step 1 was substituted for 1-methyl-5-(4,4,5,5-tetramethyl-1,3,2-dioxaborolan-2-yl)pyridin-2-one in step 4. $^1$H NMR (300 MHz, MeOH-d$_4$): δ 0.73 (3H, t, J=7.5 Hz), 1.14-1.21 (2H, m), 1.43-1.51 (2H, m), 2.45-2.64 (2H, m), 3.17 (3H, s), 3.70 (3H, s), 7.07 (1H, d, J=9.0 Hz), 7.41 (1H, s), 7.57-7.70 (3H, m), 7.82 (1H, d, J=3.0 Hz), 7.98-8.01 (1H, m), 8.44-8.47 (1H, m). LCMS: 370 (M+1)$^+$.

Example 319: 4-[2-(2-cyclopropylethyl)-5-methyl-sulfonylphenyl]-2-methylisoquinolin-1-one

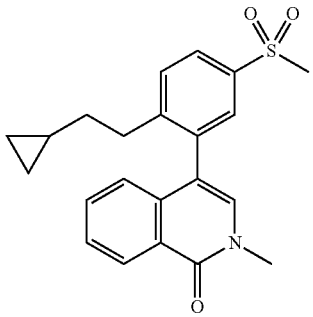 [SMILES: Cn1cc(-c2cc(S(C)(=O)=O)ccc2CCC2CC2)c2ccccc2c1=O]

The title compound of Example 315, step 3 was reacted with the title compound of Example 89, step 1 in a manner similar to Example 315, step 4 to give the title compound. $^1$H NMR (CD$_3$OD, 400 MHz): δ 8.67 (d, J=8.0 Hz, 1H), 8.21 (dd, J$_1$=2.0 Hz, J$_2$=6.0 Hz, 1H), 8.03 (d, J=2.0 Hz, 1H), 7.92-7.86 (m, 2H), 7.82-7.79 (m, 1H), 7.61 (s, 1H), 7.28 (d, J=8.0 Hz, 1H), 3.91 (s, 3H), 3.38 (s, 3H), 2.94-2.89 (m, 1H), 2.83-2.77 (m, 1H), 1.64-1.55 (m, 2H), 0.75-0.71 (m, 1H), 0.51-0.47 (m, 2H), 0.01-0.00 (m, 2H). LCMS: 382 (M+1)$^+$.

Example 320: N-[6-(cyclopropylmethoxy)-5-(2-methyl-1-oxoisoquinolin-4-yl)pyridin-3-yl]ethane-sulfonamide

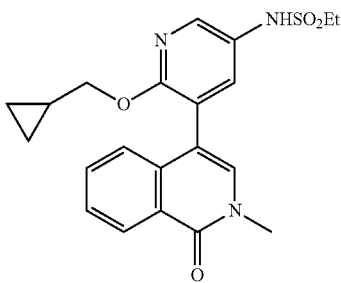

A mixture of N-[5-bromo-6-(cyclopropylmethoxy)pyridin-3-yl]ethanesulfonamide (60 mg, 0.21 mmol), 2-methyl-4-(4,4,5,5-tetramethyl-1,3,2-dioxaborolan-2-yl)isoquinolin-1-one (77 mg, 0.23 mmol), Pd$_2$(dba)$_3$ (7 mg), XPhos (7 mg), and K$_3$PO$_4$ (111 mg, 0.51 mmol) in dioxane (1.2 mL) and H$_2$O (140 uL) was purged with N$_2$, capped, and heated to 70° C. for 2 hr. After the mixture was filtered through a short bed of celite, the filtrate was concentrated in vacuo and purified by prep-HPLC to afford the title compound (45 mg, 52%) as a white solid. $^1$H NMR (400 MHz, DMSO-d$_6$): δ ppm 0.09-0.15 (m, 2H) 0.29-0.40 (m, 2H) 0.97-1.08 (m, 1H) 1.20-1.28 (m, 3H) 3.07-3.16 (m, 2H) 3.56 (s, 3H) 4.02-4.18 (m, 2H) 7.17-7.22 (m, 1H) 7.52 (s, 3H) 7.62-7.69 (m, 1H) 8.06-8.11 (m, 1H) 8.27-8.33 (m, 1H) 9.47-10.31 (m, 1H). LCMS (M+H)$^+$: 414.

Example 321: 4-[2-(cyclopropylmethoxy)-5-methyl-sulfonylpyridin-3-yl]-2-methylisoquinolin-1-one Step 1: 3-bromo-2-chloro-5-methylsulfonylpyridine

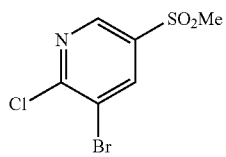 [SMILES: CS(=O)(=O)c1cnc(Cl)c(Br)c1]

A 0.5 M soln of 5-bromo-6-chloropyridine-3-sulfonyl chloride (1.5 g, 5.2 mmol) in THF was added dropwise to a mixture of NaHCO$_3$ (521 mg) and sodium sulfite (847 mg) stirred at room temp in H$_2$O (15 mL). The rxn mixture was heated to 70° C. for 2 hr. After cooling to room temp, the rxn mixture was treated with iodomethane (1.5 mL, 23 mmol) and then heated to 50° C. for 12 hr. The rxn mixture was extracted with EtOAc (20 mL×3); the combined organic layers were washed with H$_2$O, brine, dried over MgSO4, filtered, and concentrated in vacuo. The resulting solid was purified by silica gel CC (20% EtOAc in hexanes) to afford the title compound (952 mg, 68%). LCMS (M+H)$^+$: 271.

Step 2: 3-bromo-2-(cyclopropylmethoxy)-5-methyl-sulfonylpyridine

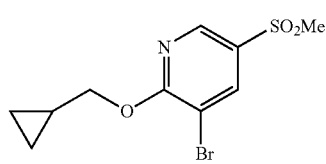 [SMILES: CS(=O)(=O)c1cnc(OCC2CC2)c(Br)c1]

A soln of cyclopropylmethanol (146 μL, 1.8 mmol) stirred in DMF (3 mL) at 0° C. was treated with NaH (75 mg, 1.9 mmol, 60% in mineral oil). After stirring at 0° C. for 30 min, the rxn mixture was treated with a soln of 3-bromo-2-chloro-5-methylsulfonylpyridine (400 mg, 1.5 mmol) in DMF (3 mL) by dropwise addition. After the icebath was removed, the mixture was stirred at room temp for 14 hr. The rxn mixture was treated with H$_2$O and extracted with EtOAc (30 mL×2). The combined organic layers were washed with brine, dried over Na$_2$SO$_4$, filtered, and concentrated in vacuo. The resulting residue was purified by silica gel CC using a gradient of EtOAc (5 to 85%) in hexanes to give the title compound (298 mg, 65%). LCMS: (M+H)$^+$307.

Step 3: 4-[2-(cyclopropylmethoxy)-5-methylsulfonylpyridin-3-yl]-2-methylisoquinolin-1-one

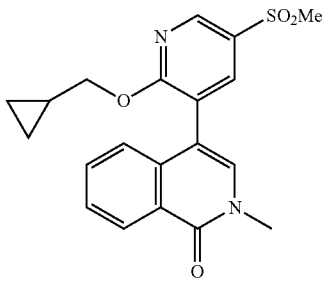 [SMILES: Cn1cc(-c2cc(S(C)(=O)=O)cnc2OCC2CC2)c2ccccc2c1=O]

A mixture of 3-bromo-2-(cyclopropylmethoxy)-5-methylsulfonylpyridine (67 mg, 0.22 mmol), 2-methyl-4-(4,4,5,5-tetramethyl-1,3,2-dioxaborolan-2-yl)isoquinolin-1-one (60 mg, 0.21 mmol), $Pd_2(dba)_3$ (6 mg), X-Phos (7 mg), and $K_3PO_4$ (111 mg, 0.51 mmol) in dioxane (1.2 mL) and $H_2O$ (140 μL) was purged with $N_2$, capped, and heated at 70° C. for 2 hr. After the mixture was filtered through a short bed of celite, the filtrate was concentrated in vacuo and purified by prep-HPLC to afford the title compound (58 mg, 73%) as a white solid. $^1$H NMR (400 MHz, DMSO-$d_6$): δ ppm 0.12-0.26 (m, 2H) 0.28-0.47 (m, 2H) 1.02-1.15 (m, 1H) 3.30-3.32 (m, 3H) 3.54-3.62 (m, 3H) 4.02-4.41 (m, 2H) 7.17-7.27 (m, 1H) 7.52-7.59 (m, 1H) 7.60-7.64 (m, 1H) 7.64-7.71 (m, 1H) 8.16-8.22 (m, 1H) 8.26-8.35 (m, 1H) 8.70-8.79 (m, 1H). LCMS (M+H)$^+$: 385.

Example 322: 4-[2-(cyclopropylmethoxy)-5-ethylsulfonylpyridin-3-yl]-2-methylisoquinolin-1-one

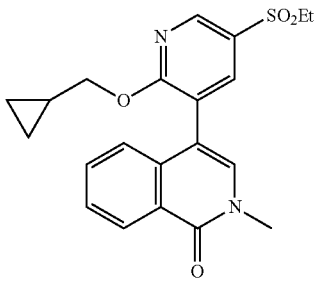

The title compound was prepared in a manner similar to Example 321, substituting iodoethane for iodomethane in Step 1. $^1$H NMR (400 MHz, DMSO-$d_6$): δ ppm 0.09-0.15 (m, 2H) 0.31-0.40 (m, 2H) 0.98-1.07 (m, 1H) 1.20-1.28 (m, 3H) 3.07-3.17 (m, 2H) 3.54-3.58 (m, 3H) 3.99-4.16 (m, 2H) 7.16-7.23 (m, 1H) 7.50-7.59 (m, 3H) 7.63-7.70 (m, 1H) 8.06-8.11 (m, 1H) 8.27-8.32 (m, 1H) 9.40-10.08 (m, 1H). LCMS (M+H)$^+$: 399.

Example 323: 5-[3-[(4-methoxyphenyl)methoxy]-5-methylsulfonylphenyl]-1,3-dimethylpyridin-2-one

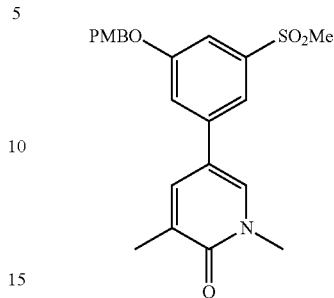

A mixture of 1-bromo-3-[(4-methoxyphenyl)methoxy]-5-methylsulfonylbenzene (450 mg, 1.2 mmol), 1,3-dimethyl-5-(4,4,5,5-tetramethyl-1,3,2-dioxaborolan-2-yl)pyridin-2-one (300 mg, 1.2 mmol), Pd(dppf)Cl$_2$ (88 mg) and $K_3PO_4$ (654 mg, 3 mmol) in dioxane (8 mL) and $H_2O$ (800 μL) was purged with $N_2$ for 7 min, capped, and heated to 75° C. for 1 hr. After the mixture was filtered through a short bed of celite, the filtrate was concentrated in vacuo and purified by silica gel CC using a gradient of EtOAc (5 to 100%) in DCM to afford the title compound (416 mg, 83%) as a tan solid. $^1$H NMR (400 MHz, DMSO-$d_6$): δ ppm 2.05-2.14 (s, 3H) 3.25-3.28 (s, 3H) 3.49-3.57 (s, 3H) 3.74-3.81 (s, 3H) 5.12-5.22 (s, 2H) 6.93-7.03 (m, 2H) 7.34-7.47 (m, 3H) 7.52-7.59 (m, 1H) 7.64-7.72 (m, 1H) 7.82-7.90 (m, 1H) 8.14-8.22 (m, 1H). LCMS (M+H)$^+$: 414.

Example 324: 1,3-dimethyl-5-(3-methylsulfonyl-5-phenylmethoxyphenyl)pyridin-2-one Step 1: 5-(3-hydroxy-5-methylsulfonylphenyl)-1,3-dimethylpyridin-2-one

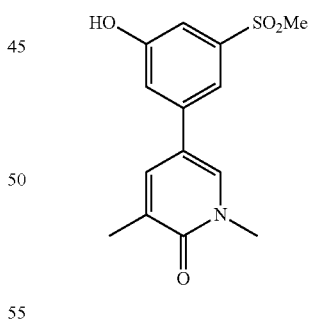

A soln of 5-[3-[(4-methoxyphenyl)methoxy]-5-methylsulfonylphenyl]-1,3-dimethylpyridin-2-one (410 mg, 1 mmol) in AcOH (10 mL) was heated to 100° C. for 8 hr. After cooling to room temp, the rxn mixture was evaporated to dryness in vacuo. The resulting residue was diluted with $H_2O$ and extracted with EtOAc (50 ml×3); the combined organic layers were washed with brine, dried over $MgSO_4$, filtered, and concentrated in vacuo. The resulting solid was suspensed in ethyl ether, sonicated for 3 min, and filtered. The filter cake was collected to afford the title compound (290 mg, 68%) as a gray solid. LCMS (M+H)$^+$: 294.

Step 2: 1,3-dimethyl-5-(3-methylsulfonyl-5-phenyl-methoxyphenyl)pyridin-2-one

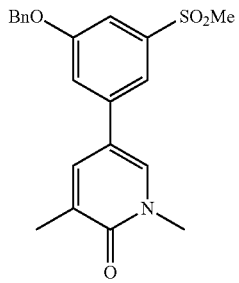 [SMILES: Cc1cc(-c2cc(OCc3ccccc3)cc(S(C)(=O)=O)c2)cn(C)c1=O]

A capped mixture of 5-(3-hydroxy-5-methylsulfonylphenyl)-1,3-dimethylpyridin-2-one (25 mg, 0.085 mmol), benzyl bromide (20 mg, 0.12 mmol), and Na$_2$CO$_3$ (18 mg, 0.17 mmol) in DMF (600 µL) was heated to 80° C. for 90 min. The mixture was filtered and the filter cake was washed with ACN (500 µL), the filtrate was purified by prep-HPLC to afford the title compound (8 mg, 25%) as a tan solid. $^1$H NMR (400 MHz, DMSO-d$_6$): δ ppm 2.08-2.13 (m, 3H) 3.26-3.28 (m, 3H) 3.51-3.57 (m, 3H) 5.22-5.34 (m, 2H) 7.33-7.47 (m, 4H) 7.48-7.53 (m, 2H) 7.54-7.60 (m, 1H) 7.67-7.71 (m, 1H) 7.83-7.88 (m, 1H) 8.17-8.22 (m, 1H). LCMS (M+H)$^+$: 384.

For Examples 325-340 in Table 18, the title compound of Step 1 in Example 324 was O-alkylated with the appropriate alkyl halide in a similar manner to Step 2 of Example 324. For Examples 332-340, Cs$_2$CO$_3$ is substituted for Na$_2$CO$_3$.

TABLE 18

| Ex. No. | R$^1$ | Name | MS (M + H) |
|---|---|---|---|
| 325 | (cyclopropylmethyl) | 5-[3-(cyclopropylmethoxy)-5-methylsulfonylphenyl]-1,3-dimethylpyridin-2-one | 348 |
| 326 | (2-phenylethyl) | 1,3-dimethyl-5-[3-methylsulfonyl-5-(2-phenylethoxy)phenyl]pyridin-2-one | 398 |
| 327 | (2-cyclopropylethyl) | 5-[3-(2-cyclopropylethoxy)-5-methylsulfonylphenyl]-1,3-dimethylpyridin-2-one | 362 |
| 328 | (2,2,2-trifluoroethyl) | 1,3-dimethyl-5-[3-methylsulfonyl-5-(2,2,2-trifluoroethoxy)phenyl]pyridin-2-one | 376 |
| 329 | (3-methyloxetan-3-yl)methyl | 1,3-dimethyl-5-[3-[(3-methyloxetan-3-yl)methoxy]-5-methylsulfonylphenyl]pyridin-2-one | 378 |
| 330 | (pyridin-2-ylmethyl) | 1,3-dimethyl-5-[3-methylsulfonyl-5-(pyridin-2-ylmethoxy)phenyl]pyridin-2-one | 385 |

TABLE 18-continued

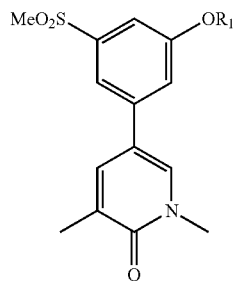

| Ex. No. | R¹ | Name | MS (M + H) |
|---|---|---|---|
| 331 | 2,6-dimethylphenylmethyl | 5-[3-[(2,6-dimethylphenyl)methoxy]-5-methylsulfonylphenyl]-1,3-dimethylpyridin-2-one | 412 |
| 332 | 2-chlorophenylmethyl | 5-[3-[(2-chlorophenyl)methoxy]-5-methylsulfonylphenyl]-1,3-dimethylpyridin-2-one | 419 |
| 333 | 2-(difluoromethoxy)phenylmethyl | 5-[3-[[2-(difluoromethoxy)phenyl]methoxy]-5-methylsulfonylphenyl]-1,3-dimethylpyridin-2-one | 450 |
| 334 | 2-cyanophenylmethyl | 2-[[3-(1,5-dimethyl-6-oxopyridin-3-yl)-5-methylsulfonylphenoxy]methyl]benzonitrile | 409 |
| 335 | 2,4-difluorophenylmethyl | 5-[3-[(2,4-difluorophenyl)methoxy]-5-methylsulfonylphenyl]-1,3-dimethylpyridin-2-one | 420 |
| 336 | 1-phenylethyl | 1,3-dimethyl-5-[3-methylsulfonyl-5-(1-phenylethoxy)phenyl]pyridin-2-one | 398 |
| 337 | 2,3-dichlorophenylmethyl | 5-[3-[(2,3-dichlorophenyl)methoxy]-5-methylsulfonylphenyl]-1,3-dimethylpyridin-2-one | 453 |
| 338 | pyridin-3-ylmethyl | 1,3-dimethyl-5-[3-methylsulfonyl-5-(pyridin-3-ylmethoxy)phenyl]pyridin-2-one | 385 |

TABLE 18-continued

MeO₂S — [ring] — OR₁ — pyridinone core (1,3-dimethyl-6-oxopyridin-3-yl at 5-position of phenyl)

| Ex. No. | R¹ | Name | MS (M + H) |
|---|---|---|---|
| 339 | 3-cyanobenzyl group | 3-[[3-(1,5-dimethyl-6-oxopyridin-3-yl)-5-methylsulfonylphenoxy]methyl]benzonitrile | 409 |
| 340 | but-2-ynyl group | 5-(3-but-2-ynoxy-5-methylsulfonylphenyl)-1,3-dimethylpyridin-2-one | 346 |

Example 341: 1,3-dimethyl-5-[3-methylsulfonyl-5-[(1R)-1-phenylethoxy]phenyl]pyridin-2-one

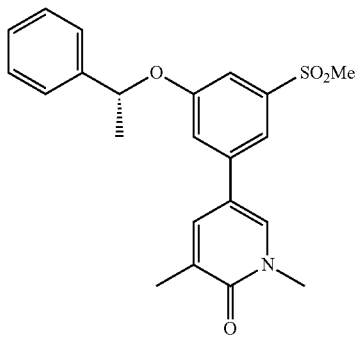 [SMILES: Cc1cc(-c2cc(O[C@H](C)c3ccccc3)cc(S(C)(=O)=O)c2)cn(C)c1=O]

A soln of (1S)-1-phenylethan-1-ol (14 mg, 0.11 mmol) in THF (1 mL) stirred at room temp under N₂ was treated with triphenylphosphine (38 mg, 0.15 mmol) and 5-(3-hydroxy-5-methylsulfonylphenyl)-1,3-dimethylpyridin-2-one (33 mg, 0.11 mmol). After 30 min, the rxn mixture was treated with DIAD (29 mg, 0.15 mmol). The N₂ inlet was removed and the mixture was stirred (closed system) for 18 hr. After the rxn mixture was diluted with EtOAc (10 ml), it was washed with H₂O, satd NaHCO₃ soln (aq), dried over Na2SO4, filtered, and concentrated in vacuo. The crude residue was diluted with ACN (1 mL) and was purified by prep-HPLC to afford the title compound (21 mg, 48%) as an off-white solid. ¹H NMR (400 MHz, DMSO-d6): δ ppm 1.61 (d. J=6.4, 3H) 2.08 (s, 3H) 3.20 (s, 3H) 3.52 (s, 3H) 5.70-5.80 (q. J=6.4, 1H) 7.23-7.31 (m, 2H) 7.35-7.41 (m, 2H) 7.44-7.51 (m, 3H) 7.56-7.63 (m, 1H) 7.73-7.80 (m, 1H) 8.08-8.15 (m, 1H). LCMS (M+H)⁺: 398.

Example 342: N-[3-(2,4-difluorophenoxy)-5-(1,5-dimethyl-6-oxopyridin-3-yl)phenyl]ethanesulfonamide Step 1: 1-(3-bromo-5-nitrophenoxy)-2,4-difluorobenzene

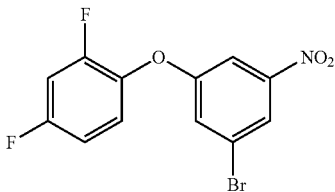 [SMILES: O=[N+]([O-])c1cc(Br)cc(Oc2ccc(F)cc2F)c1]

A mixture of 2,4-difluorophenol (286 mg, 2.2 mmol) and 1-bromo-3-fluoro-5-nitrobenzene (440 mg, 2 mmol) in DMF (4.5 mL) was treated with K₂CO₃ (304 mg, 2.2 mmol). The mixture was heated at 100° C. by microwave irradiation (normal) for 5 hr. The resulting suspension was diluted with H₂O and extracted with EtOAc (15 mL×3). The combined organic layers were washed with 1N NaOH (aq) (15 mL), H₂O (15 mL), brine, dried over MgSO₄, and concentrated in vacuo. The crude solid was purified by CC using EtOAc (5% to 25%) in hexanes to afford the title compound (200 mg, 30%) as a yellow solid. LCMS (M+H)⁺: 339.

Step 2: 3-bromo-5-(2,4-difluorophenoxy)aniline

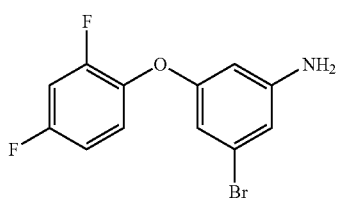 [SMILES: Nc1cc(Br)cc(Oc2ccc(F)cc2F)c1]

A mixture of 1-(3-bromo-5-nitrophenoxy)-2,4-difluorobenzene (54 mg, 0.16 mmol), ammonium chloride (18 mg, 0.32 mmol), and iron powder (45 mg, 0.80 mmol) suspended in THF (300 μL), H$_2$O (100 μL) and ethanol (300 μL) was heated at 100° C. using microwave irradiation (normal) for 3 hr. The crude rxn mixture was filtered through a short plug of celite; the celite plug was washed with MeOH (~5 mL). The resulting filtrate was concentrated in vacuo. The resulting residue was diluted with EtOAc (50 ml) and washed with satd bicarbonate soln (aq), dried over anhydrous magnesium sulfate, filtered, and concentrated in vacuo. The crude solid was purified by silica gel CC using a gradient of EtOAc (5 to 20%) in hexanes to afford the title compound (48 mg, 100%) as a yellow solid. LCMS (M+H)$^+$: 301.

Step 3: N-[3-bromo-5-(2,4-difluorophenoxy)phenyl]ethanesulfonamide

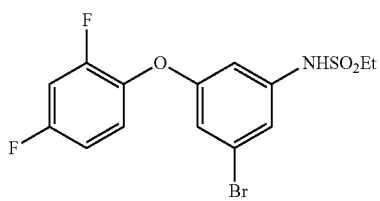

Ethylsulfonyl chloride (15 μL, 0.16 mmol) was added dropwise to a stirred soln of 3-bromo-5-(2,4-difluorophenoxy)aniline (48 mg, 0.16 mmol) and pyridine (40 μL, 0.48 mmol) in DCM (320 μL) at 0° C. under N$_2$. After the mixture was allowed to warm to room temp and stirred for 12 hr, it was treated with 1N HCl (1 mL) and extracted with DCM (3×5 mL); the combined organic extracts were washed with satd bicarbonate soln (aq), dried over Na$_2$SO$_4$, filtered and concentrated in vacuo. The crude solid was purified by silica gel CC using a gradient of EtOAc (5 to 60%) in hexanes to afford the title compound (60 mg, 95%) as a tan solid. LCMS (M+H)$^+$: 393.

Step 4: N-[4-(2,4-difluorophenoxy)-5-(1,5-dimethyl-6-oxopyridin-3-yl)phenyl]ethanesulfonamide

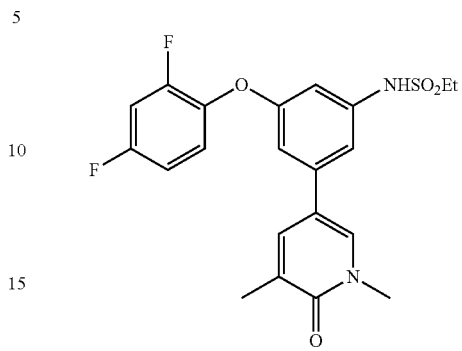

A mixture of N-[3-bromo-5-(2,4-difluorophenoxy)phenyl]ethanesulfonamide (70 mg, 0.17 mmol), 1,3-dimethyl-5-(4,4,5,5-tetramethyl-1,3,2-dioxaborolan-2-yl)pyridin-2-one (44 mg, 0.18 mmol), Pd(dppf)Cl$_2$ (12 mg) and K$_3$PO$_4$ (92 mg, 0.42 mmol) in dioxane (1 mL) and H$_2$O (133 μL) was purged with N$_2$, capped, and heated to 75° C. for 1 hr. After the mixture was filtered through a short bed of celite, the filtrate was concentrated in vacuo and purified by silica gel CC using a gradient of MeOH (0 to 10%) in DCM to afford the title compound (69 mg, 94%) as an off-white solid. $^1$H NMR (400 MHz, DMSO-d$_6$): δ ppm 1.13-1.22 (m, 3H) 2.07 (s, 3H) 3.08-3.20 (m, 2H) 3.50 (s, 3H) 6.65-6.70 (m, 1H) 6.92-6.96 (m, 1H) 7.05-7.10 (m, 1H) 7.12-7.19 (m, 1H) 7.28-7.37 (m, 1H) 7.47-7.55 (m, 1H) 7.56-7.59 (m, 1H) 7.87-7.95 (m, 1H) 9.76-9.94 (m, 1H). LCMS (M+H)$^+$: 435.

Example 343: 4-[3-[(4-methoxyphenyl)methoxy]-5-methylsulfonylphenyl]-2-methylisoquinolin-1-one

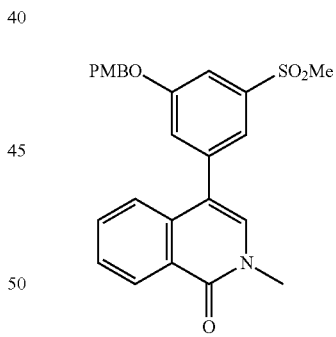

A mixture of 1-bromo-3-[(4-methoxyphenyl)methoxy]-5-methylsulfonylbenzene (103 mg, 0.28 mmol), 2-methyl-4-(4,4,5,5-tetramethyl-1,3,2-dioxaborolan-2-yl)isoquinolin-1-one (79 mg, 0.28 mmol), Pd(dppf)Cl$_2$ (20 mg) and K$_3$PO$_4$ (153 mg, 0.7 mmol) in dioxane (1.9 mL) and H$_2$O (100 μL) was purged with N$_2$ for 10 min, capped, and heated to 75° C. for 15 hr. After the mixture was filtered through a short bed of celite, the filtrate was concentrated in vacuo and purified by CC using EtOAc (5% to 100%) in DCM to afford the title compound (100 mg, 80%) as a tan solid. $^1$H NMR (400 MHz, DMSO-d$_6$): δ ppm 3.30 (s, 3H) 3.58 (s, 3H) 3.77 (s, 3H) 5.14-5.28 (m, 2H) 6.88-7.04 (m, 2H) 7.32-7.80 (m, 9H) 8.29-8.43 (m, 1H). LCMS (M+H)$^+$: 450.

Example 344: 2-methyl-4-(3-methylsulfonyl-5-phenylmethoxyphenyl)isoquinolin-1-one

Step 1: 4-(3-hydroxy-5-methylsulfonylphenyl)-2-methylisoquinolin-1-one

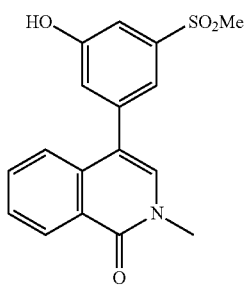 [SMILES: Cn1cc(-c2cc(O)cc(S(C)(=O)=O)c2)c2ccccc2c1=O]

The title compound was prepared in a manner similar to Example 324, substituting 4-[3-[(4-methoxyphenyl)methoxy]-5-methylsulfonylphenyl]-2-methylisoquinolin-1-one for 5-[3-[(4-methoxyphenyl)methoxy]-5-methylsulfonylphenyl]-1,3-dimethylpyridin-2-one in Step 1. LCMS (M+H)$^+$: 330.

Step 2: 2-methyl-4-(3-methylsulfonyl-5-phenylmethoxyphenyl)isoquinolin-1-one

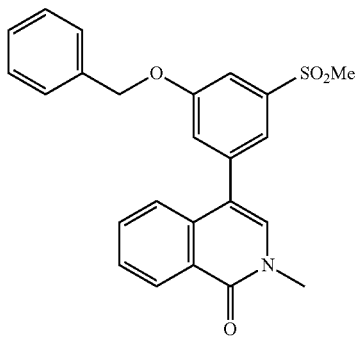 [SMILES: Cn1cc(-c2cc(OCc3ccccc3)cc(S(C)(=O)=O)c2)c2ccccc2c1=O]

A capped mixture of 4-(3-hydroxy-5-methylsulfonylphenyl)-2-methylisoquinolin-1-one (25 mg, 0.076 mmol), benzyl bromide (20 mg, 0.12 mmol), and Cs$_2$CO$_3$ (50 mg, 0.15 mmol) in DMF (600 µL) was heated to 80° C. for 3 hr. The mixture was filtered and the filter cake was washed with ACN (500 µL), the filtrate was purified by prep-HPLC to afford the title compound (12 mg, 38%) as a tan solid. LCMS (M+H)$^+$: 420.

Example 345: 4-[3-(cyclopropylmethoxy)-5-methylsulfonylphenyl]-2-methylisoquinolin-1-one

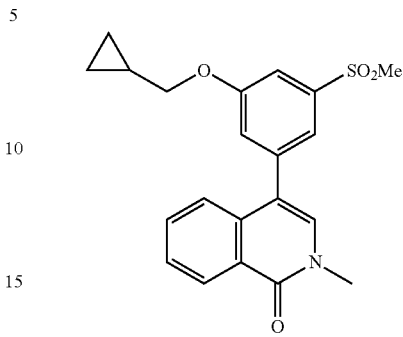

The title compound was prepared in a manner similar to Example 344, substituting cyclopropylmethyl bromide for benzyl bromide in Step 2. LCMS (M+H)$^+$: 384.

Example 346: N-[4-(2,4-difluorophenoxy)-6-(1,5-dimethyl-6-oxopyridin-3-yl)pyrimidin-2-yl]ethanesulfonamide

Step 1: 5-(2,6-dichloropyrimidin-4-yl)-1,3-dimethylpyridin-2-one

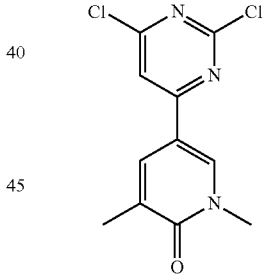

A mixture of 2,4,6-trichloropyrimidine (275 mg, 1.5 mmol), 1,3-dimethyl-5-(4,4,5,5-tetramethyl-1,3,2-dioxaborolan-2-yl)pyridin-2-one (246 mg, 1 mmol), Pd(OAc)$_2$ (20 mg), triphenylphosphine (16 mg), and 2M Na$_2$CO$_3$ (1 mL, 2 mmol) in THF (6.7 mL) was purged with N$_2$ for 5 min, capped, and heated to 80° C. for 3 hr. After the mixture was filtered through a short bed of celite, the filtrate was concentrated in vacuo and purified by CC using 0% to 100% EtOAc in DCM to afford the title compound (150 mg, 55%) as a white solid. LCMS (M+H)$^+$: 271.

Step 2: 5-[2-chloro-6-(2,4-difluorophenoxy)pyrimidin-4-yl]-1,3-dimethylpyridin-2-one and 5-[6-chloro-2-(2,4-difluorophenoxy)pyrimidin-4-yl]-1,3-dimethylpyridin-2-one

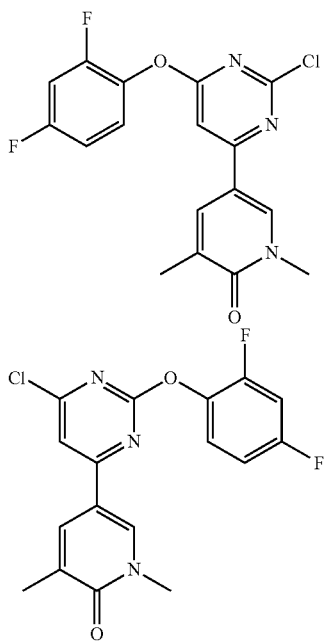

A mixture of 2,4-difluorophenol (25 mg, 0.19 mmol) and 5-(2,6-dichloropyrimidin-4-yl)-1,3-dimethylpyridin-2-one (50 mg, 0.19 mmol) in DMF (0.5 mL) and THF (0.5 mL) was treated with K$_2$CO$_3$ (304 mg, 0.23 mmol). The mixture was stirred at room temp for 3 hr. The resulting suspension was diluted with H$_2$O and extracted with EtOAc (10 mL×3). The combined organic layers were washed with 1N NaOH$_{(aq)}$ (5 mL), H$_2$O (15 mL), brine, dried over MgSO$_4$, and concentrated in vacuo. The crude solid was purified by silica gel CC using EtOAc (0% to 50%) in DCM to afford an unseparated mixture of regioisomeric title compounds (66 mg, 96% combined) as a white solid. LCMS (M+H)$^+$: 364 for both regioisomers.

Step 3: N-[4-(2,4-difluorophenoxy)-6-(1,5-dimethyl-6-oxopyridin-3-yl)pyrimidin-2-yl]ethanesulfonamide

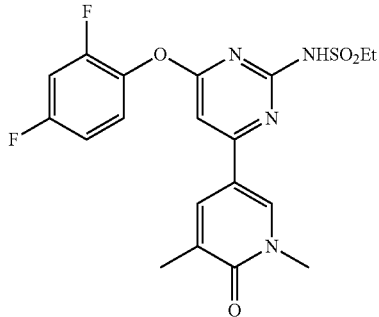

A soln of ethanesulfonamide (80 mg, 0.73 mmol) in DMF (2 mL) was treated with NaH (27 mg, 0.68 mmol, 60% by weight). After 15 min, the mixture was treated with a DMF (1 mL) soln of title compounds obtained from Step 2. The rxn mixture was stirred at 50° C. for 14 hr. The resulting suspension was diluted with H$_2$O and extracted with EtOAc (10 mL×3). The combined organic layers were washed with brine, dried over Na$_2$SO$_4$, and concentrated in vacuo. Preparative HPLC isolated both regioisomers as Examples 346 and 347. The title compound (6 mg, 8%) was obtained as a white solid. $^1$H NMR (400 MHz, DMSO-d$_6$): δ ppm 1.08 (t, J=7.1 Hz, 3H) 2.07 (s, 3H) 3.11 (q, J=7.1 Hz, 2H) 3.54 (s, 3H) 6.81 (s, 1H) 7.17 (m, 1H) 7.47 (s, 2H) 7.79 (s, 1H) 8.37 (s, 1H) 11.37 (bs, 1H). LCMS (M+H)$^+$: 437.

Example 347: N-[2-(2,4-difluorophenoxy)-6-(1,5-dimethyl-6-oxopyridin-3-yl)pyrimidin-4-yl]ethanesulfonamide

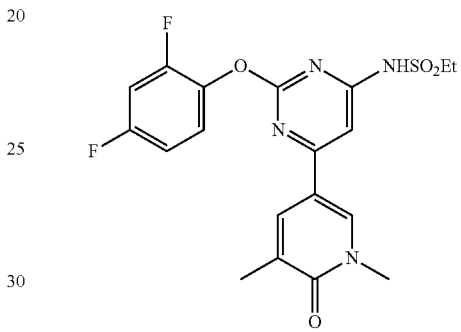

The preparative HPLC of Example 346, step 3 also isolated this regioisomer. The title compound (2 mg, 3%) was obtained as a white solid. $^1$H NMR (400 MHz, DMSO-d$_6$): δ ppm 1.06-1.13 (m, 3H) 2.08-2.12 (m, 3H) 3.11-3.23 (m, 2H) 3.54-3.57 (m, 3H) 7.14-7.28 (m, 2H) 7.45-7.54 (m, 2H) 8.04-8.09 (m, 1H) 8.52-8.57 (m, 1H) 10.92-11.26 (m, 1H), both as a white solids. LCMS (M+H)$^+$: 437.

Example 348: 4-[3-[[2-(difluoromethoxy)phenyl]methoxy]-5-methylsulfonylphenyl]-6-methylfuro[2,3-c]pyridin-7-one

Step 1: 4-[3-[(4-methoxyphenyl)methoxy]-5-methylsulfonylphenyl]-6-methylfuro[2,3-c]pyridin-7-one

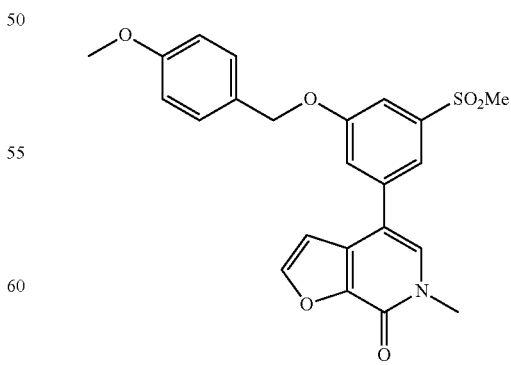

A mixture of 1-bromo-3-[(4-methoxyphenyl)methoxy]-5-methylsulfonylbenzene (470 mg, 1.27 mmol), 6-methyl-4-(4,4,5,5-tetramethyl-1,3,2-dioxaborolan-2-yl)furo[2,3-c]

pyridin-7-one (316 mg, 1.15 mmol), Pd(dppf)Cl$_2$ (84 mg) and K$_3$PO$_4$ (610 mg, 2.9 mmol) in dioxane (7 mL) and H$_2$O (700 µL) was purged with N$_2$ for 7 min, capped, and heated to 70° C. for 2 hr and room temp for 48 hr. After the mixture was diluted with EtOAc (5 mL) and H$_2$O (5 mL), it was filtered through a short bed of celite. After the filtrate was separated, the aq layer was washed with EtOAc (25 mL×3). The combined organic layers were washed with H$_2$O and brine, dried over MgSO$_4$, and concentrated in vacuo. The crude solid was purified by CC using EtOAc (0% to 100%) in DCM to afford the title compound (375 mg, 74%) as a white solid. LCMS (M+H)$^+$: 440.

Step 2: 4-(3-hydroxy-5-methylsulfonylphenyl)-6-methylfuro[2,3-c]pyridin-7-one

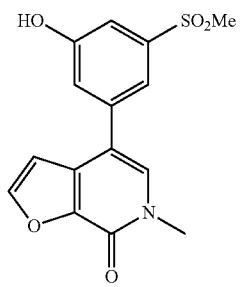 [SMILES: Cn1cc(-c2cc(O)cc(S(C)(=O)=O)c2)c2ccoc2c1=O]

A soln of 4-[3-[(4-methoxyphenyl)methoxy]-5-methylsulfonylphenyl]-6-methylfuro[2,3-c]pyridin-7-one (370 mg, 0.84 mmol) in AcOH (6 mL) was heated to 100° C. for 12 hr. After cooling to room temp, the rxn mixture was evaporated to dryness in vacuo. The resulting residue was diluted with H$_2$O and extracted with EtOAc (20 ml×3); the combined organic layers were washed with brine, dried over MgSO4, filtered, and concentrated in vacuo. The resulting solid was suspended in a 1:1 mixture of EtOAc:hexanes, sonicated for 1 min, and filtered. The filter cake was collected to afford the title compound (210 mg, 78%) as a gray solid. LCMS (M+H)$^+$: 320.

Step 3: 4-[3-[[2-(difluoromethoxy)phenyl]methoxy]-5-methylsulfonylphenyl]-6-methylfuro[2,3-c]pyridin-7-one

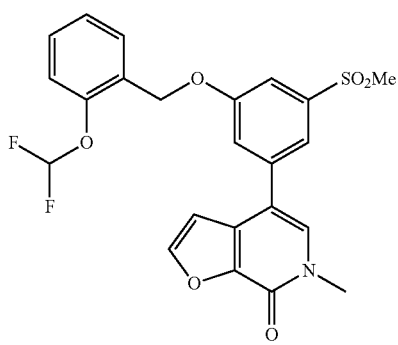 [SMILES: Cn1cc(-c2cc(OCc3ccccc3OC(F)F)cc(S(C)(=O)=O)c2)c2ccoc2c1=O]

A capped mixture of 4-(3-hydroxy-5-methylsulfonylphenyl)-6-methylfuro[2,3-c]pyridin-7-one (25 mg, 0.08 mmol), 1-(bromomethyl)-2-(difluoromethoxy)benzene (28 mg, 0.12 mmol), and Cs$_2$CO$_3$ (50 mg, 0.15 mmol) in DMF (900 µL) was heated to 80° C. for 3 hr. The mixture was filtered and the filter cake was washed with ACN (500 µL), the filtrate was purified by prep-HPLC to afford the title compound (22 mg, 58%) as a white solid. LCMS (M+H)$^+$: 476.

Example 349: 6-methyl-4-(3-methylsulfonyl-5-phenylmethoxyphenyl)furo[2,3-c]pyridin-7-one

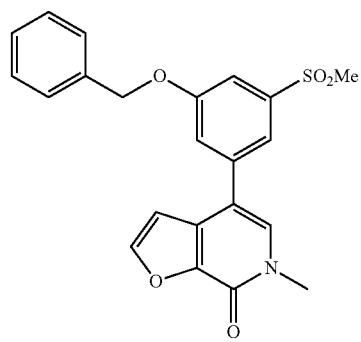 [SMILES: Cn1cc(-c2cc(OCc3ccccc3)cc(S(C)(=O)=O)c2)c2ccoc2c1=O]

The title compound was prepared in a manner similar to Example 348, substituting benzyl bromide for 1-(bromomethyl)-2-(difluoromethoxy)benzene in Step 2. LCMS (M+H)$^+$: 410.

Example 350: 4-[3-(cyclopropylmethoxy)-5-methylsulfonylphenyl]-6-methylfuro[2,3-c]pyridine-7-one

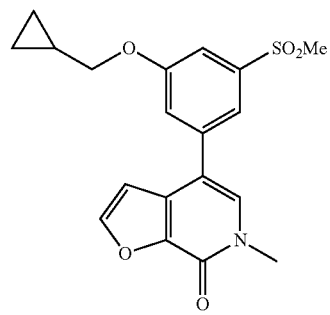 [SMILES: Cn1cc(-c2cc(OCC3CC3)cc(S(C)(=O)=O)c2)c2ccoc2c1=O]

The title compound was prepared in a manner similar to Example 348, substituting bromomethylcyclopropane for 1-(bromomethyl)-2-(difluoromethoxy)benzene in Step 3. LCMS (M+H)$^+$: 374.

Examples 351-356 in Table 19 were prepared in a similar multi-step manner as Example 300, step 1, wherein either ethyl pentanoate was converted to 4-chloro-2-methylsulfonyl-5-propylpyrimidine or ethyl hexanoate was converted to 5-butyl-4-chloro-2-methylsulfonylpyrimidine which were then each reacted with (a) 3-methoxy-1-methyl-5-(4,4,5,5-tetramethyl-1,3,2-dioxaborolan-2-yl)pyridin-2-one (described in Example 146, step 3); (b) the title compound of Example 98, step 1; or (c) 3-chloro-1-methyl-5-(4,4,5,5-tetramethyl-1,3,2-dioxaborolan-2-yl)pyridin-2-one (described in Example 134) in a manner similar to Example 152, step 5, to give the title compound.

TABLE 19

| Chemical Synthesis Example | Structure | Name | ¹H NMR (ppm (δ), 400 MHz) | MS (M + H) |
|---|---|---|---|---|
| 351 | 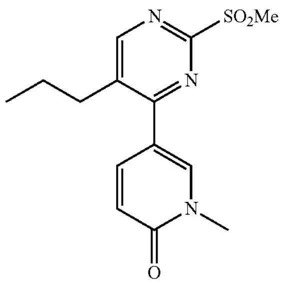 [SMILES: CCCc1cnc(S(C)(=O)=O)nc1-c1ccc(=O)n(C)c1] | 1-methyl-5-(2-methylsulfonyl-5-propylpyrimidin-4-yl)pyridin-2-one | (CDCl₃, 400 MHz) δ 8.72 (s, 1H), 8.00 (s, 1H), 7.67 (q, J = 6.8 Hz, 1H), 6.67 (d, J = 9.6 Hz, 1H), 3.68 (s, 3H), 3.38 (s, 3H), 2.82 (t, J = 8.0 Hz, 2H), 1.73 (m, 2H), 1.00 (t, J = 7.2 Hz, 3H). | 308 |
| 352 | 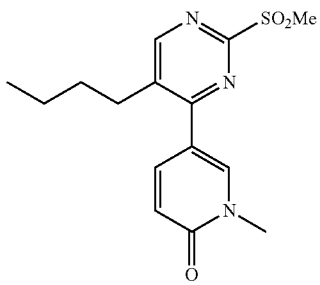 [SMILES: CCCCc1cnc(S(C)(=O)=O)nc1-c1ccc(=O)n(C)c1] | 5-(5-butyl-2-methyl-sulfonylpyrimidin-4-yl)-1-methylpyridin-2-one | | 322 |
| 353 | 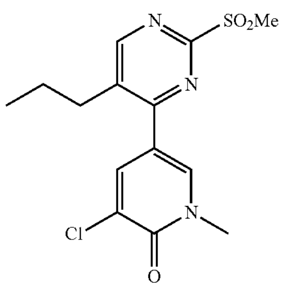 [SMILES: CCCc1cnc(S(C)(=O)=O)nc1-c1cc(Cl)c(=O)n(C)c1] | 3-chloro-1-methyl-5-(2-methylsulfonyl-5-propylpyrimidin-4-yl)pyridin-2-one | | 342 |
| 354 | 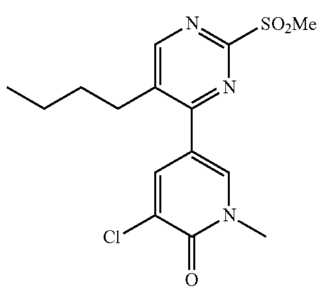 [SMILES: CCCCc1cnc(S(C)(=O)=O)nc1-c1cc(Cl)c(=O)n(C)c1] | 5-(5-butyl-2-methyl-sulfonylpyrimidin-4-yl)-3-chloro-1-methyl-pyridin-2-one | | 356 |
| 355 | 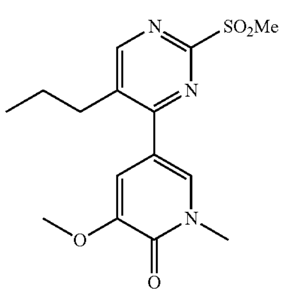 [SMILES: CCCc1cnc(S(C)(=O)=O)nc1-c1cc(OC)c(=O)n(C)c1] | 3-methoxy-1-methyl-5-(2-methylsulfonyl-5-propylpyrimidin-4-yl)pyridin-2-one | | 338 |

TABLE 19-continued

| Chemical Synthesis Example | Structure | Name | ¹H NMR (ppm (δ), 400 MHz) | MS (M + H) |
|---|---|---|---|---|
| 356 | 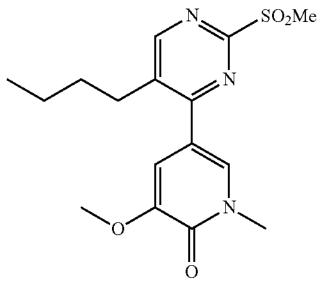 [SMILES: CCCCc1cnc(S(C)(=O)=O)nc1-c1cc(OC)c(=O)n(C)c1] | 5-(5-butyl-2-methyl-sulfonylpyrimidin-4-yl)-3-methoxy-1-methyl-pyridin-2-one | | 352 |

Examples 357-362 in Table 20 were prepared in a similar manner as Example 300, step 2 wherein Examples 351-356 were each treated with EtSO$_2$NH$_2$ to give the title compound.

Example 363 in Table 20 was prepared in a similar manner as Example 152, step 6 wherein Example 305 was treated with MeSO$_2$NH$_2$ to give the title compound.

TABLE 20

| Chemical Synthesis Example | Structure | Name | 1H NMR (ppm (δ), 400 MHz) | MS (M + H) | Prepared from Ex. No. |
|---|---|---|---|---|---|
| 357 | 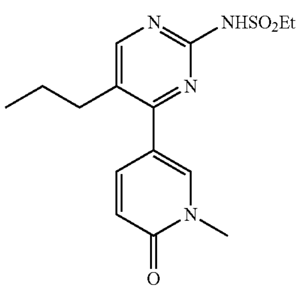 | N-[4-(1-methyl-6-oxopyridin-3-yl)-5-propylpyrimidin-2-yl]ethanesulfonamide | (CDCl$_3$, 400 MHz) δ 8.45 (s, 1H), 7.84 (s, 1H), 7.68 (d, J = 9.6 Hz, 1H), 6.68 (d, J = 9.2 Hz, 1H), 3.68 (s, 3H), 3.64 (t, J = 7.6 Hz, 2H), 2.67 (t, J = 8.0 Hz, 2H), 1.64 (q, J = 7.6 Hz, 2H), 1.45 (t, J = 7.2 Hz, 3H), 0.98 (t, J = 7.2 Hz, 3H) | 337 | 351 |
| 358 | 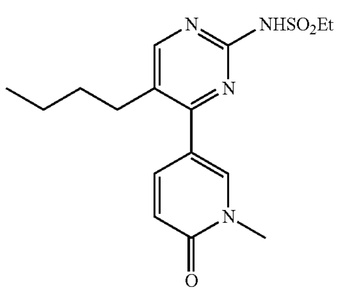 | N-[5-butyl-4-(1-methyl-6-oxopyridin-3-yl)pyrimidin-2-yl]ethanesulfonamide | (CDCl$_3$, 400 MHz) δ 8.44 (s, 1H), 7.84 (s, 1H), 7.69 (d, J = 9.6 Hz, 1H), 6.68 (d, J = 9.2 Hz, 1 H), 3.68 (s, 3H), 3.64 (t, J = 7.6 Hz, 2H), 2.68 (t, J = 7.6 Hz, 2H), 1.57 (t, J = 8.0 Hz, 2H), 1.46 (d, J = 7.6 Hz, 3H), 1.41 (t, J = 8.4 Hz, 2H), 0.93 (t, J = 7.2 Hz, 3H) | 351 | 352 |
| 359 | 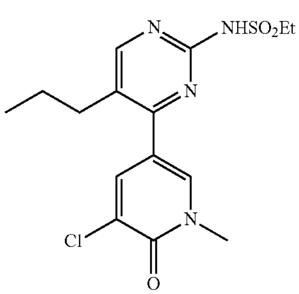 | N-[4-(5-chloro-1-methyl-6-oxopyridin-3-yl)-5-propyl-pyrimidin-2-yl]ethanesulfonamide | (CDCl$_3$, 400 MHz) δ 8.47 (s, 1H), 7.87 (d, J = 2.8 Hz, 1H), 7.78 (d, J = 2.0 Hz, 1H), 3.72 (s, 3H), 3.65 (q, J = 7.2 Hz, 2H), 2.67 (t, J = 8.0 Hz, 2H), 1.65 (d, J = 8.0 Hz, 2H), 1.45 (t, J = 7.2 Hz, 3H), 1.00 (t, J = 7.2 Hz, 3H) | 371 | 353 |

TABLE 20-continued

| Chemical Synthesis Example | Structure | Name | 1H NMR (ppm (δ), 400 MHz) | MS (M + H) | Prepared from Ex. No. |
|---|---|---|---|---|---|
| 360 | 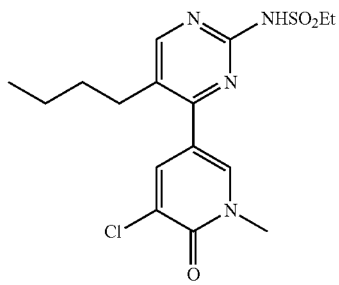 | N-[5-butyl-4-(5-chloro-1-methyl-6-oxopyridin-3-yl)pyrimidin-2-yl]ethanesulfonamide | (CDCl$_3$, 400 MHz) δ 8.48 (s, 1H), 7.90 (d, J = 2.4 Hz, 1H), 7.80 (d, J = 2.4 Hz, 1H), 3.74 (s, 3H), 3.66 (q, J = 7.2 Hz, 2H), 2.70 (t, J = 8.0 Hz, 2 H), 1.61 (m, 2H), 1.47 (t, J = 7.2 Hz, 3H), 1.42 (q, J = 8.0 Hz, 2H), 1.00 (t, J = 7.2 Hz, 3H) | 385 | 354 |
| 361 | 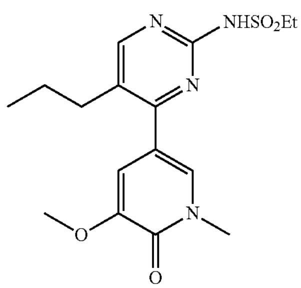 | N-[4-(5-methoxy-1-methyl-6-oxopyridin-3-yl)-5-propyl-pyrimidin-2-yl]ethanesulfonamide | (CDCl$_3$, 400 MHz) δ 8.46 (s, 1H), 7.40 (d, J = 1.6 Hz, 1H), 7.05 (s, 1H), 3.89 (s, 3H), 3.68 (s, 3H), 3.65 (t, J = 8.0 Hz, 2H), 2.69 (t, J = 8.0 Hz, 2H), 1.67 (m, 2H), 1.44 (t, J = 7.2 Hz, 3H), 1.00 (t, J = 7.2 Hz, 3H) | 367 | 355 |
| 362 | 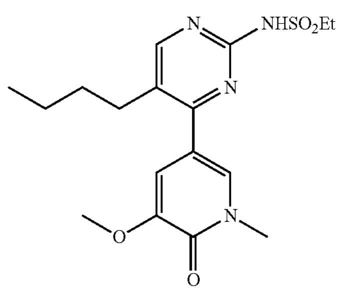 | N-[5-butyl-4-(5-methoxy-1-methyl-6-oxopyridin-3-yl)pyrimidin-2-yl]ethanesulfonamide | (CDCl$_3$, 400 MHz) δ 8.43 (s, 1H), 7.39 (d, J = 2.0 Hz, 1H), 7.03 (d, J = 2 Hz, 1H), 3.89 (s, 3H), 3.68 (s, 3H), 3.64 (d, J = 8.0 Hz, 2H), 2.71 (t, J = 8.0 Hz, 2H), 1.67 (m, 2H, overlapped with H$_2$O peak), 1.45 (t, J = 7.2 Hz, 3H), 1.39 (q, J = 7.2 Hz, 2H), 0.94 (t, J = 7.2 Hz, 3H) | 381 | 356 |
| 363 | 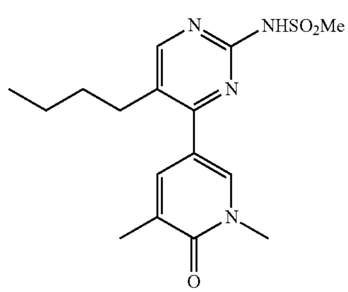 | N-[5-butyl-4-(1,5-dimethyl-6-oxopyridin-3-yl)pyrimidin-2-yl]methanesulfonamide | (CDCl$_3$, 400 MHz) δ 8.47 (s, 1H), 7.70 (d, J = 2 Hz, 1H), 7.55 (s, 1H), 3.66 (s, 3H), 3.46 (s, 3H), 2.69 (t, J = 8.0 Hz, 2H), 2.23 (s, 3H), 1.56 (q, J = 8.0 Hz, 2H), 1.38 (q, J = 7.2 Hz, 2H), 0.94 (t, J = 7.2 Hz, 3H) | 351 | 305 |

Example 364: 4-[2-(cyclopropylmethoxy)-5-propan-2-ylsulfonylphenyl]-2-methylisoquinolin-1-one Step 1: 5-bromo-7H-[1,2,4]triazolo[4,3-a]pyrazin-8-one

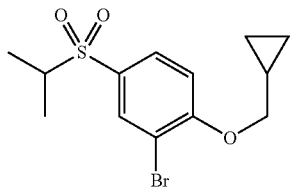 [SMILES: CC(C)S(=O)(=O)c1ccc(OCC2CC2)c(Br)c1]

The title compound was prepared in three steps from 3-bromo-4-fluorobenzenethiol in a manner similar to Example 79, steps 1-3 except that 2-iodopropane was substituted for ethyl iodide in step 1 and the alkoxide of cyclopropylmethanol was substituted for sodium methoxide in step 3. $^1$H NMR (CDCl$_3$, 400 MHz): δ 8.05 (d, J=2.4 Hz, 1H), 7.76 (dd, J$_1$=2.4 Hz, J$_2$=8.4, 1H), 6.97 (d, J=8.4 Hz, 1H), 3.18 (m, 1H), 1.29 (d, J=6.8 Hz, 6H), 0.86 (m, 1H), 0.71 (d, J=6.8 Hz, 2H), 0.45 (d, J=5.6 Hz, 2H). LCMS (M+H$^+$): 333.0; 335.0.

Step 2: 4-[2-(cyclopropylmethoxy)-5-propan-2-ylsulfonylphenyl]-2-methylisoquinolin-1-one

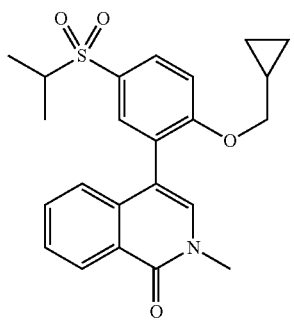 [SMILES: CC(C)S(=O)(=O)c1ccc(OCC2CC2)c(-c2cn(C)c(=O)c3ccccc23)c1]

The title compound of step 1 was coupled to the title compound of Example 89, step 1 in a manner similar Example 89, step 2 to give the title compound as a white solid. $^1$H NMR (CDCl$_3$, 400 MHz): δ 8.52 (d, J=7.2 Hz, 1H), 7.91 (dd, J$_1$=6.4 Hz, J$_2$=8.4, 1H), 7.80 (d, J=2.4 Hz, 1H), 7.51-7.57 (m, 2H), 7.15 (d, J=8.0 Hz, 1H), 7.09 (t, J=8.4 Hz, 1H), 3.89 (s, 2H), 3.67 (s, 3H), 3.18-3.25 (m, 1H), 1.33 (d, J=6.8 Hz, 6H), 0.99-1.02 (m, 1H), 0.414 (m, 2H), 0.11 (s, 2H). LCMS (M+H$^+$): 412.

Example 365: 8-[2-(cyclopropylmethoxy)-5-ethyl-sulfonylphenyl]-6-methyl-4H-pyrido[4,3-b][1,4]oxazine-3,5-dione Step 1: 6-methyl-4H-pyrido[4,3-b][1,4]oxazine-3,5-dione

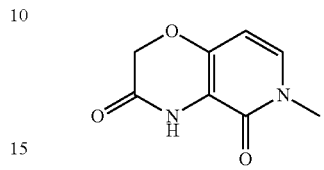

To a soln of the title compound of Example 237, step 3 (1.6 g, 9.01 mmol, 1.00 Eq) in CH$_2$Cl$_2$ (150 mL) at 0° C. under N$_2$ is added chloroacetyl chloride (0.75 mL, 9 mmol) dropwise. Pyridine (2.2 mL, 37 mmol) is then added, and the mixture was stirred for 5 hr at room temp. Satd aq KHSO$_4$ (100 mL) was added and the aq layer was extracted a total of three times with CH$_2$Cl$_2$. The combined organic layers were dried over Na$_2$SO$_4$, filtered, and then acetone (200 mL) followed by cesium carbonate (14.6 g, 45 mmol) were added directly to the filtrate (250 mL). The mixture was then heated at 50° C. for 2 hr. The volume was reduced and H$_2$O was added. Extractive work-up with 3:1 CH$_2$Cl$_2$:isopropanol followed by trituration with 1:2 EA:PE gave the title compound (400 mg, yield: 24.67%) as a yellow solid. $^1$H NMR (CDCl$_3$, 400 MHz): δ 8.17-8.14 (br, 1H), 7.01 (d, J=7.2 Hz, 1H), 6.07 (d, J=7.2 Hz, 1H), 4.69 (s, 1H), 3.59 (s, 3H). LCMS: 181.0 (M+H)$^+$.

Step 2: 8-bromo-6-methyl-4H-pyrido[4,3-b][1,4]oxazine-3,5-dione

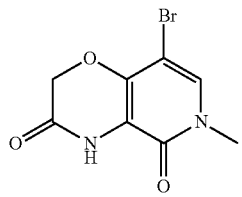

At room temp, to the title compound of step 1 (90 mg, 0.5 mmol) in anhydrous CH$_3$CN (1 mL) was added NBS (89 mg, 0.5 mmol). After stirring about 2 h, additional NBS (75 mg, 0.4 mmol) was added and the rxn was complete within 20 min. EA extractive work-up and silica gel chromatography gave the title compound (51 mg, 0.39 mmol) in 39% yield.

681

Step 3: 8-[2-(cyclopropylmethoxy)-5-ethylsulfonyl-phenyl]-6-methyl-4H-pyrido[4,3-b][1,4]oxazine-3,5-dione

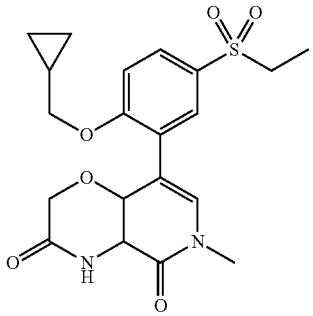 [SMILES: CCS(=O)(=O)c1ccc(OCC2CC2)c(C2=CN(C)C(=O)C3NC(=O)COC23)c1]

The title compound of step 2 was reacted with 2-[2-(cyclopropylmethoxy)-5-ethylsulfonylphenyl]-4,4,5,5-tetramethyl-1,3,2-dioxaborolane in a manner similar to Example 224, step 5. Silica gel chromatography (40-100% EA in hexane over 8 min) gave the title compound. $^1$H NMR (DMSO-d6, 400 MHz): δ ppm 0.27-0.33 (m, 2H) 0.51-0.57 (m, 2H) 1.11 (t, J=7.33 Hz, 3H) 1.14-1.22 (m, 1H, partially obscured) 3.22-3.28 (m, 2H) 3.51 (s, 3H) 3.96 (d, J=7.07 Hz, 2H) 4.54 (s, 2H) 7.27 (d, J=8.84 Hz, 1H) 7.52 (s, 1H) 7.67 (d, J=2.02 Hz, 1H) 7.79-7.92 (m, 1H) 10.10 (s, 1H). LCMS: 419 (M+H)$^+$.

Example 366: 8-[2-(cyclopropylmethoxy)-5-ethyl-sulfonylphenyl]-6-methyl-3,4,4a,8a-tetrahydro-2H-pyrido[4,3-b][1,4]oxazin-5-one

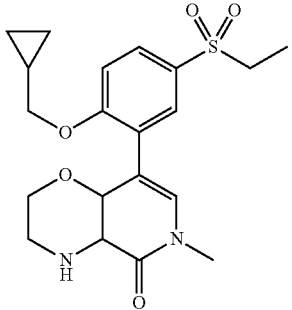 [SMILES: CCS(=O)(=O)c1ccc(OCC2CC2)c(C2=CN(C)C(=O)C3NCCOC23)c1]

The title compound of Example 365, step 3, in anhydrous THF was treated with excess 1M LAH in THF at room temp. After about 30 min, ice, H$_2$O, MeOH, and 1M HCl were added followed by satd aq NaHCO$_3$ and EA extractive work-up. Silica gel chromatography (EA, followed by 5% methanol in EA) gave the title compound as a clear glass. $^1$H NMR: (DMSO-d$_6$, 400 MHz) δ ppm 0.32 (brs, 2H) 0.54 (brs, 2H) 1.03-1.30 (m, 4H) 3.45 (brs, 3H) 3.94 (brs, 2H) 4.09 (brs, 2H) 5.03 (brs, 1H) 7.05 (brs, 1H) 7.22 (brs, 1H) 7.62 (brs, 1H) 7.78 (brs, 1H). $^1$H NMR: (DMSO-d$_6$/DCl, 400 MHz) δ ppm 0.29 (brs, 2H) 0.55 (brs, 2H) 1.10 (brs, 4H) 3.25 (brs, 2H) 3.45 (brs, 2H) 3.51 (brs, 3H) 3.93 (brs, 2H) 4.43 (brs, 2H) 7.27 (brs, 1H) 7.69 (brs, 2H) 7.84 (brs, 2H). LCMS: 405 (M+H)$^+$.

682

Example 367: N-[4-(2,4-difluorophenoxy)-3-(7-methyl-8-oxoimidazo[1,5-a]pyrazin-5-yl)phenyl]methanesulfonamide

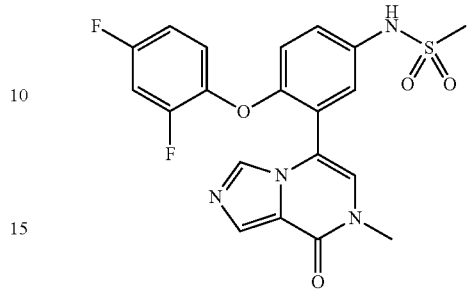

To a soln of the title compound from Example 129, Step 2 (140 mg, 0.38 mmol) in THF (20 ml) was added pyridine (152 mg, 1.90 mmol). Then methanesulfonyl chloride (48 mg, 0.46 mmol) was added to the soln at 0° C. The soln was allowed to warm up to room temp and heated to reflux for overnight. The rxn mixture was concentrated under reduced pressure to yield the crude product that was purified by prep-HPLC to give the title compound (75.26 mg, 44%) as a yellow solid. $^1$H NMR (CDCl$_3$, 400 MHz): δ 8.60 (s, 1H), 8.15 (s, 1H), 7.50 (d, J=2.8 Hz, 1H), 7.30 (dd, J=8.8, 2.4 Hz, 1H), 7.18 (td, J=8.8, 5.3 Hz, 1H), 7.00-6.88 (m, 2H), 6.83 (s, 1H), 6.78 (d, J=8.8 Hz, 1H), 3.60 (s, 3H), 3.03 (s, 3H). LCMS: 447.0 (M+1)$^+$.

Example 368: 5-[2-(cyclopropylmethoxy)-5-ethyl-sulfonylphenyl]-7-methylimidazo[1,5-a]pyrazine-8-one

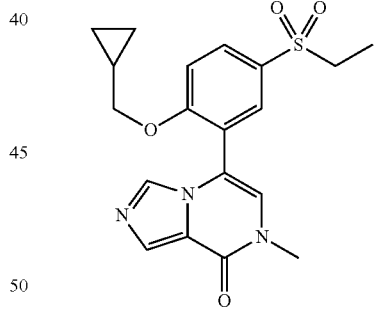

To a microwave vial containing 5-bromo-7-methylimidazo[1,5-a]pyrazin-8-one (150 mg, 0.66 mmol), 2-[2-(cyclopropylmethoxy)-5-ethylsulfonylphenyl]-4,4,5,5-tetramethyl-1,3,2-dioxaborolane (290 mg, 0.80 mmol) and NaHCO$_3$ (1 mL, 2M) in dioxane (3 mL) was added Pd(dppf)Cl$_2$ (80 mg, 0.10 mmol). The mixture was purge with N$_2$ for 2 min and sealed. The rxn was irradiated in microwave at 100° C. for 2 hr. H$_2$O (20 mL) was added and the mixture was extracted with EtOAc (20 mL×3). The combined organic layers were washed with brine (20 mL), dried with Na$_2$SO$_4$, filtered, and concentrated in vacuum. The residue was purified by CC (PE:EA=5:1 to 1:1) to afford the title compound (55.3 mg, 22%) as a light yellow solid. $^1$H NMR (CDCl$_3$, 400 MHz): δ 8.03 (dd, J$_1$=8.4 Hz, J$_2$=2.0 Hz, 2H), 7.94 (d, J=2.0 Hz, 1H), 7.56 (s, 1H), 7.15 (d, J=8.8 Hz, 1H), 6.49 (s, 1H), 3.96 (d, J=6.4 Hz, 2H), 3.54 (s, 3H), 3.16 (q, J=7.6 Hz, 1H), 1.33 (t, J=7.6 Hz, 1H), 1.08 (s, 1H), 0.54 (d, J=7.2 Hz, 2H), 0.54 (d, J=4.4 Hz, 2H). LCMS: 388.1 (M+1)⁺.

Example 369: 5-[2-(2,4-difluorophenoxy)-5-(ethylsulfonylmethyl)phenyl]-7-methylimidazo[1,5-a]pyrazin-8-one Step 1: 2-[2-(2,4-difluorophenoxy)-5-(ethylsulfonylmethyl)phenyl]-4,4,5,5-tetramethyl-1,3,2-dioxaborolane

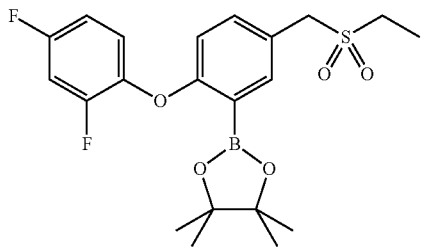 [SMILES: CCS(=O)(=O)Cc1ccc(Oc2ccc(F)cc2F)c(B2OC(C)(C)C(C)(C)O2)c1]

A mixture of 2-bromo-1-(2,4-difluorophenoxy)-4-(ethylsulfonylmethyl)benzene (250 mg, 0.64 mmol), bis(pinacolato)diboron (255 mg, 0.96 mmol), KOAc (189 mg, 1.92 mmol) and Pd(dppf)Cl₂ (44 mg, 0.06 mmol) in dioxane (5 mL) was stirred at 70° C. for 18 hr under N₂. The mixture was concentrated and the residue was purified by CC to give the title compound (150 mg, 53.4%) as yellow solid. LCMS: 439.2 (M+1)⁺.

Step 2: 5-[2-(2,4-difluorophenoxy)-5-(ethylsulfonylmethyl)phenyl]-7-methylimidazo[1,5-a]pyrazin-8-one

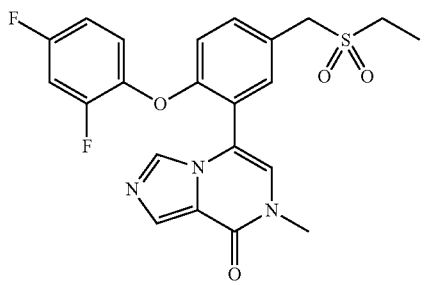 [SMILES: CCS(=O)(=O)Cc1ccc(Oc2ccc(F)cc2F)c(-c2cn(C)c(=O)c3cncn23)c1]

A mixture of the title compound from Step 1 (150 mg, 0.34 mmol), the title compound from Example 129 Step 1 (87 mg, 0.38 mmol), K₃PO₄ (217 mg, 1.02 mmol) and Pd(dppf)Cl₂ (22 mg, 0.03 mmol) in dioxane (5 mL) and H₂O (1 mL) was stirred at 70° C. for 18 hr under N₂. The resulting mixture was filtered and concentrated. The residue was purified by prep-HPLC to give the title compound (70.0 mg, 45%) as a yellow solid. ¹H NMR (DMSO-d6, 400 MHz): δ 8.83 (s, 1H), 8.33 (s, 1H), 7.64 (d, J=2.0 Hz, 1H), 7.57 (dd, J₁=8.8 Hz, J₂=2.0 Hz, 1H), 7.53-7.41 (m, 2H), 7.37 (s, 1H), 7.20-7.12 (m, 1H), 6.93 (d, J=8.8 Hz, 1H), 4.54 (s, 2H), 3.45 (s, 3H), 3.09 (q, J=7.6 Hz, 2H), 1.23 (t, J=7.6 Hz, 3H). LCMS: 460.1 (M+1)⁺.

Example 370: 7-methyl-5-[5-(methylsulfonylmethyl)-2-(2,2,2-trifluoroethoxy)phenyl]imidazo[1,5-a]pyrazin-8-one Step 1: 4,4,5,5-tetramethyl-2-[5-(methylsulfonylmethyl)-2-(2,2,2-trifluoroethoxy)phenyl]-1,3,2-dioxaborolane

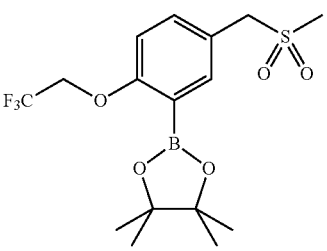 [SMILES: CC1(C)OB(c2cc(CS(C)(=O)=O)ccc2OCC(F)(F)F)OC1(C)C]

The title compound was prepared in a manner similar to Example 369, Step 1, by substituting 2-bromo-4-(methylsulfonylmethyl)-1-(2,2,2-trifluoroethoxy)benzene for 2-bromo-1-(2,4-difluorophenoxy)-4-(ethylsulfonylmethyl)benzene. LCMS: 395.2 (M+1)⁺.

Step 2: 7-methyl-5-[5-(methylsulfonylmethyl)-2-(2,2,2-trifluoroethoxy)phenyl]imidazo[1,5-a]pyrazin-8-one

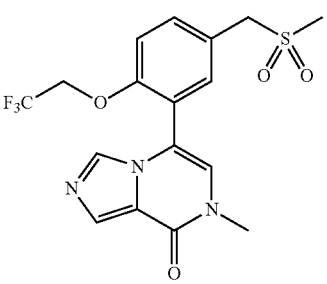 [SMILES: Cn1cc(-c2cc(CS(C)(=O)=O)ccc2OCC(F)(F)F)n2cncc2c1=O]

The title compound was prepared in a manner similar to Example 369, Step 2, by substituting 4,4,5,5-tetramethyl-2-[5-(methylsulfonylmethyl)-2-(2,2,2-trifluoroethoxy)phenyl]-1,3,2 dioxaborolane for 2-[2-(2,4-difluorophenoxy)-5-(ethylsulfonylmethyl)phenyl]-4,4,5,5-tetramethyl-1,3,2-dioxaborolane. ¹H NMR (DMSO-d₆, 400 MHz): δ 8.64 (s, 1H), 8.32 (s, 1H), 7.64 (dd, J₁=8.8 Hz, J₂=2.0 Hz, 1H), 7.56 (s, 1H), 7.39 (d, J=8.8 Hz, 1H), 7.25 (s, 1H), 4.86 (q, J=8.8 Hz, 2H), 4.53 (s, 2H), 3.44 (s, 3H), 2.94 (s, 3H). LCMS: 416.1 (M+1)⁺.

Example 371: 5-[5-(ethylsulfonylmethyl)-2-(2,2,2-trifluoroethoxy)phenyl]-7-methylimidazo[1,5-a]pyrazin-8-one

Step 1: 2-[5-(ethylsulfonylmethyl)-2-(2,2,2-trifluoroethoxy)phenyl]-4,4,5,5-tetramethyl-1,3,2-dioxaborolane

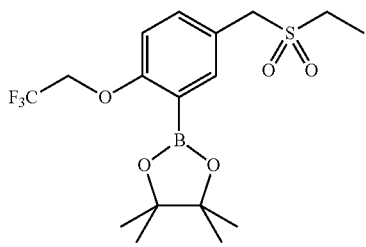 [SMILES: CCS(=O)(=O)Cc1ccc(OCC(F)(F)F)c(B2OC(C)(C)C(C)(C)O2)c1]

The title compound was prepared in a manner similar to Example 369, Step 1, by substituting 2-bromo-4-(ethylsulfonylmethyl)-1-(2,2,2-trifluoroethoxy)benzene for 2-bromo-1-(2,4-difluorophenoxy)-4-(ethylsulfonylmethyl)benzene. LCMS: 409.2 (M+1)+.

Step 2: 5-[5-(ethylsulfonylmethyl)-2-(2,2,2-trifluoroethoxy)phenyl]-7-methylimidazo[1,5-a]pyrazin-8-one

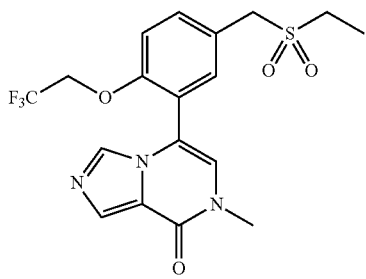 [SMILES: CCS(=O)(=O)Cc1ccc(OCC(F)(F)F)c(-c2cn(C)c(=O)c3cncn23)c1]

The title compound was prepared in a manner similar to Example 369, Step 2, by substituting 2-[5-(ethylsulfonylmethyl)-2-(2,2,2-trifluoroethoxy)phenyl]-4,4,5,5-tetramethyl-1,3,2-dioxaborolane for 2-[2-(2,4-difluorophenoxy)-5-(ethylsulfonylmethyl)phenyl]-4,4,5,5-tetramethyl-1,3,2-dioxaborolane. $^1$H NMR (DMSO-d6, 400 MHz) δ 8.99 (s, 1H), 8.47 (s, 1H), 7.61 (d, J=8.8 Hz, 1H), 7.52 (s, 1H), 7.35 (d, J=8.8 Hz, 1H), 7.31 (s, 1H), 4.82 (q, J=8.4 Hz, 2H), 4.48 (s, 2H), 3.42 (s, 3H), 3.04 (q, J=7.2 Hz, 2H), 2.94 (t, J=7.2 Hz, 3H). LCMS: 430.1 (M+1)$^+$.

Example 372: 5-[2-(2,4-difluorophenoxy)-5-(methylsulfonylmethyl)phenyl]-7-methylimidazo[1,5-a]pyrazin-8-one

Step 1: 2-[2-(2,4-difluorophenoxy)-5-(methylsulfonylmethyl)phenyl]-4,4,5,5-tetramethyl-1,3,2-dioxaborolane

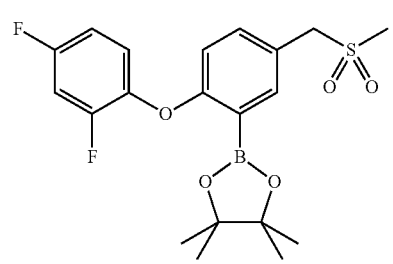 [SMILES: CC1(C)OB(c2cc(CS(C)(=O)=O)ccc2Oc2ccc(F)cc2F)OC1(C)C]

The title compound was prepared in a manner similar to Example 369, Step 1, by substituting 2-bromo-1-(2,4-difluorophenoxy)-4-(methylsulfonylmethyl)benzene for 2-bromo-1-(2,4-difluorophenoxy)-4-(ethylsulfonylmethyl)benzene. LCMS: 442.2 (M+18)$^+$.

Step 2: 5-[2-(2,4-difluorophenoxy)-5-(methylsulfonylmethyl)phenyl]-7-methylimidazo[1,5-a]pyrazin-8-one

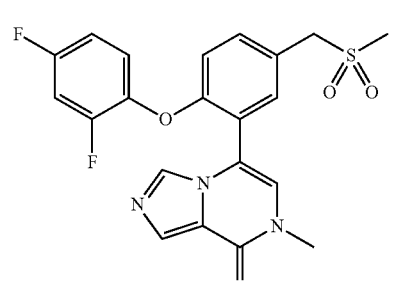

The title compound was prepared in a manner similar to Example 369, Step 2, by substituting 2-[2-(2,4-difluorophenoxy)-5-(methylsulfonylmethyl)phenyl]-4,4,5,5-tetramethyl-1,3,2-dioxaborolane for 2-[2-(2,4-difluorophenoxy)-5-(ethylsulfonylmethyl)phenyl]-4,4,5,5-tetramethyl-1,3,2-dioxaborolane. $^1$H NMR (DMSO-d6, 400 MHz) δ 8.59 (s, 1H), 8.19 (s, 1H), 7.65 (d, J=2.0 Hz, 1H), 7.57 (dd, J$_1$=8.8 Hz, J$_2$=2.0 Hz, 1H), 7.52-7.39 (m, 2H), 7.30 (s, 1H), 7.18-7.11 (m, 1H), 6.94 (d, J=8.8 Hz, 1H), 4.55 (s, 2H), 3.44 (s, 3H), 2.96 (s, 3H). LCMS: 446.1 (M+1)$^+$.

Example 373: 5-[2-(4,4-difluorocyclohexyl)oxy-5-ethylsulfonylphenyl]-7-methylimidazo[1,5-a]pyrazin-8-one Step 1: 2-(5-ethylsulfonyl-2-fluorophenyl)-4,4,5,5-tetramethyl-1,3,2-dioxaborolane

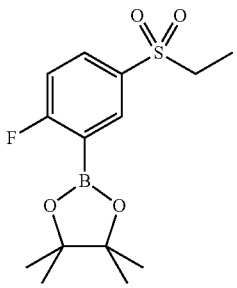 [SMILES: CCS(=O)(=O)c1ccc(F)c(B2OC(C)(C)C(C)(C)O2)c1]

Bromo-4-ethylsulfonyl-1-fluorobenzene (5.00 g, 18.72 mmol), AcOK (3.88 g, 56.16 mmol, 3 eq), pinacol ester (9.51 g, 37.44 mmol, 2 eq), Pd$_2$(dba)$_3$ (17.14 g, 18.72 mmol, 1 eq) and X-Phos (9.24 g, 18.72 mmol, 1 eq) in dioxane (300 mL) was degassed and then heated to 60° C. overnight under N$_2$. The rxn mixture was poured into H$_2$O (300 mL). The mixture was extracted with EA (3×250 mL). The combined organic phase were washed with satd brine (300 mL), dried over anhydrous MgSO$_4$, filtered and concentrated under reduced pressure to give a residue that was purified by silica gel CC to afford the title compound (1.87 g, 32%) as a gray solid. $^1$H NMR (CDCl$_3$, 400 MHz): δ 8.34-8.31 (m, 1H), 8.01-7.98 (m, 1H), 7.22 (d, J=8.8 Hz, 1H), 3.14 (q, J=7.6 Hz, 2H), 1.37 (s, 12H), 1.27 (t, J=7.6 Hz, 3H).

Step 2: 5-(5-ethylsulfonyl-2-fluorophenyl)-7-methylimidazo[1,5-a]pyrazin-8-one

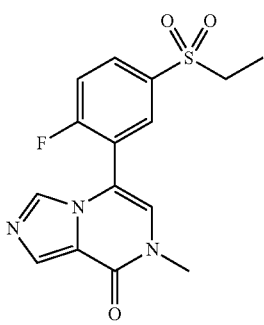 [SMILES: CCS(=O)(=O)c1ccc(F)c(-c2cn(C)c(=O)c3cncn23)c1]

5-bromo-7-methylimidazo[1,5-a]pyrazin-8-one (600 mg, 2.63 mmol, 0.83 Eq), the title compound from Step 2 (1.00 g, 3.18 mmol, 1.00 Eq), K$_3$PO$_4$ (2.03 g, 9.55 mmol, 3.00 Eq) and Pd(dppf)Cl$_2$ (118 mg, 0.16 mmol, 0.05 Eq) in dioxane (20 mL) was degassed and then heated at 60° C. overnight under N$_2$. The rxn mixture was poured into H$_2$O. The mixture was extracted with EA (3×25 mL). The organic phase was washed with brine (30 mL), dried over anhydrous MgSO$_4$, filtered and concentrated under vacuum to give a residue which was purified by silica gel chromatography to afford the title compound (600 mg, yield: 56.24%). $^1$H NMR (CDCl$_3$, 400 MHz): δ 8.50 (s, 1H), 8.17 (s, 1H), 8.12-8.08 (m, 2H), 7.50 (t, J=8.8 Hz, 1H), 6.90 (s, 1H), 3.59 (s, 3H), 3.17 (q, J=7.2 Hz, 2H), 0.89-0.83 (m, 3H).

Step 3: 5-[2-(4,4-difluorocyclohexyl)oxy-5-ethylsulfonylphenyl]-7-methylimidazo[1,5-a]pyrazin-8-one

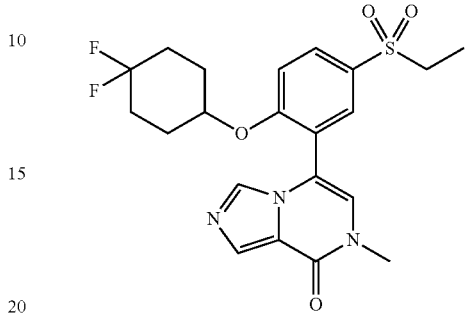

To a soln of 4,4-difluorocyclohexan-1-ol (162 mg, 1.19 mmol) in THF (10 mL) was added NaH (48 mg, 1.19 mmol, 60% in mineral oil) in one portion at 25° C. under N$_2$. The mixture was stirred at 25° C. for 30 min. Then the title compound from Step 2 (200 mg, 0.6 mmol) was added and the mixture was stirred at 25° C. for 18 hr. The rxn contents were poured into ice/water (v/v=1/1) (150 mL) and stirred for 20 min. The aq phase was extracted with EA (40 mL×3). The combined organic phase was washed with brine (20 mL×2), dried over anhydrous Na$_2$SO$_4$, filtered and concentrated under reduced pressure. The residue was purified by prep-HPLC to afford the title compound (57.35 mg, 22%) as a white solid. $^1$H NMR (DMSO-d$_6$, 400 MHz): δ 8.63 (s, 1H), 8.26 (s, 1H), 8.04 (dd, J$_1$=8.8 Hz, J$_2$=2.4 Hz 1H), 7.95 (d, J=2.4 Hz, 1H), 7.56 (d, J=8.8 Hz, 1H), 7.31 (s, 1H), 4.90-4.84 (brs, 1H), 3.44 (s, 3H), 3.32 (q, J=7.2 Hz, 2H), 1.85-1.83 (m, 4H), 1.69-1.61 (m, 4H), 1.15 (t, J=7.2 Hz, 3H). LCMS: 452.2 (M+H)$^+$.

Example 374: 5-(2-cyclopentyloxy-5-ethylsulfonylphenyl)-7-methylimidazo[1,5-a]pyrazin-8-one

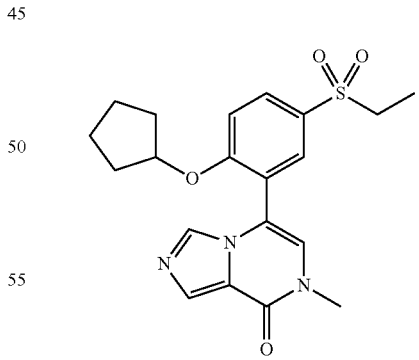

The title compound was prepared in a manner similar to Example 373, by substituting cyclopentanol for 4,4-difluorocyclohexan-1-ol in Step 3. $^1$H NMR (DMSO-d$_6$, 400 MHz): δ 8.34 (s, 1H), 8.16 (s, 1H), 8.02 (d, J=8.8 Hz, 1H), 7.91 (s, 1H), 7.42 (d, J=8.8 Hz, 1H), 7.24 (s, 1H), 5.04-5.01 (brs, 1H), 3.43 (s, 3H), 3.31 (q, J=6.8 Hz, 2H), 1.91-1.80 (m, 2H), 1.62-1.30 (m, 6H), 1.14 (t, J=6.8 Hz, 3H). LCMS: 402.2 (M+H)$^+$.

Example 375: 5-[2-(cyclopropylmethylamino)-5-ethylsulfonylphenyl]-7-methylimidazo[1,5-a]pyrazin-8-one

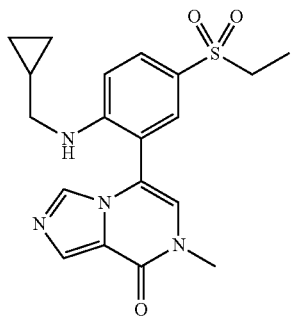 [SMILES: CCS(=O)(=O)c1ccc(NCC2CC2)c(-c2cn(C)c(=O)c3cncn23)c1]

The title compound was prepared in a manner similar to Example 373, by substituting cyclopropylmethanamine for 4,4-difluorocyclohexan-1-ol in Step 3. $^1$H NMR (DMSO-$d_6$, 400 MHz): δ 8.28-8.24 (m, 2H), 7.76 (d, J=8.8 Hz, 1H), 7.64 (s, 1H), 6.98 (d, J=8.8 Hz, 1H), 6.47-6.41 (brs, 1H), 3.44 (s, 3H), 3.18 (q, J=7.2 Hz, 2H), 3.06-3.01 (m, 2H), 1.12 (t, J=6.8 Hz, 3H), 1.06-0.98 (m, 1H), 0.42-0.37 (m, 2H), 0.16-0.11 (m, 2H). LCMS: 387.2 (M+H)$^+$.

Example 376: 5-[2-(2,4-difluorophenoxy)-5-ethylsulfonylphenyl]-7-methylimidazo[1,5-a]pyrazin-8-one

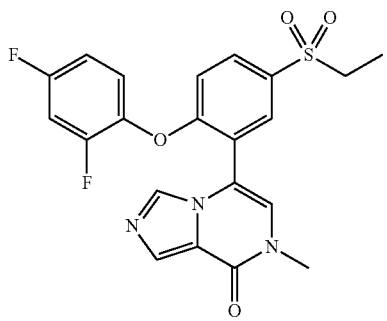 [SMILES: CCS(=O)(=O)c1ccc(Oc2ccc(F)cc2F)c(-c2cn(C)c(=O)c3cncn23)c1]

The title compound was prepared in a manner similar to Example 373, by substituting 2,4-difluorophenol for 4,4-difluorocyclohexan-1-ol in Step 3. $^1$H NMR (CDCl$_3$, 400 MHz): δ 8.05 (d, J=2.4 Hz, 1H), 8.03 (s, 1H), 7.97 (dd, J$_1$=8.8 Hz, J$_2$=2.4 Hz 1H), 7.16-7.10 (m, 1H), 7.05-7.00 (m, 1H), 6.98-6.93 (m, 1H), 7.97 (dd, J$_1$=8.8 Hz, J$_2$=1.2 Hz 1H), 3.55 (s, 3H), 3.18 (q, J=7.2 Hz, 2H), 1.36 (t, J=7.2 Hz, 3H). LCMS: 446.1 (M+H)$^+$.

Example 377: 7-[2-(cyclopropylmethoxy)-5-methylsulfonylphenyl]-5-methylfuro[3,2-c]pyridine-4-one Step 1: 7-bromo-5-methylfuro[3,2-c]pyridin-4-one

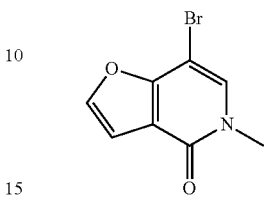

To a suspension of 7-bromo-5H-furo[3,2-c]pyridin-4-one (250 mg, 1.17 mmol) in DMF (5 mL) cooled to 0° C. was added HNa (56 mg, 1.4 mmol, 60% dispersion in mineral oil) in three portions. After stirring at room temp for 45 min, MeI (87 μL, 1.4 mmol) was added drop wise over 5 min. The rxn was allowed to warm up to room temp stirred for 2 hr. It was then cooled to 0° C. followed by addition of sat. aq NH$_4$Cl (5 mL) drop wise. The resulting mixture was extracted with EtOAc (3×5 mL). The combined organic layers were dried over Na$_2$SO$_4$, filtered and concentrated under reduced pressure. The residue was purified by silica gel CC to afford the title compound. LCMS: 227.9 (M+H)$^+$.

Step 2: 5-methyl-7-(4,4,5,5-tetramethyl-1,3,2-dioxaborolan-2-yl)furo[3,2-c]pyridin-4-one

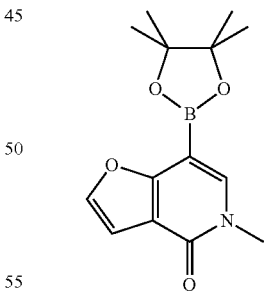

The title compound was prepared in a manner similar to Example 255, step 4, by substituting 7-bromo-5-methylfuro[3,2-c]pyridin-4-one for N-[4-(cyclopropylmethoxy)-3-(tetramethyl-1,3,2-dioxaborolan-2-yl)phenyl]ethane-1-sulfonamide. LCMS: 276.1 (M+H)$^+$.

Step 3: 7-[2-(cyclopropylmethoxy)-5-methylsulfonylphenyl]-5-methylfuro[3,2-c]pyridin-4-one

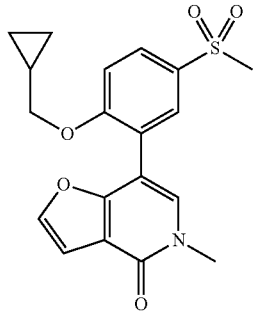

The title compound was prepared in a manner similar to Example 197, by substituting 5-methyl-7-(4,4,5,5-tetramethyl-1,3,2-dioxaborolan-2-yl)furo[3,2-c]pyridin-4-one for 2-[2-(cyclopropylmethoxy)-5-methylsulfonylphenyl]-4,4,5,5-tetramethyl-1,3,2-dioxaborolane, and 2-bromo-1-(cyclopropylmethoxy)-4-methylsulfonylbenzene for 4-bromo-2-methyl-6-(trifluoro-methyl)isoquinolin-1-one. $^1$H NMR (CDCl$_3$, 400 MHz): δ 8.05 (s, 1H), 7.92 (dd, $J_1$=8.6 Hz, $J_2$=1.8 Hz, 1H), 7.50 (m, 2H), 7.07 (m, 2H), 3.95 (d, J=6.7 Hz, 2H), 3.70 (s, 3H), 3.1 (s, 3H), 1.15 (m, 1H), 0.57 (m, 2H), 0.28 (m, 2H). LCMS: 374.1 (M+H)$^+$.

Example 378: 7-[2-(cyclopropylmethoxy)-5-ethylsulfonylphenyl]-5-methylfuro[3,2-c]pyridine-4-one

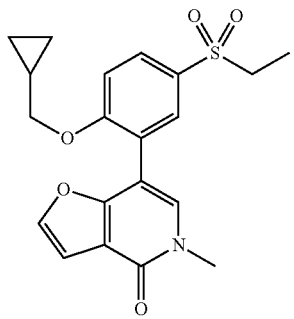 [SMILES: CCS(=O)(=O)c1ccc(OCC2CC2)c(-c2cn(C)c(=O)c3ccoc23)c1]

The title compound was prepared in a manner similar to Example 197, by substituting 2-[2-(cyclopropylmethoxy)-5-ethylsulfonylphenyl]-4,4,5,5-tetramethyl-1,3,2-dioxaborolane for 2-[2-(cyclopropylmethoxy)-5-methylsulfonylphenyl]-4,4,5,5-tetramethyl-1,3,2-dioxaborolane, and 7-bromo-5-methylfuro[3,2-c]pyridin-4-one for 4-bromo-2-methyl-6-(trifluoromethyl)isoquinolin-1-one. $^1$H NMR (DMSO-d$_6$, 400 MHz): δ 7.88 (m, 4H), 7.33 (d, J=9.4 Hz, 1H), 7.01 (d, J=2.0 Hz, 1H), 4.02 (d, J=6.8 Hz, 2H), 3.58 (s, 3H), 3.28 (m, 2H), 1.12 (t, J=7.4 Hz, 3H), 1.08 (m, 1H), 0.45 (m, 2H), 0.24 (m, 2H). LCMS: 388.1 (M+H)$^+$.

Example 379: N-[4-(2,4-difluorophenoxy)-3-(5-methyl-4-oxofuro[3,2-c]pyridin-7-yl)phenyl]ethanesulfonamide

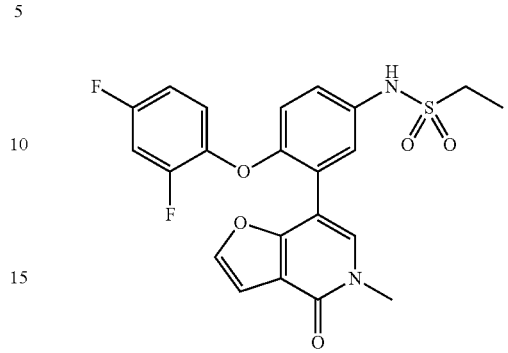

The title compound was prepared in a manner similar to Example 197, by substituting N-[4-(2,4-difluorophenoxy)-3-(4,4,5,5-tetramethyl-1,3,2-dioxaborolan-2-yl)phenyl]ethane-sulfonamide for 2-[2-(cyclopropylmethoxy)-5-methylsulfonylphenyl]-4,4,5,5-tetramethyl-1,3,2-dioxaborolane, and 7-bromo-5-methylfuro[3,2-c]pyridin-4-one for 4-bromo-2-methyl-6-(trifluoro-methyl)isoquinolin-1-one. $^1$H NMR (DMSO-d$_6$, 400 MHz): δ 9.83 (s, 1H), 7.85 (d, J=2.0 Hz, 1H), 7.78 (s, 1H), 7.37 (m, 2H), 7.24 (dd, $J_1$=8.8 Hz, $J_2$=2.7 Hz, 1H), 7.14 (m, 1H), 7.03 (m, 1H), 6.97 (d, J=2.1 Hz, 1H), 6.93 (d, J=8.8 Hz, 1H), 3.54 (s, 3H), 3.12 (q, J=7.3 Hz, 2H), 1.12 (t, J=7.3 Hz, 3H). LCMS: 461.2 (M+H)$^+$.

Example 380: N-[4-(2,4-difluorophenoxy)-3-(5-methyl-4-oxofuro[3,2-c]pyridin-7-yl)phenyl]methanesulfonamide

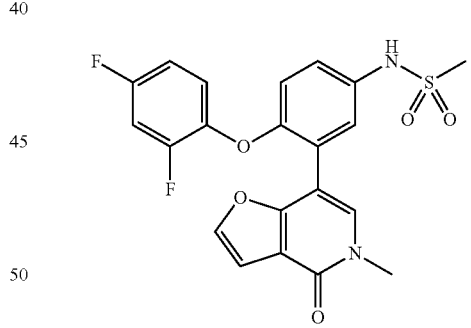

The title compound was prepared in a manner similar to Example 197, by substituting N-[4-(2,4-difluorophenoxy)-3-(4,4,5,5-tetramethyl-1,3,2-dioxaborolan-2-yl)phenyl]methanesulfonamide for 2-[2-(cyclopropylmethoxy)-5-methylsulfonylphenyl]-4,4,5,5-tetramethyl-1,3,2-dioxaborolane and 7-bromo-5-methylfuro[3,2-c]pyridin-4-one for 4-bromo-2-methyl-6-(trifluoro-methyl)isoquinolin-1-one. $^1$H NMR (DMSO-d$_6$, 400 MHz): δ 9.77 (s, 1H), 7.85 (d, J=2.1 Hz, 1H), 7.79 (s, 1H), 7.38 (m, 2H), 7.25 (dd, $J_1$=8.8 Hz, $J_2$=2.8 Hz, 1H), 7.12 (m, 1H), 7.04 (m, 1H), 6.97 (d, J=2.1 Hz, 1H), 6.94 (d, J=8.8 Hz, 1H), 3.54 (s, 3H), 3.02 (s, 3H). LCMS: 447.1 (M+H)$^+$.

Example 381: 4-(cyclopropylmethoxy)-5-(1-methyl-6-oxopyridin-3-yl)-1-(methylsulfonylmethyl)pyridin-2-one

Step 1: 5-bromo-4-(cyclopropylmethoxy)-2-methoxypyridine

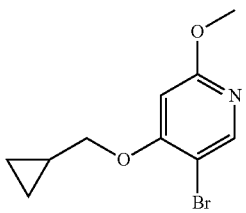

To a soln of cyclopropylmethanol (446 mg, 6.18 mmol) in THF (10 mL) was added NaH (247 mg, 6.18 mmol, 60% in mineral oil) in one portion at 0° C. The rxn mixture was warmed up to 20° C. over a period of 30 min and stirred at 20° C. for 10 min. Then 5-bromo-4-chloro-2-methoxypyridine (550 mg, 2.47 mmol) was added in one portion and the mixture was stirred at 70° C. for 4 hr. The mixture was diluted with satd ammonium aq soln (50 mL) and extracted by EtOAc (2×30 mL). The combined organic layers were dried over anhydrous $Na_2SO_4$, filtered, and concentrated to give the crude product which was purified by CC (PE:EA=20:1 to 10:1) to afford the title compound (450 mg, 70.6%) as colorless oil. $^1$H NMR (CDCl$_3$, 400 MHz): δ 8.11 (s, 1H), 6.18 (s, 1H), 3.90 (s, 3H), 3.89-3.88 (m, 2H), 1.39-1.27 (m, 1H), 0.70-0.67 (m, 2H), 0.46-0.43 (m, 2H). LCMS (M+H)$^+$: 258.0; (M+1)$^+$: 260.0.

Step 2: 5-bromo-4-(cyclopropylmethoxy)pyridin-2-ol

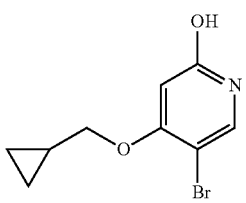 [SMILES: Oc1cc(OCC2CC2)c(Br)cn1]

To a soln of the title compound from step 1 (450 mg, 1.74 mmol) in DMF (5 mL) was added LiCl (370 mg, 8.72 mmol) and TsOH.H$_2$O (1.52 g, 8.72 mmol) at room temp. The mixture was heated to 120° C. and stirred for 1 hr, then diluted with H$_2$O (100 mL) and extracted with EtOAc (3×100 mL). The combined organic phase was washed with satd brine (2×200 mL), dried over anhydrous Na$_2$SO$_4$, filtered and concentrated under reduced pressure to afford the title compound (380 mg, yield: 88.9%) as yellow solid which used directly for the next step without further purification. $^1$H NMR (CDCl$_3$, 400 MHz) δ 7.49 (s, 1H), 5.91 (s, 1H), 3.87 (d, J=6.8 Hz, 2H), 1.36-1.22 (m, 1H), 0.71-0.67 (m, 2H), 0.46-0.42 (m, 2H). LCMS: 244.0 (M+1)$^+$; 246.0 (M+1)$^+$.

Step 3: 5-bromo-4-(cyclopropylmethoxy)-1-(methylsulfanylmethyl)pyridin-2-one

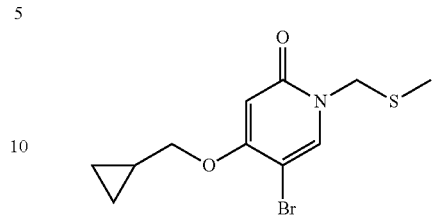

To a soln of the title compound from Step 2 (330 mg, 1.35 mmol) in DMF (5 mL) was added NaH (40 mg, 2 mmol, 60% in mineral oil) at 0° C. The mixture was stirred at 0° C. for 30 min. Then, chloromethyl methyl sulfide (131 mg, 1.35 mmol) was added. The mixture was warmed to room temp and stirred for 5 hr. The mixture was quenched with sat. aq NH$_4$Cl (30 mL) and extracted with EA (10 mL×3). The combined organic layers were washed with satd brine (20 mL×2), dried over anhydrous Na$_2$SO$_4$, filtered and concentrated under vacuum. The residue was purified by CC (PE:EA=3:1) to afford the title compound (205 mg, 50%) as yellow oil. $^1$H NMR (CDCl$_3$, 400 MHz): δ 7.60 (s, 1H), 5.86 (s, 1H), 4.96 (s, 1H), 3.84 (d, J=6.8 Hz, 2H), 2.17 (s, 3H), 1.32-1.25 (m, 1H), 0.70-0.67 (m, 2H), 0.41-0.39 (m, 2H).

Step 4: 5-bromo-4-(cyclopropylmethoxy)-1-(methylsulfonylmethyl)pyridin-2-one

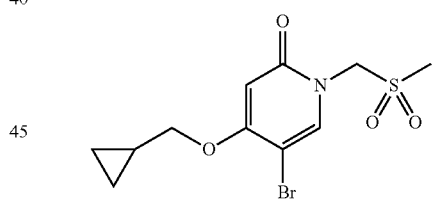

To a soln of the title compound from Step 3 (150 mg, 0.5 mmoL) in DCM (5 mL), was added mCPBA (340 mg, 1.9 mmol). The mixture was stirred at 15° C. for 2.5 hr. H$_2$O (30 mL) was added and the resulting mixture was extracted with EtOAc (120 mL×3). The combined organic phases were washed with satd brine (40 mL×2), dried over anhydrous Na$_2$SO$_4$, filtered and concentrated under reduced pressure. The residue was purified by CC on silica gel (PE:EA=5:1 to 2:1) to afford the title compound (120 mg, 72%) as a yellow solid. $^1$H NMR (CDCl$_3$, 400 MHz): δ 7.60 (s, 1H), 5.91 (s, 1H), 5.10 (s, 2H), 3.89 (d, J=6.8 Hz, 2H), 2.98 (s, 3H), 0.90-0.86 (m, 1H), 0.75-0.70 (m, 2H), 0.45-0.42 (m, 2H). LCMS: 335.9 (M+1)$^+$; 337 (M+1)$^+$.

Step 5: 4-(cyclopropylmethoxy)-5-(1-methyl-6-oxopyridin-3-yl)-1-(methylsulfonylmethyl)pyridin-2-one

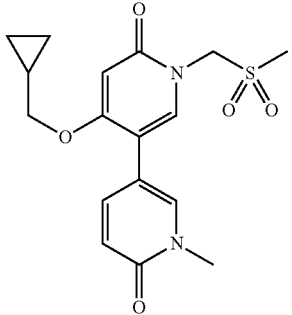 [SMILES: Cn1cc(-c2cn(CS(C)(=O)=O)c(=O)cc2OCC2CC2)ccc1=O]

The title compound from step 4 (50 mg, 0.15 mmol), 1-methyl-5-(4,4,5,5-tetramethyl-1,3,2-dioxaborolan-2-yl)pyridin-2-one (42 mg, 0.18 mmol), Pd(dppf)Cl$_2$ (11 mg, 14.9 umol) and K$_3$PO$_4$ (63 mg, 0.3 mmol) in dioxane (5 mL) and H$_2$O (5 drops) were degassed and then heated to 70° C. under N$_2$ overnight. The rxn mixture was then concentrated under reduced pressure. The residue was purified by CC (PE:DCM:EA=3:0:1 to 0:1:4) followed by preparative HPLC to afford the title compound (17.09 mg, 31.5%) as an off-white solid. $^1$H NMR (CDCl$_3$, 400 MHz): δ 7.50 (dd, J$_1$=9.2 Hz, J$_2$=2.4 Hz, 1H), 7.43 (d, J=2.4 Hz, 1H), 6.71 (d, J=9.2 Hz, 1H), 5.96 (s, 1H), 5.16 (s, 2H), 3.86 (d, J=6.8 Hz, 1H), 3.63 (s, 3H), 2.99 (s, 3H), 1.26-1.21 (m, 1H), 0.70-0.66 (m, 2H), 0.36-0.32 (m, 2H). LCMS: 365.0 (M+1)$^+$.

Example 382: 5-[4-(cyclopropylmethoxy)-1-(methylsulfonylmethyl)-6-oxopyridin-3-yl]-1,3-dimethylpyridin-2-one

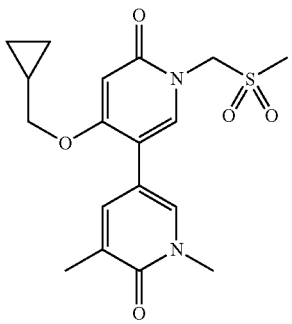 [SMILES: Cc1cc(-c2cn(CS(C)(=O)=O)c(=O)cc2OCC2CC2)cn(C)c1=O]

The title compound was prepared in a manner similar to Example 381, by substituting 1,3-dimethyl-5-(4,4,5,5-tetramethyl-1,3,2-dioxaborolan-2-yl)pyridin-2-one for 1-methyl-5-(4,4,5,5-tetramethyl-1,3,2-dioxaborolan-2-yl)pyridin-2-one in step 5. $^1$H NMR (CDCl$_3$, 400 MHz): δ 7.35 (s, 1H), 7.32 (s, 2H), 5.97 (s, 1H), 5.16 (s, 2H), 3.87 (s, J=7.2 Hz, 2H), 3.62 (s, 3H), 2.99 (s, 3H), 2.20 (s, 3H), 1.25-0.24 (m, 1H), 0.70-0.65 (m, 2H), 0.36-0.35 (m, 2H). LCMS: 379.0 (M+1)$^+$.

Example 383: 4-[4-(cyclopropylmethoxy)-1-(methylsulfonylmethyl)-6-oxopyridin-3-yl]-7-fluoro-2-methylisoquinolin-1-one

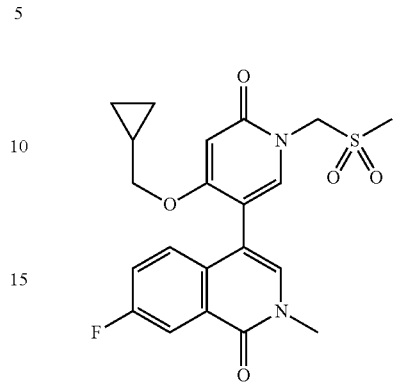

The title compound was prepared in a manner similar to Example 381, by substituting 7-fluoro-2-methyl-4-(4,4,5,5-tetramethyl-1,3,2-dioxaborolan-2-yl)isoquinolin-1-one for 1-methyl-5-(4,4,5,5-tetramethyl-1,3,2-dioxaborolan-2-yl)pyridin-2-one in step 5. $^1$H NMR (CDCl$_3$, 400 MHz): δ 8.13 (dd, J$_1$=9.2 Hz, J$_2$=2.4 Hz, 1H), 7.37 (s, 1H), 7.35-7.32 (m, 1H), 7.30-7.28 (m, 1H), 7.03 (s, 1H), 5.99 (s, 3H), 5.13 (d, J=13.6 Hz, 1H), 4.91 (d, J=13.6 Hz, 1H), 3.78 (t, J=6.4 Hz, 2H), 3.65 (s, 3H), 3.04 (s, 3H), 1.03-0.97 (m, 1H), 0.48-0.42 (m, 2H), 0.11 (s, 2H). LCMS: 433.1 (M+1)$^+$.

Example 384: 4-[4-(cyclopropylmethoxy)-1-(methylsulfonylmethyl)-6-oxopyridin-3-yl]-2-methylisoquinolin-1-one

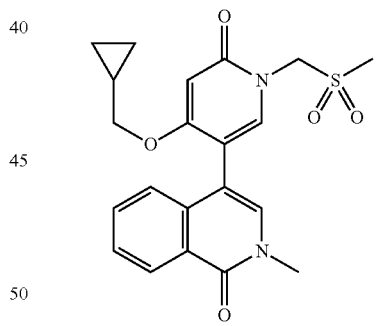

The title compound was prepared in a manner similar to Example 381, by substituting 2-methyl-4-(4,4,5,5-tetramethyl-1,3,2-dioxaborolan-2-yl)isoquinolin-1-one for 1-methyl-5-(4,4,5,5-tetramethyl-1,3,2-dioxaborolan-2-yl)pyridin-2-one in step 5. $^1$H NMR (CDCl$_3$, 400 MHz): δ 8.49 (d, J=8.0 Hz, 1H), 7.61 (t, J=7.2 Hz, 1H), 7.52 (t, J=7.2 Hz, 1H), 7.38 (s, 1H), 7.27 (d, J=8.0 Hz, 1H), 7.07 (s, 1H), 5.99 (s, 1H), 5.45 (d, J=14.4 Hz, 1H), 4.89 (d, J=14.4 Hz, 1H), 3.79 (t, J=8.0 Hz, 2H), 3.65 (s, 3H), 3.04 (s, 3H), 1.02-0.96 (m, 1H), 0.46-0.39 (m, 2H), 0.10 (s, 2H). LCMS: 415.1 (M+1)$^+$.

Example 385: 5-[4-(2,4-difluorophenoxy)-1-(methylsulfonylmethyl)-6-oxopyridin-3-yl]-1,3-dimethylpyridin-2-one

Step 1: 5-bromo-4-(2,4-difluorophenoxy)-1-(methylsulfonylmethyl)pyridin-2-one

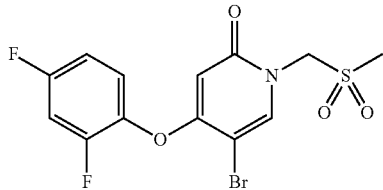 [SMILES: CS(=O)(=O)Cn1cc(Br)c(Oc2ccc(F)cc2F)cc1=O]

The title compound was prepared in a manner similar to Example 381 Steps 1 through 4, by substituting 2,4-difluorophenol for cyclopropylmethanol in step 1. $^1$H NMR (CDCl$_3$, 400 MHz) δ 7.71 (s, 1H), 7.21 (m, 1H), 7.01 (m, 2H), 5.66 (s, 1H), 5.1 (s, 2H), 2.96 (s, 3H).

Step 2: 5-[4-(2,4-difluorophenoxy)-1-(methylsulfonylmethyl)-6-oxopyridin-3-yl]-1,3-dimethylpyridin-2-one

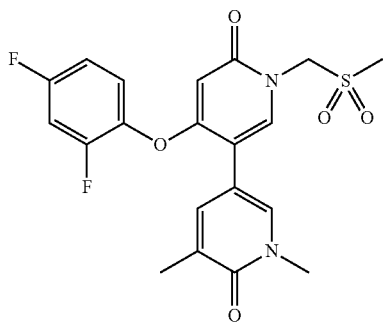

The title compound was prepared in a manner similar to Example 382, by substituting the title compound from Step 1 for 5-bromo-4-(cyclopropylmethoxy)-1-(methylsulfonylmethyl)pyridin-2-one. $^1$H NMR (CDCl$_3$, 400 MHz) δ 7.40 (s, 1H), 7.37 (s, 1H), 7.33 (s, 1H), 7.21-7.11 (m, 1H), 7.07-6.93 (m, 2H), 5.68 (s, 1H), 5.16 (s, 2H), 3.61 (s, 3H), 2.99 (s, 3H), 2.20 (s, 3H). LCMS: 437.0 (M+1)$^+$.

Example 386: 4-(2,4-difluorophenoxy)-5-(1-methyl-6-oxopyridin-3-yl)-1-(methylsulfonylmethyl)pyridin-2-one

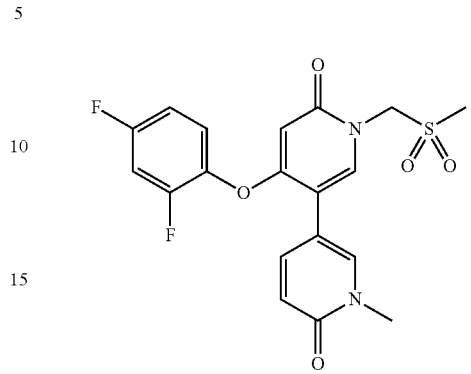

The title compound was prepared in a manner similar to Example 381, by substituting 5-bromo-4-(2,4-difluorophenoxy)-1-(methylsulfonylmethyl)pyridin-2-one for 5-bromo-4-(cyclo-propylmethoxy)-1-(methylsulfonylmethyl)pyridin-2-one in step 5. $^1$H NMR (CDCl$_3$, 400 MHz): δ 7.53 (dd, J$_1$=2.4 Hz, J$_2$=9.6 Hz, 1H), 7.46 (d, J=2.4 Hz, 1H), 7.44 (s, 1H), 7.19-7.13 (m, 1H), 7.07-7.00 (m, 1H), 7.00-6.93 (m, 1H), 6.64 (d, J=9.2 Hz, 1H), 5.68 (s, 1H), 5.17 (s, 2H), 3.61 (s, 3H), 2.98 (s, 3H). LCMS: 423.0 (M+1)$^+$.

Example 387: 4-[4-(2,4-difluorophenoxy)-1-(methylsulfonylmethyl)-6-oxopyridin-3-yl]-2-methylisoquinolin-1-one

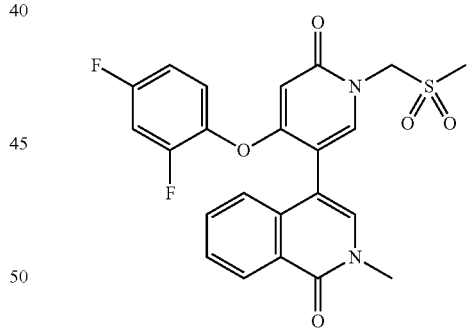

The title compound was prepared in a manner similar to Example 384, by substituting 5-bromo-4-(2,4-difluorophenoxy)-1-(methylsulfonylmethyl)pyridin-2-one for 5-bromo-4-(cyclo-propylmethoxy)-1-(methylsulfonylmethyl)pyridin-2-one. $^1$H NMR (CDCl$_3$, 400 MHz): δ 8.50 (d, J=8.0 Hz, 1H), 7.72-7.67 (m, 1H), 7.57-7.52 (m, 1H), 7.49 (d, J=9.2 Hz, 2H), 7.20 (s, 1H), 7.08-7.02 (m, 1H), 7.01-6.94 (m, 1H), 6.93-6.86 (m, 1H), 5.74 (s, 1H), 5.46 (d, J=14.4 Hz, 1H), 4.92 (d, J=14.4 Hz, 1H), 3.68 (s, 3H), 3.05 (s, 3H). LCMS: 473.0 (M+1)$^+$.

Example 388: 5-(2-but-2-ynoxy-5-methylsulfonyl-phenyl)-1,3-dimethylpyridin-2-one

Step 1: 5-(2-fluoro-5-methylsulfonylphenyl)-1,3-dimethylpyridin-2-one

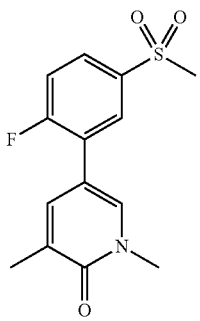

A mixture of 1,3-dimethyl-5-(4,4,5,5-tetramethyl-1,3,2-dioxaborolan-2-yl)pyridin-2-one (2.50 g, 10.0 mmol), 2-bromo-1-fluoro-4-methylsulfonylbenzene (2.54 g, 10.0 mmol), CsF (3.8 g, 25.0 mmol), Pd(dppf)Cl$_2$ (0.73 g, 1.0 mmol) in DME (50 mL), and MeOH (25 ml) was stirred at 80° C. for 18 hr under N$_2$. The mixture was concentrated and the residue was purified by CC (PE:EA=2:1 to 0:1) to give the title compound (1.8 g, 61%) as a red solid. LCMS: 295.9 (M+H)$^+$.

Step 2: 5-(2-but-2-ynoxy-5-methylsulfonylphenyl)-1,3-dimethylpyridin-2-one

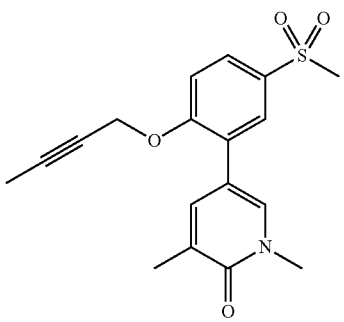 [SMILES: CC#CCOc1ccc(S(C)(=O)=O)cc1-c1cc(C)c(=O)n(C)c1]

To a soln of but-2-yn-1-ol (191 mg, 2.72 mmol) in anhydrous DMF (3 mL) was added NaH (109 mg, 2.72 mmol, 60% in mineral oil) at 0° C. The mixture was stirred at this temp for 1 hr. The title compound from Step 1 (200 mg, 0.68 mmol) was added and the rxn mixture was stirred at 0° C. for 2 hr. After this time, it was quenched with sat. NH$_4$Cl soln (20 mL) and extracted with EtOAc (20 mL×3). The combined organic layers were washed with brine (40 mL), dried over Na$_2$SO$_4$, filtered and concentrated to give a crude product that was purified by prep-HPLC to give the title compound (56.01 mg, 23.9%) as a light yellow solid. $^1$H NMR (CDCl$_3$, 400 MHz): δ 7.88 (dd, J$_1$=8.8 Hz, J$_2$=2.0 Hz, 1H), 7.81 (d, J=2.0 Hz, 1H), 7.46 (s, 2H), 7.24 (d, J=8.8 Hz, 1H), 4.79 (d, J=2.0 Hz, 2H), 3.62 (s, 3H), 3.08 (s, 3H), 2.22 (s, 3H), 1.87 (s, 3H). LCMS: 346.0 (M+H)$^+$.

Example 389: 5-(2-but-2-ynoxy-5-ethylsulfonylphenyl)-3-methoxy-1-methylpyridin-2-one

Step 1: 5-(5-ethylsulfonyl-2-fluorophenyl)-3-methoxy-1-methylpyridin-2-one

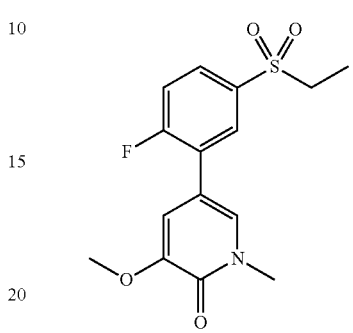

To a soln of 5-bromo-3-methoxy-1-methylpyridin-2-one (694 mg, 3.18 mmol), 2-(5-ethylsulfonyl-2-fluorophenyl)-4,4,5,5-tetramethyl-1,3,2-dioxaborolane (1 g, 3.18 mmol), Pd(dppf)Cl$_2$ (233 mg, 318.00 μmol) in C$_4$H$_8$O$_2$ (26 mL) and H$_2$O (2.6 mL) was added K$_3$PO$_4$ (2.02 g, 9.54 mmol, 3.00 Eq). The rxn was stirred at 70° C. under N$_2$ for 6 hr; then concentrated and the residue purified by CC (PE:EA=3:1 to 1:2) to afford the title compound (0.9 g, 87%) as a brown solid. $^1$H NMR (CDCl$_3$, 400 MHz): δ 7.93 (dd, J$_1$=7.2 Hz, J$_2$=2.0 Hz, 1H), 7.88-7.84 (m, 1H), 7.35 (dd, J$_1$=10.0 Hz, J$_2$=8.8 Hz, 1H), 7.23 (d, J=1.6 Hz, 1H), 6.83 (s, 1H), 3.89 (s, 3H), 3.67 (s, 3H), 3.16 (q, J=7.6 Hz, 2H), 1.33 (t, J=7.6 Hz, 3H). LCMS: 325.9 (M+H)$^+$.

Step 2: 5-(2-but-2-ynoxy-5-ethylsulfonylphenyl)-3-methoxy-1-methylpyridin-2-one

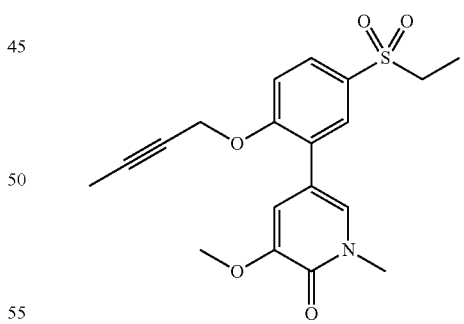

The title compound was prepared in a manner similar to Example 388, Step 2, by substituting 5-(5-ethylsulfonyl-2-fluorophenyl)-3-methoxy-1-methylpyridin-2-one for 5-(2-fluoro-5-methylsulfonylphenyl)-1,3-dimethylpyridin-2-one. $^1$H NMR (CDCl$_3$, 400 MHz): δ 7.88 (d, J=8.8 Hz, 1H), 7.80 (s, 1H), 7.23 (d, J=8.4 Hz, 1H), 7.19 (s, 1H), 6.97 (s, 1H), 4.78 (s, 2H), 3.83 (s, 3H), 3.70 (s, 3H), 3.15 (q, J=7.2 Hz, 2H), 1.87 (s, 3H), 1.32 (t, J=7.2 Hz, 3H). LCMS: 376.0 (M+H)$^+$.

701

Example 390: 5-(5-ethylsulfonyl-2-pent-2-ynoxy-phenyl)-3-methoxy-1-methylpyridin-2-one

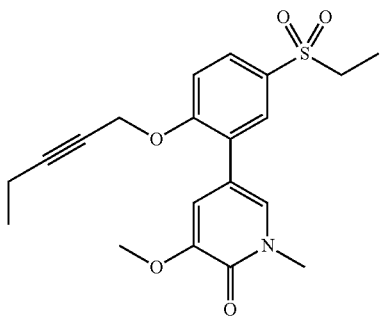 [SMILES: CCC#CCOc1ccc(S(=O)(=O)CC)cc1-c1cc(OC)c(=O)n(C)c1]

The title compound was prepared in a manner similar to Example 389, by substituting pent-2-yn-1-ol for but-2-yn-1-ol in Step 2. $^1$H NMR (CDCl$_3$, 400 MHz) δ 7.86 (dd, J$_1$=8.8 Hz, J$_2$=2.0 Hz, 1H), 7.79 (d, J=2.4 Hz, 1H), 7.23 (d, J=8.8 Hz, 1H), 7.18 (d, J=2.0 Hz, 1H), 6.94 (d, J=1.6 Hz, 1H), 4.80 (s, 2H), 3.87 (s, 3H), 3.67 (s, 3H), 3.15 (q, J=7.6 Hz, 2H), 2.24 (q, J=7.6 Hz, 2H), 1.32 (t, J=7.6 Hz, 3H), 1.14 (t, J=7.6 Hz, 3H). LCMS: 390.2 (M+H)$^+$.

Example 391: 5-[2-(3-cyclopropylprop-2-ynoxy)-5-ethylsulfonylphenyl]-3-methoxy-1-methylpyridin-2-one

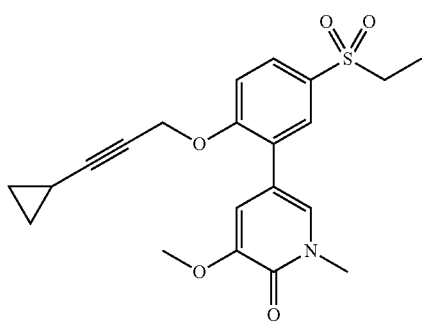 [SMILES: CCS(=O)(=O)c1ccc(OCC#CC2CC2)c(-c2cc(OC)c(=O)n(C)c2)c1]

The title compound was prepared in a manner similar to Example 389, by substituting 3-cyclopropylprop-2-yn-1-ol for but-2-yn-1-ol in Step 2. $^1$H NMR (CDCl$_3$, 400 MHz) δ 7.87 (d, J=8.8 Hz, 1H), 7.79 (s, 1H), 7.22-7.20 (m, 2H), 7.00 (s, 1H), 4.77 (s, 2H), 3.88 (s, 3H), 3.70 (s, 3H), 3.15 (q, J=7.2 Hz, 2H), 1.32 (t, J=7.2 Hz, 3H), 1.31-1.29 (m, 1H), 0.84-0.81 (m, 2H), 0.69-0.67 (m, 2H). LCMS: 402.0 (M+H)$^+$.

702

Example 392: N-[4-(2,4-difluorophenoxy)-3-[1-methyl-6-oxo-5-(trifluoromethyl)pyridin-3-yl]phenyl]ethanesulfonamide Step 1: 5-bromo-1-methyl-3-(trifluoromethyl)pyridin-2-one

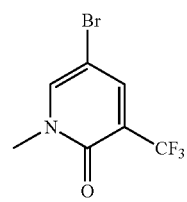

To a soln of 5-bromo-3-(trifluoromethyl)pyridin-2-ol (6 g, 25 mmol) stirred at room temp in THF (5 mL) was added NaH (1.5 g, 37 mmol, 60% in mineral oil). After stirring for 30 min, methyl iodide (7.1 g, 50 mmol) was added. After stirring at room temp for 3 hr, the rxn mixture was treated with H$_2$O (100 mL) and extracted with EtOAc (100 mL×3). The combined organic layers were washed with brine (100 mL), dried over Na$_2$SO$_4$, filtered, and concentrated in vacuo to afford the title compound (6 g, 97%) as a tan solid. The solid was carried forward without any further purification. $^1$H NMR (CDCl3, 400 MHz): δ 7.79 (d, J=2.0 Hz, 1H), 7.65 (d, J=2.0 Hz, 1H), 3.60 (s, 3H). LCMS (M+H)$^+$: 256.

Step 2: 1-methyl-5-(3,3,4,4-tetramethylborolan-1-yl)-3-(trifluoromethyl)pyridin-2-one

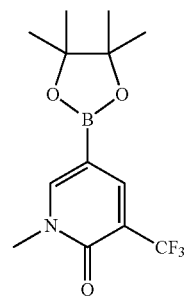 [SMILES: Cn1cc(B2OC(C)(C)C(C)(C)O2)cc(C(F)(F)F)c1=O]

A suspension of compound 5-bromo-1-methyl-3-(trifluoromethyl)pyridin-2-one (3 g, 11.8 mmol), 4,4,5,5-tetramethyl-2-(tetramethyl-1,3,2-dioxaborolan-2-yl)-1,3,2-dioxaborolane (3.6 g, 14.1 mmol), KOAc (3 g, 30.6 mmol), and Pd(dppf)$_2$Cl$_2$ (200 mg) in dioxane (50 mL) was stirred at 90° C. for 4 hr. After the rxn mixture was concentrated in vacuo, the resulting residue was purified by CC (PE:EA=3:1 to 1:1) to give the title compound (1.2 g, 34%) as a red solid. $^1$H NMR (CDCl$_3$, 400 MHz): δ 8.02 (d, J=2.0 Hz, 1H), 7.94 (d, J=2.0 Hz, 1H), 3.60 (s, 3H), 1.32 (s, 12H). LCMS (M+H)$^+$: 304.

Step 3: 5-[2-(2,4-difluorophenoxy)-5-ethylsulfonyl-phenyl]-1-methyl-3-(trifluoromethyl)pyridin-2-one

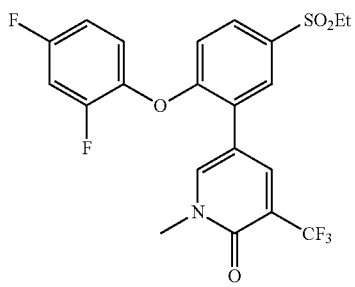

A mixture of 1-methyl-5-(3,3,4,4-tetramethylborolan-1-yl)-3-(trifluoromethyl)pyridin-2-one (100 mg, 0.33 mmol), 1-(2-bromo-4-ethylsulfonylphenoxy)-2,4-difluorobenzene (100 mg, 0.27 mmol), Pd(dppf)Cl$_2$ (24 mg) and K$_3$PO$_4$ (107 mg, 0.80 mmol) in dioxane (4 mL) and H$_2$O (1 mL) was purged with N$_2$, capped, and heated to 90° C. for 4 hr. After the mixture was filtered through a short bed of celite, the filtrate was concentrated in vacuo and purified by prep-HPLC afford the title compound (43 mg, 34%) as a white solid. $^1$H NMR (CDCl$_3$, 400 MHz): δ ppm 8.11 (s, 1H) 7.88 (s, 2H) 7.80 (m, 1H), 7.23-7.10 (m, 1H) 7.09-6.91 (m, 2H) 6.91-6.78 (m, 1H) 6.25 (s, 1H) 3.70 (s, 3H) 3.15 (q, J=7.2 Hz, 2H) 1.31 (t, J=7.2 Hz, 3H). LCMS (M+H)$^+$: 474.

Example 393: 4-[2-(cyclopropylmethoxy)-5-propan-2-ylsulfonylphenyl]-6-methoxy-2-methylisoquinolin-1-one

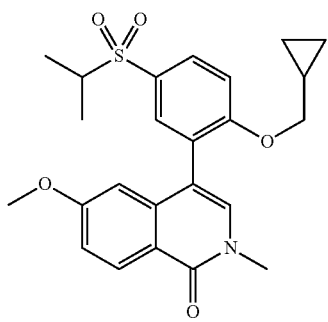 [SMILES: COc1ccc2c(=O)n(C)cc(-c3cc(S(=O)(=O)C(C)C)ccc3OCC3CC3)c2c1]

Bromo-6-methoxy-2-methylisoquinolin-1-one (prepared as reported previously in WO 2013/142390) was reacted with 4,4,5,5-tetramethyl-2-(tetramethyl-1,3,2-dioxaborolan-2-yl)-1,3,2-dioxaborolane in a manner similar to Example 248, step 2, to give 6-methoxy-2-methyl-4-(4,4,5,5-tetramethyl-1,3,2-dioxaborolan-2-yl)isoquinolin-1-one which was then reacted with the title compound of Example 364, step 1, in a manner similar to Example 364, step 2, to give the title compound. $^1$H NMR (CDCl$_3$, 400 MHz): δ 8.45 (d, J=8.4 Hz, 1H), 7.91 (dd, J$_1$=2.0 Hz, J$_2$=8.8, 1H), 7.06-7.27 (m, 3H), 6.53 (d, J=2.8 Hz, 1H), 3.89 (m, 2H), 3.78 (s, 3H), 3.65 (s, 3H), 3.22 (m, 1H), 1.33 (d, J=6.4 Hz, 6H), 1.03 (q, J=6.8 Hz, 1H), 0.45 (m, 2H), 0.14 (s, 2H). LCMS: 442.0 (M+H)$^+$.

Example 394: 5-[2-(cyclopropylmethoxy)-5-propan-2-ylsulfonylphenyl]-1,3-dimethylpyridin-2-one

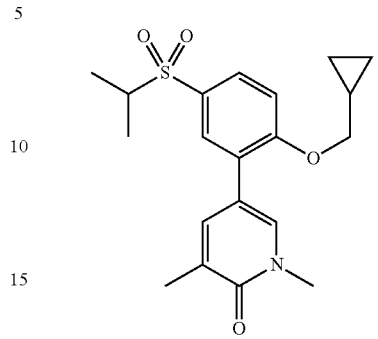

The title compound of Example 364, step 1 was reacted with 1,3-dimethyl-5-(4,4,5,5-tetramethyl-1,3,2-dioxaborolan-2-yl)pyridin-2-one in a manner similar to Example 364, step 2 to give the title compound. $^1$H NMR (CDCl3, 400 MHz): δ 7.75-7.79 (m, 2H), 7.59 (s, 1H), 7.03 (d, J=8.4 Hz, 1H), 3.96 (d, J=6.8 Hz, 2H), 3.67 (s, 3H), 3.15-3.25 (m, 1H), 2.24 (s, 3H), 1.31 (d, J=7.2 Hz, 6H), 1.27 (d, J=7.2 Hz, 1H), 0.66-0.70 (m, 2H), 0.38 (q, J=5.2 Hz, 2H). LCMS: 376.0 (M+H)$^+$.

Example 395: N-[3-(1,5-dimethyl-6-oxopyridin-3-yl)-5-phenylmethoxyphenyl]ethanesulfonamide

Step 1: N-(3-bromo-5-phenylmethoxyphenyl)ethanesulfonamide

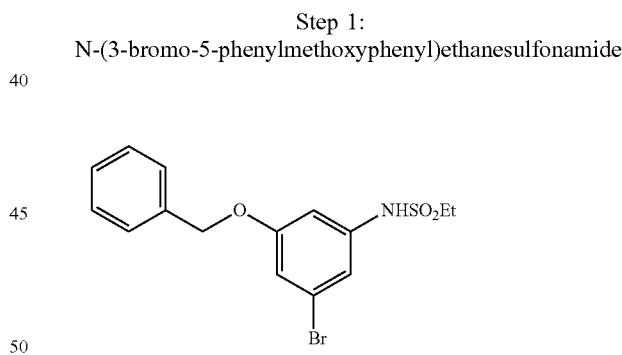

Ethylsulfonyl chloride (113 μL, 1.2 mmol) was added dropwise to a stirred soln of 3-bromo-5-phenylmethoxyaniline (284 mg, 1.0 mmol) and pyridine (247 μL, 3.1 mmol) in DCM (5 mL) at 0° C. under N$_2$. After the mixture was warmed to room temp and stirred for 14 hr, it was treated with 1N HCl (1 mL) and extracted with DCM (3×5 mL); the combined organic extracts were washed with satd bicarbonate soln (aq), dried over Na$_2$SO$_4$, filtered and concentrated in vacuo. The crude solid was purified by CC using EtOAc (5% to 95%) in hexanes to afford the title compound (345 mg, 94%) as an amber oil that solidified upon standing. LCMS (M+H)$^+$: 371.

Step 2: N-[3-(1,5-dimethyl-6-oxopyridin-3-yl)-5-phenylmethoxyphenyl]ethanesulfonamide

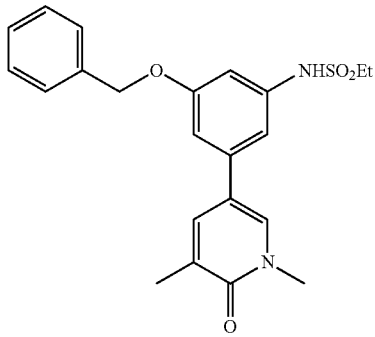

A mixture of N-(3-bromo-5-phenylmethoxyphenyl)ethanesulfonamide (60 mg, 0.16 mmol), 1,3-dimethyl-5-(4,4,5,5-tetramethyl-1,3,2-dioxaborolan-2-yl)pyridin-2-one (40 mg, 0.16 mmol), Pd(dppf)Cl$_2$ (12 mg) and K$_3$PO$_4$ (88 mg, 0.40 mmol) in dioxane (1.5 mL) and H$_2$O (150 μL) was purged with N$_2$, capped, and heated to 75° C. for 2 hr. After the mixture was filtered through a short bed of celite, the filtrate was concentrated in vacuo and purified by silica gel CC using MeOH (0% to 10%) in DCM to afford the title compound (69 mg, 94%) as an off-white solid. $^1$H NMR (400 MHz, DMSO-d$_6$): δ ppm 1.15-1.24 (m, 3H) 2.04-2.13 (m, 3H) 3.04-3.17 (m, 2H) 3.48-3.54 (m, 3H) 5.08-5.17 (m, 2H) 6.74-6.80 (m, 1H) 6.90-6.98 (m, 2H) 7.33-7.49 (m, 5H) 7.59-7.63 (m, 1H) 7.90-7.95 (m, 1H) 9.57-10.01 (bs, 1H). LCMS (M+H)$^+$: 413.

Examples 396-482 in Table 21 were prepared using Suzuki conditions to append an appropriately substituted aryl group to an appropriately substituted pyridinone. Chemical manipulation subsequent to the Suzuki reaction was also carried out as needed to give the title compound.

TABLE 21

| Chemical Synthesis Example | Structure | Name | MS (M + H) |
|---|---|---|---|
| 396 | 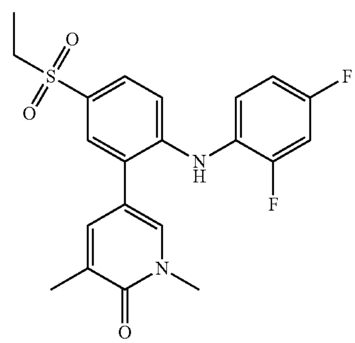 [SMILES: CCS(=O)(=O)c1ccc(Nc2ccc(F)cc2F)c(-c2cc(C)c(=O)n(C)c2)c1] | 5-[2-(2,4-difluoroanilino)-5-ethylsulfonylphenyl]-1,3-dimethylpyridin-2-one | 419.1 |
| 397 | 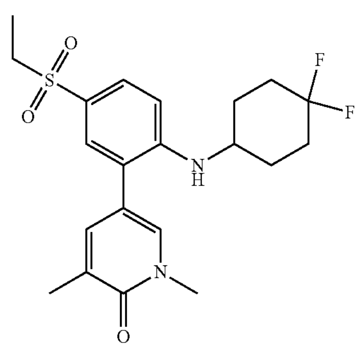 [SMILES: CCS(=O)(=O)c1ccc(NC2CCC(F)(F)CC2)c(-c2cc(C)c(=O)n(C)c2)c1] | 5-[2-[(4,4-difluorocyclohexyl)amino]-5-ethylsulfonylphenyl]-1,3-dimethylpyridin-2-one | 425.1 |
| 398 | 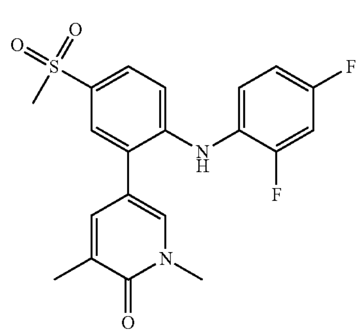 [SMILES: Cc1cc(-c2cc(S(C)(=O)=O)ccc2Nc2ccc(F)cc2F)cn(C)c1=O] | 5-[2-(2,4-difluoroanilino)-5-methylsulfonylphenyl]-1,3-dimethylpyridin-2-one | 405.1 |

TABLE 21-continued

| Chemical Synthesis Example | Structure | Name | MS (M + H) |
|---|---|---|---|
| 399 | 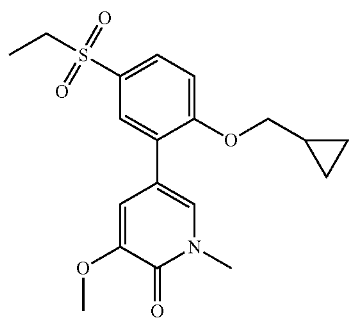 [SMILES: CCS(=O)(=O)c1ccc(OCC2CC2)c(-c2cc(OC)c(=O)n(C)c2)c1] | 5-[2-(cyclopropylmethoxy)-5-ethylsulfonylphenyl]-3-methoxy-1-methylpyridin-2-one | 378.1 |
| 400 | 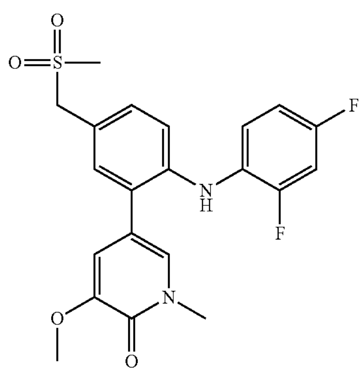 [SMILES: COc1cc(-c2cc(CS(C)(=O)=O)ccc2Nc2ccc(F)cc2F)cn(C)c1=O] | 5-[2-(2,4-difluorophenoxy)-5-(methylsulfonylmethyl)phenyl]-3-methoxy-1-methylpyridin-2-one | 436.0 |
| 401 | 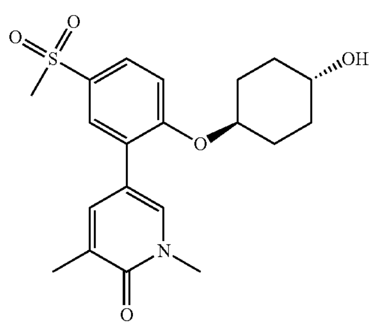 [SMILES: Cc1cc(-c2cc(S(C)(=O)=O)ccc2O[C@H]2CC[C@H](O)CC2)cn(C)c1=O] | 5-[2-(4-trans-hydroxycyclohexyl)oxy-5-methylsulfonylphenyl]-1,3-dimethylpyridin-2-one | 392.1 |
| 402 | 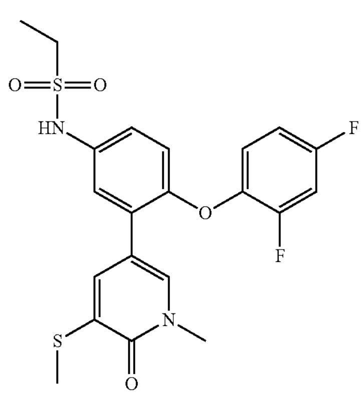 [SMILES: CCS(=O)(=O)Nc1ccc(Oc2ccc(F)cc2F)c(-c2cc(SC)c(=O)n(C)c2)c1] | N-[4-(2,4-difluorophenoxy)-3-(1-methyl-5-methylsulfanyl-6-oxopyridin-3-yl)phenyl]ethanesulfonamide | 467.10 |

TABLE 21-continued
| Chemical Synthesis Example | Structure | Name | MS (M + H) |
|---|---|---|---|
| 403 | 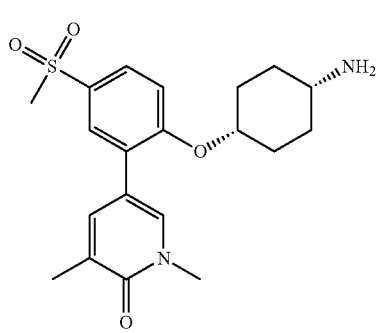 [SMILES: Cc1cc(-c2cc(S(C)(=O)=O)ccc2O[C@H]2CC[C@@H](N)CC2)cn(C)c1=O] | 5-[2-(4-cis-aminocyclohexyl)oxy-5-methylsulfonylphenyl]-1,3-dimethylpyridin-2-one | 391.2 |
| 404 | 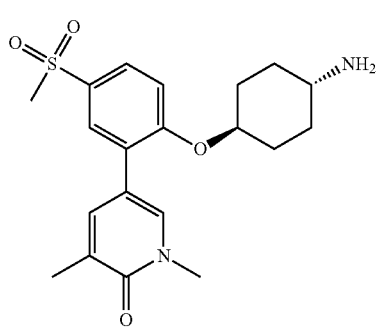 [SMILES: Cc1cc(-c2cc(S(C)(=O)=O)ccc2O[C@H]2CC[C@H](N)CC2)cn(C)c1=O] | 5-[2-(4-trans-aminocyclohexyl)oxy-5-methylsulfonylphenyl]-1,3-dimethylpyridin-2-one | 391.1 |
| 405 | 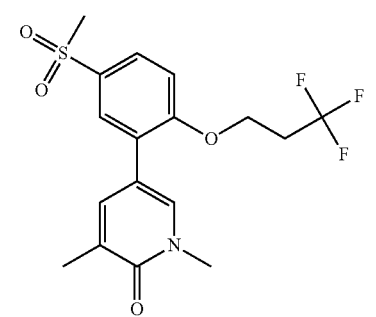 [SMILES: Cc1cc(-c2cc(S(C)(=O)=O)ccc2OCCC(F)(F)F)cn(C)c1=O] | 1,3-dimethyl-5-[5-methylsulfonyl-2-(3,3,3-trifluoropropoxy)phenyl]pyridin-2-one | 390.0 |
| 406 | 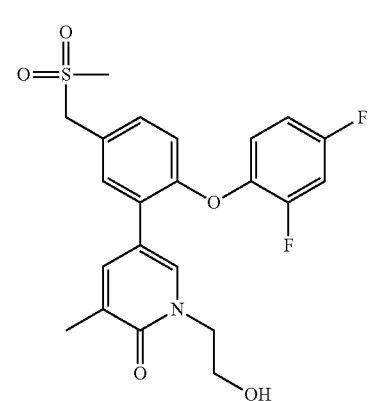 [SMILES: Cc1cc(-c2cc(CS(C)(=O)=O)ccc2Oc2ccc(F)cc2F)cn(CCO)c1=O] | 5-[2-(2,4-difluorophenoxy)-5-(methylsulfonylmethyl)phenyl]-1-(2-hydroxyethyl)-3-methylpyridin-2-one | 450.2 |

TABLE 21-continued

| Chemical Synthesis Example | Structure | Name | MS (M + H) |
|---|---|---|---|
| 407 | 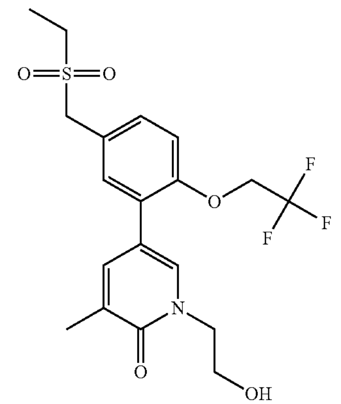 [SMILES: CCS(=O)(=O)Cc1ccc(OCC(F)(F)F)c(-c2cc(C)c(=O)n(CCO)c2)c1] | 5-[5-(ethylsulfonylmethyl)-2-(2,2,2-trifluoroethoxy)phenyl]-1-(2-hydroxyethyl)-3-methylpyridin-2-one | 434.1 |
| 408 | 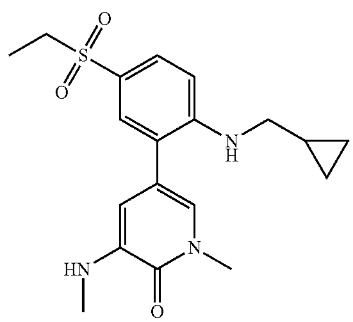 [SMILES: CCS(=O)(=O)c1ccc(NCC2CC2)c(-c2cc(NC)c(=O)n(C)c2)c1] | 5-[2-(cyclopropylmethylamino)-5-ethylsulfonylphenyl]-1-methyl-3-(methylamino)pyridin-2-one | 376.2 |
| 409 | 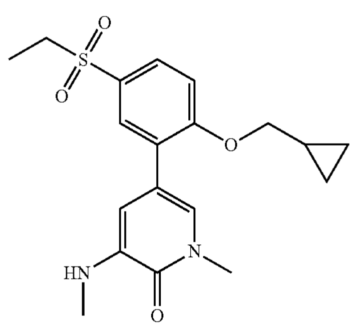 [SMILES: CCS(=O)(=O)c1ccc(OCC2CC2)c(-c2cc(NC)c(=O)n(C)c2)c1] | 5-[2-(cyclopropylmethoxy)-5-ethylsulfonylphenyl]-1-methyl-3-(methylamino)pyridin-2-one | 377.2 |
| 410 | 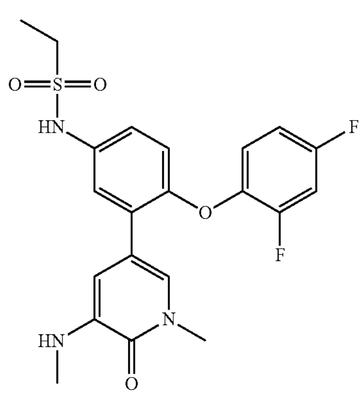 [SMILES: CCS(=O)(=O)Nc1ccc(Oc2ccc(F)cc2F)c(-c2cc(NC)c(=O)n(C)c2)c1] | N-[4-(2,4-difluorophenoxy)-3-[1-methyl-5-(methylamino)-6-oxopyridin-3-yl]phenyl]ethanesulfonamide | 450.1 |

TABLE 21-continued

| Chemical Synthesis Example | Structure | Name | MS (M + H) |
|---|---|---|---|
| 411 | 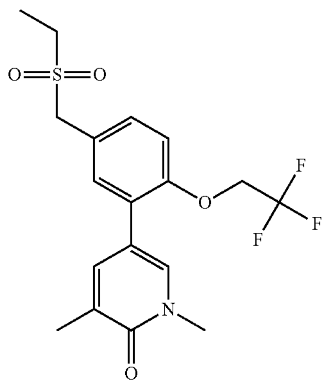 [SMILES: CCS(=O)(=O)Cc1ccc(OCC(F)(F)F)c(-c2cc(C)c(=O)n(C)c2)c1] | 5-[5-(ethylsulfonylmethyl)-2-(2,2,2-trifluoroethoxy)phenyl]-1,3-dimethylpyridin-2-one | 404.1 |
| 412 | 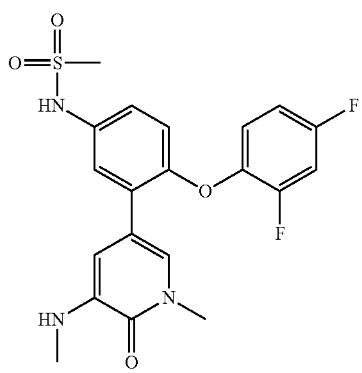 [SMILES: CNc1cc(-c2cc(NS(C)(=O)=O)ccc2Oc2ccc(F)cc2F)cn(C)c1=O] | N-[4-(2,4-difluorophenoxy)-3-[1-methyl-5-(methylamino)-6-oxopyridin-3-yl]phenyl]methanesulfonamide | 436.0 |
| 413 | 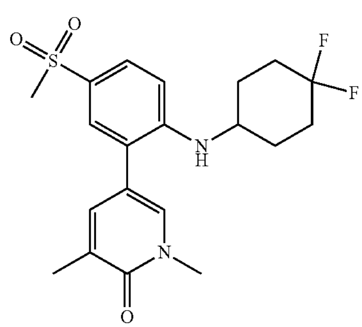 [SMILES: Cc1cc(-c2cc(S(C)(=O)=O)ccc2NC2CCC(F)(F)CC2)cn(C)c1=O] | 5-[2-[(4,4-difluorocyclohexyl)amino]-5-methylsulfonylphenyl]-1,3-dimethylpyridin-2-one | 411.0 |
| 414 | 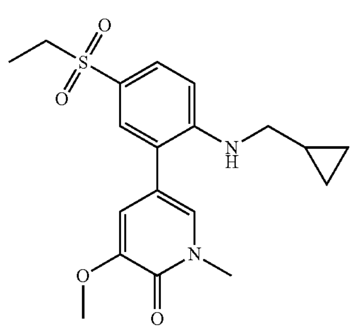 [SMILES: CCS(=O)(=O)c1ccc(NCC2CC2)c(-c2cc(OC)c(=O)n(C)c2)c1] | 5-[2-(cyclopropylmethylamino)-5-ethylsulfonylphenyl]-3-methoxy-1-methylpyridin-2-one | 377.1 |

TABLE 21-continued

| Chemical Synthesis Example | Structure | Name | MS (M + H) |
|---|---|---|---|
| 415 | 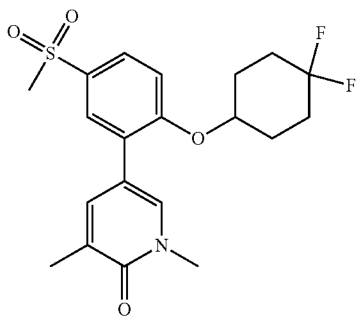 [SMILES: Cc1cc(-c2cc(S(C)(=O)=O)ccc2OC2CCC(F)(F)CC2)cn(C)c1=O] | 5-[2-(4,4-difluorocyclohexyl)oxy-5-methylsulfonylphenyl]-1,3-dimethylpyridin-2-one | 412.1 |
| 416 | 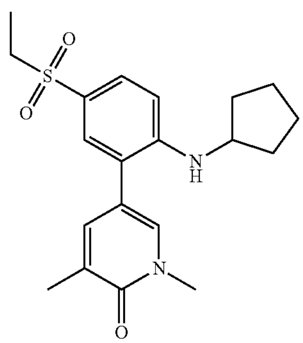 [SMILES: CCS(=O)(=O)c1ccc(NC2CCCC2)c(-c2cc(C)c(=O)n(C)c2)c1] | 5-[2-(cyclopentylamino)-5-ethylsulfonylphenyl]-1,3-dimethylpyridin-2-one | 375.2 |
| 417 | 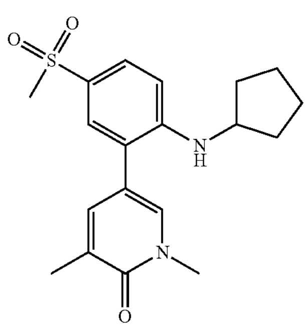 [SMILES: Cc1cc(-c2cc(S(C)(=O)=O)ccc2NC2CCCC2)cn(C)c1=O] | 5-[2-(cyclopentylamino)-5-methylsulfonylphenyl]-1,3-dimethylpyridin-2-one | 361.1 |
| 418 | 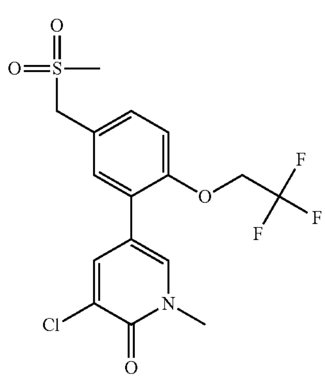 [SMILES: Cn1cc(-c2cc(CS(C)(=O)=O)ccc2OCC(F)(F)F)cc(Cl)c1=O] | 3-chloro-1-methyl-5-[5-(methylsulfonylmethyl)-2-(2,2,2-trifluoroethoxy)phenyl]pyridin-2-one | 410.0 |

TABLE 21-continued

| Chemical Synthesis Example | Structure | Name | MS (M + H) |
|---|---|---|---|
| 419 | 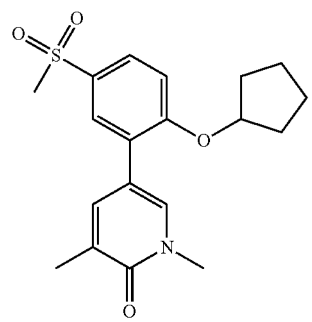 [SMILES: Cc1cc(-c2cc(S(C)(=O)=O)ccc2OC2CCCC2)cn(C)c1=O] | 5-(2-cyclopentyloxy-5-methylsulfonylphenyl)-1,3-dimethylpyridin-2-one | 362.1 |
| 420 | 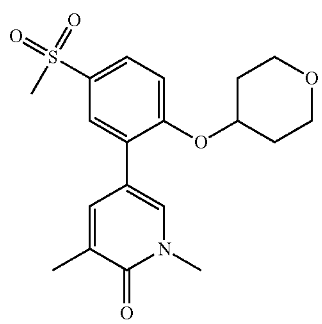 [SMILES: Cc1cc(-c2cc(S(C)(=O)=O)ccc2OC2CCOCC2)cn(C)c1=O] | 1,3-dimethyl-5-[5-methylsulfonyl-2-(oxan-4-yloxy)phenyl]pyridin-2-one | 378.1 |
| 421 | 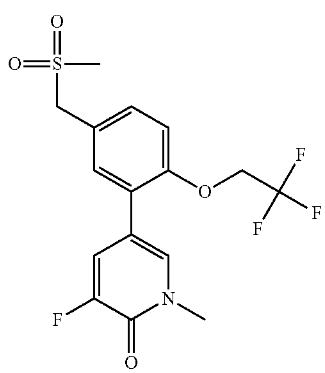 [SMILES: Cn1cc(-c2cc(CS(C)(=O)=O)ccc2OCC(F)(F)F)cc(F)c1=O] | 3-fluoro-1-methyl-5-[5-(methylsulfonylmethyl)-2-(2,2,2-trifluoroethoxy)phenyl]pyridin-2-one | 394.1 |
| 422 | 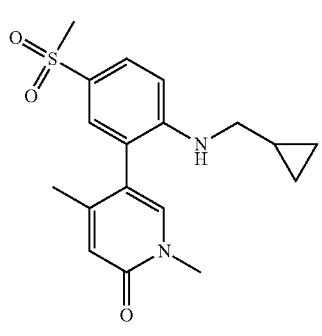 [SMILES: Cc1cc(=O)n(C)cc1-c1cc(S(C)(=O)=O)ccc1NCC1CC1] | 5-[2-(cyclopropylmethylamino)-5-methylsulfonylphenyl]-1,4-dimethylpyridin-2-one | 347.0 |

TABLE 21-continued

| Chemical Synthesis Example | Structure | Name | MS (M + H) |
|---|---|---|---|
| 423 | 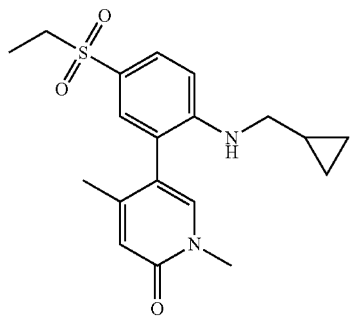 [SMILES: CCS(=O)(=O)c1ccc(NCC2CC2)c(-c2cn(C)c(=O)cc2C)c1] | 5-[2-(cyclopropylmethylamino)-5-ethylsulfonylphenyl]-1,4-dimethylpyridin-2-one | 361.1 |
| 424 | 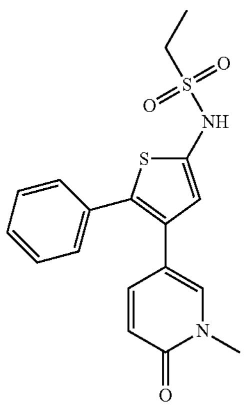 [SMILES: CCS(=O)(=O)Nc1cc(-c2ccc(=O)n(C)c2)c(-c2ccccc2)s1] | N-[4-(1-methyl-6-oxopyridin-3-yl)-5-phenylthiophen-2-yl]ethanesulfonamide | 375.0 |
| 425 | 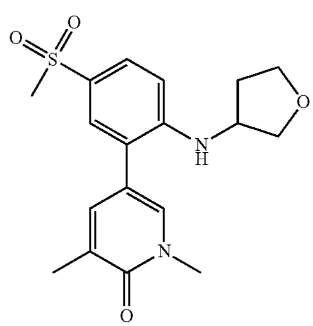 [SMILES: Cc1cc(-c2cc(S(C)(=O)=O)ccc2NC2CCOC2)cn(C)c1=O] | 1,3-dimethyl-5-[5-methylsulfonyl-2-(oxolan-3-ylamino)phenyl]pyridine-2-one | 363.1 |
| 426 | 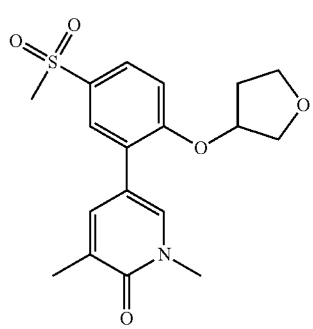 [SMILES: Cc1cc(-c2cc(S(C)(=O)=O)ccc2OC2CCOC2)cn(C)c1=O] | 1,3-dimethyl-5-[5-methylsulfonyl-2-(oxolan-3-yloxy)phenyl]pyridin-2-one | 364.0 |

TABLE 21-continued

| Chemical Synthesis Example | Structure | Name | MS (M + H) |
|---|---|---|---|
| 427 | 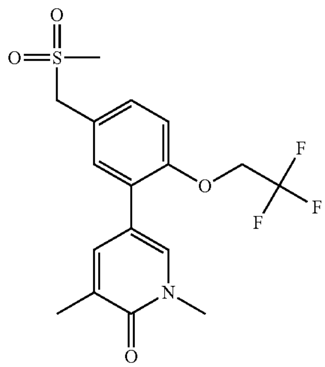 [SMILES: Cc1cc(-c2cc(CS(C)(=O)=O)ccc2OCC(F)(F)F)cn(C)c1=O] | 1,3-dimethyl-5-[5-(methylsulfonylmethyl)-2-(2,2,2-trifluoroethoxy)phenyl]pyridin-2-one | 390.0 |
| 428 | 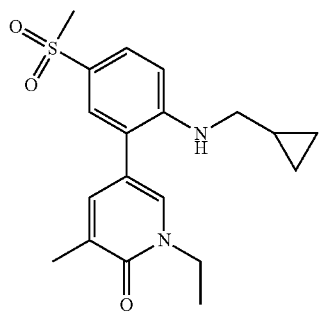 [SMILES: CCn1cc(-c2cc(S(C)(=O)=O)ccc2NCC2CC2)cc(C)c1=O] | 5-[2-(cyclopropylmethylamino)-5-methylsulfonylphenyl]-1-ethyl-3-methylpyridin-2-one | 361.1 |
| 429 | 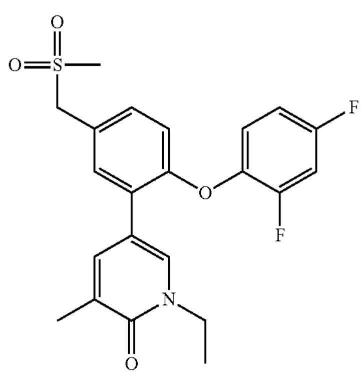 [SMILES: CCn1cc(-c2cc(CS(C)(=O)=O)ccc2Oc2ccc(F)cc2F)cc(C)c1=O] | 5-[2-(2,4-difluorophenoxy)-5-(methylsulfonylmethyl)phenyl]-1-ethyl-3-methylpyridin-2-one | 434.0 |
| 430 | 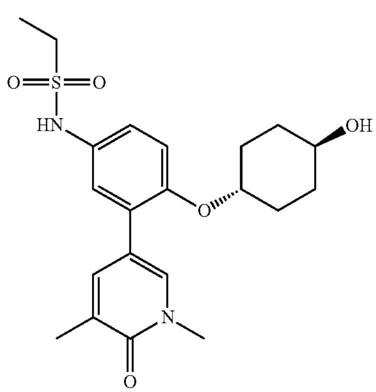 [SMILES: CCS(=O)(=O)Nc1ccc(O[C@H]2CC[C@H](O)CC2)c(-c2cc(C)c(=O)n(C)c2)c1] | N-[3-(1,5-dimethyl-6-oxopyridin-3-yl)-4-(4-trans-hydroxycyclohexyl)oxyphenyl]ethanesulfonamide | 421.1 |

TABLE 21-continued

| Chemical Synthesis Example | Structure | Name | MS (M + H) |
|---|---|---|---|
| 431 | 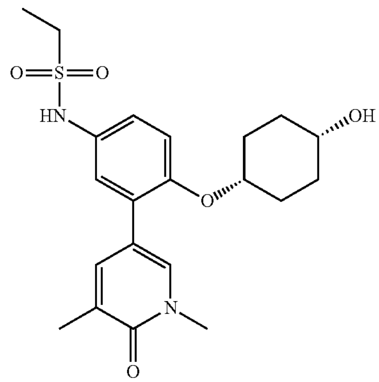 [SMILES: CCS(=O)(=O)Nc1ccc(O[C@H]2CC[C@@H](O)CC2)c(-c2cc(C)c(=O)n(C)c2)c1] | N-[3-(1,5-dimethyl-6-oxopyridin-3-yl)-4-(4-cis-hydroxycyclohexyl)oxyphenyl]ethanesulfonamide | 421.1 |
| 432 | 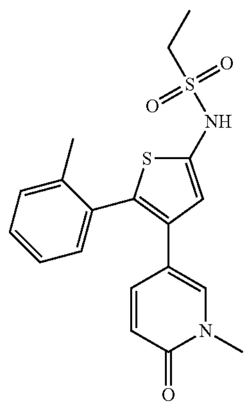 [SMILES: CCS(=O)(=O)Nc1cc(-c2ccc(=O)n(C)c2)c(-c2ccccc2C)s1] | N-[4-(1-methyl-6-oxopyridin-3-yl)-5-(2-methylphenyl)thiophen-2-yl]ethanesulfonamide | 389.1 |
| 433 | 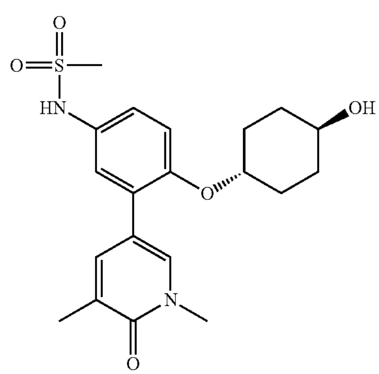 [SMILES: Cc1cc(-c2cc(NS(C)(=O)=O)ccc2O[C@H]2CC[C@H](O)CC2)cn(C)c1=O] | N-[3-(1,5-dimethyl-6-oxopyridin-3-yl)-4-(4-trans-hydroxycyclohexyl)oxyphenyl]methanesulfonamide | 407.1 |
| 434 | 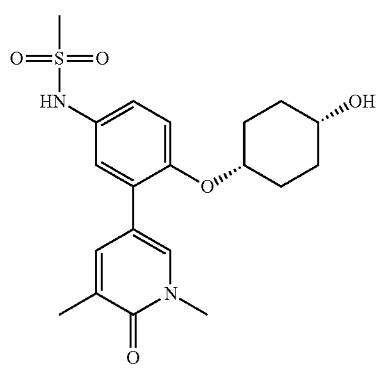 [SMILES: Cc1cc(-c2cc(NS(C)(=O)=O)ccc2O[C@H]2CC[C@@H](O)CC2)cn(C)c1=O] | N-[3-(1,5-dimethyl-6-oxopyridin-3-yl)-4-(4-cis-hydroxycyclohexyl)oxyphenyl]methanesulfonamide | 407.1 |

TABLE 21-continued

| Chemical Synthesis Example | Structure | Name | MS (M + H) |
|---|---|---|---|
| 435 | 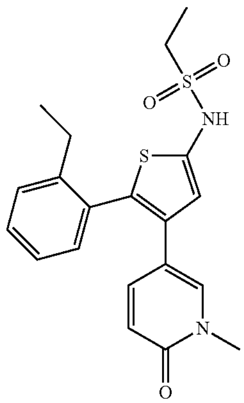 [SMILES: CCc1ccccc1-c1sc(NS(=O)(=O)CC)cc1-c1ccc(=O)n(C)c1] | N-[5-(2-ethylphenyl)-4-(1-methyl-6-oxopyridin-3-yl)thiophen-2-yl]ethanesulfonamide | 403.1 |
| 436 | 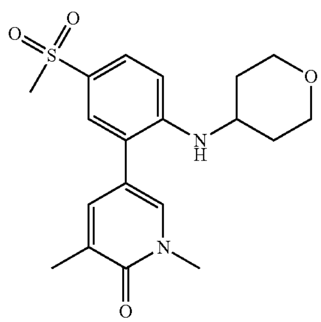 [SMILES: Cc1cc(-c2cc(S(C)(=O)=O)ccc2NC2CCOCC2)cn(C)c1=O] | 1,3-dimethyl-5-[5-methylsulfonyl-2-(oxan-4-ylamino)phenyl]pyridin-2-one | 377.1 |
| 437 | 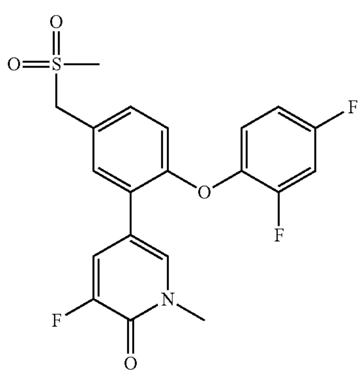 [SMILES: Cn1cc(-c2cc(CS(C)(=O)=O)ccc2Oc2ccc(F)cc2F)cc(F)c1=O] | 5-[2-(2,4-difluorophenoxy)-5-(methylsulfonylmethyl)phenyl]-3-fluoro-1-methylpyridin-2-one | 424.1 |
| 438 | 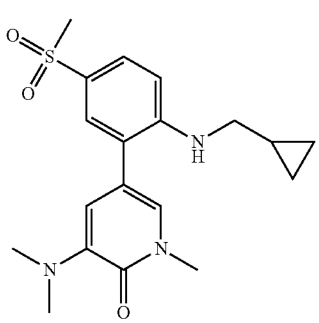 [SMILES: CN(C)c1cc(-c2cc(S(C)(=O)=O)ccc2NCC2CC2)cn(C)c1=O] | 5-[2-(cyclopropylmethylamino)-5-methylsulfonylphenyl]-3-(dimethylamino)-1-methylpyridin-2-one | 376.2 |

TABLE 21-continued

| Chemical Synthesis Example | Structure | Name | MS (M + H) |
|---|---|---|---|
| 439 | 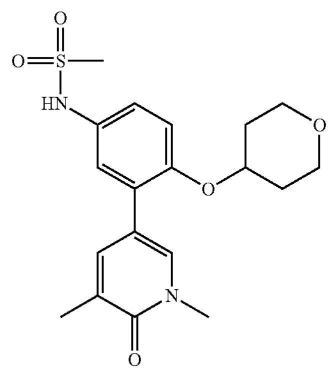 [SMILES: Cc1cc(-c2cc(NS(C)(=O)=O)ccc2OC2CCOCC2)cn(C)c1=O] | N-[3-(1,5-dimethyl-6-oxopyridin-3-yl)-4-(oxan-4-yloxy)phenyl]methanesulfonamide | 393.1 |
| 440 | 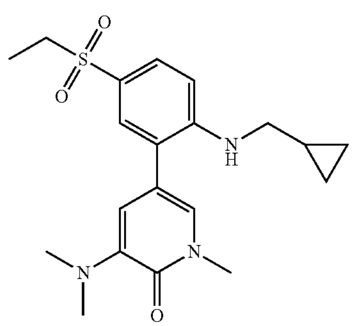 [SMILES: CCS(=O)(=O)c1ccc(NCC2CC2)c(-c2cc(N(C)C)c(=O)n(C)c2)c1] | 5-[2-(cyclopropylmethylamino)-5-ethylsulfonylphenyl]-3-(dimethylamino)-1-methylpyridin-2-one | 390.2 |
| 441 | 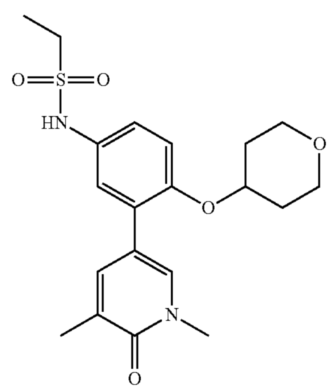 [SMILES: CCS(=O)(=O)Nc1ccc(OC2CCOCC2)c(-c2cc(C)c(=O)n(C)c2)c1] | N-[3-(1,5-dimethyl-6-oxopyridin-3-yl)-4-(oxan-4-yloxy)phenyl]ethanesulfonamide | 407.1 |
| 442 | 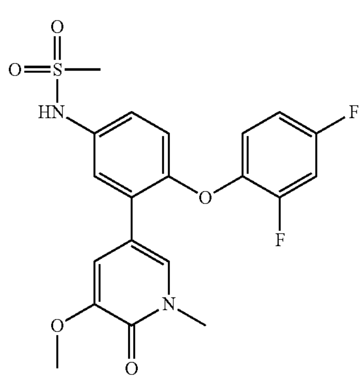 [SMILES: COc1cc(-c2cc(NS(C)(=O)=O)ccc2Oc2ccc(F)cc2F)cn(C)c1=O] | N-[4-(2,4-difluorophenoxy)-3-(5-methoxy-1-methyl-6-oxopyridin-3-yl)phenyl]methanesulfonamide | 437.1 |

TABLE 21-continued

| Chemical Synthesis Example | Structure | Name | MS (M + H) |
|---|---|---|---|
| 443 | 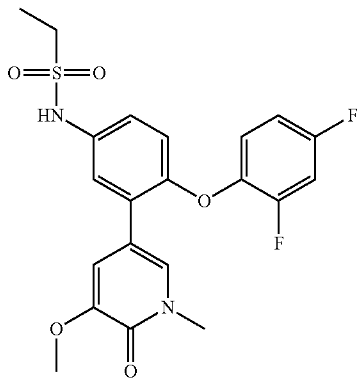 [SMILES: CCS(=O)(=O)Nc1ccc(Oc2ccc(F)cc2F)c(-c2cc(OC)c(=O)n(C)c2)c1] | N-[4-(2,4-difluorophenoxy)-3-(5-methoxy-1-methyl-6-oxopyridin-3-yl)phenyl]ethanesulfonamide | 451.1 |
| 444 | 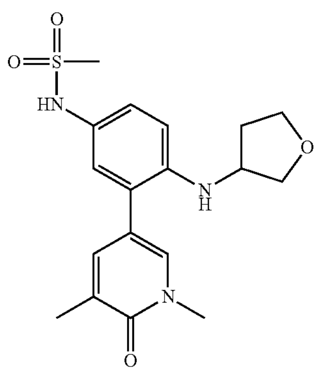 [SMILES: Cc1cc(-c2cc(NS(C)(=O)=O)ccc2NC2CCOC2)cn(C)c1=O] | N-[3-(1,5-dimethyl-6-oxopyridin-3-yl)-4-(oxolan-3-yloxy)phenyl]methanesulfonamide | 379.0 |
| 445 | 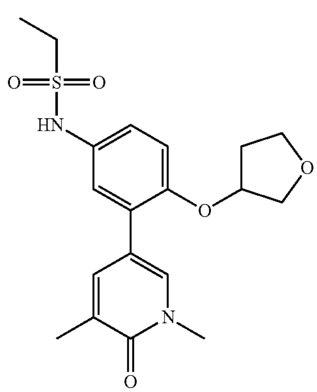 [SMILES: CCS(=O)(=O)Nc1ccc(OC2CCOC2)c(-c2cc(C)c(=O)n(C)c2)c1] | N-[3-(1,5-dimethyl-6-oxopyridin-3-yl)-4-(oxolan-3-yloxy)phenyl]ethanesulfonamide | 393.2 |
| 446 | 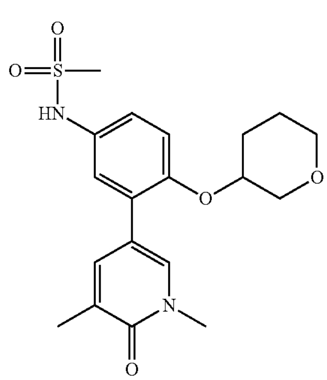 [SMILES: Cc1cc(-c2cc(NS(C)(=O)=O)ccc2OC2CCCOC2)cn(C)c1=O] | N-[3-(1,5-dimethyl-6-oxopyridin-3-yl)-4-(oxan-3-yloxy)phenyl]methanesulfonamide | 393.1 |

TABLE 21-continued

| Chemical Synthesis Example | Structure | Name | MS (M + H) |
|---|---|---|---|
| 447 | 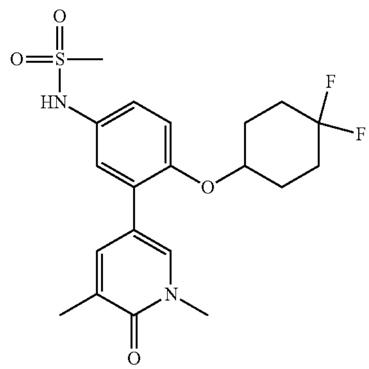 [SMILES: Cc1cc(-c2cc(NS(C)(=O)=O)ccc2OC2CCC(F)(F)CC2)cn(C)c1=O] | N-[4-(4,4-difluorocyclohexyl)oxy-3-(1,5-dimethyl-6-oxopyridin-3-yl)phenyl]methanesulfonamide | 427.1 |
| 448 | 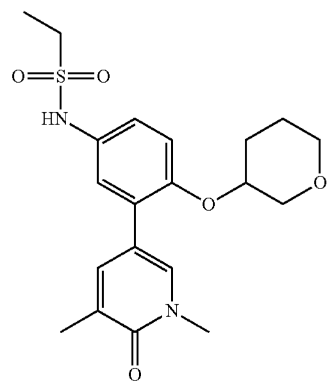 [SMILES: CCS(=O)(=O)Nc1ccc(OC2CCCOC2)c(-c2cc(C)c(=O)n(C)c2)c1] | N-[3-(1,5-dimethyl-6-oxopyridin-3-yl)-4-(oxan-3-yloxy)phenyl]ethanesulfonamide | 407.1 |
| 449 | 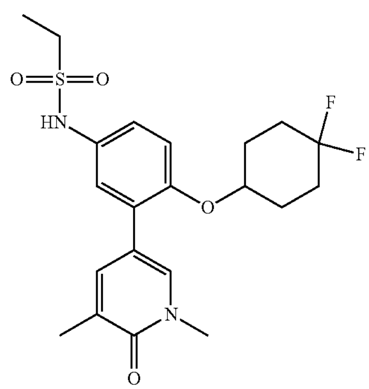 [SMILES: CCS(=O)(=O)Nc1ccc(OC2CCC(F)(F)CC2)c(-c2cc(C)c(=O)n(C)c2)c1] | N-[4-(4,4-difluorocyclohexyl)oxy-3-(1,5-dimethyl-6-oxopyridin-3-yl)phenyl]ethanesulfonamide | 441.1 |
| 450 | 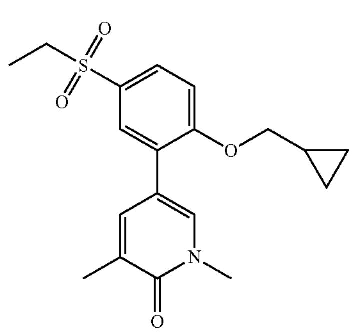 [SMILES: CCS(=O)(=O)c1ccc(OCC2CC2)c(-c2cc(C)c(=O)n(C)c2)c1] | 5-[2-(cyclopropylmethoxy)-5-ethylsulfonylphenyl]-1,3-dimethylpyridin-2-one | 362.1 |

TABLE 21-continued

| Chemical Synthesis Example | Structure | Name | MS (M + H) |
|---|---|---|---|
| 451 | 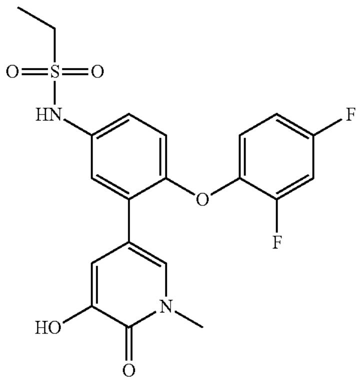 [SMILES: CCS(=O)(=O)Nc1ccc(Oc2ccc(F)cc2F)c(-c2cc(O)c(=O)n(C)c2)c1] | N-[4-(2,4-difluorophenoxy)-3-(5-hydroxy-1-methyl-6-oxopyridin-3-yl)phenyl]ethanesulfonamide | 437.0 |
| 452 | 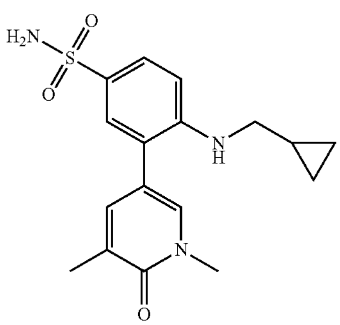 [SMILES: Cc1cc(-c2cc(S(N)(=O)=O)ccc2NCC2CC2)cn(C)c1=O] | 4-(cyclopropylmethylamino)-3-(1,5-dimethyl-6-oxopyridin-3-yl)benzenesulfonamide | 348.1 |
| 453 | 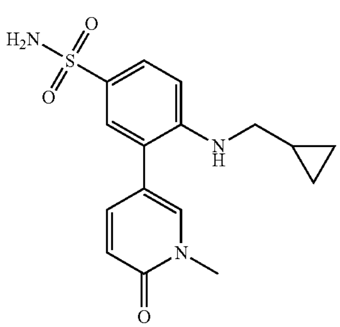 [SMILES: Cn1cc(-c2cc(S(N)(=O)=O)ccc2NCC2CC2)ccc1=O] | 4-(cyclopropylmethylamino)-3-(1-methyl-6-oxopyridin-3-yl)benzenesulfonamide | 334.1 |
| 454 | 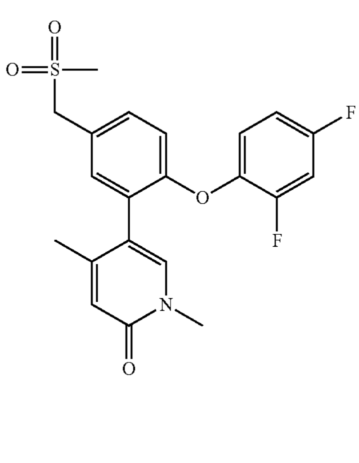 [SMILES: Cc1cc(=O)n(C)cc1-c1cc(CS(C)(=O)=O)ccc1Oc1ccc(F)cc1F] | 5-[2-(2,4-difluorophenoxy)-5-(methylsulfonylmethyl)phenyl]-1,4-dimethylpyridin-2-one | 420.0 |

TABLE 21-continued

| Chemical Synthesis Example | Structure | Name | MS (M + H) |
|---|---|---|---|
| 455 | 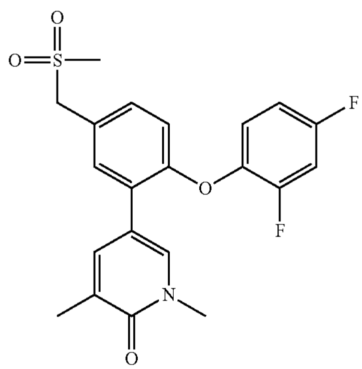 [SMILES: Cc1cc(-c2cc(CS(C)(=O)=O)ccc2Oc2ccc(F)cc2F)cn(C)c1=O] | 5-[2-(2,4-difluorophenoxy)-5-(methylsulfonylmethyl)phenyl]-1,3-dimethylpyridin-2-one | 420.1 |
| 456 | 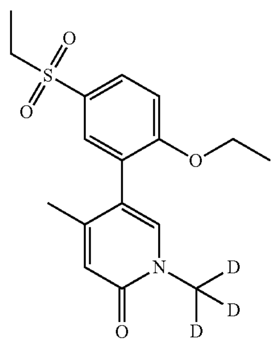 [SMILES: [2H]C([2H])([2H])n1cc(-c2cc(S(=O)(=O)CC)ccc2OCC)c(C)cc1=O] | 5-(2-ethoxy-5-ethylsulfonylphenyl)-1-($^2$H$_3$)methyl-4-methylpyridin-2-one | 339.0 |
| 457 | 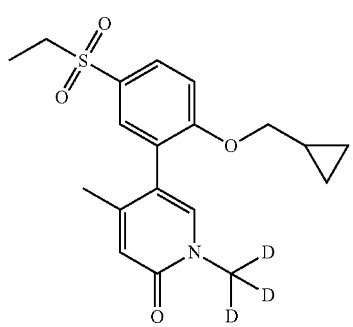 [SMILES: [2H]C([2H])([2H])n1cc(-c2cc(S(=O)(=O)CC)ccc2OCC2CC2)c(C)cc1=O] | 5-[2-(cyclopropylmethoxy)-5-ethylsulfonylphenyl]-1-($^2$H$_3$)methyl-4-methylpyridin-2-one | 365.0 |
| 458 | 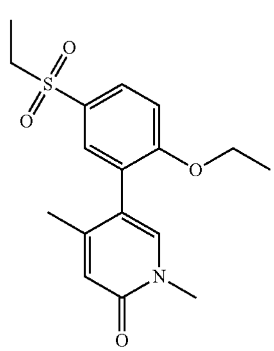 [SMILES: CCOc1ccc(S(=O)(=O)CC)cc1-c1cn(C)c(=O)cc1C] | 5-(2-ethoxy-5-ethylsulfonylphenyl)-1,4-dimethylpyridin-2-one | 336.1 |

TABLE 21-continued

| Chemical Synthesis Example | Structure | Name | MS (M + H) |
|---|---|---|---|
| 459 | 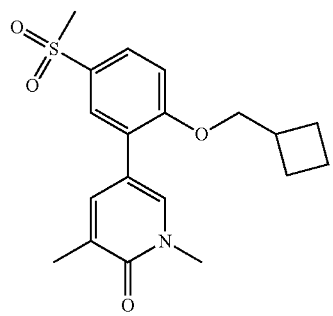 [SMILES: Cc1cc(-c2cc(S(C)(=O)=O)ccc2OCC2CCC2)cn(C)c1=O] | 5-[2-(cyclobutylmethoxy)-5-methylsulfonylphenyl]-1,3-dimethylpyridin-2-one | 362.1 |
| 460 | 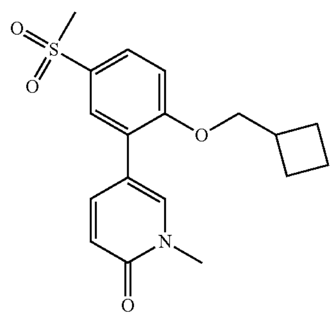 [SMILES: Cn1cc(-c2cc(S(C)(=O)=O)ccc2OCC2CCC2)ccc1=O] | 5-[2-(cyclobutylmethoxy)-5-methylsulfonylphenyl]-1-methylpyridin-2-one | 348.1 |
| 461 | 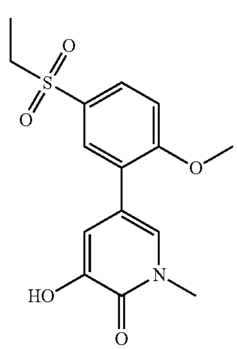 [SMILES: CCS(=O)(=O)c1ccc(OC)c(-c2cc(O)c(=O)n(C)c2)c1] | 5-(5-ethylsulfonyl-2-methoxyphenyl)-3-hydroxy-1-methylpyridin-2-one | 323.9 |
| 462 | 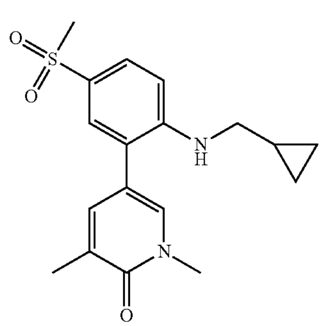 [SMILES: Cc1cc(-c2cc(S(C)(=O)=O)ccc2NCC2CC2)cn(C)c1=O] | 5-[2-(cyclopropylmethylamino)-5-methylsulfonylphenyl]-1,3-dimethylpyridin-2-one | 347.1 |

TABLE 21-continued

| Chemical Synthesis Example | Structure | Name | MS (M + H) |
|---|---|---|---|
| 463 | 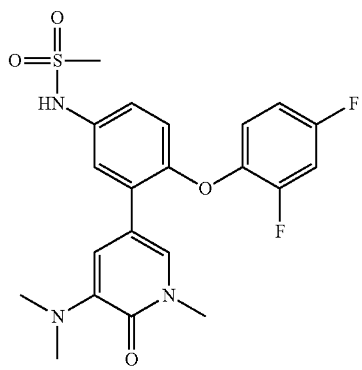 [SMILES: CN(C)c1cc(-c2cc(NS(C)(=O)=O)ccc2Oc2ccc(F)cc2F)cn(C)c1=O] | N-[4-(2,4-difluorophenoxy)-3-[5-(dimethylamino)-1-methyl-6-oxopyridin-3-yl]phenyl] methanesulfonamide | 450.1 |
| 464 | 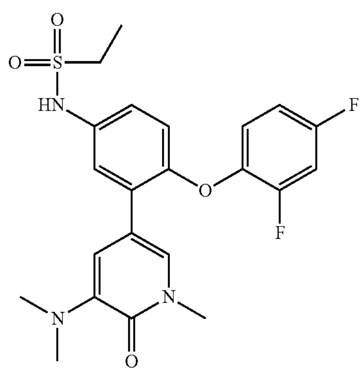 [SMILES: CCS(=O)(=O)Nc1ccc(Oc2ccc(F)cc2F)c(-c2cc(N(C)C)c(=O)n(C)c2)c1] | N-[4-(2,4-difluorophenoxy)-3-[5-(dimethylamino)-1-methyl-6-oxopyridin-3-yl]phenyl] ethanesulfonamide | 464.1 |
| 465 | 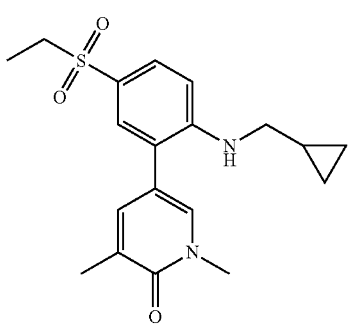 [SMILES: CCS(=O)(=O)c1ccc(NCC2CC2)c(-c2cc(C)c(=O)n(C)c2)c1] | 5-[2-(cyclopropylmethylamino)-5-ethylsulfonylphenyl]-1,3-dimethylpyridin-2-one | 361.1 |
| 466 | 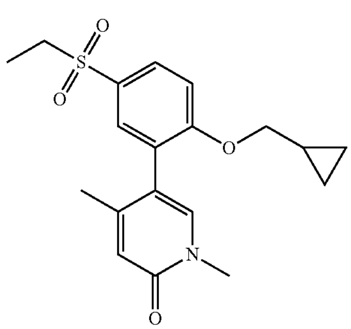 [SMILES: CCS(=O)(=O)c1ccc(OCC2CC2)c(-c2cn(C)c(=O)cc2C)c1] | 5-[2-(cyclopropylmethoxy)-5-ethylsulfonylphenyl]-1,4-dimethylpyridin-2-one | 362.1 |

TABLE 21-continued

| Chemical Synthesis Example | Structure | Name | MS (M + H) |
|---|---|---|---|
| 467 | 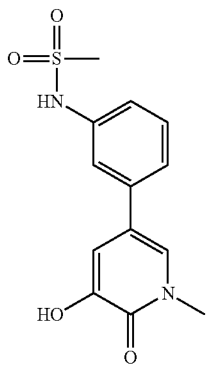 [SMILES: Cn1cc(-c2cccc(NS(C)(=O)=O)c2)cc(O)c1=O] | N-[3-(5-hydroxy-1-methyl-6-oxopyridin-3-yl)phenyl]methanesulfonamide | 295.0 |
| 468 | 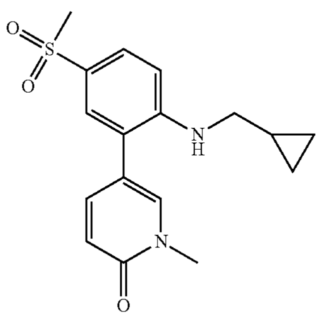 [SMILES: Cn1cc(-c2cc(S(C)(=O)=O)ccc2NCC2CC2)ccc1=O] | 5-[2-(cyclopropylmethylamino)-5-methylsulfonylphenyl]-1-methylpyridin-2-one | 333.1 |
| 469 | 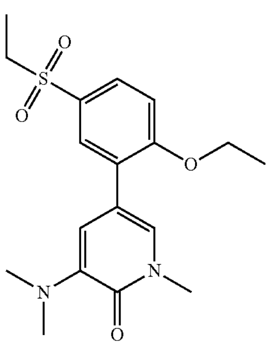 [SMILES: CCOc1ccc(S(=O)(=O)CC)cc1-c1cc(N(C)C)c(=O)n(C)c1] | 3-(dimethylamino)-5-(2-ethoxy-5-ethylsulfonylphenyl)-1-methyl-pyridin-2-one | 365.1 |
| 470 | 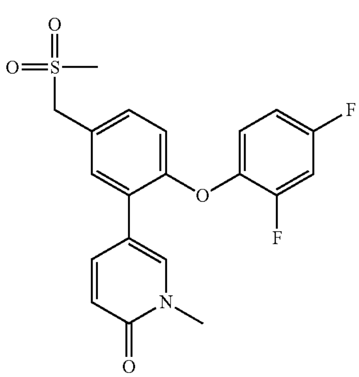 [SMILES: Cn1cc(-c2cc(CS(C)(=O)=O)ccc2Oc2ccc(F)cc2F)ccc1=O] | 5-[2-(2,4-difluorophenoxy)-5-(methylsulfonylmethyl)phenyl]-1-methylpyridin-2-one | 406.0 |

TABLE 21-continued

| Chemical Synthesis Example | Structure | Name | MS (M + H) |
|---|---|---|---|
| 471 | 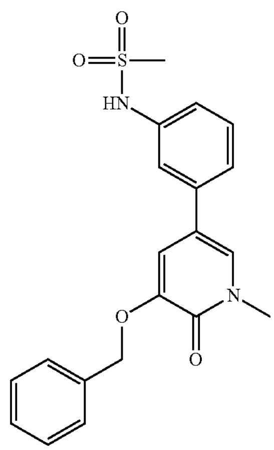 [SMILES: Cn1cc(-c2cccc(NS(C)(=O)=O)c2)cc(OCc2ccccc2)c1=O] | N-[3-(1-methyl-6-oxo-5-phenylmethoxypyridin-3-yl)phenyl]methanesulfonamide | 385.0 |
| 472 | 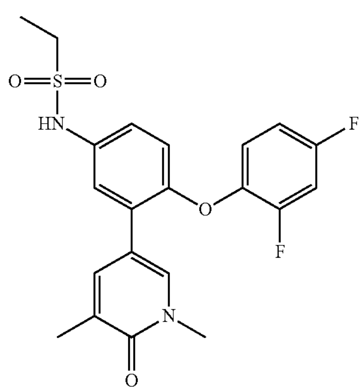 [SMILES: CCS(=O)(=O)Nc1ccc(Oc2ccc(F)cc2F)c(-c2cc(C)c(=O)n(C)c2)c1] | N-[4-(2,4-difluorophenoxy)-3-(1,5-dimethyl-6-oxopyridin-3-yl)phenyl]ethanesulfonamide | 435.1 |
| 473 | 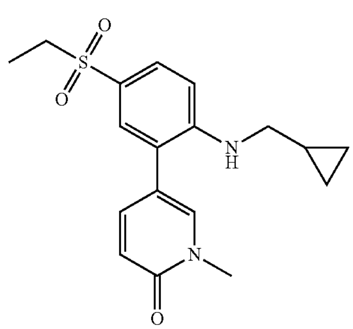 [SMILES: CCS(=O)(=O)c1ccc(NCC2CC2)c(-c2ccc(=O)n(C)c2)c1] | 5-[2-(cyclopropylmethylamino)-5-ethylsulfonylphenyl]-1-methylpyridin-2-one | 347.1 |
| 474 | 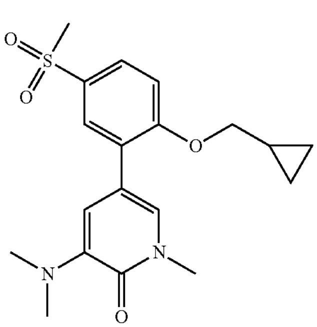 [SMILES: CN(C)c1cc(-c2cc(S(C)(=O)=O)ccc2OCC2CC2)cn(C)c1=O] | 5-[2-(cyclopropylmethoxy)-5-methylsulfonylphenyl]-3-(dimethylamino)-1-methylpyridin-2-one | 377.1 |

TABLE 21-continued

| Chemical Synthesis Example | Structure | Name | MS (M + H) |
|---|---|---|---|
| 475 | 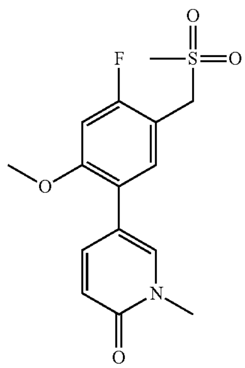 [SMILES: COc1cc(F)c(CS(C)(=O)=O)cc1-c1ccc(=O)n(C)c1] | 5-[4-fluoro-2-methoxy-5-(methylsulfonylmethyl)phenyl]-1-methylpyridin-2-one | 326.0 |
| 476 | 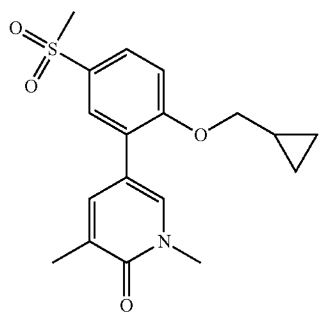 [SMILES: Cc1cc(-c2cc(S(C)(=O)=O)ccc2OCC2CC2)cn(C)c1=O] | 5-[2-(cyclopropylmethoxy)-5-methylsulfonylphenyl]-1,3-dimethylpyridin-2-one | 348.1 |
| 477 | 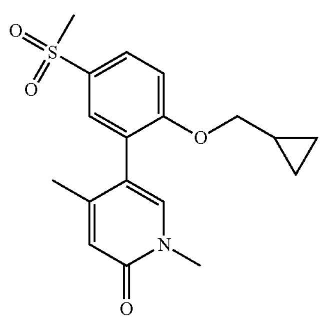 [SMILES: Cc1cc(=O)n(C)cc1-c1cc(S(C)(=O)=O)ccc1OCC1CC1] | 5-[2-(cyclopropylmethoxy)-5-methylsulfonylphenyl]-1,4-dimethylpyridin-2-one | 348.1 |
| 478 | 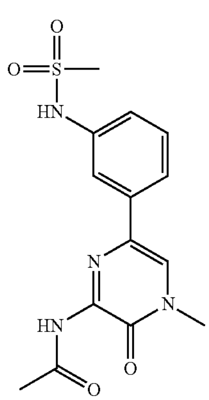 [SMILES: CC(=O)Nc1nc(-c2cccc(NS(C)(=O)=O)c2)cn(C)c1=O] | N-[6-[3-(methanesulfonamido)phenyl]-4-methyl-3-oxopyrazin-2-yl]acetamide | 337.0 |

TABLE 21-continued

| Chemical Synthesis Example | Structure | Name | MS (M + H) |
|---|---|---|---|
| 479 | 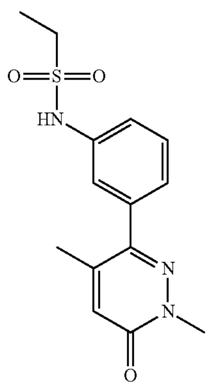 [SMILES: CCS(=O)(=O)Nc1cccc(-c2nn(C)c(=O)cc2C)c1] | N-[3-(1,4-dimethyl-6-oxopyridazin-3-yl)phenyl]ethanesulfonamide | 308.0 |
| 480 | 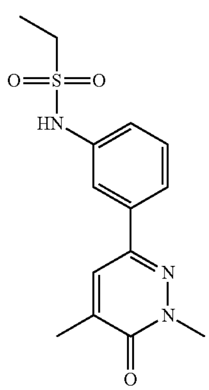 [SMILES: CCS(=O)(=O)Nc1cccc(-c2cc(C)c(=O)n(C)n2)c1] | N-[3-(1,5-dimethyl-6-oxopyridazin-3-yl)phenyl]ethanesulfonamide | 308.0 |
| 481 | 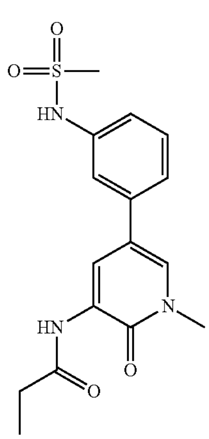 [SMILES: CCC(=O)Nc1cc(-c2cccc(NS(C)(=O)=O)c2)cn(C)c1=O] | N-[5-[3-(methanesulfonamido)phenyl]-1-methyl-2-oxopyridin-3-yl]propanamide | 350.0 |

TABLE 21-continued

| Chemical Synthesis Example | Structure | Name | MS (M + H) |
|---|---|---|---|
| 482 | 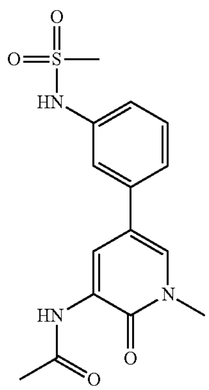 [SMILES: CC(=O)Nc1cc(-c2cccc(NS(C)(=O)=O)c2)cn(C)c1=O] | N-[5-[3-(methanesulfonamido)phenyl]-1-methyl-2-oxopyridin-3-yl]acetamide | 336.0 |

Example 483: 1-cyclobutyl-5-[2-(cyclopropyl-methoxy)-5-methylsulfonylphenyl]-3-methylpyridin-2-one Step 1: 1-cyclobutyl-3-methylpyridin-1-ium Chloride

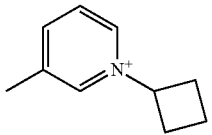

Cyclobutylamine (2.3 g, 32 mmol) was added to 1-(2,4-dinitrophenyl)-3-methyl-pyridinium chloride (J. Org. Chem. 1997, 62:729) (8.0 g, 31 mmol) in n-butanol (120 mL) at 20° C. and the deep red soln was refluxed overnight. Concentration under vacuum left a residue that was treated with $H_2O$ (20 mL) and the precipitate was removed by filtration, and the operation was repeated twice. The combined aq phase was basified with concentrated ammonia (2 mL) and washed twice with EtOAc. Evaporation of the $H_2O$ to gave the title compound (3.2 g, 70%) as a brown oil. LCMS: 148 $M^+$.

Step 2: 1-cyclobutyl-3-methylpyridin-2-one

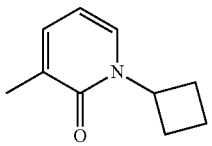

A stirred soln of the title compound from step 2 (2.8 g, 18.9 mmol) in $H_2O$ (30 mL) was cooled to 5° C. and $K_3Fe(CN)_6$ in $H_2O$ (30 mL) was added dropwise over 1 hr. Then KOH (16.7 g, 298.6 mmol) in $H_2O$ (5 mL) and toluene (30 mL) were added, and the mixture was heated at 40° C. for 30 min. The organic layer was separated, and the aq layer was extracted with DCM. The combined organic layers were washed with $H_2O$, brine and dried over $Na_2SO_4$, filtered and concentrated. Silica gel chromatography (DCM) gave the title compound (1.9 g, 62%) as a yellow oil. LCMS: 164 $(M+H)^+$.

Step 3: 5-bromo-1-cyclobutyl-3-methylpyridin-2-one

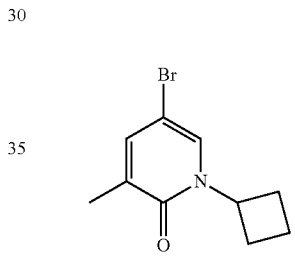

The title compound of step 3 (1.5 g, 9.2 mmol) in acetic acid (30 mL) was stirred at room temp for 10 min. Bromine (1.51 g, 9.5 mmol) was then added slowly, and after about 2 hr, the mixture was diluted with $H_2O$ and extracted with DCM. The organic soln was washed with $H_2O$, brine and dried over $Na_2SO_4$, filtered, concentrated and purified by silica gel chromatography (DCM) to give the title compound (2.0 g, 82%) as a yellow oil. LCMS: 242, 244 $(M+H)^+$.

Step 4: 1-cyclobutyl-5-[2-(cyclopropylmethoxy)-5-methylsulfonylphenyl]-3-methylpyridin-2-one

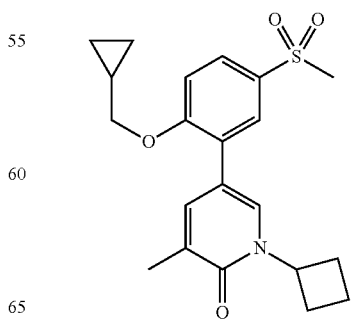

The title compound of step 4 (27 mg, 0.11 mmol), the title compound of Example 90, step 1 (46 mg, 0.13 mmol), $K_2CO_3$ (46 mg, 0.33 mmol) and $Pd(dppf)_2Cl_2$ (8 mg, 0.011 mmol) in DMF (2 mL) was $N_2$ purged and microwaved at 100° C. After 2 hr, the mixture was concentrated under vacuum and DCM was added, then washed with $H_2O$, brine and dried over $Na_2SO_4$. Purification by preparative TLC gave the title compound (25 mg, 58%) as a white solid. $^1H$ NMR ($CDCl_3$, 400 MHz): δ 7.85-7.81 (m, 2H), 7.79 (d, J=1.6 Hz, 1H), 7.47 (s, 1H), 7.02 (d, J=8.4 Hz, 1H), 5.27-5.23 (m, 1H), 3.94 (d, J=8.0 Hz, 2H), 3.07 (s, 3H), 2.57-2.50 (m, 2H), 2.32-2.24 (m, 2H), 2.21 (s, 3H), 1.93-1.84 (m, 2H), 1.31-1.25 (m, 1H), 0.70-0.65 (m, 2H), 0.40-0.36 (m, 2H). LCMS: 388 (M+H)$^+$.

Example 484: N-[3-(1-cyclobutyl-5-methyl-6-oxopyridin-3-yl)-4-(2,4-difluorophenoxy)phenyl]methanesulfonamide

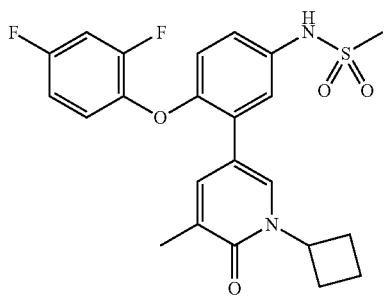 [SMILES: Cc1cc(-c2cc(NS(C)(=O)=O)ccc2Oc2ccc(F)cc2F)cn(C2CCC2)c1=O]

The title compound of Example 483, step 3 (27 mg, 0.11 mmol), N-[4-(2,4-difluoro-phenoxy)-3-(4,4,5,5-tetramethyl-1,3,2-dioxaborolan-2-yl)phenyl]methanesulfonamide (55 mg, 0.13 mmol), $K_2CO_3$ (46 mg, 0.33 mmol) and $Pd(dppf)_2Cl_2$ (8 mg, 0.011 mmol) in DMF (2 mL) were reacted and purified in a manner similar to Example 483, step 4 to give the title compound (16 mg, 32%) as a white solid. $^1H$ NMR ($CDCl_3$, 400 MHz): δ 7.65 (s, 1H), 7.42 (s, 1H), 7.26-7.27 (m, 1H), 7.13 (dd, J=8.8, 2.8 Hz, 1H), 6.97-6.89 (m, 2H), 6.83 (d, J=9.2 Hz, 2H), 6.54 (s, 1H), 5.09-5.18 (m, 1H), 3.04 (s, 3H), 2.53-2.46 (m, 2H), 2.23-2.18 (m, 2H), 2.16 (s, 3H), 1.87-1.81 (m, 2H). LCMS: 461 (M+H)$^+$.

Example 485: 1-benzyl-5-[2-(cyclopropylmethoxy)-5-methylsulfonylphenyl]-3-methylpyridin-2-one

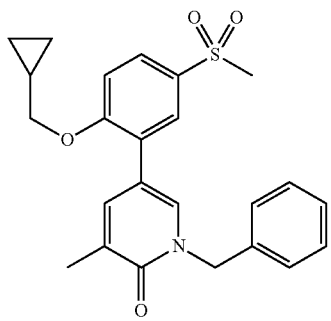 [SMILES: Cc1cc(-c2cc(S(C)(=O)=O)ccc2OCC2CC2)cn(Cc2ccccc2)c1=O]

The title compound was prepared in a manner similar to Example 483, steps 1-4 except that benzylamine was substituted for cyclobutylamine in step 1. $^1H$ NMR ($CDCl_3$, 400 MHz): δ 7.79 (s, 1H), 7.62 (d, J=2.8 Hz, 1H), 7.49-7.51 (m, 1H), 7.34-7.38 (m, 4H), 7.29-7.32 (m, 2H), 6.98 (d, J=8.8 Hz, 1H), 5.20 (s, 2H), 3.89-3.94 (m, 2H), 3.04 (s, 3H), 2.22 (s, 3H), 1.13-1.18 (m, 1H), 0.58-0.62 (m, 2H), 0.28-0.34 (m, 2H). LCMS: 424 (M+H)$^+$.

Example 486: 1,3-dimethyl-5-(2-methyl-5-methylsulfonyl-2,3-dihydro-1-benzofuran-7-yl)pyridine-2-one Step 1: 2-methyl-5-methylsulfonyl-2,3-dihydro-1-benzofuran

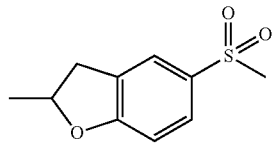

A mixture of 5-bromo-2-methyl-2,3-dihydro-1-benzofuran (1.0 g, 4.72 mmol), $CH_3SO_2Na$ (730 mg, 7.08 mmol), L-proline (110 mg, 0.94 mmol), $K_2CO_3$ (120 mg, 0.94 mmol) and CuI (89 mg, 0.47 mmol) in DMSO (10 mL) was irradiated at 140° C. for 2 hr under microwave. The mixture was extracted with EtOAc (2×30 mL). The combined organic layers were washed with brine (30 mL), dried over $Na_2SO_4$, filtered, and concentrated to give the crude product that was purified by CC on silica gel (PE:EA=2:1) to give the title compound (500 mg, 50%). $^1H$ NMR ($CDCl_3$, 400 MHz) δ 7.71-7.70 (m, 2H), 6.86-6.82 (m, 1H), 5.08-5.03 (m, 1H), 3.41-3.35 (m, 1H), 3.02 (s, 3H), 2.89-2.83 (m, 1H), 1.56 (d, J=6.4 Hz, 3H).

Step 2: 7-bromo-2-methyl-5-methylsulfonyl-2,3-dihydro-1-benzofuran

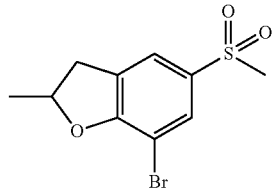

To a mixture of the title compound from Step 1 (300 mg, 1.42 mmol) in DCM (10 mL) was added Fe (159 mg, 2.84 mmol) and $Br_2$ (454 mg, 2.84 mmol) in one portion under $N_2$. The mixture was stirred at room temp for 6 hr. The rxn mixture was washed with satd aq $Na_2SO_3$ (200 mL) and extracted with DCM (30 mL×2). The combined organic layers were washed with brine (20 mL×2), dried with anhydrous $Na_2SO_4$, filtered, and concentrated under reduced pressure. The residue was purified by CC (PE:EA=3:1) to give the title compound (300 mg, 73%) as a yellow solid. $^1H$ NMR ($CDCl_3$, 400 MHz): δ 7.90 (d, J=1.6 Hz, 1H), 7.64 (d, J=1.6 Hz, 1H), 5.20-5.14 (m, 1H), 3.53-3.47 (m, 1H), 3.01-2.95 (m, 1H), 3.04 (s, 3H), 1.56 (d, J=6.4 Hz, 3H). LCMS: 291.0 (M+1)$^+$; 293.0.

Step 3: 1,3-dimethyl-5-(2-methyl-5-methylsulfonyl-2,3-dihydro-1-benzofuran-7-yl)pyridin-2-one

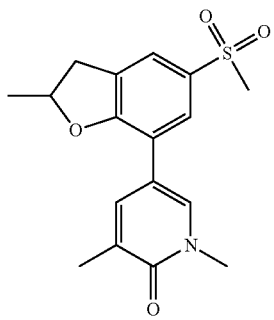 [SMILES: Cc1cc(-c2cc(S(C)(=O)=O)cc3c2OC(C)C3)cn(C)c1=O]

A soln of the title compound in Step 2 (300 mg, 1.03 mmol), 1,3-dimethyl-5-(4,4,5,5-tetramethyl-1,3,2-dioxaborolan-2-yl)pyridin-2-one (309 mg, 1.24 mmol), Pd(dppf)Cl$_2$ (76 mg, 0.103 mmol), Na$_2$CO$_3$ (328 mg, 3.09 mmol) in dioxane (8 mL) and H$_2$O (1 mL) was stirred at 80° C. under N$_2$ for 16 hr. The solvent was removed under reduced pressure to give a residue that was purified by CC (PE:EA=1:2) to give the title compound (60.0 mg, 18%) as a yellow solid. $^1$H NMR (DMSO-d6, 400 MHz): δ 8.02 (s, 1H), 7.76 (s, 1H), 7.74 (s, 1H), 7.66 (s, 1H), 5.15-5.13 (m, 1H), 3.51 (s, 3H), 3.49-3.42 (m, 1H), 3.19 (s, 3H), 2.94-2.88 (m, 1H), 2.07 (s, 3H), 1.44 (d, J=5.2 Hz, 3H). LCMS: 334.1 (M+1)$^+$.

Example 487: 4-[5-(ethylsulfonylmethyl)-2-(2,2,2-trifluoroethoxy)phenyl]-2-methylisoquinolin-1-one

Step 1: Methyl 3-bromo-4-(2,2,2-trifluoroethoxy)benzoate

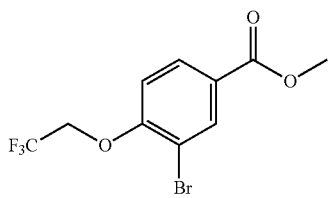 [SMILES: COC(=O)c1ccc(OCC(F)(F)F)c(Br)c1]

To a soln of methyl 3-bromo-4-fluorobenzoate (100 mg, 0.43 mmol) in DMF was added 2,2,2-trifluoroethanol (52 mg, 0.52 mmol), K$_2$CO$_3$ (119 mg, 0.86 mmol), and the mixture was stirred at 60° C. for 2 hr. The mixture was cooled and H$_2$O (50 mL) was added. The aq layer was extracted with EtOAc (30 mL×3). The combined organic layers were washed with H$_2$O (30 mL×3), brine (30 mL), dried over anhydrous Na$_2$SO$_4$, filtered, concentrated, and purified by chromatog. (PE:EA=20:1) to afford compound 3 (95 mg, 88%) as a white solid. $^1$H NMR (CDCl$_3$, 400 MHz) δ 8.29 (d, J=2.0 Hz, 1H), 8.00 (dd, J$_1$=8.4 Hz, J$_2$=2.0 Hz, 1H), 6.93 (d, J=8.4 Hz, 1H), 4.48 (q, J=8.0 Hz, 2H), 3.92 (s, 3H). LCMS: 313.0 (M+1)$^+$.

Step 2: [3-bromo-4-(2,2,2-trifluoroethoxy)phenyl]methanol

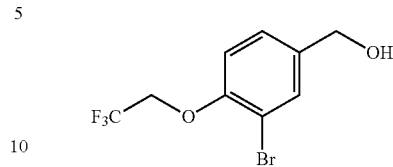

To soln of the title compound from Step 1 (2.00 g, 5.85 mmol) in THF (20.0 mL) was added LiAlH$_4$ (0.18 g, 4.68 mmol) in several portions at −40° C. The mixture was kept at −40° C. and stirred for 45 min. The rxn was quenched with H$_2$O (0.2 mL), 15% NaOH aq (0.2 mL) and additional H$_2$O (0.6 mL), and the mixture stirred at room temp for 15 min, then dried over Na$_2$SO$_4$, and filtered. The filtrate was concentrated and the residue purified by silica gel chromatography (PE:EA=5:1 to 3:1) to give the title compound (1.62 g, 89%) as a white solid. $^1$H NMR (DMSO-d$_6$, 400 MHz): δ 7.55 (d, J=2.0 Hz, 1H), 7.31-7.28 (m, 1H), 7.19 (d, J=8.4 Hz, 1H), 4.83 (q, J=8.8 Hz, 2H), 4.44 (s, 2H).

Step 3: 2-bromo-4-(chloromethyl)-1-(2,2,2-trifluoroethoxy)benzene

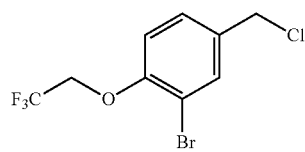 [SMILES: FC(F)(F)COc1ccc(CCl)cc1Br]

A soln of the title compound from Step 2 (300 mg, 1.05 mmol) in DCM (10 mL) was cooled to 0° C. and treated with triethylamine (91 mg, 1.15 mmol) and methanesulfonyl chloride (142 mg, 1.25 mmol). The rxn mixture was warmed to room temp and stirred overnight. It was then diluted with DCM (10 mL) and washed with 1M HCl (10 mL) and sat. NaHCO$_3$ (10 mL). The organic phase was dried over Na$_2$SO$_4$, filtered and conc under reduced press. The crude residue was purified by silica gel chromatography to afford the title compound (260 mg, 82%) as a white solid. $^1$H NMR (CDCl3, 400 MHz): δ 7.63 (d, J=2.0 Hz, 1H), 7.32 (dd, J$_1$=8.4 Hz, J$_2$=2.0 Hz, 1H), 6.92 (d, J=8.4 Hz, 1H), 4.53 (s, 2H), 4.42 (q, J=8.0 Hz, 2H).

Step 4: 2-bromo-4-(ethylsulfanylmethyl)-1-(2,2,2-trifluoroethoxy)benzene

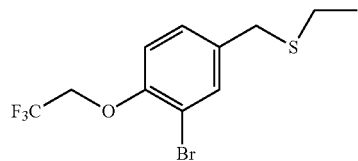 [SMILES: CCSCc1ccc(OCC(F)(F)F)c(Br)c1]

To a soln of the title compound from Step 3 (2.00 g, 6.59 mmol) in DCM (200 mL) was added TEA (1 g, 9.89 mmol), NaI (898 mg, 5.99 mmol) and EtSH (613 mg, 9.89 mmol). The mixture was stirred at 30° C. for 4 hr. The rxn was poured into H₂O (10 mL) and extracted with EtOAc (10 mL×3). The combined organic layers were washed with brine (30 mL), dried over anhydr. Na₂SO₄ and filtered. Solvents were removed under reduced pressure and the residue was purified by chromatography (PE:EA=1:0 to 3:1) to give the title compound (2.1 g, 96.8%) as a white solid. ¹H NMR (CDCl₃, 400 MHz): δ 7.55 (d, J=2.0 Hz, 1H), 7.24 (dd, J₁=8.4 Hz, J₂=2.0 Hz, 1H), 6.89 (d, J=8.4 Hz, 1H), 4.42 (q, J=8.0 Hz, 2H), 3.66 (s, 2H), 2.47-2.41 (m, 2H), 1.26-1.22 (m, 3H).

Step 5: 2-bromo-4-(ethylsulfonylmethyl)-1-(2,2,2-trifluoroethoxy)benzene

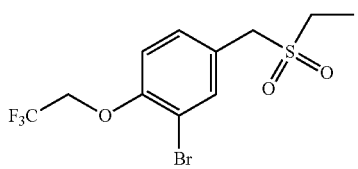 [SMILES: CCS(=O)(=O)Cc1ccc(OCC(F)(F)F)c(Br)c1]

To a soln of the title compound from Step 4 (2.10 g, 6.38 mmol) in DCM (210 mL) was added MCPBA (4.41 g, 25.53 mmol) in several portions. The mixture was stirred at 25° C. for 12 hr. The rxn was poured into sat. aq Na₂SO₃ (100 mL) and extracted with DCM (80 mL×3). The combined organic layers were washed with sat. NaHCO₃ (100 mL×2) and brine (100 mL), dried over anhydrous Na₂SO₄, filtered and concentrated under reduced pressure. The residue was purified by silica gel chromatography (PE:EA=1:0-2:1) to give the title compound (2.10 g, 91%) as a white solid. ¹H NMR (CDCl3, 400 MHz) δ 7.64 (d, J=2.0 Hz, 1H), 7.37 (dd, J₁=8.4 Hz, J₂=2.4 Hz, 1H), 6.95 (d, J=8.4 Hz, 1H), 4.43 (q, J=8.0 Hz, 2H), 4.15 (s, 2H), 2.91 (q, J=7.6 Hz, 2H), 1.39 (t, J=7.6 Hz, 3H).

Step 6: 4-[5-(ethylsulfonylmethyl)-2-(2,2,2-trifluoroethoxy)phenyl]-2-methylisoquinolin-1-one

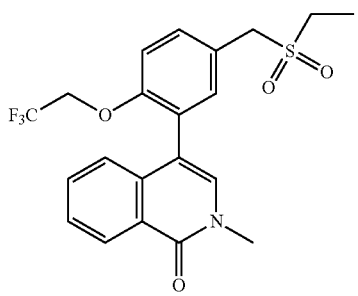 [SMILES: CCS(=O)(=O)Cc1ccc(OCC(F)(F)F)c(-c2cn(C)c(=O)c3ccccc23)c1]

The title compound from Step 5 (200 mg, 0.58 mmol), 2-methyl-4-(4,4,5,5-tetramethyl-1,3,2-dioxaborolan-2-yl)isoquinolin-1-one (197 mg, 0.69 mmol), Pd(PPh₃)₄ (67 mg, 58.0 umol) and Na₂CO₃ (184 mg, 1.74 mmol) in dioxane (6 mL) and H₂O (6 drops) was degassed and then heated to 70° C. for 18 hr under N₂. The rxn mixture was concentrated under reduced pressure and the residue was purified by CC (PE:EA=5:1 to 1:1) followed by prep-HPLC purification to afford the title compound (164.44 mg, 67%) as an off-white solid. ¹H NMR (CDCl₃, 400 MHz): δ 8.52 (d, J=8.0 Hz, 1H), 7.58-7.48 (m, 3H), 7.40 (d, J=2.4 Hz, 1H), 7.22 (d, J=8.0, 1H), 7.07 (t, J=8.0, 2H), 4.30 (q, J=8.0 Hz, 2H), 4.23 (s, 2H), 3.67 (s, 3H), 2.98 (q, J=7.6 Hz, 2H), 1.43 (t, J=7.6 Hz, 3H). LCMS: 440.0 (M+1)⁺.

Example 488: 2-methyl-4-[5-(methylsulfonylmethyl)-2-(2,2,2-trifluoroethoxy)phenyl]isoquinolin-1-one Step 1: 2-bromo-4-(methylsulfanylmethyl)-1-(2,2,2-trifluoroethoxy)benzene

The title compound was prepared in a manner similar to Example 487 Step 4, by substituting methanethiol for ethanethiol. ¹H NMR (CDCl3, 400 MHz): δ 7.56 (d, J=2.0 Hz, 1H), 7.25 (dd, J₁=8.4 Hz, J₂=2.0 Hz, 1H), 6.93-6.90 (m, 1H), 4.44-4.35 (m, 2H), 3.63 (s, 2H), 2.02 (s, 3H).

Step 2: 2-bromo-4-(methylsulfonylmethyl)-1-(2,2,2-trifluoroethoxy)benzene

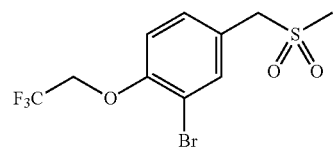 [SMILES: CS(=O)(=O)Cc1ccc(OCC(F)(F)F)c(Br)c1]

The title compound was prepared in a manner similar to Example 487 Step 5, by substituting 2-bromo-4-(methylsulfanylmethyl)-1-(2,2,2-trifluoroethoxy)benzene for 2-bromo-4-(ethylsulfanylmethyl)-1-(2,2,2-trifluoroethoxy)benzene. ¹H NMR (CDCl3, 400 MHz): δ 7.65 (d, J=2.0 Hz, 1H), 7.38 (dd, J₁=8.4 Hz, J₂=2.4 Hz, 1H), 7.12-7.06 (m, 1H), 4.43 (q, J=8.0 Hz, 2H), 4.19 (s, 2H), 2.82 (s, 3H).

Step 3: 2-methyl-4-[5-(methylsulfonylmethyl)-2-(2,2,2-trifluoroethoxy)phenyl]isoquinolin-1-one

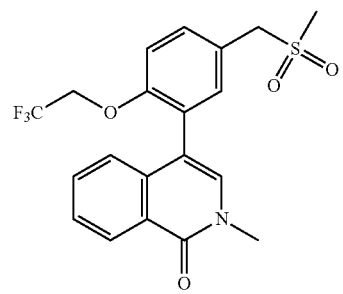 [SMILES: Cn1cc(-c2cc(CS(C)(=O)=O)ccc2OCC(F)(F)F)c2ccccc2c1=O]

The title compound was prepared in a manner similar to Example 487 Step 6, by substituting 2-bromo-4-(methylsulfonylmethyl)-1-(2,2,2-trifluoroethoxy)benzene for 2-bromo-4-(ethylsulfonylmethyl)-1-(2,2,2-trifluoroethoxy)benzene.

¹H NMR (CDCl₃, 400 MHz): δ 8.52 (d, J=8.0 Hz, 1H), 7.60-7.49 (m, 3H), 7.41 (d, J=2.0 Hz, 1H), 7.22 (d, J=8.0, 1H), 7.08-7.06 (m, 2H), 4.33-4.27 (m, 4H), 3.67 (s, 3H), 2.87 (s, 3H). LCMS: 426.0 (M+1)⁺.

Example 489: 1,3-dimethyl-5-(7-methylsulfonyl-2,3-dihydro-1,4-benzodioxin-5-yl)pyridin-2-one Step 1: 3,4-dihydro-2H-chromen-2-ylmethanol

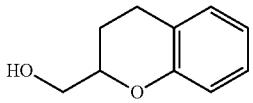

A mixture of 4-oxochromene-2-carboxylic acid (20.0 g, 105 mmol) and Pd/C (3.0 g, 10% (w/w)) in AcOH (200 mL) was placed in Parr hydrogenation apparatus under H₂ (50 psi) and stirred for 25 hr at room temp. It was then filtered and concentrated. The residue was suspended in H₂O (300 mL), stirred for 10 min, filtered and dried to give 3,4-dihydro-2H-chromene-2-carboxylic acid (13.5 g, 72%) as a white solid. BH₃ (57 mL, 114 mmol, 2.0 M in THF) was added slowly to a soln of this carboxylic acid in THF (120 mL) at 0° C. The rxn mixture was then warmed to room temp and stirred for 5 hr at this temp. THF:H₂O (30 mL, 1:1) was added drop-wise while keeping the temp between 0-5° C. and stirred for 20 min. K₂CO₃ (26.0 g, 189 mmol) was added and the rxn was vigorously stirred for 30 min. The THF layer was separated and concentrated to give the title compound (11.0 g, 89%) as a brown oil. ¹H NMR (400 MHz, CDCl₃): δ 7.10-7.03 (m, 2H), 6.86-6.81 (m, 2H), 4.14-4.08 (m, 1H), 3.85-3.68 (m, 2H), 2.92-2.84 (m, 1H), 2.80-2.73 (m, 1H), 1.98-1.92 (m, 1H), 1.90-1.79 (m, 1H). LCMS: 165 (M+1)⁺.

Step 2: 3,4-dihydro-2H-chromen-2-ylmethyl trifluoromethanesulfonate

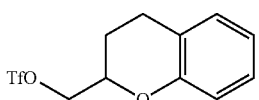

Trifluoromethanesulfonic anhydride (19.6 g, 69.5 mmol) in DCM (15 mL) was added to a soln of the title compound from Step 1 (9.50 g, 57.9 mmol) in DCM (100 mL) and pyridine (11.0 g, 139 mmol) cooled to -5° C. The rxn was then stirred at 0° C. for 1 hr. H₂O (150 mL) was added and the rxn was extracted with DCM (150 mL). The organic layer was washed with 1M HCl (180 mL), H₂O (100 mL), and NaHCO₃ (100 mL aq). The organic phase was dried over Na₂SO₄, filtered and concentrated to give the title compound (13.5 g, 79%) as a pale-brown oil. ¹H NMR (400 MHz, CDCl₃): δ 7.12-7.04 (m, 2H), 6.90-6.83 (m, 2H), 4.66-4.61 (m, 2H), 4.36-4.31 (m, 1H), 2.96-2.79 (m, 2H), 2.09-2.03 (m, 1H), 1.95-1.84 (m, 1H). LCMS: 314 (M+NH₄)⁺.

Step 3: 2-ethyl-3,4-dihydro-2H-chromene

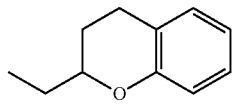

MeMgBr (45.6 mL, 137 mmol, 3M in ether) was added to a mixture of the title compound from Step 2 (13.5 g, 45.6 mmol) and CuBr-Me₂S (1.61 g, 7.74 mmol) in THF (150 mL) at -5° C. The rxn was stirred at room temp for 2 hr. It was then poured onto a soln of NH₄Cl (55 g, 1.04 mol) in H₂O (200 mL) and extracted with DCM (3×150 mL). The organic layer was dried over Na₂SO₄, filtered and concentrated under reduced pressure to give the title compound (6.66 g, 90%) as a brown oil. ¹H NMR (400 MHz, CDCl₃): δ 7.09-7.02 (m, 2H), 6.82-6.78 (m, 2H), 3.93-3.87 (m, 1H), 2.84-2.72 (m, 2H), 2.02-1.96 (m, 1H), 1.81-1.61 (m, 3H), 1.04 (t, J=7.2 Hz, 3H).

Step 4: 2-ethyl-6-nitro-3,4-dihydro-2H-chromene and 2-ethyl-8-nitro-3,4-dihydro-2H-chromene

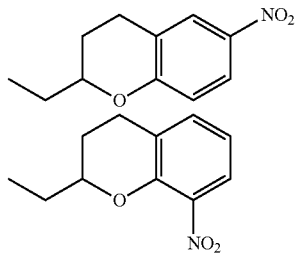

The title compound from Step 3 (1.0 g, 6.17 mmol) was added to HNO₃ (5 mL, 65-68%) at 0° C., warmed to room temp and stirred for 1 hr. It was then poured onto an ice-water mixture, extracted with EtOAc (50 mL), dried over Na₂SO₄ and concentrated under reduced pressure. The residue was purified by silica gel CC (PE:EA 100:1 to 50:1) to give a mixture of the title compounds (600 mg) which was used in the next step.

Step 5: N-(2-ethyl-3,4-dihydro-2H-chromen-6-yl)methanesulfonamide

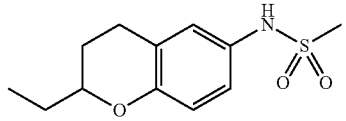 [SMILES: CCC1CCc2cc(NS(C)(=O)=O)ccc2O1]

The mixture of the title compounds from Step 4 (600 mg) was suspended in MeOH (6 mL) and sat. NH₄Cl soln (2 mL). Fe (810 mg, 14.5 mmol) was added and the mixture heated to 85° C. for 2.5 hr. It was then filtered and extracted with EtOAc. The organic layer was dried and conc under reduced press. to give a crude mixture of 2-ethyl-3,4-dihydro-2H-chromen-6-amine and 2-ethyl-3,4-dihydro-2H-chromen-8-amine. This mixture was dissolved in DCM (10 mL), then TEA (0.8 mL) and methanesulfonyl chloride (400 mg, 3.50 mmol) added; this was stirred at room temp for 1 hr; then extracted with DCM (45 mL×2), dried over Na₂SO₄, filtered, concentrated under reduced pressure, and purified by CC (PE:EA=50:1 to 20:1 to 10:1) to give the title compound (190 mg, 12% for three steps) as a yellow solid. ¹H NMR (300 MHz, CDCl₃): δ 6.99-6.80 (m, 2H), 6.78 (d, J=8.7 Hz, 1H), 6.16 (s, 1H), 3.95-3.90 (m, 1H), 2.96 (s, 3H), 2.83-2.76 (m, 2H), 2.04-1.97 (m, 1H), 1.81-1.64 (m, 3H), 1.05 (t, J=7.2 Hz, 3H). LCMS: 273 (M+NH₄)⁺.

Step 6: N-(8-bromo-2-ethyl-3,4-dihydro-2H-chromen-6-yl)methanesulfonamide

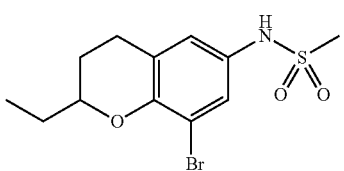 [SMILES: CCC1CCc2cc(NS(C)(=O)=O)cc(Br)c2O1]

To a soln of the title compound from Step 5 (170 mg, 0.667 mmol) in ACN (6 mL) was added NBS (156 mg, 0.867 mmol). The mixture was stirred for 7 hr at room temp; then extracted with DCM, dried over Na₂SO₄, filtered, and conc under reduced press. The residue was purified with prep-TLC (PE:EA 3:1) to give the title compound (105 mg, 47%) as a gray solid. ¹H NMR (400 MHz, CDCl₃): δ 7.23 (d, J=2.4 Hz, 1H), 6.96 (d, J=2.4 Hz, 1H), 6.24 (s, 1H), 4.01-3.99 (m, 1H), 2.97 (s, 3H), 2.84-2.77 (m, 2H), 2.04-1.99 (m, 1H), 1.85-1.66 (m, 3H), 1.09 (t, J=7.2 Hz, 3H).

Step 7: N-[2-ethyl-8-(2-methyl-1-oxoisoquinolin-4-yl)-3,4-dihydro-2H-chromen-6-yl]methanesulfonamide

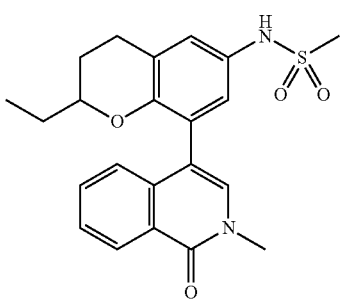 [SMILES: CCC1CCc2cc(NS(C)(=O)=O)cc(-c3cn(C)c(=O)c4ccccc34)c2O1]

A mixture of the title compound from Step 6 (105 mg, 0.315 mmol), 2-methyl-4-(4,4,5,5-tetramethyl-1,3,2-dioxaborolan-2-yl)isoquinolin-1-one (108 mg, 0.379 mmol), K₂CO₃ (131 mg, 0.949 mmol) and Pd(dppf)Cl₂ (23.1 mg, 0.032 mmol) in dioxane/H₂O (10 mL/3 mL) was heated to 85° C. for 2 hr, then filtered and extracted with EtOAc. The organic layer was conc under reduced press. The residue was purified by CC (PE:EA 50:1 to 20:1 to 10:1) to give the title compound (25 mg, 19%). ¹H NMR (400 MHz, CD₃OD): δ 8.31 (d, J=8.4 Hz, 1H), 7.59-7.55 (m, 1H), 7.47-7.43 (m, 1H), 7.31-7.23 (m, 2H), 7.05 (s, 1H), 6.95 (d, J=2.8 Hz, 1H), 3.77-3.71 (m, 1H), 3.60 (s, 3H), 2.95-2.75 (m, 5H), 1.95-1.92 (m, 1H), 1.66-1.54 (m, 1H), 1.38-1.22 (m, 2H), 0.59-0.55 (m, 1.25H), 0.42-0.38 (m, 1.75H). LCMS: 413.0 (M+1)⁺.

Example 491: N-[2-ethyl-8-(2-methyl-1-oxoisoquinolin-4-yl)-3,4-dihydro-2H-chromen-6-yl]ethanesulfonamide

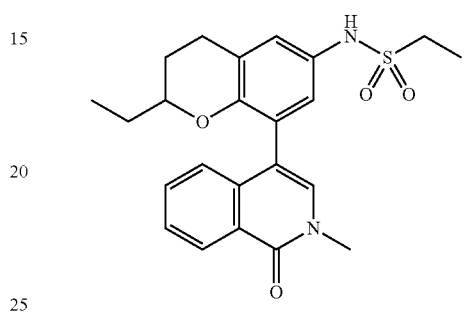

The title compound was prepared in a manner similar to Example 490 by substituting ethanesulfonyl chloride for methanesulfonyl chloride in Step 5. ¹H NMR (400 MHz, CD₃OD): δ 8.39 (d, J=7.6 Hz, 1H), 7.67-7.63 (m, 1H), 7.56-7.52 (m, 1H), 7.37-7.30 (m, 2H), 7.12 (s, 1H), 7.03 (d, J=2.8 Hz, 1H), 3.86-3.81 (m, 1H), 3.69 (s, 3H), 3.10 (q, J=7.2 Hz, 2H), 3.02-2.81 (m, 2H), 2.03-1.99 (m, 1H), 1.75-1.41 (m, 3H), 1.36 (t, J=7.6 Hz, 3H), 0.67-0.62 (m, 1.25H), 0.51-0.48 (m, 1.75H). LCMS: 427.0 (M+1)⁺.

Example 492: N-[8-(1,5-dimethyl-6-oxopyridin-3-yl)-2-ethyl-3,4-dihydro-2H-chromen-6-yl]ethanesulfonamide

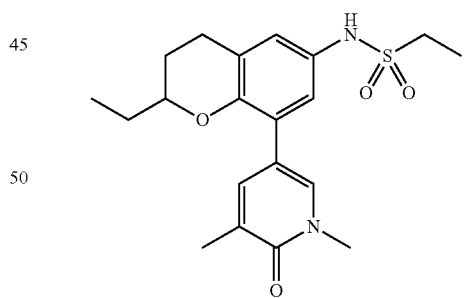

The title compound was prepared in a manner similar to Example 491 by substituting 1,3-dimethyl-5-(4,4,5,5-tetramethyl-1,3,2-dioxaborolan-2-yl)pyridin-2-one for 2-methyl-4-(4,4,5,5-tetramethyl-1,3,2-dioxaborolan-2-yl)isoquinolin-1-one. ¹H NMR (400 MHz, CD₃OD): δ 7.69 (s, 1H), 7.66 (s, 1H), 7.02 (m, 1H), 7.0 (s, 1H), 3.96-3.93 (m, 1H), 3.65 (s, 3H), 3.07 (q, J=7.5 Hz, 2H), 2.93-2.82 (m, 2H), 2.18 (s, 3H), 2.08-2.04 (m, 1H), 1.72-1.66 (m, 3H), 1.34 (t, J=7.6 Hz, 3H), 1.04 (t, J=7.2 Hz, 3H). LCMS: 391.0 (M+1)⁺.

Example 493: 4-(2-cyclopropyl-5-methylsulfonyl-2,3-dihydro-1-benzofuran-7-yl)-2-methylisoquinolin-1-one Step 1: 7-bromo-2-cyclopropyl-5-methylsulfonyl-1-benzofuran

To a soln of 2,6-dibromo-4-methylsulfonylphenol (1 g, 3.30 mmol) in pyridine (40 mL) was added ethynylcyclopropane (240 mg, 3.64 mmol) and Cu$_2$O (260 mg, 1.82 mmol). The rxn mixture was degassed with N$_2$. The mixture was heated to 130° C. for 3 hr. It was then concentrated and purified by CC (PE to PE/EA=3/1) to give the title product (510 mg, 53%) as a gray solid. $^1$H NMR (CDCl$_3$, 400 MHz) δ 7.99 (s, 1H), 7.93 (s, 1H), 6.52 (s, 1H), 3.07 (s, 3H), 2.13-2.11 (m, 1H), 1.13-1.05 (m, 4H).

Step 2: 7-bromo-2-cyclopropyl-5-methylsulfonyl-2,3-dihydro-1-benzofuran

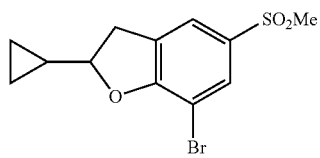 [SMILES: CS(=O)(=O)c1cc(Br)c2c(c1)CC(C1CC1)O2]

To a soln of the title compound from Step 1 (250 mg, 0.79 mmol) in Et$_3$SiH (516 mg, 4.44 mmol) at 0° C. was added TFA (5.43 g, 47.59 mmol) in one portion. The rxn mixture was warmed up to room temp and stirred for 48 hr. Aq NaOH soln (10 mL, 1N) was added slowly to the above soln. The mixture was extracted with EtOAc (10 mL). The organic layer was dried over Na$_2$SO$_4$, filtered and concentrated. The residue was purified by CC (PE to PE/EA=2/1) to give the title compound (83 mg, 33%) as a white solid. $^1$H NMR (CDCl$_3$, 400 MHz) δ 7.90 (s, 1H), 7.64 (s, 1H), 4.47-4.43 (m, 1H), 3.51-3.47 (m, 1H), 3.23-3.17 (m, 1H), 3.04 (s, 3H), 1.24-1.22 (m, 1H), 0.74-0.55 (m, 3H), 0.44-0.41 (m, 1H).

Step 3: 4-(2-cyclopropyl-5-methylsulfonyl-2,3-dihydro-1-benzofuran-7-yl)-2-methylisoquinolin-1-one

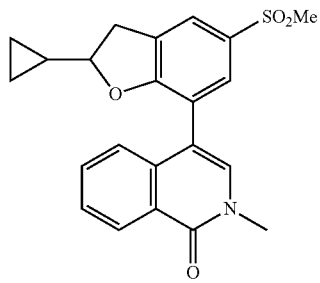 [SMILES: Cn1cc(-c2cc(S(C)(=O)=O)cc3c2OC(C2CC2)C3)c2ccccc2c1=O]

Example 494: 4-(2-ethyl-5-methylsulfonyl-2,3-dihydro-1-benzofuran-7-yl)-2-methylisoquinolin-1-one Step 1: 2-ethyl-7-iodo-5-methylsulfonyl-1-benzofuran

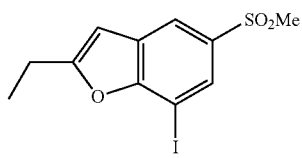 [SMILES: CCc1cc2cc(S(C)(=O)=O)cc(I)c2o1]

To a soln of 2,6-diiodo-4-methylsulfonylphenol (1.00 g, 2.36 mmol) in pyridine (10 mL) at 25° C. was added but-1-yne (128 mg, 2.36 mmol) and Cu$_2$O (135 mg, 0.944 mmol). The mixture was stirred at 130° C. for 3 hr under a N$_2$, then cooled to 25° C., diluted with 1N HCl (200 ml) and extracted with EtOAc (30 mL×2). The combined organic layers were washed by brine (100 mL), dried over Na$_2$SO$_4$, filtered and concentrated. The residue was purified by CC (PE:EA=10:1 to 5:1) to afford the title compound (400 mg, 48%) as a solid. $^1$H NMR (CDCl$_3$, 400 MHz): δ 8.14 (d, J=1.6 Hz, 1H), 8.06 (d, J=1.6 Hz, 1H), 6.62 (s, 1H), 3.09 (s, 3H), 2.90 (q, J=7.6 Hz, 2H), 1.38 (t, J=7.6 Hz, 3H). LCMS: 350.9 (M+H$^+$).

Step 2: 4-(2-ethyl-5-methylsulfonyl-1-benzofuran-7-yl)-2-methylisoquinolin-1-one

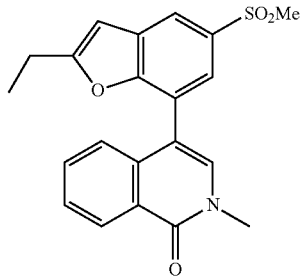 [SMILES: CCc1cc2cc(S(C)(=O)=O)cc(-c3cn(C)c(=O)c4ccccc34)c2o1]

To a soln of 2-methyl-4-(4,4,5,5-tetramethyl-1,3,2-dioxaborolan-2-yl)isoquinolin-1-one (82 mg, 286 μmol) and the title compound from Step 1 (100 mg, 286 μmol) in H$_2$O (2 mL) and dioxane (20 mL) was added Pd(dppf)Cl$_2$ (21 mg, 28.6 μmol, 0.10 Eq) and Na$_2$CO$_3$ (61 mg, 572 μmol). The mixture was degassed with N$_2$ and heated to 90° C. for 4 hr; then cooled to room temp and concentrated under reduced pressure. The residue was purified by CC (PE:EA 3:1 to 1:1) followed by prep-HPLC to afford the title compound (35.57 mg, 33%) as a white solid. $^1$H NMR (CDCl$_3$, 400 MHz): δ 8.56 (d, J=7.2 Hz, 1H), 8.19 (d, J=1.6 Hz, 1H), 7.83 (d, J=1.6 Hz, 1H), 7.60-7.57 (m, 2H), 7.29-7.27 (m, 2H), 6.60 (s, 1H), 3.73 (s, 3H), 3.15 (s, 3H) 2.75 (q, J=7.2 Hz, 2H), 1.28 (t, J=7.2 Hz, 3H). LCMS: 382.0 (M+H$^+$).

Step 3: 4-(2-ethyl-5-methylsulfonyl-2,3-dihydro-1-benzofuran-7-yl)-2-methylisoquinolin-1-one

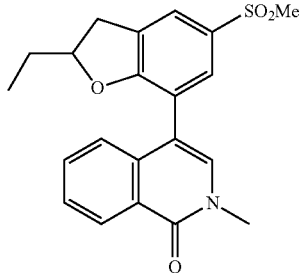 [SMILES: CCC1Cc2cc(S(C)(=O)=O)cc(-c3cn(C)c(=O)c4ccccc34)c2O1]

To a soln of the title compound from Step 2 (130 mg, 340 umol) in MeOH (3 mL) was added Pd/C (70 mg, 10% w/w) in one portion. The rxn mixture was stirred at 25° C. under $H_2$ atmosphere (15 psi) for 8 hr; then filtered through celite. The solvent was removed under reduced pressure and the residue purified by prep-HPLC to give the title compound (12.4 mg) as a gray solid. $^1$H NMR (CDCl$_3$, 300 MHz): δ 8.54-8.51 (d, J=7.5 Hz, 1H), 7.79-7.75 (m, 2H), 7.75-7.54 (m, 2H), 7.32-7.29 (d, J=8.1 Hz, 1H), 7.16 (s, 1H), 4.90-4.85 (m, 1H), 3.69 (s, 3H), 3.49-3.41 (m, 1H), 3.06-3.00 (m, 1H), 1.85-1.70 (m, 2H), 0.96-0.91 (t, J=7.5 Hz, 3H). LCMS: 384.0 (M+1).

Example 495: N-[7-(1,5-dimethyl-6-oxopyridin-3-yl)-2-propyl-2,3-dihydro-1-benzofuran-5-yl]ethanesulfonamide Step 1: 2-cyclopropyl-7-iodo-5-nitro-1-benzofuran

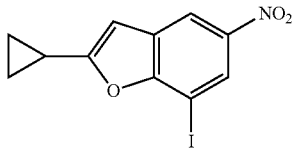 [SMILES: O=[N+]([O-])c1cc(I)c2oc(C3CC3)cc2c1]

A soln of 2,6-diiodo-4-nitrophenol (10 g, 25.6 mmol), ethynylcyclopropane (1.9 g, 28.8 mmol) and Cu$_2$O (1.9 mg, 13.2 mmol) in 100 mL of dry pyridine was refluxed for 2 hr. The rxn mixture was poured into 1 L of H$_2$O and stirred for 10 min. The resulting mixture was filtered. The cake was purified by CC on silica gel eluting with EtOAc:PE (0% to 20%) to give the title compound (6.6 g, 78% yield) as a yellow solid. $^1$H NMR (CDCl$_3$, 400 MHz): δ 8.47 (d, J=2.4 Hz, 1H), 8.32 (d, J=2.4 Hz, 1H), 6.58 (s, 1H), 2.13-2.07 (m, 1H), 1.14-1.04 (m, 4H).

Step 2: 2-cyclopropyl-7-iodo-1-benzofuran-5-amine

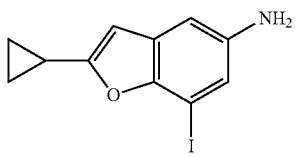 [SMILES: Nc1cc(I)c2oc(C3CC3)cc2c1]

To a soln of the title compound from Step 1 (2.0 g, 6.0 mmol) and Fe (1.0 g, 18 mmol) in MeOH (80 mL) was added sat. NH$_4$Cl soln (10 mL). The rxn mixture was refluxed for 1 hr. The mixture was cooled to room temp and poured into 400 mL of DCM. The resulting mixture was filtered and the filtrate was washed with H$_2$O (100 mL) and brine. The organic layer was dried over anhydrous Na$_2$SO$_4$, filtered and concentrated under reduced pressure to give the crude title compound (1.5 g, 83% yield) as red oil that was used for the next step directly. $^1$H NMR (CDCl$_3$, 400 MHz): δ 6.87 (d, J=2.4 Hz, 1H), 6.61 (d, J=2.0 Hz, 1H), 6.19 (s, 1H), 3.45 (br, 2H), 1.97-1.90 (m, 1H), 0.95-0.85 (m, 4H). LCMS: 300 (M+1)$^+$.

Step 3: N-(2-cyclopropyl-7-iodo-1-benzofuran-5-yl)ethanesulfonamide

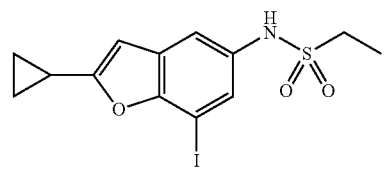 [SMILES: CCS(=O)(=O)Nc1cc(I)c2oc(C3CC3)cc2c1]

To a soln of the title compound from Step 2 (1.0 g, 3.3 mmol) in 20 mL of dry DCM was added a soln of pyridine (793 mg, 10 mmol) in DCM (10 mL), followed by addition of EtSO$_2$Cl (473 mg, 3.7 mmol). The rxn mixture was stirred at room temp for 1 hr, then diluted with DCM (20 mL), and washed with H$_2$O (20 mL×2) and brine. The organic layer was dried over Na$_2$SO$_4$, filtered and concentrated under reduced pressure to give the crude title compound (1.3 g, 100% yield) that was used directly in the next step. $^1$H NMR (CDCl$_3$, 400 MHz): δ 7.42 (d, J=2.0 Hz, 1H), 7.38 (d, J=2.0 Hz, 1H), 6.88 (br, 1H), 6.40 (s, 1H), 3.09 (q, J=7.2 Hz, 2H), 1.37 (t, J=7.2 Hz, 3H), 2.04-2.08 (m, 1H), 1.06-0.97 (m, 4H). LCMS: 409 (M+18)$^+$.

Step 4: N-[2-cyclopropyl-7-(1,5-dimethyl-6-oxopyridin-3-yl)-1-benzofuran-5-yl]ethanesulfonamide

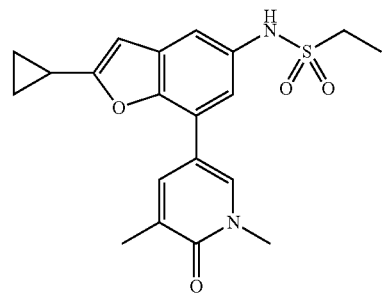 [SMILES: CCS(=O)(=O)Nc1cc(-c2cc(C)c(=O)n(C)c2)c2oc(C3CC3)cc2c1]

To a soln of the title compound from Step 3 (500 mg, 1.3 mmol) and 1,3-dimethyl-5-(4,4,5,5-tetramethyl-1,3,2-dioxaborolan-2-yl)pyridin-2-one (380 mg, 1.5 mmol) in 10 mL of DMF was added K$_2$CO$_3$ (50 mg, 3.8 mmol), H$_2$O (2 mL) and Pd(dppf)Cl$_2$ (30 mg) under N$_2$. The rxn mixture was heated to 100° C. for 1 hr, and the resulting mixture poured into 100 mL of H$_2$O then extracted with DCM (100 mL×2). The combined organic layers were dried over anhydrous Na$_2$SO$_4$, filtered and concentrated under reduced pressure.

The residue was purified by CC on silica gel eluting with EtOAc to give the title compound (230 mg, 47% yield) as a white solid. $^1$H NMR (CDCl$_3$, 400 MHz): δ 7.81 (d, J=3.6 Hz, 1H), 7.67-7.66 (m, 1H), 7.26 (t, J=1.2 Hz, 1H), 7.12 (d, J=3.2 Hz, 1H), 6.54 (br, 1H), 6.36 (d, J=0.8 Hz, 1H), 3.67 (s, 3H), 3.14-3.06 (m, 2H), 2.25 (s, 3H), 2.11-2.00 (m, 1H), 1.38-1.43 (m, 3H), 1.09-0.92 (m, 4H). LCMS: 387 (M+1)$^+$.

Step 5: N-[7-(1,5-dimethyl-6-oxopyridin-3-yl)-2-propyl-2,3-dihydro-1-benzofuran-5-yl]ethanesulfonamide

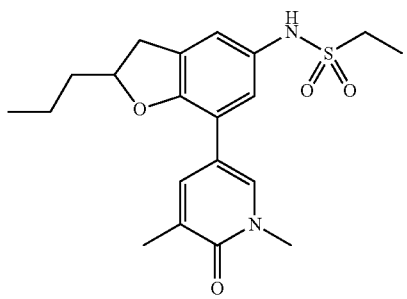 [SMILES: CCCC1Cc2cc(NS(=O)(=O)CC)cc(-c3cc(C)c(=O)n(C)c3)c2O1]

A mixture of the title compound from Step 4 (70 mg, 0.18 mmol) and 10 mg of Pd/C in 40 mL MeOH was stirred under a H$_2$ atmosphere at room temp for 1 hr. The resulting mixture was filtered and the filtrate was concentrated under reduced pressure. The residue was purified by prep-HPLC to give the title compound (10 mg, 14% yield) as a white solid. $^1$H NMR (CDCl$_3$, 300 MHz): δ 7.77 (d, J=2.1 Hz, 1H), 7.56 (s, 1H), 7.04 (s, 1H), 7.01 (s, 1H), 6.26 (d, J=2.7 Hz, 1H), 4.88-4.84 (m, 1H), 3.61 (s, 3H), 3.34-3.26 (m, 1H), 3.09 (q, J=7.5 Hz, 2H), 2.90-2.84 (m, 1H), 2.21 (s, 3H), 1.87-1.82 (m, 1H), 1.72-1.63 (m, 1H), 1.56-1.43 (m, 2H), 1.38 (t, J=7.2 Hz, 3H), 0.98 (t, J=7.5 Hz, 3H). LCMS: 391 (M+1)$^+$.

Example 496: N-[2-cyclopropyl-7-(1,5-dimethyl-6-oxopyridin-3-yl)-2,3-dihydro-1-benzofuran-5-yl]ethanesulfonamide

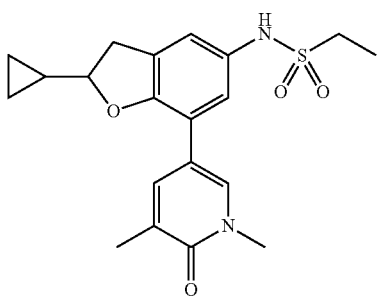 [SMILES: CCS(=O)(=O)Nc1cc2c(c(-c3cc(C)c(=O)n(C)c3)c1)OC(C1CC1)C2]

To a mixture of the title compound from Example 495, Step 4 (30 mg, 0.08 mmol) in Et$_3$SiH (1 mL) in a sealed tube was added TFA (0.2 mL) at 0° C. This was warmed to room temp and stirred overnight, then diluted with DCM (30 mL) and washed with 1N NaOH, H$_2$O, and brine. The organic phase was dried over Na$_2$SO$_4$, filtered, and conc under reduced press. The residue was recrystallized from EtOAc to give the title compound (3 mg, 10% yield) as a white solid. $^1$H NMR (CDCl$_3$, 300 MHz): δ 7.77 (s, 1H), 7.57 (s, 1H), 7.04 (d, J=3.0 Hz, 2H), 6.44 (s, 1H), 4.37-4.29 (m, 1H), 3.63 (s, 3H), 3.37-3.29 (m, 1H), 3.13-3.03 (m, 3H), 2.22 (s, 3H), 1.40 (t, J=7.5 Hz, 3H), 1.26-1.14 (m, 1H), 0.71-0.33 (m, 4H). LCMS: 389 (M+1)$^+$.

Example 497: 4-[3-(methoxymethyl)-7-methylsulfonyl-2,3-dihydro-1,4-benzodioxin-5-yl]-2-methylisoquinolin-1-one Step 1: (6-bromo-2,3-dihydro-1,4-benzodioxin-2-yl)methanol and (6-bromo-2,3-dihydro-1,4-benzodioxin-3-yl)methanol

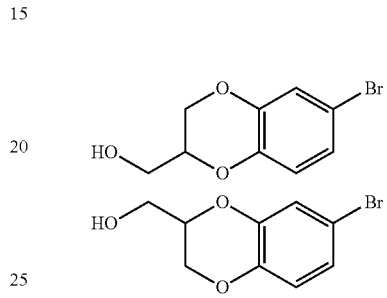

To a mixture of NaOH (1.6 g, 39.7 mmol) in THF (120 mL) and H$_2$O (40 mL) was added 4-bromobenzene-1,2-diol (5 g, 26.5 mmol). Oxiran-2-ylmethanol (7.35 g, 79.5 mmol) was added portion-wise at room temp under N$_2$. The rxn was stirred at 100° C. for 4 hr; then cooled to room temp; and extracted with EtOAc (50 mL×2). The organic layers were washed with brine (40 mL×2), dried over anhydrous Na$_2$SO$_4$, filtered, and conc under reduced press. The residue was purified by CC (PE:EA 5:1) to give the title compounds (4.7 g, 73%). LCMS: 166 (M−80)$^+$.

Step 2: (6-methylsulfonyl-2,3-dihydro-1,4-benzodioxin-2-yl)methanol and (6-methylsulfonyl-2,3-dihydro-1,4-benzodioxin-3-yl)methanol

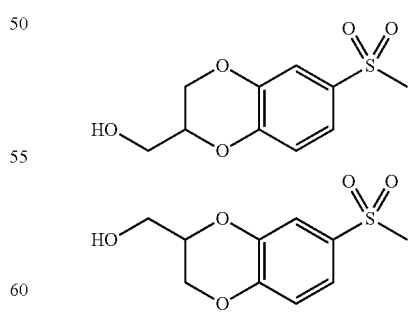

The mixture from Step 1 (1 g, 4.08 mmol) was submitted to the experimental conditions described in Example 486, Step 1, to give a mixture of the title compounds (650 mg, 65%). LCMS: 245.1 (M+1)$^+$.

Step 3: 2-(methoxymethyl)-6-methylsulfonyl-2,3-dihydro-1,4-benzodioxine and 3-(methoxymethyl)-6-methylsulfonyl-2,3-dihydro-1,4-benzodioxine

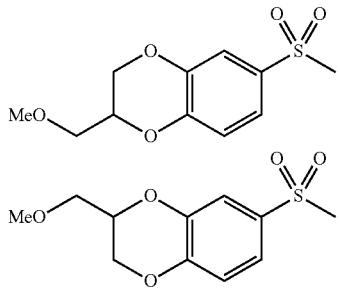

To a soln of the mixture from Step 2 (2.5 g, 10.23 mmol) in THF (30 mL) was added NaH (614 mg, 15.35 mmol) at 0° C. The rxn was stirred at 0° C. for 1 hr. CH$_3$I (1.45 g, 10.23 mmol) was added to the rxn mixture while keeping the internal temp ~0° C. The rxn mixture was stirred at room temp for another 3 hr, then quenched with ice and extracted with EtOAc (30 mL×3). The combined organic phases were washed with satd brine (20 mL×2), dried over anhydrous Na$_2$SO$_4$, filtered and conc under reduced press. The residue was purified by CC (PE:EA=3:1) to give a mixture of the title compounds (1.5 g, 57%) as an oil. The mixture was further separated into its four individual components by chiral phase SFC to give the two enantiomers of 2-(methoxymethyl)-6-methyl-sulfonyl-2,3-dihydro-1,4-benzodioxine (200 mgs each) and the two enantiomers of 3-(methoxy-methyl)-6-methylsulfonyl-2,3-dihydro-1,4-benzodioxine (200 and 120 mgs, respectively). Their absolute stereochemistry was not assigned. 2-(methoxymethyl)-6-methylsulfonyl-2,3-dihydro-1,4-benzodioxine $^1$H NMR (CDCl$_3$, 400 MHz): δ7.44 (d, J=1.6 Hz, 1H), 7.41 (dd, J$_1$=8.8 Hz, J$_2$=2.0 Hz, 1H), 7.03 (d, J=8.0 Hz, 1H), 4.42-4.31 (m, 2H), 4.10 (dd, J$_1$=11.6 Hz, J$_2$=7.6 Hz, 1H), 3.71-3.58 (m, 2H), 3.42 (s, 3H), 3.01 (s, 3H). LCMS: 259 (M+1)$^+$. 3-(methoxymethyl)-6-methylsulfonyl-2,3-dihydro-1,4-benzodioxine $^1$H NMR (CDCl$_3$, 400 MHz): δ 7.47 (d, J=2.0 Hz, 1H), 7.41 (dd, J$_1$=8.8 Hz, J$_2$=2.0 Hz, 1H), 7.00 (d, J=8.4 Hz, 1H), 4.40-4.30 (m, 2H), 4.18-4.10 (dd, J$_1$=11.2 Hz, J$_2$=7.2 Hz, 1H), 3.70-3.58 (m, 2H), 3.42 (s, 3H), 3.00 (s, 3H). LCMS: 259 (M+1)$^+$.

Step 4: 5-bromo-3-(methoxymethyl)-7-methylsulfonyl-2,3-dihydro-1,4-benzodioxine

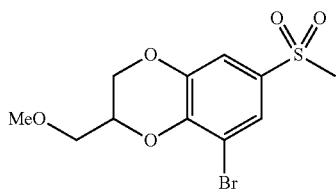 [SMILES: COCC1COc2cc(S(C)(=O)=O)cc(Br)c2O1]

The title compound (single enantiomer, absolute stereochemistry not assigned) was prepared in a manner similar to Example 486, Step 2, by substituting 2-(methoxymethyl)-6-methylsulfonyl-2,3-dihydro-1,4-benzodioxine for 2-methyl-5-methylsulfonyl-2,3-dihydro-1-benzofuran. $^1$H NMR (CDCl$_3$, 400 MHz) δ 7.70 (d, J=2.0 Hz, 1H), 7.46 (d, J=2.0 Hz, 1H), 4.53 (dd, J$_1$=2.2 Hz, J$_2$=11.4 Hz, 1H), 4.39-4.34 (m, 1H), 4.26-4.21 (m, 1H), 3.73-3.63 (m, 2H), 3.45 (s, 3H), 3.03 (s, 3H).

Step 5: 4-[3-(methoxymethyl)-7-methylsulfonyl-2,3-dihydro-1,4-benzodioxin-5-yl]-2-methylisoquinolin-1-one

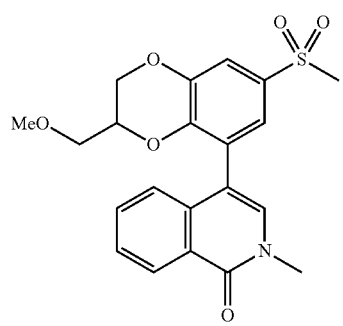 [SMILES: COCC1COc2cc(S(C)(=O)=O)cc(-c3cn(C)c(=O)c4ccccc34)c2O1]

A mixture of the title compound from Step 4 (20 mg, 0.06 mmol), 2-methyl-4-(4,4,5,5-tetramethyl-1,3,2-dioxaborolan-2-yl)isoquinolin-1-one (20 mg, 0.07 mmol), Na$_2$CO$_3$ (19 mg, 0.18 mmol), Pd(dppf)Cl$_2$ (7 mg, 0.01 mmol) in dioxane (2 mL) and H$_2$O (0.2 mL) was stirred at 80° C. for 12 hr under N$_2$. The rxn mixture was poured over H$_2$O (10 mL) and extracted with EtOAc (3×10 mL). The combined organic phases were washed with brine (10 mL), dried over anhydrous Na$_2$SO$_4$, filtered, and concentrated under reduced pressure to give a residue; then purified by CC followed by prep-HPLC to afford the title compound (12 mg, 24%). Absolute stereochemistry not assigned. $^1$H NMR (DMSO-d6, 400 MHz) δ 8.30 (d, J=8.0 Hz, 1H), 7.68-7.63 (m, 1H), 7.55-7.52 (m, 3H), 7.42 (s, 1H), 7.28 (d, J=8.4 Hz, 1H), 4.43-4.35 (m, 2H), 4.21-4.12 (m, 1H), 3.56 (s, 3H), 3.44-3.41 (m, 2H), 3.23 (s, 3H), 3.09 (s, 3H). LCMS: 416.0 (M+H)$^+$.

Example 498: 5-[3-(methoxymethyl)-7-methylsulfonyl-2,3-dihydro-1,4-benzodioxin-5-yl]-1,3-dimethylpyridin-2-one

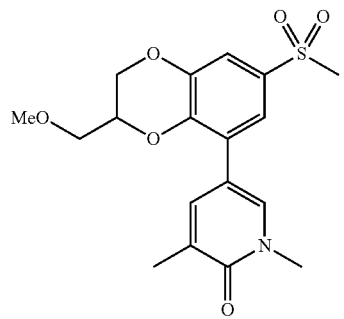 [SMILES: COCC1COc2cc(S(C)(=O)=O)cc(-c3cc(C)c(=O)n(C)c3)c2O1]

The title compound (single enantiomer, absolute stereochemistry not assigned) was prepared in a manner similar to Example 497, by substituting 1,3-dimethyl-5-(4,4,5,5-tetramethyl-1,3,2-dioxaborolan-2-yl)pyridin-2-one for 2-methyl-4-(4,4,5,5-tetramethyl-1,3,2-dioxaborolan-2-yl)

isoquinolin-1-one in Step 5. ¹H NMR (CDCl₃, 400 MHz): δ 7.53 (s, 1H), 7.49 (s, 1H), 7.43 (m, 2H), 4.45-4.37 (m, 2H), 4.18-4.17 (m, 1H), 3.68-3.62 (m, 5H), 3.44 (s, 3H), 3.07 (s, 3H), 2.21 (s, 3H). LCMS: 380 (M+H)⁺.

Example 499: 4-[3-(methoxymethyl)-7-methylsulfonyl-2,3-dihydro-1,4-benzodioxin-5-yl]-2-methylisoquinolin-1-one

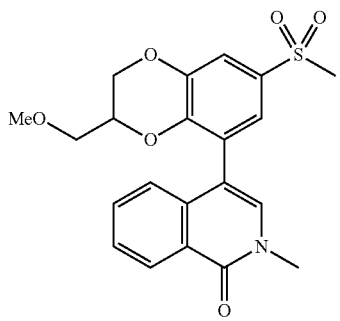 [SMILES: COCC1COc2cc(S(C)(=O)=O)cc(-c3cn(C)c(=O)c4ccccc34)c2O1]

The title compound (single enantiomer, absolute stereochemistry not assigned) was prepared in a manner similar to Example 497, by substituting the compound used in Step 4 for its enantiomer. ¹H NMR (DMSO-d6, 400 MHz): δ 8.30 (d, J=8.0 Hz, 1H), 7.68 (t, J=8.0 Hz, 1H), 7.55-7.51 (m, 3H), 7.42 (s, 1H), 7.28 (d, J=8.0 Hz, 1H), 4.42-4.35 (m, 2H), 4.21-4.14 (m, 1H), 3.56 (s, 3H), 3.44-3.39 (m, 2H), 3.24 (s, 3H), 3.09 (s, 3H). LCMS: 416.0 (M+H)⁺.

Example 500: 5-[3-(methoxymethyl)-7-methylsulfonyl-2,3-dihydro-1,4-benzodioxin-5-yl]-1,3-dimethylpyridin-2-one

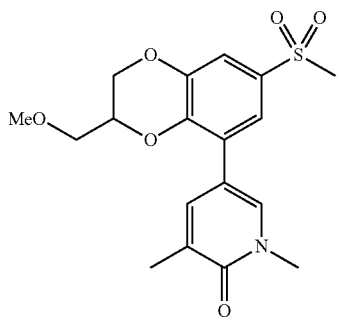 [SMILES: COCC1COc2cc(S(C)(=O)=O)cc(-c3cc(C)c(=O)n(C)c3)c2O1]

The title compound (single enantiomer, absolute stereochemistry not assigned) was prepared in a manner similar to Example 498, but using the other enantiomer of 5-bromo-3-(methoxymethyl)-7-methylsulfonyl-2,3-dihydro-1,4-benzodioxine. ¹H NMR (CDCl₃, 400 MHz) δ 7.59 (s, 1H), 7.58 (s, 1H), 7.44 (m, 2H), 4.41-4.37 (m, 2H), 4.20-4.18 (m, 1H), 3.71-3.63 (m, 5H), 3.44 (s, 3H), 3.07 (s, 3H), 2.24 (s, 3H). LCMS: 380.0 (M+H)⁺.

Example 501: 4-[2-(methoxymethyl)-7-methylsulfonyl-2,3-dihydro-1,4-benzodioxin-5-yl]-2-methylisoquinolin-1-one

Step 1: 5-bromo-2-(methoxymethyl)-7-methylsulfonyl-2,3-dihydro-1,4-benzodioxine

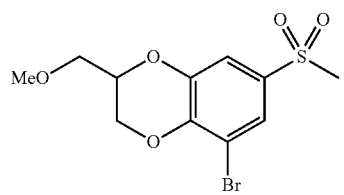 [SMILES: COCC1COc2c(Br)cc(S(C)(=O)=O)cc2O1]

The title compound (single enantiomer, absolute stereochemistry not assigned) was prepared in a manner similar to Example 497, Step 4, by substituting 2-(methoxymethyl)-6-methylsulfonyl-2,3-dihydro-1,4-benzodioxine for 3-(methoxymethyl)-6-methylsulfonyl-2,3-dihydro-1,4-benzodioxine. LCMS: 359 (M+23)⁺.

Step 2: 4-[2-(methoxymethyl)-7-methylsulfonyl-2,3-dihydro-1,4-benzodioxin-5-yl]-2-methylisoquinolin-1-one

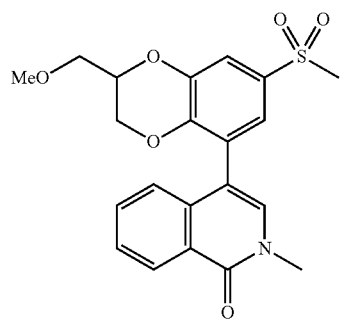 [SMILES: COCC1COc2c(cc(S(C)(=O)=O)cc2-c2cn(C)c(=O)c3ccccc23)O1]

The title compound (single enantiomer, absolute stereochemistry not assigned) was prepared in a manner similar to Example 497, Step 5, by substituting 5-bromo-2-(methoxymethyl)-7-methylsulfonyl-2,3-dihydro-1,4-benzodioxine for 5-bromo-3-(methoxymethyl)-7-methylsulfonyl-2,3-dihydro-1,4-benzodioxine. ¹H NMR (DMSO-d₆, 400 MHz): δ 8.31 (d, J=8.0 Hz, 1H), 7.66-7.63 (m, 1H), 7.56-7.51 (m, 3H), 7.40 (s, 1H), 7.30-7.16 (m, 1H), 4.53-4.44 (m, 1H), 4.36-4.28 (m, 1H), 4.12-4.01 (m, 1H), 3.61-3.56 (m, 5H), 3.34 (s, 3H), 3.24 (s, 3H). LCMS: 416.0 (M+H)⁺.

Example 502: 5-[2-(methoxymethyl)-7-methylsulfonyl-2,3-dihydro-1,4-benzodioxin-5-yl]-1,3-dimethyl-pyridin-2-one

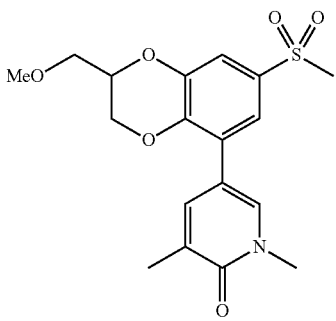 [SMILES: COCC1COc2c(cc(S(C)(=O)=O)cc2-c2cc(C)c(=O)n(C)c2)O1]

The title compound (single enantiomer, absolute stereochemistry not assigned) was prepared in a manner similar to Example 501, by substituting 1,3-dimethyl-5-(4,4,5,5-tetramethyl-1,3,2-dioxaborolan-2-yl)pyridin-2-one for 2-methyl-4-(4,4,5,5-tetramethyl-1,3,2-dioxaborolan-2-yl)isoquinolin-1-one. $^1$H NMR (CDCl$_3$, 400 MHz) δ 7.48 (m, 3H), 7.41 (d, J=2.4 Hz, 1H), 4.47-4.34 (m, 2H), 4.19-4.16 (m, 1H), 3.71-3.65 (m, 5H), 3.45 (s, 3H), 3.05 (s, 3H), 2.22 (s, 3H). LCMS: 380.0 (M+H)$^+$.

Example 503: 4-[2-(methoxymethyl)-7-methylsulfonyl-2,3-dihydro-1,4-benzodioxin-5-yl]-2-methylisoquinolin-1-one

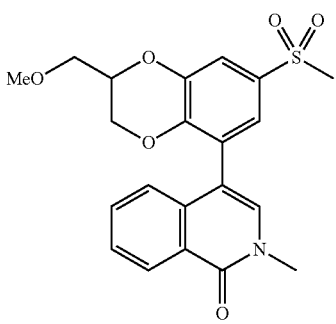 [SMILES: COCC1COc2c(cc(S(C)(=O)=O)cc2-c2cn(C)c(=O)c3ccccc23)O1]

The title compound (single enantiomer, absolute stereochemistry not assigned) was prepared in a manner similar to Example 501, by substituting the compound used in Step 1 for its enantiomer. $^1$H NMR (CD$_3$OD, 400 MHz) δ8.41 (d, J=8.0 Hz, 1H), 7.70 (t, J=7.6 Hz, 1H), 7.58-7.54 (m, 2H), 7.48 (s, 1H), 7.42 (s, 1H), 7.33-7.30 (m, 1H), 4.52-4.41 (m, 2H), 4.20-4.12 (m, 1H), 3.67 (s, 3H), 3.47 (m, 2H), 3.19-3.15 (m, 6H). LCMS: 416.0 (M+H)$^+$.

Example 504: 4-[2-(cyclopropylmethoxy)-5-methylsulfonylphenyl]-2-methyl-6,7-dihydro-5H-cyclopenta[c]pyridin-1-one

Step 1: Ethyl 6,7-dihydro-5H-cyclopenta[c]pyridine-1-carboxylate

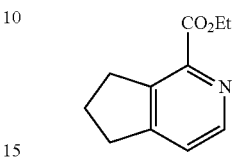

Ethyl 1,2,4-triazine-3-carboxylate (7 g, 45.8 mmol), cyclopentanone (4.9 mL, 55.0 mmol), and pyrrolidine (4.6 mL, 55.0 mmol) in toluene (100 mL) were heated to reflux for 12 hr. The mixture was purified by column on silica gel chromatography (PE/EtOAc=5:1) to give the title compound (2.02 g, 25%) as a brown oil. LCMS: 192 (M+1)$^+$.

Step 2: 6,7-dihydro-5H-cyclopenta[c]pyridine-1-carboxylic Acid

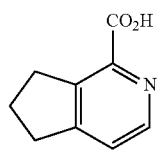 [SMILES: O=C(O)c1nccc2c1CCC2]

A 2N soln of LiOH (50 mL) in H$_2$O was slowly added to the title compound of step 1 (10 g, 52.4 mmol) in MeOH (250 mL) at 0° C. The mixture was warmed to room temp and stirred for 30 min. The MeOH was reduced under vacuum and the residual aq soln was washed with EtOAc. The organic phase was re-extracted with H$_2$O. The combined aq extracts were acidified to pH 2 with 1N HCl. The H$_2$O was removed and preparative HPLC gave the title compound (5.4 g, 63%) as a white solid. $^1$H NMR (CD$_3$OD, 400 MHz): δ 8.45 (d, J=5.6 Hz, 1H), 7.88 (d, J=5.6 Hz, 1H), 3.39 (t, J=8.0, 7.6 Hz, 2H), 3.16 (d, t, J=8.0, 7.6 Hz, 2H), 2.16-2.20 (m, 2H).

Step 3: Tert-Butyl N-(6,7-dihydro-5H-cyclopenta[c]pyridin-1-yl)carbamate

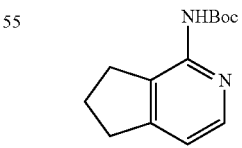

The title compound of step 2 (1.0 g, 6.1 mmol), diphenylphosphoryl azide (2.64 mL 12.2 mmol), and triethylamine (1.64 mL, 12.2 mmol) in tBuOH (50 mL), under N$_2$, were heated at 80° C. for 2 hr. Silica gel chromatography (PE:EtOAc 5:1) gave the title compound (570 mg, 40%) as a white solid. $^1$H NMR (CDCl$_3$, 300 MHz): δ 8.18 (d, J=4.8

Hz, 1H), 7.04 (d, J=4.8 Hz, 1H), 2.90-2.97 (m, 4H), 2.06-2.12 (m, 2H), 1.49 (s, 9H). LCMS: 235 (M+1)+.

Step 4: 6,7-dihydro-5H-cyclopenta[c]pyridin-1-amine Hydrochloride

Anhydrous 1M HCl in DCM (20 mL) was added slowly to the title compound of step 3 (570 mg, 2.43 mmol) in DCM (10 mL) at 0° C. After stirring at room temp for 1.5 hr, evaporation of the volatile components gave the title compound (400 mg, 96%) as a white solid. $^1$H NMR (CD$_3$OD, 300 MHz): δ 7.66 (d, J=6.6 Hz, 1H), 6.88 (d, J=6.6 Hz, 1H), 3.04 (t, J=7.8, 7.2 Hz, 2H), 2.86 (t, J=7.8, 7.2 Hz, 2H), 2.17-2.27 (m, 2H). LCMS: 135 (M+1)+.

Step 5: 2,5,6,7-tetrahydrocyclopenta[c]pyridin-1-one

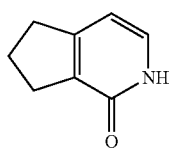

The title compound of step 4 (400 mg, 2.33 mmol) was dissolved in H$_2$O (6.5 mL) and H$_3$PO$_2$ (2 mL, 50% w/w in H$_2$O, 18.64 mmol) was added. The mixture was cooled to 0° C. and a soln of NaNO$_2$ (180 mg 2.68 mmol) in H$_2$O (6.5 mL) was added dropwise. The mixture was stirred at 0° C. for 1 hr and then at room temp overnight. The pH 7 was obtained by careful addition of NaHCO$_3$. Extractive work-up using EtOAc gave the title compound (300 mg, 95%) as a yellow solid. $^1$H NMR (CDCl$_3$, 300 MHz): δ 12.55 (s, 1H), 7.24 (d, J=6.3 Hz, 1H), 6.26 (d, J=6.3 Hz, 1H), 2.84-2.89 (m, 4H), 2.04-2.11 (m, 2H). LCMS: 136 (M+1)+.

Step 6: 2-methyl-6,7-dihydro-5H-cyclopenta[c]pyridin-1-one

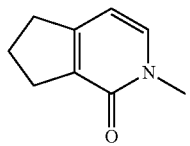

The title compound of step 5 (260 mg, 1.93 mmol) was dissolved in DMF (5 mL) and cooled to 0° C. NaH (94 mg, 2.31 mmol) was added and the mixture was stirred for 30 min. Methyl iodide (146 μL, 2.31 mmol) was added and the mixture stirred at room temp for 2 hr. The volatile components were removed under vacuum and silica gel chromatography (PE:EtOAc 1:1) gave the title compound (192.6 mg, 67%) as a brown oil. $^1$H NMR (CD$_3$Cl, 300 MHz): δ 7.13 (d, J=6.6 Hz, 1H), 6.13 (d, J=6.6 Hz, 1H), 3.53 (s, 3H), 2.79-2.85 (m, 4H), 2.01-2.11 (m, 2H). LCMS: 150 (M+1)+.

Step 7: 4-bromo-2-methyl-6,7-dihydro-5H-cyclopenta[c]pyridin-1-one

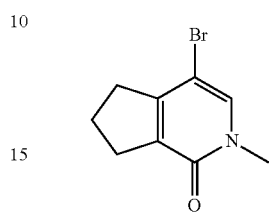

The title compound of step 6 (140 mg, 1.04 mmol) was dissolved in ACN (5 mL) and NBS (188 mg, 1.06 mmol) was added. After stirring at room temp for 1.5 hr, purification by silica gel chromatography (PE:EtOAc 1:1) gave the title compound (196 mg, 89.5%) as a white solid. $^1$H NMR (CD$_3$Cl, 300 MHz): δ 7.33 (s, 1H), 3.53 (s, 3H), 2.85-2.97 (m, 4H), 2.05-2.13 (m, 2H). LCMS: 228, 230 (M+1)+.

Step 8: 4-[2-(cyclopropylmethoxy)-5-methylsulfonylphenyl]-2-methyl-6,7-dihydro-5H-cyclopenta[c]pyridin-1-one

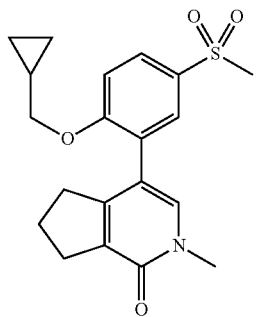

To a soln of the title compound of step 7 (60 mg, 0.26 mmol), the title compound of Example 90, step 1 (111.2 mg, 0.32 mmol) and K$_2$CO$_3$ (107 mg, 0.78 mmol) in dioxane (4 mL) and H$_2$O (1 mL) was added Pd(dppf)Cl$_2$ (6 mg) under N$_2$. The mixture was heated at 85° C. overnight. EA extractive work-up followed by prep-TLC (DCM:MeOH=25:1) gave the title compound (47 mg, 48%) as a yellow solid. $^1$H NMR (DMSO-d$_6$, 300 MHz): δ 7.83 (dd, J=8.7, 2.7 Hz, 1H), 7.66 (d, J=2.9 Hz, 1H), 7.58 (s, 1H), 7.25 (d, J=8.7 Hz, 1H), 3.95 (d, J=6.9 Hz, 2H). 3.46 (s, 3H), 3.17 (s, 3H), 2.65-2.70 (m, 4H), 1.91-1.97 (m, 2H), 1.13-1.18 (m, 1H), 0.50-0.54 (m, 2H), 0.26-0.30 (m, 2H). LCMS: 374 (M+1)+.

Example 505: 4-[2-(cyclopropylmethoxy)-5-ethyl-sulfonylphenyl]-2-methyl-6,7-dihydro-5H-cyclopenta[c]pyridin-1-one

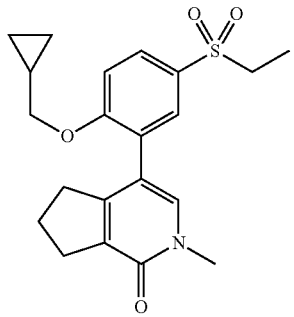 [SMILES: CCS(=O)(=O)c1ccc(OCC2CC2)c(-c2cn(C)c(=O)c3c2CCC3)c1]

The title compound was prepared in a similar manner to Example 504, step 8 except that 2-[2-(cyclopropylmethoxy)-5-ethylsulfonylphenyl]-4,4,5,5-tetramethyl-1,3,2-dioxaborolane was substituted for the title compound of Example 90, step 1. $^1$H NMR (CD$_3$OD, 400 MHz): δ 7.91 (dd, J=8.4, 2.0 Hz, 1H), 7.73 (d, J=2.0 Hz, 1H), 7.56 (s, 1H), 7.27 (d, J=8.4 Hz, 1H), 4.01 (d, J=6.8 Hz, 2H), 3.66 (s, 3H), 3.23 (q, J=7.6 Hz, 2H), 2.88 (t, J=7.6 Hz, 2H), 2.82 (t, J=7.6 Hz, 2H), 2.08-2.14 (m, 2H), 1.26 (t, J=7.6 Hz, 3H), 1.08-1.27 (m, 1H), 0.60-0.65 (m, 2H), 0.33-0.37 (m, 2H). LCMS: 388 (M+1)$^+$.

Example 506: N-[4-(2,4-difluorophenoxy)-3-(2-methyl-1-oxo-6,7-dihydro-5H-cyclopenta[c]pyridin-4-yl)phenyl]methanesulfonamide

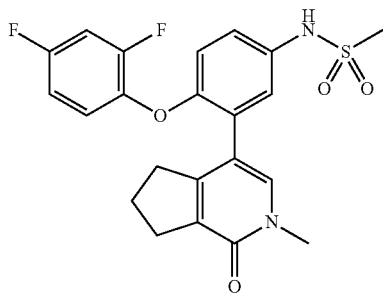 [SMILES: Cn1cc(-c2cc(NS(C)(=O)=O)ccc2Oc2ccc(F)cc2F)c2c(c1=O)CCC2]

The title compound was prepared in a similar manner to Example 504, step 8, except that N-[4-(2,4-difluorophenoxy)-3-(4,4,5,5-tetramethyl-1,3,2-dioxaborolan-2-yl)phenyl]methanesulfonamide was substituted for the title compound of Example 90, step 1. $^1$H NMR (DMSO-d6, 400 MHz): δ 9.72 (s, 1H), 7.58 (s, 1H), 7.34-7.42 (m, 1H), 7.24-7.10 (m, 2H), 7.00-7.08 (m, 2H), 6.91 (d, J=8.4 Hz, 1H), 3.43 (s, 3H), 3.01 (s, 3H), 2.71 (t, J=7.2 Hz, 2H), 2.65 (t, J=7.2 Hz, 2H), 1.88-1.96 (m, 2H). LCMS: 447 (M+1)$^+$.

Example 507: N-[4-(2,4-difluorophenoxy)-3-(2-methyl-1-oxo-6,7-dihydro-5H-cyclopenta[c]pyridin-4-yl)phenyl]ethanesulfonamide

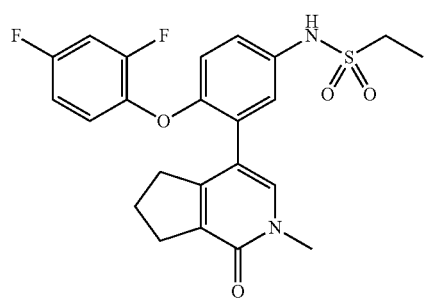 [SMILES: CCS(=O)(=O)Nc1ccc(Oc2ccc(F)cc2F)c(-c2cn(C)c(=O)c3c2CCC3)c1]

The title compound was prepared in a similar manner to Example 504, step 8 except that N-[4-(2,4-difluorophenoxy)-3-(4,4,5,5-tetramethyl-1,3,2-dioxaborolan-2-yl)phenyl]ethane-sulfonamide was substituted for the title compound of Example 90, step 1. $^1$H NMR (CD$_3$Cl, 400 MHz): δ 7.30 (s, 1H), 7.19 (d, J=3.2 Hz, 1H), 7.14 (dd, J=8.8, 3.2 Hz, 1H), 6.89-6.96 (m, 2H), 6.79-6.85 (m, 1H); 6.77 (d, J=8.8 Hz, 1H), 6.60 (s, 1H), 3.65 (s, 3H), 3.15 (q, J=7.6 Hz, 2H), 2.96 (t, J=7.6 Hz, 2H), 2.82 (t, J=7.6 Hz, 2H), 2.02-2.06 (m, 2H), 1.41 (t, J=7.6 Hz, 3H). LCMS: 461 (M+1)$^+$.

Examples 508-511 as described in Table 22 were prepared in three steps. Using conditions similar to those described in WO 2005/40151 (Preparation 6), 5-bromo-3-methylpyridin-2-ol was N-alkylated with isopropyl bromide to give 5-bromo-3-methyl-1-propan-2-ylpyridin-2-one which was then reacted with 4,4,5,5-tetramethyl-2-(tetramethyl-1,3,2-dioxaborolan-2-yl)-1,3,2-dioxaborolane using conditions similar to those described in Example 248, step 2 to give the pinacol ester, 3-methyl-1-propan-2-yl-5-(4,4,5,5-tetramethyl-1,3,2-dioxaborolan-2-yl)pyridin-2-one. This pinacol ester was then substituted for the pinacol ester of the example shown under Synthetic Method in Table 22 and reacted in the same way as the example to obtain the title compounds.

TABLE 22

[Structure: 5-R¹-3-methyl-1-(propan-2-yl)pyridin-2(1H)-one]

| Ex. No. | R¹ | Name | MS (M + H) | Synthetic Method |
|---|---|---|---|---|
| 508 | MeO₂S-pyrimidine with butyl | 5-(5-butyl-2-methylsulfonylpyrimidin-4-yl)-3-methyl-1-propan-2-ylpyridin-2-one | 364 | Example 305 |
| 509 | EtO₂SHN-pyrimidine-O-(2,4-difluorophenyl) | N-[5-(2,4-difluorophenoxy)-4-(5-methyl-6-oxo-1-propan-2-ylpyridin-3-yl)pyrimidin-2-yl]ethanesulfonamide | 465 | Example 169 |
| 510 | MeO₂S-pyrimidine-O-(2,4-difluorophenyl) | 5-[5-(2,4-difluorophenoxy)-2-methyl]sulfonylpyrimidin-4-yl]-3-methyl-1-propan-2-ylpyridin-2-one | 436 | Example 149, step 4 |
| 511 | EtO₂SHN-pyrimidine with butyl | N-[5-butyl-4-(5-methyl-6-oxo-1-propan-2-ylpyridin-3-yl)pyrimidin-2-yl]ethanesulfonamide | 393 | Example 310 |

Examples 512-514 as described in Table 23 were prepared in three steps. Using conditions similar to those described by Malhotra et. al., 15(24) Organic Letters 3698 (2013), (supporting information, compounds 4c and 3a), 3,5-dibromo-1-methylpyridin-2-one was alkylated at the 3-position using isopropylmagnesium bromide to give 5-bromo-1-methyl-3-propan-2-yl-pyridin-2-one which was then reacted with 4,4,5,5-tetramethyl-2-(tetramethyl-1,3,2-dioxaborolan-2-yl)-1,3,2-dioxaborolane using conditions similar to those described in Example 248, step 2 to give the pinacol ester, 1-methyl-3-propan-2-yl-5-(4,4,5,5-tetramethyl-1,3,2-dioxaborolan-2-yl)pyridin-2-one. This pinacol ester was then substituted for the pinacol ester of the example shown under Synthetic Method in Table 23 and reacted in the same way as the example to obtain the title compounds.

TABLE 23

[Structure: 5-R¹-3-isopropyl-1-methylpyridin-2(1H)-one]

| Ex. No. | R¹ | Name | MS (M + H) | Synthetic Method |
|---|---|---|---|---|
| 512 | EtO₂SHN-pyrimidine with butyl | N-[5-butyl-4-(1-methyl-6-oxo-5-propan-2-ylpyridin-3-yl)pyrimidin-2-yl]ethanesulfonamide | 393 | Example 310 |

TABLE 23-continued

| Ex. No. | R¹ | Name | MS (M + H) | Synthetic Method |
|---|---|---|---|---|
| 513 | MeO₂S-pyrimidine with butyl | 5-(5-butyl-2-methylsulfonylpyrimidin-4-yl)-1-methyl-3-propan-2-ylpyridin-2-one | 364 | Example 305 |
| 514 | EtO₂SHN-pyrimidine-O-(2,4-difluorophenyl) | N-[5-(2,4-difluorophenoxy)-4-(1-methyl-6-oxo-5-propan-2-ylpyridin-3-yl)pyrimidin-2-yl]ethanesulfonamide | 465 | Example 169 |

II. Biological Evaluation

Example 1: In Vitro Enzyme Inhibition Assay

Determination of the $IC_{50}$ for the heterocyclic derivative BRD4 inhibitors disclosed herein was performed as follows. His-tagged BRD4 was cloned, expressed and purified to homogeneity. Filipakopoulos et al., Nature 468:1067 (2010). BRD4 binding and inhibition was assessed by monitoring the interaction of biotinylated H4-tetraacetyl peptide (AnaSpec, H4K5/8/12/16(Ac), biotin-labeled) with the target using the AlphaScreen technology (Life Technologies). In a 384-well ProxiPlate BRD4(BD1) (2 nM final) was combined with peptide (15 nM final) in 50 mM HEPES (pH 7.3), 10 mM NaCl, 0.25 mM TCEP, 0.1% (w/v) BSA, and 0.005% (w/v) Brij-35 either in the presence of DMSO (final 0.4% DMSO) or compound dilution series in DMSO. After 20 min incubation at room temp, Alpha streptavidin donor beads and Nickel Chelate acceptor beads were added to a final concentration of 5 μg/mL. After 2 hr of equilibration, plates were read on an Envision instrument and the $IC_{50}$ was calculated using a four parameter non-linear curve fit. Chemistry Example 1 (2-methyl-4-phenylisoquinolin-1-one) had an $IC_{50}$ of 2.782 μM in this assay format.

The ability of the compounds disclosed herein to inhibit BRD4 activity was quantified and the respective $IC_{50}$ value was determined. The $IC_{50}$ values of various compounds disclosed herein is provided in Table 24.

Example 2: In Vitro Cell-based Assay

A colorimetric cellular proliferation assay (Cell-MTS assay) was performed to assess the ability of the heterocyclic derivative BRD4 inhibitors disclosed herein to effect the proliferation of established cancer cell lines.

Assay Principle

The Cell-MTS assay is a 7-day plate-based colorimetric assay which quantifies the amount of newly generated NADH in the presence or absence of test compound. The NADH level is used for the quantification of cancer cell proliferation.

Assay Method

Established cancer cell lines with a variety of driving mutations were obtained from American Type Culture Collection (ATCC) and routinely passaged according to ATCC protocols. For routine assay, these cells were seeded at densities which enabled ~90% confluence after 7 days of culture. Raji, human Burkitts lymphoma cells, (cMYC) were seeded at 15,000 cells per 96-well. HL-60, human proleukemia cells, (NRAS, p16, p53, c-Myc amplified) were seeded at 5,000 cells per 96-well. NCI-H460, human non-small cell lung cancer cells, (KRAS, PIK3CA, STLK11, p16) were seeded at 3,000 cells per 96-well. 24 hr after plating, cells received an 11-point dilution of test compound with final concentration ranges from 100 μM to 2.0 nM. Cells were incubated in the presence of compound for 168 hr at 37° C., and 5% $CO_2$. At the end of this incubation period, 80 μL of media is removed and 20 μL of CellTiter 96® AQueous Non-Radioactive Cell Proliferation Assay soln (Promega) was added. The cells were incubated until the $OD_{490}$ was >0.6. $IC_{50}$ values were calculated using the IDBS XLfit software package and include background subtracted $OD_{490}$ values and normalization to DMSO controls. Cellular proliferation $IC_{50}$ values were uploaded and archived using the Chem Biography Platform.

Table 24 provides the results of the in vitro enzyme inhibition assay experiments and the in vitro cell-based assay experiments performed with the compounds disclosed herein.

TABLE 24

| Chem. Synth. Example | Name | BRD4 IC$_{50}$ (μM) | Raji IC$_{50}$ (μM) | HL-60 IC$_{50}$ (μM) | H460 IC$_{50}$ (μM) |
|---|---|---|---|---|---|
| 1 | 4-(3-methoxyphenyl)-2-methylisoquinolin-1-one | B | | | |
| 2 | 2-methyl-4-phenylisoquinolin-1-one | B | | | |
| 3 | 4-(2-fluorophenyl)-2-methylisoquinolin-1-one | C | | | |
| 4 | 4-(2-methoxyphenyl)-2-methylisoquinolin-1-one | C | | | |
| 5 | 4-(3-aminophenyl)-2-methylisoquinolin-1-one | B | | | |
| 6 | N-cyclopropyl-3-(2-methyl-1-oxoisoquinolin-4-yl)benzenesulfonamide | B | | | |
| 7 | 2-methyl-4-(3-pyrrolidin-1-ylsulfonylphenyl)isoquinolin-1-one | B | A | B | |
| 8 | N-[[3-(2-methyl-1-oxoisoquinolin-4-yl)phenyl]methyl]methanesulfonamide | B | | | |
| 9 | N-[3-(2-methyl-1-oxoisoquinolin-4-yl)phenyl]methanesulfonamide | A | A | A | C |
| 10 | N-ethyl-3-(2-methyl-1-oxoisoquinolin-4-yl)benzenesulfonamide | B | | | |
| 11 | 4-(3-ethylsulfonylphenyl)-2-methylisoquinolin-1-one | B | A | B | |
| 12 | 4-[3-(dimethylsulfamoylamino)phenyl]-2-methyl-1-oxoisoquinoline | A | A | A | |
| 13 | N-[3-(2-methyl-1-oxoisoquinolin-4-yl)phenyl]ethanesulfonamide | A | A | A | |
| 14 | 2-methyl-4-(3-morpholin-4-yl-sulfonylphenyl)isoquinolin-1-one | B | | | |
| 15 | N-benzyl-2-methoxy-5-(2-methyl-1-oxoisoquinolin-4-yl)benzenesulfonamide | B | A | B | |
| 16 | 2-methoxy-5-(2-methyl-1-oxoisoquinolin-4-yl)benzenesulfonamide | B | | | |
| 17 | N-[2-methyl-5-(2-methyl-1-oxoisoquinolin-4-yl)phenyl] methanesulfonamide | A | B | A | |
| 18 | N-benzyl-2-methoxy-5-(2-methyl-1-oxoisoquinolin-4-yl)benzamide | B | B | B | |
| 19 | 4-(3,4-dihydro-2H-1,4-benzoxazin-6-yl)-2-methylisoquinolin-1-one | B | | | |
| 20 | 2-methyl-4-(2-oxo-1,3-dihydroindol-6-yl)isoquinolin-1-one | C | A | A | |
| 21 | 3-(2-methyl-1-oxoisoquinolin-4-yl)benzenesulfonamide | B | B | B | |
| 22 | N-(2-hydroxyethyl)-3-(2-methyl-1-oxoisoquinolin-4-yl)benzenesulfonamide | B | B | B | |
| 23 | 4-(5-amino-2-fluorophenyl)-2-methylisoquinolin-1-one | B | | | |
| 24 | 4-(5-amino-2,4-difluorophenyl)-2-methylisoquinolin-1-one | B | | | |
| 25 | 4-(3-amino-5-fluorophenyl)-2-methylisoquinolin-1-one | B | | | |
| 26 | 4-(3-amino-4-fluorophenyl)-2-methylisoquinolin-1-one | B | | | |
| 27 | N-benzyl-3-(2-methyl-1-oxoisoquinolin-4-yl)benzenesulfonamide | B | | | |
| 28 | N-[3-(2-methyl-1-oxoisoquinolin-4-yl)phenyl]propane-1-sulfonamide | A | B | B | |
| 29 | N-[3-(2-methyl-1-oxoisoquinolin-4-yl)phenyl]butane-1-sulfonamide | A | B | B | |
| 30 | N-[2-methoxy-5-(2-methyl-1-oxoisoquinolin-4-yl)phenyl]methanesulfonamide | A | B | A | |
| 31 | tert-butyl N-methyl-N-[3-(2-methyl-1-oxoisoquinolin-4-yl)phenyl]carbamate | B | B | B | |
| 32 | 2-methyl-4-[3-(methylamino)phenyl]isoquinolin-1-one | B | | | |
| 33 | N-methyl-N-[3-(2-methyl-1-oxoisoquinolin-4-yl)phenyl]methanesulfonamide | A | B | B | |

TABLE 24-continued

| Chem. Synth. Example | Name | BRD4 IC$_{50}$ (μM) | Raji IC$_{50}$ (μM) | HL-60 IC$_{50}$ (μM) | H460 IC$_{50}$ (μM) |
|---|---|---|---|---|---|
| 34 | N-[4-fluoro-3-(2-methyl-1-oxoisoquinolin-4-yl)phenyl]methanesulfonamide | A | A | A | |
| 35 | N-[2,4-difluoro-5-(2-methyl-1-oxoisoquinolin-4-yl)phenyl]methanesulfonamide | B | B | B | |
| 36 | N-[3-fluoro-5-(2-methyl-1-oxoisoquinolin-4-yl)phenyl]methanesulfonamide | B | B | B | |
| 37 | N-[2-fluoro-5-(2-methyl-1-oxoisoquinolin-4-yl)phenyl]methanesulfonamide | A | B | B | |
| 38 | N-[4-chloro-3-(2-methyl-1-oxoisoquinolin-4-yl)phenyl]methanesulfonamide | A | B | A | |
| 39 | N-[4-methyl-3-(2-methyl-1-oxoisoquinolin-4-yl)phenyl]methanesulfonamide | A | B | A | |
| 40 | N-[3-(2-methyl-1-oxoisoquinolin-4-yl)-5-(trifluoromethyl)phenyl]methanesulfonamide | B | B | B | |
| 41 | N-[4-fluoro-3-[2-methyl-6-(1-methyl-pyrazol-4-yl)-1-oxoisoquinolin-4-yl]phenyl]methanesulfonamide | A | A | A | |
| 42 | N-[3-[2-methyl-6-(1-methylpyrazol-4-yl)-1-oxoisoquinolin-4-yl]phenyl]methanesulfonamide | A | A | A | |
| 43 | N-[2,4-difluoro-5-[2-methyl-6-(1-methylpyrazol-4-yl)-1-oxoisoquinolin-4-yl]phenyl]methanesulfonamide | A | A | A | |
| 44 | 4-(3-ethylsulfonylphenyl)-2-methyl-6-(1-methylpyrazol-4-yl)isoquinolin-1-one | A | B | A | C |
| 45 | N-[4-chloro-3-[2-methyl-6-(1-methylpyrazol-4-yl)-1-oxoisoquinolin-4-yl]phenyl]ethanesulfonamide | A | A | A | B |
| 46 | 4-[2-(cyclopropylmethoxy)-5-methylsulfonylphenyl]-2-methyl-6-(1-methylpyrazol-4-yl)isoquinolin-1-one | A | A | A | C |
| 47 | N-[3-(6-fluoro-2-methyl-1-oxoisoquinolin-4-yl)phenyl]methanesulfonamide | A | A | A | |
| 48 | 3-(6-fluoro-2-methyl-1-oxoisoquinolin-4-yl)benzenesulfonamide | B | B | B | |
| 49 | N-ethyl-3-(6-fluoro-2-methyl-1-oxoisoquinolin-4-yl)benzenesulfonamide | B | B | B | |
| 50 | N-[4-chloro-3-(6-fluoro-2-methyl-1-oxoisoquinolin-4-yl)phenyl]ethanesulfonamide | A | B | A | B |
| 51 | N-[3-(2-methyl-1-oxo-2,7-naphthyridin-4-yl)phenyl]methanesulfonamide | B | C | B | |
| 52 | N-[3-(2-methyl-1-oxo-2,7-naphthyridin-4-yl)phenyl]ethanesulfonamide | B | B | B | |
| 53 | N-ethyl-3-(2-methyl-1-oxo-2,7-naphthyridin-4-yl)benzenesulfonamide | B | C | C | |
| 54 | N-benzyl-2-methoxy-5-(2-methyl-1-oxo-2,7-naphthyridin-4-yl)benzenesulfonamide | C | C | B | C |
| 55 | 3-(2-methyl-1-oxo-2,7-naphthyridin-4-yl)benzenesulfonamide | C | | | |
| 56 | 2-methoxy-5-(2-methyl-1-oxo-2,7-naphthyridin-4-yl)benzenesulfonamide | C | | | |
| 57 | N-[4-(2,4-difluorophenoxy)-3-(2-methyl-1-oxo-2,7-naphthyridin-4-yl)phenyl]ethanesulfonamide | A | A | A | C |

TABLE 24-continued

| Chem. Synth. Example | Name | BRD4 IC$_{50}$ (μM) | Raji IC$_{50}$ (μM) | HL-60 IC$_{50}$ (μM) | H460 IC$_{50}$ (μM) |
|---|---|---|---|---|---|
| 58 | N-[3-(7-fluoro-2-methyl-1-oxoisoquinolin-4-yl)phenyl] methanesulfonamide | A | B | A | |
| 59 | N-ethyl-3-(7-fluoro-2-methyl-1-oxoisoquinolin-4-yl)benzenesulfonamide | B | B | B | |
| 60 | N-benzyl-5-(7-fluoro-2-methyl-1-oxoisoquinolin-4-yl)-2-methoxybenzenesulfonamide | B | A | B | C |
| 61 | 3-(7-fluoro-2-methyl-1-oxoisoquinolin-4-yl)benzenesulfonamide | A | B | B | |
| 62 | N-[3-(7-fluoro-2-methyl-1-oxoisoquinolin-4-yl)phenyl] ethanesulfonamide | A | B | A | |
| 63 | 4-(3-ethylsulfonylphenyl)-7-fluoro-2-methylisoquinolin-1-one | B | B | B | C |
| 64 | 5-(7-fluoro-2-methyl-1-oxoisoquinolin-4-yl)-2-methoxybenzenesulfonamide | B | | | |
| 65 | 2-methyl-4-(1-methylpyrazol-4-yl)isoquinolin-1-one | B | | | |
| 66 | 4-(furan-2-yl)-2-methylisoquinolin-1-one | C | | | |
| 67 | 2-methyl-4-(1,3-oxazol-2-yl)isoquinolin-1-one | C | | | |
| 68 | 2-methyl-4-(1H-pyrazol-5-yl)isoquinolin-1-one | C | | | |
| 69 | 2-methyl-4-(1-methylimidazol-2-yl)isoquinolin-1-one | C | | | |
| 70 | 2-methyl-4-pyridin-2-ylisoquinolin-1-one | C | | | |
| 71 | 2-methyl-4-pyrimidin-2-ylisoquinolin-1-one | C | | | |
| 72 | N-[3-[2-methyl-6-(6-methylpyridin-3-yl)-1-oxoisoquinolin-4-yl]phenyl]ethanesulfonamide | A | A | A | B |
| 73 | N-[3-(2-methyl-1-oxo-6-phenylisoquinolin-4-yl)phenyl]ethanesulfonamide | B | | | |
| 74 | N-[3-(2-methyl-1-oxo-6-phenylisoquinolin-4-yl)phenyl]methanesulfonamide | B | B | B | C |
| 75 | N-[3-(2,6-dimethyl-1-oxoisoquinolin-4-yl)phenyl]ethanesulfonamide | A | A | A | C |
| 76 | N-[3-(6-ethyl-2-methyl-1-oxoisoquinolin-4-yl)phenyl]ethanesulfonamide | A | | | |
| 77 | N-[3-(6-ethyl-2-methyl-1-oxoisoquinolin-4-yl)phenyl]methanesulfonamide | A | A | A | C |
| 78 | N-[3-(2,6-dimethyl-1-oxoisoquinolin-4-yl)phenyl]methanesulfonamide | A | A | A | C |
| 79 | 4-(5-ethylsulfonyl-2-methoxyphenyl)-2-methyl-6-(1-methylpyrazol-4-yl) isoquinolin-1-one | A | A | A | C |
| 80 | 4-(5-ethylsulfonyl-2-hydroxyphenyl)-2-methyl-6-(1-methylpyrazol-4-yl)isoquinolin-1-one | A | | | |
| 81 | 4-(2-ethoxy-5-ethylsulfonylphenyl)-2-methyl-6-(1-methylpyrazol-4-yl) isoquinolin-1-one | A | A | A | A |
| 82 | 4-[2-(cyclopropylmethoxy)-5-ethylsulfonylphenyl]-2-methyl-6-(1-methylpyrazol-4-yl)isoquinolin-1-one | A | A | A | B |
| 83 | 4-(5-ethylsulfonyl-2-propoxyphenyl)-2-methyl-6-(1-methylpyrazol-4-yl) isoquinolin-1-one | A | A | A | A |

TABLE 24-continued

| Chem. Synth. Example | Name | BRD4 IC$_{50}$ (μM) | Raji IC$_{50}$ (μM) | HL-60 IC$_{50}$ (μM) | H460 IC$_{50}$ (μM) |
|---|---|---|---|---|---|
| 84 | 4-[5-ethylsulfonyl-2-(2-hydroxyethoxy)phenyl]-2-methyl-6-(1-methylpyrazol-4-yl)isoquinolin-1-one | A | B | A | B |
| 85 | 4-[2-(2-aminoethoxy)-5-ethylsulfonylphenyl]-2-methyl-6-(1-methylpyrazol-4-yl)isoquinolin-1-one | A | C | B | C |
| 86 | N-[2-fluoro-4-methoxy-5-[2-methyl-6-(1-methylpyrazol-4-yl)-1-oxoisoquinolin-4-yl]phenyl]ethanesulfonamide | A | A | A | B |
| 87 | N-[3-(2-methyl-1-oxo-6-pyridin-2-ylisoquinolin-4-yl)phenyl] ethanesulfonamide | B | B | A | C |
| 88 | 4-[4-fluoro-2-methoxy-5-(methylsulfonylmethyl)phenyl]-2-methyl-6-(1-methylpyrazol-4-yl) isoquinolin-1-one | A | A | A | C |
| 89 | 4-[2-(cyclopropylmethoxy)-5-methylsulfonylphenyl]-2-methylisoquinolin-1-one | A | A | A | C |
| 90 | 4-[2-(cyclopropylmethoxy)-5-methylsulfonylphenyl]-6-fluoro-2-methylisoquinolin-1-one | A | A | A | |
| 91 | 4-[2-(cyclopropylmethoxy)-5-methylsulfonylphenyl]-7-fluoro-2-methylisoquinolin-1-one | A | A | A | C |
| 92 | 4-[2-(2,4-difluorophenoxy)-5-methylsulfonylphenyl]-2-methylisoquinolin-1-one | A | A | A | C |
| 93 | N-[4-(2,4-difluorophenoxy)-3-(2-methyl-1-oxoisoquinolin-4-yl)phenyl] ethanesulfonamide | A | A | A | C |
| 94 | N-[3-(1-methyl-6-oxopyridin-3-yl)phenyl]methanesulfonamide | B | A | C | |
| 95 | N-[3-(1,4-dimethyl-6-oxopyridin-3-yl)phenyl]methanesulfonamide | B | | | |
| 96 | N-[3-(1,5-dimethyl-6-oxopyridin-3-yl)phenyl]methanesulfonamide | B | | | |
| 97 | N-[3-(1,4,5-trimethyl-6-oxopyridin-3-yl)phenyl]methanesulfonamide | B | | | |
| 98 | 5-[2-(cyclopropylmethoxy)-5-methylsulfonylphenyl]-1-methylpyridin-2-one | B | B | B | C |
| 99 | N-[4-(2,4-difluorophenoxy)-3-(1-methyl-6-oxopyridin-3-yl)phenyl]ethanesulfonamide | A | A | A | C |
| 100 | N-[4-(2,4-difluorophenoxy)-3-(1-methyl-6-oxopyridin-3-yl)phenyl] methanesulfonamide | A | A | A | C |
| 101 | N-[4-(2,4-difluorophenoxy)-3-(1,4-dimethyl-6-oxopyridin-3-yl)phenyl]methanesulfonamide | A | A | A | C |
| 102 | N-[4-(2,4-difluorophenoxy)-3-(1,5-dimethyl-6-oxopyridin-3-yl)phenyl]methanesulfonamide | A | A | A | C |
| 103 | N-[4-(2,4-difluorophenoxy)-3-(1,4,5-trimethyl-6-oxopyridin-3-yl)phenyl]methanesulfonamide | A | B | A | C |
| 104 | 3-amino-1-methyl-5-(3-methylsulfonylphenyl)pyrazin-2-one | C | | | |
| 105 | 3-amino-5-(3-ethylsulfonylphenyl)-1-methylpyrazin-2-one | C | | | |
| 106 | N-[5-(6-amino-4-methyl-5-oxopyrazin-2-yl)-2-methoxyphenyl] methanesulfonamide | C | | | |
| 107 | 3-amino-1-methyl-5-(3-methylsulfonylphenyl)pyridin-2-one | C | | | |
| 108 | 3-amino-5-(3-ethylsulfonylphenyl)-1-methylpyridin-2-one | C | | | |
| 109 | N-[5-(5-amino-1-methyl-6-oxopyridin-3-yl)-2-methoxyphenyl] methanesulfonamide | B | C | C | C |
| 110 | N-[2-methoxy-5-[1-methyl-5-(methylamino)-6-oxopyridin-3-yl]phenyl]methanesulfonamide | A | C | B | C |

TABLE 24-continued

| Chem. Synth. Example | Name | BRD4 IC$_{50}$ (μM) | Raji IC$_{50}$ (μM) | HL-60 IC$_{50}$ (μM) | H460 IC$_{50}$ (μM) |
|---|---|---|---|---|---|
| 111 | N-[5-[5-(ethylamino)-1-methyl-6-oxopyridin-3-yl]-2-methoxyphenyl] methanesulfonamide | B | | | |
| 112 | N-[5-[5-(cyclopropylmethylamino)-1-methyl-6-oxopyridin-3-yl]-2-methoxyphenyl]methanesulfonamide | B | | | |
| 113 | N-[5-[5-(dimethylamino)-1-methyl-6-oxopyridin-3-yl]-2-methoxyphenyl] methanesulfonamide | A | B | A | B |
| 114 | N-[5-[5-(diethylamino)-1-methyl-6-oxopyridin-3-yl]-2-methoxyphenyl]methanesulfonamide | B | | | |
| 115 | N-[3-(5-amino-1-methyl-6-oxopyridin-3-yl)-4-(2,4-difluorophenoxy)phenyl] ethane-sulfonamide | A | A | A | C |
| 116 | 3-amino-5-[2-(cyclopropylmethoxy)-5-methylsulfonylphenyl]-1-methylpyridin-2-one | A | C | B | C |
| 117 | 4-ethoxy-3-(1-methyl-6-oxopyridin-3-yl) benzenesulfonamide | A | B | B | C |
| 118 | 4-(2,4-difluorophenoxy)-3-(1-methyl-6-oxopyridin-3-yl)benzenesulfonamide | A | A | A | C |
| 119 | 5-[2-(cyclopropylmethoxy)-5-methylsulfonylphenyl]-3-fluoro-1-methylpyridin-2-one | B | B | B | C |
| 120 | 5-[2-(2,4-difluorophenoxy)-5-methylsulfonylphenyl]-3-fluoro-1-methylpyridin-2-one | B | C | B | C |
| 121 | 5-[2-(2,4-difluorophenoxy)-5-ethylsulfonylphenyl]-3-fluoro-1-methylpyridin-2-one | A | B | A | C |
| 122 | N-[4-(2,4-difluorophenoxy)-3-(5-fluoro-1-methyl-6-oxopyridin-3-yl)phenyl]ethanesulfonamide | A | A | A | C |
| 123 | N-[3-(2-methyl-1-oxo-2,6-naphthyridin-4-yl)phenyl]ethanesulfonamide | B | B | B | C |
| 124 | N-ethyl-3-(2-methyl-1-oxo-2,6-naphthyridin-4-yl)benzenesulfonamide | B | | | |
| 125 | N-[3-(2-methyl-1-oxo-2,6-naphthyridin-4-yl)phenyl]methanesulfonamide | B | | | |
| 126 | 4-(3-ethylsulfonylphenyl)-2-methyl-2,6-naphthyridin-1-one | C | | | |
| 127 | N-[4-(2,4-difluorophenoxy)-3-(2-methyl-1-oxo-2,6-naphthyridin-4-yl)phenyl]ethanesulfonamide | A | A | A | C |
| 128 | 4-[2-(cyclopropylmethoxy)-5-methylsulfonylphenyl]-2-methyl-6-(4-methylpyrazol-1-yl)isoquinolin-1-one | A | A | A | C |
| 129 | N-[4-(2,4-difluorophenoxy)-3-(7-methyl-8-oxoimidazo[1,5-a]pyrazin-5-yl) phenyl]ethanesulfonamide | A | A | A | C |
| 130 | 5-[2-(cyclopropylmethoxy)-5-methylsulfonylphenyl]-7-methylimidazo[1,5-a]pyrazin-8-one | A | B | A | C |
| 131 | 7-methyl-5-(3-methylsulfonylphenyl) imidazo [1,5-a]pyrazin-8-one | C | | | |
| 132 | N-[2-methoxy-5-(7-methyl-8-oxoimidazo[1,5-a]pyrazin-5-yl)phenyl]methanesulfonamide | B | C | B | B |
| 133 | 5-(3-ethylsulfonylphenyl)-7-methylimidazo[1,5-a]pyrazin-8-one | C | | | |
| 134 | N-[3-(5-chloro-1-methyl-6-oxopyridin-3-yl)-4-(2,4-difluorophenoxy)phenyl] ethane-sulfonamide | A | A | A | B |
| 135 | 4-[2-(cyclopropylmethoxy)-5-ethylsulfonylphenyl]-2-methylisoquinolin-1-one | A | A | A | B |

TABLE 24-continued

| Chem. Synth. Example | Name | BRD4 IC$_{50}$ (μM) | Raji IC$_{50}$ (μM) | HL-60 IC$_{50}$ (μM) | H460 IC$_{50}$ (μM) |
|---|---|---|---|---|---|
| 136 | 6-[2-(cyclopropylmethoxy)-5-methylsulfonylphenyl]-2,4-dimethylpyridazin-3-one | B | C | B | C |
| 137 | 6-[2-(cyclopropylmethoxy)-5-methylsulfonylphenyl]-2,5-dimethylpyridazin-3-one | B | | | |
| 138 | N-[4-(2,4-difluorophenoxy)-3-[1-methyl-6-oxo-5-(trifluoromethyl)pyridin-3-yl] phenyl]ethanesulfonamide | A | A | A | C |
| 139 | N-[4-(2,4-difluorophenoxy)-3-(4-fluoro-1-methyl-6-oxopyridin-3-yl) phenyl]ethanesulfonamide | A | A | A | C |
| 140 | N-[3-(5-cyclopropyl-1-methyl-6-oxopyridin-3-yl)-4-(2,4-difluorophenoxy) phenyl]ethanesulfonamide | A | A | A | C |
| 141 | N-{4-(2,4-difluorophenoxy)-3-[1-($^2$H$_3$)methyl-6-oxopyridin-3-yl]phenyl} ethanesulfonamide | A | | | |
| 142 | N-[4-(2,4-difluorophenoxy)-3-(2-methyl-1-oxo-5,6,7,8-tetrahydro-2,6-naph-thyridin-4-yl)phenyl] ethanesulfonamide | B | | | |
| 143 | 4-[5-(cyclopropylmethoxy)-2-(methylsulfonylmethyl)pyrimidin-4-yl]-2-methylisoquinolin-1-one | A | B | B | C |
| 144 | 5-[5-(cyclopropylmethoxy)-2-(methylsulfonylmethyl)pyrimidin-4-yl]-1,3-dimethylpyridin-2-one | A | C | B | C |
| 145 | 4-[5-(cyclopropylmethoxy)-2-(methylsulfonylmethyl)pyrimidin-4-yl]-2-methyl-6-(1-methylpyrazol-4-yl) isoquinolin-1-one | A | B | A | C |
| 146 | 5-[5-(2,4-difluorophenoxy)-2-(methylsulfonylmethyl)pyrimidin-4-yl]-3-methoxy-1-methylpyridin-2-one | A | B | | C |
| 147 | 5-[5-(2,4-difluorophenoxy)-2-(methylsulfonylmethyl)pyrimidin-4-yl]-1,3-dimethylpyridin-2-one | A | B | | C |
| 148 | 4-[5-(2,4-difluorophenoxy)-2-(methylsulfonylmethyl)pyrimidin-4-yl]-2-methylisoquinolin-1-one | A | C | | |
| 149 | 5-[5-(2,4-difluorophenoxy)-2-methylsulfonylpyrimidin-4-yl]-1,3-dimethylpyridin-2-one | B | C | C | C |
| 150 | 5-[5-(2,4-difluorophenoxy)-2-methylsulfonylpyrimidin-4-yl]-3-methoxy-1-methylpyridin-2-one | A | B | B | C |
| 151 | 4-[5-(2,4-difluorophenoxy)-2-methylsulfonylpyrimidin-4-yl]-2-methylisoquinolin-1-one | A | | | |
| 152 | N-[5-(cyclopropylmethoxy)-4-(2-methyl-1-oxoisoquinolin-4-yl)pyrimidin-2-yl] methanesulfonamide | A | A | A | C |
| 153 | N-[5-(cyclopropylmethoxy)-4-(1,5-dimethyl-6-oxopyridin-3-yl)pyrimidin-2-yl] methanesulfonamide | A | B | B | C |
| 154 | N-[5-(cyclopropylmethoxy)-4-[2-methyl-6-(1-methylpyrazol-4-yl)-1-oxoisoquinolin-4-yl]pyrimidin-2-yl] methanesulfonamide | A | A | A | C |
| 155 | N-[5-(cyclopropylmethoxy)-4-(2-methyl-1-oxoisoquinolin-4-yl)pyrimidin-2-yl] ethanesulfonamide | A | A | A | C |
| 156 | 4-[5-(cyclopropylmethoxy)-2-(1,1-dioxo-1,2-thiazolidin-2-yl)pyrimidin-4-yl]-2-methylisoquinolin-1-one | A | | | |
| 157 | N-[5-(cyclopropylmethoxy)-4-(6-fluoro-2-methyl-1-oxoisoquinolin-4-yl)pyrimidin-2-yl]ethanesulfonamide | A | A | A | C |

TABLE 24-continued

| Chem. Synth. Example | Name | BRD4 IC$_{50}$ (μM) | Raji IC$_{50}$ (μM) | HL-60 IC$_{50}$ (μM) | H460 IC$_{50}$ (μM) |
|---|---|---|---|---|---|
| 158 | N-[5-(cyclopropylmethoxy)-4-(7-fluoro-2-methyl-1-oxoisoquinolin-4-yl)pyrimidin-2-yl]methanesulfonamide | A | A | A | C |
| 159 | N-[5-(cyclopropylmethoxy)-4-(6-fluoro-2-methyl-1-oxoisoquinolin-4-yl)pyrimidin-2-yl]methanesulfonamide | A | A | A | C |
| 160 | N-[5-(cyclopropylmethoxy)-4-(7-fluoro-2-methyl-1-oxoisoquinolin-4-yl)pyrimidin-2-yl]ethanesulfonamide | A | A | A | C |
| 161 | N-[5-(cyclopropylmethoxy)-4-(2-methyl-1-oxoisoquinolin-4-yl)pyrimidin-2-yl]-N-ethylmethanesulfonamide | A | A | A | C |
| 162 | N-[5-(cyclopropylmethoxy)-4-(1,5-dimethyl-6-oxopyridin-3-yl)pyrimidin-2-yl]-N-ethylmethanesulfonamide | A | A | A | C |
| 163 | N-[5-(cyclopropylmethoxy)-4-(2-methyl-1-oxo-5,6,7,8-tetrahydroisoquinolin-4-yl)pyrimidin-2-yl]methanesulfonamide | A | A | B | C |
| 164 | N-[5-(cyclopropylmethoxy)-4-(2-methyl-1-oxo-5,6,7,8-tetrahydroisoquinolin-4-yl)pyrimidin-2-yl]ethanesulfonamide | A | A | B | C |
| 165 | N-[5-(2,4-difluorophenoxy)-4-(2-methyl-1-oxoisoquinolin-4-yl)pyrimidin-2-yl]methanesulfonamide | A | B | | C |
| 166 | N-[5-(2,4-difluorophenoxy)-4-(1,5-dimethyl-6-oxopyridin-3-yl)pyrimidin-2-yl]methanesulfonamide | A | A | A | C |
| 167 | N-[5-(2,4-difluorophenoxy)-4-(5-methoxy-1-methyl-6-oxopyridin-3-yl) pyrimidin-2-yl]methanesulfonamide | A | B | | C |
| 168 | N-[5-(2,4-difluorophenoxy)-4-(5-methoxy-1-methyl-6-oxopyridin-3-yl) pyrimidin-2-yl]ethanesulfonamide | A | A | A | C |
| 169 | N-[5-(2,4-difluorophenoxy)-4-(1,5-dimethyl-6-oxopyridin-3-yl)pyrimidin-2-yl] ethanesulfonamide | A | A | A | C |
| 170 | N-[5-(2,4-difluorophenoxy)-4-(2-methyl-1-oxoisoquinolin-4-yl)pyrimidin-2-yl] ethanesulfonamide | A | A | A | C |
| 171 | 4-[5-(2,4-difluorophenoxy)-2-(1,1-dioxo-1,2-thiazolidin-2-yl)pyrimidin-4-yl]-2-methylisoquinolin-1-one | A | | | |
| 172 | N-[5-(2,4-difluorophenoxy)-4-(2-methyl-1-oxo-5,6,7,8-tetrahydroisoquinolin-4-yl)pyrimidin-2-yl]methanesulfonamide | A | B | B | C |
| 173 | N-[5-(2,4-difluorophenoxy)-4-(2-methyl-1-oxo-5,6,7,8-tetrahydroisoquinolin-4-yl)pyrimidin-2-yl]ethanesulfonamide | A | B | B | C |
| 174 | 4-[2-(cyclopropylmethoxy)-5-ethylsulfonylphenyl]-6-fluoro-2-methylisoquinolin-1-one | A | A | A | C |
| 175 | 2-methyl-4-[5-methylsulfonyl-2-(oxolan-3-yloxy)phenyl]isoquinolin-1-one | A | A | A | C |
| 176 | 2-methyl-4-[5-methylsulfonyl-2-(oxan-4-yloxy)phenyl]isoquinolin-1-one | A | A | A | C |

TABLE 24-continued

| Chem. Synth. Example | Name | BRD4 IC$_{50}$ (μM) | Raji IC$_{50}$ (μM) | HL-60 IC$_{50}$ (μM) | H460 IC$_{50}$ (μM) |
|---|---|---|---|---|---|
| 177 | 4-(2-ethoxy-5-methylsulfonylphenyl)-2-methylisoquinolin-1-one | A | B | A | C |
| 178 | 2-methyl-4-(5-methylsulfonyl-2-propoxyphenyl)isoquinolin-1-one | A | A | A | C |
| 179 | 2-methyl-4-[5-methylsulfonyl-2-(oxan-3-yloxy)phenyl]isoquinolin-1-one | A | A | A | C |
| 180 | 4-[2-(trans-4-hydroxycyclohexyl)oxy-5-methylsulfonylphenyl]-2-methylisoquinolin-1-one | A | A | A | C |
| 181 | 4-[5-ethylsulfonyl-2-(trans-4-hydroxycyclohexyl)oxyphenyl]-2-methylisoquinolin-1-one | A | A | A | C |
| 182 | 4-[2-(trans-4-aminocyclohexyl)oxy-5-methylsulfonylphenyl]-2-methylisoquinolin-1-one | A | A | A | C |
| 183 | 4-[2-(cis-4-aminocyclohexyl)oxy-5-methylsulfonylphenyl]-2-methylisoquinolin-1-one | A | C | B | C |
| 184 | 4-(2-but-2-ynoxy-5-methylsulfonylphenyl)-2-methylisoquinolin-1-one | A | B | A | B |
| 185 | 4-(2-but-2-ynoxy-5-ethylsulfonylphenyl)-2-methylisoquinolin-1-one | A | A | A | C |
| 186 | 6-fluoro-4-[2-(trans-4-hydroxycyclohexyl)oxy-5-methylsulfonylphenyl]-2-methylisoquinolin-1-one | A | A | A | C |
| 187 | 7-fluoro-4-[2-(trans-4-hydroxycyclohexyl)oxy-5-methylsulfonylphenyl]-2-methylisoquinolin-1-one | A | A | A | C |
| 188 | 4-[5-ethylsulfonyl-2-(trans-4-hydroxycyclohexyl)oxyphenyl]-6-fluoro-2-methylisoquinolin-1-one | A | A | | |
| 189 | 4-[5-ethylsulfonyl-2-(trans-4-hydroxycyclohexyl)oxyphenyl]-7-fluoro-2-methylisoquinolin-1-one | A | A | | |
| 190 | 2-methyl-4-[5-methylsulfonyl-2-(oxolan-3-ylamino)phenyl]isoquinolin-1-one | A | B | B | C |
| 191 | 2-methyl-4-[5-methylsulfonyl-2-(oxan-4-ylamino)phenyl]isoquinolin-1-one | A | A | A | C |
| 192 | 4-[2-[(trans-4-hydroxycyclohexyl)amino]-5-methylsulfonylphenyl]-2-methylisoquinolin-1-one | A | A | A | C |
| 193 | 4-[2-(cyclopropylmethylamino)-5-ethylsulfonylphenyl]-2-methylisoquinolin-1-one | A | A | A | C |
| 194 | 4-[2-(cyclopropylmethylamino)-5-methylsulfonylphenyl]-2-methylisoquinolin-1-one | A | A | A | C |
| 195 | 4-[2-(cyclopropylmethylamino)-5-ethylsulfonylphenyl]-7-fluoro-2-methylisoquinolin-1-one | A | A | A | C |
| 196 | 4-[2-(cyclopropylmethylamino)-5-methylsulfonylphenyl]-7-fluoro-2-methylisoquinolin-1-one | A | A | A | C |
| 197 | 4-[2-(cyclopropylmethoxy)-5-methylsulfonylphenyl]-2-methyl-6-(trifluoromethyl)isoquinolin-1-one | A | B | | C |
| 198 | 4-[2-(cyclopropylmethoxy)-5-methylsulfonylphenyl]-6-methoxy-2-methylisoquinolin-1-one | A | A | A | C |
| 199 | 4-[3-(cyclopropylmethoxy)-6-methylsulfonylpyridin-2-yl]-2-methylisoquinolin-1-one | A | A | A | C |
| 200 | 4-[5-(cyclopropylmethoxy)-2-methylsulfonylpyridin-4-yl]-2-methylisoquinolin-1-one | A | B | A | C |

TABLE 24-continued

| Chem. Synth. Example | Name | BRD4 IC$_{50}$ (μM) | Raji IC$_{50}$ (μM) | HL-60 IC$_{50}$ (μM) | H460 IC$_{50}$ (μM) |
|---|---|---|---|---|---|
| 201 | 4-[3-(cyclopropylmethoxy)-6-methylsulfonylpyridin-2-yl]-7-fluoro-2-methylisoquinolin-1-one | A | A | A | C |
| 202 | 4-[3-(cyclopropylmethoxy)-6-methylsulfonylpyridin-2-yl]-6-fluoro-2-methylisoquinolin-1-one | A | A | | C |
| 203 | 4-[5-(cyclopropylmethoxy)-2-methylsulfonylpyridin-4-yl]-7-fluoro-2-methylisoquinolin-1-one | A | A | A | C |
| 204 | 4-(2-ethoxy-5-ethylsulfonylthiophen-3-yl)-2-methylisoquinolin-1-one | A | B | B | C |
| 205 | 4-[2-(cyclopropylmethylamino)-5-ethylsulfonylthiophen-3-yl]-2-methylisoquinolin-1-one | A | B | B | C |
| 206 | 4-[3-(cyclopropylmethoxy)-6-ethylsulfonylpyridin-2-yl]-2-methylisoquinolin-1-one | A | A | A | C |
| 207 | 4-[5-(cyclopropylmethoxy)-2-ethylsulfonylpyridin-4-yl]-2-methylisoquinolin-1-one | A | A | A | C |
| 208 | 4-[5-(2-hydroxyethylsulfonyl)-2-methoxyphenyl]-2-methyl-6-(1-methylpyrazol-4-yl)isoquinolin-1-one | A | B | A | C |
| 209 | N-[4-(cyclopropylmethoxy)-2-fluoro-5-[2-methyl-6-(1-methylpyrazol-4-yl)-1-oxoisoquinolin-4-yl]phenyl] ethanesulfonamide | A | A | A | C |
| 210 | 4-(5-ethylsulfonyl-2-methoxyphenyl)-2-methyl-6-(1H-pyrazol-4-yl) isoquinolin-1-one | A | A | A | C |
| 211 | 4-(2-ethoxy-5-methylsulfonylphenyl)-2-methyl-6-(1-methylpyrazol-4-yl) isoquinolin-1-one | A | | | |
| 212 | 2-methyl-6-(1-methylpyrazol-4-yl)-4-(5-methylsulfonyl-2-propoxyphenyl) isoquinolin-1-one | A | | | |
| 213 | N-[2-[2-methyl-6-(1-methylpyrazol-4-yl)-1-oxoisoquinolin-4-yl]pyridin-4-yl] ethanesulfonamide | A | B | B | C |
| 214 | [4-(cyclopropylmethoxy)-3-(2-methyl-1-oxoisoquinolin-4-yl)phenyl] sulfamate | A | A | A | C |
| 215 | [4-(cyclopropylmethoxy)-3-(1,5-dimethyl-6-oxopyridin-3-yl) phenyl]sulfamate | A | A | A | C |
| 216 | 4-(2-ethoxy-5-methylsulfonylphenyl)-2-methyl-5,6,7,8-tetrahydroisoquinolin-1-one | A | | | |
| 217 | 4-[2-(cyclopropylmethoxy)-5-methylsulfonylphenyl]-2-methyl-5,6,7,8-tetrahydroisoquinolin-1-one | A | A | A | C |
| 218 | N-[4-(cyclopropylmethoxy)-2-fluoro-5-(2-methyl-1-oxo-5,6,7,8-tetrahydroisoquinolin-4-yl)phenyl] methanesulfonamide | A | B | A | C |
| 219 | 4-[2-(cyclopropylmethoxy)-5-ethylsulfonylphenyl]-2-methyl-5,6,7,8-tetrahydroisoquinolin-1-one | A | A | A | C |
| 220 | N-[2-(2-methyl-1-oxoisoquinolin-4-yl)-4-methylsulfonylphenyl] cyclopropanecarboxamide | B | C | C | C |
| 221 | N-[2-(2-methyl-1-oxoisoquinolin-4-yl)-4-methylsulfonylphenyl]propanamide | C | C | C | C |
| 222 | N-[2-(2-methyl-1-oxoisoquinolin-4-yl)-4-methylsulfonylphenyl]acetamide | C | C | C | C |
| 223 | 4-[2-(cyclopropylmethylamino)-5-methylsulfonylphenyl]-2-methyl-5,6,7,8-tetrahydroisoquinolin-1-one | A | B | A | C |

TABLE 24-continued

| Chem. Synth. Example | Name | BRD4 IC$_{50}$ (μM) | Raji IC$_{50}$ (μM) | HL-60 IC$_{50}$ (μM) | H460 IC$_{50}$ (μM) |
|---|---|---|---|---|---|
| 224 | 8-[2-(cyclopropylmethoxy)-5-methylsulfonylphenyl]-6-methyl-2-(1-methylpyrazol-4-yl)pyrido[4,3-d] pyrimidin-5-one | A | A | A | C |
| 225 | 8-(5-ethylsulfonyl-2-propoxyphenyl)-6-methyl-2-(1-methylpyrazol-4-yl) pyrido[4,3-d]pyrimidin-5-one | A | A | A | C |
| 226 | 8-[2-(cyclopropylmethoxy)-5-ethylsulfonylphenyl]-6-methyl-2-(1-methylpyrazol-4-yl)pyrido[4,3-d]pyrimidin-5-one | A | A | A | C |
| 227 | 8-(2-ethoxy-5-ethylsulfonylphenyl)-6-methyl-2-(1-methylpyrazol-4-yl)pyrido[4,3-d]pyrimidin-5-one | A | B | A | C |
| 228 | 6-methyl-2-(1-methylpyrazol-4-yl)-8-(5-methylsulfonyl-2-propoxyphenyl)pyrido[4,3-d]pyrimidin-5-one | A | B | A | C |
| 229 | N-[4-(2,4-difluorophenoxy)-3-(1,5-dimethyl-6-oxopyridin-3-yl)phenyl]-N-methylmethanesulfonamide | A | A | A | C |
| 230 | N-[4-(2,4-difluorophenoxy)-3-(1,5-dimethyl-6-oxopyridin-3-yl)phenyl]-N-(oxetan-3-yl)methanesulfonamide | A | A | A | C |
| 231 | 8-[2-(cyclopropylmethoxy)-5-methylsulfonylphenyl]-6-methylpyrido[4,3-d]pyrimidin-5-one | B | | | |
| 232 | 8-[2-(cyclopropylmethoxy)-5-ethylsulfonylphenyl]-6-methylpyrido[4,3-d] pyrimidin-5-one | A | | | |
| 233 | 8-[2-(2,4-difluorophenoxy)-5-methylsulfonylphenyl]-6-methylpyrido[4,3-d]pyrimidin-5-one | B | | | |
| 234 | 8-[2-(2,4-difluorophenoxy)-5-ethylsulfonylphenyl]-6-methylpyrido[4,3-d] pyrimidin-5-one | B | | | |
| 235 | 5-[2-(cyclopropylmethoxy)-5-methylsulfonylphenyl]-7-methyl-[1,2,4]triazolo[4,3-a]pyrazin-8-one | C | C | C | C |
| 236 | N-[4-(2,4-difluorophenoxy)-3-(7-methyl-8-oxo-[1,2,4]triazolo[4,3-a]pyrazin-5-yl)phenyl]ethanesulfonamide | A | C | B | C |
| 237 | 7-[2-(cyclopropylmethoxy)-5-methylsulfonylphenyl]-5-methyl-[1,3]oxazolo[4,5-c]pyridin-4-one | A | | | |
| 238 | 7-[2-(cyclopropylmethoxy)-5-methylsulfonylphenyl]-2,5-dimethyl-[1,3]oxazolo[4,5-c]pyridin-4-one | A | B | A | C |
| 239 | 5-methyl-7-[5-(methylsulfonylmethyl)-2-(2,2,2-trifluoroethoxy)phenyl]-[1,3]oxazolo[4,5-c]pyridin-4-one | A | | | |
| 240 | N-[4-(2,4-difluorophenoxy)-3-(5-methyl-4-oxo-[1,3]oxazolo[4,5-c]pyridin-7-yl) phenyl]ethanesulfonamide | A | A | A | C |
| 241 | N-[4-(2,4-difluorophenoxy)-3-(2,5-dimethyl-4-oxo-[1,3]oxazolo[4,5-c]pyridin-7-yl)phenyl]ethanesulfonamide | A | A | A | C |
| 242 | 5-[2-(cyclopropylmethoxy)-5-methylsulfonylphenyl]-1-(cyclopropylmethyl)-3-methylpyridin-2-one | A | B | A | C |
| 243 | 5-[2-(cyclopropylmethoxy)-5-methylsulfonylphenyl]-3-methyl-1-(2-methylpropyl)pyridin-2-one | B | C | B | C |

TABLE 24-continued

| Chem. Synth. Example | Name | BRD4 IC$_{50}$ (μM) | Raji IC$_{50}$ (μM) | HL-60 IC$_{50}$ (μM) | H460 IC$_{50}$ (μM) |
|---|---|---|---|---|---|
| 244 | 5-[2-(cyclopropylmethoxy)-5-methylsulfonylphenyl]-1-(2-methoxyethyl)-3-methylpyridin-2-one | B | C | B | C |
| 245 | 5-[2-(cyclopropylmethoxy)-5-methylsulfonylphenyl]-3-methyl-1-(oxetan-3-ylmethyl)pyridin-2-one | B | C | C | C |
| 246 | 5-[2-(cyclopropylmethoxy)-5-methylsulfonylphenyl]-3-methyl-1-(1,3-oxazol-4-ylmethyl)pyridin-2-one | B | C | C | C |
| 247 | N-[3-[1-(cyclopropylmethyl)-5-methyl-6-oxopyridin-3-yl]-4-(2,4-difluorophenoxy) phenyl]ethanesulfonamide | A | A | A | C |
| 248 | N-[4-[1-(cyclopropylmethyl)-5-methyl-6-oxopyridin-3-yl]-5-(2,4-difluorophenoxy) pyrimidin-2-yl]methanesulfonamide | A | A | A | C |
| 249 | N-[4-[1-(cyclopropylmethyl)-5-methyl-6-oxopyridin-3-yl]-5-(2,4-difluorophenoxy)pyrimidin-2-yl]ethanesulfonamide | A | A | A | C |
| 250 | 1-(cyclopropylmethyl)-5-[4-(2,4-difluorophenoxy)-1-(methylsulfonylmethyl)-6-oxopyridin-3-yl]-3-methylpyridin-2-one | A | B | A | C |
| 251 | 1-cyclopropyl-5-[2-(cyclopropylmethoxy)-5-ethylsulfonylphenyl]-3-methylpyridin-2-one | A | B | A | C |
| 252 | 4-[2-(cyclopropylmethoxy)-5-ethylsulfonylphenyl]-6-methylfuro[2,3-c]pyridin-7-one | A | A | A | C |
| 253 | N-[4-(2,4-difluorophenoxy)-3-(6-methyl-7-oxofuro[2,3-c]pyridin-4-yl)phenyl]ethanesulfonamide | A | A | A | C |
| 254 | 4-[2-(cyclopropylmethoxy)-5-methylsulfonylphenyl]-6-methylfuro[2,3-c]pyridin-7-one | A | A | A | C |
| 255 | N-[4-(cyclopropylmethoxy)-3-(6-methyl-7-oxofuro[2,3-c]pyridin-4-yl) phenyl]ethanesulfonamide | A | A | A | C |
| 256 | N-[6-(2,4-difluorophenoxy)-5-(6-methyl-7-oxofuro[2,3-c]pyridin-4-yl)pyridin-3-yl]ethanesulfonamide | A | A | A | C |
| 257 | N-[6-(cyclopropylmethoxy)-5-(6-methyl-7-oxofuro[2,3-c]pyridin-4-yl)pyridin-3-yl]ethanesulfonamide | A | A | A | C |
| 258 | 6-methyl-4-[5-(methylsulfonylmethyl)-2-(2,2,2-trifluoroethoxy)phenyl]furo[2,3-c] pyridin-7-one | A | B | A | B |
| 259 | 4-[3-(cyclopropylmethoxy)-6-methylsulfonylpyridin-2-yl]-6-methylfuro[2,3-c]pyridin-7-one | A | B | A | C |
| 260 | 2-chloro-4-[2-(cyclopropylmethoxy)-5-methylsulfonylphenyl]-6-methylfuro[2,3-c]pyridin-7-one | A | A | A | B |
| 261 | N-[6-(cyclopropylmethoxy)-5-(2-fluoro-6-methyl-7-oxofuro[2,3-c]pyridin-4-yl)pyridin-3-yl]ethanesulfonamide | A | A | A | C |
| 262 | N-[5-(2,4-difluorophenoxy)-4-(6-methyl-7-oxofuro[2,3-c]pyridin-4-yl)pyrimidin-2-yl]methanesulfonamide | A | A | A | C |
| 263 | N-[5-(2,4-difluorophenoxy)-4-(6-methyl-7-oxofuro[2,3-c]pyridin-4-yl)pyrimidin-2-yl]ethanesulfonamide | A | A | A | C |
| 264 | N-[5-(cyclopropylmethoxy)-4-(6-methyl-7-oxofuro[2,3-c]pyridin-4-yl)pyrimidin-2-yl]ethanesulfonamide | A | A | A | C |

TABLE 24-continued

| Chem. Synth. Example | Name | BRD4 IC$_{50}$ (μM) | Raji IC$_{50}$ (μM) | HL-60 IC$_{50}$ (μM) | H460 IC$_{50}$ (μM) |
|---|---|---|---|---|---|
| 265 | 4-[2-(cyclopropylmethoxy)-5-ethylsulfonylphenyl]-6-methyl-7-oxothieno[2,3-c]pyridine-2-carboxamide | A | A | A | C |
| 266 | 4-[2-(cyclopropylmethoxy)-5-(ethylsulfonylamino)phenyl]-6-methyl-7-oxothieno[2,3-c]pyridine-2-carboxamide | A | A | A | C |
| 267 | 4-[2-(cyclopropylmethoxy)-5-methylsulfonylphenyl]-6-methyl-7-oxothieno[2,3-c]pyridine-2-carboxamide | A | B | A | C |
| 268 | 4-[2-(cyclopropylmethoxy)-5-(ethylsulfonylamino)pyridin-3-yl]-6-methyl-7-oxothieno[2,3-c]pyridine-2-carboxamide | A | B | A | C |
| 269 | N-[4-(2,4-difluorophenoxy)-3-(2,6-dimethyl-7-oxofuro[2,3-c]pyridin-4-yl)phenyl]ethanesulfonamide | A | A | A | C |
| 270 | 4-[2-(cyclopropylmethoxy)-5-ethylsulfonylphenyl]-2,6-dimethylfuro[2,3-c]pyridin-7-one | A | A | A | B |
| 271 | N-[4-(2,4-difluorophenoxy)-3-(5-fluoro-1-methyl-6-oxopyridin-3-yl)phenyl] methanesulfonamide | A | A | A | C |
| 272 | 3-chloro-5-[2-(cyclopropylmethoxy)-5-ethylsulfonylphenyl]-1-methylpyridin-2-one | A | A | A | C |
| 273 | 5-[5-(2,4-difluorophenoxy)-2-methylsulfonylpyrimidin-4-yl]-1-methyl-3-propan-2-ylpyridin-2-one | B | | | |
| 274 | 5-[2-(cyclopropylmethoxy)-5-ethylsulfonylphenyl]-3-fluoro-1-methylpyridin-2-one | A | B | B | C |
| 275 | 3-chloro-5-[2-(cyclopropylmethylamino)-5-ethylsulfonylphenyl]-1-methylpyridin-2-one | A | A | A | C |
| 276 | 5-[2-(2,4-difluorophenoxy)-5-(methanesulfonylmethyl)phenyl]-3-($^{2}$H$_3$)methyl-1-methyl-1,2-dihydropyridin-2-one | A | A | | |
| 277 | N-[4-(2,4-difluorophenoxy)-3-[5-($^{2}$H$_3$)methyl-1-methyl-6-oxo-1,6-dihydropyridin-3-yl]phenyl] methanesulfonamide | A | A | | |
| 278 | N-[4-(2,4-difluorophenoxy)-3-[5-($^{2}$H$_3$)methyl-1-methyl-6-oxo-1,6-dihydropyridin-3-yl]phenyl] ethane-1-sulfonamide | A | A | | |
| 279 | N-[3-(5-cyclopropyl-1-methyl-6-oxopyridin-3-yl)-4-(2,4-difluorophenoxy)phenyl]methanesulfonamide | A | A | A | C |
| 280 | 3-cyclopropyl-5-[2-(cyclopropyl-methoxy)-5-ethylsulfonylphenyl]-1-methylpyridin-2-one | A | A | A | C |
| 281 | N-[4-(2,4-difluorophenoxy)-3-(1-methyl-6-oxo-5-pyrrolidin-1-ylpyridin-3-yl)phenyl]methanesulfonamide | B | | | |
| 282 | 5-[2-(cyclopropylmethoxy)-5-ethylsulfonylphenyl]-1-methyl-3-pyrrolidin-1-ylpyridin-2-one | B | | | |
| 283 | N-[4-(2,4-difluorophenoxy)-3-(5-ethynyl-1-methyl-6-oxopyridin-3-yl)phenyl]ethanesulfonamide | A | B | A | C |
| 284 | 5-[2-(cyclopropylmethoxy)-5-ethylsulfonylphenyl]-3-ethynyl-1-methylpyridin-2-one | A | B | B | C |
| 285 | 5-[2-(cyclopropylmethoxy)-5-methylsulfonylphenyl]-3-ethynyl-1-methylpyridin-2-one | B | | | |

TABLE 24-continued

| Chem. Synth. Example | Name | BRD4 IC$_{50}$ (μM) | Raji IC$_{50}$ (μM) | HL-60 IC$_{50}$ (μM) | H460 IC$_{50}$ (μM) |
|---|---|---|---|---|---|
| 286 | N-[4-(2,4-difluorophenoxy)-3-(5-ethynyl-1-methyl-6-oxopyridin-3-yl) phenyl]methanesulfonamide | A | B | | C |
| 287 | 5-[2-(cyclopropylmethoxy)-5-ethylsulfonylphenyl]-3-(difluoromethoxy)-1-methylpyridin-2-one | A | B | A | C |
| 288 | 5-[2-(cyclopropylmethoxy)-5-ethylsulfonylphenyl]-1-methyl-3-(2,2,2-trifluoroethoxy)pyridin-2-one | A | B | | |
| 289 | N-[3-[5-(difluoromethoxy)-1-methyl-6-oxopyridin-3-yl]-4-(2,4-difluorophenoxy) phenyl]ethanesulfonamide | A | A | A | C |
| 290 | N-[4-(2,4-difluorophenoxy)-3-[1-methyl-6-oxo-5-(2,2,2-trifluoroethoxy)pyridin-3-yl] phenyl]ethanesulfonamide | A | A | A | C |
| 291 | 3-(difluoromethoxy)-5-[2-(2,4-difluorophenoxy)-5-(ethylsulfonylmethyl) phenyl]-1-methylpyridin-2-one | A | A | A | C |
| 292 | 5-[2-(2,4-difluorophenoxy)-5-(ethylsulfonylmethyl)phenyl]-1-methyl-3-(2,2,2-trifluoroethoxy)pyridin-2-one | A | B | A | C |
| 293 | 5-[2-(cyclopropylmethoxy)-5-methylsulfonylphenyl]-1-methyl-3-(1-methylpyrazol-4-yl)oxypyridin-2-one | A | B | B | C |
| 294 | 5-[2-(cyclopropylmethoxy)-5-methylsulfonylphenyl]-1-methyl-3-(1-propan-2-ylpyrazol-4-yl)oxypyridin-2-one | A | C | B | C |
| 295 | 5-[2-(cyclopropylmethoxy)-5-methylsulfonylphenyl]-1-methyl-3-phenoxypyridin-2-one | A | B | B | B |
| 296 | N-[4-(1-butyl-5-methyl-6-oxopyridin-3-yl)-5-(2,4-difluorophenoxy)pyrimidin-2-yl]methanesulfonamide | A | | | |
| 297 | N-[4-(1-butyl-5-methyl-6-oxopyridin-3-yl)-5-(2,4-difluorophenoxy)pyrimidin-2-yl]ethanesulfonamide | A | | | |
| 298 | N-[4-[1-(cyclobutylmethyl)-5-methyl-6-oxopyridin-3-yl]-5-(2,4-difluorophenoxy)pyrimidin-2-yl]methanesulfonamide | B | | | |
| 299 | N-[4-[1-(cyclobutylmethyl)-5-methyl-6-oxopyridin-3-yl]-5-(2,4-difluorophenoxy)pyrimidin-2-yl]ethanesulfonamide | B | | | |
| 300 | N-[5-ethyl-4-(2-methyl-1-oxoisoquinolin-4-yl)pyrimidin-2-yl]ethanesulfonamide | A | | | |
| 301 | 2-methyl-4-(2-methylsulfonyl-5-propylpyrimidin-4-yl)isoquinolin-1-one | | | | |
| 302 | 5-(5-ethyl-2-methylsulfonylpyrimidin-4-yl)-1,3-dimethylpyridin-2-one | | | | |
| 303 | 1,3-dimethyl-5-(2-methylsulfonyl-5-propylpyrimidin-4-yl)pyridin-2-one | | | | |
| 304 | 4-(5-butyl-2-methylsulfonylpyrimidin-4-yl)-2-methylisoquinolin-1-one | A | | | |
| 305 | 5-(5-butyl-2-methylsulfonylpyrimidin-4-yl)-1,3-dimethylpyridin-2-one | A | | | |
| 306 | N-[4-(2-methyl-1-oxoisoquinolin-4-yl)-5-propylpyrimidin-2-yl]ethanesulfonamide | A | | | |
| 307 | N-[4-(1,5-dimethyl-6-oxopyridin-3-yl)-5-ethylpyrimidin-2-yl]ethanesulfonamide | A | A | A | C |

TABLE 24-continued

| Chem. Synth. Example | Name | BRD4 IC$_{50}$ (μM) | Raji IC$_{50}$ (μM) | HL-60 IC$_{50}$ (μM) | H460 IC$_{50}$ (μM) |
|---|---|---|---|---|---|
| 308 | N-[4-(1,5-dimethyl-6-oxopyridin-3-yl)-5-propylpyrimidin-2-yl]ethanesulfonamide | A | A | A | C |
| 309 | N-[5-butyl-4-(2-methyl-1-oxoisoquinolin-4-yl)pyrimidin-2-yl] ethanesulfonamide | A | A | A | C |
| 310 | N-[5-butyl-4-(1,5-dimethyl-6-oxopyridin-3-yl)pyrimidin-2-yl]ethanesulfonamide | A | A | A | C |
| 311 | 4-[5-(cyclopropylmethoxy)-2-methylsulfonylpyrimidin-4-yl]-2-methylisoquinolin-1-one | A | | | |
| 312 | 5-(2-ethyl-5-methylsulfonylphenyl)-1-methylpyridin-2-one | B | C | C | C |
| 313 | 1-methyl-5-(5-methylsulfonyl-2-propylphenyl)pyridin-2-one | B | C | B | C |
| 314 | 2-methyl-4-(5-methylsulfonyl-2-propylphenyl)isoquinolin-1-one | A | | | |
| 315 | 5-[2-(2-cyclopropylethyl)-5-methylsulfonylphenyl]-1-methylpyridin-2-one | A | | | |
| 316 | 4-(2-ethyl-5-methylsulfonylphenyl)-2-methylisoquinolin-1-one | A | | | |
| 317 | 5-(2-butyl-5-methylsulfonylphenyl)-1-methylpyridin-2-one | A | | | |
| 318 | 4-(2-butyl-5-methylsulfonylphenyl)-2-methylisoquinolin-1-one | A | | | |
| 319 | 4-[2-(2-cyclopropylethyl)-5-methylsulfonylphenyl]-2-methylisoquinolin-1-one | A | | | |
| 320 | N-[6-(cyclopropylmethoxy)-5-(2-methyl-1-oxoisoquinolin-4-yl)pyridin-3-yl]ethanesulfonamide | A | A | A | C |
| 321 | 4-[2-(cyclopropylmethoxy)-5-methylsulfonylpyridin-3-yl]-2-methylisoquinolin-1-one | A | A | A | C |
| 322 | 4-[2-(cyclopropylmethoxy)-5-ethylsulfonylpyridin-3-yl]-2-methylisoquinolin-1-one | A | A | A | C |
| 323 | 5-[3-[(4-methoxyphenyl)methoxy]-5-methylsulfonylphenyl]-1,3-dimethylpyridin-2-one | A | | | |
| 324 | 1,3-dimethyl-5-(3-methylsulfonyl-5-phenylmethoxyphenyl)pyridin-2-one | A | B | A | C |
| 325 | 5-[3-(cyclopropylmethoxy)-5-methylsulfonylphenyl]-1,3-dimethylpyridin-2-one | A | B | B | C |
| 326 | 1,3-dimethyl-5-[3-methylsulfonyl-5-(2-phenylethoxy)phenyl]pyridin-2-one | A | B | B | C |
| 327 | 5-[3-(2-cyclopropylethoxy)-5-methylsulfonylphenyl]-1,3-dimethylpyridin-2-one | A | B | B | C |
| 328 | 1,3-dimethyl-5-[3-methylsulfonyl-5-(2,2,2-trifluoroethoxy)phenyl] pyridin-2-one | A | | | |
| 329 | 1,3-dimethyl-5-[3-[(3-methyloxetan-3-yl)methoxy]-5-methylsulfonylphenyl]pyridin-2-one | A | | | |
| 330 | 1,3-dimethyl-5-[3-methylsulfonyl-5-(pyridin-2-ylmethoxy) phenyl] pyridin-2-one | A | | | |
| 331 | 5-[3-[(2,6-dimethylphenyl)methoxy]-5-methylsulfonylphenyl]-1,3-dimethylpyridin-2-one | A | B | A | C |
| 332 | 5-[3-[(2-chlorophenyl)methoxy]-5-methylsulfonylphenyl]-1,3-dimethylpyridin-2-one | A | | | |

TABLE 24-continued

| Chem. Synth. Example | Name | BRD4 IC$_{50}$ (μM) | Raji IC$_{50}$ (μM) | HL-60 IC$_{50}$ (μM) | H460 IC$_{50}$ (μM) |
|---|---|---|---|---|---|
| 333 | 5-[3-[[2-(difluoromethoxy)phenyl]methoxy]-5-methylsulfonylphenyl]-1,3-dimethylpyridin-2-one | A | B | A | C |
| 334 | 2-[[3-(l,5-dimethyl-6-oxopyridin-3-yl)-5-methylsulfonyl-phenoxy] methyl]benzonitrile | A | B | A | C |
| 335 | 5-[3-[(2,4-difluorophenyl)methoxy]-5-methylsulfonylphenyl]-1,3-dimethylpyridin-2-one | A | | | |
| 336 | 1,3-dimethyl-5-[3-methylsulfonyl-5-(1-phenylethoxy)phenyl]pyridin-2-one | A | B | A | C |
| 337 | 5-[3-[(2,3-dichlorophenyl)methoxy]-5-methylsulfonylphenyl]-1,3-dimethylpyridin-2-one | B | | | |
| 338 | 1,3-dimethyl-5-[3-methylsulfonyl-5-(pyridin-3-ylmethoxy) phenyl]pyridin-2-one | A | | | |
| 339 | 3-[[3-(1,5-dimethyl-6-oxopyridin-3-yl)-5-methylsulfonyl-phenoxy]methyl] benzonitrile | A | | | |
| 340 | 5-(3-but-2-ynoxy-5-methylsulfonylphenyl)-1,3-dimethylpyridin-2-one | A | | | |
| 341 | 1,3-dimethyl-5-[3-methylsulfonyl-5-(1-phenylethoxy)phenyl]pyridin-2-one | A | A | A | C |
| 342 | N-[3-(2,4-difluorophenoxy)-5-(1,5-dimethyl-6-oxopyridin-3-yl) phenyl]ethanesulfonamide | A | A | A | B |
| 343 | 4-[3-[(4-methoxyphenyl)methoxy]-5-methylsulfonylphenyl]-2-methylisoquinolin-1-one | B | | | |
| 344 | 2-methyl-4-(3-methylsulfonyl-5-phenylmethoxyphenyl)isoquinolin-1-one | A | | | |
| 345 | 4-[3-(cyclopropylmethoxy)-5-methylsulfonylphenyl]-2-methylisoquinolin-1-one | A | | | |
| 346 | N-[4-(2,4-difluorophenoxy)-6-(1,5-dimethyl-6-oxopyridin-3-yl)pyrimidin-2-yl]ethanesulfonamide | B | | | |
| 347 | N-[2-(2,4-difluorophenoxy)-6-(1,5-dimethyl-6-oxopyridin-3-yl)pyrimidin-4-yl]ethanesulfonamide | B | | | |
| 348 | 4-[3-[[2-(difluoromethoxy)phenyl] methoxy]-5-methylsulfonylphenyl]-6-methylfuro[2,3-c]pyridin-7-one | A | A | A | B |
| 349 | 6-methyl-4-(3-methylsulfonyl-5-phenylmethoxyphenyl)furo[2,3-c]pyridin-7-one | A | A | A | C |
| 350 | 4-[3-(cyclopropylmethoxy)-5-methylsulfonylphenyl]-6-methylfuro[2,3-c]pyridin-7-one | A | | | |
| 351 | 1-methyl-5-(2-methylsulfonyl-5-propylpyrimidin-4-yl)pyridin-2-one | | | | |
| 352 | 5-(5-butyl-2-methylsulfonylpyrimidin-4-yl)-1-methylpyridin-2-one | | | | |
| 353 | 3-chloro-1-methyl-5-(2-methylsulfonyl-5-propylpyrimidin-4-yl)pyridin-2-one | | | | |
| 354 | 5-(5-butyl-2-methylsulfonylpyrimidin-4-yl)-3-chloro-1-methylpyridin-2-one | | | | |
| 355 | 3-methoxy-1-methyl-5-(2-methyl-sulfonyl-5-propylpyrimidin-4-yl) pyridin-2-one | | | | |
| 356 | 5-(5-butyl-2-methylsulfonylpyrimidin-4-yl)-3-methoxy-1-methylpyridin-2-one | | | | |

TABLE 24-continued

| Chem. Synth. Example | Name | BRD4 IC$_{50}$ (µM) | Raji IC$_{50}$ (µM) | HL-60 IC$_{50}$ (µM) | H460 IC$_{50}$ (µM) |
|---|---|---|---|---|---|
| 357 | N-[4-(1-methyl-6-oxopyridin-3-yl)-5-propylpyrimidin-2-yl]ethanesulfonamide | A | | | |
| 358 | N-[5-butyl-4-(1-methyl-6-oxopyridin-3-yl)pyrimidin-2-yl]ethanesulfonamide | A | | | |
| 359 | N-[4-(5-chloro-1-methyl-6-oxopyridin-3-yl)-5-propylpyrimidin-2-yl] ethanesulfonamide | A | | | |
| 360 | N-[5-butyl-4-(5-chloro-1-methyl-6-oxopyridin-3-yl)pyrimidin-2-yl] ethanesulfonamide | A | | | |
| 361 | N-[4-(5-methoxy-1-methyl-6-oxopyridin-3-yl)-5-propylpyrimidin-2-yl] ethanesulfonamide | A | | | |
| 362 | N-[5-butyl-4-(5-methoxy-1-methyl-6-oxopyridin-3-yl)pyrimidin-2-yl] ethanesulfonamide | A | | | |
| 363 | N-[5-butyl-4-(1,5-dimethyl-6-oxopyridin-3-yl)pyrimidin-2-yl]methanesulfonamide | A | | | |
| 364 | 4-[2-(cyclopropylmethoxy)-5-propan-2-ylsulfonylphenyl]-2-methylisoquinolin-1-one | A | | | |
| 365 | 8-[2-(cyclopropylmethoxy)-5-ethylsulfonylphenyl]-6-methyl-4H-pyrido[4,3-b][1,4]oxazine-3,5-dione | A | A | A | C |
| 366 | 8-[2-(cyclopropylmethoxy)-5-ethylsulfonylphenyl]-6-methyl-3,4-dihydro-2H-pyrido[4,3-b][1,4] oxazin-5-one | A | | | |
| 367 | N-[4-(2,4-difluorophenoxy)-3-(7-methyl-8-oxoimidazo[1,5-a]pyrazin-5-yl)phenyl]methanesulfonamide | A | A | A | C |
| 368 | 5-[2-(cyclopropylmethoxy)-5-ethylsulfonylphenyl]-7-methylimidazo[1,5-a]pyrazin-8-one | A | A | A | B |
| 369 | 5-[2-(2,4-difluorophenoxy)-5-(ethylsulfonylmethyl)phenyl]-7-methylimidazo[1,5-a]pyrazin-8-one | A | B | A | C |
| 370 | 7-methyl-5-[5-(methylsulfonylmethyl)-2-(2,2,2-trifluoroethoxy)phenyl] imidazo[1,5-a]pyrazin-8-one | A | B | B | C |
| 371 | 5-[5-(ethylsulfonylmethyl)-2-(2,2,2-trifluoroethoxy)phenyl]-7-methylimidazo[1,5-a]pyrazin-8-one | B | B | B | C |
| 372 | 5-[2-(2,4-difluorophenoxy)-5-(methylsulfonylmethyl)phenyl]-7-methylimidazo[1,5-a]pyrazin-8-one | A | A | A | C |
| 373 | 5-[2-(4,4-difluorocyclohexyl)oxy-5-ethylsulfonylphenyl]-7-methylimidazo[1,5-a]pyrazin-8-one | A | B | A | C |
| 374 | 5-(2-cyclopentyloxy-5-ethylsulfonylphenyl)-7-methylimidazo[1,5-a]pyrazin-8-one | A | A | A | C |
| 375 | 5-[2-(cyclopropylmethylamino)-5-ethylsulfonylphenyl]-7-methylimidazo[1,5-a]pyrazin-8-one | A | | | |
| 376 | 5-[2-(2,4-difluorophenoxy)-5-ethylsulfonylphenyl]-7-methylimidazo[1,5-a]pyrazin-8-one | A | B | A | C |
| 377 | 7-[2-(cyclopropylmethoxy)-5-methylsulfonylphenyl]-5-methylfuro[3,2-c]pyridin-4-one | A | A | A | C |
| 378 | 7-[2-(cyclopropylmethoxy)-5-ethylsulfonylphenyl]-5-methylfuro[3,2-c] pyridin-4-one | A | A | A | B |
| 379 | N-[4-(2,4-difluorophenoxy)-3-(5-methyl-4-oxofuro[3,2-c]pyridin-7-yl)phenyl] ethanesulfonamide | A | A | A | C |
| 380 | N-[4-(2,4-difluorophenoxy)-3-(5-methyl-4-oxofuro[3,2-c]pyridin-7-yl)phenyl] methanesulfonamide | A | A | A | C |

TABLE 24-continued

| Chem. Synth. Example | Name | BRD4 IC$_{50}$ (μM) | Raji IC$_{50}$ (μM) | HL-60 IC$_{50}$ (μM) | H460 IC$_{50}$ (μM) |
|---|---|---|---|---|---|
| 381 | 4-(cyclopropylmethoxy)-5-(1-methyl-6-oxopyridin-3-yl)-1-(methylsulfonylmethyl)pyridin-2-one | A | C | B | C |
| 382 | 5-[4-(cyclopropylmethoxy)-1-(methylsulfonylmethyl)-6-oxopyridin-3-yl]-1,3-dimethylpyridin-2-one | A | B | A | C |
| 383 | 4-[4-(cyclopropylmethoxy)-1-(methylsulfonylmethyl)-6-oxopyridin-3-yl]-7-fluoro-2-methylisoquinolin-1-one | A | B | A | C |
| 384 | 4-[4-(cyclopropylmethoxy)-1-(methylsulfonylmethyl)-6-oxopyridin-3-yl]-2-methylisoquinolin-1-one | A | B | A | C |
| 385 | 5-[4-(2,4-difluorophenoxy)-1-(methylsulfonylmethyl)-6-oxopyridin-3-yl]-1,3-dimethylpyridin-2-one | A | A | A | C |
| 386 | 4-(2,4-difluorophenoxy)-5-(1-methyl-6-oxopyridin-3-yl)-1-(methylsulfonylmethyl)pyridin-2-one | A | B | B | C |
| 387 | 4-[4-(2,4-difluorophenoxy)-1-(methylsulfonylmethyl)-6-oxopyridin-3-yl]-2-methylisoquinolin-1-one | A | A | A | C |
| 388 | 5-(2-but-2-ynoxy-5-methylsulfonylphenyl)-1,3-dimethylpyridin-2-one | A | A | A | C |
| 389 | 5-(2-but-2-ynoxy-5-ethylsulfonylphenyl)-3-methoxy-1-methylpyridin-2-one | A | B | A | C |
| 390 | 5-(5-ethylsulfonyl-2-pent-2-ynoxyphenyl)-3-methoxy-1-methylpyridin-2-one | A | | | |
| 391 | 5-[2-(3-cyclopropylprop-2-ynoxy)-5-ethylsulfonylphenyl]-3-methoxy-1-methylpyridin-2-one | A | B | A | C |
| 392 | 5-[2-(2,4-difluorophenoxy)-5-ethylsulfonylphenyl]-1-methyl-3-(trifluoromethyl)pyridin-2-one | B | | | |
| 393 | 4-[2-(cyclopropylmethoxy)-5-propan-2-ylsulfonylphenyl]-6-methoxy-2-methylisoquinolin-1-one | A | | | |
| 394 | 5-[2-(cyclopropylmethoxy)-5-propan-2-ylsulfonylphenyl]-1,3-dimethylpyridin-2-one | A | | | |
| 395 | N-[3-(1,5-dimethyl-6-oxopyridin-3-yl)-5-phenylmethoxyphenyl]ethanesulfonamide | A | | | |
| 396 | 5-[2-(2,4-difluoroanilino)-5-ethylsulfonylphenyl]-1,3-dimethylpyridin-2-one | A | A | A | C |
| 397 | 5-[2-[(4,4-difluorocyclohexyl)amino]-5-ethylsulfonylphenyl]-1,3-dimethylpyridin-2-one | A | A | A | C |
| 398 | 5-[2-(2,4-difluoroanilino)-5-methylsulfonylphenyl]-1,3-dimethylpyridin-2-one | A | B | A | C |
| 399 | 5-[2-(cyclopropylmethoxy)-5-ethylsulfonylphenyl]-3-methoxy-1-methylpyridin-2-one | A | A | A | C |
| 400 | 5-[2-(2,4-difluorophenoxy)-5-(methylsulfonylmethyl)phenyl]-3-methoxy-1-methylpyridin-2-one | A | A | A | C |
| 401 | 5-[2-(4-hydroxycyclohexyl)oxy-5-methylsulfonylphenyl]-1,3-dimethylpyridin-2-one | A | B | A | C |
| 402 | N-[4-(2,4-difluorophenoxy)-3-(1-methyl-5-methylsulfanyl-6-oxopyridin-3-yl)phenyl]ethanesulfonamide | A | A | A | C |

TABLE 24-continued

| Chem. Synth. Example | Name | BRD4 IC$_{50}$ (μM) | Raji IC$_{50}$ (μM) | HL-60 IC$_{50}$ (μM) | H460 IC$_{50}$ (μM) |
|---|---|---|---|---|---|
| 403 | 5-[2-(cis-4-aminocyclohexyl)oxy-5-methylsulfonylphenyl]-1,3-dimethylpyridin-2-one | A | | | |
| 404 | 5-[2-(trans-4-aminocyclohexyl)oxy-5-methylsulfonylphenyl]-1,3-dimethylpyridin-2-one | A | C | A | C |
| 405 | 1,3-dimethyl-5-[5-methylsulfonyl-2-(3,3,3-trifluoropropoxy) phenyl]pyridin-2-one | A | | | |
| 406 | 5-[2-(2,4-difluorophenoxy)-5-(methylsulfonylmethyl)phenyl]-1-(2-hydroxyethyl)-3-methylpyridin-2-one | A | | | |
| 407 | 5-[5-(ethylsulfonylmethyl)-2-(2,2,2-trifluoroethoxy)phenyl]-1-(2-hydroxyethyl)-3-methylpyridin-2-one | B | | | |
| 408 | 5-[2-(cyclopropylmethylamino)-5-ethylsulfonylphenyl]-1-methyl-3-(methylamino)pyridin-2-one | A | | | |
| 409 | 5-[2-(cyclopropylmethoxy)-5-ethylsulfonylphenyl]-1-methyl-3-(methylamino)pyridin-2-one | A | | | |
| 410 | N-[4-(2,4-difluorophenoxy)-3-[1-methyl-5-(methylamino)-6-oxopyridin-3-yl]phenyl]ethanesulfonamide | A | | | |
| 411 | 5-[5-(ethylsulfonylmethyl)-2-(2,2,2-trifluoroethoxy)phenyl]-1,3-dimethylpyridin-2-one | A | | | |
| 412 | N-[4-(2,4-difluorophenoxy)-3-[1-methyl-5-(methylamino)-6-oxopyridin-3-yl]phenyl]methanesulfonamide | A | | | |
| 413 | 5-[2-[(4,4-difluorocyclohexyl)amino]-5-methylsulfonylphenyl]-1,3-dimethylpyridin-2-one | A | | | |
| 414 | 5-[2-(cyclopropylmethylamino)-5-ethylsulfonylphenyl]-3-methoxy-1-methylpyridin-2-one | A | | | |
| 415 | 5-[2-(4,4-difluorocyclohexyl)oxy-5-methylsulfonylphenyl]-1,3-dimethylpyridin-2-one | A | A | A | C |
| 416 | 5-[2-(cyclopentylamino)-5-ethylsulfonylphenyl]-1,3-dimethylpyridin-2-one | A | A | A | C |
| 417 | 5-[2-(cyclopentylamino)-5-methylsulfonylphenyl]-1,3-dimethylpyridin-2-one | A | A | A | C |
| 418 | 3-chloro-1-methyl-5-[5-(methylsulfonylmethyl)-2-(2,2,2-trifluoroethoxy)phenyl]pyridin-2-one | A | B | A | C |
| 419 | 5-(2-cyclopentyloxy-5-methylsulfonylphenyl)-1,3-dimethylpyridin-2-one | A | B | A | C |
| 420 | 1,3-dimethyl-5-[5-methylsulfonyl-2-(oxan-4-yloxy)phenyl]pyridin-2-one | A | B | A | C |
| 421 | 3-fluoro-1-methyl-5-[5-(methylsulfonylmethyl)-2-(2,2,2-trifluoroethoxy)phenyl]pyridin-2-one | A | | | |
| 422 | 5-[2-(cyclopropylmethylamino)-5-methylsulfonylphenyl]-1,4-dimethylpyridin-2-one | B | | | |
| 423 | 5-[2-(cyclopropylmethylamino)-5-ethylsulfonylphenyl]-1,4-dimethylpyridin-2-one | B | | | |
| 424 | N-[4-(1-methyl-6-oxopyridin-3-yl)-5-phenylthiophen-2-yl]ethanesulfonamide | C | | | |
| 425 | 1,3-dimethyl-5-[5-methylsulfonyl-2-(oxolan-3-ylamino)phenyl]pyridin-2-one | A | | | |
| 426 | 1,3-dimethyl-5-[5-methylsulfonyl-2-(oxolan-3-yloxy)phenyl]pyridin-2-one | A | B | B | C |

TABLE 24-continued

| Chem. Synth. Example | Name | BRD4 IC$_{50}$ (μM) | Raji IC$_{50}$ (μM) | HL-60 IC$_{50}$ (μM) | H460 IC$_{50}$ (μM) |
|---|---|---|---|---|---|
| 427 | 1,3-dimethyl-5-[5-(methylsulfonylmethyl)-2-(2,2,2-trifluoroethoxy)phenyl]pyridin-2-one | A | A | A | C |
| 428 | 5-[2-(cyclopropylmethylamino)-5-methylsulfonylphenyl]-1-ethyl-3-methylpyridin-2-one | A | B | B | C |
| 429 | 5-[2-(2,4-difluorophenoxy)-5-(methylsulfonylmethyl)phenyl]-1-ethyl-3-methylpyridin-2-one | A | A | A | C |
| 430 | N-[3-(1,5-dimethyl-6-oxopyridin-3-yl)-4-(trans-4-hydroxycyclohexyl)oxy-phenyl]ethanesulfonamide | A | A | A | C |
| 431 | N-[3-(1,5-dimethyl-6-oxopyridin-3-yl)-4-(cis-4-hydroxycyclohexyl)oxyphenyl]ethanesulfonamide | A | B | A | C |
| 432 | N-[4-(1-methyl-6-oxopyridin-3-yl)-5-(2-methylphenyl)thiophen-2-yl]ethanesulfonamide | C | | | |
| 433 | N-[3-(1,5-dimethyl-6-oxopyridin-3-yl)-4-(trans-4-hydroxycyclohexyl) oxyphenyl]methane-sulfonamide | A | A | A | C |
| 434 | N-[3-(1,5-dimethyl-6-oxopyridin-3-yl)-4-(cis-4-hydroxycyclohexyl)oxyphenyl] methane-sulfonamide | A | B | B | C |
| 435 | N-[5-(2-ethylphenyl)-4-(1-methyl-6-oxopyridin-3-yl)thiophen-2-yl] ethanesulfonamide | C | | | |
| 436 | 1,3-dimethyl-5-[5-methylsulfonyl-2-(oxan-4-ylamino)phenyl]pyridin-2-one | A | B | A | C |
| 437 | 5-[2-(2,4-difluorophenoxy)-5-(methylsulfonylmethyl)phenyl]-3-fluoro-1-methylpyridin-2-one | A | A | A | C |
| 438 | 5-[2-(cyclopropylmethylamino)-5-methylsulfonylphenyl]-3-(dimethylamino)-1-methylpyridin-2-one | A | A | A | C |
| 439 | N-[3-(1,5-dimethyl-6-oxopyridin-3-yl)-4-(oxan-4-yloxy)phenyl] methanesulfonamide | A | A | A | C |
| 440 | 5-[2-(cyclopropylmethylamino)-5-ethylsulfonylphenyl]-3-(dimethylamino)-1-methylpyridin-2-one | A | A | A | C |
| 441 | N-[3-(1,5-dimethyl-6-oxopyridin-3-yl)-4-(oxan-4-yloxy)phenyl]ethanesulfonamide | A | A | A | C |
| 442 | N-[4-(2,4-difluorophenoxy)-3-(5-methoxy-1-methyl-6-oxopyridin-3-yl)phenyl]methanesulfonamide | A | A | A | C |
| 443 | N-[4-(2,4-difluorophenoxy)-3-(5-methoxy-1-methyl-6-oxopyridin-3-yl)phenyl]ethanesulfonamide | A | A | A | C |
| 444 | N-[3-(1,5-dimethyl-6-oxopyridin-3-yl)-4-(oxolan-3-yloxy)phenyl] methanesulfonamide | A | A | A | C |
| 445 | N-[3-(1,5-dimethyl-6-oxopyridin-3-yl)-4-(oxolan-3-yloxy)phenyl]ethanesulfonamide | A | A | A | C |
| 446 | N-[3-(1,5-dimethyl-6-oxopyridin-3-yl)-4-(oxan-3-yloxy)phenyl] methanesulfonamide | A | A | A | C |
| 447 | N-[4-(4,4-difluorocyclohexyl)oxy-3-(1,5-dimethyl-6-oxopyridin-3-yl)phenyl]methanesulfonamide | A | A | A | C |
| 448 | N-[3-(1,5-dimethyl-6-oxopyridin-3-yl)-4-(oxan-3-yloxy)phenyl]ethanesulfonamide | A | A | A | C |
| 449 | N-[4-(4,4-difluorocyclohexyl)oxy-3-(1,5-dimethyl-6-oxopyridin-3-yl)phenyl] ethanesulfonamide | A | A | A | C |
| 450 | 5-[2-(cyclopropylmethoxy)-5-ethylsulfonylphenyl]-1,3-dimethylpyridin-2-one | A | A | A | C |

TABLE 24-continued

| Chem. Synth. Example | Name | BRD4 IC$_{50}$ (μM) | Raji IC$_{50}$ (μM) | HL-60 IC$_{50}$ (μM) | H460 IC$_{50}$ (μM) |
|---|---|---|---|---|---|
| 451 | N-[4-(2,4-difluorophenoxy)-3-(5-hydroxy-1-methyl-6-oxopyridin-3-yl)phenyl]ethanesulfonamide | A | ND | A | C |
| 452 | 4-(cyclopropylmethylamino)-3-(1,5-dimethyl-6-oxopyridin-3-yl) benzenesulfonamide | B | ND | B | C |
| 453 | 4-(cyclopropylmethylamino)-3-(1-methyl-6-oxopyridin-3-yl)benzenesulfonamide | C | C | C | C |
| 454 | 5-[2-(2,4-difluorophenoxy)-5-(methylsulfonylmethyl)phenyl]-1,4-dimethylpyridin-2-one | A | A | A | C |
| 455 | 5-[2-(2,4-difluorophenoxy)-5-(methylsulfonylmethyl)phenyl]-1,3-dimethylpyridin-2-one | A | A | A | C |
| 456 | 5-(2-ethoxy-5-ethylsulfonylphenyl)-1-($^2$H$_3$)methyl-4-methylpyridin-2-one | A | | | |
| 457 | 5-[2-(cyclopropylmethoxy)-5-ethylsulfonylphenyl]-1-($^2$H$_3$)methyl-4-methylpyridin-2-one | A | A | | |
| 458 | 5-(2-ethoxy-5-ethylsulfonylphenyl)-1,4-dimethylpyridin-2-one | A | | | |
| 459 | 5-[2-(cyclobutylmethoxy)-5-methylsulfonylphenyl]-1,3-dimethylpyridin-2-one | A | A | A | C |
| 460 | 5-[2-(cyclobutylmethoxy)-5-methylsulfonylphenyl]-1-methylpyridin-2-one | A | | | |
| 461 | 5-(5-ethylsulfonyl-2-methoxyphenyl)-3-hydroxy-1-methylpyridin-2-one | B | | | |
| 462 | 5-[2-(cyclopropylmethylamino)-5-methylsulfonylphenyl]-1,3-dimethylpyridin-2-one | A | A | A | C |
| 463 | N-[4-(2,4-difluorophenoxy)-3-[5-(dimethylamino)-1-methyl-6-oxopyridin-3-yl]phenyl]methanesulfonamide | A | A | A | C |
| 464 | N-[4-(2,4-difluorophenoxy)-3-[5-(dimethylamino)-1-methyl-6-oxopyridin-3-yl]phenyl]ethanesulfonamide | A | A | A | C |
| 465 | 5-[2-(cyclopropylmethylamino)-5-ethylsulfonylphenyl]-1,3-dimethylpyridin-2-one | A | A | A | C |
| 466 | 5-[2-(cyclopropylmethoxy)-5-ethylsulfonylphenyl]-1,4-dimethylpyridin-2-one | A | A | A | C |
| 467 | N-[3-(5-hydroxy-1-methyl-6-oxopyridin-3-yl)phenyl]methanesulfonamide | B | C | C | C |
| 468 | 5-[2-(cyclopropylmethylamino)-5-methylsulfonylphenyl]-1-methylpyridin-2-one | A | C | B | C |
| 469 | 3-(dimethylamino)-5-(2-ethoxy-5-ethylsulfonylphenyl)-1-methylpyridin-2-one | A | A | A | C |
| 470 | 5-[2-(2,4-difluorophenoxy)-5-(methylsulfonylmethyl)phenyl]-1-methylpyridin-2-one | A | A | A | B |
| 471 | N-[3-(1-methyl-6-oxo-5-phenylmethoxypyridin-3-yl)phenyl]methanesulfonamide | C | | | |
| 472 | N-[4-(2,4-difluorophenoxy)-3-(1,5-dimethyl-6-oxopyridin-3-yl)phenyl]ethanesulfonamide | A | A | A | C |
| 473 | 5-[2-(cyclopropylmethylamino)-5-ethylsulfonylphenyl]-1-methylpyridin-2-one | A | B | A | C |
| 474 | 5-[2-(cyclopropylmethoxy)-5-methylsulfonylphenyl]-3-(dimethylamino)-1-methylpyridin-2-one | A | A | A | C |

TABLE 24-continued

| Chem. Synth. Example | Name | BRD4 IC$_{50}$ (μM) | Raji IC$_{50}$ (μM) | HL-60 IC$_{50}$ (μM) | H460 IC$_{50}$ (μM) |
|---|---|---|---|---|---|
| 475 | 5-[4-fluoro-2-methoxy-5-(methylsulfonylmethyl)phenyl]-1-methylpyridin-2-one | B | | | |
| 476 | 5-[2-(cyclopropylmethoxy)-5-methylsulfonylphenyl]-1,3-dimethylpyridin-2-one | A | B | A | C |
| 477 | 5-[2-(cyclopropylmethoxy)-5-methylsulfonylphenyl]-1,4-dimethylpyridin-2-one | A | B | A | C |
| 478 | N-[6-[3-(methanesulfonamido)phenyl]-4-methyl-3-oxopyrazin-2-yl]acetamide | C | | | |
| 479 | N-[3-(1,4-dimethyl-6-oxopyridazin-3-yl)phenyl]ethanesulfonamide | C | | | |
| 480 | N-[3-(1,5-dimethyl-6-oxopyridazin-3-yl)phenyl]ethanesulfonamide | B | | | |
| 481 | N-[5-[3-(methanesulfonamido)phenyl]-1-methyl-2-oxopyridin-3-yl]propanamide | C | | | |
| 482 | N-[5-[3-(methanesulfonamido)phenyl]-1-methyl-2-oxopyridin-3-yl]acetamide | C | | | |
| 483 | 1-cyclobutyl-5-[2-(cyclopropylmethoxy)-5-methylsulfonylphenyl]-3-methylpyridin-2-one | A | | | |
| 484 | N-[3-(1-cyclobutyl-5-methyl-6-oxopyridin-3-yl)-4-(2,4-difluorophenoxy)phenyl]methane-sulfonamide | A | | | |
| 485 | 1-benzyl-5-[2-(cyclopropylmethoxy)-5-methylsulfonylphenyl]-3-methylpyridin-2-one | B | | | |
| 486 | 1,3-dimethyl-5-(2-methyl-5-methylsulfonyl-2,3-dihydro-1-benzofuran-7-yl)pyridin-2-one | B | C | B | C |
| 487 | 4-[5-(ethylsulfonylmethyl)-2-(2,2,2-trifluoroethoxy)phenyl]-2-methylisoquinolin-1-one | A | A | A | C |
| 488 | 2-methyl-4-[5-(methylsulfonylmethyl)-2-(2,2,2-trifluoroethoxy) phenyl]isoquinolin-1-one | A | A | A | C |
| 489 | 1,3-dimethyl-5-(7-methylsulfonyl-2,3-dihydro-1,4-benzodioxin-5-yl)pyridin-2-one | B | | | |
| 490 | N-[2-ethyl-8-(2-methyl-1-oxoisoquinolin-4-yl)-3,4-dihydro-2H-chromen-6-yl] methanesulfonamide | A | | | |
| 491 | N-[2-ethyl-8-(2-methyl-1-oxoisoquinolin-4-yl)-3,4-dihydro-2H-chromen-6-yl]ethanesulfonamide | A | | | |
| 492 | N-[8-(1,5-dimethyl-6-oxopyridin-3-yl)-2-ethyl-3,4-dihydro-2H-chromen-6-yl] ethanesulfonamide | A | | | |
| 493 | 4-(2-cyclopropyl-5-methylsulfonyl-2,3-dihydro-1-benzofuran-7-yl)-2-methylisoquinolin-1-one | A | | | |
| 494 | 4-(2-ethyl-5-methylsulfonyl-2,3-dihydro-1-benzofuran-7-yl)-2-methylisoquinolin-1-one | A | B | | |
| 495 | N-[7-(1,5-dimethyl-6-oxopyridin-3-yl)-2-propyl-2,3-dihydro-1-benzofuran-5-yl] ethanesulfonamide | A | | | |
| 496 | N-[2-cyclopropyl-7-(1,5-dimethyl-6-oxopyridin-3-yl)-2,3-dihydro-1-benzofuran-5-yl]ethanesulfonamide | A | A | | |
| 497 | 4-[3-(methoxymethyl)-7-methylsulfonyl-2,3-dihydro-1,4-benzodioxin-5-yl]-2-methylisoquinolin-1-one | A | B | B | C |

TABLE 24-continued

| Chem. Synth. Example | Name | BRD4 IC$_{50}$ (μM) | Raji IC$_{50}$ (μM) | HL-60 IC$_{50}$ (μM) | H460 IC$_{50}$ (μM) |
|---|---|---|---|---|---|
| 498 | 5-[3-(methoxymethyl)-7-methylsulfonyl-2,3-dihydro-1,4-benzodioxin-5-yl]-1,3-dimethylpyridin-2-one | A | C | B | C |
| 499 | 4-[3-(methoxymethyl)-7-methylsulfonyl-2,3-dihydro-1,4-benzodioxin-5-yl]-2-methylisoquinolin-1-one | A | | | |
| 500 | 5-[3-(methoxymethyl)-7-methylsulfonyl-2,3-dihydro-1,4-benzodioxin-5-yl]-1,3-dimethylpyridin-2-one | A | | | |
| 501 | 4-[2-(methoxymethyl)-7-methylsulfonyl-2,3-dihydro-1,4-benzodioxin-5-yl]-2-methylisoquinolin-1-one | A | B | B | C |
| 502 | 5-[2-(methoxymethyl)-7-methylsulfonyl-2,3-dihydro-1,4-benzodioxin-5-yl]-1,3-dimethylpyridin-2-one | A | | | |
| 503 | 4-[2-(methoxymethyl)-7-methylsulfonyl-2,3-dihydro-1,4-benzodioxin-5-yl]-2-methylisoquinolin-1-one | A | | | |
| 504 | 4-[2-(cyclopropylmethoxy)-5-methylsulfonylphenyl]-2-methyl-6,7-dihydro-5H-cyclopenta[c]pyridin-1-one | A | A | | |
| 505 | 4-[2-(cyclopropylmethoxy)-5-ethylsulfonylphenyl]-2-methyl-6,7-dihydro-5H-cyclopenta[c]pyridin-1-one | A | | | |
| 506 | N-[4-(2,4-difluorophenoxy)-3-(2-methyl-1-oxo-6,7-dihydro-5H-cyclopenta[c]pyridin-4-yl)phenyl]methanesulfonamide | A | | | |
| 507 | N-[4-(2,4-difluorophenoxy)-3-(2-methyl-1-oxo-6,7-dihydro-5H-cyclopenta[c] pyridin-4-yl)phenyl]ethanesulfonamide | A | | | |
| 508 | 5-(5-butyl-2-methylsulfonylpyrimidin-4-yl)-3-methyl-1-propan-2-ylpyridin-2-one | A | | | |
| 509 | N-[5-(2,4-difluorophenoxy)-4-(5-methyl-6-oxo-1-propan-2-ylpyridin-3-yl)pyrimidin-2-yl]ethanesulfonamide | A | A | | |
| 510 | 5-[5-(2,4-difluorophenoxy)-2-methylsulfonylpyrimidin-4-yl]-3-methyl-1-propan-2-ylpyridin-2-one | B | | | |
| 511 | N-[5-butyl-4-(5-methyl-6-oxo-1-propan-2-ylpyridin-3-yl)pyrimidin-2-yl] ethanesulfonamide | A | A | | |
| 512 | N-[5-butyl-4-(1-methyl-6-oxo-5-propan-2-ylpyridin-3-yl)pyrimidin-2-yl] ethanesulfonamide | A | A | | |
| 513 | 5-(5-butyl-2-methylsulfonylpyrimidin-4-yl)-1-methyl-3-propan-2-ylpyridin-2-one | A | | | |
| 514 | N-[5-(2,4-difluorophenoxy)-4-(1-methyl-6-oxo-5-propan-2-ylpyridin-3-yl) pyrimidin-2-yl]ethanesulfonamide | A | | | |

Note:
IC$_{50}$ data are designated within the following ranges:
A: ≤0.5 μM;
B: >0.5 μM to ≤5.0 μM;
C: >5.0 μM Example 3: In Vivo Xenograph Study—Antitumor Efficacy in Xenograft Models of NUT Midline Carcinoma (NMC)

Xenograft models of NMC in mice are used in this study. Matched cohorts of mice with established tumors are randomized to treatment with a test compound or vehicle, administered by daily intraperitoneal injection. Before randomization and after 4 days of therapy, mice are evaluated by $^{18}$F-fluorodeoxyglucose (FDG)-PET imaging. Tumor-volume measurements are also made, as are measures of toxicity or weight loss. Tumors are obtained and sectioned and immunohisto-chemically examined for the BRD4-NUT oncoprotein, cell spreading, keratin expression, nuclear Ki67, and TUNEL staining. Paired samples from treated and untreated mice are prepared and analyzed using standardized protocols and commercially available software (i.e., ImageScopt; Aperio Technologies).

Example 4: In Vivo Xenograph Study—Antitumor Efficacy in Xenograft Models of MCF-7 Breast Cancer Time release pellets containing 0.72 mg 1743 Estradiol are subcutaneously implanted into nu/nu mice. MCF-7 cells are grown in RPMI containing 10% FBS at 5% $CO_2$, 37° C. Cells are spun down and re-suspended in 50% RPMI (serum free) and 50% Matrigel at $1\times10^7$ cells/mL. MCF-7 cells are subcutaneously injected (100 μL/animal) on the right flank 2-3 days post pellet implantation and tumor volume (length× width$^2$/2) is monitored bi-weekly. When tumors reach an average volume of ~200 mm$^3$ animals are randomized and treatment is started. Animals are treated with a test compound or vehicle daily for 4 weeks. Tumor volume and body weight are monitored bi-weekly throughout the study. At the conclusion of the treatment period, plasma and tumor samples are taken for pharmacokinetic and pharmacodynamic analyses, respectively.

Example 5: In Vivo Xenograph Study—Antitumor Efficacy in Xenograft Model of Raji Human Burkitts Lymphoma Model Procedure:

Female SCID CB17 mice (6-8 weeks old, Charles River Laboratories) were inoculated subcutaneously in the right flank region with Raji cells (at 3.5×106 cells/mouse) and the tumor was allowed to grow to approximately 150 mm$^3$. Mice were then randomized into treatment cohorts (N=8) and treated orally once daily with vehicle control or test compound for 21 days. Test compound was administered as a suspension in 1% Tween 80, 40% PEG400 and either: 59% of 0.5% HPMC, or 9% DMSO+50% of 0.5% HPMC. Tumors length and width were measured in millimeters three times per week. Tumor volumes were calculated by the formula V=L×W$^2$/2. Tumor growth inhibition (TGI) was calculated with the formula:

TGI=100−(median tumor volume of treatment group/ median tumor volume of vehicle control group)×100

TGI measurements were performed until the volume of a tumor in the control group reached 3,000 mm$^3$. Statistical analysis was performed using 2-tailed T-test. P values <0.05 were considered as statistically significant.

Preliminary Results:

Seven compounds from Table 1 were selected and administered at doses ranging from 5 mg/kg to 50 mg/kg. TGI was determined to range from 42% to 80%. Results are preliminary and do not reflect optimized dosing schedules.

III. Preparation of Pharmaceutical Dosage Forms

Example 1: Oral Tablet

A tablet is prepared by mixing 48% by weight of a compound of Formula (I), or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

I claim:

1. A method for inhibiting a histone demethylase enzyme comprising contacting a histone demethylase enzyme with a compound of Formula (XXIV)

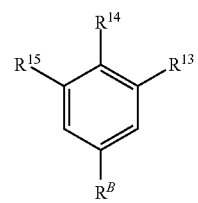

Formula (XXIV)

wherein the compound of Formula (XXIV) includes a pharmaceutically acceptable salt thereof, and wherein:

$R^{13}$ is —Y—Z; wherein

Y is a bond or —$CH_2$—; and

Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$COR^{21}$, —$OC(O)N(R^{22})_2$, —$OSO_2N(R^{22})_2$, —$N(R^{22})SO_3R^{21}$, or —$N(R^{22})_2$, wherein each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl;

$R^{14}$ is hydrogen, halogen, $C_1$-$C_3$ alkyl, or $C_1$-$C_3$ alkoxy;

$R^{15}$ is halogen or U—V, wherein

U is a bond, —O—, or —$CH_2$—, and

V is —CN, alkyl, alkynyl, aryl, aralkyl, cycloalkyl, cycloalkylalkyl, heterocyclyl, heterocyclylalkyl, heteroaryl, or heteroarylalkyl; and $R^B$ is

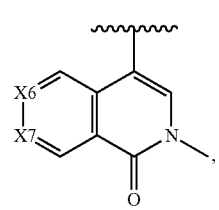

wherein

X6 is C—$R^7$, wherein $R^7$ is hydrogen or halogen, and

X7 is C—$R^8$, wherein $R^8$ is hydrogen or halogen;

or
R$^B$ is

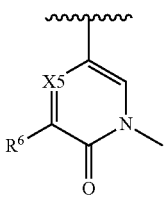

wherein
X5 is C—R$^5$, wherein R$^5$ is hydrogen or halogen, and R$^6$ is hydrogen, alkyl, alkoxy, or halogen;
or

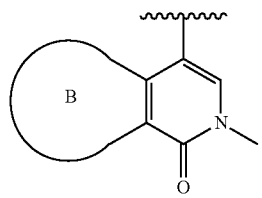

wherein
Ring B is optionally substituted 5-membered heterocyclyl ring containing at least one oxygen or sulfur atom.

2. The method of claim 1, wherein Z is —SO$_2$R$^{21}$, —N(R$^{22}$)SO$_2$R$^{21}$, —SO$_2$R$^{21}$, or —N(R$^{22}$)$_2$.

3. The method of claim 1, wherein R$^{21}$ is heterocyclyl or heterocyclylalkyl.

4. The method of claim 1, wherein R$^{21}$ is alkyl, cycloalkyl, or cycloalkylalkyl.

5. The method of claim 1, wherein R$^{21}$ is alkyl, and the alkyl is C$_1$-C$_4$ alkyl.

6. The method of claim 1, wherein R$^{22}$ is alkyl, cycloalkyl, or aralkyl.

7. The method of claim 1, wherein R$^{22}$ is hydrogen or methyl.

8. The method of claim 1, wherein V is alkyl, aryl, aralkyl, cycloalkylalkyl, heterocyclylalkyl, heteroaryl, heteroarylalkyl, or alkynyl.

9. The method of claim 1, wherein Y is a bond; Z is —N(R$^{22}$)SO$_2$R$^{21}$; U is —O—; and V is aryl, aralkyl, or cycloalkylalkyl.

10. The method of claim 1, wherein Y is a bond; Z is —SO$_2$R$^{21}$; U is —O—; and V is aryl, aralkyl, or cycloalkylalkyl.

11. The method of claim 1, wherein R$^B$ is

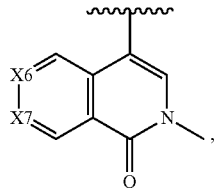

wherein X6 is C—R$^7$, wherein R$^7$ is hydrogen or halogen, and X7 is C—R$^8$, wherein R$^8$ is hydrogen or halogen.

12. The method of claim 11, wherein R$^7$ is halogen and R$^8$ is hydrogen.

13. The method of claim 11, wherein R$^7$ is hydrogen and R$^8$ is halogen.

14. The method of claim 11, wherein both R$^7$ and R$^8$ are hydrogen.

15. A method of treating a histone demethylase-associated cancer wherein the cancer is selected from Burkitt lymphoma, promyelocytic leukemia, non-small cell lung cancer, NUT midline carcinoma, or breast cancer in a subject comprising administering a therapeutically effective dose of a compound of Formula (XXIV)

Formula (XXIV)

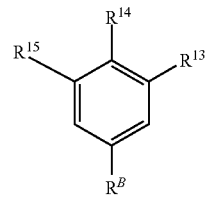

wherein the compound of Formula (XXIV) includes a pharmaceutically acceptable salt thereof, and wherein:

R$^{13}$ is —Y—Z; wherein
  Y is selected from a bond or —CH$_2$—, and
  Z is selected from —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —COR$^{21}$, —OC(O)N(R$^{22}$)$_2$, —OSO$_2$N(R$^{22}$)$_2$, —N(R$^{22}$)SO$_3$R$^{21}$, or —N(R$^{22}$)$_2$, and wherein
  each R$^{21}$ is independently selected from alkyl, cycloalkyl, cycloalkylalkyl, aryl, aralkyl, heterocyclyl, heterocyclylalkyl, heteroaryl, or heteroarylalkyl, and
  each R$^{22}$ is independently selected from hydrogen, alkyl, cycloalkyl, cycloalkylalkyl, aryl, aralkyl, heterocyclyl, heterocyclylalkyl, heteroaryl, or heteroarylalkyl;

R$^{14}$ is hydrogen, halogen, C$_1$-C$_3$ alkyl, or C$_1$-C$_3$ alkoxy;

R$^{15}$ is halogen or U—V, wherein
  U is a bond, —O—, or —CH$_2$—, and
  V is —CN, alkyl, alkynyl, aryl, aralkyl, cycloalkyl, cycloalkylalkyl, heterocyclyl, heterocyclylalkyl, heteroaryl, or heteroarylalkyl; and R$^B$ is

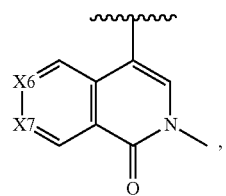

wherein
  X6 is C—R$^7$, wherein R$^7$ is hydrogen or halogen, and
  X7 is C—R$^5$, wherein R$^8$ is hydrogen or halogen;

or
R$^B$ is

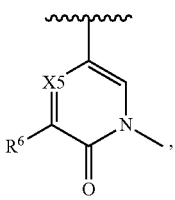

wherein
X5 is C—R$^5$, wherein R$^5$ is hydrogen or halogen, and R$^6$ is hydrogen, alkyl, alkoxy, or halogen;
or
R$^B$ is

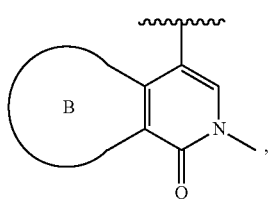

wherein
Ring B is an optionally substituted 5-membered heterocyclyl ring containing at least one oxygen or sulfur atom.

16. The method of claim 15, wherein Z is —SO$_2$R$^{21}$, —N(R$^{22}$)SO$_2$R$^{21}$, or —N(R$^{22}$)$_2$.

17. The method of claim 15, wherein R$^{21}$ is heterocyclyl or heterocyclylalkyl.

18. The method of claim 15, wherein R$^{21}$ is alkyl, cycloalkyl, or cycloalkylalkyl.

19. The method of claim 15, wherein R$^{21}$ is alkyl, and the alkyl is C$_1$-C$_4$ alkyl.

20. The method of claim 15, wherein R$^{22}$ is alkyl, cycloalkyl, or aralkyl.

21. The method of claim 15, wherein R$^{22}$ is hydrogen or methyl.

22. The method of claim 15, wherein R$^{14}$ is hydrogen.

23. The method of claim 15, wherein V is alkyl, aryl, aralkyl, cycloalkylalkyl, heterocyclylalkyl, heteroaryl, heteroarylalkyl, or alkynyl.

24. The method of claim 15, wherein Y is a bond; Z is —N(R$^{22}$)SO$_2$R$^{21}$; U is —O—; and V is aryl, aralkyl, or cycloalkylalkyl.

25. The method of claim 15, wherein Y is a bond; Z is —SO$_2$R$^{21}$; U is —O—; and V is aryl, aralkyl, or cycloalkylalkyl.

26. The method of claim 15, wherein R$^B$ is

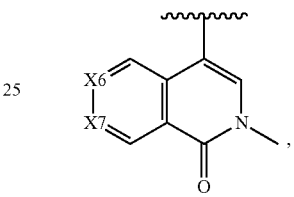

wherein X6 is C—R$^7$, wherein R$^7$ is hydrogen or halogen; and X7 is C—R$^8$, wherein R$^8$ is hydrogen or halogen.

27. The method of claim 26, wherein R$^7$ is halogen and R$^8$ is hydrogen.

* * * * *